United States Patent
Fu et al.

(10) Patent No.: US 12,187,742 B2
(45) Date of Patent: Jan. 7, 2025

(54) DUAL ATM AND DNA-PK INHIBITORS FOR USE IN ANTI-TUMOR THERAPY

(71) Applicant: XRAD Therapeutics, Inc., New York, NY (US)

(72) Inventors: Jianmin Fu, Beijing (CN); Yaode Wang, Beijing (CN); Yue Sun, Beijing (CN); Guosheng Wu, Beijing (CN); Aijun Lu, Beijing (CN); Shuang Zhang, Beijing (CN); Robert Goodnow, Concord, MA (US); Tona Gilmer, Rougemont, NC (US); Michael Kastan, Chapel Hill, NC (US); David Kirsch, Durham, NC (US)

(73) Assignee: XRAD Therapeutics, Inc., Orlando, FL (US)

( * ) Notice: Subject to any disclaimer, the term of this patent is extended or adjusted under 35 U.S.C. 154(b) by 1028 days.

(21) Appl. No.: 17/074,425

(22) Filed: Oct. 19, 2020

(65) Prior Publication Data
US 2022/0315606 A1   Oct. 6, 2022

Related U.S. Application Data

(63) Continuation of application No. PCT/CN2019/083104, filed on Apr. 17, 2019.

(60) Provisional application No. 62/665,296, filed on May 1, 2018.

(30) Foreign Application Priority Data

Apr. 20, 2018 (CN) .......................... 201810359447.6

(51) Int. Cl.
C07D 519/00 (2006.01)
C07D 471/04 (2006.01)
C07D 491/20 (2006.01)

(52) U.S. Cl.
CPC ......... *C07D 519/00* (2013.01); *C07D 471/04* (2013.01); *C07D 491/20* (2013.01)

(58) Field of Classification Search
None
See application file for complete search history.

(56) References Cited

U.S. PATENT DOCUMENTS

| | | |
|---|---|---|
| 8,815,830 B2 | 8/2014 | Wagner |
| 2017/0129888 A1 | 5/2017 | Guan et al. |
| 2018/0072715 A1 | 3/2018 | Fuchss et al. |
| 2018/0280377 A1 | 10/2018 | Pike et al. |
| 2022/0142995 A1 | 5/2022 | Fu et al. |

FOREIGN PATENT DOCUMENTS

| | | |
|---|---|---|
| CN | 102256966 A | 11/2011 |
| CN | 102399218 A | 4/2012 |
| CN | 103880844 A | 6/2014 |
| CN | 103936762 A | 7/2014 |
| CN | 105461711 A | 4/2016 |
| CN | 105461712 A | 4/2016 |
| CN | 106255692 A | 12/2016 |
| EP | 3159341 A1 | 4/2017 |
| EP | 3159342 A1 | 4/2017 |
| EP | 3845532 A1 | 7/2021 |
| RU | 2478620 C2 | 4/2013 |

(Continued)

OTHER PUBLICATIONS

Extended European Search Report for European Patent Application No. 23202655.9, dated Mar. 25, 2024 (14 pages).

(Continued)

*Primary Examiner* — Jeffrey S Lundgren
*Assistant Examiner* — Michael J Schmitt
(74) *Attorney, Agent, or Firm* — Clark & Elbing LLP

(57) ABSTRACT

Provided herein are compounds of the Formula (I), (II), and (III):

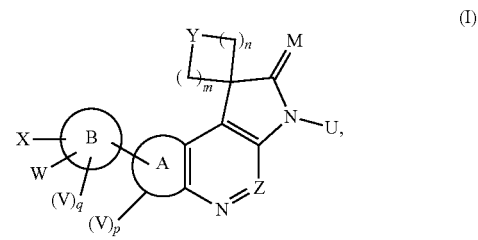

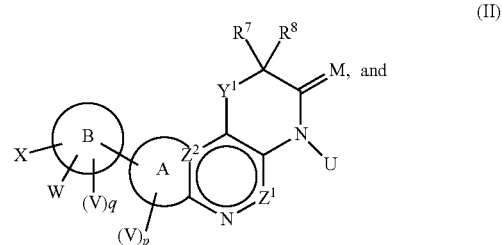

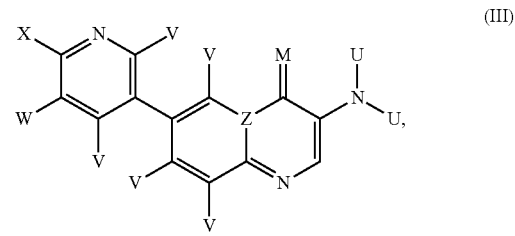

as well as pharmaceutically acceptable salts thereof, wherein the substituents are those disclosed in the specification. These compounds, and the pharmaceutical compositions containing them, are useful for the treatment of oncologic diseases.

25 Claims, No Drawings

(56) References Cited

FOREIGN PATENT DOCUMENTS

| WO | WO-2006/063149 A1 | 6/2006 |
| WO | WO-2007/137738 A1 | 12/2007 |
| WO | WO-2008/051493 A2 | 5/2008 |
| WO | WO-2009/155527 A2 | 12/2009 |
| WO | WO-2010/044885 A2 | 4/2010 |
| WO | WO-2016/155884 A1 | 10/2016 |
| WO | WO-2016/186453 A1 | 11/2016 |
| WO | WO-2017/076895 A1 | 5/2017 |
| WO | WO-2017/076898 A1 | 5/2017 |
| WO | WO-2017/162611 A1 | 9/2017 |
| WO | WO-2017/192385 A1 | 11/2017 |
| WO | WO-2017/194632 A1 | 11/2017 |
| WO | WO-2021/022078 A1 | 2/2021 |

OTHER PUBLICATIONS

Office Action with English translation for Russian Application No. 2020137874 dated Jan. 11, 2023 (33 pages).

Communication Pursuant to Rule 114(2) EPC transmitting Third Party Observations pursuant to Article 115 EPC, against European Application No. EP19787882.0, dated Mar. 24, 2023 (5 Pages).

Communication pursuant to Rule 114(2) EPC transmitting Third Party Observations pursuant to Article 115 EPC, against European Application No. EP19787882.0, dated Mar. 27, 2023 (17 Pages).

International Search Report and Written Opinion for International Patent Application No. PCT/CN19/083104, mailed on Jul. 23, 2019(17 pages).

Mukherjee et al., "The Dual PI3K/mTOR Inhibitor NVP-BEX235 is a Potent Inhibitor of ATM- and DNA-PLCs-Medicated DNA Damage Responses," Neoplasia. 14(1):34-43(2012).

Extended European Search Report for European Patent Application No. 19787882.0, dated Oct. 20, 2021 (14 pages).

First Examination Report for Australian Application No. 2019254980, dated Oct. 11, 2022 (8 pages).

First Examination Report with English translation for Indian Application No. 202017049350, dated Apr. 29, 2022 (7 pages).

Office Action for Mexican Application No. MX/a/2020/010942, dated Sep. 23, 2022 (4 pages).

Office Action with English translation for Russian Application No. 2020137874 dated Feb. 28, 2022 (30 pages).

Search Report with English translation for Russian Application No. 2020137874, dated Feb. 28, 2022 (4 pages).

Toledo et al., "A cell-based screen identifies ATR inhibitors with synthetic lethal properties for cancer-associated mutations," Nat Struct Mol Biol. 18(6):721-7 (2011) (8 pages).

DUAL ATM AND DNA-PK INHIBITORS FOR USE IN ANTI-TUMOR THERAPY

FIELD OF THE INVENTION

The invention relates to compounds and pharmaceutically acceptable salts thereof and methods of their use for the treatment of cancer as a monotherapy or in combination with radiotherapy, chemotherapy, and/or immunotherapy.

BACKGROUND OF THE INVENTION

Several members of the PIKK (PI-3K-like Kinase) family of serine-threonine kinases are known mediators of DNA damage signaling.

Radiation therapy (RT) is used to treat >50% of all cancer patients at some point during their illness. Despite significant effort, previous approaches to develop clinical radiosensitizers have not been highly effective, primarily as a result of targeting non-specific pathways which are not direct regulators of the cellular response to radiation. There is a need for new therapies for oncological diseases.

SUMMARY OF THE INVENTION

In general, the present invention provides a compound of Formula (I):

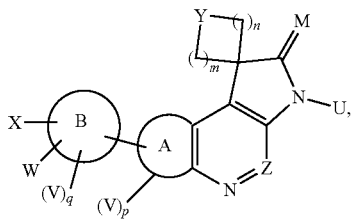

(I)

or a stereoisomer, enantiomer, or tautomer thereof or a mixture thereof;
or a pharmaceutically acceptable salt or solvate thereof; wherein
m and n are each independently 0, 1, 2, 3, or 4;
p and q are each independently 0, 1, 2, or 3;

is a fused cyclyl, a fused heterocyclyl, a fused aryl, or a fused heteroaryl;

is a mono-cyclic or bi-cyclic ring, a mono-heterocyclic or bi-heterocyclic ring, or an aryl or heteroaryl;
Y is $-(C(R^{1a})H)-$, $-C(O)-$, $-O-$, $-N(R^5)-$, $-S(O)_r-$ (where r is 0, 1 or 2), $-S(O)_t(NR^3)-$ (where t is 1 or 2), $-P(O)(R^3)-O-$, $-O-P(O)(R^3)-$, $-P(O)(R^3)-N(R^5)-$, $-N(R^5)-P(O)(R^3)-$, $-CHF-$, $-CF_2-$, $-OC(O)-$, $-C(O)O-$, $-C(O)N(R^5)-$ or $-N(R^5)C(O)-$,
M is O, S, or $NR^5$;
U is hydrogen or alkyl;
V, W, and X are each independently selected from the group consisting of hydrogen, optionally substituted alkyl, optionally substituted alkenyl, optionally substituted alkynyl, halo, optionally substituted haloalkyl, optionally substituted haloalkenyl, optionally substituted haloalkoxy, optionally substituted cycloalkyl, optionally substituted aryl, optionally substituted heterocyclyl, optionally substituted heteroaryl, $-R^6-CN$, $-R^6-NO_2$, $-R^6-OR^5$, $-R^6-N(R^4)R^5$, $-O-R^6-N(R^4)R^5$, $-N=C(R^4)R^5$, $-S(O)_rR^4$, $-OS(O)_2CF_3$, $-R^6-C(O)R^4$, $-C(S)R^4$, $-R^6-C(O)OR^4$, $-C(S)OR^4$, $-R^6-C(O)N(R^4)R^5$, $-C(S)N(R^4)R^5$, $-N(R^5)C(O)R^4$, $-N(R^5)C(S)R^4$, $-N(R^5)C(O)OR^4$, $-N(R^5)C(S)OR^4$, $-N(R^5)C(O)N(R^4)R^5$, $-N(R^5)C(S)N(R^4)R^5$, $-N(R^5)S(O)_tR^4$, $-N(R^5)S(O)_tN(R^4)R^5$, $-R^6-S(O)_tN(R^4)R^5$, $-O-P(O)(R^4)R^5$, $-O-P(O)R^4O(R^4)$, $-O-P(O)R^4N(R^4)R^5$, $-N(R^5)-P(O)(R^4)R^5$, $-N(R^5)-P(O)R^4O(R^4)$, $-N(R^5)-P(O)R^4N(R^4)R^5$, $-N(R^5)-P(O)O(R^4)N(R^4)R^5$, $-N(R^5)-P(O)N(R^4)R^5N(R^4)R^5$, $-N(R^5)C(=NR^5)R^4$, $-N(R^5)C(=NR^5)N(R^4)R^5$, and $-N(R^5)C(=N-CN)N(R^4)R^5$, wherein each r is independently 0, 1, or 2 and each t is independently 1 or 2;
or two adjacent V, or W, or X together with the carbon ring atoms to which they are directly attached, form a fused ring selected from optionally substituted cycloalkyl, optionally substituted aryl, optionally substituted heterocyclyl, and optionally substituted heteroaryl;
Z is $C(R^{1a})$ or N;
$R^{1a}$ is a hydrogen, alkyl, halo, CN, $NO_2$, or $-OR^5$;
$R^3$ is an alkyl, $-OR^5$, or $-N(R^4)R^5$;
each of $R^4$ and $R^5$ is independently selected from group consisting of hydrogen, optionally substituted alkyl, optionally substituted alkenyl, optionally substituted alkynyl, optionally substituted haloalkyl, optionally substituted alkoxyalkyl, optionally substituted cycloalkyl, optionally substituted aryl, optionally substituted heterocyclyl, and optionally substituted heteroaryl;
or, when $R^4$ and $R^5$ are each attached to the same nitrogen atom, $R^4$ and $R^5$, together with the nitrogen atom to which they are attached, form an optionally substituted heterocyclyl or optionally substituted heteroaryl; and
each $R^6$ is a direct bond or a linear or branched optionally substituted alkylene chain, a linear or branched optionally substituted alkenylene chain, a linear or branched optionally substituted alkynylene chain, or optionally substituted heterocyclylene.

The ATM (ataxia-telangiectasia, mutated) and DNA-PK kinases, in particular, are important modulators of cellular responses to DNA breakage and inhibition of either of these molecules markedly increases the sensitivity of cells to ionizing radiation. Thus, effective inhibitors of the actions of ATM and DNA-PK with or without radiation and with or without chemotherapy and with or without immunotherapy provide effective therapy for the treatment of oncologic tumors. The treatment of a patient with dual ATM and DNA-PK inhibitors is a means to delay or eliminate the repair of DNA damage by radiation therapy. As a result, lower doses of ionizing radiation may have enhanced therapeutic benefit, thereby causing less damage to nearby non-cancerous tissues.

Humans and mice containing loss-of-function mutations in the ATM or PRKDC genes, which encode Ataxia Telangiectasia Mutated (ATM) kinase and DNA-dependent Protein Kinase (DNA-PK), respectively, are hypersensitive to ionizing radiation. Accordingly, inhibition of ATM and DNA-PK kinases together will more effectively sensitize tumor cells to radiation or other DNA damaging agents than inhibiting either kinase by itself. In addition, minimizing inhibition of the related kinases, ATR and mTOR, will reduce toxicity of small molecule inhibitors of this class of kinases. Thus, we have developed molecules with dual inhibition of ATM and DNA-PK while minimizing inhibition of other related kinases, like ATR and mTOR. Such optimized molecules will sensitize tumor cells to radiation and select chemotherapeutic agents.

A preferred set of compounds of this invention also included the following structures.

The invention also provides a compound of formula (I):

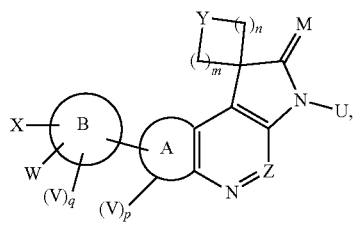

(I)

or a pharmaceutically acceptable salt or solvate thereof;
wherein
m and n are each independently 0, 1, 2, 3, 4;
p and q are each independently 0, 1, 2, 3;

is a fused cyclyl, a fused heterocyclyl, a fused aryl or a fused heteroaryl;

is a mono-cyclic or bi-cyclic ring, a mono-heterocyclic or bi-heterocyclic ring, an aryl or heteroaryl;
Y is —$(C(R^{1a})H)$—;
M is O;
U is hydrogen or alkyl;
V, W, and X are each independently selected from the group consisting of hydrogen, optionally substituted alkyl, halo, optionally substituted haloalkyl, optionally substituted cycloalkyl, optionally substituted aryl, optionally substituted heterocyclyl, optionally substituted heteroaryl, —$R^6$—CN, —$R^6$—$NO_2$, —$R^6$—$OR^5$, —$R^6$—$N(R^4)R^5$, —O—$R^6$—$N(R^4)R^5$, —$S(O)_rR^4$, —$OS(O)_2CF_3$, —$R^6$—$C(O)R^4$, —$C(S)R^4$, —$R^6$—$C(O)OR^4$, —$C(S)OR^4$, —$R^6$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_rR^4$, —$N(R^5)S(O)_rN(R^4)R^5$, —$N(R^4)$—$P(O)(R^4)R^5$, —$N(R^5)$—$P(O)R^4O(R^4)$, —$N(R^5)$—$P(O)R^4N(R^4)R^5$, —$N(R^5)$—$P(O)O(R^4)N(R^4)R^5$, —$N(R^5)$—$P(O)N(R^4)$ $R^5N(R^4)R^5$, —$N(R^5)C(=NR^5)R^4$, —$N(R^5)C(=NR^5)N(R^4)R^5$, and —$N(R^5)C(=N$—$CN)N(R^4)R^5$, wherein each r is independently 0, 1, or 2 and each t is independently 1 or 2; or two adjacent V, or W, or X together with the carbon ring atoms to which they are directly attached, form a fused ring selected from optionally substituted cycloalkyl, optionally substituted aryl, optionally substituted heterocyclyl, and optionally substituted heteroaryl;
Z is $C(R^{1a})$, or N;
$R^{1a}$ is a hydrogen, alkyl, halo, CN, or —OR;
each $R^4$ and $R^5$ is independently selected from group consisting of hydrogen, optionally substituted alkyl, optionally substituted alkenyl, optionally substituted alkynyl, optionally substituted haloalkyl, optionally substituted alkoxyalkyl, optionally substituted cycloalkyl, optionally substituted aryl, optionally substituted heterocyclyl, and optionally substituted heteroaryl;
or, when $R^4$ and $R^5$ are each attached to the same nitrogen atom, $R^4$ and $R^5$, together with the nitrogen atom to which they are attached, form a optionally substituted heterocyclyl or optionally substituted heteroaryl; and
each $R^6$ is a direct bond or a linear or branched optionally substituted alkylene chain, a linear or branched optionally substituted alkenylene chain, a linear or branched optionally substituted alkynylene chain, or optionally substituted heterocyclylene.

In some embodiments, the compound is a compound of formula (IA):

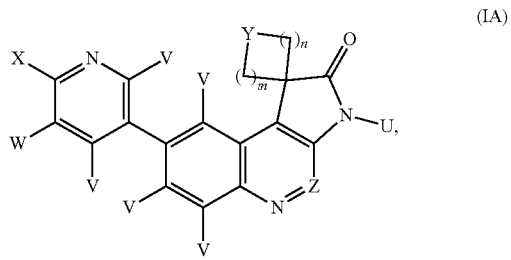

(IA)

where all variables are as described herein.
The invention also provides a compound of Formula (II):

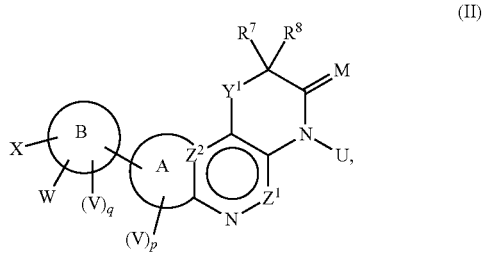

(II)

or a stereoisomer, enantiomer, or tautomer thereof or a mixture thereof;
or a pharmaceutically acceptable salt or solvate thereof;
wherein
p and q are each independently 0, 1, 2, or 3;

is a fused cyclyl, a fused heterocyclyl, a fused aryl, or a fused heteroaryl;

is a mono-cyclic or bi-cyclic ring, a mono-heterocyclic or bi-heterocyclic ring, or an aryl or heteroaryl;

$Y^1$ is a bond, $NR^5$, or $C(R^{1a})_2$;

M is O, S, or $NR^5$, and U is hydrogen or optionally substituted alkyl; or M and U, together with the atoms to which they are attached combine to form an optionally substituted heterocyclyl (e.g., 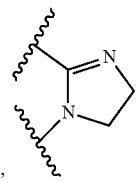 );

V, W, and X are each independently selected from the group consisting of optionally substituted alkyl, optionally substituted alkenyl, optionally substituted alkynyl, halo, optionally substituted haloalkyl, optionally substituted haloalkenyl, optionally substituted haloalkoxy, optionally substituted cycloalkyl, optionally substituted aryl, optionally substituted heterocyclyl, optionally substituted heteroaryl, $-R^6-CN$, $-R^6-NO_2$, $-R^6-OR^5$, $-R^6-N(R^4)R^5$, $-O-R^6-N(R^4)R^5$, $-N=C(R^4)R^5$, $-S(O)_rR^4$, $-OS(O)_2CF_3$, $-R^6-C(O)R^4$, $-C(S)R^4$, $-R^6-C(O)OR^4$, $-C(S)OR^4$, $-R^6-C(O)N(R^4)R^5$, $-C(S)N(R^4)R^5$, $-N(R^5)C(O)R^4$, $-N(R^5)C(S)R^4$, $-N(R^5)C(O)OR^4$, $-N(R^5)C(S)OR^4$, $-N(R^5)C(O)N(R^4)R^5$, $-N(R^5)C(S)N(R^4)R^5$, $-N(R^5)S(O)_tR^4$, $-N(R^5)S(O)_tN(R^4)R^5$, $-R^6-S(O)_tN(R^4)R^5$, $-O-P(O)(R^4)R^5$, $-O-P(O)R^4O(R^4)$, $-O-P(O)R^4N(R^4)R^5$, $-N(R^5)-P(O)(R^4)R^5$, $-N(R^5)-P(O)R^4O(R^4)$, $-N(R^5)-P(O)R^4N(R^4)R^5$, $-N(R^5)-P(O)O(R^4)N(R^4)R^5$, $-N(R^5)-P(O)N(R^4)R^5N(R^4)R^5$, $-N(R^5)C(=NR^5)R^4$, $-N(R^5)C(=NR^5)N(R^4)R^5$, and $-N(R^5)C(=N-CN)N(R^4)R^5$, wherein each r is independently 0, 1, or 2 and each t is independently 1 or 2; or two adjacent groups selected from the group consisting of V, W, and X, together with the carbon ring atoms to which they are directly attached, form a fused ring selected from optionally substituted cycloalkyl, optionally substituted aryl, optionally substituted heterocyclyl, and optionally substituted heteroaryl;

$Z^1$ is $C(R^{1a})$ or N;

$Z^2$ is C or N;

each $R^{1a}$ is independently a hydrogen, optionally substituted alkyl, halo, CN, $NO_2$, $-OR^5$, or $-N(R^4)R^5$;

each of $R^4$ and $R^5$ is independently selected from group consisting of hydrogen, optionally substituted alkyl, optionally substituted alkenyl, optionally substituted alkynyl, optionally substituted haloalkyl, optionally substituted alkoxyalkyl, optionally substituted cycloalkyl, optionally substituted aryl, optionally substituted heterocyclyl, and optionally substituted heteroaryl; or, when $R^4$ and $R^5$ are each attached to the same nitrogen atom, $R^4$ and $R^5$, together with the nitrogen atom to which they are attached, form an optionally substituted heterocyclyl or optionally substituted heteroaryl;

each $R^6$ is a direct bond or a linear or branched optionally substituted alkylene chain, a linear or branched optionally substituted alkenylene chain, a linear or branched optionally substituted alkynylene chain, or optionally substituted heterocyclylene; and each of $R^7$ and $R^8$ is independently selected from group consisting of hydrogen, optionally substituted alkyl, optionally substituted alkenyl, optionally substituted alkynyl, optionally substituted haloalkyl, optionally substituted alkoxyalkyl, optionally substituted cycloalkyl, optionally substituted aryl, optionally substituted heterocyclyl, and optionally substituted heteroaryl; or $R^7$ and $R^8$, together with the atom to which they are attached, combine to form an optionally substituted cycloalkylene or optionally substituted heterocyclylene.

The invention also provides a compound of formula (II):

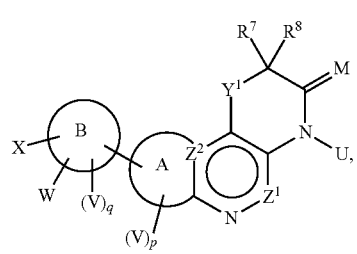

(II)

or a pharmaceutically acceptable salt or solvate thereof; wherein p and q are each independently 0, 1, 2, or 3;

is a fused cyclyl, a fused heterocyclyl, a fused aryl, or a fused heteroaryl;

is a mono-cyclic or bi-cyclic ring, a mono-heterocyclic or bi-heterocyclic ring, or an aryl or heteroaryl;

$Y^1$ is a bond, $NR^5$, or $C(R^{1a})_2$;

M is O, and U is hydrogen or optionally substituted alkyl; or M and U, together with the atoms to which they are attached combine to form an optionally substituted heterocyclyl (e.g., 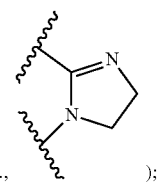 );

V, W, and X are each independently selected from the group consisting of optionally substituted alkyl, halo, optionally substituted haloalkyl, optionally substituted cycloalkyl, optionally substituted aryl, optionally substituted heterocyclyl, optionally substituted heteroaryl, —$R^6$—CN, —$R^6$—$NO_2$, —$R^6$—$OR^5$, —$R^6$—$N(R^4)R^5$, —O—$R^6$—$N(R^4)R^5$, —$S(O)_rR^4$, —$OS(O)_2CF_3$, —$R^6$—$C(O)R^4$, —$C(S)R^4$, —$R^6$—$C(O)OR^4$, —$C(S)OR^4$, —$R^6$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_rR^4$, —$N(R^5)S(O)_tN(R^4)R^5$, —$N(R^5)$—$P(O)(R^4)R^5$, —$N(R^5)$—$P(O)R^4O(R^4)$, —$N(R^5)$—$P(O)R^4N(R^4)R^5$, —$N(R^5)$—$P(O)O(R^4)N(R^4)R^5$, —$N(R^5)$—$P(O)N(R^4)R^5N(R^4)R^5$, —$N(R^5)C(=NR^5)R^4$, —$N(R^5)C(=NR^5)N(R^4)R^5$, and —$N(R^5)C(=N-CN)N(R^4)R^5$, wherein each r is independently 0, 1, or 2 and each t is independently 1 or 2; or two adjacent groups selected from the group consisting of V, W, and X, together with the carbon ring atoms to which they are directly attached, form a fused ring selected from optionally substituted cycloalkyl, optionally substituted aryl, optionally substituted heterocyclyl, and optionally substituted heteroaryl;

$Z^1$ is $C(R^{1a})$ or N;

$Z^2$ is C or N;

each $R^{1a}$ is independently a hydrogen, optionally substituted alkyl, halo, CN, $NO_2$, —$OR^5$, or —$N(R^4)R^5$;

each of $R^4$ and $R^5$ is independently selected from group consisting of hydrogen, optionally substituted alkyl, optionally substituted alkenyl, optionally substituted alkynyl, optionally substituted haloalkyl, optionally substituted alkoxyalkyl, optionally substituted cycloalkyl, optionally substituted aryl, optionally substituted heterocyclyl, and optionally substituted heteroaryl;

or, when $R^4$ and $R^5$ are each attached to the same nitrogen atom, $R^4$ and $R^5$, together with the nitrogen atom to which they are attached, form an optionally substituted heterocyclyl or optionally substituted heteroaryl;

each $R^6$ is a direct bond or a linear or branched optionally substituted alkylene chain, a linear or branched optionally substituted alkenylene chain, a linear or branched optionally substituted alkynylene chain, or optionally substituted heterocyclylene; and each of $R^7$ and $R^8$ is independently selected from group consisting of hydrogen, optionally substituted alkyl, optionally substituted alkenyl, optionally substituted alkynyl, optionally substituted haloalkyl, optionally substituted alkoxyalkyl, optionally substituted cycloalkyl, optionally substituted aryl, optionally substituted heterocyclyl, and optionally substituted heteroaryl; or $R^7$ and $R^8$, together with the atom to which they are attached, combine to form an optionally substituted cycloalkylene or optionally substituted heterocyclylene.

In particular embodiments, $Z^2$ is C. In further embodiments, $Z^1$ is $C(R^{1a})$.

In some embodiments, the compound is a compound of formula (IIA):

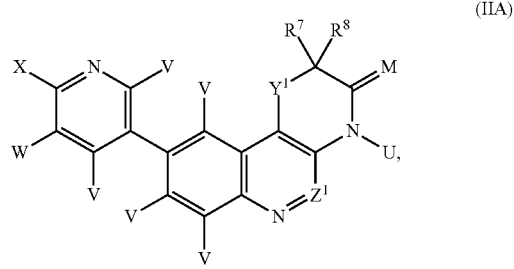

(IIA)

where all variables are as described herein.

The invention also provides a compound of formula (III):

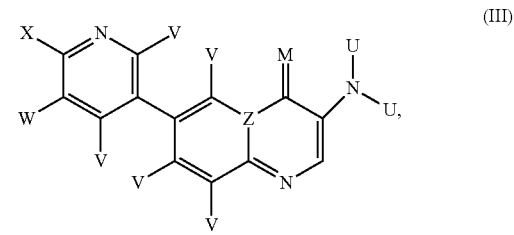

(III)

or a stereoisomer, enantiomer, or tautomer thereof or a mixture thereof;

or a pharmaceutically acceptable salt or solvate thereof; wherein

M is O, S, or $NR^5$, and U is hydrogen, optionally substituted alkyl, optionally substituted heteroaryl, or optionally substituted aryl;

V, W, and X are each independently selected from the group consisting of optionally substituted alkyl, halo, optionally substituted haloalkyl, optionally substituted cycloalkyl, optionally substituted aryl, optionally substituted heterocyclyl, optionally substituted heteroaryl, —$R^6$—CN, —$R^6$—$NO_2$, —$R^6$—$OR^5$, —$R^6$—$N(R^4)R^5$, —O—$R^6$—$N(R^4)R^5$, —$S(O)_rR^4$, —$OS(O)_2CF_3$, —$R^6$—$C(O)R^4$, —$C(S)R^4$, —$R^6$—$C(O)OR^4$, —$C(S)OR^4$, —$R^6$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_rR^4$, —$N(R^5)S(O)_tN(R^4)R^5$, —$N(R^5)$—$P(O)(R^4)R^5$, —$N(R^5)$—$P(O)R^4O(R^4)$, —$N(R^5)$—$P(O)R^4N(R^4)R^5$, —$N(R^5)$—$P(O)O(R^4)N(R^4)R^5$, —$N(R^5)$—$P(O)N(R^4)R^5N(R^4)R^5$, —$N(R^5)C(=NR^5)R^4$, —$N(R^5)C(=NR^5)N(R^4)R^5$, and —$N(R^5)C(=N-CN)N(R^4)R^5$, wherein each r is independently 0, 1, or 2 and each t is independently 1 or 2; or two adjacent groups selected from the group consisting of V, W, and X, together with the carbon ring atoms to which they are directly attached, form a fused ring selected from optionally substituted cycloalkyl, optionally substituted aryl, optionally substituted heterocyclyl, and optionally substituted heteroaryl;

Z is C or N;

each of $R^4$ and $R^5$ is independently selected from group consisting of hydrogen, optionally substituted alkyl, optionally substituted alkenyl, optionally substituted alkynyl, optionally substituted haloalkyl, optionally substituted alkoxyalkyl, optionally substituted cycloalkyl, optionally substituted aryl, optionally substituted heterocyclyl, and optionally substituted heteroaryl;

or, when $R^4$ and $R^5$ are each attached to the same nitrogen atom, $R^4$ and $R^5$, together with the nitrogen atom to which they are attached, form an optionally substituted heterocyclyl or optionally substituted heteroacyl; and each $R^6$ is a direct bond or a linear or branched optionally substituted alkylene chain, a linear or branched optionally substituted alkenylene chain, a linear or branched optionally substituted alkynylene chain, or optionally substituted heterocyclylene.

In some embodiments, the compound is any one of the compounds disclosed in the Examples section.

In certain embodiments, X is optionally substituted alkyl, halo, optionally substituted haloalkyl, optionally substituted cycloalkyl, optionally substituted heterocyclyl, optionally substituted heteroaryl, or —O—$R^6$—$N(R^4)R^5$. In particular embodiments, W is optionally substituted heterocyclyl, optionally substituted heteroaryl, —$R^6$—$N(R^4)R^5$, —$S(O)_tR^4$, —$OS(O)_2CF_3$, —$R^6$—$C(O)R^4$, —$C(S)R^4$, —$R^6$—$C(O)OR^4$, —$C(S)OR^4$, —$R^6$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_tR^4$, —$N(R^5)S(O)_tN(R^4)R^5$, —$N(R^5)$—$P(O)(R^4)R^5$, —$N(R^5)$—$P(O)R^4O(R^4)$, —$N(R^5)$—$P(O)R^4N(R^4)R^5$, —$N(R^5)$—$P(O)O(R^4)N(R^4)R^5$, —$N(R^5)$—$P(O)N(R^4)R^5N(R^4)R^5$, —$N(R^5)C(=NR^5)R^4$, —$N(R^5)C(=NR^5)N(R^4)R^5$, and —$N(R^5)C(=N$—$CN)N(R^4)R^5$, wherein each r is independently 0, 1, or 2 and each t is independently 1 or 2.

In some embodiments, Y is —$C(R^{1a})H)$—, —O—, —$N(R^5)$—, —CHF—, or —$CF_2$—. In further embodiments, Y is —$C(R^{1a})H)$—. In yet further embodiments, M is O. In particular embodiments, $R^{1a}$ is a hydrogen, alkyl, halo, CN, or —$OR^5$. In certain embodiments, V, W, and X are each independently selected from the group consisting of hydrogen, optionally substituted alkyl, halo, optionally substituted cycloalkyl, optionally substituted aryl, optionally substituted heterocyclyl, optionally substituted heteroaryl, —$R^6$—$N(R^4)R^5$, —O—$R^6$—$N(R^4)R^5$, —$N(R^5)S(O)_tR^4$, and —$N(R^5)S(O)_tN(R^4)R^5$, wherein each r is independently 0, 1, or 2, and each t is independently 1 or 2; or two adjacent V, or W, or X together with the carbon ring atoms to which they are directly attached, form a fused ring selected from optionally substituted cycloalkyl, optionally substituted aryl, optionally substituted heterocyclyl, and optionally substituted heteroaryl. In other embodiments, V, W, and X are each independently selected from the group consisting of hydrogen, optionally substituted alkyl, halo, optionally substituted heterocyclyl, —$R^6$—$N(R^4)R^5$, —O—$R^6$—$N(R^4)R^5$, —$N(R^5)S(O)_tR^4$, and —$N(R^5)S(O)_tN(R^4)R^5$, wherein each r is independently 0, 1, or 2 and each t is independently 1 or 2; or two adjacent V, or W, or X together with the carbon ring atoms to which they are directly attached, form a fused ring selected from optionally substituted cycloalkyl, optionally substituted aryl, optionally substituted heterocyclyl, and optionally substituted heteroaryl.

In another aspect, the invention provides methods for the treatment of cancer in a mammal, preferably human or canine, wherein the methods comprise administering to the mammal in need thereof a therapeutically effective amount of a compound of the invention. In some embodiments, the compound is administered to the mammal receiving radiotherapy.

In another aspect, the invention provides methods for the treatment of cancer in a mammal, wherein the methods comprise administering to the mammal in need thereof a therapeutically effective amount of a compound of the invention. In some embodiments, the compound is administered to the mammal in combination with a DNA-damaging agent. Non-limiting examples of DNA-damaging agents include cisplatin, oxaliplatin, carboplatin, valrubicin, idarubicin, calicheamicin, PARP inhibitors.

In another aspect, the invention provides pharmaceutical compositions comprising the compounds of the invention and pharmaceutically acceptable excipients. In one embodiment, the pharmaceutical composition comprises a compound of the invention in a pharmaceutically acceptable carrier and in an amount effective to treat an oncology disease or disorder in an animal, preferably a mammal.

A compound of the invention, when used in a combination therapy, may increase the potency of the other drug therapy or may reduce the frequency and/or severity of adverse events associated with the other drug therapy. For example, side effects of radiation (e.g., oral or gastrointestinal mucositis, dermatitis, pneumonitis, or fatigue) may be reduced in patients receiving a combination therapy including a compound of the invention and radiotherapy (e.g., incidence of the adverse events may be reduced by at least 1%, 54, 10%, or 20%) relative to patients receiving radiotherapy without a compound of the invention. Additionally, other adverse events that may be reduced in patients receiving a combination therapy including a compound of the invention and radiotherapy (e.g., incidence of the adverse events may be reduced by at least 1%, 5%, 10%, or 20%) relative to patients receiving radiotherapy without a compound of the invention may be late effects of radiation, e.g., radiation-induced lung fibrosis, cardiac injury, bowel obstruction, nerve injury, vascular injury, lymphedema, brain necrosis, or radiation-induced cancer. Similarly, when the compound is administered in a combination therapy with another anti-cancer drug (e.g., those described herein), the combined therapy may cause the same or even increased tumor cell death, even when the dose of the other anti-cancer drug is lowered. Reduced dosages of other anti-cancer drugs thus may reduce the severity of adverse events caused by the other anti-cancer drugs.

In another aspect, this invention is directed to the use of the compounds of the invention, as set forth above, as a stereoisomer, enantiomer, tautomer thereof or mixtures thereof, or a pharmaceutically acceptable salt or solvate thereof, or the use of a pharmaceutical composition comprising a pharmaceutically acceptable excipient and a compound of the invention, as set forth above, as a stereoisomer, enantiomer, tautomer thereof or mixtures thereof, or a pharmaceutically acceptable salt or solvate thereof, in the preparation of a medicament for use in the treatment of a disease. In some embodiments, the compound of the invention is administered in combination with radiotherapy. In other embodiments, the compound of the invention is administered in combination with a DNA damaging agent. In certain embodiments, the disease is cancer.

In further embodiments, examples of cancer to be treated using methods and uses disclosed herein include but are not limited to leukemias and lymphomas-acute myelogenous leukemia, acute lymphoblastic leukemia, acute megakaryocytic leukemia, promyelocytic leukemia, erythroleukemia, lymphoblastic T cell leukemia, chronic myelogenous leukemias, chronic lymphocytic leukemia, hairy-cell leukemia, chronic neutrophilic leukemia, plasmacytoma, immunoblastic large cell leukemia, mantle cell leukemia, multiple myelomas, malignant lymphoma, diffuse large B-cell lymphoma, Hodgkins lymphoma, non-Hodgkins lymphoma, lymphoblastic T cell lymphoma, Burkitt's lymphoma and follicular lymphoma.

In yet further embodiments, examples of cancer to be treated using methods and uses disclosed herein include but are not limited to brain cancers (e.g., astrocytoma, glioma, glioblastoma, medulloblastoma, ependymoma), bladder cancer, breast cancer, central nervous system cancers, cervical cancer, colon cancer, endometrial cancer, esophageal cancer, gastrointestinal stromal tumor, gastric cancer, head and neck cancers, buccal cancer, cancer of the mouth, hepatocellular cancer, lung cancer, melanoma, mesothelioma, nasopharyngeal cancer, neuroblastoma, osteosaroma, ovarian cancer, pancreatic cancer, prostate cancer, renal cancer, salivary gland cancer, sarcomas, testicular cancer, urothelial cancer, vulvar cancer and Wilms tumor.

In still further embodiments, examples of cancer to be treated using methods and uses disclosed herein but are not limited to metastases and metastatic cancer. For example, the methods and uses disclosed herein for treating cancer may involve treatment of both primary tumors and metastases.

In some embodiments, the methods and uses disclosed herein comprise the pre-treatment of a subject with a dual an ATM and DNA-PK inhibitor prior to administration of radiation therapy or a DNA damaging agent. Pre-treatment of the subject with a dual ATM and DNA-PK inhibitor may delay or eliminate the repair of DNA damage following radiation therapy.

Radiation therapy includes, but is not limited to, external beam radiation therapy with X-rays (photons), gamma rays from $^{60}$cobalt or other radioactive isotopes, neutrons, electrons, protons, carbon ions, helium ions, and other charged particles. Radiation therapy also includes brachytherapy and radio-pharmaceuticals that emits gamma rays, alpha particles, beta particles, Auger electrons, or other types of radioactive particles from isotopes including $^{192}$Iridium, $^{125}$Iodine, $^{137}$Cesium, $^{103}$Palladium, $^{32}$Phosphate, $^{90}$Yttrium, $^{67}$Gallium, $^{211}$Astatine, $^{223}$Radium, and other radioactive isotopes. Radiation therapy also includes radioimmunotherapy (RIT) with antibodies or small molecules that are conjugated to radioactive isotopes including $^{131}$Iodine, $^{90}$Yttrium, $^{225}$Actinium, $^{211}$Astatine, $^{67}$Gallium, and other radioactive isotopes.

In some embodiments, the combination therapy comprises administration to a subject of an ATM and DNA-PK inhibitor and an anti-tumor agent, e.g., cisplatin, oxaliplatin, carboplatin, topoisomerase I inhibitors, topoisomerase II inhibitors, anthracyclines, valrubicin, idarubicin, calicheamicin, PARP inhibitors (e.g., olaparib, rucaparib, niraparib, veliparib, talazoparib), as well as other anti-cancer agents known to those skilled in the art.

In certain embodiments, the combination therapy comprises administration to a subject of an ATM and DNA-PK inhibitor and an anti-tumor immunotherapeutic agents including by not limited to ipilimumab, ofatumumab, nivolumab, pembrolizumab, atezolizumab, avelumab, durvalumab, etc.

In the combination therapies described herein, an ATM and DNA-PK inhibitor may be administered to the subject simultaneously or sequentially (e.g., before or after) the other drug.

DETAILED DESCRIPTION

Definitions

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described. In addition to the foregoing, as used in the specification and appended claims, unless specified to the contrary, the following terms have the meaning indicated:

"Amino" refers to the —NH$_2$ radical.
"Cyano" refers to the —CN radical.
"Hydroxyl" refers to the —OH radical.
"Imino" refers to the =NH substituent.
"Nitro" refers to the —NO$_2$ radical.
"Oxo" refers to the =O substituent.
"Thioxo" refers to the =S substituent.
"Trifluoromethyl" refers to the —CF$_3$ radical.

"Alkyl" refers to a linear, saturated, acyclic, monovalent hydrocarbon radical or branched, saturated, acyclic, monovalent hydrocarbon radical, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl and the like. An optionally substituted alkyl radical is an alkyl radical that is optionally substituted, valence permitting, by one, two, three, four, or five substituents independently selected from the group consisting of halo, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{15}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 or 2), —S(O)$_t$R$^{16}$ (where t is 1 or 2), —S(O)$_p$R$^{16}$ (where p is 0, 1, or 2) and —S(O)$_t$N(R$^{14}$)$_2$ (where t is 1 or 2), where each R$^{14}$ is independently hydrogen, alkyl, haloalkyl, cycloalkyl, cycloalkylalkyl, aryl, aralkyl, heterocyclyl, or heteroaryl; each R$^{15}$ is independently hydrogen, cycloalkyl, aryl, heterocyclyl, or heteroaryl; and each R$^{16}$ is independently alkyl, haloalkyl, cycloalkyl, aryl, heterocyclyl, or heteroaryl.

"Alkenyl" refers to a linear, acyclic, monovalent hydrocarbon radical or branched, acyclic, monovalent hydrocarbon radical, containing one, two, or three carbon-carbon double bonds, having from two to twelve carbon atoms, preferably two to eight carbon atoms and which is attached to the rest of the molecule by a single bond, e.g., ethenyl, prop-1-enyl, but-1-enyl, pent-1-enyl, penta-1, 4-dienyl and the like. An optionally substituted alkenyl radical is an alkenyl radical that is optionally substituted, valence permitting, by one, two, three, four, or five substituents independently selected from the group consisting of: halo, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{15}$, —C(O)OR$^{14}$, —C(O)N(R$^{14}$)$_2$, —N(R$^{14}$)C(O)R$^{16}$, —N(R$^{14}$)C(O)R$^{16}$, —N(R$^{14}$)S(O)$_t$R$^{16}$ (where t is 1 or 2), —S(O)$_t$OR$^{16}$ (where t is 1 or 2), —S(O)$_p$R$^{16}$ (where p is 0, 1, or 2) and —S(O)$_t$N(R$^{14}$)$_2$ (where t is 1 or 2), where each R$^{14}$ is independently hydrogen, alkyl, haloalkyl, cycloalkyl, aryl, heterocyclyl, or heteroaryl; each R$^{15}$ is independently hydrogen, cycloalkyl, aryl, heterocyclyl, or heteroaryl; and each R$^{16}$ is independently alkyl, haloalkyl, cycloalkyl, cycloalkylalkyl, aryl, heterocyclyl, or heteroaryl.

"Alkynyl" refers to a linear, acyclic, monovalent hydrocarbon radical or branched, acyclic, monovalent hydrocarbon radical, containing one or two carbon-carbon triple bonds and, optionally, one, two, or three carbon-carbon double bonds, and having from two to twelve carbon atoms, preferably two to eight carbon atoms and which is attached to the rest of the molecule by a single bond, e.g., ethynyl, prop-1-ynyl, but-1-ynyl, pent-1-ynyl, penta-1-en-4-ynyl and the like. An optionally substituted alkynyl radical is an alkynyl radical that is optionally substituted by one, two, three, four, or five substituents independently selected from the group consisting of: halo, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{15}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 or 2), —S(O)$_t$OR$^{16}$ (where t is 1 or 2), —S(O)$_p$R$^{16}$ (where p is 0, 1, or 2) and —S(O)$_t$N(R$^{14}$)$_2$ (where t is 1 or 2) where each R$^{14}$ is independently hydrogen, alkyl, haloalkyl, cycloalkyl, aryl, heterocyclyl, or heteroaryl; each R$^{15}$ is independently hydrogen, cycloalkyl, aryl, heterocyclyl, or heteroaryl; and each R$^{16}$ is independently alkyl, haloalkyl, cycloalkyl, aryl, heterocyclyl, or heteroaryl.

"Alkylene" or "alkylene chain" refers to a linear, acyclic, saturated, divalent hydrocarbon chain or branched, acyclic, saturated, divalent hydrocarbon chain, having from one to twelve carbon atoms, e.g., methylene, ethylene, propylene, n-butylene, and the like. The alkylene chain is attached through single bonds. The points of attachment of the alkylene chain may be on the same carbon atom or on different carbon atoms within the alkylene chain. An optionally substituted alkylene chain is an alkylene chain that is optionally substituted, valence permitting, by one, two, three, four, or five substituents independently selected from the group consisting of: halo, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{15}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 or 2), —S(O)$_t$OR$^{16}$ (where t is 1 or 2), —S(O)$_p$R$^{16}$ (where p is 0, 1, or 2) and —S(O)$_t$N(R$^{14}$)$_2$ (where t is 1 or 2) where each R$^{14}$ is independently hydrogen, alkyl, haloalkyl, cycloalkyl, aryl, heterocyclyl, or heteroaryl; each R$^{15}$ is independently hydrogen, cycloalkyl, aryl, heterocyclyl, or heteroaryl; and each R$^{16}$ is independently alkyl, haloalkyl, cycloalkyl, aryl, heterocyclyl, or heteroaryl.

"Alkenylene" or "alkenylene chain" refers to a linear, acyclic, divalent hydrocarbon chain or branched, acyclic, divalent hydrocarbon chain, containing one, two, or three carbon-carbon double bonds and having from two to twelve carbon atoms, e.g., ethenylene, propenylene, n-butenylene and the like. The alkenylene chain is attached through single bonds. The points of attachment of the alkenylene chain may be on the same carbon atom or on different carbon atoms within the alkenylene chain. An optionally substituted alkenylene chain is an alkenylene chain that is optionally substituted, valence permitting, by one, two, three, four, or five substituents independently selected from the group consisting of: halo, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{15}$, —C(O)OR$^{14}$, —C(O)N(R$^{14}$)$_2$, —N(R$^4$)C(O)OR$^{16}$, —N(R$^{14}$)C(O)R$^{16}$, —N(R$^{14}$)S(O)$_t$R$^{16}$ (where t is 1 or 2), —S(O)$_t$R$^{16}$ (where t is 1 or 2), —S(O)$_p$R$^{16}$ (where p is 0, 1, or 2) and —S(O)$_t$N(R$^{14}$)$_2$ (where t is 1 or 2) where each R$^{14}$ is independently hydrogen, alkyl, haloalkyl, cycloalkyl, aryl, heterocyclyl, or heteroaryl; each R$^{15}$ is independently hydrogen, cycloalkyl, aryl, heterocyclyl, or heteroaryl; and each R$^{16}$ is independently alkyl, haloalkyl, cycloalkyl, aryl, heterocyclyl, or heteroaryl.

"Alkynylene" or "alkynylene chain" refers to a linear, acyclic, divalent, hydrocarbon chain or branched, acyclic, divalent hydrocarbon chain, containing one or two carbon-carbon triple bonds and, optionally, one, two, or three carbon-carbon double bonds, and having from two to twelve carbon atoms, e.g., propynylene, n-butynylene and the like. The alkynylene chain is attached through single bonds. The points of attachment of the alkynylene may be on the same carbon atom or on different carbon atoms within the alkynylene chain. An optionally substituted alkynylene chain is an alkynelene chain that is optionally substituted by one, two, three, four, or five substituents independently selected from the group consisting of: halo, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{15}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 or 2), —S(O)$_t$OR$^{16}$ (where t is 1 or 2), —S(O)$_p$R$^{16}$ (where p is 0, 1, or 2) and —S(O)$_t$N(R$^{14}$)$_2$ (where t is 1 to 2) where each R$^{14}$ is independently hydrogen, alkyl, haloalkyl, cycloalkyl, aryl, heterocyclyl, or heteroaryl; each R$^{15}$ is independently hydrogen, cycloalkyl, aryl, heterocyclyl, or heteroaryl; and each R$^{16}$ is independently alkyl, haloalkyl, cycloalkyl, aryl, heterocyclyl, or heteroaryl.

"Alkoxy" refers to a radical of the formula —OR$_a$ where R$_a$ is an alkyl radical as defined above containing one to twelve carbon atoms. The alkyl part of the optionally substituted alkoxy radical is optionally substituted as defined above for an alkyl radical.

"Alkoxyalkyl" refers to a radical of the formula —R$_a$—O—R$_b$ where R$_a$ is alkylene and R$_b$ is alkyl as defined above. Alkyl and alkylene parts of the optionally substituted alkoxyalkyl radical are optionally substituted as defined above for an alkyl radical and alkylene chain, respectively.

"Aralkyl" refers to a radical of the formula —R$_a$—R$_b$, where R$_a$ is alkylene and R$_b$ is aryl as described herein. Alkylene and aryl portions of optionally substituted aralkyl are optionally substituted as described herein for alkylene and aryl, respectively.

"Aryl" refers to an aromatic monocyclic or multicyclic hydrocarbon ring system radical containing from 6 to 18 carbon atoms, where the multicyclic aryl ring system is a bicyclic, tricyclic, or tetracyclic ring system. Aryl radicals include, but are not limited to, groups such as fluorenyl, phenyl and naphthyl. An optionally substituted aryl is an aryl radical that is optionally substituted by one, two, three, four, or five substituents independently selected from the group consisting of alkyl, akenyl, halo, haloalkyl, haloalkenyl, cyano, nitro, aryl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)S(O)$_t$R$^{16}$ (where t is 1 or 2), —R$^{15}$—S(O)$_t$OR$^{16}$ (where t is 1 or 2), —R$^{15}$—S(O)$_p$R$^{16}$ (where p is 0, 1, or 2), and —R$^{15}$—S(O)$_t$N(R$^{14}$)$_2$ (where t is 1 or 2), where each R$^{14}$ is independently hydrogen, alkyl, haloalkyl, cycloalkyl, aryl, heterocyclyl, or heteroaryl; each R$^{15}$ is independently a direct bond or a linear or branched alkylene or alkenylene chain; and each R$^{16}$ is independently alkyl, haloalkyl, cycloalkyl, cycloalkylalkyl, aryl, heterocyclyl, or heteroaryl.

"Cycloalkyl" refers to a stable non-aromatic monocyclic or polycyclic hydrocarbon radical having from three to fifteen carbon atoms, preferably having from three to ten carbon atoms, and which is saturated or unsaturated, and which attaches to the rest of the molecule by a single bond. A polycyclic hydrocarbon radical is bicyclic, tricyclic, or tetracyclic ring system. An unsaturated cycloalkyl contains one, two, or three carbon-carbon double bonds and/or one carbon-carbon triple bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, and the like. An optionally substituted cycloalkyl is a cycloalkyl radical that is optionally substituted by one, two, three, four, or five substituents independently selected from the group consisting of alkyl, alkenyl, halo, haloalkyl, haloalkenyl, cyano, nitro, oxo, aryl, aralkyl, cycloalkyl, heterocyclyl, heteroaryl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})S(O)_tR^{16}$ (where t is 1 or 2), $-R^{15}-S(O)_tOR^{16}$ (where t is 1 or 2), $-R^{15}-S(O)_pR^{16}$ (where p is 0, 1, or 2) and $-R^{15}-S(O)_tN(R^{14})_2$ (where t is 1 or 2) where each $R^{14}$ is independently hydrogen, alkyl, haloalkyl, cycloalkyl, aryl, heterocyclyl, or heteroaryl; each $R^{15}$ is independently a direct bond or a linear or branched alkylene or alkenylene chain, and each $R^{16}$ is independently alkyl, haloalkyl, cycloalkyl, cycloalkylalkyl, aryl, aralkyl, heterocyclyl, or heteroaryl.

"Cycloalkylene" refers to a stable non-aromatic monocyclic or polycyclic hydrocarbon radical having from three to fifteen carbon atoms, preferably having from three to ten carbon atoms, and which is saturated or unsaturated, and which attaches to the rest of the molecule by two single bonds. An optionally substituted cycloalkylene is a cycloalkylene that is substituted as described herein for cycloalkyl.

"Fused" refers to any ring system described herein which is fused to an existing ring structure in the compounds of the invention. When the fused ring system is a heterocyclyl or a heteroaryl, any carbon atom on the existing ring structure which becomes part of the fused ring system may be replaced with a nitrogen atom.

"Halo" refers to the halogen substituents: bromo, chloro, fluoro, and iodo.

"Haloalkyl" refers to an alkyl radical, as defined above, that is further substituted by one or more halogen substituents. The number of halo substituents included in haloalkyl is from one and up to the total number of the hydrogen atoms available for replacement with the halo substituents (e.g., perfluoroalkyl). Non-limiting examples of haloalkyl include trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl and the like. For an optionally substituted haloalkyl, the hydrogen atoms bonded to the carbon atoms of the alkyl part of the haloalkyl radical may be optionally replaced with substituents as defined above for an optionally substituted alkyl.

"Haloalkenyl" refers to an alkenyl radical, as defined above, that is further substituted by one or more halo substituents. The number of halo substituents included in haloalkenyl is from one and up to the total number of the hydrogen atoms available for replacement with the halo substituents (e.g., perfluoroalkenyl). Non-limiting examples of haloalkenyl include 2,2-difluoroethenyl, 3-chloroprop-1-enyl, and the like. For an optionally substituted haloalkenyl, the hydrogen atoms bonded to the carbon atoms of the alkenyl part of the haloalkenyl radical may be optionally replaced with substitutents as defined above for an optionally substituted alkenyl group.

"Haloalkynyl" refers to an alkynyl radical, as defined above, that is further substituted by one or more halo substituents. The number of halo substituents included in haloalkynyl is from one and up to the total number of the hydrogen atoms available for replacement with the halo substituents (e.g., perfluoroalkynyl). Non-limiting examples of haloalkynyl include 3-chloroprop-1-ynyl and the like. The alkynyl part of the haloalkynyl radical may be additionally optionally substituted as defined above for an alkynyl group.

"Heteroarylalkyl" refers to a radical of the formula $-R_a-R_b$, where $R_a$ is alkylene and $R_b$ is heteroaryl as described herein. Alkylene and heteroaryl portions of optionally substituted heteroarylalkyl are optionally substituted as described herein for alkylene and heteroaryl, respectively.

"Heterocyclyl" refers to a stable 3- to 18-membered non-aromatic ring system radical having the carbon count of two to twelve and containing a total of one to six heteroatoms independently selected from the group consisting of nitrogen, oxygen, phosphorus, and sulfur. A heterocyclyl radical is a monocyclic, bicyclic, tricyclic, or tetracyclic ring system. A bicyclic, tricyclic, or tetracyclic heterocyclyl is a fused, spiro, and/or bridged ring system. The heterocyclyl radical may be saturated or unsaturated. An unsaturated heterocyclyl contains one, two, or three carbon-carbon double bonds and/or one carbon-carbon triple bond. An optionally substituted heterocyclyl is a heterocyclyl radical that is optionally substituted by one, two, three, four, or five substituents independently selected from the group consisting of alkyl, alkenyl, halo, haloalkyl, haloalkenyl, cyano, oxo, thioxo, nitro, aryl, aralkyl, cycloalkyl, heterocyclyl, heteroaryl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})S(O)_tR^{16}$ (where t is 1 or 2), $-R^{15}-S(O)_tOR^{16}$ (where t is 1 or 2), $-R^{15}-S(O)_pR^{16}$ (where p is 0, 1, or 2), and $-R^{15}-S(O)_tN(R^{14})_2$ (where t is 1 or 2), where each $R^{14}$ is independently hydrogen, alkyl, alkenyl, haloalkyl, cycloalkyl, aryl, heterocyclyl, or heteroaryl; each $R^{15}$ is independently a direct bond or a linear or branched alkylene or alkenylene chain; and each $R^{16}$ is independently alkyl, alkenyl, haloalkyl, cycloalkyl, aryl, heterocyclyl, or heteroaryl. The nitrogen, carbon, or sulfur atoms in the heterocyclyl radical may be optionally oxidized (when the substituent is oxo and is present on the heteroatom); the nitrogen atom may be optionally quaternized (when the substituent is alkyl, alkenyl, aryl, aralkyl, cycloalkyl, heterocyclyl, heteroaryl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})S(O)_tR^{16}$ (where t is 1 or 2), $-R^{15}-S(O)_tOR^{16}$ (where t is 1 or 2), $-R^{15}-S(O)_pR^{16}$ (where p is 0, 1, or 2), and $-R^{15}-S(O)_tN(R^{14})_2$ (where t is 1 or 2), where $R^{15}$ is a linear or branched alkylene or alkenylene chain, and $R^{14}$ and $R^{16}$ are as defined above). Examples of optionally substituted heterocyclyl radicals include, but are not limited to, azetidinyl, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

"Heterocyclylene" refers to a heterocyclyl in which one hydrogen atom is replaced with a valency. An optionally substituted heterocyclylene is optionally substituted as described herein for heterocyclyl.

"Heteroaryl" refers to a 5- to 18-membered ring system radical containing at least one aromatic ring, having the carbon count of one to seventeen carbon atoms, and containing a total of one to ten heteroatoms independently selected from the group consisting of nitrogen, oxygen, and sulfur. The heteroaryl radical is a monocyclic, bicyclic, tricyclic, or tetracyclic ring system. The bicyclic, tricyclic, or tetracyclic heteroaryl radical is a fused and/or bridged ring system. An optionally substituted heteroaryl is a heteroaryl radical that is optionally substituted by one, two, three, four, or five substituents independently selected from the group consisting of alkyl, alkenyl, alkoxy, halo, haloalkyl, haloalkenyl, cyano, oxo, thioxo, nitro, oxo, aryl, aralkyl, cycloalkyl, heterocyclyl, heteroaryl, or heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})S(O)_tR^{16}$ (where t is 1 or 2), —$R^{15}$—$S(O)_tOR^{16}$ (where t is 1 or 2), —$R^{15}$—$S(O)_pR^{16}$ (where p is 0, 1, or 2), and —$R^{15}$—$S(O)_tN(R^{14})_2$ (where t is 1 or 2), where each $R^{14}$ is independently hydrogen, alkyl, alkenyl, haloalkyl, cycloalkyl, aryl, heterocyclyl, or heteroaryl; each $R^{15}$ is independently a direct bond or a linear or branched alkylene or alkenylene chain; and each $R^{16}$ is alkyl, alkenyl, haloalkyl, cycloalkyl, aryl, heterocyclyl, or heteroaryl. The nitrogen, carbon, or sulfur atoms in the heterocyclyl radical may be optionally oxidized (when the substituent is oxo and is present on the heteroatom), provided that at least one ring in heteroaryl remains aromatic; the nitrogen atom may be optionally quaternized (when the substituent is alkyl, alkenyl, aryl, aralkyl, cycloalkyl, heterocyclyl, heteroaryl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})S(O)_tR^{16}$ (where t is 1 or 2), —$R^{15}$—$S(O)_tOR^{16}$ (where t is 1 or 2), —$R^{15}$—$S(O)_pR^{16}$ (where p is 0, 1, or 2), and —$R^{15}$—$S(O)_tN(R^{14})_2$ (where t is 1 or 2), where $R^{15}$ is a linear or branched alkylene or alkenylene chain, and $R^{14}$ and $R^{16}$ are as defined above), provided that at least one ring in heteroaryl remains aromatic. Examples of optionally substituted heteroaryl radicals include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyl, naphthyridinyl, oxadiazolyl, 2-oxoazepinyl, oxazolyl, oxiranyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl and thiophenyl (i.e. thienyl).

The invention disclosed herein is also meant to encompass all pharmaceutically acceptable compounds of formula (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action on ATM and DNA-PK enzymes, or binding affinity to pharmacologically important site of action on ATM and DNA-PK enzymes. Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples and Preparations as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically identified by administering a radiolabelled compound of the invention in a detectable dose to an animal, such as rat, mouse, guinea pig, canine, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g. cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals. e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, in the mammal, preferably a human or canine. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;
(ii) inhibiting the disease or condition, i.e., arresting its development;
(iii) relieving the disease or condition, i.e., causing regression of the disease or condition; or
(iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Also within the scope of the invention are intermediate compounds of formula (I) and all polymorphs of the aforementioned species and crystal habits thereof.

In one embodiment, there is provided a compound of Formula (I), wherein the compound is selected from the group consisting of:

8'-(6-(3-(Dimethylamino)propoxy)pyridin-3-yl)-3'-methylspiro[cyclopropane-1,1'-pyrrolo[2,3-c]quinolin]-2'(3'H)-one
N-(2-(3-(Dimethylamino)propoxy)-5-(3'-methyl-2'-oxo-2',3'-dihydrospiro[cyclopentane-1,1'-pyrrolo[2,3-c]quinolin]-8'-yl)pyridin-3-yl)benzenesulfonamide
N-(2-(3-(Dimethylamino)propoxy)-5-(3'-methyl-2'-oxo-2',3'-dihydrospiro[cyclohexane-1,1'-pyrrolo[2,3-c]quinolin]-8'-yl)pyridin-3-yl)benzenesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide
N-(2-(3-(Dimethylamino)propoxy)-5-(3'-methyl-2'-oxo-2',3'-dihydrospiro[cyclobutane-1,1'-pyrrolo[2,3-c,]quinolin]-8'-yl)pyridin-3-yl)benzenesulfonamide
N-(2-(2-(Dimethylamino)ethoxy)-5-(3'-methyl-2'-oxo-2',3'-dihydrospiro[cyclopentane-1,1'-pyrrolo[2,3-c]quinolin]-8'-yl)pyridin-3-yl)benzenesulfonamide
N-(2-(3-(Dimethylamino)propoxy)-5-(3'-methyl-2'-oxo-2',3'-dihydrospiro[cyclopentane-1,1'-pyrrolo[2,3-c]quinolin]-8'-yl)pyridin-3-yl)benzamide
N-(2-Methoxy-5-(3'-methyl-2'-oxo-2',3'-dihydrospiro[oxetane-3,1'-pyrrolo[2,3-c]quinolin]-8'-yl)pyridin-3-yl)benzenesulfonamide
3-Chloro-N-(2-methoxy-5-(3'-methyl-2'-oxo-2',3'-dihydrospiro[cyclopropane-1,1'-pyrrolo[2,3-c]quinolin]-8'-yl)pyridin-3-yl)benzenesulfonamide
N-(2-(Dimethylamino)-5-(3'-methyl-2'-oxo-2',3'-dihydrospiro[cyclobutane-1,1'-pyrrolo[2,3-c]quinolin]-8'-yl)pyridin-3-yl)benzenesulfonamide
N-(5-(3'-((1H-pyrazol-4-yl)methyl)-2'-oxo-2',3'-dihydrospiro[cyclopropane-1,1'-pyrrolo[2,3-c]quinolin]-8'-yl)-2-methoxypyridin-3-yl)benzenesulfonamide
N-(2-Methoxy-5-(3'-methyl-2'-oxo-2',3'-dihydrospiro[cyclopropane-1,1'-pyrrolo[2,3-c]quinolin]-8'-yl)pyridin-3-yl)-4-nitrobenzenesulfonamide
3-Acetyl-N-(2-methoxy-5-(3'-methyl-2'-oxo-2',3'-dihydrospiro[cyclopropane-1,1'-pyrrolo[2,3-c]quinolin]-8'-yl)pyridin-3-yl)benzenesulfonamide
N-(2-Methoxy-5-(3'-methyl-2'-oxo-2',3'-dihydrospiro[cyclopropane-1,1'-pyrrolo[2,3-c]quinolin]-8'-yl)pyridin-3-yl)benzenesulfonamide
N-(2-Chloro-5-(3'-methyl-2'-oxo-2',3'-dihydrospiro[cyclopropane-1,1'-pyrrolo[2,3-c]quinolin]-8'-y])pyridin-3-yl)benzenesulfonamide
N-(2-Methoxy-5-(3-((1-methyl-1H-pyrazol-3-yl)amino)-4-oxo-4H-pyrido[1,2-a]pyrimidin-7-yl)pyridin-3-yl)benzenesulfonamide
N-(2-Methoxy-5-(3'-(oxetan-3-ylmethyl)-2'-oxo-2',3'-dihydrospiro[cyclopropane-1,1'-pyrrolo[2,3-c]quinolin]-8'-yl)pyridin-3-yl)benzenesulfonamide
3-(1-Hydroxyethyl)-N-(2-methoxy-5-(3'-methyl-2'-oxo-2'3'-dihydrospiro[cyclopropane-1,1'-pyrrolo[2,3-c]quinolin]-8'-yl)pyridin-3-yl)benzenesulfonamide
N-(2-Methoxy-5-(2'-oxo-2',3'-dihydrospiro[cyclopropane-1,1'-pyrrolo[2,3-c]quinolin]-8'-yl)pyridin-3-yl)benzenesulfonamide
3'-Methyl-8'-(quinolin-3-yl)spiro[cyclopropane-1,1'-pyrrolo[2,3-c]quinolin]-2'(3'H)-one
N-(5-(3'-(Cyanomethyl)-2'-oxo-2',3'-dihydrospiro[cyclopropane-1,1'-pyrrolo[2,3-c]quinolin]-8'-yl)-2-methoxypyridin-3-yl)benzenesulfonamide
3'-Methyl-8'-(quinolin-6-yl)spiro[cyclopropane-1,1'-pyrrolo[2,3-c]quinolin]-2'(3'H)-one
N-(2-Chloro-5-(1,3-dimethyl-2-oxo-1-(pyridin-4-yl)-2,3-dihydro-1H-pyrrolo[2,3-c]quinolin-8-yl)pyridin-3-yl)benzenesulfonamide
N-(2-Methyl-5-(3'-methyl-2'-oxo-2',3'-dihydrospiro[cyclopropane-1,1'-pyrrolo[2,3-c]quinolin]-8'-yl)pyridin-3-yl)benzenesulfonamide
8'-(5-(2-Hydroxypropan-2-yl)pyridin-3-yl)-3'-methylspiro[cyclopropane-1,1'-pyrrolo[2,3-c]quinolin]-2'(3'H)-one
8'-(5-(2-Hydroxypropan-2-yl)-6-methoxypyridin-3-yl)-3'-methylspiro[cyclopropane-1,1'-pyrrolo[2,3-c]quinolin]-2'(3'H)-one
N-(5-(3'-(2-Cyanoethyl)-2'-oxo-2',3'-dihydrospiro[cyclopropane-1,1'-pyrrolo[2,3-c]quinolin]-8'-yl)-2-methoxypyridin-3-yl)benzenesulfonamide
8'-(6-Chloro-5-(2-hydroxypropan-2-yl)pyridin-3-yl)-3'-methylspiro]cyclopropane-1,1'-pyrrolo[2,3-c]quinolin]-2'(3'H)-one
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide
N-(5-(3'-((1H-pyrazol-4-yl)methyl)-2'-oxo-2',3'-dihydrospiro[cyclopropane-1,1'-pyrrolo[2,3-c]quinolin]-8'-yl)-2-(3-(dimethylamino)propoxy)pyridin-3-yl)benzenesulfonamide
N-(2-(3-(Dimethylamino)propoxy)-5-(3'-isopropyl-2'-oxo-2',3'-dihydrospiro[cyclopropane-1,1'-pyrrolo[2,3-c]quinolin]-8'-yl)pyridin-3-yl)benzenesulfonamide
N-(2-(3-(Dimethylamino)propoxy)-5-(3'-methyl-2'-oxo-2',3'-dihydrospiro[oxetane-3,1'-pyrrolo[2,3-c]quinolin]-8'-yl)pyridin-3-yl)benzenesulfonamide
N-(2-(3-(Dimethylamino)propoxy)-5-(3'-methyl-2'-oxo-2,2',3,3',5,6-hexahydrospiro[pyran-4,1'-pyrrolo[2,3-c]quinolin]-8'-yl)pyridin-3-yl)benzenesulfonamide
8'-(6-(3-(Dimethylamino)propoxy)-5-(isopropylamino)pyridin-3-yl)-3'-methylspiro[cyclopropane-1,1'-pyrrolo[2,3-c]quinolin]-2'(3'H)-one
N-(2-(4-(Dimethylamino)butoxy)-5-(3'-methyl-2'-oxo-2',3'-dihydrospiro[cyclopropane-1,1'-pyrrolo[2,3-c]quinolin[-8'-yl)pyridin-3-yl)benzenesulfonamide 8'-(6-Methoxy-5-(phenylsulfonyl)pyridin-3-yl)-3'-methylspiro[cyclopropane-1,1'-pyrrolo[2,3-c]quinolin]-2'(3'H)-one
N-(2-(3-(Dimethylamino)propoxy)-5-(3'-(oxetan-3-ylmethyl)-2'-oxo-2',3'-dihydrospiro[cyclopropane-1,1'-pyrrolo[2,3-c]quinolin]-8'-yl)pyridin-3-yl)benzenesulfonamide
8'-(6-(3-(Dimethylamino)propoxy)-5-isopropoxypyridin-3-yl)-3'-methylspiro[cyclopropane-1,1'-pyrrolo[2,3-c]quinolin]-2'(3'H)-one
3'-Methyl-8'-(quinoxalin-6-yl)spiro[cyclopropane-1,1'-pyrrolo[2,3-c]quinolin]-2'(3'H)-one
3'-Methyl-8'-(2-oxo-1,2,4a,8a-tetrahydroquinolin-6-yl)spiro[cyclopropane-1,1'-pyrrolo[2,3-c]quinolin]-2'(3'H)-one
8'-(2-Chloroquinolin-6-yl)-3'-methylspiro[cyclopropane-1,1'-pyrrolo[2,3-c]quinolin]-2'(3'H)-one
N-(2-(3-(Dimethylamino)propoxy)-5-(3'-ethyl-2'-oxo-2',3'-dihydrospiro[cyclopropane-1,1'-pyrrolo[2,3-c]quinolin]-8'-yl)pyridin-3-yl)benzenesulfonamide
N-(5-(3'-Methyl-2'-oxo-2',3'-dihydrospiro[cyclopropane-1,1'-pyrrolo[2,3-c]quinolin]-8'-yl)-2-(2-(methylamino)ethoxy)pyridin-3-yl)benzenesulfonamide
8'-(2-Methoxyquinolin-6-yl)-3'-methylspiro[cyclopropane-1,1'-pyrrolo[2,3-c]quinolin]-2'(3'H)-one
3'-Methyl-8'-(1-methyl-2-oxo-1,2-dihydroquinolin-6-yl)spiro[cxclopropane-1,1'-pyrrolo[2,3-c]quinolin]-2'(3'H)-one
3-(1-Cyanoethyl)-N-(2-(3-(Dimethylamino)propoxy)-5-(3'-methyl-2'-oxo-2',3'-dihydiospiro[cyclopropane-1,1'-pyrrolo[2,3-c]quinolin]-8'-yl)pyridin-3-yl)benzenesulfonamide
N-(2-(3-(Dimethylamino)propoxy)-5-(3'-methyl-2'-oxo-2',3'-dihydrospiro[oxetane-3,1'-pyrrolo[2,3-c]quinolin]-8'-yl)pyridin-3-yl)cyclopropanesulfonamide
8'-(2-Aminopyrimidin-5-yl)-3'-methylspiro[cyclopropane-1,1'-pyrrolo[2,3-c]quinolin]-2'(3'H)-one
N-(5-(3'-Methyl-2'-oxo-2',3'-dihydrospiro[cyclopropane-1,1'-pyrrolo[2,3-c]quinolin]-8'-yl)-2-(4-methylpiperazin-1-yl)pyridin-3-yl)benzenesulfonamide
8'-(1H-indazol-4-yl)-3'-methylspiro[cyclopropane-1,1'-pyrrolo[2,3-c]quinolin]-2'(3'H)-one
3'-Methyl-8'-(pyrimidin-5-yl)spiro[cyclopropane-1,1'-pyrrolo[2,3-c]quinolin]-2'(3'H)-one
2-(3-(Dimethylamino)propoxy)-5-(3'-methyl-2'-oxo-2',1'-dihydrospiro[cyclopropane-1,1'-pyrrolo[2,3-c]quinolin]-8'-yl)nicotinamide
N-(2-(4-Methyl-1,4-diazepan-1-yl)-5-(3'-methyl-2'-oxo-2',3'-dihydrospiro[cyclopropane-1,1'-pyrrolo[2,3-c]quinolin]-8'-yl)pyridin-3-yl)benzenesulfonamide
8'-(6-(3-(Dimethylamino)propoxy)-5-methoxypyridin-3-yl)-3'-methylspiro[cyclopropane-1,1'-pyrrolo[2,3-c]quinolin]-2'(3'H)-one
8'-(5-Chloro-6-(3-(dimethylamino)propoxy)pyridin-3-yl)-3'-methylspiro[cyclopropane-1,1'-pyrrolo[2,3-c]quinolin]-2'(3'H)-one
N-(2-(4-(Dimethylamino)butoxy)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide
8'-(6-(3-(Dimethylamino)propoxy)-5-methylpyridin-3-yl)-3'-methylspiro[cyclopropane-1,1'-pyrrolo[2,3-c]quinolin]-2'(3'H)-one
N-(5-(3'-Methyl-2'-oxo-2',3'-dihydrospiro[cyclopropane-1,1'-pyrrolo[2,3-c]quinolin]-8'-yl)-2-(3-(pyrrolidin-1-yl)propoxy)pyridin-3-yl)benzenesulfonamide
8'-(5-(Benzyloxy)-6-(3-((dimethylamino)propoxy)pyridin-3-yl)-3'-methylspiro[cyclopropane-1,1'-pyrrolo[2,3-c]quinolin]-2'(3'H)-one
N-(5-(3'-Methyl-2'-oxo-2',3'-dihydrospiro[cyclopropane-1,1'-pyrrolo[2,3-c]quinolin]-8'-yl)-2-(3-(pyrrolidin-1-yl)propoxy)pyridin-3-yl)cyclopropanesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)ethanesulfonamide hydrochloride
3'-Methyl-8'-(1,8-naphthyridin-3-yl)spiro[cyclopropane-1,1'-pyrrolo[2,3-c]quinolin]-2'(3'H)-one
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)phenyl)benzenesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)methanesulfonamide
N-(2-(3-(Dimethylamino)propoxy)-5-(7'-fluoro-3'-methyl-2'-oxo-2',3'-dihydrospiro[cyclopropane-1,1'-pyrrolo[2,3-c]quinolin]-8'-yl)pyridin-3-yl)benzenesulfonamide
N-(2-(3-(Dimethylamino)propoxy)-5-(7'-fluoro-3'-methyl-2'-oxo-2',3'-dihydrospiro[cyclopropane-1,1'-pyrrolo[2,3-c]quinolin]-8'-yl)pyridin-3-yl)cyclopropanesulfonamide
N-(5-(3'-Methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)benzenesulfonamide
N-(5-(3'-Methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)cyclopropanesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)cyclobutanesulfonamide
8'-(2-((3-(Dimethylamino)propyl)amino)pyrimidin-5-yl)-3'-methylspiro[cyclopropane-1,1'-pyrrolo[2,3-c]quinolin]-2'(3'H)-one
8'-(2-(3-(Dimethylamino)propoxy)pyrimidin-5-yl)-3'-methylspiro[cyclopropane-1,1'-pyrrolo[2,3-c]quinolin]-2'(3'H)-one
8'-(6-(3-(Dimethylamino)propoxy)-5-phenylpyridin-3-yl)-3'-methylspiro[cyclopropane-1,1'-pyrrolo[2,3-c]quinolin]-2'(3'H)-one
N-(2-(3-(Dimethylamino)propoxy)-5-(4-methyl-3-oxo-3,4-dihydro-1H-spiro[benzo[f][1,7]naphthyridine-2,1'-cyclobutan]-9-yl)pyridin-3-yl)benzenesulfonamide
N-(5-(1',4'-Dimethyl-3'-oxo-3',4'-dihydro-1H-spiro[cyclopropane-1,2'-pyrazino[2,3-c]quinolin]-9'-yl)-2-(3-(dimethylamino)propoxy)pyridin-3-yl)benzenesulfonamide
N-(5-(3'-Methyl-2'-oxo-2',3'-dihydrospiro[cyclopropane-1,1'-pyrrolo[2,3-c]quinolin]-8'-yl)-2-(4-(methylamino)butoxy)pyridin-3-yl)benzenesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)oxetane-3-sulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)propane-1-sulfonamide
N-(5-(3'-Methyl-2'-oxo-2',3'-dihydrospiro[cyclopropane-1,1'-pyrrolo[2,3-c]quinolin]-8'-yl)-2-(2-(1-methylpyrrolidin-2-yl)ethoxy)pyridin-3-yl)benzenesulfonamide
N-(5-(3'-Methyl-2'-oxo-2',3'-dihydrospiro[cyclopropane-1,1'-pyrrolo[2,3-c]quinolin]-8'-yl)-2-(2-(1-methylpyrrolidin-2-yl)ethoxy)pyridin-3-yl)cyclopropanesulfonamide
N-(5-(3'-Methyl-2'-oxo-2',3'-dihydrospiro[cyclopropane-1,1'-pyrrolo[2,3-c]quinolin]-8'-yl)-2-(2-(1-methylpiperidin-2-yl)ethoxy)pyridin-3-yl)cyclopropanesulfonamide
N-(5-(3,-Methyl-2'-oxo-2',3'-dihydrospiro[cyclopropane-1,1'-pyrrolo[2,3-c]quinolin]-8'-yl)-2-(2-(1-methylpiperidin-2-yl)ethoxy)pyridin-3-yl)benzenesulfonamide
N-(2-(3-(Dimethylamino)propoxy)-5-(7'-methoxy-3'-methyl-2'-oxo-2',3'-dihydrospiro[cyclopropane-1,1'-pyrrolo[2,3-c]quinolin]-8'-yl)pyridin-3-yl)benzenesulfonamide N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-2-methoxyethane-1-sulfonamide
N-(5-(3'-Methyl-2'-oxo-2',3'-dihydrospiro[cyclopropane-1,1'-pyrrolo[2,3-c]quinolin]-8'-yl)-2-((1-methylpiperidin-3-yl)methoxy)pyridin-3-yl)benzenesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)pyridine-3-sulfonamide
N-(5-(3'-Methyl-2'-oxo-2',3'-dihydrospiro[cyclopropane-1,1'-pyrrolo[2,3-c]quinolin]-8'-yl)-2-((1-methylpiperidin-3-yl)methoxy)pyridin-3-yl)cyclopropanesulfonamide
N-(2-(3-(Dimethylamino)propoxy)-5-(1'-methyl-3'-oxo-3',4'-dihydro-1'H-spiro[cyclopropane-1,2'-pyrazino[2,3-c]quinolin]-9'-yl)pyridin-3-yl)benzenesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-fluorobenzenesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)pyrrolidine-1-sulfonamide hydrochloride
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)phenyl)-3-fluorobenzenesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-1-methyl-1H-pyrazole-4-sulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)thiophene-3-sulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-methoxybenzenesulfonamide
8'-(6-((3-(Dimethylamino)propyl)amino)pyridin-3-yl)-3'-methylspiro[cyclopropane-1,1'-pyrrolo[2,3-c]quinolin]-2'(3'H)-one
8'-(6-(3-(Dimethylamino)propoxy)-5-(1-phenylethoxy)pyridin-3-yl)-3'-methylspiro[cyclopropane-1,1'-pyrrolo[2,3-c]quinolin]-2'(3'H)-one
3-Cyano-N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide
N-(2-(3-(Dimethylamino)propoxy)-3-fluoro-5-(3'-methyl-2'-oxo-2',3'-dihydrospiro[cyclopropane-1,1'-pyrrolo[2,3-c]quinolin]-8'-yl)phenyl)benzenesulfonamide
3-Chloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)phenyl)benzenesulfonamide
N-(2-(3-(Dimethylamino)propoxy)-5-(3'-methyl-2'-oxo-2',3'-dihydrospiro[cyclopropane-1,1'-pyrrolo[2,3-c]qiunolin]-8'-yl)pyridin-3-yl)-5-methylisoxazole-4-sulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-methylbenzenesulfonamide
N-(4-(N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)sulfamoyl)phenyl)acetamide
N-(2-(3-(Dimethylamino)cyclobutoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-1-phenylmethanesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-3-methoxybenzenesulfonamide
6-Chloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)pyridine-3-sulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-3-(trifluoromethyl)benzenesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-2-fluorobenzenesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-(trifluoromethyl)benzenesulfonamide
8'-{6-[3-(Dimethylamino)propoxy]-5-[(dimethylsulfamoyl)amino]pyridine-3-yl}-3'-methyl-2',3'-dihydrospiro[cyclopropane-1,1'-pyrrolo[2,3-c]quinoline]-2'-one
N-(5-(3'-Methyl-2'-oxo-2',3'-dihydrospiro[cyclopropane-1,1'-pyrrolo[2,3-c]quinolin]-8'-yl)-2-((1-methylazetidin-3-yl)methoxy)pyridin-3-yl)benzenesulfonamide
3-Cyano-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-fluorobenzenesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-1-methyl-1H-pyrazole-3-sulfonamide
N-(2-(4-(Dimethylamino)piperidin-1-yl)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide
N-(2-(3-(Dimethylamino)propoxy)-5-(3'-methyl-2'-oxo-1-phenyl-2',3'-dihydrospiro[azetidine-3,1'-pyrrolo[2,3-c]quinolin]-8'-yl)pyridin-3-yl)benzenesulfonamide
N-(2-(4-((Dimethylamino)methyl)piperidin-1-yl)-5-(3'-methyl-2'-oxo-2',3'-dihydrospirolcyclopropane-1,1'-pyrrolo[2,3-c]quinolin]-8'-yl)pyridin-3-yl)cyclopropanesulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-2-(trifluoromethoxy)benzenesulfonamide
N-(5-(7'-Fluoro-3'-methyl-2'-oxo-2',3'-dihydrospiro[cyclopropane-1,1'-pyrrolo[2,3-c]quinolin]-8'-yl)-2-(4-methylpiperazin-1-yl)pyridin-3-yl)benzenesulfonamide hydrochloride
N-(5-(7'-Fluoro-3'-methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)benzenesulfonamide hydrochloride
4-Methoxy-N-(5-(3'-methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)benzenesulfonamide hydrochloride
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)thiophene-2-sulfonamide
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-(trifluoromethoxy)benzenesulfonamide
N-(2-(3-((Dimethylamino)methyl)azetidin-1-yl)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide -continued 8'-(6-(3-(Dimethylamino)propoxy)-5-(phenylsulfonamido)pyridin-3-yl)-3'-methyl-2'-oxo-2',3'-dihydrospiro[cyclopropane-1,1'-pyrrolo[2,3-c]quinoline] 5'-oxide N-(5-(7'-Fluoro-3'-methyl-2'-oxo-2',3'-dihydrospiro[cyclopropane-1,1'-pyrrolo[2,3-c]quinoline]-8'-yl)-2-(3-(pyrrolidin-1-yl)propoxy)pyridin-3-yl)benzenesulfonamide 3,5-Dichloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide 4-(Difluoromethoxy)-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide 4-(tert-Butyl)-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide 4-Chloro-N-(2-(3-(dimethylamino)propoxy)-5-(3'-methyl-2'-oxo-2',3,-dihydrospiro[cyclopropane-1,1'-pyrrolo[2,3-c]quinolin]-8'-yl)pyridin-3-yl)benzenesulfonamide hydrochloride 4-Chloro-N-(2-(3-(dimethylamino)propoxy)-5-(7'-nuoro-3'-methyl-2'-oxo-2',3'-dihydrospiro[cyclopropane-1,1'-pyrrolo[2,3-c]quinolin]-8'-yl)pyridin-3-yl)benzenesulfonamide hydrochloride 5-Chloro-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyridine-3-sulfonamide hydrochloride N-(5-(3'-Methyl-2'-oxo-2',3'-dihydrospiro[cyclobutane-1,1'-pyrrolo[2,3-c]quinolin]-8'-yl)-2-(3-morpholinopropoxy)pyridin-3-yl)benzenesulfonamide hydrochloride N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)benzenesulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-6-methoxypyridine-3-sulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-(pentafluoro-16-sulfaneyl)benzenesulfonamide N-(2-(1,1-Dioxidothiomorpholino)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)morpholine-4-sulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide hydrochloride N-(2-(1-Imino-1-oxido-116-thiomorpholino)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3,4-dihydroquinoline-1(2H)-sulfonamide N,N-Dimethyl-3-((5-(3'-methyl-2'-oxo-2',3'-dihydrospiro[cyclopropane-1,1'-pyrrolo[2,3-c]quinolin]-8'-yl)-3-(phenylsulfonamido)pyridin-2-yl)oxy)propan-1-amine oxide N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-5-(trifluoromethyl)pyridine-3-sulfonamide hydrochloride 6-Methyl-N-(5-(3'-methyl-2,-oxo-2',3'-dihydrospiro[cyclobutane-1,1'-pyrrolo[2,3-c]quinolin]-8'-yl)-2-(3-(piperidin-1-yl)propoxy)pyridin-3-yl)pyridine-3-sulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-(trifluoromethoxy)benzenesulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methoxybenzenesulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methylbenzenesulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-6-(trifluoromethyl)pyridine-3-sulfonamide hydrochloride 6-Cyano-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyridine-3-sulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyridine-2-sulfonamide hydrochloride 8'-{6-[3-(Dimethylamino)propoxy]-5-[(dimethylsulfamoyl)amino]pyridine-3-yl}-3'-methyl-2',3'-dihydrospiro[cyclobutane-1,1'-pyrrolo[2,3-c]quinoline]-2'-one hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3-(trifluoromethyl)benzenesulfonamide 8'-(6-Methoxy-5-(phenylsulfonimidoyl)pyridin-3-yl)-3'-methylspiro[cyclobutane-1,1'-pyrrolo[2,3-c]quinolin]-2'(3'H)-one N-(2-(3-(4,4-Difluoropiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3,5-difluorobenzenesulfonamide 3-Chloro-N-(2-(3-(dimethylamino)propoxy)-5-(3'-methyl-2,-oxo-2',3'-dihydrospiro[cyclobutane-1,1'-pyrrolo[2,3-c]quinolin]-8'-yl)pyridin-3-yl)-5-(trifluoromethyl)benzenesulfonamide hydrochloride N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3-fluoro-5-(trifluoromethyl)benzenesulfonamide hydrochloride 3,5-Dichloro-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-fluorobenzenesulfonamide hydrochloride 3-Cyano-N-(2-(3-(dimethylamino)propoxy)-5-(3'-methyl-2,-oxo-2',3'-dihydrospiro[cyclobutane-1,1'-pyrrolo[2,3-c]quinolin]-8'-yl)pyridin-3-yl)-4-fluorobenzenesulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)thiazole-4-sulfonamide hydrochloride N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-oxo-1,2-dihydropyridine-4-sulfonamide N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methylpiperazine-1-sulfonamide hydrochloride -continued 8'-{6-[3-(Dimethylamino)propoxy)-5-{[ethyl(methyl)sulfamoyl]amino}pyridin-3-yl}-3'-Methyl-2',3'-dihydrospiro[cyclobutane-1,1'-pyrrolo[2,3-c]quinoline]-2'-one
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)azetidine-1-sulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methylpiperidine-1-sulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1-methyl-1H-pyrazole-4-sulfonamide hydrochloride
4-Methyl-N-(5-(3'-methyl-2'-oxo-2',3'-dihydrospiro[cyclobutane-1,1'-pyrrolo[2,3-c]quinolin]-8'-yl)-2-(4-morpholinopiperidin-1-yl)pyridin-3-yl)benzenesulfonamide hydrochloride
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-fluorobenzenesulfonamide hydrochloride
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)thiazole-5-sulfonamide hydrochloride
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3-methylisothiazole-5-sulfonamide
3-Chloro-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-5-fluorobenzenesulfonamide hydrochloride
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-methylpyrrolidine-1-sulfonamide
N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide hydrochloride
5-Cyano-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyridine-3-sulfonamide hydrochloride
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3-methylpiperidine-1-sulfonamide
8'-(5-{[Butyl(methyl)sulfamoyl]amino}-6-[3-(dimethylamino)propoxy]pyridin-3-yl)-3'-methyl-2',3'-dihydrospiro[cyclobutane-1,1'-pyrrolo[2,3-c]quinoline]-2'-one
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)piperazine-1-sulfonamide
N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)-4-methylbenzenesulfonamide 2,2,2-trifluoroacetate
N-Methyl-N-(piperidin-4-yl)({2-[3-(dimethylamino)propoxy]-5-{3'-methyl-2'-oxo-2',3'-dihydrospiro[cyclobutane-1,1'-pyrrolo[2,3-c]quinolin]-8'-yl}pyridin-3-yl}amino)sulfonamide 2,2,2-trifluoroacetate
8'-(5-{[(Dimethylsulfamoyl)amino]-6-[3-(piperidin-1-yl)propoxy]pyridin-3-yl}-3'-methyl-2',3'-dihydrospiro[cyclobutane-1,1'-pyrrolo[2,3-c]quinoline]-2'-one hydrochloride
8'-(5-{[Bis(2-methoxyethyl)sulfamoyl]amino}-6-[3-(dimethylamino)propoxy]pyridine-3-yl)-3'-methyl-2',3'-dihydrospiro[cyclobutane-1,1'-pyrrolo[2,3-c]quinoline]-2'-one
N-Benzyl-N-methyl({2-[3-(dimethylamino)propoxy]-5-{3'-methyl-2'-oxo-2',3'-dihydrospiro[cyclobutane-1,1'-pyrrolo[2,3-c]quinoline]-8'-yl}pyridin-3-yl}amino)sulfonamide
8'-(5-{[(Diethylsulfamoyl)amino]-6-[3-(dimethylamino)propoxy]pyridin-3-yl}-3'-methyl-2',3'-dihydrospiro[cyclobutane-1,1'-pyrrolo[2,3-c]quinoline]-2'-one
N-(2-(3-(Dimethylamino)propoxy)-5-(3'-methyl-2'-oxo-2',3'-dihydrospiro[cyclobutane-1,1'-pyrrolo[2,3-c']quinolin]-8'-yl)pyridin-3-yl)-2,6-dimethylmorpholine-4-sulfonamide
N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide hydrochloride
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-(trifluoromethyl)benzenesulfonamide hydrochloride
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methoxypiperidine-1-sulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)isothiazole-5-sulfonamide hydrochloride
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide
N,6-Dimethyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)pyridine-3-sulfonamide 2,2,2-trifluoroacetate
N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-4-methylbenzenesulfonamide hydrochloride
N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)thiazole-4-sulfonamide hydrochloride
3-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)isothiazole-5-sulfonamide hydrochloride
2-Fluoro-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)benzenesulfonamide hydrochloride
3-Chloro-5-fluoro-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)benzenesulfonamide hydrochloride
N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)cyclopropanesulfonamide hydrochloride
N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide hydrochloride
N-(5-(3,-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)thiazole-5-sulfonamide hydrochloride
4-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)piperazine-1-sulfonamide
6-Methyl-N-(5-(3'-methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)pyridine-3-sulfonamide N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)piperazine-1-sulfonamide
N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-2-fluorobenzenesulfonamide
N-(2-(3-(Dimethylamino)propoxy)-5-(9'-fluoro-3'-methyl-2'-oxo-2',3'-dihydrospiro[cyclobutane-1,1'-pyrrolo[2,3-c]quinolin]-8'-yl)pyridin-3-yl)-4-methylbenzenesulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)oxetane-3-sulfonamide
N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-2,4-difluorobenzenesulfonamide hydrochloride
N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide hydrochloride
8'-(6-{[1,4'-Bipiperidine]-1'-yl}-5-[(dimethylsulfamoyl)amino]pyridin-3-yl)-3'-methyl-2',3'-dihydrospiro[cyclobutane-1,1'-pyrrolo[2,3-c]quinoline]-2'-one
8'-(6-Methoxy-5-(((6-methylpyridin-3-yl)sulfonyl)methyl)pyridin-3-yl)-3'-methylspiro[cyclopropane-1,1'-pyrrolo[2,3-c]quinolin]-2'(3'H)-one
N-(2-(3-(2,6-Dimethylpiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide
6-Methyl-N-(5-(3'-methyl-2'-oxo-2',3'-dihydrospiro[cyclobutane-1,1'-pyrrolo[2,3-c]quinolin]-8'-yl)-2-(3-(2,2,6,6-tetramethylpiperidin-1-yl)propoxy)pyridin-3-yl)pyridine-3-sulfonamide
8'-6-{[1,4'-Bipiperidine]-1'-yl}-5-{[ethyl(methyl)sulfamoyl]amino}pyridin-3-yl)-3'-methyl-2',3'-dihydrospiro[cyclobutane-1,1'-pyrrolo[2,3-c]quinoline]-2'-one
N-(2-([1,4'-Bipipendin]-1'-yl)-5-(3'-methyl-2'-oxo-2',3'-dihydrospiro[cyclopropane-1,1'-pyrrolo[2,3-c]quinolin]-8'-yl)pyridin-3-yl)benzenesulfonamide methanesulfonate
8'-(6-{[1,4'-Bipiperidine]-1'-yl}-5-{[ethyl(methyl)sulfamoyl]amino}pyridin-3-yl)-3'-methyl-2',3'-dihydrospiro[cyclopropane-1,1'-pyrrolo[2,3-c]quinoline]-2'-one
N-(2-(3-(Dimethylamino)propoxy)-5-(9'-fluoro-3'-methyl-2'-oxo-2',3'-dihydrospiro[cyclopropane-1,1'-pyrrolo[2,3-c]quinolin]-8'-yl)pyridin-3-yl)-4-methylbenzenesulfonamide
3'-Methyl-8'-(1-((6-methylpyridin-3-yl)sulfonyl)-2-(2-(piperidin-1-yl)ethyl)-1H-pyrrolo[3,2-b]pyridin-6-yl)spiro[cyclobutane-1,1'-pyrrolo[2,3-c]quinolin]-2'(3'H)-one
N-(5-(7'-Fluoro-3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)-6-methylpyridine-3-sulfonamide hydrochloride
N-(2-([1,4'-Bipiperidin]-1'-yl)-5-(3'-methyl-2'-oxo-2',3'-dihydrospiro[cyclopropane-1,1'-pyrrolo[2,3-c]quinolin]-8'-yl)pyridin-3-yl)-6-methylpyridine-3-sulfonamide
6-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy-2,2-d2)pyridin-3-yl)pyridine-3-sulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-hydroxybenzenesulfonamide hydrochloride
6-Methyl-N-(5-(3'-methyl-2'-oxo-2',3'-dihydrospiro[cyclobutane-1,1'-pyrrolo[2,3-c]quinolin]-8'-yl)-2-3'-(piperidin-1-yl-d10)propoxy)pyridin-3-yl)pyridine-3-sulfonamide hydrochloride
8'-(5-{[Ethyl(methyl)sulfamoyl]amino}-6-[3-(piperidin-1-yl)1,1'propoxy]pyridin-3-yl)1,1'-3'-methyl-2',3'-dihydrospiro[cyclobutane-1,1'-pyrrolo[2,3-c]quinoline]-2'-one
2-Amino-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)ethane-1-sulfonamide
N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)methanesulfonamide
8'-{6-[4-(Dimethylamino)piperidin-1-yl]-5-[(dimethylsulfamoyl)amino]pyridin-3-yl}-3'-methyl-2',3'-dihydrospiro[cyclobutane-1,1'-pyrrolo[2,3-c]quinoline]-2'-one
N-(5-(3'-Methyl-2'-oxo-2',3'-dihydrospiro[cyclobutane-1,1'-pyrroio[2,3-c]quinolin]-8'-yl)-2-(4-methylpiperazin-1-yl)pyridin-3-yl)cyclopropanesulfonamide hydrochloride
N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(5-(3'-Methyl-2'-oxo-2',3'-dihydrospiro[cyclobutane-1,1'-pyrroio[2,3-c]quinolin]-8'-yl)-2-(4-methylpiperazin-1-yl)pyridin-3-yl)methanesulfonamide
8'-{5-[(Dimethylsulfamoyl)amino]-6-(4-methylpiperazin-1-yl)pyridin-3-yl}-3'-methyl-2',3'-dihydrospiro[cyclobutane-1,1 pyrrolo[2,3-c]quinoline]-2'-one
N-(2-(3-Methyl(2,2,2-trifluoroethyl)amino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(5-(3'-Methyl-2'-oxo-2',3'-dihydrospiro[cyclobutane-1,1'-pyrroio[2,3-c]quinolin]-8'-yl)-2-(3-(pyrrolidin-1-yl)propoxy)pyridin-3-yl)benzenesulfonamide
N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)-3-methylisothiazole-5-sulfonamide
2-(3-(Dimethylamino)propoxy)-N,N-dimethyl-5-(3'-methyl-2'-oxo-2',3'-dihydrospiro[cyclobutane-1,1'-pyrrolo[2,3-c]quinolin]-8'-yl)pyridine-3-sulfonamide
N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)propoxy)pyridin-3-yl)cyclopropanesulfonamide
N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)propoxy)pyridin-3-yl)methanesulfonamide
N-(2-(3-(Dimethylamino)propoxy)-5-(2'-oxo-2'3'-dihydrospiro[cyclobutane-1,1'-pyrrolo[2,3-c]quinolin]-8'-yl)pyridin-3-yl)methanesulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)ethanesulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1,1,1-trifluoromethanesulfonamide
N-(5-(3'-Methyl-2'-oxo-2',3'-dihydrospiro[cyclobutane-1,1'-pyrrolo[2,3-c]quinolin]-8'-yl)-2-(3-(methylamino)propoxy)pyridin-3-yl)methanesulfonamide formate N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)propane-1-sulfonarnide
8'-{5-[(Dimethylsulfamoyl)amino]-6-[3-(pyrrolidin-1-yl)propoxy]pyridin-3-yl}-3'-methyl-2',3'-dihydrospiro[cyclobutane-1,1'-pyrrolo[2,3-c]quinoline]-2'-one
N-(5-(3'-Methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)benzenesulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyrrolidine-1-sulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-ethylthiazole-5-sulfonamide
3-Methyl-N-(5-(3'-methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)isothiazole-5-sulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1,1-difluoromethanesulfonamide
N-(2-(2-(Ethylamino)ethoxy)-5-(3'-methyl-2'-oxo-2',3'-dihydrospiro[cyclobutane-l,1'-pyrrolo[2,3-c]quinolin]-8'-yl)pyridin-3-yl)methanesulfonamide
N-(5-(3'-Methyl-2'-oxo-2',3'-dihydrospiro[cyclobutane-1,1'-pyrrolo[2,3-c]quinolin]-8'-yl)-2-(2-(methylamino)ethoxy)pyridin-3-yl)methanesulibnamide
N-(5-(3'-Methyl-2'-oxo-2',3'-dihydrospiro[cyclobutane-1,1'-pyrrolo[2,3-c]quinolin]-8'-yl)-2-(2-(methylamino)ethoxy)pyridin-3-yl)benzenesulfonamide
N-(2-(3,3-Difluoro-[1,4'-bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)pyridine-3-sulfonamide
N-(2-(3-(Dimethylamino)propoxy)-5-(3'-methyl-2'-oxo-2',3'-dihydrospiro[cyclobnlane-1,1'-pyrrolo[2,3-c]quinolin]-8'-yl)pyridin-3-yl)cyclobutanesulfonamide
N-(2-(3-Hydroxypropoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
2-(3-(Dimethylamino)propoxy)-5-(3'-methyl-2'-oxo-2',3'-dihydrospiro[cyciobutane-1,1'-pyrrolo[2,3-c]quinolin]-8'-yl)pyridine-3-sulfonamide
N-(2-(2,2-Difluoro-3-(piperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(5-(8',9'-dihydrospiro[cyclopentane-1,11'-imidazo[1',2':1,5]pyrrolo[2,3-c]quinolin]-2'-yl)-2-(2-(isopropylamino)ethoxy)pyridin-3-yl)methanesulfonamide
N-(2-(3-(Dimethylamino)propoxy)-5-(3'-methyl-2',3-dioxo-2',3'-dihydrospiro[cyclobutane-1,1'-pyrrolo[2,3-c]quinolin]-8'-yl)pyridin-3-yl)methanesulfonamide
N-(2-((3-(Dimethylamino)propyl)amino)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(5-(3'-Methyl-2'-oxo-2',3'-dihydrospiro[cyclobutane-1,1'-pyrrolo[2,3-c]quinolin]-8'-yl)-2-(4-methylpiperidin-1-yl)pyridin-3-yl)methanesulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-(1,3-dioxoisoindolin-2-yl)ethane-1-sulfonamide
N-(2-(3-(Dimethylamino)propoxy)-5-(3-fluoro-3'-methyl-2'-oxo-2',3'-dihydrospiro[cyclobutane-1,1'-pyrrolo[2,3-c]quinolin]-8'-yl)pyridin-3-yl)methanesulfonamide
N-(3-(3-(Dimethylamino)propoxy)-6-(3'-methyl-2'-oxo-2',3'-dihydrospiro[cyclobutane-1,1'-pyrrolo[2,3-c]quinolin]-8'-yl)pyrazin-2-yl)methanesulfonamide
2-(Dimethylamino)-N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)ethane-1-sulfonamide
N-(2-((2-(Dimethylandno)ethoxy)methyl)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-methoxyethane-1-sulfonamide
2-(3-(Dimethylamino)propoxy)-N-methyl-5-(3'-methyl-2'-oxo-2',3'-dihydrospiro[cyclobutane-1,1'-pyrrolo[2,3-c]quinolin]-8'-yl)pyridine-3-sulfonamide
N-(2-(3-(Dimethylamino)propoxy)-5-(9'-fluoro-3'-methyl-2'-oxo-2',3'-dihydrospiro[cyclobutane-1,1'-pyrrolo[2,3-c]quinolin]-8'-yl)pyridin-3-yl)methanesulfonamide
N-(5-(3'-Methyl-2'-oxo-2',3'-dihydrospiro[cyclobutane-1,1'-pyrrolo[2,3-c]quinolni]-8'-yl)-2-(4-(piperidin-1-yl)butyl)pyridin-3-yl)methanesulfonamide
N-(2-(3-(3-Hydroxypiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(6'-(Dimethylamino)-5-(3'-methyl-2'-oxo-2',3'-dihydrospiro[cyclobutane-1,1'-pyrrolo[2,3-c]quinolin]-8'-yl)-[2,3'-bipyridin]-3-yl)methanesulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)thiophene-3-sulfonamide
1-Cyano-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1-(methylsulfonyl)methanesulfonamide
2-Ethyl-N-(5-(3'-methyl-2'-oxo-2',3'-dihydrospiro[cyclobutane-1,1'-pyrrolo[2,3-c]quinolin]-8'-yl)-2-(2-(methylamino)ethoxy)pyridin-3-yl)thiazole-5-sulfonamide
N-(1'-Methyl-5-(3'-methyl-2,-oxo-2',3'-dihydrospiro[cyclobutane-1,1'-pyrrolo[2,3-c]quinolin]-8'-yl)-1',2',3',6'-tetrahydro-[2,4'-bipyridin]-3-yl)methanesulfonamide
N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)azetidin-1-yl)pyridin-3-yl)methanesulfonamide
N-(2-(3-((2-Methoxyethyl)(methyl)amino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide -continued N-(2-(3-(3-Fluoropyrrolidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(2-(3-(3-Methoxypiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(2-(2-(Isopropylamino)ethoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(2-(3-(3-Fluoropiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(2-(3-(3-Methoxypyrrolidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(2-(3-Hydroxy-2-(piperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(5-(3'-Methyl-2'-oxo-2',3'-dihydrospiro[cyclobutane-1,1'-pyrrolo[2,3-c]quinolin]-8'-yl)-2-(1-methylpiperidin-4-yl)pyridin-3-yl)methanesulfonamide
N-(2-(3-(4-Fluoropiperidin-1-yl)propoxy)-5-(3'-methyl-2,-oxo-2',3,-dihydrospiro[cyclobutane-1,1'-pyrrolo[2,3-c]quinoHn]-8'-yl)pyridin-3-yl)methanesulfonamide
N-(2-(2-Hydroxy-3-(piperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
8'-{6-[3-(Dimethylamino)azetidin-1-yl]-5-[(dimethylsulfamoyl)amino]pyridin-3-yl}-3'-methyl-2',3'-dihydrospiro[cyclobutane-1,1'-pyrrolo[2,3-c]quinoline]-2'-one
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-methylthiazole-5-sulfonamide
8'-{6-[3-(Dimethylamino)propoxy]-5-[(dimethylsulfamoyl)amino]pyridin-3-yl}-7'-fluoro-3'-methyl-2',3'-dihydrospiro[cyclobutane-1,1'-pyrrolo[2,3-c]quinoline]-2'-one hydrochloride
N-(2-(3-(Dimethylamino)propoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride
N-(2-(3-(Dimethylamino)butoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(2-(3-((2-Cyanoethyl)(methyl)amino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(5-(7'-Fluoro-3'-methyl-2'-oxo-2',3'-dihydrospiro[cyclobutane-1,1'-pyrrolo[2,3-c]quinolin]-8'-yl)-2-(3-((2-methoxyethyl)(methyl)amino)propoxy)pyridin-3-yl)morpholine-4-sulfonamide
N-(2-(3-(Dimethylamino)-2-hydroxypropoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(2-(2-(Dimethylamino)-3-hydroxypropoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(5-(7'-Fluoro-3'-methyl-2'-oxo-2',3'-dihydrospiro[cyclobutane-1,1'-pyrrolo[2,3-c]quinolin]-8'-yl)-2-(3-(4-fluoropiperidin-1-yl)propoxy)pyridin-3-yl)methanesulfonamide hydrochloride
N-(2-(3-(3,3-Difluoropipendin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(5-(3'-Methyl-2'-oxo-2',3'-dihydrospiro[cyclobutane-1,1'-pyrrolo[2,3-c]quinolin]-8'-yl)-2-(3-(4-methylpiperazin-1-yl)propoxy)pyridin-3-yl)methanesulfonamide
N-(5-(3'-Methyl-2'-oxo-2',3'-dihydrospiro[cyclobutane-1,1'-pyrrolo[2,3-c]quinolin]-8'-yl)-2-(3-(piperazin-1-yl)propoxy)phenyl)methanesulfonamide hydrochloride
1-Fluoro-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)methanesulfonamide
1,1-Difluoro-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)methanesulfonamide
N-(2-(3-(6-Oxa-3-azabicyclo[3.1.1]heptan-3-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
8'-{5-[(Dimethylsulfamoyl)amino]-6-[3-(morpholin-4-yl)propoxy]pyridin-3-yl}-3'-methyl-2',3'-dihydrospiro[cyclobutane-1,1'-pyrrolo[2,3-c]quinoline]-2'-one
N-(5-(3'-Methyl-2'-oxo-2',3'-dihydrospiro[cyclobutane-1,1'-pyrrolo[2,3-c]quinolin]-8'-yl)-2-(3-morpholinopropoxy)pyridin-3-yl)methanesulfonamide
N-(5-(3'-Methyl-2'-oxo-2',3'-dihydrospiro[cyclobutane-1,1'-pyrrolo[2,3-c]quinolin]-8'-yl)-2-(3-morpholinopropoxy)pyridin-3-yl)cyclopropanesulfonamide
N-(2-(3-(3,3-Difluoroazetidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide formate
N-(5-(3'-Ethyl-2'-oxo-2',3'-dihydrospiro[cyclobutane-1,1'-pyrrolo[2,3-c]quinolin]-8'-yl)-2-(2-(methylamino)ethoxy)pyridin-3-yl)methanesulfonamide hydrochloride
N-(2-(2-(tert-Butylamino)ethoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(2-(Azetidin-3-ylmethoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide hydrochloride
N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)-3-methoxyazetidine-1-sulfonamide formate
N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)morpholine-4-sulfonamide hydrochloride
N-(2-(3-(Ethyl(methyl)amino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride
N-(5-(7'-Fluoro-3'-methyl-2'-oxo-2',3'-dihydrospiro[cyclobutane-1,1'-pyrrolo[2,3-c]quinolin]-8'-yl)-2-(3-((2-methoxyethyl)(methyl)amino)azetidin-1-yl)pyridin-3-yl)methanesulfonamide hydrochloride
N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)-2,4-difluorobenzenesulfonamide hydrochloride
8'-{6-[3-(Dimethylamino)azetidin-1-yl]-5-[(dimethylsulfamoyl)amino]pyridin-3-yl}-7'-fluoro-3'-methyl-2',3'-dihydrospiro[cyclobutaue-1,1'-pyrrolo[2,3-c]quinoline]-2'-one hydrochloride
N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride N-(2-(3-(Dimethylamino)azetidin-1-yl)-5-(3'-methyl-2'-oxo-2',3'-dihydrospiro[cyclobutane-1,1'-pyrrolo[2,3-c]quinolin]-8'-yl)pyridin-3-yl)ethanesulfonamide
N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)cyclopropanesulfonamide hydrochloride
N-(2-(3-(Dimethylamino)azetidin-1-yl)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide
N-(5-(3'-Methyl-2'-oxo-2',3'-dihydrospiro[cyclobutane-1,1'-pyrrolo[2,3-c]quinolin]-8'-yl)-2-(3-(piperidin-1-yl)azetidin-1-yl)pyridin-3-y))methauesulfonamide hydrochloride
N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)-2-fluorobenzenesulfonamide hydrochloride
N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)-4-methylbenzenesulfonamide hydrochloride
N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)benzenesulfonamide hydrochloride
N-(5-(2,3'-Dimethyl-2'-oxo-2',3'-dihydrospiro[cyclobutane-1,1'-pyrrolo[2,3-c]quinolin]-8'-yl)-2-(3-(dimethylamino)azetidin-1-yl)pyridin-3-yl)methanesulfonamide formate
N-(2-(3-(Ethyl(methyl)amino)azetidin-1-yl)-5-(3'-methyl-2,-oxo-2',3'-dihydrospiro[cyclobutane-1,1'-pyrrolo[2,3-c]quinolin]-8'-yl)pyridin-3-yl)methanesulfonamide hydrochloride
N-(5-(4'-Amino-3'-methyl-2'-oxo-2',3'-dihydrospiro[cyclobutane-1,1'-pyrrolo[2,3-c]quinolin]-8'-yl)-2-(3-(dimethylamino)azetidin-1-yl)pyridin-3-yl)methanesulfonamide hydrochloride
N-(5-(7'-Fluoro-3'-methyl-2'-oxo-2',3'-dihydrospiro[cyclobutane-1,1'-pyrrolo[2,3-c]quinolin]-8'-yl)-2-(3-(isopropylamino)azetidin-1-yl)pyridin-3-yl)methanesulfonamide hydrochloride
N-(5-(3'-Methyl-2'-oxo-2',3'-dihydrospiro[cyclobutane-1,1'-pyrrolo[2,3-c]quinolin]-8'-yl)-2-(3-(methylamino)azetidin-1-yl)pyridin-3-yl)methanesulfonamide formate
N-(5-(7'-Fluoro-3'-methyl-2'-oxo-2',3'-dihydrospiro[cyclobutane-1,1'-pyrrolo[2,3-c]quinolin]-8'-yl)-2-(3-(methylamino)azetidin-1-yl)pyridin-3-yl)methanesulfonamide formate
N-(2-(3-(Ethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide
8'-{5-[(Dimethylsulfamoyl)amino]-6-[3-(methylamino)azetidin-1-yl]pyridin-3-yl}-7'-fluoro-3'-methyl-2',3'-dihydrospiro[cyclobutane-1,1'-pyrrolo[2,3-c]quinoline]-2'-one
N-(5-(7'-Fluoro-3'-methyl-2,-oxo-2',3,-dihydrospiro[cyclobutane-1,1'-pyrrolo[2,3-c]quinolin]-8'-yl)-2-(3-(methylamino)azetidin-1-yl)pyridin-3-yl)cyclopropanesulfonamide
N-(5-(7'-Fluoro-3'-methyl-2'-oxo-2',3'-dihydrospiro[cyclobutane-1,1'-pyrrolo[2,3-c]quinolin]-8'-yl)-2-(3-(methylamino)azetidin-1-yl)pyridin-3-yl)ethanesulfonamide
N-(5-(3',7-Dimethyl-2'-oxo-2',3'-dihydrospiro[cyclobutane-1,1'-pyrrolo[2,3-c]quinolin]-8'-yl)-2-(3-(dimethylamino)azetidin-1-yl)pyridin-3-yl)methanesulfonamide
N-(2-(3-(Dimethylamino)azetidin-1-yl)-5-(3'-ethyl-2'-oxo-2',3'-dihydrospiro[cyclobtitane-1,1'-pyrrolo[2,3-c]quinolin]-8'-yl)pyridin-3-yl)methanesulfonamide
N-(2-(3-(Dimethylamino)azetidin-1-yl)-5-(3'-ethyl-2'-oxo-2',3'-dihydrospiro[cyclobutane-1,1'-pyrrolo[2,3-c3quinolin]-8'-yl)pyridin-3-yl)benzenesulfonamide
N-(2-(3-(Dimethylamino)azetidin-1-yl)-5-(3'-methyl-2,-oxo-2',3'-dihydrospiro[cyclobutane-1,1'-pyrrolo[2,3-c]quinolin]-8'-yl)pyridin-3-yl)-2-methylthiazole-5-sulfonamide
8'-{6-[3-(Dimethylamino)azetidin-1-yl]-5-{[ethyl(methyl)sulfamoyl]amino}pyridin-3-yl}-3'-methyl-2',3'-dihydrospiro[cyclobutane-l,1'-pyrrolo[2,3-c]quinoline]-2'-one
8'-{6-[3-(Dimethylamino)azetidin-1-yl]-5-[(methylsulfamoyl)amino]pyridin-3-yl}-7'-fluoro-3'-methyl-2',3'-dihydrospiro[cyclobutane-1,1'-pyrrolo[2,3-c]quinoline]-2'-one
N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)-1,1-difluoromethanesulfonamide formate
1-Cyano-N-(2-(3-(dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride
N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)ethanesulfonamide formate
N-(5-(7'-Fluoro-3'-methyl-2'-oxo-2',3'-dihydrospiro[cyclobutane-1,1'-pyrrolo[2,3-c]quinolin]-8'-yl)-2-(3-(morpholinomethyl)azetidin-1-yl)pyridin-3-yl)methanesulfonamide formate
N-(5-(3'-Methyl-2'-oxo-2',3'-dihydrospiro[cyclobutane-1,1'-pyrrolo[2,3-c]quinolin]-8'-yl)-2-(6-methyl-2,6-diazaspiro[3.3]heptan-2-yl)pyridin-3-yl)methanesulfonamide formate
N-(5-(3'-Methyl-2'-oxo-2',3'-dihydrospiro[cyclobutane-1,1'-pyrrolo[2,3-c]quinolin]-8'-yl)-2-(2,6-diazaspiro[3.3]heptan-2-yl)pyridin-3-yl)methanesulfonamide formate
tert-Butyl 6-(5-(3'-methyl-2'-oxo-2',3'-dihydrospiro[cyclobutane-1,1'-pyrrolo[2,3-c]quinolin]-8'-yl)-3-(methylsulfonamido)pyridin-2-yl)-2,6-diazaspiro[3.3]heptane-2-carboxylate
tert-Butyl 5-(5-(3'-methyl-2'-oxo-2',3'-dihydrospiro[cyclobutane-1,1'-pyrrolo[2,3-c]quinolin]-8'-yl)-3-(methylsulfonamido)pyridin-2-yl)hexahydropyrrolo[3,4-c]pyrrolo-2(1H)-carboxylate
N-(2-(Hexahydropyrrolo[3,4-c]pyrrol-2(1H)-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide formate
N-(5-(3'-Methyl-2'-oxo-2',3'-dihydrospiro[cyclobutane-1,1'-pyrrolo[2,3-c]quinolin]-8'-yl)-2-(5-methylhexahydropyrrolo[3,4-c]pyrrol-2(1H)-yl)pyridin-3-yl)methanesulfonamide formate
N-(2-(3-(Dimethylamino)pyrrolidin-1-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide
N-(5-(3'-Methyl-2'-oxo-2',3'-dihydrospiro[cyclobutane-1,1'-pyrrolo[2,3-c]quinolin]-8'-yl)-2-(3-(piperidin-1-yl)pyrrolidin-1-yl)pyridin-3-yl)methanesulfonamide hydrochloride
N-(5-(3'-Methyl-2'-oxo-2',3'-dihydrospiro[cyclobutane-1,1'-pyrrolo[2,3-c]quinolin]-8'-yl)-2-(3-methyl-3-(piperidin-1-yl)pyrrolidin-1-yl)pyridin-3-yl)methanesulfonamide hydrochloride
N-(5-(3'-Methyl-2'-oxo-2',3'-dihydrospiro[cyclobutane-1,1'-pyrrolo[2,3-c]quinolin]-8'-yl)-2-(4'-methyl-[1,4'-bipiperidin]-1'-yl)pyridin-3-yl)methanesulfonamide -continued 8'-{5-[(Dimethylsulfamoyl)amino]-6-[4-(morpholin-4-yl)piperidin-1-yl]pyridin-3-yl}-3'-methyl-2',3'-dihydrospiro[cyclobutane-1,1'-pyrrolo[2,3-c]quinoline]-2'-one
N-(5-(3'-Methyl-2'-oxo-2',3'-dihydrospiro[cyclobutane-1,1'-pyrrolo[2,3-c]quinolin]-8'-yl)-2-(4-morpholinopiperidin-1-yl)pyridin-3-yl)cyclopropanesulfonamide hydrochloride
N-(5-(3'-Methyl-2'-oxo-2',3'-dihydrospiro[cyclobutane-1,1'-pyrrolo[2,3-c]quinolin]-8'-yl)-2-(4-morpholinopiperidin-1-yl)pyridin-3-yl)methanesulfonamide hydrochloride
N-(2-([1,4'-Bipiperidin]-1'-yl)-5-(7'-fluoro-3'-methy]-2'-oxo-2',3'-dihydrospiro[cyclobutane-1,1'-pyrrolo[2,3-c]quinolin]-8'-yl)pyridin-3-yl)methanesulfonamide hydrochloride
tert-Butyl 3-(5-(3'-methyl-2'-oxo-2',3'-dihydrospiro[cyclobutane-1,1'-pyrrolo[2,3-c]quinolin]-8'-yl)-3-(methylsulfonamido)pyridin-2-yl)-3,6-diazabicyclo[3.1.1]heptane-6-carboxylate
N-(2-(3,6-Diazabicyclo[3.1.1]heptan-3-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide formate
N-(5-(3'-Methyl-2,-oxo-2',3'-dihydrospiro[cyclobutane-1,1'-pyrrolo[2,3-c]quinolin]-8'-yl)-2-(6-methyl-3,6-diazabicyclo[3.1.1]heptan-3-yl)pyridin-3-yl)methanesulfonamide formate
N-(2-((3-(Dimethylamino)propyl)(methyl)amino)-5-(3'-methyl-2'-oxo-2',3'-dihydrospiro[cyclobutane-1,1'-pyrrolo[2,3-c]quinolin]-8'-yl)pyridin-3-yl)methanesulfonamide hydrochloride
N-(2-((2-(Dimethylamino)ethyl)(methyl)amino)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride
8'-(2-(Dimethylamino)pyrimidin-5-yl)-7'-fluoro-3'-methylspiro[cyclobutane-1,1'-pyrrolo[2,3-c]quinolin]-2'(3'H)-one
N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)cyclopropanesulfonamide hydrochloride
N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)-2-methylpropane-2-sulfonarmde
N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)-1-methylcyclopropane-1-sulfonamide
1,1-Difluoro-N-(5-(7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
8'-{5-[(Dimethylsulfamoyl)amino]-6-{2-[(propan-2-yl)amino]ethoxy}pyridin-3-yl}-7'-fluoro-3'-methyl-2',3'-dihydrospiro[cyclobutane-1,1'-pyrrolo[2,3-c]quinoline]-2'-one hydrochloride
N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)azetidine-1-sulfonamide
3-Fluoro-N-(5-(7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)azetidine-1-sulfonamide
3-Cyano-N-(5-(7'-nuoro-3'-methyl-2'-oxo-2',3'-dihydrospiro[cyclobutane-1,1'-pyrrolo[2,3-c]quinolin]-8'-yl)-2-(2-(isopropylamino)ethoxylpyridin-3-yl)azetidine-1-sulfonamide
N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)morpholine-4-sulfonamide hydrochloride
1-Cyano-N-(5-(7'-fluoro-3'-methyl-2'-oxo-2',3'-dihydrospiro[cyclobulane-1,1'-pyrrolo[2,3-c]quinolin]-8'-yl)-2-(2-(isopropylamino)ethoxy)pyridin-3-yl)methanesulfonamide hydrochloride
2-(Dimethylamino)-N-(5-(7'-fluoro-3'-methyl-2'-oxo-2',3'-dihydrospiro[cyclobutane-1,1'-pyrrolo[2,3-c,]quinolin]-8'-yl)-2-(2-(isopropylamino)ethoxy)pyridin-3-yl)ethane-1-sulfonamide
hydrochloride
N-(2-(2-(Cyclopropylamino)ethoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride
N-(2-(2-(Cyclobutylamino(ethoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide
N-(5-(7'-Fluoro-3'-methyl-2'-oxo-2',3'-dihydrospiro[cyclobutane-1,1'-pyrrolo[2,3-c]quinolin]-8'-yl)-2-(2-((2,2,2-trifluoroethyl)amino)ethoxy)pyridin-3-yl)methanesulfonamide
N-(2-(2-((2,2-Difluoroethyl)amino)ethoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide
N-(5-(7'-Fluoro-3'-methyl-2'-oxo-2',3'-dihydrospiro[cyclobutane-1,1'-pyrrolo[2,3-c]quinolin]-8'-yl)-2-(2-((2-fluoroethyl)amino)ethoxy)pyridin-3-yl)methanesulfonamide hydrochloride
cis-N-(5-(7'-Fluoro-3-hydroxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride
trans-N-(5-(7'-Fluoro-3-hydroxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(2-(3-(Dimethylamino(propoxy)-5-(3-hydroxy-3'-methyl-2'-oxo-2',3'-dihydrospiro[cyclobutane-1,1'-pyrrolo[2,3-c]quinolin]-8'-yl)pyridin-3-yl)methanesulfonamide
trans-N-(2-(2-(Isopropylamino)ethoxy)-5-(3-methoxy-3'-methyl-2'-oxo-2',3'-dihydrospiro[cyclobutane-1,1'-pyrrolo[2,3-c]quinolin]-8'-yl)pyridin-3-yl)methanesulfonamide hydrochloride
cis-N-(5-(7'-Fluoro-3-methoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3-methoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3-methoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)cyclopropanesulfonamid
trans-N-(5-(7'-Fluoro-3-methoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)cyclopropanesulfonamide
cis-8'-{5-[(Dimethylsulfamoyl)amino]-6-{2-[(propan-2-yl)amino]ethoxy}pyridine-3-yl}-7'-fluoro-3-Methoxy-3'-methyl-2',3'-dihydrospiro[cyclobutane-1,1'-pyrrolo[2,3-c]quinoline]-2'-one
trans-8'-{5-[(Dimethylsulfamoyl)amino]-6-{2-[(propan-2-yl)amino]ethoxy}pyridine-3-yl}-7'-fluoro-3-Methoxy-3'-methyl-2',3'-dihydrospiro[cyclobutane-1,1'-pyrrolo[2,3-c]quinoline]-2'-one
cis-N-(2-([1,4'-Bipiperidin]-1'-yl)-5-(7'-fluoro-3-methoxy-3'-methyl-2'-oxo-2',3'-dihydrospiro[cyclobutane-1,1'-pyrrolo[2,3-c]quinolin]-8'-yl)pyridin-3-yl)methanesulfonamide
trans-N-(2-([1,4'-Bipiperidin]-1'-yl)-5-(7'-fluoro-3-methoxy-3'-methyl-2'-oxo-2',3'-dihydrospiro[cyclobutane-1,1'-pyrrolo[2,3-c]quinolin]-8'-yl)pyridin-3-yl)methanesulfonamide
cis-N-(5-(3-Ethoxy-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide -continued trans-N-(5-(3-Ethoxy-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3-isopropoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3-isopropoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3'-methyl-2'-oxo-3-(1-phenylethoxy)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-(1-phenylethoxy)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
2-(3-(Dimethylamino)propoxy)-5-(3'-methyl-2'-oxo-2',3'-dihydrospiro[cyclobutane-1,1'-pyrrolo[2,3-c]quinolin]-8'-yl)-3-(methylsulfonamido)benzoic acid
cis-N-(5-(7'-Fluoro-3'-methyl-2'-oxo-3-phenoxy-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-phenoxy-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-8'-{5-[(Dimethylsulfamoyl)amino]-6-{2-[(propan-2-yl)amino]ethoxy}pyridine-3-yl}-7'-fluoro-3'-methyl-3-phenoxy-2',3'-dihydrospiro[cyclobutane-1,1'-pyrrolo[2,3-c]quinoline]-2'-one hydrochloride
trans-8'-{5-[(Dimethylsulfamoyl)amino]-6-{2-[(propan-2-yl)amino]ethoxy}pyridine-3-yl}-7'-fluoro-3'-methyl-3-phenoxy-2',3'-dihydrospiro[cyclobutane-1,1'-pyrrolo[2,3-c]quinoline]-2'-one hydrochloride
cis-N-(5-(7'-Fluoro-3-(methoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3-(methoxymethyl)-3'-methyl-2'-oxo-2',3'-dihydrospiro[cylclobutane-1,1'-pyrrolo[2,3-c]quinolin]-8'-yl)-2-(2-(isopropylamino)ethoxy)pyridin-3-yl)methanesulfonamide
cis-N-(5-(3-(Ethoxymethyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(3-(Ethoxymethyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-(phenoxymethyl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3'-methyl-2'-oxo-3-(phenoxymethyl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)propane-2-sulfonamide
trans-N-(5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)propane-2-sulfonamide
cis-N-(5-(7'-Fluoro-3'-methyl-2'-oxo-3-phenyl-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride
trans-N-(5-(7'-Fluoro-3'-methyl-2'-oxo-3-phenyl-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride
cis-N-(5-(3-(4-Chlorophenyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(3-(4-Chlorophenyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(3-(3-Chlorophenyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(3-(3-Chlorophenyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3-(4-methoxyphenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride
trans-N-(5-(7'-Fluoro-3-(4-methoxyphenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride
cis-N-(5-(7'-Fluoro-3-(4-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3-(4-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3-(3-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3-(3-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3-(2-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3-(2-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3-(6-methoxypyridin-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3-(6-methoxypyridin-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3-(6-methoxypyrridin-3-yl)-3'-methyl-2'-oxo-2',3'-dihydrospiro[cyclobutane-1,1'-pyrrolo[2,3-c]quinolin]-8'-yl)-2-(2-(isopropylamino)ethoxyl)pyridin-3-yl)methanesulfonamide
trans-N-(5-(7'-Fluoro-3-(6-methoxypyridin-3-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3-(2-methoxypyridin-4-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide -continued trans-N-(5-(7'-Fluoro-3-(2-methoxypyridin-4-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-Fluoro-3'-methyl-2'-oxo-3-(pyridin-2-yl)-2',3'-dihydrospiro[cyclobutane-1,1'-pyrrolo[-(5-(72,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-(pyridin-2-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3'-methyl-2'-oxo-3-(pyridin-3-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-(pyridin-3-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3'-methyl-2'-oxo-3-(pyridin-4-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-(pyridin-4-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3'-methyl-2'-oxo-3-(6-oxo-1,6-dihydropyridin-2-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-(6-oxo-1,6-dihydropyridin-2-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3'-methyl-2'-oxo-3-(6-oxo-1,6-dihydropyridin-3-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-(6-oxo-1,6-dihydropyridin-3-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3'-methyl-2'-oxo-3-(2-oxo-l,2-dihydropyridin-4-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-(2-oxo-l,2-dihydropyridin-4-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
N-(5-(7'-Fluoro-3,3,3'-trimethyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3,3'-dimethyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3,3'-dimethyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
2-(3-(Dimethylamino)propoxy)-5-(3'-methyl-2'-oxo-2',3'-dihydrospiro[cyclobutane-1,1'-pyrrolo[2,3-c]quinolin]-8'-yl)-3-(methylsulfonamido)benzamide
trans-N-(5-(3-Benzyl-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(3-Benzyl-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(3-((Dimethylamino)methyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(3-((Dimethylamino)methyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3'-methyl-3-((methylamino)methyl)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-3-((methylamino)methyl)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride
cis-N-(5-(7'-Fluoro-3-(2-hydroxypropan-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy(pyridin-3-yl)methanesulfonamide
trans-N-(5-(7'-Fluoro-3-(2-hydroxypropan-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
N-(5-(7''-Fluoro-3''-methyl-2''-oxo-2'',3''-dihydrodispiro[piperidine-4,1'-cyclobutane-3',1''-pyrrolo[2,3-c]quinolin]-8''-yl)-2-(2-(isopropylamino)ethoxy)pyridin-3-yl)methanesulfonamide
cis-N-(5-(7'-Fluoro-3'-methyl-2'-oxo-3-(phenylamino)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-(phenylamino)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride
cis-N-(5-(3-((4-Chlorophenyl)amino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(3-((4-Chlorophenyl)amino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(7'-Fluoro-3'-methyl-3-(methyl(phenyl)amino)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-3-(methyl(phenyl)amino)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-N-(5-(3-(Dimethylamino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(3-(Dimethylamino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
cis-V-(5-(7'-Fluoro-3'-methyl-2'-oxo-3-(pyrrolidin-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-(pyrrolidin-1-yl)-2',3'-dihydrospiro[cyclobutane-1,1'-pyrrolo[2,3-c]qinnolin]-8'-yl)-2-(2-(isopropylamino)ethoxy)pyridin-3-yl)methanesulfonamide
cis-N-(5-(7'-Fluoro-3'-methyl-2'-oxo-3-(piperidin-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
trans-N-(5-(7'-Fluoro-3'-methyl-2'-oxo-3-(piperidin-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonarmde hydrochloride
cis-N-(5-(7'-Fluoro-3'-methyl-3-morpholino-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide -continued trans-N-(5-(7'-Fluoro-3'-methyl-3-morpholino-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide trans-N-(5-(7'-Fluoro-3'-methyl-3-(methylamino)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide trans-N-(5-(7'-Fluoro-3-((2-methoxyethyl)amino)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonaimde cis-N-(5-(7'-Fluoro-3'-methyl-2'-oxo-3-(2-oxopyridin-1(2H)-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide cis-N-(5-(7'-Fluoro-3'-methyl-2'-oxo-3-(1H-pyrazrol-1-yl)-2',3'-dihydrospiro[cyclobutaue-1,1'-pyrrolo[2,3-c]quinolin]-8'-yl)-2-(2-(isopropylamino)ethoxy)pyridin-3-yl)methanesulfonamide N-(2-(3-(Dimethylamino)propoxy)-5-(3'-methyl-2'-oxo-2',3'-dihydrospiro[azetidine-3,1'-pyrrolo[2,3-c]quinolin]-8'-yl)pyridin-3-yl)methanesulfonamide N-(5-(1,3'-Dimethyl-2'-oxo-2',3'-dihydrospiro[azetidine-3,1'-pyrrolo[2,3-c]quinolin]-8'-yl)-2-(3-(dimethylamino)propoxy)pyridin-3-yl)methanesulfonamide tert-Butyl 8'-(6-(3-(dimethylamino)propoxy)-5-(methylsulfonamido)pyridin-3-yl)-3'-methyl-2'-oxo-2',3'-dihydrospiro[azetidine-3,1'-pyrrolo[2,3-c]quinoline]-1-carboxylate N-(2-(3-(Dimethylamino)azetidin-1-yl)-5-(3'-methyl-2'-oxo-1-(2,2,2-trifluoroethyl)-2',3'-dihydrospiro[azetidine-3,1'-pyrrolo[2,3-c]quinolin]-8'-yl)pyridin-3-yl)methanesulfonamide N-(5-(7'-Fluoro-1,3'-dimethyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride N-(5-(1-Ethyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(7'-Fluoro-1-isopropyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)ethanesulfonamide N-(5-(7'-Fluoro-1-isopropyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)cyclopropanesulfonamide N-(5-(7'-Fluoro-1-isopropyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)propane-2-sulfonamide N-([1,4'-Bipiperidin]-1'-yl)-5-(7'-fluoro-1-isopropyl-3'-methyl-2'-oxo-2',3'-dihydrospiro[azetidine-3,1'-pyrrolo[2,3-c]quinolin]-8'-yl)pyridin-3-yl)methanesulfonamide N-(5-(1-(sec-Butyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(7'-Fluoro-3'-methyl-2'-oxo-1-propyl-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(1-Butyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(7'-Fluoro-3'-methyl-2'-oxo-1-(pentan-3-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(7'-Fluoro-1-isobutyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(7'-Fluoro-1-isopentyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide (S)-N-(5-(7'-Fluoro-3'-methyl-2'-oxo-1-(1-phenylethyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide (R)-N-(5-(7'-Fluoro-3'-methyl-2'-oxo-1-(1-phenylethyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(1-Benzyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(1-Cyclopropyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(1-Cyclobutyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride N-(5-(1-Cyclopentyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(1-Cyclohexyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(7'-Fluoro-3'-methyl-2'-oxo-1-(tetrahydro-2H-pylan-4-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride N-(5-(7'-Fluoro-3'-methyl-2'-oxo-1-(piperidin-4-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(7'-Fluoro-3'-methyl-1-(1-methylpiperidin-4-yl)-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(1-(1-Acetylpiperidin-4-yl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(7'-Fluoro-1-((1s,4s)''4-hydroxycyclohexyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(7'-Fluoro-1-((1r,4r)-4-hydroxycyclohexyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(7'-Fluoro-1-(2-hydroxyethyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(7'-Fluoro-1-(2-methoxyethyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide N-(5-(1-(2,2-Difluoroethyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide (R)-N-(5-(1-(2,3-Dihydroxypropyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide (S)-N-(5-(1-(2,3-Dihydroxylpropyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide -continued N-(5-(1-Acetyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-1-isobutylyl-3'-methyl-2'-oxo-2',3'-dihydrospiro[azetidine-3,1'-pyriOio[2,3-c]quinolin]-8'-yl)-2-(2-(isopropylamino)ethoxy)pyridin-3-yl)methanesulfonamide
Methyl 7'-fluoro-8'-(6-(2-(isopropylamino)ethoxy)-5-(methylsulfonamido)pyridin-3-yl)-3'-methyl-2'-oxo-2',3'-dihydrospiro[azetidine-3,1'-pyrrolo[2,3-c]quinoline]-1-carboxylate
Isopropyl 7'-fluoro-8'-(6-(2-(isopropylamino)ethoxy)-5-(methylsulfonamido)pyridin-3-yl)-3'-methyl-2'-oxo-2',3'-dihydrospiro[azetidine-3,1'-pyrrolo[2,3-c]quinoline]-1-carboxylate
N-(5-(7'-Fluoro-3'-methyl-2'-oxo-1-(phenylsulfonyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(1-Benzoyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
7'-Fluoro-8'-(6-(2-(isopropylamino)ethoxy)-5-(methylsulfonamido)pyridin-3-yl)-3'-methyl-2'-oxo-2',3'-dihydrospiro[azetidine-3,1'-pyrrolo[2,3-c]quinoline]-1-carboxamide
7'-Fluoro-8'-(6-(2-(isopropylamino)ethoxy)-5-(methylsulfonamido)pyridin-3-yl)-N,N,3'-trimethyl-2'-oxo-2',3'-dihydrospiro[azetidine-3,1'-pyrrolo[2,3-c]quinoline]-1-carboxamide
N-(5-(7'-Fluoro-3'-methyl-2'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride
N-(5-(7'-Fluoro-3'-methyl-2'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)-2-methylthiazole-5-sulfonamide
N-(5-(7'-Fluoro-3'-methyl-2'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)-3-methylisothiazole-5-sulfonamide
N-(5-(7'-Fluoro-3'-methyl-2'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)ethanesulfonamide hydrochloride
N-(5-(1-(4-Chlorophenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride
N-(5-(1-(3-Chlorophenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(1-(2-Chlorophenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-3'-methyl-2'-oxo-1-(p-tolyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride
N-(5-(7'-Fluoro-3'-methyl-2'-oxo-1-(m-tolyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-3'-methyl-2'-oxo-1-(o-tolyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(1-(4-Ethylphenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-1-(4-isopropylphenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(1-(4-(tert-butyl)phenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-1-(4-(methoxymethyl)phenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-1-(4-methoxyphenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-1-(3-methoxyphenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-1-(2-methoxyphenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-3'-methyl-2'-oxo-1-(4-(trifluoromethyl)phenyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride
N-(5-(7'-Fluoro-3'-methyl-2'-oxo-1-(3-(trifluoromethyl)phenyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-1-(4-fluorophenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride
N-(5-(7'-Fluoro-1-(3-fluorophenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-1-(2-fluorophenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-3'-methyl-2'-oxo-1-(4-(trifluoromethoxy)phenyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-3'-methyl-2'-oxo-1-(3-(trifluoromethoxy)phenyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(1-([1,1'-Biphenyl]4-yl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(1-Benzo[d][1,3]dioxol-5-yl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(1-(2,3-Dihydrobenzo[b][1,4]dioxin-6-yl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(1-(3,4-Dimethoxyphenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-3'-methyl-2'-oxo-1-(pyridin-4-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-3'-methyl-2'-oxo-1-(pyridin-3-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride
N-(5-(7'-Fluoro-3'-methyl-2'-oxo-1-(pyrimidin-5-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide -continued N-(5-(7'-Fluoro-3'-methyl-2'-oxo-1-(2H-tetrazol-5-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-3'-methyl-2'-oxo-1-(pyrimidin-2-yl)-2',3'-dihydrospiro[azetidine-3,1'-pyrrolo[2,3-c]quniolin]-8'-yl)-2-(2-(isopropylamino)ethoxy)pyridin-3-yl)methanesulfonamide hydrochloride
N-(5-(7'-Fluoro-3'-methyl-1-(2-methyl-2H-tetrazol-5-yl)-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(7'-Fluoro-3'-methyl-1-(1-methyl-1H-tetrazol-5-yl)-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide
N-(5-(3'3-Difluoro-3'-methtyl-2'-oxo-2',3'-dihydrospiro[cyclobutane-1,1'-pyrrolo[2,3-c]quinolin]-8'-yl)-2-(3-(dimethylamino)propoxy)pyridin-3-yl)methanesulfonamide
N-(5-(7'-Fluoro-3'-methyl-2'-oxo-2',3'-dihydrospiro[oxetane-3,1'-pyrrolo[2,3-c]quinolin]-8'-yl)-2-(2-(Isopropylamino)ethoxy)pyridin-3-yl)methanesulfonamide hydrochloride
N-(5-(9'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride
8'-{6-[3-(Dimethylamino)propoxy]-5-[(dimethylsulfamoyl)amino]pyridin-3-yl}-6'-fluoro-3'-methyl-2',3'-dihydrospiro[cyclobutane-1,1'-pyrrolo[2,3-c]quinoline]-2'-one
N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
Methyl 2-(3-(dimethylamino)propoxy)-5-(3'-methyl-2'-oxo-2',3'-dihydrospiro[cyclobutane-1,1'-pyrrolo[2,3-c]quinolin]-8'-yl)-3-(methylsulfonamido)benzoate
cis-N-(5-(3,7'-Difluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide
N-(5-[7-Methyl-8-oxo-7'8-dihydrospiro[cyclobutane-1,9-pyrrolo[2,3-c]1,5-naphthyridin]-2-yl]-2-[2-[(propan-2-yl)amino]ethoxy]pyridin-3-yl)methanesulfonamide
N-(2-(2-(Isopropylamino)ethoxy)-5-(3'-methyl-2'-oxo-2',3'-dihydrospiro[cyclobutane-1,1'-pyrrolo[2,3-c][1,7]naphthyridin]-8'-yl)pyridin-3-yl)methanesulfonamide
N-(3-cyano-2-(3-(Dimethylamino)propoxy)-5-(3'-methyl-2'-oxo-2',3'-dihydrospiro[cyclobutane-1,1'-pyrrolo[2,3-c]quinolin]-8'-yl)phenyl)methanesulfonamide
2-(3-(Dimethylamino)propoxy)-N,N-dimethyl-5-(3'-methyl-2'-oxo-2',3'-dihydrospiro[cyclobutane-1,1'-pyrrolo[2,3-c]quinolin]-8'-yl)-3-(methy)sulfonamido)benzamide
2-(3-(Dimethylamino)propoxy)-N-methyl-5-(3'-methyl-2'-oxo-2',3'-dihydrospiro[cyclobutane-1,1'-pyrrolo[2,3-c]quinolin]-8'-yl)-3-(methylsulfonamido)benzamide

Preparation of the Compounds of the Invention

The compounds of the present invention can be prepared using methods and techniques known in the art. Suitable processes for synthesizing these compounds are provided in the Examples. Generally, compounds of Formula (I) can be prepared according to the Schemes described below. The sources of the starting materials for these reactions are also described.

Protecting groups may be added or removed in the preparation of the compounds of the invention in accordance with standard techniques, which are known to one skilled in the art and as described herein. The use of protecting groups is described in detail in Greene, T. W. and P. G. M. Wuts, Greene's *Protective Groups in Organic Synthesis* (2000), 4th Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active.

All of the compounds described below as being prepared which may exist in free base or acid form may be converted to their pharmaceutically acceptable salts by treatment with the appropriate inorganic or organic base or acid. Salts of the compounds prepared below may be converted to their free base or acid form by standard techniques. It is understood that all polymorphs, amorphous forms, anhydrates, hydrates, solvates and salts of the compounds of the invention are intended to be within the scope of the invention. Furthermore, all compounds of the invention which contain an acid or an ester group can be converted to the corresponding ester or acid, respectively, by methods known to one skilled in the art or by methods described herein.

A general representation of preparation of many of these compounds is shown below in Scheme 1. Compounds are prepared through the coupling of various components of the molecule: Suzuki coupling of halo substituted compound 3 (or 2') with a boronic acid or borate compound 2 (3'). Further reactions may or may not be needed to furnish the synthesis of the compounds of this invention. Preparations of specific compounds of this invention are shown in the following Schemes.

Scheme 1

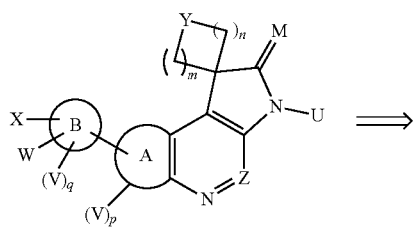

Formula I

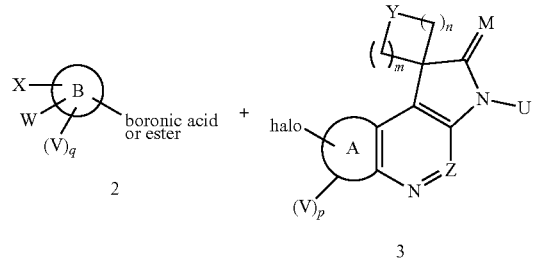

-continued

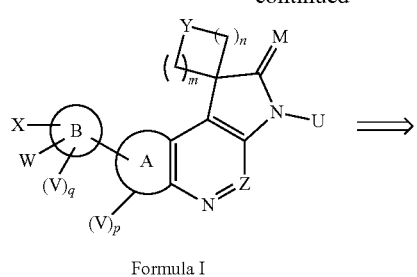

Formula I

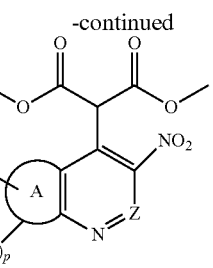

6

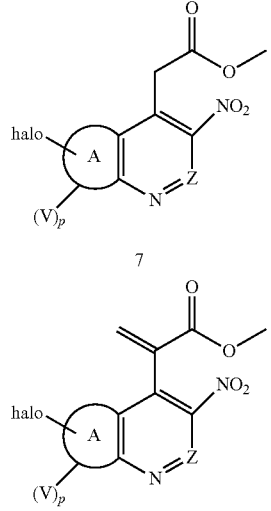

7

8

9

10

In aryl-aryl coupling reactions, halogen may be iodo, bromo, or chloro, preferable bromo or iodo. In this method, halogen substitutions may be transformed to aryl substitutions using Suzuki coupling reaction conditions. The conditions of this method are disclosed in many publications which have been reviewed by A. Suzuki in an article entitled "The Suzuki reaction with arylboron compounds in arene chemistry" in *Modern Arene Chemistry* 2002, 53-106. In carrying out this reaction any of the suitable conditions conventional in a Suzuki reaction can be utilized. Generally, Suzuki coupling reactions are carried out in the presence of a transition metal catalyst such as a palladium catalyst utilizing any conventional organic solvent for this reaction and a weak inorganic or organic base. Among the preferred organic solvents are the polar aprotic solvents. Any conventional polar aprotic solvents can be utilized in preparing compounds of the invention. Suitable solvents are customary, especially higher-boiling solvents. e.g. dimethoxyethane. The weak inorganic base can be a carbonate or bicarbonate, such as potassium carbonate or cesium carbonate. The organic base can be an amine such as triethylamine.

Scheme 2

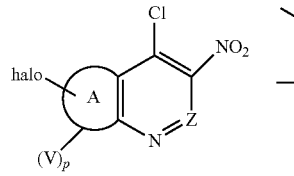 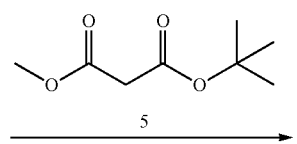

4

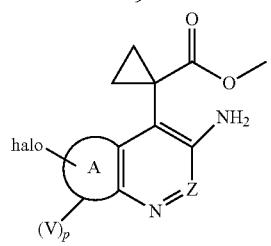

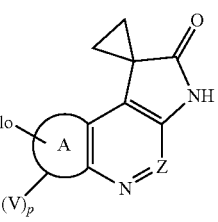

11

Specifically, the construction of the spirocyclopropryl ring in Formula (I) is demonstrated in Scheme 2. Starting material 4 can be either commercially available or prepared by those skilled in the art following the literature described methods. Reaction of compound 4 with tert-butyl methyl malonate (5) provides compound 6, which upon treatment under acidic conditions, leads to the decarboxylation product 7. The spirocyclopropyl group is created by reaction of the alkene ester 7 with a cyclopropanation method, such as, but not limited to using trimethylsulfoxonium iodide in the presence of strong base such as potassium tert-butoxide in aprotic solvent such as tetrahydrofuran at zero degree Celsius to ambient temperature to provide the cyclopropyl compound 9. The nitro group in compound 9 is reduced to amino group using a reducing reagent such as, but not limited to iron to provide the amino intermediate 10. Compound 10 was treated with a strong base such as, but not limited to, sodium tert-butoxide to provide the cyclized spirocyclopropyl compound 11.

reagent such as, but not limited to, iron to give the corresponding amino intermediate which cyclizes to provide the oxindole compound 14 in situ. Thus, the compound 14 (or intermediate 11 from Scheme 2) is then N-akylated with an alkylating reagent in the presence of a base such as, but not limited to, potassium carbonate or sodium hydride in a polar solvent such as, but not limited to, N,N-dimethylformamide or tetrahydrofuran thereby to generate the spiro oxindole intermediate 15.

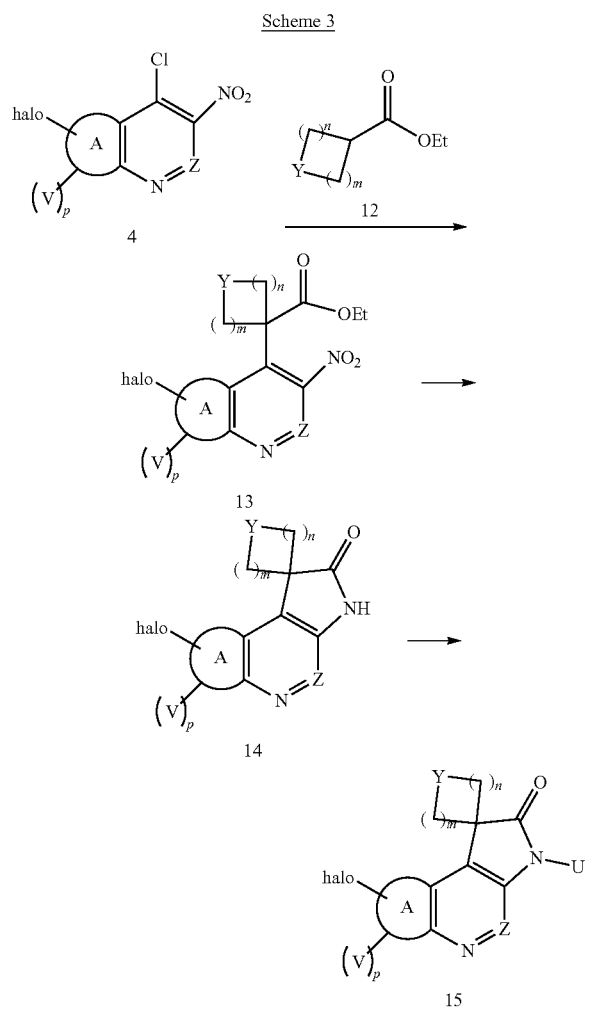

Scheme 3

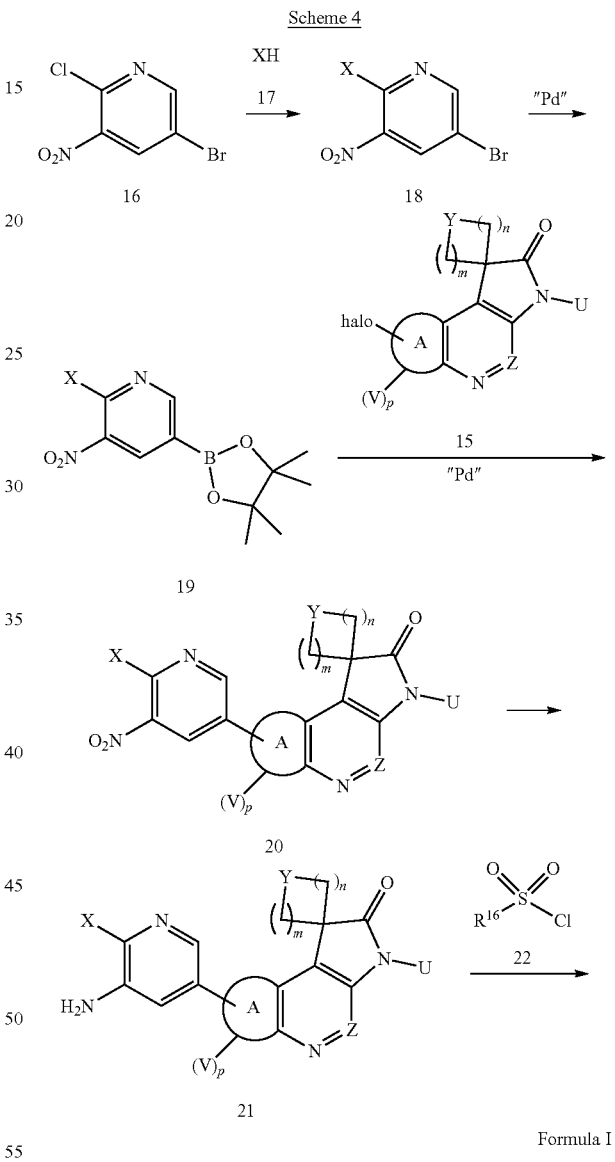

Scheme 4

Specifically, the other spiro oxindole intermediate 15 is synthesized as shown in Scheme 3. The cyclyl or heterocyclyl substituted ester 12 is treated with a strong base such as, but not limited to, lithium diisopropylamide at low temperature in anhydrous solvent such as, but not limited to, tetrahydrofurn to react with starting material 4, which is either commercially available or prepared by those skilled in the art following the literature described methods to provide intermediate 13. Intermediate 13 is reduced by a reducing Specifically, the compounds of Formula (I) in this invention can be synthesized as shown in Scheme 4. Commercially available 5-bromo-2-chloro-3-nitro-pyridine (16) reacts with a nucleophile XH (17) in the presence of a strong base such as, but not limited to, sodium hydride to provide intermediate 18. Under palladium catalyzed conditions, borate 19 can be prepared, which then reacts with the spiro intermediate 15 to provide the cross coupled product 20. The nitro group in compound 20 is reduced to amino group using a reducing reagent such as, but not limited to, iron to provide intermediate 21. Reaction of 21 with different sulphonyl chlorides (22) furnishes the synthesis of compounds of Formula (I).

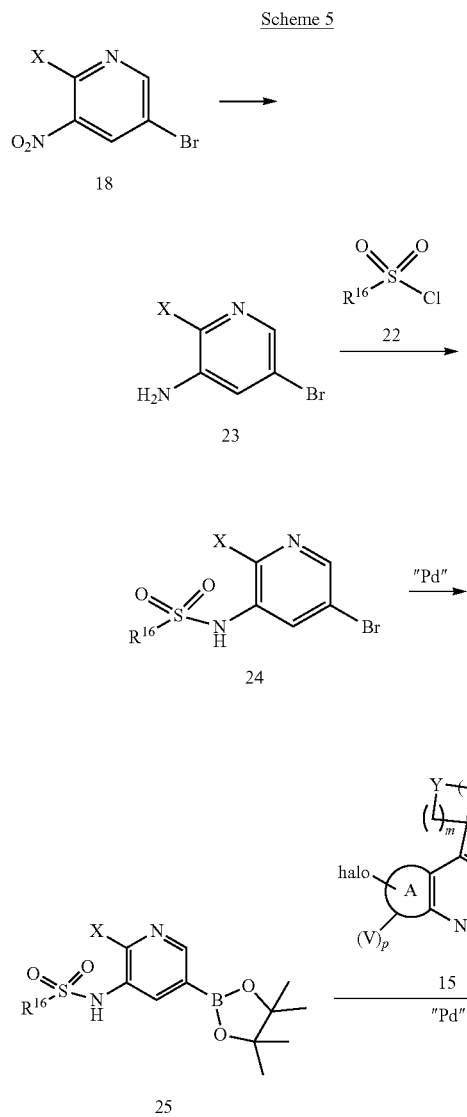

Scheme 5

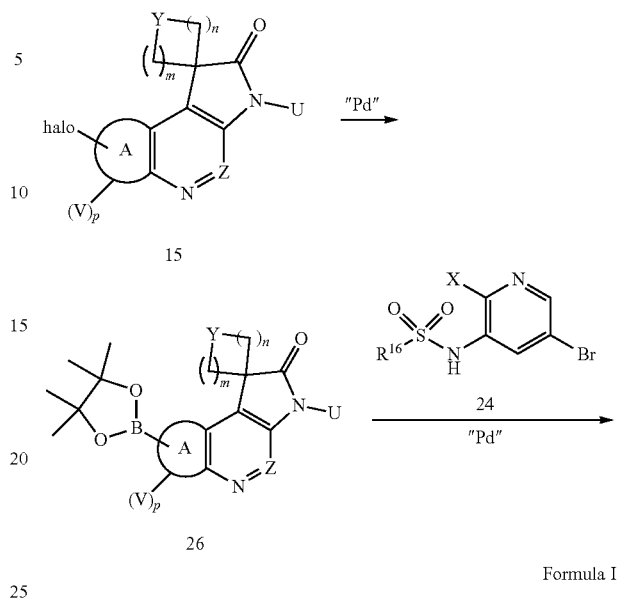

Scheme 6

Specifically, the compounds of Formula (I) in this invention can also be synthesized as shown in Scheme 6. The halo compound 15 can be converted to its corresponding borate 26 under palladium catalysis. Borate 26 can couple with the halo compound 24 under Suzuki reaction conditions to provide the compounds of Formula (I).

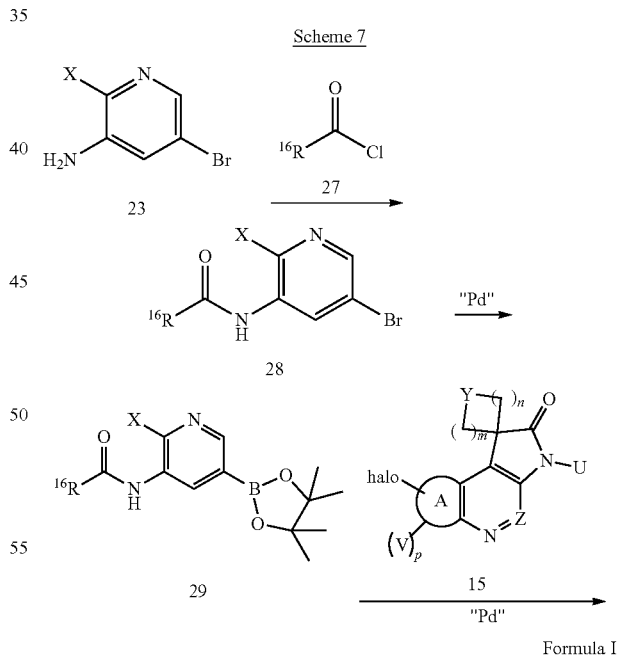

Scheme 7

Specifically, the compounds of Formula (I) in this invention can also be synthesized as shown in Scheme. The nitro group in compound 18 is reduced to amino group using a reducing reagent such as, but not limited to, iron to provide intermediate 23. Reaction of 23 with different sulphonyl chlorides (22) provides the sulphonamide intermediate 24, which is converted to its corresponding borate 25 under palladium catalysis. Borate 25 can couple with the halo compound 15 under Suzuki reaction conditions to provide the compounds of Formula (I).

In Scheme 4 and Scheme 5, the cross coupled compounds are also synthesizable using Suzuki coupling chemistry with components having reversed the halogen and boronate/boronic acid substitution patterns, for example, as shown in Scheme 6

Specifically, the compounds of Formula (I) in this invention can also be synthesized as shown in Scheme 7. The amino compound 23 can react with a carboxyl chloride compound 27 to provide the amide compound 28. Compound 28 can be converted to its corresponding borate 29 under palladium catalysis. Borate 29 couples with the halo compound 15 under Suzuki reaction conditions to provide the compounds of Formula (I).

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad lithium. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions thereof, can be solids, liquids or gases, thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount".

The invention will now be further described in the Examples below, which are intended as an illustration only and do not limit the scope of the invention.

EXAMPLES

Reagents were purchased from Aldrich, Sigma, TCI (Shanghai) Development, Chembon Pharmaceutical Co., Ltd, Zhangjiagang Aimate Huaxue Youxiangongsi, Changzhou Qinuo BioTech Co. Ltd, and Shanghai Weiyuan Fine Fluorine Technology Development Co., Ltd or other suppliers as indicated below and used without further purification. Reactions using microwave irradiation for heating were conducted using a Biotage Initiator+. The purification of multi-milligram to multi-gram scale was conducted by methods known to those skilled in the art such as elution of silica gel flash column chromatography, preparative flash column chromatography purifications were also affected in some cases by use of disposal pre-packed silica gel columns (Welch/Agela) eluted with a Biotage CombiFlash system.

For the purpose of judging compound identity and purity, typically, the analytical LC-MS (liquid chromatography/mass spectroscopy) system was used consisted of a Waters ZQ® platform with electrospray ionization in positive ion detection mode with an Agilent 1100 series HPLC with autosampler. The column was usually a Water Xterra MS C18, 3.0×50 mm, 5 µm. The flow rate was 1 mL/min, and the injection volume was 10 µL. UV detection was in the range 210-400 nm. The mobile phase consisted of solvent A (water plus 0.06% TRIFLUOROACETIC ACID) and solvent B (acetonitrile plus 0.05% TRIFLUOROACETIC ACID) with a gradient of 100% solvent A for 0.7 min changing to 100% solvent B over 3.75 min, maintained for 1.1 min, then reverting to 100% solvent A over 0.2 min For some separations, the use of super critical fluid chromatography may also be useful. Super critical fluid chromatography separations were performed using a Mettler-Toledo Minigram system with the following typical conditions: 100 bar, 30° C. 2.0 mL/min eluted a 12 mm AD column with 40% MeOH in super critical fluid $CO_2$. In the case of analytes with basic amino groups, 0.2% isopropyl amine was added to the methanol modifier.

Many compounds of Formula (I) were also purified by reverse phase HPLC, using methods well known to those skilled in the art. In some cases, preparative HPLC purification was conducted using PE Sciex 150 EX Mass Spec controlling a Gilson 215 collector attached to a Shimadzu preparative HPLC system and a Leap auto-injector. Compounds were collected from the elution stream using MS detection in the positive ion detection:

The elution of compounds from C-18 columns (2.0×10 cm eluted at 20 mL/min) was affected using appropriate linear gradation mode over 10 minutes of Solvent (A) 0.05% TRIFLUOROACETIC ACID/$H_2O$ and Solvent (B) 0.035% TRIFLUOROACETIC ACID/acetyl nitrile. For injection on to HPLC systems, the crude samples were dissolved in mixtures of methanol, acetyl nitrile and DMSO.

Compounds were characterized either by $^1$H-NMR using a Bruker ADVANCE III HD 400 MHz Spectrometer or Bruker AVANCE 300 MHz Spectrometer.

List of Abbreviations

DCE 1,2-dichloroethane
DCM dichloromethane
DIPEA diisopropylethylamine
DMF N, N-dimethylformamide
DMSO dimethylsulfoxide
EtOAc ethyl acetate
HOAc Acetic acid
HPLC high pressure liquid chromatography
MeI methyl iodide
MeOH methyl alcohol
MW microwave
NMP 1-methyl-2-pyrrolidinone rt ambient temperature
TBDMS tert-butyl-dimethylsilyl
TEA triethylamine
TRIFLUOROACETIC ACID trifluoroacetic acid
TEMPO 2,2,6,6-tetramethyl-1-piperidinyloxy
THF tetrahydrofuran Preparation of Preferred Intermediates Intermediate A

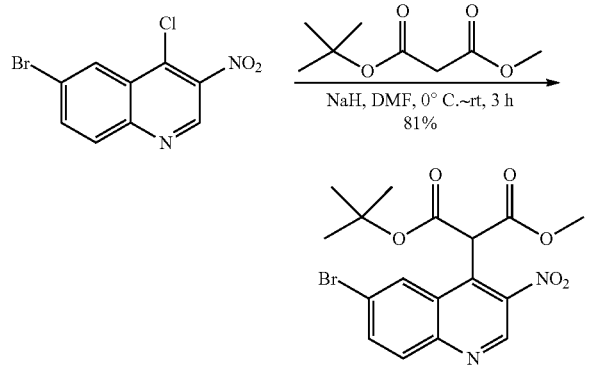

1-(tert-Butyl) 3-methyl 2-(6-bromo-3-nitroquinolin-4-yl) malonate: A solution of 1-tert-butyl 3-methyl propanedioate (26.1 g, 150 mmol) in anhydrous N,N-dimethylformamide (500 mL) was treated with sodium hydride (6.40 g, 160 mmol, 60% w/w dispersed in mineral oil) for 1 hour at 0° C. under nitrogen atmosphere followed by the addition of 6-bromo-4-chloro-3-nitroquinoline (28.8 g, 100 mmol). The resulting mixture was stirred for 3 hours at ambient temperature. The reaction was quenched by saturated aqueous of ammonium chloride (300 mL) and diluted with water (2.00 L). The mixture was extracted with ethyl acetate (3×500 mL). The combined organic layers was washed with brine (3×200 mL), dried over anhydrous sodium sulfate and filtered. The filtrate was concentrated under reduced pressure and the residue was purified by silica gel column chromatography, eluted with 5%~20% ethyl acetate in petroleum ether. Desired fractions were collected and concentrated under reduced pressure to afford the title compound as a light brown solid (34.4 g, 81%): $^1$H NMR (300 MHz, CDCl$_3$) δ 9.38 (s, 1H), 8.36 (d, J=2.0 Hz, 1H), 8.13 (d, J=9.0 Hz, 1H), 7.99 (dd, J=9.0, 1.9 Hz, 1H), 5.59 (s, 1H), 3.85 (s, 3H), 1.47 (s, 9H); MS: [(M+1)]$^+$=425.05, 427.05.

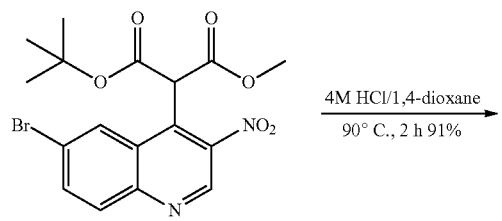

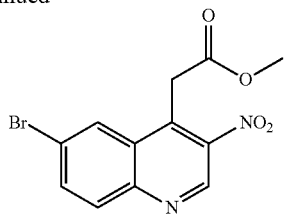

Methyl 2-(6-bromo-3-nitroquinolin-4-yl)acetate: 1-tert-butyl 3-methyl 2-(6-bromo-3-nitroquinolin-4-yl)propanedioate (34.4 g, 80.9 mmol) was treated with 4M HCl (g) in 1,4-dioxane (800 mL) for 3 hours at 90° C. After cooling down to ambient temperature, the reaction mixture was concentrated under reduced pressure and the residue was taken up with ethyl acetate (300 mL) and water (200 mL), neutralized with saturated aqueous of sodium bicarbonate. The organic layer was collected, dried over anhydrous sodium sulfate and filtered. The filtrate was concentrated under reduced pressure. The residue was purified by silica gel column chromatography, eluted with 5%~15% ethyl acetate in petroleum ether. Desired fractions were collected and concentrated under reduced pressure to afford the title compound as a brown solid (23.7 g, 91%): $^1$H NMR (300 MHz, CDCl$_3$) δ 9.43 (s, 1H), 8.30 (d, J=2.1 Hz, 1H), 8.14 (d, J=8.9 Hz, 1H), 8.01 (dd, J=9.0, 2.0 Hz, 1H), 4.47 (s, 2H), 3.80 (s, 3H); MS: [(M+1)]$^+$=324.95, 326.95.

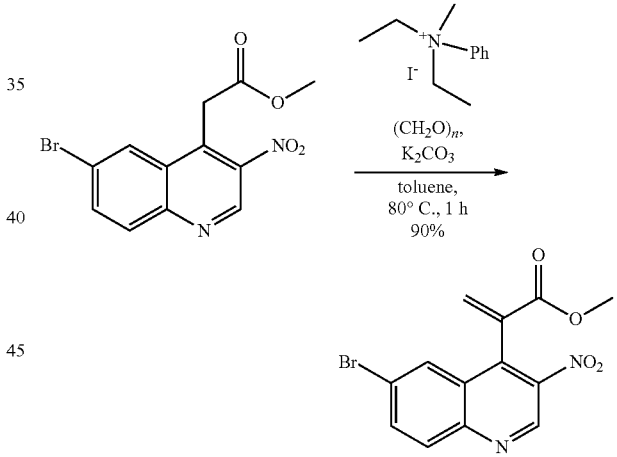

Methyl 2-(6-bromo-3-nitroquinolin-4-yl)acrylate: To a stirred mixture of methyl 2-(6-bromo-3-nitroquinolin-4-yl) acetate (18.3 g, 56.3 mmol), potassium carbonate (15.7 g, 113 mmol) and N,N,N-triethylbenzenaminium iodide (20.6 g, 67.6 mmol) in anhydrous toluene (450 mL) was added paraformaldehyde (11.0 g, 366 mmol) at ambient temperature. The resulting mixture was warmed to 80° C. slowly (over 20 min) and stirred for additional 1 hour at 80° C. After cooling down to ambient temperature, the resulting mixture was concentrated under reduced pressure. The residue was purified by silica gel column chromatography, eluted with 5%~20% ethyl acetate in petroleum ether. Desired fractions were collected and concentrated under reduced pressure to afford the title compound as a light yellow solid (17.0 g, 90%): $^1$H NMR (300 MHz, CDCl$_3$) δ 9.55 (s, 1H), 8.23-8.09 (m, 2H), 8.01 (dd, J=9.0, 2.1 Hz, 1H), 7.01 (s, 1H), 5.89 (s, 1H), 3.81 (s, 3H); MS: [(M+1)]$^+$=336.95, 338.95.

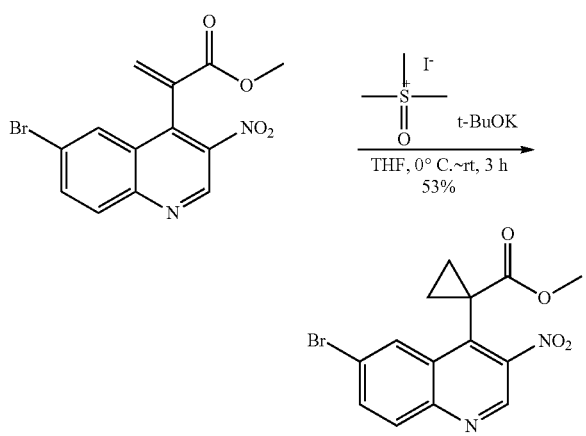

Methyl 1-(6-bromo-3-nitroquinolin-4-yl)cyclopropane-1-carboxylate: To a suspension of trimethylsulfoxonium iodide (16.6 g, 75.7 mmol) in anhydrous tetrahydrofuran (600 mL) was added sodium tert-butoxide (8.50 g, 75.7 mmol) at 0° C. under nitrogen atmosphere. The resulting mixture was stirred for 0.5 hours at ambient temperature followed by the addition of methyl 2-(6-bromo-3-nitroquinolin-4-yl)prop-2-enoate (17.0 g, 50.4 mmol) at 0° C. in portions. The resulting mixture was stirred for 3 hours at ambient temperature. The reaction was quenched by a saturated aqueous of ammonium chloride (100 mL) and diluted with water (500 mL). The organic layer was separated and the aqueous layer was extracted with ethyl acetate (3×200 mL). The combined organic layers was washed with brine (200 mL), dried over anhydrous sodium sulfate and filtered. The filtrate was concentrated under reduced pressure. The residue was purified by silica gel column chromatography, eluted with 5%~15% ethyl acetate in petroleum ether. Desired fractions were collected and concentrated under reduced pressure to afford the title compound as a light yellow solid (9.30 g, 53%): $^1$H NMR (300 MHz, CDCl$_3$) δ 9.27 (s, 1H), 8.48 (d, J=2.1 Hz, 1H), 8.15 (d, J=9.0 Hz, 1H), 7.99 (dd, J=9.0, 2.1 Hz, 1H), 3.72 (s, 3H), 2.15 (ddd, J=9.9, 7.2, 4.4 Hz, 1H), 2.02-1.87 (m, 1H), 1.32 (ddd, J=10.0, 7.5, 4.5 Hz, 1H), 1.10 (ddd, J=10.0, 7.3, 4.8 Hz, 1H); MS: $[(M+1)]^+$=351.00, 353.00.

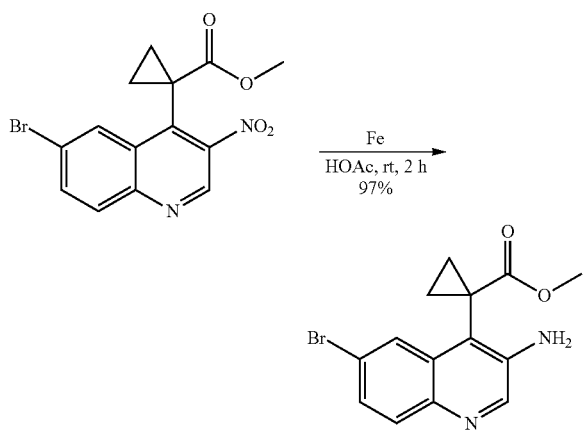

Methyl 1-(3-amino-6-bromoquinolin-4-yl)cyclopropane-1-carboxylate: To a solution of methyl 1-(6-bromo-3-nitroquinolin-4-yl)cyclopropane-1-carboxylate (9.30 g, 26.5 mmol) in acetic acid (250 mL) was added iron powder (14.8 g, 265 mmol) at ambient temperature. After stirring for 1 hour at ambient temperature, the resulting mixture was filtered and the filtered cake was washed with tetrahydrofuran (6×100 mL). The filtrate was concentrated under reduced pressure and the residue was taken up with ethyl acetate (300 mL) and water (200 mL). The organic layer was separated, dried over anhydrous sodium sulfate and filtered. The filtrate was concentrated under reduced pressure to afford the title compound as a light brown solid (8.20 g, 97%): $^1$H NMR (300 MHz, DMSO-d$_6$) δ 8.50 (s, 1H), 7.93 (d, J=2.2 Hz, 1H), 7.73 (d, J=8.7 Hz, 1H), 7.43 (dd, J=8.8, 2.2 Hz, 1H), 5.93 (s, 2H), 3.54 (s, 3H), 1.99-1.89 (m, 1H), 1.83-1.73 (m, 1H), 1.20-1.08 (m, 2H); MS: $[(M+1)]^+$=321.05, 323.05.

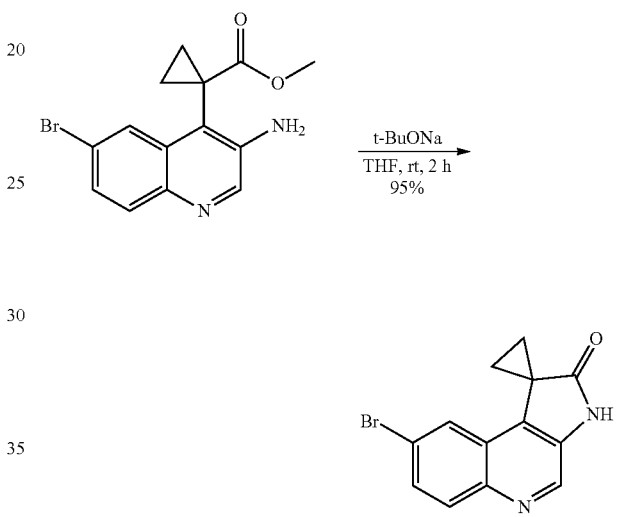

8'-Bromospiro[cyclopropane-1,1'-pyrrolo[2,3-c]quinolin]-2'(3'H)-one: A solution of methyl 1-(3-amino-6-bromoquinolin-4-yl)cyclopropane-1-carboxylate (8.20 g, 25.5 mmol) in tetrahydrofuran (600 mL) was treated with sodium tert-butoxide (12.3 g, 128 mmol) for 2 hours at ambient temperature. The reaction was quenched with saturated aqueous ammonium chloride (300 mL). The organic layer was separated and the aqueous layer was extracted by ethyl acetate (3×300 mL). The combined organic layers was washed with brine (3×100 mL), dried over anhydrous sodium sulfate and filtered. The filtrate was concentrated under reduced pressure to afford the title compound as a light yellow solid (7.00 g, 95%): $^1$H NMR (300 MHz, DMSO-d$_6$) δ 11.11 (s, 1H), 8.71 (s, 1H), 7.95 (d, J=9.0 Hz, 1H), 7.70 (dd, J=9.0, 2.1 Hz, 1H), 7.59 (d, J=2.1 Hz, 1H), 2.32 (q, J=4.4 Hz, 2H), 1.70 (q, J=4.3 Hz, 2H); MS: $[(M+1)]^+$=289.0, 291.0.

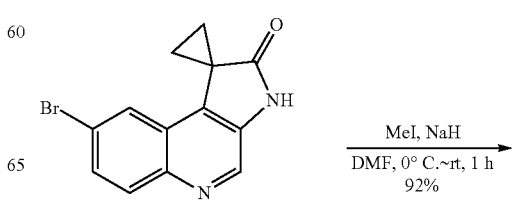

-continued

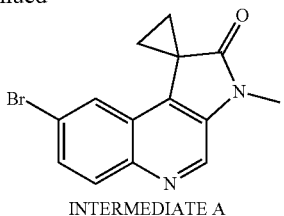

INTERMEDIATE A

8-Bromo-3'-methylspiro[cyclopropane-1,1'-pyrrolo[2,3-c]quinolin]-2'(3'H)-one: A solution of 8-bromo-2,3-dihydrospiro[cyclopropane-1,1-pyrrolo[2,3-c]quinoline]-2-one (3.00 g, 10.4 mmol) in anhydrous N,N-dimethylformamide (60.0 mL) was treated with sodium hydride (540 mg, 13.5 mol, 60% w/w dispersed in mineral oil) for 1 hour at 0° C. followed by the addition of iodomethane (1.80 g, 12.5 mmol). The resulting mixture was stirred for additional 1 hour at ambient temperature. The reaction was quenched by saturated aqueous ammonium chloride (100 mL) and diluted with water (500 mL). The precipitated solid was collected by filtration and washed with water (3×50.0 mL) to afford the title compound as an off-white solid: (2.90 g, 92%): $^1$H NMR (300 MHz, DMSO-$d_6$) δ 8.96 (s, 1H), 7.99 (d, J=9.1 Hz, 1H), 7.73 (dd, J=9.0, 2.1 Hz, 1H), 7.63 (d, J=2.2 Hz, 1H), 3.41 (s, 3H), 2.38 (q, J=4.5 Hz, 2H), 1.76 (q, J=4.4 Hz, 2H); MS: [(M+1)]$^+$=303.9, 305.9.

The following intermediates were prepared according to the procedure described above:

| Intermediate | Structure | Name | MS: [(M + 1)]$^+$ | $^1$H NMR |
|---|---|---|---|---|
| A1 | 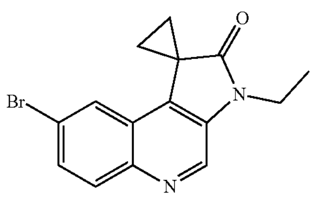 [SMILES: CCN1C(=O)C2(CC2)c2c1cnc1ccc(Br)cc21] | 8'-Bromo-3'-ethylspiro[cyclopropane-1,1'-pyrrolo[2,3-c]quinolin]-2'(3'H)-one | 317.10 319.10 | $^1$H NMR (400 MHz, DMSO-$d_6$) δ 9.00 (s, 1H), 7.98 (d, J = 9.0 Hz, 1H), 7.72 (dd, J = 9.0, 2.1 Hz, 1H), 7.61 (d, J = 2.1 Hz, 1H), 3.97 (q, J = 7.2 Hz, 2H), 2.37 (q, J = 4.5 Hz, 2H), 1.76 (q, J = 4.4 Hz, 2H), 1.26 (t, J = 7.2 Hz, 3H). |
| A2$^a$ | | 8'-Bromo-3'-isopropylspiro[cyclopropane-1,1'-pyrrolo[2,3-c]quinolin]-2'(3'H)-one | 331.05 333.05 | $^1$H NMR (300 MHz, CDCl$_3$) δ 8.87 (s, 1H), 8.22 (s, 1H), 7.72 (d, J = 8.8 Hz, 1H), 7.56 (d, J = 2.0 Hz, 1H), 4.92-4.82 (m, 1H), 2.37-2.29 (m, 2H), 2.13-2.06 (m, 2H), 1.59 (d, J = 7.0 Hz, 6H). |
| A3 | 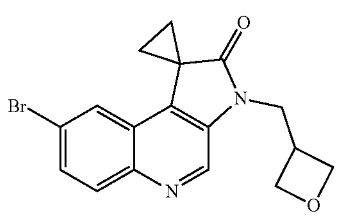 [SMILES: O=C1N(CC2COC2)c2cnc3ccc(Br)cc3c2C12CC2] | 8'-Bromo-3'-(oxetan-3-ylmethyl)spiro[cyclopropane-1,1'-pyrrolo[2,3-c]quinolin]-2'(3'H)-one | 358.95 360.95 | $^1$H NMR (300 MHz, DMSO-$d_6$) δ 8.99 (s, 1H), 7.94 (d, J = 9.0 Hz, 1H), 7.69 (dd, J = 9.0, 2.1 Hz, 1H), 7.58 (d, J = 2.1 Hz, 1H), 4.61 (dd, J = 7.8, 6.1 Hz, 2H), 4.38 (t, J = 6.1 Hz, 2H), 4.22 (d, J = 7.2 Hz, 2H), 3.48-3.40 (m, 1H), 2.36 (q, J = 4.4 Hz, 2H), 1.74 (q, J = 4.4 Hz, 2H). |
| A4 | 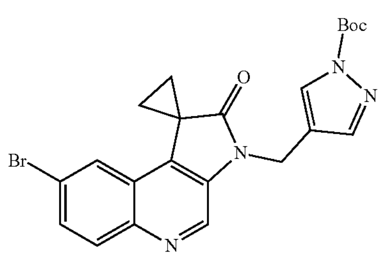 [SMILES: CC(C)(C)OC(=O)n1cc(CN2C(=O)C3(CC3)c3c2cnc2ccc(Br)cc32)cn1] | tert-Butyl 4-((8'-bromo-2'-oxospiro[cyclopropane-1,1'-pyrrolo[2,3-c]quinolin]-3'(2'H)-yl)methyl)-1H-pyrazole-1-carboxylate | 469.00 471.00 | $^1$H NMR (300 MHz, CDCl$_3$) δ 8.69 (s, 1H), 8.11 (s, 1H), 7.99 (d, J = 9.1 Hz, 1H), 7.73 (s, 1H), 7.65 (dd, J = 9.1, 2.0 Hz, 1H), 7.51 (d, J = 2.1 Hz, 1H), 5.02 (s, 2H), 2.30 (q, J = 4.5 Hz, 2H), 2.09-2.03 (m, 2H), 1.63 (s, 9H). |

Note:
$^a$reaction conditions:
1) DMF, NaH, 0° C.~rt, 30 min;
2) 2-iodopropane, 55° C., 3 hours.

Intermediate A5

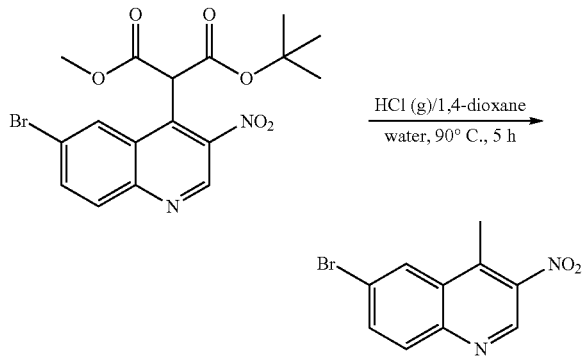

6-Bromo-4-methyl-3-nitroquinoline: A solution of 1-tert-butyl 3-methyl 2-(6-bromo-3-nitroquinolin-4-yl)propanedioate (9.40 g, 22.1 mmol) in HCl (gas)/1,4-dioxane (110 mL, 4M) and water (11.0 mL) was stirred for 5 hours at 90° C. The resulting mixture was concentrated under reduced pressure. The residue was basified to pH=8 with saturated aqueous sodium bicarbonate. The aqueous layer was extracted with ethyl acetate (3×100 mL). The combined organic layers was washed with brine (100 mL) and dried over anhydrous sodium sulfate. After filtration, the filtrate was concentrated under reduced pressure. The residue was purified by silica gel column chromatography, eluted with 2%~5% ethyl acetate in petroleum ether. The desired fractions were collected and concentrated under reduced pressure to afford the title compound as a yellow solid (5.46 g, 93%): $^1$H NMR (400 MHz, DMSO-$d_6$) δ 9.26 (s, 1H), 8.60 (d, J=2.0 Hz, 1H), 8.13-8.05 (m, 2H), 2.85 (s, 3H); MS: $[(M+1)]^+$=267.05, 269.05.

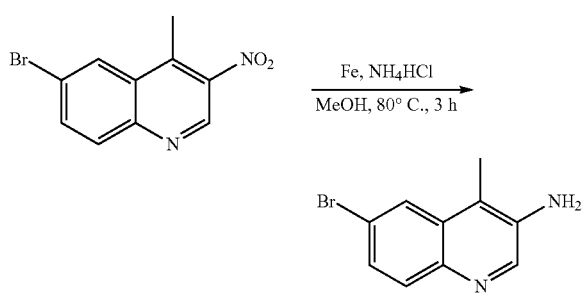

6-Bromo-4-methylquinolin-3-amine: A mixture of 6-bromo-4-methyl-3-nitroquinoline (2.15 g, 8.05 mmol), ammonium chloride (2.13 g, 39.8 mmol) and iron powder (2.26 g, 40.3 mmol) in methanol (60.0 mL) and water (6.00 mL) was stirred for 3 hours at 80° C. The resulting mixture was concentrated under reduced pressure. The residue was purified by silica gel column chromatography, eluted with 1%~5% methanol in dichloromethane. The desired fractions were collected and concentrated under reduced pressure to afford the title compound as a colorless solid (1.65 g, 86%): $^1$H NMR (300 MHz, CDCl$_3$) δ 8.44 (s, 1H), 7.98 (d, J=2.1 Hz, 1H), 7.80 (d, J=8.8 Hz, 1H), 7.49 (dd, J=8.9, 2.1 Hz, 1H), 3.88 (s, 2H), 2.36 (s, 3H); MS: $[(M+1)]^+$=236.95, 238.95.

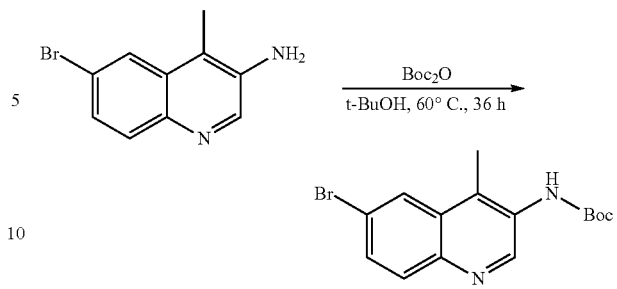

tert-Butyl (6-bromo-4-methylquinolin-3-yl)carbamate: A mixture of 6-bromo-4-methylquinolin-3-amine (1.56 g, 6.58 mol) and di-tert-butyl dicarbonate (2.15 g, 10.0 mmol) in tert-butyl alcohol (50.0 mL) was stirred for 36 hours at 60° C. The reaction mixture was cooled down to ambient temperature, diluted with water (100 mL), then extracted with ethyl acetate (3×200 mL). The combined organic layers was washed with brine (200 mL) and dried over anhydrous sodium sulfate. After filtration, the filtrate was concentrated under reduced pressure. The residue was purified by silica gel column chromatography, eluted with 2%~20% ethyl acetate in petroleum ether. The desired fractions were collected and concentrated under reduced pressure to afford the title compound as a light yellow solid (1.83 g, 83%): $^1$H NMR (400 MHz, CDCl$_3$) δ 9.04 (s, 1H), 8.09 (d, J=2.0 Hz, 1H), 7.92 (d, J=8.8 Hz, 1H), 7.73-7.65 (m, 1H), 6.58 (s, 1H), 2.52 (s, 3H), 1.53 (s, 9H); MS: $[(M+1)]^+$=337.00, 339.00.

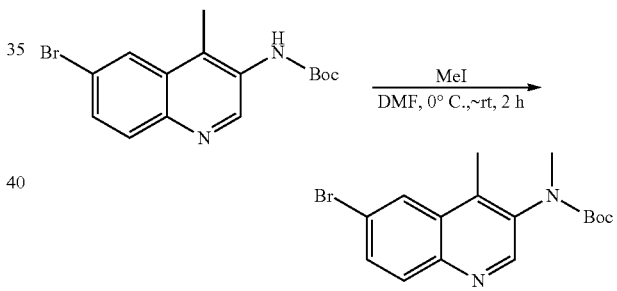

tert-Butyl (6-bromo-4-methylquinolin-3-yl)(methyl)carbamate: A solution of tert-butyl 6-bromo-4-methylquinolin-3-ylcarbamate (1.78 g, 5.28 mol) in N,N-dimethylformamide (40.0 mL) was treated with sodium hydride (275 mg, 6.86 mmol, 60% dispersed in mineral oil) for 30 min at 0° C. followed by the addition of iodomethane (899 mg, 6.33 mmol). After stirring for 2 hours at ambient temperature, the reaction was quenched with saturated aqueous ammonium chloride (10.0 mL). The resulting mixture diluted with water (300 mL) and extracted with ethyl acetate (3×200 mL). The combined organic layers was washed with brine (2×200 mL) and dried over anhydrous sodium sulfate. After filtration, the filtrate was concentrated under reduced pressure. The residue was purified by silica gel column chromatography, eluted with 4%~20% ethyl acetate in petroleum ether. The desired fractions were collected and concentrated under reduced pressure to afford the title compound as a yellow solid (1.82 g, 99%): $^1$H NMR (400 MHz, CDCl$_3$) δ 8.66 (s, 1H), 8.18 (d, J=2.1 Hz, 1H), 8.01 (d, J=8.9 Hz, 1H), 7.83-7.76 (m, 1H), 3.25 (s, 3H), 2.54 (s, 3H), 1.33 (s, 9H), 1.25 (s, 1H); MS: $[(M+1)]^+$=351.20, 353.20.

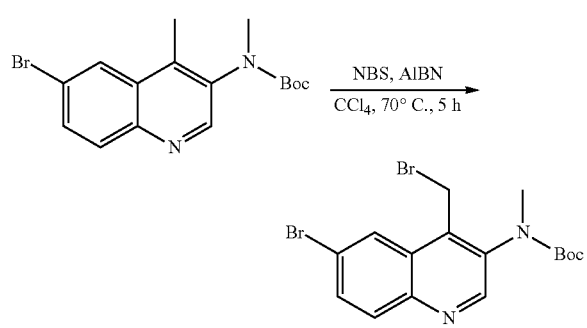

tert-Butyl (6-bromo-4-(bromomethyl)quinolin-3-yl)(methyl)carbamate: To a solution of tert-butyl N-(6-bromo-4-methylquinolin-3-yl)-N-methylcarbamate (700 mg, 1.99 mmol) in tetrachloromethane (50.0 mL) were added boranylidene(sulfanyl)amine (141 mg, 2.39 mmol) and azodiisobutyronitrile (49.1 mg, 0.30 mmol) at ambient temperature. After stirring for 5 hours at 70° C., the resulting mixture was concentrated under reduced pressure. The residue was purified by silica gel column chromatography, eluted with 10% ethyl acetate in petroleum ether. The desired fractions were collected and concentrated under reduced pressure to afford the title compound as an off-white solid (410 mg, 48%): $^1$H NMR (300 MHz, CDCl$_3$) δ 8.67 (s, 1H), 8.26 (d, J=2.0 Hz, 1H), 8.02 (d, J=9.0 Hz, 1H), 7.81 (dd, J=9.0, 2.0 Hz, 1H), 1 4.73 (s, 2H), 3.30 (s, 3H), 1.31 (s, 9H); MS: [(M+1)]$^+$=428.30, 430.80.

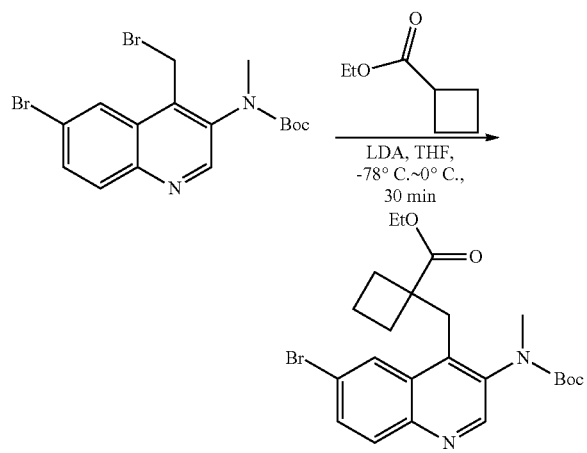

Ethyl 1-((6-bromo-3-((tert-butoxycarbonyl)(methyl)amino)quinolin-4-yl)methyl)cyclobutane-1-carboxylate To a solution of bis(propan-2-yl)amine (424 mg, 4.19 mmol) in anhydrous tetrahydrofuran (15.0 mL) was added n-butyllithium (1.70 mL, 4.19 mmol, 2.5 M in hexane) at −78° C. under nitrogen atmosphere. The resulting mixture was stirred at −30° C. for 30 min followed by the addition of ethyl cyclobutanecarboxylate (537 mg, 4.19 mmol) at −78° C. After stirring for 30 min at −78° C., to the above mixture was added a solution of tert-butyl (6-bromo-4-(bromomethyl)quinolin-3-yl)(methyl)carbamate (150 mg, 0.35 mmol) in anhydrous tetrahydrofuran (3 mL) at −30° C. The resulting mixture was stirred for additional 30 min at 0° C. The reaction was quenched with saturated aqueous ammonium chloride (5.00 mL). The resulting mixture was diluted with water (50.0 mL) and extracted with ethyl acetate (3×20.0 mL). The combined organic layers was washed with brine (2×20.0 mL) and dried over anhydrous sodium sulfate. After filtration, the filtrate was concentrated under reduced pressure. The residue was purified by Prep-TLC (petroleum ether/ethyl acetate=1/1, v/v) to afford the title compound as an off-white solid (82.7 mg, 50%): $^1$H NMR (300 MHz, CDCl$_3$) δ 8.68 (s, 1H), 8.20 (s, 1H), 7.86-7.74 (m, 2H), 4.25-4.03 (m, 2H), 3.49 (s, 2H), 2.57 (s, 3H), 2.43-2.27 (m, 2H), 2.11-1.80 (m, 4H), 1.17 (t, J=6.8 Hz, 3H); MS: [(M+1)]$^+$=477.15, 479.15.

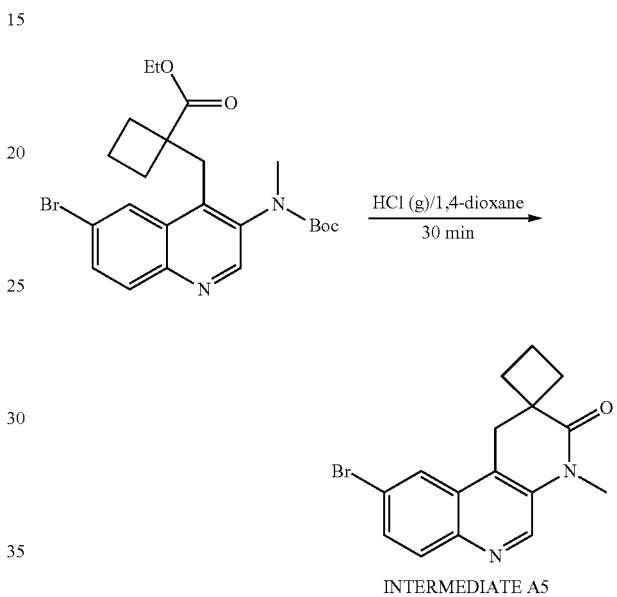

INTERMEDIATE A5

9-Bromo-4-methyl-1,4-dihydro-3H-spiro[benzo[f][1,7]naphthyridine-2,1'-cyclobutan]-3-one: A mixture of ethyl 1-((6-bromo-3-((tert-butoxycarbonyl)(methyl)amino)quinolin-4-yl)methyl)cyclobutane-1-carboxylate (109 mg, 0.23 mmol) in HCl (g)/1,4-dioxane (20.0 mL, 4 M) was stirred at ambient temperature for 30 min The reaction mixture was concentrated under reduced pressure to afford the title compound as a brown solid (63 mg, 84%): $^1$H NMR (300 MHz, CDCl$_3$) δ 8.79 (s, 1H), 8.18 (d, J=2.0 Hz, 1H), 7.98 (d, J=8.9 Hz, 1H), 7.73 (dd, J=8.9, 2.1 Hz, 1H), 3.57 (s, 3H), 3.40 (s, 2H), 2.68-2.52 (m, 2H), 2.11 (dd, J=9.9, 6.3 Hz, 2H), 1.88 (dd, J=11.5, 6.8 Hz, 2H); MS: [(M+1)]$^+$=331.00, 333.00.

Intermediate A6

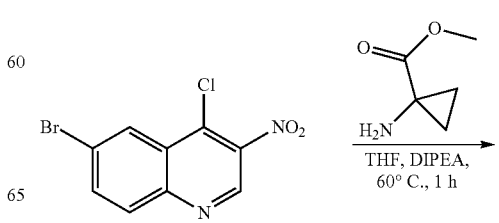

-continued

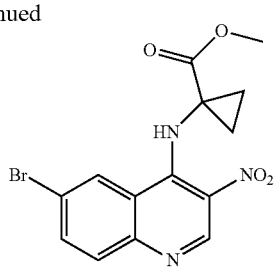

Methyl 1-((6-bromo-3-nitroquinolin-4-yl)amino)cyclopropane-1-carboxylate: A mixture of 6-bromo-4-chloro-3-nitroquinoline (2.00 g, 6.% mmol), methyl 1-aminocyclopropane-1-carboxylate (1.60 g, 13.9 mmol) and N,N-diisopropylethylamine (1.80 g, 13.9 mmol) in tetrahydrofuran (60.0 mL) was stirred for 1 hour at 60° C. The mixture was concentrated under reduced pressure. The residue was purified by silica gel column chromatography, eluted with 2%~17% ethyl acetate in petroleum ether. The desired fractions were collected and concentrated under reduced pressure to afford the title compound as a yellow solid (2.50 g, 99%): $^1$H NMR (400 MHz, DMSO-$d_6$) δ 9.08 (s, 1H), 8.89 (s, 1H), 8.84 (d, J=2.1 Hz, 1H), 7.96 (dd, J=8.9, 2.1 Hz, 1H), 7.84 (d, J=8.9 Hz, 1H), 3.73 (s, 3H), 1.41 (s, 2H), 1.30 (s, 2H); MS: [(M+1)]$^+$=366.05, 368.05.

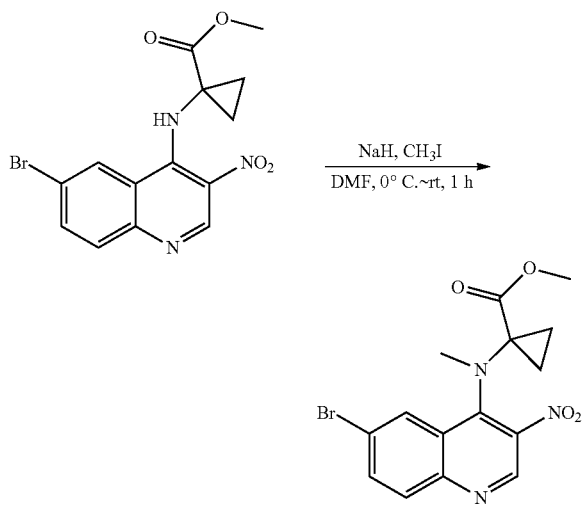

Methyl 1-((6-bromo-3-nitroquinolin-4-yl)(methyl)amino)cyclopropane-1-carboxylate: To a solution of methyl 1-((6-bromo-3-nitroquinolin-4-yl)amino)cyclopropane-1-carboxylate (2.50 g, 6.83 mmol) in N,N-dimethylformamide (30.0 mL) was added sodium hydride (410 mg, 10.2 mmol, 60% dispersed in mineral oil) at 0° C., followed by the addition of iodomethane (1.5 g, 10.2 mmol). After stirring for 1 hour at ambient temperature, the reaction was quenched with saturated aqueous ammonium chloride (20.0 mL). The resulting mixture was diluted with water (200 mL) and extracted with ethyl acetate (3×200 mL). The combined organic layers was washed with brine (3×200 mL) and dried over anhydrous sodium sulfate. After filtration, the filtrate was concentrated under reduced pressure. The residue was purified by silica gel column chromatography, eluted with 3%~50% ethyl acetate in petroleum ether. The desired fractions were collected and concentrated under reduced pressure to afford the title compound as a yellow solid (1.50 g, 58%): $^1$H NMR (400 MHz, DMSO-$d_6$) δ 8.86 (s, 1H), 8.45 (d, J=2.5 Hz, 1H), 7.83 (dd, J=8.9, 2.5 Hz, 1H), 7.54 (d, J=9.0 Hz, 1H), 3.80 (s, 3H), 3.57 (s, 3H), 1.46 (d, J=3.4 Hz, 2H), 1.09 (d, J=3.7 Hz, 2H); MS: [(M+1)]$^+$=379.95, 381.95.

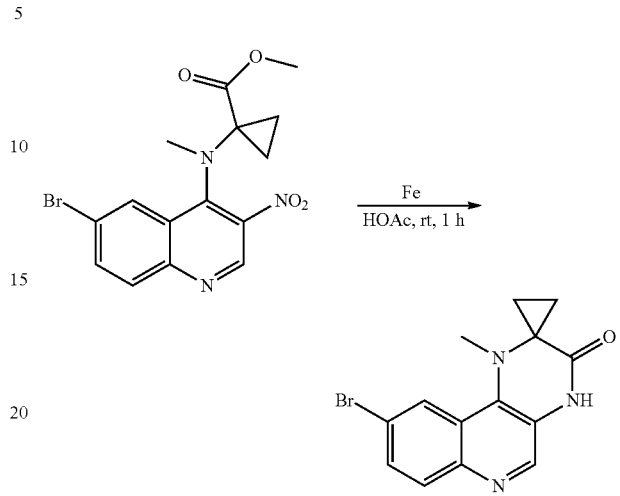

9'-Bromo-1'-methyl-1',4'-dihydro-3'H-spiro[cyclopropane-1,2'-pyrazino[2,3-c]quinolin]-3'-one: To a solution of methyl 1-((6-bromo-3-nitroquinolin-4-yl)(methyl)amino) cyclopropane-1-carboxylate (600 mg, 1.58 mmol) in acetic acid (30.0 mL) was added iron powder (881 mg, 15.8 mmol) at ambient temperature. The resulting mixture was stirred for 1 hour at ambient temperature. The mixture was filtered and the filtered cake was washed with tetrahydrofuran (6×100 mL). The filtrate was concentrated under reduced pressure. The residue was basified to pH=8 with saturated aqueous sodium bicarbonate. The resulting mixture was extracted with ethyl acetate (3×200 mL). The combined organic layers was washed with brine (3×200 mL) and dried over anhydrous sodium sulfate. After filtration, the filtrate was concentrated under reduced pressure and the residue was purified by trituration with dichloromethane and n-hexane (v/v=1/1) to afford the title compound as a yellow solid (450 mg, 82%): $^1$H NMR (400 MHz, DMSO-$d_6$) δ 10.08 (s, 1H), 8.07 (d, J=2.5 Hz, 1H), 7.59 (dd, J=9.1, 2.5 Hz, 1H), 7.24 (d, J=9.1 Hz, 1H), 6.61 (s, 1H), 3.46 (s, 3H), 1.51 (q, J=3.6 Hz, 2H), 0.99 (q, J=3.6 Hz, 2H); MS: [(M+1)]$^+$=318.00, 320.00.

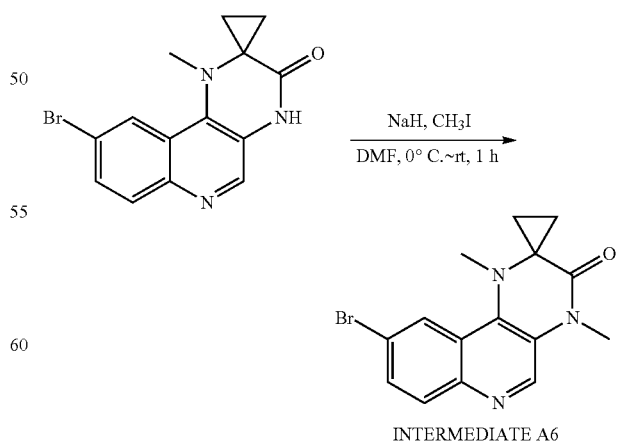

INTERMEDIATE A6

9'-Bromo-1',4'-dimethyl-1',4'-dihydro-3'H-spiro[cyclopropane-1,2'-pyrazino[2,3-c]quinolin]-3'-one: To solution of 9-bromo-1-methyl-3,4-dihydro-1H-spiro[cyclopropane-1,2-pyrazino[2,3-c]quinoline]-3-one (60.0 mg, 0.19 mmol) in N,N-dimethylformamide (10.0 mL) was added sodium hydride (10.0 mg, 0.25 mmol, 60% dispersed in mineral oil) at 0° C. under nitrogen atmosphere. The resulting mixture was stirred for 1 hour at 25° C. followed by the addition of iodomethane (36.0 mg, 0.25 mmol) at 0° C. After stirring for additional 1.5 hours at 25° C., the reaction was quenched with saturated aqueous ammonium chloride (20.0 mL) and diluted with water (100 mL). The resulting mixture was extracted with ethyl acetate (3×200 mL). The combined organic layers was washed with brine (2×200 mL) and dried over anhydrous sodium sulfate. After filtration, the filtrate was concentrated under reduced pressure. The residue was purified by Prep-TLC (DCM/MeOH=15/1, v/v) to afford the title compound as a yellow solid (45.0 mg, 72%): $^1$H NMR (400 MHz, CDCl$_3$) δ 8.32 (s, 1H), 7.49 (d, J=9.0 Hz, 1H), 6.91 (s, 1H), 6.18 (s, 1H), 3.50 (s, 3H), 3.15 (s, 3H), 1.78 (q, J=3.8 Hz, 2H), 1.55 (q, J=3.8 Hz, 2H); MS: [(M+1)]$^+$=332.00, 334.00.

Intermediate A8

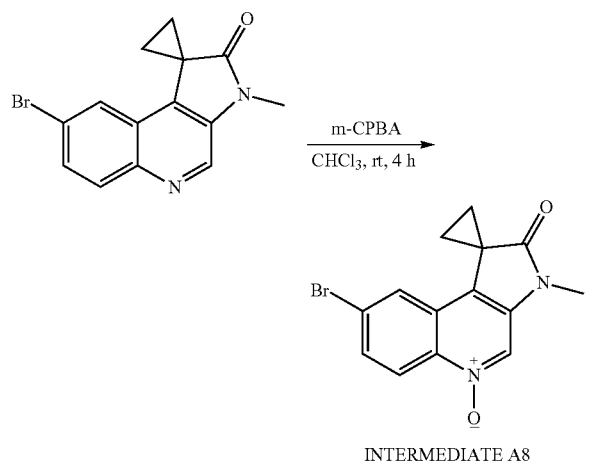

INTERMEDIATE A8

8'-Bromo-3'-methyl-2'-oxo-2',3'-dihydrospiro[cyclopropane-1,1'-pyrrolo[2,3-c]quinoline] 5'-oxide: To a stirred mixture of 8-bromo-3-methyl-2,3-dihydrospiro[cyclopropane-1,1-pyrrolo[2,3-c]quinoline]-2-one (200 mg, 0.66 mmol) in trichloromethane (20.0 mL) was added 3-chloroperbenzoic acid (171 mg, 0.99 mmol) at 25° C. under nitrogen atmosphere. After stirring for 4 hours at 25° C., the reaction was quenched with saturated aqueous sodium bicarbonate (20.0 mL) and saturated aqueous sodium sulfite solution (20.0 mL). The resulting mixture was extracted with trichloromethane (3×50.0 mL). The combined organic layers was washed with brine (60.0 mL) and dried over anhydrous sodium sulfate. After filtration, the filtrate was concentrated under reduced pressure. The residue was purified by silica gel column chromatography, eluted with 1%~5% methanol in dichloromethane. The desired fractions were collected and concentrated under reduced pressure to afford the title compound as a yellow solid (150 mg, 72%): $^1$H NMR (400 MHz, DMSO-d$_6$) δ 8.92 (s, 1H), 8.47 (d, J=9.4 Hz, 1H), 7.75 (dd, J=9.4, 1.9 Hz, 1H), 7.61 (d, J=2.0 Hz, 1H), 3.30 (s, 3H), 2.36-2.30 (m, 2H), 1.71 (q, J=4.5 Hz, 2H); MS: [(M+1)]$^+$=318.80, 320.80.

Intermediate A9

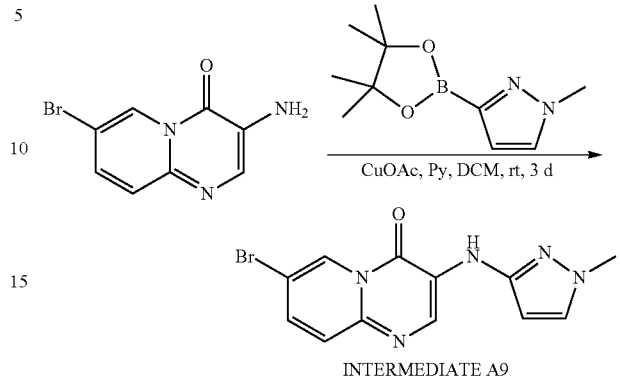

INTERMEDIATE A9

7-Bromo-3-((1-methyl-1H-pyrazol-3-yl)amino)-4H-pyrido[1,2-a]pyrimidin-4-one: To a solution of 3-amino-7-bromo-4H-pyrido[1,2-a]pyrimidin-4-one (170 mg, 0.71 mmol) (Prepared according to the published literature: PCT Int. Appl., 2015192761, 23 Dec. 2015) and 1-methy-3-(tetramethyl-1,3,2-dioxaborolan-2-yl)-1H-pyrazole (221 mg, 1.06 mmol) in dichloromethane (20.0 mL) were added cupric acetate (193 mg, 1.06 mmol) and pyridine (112 mg, 1.42 mmol) at ambient temperature. After stirring for 3 days at ambient temperature under air atmosphere, the resulting mixture was filtered. The filtrate was concentrated under reduced pressure. The residue was purified by Prep-TLC with ethyl acetate to give the title compound as a colorless solid (100 mg, 42%): $^1$H NMR (300 MHz, CDCl$_3$) δ 9.19 (s, 1H), 9.02 (d, J=2.1 Hz, 1H), 7.52 (d, J=9.8 Hz, 1H), 7.40 (dd, J=9.5, 2.1 Hz, 1H), 7.25 (d, J=2.3 Hz, 1H), 7.02 (s, 1H), 5.91 (d, J=2.3 Hz, 1H), 3.85 (s, 3H); MS: [(M+1)]$^+$=320.10, 322.10.

Intermediate A10

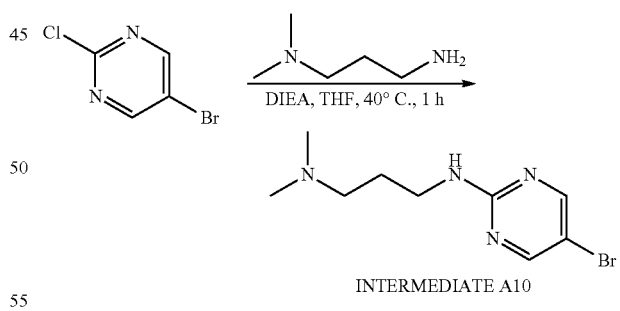

INTERMEDIATE A10

N$^1$-(5-Bromopyrimidin-2-yl)-N$^3$,N$^3$-dimethylpropane-1,3-diamine: A mixture of 5-bromo-2-chloropyrimidine (500 mg, 2.58 mmol), N,N-diisopropylethylamine (668 mg, 5.17 mmol) and (3-aminopropyl)dimethylamine (528 mg, 5.17 mmol) in tetrahydrofuran (20.0 mL) was stirred for 1 hour at 40° C. The resulting mixture was concentrated under reduced pressure. The residue was purified by silica gel column chromatography, eluted with 2%~17% methanol in dichloromethane. The desired fractions were collected and concentrated under reduced pressure to afford the title compound as a colorless solid (660 mg, 99%): $^1$H NMR (400 MHz, DMSO-$d_6$) δ 8.34 (s, 2H), 7.49 (t, J=5.7 Hz, 1H), 3.24 (q, J=6.6 Hz, 2H), 2.52-2.42 (m, 5H), 2.28 (s, 6H), 1.68 (p, J=7.1 Hz, 2H); MS: [(M+1)]$^+$=259.10, 261.10.

Intermediate A11

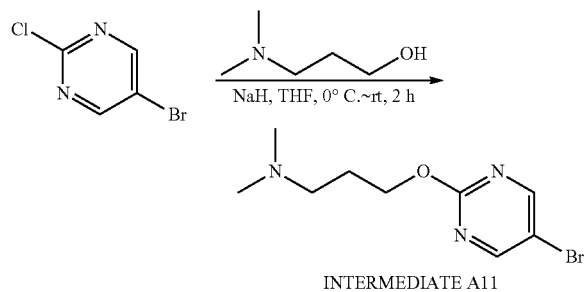

INTERMEDIATE A11

3-((5-Bromopyrimidin-2-yl)oxy)-N,N-dimethylpropan-1-amine: To solution of 3-(dimethylamino)propan-1-ol (347 mg, 3.36 mmol) in anhydrous tetrahydrofuran (15.0 mL) was added sodium hydride (135 mg, 3.36 mmol, 60% dispersed in mineral oil) at 0° C. under nitrogen atmosphere. The resulting mixture was stirred for 1 hour at 25° C. followed by the addition of 5-bromo-2-chloropyrimidine (500 mg, 2.58 mmol) at 0° C. After stirring for additional 1.5 hours at 25° C. the reaction was quenched with saturated aqueous ammonium chloride (5.00 mL). The resulting mixture was diluted with water (50.0 mL) and extracted with ethyl acetate (3×20.0 mL). The combined organic layers was washed with brine (2×30.0 mL) and dried over anhydrous sodium sulfate. After filtration, the filtrate was concentrated under reduced pressure. The residue was purified by silica gel column chromatography, eluted with 7%~10% methanol in dichloromethane. The desired fractions were collected and concentrated under reduced pressure to afford the title compound as an off-white solid (640 mg, 96%): $^1$H NMR (300 MHz, DMSO-$d_6$) δ 8.78 (s, 2H), 4.36 (t, J=6.1 Hz, 2H), 3.22-3.14 (m, 2H), 2.76 (s, 6H), 2.20-2.09 (m, 2H); MS: [(M+1)]$^+$=260.10, 262.10.

Intermediate A12

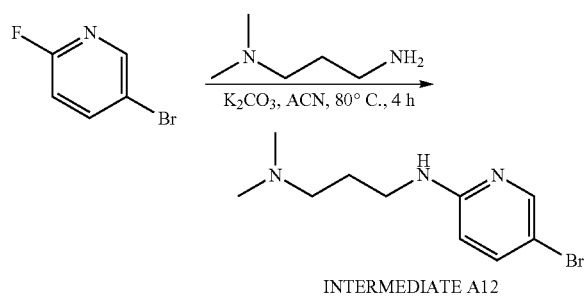

INTERMEDIATE A12

N$^1$-(5-Bromopyridin-2-yl)-N$^3$,N$^3$-dimethylpropane-1,3-diamine: A mixture of (3-aminopropyl)dimethylamine (1.00 g, 9.78 mmol), 5-bromo-2-fluoropyridine (1.60 g, 9.09 mmol) and potassium carbonate (2.60 g, 18.8 mmol) in acetonitrile (30.0 mL) was stirred at 80° C. for 4 hours. The resulting mixture was concentrated under reduced pressure. The residue was purified by silica gel column chromatography, eluted with 3%~10% methanol in dichloromethane. The desired fractions were collected and concentrated under reduced pressure to afford the title compound as a colorless oil (260 mg, 12%): $^1$H NMR (300 MHz, CDCl$_3$) δ 8.08 (dd, J=2.5, 0.7 Hz, 1H), 7.44 (dd, J=8.9, 2.5 Hz, 1H), 6.31 (dd, J=8.8, 0.7 Hz, 1H), 5.46 (s, 1H), 3.34 (t, J=5.8 Hz, 2H), 2.49 (t, J=6.6 Hz, 2H), 2.31 (s, 6H), 1.82 (p, J=6.6 Hz, 2H); MS: [(M+1)]$^+$=258.10, 260.10.

Intermediate A13

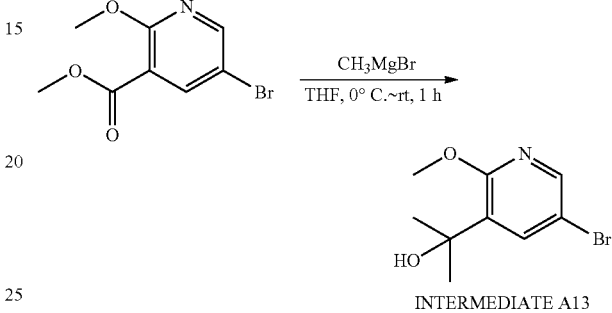

INTERMEDIATE A13

2-(5-Bromo-2-methoxypyridin-3-yl)propan-2-ol: To a solution of methyl 5-bromo-2-methoxypyridine-3-carboxylate (580 mg, 2.36 mmol) (Prepared according to the published literature: PCT Int. Appl., 2016044662, 24 Mar. 2016) in anhydrous tetrahydrofuran (10.0 mL) was added methylmagnesium bromide (7.10 mL, 7.07 mmol, 1 M in tetrahydrofuran) dropwise at 0° C. After stirring for 1 hour at ambient temperature, the reaction was quenched with saturated aqueous ammonium chloride (10.0 mL). The resulting mixture was diluted by water (100 mL) and extracted with ethyl acetate (4×50.0 mL). The combined organic layers was dried over anhydrous sodium sulfate and filtered. The filtrate was concentrated under reduced pressure to give the title compound as a yellow solid (500 mg 87%): $^1$H NMR (400 MHz, CDCl$_3$) δ 8.10 (d, J=2.4 Hz, 1H), 7.73 (d, J=2.4 Hz, 1H), 4.01 (s, 3H), 1.58 (s, 6H); MS: [(M+1)]$^+$=246.10, 248.10.

Intermediate A14

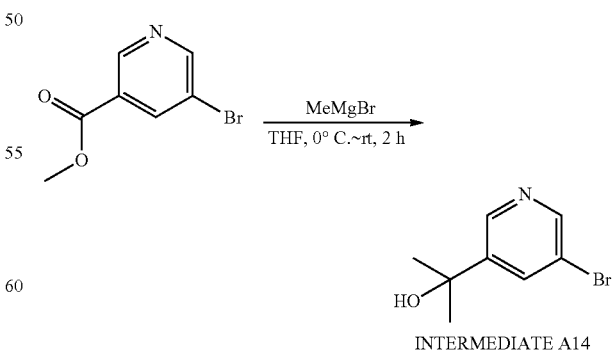

INTERMEDIATE A14

2-(5-Bromopyridin-3-yl)propan-2-ol: This compound was prepared according to the literature: PCT Int. Appl., 2012097039, 19 Jul. 2012): $^1$H NMR (400 MHz, CDCl$_3$) δ

8.68-8.63 (m, 1H), 8.60-8.55 (m, 1H), 8.03 (t, J=2.0 Hz, 1H), 1.61 (s, 6H); MS: [(M+1)]⁺=215.80, 217.80.

Intermediate A15

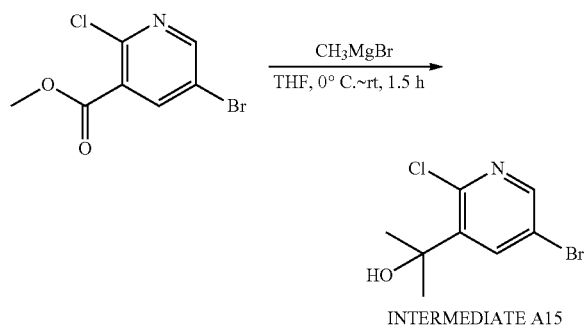

INTERMEDIATE A15

2-(5-Bromo-2-chloropyridin-3-yl)propan-2-ol: To a solution of methyl 5-bromo-2-chloropyridine-3-carboxylate (1.00 g, 3.99 mmol) in anhydrous tetrahydrofuran (30.0 mL) was added methylmagnesium bromide (12.0 mmol, 1 M in tetrahydrofuran) at 0° C. After stirring for 1.5 hours at 25° C., the reaction was quenched with saturated aqueous ammonium chloride (5.00 mL) at 0° C. The resulting mixture was diluted with water (100 mL) and extracted with ethyl acetate (3×150 mL). The combined organic layers was washed with brine (200 mL) and dried over anhydrous sodium sulfate. After filtration, the filtrate was concentrated under reduced pressure. The residue was purified by silica gel column chromatography, eluted with 20% ethyl acetate in petroleum ether. The desired fractions were collected and concentrated under reduced pressure to afford the title compound as a colorless solid (930 mg, 93%): ¹H NMR (400 MHz, DMSO-d₆) δ 8.45 (d, J=2.5 Hz, 1H), 8.30 (d, J=2.5 Hz, 1H), 5.62 (s, 1H), 1.57 (s, 6H); MS: [(M+1)]⁺=250.10, 252.10.

Intermediate A16

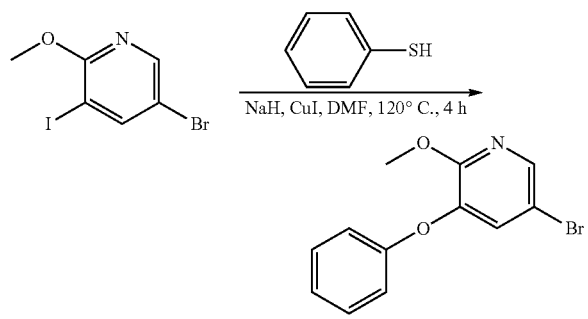

5-Bromo-2-methoxy-3-(phenylthio)pyridine: To a solution of 5-bromo-3-iodo-2-methoxypyridine (1.00 g, 3.19 mmol) and benzenethiol (386 mg, 3.50 mmol) in N-dimethylformamide (20.0 mL) were added sodium hydride (153 mg, 3.82 mmol, 60% dispersed in mineral oil) and copper(I) iodide (121 mg, 0.64 mmol) at ambient temperature. After stirring for 4 hours at 120° C. under nitrogen atmosphere, the resulting solution was cooled down to ambient temperature. The resulting mixture was diluted by water (100 mL) and extracted with ethyl acetate (3×100 mL). The combined organic layers was washed with brine (2×50 mL) and dried over anhydrous sodium sulfate. After filtration, the filtrate was concentrated under reduced pressure. The residue was purified by silica gel column chromatography, eluted with 9%~11% ethyl acetate in petroleum ether. The desired fractions were collected and concentrated under reduced pressure to afford the title compound as a yellow solid (750 mg, 80%): ¹H NMR (400 MHz, CDCl₃) δ 7.97 (d, J=2.3 Hz, 1H), 7.53-7.38 (m, 5H), 7.08 (d, J=2.3 Hz, 1H), 4.00 (s, 3H); MS: [(M+1)]⁺=296.10, 298.10.

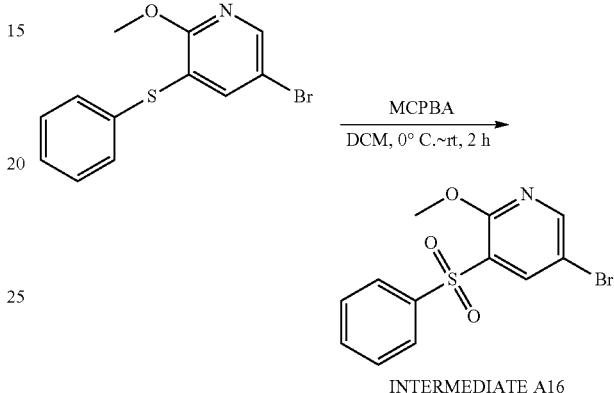

INTERMEDIATE A16

5-Bromo-2-methoxy-3-(phenylsulfonyl)pyridine: To a solution of 5-bromo-2-methoxy-3-(phenylthio)pyridine (650 mg, 2.19 mmol) in dichloromethane (30.0 mL) was added 3-chloroperbenzoic acid (947 mg, 5.49 mmol) at 0° C. The resulting mixture was stirred at ambient temperature for 2 hours. The resulting mixture was concentrated in under reduced pressure. The residue was purified by silica gel column chromatography, eluted with 9%~11% ethyl acetate in petroleum ether. The desired fractions were collected and concentrated under reduced pressure to afford the title compound as a yellow solid (600 mg, 84%): ¹H NMR (300 MHz, CDCl₃) δ 8.48 (d, J=2.5 Hz, 1H), 8.33 (d, J=2.4 Hz, 1H), 8.02-7.92 (m, 2H), 7.69-7.46 (m, 3H), 3.89 (s, 3H); MS: [(M+1)]⁺=328.00, 330.00.

Intermediate A17

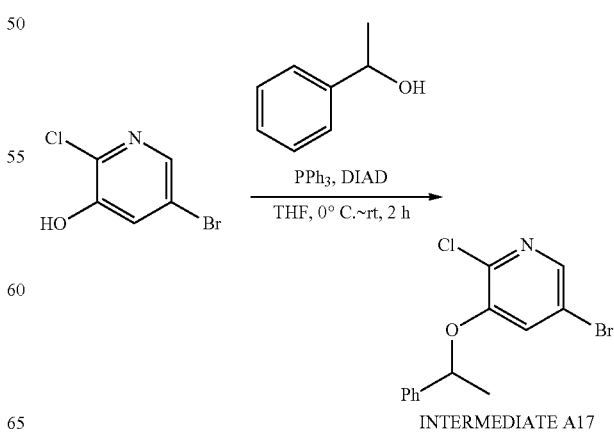

INTERMEDIATE A17

5-Bromo-2-chloro-3-(1-phenylethoxy)pyridine: To a solution of 5-bromo-2-chloropyridin-3-ol (1.00 g, 4.80 mmol), 1-phenylethan-1-ol (0.64 g, 5.28 mmol) and triphenylphosphine (1.51 g, 5.76 mmol) in anhydrous tetrahydrofuran (20.0 mL) was added diisopropyl azodiformate (1.16 g, 5.76 mmol) dropwise at 0° C. After stirring for 2 hours at 25° C. under nitrogen atmosphere, the reaction was quenched with saturated aqueous ammonium chloride (1.00 mL). The resulting mixture was concentrated under reduced pressure. The residue was purified by silica gel column chromatography, eluted with 1%~20% ethyl acetate in petroleum ether. The desired fractions were collected and concentrated under reduced pressure to afford the title compound as a colorless oil (190 mg, 13%): $^1$H NMR (400 MHz, CDCl$_3$) δ 7.98 (d, J=2.1 Hz, 1H), 7.42-7.25 (m, 5H), 7.15 (d, J=2.0 Hz, 1H), 5.32 (q, J=6.4 Hz, 1H), 1.72 (d, J=6.4 Hz, 3H); MS: [(M+1)]$^+$=312.00, 314.00.

Intermediate A18

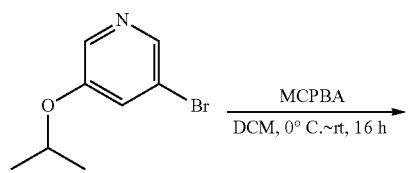

3-Bromo-5-isopropoxypyridine 1-oxide: To a solution of 3-bromo-5-(propan-2-yloxy)pyridine (1.00 g, 4.63 mol) (Prepared according to the reported procedure in *Journal of Medicinal Chemistry*, 52(14), 4126-4141; 2009.) in dichloromethane (50.0 mL) was added 3-chloroperbenzoic acid (1.60 g, 9.26 mmol) at 0° C. After stirring for 16 hours at 25° C., the reaction was quenched with saturated aqueous sodium sulfite solution (30.0 mL). The resulting mixture was extracted with dichloromethane (3×100 mL). The combined organic layers was washed with 2N aqueous sodium hydroxide solution (100 mL) and brine (100 mL), dried over anhydrous sodium sulfate. After filtration, the filtrate was concentrated under reduced pressure to afford the title compound as a yellow solid (1.00 g, 94%): $^1$H NMR (400 MHz, CDCl$_3$) δ 8.02 (s, 1H), 7.92 (s, 1H), 7.04 (s, 1H), 4.51 (p, J=6.0 Hz, 1H), 1.37 (d, J=6.0 Hz, 6H); MS: [(M+1)]$^+$=232.05, 234.05.

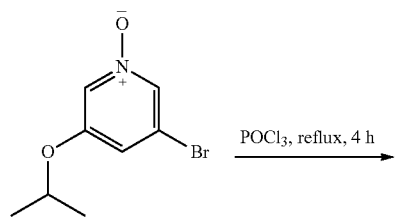

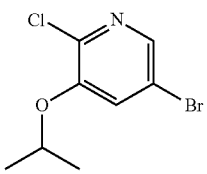

5-Bromo-2-chloro-3-isopropoxypyridine: A solution of 3-bromo-5-(propan-2-yloxy)pyridin-1-ium-1-olate (900 mg, 3.88 mmol) in phosphoroyl trichloride (20.0 mL) was refluxed for 4 hours. The reaction mixture was concentrated under reduced pressure. The residue was diluted with dichloromethane (20.0 mL). The resulting mixture was poured into ice-water (100 mL) and extracted with ethyl acetate (3×120 mL). The combined organic layers was concentrated under reduced pressure and the residue was purified by silica gel column chromatography, eluted with 1% ethyl acetate in petroleum ether. The desired fractions were collected and concentrated under reduced pressure to afford the title compound as a yellow oil (660 mg, 68%): $^1$H NMR (300 MHz, CDCl$_3$) δ 8.06 (d, J=2.0 Hz, 1H), 7.34 (dd, J=2.1, 0.6 Hz, 1H), 4.66-4.49 (m, 1H), 1.44 (d, J=6.1 Hz, 6H); MS: [(M+1)]$^+$=250.00, 252.00.

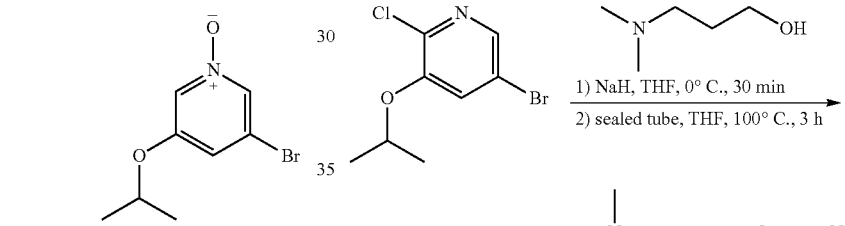

INTERMEDIATE A18

3-((5-Bromo-3-isopropoxypyridin-2-yl)oxy)-N,N-dimethylpropan-1-amine: A solution of 3-(dimethylamino)propan-1-ol (247 mg, 2.40 mmol) in tetrahydrofuran (15.0 mL) was treated with sodium hydride (120 mg, 2.99 mmol, 60% dispersed in mineral oil) for 30 min at 0° C. followed by the addition of 5-bromo-2-chloro-3-(propan-2-yloxy)pyridine (300 mg, 1.20 mmol). After stirring for 3 hours at 100° C. in a sealed tube, the reaction was quenched with saturated aqueous ammonium chloride (2.00 mL) at 0° C. The resulting mixture was concentrated under reduced pressure. The residue was purified by silica gel column chromatography, eluted with 5%~12% methanol in dichloromethane. The desired fractions were collected and concentrated under reduced pressure to afford the title compound as a yellow oil (220 mg, 58%): $^1$H NMR (400 MHz, CDCl$_3$) δ 7.75 (d, J=2.1 Hz, 1H), 7.16 (d, J=2.1 Hz, 1H), 4.43 (dt, J=38.2, 6.3 Hz, 3H), 2.63 (s, 2H), 2.09 (s, 2H), 1.36 (d, J=6.1 Hz, 6H); MS: [(M+1)]$^+$=317.15, 319.15.

The following intermediates were prepared according to the procedure described above:

| Intermediate | Structure | Name | MS: [(M + 1)]+ | 1H NMR |
|---|---|---|---|---|
| A18-1 | 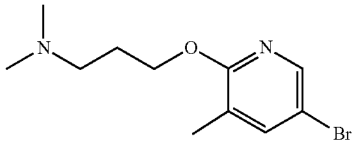 | 3-((5-Bromo-3-methylpyridin-2-yl)oxy)-N,N-dimethylpropan-1-amine | 273.00 275.00 | 1H NMR (300 MHz, CDCl$_3$,) δ 8.02 (dd, J = 2.4, 0.9 Hz, 1H), 7.50 (dq, J = 1.8, 0.8 Hz, 1H), 4.35 (t, J = 6.4 Hz, 2H), 2.57-2.45 (m, 2H), 2.32 (s, 6H), 2.19 (t, J = 0.8 Hz, 3H), 2.08-1.92 (m, 2H). |
| A18-2 | 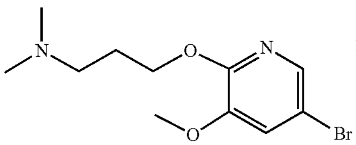 [SMILES: COc1cc(Br)cnc1OCCCN(C)C] | 3-((5-Bromo-3-methoxypyridin-2-yl)oxy)-N,N-dimethylpropan-1-amine | 289.00 291.00 | 1H NMR (400 MHz, CD$_3$OD) δ 7.71 (d, J = 2.1 Hz, 1H), 7.35 (d, J = 2.1 Hz, 1H), 4.33 (t, J = 6.3 Hz, 2H), 3.83 (s, 3H), 2.57-2.46 (m, 2H), 2.27 (s, 6H), 2.06-1.91 (m, 2H). |
| A18-3 | 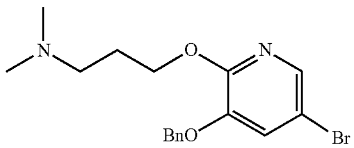 [SMILES: CN(C)CCCOc1ncc(Br)cc1OCc1ccccc1] | 3-((3-(Benzyloxy)-5-bromopyridin-2-yl)oxy)-N,N-dimethylpropan-1-amine | 365.15 367.15 | 1H NMR (300 MHz, DMSO-d$_6$) δ 7.83 (d, J = 2.0 Hz, 1H), 7.63 (d, J = 2.1 Hz, 1H), 7.49-7.33 (m, 5H), 5.18 (s, 2H), 4.33 (t, J = 6.4 Hz, 2H), 3.12-3.01 (m, 2H), 2.67 (s, 6H), 2.11 (p, J = 6.4 Hz, 2H). |
| A18-4 | 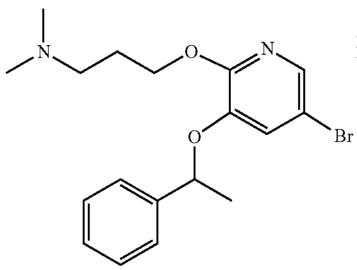 | 3-((5-Bromo-3-(1-phenylethoxy)pyridin-2-yl)oxy)-N,N-dimethylpropan-1-amine | 379.00 381.00 | 1H NMR (400 MHz, CDCl$_3$,) δ 7.71 (d, J = 2.1 Hz, 1H), 7.40-7.26 (m, 5H), 7.01 (d, J = 2.1 Hz, 1H), 5.27 (q, J = 6.4 Hz, 1H), 4.39 (td, J = 6.6, 1.2 Hz, 2H), 2.54-2.48 (m, 2H), 2.30 (s, 6H), 2.08-1.97 (m, 2H), 1.66 (d, J = 6.4 Hz, 3H). |

Intermediate A19

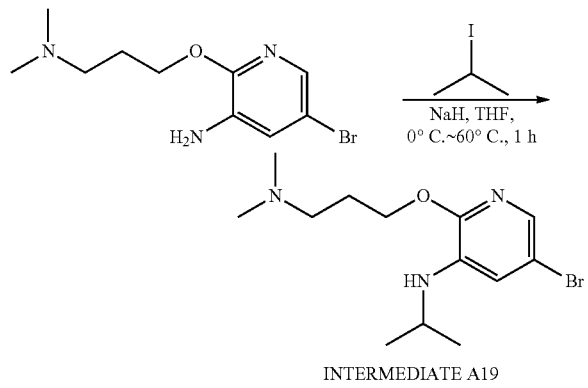

INTERMEDIATE A19

5-Bromo-2-(3-(dimethylamino)propoxy)-N-isopropylpyridin-3-amine: A solution of 5-bromo-2-[3-(dimethylamino)propoxy]pyridin-3-amine (500 mg, 1.82 mol) in anhydrous tetrahydrofuran (50.0 mL) was treated with sodium hydride (200 mg, 5.02 mol, 60% dispersed in mineral oil) for 30 min at 0° C. followed by the addition of 2-iodopropane (620 mg, 3.65 mmol). After stirring for 1 hour at 60° C., the reaction was quenched with saturated aqueous ammonium chloride (100 mL). The resulting mixture was extracted with ethyl acetate (3×200 mL). The combined organic layers was washed with brine (3×200 mL) and dried over anhydrous sodium sulfate. After filtration, the filtrate was concentrated under reduced pressure. The residue was purified by silica gel column chromatography, eluted with 2%~-9% methanol in dichloromethane. The desired fractions were collected and concentrated under reduced pressure to afford the title compound as a yellow oil (320 mg, 56%): 1H NMR (400 MHz, DMSO-d$_6$) δ 7.34 (d, J=2.1 Hz, 1H), 6.88 (d, J=2.1 Hz, 1H), 4.93 (d, J=8.5 Hz, 1H), 4.27 (t, J=6.4 Hz, 2H), 3.59 (dp, J=8.4, 6.3 Hz, 1H), 2.85 (s, 2H), 2.50 (s, 6H), 2.01 (p, J=6.7 Hz, 2H), 1.14 (d, J=6.3 Hz, 6H); MS: [(M+1)]+=316.10, 318.10.

Intermediate A20

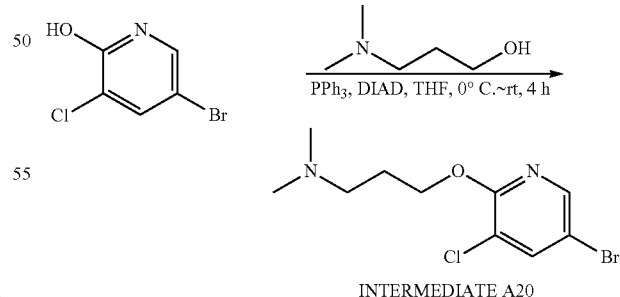

INTERMEDIATE A20

3-((5-Bromo-3-chloropyridin-2-yl)oxy)-N,N-dimethylpropan-1-ol: To a solution of 5-bromo-3-chloropyridin-2-ol (500 mg, 2.40 mmol), triphenylphosphine (944 mg, 3.60 mmol) and 3-(dimethylamino)propan-1-ol (322 mg, 3.12 mmol) in anhydrous tetrahydrofuran (20.0 mL) was added diisopropyl azodiformate (873 mg, 4.32 mmol) dropwise at 0° C. After stirring for additional 4 hours, the reaction was quenched with saturated aqueous ammonium chloride (1.00 mL). The resulting mixture was concentrated under reduced pressure. The residue was purified by silica gel column chromatography, eluted with 1%~10% methanol in dichloromethane. The desired fractions were collected and concentrated under reduced pressure to afford the title compound as a colorless solid (460 mg, 66%): $^1$H NMR (300 MHz, DMSO-d6) δ 8.33-8.19 (m, 2H), 4.35 (t, J=6.6 Hz, 2H), 3.18 (d, J=3.7 Hz, 2H), 2.34 (t, J=7.0 Hz, 2H), 2.13 (s, 6H), 1.86 (p, J=6.9 Hz, 6H). MS: [(M+1)]$^+$=292.95, 294.95.

Intermediate A21

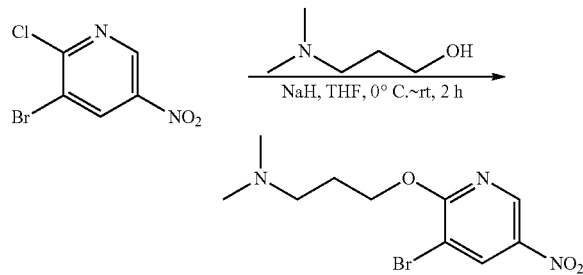

3-((3-Bromo-5-nitropyridin-2-yl)oxy)-N,N-dimethylpropan-1-amine: A solution of 3-(dimethylamino)propan-1-ol (4.00 g, 38.3 mmol) in anhydrous tetrahydrofuran (120 mL) was treated with sodium hydride (1.75 g, 43.7 mmol, 60% dispersed in mineral oil) for 0.5 hours at 0° C. under nitrogen atmosphere followed by the addition of 3-bromo-2-chloro-5-nitropyridine (7.00 g, 29.5 mmol). After stirring for additional 2 hours at 25° C., the reaction was quenched with saturated aqueous ammonium chloride (40.0 mL). The resulting mixture was diluted with water (150 mL) and extracted with ethyl acetate (3×200 mL). The combined organic layers was dried over anhydrous sodium sulfate. After filtration, the filtrate was concentrated under reduced pressure. The residue was purified by silica gel column chromatography, eluted with 2%~10% methanol in dichloromethane. The desired fractions were collected and concentrated under reduced pressure to afford the title compound as a red oil (8.60 g, 96%): $^1$H NMR (300 MHz, CDCl$_3$) δ 8.99 (d, J=2.5 Hz, 1H), 8.63 (d, J=2.5 Hz, 1H), 4.60 (t, J=6.1 Hz, 2H), 2.98 (s, 2H), 2.67 (s, 6H), 2.34 (s, 2H); MS: [(M+1)]$^+$=303.95, 305.95.

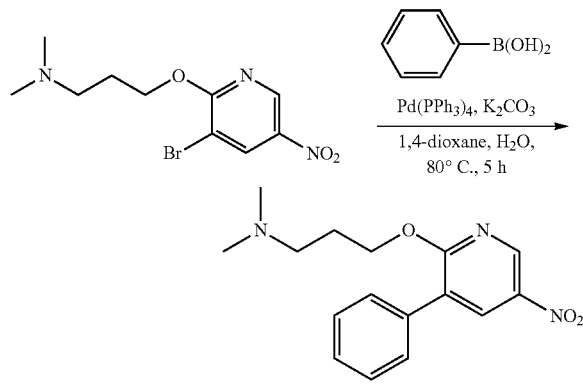

Dimethyl((3-(5-nitro-3-phenylpyridin-2-yl)oxy)propyl))amine: To a solution of 3-((3-bromo-5-nitropyridin-2-yl)oxy)-N,N-dimethylpropan-1-amine (1.00 g, 3.29 mmol), phenylboronic acid (601 mg, 4.93 mmol) and potassium carbonate (909 mg, 6.58 mmol) in 1,4-dioxane (50.0 mL) and water (2.50 mL) was added tetrakis(triphenylphosphine)palladium (0) (380 mg, 0.33 mmol) under nitrogen atmosphere. After stirring for 5 hours at 80° C., the reaction mixture was concentrated under reduced pressure. The residue was purified by silica gel column chromatography, eluted with 1%~9% methanol in dichloromethane. The desired fractions were collected and concentrated under reduced pressure to afford the title compound as a yellow oil (800 mg, 81%): $^1$H NMR (400 MHz, CDCl$_3$) δ 9.03 (d, J=2.8 Hz, 1H), 8.40 (d, J=2.8 Hz, 1H), 7.59-7.56 (m, 2H), 7.49-7.41 (m, 3H), 4.54 (t, J=6.5 Hz, 2H), 2.43 (t, J=7.4 Hz, 2H), 2.25 (s, 6H), 2.01-1.93 (m, 2H); MS: [(M+1)]$^+$=302.05.

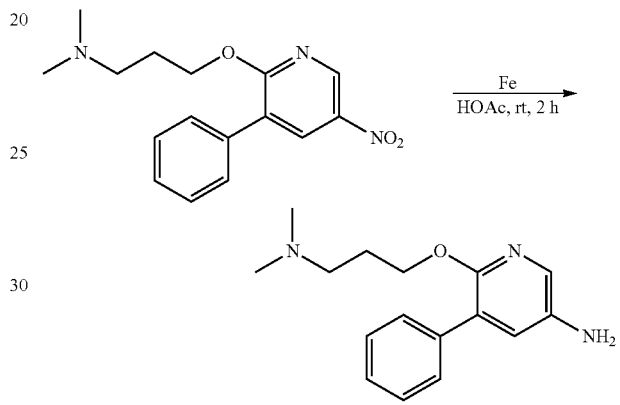

6-(3-(Dimethylamino)propoxy)-5-phenylpyridin-3-amine: To a solution of dimethyl((3-(5-nitro-3-phenylpyridin-2-yl)oxy)propyl))amine (800 mg, 2.65 mmol) in acetic acid (40.0 mL) was added iron powder (1.48 g, 26.6 mmol). After stirring for 1 hour at 25° C., the resulting mixture was filtered and the filtered cake was washed with tetrahydrofuran (6×80.0 mL). The filtrate was concentrated under reduced pressure. The residue was basified to pH=8 with saturated aqueous sodium bicarbonate. The resulting mixture was extracted with ethyl acetate (3×150 mL) and the combined organic layers was dried over anhydrous sodium sulfate. After filtration, the filtrate was concentrated under reduced pressure. The residue was purified by silica gel column chromatography, eluted with 7%~10% methanol in dichloromethane. The desired fractions were collected and concentrated under reduced pressure to afford the title compound as a brown oil (500 mg, 70%): $^1$H NMR (300 MHz, CDCl$_3$) δ 7.64 (d, J=2.9 Hz, 1H), 7.57 (d, J=2.6 Hz, 1H), 7.54-7.48 (m, 2H), 7.44-7.32 (m, 3H), 4.33 (t, J=6.3 Hz, 2H), 2.72 (t, J=7.4 Hz, 2H), 2.43 (s, 6H), 2.14-1.99 (m, 2H); MS: [(M+1)]$^+$=272.05.

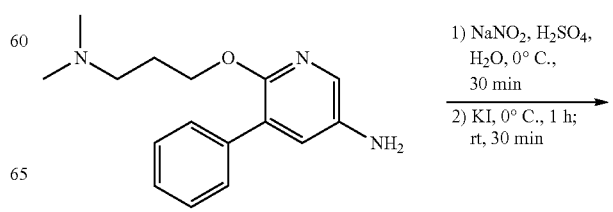

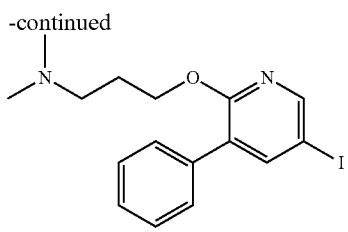

INTERMEDIATE A21

3-((5-Iodo-3-phenylpyridin-2-yl)oxy)-N,N-dimethylpropan-1-amine: To a solution of 6-[3-(dimethylamino) propoxy]-5-phenylpyridin-3-amine (300 mg, 1.11 mmol) in water (4.00 ml) and concentrated sulfuric acid (0.50 mL, 9.38 mmol) was added a solution of sodium nitrite (91.5 mg, 1.33 mmol, in water 1.00 mL) at 0° C. The resulting mixture was stirred for 30 minutes at 0° C. followed by the addition of potassium iodide (404 mg, 2.43 mmol, in water 2.00 mL). After stirring for 1 hour at 0° C. and additional 30 minutes at ambient temperature, the reaction mixture was neutralized with saturated aqueous sodium carbonate and extracted with ethyl acetate (3×50.0 ml). The combined organic layers was washed with brine (50.0 mL) and dried over anhydrous sodium sulfate. After filtration, the filtrate was concentrated under reduced pressure. The residue was purified by silica gel column chromatography, eluted with 3%~9% methanol in dichloromethane. The desired fractions were collected and concentrated under reduced pressure to afford the title compound as a yellow solid (140 mg, 34%): $^1$H NMR (400 MHz, DMSO-d$_6$) δ 8.39 (d, J=2.2 Hz, 1H), 8.05 (d, J=2.3 Hz, 1H), 7.61-7.56 (m, 2H), 7.49-7.43 (m, 2H), 7.43-7.38 (m, 1H), 4.34 (t, J=6.3 Hz, 2H), 3.09 (t, J=7.8 Hz, 2H), 2.73 (s, 6H), 2.10-2.01 (m, 2H); MS: [(M+1)]$^+$=383.10.

Intermediate A22

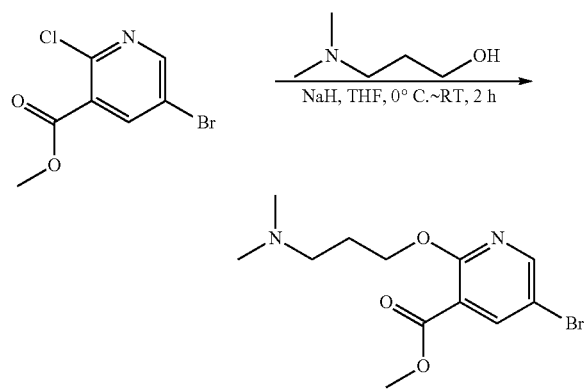

Methyl 5-bromo-2-(3-(dimethylamino)propoxy)nicotinate: To solution of 3-(dimethylamino)propan-1-ol (1.2 g, 10 mmol) in tetrahydrofuran (50 mL) was added sodium hydride (0.4 g, 10 mmol, 60% dispersed in mineral oil) at 0° C. under nitrogen atmosphere followed by the addition of methyl 5-bromo-2-chloropyridine-3-carboxylate (2.0 g, 8.0 mmol). After stirring for additional 1.5 hours at 25° C., the reaction was quenched with saturated aqueous ammonium chloride (20 mL). The resulting mixture was diluted with water (200 mL) and extracted with ethyl acetate (3×200 mL). The combined organic layers was washed with brine (2×50 mL) and dried over anhydrous sodium sulfate. After filtration, the filtrate was concentrated under reduced pressure. The residue was purified by silica gel column chromatography, eluted with 2%~12% methanol in dichlormethane. The desired fractions were collected and concentrated under reduced pressure to afford the title compound as a yellow solid (0.97 g, 27%): MS: [(M+1)]$^+$=316.95, 318.95.

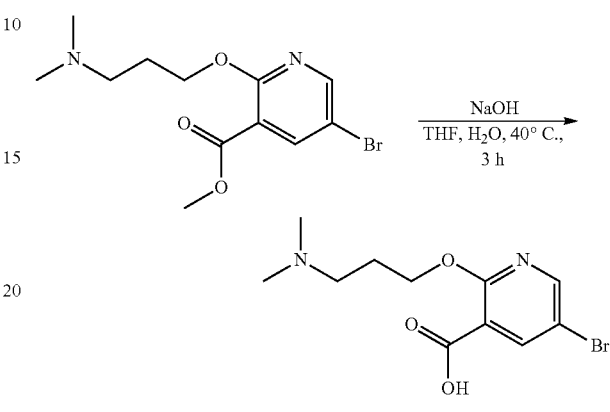

5-Bromo-2-(3-(dimethylamino)propoxy)nicotinic acid: To a stirred solution of methyl 5-bromo-2-[3-(dimethylamino)propoxy]benzoate (100 mg, 0.32 mmol) in tetrahydrofuran (30.0 mL) and water (3.00 mL) was added sodium hydroxide (50.6 mg, 1.27 mmol). The mixture was stirred at 40° C. for 3 hours. The mixture was neutralized to pH=7 with diluted hydrochloric acid. The resulting solution was concentrated under reduced pressure. The residue was purified by silica gel column chromatography, eluted with 25% methanol in dichloromethane. The desired fractions were collected and concentrated under reduced pressure to afford the title compound as a colorless solid (30.0 mg, 32%): MS: [(M+1)]$^+$=302.95, 304.95.

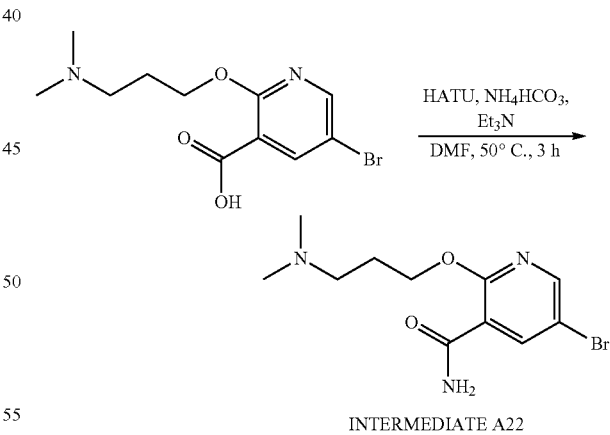

INTERMEDIATE A22

5-Bromo-2-(3-(dimethylamino)propoxy)nicotinamide:
To a solution of 5-bromo-2-[3-(dimethylamino)propoxy] pyridine-3-carboxylic acid (470 mg, 1.55 mmol) in N,N-dimethylformamide (30.0 mL) were added ammonium bicarbonate (368 mg, 4.65 mmol), triethylamine (470 mg, 4.65 mmol) and O-(7-azabenzotriazol-1-yl)-N,N,N',N'-tetramethyluronium hexafluorophosphate (0.88 g, 2.33 mmol). The resulting mixture was stirred for 3 hours at 50° C. The resulting mixture was concentrated under reduced pressure. The residue was purified by silica gel column chromatography, eluted with 17% methanol in dichloromethane. The desired fractions were collected and concentrated under reduced pressure to afford the title compound as yellow oil (270 mg, 58%): MS: [(M+1)]⁺=302.00, 304.00

Intermediate A23

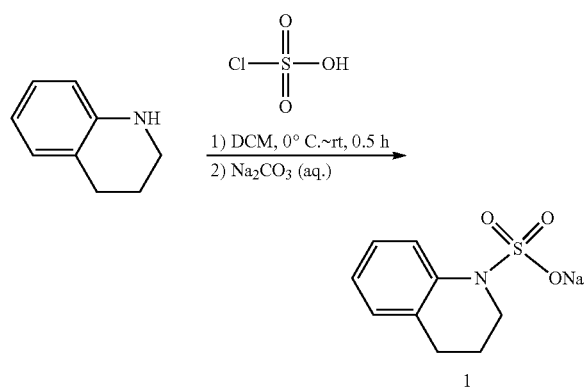

Sodium 3,4-dihydroquinoline-1(2H)-sulfonate: To a solution of 1,2,3,4-tetrahydroquinoline (5.00 g, 37.5 mmol) in dichloromethane (25.0 mL) was added chloranesulfonic acid (1.30 g, 11.3 mmol, in dichloromethane 3.30 mL) dropwise at 0° C. over 1 hour. After stirring for additional 0.5 hour, the resulting mixture was concentrated under reduced pressure. Sodium carbonate (1.60 g, 15.1 mol) in water (14.0 mL) was added into the residue. Then, the mixture was extracted with diethyl ether (3×100 mL) and the aqueous layer was concentrated under reduced pressure. The residue was dried under reduced pressure to afford the title compound as a yellow solid (2.81 g, crude) which was used in the next step without further purification.

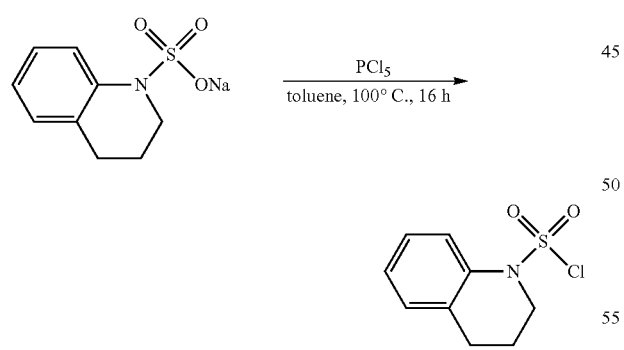

1,2,3,4-Tetrahydroquinoline-1-sulfonyl chloride: To a solution of sodium 1,2,3,4-tetrahydroquinoline-1-sulfonate (1.88 g, 7.99 mmol) in toluene (40.0 mL) was added phosphorus pentachloride (1.70 g, 7.99 mmol) under nitrogen atmosphere. After stirring for 16 hours at 100° C., the resulting mixture was cooled down to 0° C. After filtration, the filtrate was concentrated under reduced pressure to afford the title compound as a gum (1.60 g, crude), which was used in the next step without further purification.

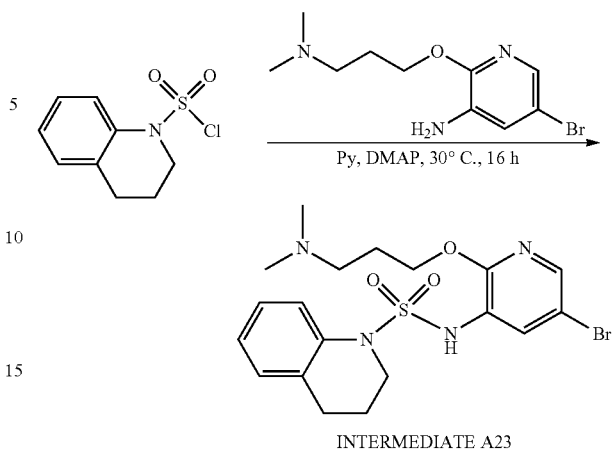

INTERMEDIATE A23

N-(5-Bromo-2-(3-(dimethylamino)propoxy)pyridin-3-yl)-3,4-dihydroquinoline-1(2H)-sulfonamide: To a stirred solution of 5-bromo-2-[3-(dimethylamino)propoxy]pyridin-3-amine (770 mg, 2.81 mmol) and N,N-4-dimethylaminopyridine (34.3 mg, 0.28 mmol) in pyridine (40.0 mL) was added 1,2,3,4-tetrahydroquinoline-1-sulfonyl chloride (1.30 g, 5.62 mmol) at ambient temperature. After stirring for 16 hours under nitrogen atmosphere at 25° C., the resulting mixture was concentrated under reduced pressure. The residue was purified by silica gel column chromatography, eluted with 2%~12% methanol in dichloromethane. The desired fractions were collected and concentrated under reduced pressure to afford the title compound as a yellow oil (220 mg, 17%): ¹H NMR (400 MHz, CDCl₃) δ 7.82 (d, J=2.3 Hz, 1H), 7.79 (d, J=2.2 Hz, 1H), 7.41-7.35 (m, 2H), 7.26 (d, J=8.7 Hz, 1H), 6.37 (d, J=8.2 Hz, 1H), 4.29 (t, J=6.2 Hz, 2H), 3.36-3.30 (m, 2H), 2.72 (t, J=6.2 Hz, 2H), 2.56-2.47 (m, 2H), 2.37 (s, 6H), 1.97-1.86 (m, 2H), 1.25 (t, J=3.6 Hz, 2H); MS: [(M+1)]⁺=469.10, 471.10.

Intermediate A24

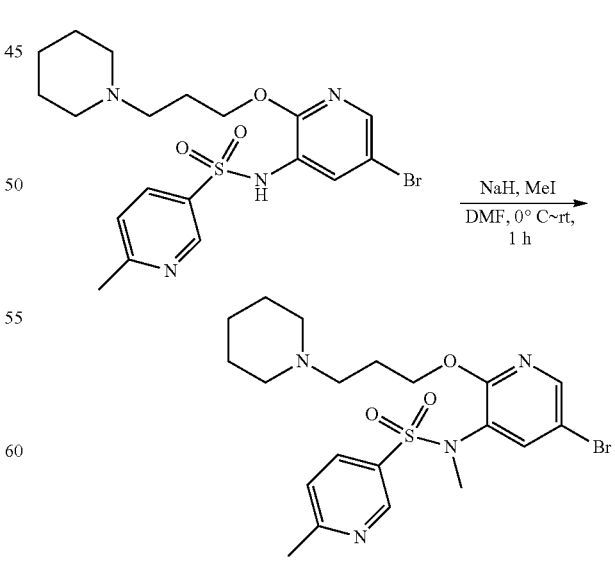

INTERMEDIATE A24

N-(5-Bromo-2-(3-(piperidin-1-yl)propoxy)pyridin-3-yl)-N,6-dimethylpyridine-3-sulfonamide: To a solution of N-(5-bromo-2-(3-(piperidin-1-yl)propoxy)pyridin-3-yl)-6-methylpyridine-3-sulfonamide (150 mg, 0.32 mmol) in N,N-dimethylformamide (10.0 mL) was added sodium hydride (19.2 mg, 0.48 mmol, 60% dispersed in mineral oil) at 0° C. under nitrogen atmosphere. The resulting mixture was stirred for 1 hour at 25° C. followed by the addition of iodomethane (63.6 mg, 0.45 mmol) at 0° C. After stirring for additional 1.5 hours at 25° C., the reaction was quenched with methanol (1.00 mL). The residue was purified by silica gel column chromatography, eluted with 2%~12% methanol in dichloromethane to afford the title compound as an off-white solid (32 mg, 21%): $^1$H NMR (300 MHz, DMSO-$d_6$) δ 8.66 (d, J=2.3 Hz, 1H), 8.30 (d, J=2.4 Hz, 1H), 7.96 (d, J=2.4 Hz, 1H), 7.91 (dd, J=8.2, 2.5 Hz, 1H), 7.49 (d, J=8.2 Hz, 1H), 3.93 (t, J=6.7 Hz, 2H), 3.14 (s, 3H), 2.58 (s, 3H), 2.25-2.17 (m, 4H), 2.12-2.05 (m, 2H), 1.50-1.41 (m, 4H), 1.40-1.32 (m, 4H); MS: [(M+1)]$^+$=483.20, 485.20.

Intermediate A25

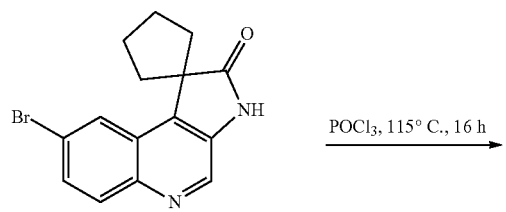

8'-Bromo-2'-chlorospiro[cyclopentane-1,1'-pyrrolo[2,3-c]quinoline]: A mixture of 8-bromo-3H-spiro[cyclopentane-1,1-pyrrolo[2,3-c]quinolin-2-one (400 mg, 1.26 mmol) in phosphorus oxychloride (7.00 mL) was stirred for 16 hours at 115° C. The resulting mixture was concentrated under reduced pressure. The residue was purified by silica gel column chromatography, eluted with 30%~50% ethyl acetate in petroleum ether. The desired fractions were collected and concentrated under reduced pressure to afford the title compound as an off-white solid (90.0 mg, 22%): MS: [(M+1)]$^+$=333.10, 335.10.

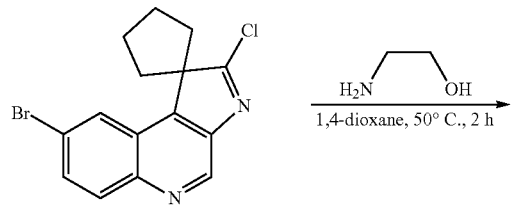

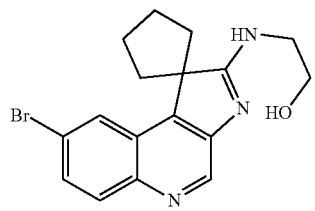

2-((8'-Bromospiro[cyclopentane-1,1'-pyrrolo[2,3-c]quinolin]-2'-yl)amino)ethan-1-ol: To a stirred solution of 8'-bromo-2'-chlorospiro[cyclopentane-1,1'-pyrrolo[2,3-c]quinoline] (90.0 mg, 0.27 mmol) in 1,4-dioxane (4.00 mL) was added ethanolamine (32.8 mg, 0.54 mmol) dropwise at ambient temperature. The resulting mixture was stirred for 2 hours at 50° C. The resulting mixture was concentrated under reduced pressure. The residue was purified by reversed phase flash chromatography with the following conditions: Column: Spherical C18, 20~40 μm, 120 g; Mobile Phase A: Water (plus 10 mM NH$_4$HCO$_3$), Mobile Phase B: acetonitrile; Flow rate: 45 mL/min; Gradient (B %): 5%~30%, 15 min; 30%~52%, 15 min; 52%~95%; 2 min; 95%, 5 min; Detector. UV 254 nm. The fractions containing desired product were collected at 56% B and concentrated under reduced pressure to afford the title compound as an off-white solid (80.0 mg, 83%): $^1$H NMR (400 MHz, CDCl$_3$) δ 8.95 (s, 1H), 7.98 (d, J=9.0 Hz, 1H), 7.86 (d, J=2.2 Hz, 1H), 7.59 (dd, J=9.0, 2.1 Hz, 1H), 5.33 (s, 1H), 3.95-3.88 (m, 2H), 3.72 (t, J=4.6 Hz, 2H), 2.49-2.29 (m, 4H), 2.15-2.03 (m, 4H); MS: [(M+1)]$^+$=360.05, 362.05.

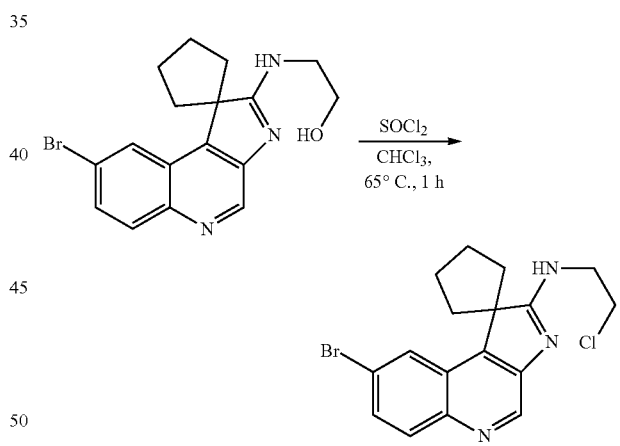

8'-Bromo-N-(2-chloroethyl)spiro[cyclopentane-1,1'-pyrrolo[2,3-c]quinolin]-2'-amine: To a stirred mixture of 2-((8'-bromospiro[cyclopentane-1,1'-pyrrolo[2,3-c]quinolin]-2'-yl)amino)ethan-1-ol (80.0 mg, 0.22 mmol) in trichloromethane (5.00 mL) was added sulfonyl chloride (150 mg, 1.11 mmol) dropwise at ambient temperature. The resulting mixture was stirred for 1 hour at 65° C. The resulting mixture was concentrated under vacuum. The residue was purified by Prep-TLC (petroleum ether/EtOAc=3/1, v/v) to afford the title compound as an off-white solid (72.0 mg, 86%): $^1$H NMR (400 MHz, CDCl$_3$) δ 9.01 (s, 1H), 8.05 (d, J=9.1 Hz, 1H), 7.89 (d, J=2.1 Hz, 1H), 7.63 (dd, J=9.1, 2.1 Hz, 1H), 3.99 (s, 2H), 3.90 (s, 2H), 2.51-2.32 (m, 4H), 2.26-2.12 (m, 4H); MS: [(M+1)]$^+$=378.05, 380.05.

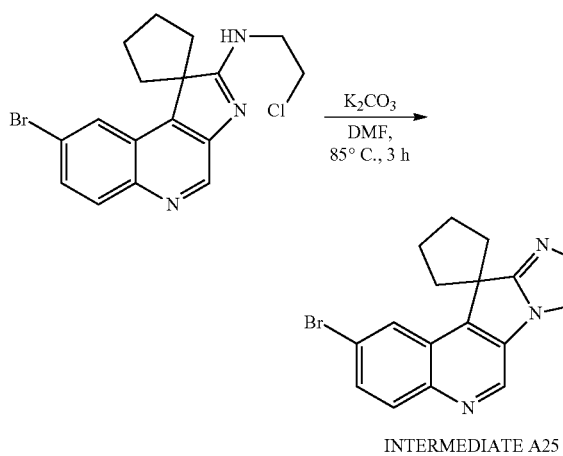

INTERMEDIATE A25

2'-Bromo-8',9'-dihydrospiro[cyclopentane-1,11'-imidazo[1',2':1,5]pyrrolo[2,3-c]quinoline]: To a solution of 8'-bromo-N-(2-chloroethyl)spiro[cyclopentane-1,1'-pyrrolo[2,3-c]quinolin]-2'-amine (72.0 mg, 0.19 mmol) in N,N-dimethylformamide (3.00 mL) was added potassium carbonate (52.6 mg, 0.38 mmol) at ambient temperature. After stirring for 3 hours at 85° C., the resulting mixture was concentrated under reduced pressure. The residue was purified by Prep-TLC (DCM/MeOH=7/1, v/v) to afford the title compound as a light yellow solid (22.0 mg, 34%): ¹H NMR (400 MHz, CDCl₃) δ 8.49 (s, 1H), 7.95 (d, J=9.0 Hz, 1H), 7.91 (d, J=2.2 Hz, 1H), 7.59 (dd, J=9.0, 2.2 Hz, 1H), 4.35 (t, J=8.8 Hz, 2H), 3.82 (t, J=8.8 Hz, 2H), 2.42-2.33 (m, 2H), 2.31-2.20 (m, 4H), 2.20-2.10 (m, 2H); MS: [(M+1)]⁺=342.10, 344.10.

Intermediate B

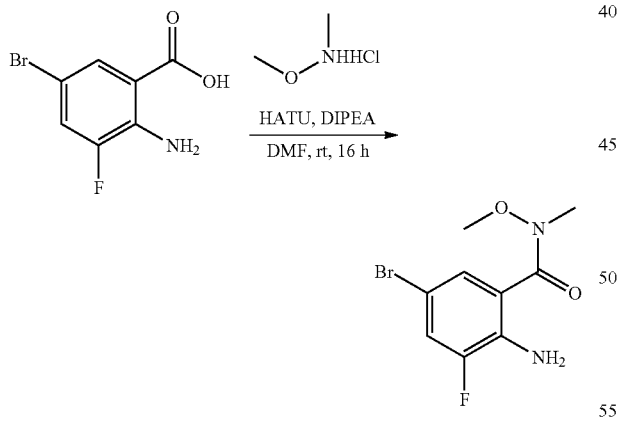

2-Amino-5-bromo-3-fluoro-N-methoxy-N-methylbenzamide: To a solution of 2-amino-5-bromo-3-fluorobenzoic acid (10.0 g, 42.7 mol) and methoxy(methyl)amine hydrochloride (5.40 g, 55.6 mmol) in N,N-dimethylformamide (200 mL) were added O-(7-azabenzotriazol-1-yl)-N,N,N',N'-tetramethyluronium hexafluorophosphate (17.8 g, 47.0 mmol) and diisopropylethylamine (12.2 g, 94.0 mmol) at 0° C. The resulting mixture was stirred for 16 hours at 25° C. The reaction was quenched with water (1.50 L) and the resulting mixture was extracted with ethyl acetate (3×500 mL). The combined organic layers was washed with brine (2×500 mL) and dried over anhydrous sodium sulfate. After filtration, the filtrate was concentrated under reduced pressure. The residue was purified by silica gel column chromatography, eluted with 2%~17% ethyl acetate in petroleum ether. The desired fractions were collected and concentrated under reduced pressure to afford the title compound as a light orange solid (11.4 g, 97%): ¹H NMR (400 MHz, CD₃OD) 7.27-7.22 (m, 2H), 3.60 (s, 3H), 3.33 (s, 3H); MS: [(M+1)]⁺=277.00, 279.00.

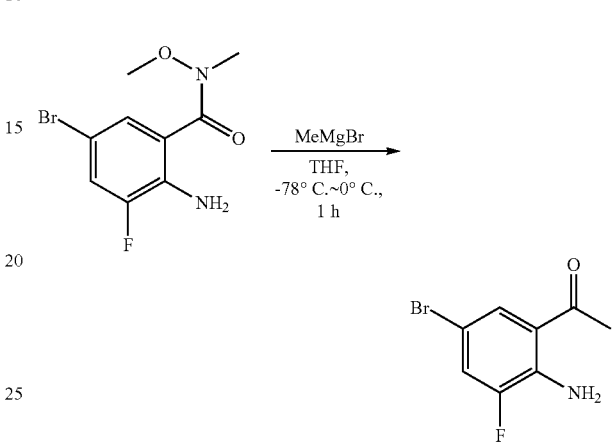

1-(2-Amino-5-bromo-3-fluorophenyl)ethan-1-one: To a solution of 2-amino-5-bromo-3-fluoro-N-methoxy-N-methylbenzamide (16.8 g, 60.6 mmol) in tetrahydrofuran (400 mL) was added bromo(methyl)magnesium (198 mL, 593 mmol, 3 M in tetrahydrofuran) dropwise at −78° C. The resulting mixture was stirred for 1 hour at 25° C. The reaction was quenched by saturated aqueous ammonium chloride (10.0 mL) and diluted with water (800 mL) at 0° C. The resulting mixture was extracted with ethyl acetate (3×250 mL). The combined organic layers was washed with brine (2×200 mL) and dried over anhydrous sodium sulfate. After filtration, the filtrate was concentrated under reduced pressure. The residue was purified by silica gel column chromatography, eluted with 1%~3% ethyl acetate in petroleum ether. The desired fractions were collected and concentrated under reduced pressure to afford the title compound as a yellow solid (8.10 g, 58%): ¹H NMR (400 MHz, DMSO-d₆) δ 7.76 (d, J=2.1 Hz, 1H), 7.55 (dt, J=11.0, 1.8 Hz, 1H), 7.20 (s, 2H), 2.55 (d, J=1.5 Hz, 3H); MS: [(M+1)]⁺=231.95, 233.95.

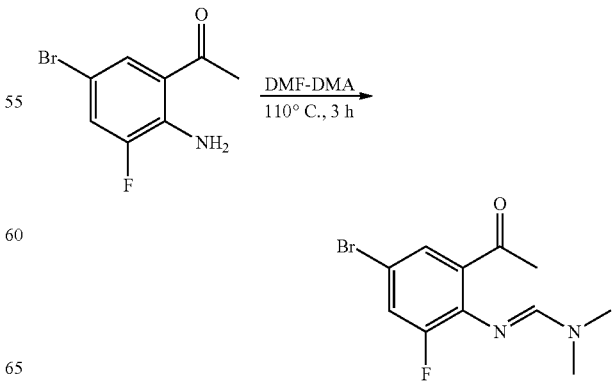

(E)-N'-(2-Acetyl-4-bromo-6-fluorophenyl)-N,N-dimethylformimidamide: A solution of 1-(2-amino-5-bromo-3-fluorophenyl)ethan-1-one (182 mg, 0.78 mmol) in N,N-dimethylformamide dimethyl acetal (6.00 mL) was stirred for 3 hours at 110° C. The resulting mixture was concentrated under reduced pressure to give the crude product which was used in the next step directly without further purification: MS: [(M+1)]⁺=287.00, 289.00.

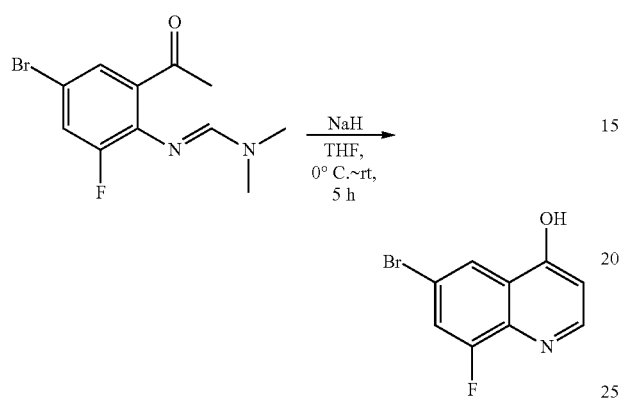

6-Bromoquinolin-4-ol: To a solution of (E)-N-(2-acetyl-4-bromo-6-fluorophenyl)-N,N'-dimethylmethanimidamide (10.0 g, 34.8 mmol) in tetrahydrofuran (250 mL) was added sodium hydride (1.70 g, 42.5 mmol, 60% dispersed in mineral oil) in portions at 0° C. under nitrogen atmosphere. After stirring for additional 5 hours at 25° C., the reaction was quenched by methanol (10.0 mL, plus 1.00 mL acetic acid). The resulting mixture was concentrated under reduced pressure. The residue was purified by silica gel column chromatography, eluted with 1%~5% methanol in dichloromethane. The desired fractions were collected and concentrated under reduced pressure to afford the title compound as a beige solid (3.40 g, 45%): ¹H NMR (400 MHz, DMSO-d₆) δ 12.04 (s, 1H), 7.99 (s, 1H), 7.91 (d, J=10.6 Hz, 2H), 6.14 (d, J=7.4 Hz, 1H); MS: [(M+1)]⁺=242.10, 244.10.

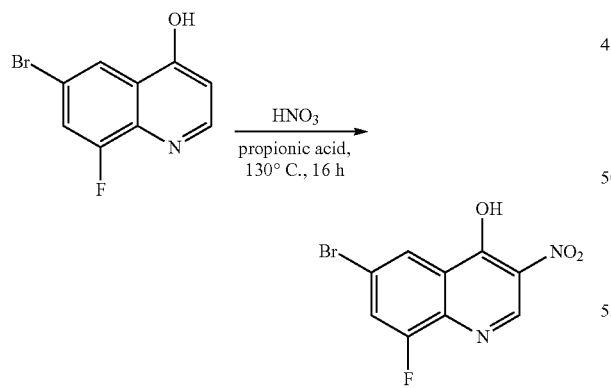

6-Bromo-8-fluoro-3-nitroquinolin-4-ol: To a solution of 6-bromo-8-fluoroquinolin-4-ol (3.40 g, 14.2 mmol) in propionic acid (40.0 mL) was added concentrated nitric acid (2.10, 21.3 mmol, 65% w/w) at ambient temperature. The resulting mixture was stirred for 16 hours at 130° C. After cooling down to ambient temperature, the resulting mixture was concentrated under reduced pressure. The product was precipitated by the addition of dichloromethane (150 mL). The precipitated solid was collected by filtration and washed with dichloromethane (3×20.0 mL) to afford the title compound as a light brown solid (2.80 g, 68%): ¹H NMR (400 MHz, DMSO-d₆) δ 13.36 (br, 1H), 8.96 (s, 1H), 8.14 (dd, J=2.1 Hz, 1H), 8.07 (dd, J=10.2, 2.2 Hz, 1H); MS: [(M+1)]⁺=287.00, 289.00.

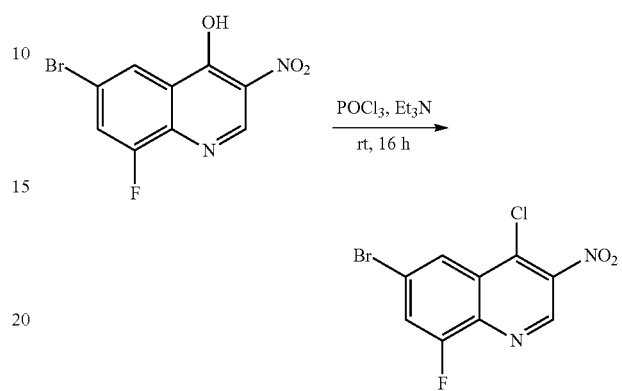

6-Bromo-4-chloro-8-fluoro-3-nitroquinoline: To a solution of 6-bromo-8-fluoro-3-nitroquinolin-4-ol (1.50 g, 5.20 mmol) in phosphoroyl trichloride (20.0 mL) was added triethylamine (2.60 g, 26.1 mmol) dropwise at 0° C. The resulting mixture was stirred for 16 hours at 25° C. The resulting mixture was concentrated under vacuum. The residue was diluted with dichloromethane (100 mL) and poured slowly into ice/water (200 g). The aqueous layer was extracted with dichloromethane (3×100 mL). The combined organic layers was washed with brine (2×50.0 mL) and dried over anhydrous sodium sulfate. After filtration, the filtrate was concentrated under reduced pressure. The residue was purified by silica gel column chromatography, eluted with 1%~10% ethyl acetate in petroleum ether. The desired fractions were collected and concentrated under reduced pressure to afford the title compound as a light yellow solid (2.80 g, 68%): ¹H NMR (400 MHz, CDCl₃) δ 9.26 (s, 1H), 8.39 (d, J=1.7 Hz, 1H), 7.78 (dd, J=8.9, 2.0 Hz, 1H); MS: [(M+1)]⁺=305.00, 307.00.

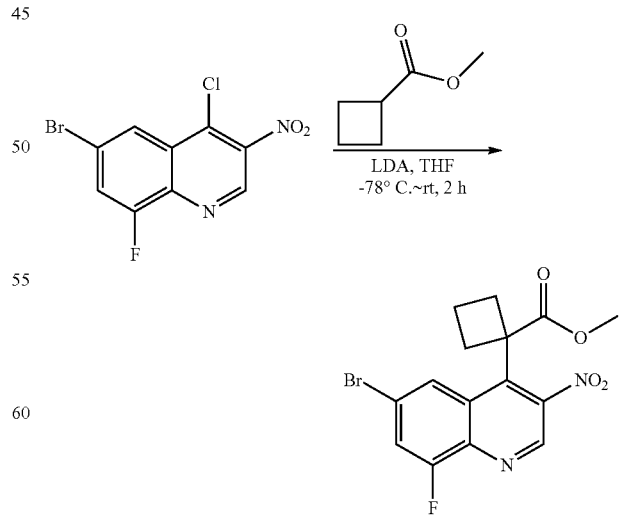

Methyl 1-(6-bromo-8-fluoro-3-nitroquinolin-4-yl)cyclobutane-1-carboxylate: A solution of bis(propan-2-yl)

amine (368 mg, 3.63 mmol) in anhydrous tetrahydrofuran (30.0 mL) was treated with n-butyllithium (1.50 mL, 22.7 mmol, 2.50 M in hexane) at −78° C. for 1 hour under nitrogen atmosphere followed by the addition of methyl cyclobutanecarboxylate (415 mg, 3.63 mmol) over 2 min After stirring for additional 1 hour at −78° C., a solution of 6-bromo-4-chloro-8-fluoro-3-nitroquinoline (555 mg, 1.82 mmol) in tetrahydrofuran (20.0 mL) was added dropwise to the reaction mixture. The resulting mixture was slowly warmed to ambient temperature. After stirring for 2 hours at ambient temperature, the reaction was quenched by saturated aqueous ammonium chloride (5.00 mL) at −30° C. The resulting mixture was diluted with water (150 mL) and the organic layer was separated. The aqueous layer was extracted with ethyl acetate (3×100 mL). The combined organic layers was washed with brine (2×50.0 mL) and dried over anhydrous sodium sulfate. After filtration, the filtrate was concentrated under reduced pressure. The residue was purified by silica gel column chromatography, eluted with 1%~10% ethyl acetate in petroleum ether. The desired fractions were collected and concentrated under reduced pressure to afford the title compound as an orange solid (220 mg, 31%): $^1$H NMR (400 MHz, CDCl$_3$) δ 9.13 (s, 1H), 7.83 (t, J=1.7 Hz, 1H), 7.66 (dd, J=8.9, 2.0 Hz, 1H), 3.81 (s, 3H), 3.11-2.99 (m, 2H), 2.57-2.46 (m, 2H), 1.93-1.81 (m, 2H); MS: [(M+1)]$^+$=383.00, 385.00.

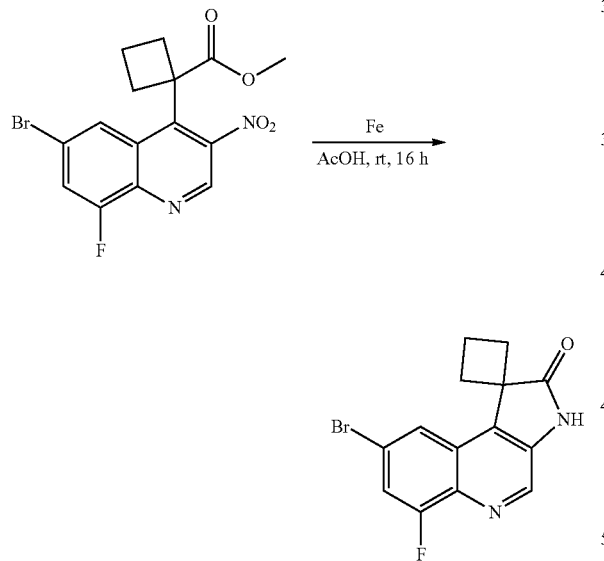

8'-Bromo-6'-fluorospiro[cyclobutane-1,1'-pyrrolo[2,3-c]quinolin]-2'(3'H)-one: To a solution of methyl 1-(6-bromo-8-fluoro-3-nitroquinolin-4-yl)cyclobutane-1-carboxylate (220 mg, 0.57 mmol) in acetic acid (20.0 mL) was added iron powder (321 mg, 5.74 mmol) at ambient temperature. After stirring for 16 hours at ambient temperature, the resulting mixture was filtered, the filtered cake was washed with tetrahydrofuran (6×20.0 mL). The filtrate was concentrated under reduced pressure. The residue was purified by Prep-TLC (DCM/MeOH=15/1, v/v) to afford the title compound as a light yellow solid (134 mg, 72%): $^1$H NMR (400 MHz, DMSO-d$_6$) δ 10.87 (s, 1H), 8.68 (s, 1H), 8.19 (d, J=1.8 Hz, 1H), 7.75 (dt, J=10.3, 1.4 Hz, 1H), 2.87-2.74 (m, 2H), 2.49-2.31 (m, 4H); MS: [(M+1)]$^+$=321.10, 323.10.

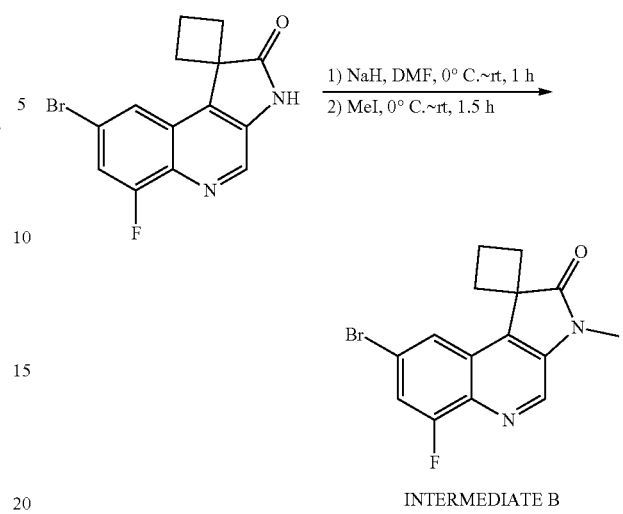

INTERMEDIATE B

8'-Bromo-6'-fluoro-3'-methylspiro[cyclobutane-1,1'-pyrrolo[2,3-c]quinolin]-2'(3'H)-one: To a solution of 8-bromo-6-fluoro-2,3-dihydrospiro[cyclobutane-1,1-pyrrolo[2,3-c]quinolin]-2-one (134 mg, 0.42 mmol) in N,N-dimethylformamide (15.0 mL) was added sodium hydride (25.0 mg, 0.63 mmol, 60% w/w dispersed in mineral oil) at 0° C. under nitrogen atmosphere. The resulting mixture was stirred for 1 hour at 25° C. followed by the addition of iodomethane (77.0 mg, 0.54 mmol). After stirring for additional 1.5 hours at 25° C., the reaction was quenched by saturated aqueous ammonium chloride (5.00 mL). The resulting mixture was diluted with water (150 mL) and extracted with ethyl acetate (3×100 mL). The combined organic layers was washed with brine (2×50.0 mL) and dried over anhydrous sodium sulfate. After filtration, the filtrate was concentrated under reduced pressure. The residue was purified by Prep-TLC (DCM/MeOH=20/1, v/v) to afford the title compound as a light yellow solid (52.0 mg, 38%): $^1$H NMR (400 MHz, DMSO-d$_6$) δ 8.92 (s, 1H), 8.22 (s, 1H), 7.78 (dd, J=10.5, 2.0 Hz, 1H), 3.31 (s, 3H), 2.85-2.79 (m, 2H), 2.57-2.52 (m, 4H); MS: [(M+1)]$^+$=335.10, 337.10.

Intermediate C

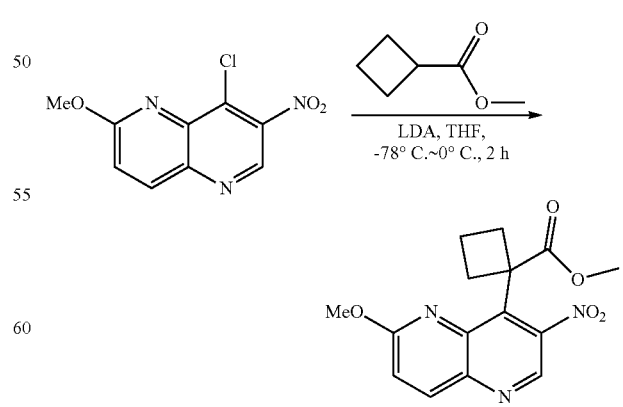

Methyl 1-(6-methoxy-3-nitro-1,5-naphthyridin-4-yl)cyclobutane-1-carboxylate: A solution of methyl cyclobutanecarboxylate (620 mg, 5.43 mmol) was treated with freshly prepared lithium diisopropylamide (5.43 mmol) in tetrahydrofuran (20.0 mL) for 1 hour at −78° C. under nitrogen atmosphere followed by the addition of 8-chloro-2-methoxy-7-nitro-1,5-naphthyridine (1.00 g, 4.17 mmol) (Prepared according to the reported procedure in PCT Int. Appl., 2013118086, 15 Aug. 2013) in portions over 2 min After stirring for additional 1 hour at 0° C., the reaction was quenched by saturated aqueous ammonium chloride (20.0 mL) and diluted with water (150 mL). The mixture was extracted with ethyl acetate (3×100 mL). The combined organic layers was washed with brine (2×50.0 mL) and dried over anhydrous sodium sulfate. After filtration, the filtrate was concentrated under reduced pressure. The residue was purified by silica gel column chromatography, eluted with 2%~10% ethyl acetate in petroleum ether to afford the title compound as a yellow solid (3.26 g, 49%): $^1$H NMR (400 MHz, CDCl$_3$) δ 9.00 (s, 1H), 8.26 (d, J=9.1 Hz, 1H), 7.23 (d, J=9.1 Hz, 1H), 4.01 (s, 3H), 3.71 (s, 3H), 3.11-3.02 (m, 2H), 2.63-2.46 (m, 3H), 1.96-1.78 (m, 1H); MS: [(M+1)]$^+$=318.30.

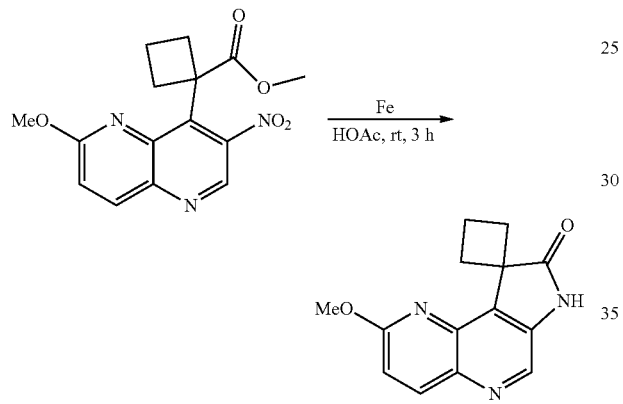

2'-Methoxyspiro[cyclobutane-1,9'-pyrrolo[2,3-c][1,5]naphthyridin]-8'(7'H)-one: To a solution of methyl 1-(6-methoxy-3-nitro-1,5-naphthyridin-4-yl)cyclobutane-1-carboxylate (1.50 g, 4.73 mmol) in acetic acid (20.0 mL) was added iron powder (1.85 g, 33.1 mmol) at ambient temperature. After stirring for 3 hours at ambient temperature, the resulting mixture was concentrated under reduced pressure. The residue was taken up with ethyl acetate (5×200 mL), washed with brine (3×100 mL) and dried over anhydrous sodium sulfate. After filtration, the filtrate was concentrated under reduced pressure. The residue was purified by silica gel column chromatography, eluted with 1%~3% methanol in dichloromethane to afford the title compound as a light yellow solid (1.18 g, 98%): $^1$H NMR (400 MHz, CDCl$_3$) δ 8.71 (s, 1H), 8.58 (s, 1H), 8.22 (d, J=9.1 Hz, 1H), 7.06 (d, J=9.1 Hz, 1H), 4.17 (s, 3H), 3.14-3.04 (m, 2H), 2.81-2.66 (m, 3H), 2.55-2.44 (m, 1H); MS: [(M+1)]$^+$=256.10.

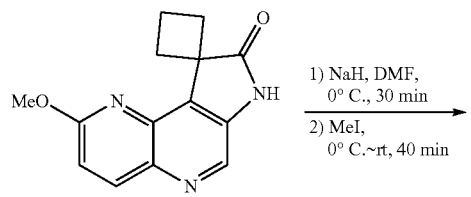

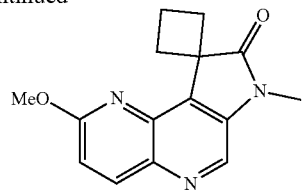

2'-Methoxy-7'-methylspiro[cyclobutane-1,9'-pyrrolo[2,3-c][1,5]naphthyridin]-8'(7'H)-one: A solution of 2-methoxy-7,8-dihydrospiro[cyclobutane-1,9-pyrrolo[2,3-c]1,5-naphthyridin]-8-one (1.30 g, 5.09 mmol) in N,N-dimethylformamide (10.0 mL) was treated with sodium hydride (265 mg, 6.62 mmol, 60% dispersed in mineral oil) for 30 min at 0° C. under nitrogen atmosphere followed by the addition of iodomethane (940 mg, 6.62 mmol) over 2 min After stirring for additional 40 min at ambient temperature, the reaction was quenched by saturated aqueous ammonium chloride (20.0 mL) and diluted with water (150 mL). The resulting mixture was extracted with ethyl acetate (3×100 mL). The combined organic layers was washed with brine (2×50.0 mL) and dried over anhydrous sodium sulfate. After filtration, the filtrate was concentrated under reduced pressure. The residue was purified by silica gel column chromatography, eluted with 2%~5% methanol in dichloromethane to afford the title compound as a light yellow solid (1.29 g, 94%): $^1$H NMR (400 MHz, CDCl$_3$) δ 8.48 (s, 1H), 8.22 (d, J=9.1 Hz, 1H), 7.07 (d, J=9.1 Hz, 1H), 4.18 (s, 3H), 3.37 (s, 3H), 3.12-3.00 (m, 2H), 2.85-2.70 (m, 1H), 2.70-2.62 (m, 2H), 2.56-2.41 (m, 1H); MS: [(M+1)]$^+$=270.10.

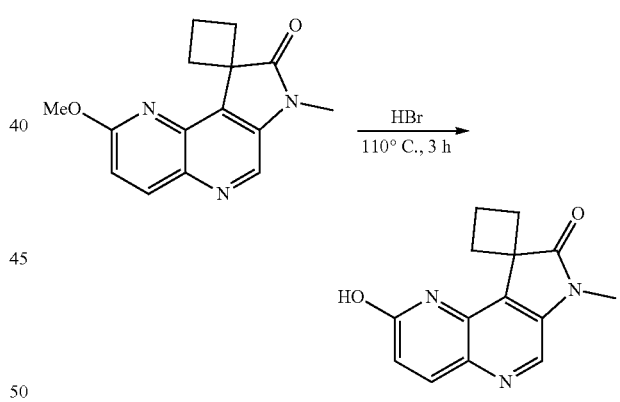

2-Hydroxy-7-methyl-7,8-dihydrospiro[cyclobutane-1,9-pyrrolo[2,3-c]1,5-naphthyridin]-8-one: A solution of 2'-methoxy-7'-methylspiro[cyclobutane-1,9'-pyrrolo[2,3-c][1,5]naphthyridin]-8'(7'H)-one (1.00 g, 3.70 mmol) in hydrobromic acid (12.0 mL, 40% in water) was stirred for 3 hours at 110° C. under nitrogen atmosphere. After cooling down to ambient temperature, the resulting mixture was neutralized with ammonium hydroxide. The resulting mixture was concentrated under reduced pressure. The residue was purified by reversed phase chromatography with the following conditions: [Column: Spherical C18, 20~40 μm, 330 g; Mobile Phase A: Water (plus 10 mM NH$_4$HCO$_3$ and 10 mM NH$_3$·H$_2$O); Mobile Phase B: Acetonitrile; Flow rate: 65 mL/min; Gradient (B %): 5%~20%, 8 min; 20%~27%, 10 min; 27%~95%; 2 min; 95%, 5 min; Detector UV 254 nm; Rt: 18 min]. The desired fractions were collected and concentrated under reduced pressure to afford the title compound as a brown yellow solid (220 mg, 24%): ¹H NMR (400 MHz, DMSO-d₆) δ 10.31 (s, 1H), 8.57 (s, 1H), 7.95 (d, J=9.7 Hz, 1H), 6.51 (d, J=9.7 Hz, 1H), 4.46-4.39 (m, 2H), 3.68 (s, 3H), 3.08 (t, J=6.2 Hz, 2H), 2.04 (p, J=6.0 Hz, 2H); MS: [(M+1)]⁺=256.20.

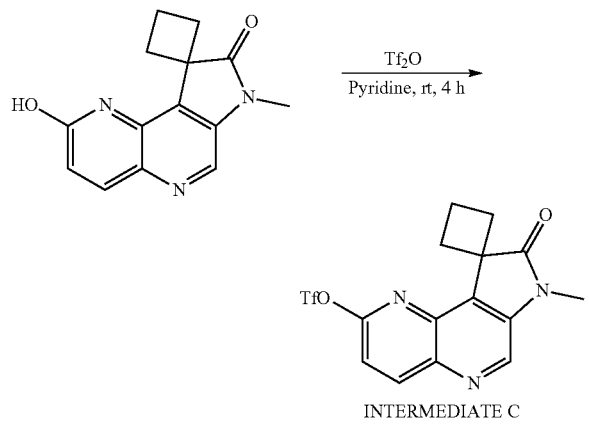

INTERMEDIATE C

7-Methyl-8-oxo-7,8-dihydrospiro[cyclobutane-1,9-pyrrolo[2,3-c]1,5-naphthyridin]-2-yl trifluoromethanesulfonate To a stirred solution of 2-hydroxy-7-methyl-7,8-dihydrospiro[cyclobutane-1,9-pyrrolo[2,3-c]1,5-naphthyridin]-8-one (20.0 mg, 0.078 mmol) in pyridine (1.00 mL) was added trifluromethanesulfonic anhydride (29.0 mg, 0.10 mmol) dropwise at ambient temperature. The resulting mixture was stirred for 4 hours at ambient temperature. The resulting mixture was diluted with water (10.0 mL). The resulting mixture was extracted with ethyl acetate (5×30.0 mL). The combined organic layers was washed with brine (3×30.0 mL), dried over anhydrous sodium sulfate and filtered. The filtrate was concentrated under reduced pressure. The residue was purified by silica gel column chromatography, eluted with 4% methanol in dichloromethane. The desired fractions were collected and concentrated under reduced pressure to afford the title compound as a yellow solid (16.0 mg, 53%): ¹H NMR (400 MHz, CDCl₃) δ 8.86 (s, 1H), 8.56 (d, J=8.9 Hz, 1H), 7.28 (d, J=8.9 Hz, 1H), 4.55-4.45 (m, 2H), 3.81 (d, J=1.1 Hz, 3H), 3.18 (t, J=6.3 Hz, 2H), 2.18 (p, J=6.0 Hz, 2H); MS: [(M+1)]⁺=388.50

Intermediate D

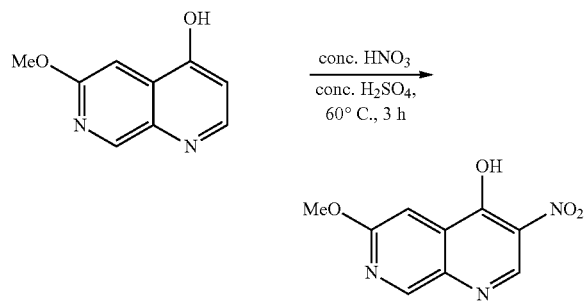

6-Methoxy-3-nitro-1,7-naphthyridin-4-ol: A solution of 6-methoxy-1,7-naphthyridin-4-ol (4.80 g, 27.2 mmol) (Prepared according to the procedure reported by *ACS Medicinal Chemistry Letters*, 6(4), 434-438; 2015) in concentrated sulfuric acid (10.0 mL, 98%) and concentrated nitric acid (5.00 mL, 65%) was stirred for 3 hours at 60° C. After cooling down to ambient temperature, the resulting mixture was diluted with ice/water (1.00 L). The precipitated solid was collected by filtration and washed with water (4×50.0 mL). The resulting solid was dried under infrared light to afford the title compound as an yellow solid (3.00 g, 50%): ¹H NMR (400 MHz, DMSO-d₆) δ 13.31 (s, 1H), 9.23 (s, 1H), 8.84 (s, 1H), 7.41 (d, J=0.9 Hz, 1H), 5.10 (s, 3H), 3.96 (s, 3H); MS: [(M+1)]⁺=222.10.

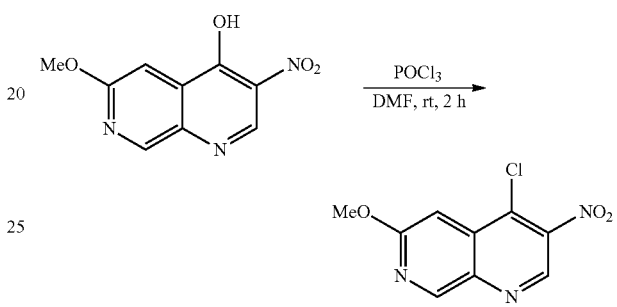

4-Chloro-6-methoxy-3-nitro-1,7-naphthyridine: To a solution of 6-methoxy-3-nitro-1,7-naphthyridin-4-ol (3.00 g, 13.6 mmol) in N,N-dimethylformamide (60.0 mL) was added phosphoryl trichloride (10.0 mL, 107 mmol) at 0° C. After stirring for 2 hours at 25° C., the resulting mixture was poured into ice/water (500 mL). The mixture was extracted with dichloromethane (3×100 mL). The combined organic layers was washed with brine (2×100 mL) and dried over anhydrous sodium sulfate. After filtration, the filtrate was concentrated under reduced pressure. The residue was purified by silica gel column chromatography, eluted with 5%~25% ethyl acetate in petroleum ether. The desired fractions were collected and concentrated under reduced pressure to afford the title compound as a yellow solid (2.00 g, 62%): ¹H NMR (400 MHz, CDCl₃) δ 9.33 (s, 1H), 9.05 (s, 1H), 7.47 (d, J=0.8 Hz, 1H), 4.14 (s, 3H); MS: [(M+1)]⁺=240.25.

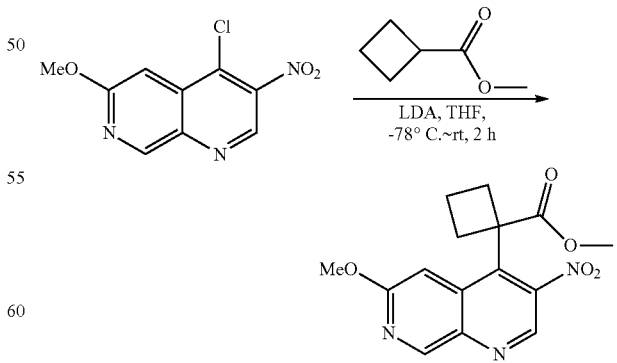

Methyl 1-(6-methoxy-3-nitro-1,7-naphthyridin-4-yl)cyclobutane-1-carboxylate: A solution of methyl cyclobutanecarboxylate (0.62 g, 5.43 mmol) in tetrahydrofuran (4.00 mL) was treated with freshly prepared lithium diisopropylamide (5.43 mmol) in tetrahydrofuran (40.0 mL) for 1 hour at −78° C. under nitrogen atmosphere followed by the addition of 4-chloro-6-methoxy-3-nitro-1,7-naphthyridine (1.00 g, 4.17 mmol) in portions over 2 min After stirring for additional 1 hour at ambient temperature, the reaction was quenched by saturated aqueous ammonium chloride (20.0 mL) and diluted with water (80.0 mL). The resulting mixture was extracted with ethyl acetate (3×150 mL). The combined organic layers was washed with brine (2×100 mL) and dried over anhydrous sodium sulfate. After filtration, the filtrate was concentrated under reduced pressure. The residue was purified by silica gel column chromatography, eluted with 2%~20% ethyl acetate in petroleum ether to afford the title compound as a purple solid (409 mg, 31%): $^1$H NMR (400 MHz, DMSO-$d_6$) δ 9.32 (d, J=0.8 Hz, 1H), 9.07 (s, 1H), 7.07 (d, J=0.8 Hz, 1H), 4.03 (s, 3H), 3.70 (s, 3H), 2.94-2.74 (m, 3H), 2.61-2.54 (m, 2H), 2.35-2.25 (m, 1H): MS: [(M+1)]$^+$=318.30.

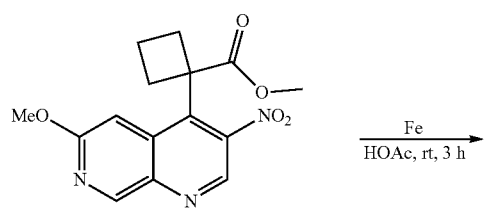

8'-Methoxyspiro[cyclobutane-1,1'-pyrrolo[2,3-c][1,7]naphthyridin]-2'(3'H)-one: To a solution of methyl 1-(6-methoxy-3-nitro-1,7-naphthyridin-4-yl)cyclobutane-1-carboxylate (409 mg, 1.29 mmol) in acetic acid (6.00 mL) was added iron powder (504 mg, 9.02 mmol) at ambient temperature. After stirring for 3 hours at ambient temperature, the resulting mixture was filtered and the filtered cake was washed with tetrahydrofuran (6×100 mL). The filtrate was concentrated under reduced pressure. The residue was purified by silica gel column chromatography, eluted with 1%~10% methanol in dichloromethane to afford the title compound as a purple solid (180 mg, 55%): $^1$H NMR (400 MHz, DMSO-$d_6$) δ 10.84 (s, 1H), 9.12 (d, J=0.8 Hz, 1H), 8.58 (s, 1H), 7.31 (d, J=0.8 Hz, 1H), 4.03 (s, 3H), 2.88-2.76 (m, 2H), 2.55-2.39 (m, 4H); MS: [(M+1)]$^+$=256.20.

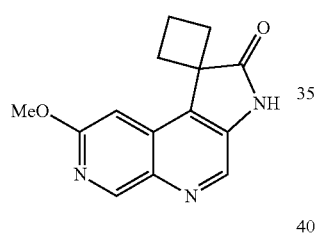

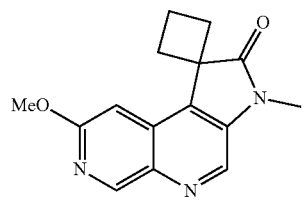

8'-Methoxy-3'-methylspiro[cyclobutane-1,1'-pyrrolo[2,3-c][1,7]naphthyridin]-2'(3'H)-one: A solution of 8-methoxy-3H-spiro[cyclobutane-1,1-pyrrolo[2,3-c]1,7-naphthyridin]-2-one (180 mg, 0.71 mmol) in N,N-dimethylformamide (5.00 mL) was treated with sodium hydride (42.3 mg, 1.06 mmol, 60% dispersed in mineral oil) for 0.5 hours at 0° C. under nitrogen atmosphere followed by the addition of iodomethane (130 mg, 0.92 mmol). After stirring for additional 0.5 hours at ambient temperature, the reaction was quenched by saturated aqueous ammonium chloride (20.0 mL) and diluted with water (150 mL). The resulting mixture was extracted with ethyl acetate (3×50.0 mL). The combined organic layers was washed with brine (2×30.0 mL) and dried over anhydrous sodium sulfate. After filtration, the filtrate was concentrated under reduced pressure. The residue was purified by silica gel column chromatography, eluted with 6% methanol in dichloromethane to afford the title compound as a purple solid (186 mg, 98%): $^1$H NMR (400 MHz, DMSO-$d_6$) δ 9.16 (d, J=0.8 Hz, 1H), 8.83 (s, 1H), 7.33 (d, J=0.9 Hz, 1H), 4.04 (s, 3H), 3.30 (s, 3H), 2.88-2.78 (m, 2H), 2.50-2.42 (m, 4H); MS: [(M+1)]$^+$=270.10.

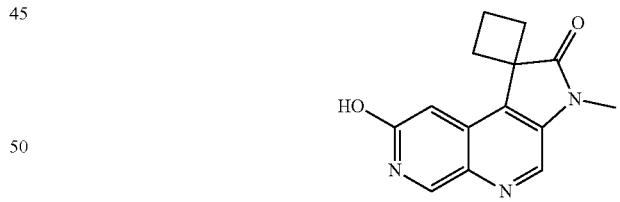

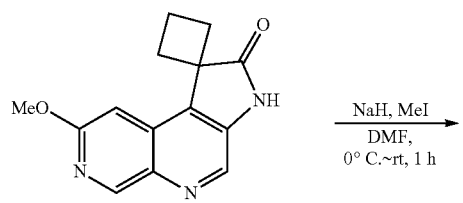

8'-Hydroxy-3'-methylspiro[cyclobutane-1,1'-pyrrolo[2,3-c][1,7]naphthyridin]-2'(3'H)-one: 8-Methoxy-3-methylspiro[cyclobutane-1,1-pyrrolo[2,3-c]1,7-naphthyridin]-2-one (100 mg, 0.37 mmol) was treated with hydrogen chloride (20.0 mL, 4 M in 1,4-dioxane) for 5 hours at 100° C. under air atmosphere. The resulting mixture was concentrated under reduced pressure. The residue was purified by silica gel column chromatography, eluted with 1%~25% methanol in dichloromethane to afford the title compound as a light yellow solid (70.0 mg, 74%): $^1$H NMR (400 MHz, DMSO-$d_6$) δ 8.78 (s, 1H), 8.74 (s, 1H), 6.98 (s, 1H), 4.46-4.42 (m, 2H), 3.73 (s, 3H), 2.99 (t, J=6.3 Hz, 2H), 2.13-2.06 (m, 2H); MS: [(M+1)]$^+$=256.10.

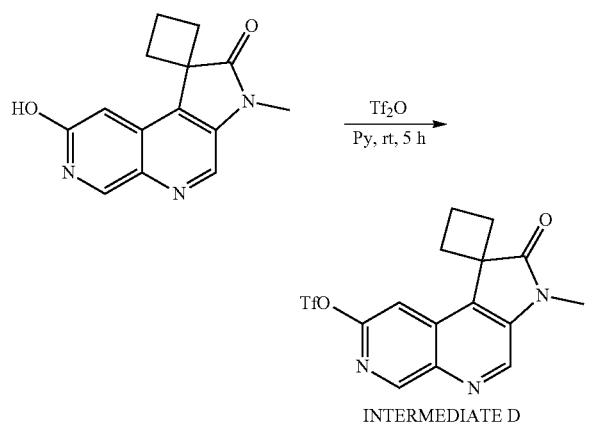

was concentrated under reduced pressure. The residue was purified by silica gel column chromatography, eluted with 2%~17% ethyl acetate in petroleum ether. The desired fractions were collected and concentrated under reduced pressure to afford the title compound as a colorless solid (25.0 g, 71%): $^1$H NMR (400 MHz, CD$_3$OD) δ 7.49 (d, J=7.7 Hz, 1H), 6.60 (d, J=11.0 Hz, 1H), 3.59 (s, 3H), 3.32 (s, 3H); MS: [(M+1)]$^+$=277.00, 279.00.

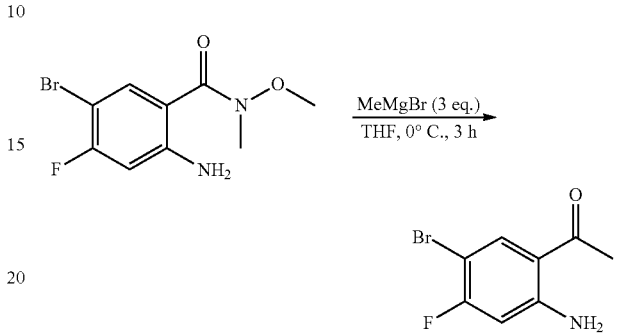

INTERMEDIATE D

3'-Methyl-2'-oxo-2',3'-dihydrospiro[cyclobutane-1,1'-pyrrolo[2,3-c][1,7]naphthyridin]-8'-yl trifluoromethanesulfonate: To a stirred solution of 8-hydroxy-3-methylspiro[cyclobutane-1,1-pyrrolo[2,3-c]1,7-naphthyridin]-2-one (65.0 mg, 0.26 mmol) in pyridine (3.00 mL) was added trifluromethanesulfonic anhydride (94.0 mg, 0.33 mmol) dropwise at ambient temperature under ambient atmosphere. After stirring for additional 5 hours the resulting mixture was diluted with water (10.0 mL) and extracted with ethyl acetate (5×30.0 mL). The combined organic layers was washed with brine (3×30.0 mL) and dried over anhydrous sodium sulfate. After filtration, the filtrate was concentrated under reduced pressure. The residue was purified by Prep-TLC (6% methanol in dichloromethane) to afford the title compound as a yellow solid (50.0 mg, 51%): $^1$H NMR (400 MHz, DMSO-d$_6$) δ 9.19 (s, 1H), 9.14 (s, 1H), 8.06 (s, 1H), 4.51 (t, J=5.9, 2H), 3.83 (s, 3H), 3.07 (t, J=6.2 Hz, 2H), 2.13 (p, J=6.0 Hz, 2H); MS: [(M+1)]$^+$=388.05.

1-(2-Amino-5-bromo-4-fluorophenyl)ethan-1-one: To a solution of 2-amino-5-bromo-4-fluoro-N-methoxy-N-methylbenzamide (25.0 g, 90.2 mmol) in anhydrous tetrahydrofuran (625 mL) was added bromo(methyl)magnesium (90.2 mL, 271 mmol, 3 M in tetrahydrofuran) dropwise at −78° C. The resulting mixture was stirred for 3 hours at 0° C. The reaction was quenched by saturated aqueous ammonium chloride (50.0 mL) at 0° C. and diluted with water (1.00 L). The resulting mixture was extracted with ethyl acetate (3×250 mL). The combined organic layers was washed with brine (2×200 mL) and dried over anhydrous sodium sulfate. After filtration, the filtrate was concentrated under reduced pressure. The residue was purified by silica gel column chromatography, eluted with 1%~9% ethyl acetate in petroleum ether. The desired fractions were collected and concentrated under reduced pressure to afford the title compound as a yellow solid (11.0 g, 53%): $^1$H NMR (400 MHz, CDCl$_3$) δ 7.87 (d, J=7.6 Hz, 1H), 6.41 (d, J=10.4 Hz, 1H), 2.54 (s, 3H); MS: [(M+1)]$^+$=232.00, 234.00.

Intermediate E

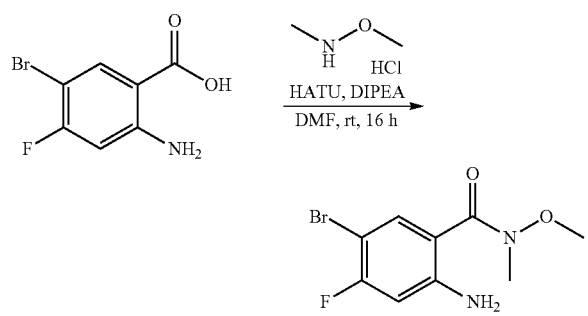

2-Amino-5-bromo-4-fluoro-N-methoxy-N-methylbenzamide: To a solution of 2-amino-5-bromo-4-fluorobenzoic acid (30.0 g, 128 mmol) and methoxy(methyl)amine hydrochloride (19.0 g, 193 mmol) in N,N-dimethylformamide (900 mL) were added O-(7-azabenzotriazol-1-yl)-N,N,N',N'-tetramethyluronium hexafluorophosphate (54.0 g, 141 mmol) and diisopropylethylamine (41.0 g, 321 mmol) at 0° C. The resulting mixture was stirred for 16 hours at 25° C. The resulting mixture was diluted with water (3.00 L) and extracted with ethyl acetate (3×1.00 L). The combined organic layers was washed with brine (2×1.00 L) and dried over anhydrous sodium sulfate. After filtration, the filtrate

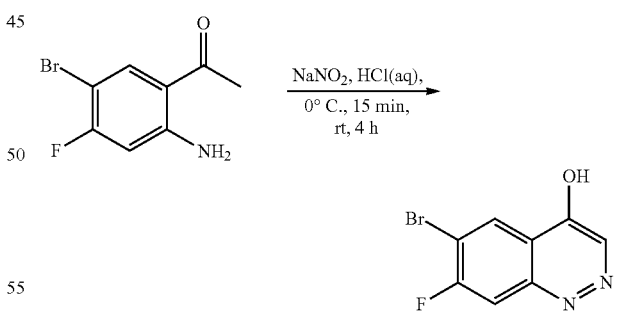

6-Bromo-7-fluorocinnolin-4-ol: A solution of 1-(2-amino-5-bromo-4-fluorophenyl)ethan-1-one (5.00 g, 21.5 mmol) in hydrochloric acid (65.0 mL, 6 N) was stirred for 1 hour at ambient temperature followed by the addition of a solution of sodium nitrite (1.49 g, 21.6 mmol, in water 13.0 mL) dropwise at 0° C.~5° C. After stirring for additional 4 hours, the mixture was neutralized with saturated aqueous sodium bicarbonate. The resulting mixture was extracted with ethyl acetate (3×200 mL). The combined organic layers was washed with brine (100 mL) and dried over anhydrous sodium sulfate. After filtration, the filtrate was concentrated under reduced pressure. The residue was purified by silica gel column chromatography, eluted with 3%~12% ethyl acetate in petroleum ether. The desired fractions were collected and concentrated under reduced pressure to afford the title compound as a yellow solid (3.00 g, 58%): $^1$H NMR (400 MHz, DMSO-$d_6$) δ 13.65 (s, 1H), 8.28 (d, J=7.5 Hz, 1H), 7.82 (s, 1H), 7.48 (d, J=9.3 Hz, 1H); MS: $[(M+1)]^+$=243.00, 245.00.

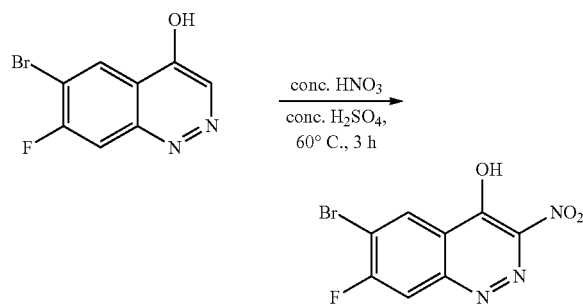

6-Bromo-7-fluoro-3-nitrocinnolin-4-ol: A solution of 6-bromo-7-fluorocinnolin-4-ol (3.00 g, 12.3 mmol) in concentrated sulfuric acid (10.0 mL, 98%) and concentrated nitric acid (5.00 mL, 65%) was stirred for 3 hours at 60° C. under ambient atmosphere. After cooling down to ambient temperature, the resulting mixture was diluted with ice/water (1.00 L). The precipitated solid was collected by filtration and washed with water (4×50.0 mL). The resulting solid was dried under infrared light to afford the title compound as a yellow solid (1.20 g, 34%): $^1$H NMR (400 MHz, CD$_3$OD) δ 8.59 (d, J=7.1 Hz, 1H), 7.57 (d, J=8.6 Hz, 1H); MS: $[(M+1)]^+$=288.00, 290.00.

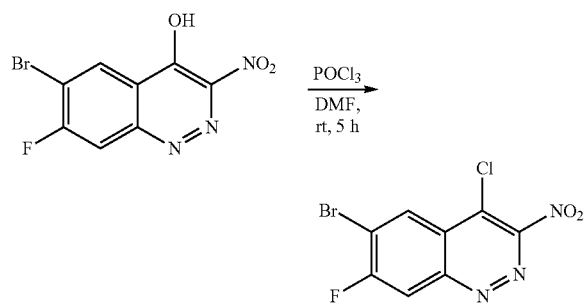

6-Bromo-7-fluoro-3-nitrocinnolin-4-ol: To a solution of 6-bromo-7-fluoro-3-nitrocinnolin-4-ol (1.20 g, 4.17 mmol) in N,N-dimethylformamide (25.0 mL) was added phosphoryl trichloride (3.20 g, 20.9 mmol) at 0° C. After stirring for 5 hours at 25° C., the resulting mixture was poured into ice/water (250 mL). The mixture was extracted with dichloromethane (3×100 mL). The combined organic layers was washed with brine (2×100 mL) and dried over anhydrous sodium sulfate. After filtration, the filtrate was concentrated under reduced pressure. The residue was purified by silica gel column chromatography, eluted with 10% ethyl acetate in dichloromethane. The desired fractions were collected and concentrated under reduced pressure to afford the title compound as a yellow solid (1.00 g, 80%): $^1$H NMR (400 MHz, CD$_3$OD) δ 8.90 (d, J=6.7 Hz, 1H), 8.51 (d, J=8.3 Hz, 1H); MS: $[(M+1)]^+$=305.95, 307.95.

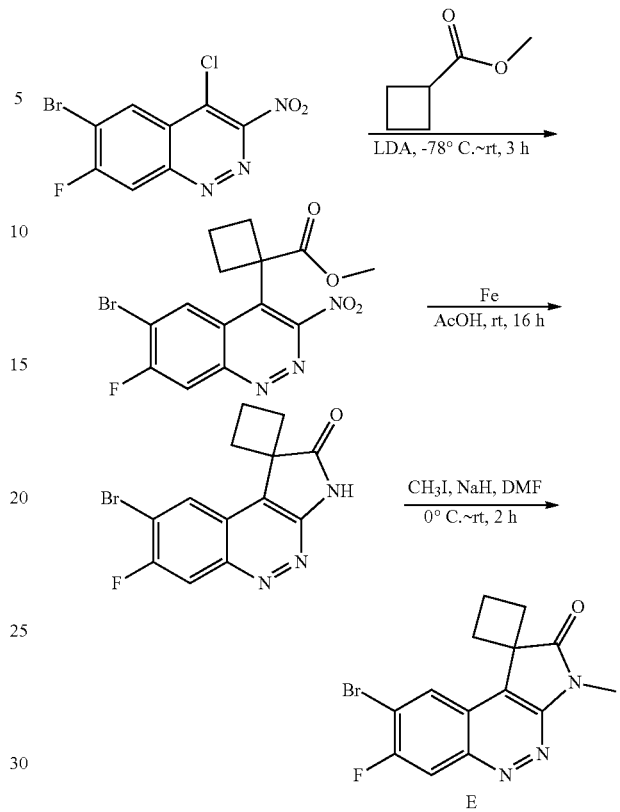

8'-Bromo-7'-fluoro-3'-methylspiro[cyclobutane-1,1'-pyrrolo[2,3-c]cinnolin]-2'(3'H)-one: A solution of methyl cyclobutanecarboxylate (0.48 g, 4.24 mmol) in tetrahydrofuran (5.00 mL) was treated with freshly prepared lithium diisopropylamide (4.24 mmol) in tetrahydrofuran (43.0 mL) at −78° C. for 1 hour under nitrogen atmosphere followed by the addition of 6-bromo-4-chloro-7-fluoro-3-nitrocinnoline (1.00 g, 3.26 mmol) over 2 min at −78° C. After stirring for additional 2 hours at ambient temperature, the reaction was quenched by saturated aqueous ammonium chloride (20.0 mL). The resulting mixture was diluted with water (150 mL) and extracted with ethyl acetate (3×50.0 mL). The combined organic layers was washed with brine (2×30.0 mL) and dried over anhydrous sodium sulfate. After filtration, the filtrate was concentrated under reduced pressure. The residue was dissolved in acetic acid (10.0 mL) followed by the addition of iron powder (1.00 g, 17.8 mmol). After stirring for 16 hours at ambient temperature, the resulting mixture was filtered and the filtered cake was washed with tetrahydrofuran (6×100 mL). The filtrate was concentrated under reduced pressure. The residue was taken up with saturated aqueous sodium bicarbonate (100 mL). The resulting mixture was extracted with ethyl acetate (3×20.0 mL). The combined organic layers was washed with brine (3×20.0 mL) and dried over anhydrous sodium sulfate. After filtration, the filtrate was concentrated under reduced pressure. The residue was dissolved in N,N-dimethylformamide (6.00 mL) followed by the addition of sodium hydride (22.3 mg, 0.56 mmol, 60% dispersed in mineral oil) and iodomethane (68.7 mg, 0.48 mmol) at 0° C. under nitrogen atmosphere. After stirring for additional 2 hours at ambient temperature, the reaction was quenched by the addition of saturated aqueous ammonium chloride (10.0 mL) and diluted with water (50.0 mL). The resulting mixture was extracted with Ethyl acetate (3×20.0 mL). The combined organic layers was washed with brine (10.0 mL) and dried over anhydrous sodium sulfate. After filtration, the filtrate was concentrated under reduced pressure. The residue was purified by silica gel column chromatography, eluted with 5% methanol in dichloromethane the title compound as a light yellow solid (102 mg, 9%): $^1$H NMR (400 MHz, DMSO-$d_6$) δ 8.68 (d, J=7.0 Hz, 1H), 8.33 (d, J=9.4 Hz, 1H), 3.45 (s, 3H), 3.19-3.15 (m, 2H), 2.56-2.43 (m, 4H); MS: [(M+1)]$^+$=336.10, 338.10.

Intermediate F

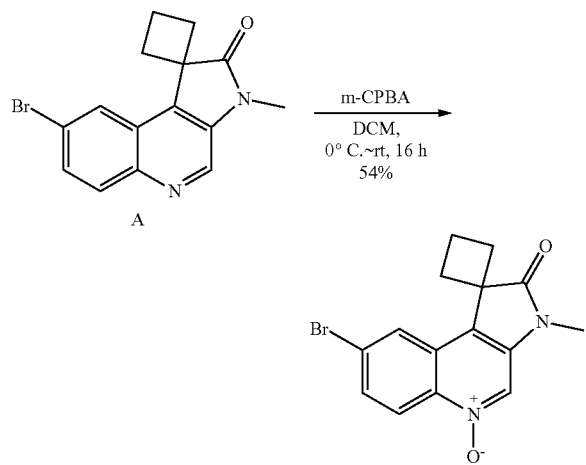

8'-Bromo-3'-methyl-2'-oxo-2',3'-dihydrospiro[cyclobutane-1,1'-pyrrolo[2,3-c]quinoline] 5'-oxide: To a stirred solution of 8-bromo-3-methyl-2,3-dihydrospiro[cyclobutane-1,1-pyrrolo[2,3-c]quinolin-2-one (1.50 g, 4.70 mmol) in trichloromethane (25.0 mL) was added 3-chloroperbenzoic acid (2.50 g, 14.2 mmol) in portions at 0° C. under nitrogen atmosphere. After stirring for additional 16 hours at ambient temperature under nitrogen atmosphere, the reaction was quenched by saturated aqueous sodium bicarbonate (20.0 mL). The resulting mixture was extracted with ethyl acetate (3×50.0 mL). The combined organic layers was washed with brine (2×50.0 mL), dried over anhydrous sodium sulfate and filtered. The filtrate was concentrated under reduced pressure. The residue was purified by silica gel column chromatography, eluted with 1%~8% methanol in dichloromethane. The desired fractions were collected and concentrated under reduced pressure to afford the title compound as a yellow solid (850 mg, 54%): $^1$H NMR (400 MHz, DMSO-$d_6$) δ 8.83 (s, 1H), 8.52 (s, 1H), 8.48 (d, J=9.3 Hz, 1H), 8.39 (d, J=2.0 Hz, 1H), 7.79 (dd, J=9.4, 2.0 Hz, 1H), 3.20 (s, 3H), 2.89-2.76 (m, 2H), 2.49-2.43 (m, 3H), 2.43-2.31 (m, 1H); MS: [(M+1)]$^+$=333.10, 335.10.

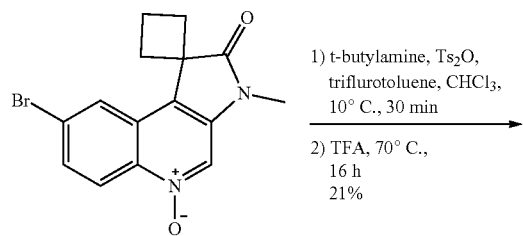

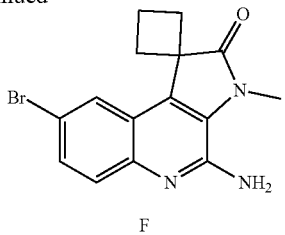

4'-Amino-8'-bromo-3'-methylspiro[cyclobutane-1,1'-pyrrolo[2,3-c]quinolin]-2'(3'H)-one: To a stirred solution of 8-bromo-3-methyl-2,3-dihydrospiro[cyclobutane-1,1-pyrrolo[2,3-c]quinoline]-2,5-dione (664 mg, 2.00 mmol) in trifluorotoluene (8.00 mL) and trichloromethane (10.0 mL) were added t-butylamine (1.17 mg, 16.0 mmol,) dropwise at 0° C. and 4-methylbenzenesulfonyl 4-methylbenzene-1-sulfonate (2.60 g, 8.00 mmol) in portions while keep the temperature at 5-12° C. The resulting mixture was stirred for 30 min at 10° C. followed by the addition of trifluoroacetic acid (4.00 mL). After stirring for 16 hours at 70° C., the resulting mixture was concentrated under reduced pressure. The mixture was basified to pH=9 with 50% sodium hydroxide solution. The resulting mixture was extracted with ethyl acetate (5×50.0 mL). The combined organic layers was washed with brine (2×50.0 mL), dried over anhydrous sodium sulfate and filtered. The filtrate was concentrated under reduced pressure. The residue was purified by silica gel column chromatography, eluted with 1%~5% methanol in dichloromethane. The desired fractions were collected and concentrated under reduced pressure to afford the title compound as a yellow solid (135 mg, 21%): $^1$H NMR (400 MHz, DMSO-$d_6$) δ 8.12 (d, J=2.0 Hz, 1H), 7.59-7.48 (m, 2H), 3.43 (s, 3H), 2.76 (dd, J=11.9, 6.9 Hz, 2H), 2.49-2.30 (m, 4H); MS: [(M+1)]$^+$=332.10, 334.10.

Intermediate G

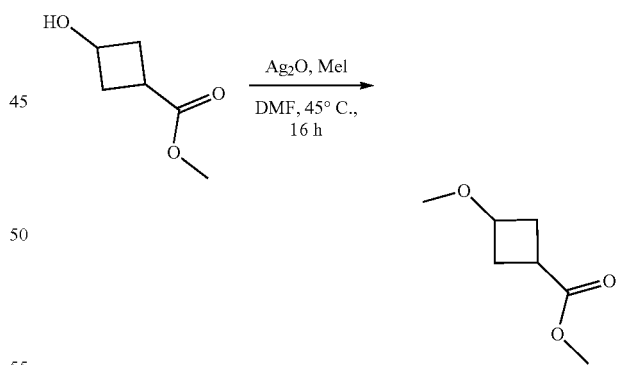

Methyl 3-methoxycyclobutane-1-carboxylate: A mixture of methyl 3-hydroxycyclobutane-1-carboxylate (14.0 g, 0.11 mol), silver oxide (50.0 g, 0.22 mol) and iodomethane (30.5 g, 0.22 mol) in N,N-dimethylformamide (100 mL) was stirred for 16 hours at 45° C. After cooling down to ambient temperature, the resulting mixture was diluted with water (1.00 L) and extracted with diethyl ether (6×200 mL). The combined organic layers was washed with brine (2×200 mL) and dried over anhydrous magnesium sulfate. After filtration, the filtrate was concentrated under reduced pressure to afford the title compound as a light yellow oil (10.0 g, 65%):

$^1$H NMR (400 MHz, DMSO-d$_6$) δ 3.75 (p, J=7.3 Hz, 1H), 3.59 (s, 3H), 3.11 (s, 3H), 2.75-2.61 (m, 1H), 2.47-2.38 (m, 2H), 2.00-1.89 (m, 2H).

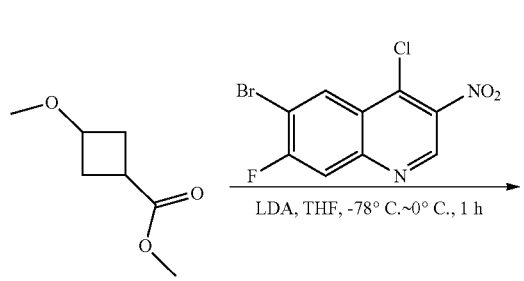

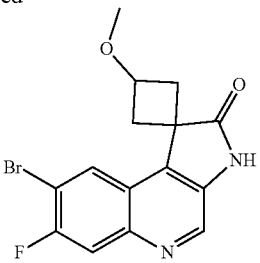

8'-Bromo-7'-fluoro-3-methoxyspiro[cyclobutane-1,1'-pyrrolo[2,3-c]quinolin]-2'(3'H)-one: To a solution of methyl 1-(6-bromo-7-fluoro-3-nitroquinolin-4-yl)-3-methoxycyclobutane-1-carboxylate (720 mg, 1.74 mmol) in acetic acid (10.0 mL) was added iron powder (681 mg, 12.2 mmol). The resulting mixture was stirred for 3 hours at ambient temperature. The resulting mixture was diluted with water (150 mL) and extracted with ethyl acetate (4×50.0 mL). The combined organic layers was washed with brine (2×50.0 mL) and dried over anhydrous sodium sulfate. After filtration, the filtrate was concentrated under reduced pressure. The residue was purified by silica gel column chromatography, eluted with 5%~30% ethyl acetate in petroleum ether to afford the title compound as a light yellow solid (550 mg, 89%): $^1$H NMR (400 MHz, CDCl$_3$) δ 8.93 (s, 0.45H), 8.88 (d, J=7.2 Hz, 0.55H), 8.84 (s, 1H), 8.78 (s, 0.55H), 8.27 (d, J=7.0 Hz, 0.45H) 7.92 (d, J=9.3 Hz, 1H), 4.67 (p, J=6.7 Hz, 0.45H), 4.53 (p, J=6.7 Hz, 0.55H), 3.48 (d, J=6.6 Hz, 3H), 3.07-2.83 (m, 4H); MS: [(M+1)]$^+$=351.00, 353.00.

Methyl 1-(6-bromo-7-fluoro-3-nitroquinolin-4-yl)-3-methoxycyclobutane-1-carboxylate: To a solution of freshly prepared lithium diisopropylamide (10.6 mmol) in anhydrous tetrahydrofuran (100 mL) was added methyl 3-methoxycyclobutane-1-carboxylate (1.53 g, 10.6 mmol) at −78° C. After stirring for additional 1 hour, a solution of 6-bromo-4-chloro-7-fluoro-3-nitroquinoline (2.50 g, 8.18 mmol) in tetrahydrofuran (5.00 mL) was added over 5 min The resulting mixture was slowly warmed to 0° C. and then quenched by saturated aqueous ammonium chloride (100 mL). The resulting mixture was diluted with water (1.00 L) and the organic layer was separated. The aqueous layer was extracted with ethyl acetate (3×200 mL). The combined organic layers was washed with brine (2×200 mL) and dried over anhydrous sodium sulfate. After filtration, the filtrate was concentrated under reduced pressure. The residue was purified by silica gel column chromatography, eluted with 5%~50% ethyl acetate in petroleum ether to afford the title compound as a brown syrup (720 mg, 21%): $^1$H NMR (400 MHz, DMSO-d$_6$) δ 9.25 (s, 1H), 8.31 (d, J=7.3 Hz, 1H), 8.17 (d, J=9.3 Hz, 1H), 4.16-4.13 (m, 1H), 3.71 (s, 3H), 3.11 (s, 3H), 2.47-2.38 (m, 2H), 2.00-1.89 (m, 2H); MS: [(M+1)]$^+$=413.2, 415.2.

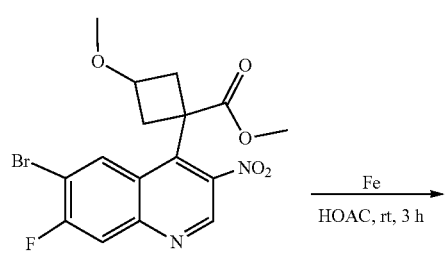

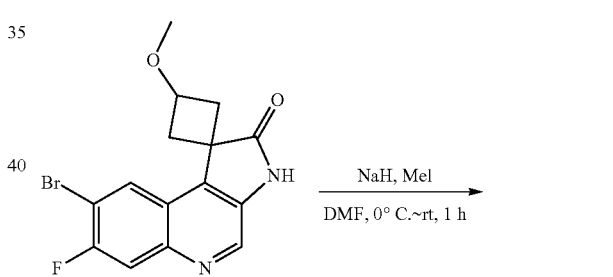

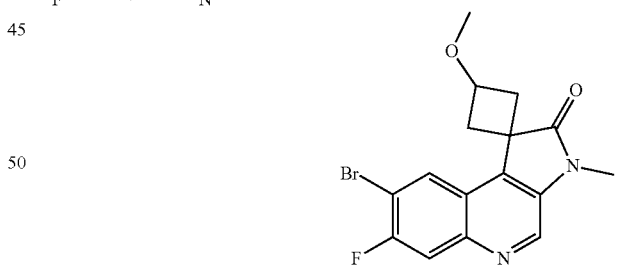

8'-Bromo-7-fluoro-3-methoxy-3'-methylspiro[cyclobutane-1,1'-pyrrolo[2,3-c]quinolin]-2'(3'H)-one: A solution of 8-bromo-7-fluoro-3-methoxy-2,3-dihydrospiro[cyclobutane-1,1-pyrrolo[2,3-c]quinolin]-2-one (550 mg, 1.56 mmol) in N,N-dimethylformamide (10.0 mL) was treated with sodium hydride (81.4 mg, 2.04 mmol 60% dispersed in mineral oil) for 0.5 hours at 0° C. followed by the addition of iodomethane (265 mg, 1.87 mmol) dropwise over 2 min at 0° C. After stirring for additional 1 hour at ambient temperature, the reaction was quenched by saturated aqueous ammonium chloride (20.0 mL) and diluted with water (150 mL). The resulting mixture was extracted with ethyl acetate (3×50.0 mL). The combined organic layers was washed with brine (2×30.0 mL) and dried over anhydrous sodium sulfate. After filtration, the filtrate was concentrated under reduced pressure. The residue was purified by silica gel column chromatography, eluted with 5%~10% ethyl acetate in petroleum ether to afford the title compound as a yellow solid (500 mg, 87%): MS: [(M+1)]⁺=365.10, 367.10.

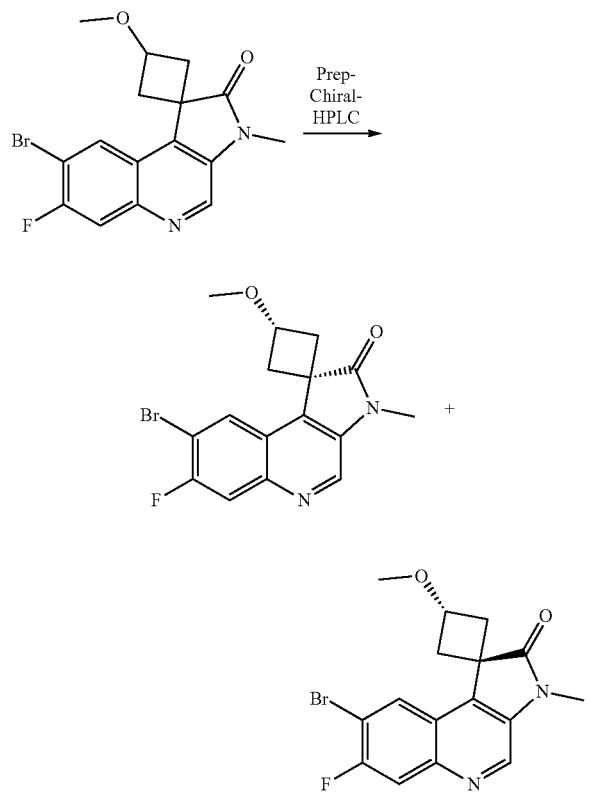

cis-8'-Bromo-7'-fluoro-3-methoxy-3'-methylspiro[cyclobutane-1,1'-pyrrolo[2,3-c]quinolin]-2' (3'H)-one: 8-bromo-7-fluoro-3-methoxy-3-methyl-2,3-dihydrospiro[cyclobutane-1,1-pyrrolo[2,3-c]quinolin]-2-one (500 mg, 1.07 mmol) was separated by Prep-Chiral-HPLC with the following conditions: [Column: CHIRALPAK IC, 2×25 cm, 5 μm; Mobile Phase A: Hexane/dichloromethane (v/v=3/1 plus 0.1% diethylamine); Mobile Phase B: EtOH; Flow rate: 20.0 mL/min; Gradient: 30 B % in 13 min; Detector UV 220/254 nm; RT1: 8.78 min; RT2: 11.34 min]. The fractions containing desired product were collected and concentrated under reduced pressure to afford cis-8'-bromo-7'-fluoro-3-methoxy-3'-methylspiro[cyclobutane-1,1'-pyrrolo[2,3-c]quinolin]-2'(3'H)-one (RT2: 11.34 min) as an off-white solid (165 mg, 33%): ¹H NMR (400 MHz, DMSO-d₆) δ 8.93 (s, 1H), 8.29 (d. J=7.3 Hz, 1H), 8.03 (d, J=10.0 Hz, 1H), 4.61 (p, J=7.0 Hz, 1H), 3.30 (s, 6H), 2.93 (dd, J=13.1, 8.5 Hz, 2H), 2.60 (dd, J=13.5, 6.8 Hz, 2H); MS: [(M+1)]⁺=365.10, 367.10; and trans-8'-bromo-7'-fluoro-3-methoxy-3'-methylspiro[cyclobutane-1,1'-pyrrolo[2,3-c]quinolin]-2'(3'H)-one (RT1: 8.78 min) as an off-white solid (200 mg, 40%): ¹H NMR (400 MHz, DMSO-d₆) δ 8.92 (s, 1H), 8.79 (d, J=7.5 Hz, 1H), 8.02 (d, J=10.2 Hz, 1H), 4.40-4.32 (m, 1H), 3.33 (s, 3H), 3.30 (s, 3H), 2.84-2.70 (m, 4H); MS: [(M+1)]⁺=365.10, 367.10.

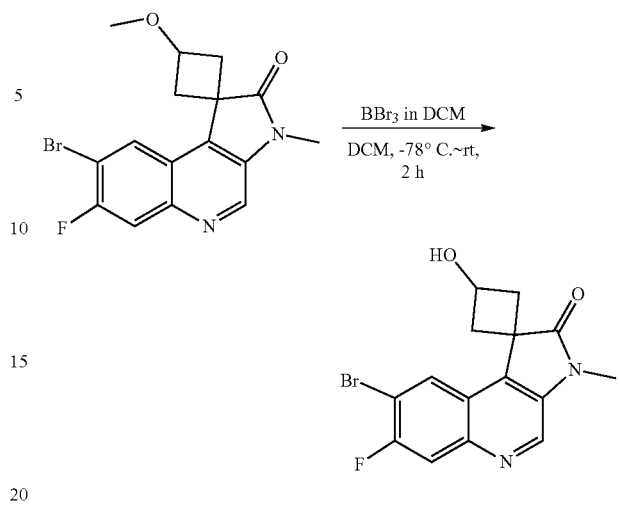

8'-Bromo-7'-fluoro-3-hydroxy-3'-methylspiro[cyclobutane-1,1'-pyrrolo[2,3-c]quinolin]-2'(3'H)-one: To a stirred solution of 8'-bromo-7'-fluoro-3-methoxy-3'-methylspiro[cyclobutane-1,1'-pyrrolo[2,3-c]quinolin]-2'(3'H)-one (900 mg, 2.46 mmol) in dichloromethane (20.0 mL) was added boron tribromide (24.6 mL, 24.6 mmol, 1M in dichloromethane) dropwise at −78° C. under nitrogen atmosphere. The resulting mixture was warmed to ambient temperature spontaneous. After stirring for additional 2 hours, the mixture was quenched with saturated aqueous sodium bicarbonate. The aqueous layer was extracted with ethyl acetate (3×100 mL). The combined organic layers was washed with brine (3×100 mL) and dried over anhydrous sodium sulfate. After filtration, the filtrate was concentrated under reduced pressure. The residue was purified by silica gel column chromatography, eluted with 1%~5% methanol in dichloromethane. The fractions containing desired product were collected and concentrated under reduced pressure to afford the title compound as a colorless solid (530 mg, 62%): ¹H NMR (400 MHz, DMSO-d₆) δ 8.96-8.89 (m, 1.6H), 8.32 (d, J=7.4 Hz, 0.4H), 8.05-7.98 (m, 1H), 5.99 (d, J=6.5 Hz, 0.6H), 5.73 (d, J=5.7 Hz, 0.4H), 4.92 (h, J=7.5 Hz, 0.4H), 4.70 (h, J=7.0 Hz, 0.6H), 3.31 (s, 1.4H), 3.29 (s, 1.6H), 2.98-2.87 (m, 0.6H), 2.81-2.67 (m, 2.4H), 2.65-2.55 (m, 0.6H); MS: [(M+1)]⁺=351.00, 353.00.

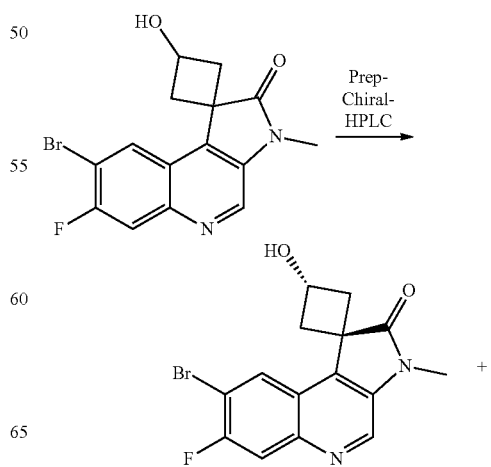

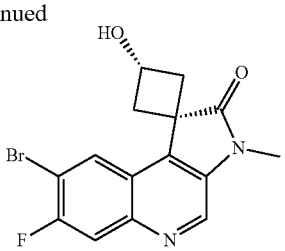

cis-8'-Bromo-7'-fluoro-3-hydroxy-3'-methylspiro[cyclobutane-1,1'-pyrrolo[2,3-c]quinolin]-2'(3'H)-one: 8-Bromo-7-fluoro-3-hydroxy-3-methyl-2,3-dihydrospiro[cyclobutane-1,1-pyrrolo[2,3-c]quinolin]-2-one (270 mg) was separated by Prep-Chiral-HPLC with the following conditions [Column: CHIRALPAK IC, 2×25 cm, 5 μm; Mobile Phase A: Hexane/dichloromethane (v/v=3/1 plus 0.1% diethylamine); Mobile Phase B: EtOH; Flow rate: 20 mL/min; Gradient: 30 B % in 19 min; Detector: UV 220/254 nm; RT1: 10.52 min; RT2: 17.38 min]. The fractions containing desired product were collected and concentrated under reduced pressure to afford trans-8'-bromo-7'-fluoro-3-hydroxy-3'-methylspiro[cyclobutane-1,1'-pyrrolo[2,3-c]quinolin]-2'(3'H)-one (RT1: 10.52 min) as a light yellow solid (98.0 mg, 37%): $^1$H NMR (400 MHz, DMSO-$d_6$) δ 8.94 (d, J=7.5 Hz, 1H), 8.90 (s, 1H), 8.01 (d, J=10.1 Hz, 1H), 5.98 (s, 1H), 4.70 (s, 1H), 3.29 (s, 3H), 2.82-2.69 (m, 4H); MS: [(M+1)]$^+$=351.00, 353.00 and cis-8'-bromo-7'-fluoro-3-hydroxy-3'-methylspiro[cyclobutane-1,1'-pyrrolo[2,3-c]quinolin]-2'(3'H)-one (RT2:17.38 min) as a light yellow solid (65.0 mg, 24%): $^1$H NMR (400 MHz, DMSO-$d_6$) δ 8.92 (s, 1H), 8.32 (d, J=7.3 Hz, 1H), 8.02 (d, J=10.0 Hz, 1H), 5.73 (d, J=5.7 Hz, 1H), 4.91 (p, J=6.9 Hz, 1H), 3.31 (s, 3H), 2.97-2.78 (m, 2H), 2.65-2.54 (m, 2H); MS: [(M+1)]$^+$=351.00, 353.00.

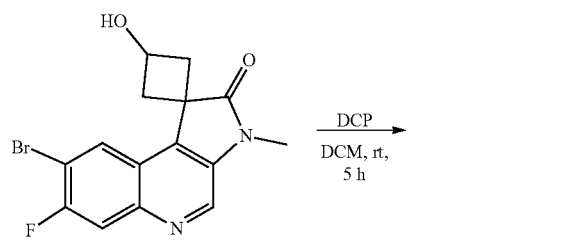

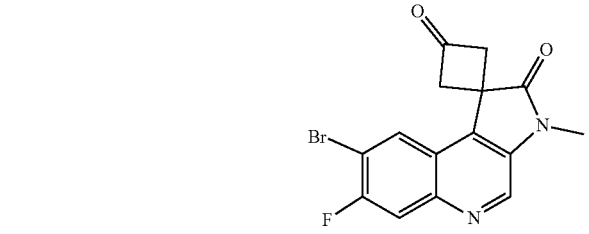

8'-Bromo-7'-fluoro-3'-methylspiro[cyclobutane-1,1'-pyrrolo[2,3-c]quinoline]-2',3(3'H)-dione: To a solution of 8-bromo-7-fluoro-3-hydroxy-3-methylspiro[cyclobutane-1,1-pyrrolo[2,3-c]quinolin]-2-one (2.00 g, 5.70 mmol) in dichloromethane (40.0 mL) was added Dess-Martin periodinane (3.62 g, 8.54 mmol) at 0° C. After stirring for 5 hours at 25° C., the reaction was quenched by a mixture of saturated aqueous sodium thiosulfate solution and saturated aqueous sodium bicarbonate (v/v=1/1) (50 mL). The resulting mixture was extracted with ethyl acetate (3×200 mL). The combined organic layers was washed with brine (3×100 mL) and dried over anhydrous sodium sulfate. After filtration, the filtrate was concentrated under reduced pressure. The residue was purified by silica gel column chromatography, eluted with 2%~5% methanol in dichloromethane. The desired fractions were collected and concentrated under reduced pressure to afford the title compound as a light yellow solid (1.65 g, 83%): $^1$H NMR (400 MHz, DMSO-$d_6$) δ 9.01 (s, 1H), 8.29 (d, J=7.3 Hz, 1H), 8.04 (d, J=10.1 Hz, 1H), 4.09-4.00 (m, 2H), 3.60-3.50 (m, 2H); MS: [(M+1)]$^+$=349.00, 351.00.

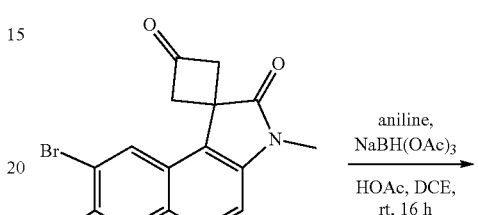

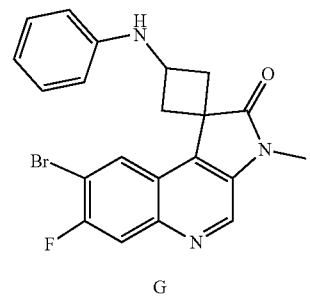

8'-Bromo-7'-fluoro-3'-methyl-3-(phenylamino)spiro[cyclobutane-1,1'-pyrrolo[2,3-c]quinolin]-2'(3'H)-one: To a solution of 8'-bromo-7'-fluoro-3'-methylspiro[cyclobutane-1,1'-pyrrolo[2,3-c]quinoline]-2',3(3'H)-dione (100 mg, 0.29 mmol) in 1,2-dichloroethane (5.00 mL) were added aniline (80.0 mg, 0.86 mmol) and acetic acid (18.0 mg, 0.29 mmol) at ambient temperature under nitrogen atmosphere. The resulting mixture was stirred for 2 hours at ambient temperature under nitrogen atmosphere followed by the addition of sodium triacetoxyborohydride (304 mg, 1.43 mmol). The resulting mixture was stirred for additional 16 hours at 25° C. The reaction was quenched by water (20.0 mL). The resulting mixture was extracted with ethyl acetate (5×50.0 mL). The combined organic layers was washed with brine (2×50.0 mL) and dried over anhydrous sodium sulfate. After filtration, the filtrate was concentrated under reduced pressure. The residue was purified by silica gel column chromatography, eluted with 1%~4% methanol in dichloromethane. The desired fractions were collected and concentrated under reduced pressure to afford the title compound as a yellow solid (45.0 mg, 37%): $^1$H NMR (400 MHz, DMSO-$d_6$) δ 8.96-8.91 (m, 1.4H), 8.56 (d, J=7.4 Hz, 0.6H), 8.08-8.00 (m, 1H), 7.19-7.11 (m, 2H), 6.70-6.58 (m, 3H), 4.61-4.52 (m, 0.6H), 4.45-4.37 (m, 0.4H), 3.34 (s, 1.2H), 3.33 (s, 1.8H), 3.18 (dd, J=13.3, 8.4 Hz, 1.2H), 2.93 (dd, J=12.8, 7.8 Hz, 0.8H), 2.83-2.75 (m, 0.8H), 2.57 (dd, J=13.4, 6.6 Hz, 1.2H): MS: [(M+1)]$^+$=426.05, 428.05.

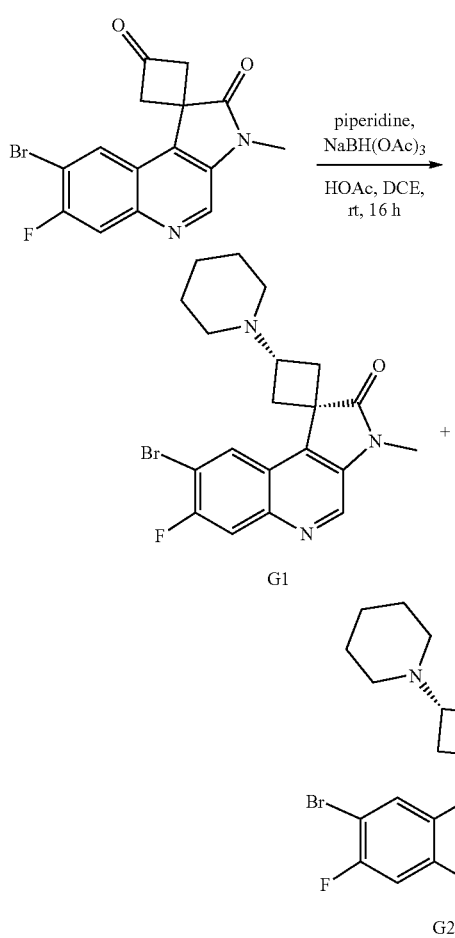

cis-8'-Bromo-7'-fluoro-3'-methyl-3-(piperidin-1-yl)spiro[cyclobutane-1,1'-pyrrolo[2,3-c]quinolin]-2'(3'H)-one and trans-8'-Bromo-7'-fluoro-3'-methyl-3-(piperidin-1-yl)spiro[cyclobutane-1,1'-pyrrolo[2,3-c]quinolin]-2'(3'H)-one To a solution of 8'-bromo-7'-fluoro-3'-methylspiro[cyclobutane-1,1'-pyrrolo[2,3-c]quinoline]-2',3(3'H)-dione (100 mg, 0.29 mmol) in 1,2-dichloroethane (3.00 mL) were added piperidine (49.0 mg, 0.57 mmol) and acetic acid (18.0 mg, 0.29 mmol) at ambient temperature under nitrogen atmosphere. The resulting mixture was stirred for 2 hours at ambient temperature under nitrogen atmosphere followed by the addition of sodium triacetoxyborohydride (304 mg, 1.43 mmol). The resulting mixture was stirred for additional 16 hours at 25° C. The reaction was quenched by water (20.0 mL). The resulting mixture was extracted with ethyl acetate (5×50.0 mL). The combined organic layers was washed with brine (2×50.0 mL) and dried over anhydrous sodium sulfate. After filtration, the filtrate was concentrated under reduced pressure. The residue was purified by Prep-TLC (DCM/MeOH=20/1, v/v) to afford cis-8'-bromo-7'-fluoro-3'-methyl-3-(piperidin-1-yl)spiro[cyclobutane-1,1'-pyrrolo[2,3-c]quinolin]-2'(3'H)-one (high polarity) as a yellow solid (40.0 mg, 34%): $^1$H NMR (400 MHz, CDCl$_3$) δ 8.70 (s, 1H), 8.40 (d, J=7.1 Hz, 1H), 7.89 (d, J=9.4 Hz, 1H), 3.97-2.85 (m, 1H), 3.39 (s, 3H), 3.10 (dd, J=13.4, 8.5 Hz, 2H), 2.84-2.66 (m, 6H), 1.84 (s, 4H), 1.60 (s, 2H); MS: [(M+1)]$^+$=418.20, 420.20; and trans-8'-bromo-7'-fluoro-3'-methyl-3-(piperidin-1-yl)spiro[cyclobutane-1,1'-pyrrolo[2,3-c]quinolin]-2'(3'H)-one (low polarity) as a yellow solid (24.3 mg, 21%): $^1$H NMR (400 MHz, CDCl$_3$) δ 9.73 (d, J=7.5 Hz, 1H), 8.66 (s, 1H), 7.83 (d, J=9.5 Hz, 1H), 3.39 (s, 3H), 3.2-3.16 (m, 1H), 2.81 (dd, J=13.3, 7.9 Hz, 2H), 2.69 (dd, J=13.5, 5.9 Hz, 2H), 2.43 (s, 4H), 1.85-1.77 (m, 4H), 1.62-1.60 (m, 2H); MS: [(M+1)]$^+$=418.20, 420.20.

The following intermediates were prepared according to the procedure described above:

| Intermediate | Structure | Name | MS: [(M + 1)]$^+$ | $^1$H NMR |
|---|---|---|---|---|
| G3 | 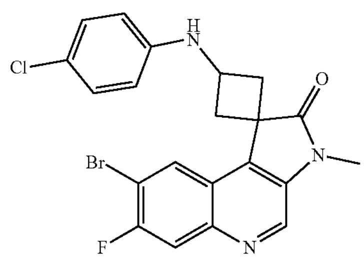 [SMILES: CN1C(=O)C2(CC(Nc3ccc(Cl)cc3)C2)c2c1cnc1cc(F)c(Br)cc21] | 8'-Bromo-3-((4-chlorophenyl)amino)-7'-fluoro-3'-methylspiro[cyclobutane-1,1'-pyrrolo[2,3-c]quinolin]-2'(3'H)-one | 460.05 462.05 | $^1$H NMR (400 MHz, CDCl$_3$) δ 8.35 (d, J = 7.1 Hz, 0.4H), 8.68 (d, J = 2.8 Hz, 1H), 8.35 (d, J = 7.1 Hz, 0.6H), 7.89 (t, J = 9.7 Hz, 1H), 7.23-7.17 (m, 2H), 6.72-6.62 (m, 2H), 4.66-4.55 (m, 1H), 3.40 (s, 1.2H), 3.39 (s, 1.8H), 3.29 (dd, J = 13.9, 8.3 Hz, 1.2H), 3.15-3.08 (m, 0.8H), 2.79 (dd, J = 13.4, 6.9 Hz, 0.8H), 2.61 (dd, J = 14.3, 4.4 Hz, 1.2H). |
| G4$^a$ | | cis-8'-Bromo-7'-fluoro-3'-methyl-3-(methyl(phenyl)amino)spiro[cyclobutane-1,1'-pyrrolo[2,3-c]quinolin]-2'(3'H)-one | 440.20 442.20 | $^1$H NMR (400 MHz, DMSO-d$_6$) δ 8.95 (s, 1H), 8.55 (d, J = 7.3 Hz, 1H), 8.06 (d, J = 10.1 Hz, 1H), 7.24 (t, J = 7.8 Hz, 2H), 6.92 (d, J = 8.2 Hz, 2H), 6.76 (t, J = 7.2 Hz, 1H), 4.83 (p, J = 8.3 Hz, 1H), 3.32 (s, 3H), 3.11-3.03(m, 5H), 2.84 (dd, J = 13.8, 8.0 Hz, 2H). |

-continued

| Intermediate | Structure | Name | MS: [(M + 1)]+ | 1H NMR |
|---|---|---|---|---|
| G5[a] | 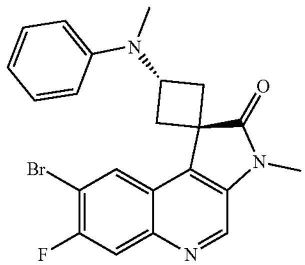 [SMILES: CN1c2cnc3cc(F)c(Br)cc3c2[C@]2(C[C@@H](N(C)c3ccccc3)C2)C1=O] | trans-8'-Bromo-7'-fluoro-3'-methyl-3-(methyl(phenyl)amino)spiro[cyclobutane-1,1'-pyrrolo[2,3-c]quinolin]-2'(3'H)-one | 440.20 442.20 | 1H NMR (400 MHz, DMSO-d$_6$) δ 9.02 (d, J = 7.7 Hz, 1H), 8.92 (s, 1H), 8.00 (d, J = 10.1 Hz, 1H), 7.28 (t, J = 7.9 Hz, 2H), 7.00 (d, J = 8.2 Hz, 2H), 7.28 (t, J =7.4 Hz, 1H), 4.29 (p, J = 7.3 Hz, 1H), 3.32 (s, 3H), 2.96 (s, 3H), 2.91-2.75 (m, 4H). |
| G6 | 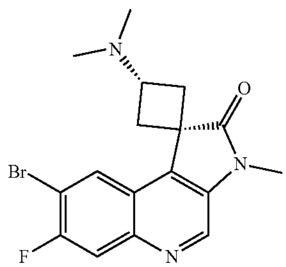 [SMILES: CN1c2cnc3cc(F)c(Br)cc3c2[C@]2(C[C@H](N(C)C)C2)C1=O] | cis-8'-Bromo-3-(dimethylamino)-7'-fluoro-3'-methylspiro[cyclobutane-1,1'-pyrrolo[2,3-c]quinolin]-2'(3'H)-one | 378.20 380.20 | 1H NMR (400 MHz, DMSO-d$_6$) δ 8.94 (s, 1H), 8.41 (d, J = 7.4 Hz, 1H), 8.05 (d, J = 10.0 Hz, 1H), 3.31 (s, 4H), 2.86-2.75(m, 2H), 2.71-2.61 (m, 2H), 2.81 (s, 2H), 2.37 (s, 6H). |
| G7 | 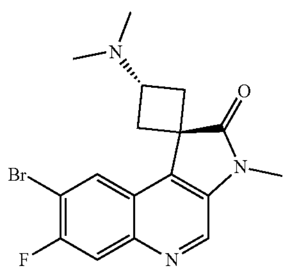 [SMILES: CN1c2cnc3cc(F)c(Br)cc3c2[C@]2(C[C@@H](N(C)C)C2)C1=O] | trans-8'-Bromo-3-(dimethylamino)-7'-fluoro-3'-methylspiro[cyclobutane-1,1'-pyrrolo[2,3-c]quinolin]-2'(3'H)-one | 378.20 380.20 | 1H NMR (400 MHz, DMSO-d$_6$) δ 9.35 (d, J = 7.7 Hz, 1H), 8.91 (s, 1H), 8.00 (d, J = 10.2 Hz, 1H), 3.30 (s, 3H), 3.04 (p, J = 7.2 Hz, 1H), 2.65-2.58 (m, 4H), 2.22 (s, 6H). |
| G8 | 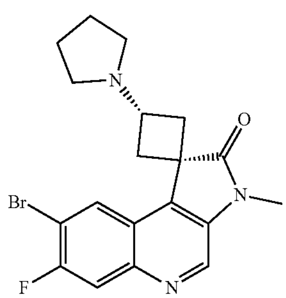 [SMILES: CN1c2cnc3cc(F)c(Br)cc3c2[C@]2(C[C@H](N3CCCC3)C2)C1=O] | cis-8'-Bromo-7'-fluoro-3' methyl-3-(pyrrolidin-1-yl)spiro[cyclobutane-1,1'-pyrrolo[2,3-c]quinolin]-2'(3'H)-one | 404.00 406.00 | 1H NMR (400 MHz, CDCl$_3$) δ 8.68 (s, 1H), 8.33 (s, 1H), 7.87 (d, J = 9.5 Hz, 1H), 4.16 (s, 1H), 3.37 (s, 3H), 3.28-2.62 (m, 8H), 1.99 (s, 4H). |
| G9 | 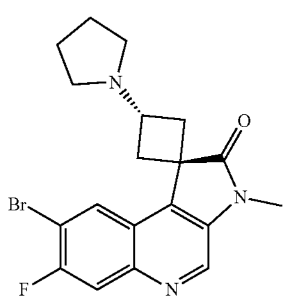 [SMILES: CN1c2cnc3cc(F)c(Br)cc3c2[C@]2(C[C@@H](N3CCCC3)C2)C1=O] | trans-8'-Bromo-7'-fluoro-3'-methyl-3-(pyrrolidin-1-yl)spiro[cyclobutane-1,1'-pyrrolo[2,3-c]quinolin]-2'(3'H)-one | 404.00 406.00 | 1H NMR (400 MHz, CDCl$_3$) δ 9.89 (d, J = 7.2 Hz, 1H), 8.65 (s, 1H), 7.80 (d, J = 9.5 Hz, 1H), 4.59-4.49 (m, 1H), 3.82 (s, 2H), 3.37 (d, J = 7.0 Hz, 3H), 2.89-2.79 (m, 2H), 2.79-2.67 (m, 2H), 2.59 (s, 2H), 2.32 (s, 1H), 2.14 (s, 1H), 1.96 (s, 2H). |

-continued

| Intermediate | Structure | Name | MS: [(M + 1)]+ | 1H NMR |
|---|---|---|---|---|
| G10 | 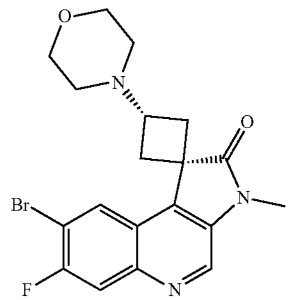 [SMILES: CN1c2cnc3cc(F)c(Br)cc3c2[C@]2(C[C@H](N3CCOCC3)C2)C1=O] | 8'-Bromo-7'-fluoro-3'-methyl-3-morpholinospiro[cyclobutane-1,1'-pyrrolo[2,3-c]quinolin]-2'(3'H)-one | 420.30 422.30 | 1H NMR (400 MHz, CDCl3) δ 8.67 (s, 1H), 8.41 (s, 1H), 7.87 (d, J = 9.2 Hz, 1H), 3.83 (s, 4H), 3.70-3.57 (m, 1H), 3.37 (s, 3H), 2.96-2.85 (m, 2H), 2.79-2.65 (m, 2H), 2.59 (s, 4H). |
| G11 | 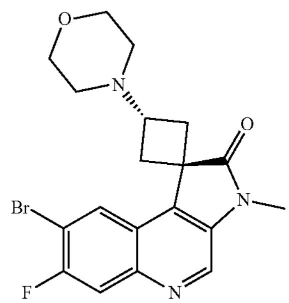 [SMILES: CN1c2cnc3cc(F)c(Br)cc3c2[C@]2(C[C@@H](N3CCOCC3)C2)C1=O] | trans-8'-Bromo-7'-fluoro-3'methyl-3-morpholinospiro[cyclobutane-1,1'-pyrrolo[2,3-c]quinolin]-2'(3'H)-one | 420.30 422.10 | 1H NMR (400 MHz, CDCl3) δ 9.61 (d, J = 7.5 Hz, 1H), 8.65 (s, 1H), 7.83 (d, J = 9.9 Hz, 1H), 3.95 (t, J = 4.6 Hz, 4H), 3.37 (s, 3H), 3.27 (p, J = 6.5 Hz, 1H), 2.81 (dd, J = 13.6, 8.1 Hz, 2H), 2.68 (dd, J = 13.4, 5.8 Hz, 2H), 2.51 (s, 4H). |
| G12[b] | 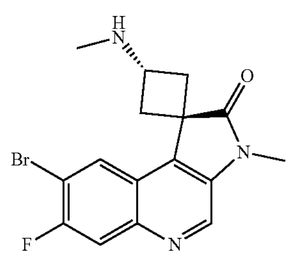 [SMILES: CN[C@H]1C[C@@]2(C1)C(=O)N(C)c1cnc3cc(F)c(Br)cc3c12] | 8'-Bromo-7'-fluoro-3'-methyl-3-(methylamino)spiro[cyclobutane-1,1'-pyrrolo[2,3-c]quinolin]-2'(3'H)-one | 364.00 366.00 | 1H NMR (400 MHz, CDCl3) δ 9.12 (d, J = 7.1 Hz, 1H), 8.66 (s, 1H), 7.80 (d, J = 9.4 Hz, 1H), 4.43 (p, J = 8.3 Hz, 1H), 3.37 (s, 3H), 3.21 (t, J = 10.4 Hz, 2H), 2.85 (t, J = 10.0 Hz, 2H), 2.64 (s, 3H). |
| G13[b] | 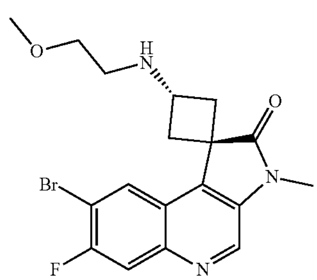 | 8'-Bromo-7'-fluoro-3-((2-methoxyethyl)amino)-3'-methylspiro[cyclobutane-1,1'-pyrrolo[2,3-c]quinolin]-2'(3'H)-one | 408.10 410.10 | 1H NMR (400 MHz, CDCl3) δ 9.05 (d, J = 7.1 Hz, 1H), 8.65 (s, 1H), 7.76 (d, J = 9.4 Hz, 1H), 4.49 (p, J = 8.2 Hz, 1H), 3.71 (t, J = 5.0 Hz, 2H), 3.40 (s, 3H), 3.37 (s, 3H), 3.24-3.14 (m, 2H), 3.09 (t, J = 5.1 Hz, 2H), 2.89-2.81 (m, 2H). |

Note: a: The two isomers was separated by reversed phase chromatography with the following condition: [Column: Spherical C18 Column, 20-40 μm, 120 g; Mobile Phase A: Water (plus 10 mM NH4HCO3); Mobile Phase B: Acetonitrile; Flow rate: 50 mL/min; Gradient of B: 5%~30%, 4 min, 30%~73% 23 min, 73%, 5 min, 73%~95% 3 min, 95%, 4 min; Detector: 254 nm], cis-isomer: RT: 29 min; trans-isomer: RT: 31 min; b: Only one trans isomer was obtained; others: The two isomers as separated by Prep-TLC (DCM/MeOH=20/1, v/v), cis-isomer: high polarity, trans-isomer low polarity.

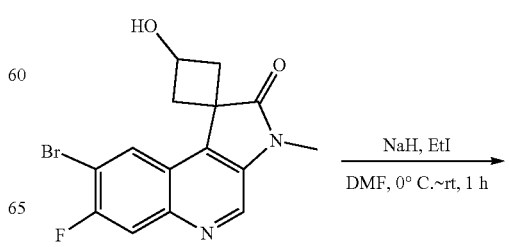

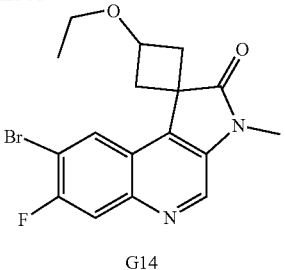

G14

8'-Bromo-3-ethoxy-7'-fluoro-3'-methylspiro[cyclobutane-1,1'-pyrrolo[2,3-c]quinolin]-2' (3'H)-one: A solution of 8'-bromo-7'-fluoro-3-hydroxy-3'-methylspiro[cyclobutane-1,1'-pyrrolo[2,3-c]quinolin]-2'(3'H)-one (200 mg, 0.57 mmol) in N,N-dimethylformamide (5.00 mL) was treated with sodium hydride (30.0 mg, 0.74 mmol, 60% w/w dispersed in mineral oil) for 0.5 hours at 0° C. under nitrogen atmosphere followed by the addition of iodoethane (115 mg, 0.74 mmol). After stirring for additional 1 hour at 25° C., the reaction was quenched by saturated aqueous ammonium chloride (2.00 mL) and diluted with water (30.0 mL). The resulting mixture was extracted with ethylacetate (3×50.0 mL). The combined organic layers was washed with brine (2×30.0 mL) and dried over anhydrous sodium sulfate. After filtration, the filtrate was concentrated under reduced pressure. The residue was purified by silica gel column chromatography, eluted with 1%~5% methanol in dichloromethane. The desired fractions were collected and concentrated under reduced pressure to afford the title compound as a yellow solid (40.0 mg, 19%): $^1$H NMR (400 MHz, CDCl$_3$) δ 8.96 (d, J=7.3 Hz, 0.6H), 8.66 (d, J=5.8 Hz, 1H), 8.27 (d, J=7.2 Hz, 0.4H), 7.85 (t, J=9.3 Hz, 1H), 4.74 (p, J=7.2 Hz, 0.35H), 4.56 (p, J=6.9 Hz, 0.7H), 3.59 (q, J=6.9 Hz, 2H), 3.37 (d, J=4.8 Hz, 3H), 3.02-2.77 (m, 4H), 1.43-1.29 (m, 3H); MS: [(M+1)]$^+$=379.00, 381.00.

The following intermediates were prepared according to the procedure described above:

| Intermediate | Structure | Name | MS: [(M + 1)]$^+$ | $^1$H NMR |
|---|---|---|---|---|
| G15 | | 8'-Bromo-7'-fluoro-3-isopropoxy-3'methylspiro[cyclobutane-1,1'-pyrrolo[2,3-c]quinolin]-2'(3'H)-one | 393.00 395.00 | $^1$H NMR (400 MHz, CDCl$_3$) δ 8.99 (d, J = 7.6 Hz, 0.7H), 8.66 (d, J = 5.6 Hz, 1H), 8.31 (d, J = 6.8 Hz, 0.35H), 7.92-7.84 (m, 1H), 7.87 (d, J = 8.3 Hz, 1H), 4.71-4.62 (m, 0.35H), 3.83-3.75 (m, 0.7H), 3.37 (d, J = 3.9 Hz, 3H), 3.04-2.78 (m, 4H), 1.32-1.27 (m, 6H). |
| G16$^a$ | | cis-8'-Bromo-7'-fluoro-3'-methyl-3-(1-phenylethoxy)spiro[cyclobutane-1,1'-pyrrolo[2,3-c]quinolin]-2'(3'H)-one | 455.30 457.30 | $^1$H NMR (400 MHz, CDCl$_3$) δ 8.64 (s, 1H), 8.06 (d, J = 7.1 Hz, 1H), 7.81 (d, J = 9.5 Hz, 1H), 7.45-7.37 (m, 4H), 7.34-7.28 (m, 1H), 4.68 (p, J = 7.3 Hz, 1H), 4.59 (q, J = 6.5 Hz, 1H), 3.35 (s, 3H), 2.96 (dd, J = 12.9, 6.8 Hz, 1H), 2.89-2.78 (m, 2H), 2.63-2.55 (m, 1H), 1.58 (d, J = 6.5 Hz, 3H). |
| G17$^a$ | | trans-8'-Bromo-7'-fluoro-3'-methyl-3-(1-phenylethoxy)spiro[cyclobutane-1,1'-pyrrolo[2,3-c]quinolin]-2'(3'H)-one | 455.30 457.30 | $^1$H NMR (400 MHz, CDCl$_3$) δ 8.98 (d, J = 7.3 Hz, 1H), 8.62 (s, 1H), 7.85 (d, J = 9.6 Hz, 1H), 7.44-7.40 (m 2H), 7.39-7.33 (m, 2H), 7.30-7.26 (m, 1H), 4.61-4.50 (m, 2H), 3.32 (s, 3H), 2.98-2.83 (m, 2H), 2.75-2.62 (m, 2H), 1.65 (d, J =6.5 Hz, 3H). |

| Intermediate | Structure | Name | MS: [(M + 1)]+ | 1H NMR |
|---|---|---|---|---|
| G18 | 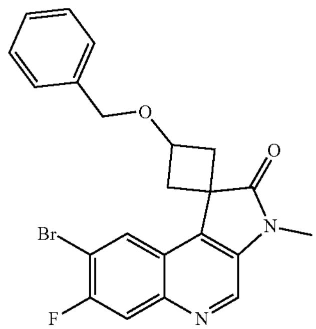 [SMILES: CN1C(=O)C2(CC(OCc3ccccc3)C2)c2c1cnc1cc(F)c(Br)cc21] | 3-(Benzyloxy)-8'-bromo-7'-fluoro-3'-methylspiro[cyclobutane-1,1'-pyrrolo[2,3-c]quinolin]-2'(3'H)-one | 441.00 443.00 | 1H NMR (400 MHz, DMSO-$d_6$) δ 8.92 (d, J = 3.6 Hz, 1H), 8.79 (d, J = 7.6 Hz, 0.5H), 8.25 (d, J = 7.2 Hz, 0.5H), 8.03 (d, J = 10.1 Hz, 1H), 7.50 (d, J = 7.0 Hz, 1H), 7.46-7.37 (m, 3H), 7.37-7.30 (m, 1H), 4.83 (p, J = 6.8 Hz, 0.5H), 4.62-4.50 (m, 2.5H), 3.30 (d, J = 5.7 Hz, 3H), 2.98-2.90 (m, 1H), 2.80 (d, J = 6.7 Hz, 2H), 2.72-2.64 (m, 1H). |

Note:
aThe two isomers was separated by reversed phase chromatography with the following conditions:
[Column: Spherical C18 Column, 20-40 μm, 120 g; Mobile Phase A: Water (plus 10 mM NH$_4$HCO$_3$); Mobile Phase B: Acetonitrile; Flow rate: 50 mL/min; Gradient of B: 5%~33%, 4 min, 30%~40%, 6 min, 40%~68%, 28 min, 68%, 3 min, 68%~5%, 5 min, 85%, 3 min, 85%~95%, 3 min, 95%, 4 min Detector: UV 254 nm]; cis-isomer: RT: 38 min; trans-isomer: RT: 46 min Intermediate H

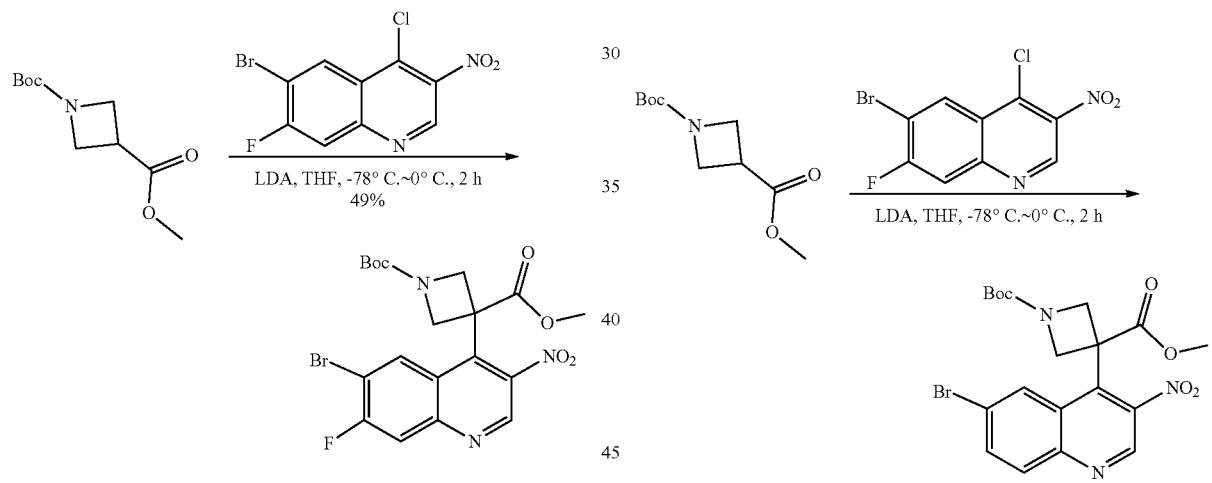

1-(tert-Butyl) 3-methyl 3-(6-bromo-7-fluoro-3-nitroquinolin-4-yl)azetidine-1,3-dicarboxylate: To a solution of freshly prepared lithium diisopropylamide (137 mmol) in anhydrous tetrahydrofuran (110 mL) was added a solution of 1-tert-butyl 3-methyl azetidine-1,3-dicarboxylate (29.3 g, 137 mmol) in tetrahydrofurn (100 mL) at −78° C. After stirring for 1 hour, a solution of 6-bromo-4-chloro-7-fluoro-3-nitroquinoline (32.0 g, 105 mmol) in tetrahydrofuran (100 mL) was added to the reaction mixture over 20 min The resulting mixture was slowly warmed to 0° C. The reaction was quenched by saturated aqueous ammonium chloride (20.0 mL) and diluted with water (800 mL). The resulting mixture was extracted with ethyl acetate (3×150 mL). The combined organic layers was washed with brine (2×100 mL) and dried over anhydrous sodium sulfate. After filtration, the filtrate was concentrated under reduced pressure. The residue was purified by silica gel column chromatography, eluted with 5%~20% ethyl acetate in petroleum ether to afford the title compound as a light yellow solid (25.0 g, 49%): 1H NMR (400 MHz, DMSO-$d_6$) δ 9.35 (s, 1H), 8.21 (d, J=9.3 Hz, 1H), 8.14 (d, J=7.1 Hz, 1H), 4.18-4.11 (m, 2H), 3.87-3.74 (m, 2H), 3.66 (s, 3H), 1.37 (s, 9H); MS: [(M+1)]+=484.20, 486.20.

1-(tert-Butyl) 3-methyl 3-(6-bromo-3-nitroquinolin-4-yl) azetidine-1,3-dicarboxylate. The title compound was prepared according to the procedure described above as an orange solid (1.90 g, 58%): 1H NMR (400 MHz, CDCl$_3$) δ 9.32 (s, 1H), 8.14 (d, J=8.9 Hz, 1H), 7.98 (dd, J=9.0, 2.0 Hz, 1H), 7.65 (d, J=2.1 Hz, 1H), 4.75 (d, J=8.0 Hz, 2H), 4.14 (d, J=7.1 Hz, 2H), 3.90 (s, 3H), 1.37 (s, 9H); MS: [(M+1)]+=466.20, 468.20.

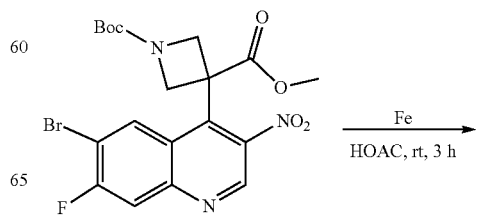

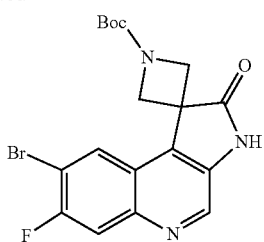

tert-Butyl 8'-bromo-7'-fluoro-2'-oxo-2',3'-dihydrospiro[azetidine-3,1'-pyrrolo[2,3-c]quinoline]-1-carboxylate To a solution of 1-tert-butyl 3-methyl 3-(6-bromo-7-fluoro-3-nitroquinolin-4-yl)azetidine-1,3-dicarboxylate (12.0 g, 24.8 mmol) in acetic acid (300 mL) was added iron powder (9.69 g, 174 mmol) at ambient temperature. After stirring for 3 hours at ambient temperature, the resulting mixture was concentrated under reduced pressure. The residue was taken up with water (200 mL) and extracted with ethyl acetate (4×100 mL). The combined organic layers was washed with brine (2×100 mL) and dried over anhydrous sodium sulfate. After filtration, the filtrate was concentrated under reduced pressure. The residue was purified by silica gel column chromatography, eluted with 1%~5% methanol in dichloromethane to afford the title compound as an off-white solid (10.4 g, 99%): $^1$H NMR (400 MHz, DMSO-$d_6$) δ 11.02 (br, 1H), 8.71 (s, 1H), 8.24 (d, J=7.3 Hz, 1H), 8.03 (d, J=10.1 Hz, 1H), 4.29 (d, J=9.0 Hz, 2H), 4.21 (d, J=9.0 Hz, 2H), 1.49 (s, 9H); MS: [(M+1)]$^+$=422.20, 424.20.

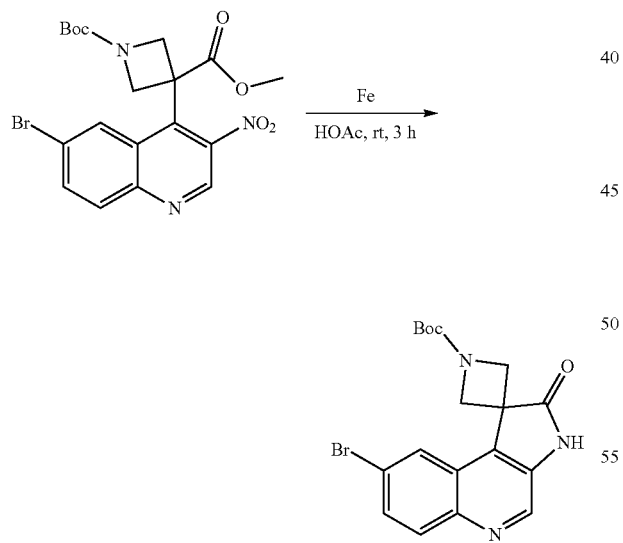

tert-Butyl 8'-bromo-2'-oxo-2',3'-dihydrospiro[azetidine-3,1'-pyrrolo[2,3-c]quinoline]-1-carboxylate.

It was prepared according to the procedure described above as a colorless solid (780 mg, 88%): $^1$H NMR (400 MHz, DMSO-$d_6$) δ 11.01 (br, 1H), 8.70 (s, 1H), 8.12 (s, 1H), 8.02 (d, J=9.0 Hz, 1H), 7.80 (d, J=9.1 Hz, 1H), 4.30 (d, J=8.8 Hz, 2H), 4.22 (d, J=9.1 Hz, 2H), 1.51 (s, 9H); MS: [(M+1)]$^+$=404.20, 406.20.

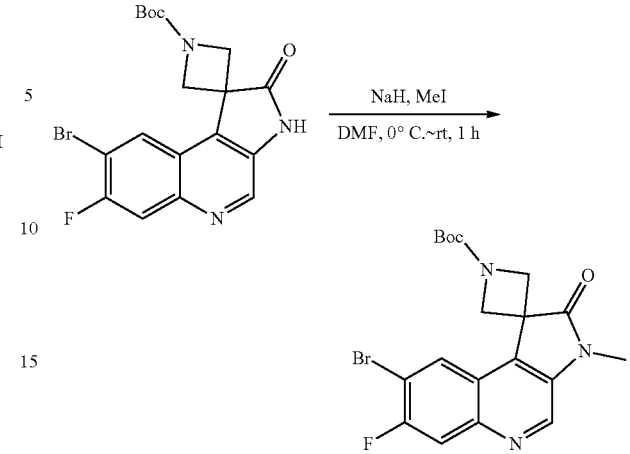

tert-Butyl 8'-bromo-7'-fluoro-3'-methyl-2'-oxo-2',3'-dihydrospiro[azetidine-3,1'-pyrrolo[2,3-c]quinoline]-1-carboxylate: To a stirred solution of tert-butyl 8-bromo-7-fluoro-2-oxo-2,3-dihydrospiro[azetidine-3,1-pyrrol[2,3-c]quinoline]-1-carboxylate (4.22 g, 9.99 mmol) in N,N-dimethylformamide (100 mL) was added sodium hydride (0.52 g, 13.0 mmol, 60% dispersed in mineral oil) at 0° C. under nitrogen atmosphere. The resulting mixture was stirred for 1 hour at ambient temperature followed by the addition of iodomethane (1.70 g, 12.0 mmol). After stirring for additional 1 hour at ambient temperature, the reaction was quenched by saturated aqueous ammonium chloride (20.0 mL) and diluted with water (1.00 L). The precipitated solid was collected by filtration, washed with water (3×30.0 mL) and hexane (2×30.0 mL). The resulting solid was dried under infrared light to afford the title compound as a light yellow solid (3.93 g, 90%): $^1$H NMR (400 MHz, CDCl$_3$) δ 8.71 (s, 1H), 8.47 (d, J=7.0 Hz, 1H), 7.94 (d, J=9.1 Hz, 1H), 4.54 (d, J=9.1 Hz, 2H), 4.31 (d, J=9.0 Hz, 2H), 3.40 (s, 3H), 1.56 (s, 9H); MS: [(M+1)]$^+$=436.15, 438.15.

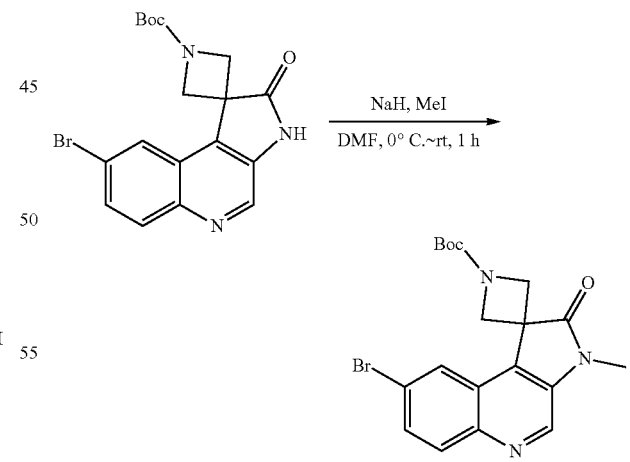

tert-Butyl 8'-bromo-3'-methyl-2-oxo-2',3'-dihydrospiro[azetidine-3,1'-pyrrolo[2,3-c]quinoline]-1-carboxylate The title compound was prepared according to the procedure described above as a colorless solid (289 mg, 92%):

¹H NMR (400 MHz, DMSO-d₆) δ 8.94 (s, 1H), 8.13 (d, J=2.2 Hz, 1H), 8.05 (d, J=9.0 Hz, 1H), 7.81 (dd, J=9.1, 2.2 Hz, 1H), 4.33-4.17 (m, 4H), 3.31 (s, 3H), 1.50 (s, 9H); MS: [(M+1)]⁺=418.20, 420.20.

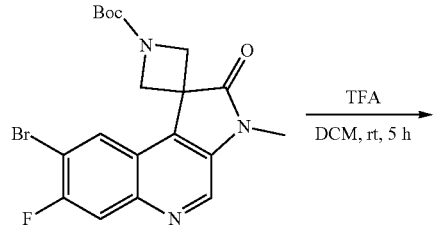

8-Bromo-7-fluoro-3-methyl-2,3-dihydrospiro[azetidine-3,1-pyrrolo[2,3-c]quinolin]-2-one: A solution of tert-butyl 8-bromo-7-fluoro-3-methyl-2-oxo-2,3-dihydrospiro[azetidine-3,1-pyrrolo[2,3-c]quinoline]-1-carboxylate (3.93 g, 9.01 mmol) and trifluoroacetic acid (20.0 mL) in dichloromethane (100 mL) was stirred for 5 hours at ambient temperature. The resulting mixture was concentrated under reduced pressure. The residue was basified to pH=8 with saturated aqueous sodium bicarbonate. The resulting mixture was extracted with ethyl acetate (6×300 mL). The combined organic layers was washed with brine (2×300 mL) and dried over anhydrous sodium sulfate. After filtration, the filtrate was concentrated under reduced pressure to afford the title compound as a light yellow solid (3.00 g, 99%): ¹H NMR (400 MHz, DMSO-d₆) δ 9.56 (d, J=7.7 Hz, 1H), 8.92 (s, 1H), 8.02 (d, J=10.2 Hz, 1H), 4.18 (d, J=7.5 Hz, 2H), 3.59 (d, J=7.5 Hz, 2H), 3.29 (s, 3H); MS: [(M+1)]⁺=335.95, 337.95.

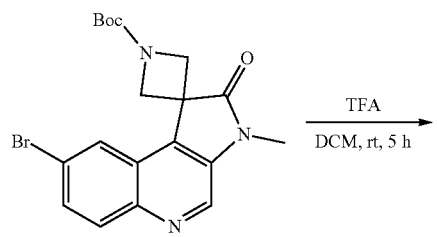

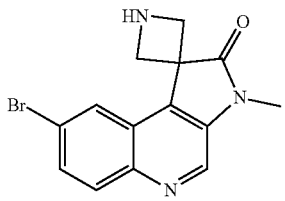

8'-Bromo-3'-methylspiro[azetidine-3,1'-pyrrolo[2,3-c]quinolin]-2'(3'H)-one: It was prepared according to the procedure described above as a colorless solid: ¹H NMR (400 MHz, DMSO-d₆) δ 9.36 (s, 1H), 8.89 (s, 1H), 8.01 (d, J=9.0 Hz, 1H), 7.78 (d, J=9.0 Hz, 1H), 4.18 (d, J=8.0 Hz, 2H), 3.61 (d, J=7.6 Hz, 2H), 3.29 (s, 3H); MS: [(M+1)]⁺=317.95, 319.95.

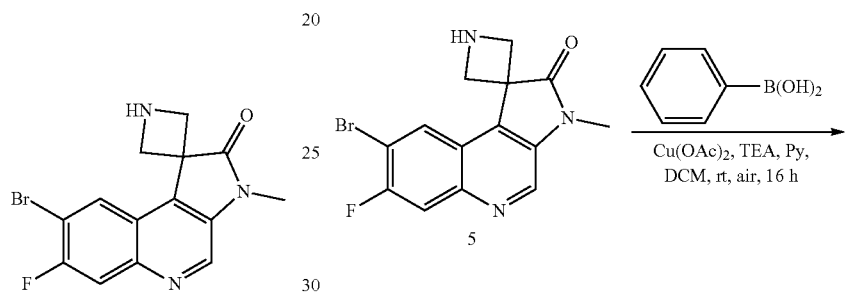

8'-Bromo-7'-fluoro-3'-methyl-1-phenylspiro[azetidine-3,1'-pyrrolo[2,3-c]quinolin]-2'(3'H)-one: To a mixture of 8'-bromo-7'-fluoro-3'-methylspiro[azetidine-3,1'-pyrrolo[2,3-c]quinolin]-2'(3'H)-one (253 mg, 0.75 mmol), triethylamine (229 mg, 2.26 mmol) and pyridine (179 mg, 2.26 mmol) in dichloromethane (20.0 mL) were added phenylboronic acid (183 mg, 1.51 mmol) and cupric acetate (273 mg, 1.51 mmol). The resulting mixture was stirred at 25° C. for 16 hours under air atmosphere. The resulting mixture was concentrated under vacuum. The residue was purified by silica gel column chromatography, eluted with 1%~4% methanol in dichlormethane. The fractions containing desired product were collected and concentrated under reduced pressure to afford the title compound as alight yellow solid (100 mg, 33%): ¹H NMR (400 MHz, CDCl₃) δ 9.05 (d, J=7.3 Hz, 1H), 8.73 (s, 1H), 7.96 (d, J=9.2 Hz, 1H), 7.35 (dd, J=8.4, 7.3 Hz, 2H), 6.94 (t, J=7.4 Hz, 1H), 6.72-6.66 (m, 2H), 4.39 (q, J=7.0 Hz, 4H), 3.40 (s, 3H), MS: [(M+1)]⁺=412.10, 414.10.

| Intermediate | Structure | Name | MS: [(M + 1)]+ | 1H-NMR |
|---|---|---|---|---|
| H1 | 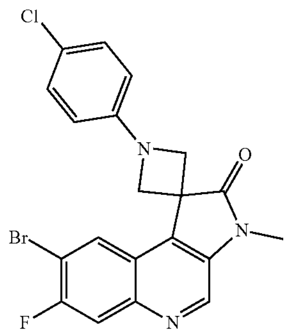 [SMILES: CN1C(=O)C2(CN(c3ccc(Cl)cc3)C2)c2c1cnc1cc(F)c(Br)cc21] | 8'-Bromo-1-(4-chlorophenyl)-7'-fluoro-3'-methylspiro[azetidine-3,1'-pyrrolo[2,3-c]quinolin]-2'(3'H)-one | 446.05 448.05 | $^1$H-NMR (400 MHz, CDCl$_3$) δ 9.07 (d, J = 7.3 Hz, 1H), 8.76 (s, 1H), 8.17 (d, J = 9.2 Hz, 1H), 7.30 (d, J = 8.1 Hz, 2H), 6.62 (d, J = 8.1 Hz, 2H), 4.40-4.33 (m, 4H), 3.43 (s, 3H). |
| H2 | 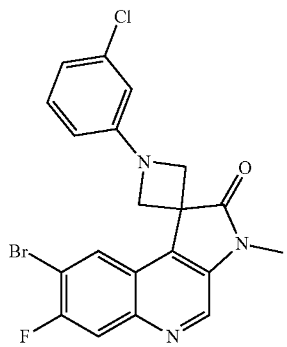 [SMILES: CN1C(=O)C2(CN(c3cccc(Cl)c3)C2)c2c1cnc1cc(F)c(Br)cc21] | 8'-Bromo-1-(3-chlorophenyl)-7'-fluoro-3'-methylspiro[azetidine-3,1'-pyrrolo[2,3-c]quinolin]-2'(3'H)-one | 445.90 447.90 | $^1$H NMR (400 MHz, DMSO-d$_6$) δ 9.00 (s, 1H), 8.74 (d, J = 7.5 Hz, 1H), 8.07 (d, J = 10.1 Hz, 1H), 7.32 (t, J = 8.0 Hz, 1H), 6.89 (d, J = 8.0 Hz, 1H), 6.79 (s, 1H), 6.68 (d, J = 8.3 Hz, 1H), 4.42 (d, J = 8.1 Hz, 2H), 4.14 (d, J = 8.1 Hz, 2H), 3.32 (s, 3H). |
| H3 | 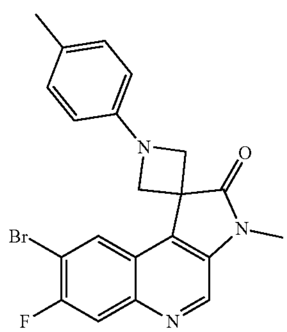 [SMILES: Cc1ccc(N2CC3(C2)C(=O)N(C)c2cnc4cc(F)c(Br)cc4c23)cc1] | 8'-Bromo-7'-fluoro-3'-methyl-1-(p-tolyl)spiro[azetidine-3,1'-pyrrolo[2,3-c]quinolin]-2'(3'H)-one | 426.05 428.05 | $^1$H NMR (400 MHz, DMSO-d$_6$) δ 9.00 (s, 1H), 8.94 (d, J = 7.6 Hz, 1H), 8.07 (d, J = 10.1 Hz, 1H), 7.13 (d, J = 8.1 Hz, 2H), 6.64 (d, J = 8.3 Hz, 2H), 4.35 (d, J = 7.8 Hz, 2H), 4.06 (d, J = 7.8 Hz, 2H), 3.32 (s, 3H), 2.27 (s, 3H). |
| H4 | 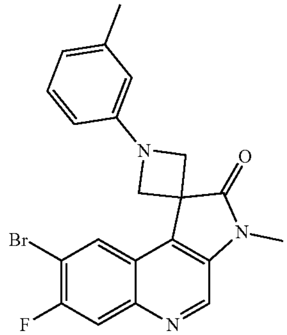 [SMILES: Cc1cccc(N2CC3(C2)C(=O)N(C)c2cnc4cc(F)c(Br)cc4c23)c1] | 8'-Bromo-7'-fluoro-3'-methyl-1-(m-tolyl)spiro[azetidine-3,1'-pyrrolo[2,3-c]quinolin]-2'(3'H)-one | 426.10 428.10 | $^1$H NMR (400 MHz, DMSO-d$_6$) δ 8.99 (s, 1H), 8.88 (d, J = 7.6 Hz, 1H), 8.06 (d, J = 10.1 Hz, 1H), 7.18 (t, J = 7.7 Hz, 1H), 6.69 (d, J = 7.5 Hz, 1H), 6.55-6.48 (m, 2H), 4.36 (d, J = 7.8 Hz, 2H), 4.09 (d, J = 7.8 Hz, 2H), 3.32 (s, 3H), 2.30 (s, 3H). |

| Intermediate | Structure | Name | MS: [(M + 1)]+ | 1H-NMR |
|---|---|---|---|---|
| H5 | 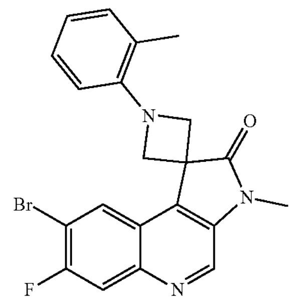 [SMILES: Cc1ccccc1N1CC2(C1)C(=O)N(C)c1cnc3cc(F)c(Br)cc3c12] | 8'-Bromo-7'-fluoro-3'-methyl-1-(o-tolyl)spiro[azetidine-3,1'-pyrrolo[2,3-c]quinolin]-2'(3'H)-one | 426.00 428.00 | 1H NMR (400 MHz, CDCl3) δ 9.49 (d, J = 7.5 Hz, 1H), 8.73 (s, 1H), 7.88 (d, J = 9.5 Hz, 1H), 7.17 (t, J = 7.6 Hz, 1H), 7.11 (d, J = 7.5 Hz, 1H), 6.95 (t, J = 7.4 Hz, 1H), 6.77 (d, J = 7.5 Hz, 1H), 4.48 (d, J = 7.1 Hz, 2H), 4.31 (d, J = 7.2 Hz, 2H), 3.39 (s, 3H), 2.25 (s, 3H). |
| H6 | 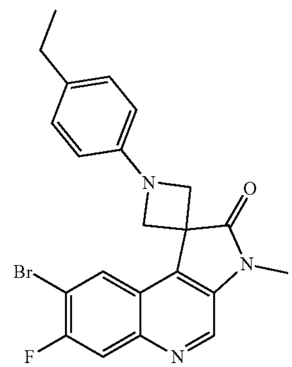 [SMILES: CCc1ccc(N2CC3(C2)C(=O)N(C)c2cnc4cc(F)c(Br)cc4c23)cc1] | 8'-Bromo-1-(4-ethylphenyl)-7'-fluoro-3'-methylspiro[azetidine-3,1'-pyrrolo[2,3-c]quinolin]-2'(3'H)-one | 440.10 442.10 | 1H NMR (400 MHz, DMSO-d6) δ 8.99 (s, 1H), 8.94 (d, J = 7.5 Hz, 1H), 8.06 (d, J = 10.3 Hz, 1H), 7.15 (d, J = 8.0 Hz, 2H), 6.65 (d, J = 8.0 Hz, 2H), 4.12-4.05 (m, 4H), 3.17 (s, 3H), 2.57 (q, J = 7.5 Hz, 2H), 1.18 (t, J = 7.5 Hz, 3H). |
| H7 | 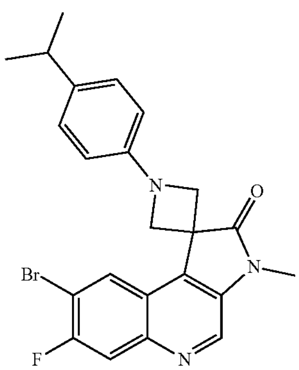 [SMILES: CC(C)c1ccc(N2CC3(C2)C(=O)N(C)c2cnc4cc(F)c(Br)cc4c23)cc1] | 8'-Bromo-7'-fluoro-1-(4-isopropylphenyl)-3'-methylspiro[azetidine-3,1'-pyrrolo[2,3-c]quinolin]-2'(3'H)-one | 454.10 456.10 | 1H NMR (400 MHz, CDCl3) δ 9.09 (d, J = 7.5 Hz, 1H), 8.74 (s, 1H), 7.90 (d, J = 9.4 Hz, 1H), 7.24 (d, J = 8.0 Hz, 2H), 6.69-6.64 (m, 2H), 4.37 (q, J = 7.0 Hz, 4H), 3.41 (d, J = 1.7 Hz, 3H), 2.97-2.88 (m, 1H), 1.30 (d, J = 1.8 Hz, 3H), 1.29 (d, J = 1.6 Hz, 3H). |
| H8 | 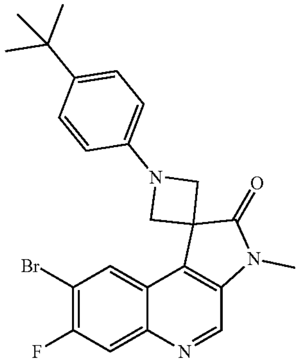 [SMILES: CN1C(=O)C2(CN(c3ccc(C(C)(C)C)cc3)C2)c2c1cnc1cc(F)c(Br)cc21] | 8'-Bromo-1-(4-(tert-butyl)phenyl)-7'-fluoro-3'-methylspiro[azetidine-3,1'-pyrrolo[2,3-c]quinolin]-2'(3'H)-one | 468.20 470.20 | 1H NMR (400 MHz, DMSO-d6) δ 8.99 (s, 1H), 8.94 (d, J = 7.6 Hz, 1H), 8.06 (d, J = 10.1 Hz, 1H), 7.36-7.29 (m, 2H), 6.70-6.62 (m, 2H), 4.35 (d, J = 7.7 Hz, 2H), 4.07 (d, J = 7.7 Hz, 2H), 3.32 (s, 3H), 1.29 (s, 9H), 1.23 (d, J = 5.0 Hz, 6H). |

-continued

| Intermediate | Structure | Name | MS: [(M + 1)]⁺ | ¹H-NMR |
|---|---|---|---|---|
| H9 | 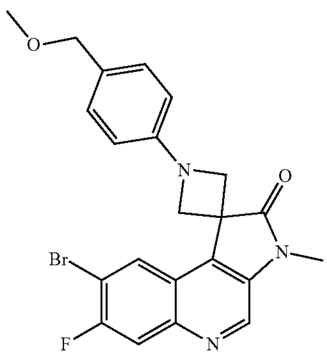 | 8'-Bromo-7'-fluoro-1-(4-(methoxymethyl)phenyl)-3'-methylspiro[azetidine-3,1'-pyrrolo[2,3-c]quinolin]-2'(3'H)-one | 456.20 458.20 | ¹H NMR (400 MHz, DMSO-$d_6$) δ 8.99 (s, 1H), 8.87 (d, J = 7.6 Hz, 1H), 8.07 (d, J = 10.1 Hz, 1H), 7.26 (d, J = 8.1 Hz, 2H), 6.70 (d, J = 8.1 Hz, 2H), 4.39 (d, J = 7.9 Hz, 2H), 4.34 (s, 2H), 4.10 (d, J = 7.9 Hz, 2H), 3.27 (s, 3H). |
| H10 | 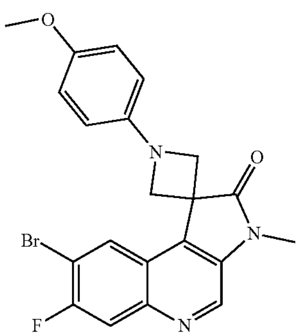 | 8'-Bromo-7'-fluoro-1-(4-methoxyphenyl)-3'-methylspiro[azetidine-3,1'-pyrrolo[2,3-c]quinolin]-2'(3'H)-one | 442.20, 444.20 | ¹H NMR (400 MHz, CDCl$_3$) δ 9.20 (d, J = 7.3 Hz, 1H), 8.72 (s, 1H), 8.02 (d, J = 9.2 Hz, 1H), 6.93 (d, J = 8.9 Hz, 2H), 6.65 (d, J = 8.9 Hz, 2H), 4.38-4.30 (m, 4H), 3.81 (s, 3H), 3.40 (s, 3H). |
| H11 | 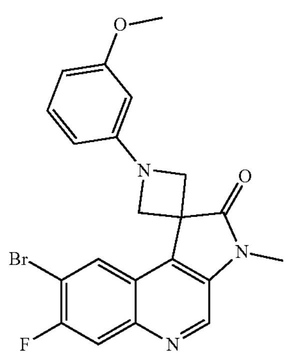 [SMILES: COc1cccc(N2CC3(C2)C(=O)N(C)c2cnc4cc(F)c(Br)cc4c23)c1] | 8'-Bromo-7'-fluoro-1-(3-methoxyphenyl)-3'-methylspiro[azetidine-3,1'-pyrrolo[2,3-c]quinolin]-2'(3'H)-one | 442.00 444.00 | ¹H-NMR (400 MHz, DMSO-$d_6$) δ 8.99 (s, 1H), 8.84 (d, J = 7.6 Hz, 1H), 8.07 (d, J = 10.1 Hz, 1H), 7.20 (t, J = 8.1 Hz, 1H), 6.45 (dd, J = 7.9, 2.3 Hz, 1H), 6.33-6.28 (m, 1H), 6.25 (t, J = 2.2 Hz, 1H), 4.37 (d, J = 7.9 Hz, 2H), 4.11 (d, J = 7.9 Hz, 2H), 3.76 (s, 3H), 3.32 (s, 3H). |
| H12 | 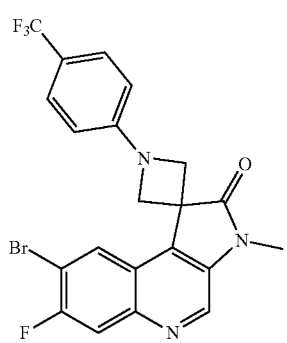 | 8'-Bromo-7'-fluoro-3'-methyl-1-(4-(trifluoromethyl)phenyl)spiro[azetidine-3,1'-pyrrolo[2,3-c]quinolin]-2'(3'H)-one | 480.10 482.10 | ¹H-NMR (400 MHz, CDCl$_3$) δ 8.81 (d, J = 7.2 Hz, 1H), 8.74 (s, 1H), 7.91 (d, J = 9.3 Hz, 1H), 7.58 (d, J = 8.2 Hz, 2H), 6.71 (d, J = 8.3 Hz, 2H), 4.44 (s, 4H), 3.41 (s, 3H). |

-continued

| Intermediate | Structure | Name | MS: [(M + 1)]+ | 1H-NMR |
|---|---|---|---|---|
| H13 | 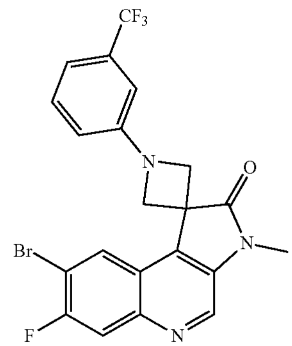 [SMILES: CN1C(=O)C2(CN(c3cccc(C(F)(F)F)c3)C2)c2c1cnc1cc(F)c(Br)cc21] | 8'-Bromo-7'-fluoro-3'-methyl-1-(3-(trifluoromethyl)phenyl)spiro[azetidine-3,1'-pyrrolo[2,3-c]quinolin]-2'(3'H)-one | 480.10 482.10, | 1H NMR (400 MHz, CDCl3) δ 8.91 (d, J = 7.1 Hz, 1H), 8.75 (s, 1H), 7.95 (d, J = 9.2 Hz, 1H), 7.44 (t, J = 7.9 Hz, 1H), 7.18 (d, J = 7.8 Hz, 1H), 6.87 (s, 1H), 6.83 (d, J = 8.1 Hz, 1H), 4.42 (s, 4H), 3.41 (s, 3H). |
| H14 | 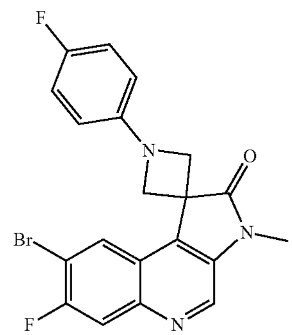 [SMILES: CN1C(=O)C2(CN(c3ccc(F)cc3)C2)c2c1cnc1cc(F)c(Br)cc21] | 8'-Bromo-7'-fluoro-1-(4-fluorophenyl)-3'-methylspiro[azetidine-3,1'-pyrrolo[2,3-c]quinolin]-2'(3'H)-one | 430.20 432.05 | 1H NMR (400 MHz, DMSO-d6) δ 8.99 (s, 1H), 8.89 (d, J = 7.3 Hz, 1H), 8.07 (d, J = 10.0 Hz, 1H), 7.15 (t, J = 8.8 Hz, 2H), 6.74 (s, 2H), 4.37 (d, J = 7.6 Hz, 2H), 4.08 (d, J = 7.6 Hz, 2H), 3.31 (s, 3H). |
| H15 | 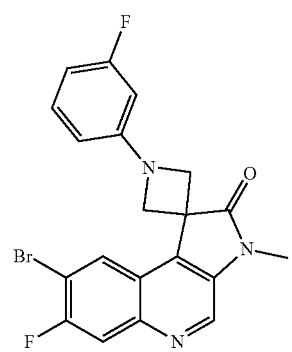 [SMILES: CN1C(=O)C2(CN(c3cccc(F)c3)C2)c2c1cnc1cc(F)c(Br)cc21] | 8'-Bromo-7'-fluoro-1-(3-fluorophenyl)-3'-methylspiro[azetidine-3,1'-pyrrolo[2,3-c]quinolin]-2'(3'H)-one | 430.15 432.15 | 1H NMR (400 MHz, CD3OD) δ 8.97 (d, J = 7.6 Hz, 1H), 8.86 (s, 1H), 7.89 (s, 1H), 7.32-7.25 (m, 1H), 6.60 (t, J = 8.2 Hz, 1H), 6.49-6.42 (m, 2H), 4.40 (d, J = 7.6 Hz, 2H), 4.28 (d, J = 7.9 Hz, 2H), 3.39 (s, 3H). |
| H16 | 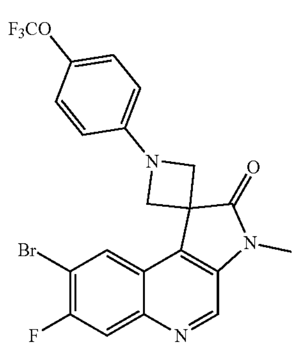 [SMILES: CN1C(=O)C2(CN(c3ccc(OC(F)(F)F)cc3)C2)c2c1cnc1cc(F)c(Br)cc21] | 8'-Bromo-7'-fluoro-3'-methyl-1-(4-(trifluoromethoxy)phenyl)spiro[azetidine-3,1'-pyrrolo[2,3-c]quinolin]-2'(3'H)-one | 496.00, 498.00 | 1H NMR (400 MHz, CDCl3) δ 8.91 (d, J = 7.6 Hz, 1H), 8.73 (s, 1H), 7.88 (d, J = 9.5 Hz, 1H), 7.20 (d, J = 9.0 Hz, 2H), 6.65 (d, J = 9.0 Hz, 2H), 4.40-4.35 (m, 4H), 3.40 (s, 3H). |

-continued

| Intermediate | Structure | Name | MS: [(M + 1)]+ | 1H-NMR |
|---|---|---|---|---|
| H17 | 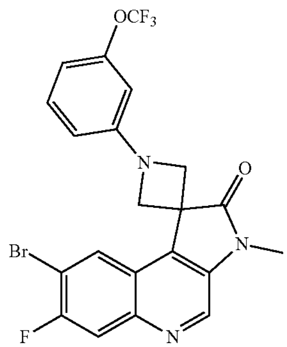 [SMILES: CN1C(=O)C2(CN(c3cccc(OC(F)(F)F)c3)C2)c2c1cnc1cc(F)c(Br)cc21] | 8'-Bromo-7'-fluoro-3'-methyl-1-(3-(trifluoromethoxy)phenyl)spiro[azetidine-3,1'-pyrrolo[2,3-c]quinolin]-2'(3'H)-one | 496.05 498.05 | 1H NMR (400 MHz, DMSO-$d_6$) δ 9.01 (s, 1H), 8.73 (d, J = 7.6 Hz, 1H), 8.08 (d, J = 10.1 Hz, 1H), 7.42 (t, J = 8.2 Hz, 1H), 6.82 (d, J = 8.4 Hz, 1H), 6.75 (d, J = 8.4 Hz, 1H), 6.69 (s, 1H), 4.45 (d, J = 8.2 Hz, 2H), 4.15 (d, J = 8.2 Hz, 2H), 3.31 (s, 3H). |
| H18 | 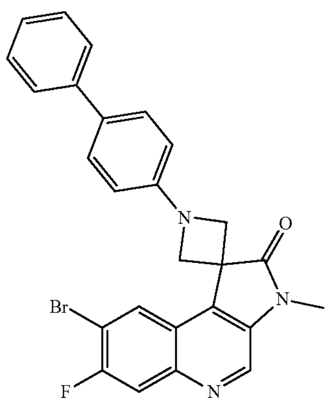 [SMILES: CN1C(=O)C2(CN(c3ccc(-c4ccccc4)cc3)C2)c2c1cnc1cc(F)c(Br)cc21] | 1-([1,1'-Biphenyl]-4-yl)-8'-Bromo-7'-fluoro-3'-methylspiro[azetidine-3,1'-pyrrolo[2,3-c]quinolin]-2'(3'H)-one | 488.20, 490.05 | 1H NMR (400 MHz, CDCl$_3$) δ 9.11 (s, 1H), 8.75 (s, 1H), 8.10 (s, 1H), 7.63-7.56 (m, 4H), 7.44 (t, J = 7.6 Hz, 2H), 7.33 (d, J = 7.4 Hz, 1H), 6.77 (d, J = 8.2 Hz, 2H), 4.50-4.39 (m, 4H), 3.43 (s, 3H). |
| H19 | 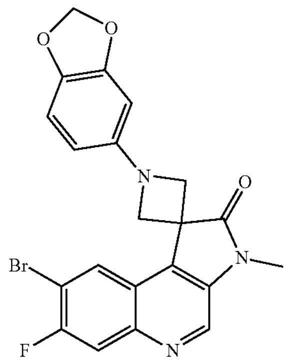 [SMILES: CN1C(=O)C2(CN(c3ccc4c(c3)OCO4)C2)c2c1cnc1cc(F)c(Br)cc21] | 1-(Benzo[d][1,3]dioxol-5-yl)-8'-Bromo-7'-fluoro-3'-methylspiro[azetidine-3,1'-pyrrolo[2,3-c]quinolin]-2'(3'H)-one | 456.05 458.05 | 1H-NMR (400 MHz, CDCl$_3$) δ 9.09 (d, J = 7.2 Hz, 1H), 8.73 (s, 1H), 7.96 (d, J = 9.3 Hz, 1H), 6.80 (d, J = 8.2 Hz, 1H), 6.28 (d, J = 2.1 Hz, 1H), 6.08 (dd, J = 8.2, 2.3 Hz, 1H), 5.94 (s, 2H), 4.34-4.27 (m, 4H), 3.40 (s, 3H). |
| H20 | 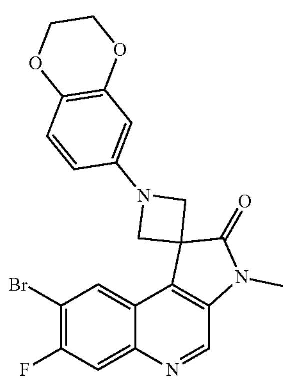 [SMILES: CN1C(=O)C2(CN(c3ccc4c(c3)OCCO4)C2)c2c1cnc1cc(F)c(Br)cc21] | 8'-Bromo-1-(2,3-dihydrobenzo[b][1,4]dioxin-6-yl)-7'-fluoro-3'-methylspiro[azetidine-3,1'-pyrrolo[2,3-c]quinolin]-2'(3'H)-one | 470.00, 472.00 | 1H NMR (400 MHz, CDCl$_3$) δ 9.09 (d, J = 7.2 Hz, 1H), 8.73 (s, 1H), 7.96 (d, J = 9.3 Hz, 1H), 6.80 (d, J = 8.2 Hz, 1H), 6.28 (d, J = 2.1 Hz, 1H), 6.08 (dd, J = 8.2, 2.3 Hz, 1H), 5.94 (s, 2H), 4.34-4.27 (m, 4H), 3.40 (s, 3H). |

-continued

| Intermediate | Structure | Name | MS: [(M + 1)]+ | 1H-NMR |
|---|---|---|---|---|
| H21 | 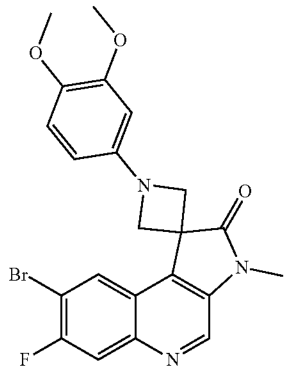 [SMILES: COc1ccc(N2CC3(C2)C(=O)N(C)c2cnc4cc(F)c(Br)cc4c23)cc1OC] | 8'-Bromo-1-(3,4-dimethoxyphenyl)-7'-fluoro-3'-methylspiro[azetidine-3,1'-pyrrolo[2,3-c]quinolin]-2'(3'H)-one | 472.00, 474.00 | 1H NMR (400 MHz, DMSO-d$_6$) δ 9.00 (s, 1H), 8.98 (d, J = 7.5 Hz, 1H), 8.07 (d, J = 10.1 Hz, 1H), 6.92 (d, J = 8.5 Hz, 1H), 6.39 (d, J = 2.5 Hz, 1H), 6.20 (dd, J = 8.6, 2.6 Hz, 1H), 4.33 (d, J = 7.7 Hz, 2H), 4.08 (d, J = 7.7 Hz, 2H), 3.79 (s, 3H), 3.72 (s, 3H), 3.31 (s, 3H). |
| H22 | 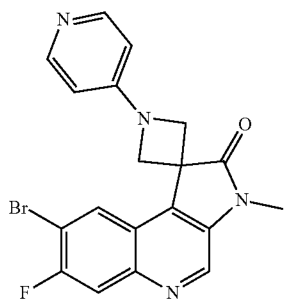 [SMILES: CN1C(=O)C2(CN(c3ccncc3)C2)c2c1cnc1cc(F)c(Br)cc21] | 8'-Bromo-7'-fluoro-3-methyl-1-(pyridin-4-yl)spiro[azetidine-3,1'-pyrrolo[2,3-c]quinolin]-2'(3'H)-one | 413.10 415.10 | 1H NMR (400 MHz, CDCl$_3$) δ 8.77 (s, 1H), 8.29 (d, J = 7.0 Hz, 1H), 7.91 (d, J = 9.1 Hz, 1H), 7.72-7.65 (m, 2H), 6.59-6.52 (m, 2H), 4.59 (s, 4H), 3.43 (s, 3H). |
| H23 | 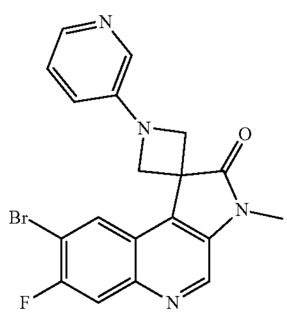 [SMILES: CN1C(=O)C2(CN(c3cccnc3)C2)c2c1cnc1cc(F)c(Br)cc21] | 8'-Bromo-7'-fluoro-3'-methyl-1-(pyridin-3-yl)spiro[azetidine-3,1'-pyrrolo[2,3-c]quinolin]-2'(3'H)-one | 413.10 415.10 | 1H NMR (400 MHz, DMSO-d$_6$) δ 9.00 (s, 1H), 8.81 (d, J = 7.6 Hz, 1H), 8.12 (s, 2H), 8.08 (d, J = 10.2 Hz, 1H), 7.36-7.28 (m, 1H), 7.15 (d, J = 8.2 Hz, 1H), 4.47 (d, J = 8.1 Hz, 2H), 4.18 (d, J = 8.1 Hz, 2H), 3.32(s, 3H). |
| H64 | 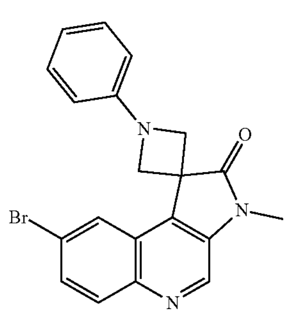 [SMILES: CN1C(=O)C2(CN(c3ccccc3)C2)c2c1cnc1ccc(Br)cc21] | 8'-Bromo-3'-methyl-1-phenylspiro[azetidine-3,1'-pyrrolo[2,3-c]quinolin]-2'(3'H)-one | 394.05 396.05 | 1H NMR (300 MHz, DMSO-d$_6$) δ 8.73 (s, 1H), 8.67 (d, J = 2.2 Hz, 1H), 8.02 (d, J = 9.0 Hz, 1H), 7.77 (dd, J = 9.0, 2.2 Hz, 1H), 7.30 (t, J = 7.7 Hz, 2H), 6.86 (t, J = 7.4 Hz, 1H), 6.70 (d, J = 7.8 Hz, 2H), 4.39 (d, J = 7.8 Hz, 2H), 4.09 (d, J = 7.9 Hz, 2H), 3.31 (s, 3H). |

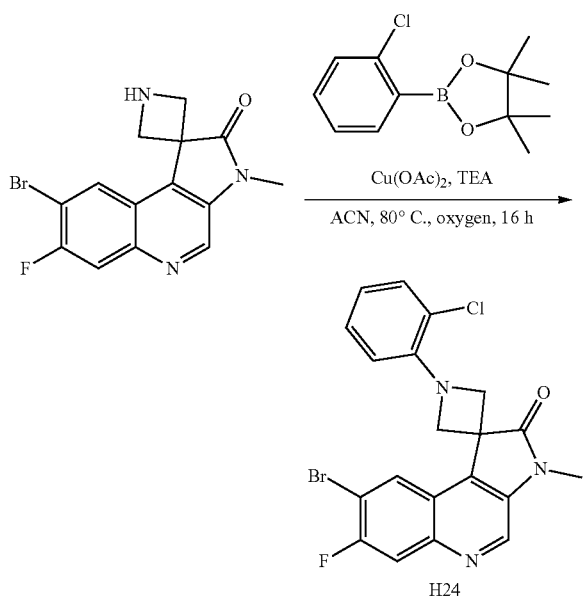

8'-Bromo-1-(2-chlorophenyl)-7'-fluoro-3'-methylspiro[azetidine-3,1'-pyrrolo[2,3-c]quinolin]-2'(3'H)-one: To a stirred mixture of 8-bromo-7'-fluoro-3'-methylspiro[azetidine-3,1'-pyrrolo[2,3-c]quinolin]-2'(3'H)-one (150 mg, 0.45 mmol,) and triethylamine (136 mg, 1.34 mmol) in acetonitrile (9.00 mL) were added cupric acetate (81.0 mg, 0.45 mmol) and 2-(2-chlorophenyl)-4,4,5,5-tetramethyl-1,3,2-dioxaborolane (320 mg, 1.34 mmol). The resulting mixture was stirred for 16 hours at 80° C. under oxygen atmosphere. The resulting mixture was concentrated under reduced pressure. The residue was purified by silica gel column chromatography, eluted with 1%~3% methanol in dichloromethane. The desired fractions were collected and concentrated under reduced pressure to afford the title compound as a yellow solid (50.0 mg, 26%): $^1$H NMR (400 MHz, CDCl$_3$) δ 9.32 (d, J=7.5 Hz, 1H), 8.73 (s, 1H), 7.88 (d, J=9.4 Hz, 1H), 7.35 (dd, J=8.0, 1.5 Hz, 1H), 6.94 (t, J=8.0 Hz, 1H), 6.80 (d, J=8.8 Hz, 1H), 4.58-4.48 (m, 4H), 3.40 (s, 3H); MS: [(M+1)]$^+$=44.05, 448.05.

The following intermediates were prepared according to the procedure described above:

| Intermediate | Structure | Name | MS: [(M + 1)]$^+$ | $^1$H-NMR |
|---|---|---|---|---|
| H25 | 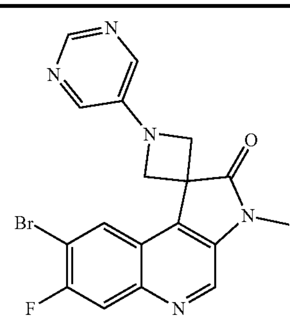 | 8'-Bromo-7'-fluoro-3'-methyl-1-(pyrimidin-5-yl)spiro[azetidine-3,1'-pyrrolo[2,3-c]quinolin]-2'(3'H)-one | 414.00 416.00 | $^1$H NMR (400 MHz, CDCl$_3$) δ 8.92 (s, 1H), 8.81 (d, J = 7.1 Hz, 1H), 8.76 (s, 1H), 8.31-8.25 (m, 2H), 7.98 (d, J = 9.2 Hz, 1H), 4.53 (s, 4H), 3.42 (s, 3H). |
| H26 | 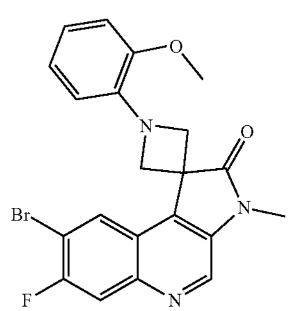 [SMILES: COc1ccccc1N1CC2(C1)C(=O)N(C)c1cnc3cc(F)c(Br)cc3c12] | 8'-Bromo-7'-fluoro-1-(2-methoxyphenyl)-3'-methylspiro[azetidine-3,1'-pyrrolo[2,3-c]quinolin]-2'(3'H)-one | 442.10 444.10 | $^1$H NMR (400 MHz, DMSO-d$_6$) δ 9.16 (d, J = 7.6 Hz, 1H), 8.98 (s, 1H), 8.05 (d, J = 10.2 Hz, 1H), 6.99 (dd, J = 7.7, 1.7 Hz, 1H), 6.97-6.86 (m, 2H), 6.67 (dd, J = 7.5, 1.8 Hz, 1H), 4.34 (d, J = 8.1 Hz, 2H), 4.17 (d, J = 8.2 Hz, 2H), 3.78 (s, 3H), 3.31 (s, 3H). |
| H27 | 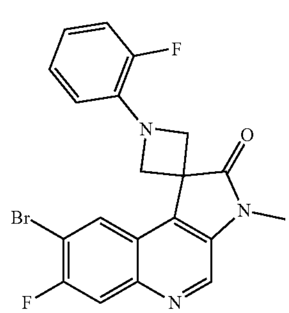 | 8'-Bromo-7'-fluoro-1-(2-fluorophenyl)-3'-methylspiro[azetidine-3,1'-pyrrolo[2,3-c]quinolin]-2'(3'H)-one | 430.10, 432.10 | $^1$H NMR (400 MHz, DMSO-d$_6$) δ 9.05-8.98 (m, 2H), 8.08 (d, J = 10.1 Hz, 1H), 7.25-7.12 (m, 2H), 6.95-6.83 (m, 2H), 4.41 (d, J = 7.6 Hz, 2H), 4.26 (d, J = 7.8 Hz, 2H), 3.31 (s, 3H). |

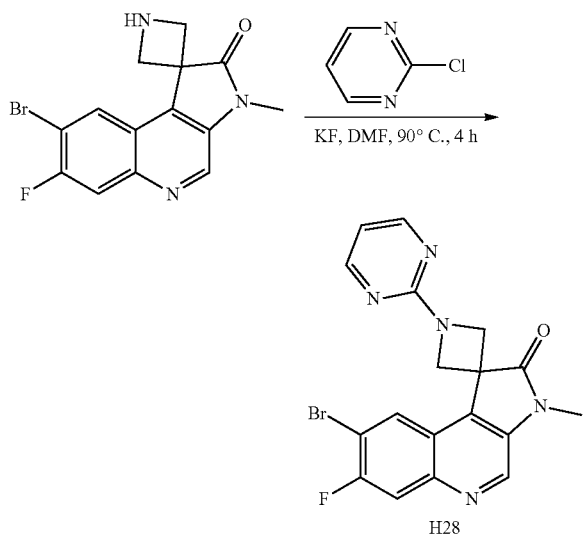

8'-Bromo-7'-fluoro-3'-methyl-1-(pyrimidin-2-yl)spiro[azetidine-3,1'-pyrrolo[2,3-c]quinolin]-2'(3'H)-one: To a stirred solution of 8-bromo-7-fluor-3-methyl-2,3-dihydrospiro[azetidine-3,1-pyrrolo[2,3-c]quinolin]-2-one (120 mg, 0.36 mmol) and 2-chloropyrimidine (41.0 mg, 0.36 mmol) in N,N-dimethylformamide (5.00 mL) was added potassium fluoride (42.0 mg, 0.72 mmol) at ambient temperature under nitrogen atmosphere. The resulting mixture was stirred for 4 hours at 90° C. under nitrogen atmosphere. After cooling down to ambient temperature, the mixture was purified by reversed phase flash chromatography with the following conditions: [Column: Spherical C18, 20~40 μm, 120 g; Mobile Phase A: Water (plus 10 mM $NH_4HCO_3$); Mobile Phase B: Acetonitrile; Flow rate: 55 min; Gradient (B): 5%~22%, 4 min 22%~45%, 20 min; 45%~95%; 2 min; 95%, 5 min; Detector: UV 254 n]. The desired fractions were collected and concentrated under reduced pressure to afford the title compound as a yellow solid (24.0 mg, 17%): $^1$H NMR (400 MHz, $CD_3OD$) δ 8.87 (s, 1H), 8.62 (d, J=7.3 Hz, 1H), 8.51 (d, J=4.9 Hz, 1H), 7.92-7.78 (m, 2H), 7.34 (s, 1H), 4.61-1.51 (m, 4H), 3.40 (s, 3H); MS: $[(M+1)]^+$=414.10, 416.10.

General Procedure 1

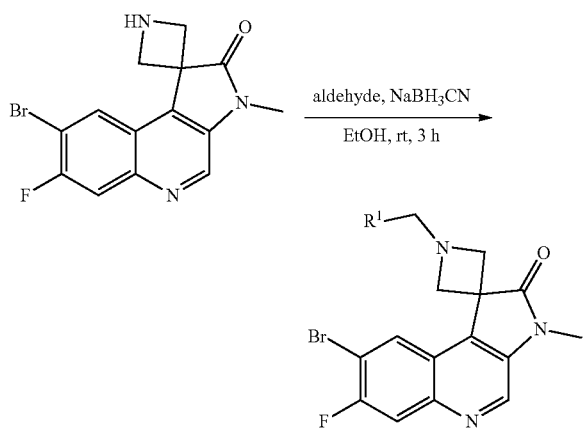

To a stirred solution of 8'-bromo-7'-fluoro-3'-methylspiro[azetidine-3,1'-pyrrolo[2,3-c]quinolin]-2'(3'H)-one (100 mg, 0.30 mmol) and aldehyde (1.50 mmol) in ethanol (8.00 mL) was added sodium cyanoborohydride (94.0 mg, 1.50 mmol) at ambient temperature. The resulting mixture was stirred for 3 hours at 25° C. under nitrogen atmosphere. The resulting mixture was purified by reversed phase flash chromatography with the following conditions: (Column: Spherical C18, 20~40 μm, 120 g; Mobile Phase A: Water (plus 10 mM $NH_4HCO_3$); Mobile Phase B: Acetonitrile; Flow rate: 50 mL/min; Gradient (B): 5%~20%, 6 min; 20%~50%, 30 min; 50%~95%, 5 min; 95%, 5 min; Detector: UV 254 nm. The desired fractions were collected and concentrated under reduced pressure to afford the corresponding product as a colorless solid.

General Procedure 2

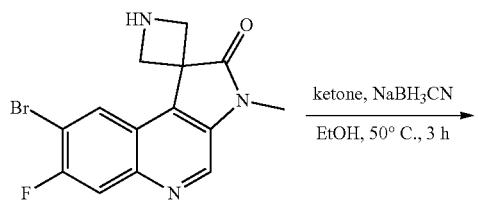

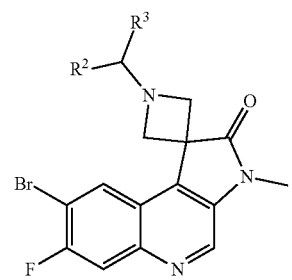

To a stirred solution of 8'-bromo-7'-fluoro-3'-methylspiro[azetidine-3,1'-pyrrolo[2,3-c]quinolin]-2'(3'H)-one (100 mg, 0.30 mmol) and ketone (1.50 mmol) in ethanol (8.00 mL) was added sodium cyanoborohydride (94.0 mg, 1.50 mmol) at ambient temperature. The resulting mixture was stirred for 3 hours at 50° C. under nitrogen atmosphere. The resulting mixture was purified by reversed phase flash chromatography with the following conditions: (Column: Spherical C18, 20~40 μm, 120 g, Mobile Phase A: Water (plus 10 mM $NH_4HCO_3$); Mobile Phase B: Acetonitrile; Flow rate: 50 mL/min; Gradient (B): 5~20%, 6 min; 20~50%, 30 min; 50%~95%, 5 min; 95%, 5 min; Detector UV 254 nm). The desired fractions were collected and concentrated under reduced pressure to afford the corresponding product as a colorless solid.

The following intermediates were prepared according to the procedure described above:

| Intermediate | Structure | Name | MS: [(M + 1)]⁺ | ¹H-NMR |
|---|---|---|---|---|
| H29 | 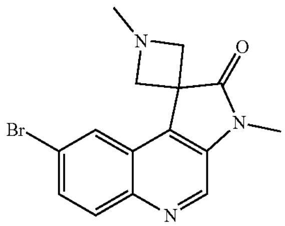 [SMILES: CN1CC2(C1)C(=O)N(C)c1cnc3ccc(Br)cc3c12] | 8'-Bromo-1,3'-dimethylspiro[azetidine-3,1'-pyrrolo[2,3-c]quinolin]-2'(3'H)-one | 332.10 334.10 | $^1$H NMR (400 MHz, DMSO-d$_6$) δ 9.36 (d, J = 2.3 Hz, 1H), 8.90 (s, 1H), 8.01 (d, J = 9.0 Hz, 1H), 7.77 (dd, J = 9.1, 2.2 Hz, 1H), 3.81 (d, J = 8.0 Hz, 2H), 3.44 (d, J = 7.9 Hz, 2H), 3.30 (s, 3H), 2.49 (s, 3H). |
| H30 | 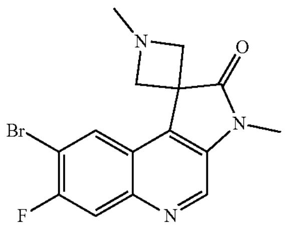 [SMILES: CN1CC2(C1)C(=O)N(C)c1cnc3cc(F)c(Br)cc3c12] | 8'-Bromo-7'-fluoro-1,3'-dimethylspiro[azetidine-3,1'-pyrrolo[2,3-c]quinolin]-2'(3'H)-one | 350.15 352.15 | $^1$H NMR (400 MHz, DMSO-d$_6$) δ 9.56 (d, J = 7.9 Hz, 1H), 8.92 (s, 1H), 8.27 (s, 2H), 8.01 (d, J = 10.4 Hz, 1H), 3.80 (d, J = 7.9 Hz, 2H), 3.44 (d, J = 7.8 Hz, 2H), 3.29 (s, 3H). |
| H31 | 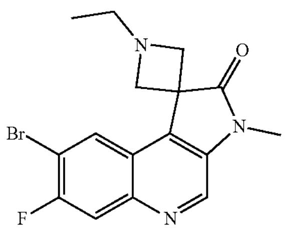 [SMILES: CCN1CC2(C1)C(=O)N(C)c1cnc3cc(F)c(Br)cc3c12] | 8'-Bromo-1-ethyl-7'-fluoro-3'-methylspiro[azetidine-3,1'-pyrrolo[2,3-c]quinolin]-2'(3'H)-one | 364.10 366.10 | $^1$H NMR (400 MHz, DMSO-d$_6$) δ 9.69 (d, J = 7.8 Hz, 1H), 8.93 (s, 1H), 8.01 (d, J = 10.2 Hz, 1H), 3.75 (d, J = 7.6 Hz, 2H), 3.42 (d, J = 7.3 Hz, 2H), 3.29 (s, 3H), 2.66 (q, J = 7.2 Hz, 2H), 1.03 (t, J = 7.2 Hz, 3H). |
| H32 | 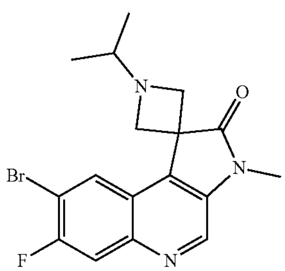 [SMILES: CC(C)N1CC2(C1)C(=O)N(C)c1cnc3cc(F)c(Br)cc3c12] | 8'-Bromo-7'-fluoro-1-isopropyl-3'-methylspiro[azetidine-3,1'-pyrrolo[2,3-c]quinolin]-2'(3'H)-one | 378.10 380.10 | $^1$H NMR (400 MHz, DMSO-d$_6$) δ 9.84 (d, J = 8.0 Hz, 1H), 8.93 (s, 1H), 8.00 (d, J = 10.2 Hz, 1H), 3.69 (d, J = 7.6 Hz, 2H), 3.46 (d, J = 7.3 Hz, 2H), 3.30 (s, 3H), 2.63-2.56 (m, 1H), 1.01 (d, J = 6.1 Hz, 6H). |
| H33 | 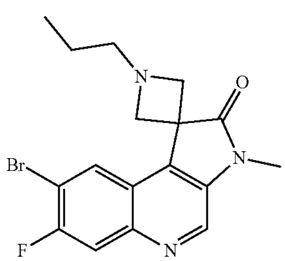 [SMILES: CCCN1CC2(C1)C(=O)N(C)c1cnc3cc(F)c(Br)cc3c12] | 8'-Bromo-7'-fluoro-3'-methyl-1-propylspiro[azetidine-3,1'-pyrrolo[2,3-c]quinolin]-2'(3'H)-one | 378.10 380.10 | $^1$H NMR (400 MHz, CDCl$_3$) δ 9.83 (d, J = 7.7 Hz, 1H), 8.65 (s, 1H), 7.81 (d, J = 9.6 Hz, 1H), 3.77 (d, J = 6.8 Hz, 2H), 3.62 (d, J = 7.1 Hz, 2H), 3.36 (s, 3H), 2.71 (t, J = 6.7 Hz, 2H), 1.54-1.46 (m, 2H), 1.08 (t, J = 7.4 Hz, 3H). |
| H34 | 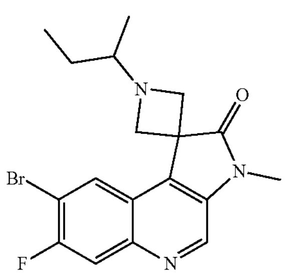 [SMILES: CCC(C)N1CC2(C1)C(=O)N(C)c1cnc3cc(F)c(Br)cc3c12] | 8'-Bromo-1-(sec-butyl)-7'-fluoro-3'-methylspiro[azetidine-3,1'-pyrrolo[2,3-c]quinolin]-2'(3'H)-one | 392.10 394.10 | $^1$H NMR (400 MHz, CDCl$_3$) δ 9.92 (d, J = 7.6 Hz, 1H), 8.66 (s, 1H), 7.81 (d, J = 9.7 Hz, 1H), 3.75-3.62 (m, 4H), 3.37 (s, 3H), 2.62 (s, 1H), 1.51-1.36 (m, 2H), 1.05 (d, J = 6.2 Hz, 3H), 1.00 (t, 7.4 Hz, 3H). |

-continued

| Intermediate | Structure | Name | MS: [(M + 1)]+ | ¹H-NMR |
|---|---|---|---|---|
| H35 | 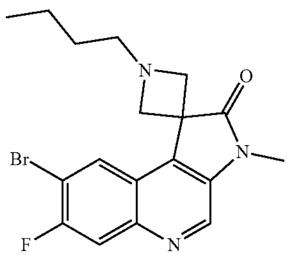 [SMILES: CCCCN1CC2(C1)C(=O)N(C)c1cnc3cc(F)c(Br)cc3c12] | 8'-Bromo-1-butyl-7'-fluoro-3'-methylspiro[azetidine-3,1'-pyrrolo[2,3-c]quinolin]-2'(3'H)-one | 392.00 394.00 | ¹H NMR (400 MHz, DMSO-d₆) δ 9.76 (d, J = 7.9 Hz, 1H), 8.93 (s, 1H), 8.01 (d, J = 10.2 Hz, 1H), 4.15 (d, J = 5.6 Hz, 2H), 3.77-3.69 (m, 2H), 2.65 (t, J = 6.5 Hz, 2H), 1.55-1.44 (m, 4H), 0.97 (t, J = 7.2 Hz, 3H). |
| H36 | 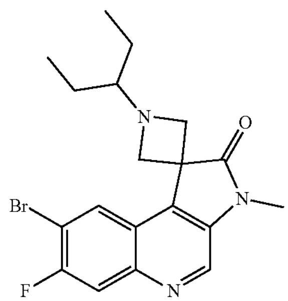 [SMILES: CCC(CC)N1CC2(C1)C(=O)N(C)c1cnc3cc(F)c(Br)cc3c12] | 8'-Bromo-7'-fluoro-3'-methyl-1-(pentan-3-yl)spiro[azetidine-3,1'-pyrrolo[2,3-c]quinolin]-2'(3'H)-one | 406.10 408.10 | ¹H NMR (400 MHz, DMSO-d₆) δ 9.88 (d, J = 8.0 Hz, 1H), 8.94 (s, 1H), 8.00 (d, J = 10.2 Hz, 1H), 3.67 (d, J = 7.6 Hz, 2H), 3.49 (d, J = 7.1 Hz, 2H), 2.39 (dq, J = 7.1, 3.6 Hz, 1H), 1.57-1.36 (m, 4H), 0.94 (t, J = 7.4 Hz, 6H). |
| H37 | 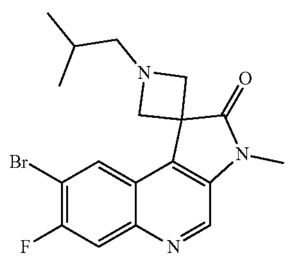 [SMILES: CC(C)CN1CC2(C1)C(=O)N(C)c1cnc3cc(F)c(Br)cc3c12] | 8'-Bromo-7'-fluoro-1-isobutyl-3'-methylspiro[azetidine-3,1'-pyrrolo[2,3-c]quinolin]-2'(3'H)-one | 392.00 394.00 | ¹H NMR (400 MHz, DMSO-d₆) δ 9.83 (d, J = 7.9 Hz, 1H), 8.93 (s, 1H), 8.01 (d, J = 10.2 Hz, 1H), 3.78-3.71 (m, 2H), 3.48-3.42 (m, 2H), 3.30 (s, 3H), 2.48 (d, J = 6.9 Hz, 2H), 1.68 (p, J = 6.8 Hz, 1H), 1.02 (d, J = 6.6 Hz, 6H). |
| H38 | 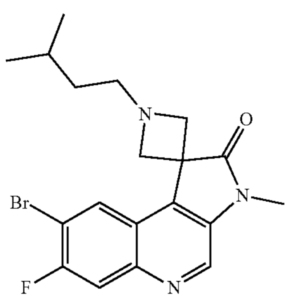 [SMILES: CC(C)CCN1CC2(C1)C(=O)N(C)c1cnc3cc(F)c(Br)cc3c12] | 8'-Bromo-7'-fluoro-1-isopentyl-3'-methylspiro[azetidine-3,1'-pyrrolo[2,3-c]quinolin]-2'(3'H)-one | 406.10 408.10 | ¹H NMR (400 MHz, CDCl₃) δ 9.79 (d, J = 7.8 Hz, 1H), 8.66 (s, 1H), 7.82 (d, J = 10.0 Hz, 1H), 3.76 (d, J = 6.8 Hz, 2H), 3.62 (d, J = 6.8 Hz, 2H), 3.37 (s, 3H), 2.75 (t, J = 7.0 Hz, 2H), 1.42-1.31 (m, 3H), 0.98 (d, J = 6.6 Hz, 6H). |
| H39 | 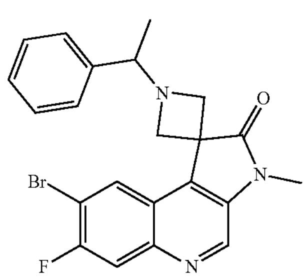 [SMILES: CC(c1ccccc1)N1CC2(C1)C(=O)N(C)c1cnc3cc(F)c(Br)cc3c12] | 8'-Bromo-7'-fluoro-3'-methyl-1-(1-phenylethyl)spiro[azetidine-3,1'-pyrrolo[2,3-c]quinolin]-2'(3'H)-one | 440.10 442.10 | ¹H NMR (400 MHz, DMSO-d₆) δ 10.00 (d, J = 7.9 Hz, 1H), 8.91 (s, 1H), 8.00 (d, J = 10.2 Hz, 1H), 7.58-7.47 (m, 2H), 7.38 (t, J = 7.5 Hz, 2H), 7.32-7.23 (m, 1H), 3.86 (dd, J = 7.2, 1.9 Hz, 1H), 3.64 (d, J = 7.0 Hz, 2H), 3.30 (d, J = 6.8 Hz, 2H), 3.29 (s, 3H), 1.28 (d, J = 6.4 Hz, 3H). |

| Intermediate | Structure | Name | MS: [(M + 1)]+ | 1H-NMR |
|---|---|---|---|---|
| H40 | 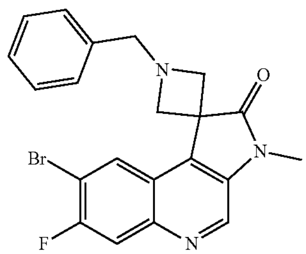 [SMILES: CN1C(=O)C2(CN(Cc3ccccc3)C2)c2c1cnc1cc(F)c(Br)cc21] | 1-Benzyl-8'-Bromo-7'-fluoro-3'-methylspiro[azetidine-3,1'-pyrrolo[2,3-c]quinolin]-2'(3'H)-one | 426.29 428.29 | 1H NMR (400 MHz, CDCl3) δ 9.92 (d, J = 7.7 Hz, 1H), 8.66 (s, 1H), 7.82 (d, J = 9.6 Hz, 1H), 7.50 (d, J = 6.9 Hz, 2H), 7.38 (t, J = 7.4 Hz, 2H), 7.30 (d, J = 7.4 Hz, 1H), 3.94 (s, 2H), 3.79-3.72 (m, 4H), 3.37 (s, 3H). |
| H41 | 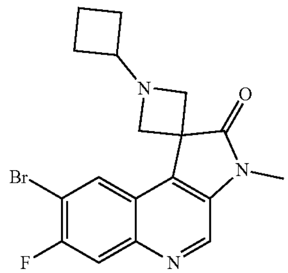 [SMILES: CN1C(=O)C2(CN(C3CCC3)C2)c2c1cnc1cc(F)c(Br)cc21] | 8'-Bromo-1-cyclobutyl-7'-fluoro-3'-methylspiro[azetidine-3,1'-pyrrolo[2,3-c]quinolin]-2'(3'H)-one | 390.10 392.10 | 1H NMR (400 MHz, CDCl3) δ 9.83 (d, J = 7.7 Hz, 1H), 8.66 (s, 1H), 7.82 (d, J = 9.6 Hz, 1H), 3.70 (s, 4H), 3.45-3.38 (m, 1H), 3.36 (s, 3H), 2.16-2.07 (m, 2H), 2.04-1.92 (m, 3H), 1.87-1.74 (m, 1H). |
| H42 | 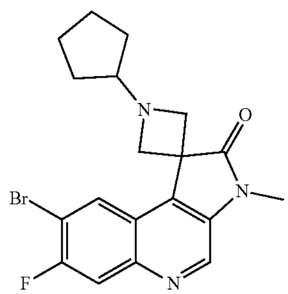 [SMILES: CN1C(=O)C2(CN(C3CCCC3)C2)c2c1cnc1cc(F)c(Br)cc21] | 8'-Bromo-1-cyclopentyl-7'-fluoro-3'-methylspiro[azetidine-3,1'-pyrrolo[2,3-c]quinolin]-2'(3'H)-one | 404.20 406.20 | 1H NMR (400 MHz, DMSO-d6) δ 9.76 (d, J = 7.9 Hz, 1H), 8.92 (s, 1H), 7.98 (d, J = 10.2 Hz, 1H), 3.67 (d, J = 7.0 Hz, 2H), 3.39 (d, J = 7.0 Hz, 2H), 3.30 (s, 3H) 3.03-2.98 (m, 1H), 1.91-1.83 (m, 2H), 1.77-1.59 (m, 6H). |
| H43 | 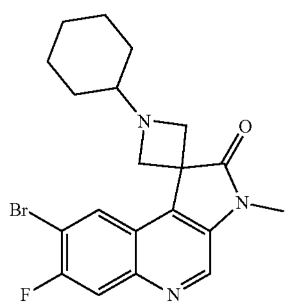 [SMILES: CN1C(=O)C2(CN(C3CCCCC3)C2)c2c1cnc1cc(F)c(Br)cc21] | 8'-Bromo-1-cyclohexyl-7'-fluoro-3'-methylspiro[azetidine-3,1'-pyrrolo[2,3-c]quinolin]-2'(3'H)-one | 418.15 420.15 | 1H NMR (400 MHz, DMSO-d6) δ 9.91 (d, J = 7.9 Hz, 1H), 8.92 (s, 1H), 7.98 (d, J = 10.2 Hz, 1H), 3.66 (d, J = 7.0 Hz, 2H), 3.44 (d, J = 7.0 Hz, 2H), 3.32 (s, 3H), 2.46 (s, 1H), 1.97-1.88 (m, 4H), 1.81-1.17(m, 6H). |
| H44 | 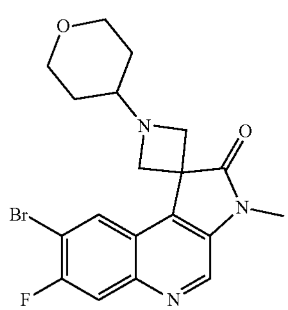 [SMILES: CN1C(=O)C2(CN(C3CCOCC3)C2)c2c1cnc1cc(F)c(Br)cc21] | 8'-Bromo-7'-fluoro-3'-methyl-1-(tetrahydro-2H-pyran-4-yl)spiro[azetidine-3,1'-pyrrolo[2,3-c]quinolin]-2'(3'H)-one | 420.10 422.10 | 1H NMR (400 MHz, CDCl3) δ 9.86 (d, J = 7.7 Hz, 1H), 8.67 (s, 1H), 7.83 (d, J = 9.6 Hz, 1H), 4.09-4.01 (m, 2H), 3.77 (d, J = 7.0 Hz, 2H), 3.69 (d, J = 7.2 Hz, 2H), 3.64-3.55 (m, 2H), 3.38 (s, 3H), 2.84-2.76 (m 1H), 1.87-1.76 (m, 2H), 1.58-1.48 (m, 2H). |

-continued

| Intermediate | Structure | Name | MS: [(M + 1)]+ | 1H-NMR |
|---|---|---|---|---|
| H45 | 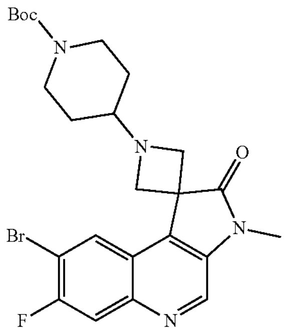 [SMILES: CN1C(=O)C2(CN(C3CCN(C(=O)OC(C)(C)C)CC3)C2)c2c1cnc1cc(F)c(Br)cc21] | tert-Butyl 4-(8'-bromo-7'-fluoro-3'-methyl-2'-oxo-2',3'-dihydrospiro[azetidine-3,1'-pyrrolo[2,3-c]quinolin-1-yl)piperidine-1-carboxylate | 519.20 521.20 | 1H NMR (400 MHz, CDCl3) δ 9.85 (d, J = 7.6 Hz, 1H), 8.69 (s, 1H), 7.84 (d, J = 9.5 Hz, 1H), 3.92-3.82 (m, 4H), 3.39 (s, 3H), 3.29-3.10 (m, 4H), 2.78 (s, 1H), 2.12-2.03 (m, 2H), 1.93-1.82 (m, 2H), 1.50 (s, 9H). |
| H46 | 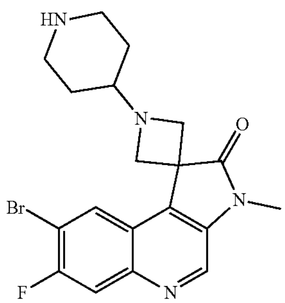 [SMILES: CN1C(=O)C2(CN(C3CCNCC3)C2)c2c1cnc1cc(F)c(Br)cc21] | 8'-Bromo-7'-fluoro-3'-methyl-1-(piperidin-4-yl)spiro[azetidine-3,1'-pyrrolo[2,3-c]quinolin]-2'(3'H)-one | 419.00 421.00 | 1H NMR (400 MHz, DMSO-d6) δ 9.76 (d, J = 7.9 Hz, 1H), 8.94 (s, 1H), 8.02 (d, J = 10.1 Hz, 1H), 3.76 (d, J = 7.4 Hz, 2H), 3.51 (d, J = 7.3 Hz, 2H), 3.24 (t, J = 9.7 Hz, 2H), 3.12-3.03 (m, 2H), 2.72 (s, 1H), 1.97-1.86 (m, 2H), 1.68-1.57 (m, 2H). |
| H47 | 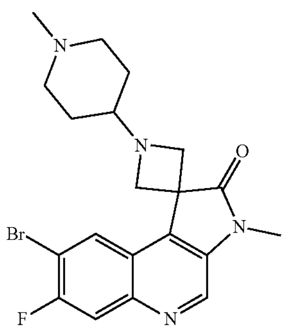 [SMILES: CN1CCC(N2CC3(C2)C(=O)N(C)c2cnc4cc(F)c(Br)cc4c23)CC1] | 8'-Bromo-7'-fluoro-3'-methyl-1-(1-methylpiperidin-4-yl)spiro[azetidine-3,1'-pyrrolo[2,3-c]quinolin]-2'(3'H)-one | 433.10 435.10 | 1H NMR (400 MHz, CDCl3) δ 9.71 (d, J = 7.6 Hz, 1H), 8.68 (s, 1H), 7.84 (d, J = 9.6 Hz, 1H), 3.79-3.73 (m, 2H), 3.68 (d, J = 7.2 Hz, 2H), 2.98-2.87 (m, 2H), 2.72 (t, J = 6.4 Hz, 2H), 2.55 (s, 3H), 2.50-2.42 (m, 1H), 2.03 (s, 2H), 1.69 (s, 2H). |
| H48 | 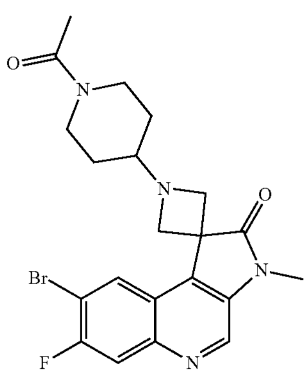 [SMILES: CC(=O)N1CCC(N2CC3(C2)C(=O)N(C)c2cnc4cc(F)c(Br)cc4c23)CC1] | 1-(1-Acetylpiperidin-4-yl)-8'-bromo-7'-fluoro-3'-methylspiro[azetidine-3,1'-pyrrolo[2,3-c]quinolin]-2'(3'H)-one | 461.00 463.00 | 1H NMR (400 MHz, DMSO-d6) δ 9.83 (d, J = 7.9 Hz, 1H), 8.94 (s, 1H), 8.02 (d, J = 10.2 Hz, 1H), 3.77-3.68 (m, 4H), 3.59-3.48 (m, 4H), 3.31 (s, 3H), 2.68 (s, 1H), 2.04 (s, 3H), 1.73 (s, 1H), 1.63 (s, 1H), 1.45 (s, 1H), 1.40-1.30 (m, 1H). |

| Intermediate | Structure | Name | MS: [(M + 1)]+ | 1H-NMR |
|---|---|---|---|---|
| H49 | 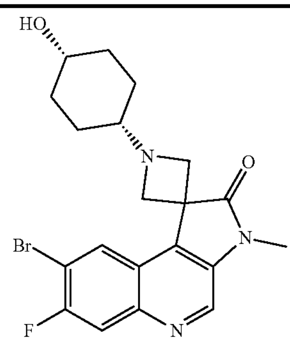 | 8'-Bromo-7'-fluoro-1-((1s,4s)-4-hydroxycyclohexyl)-3'-methylspiro[azetidine-3,1'-pyrrolo[2,3-c]quinolin]-2'(3'H)-one | 434.05 436.05 | 1H NMR (400 MHz, DMSO-d6) δ 9.82 (d, J = 7.9 Hz, 1H), 8.92 (s, 1H), 8.00 (d, J = 10.2 Hz, 1H), 4.38 (d, J = 2.9 Hz, 1H), 3.73-3.66 (m, 2H), 3.64-3.55 (m, 1H), 3.42 (d, J = 7.4 Hz, 2H), 3.30 (s, 3H), 2.42 (s, 1H), 1.73-1.64 (m, 2H), 1.64-1.50 (m, 4H), 1.50-1.41 (m, 2H). |
| H50 | 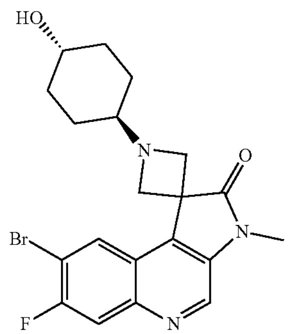 [SMILES: CN1C(=O)C2(CN([C@H]3CC[C@H](O)CC3)C2)c2c1cnc1cc(F)c(Br)cc21] | 8'-Bromo-7'-fluoro-1-((1r,4r)-4-hydroxycyclohexyl)-3'-methylspiro[azetidine-3,1'-pyrrolo[2,3-c]quinolin]-2'(3'H)-one | 434.05 436.05 | 1H NMR (400 MHz, DMSO-d6) δ 9.82 (d, J = 7.9 Hz, 1H), 8.92 (s, 1H), 7.99 (d, J = 10.2 Hz, 1H), 4.50 (s, 1H), 3.66 (d, J = 7.3 Hz, 3H), 3.46 (d, J = 7.2 Hz, 2H), 3.30 (s, 3H), 2.37 (s, 1H), 1.93-1.77 (m, 4H), 1.39-1.26 (m, 2H), 1.26-1.12 (m, 2H). |
| H51 | 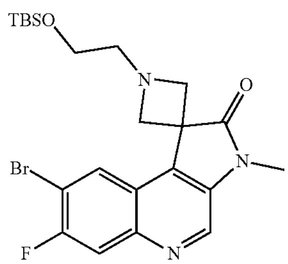 [SMILES: CN1C(=O)C2(CN(CCO[Si](C)(C)C(C)(C)C)C2)c2c1cnc1cc(F)c(Br)cc21] | 8'-Bromo-1-(2-((tert-butyldimethylsilyl)oxy)ethyl)-7'-fluoro-3'-methylspiro[azetidine-3,1'-pyrrolo[2,3-c]quinolin]-2'(3'H)-one | 494.20 496.20 | 1H NMR (400 MHz, CDCl3) δ 9.79 (d, J = 7.7 Hz, 1H), 8.65 (s, 1H), 7.82 (d, J = 9.6 Hz, 1H), 3.88-3.74 (m, 6H), 3.36 (s, 3H), 2.88 (t, J = 5.2 Hz, 2H), 0.87 (s, 9H), 0.08 (s, 6H). |
| H52 | 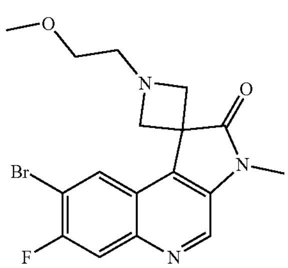 | 8'-Bromo-7'-fluoro-1-(2-methoxyethyl)-3'-methylspiro[azetidine-3,1'-pyrrolo[2,3-c]quinolin]-2'(3'H)-one | 394.10 396.10 | 1H NMR (400 MHz, CDCl3) δ 9.75 (s, 1H), 8.66 (s, 1H), 7.82 (d, J = 9.5 Hz, 1H), 3.83 (s, 4H), 3.61 (s, 2H), 3.42 (s, 3H), 3.37 (s, 3H), 3.00 (s, 2H). |

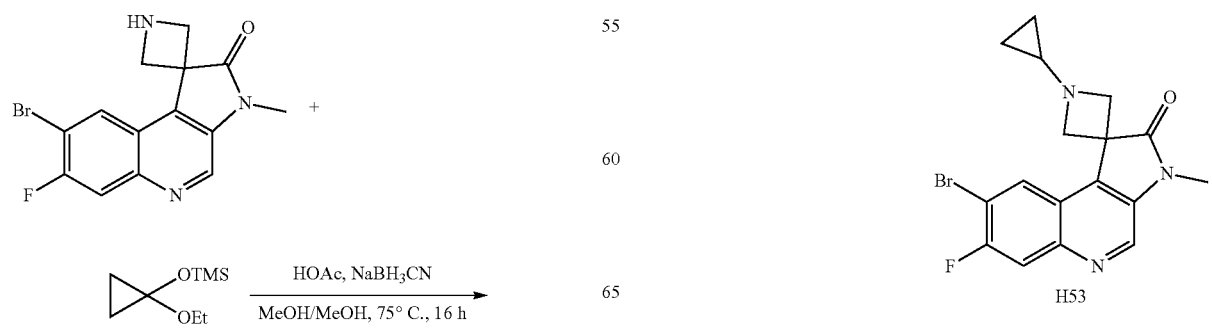

8'-Bromo-1-cyclopropyl-7'-fluoro-3'-methylspiro[azetidine-3,1'-pyrrolo[2,3-c]quinolin]-2'(3'H)-one: To a solution of 8'-bromo-7'-fluoro-3'-methylspiro[azetidine-3,1'-pyrrolo[2,3-c]quinolin]-2'(3'H)-one (100 mg, 0.30 mmol) in methanol (1.50 mL) and ethanol (1.50 mL) were added (1-ethoxycyclopropoxy)trimethylsilane (314 mg, 1.80 mmol), 4 Å molecular sieves (50.0 mg), acetic acid (180 mg, 3.00 mmol) and sodium cyanoborohydride (94.0 mg, 1.50 mmol) sequentially. The resulting mixture was stirred for 16 hours at 75° C. under nitrogen atmosphere. After cooling down to ambient temperature, the resulting suspension was filtered. The filtered cake was washed with ethyl acetate (3×15.0 mL). The filtrate was basified with saturated aqueous sodium bicarbonate to pH=8 and extracted with ethyl acetate (3×50.0 mL). The combined organic layers was washed with brine (2×30.0 mL) and dried over anhydrous sodium sulfate. After filtration, the filtrate was concentrated under reduced pressure. The residue was purified by silica gel column chromatography, eluted with 1%~4% methanol in dichloromethane. The desired fractions were collected and concentrated under reduced pressure to afford the title compound as a brown solid (30.0 mg, 27%): $^1$H NMR (400 MHz, CDCl$_3$) δ 9.56 (d, J=7.6 Hz, 1H), 8.65 (s, 1H), 7.80 (d, J=9.6 Hz, 1H), 3.88 (d, J=7.2 Hz, 2H), 3.75 (d, J=7.0 Hz, 2H), 3.37 (s, 3H), 2.04 (s, 1H), 0.54 (d, J=7.7 Hz, 4H); MS: [(M+1)]$^+$=376.05, 378.05.

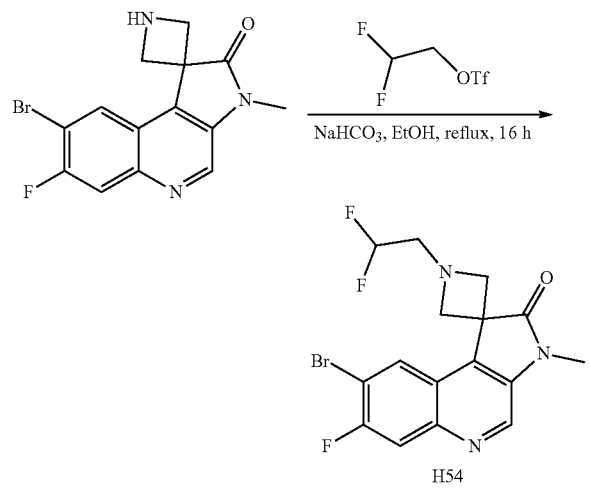

H54

8'-Bromo-1-(2,2-difluoroethyl)-7'-fluoro-3'-methylspiro[azetidine-3,1'-pyrrolo[2,3-c]quinolin]-2'(3'H)-one To a stirred mixture of 8-bromo-7-fluoro-3-methylspiro[azetidine-3,1-pyrrolo[2,3-c]quinolin]-2-one (100 mg, 0.30 mmol) and 2,2-difluoroethyl trifluoromethanesulfonate (319 mg, 1.49 mmol) in ethanol (8.00 mL) was added sodium bicarbonate (50.0 mg, 0.60 mmol) at ambient temperature. The resulting mixture was stirred for 16 hours at 80° C. under nitrogen atmosphere. The resulting mixture was concentrated under reduced pressure. The residue was purified by silica gel column chromatography, eluted with 2%~5% methanol in dichloromethane. The desired fractions were collected and concentrated under reduced pressure to afford the title compound as a colorless solid (35.0 mg, 30%): $^1$H NMR (400 MHz, DMSO-d$_6$) δ 9.61 (d, J=7.8 Hz, 1H), 8.93 (s, 1H), 8.01 (d, J=10.2 Hz, 1H), 6.13 (tt, J=55.8, 3.8 Hz, 1H), 3.84 (d, J=7.7 Hz, 2H), 3.68 (d, J=7.7 Hz, 2H), 3.29 (s, 3H), 3.13 (td, J=16.5, 3.9 Hz, 2H), MS: [(M+1)]$^+$=418.00, 420.00.

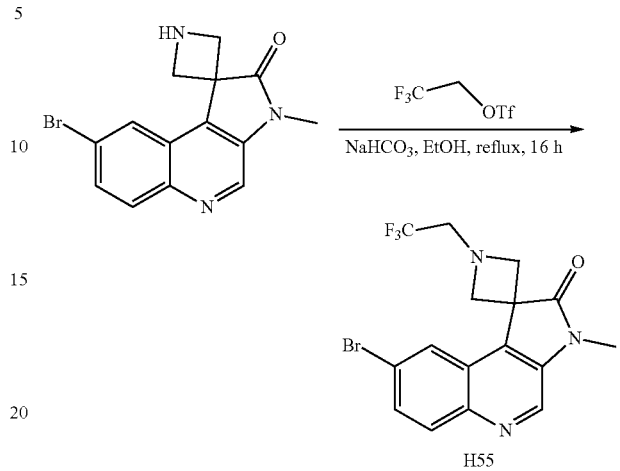

H55

8'-Bromo-3'-methyl-1-(2,2,2-trifluoroethyl)spiro[azetidine-3,1'-pyrrolo[2,3-c]quinolin]-2'(3'H)-one: To a stirred mixture of 8-bromo-7-fluoro-3-methylspiro[azetidine-3,1-pyrrolo[2,3-c]quinolin]-2-one (195 mg, 0.62 mmol) and 2,2-2,2,2-trifluoroethyl trifluoromethanesulfonate (711 mg, 3.06 mmol) in ethanol (12.0 mL) was added sodium bicarbonate (103 mg, 1.23 mmol) at ambient temperature. The resulting mixture was stirred for 16 hours at 80° C. under nitrogen atmosphere. The resulting mixture was concentrated under reduced pressure. The residue was purified by silica gel column chromatography, eluted with 1%~2% methanol in dichloromethane. The desired fractions were collected and concentrated under reduced pressure to afford the title compound as an off-white solid (110 mg, 45%): $^1$H NMR (400 MHz, CD$_3$OD) δ 9.54 (d, J=2.1 Hz, 1H), 8.78 (s, 1H), 7.97 (d, J=9.1 Hz, 1H), 7.78 (dd, J=9.1, 2.2 Hz, 1H), 3.97 (d, J=7.6 Hz, 2H), 3.88 (d, J=7.7 Hz, 2H), 3.49-3.35 (m, 5H); MS: [(M+1)]$^+$=400.00, 402.00.

General Procedure 3

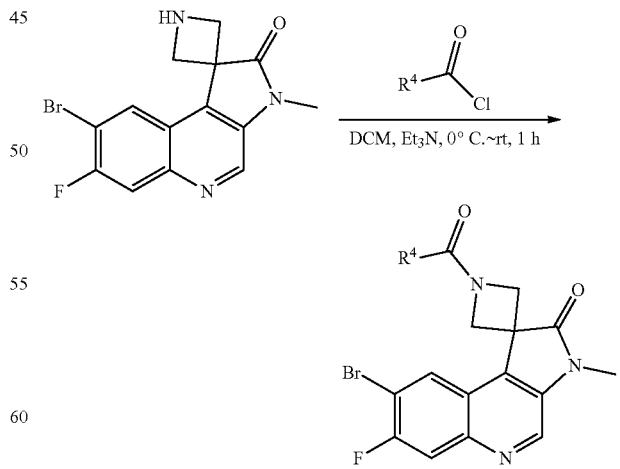

To stirred solution 3 of 8'-bromo-7'-fluoro-3'-methylspiro[azetidine-3,1'-pyrrolo[2,3-c]quinolin]-2'(3'H)-one (50.0 mg, 0.15 mmol) and triethylamine (30.0 mg, 0.30 mmol) in dichloromethane (5.00 mL) was added acyl chloride (0.30 mmol) at 0° C. The resulting mixture was stirred for 1 hour at ambient temperature. The reaction was quenched by methanol (0.50 mL) at 0. The resulted mixture was concentrated under reduced pressure. The residue was purified by silica gel column chromatography, eluted with 1%~4% methanol in dichloromethane. The desired fractions were collected and concentrated under reduced pressure to afford the corresponding product as an off-white solid.

The following intermediates were prepared according to the procedure described above:

| Intermediate | Structure | Name | MS: [(M + 1)]⁺ | ¹H-NMR |
|---|---|---|---|---|
| H56 | 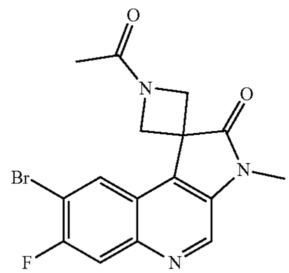 [SMILES: CC(=O)N1CC2(C1)C(=O)N(C)c1cnc3cc(F)c(Br)cc3c12] | 1-Acetyl-8'-Bromo-7'-fluoro-3'-methylspiro[azetidine-3,1'-pyrrolo[2,3-c]quinolin]-2'(3'H)-one | 378.10 380.10 | $^1$H NMR (400 MHz, DMSO-d$_6$) δ 8.98 (s, 1H), 8.21 (d, J = 7.4 Hz, 1H), 8.06 (d, J = 10.1 Hz, 1H), 4.65 (d, J = 9.0 Hz, 1H), 4.49 (d, J = 9.1 Hz, 1H), 4.28 (d, J = 9.9 Hz, 1H), 4.19 (d, J = 9.9 Hz, 1H), 3.31(s, 3H), 1.99 (s, 3H). |
| H57 | 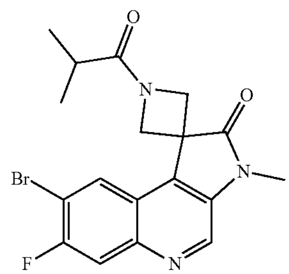 [SMILES: CC(C)C(=O)N1CC2(C1)C(=O)N(C)c1cnc3cc(F)c(Br)cc3c12] | 8'-Bromo-7'-fluoro-1-isobutyryl-3'-methylspiro[azetidine-3,1'-pyrrolo[2,3-c]quinolin]-2'(3'H)-one | 406.20 408.20 | $^1$H NMR (400 MHz, CDCl$_3$) δ 8.72 (s, 1H), 8.26 (d, J = 7.1 Hz, 1H), 7.88 (d, J = 9.4 Hz, 1H), 4.73 (d, J = 8.3 Hz, 1H), 4.58 (d, J = 9.7 Hz, 1H), 4.55 (d, J = 8.2 Hz, 1H), 4.40 (d, J = 9.6 Hz, 1H), 3.41 (s, 3H), 2.66-2.58 (m, 1H), 1.32 (d, J = 6.9 Hz, 3H), 1.24 (d, J = 6.6 Hz, 3H). |
| H58 | 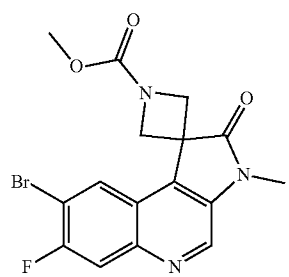 [SMILES: COC(=O)N1CC2(C1)C(=O)N(C)c1cnc3cc(F)c(Br)cc3c12] | Methyl 8'-Bromo-7'-fluoro-3'-methyl-2'-oxo-2',3'-dihydrospiro[azetidine-3,1'-pyrrolo[2,3-c]quinoline]-1-carboxylate | 394.05 396.05 | $^1$H NMR (400 MHz, DMSO-d$_6$) δ 8.98 (s, 1H), 8.33 (d, J = 7.4 Hz, 1H), 8.08 (d, J = 10.1 Hz, 1H), 4.37 (d, J = 9.1 Hz, 2H), 4.29 (d, J = 8.9 Hz, 2H), 3.74 (s, 3H), 3.32 (s, 3H). |
| H59 | 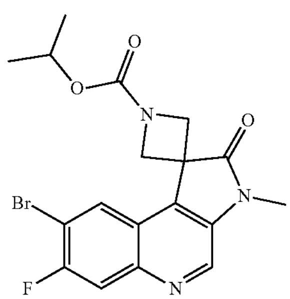 [SMILES: CC(C)OC(=O)N1CC2(C1)C(=O)N(C)c1cnc3cc(F)c(Br)cc3c12] | Isopropyl 8'-Bromo-7'-fluoro-3'-methyl-2'-oxo-2',3'-dihydrospiro[azetidine-3,1'-pyrrolo[2,3-c]quinoline]-1-carboxylate | 422.05 424.05 | $^1$H NMR (400 MHz, DMSO-d$_6$) δ 8.98 (s, 1H), 8.28 (d, J = 7.4 Hz, 1H), 8.07 (d, J = 10.1 Hz, 1H), 4.97-4.89 (m, 1H), 4.34 (d, J = 9.1 Hz, 2H), 4.26 (d, J = 9.0 Hz, 2H), 3.31 (s, 3H), 1.29 (d, J = 6.3 Hz, 6H). |
| H60 | 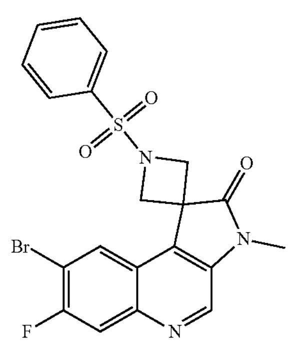 [SMILES: CN1C(=O)C2(CN(S(=O)(=O)c3ccccc3)C2)c2c1cnc1cc(F)c(Br)cc21] | 8'-Bromo-7'-fluoro-3'-methyl-1-(phenylsulfonyl)spiro[azetidine-3,1'-pyrrolo[2,3-c]quinolin]-2'(3'H)-one | 476.00 478.00 | $^1$H NMR (400 MHz, CDCl$_3$) δ 8.90 (d, J = 7.2 Hz, 1H), 8.66 (s, 1H), 8.06-7.99 (m, 2H), 7.85 (d, J = 9.4 Hz, 1H), 7.85-7.76 (m, 1H), 7.76-7.67 (m, 2H), 4.33 (d, J = 8.2 Hz, 2H), 4.25 (d, J = 8.2 Hz, 2H), 3.28 (s, 3H). |

| Intermediate | Structure | Name | MS: [(M + 1)]⁺ | ¹H-NMR |
|---|---|---|---|---|
| H61 | 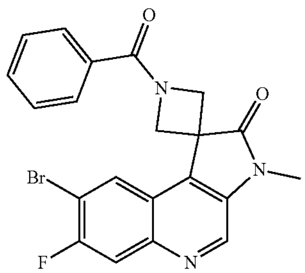 [SMILES: CN1C(=O)C2(CN(C(=O)c3ccccc3)C2)c2c1cnc1cc(F)c(Br)cc21] | 1-Benzoyl-8'-Bromo-7'-fluoro-3'-methylspiro[azetidine-3,1'-pyrrolo[2,3-c]quinolin]-2'(3'H)-one | 440.05 442.05 | ¹H NMR (400 MHz, CDCl₃) δ 8.72 (s, 1H), 8.35 (d, J = 7.1 Hz, 1H), 7.88 (d, J = 9.4 Hz, 1H), 7.83-7.75 (m, 2H), 7.57-7.47 (m, 3H), 4.79 (d, J = 9.4 Hz, 2H), 4.63 (d, J = 9.4 Hz, 2H), 3.41 (s, 3H). |
| H62 | 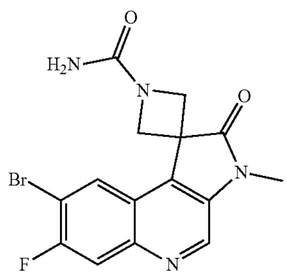 [SMILES: CN1C(=O)C2(CN(C(N)=O)C2)c2c1cnc1cc(F)c(Br)cc21] | 8'-Bromo-7'-fluoro-3'-methyl-2'-oxo-2',3'-dihydrospiro[azetidine-3,1'-pyrrolo[2,3-c]quinoline]-1-carboxamide | 379.15 381.15 | ¹H NMR (400 MHz, DMSO-d₆) δ 8.96 (s, 1H), 8.51 (d, J = 7.4 Hz, 1H), 8.07 (d, J = 10.2, 1H), 6.39 (s, 2H), 4.20 (d, J = 8.6 Hz, 2H), 4.15 (d, J = 8.7 Hz, 2H), 3.30 (s, 3H). |
| H63 | 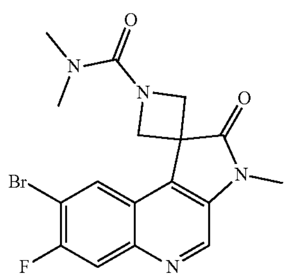 [SMILES: CN(C)C(=O)N1CC2(C1)C(=O)N(C)c1cnc3cc(F)c(Br)cc3c12] | 8'-Bromo-7'-fluoro-N,N,3'-trimethyl-2'-oxo-2',3'-dihydrospiro[azetidine-3,1'-pyrrolo[2,3-c]quinoline]-1-carboxamide | 407.15 409.15 | ¹H NMR (400 MHz, DMSO-d₆) δ 8.98 (s, 1H), 8.67 (d, J = 7.5 Hz, 1H), 8.07 (d, J = 10.1 Hz, 1H), 4.32 (d, J = 8.6 Hz, 2H), 4.23 (d, J = 8.6 Hz, 2H), 3.32 (s, 3H), 2.90 (s, 6H). |

Intermediate 64 and 65

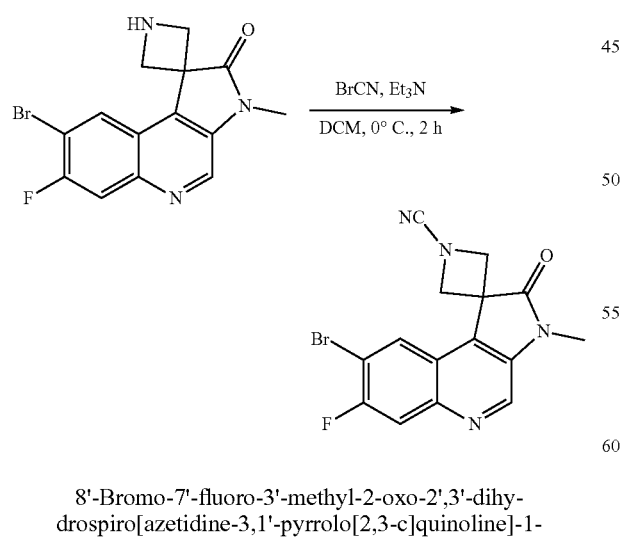

8'-Bromo-7'-fluoro-3'-methyl-2-oxo-2',3'-dihydrospiro[azetidine-3,1'-pyrrolo[2,3-c]quinoline]-1-carbonitrile To a mixture of 8-bromo-7-fluoro-3-methyl-2,3-dihydrospiro[azetidine-3,1'-pyrrolo[2,3-c]quinolin]-2-on (200 mg, 0.60 mmol) and triethylamine (0.21 mL, 1.50 mol) in dichloromethane (8.00 mL) was added cyanic bromide (95.0 mg, 0.90 mmol, in dichloromethane 1.00 mL) dropwise at 0° C. The resulting mixture was stirred for 2 hours at 0° C. The resulting mixture was concentrated under reduced pressure. The residue was purified by silica gel column chromatography, eluted with 1%~5% methanol in dichloromethane. The desired fractions were collected and concentrated under reduced pressure to afford the title compound as an off-white solid (200 mg, 94%): ¹H NMR (400 MHz, CDCl₃) δ 8.72 (s, H), 8.68 (d, J=7.0 Hz, 1H), 7.92 (d, J=9.2 Hz, 1H), 4.83 (d, J=7.8 Hz, 2H), 4.50 (d, J=7.9 Hz, 2H), 3.40 (s, 3H), MS: [(M+1)]⁺=361.00, 363.00.

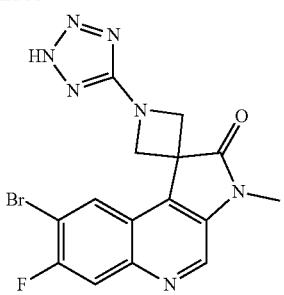

8'-Bromo-7'-fluoro-3'-methyl-1-(2H-tetrazol-5-yl)spiro[azetidine-3,1'-pyrrolo[2,3-c]quinolin]-2'(3'H)-one To a stirred solution of 8-bromo-7-fluoro-3-methyl-2-oxo-2,3-dihydrospiro[azetidine-3,1-pyrrolo[2,3-c]quinoline]-1-carbonitrile (200 mg, 0.55 mmol) in N,N-dimethylformamide (15.0 mL) was added sodium azide (72.0 mg, 1.11 mmol) and aluminium chloride (23.0 mg, 0.17 mmol) at ambient temperature under argon atmosphere. The resulting mixture was stirred for 30 min at 120° C. under argon atmosphere. After cooling down to ambient temperature, the mixture was purified by reversed phase flash chromatography with the following conditions: [Column: Spherical C18, 20-40 μm, 330 g; Mobile Phase A: Water (plus 5 mM AcOH); Mobile Phase B: Acetonitrile; Flow rate: 80 mL/min; Gradient: 38% B to 58% B in 20 min; Detector UV 254 nm]. The fractions containing desired product were collected at 48% B and concentrated under reduced pressure to afford the title compound as a light yellow solid (100 mg, 45%): $^1$H NMR (400 MHz, DMSO-$d_6$) δ 9.00 (s, 1H), 8.68 (d, J=7.5 Hz, 1H), 8.08 (d, J=10.1 Hz, 1H), 4.52 (d, J=8.6 Hz, 2H), 4.39 (d, J=8.6 Hz, 2H), 3.31 (s, 3H); MS: [(M+1)]$^+$=404.00, 406.00.

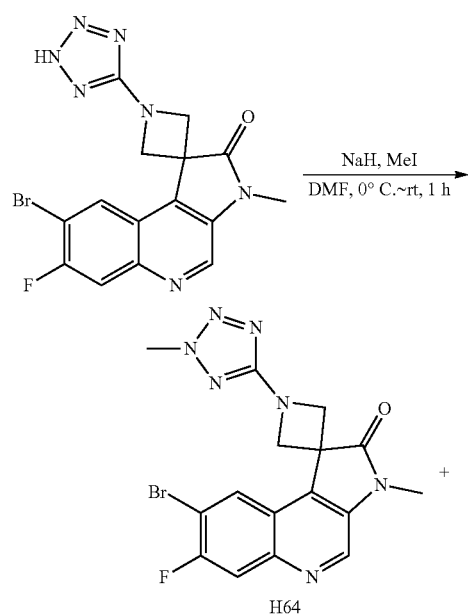

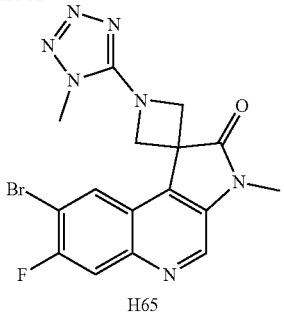

H65

8'-Bromo-7'-fluoro-3'-methyl-1-(2-methyl-2H-tetrazol-5-yl)spiro[azetidine-3,1'-pyrrolo[2,3-c]quinolin]-2'(3'H)-one and 8'-bromo-7'-fluoro-3'-methyl-1-(1-methyl-1H-tetrazol-5-yl)spiro[azetidine-3,1'-pyrrolo[2,3-c]quinolin]-2'(3'H)-one To a solution of 8-bromo-7-fluoro-3-methyl-1-(1H-1,2,3,4-tetrazol-5-yl)-2,3-dihydrospiro[azetidine-3,1-pyrrolo[2,3-c]quinolin]-2-one (60.0 mg, 0.15 mmol) in N,N-dimethylformamide (5.00 mL) was added sodium hydride (8.00 mg, 0.18 mmol, 60% w/w dispersed in mineral oil) at 0° C. under argon atmosphere. The resulting mixture was stirred for 10 min at 0° C. under argon atmosphere followed by the addition of iodomethane (105 mg, 0.75 mmol, in tetrahydrofuran 2.00 mL) dropwise at 0° C. After stirring for additional 1 hour at ambient temperature, the reaction was quenched by the addition of water (1.00 mL). The resulted mixture was concentrated under reduced pressure. The residue was purified by reversed phase flash chromatography with the following conditions: [Column: Spherical C18, 20-40 μm, 120 g; Mobile Phase A: Water (plus 10 mM NH$_4$HCO$_3$); Mobile Phase B: Acetonitrile; Flow rate: 45 mL/min, Gradient: 40% B to 60% B in 20 min; Detector: UV 254 nm]. The fractions containing desired product were collected at 49% B and concentrated under reduced pressure to afford 8-bromo-7-fluoro-3-methyl-1-(2-methyl-2H-1,2,3,4-tetrazol-5-yl)-2,3-dihydrospiro[azetidine-3,1-pyrrolo[2,3-c]quinolin]-2-one an off-white solid (18.0 mg, 29%): MS: [(M+1)]$^+$=417.95, 419.95. The fractions containing desired product were collected at 52% B and concentrated under reduced pressure to afford 8-bromo-7-fluoro-3-methyl-1-(1-methyl-1H-1,2,3,4-tetrazol-5-yl)-2,3-dihydrospiro[azetidine-3,1-pyrrolo[2,3-c]quinolin]-2-one as an off-white solid (35 mg, 57%): $^1$H NMR (400 MHz, DMSO-$d_6$) δ 8.99 (s, 1H), 8.77 (d, J=7.5 Hz, 1H), 8.08 (d, J=10.1 Hz, 1H), 4.49 (d, J=8.5 Hz, 2H), 4.34 (d, J=8.5 Hz, 2H), 4.28 (s, 3H), 3.31 (s, 3H); MS: [(M+1)]$^+$=417.95, 419.95.

Intermediate H66

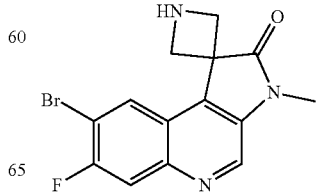 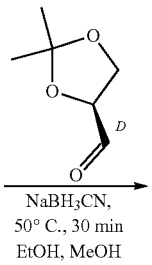

-continued

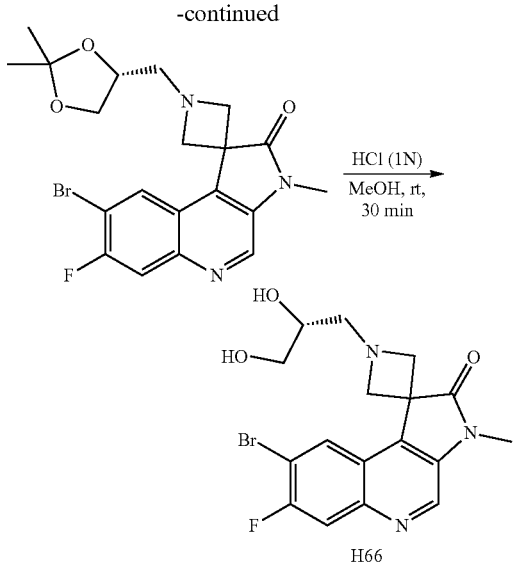

(R)-8'-Bromo-1-(2,3-dihydroxypropyl)-7'-fluoro-3'-methylspiro[azetidine-3,1'-pyrrolo[2,3-c]quinolin]-2'(3'H)-one To a stirred mixture of 8-bromo-7-fluoro-3-methyl-2,3-dihydrospiro[azetidine-3,1-pyrrolo[2,3-c]quinolin]-2-one (40.0 mg, 0.12 mmol) and (4S)-2,2-dimethyl-1,3-dioxolane-4-carbaldehyde (92.9 mg, 0.71 mmol) in methanol (1.50 mL) and ethanol (1.50 mL) was added sodium cyanoborohydride (15.0 mg, 0.24 mmol) at ambient temperature. The resulting mixture was stirred for 30 min at 50° C. The resulting mixture was concentrated under reduced pressure. The residue was dissolved in methanol (1.00 mL) and hydrochloric acid (4.00 mL, 1 N) and stirred for 30 min at ambient temperature. The resulting mixture was concentrated under reduced pressure to give crude product which was used in the next step without further purification: MS: [(M+1)]$^+$=410.20, 412.20.

Intermediate H67

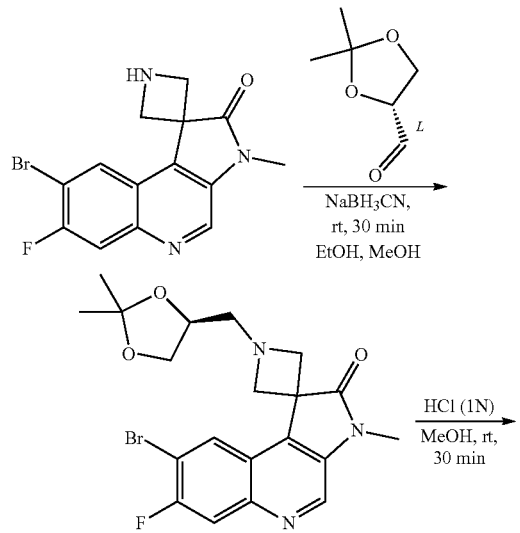

-continued

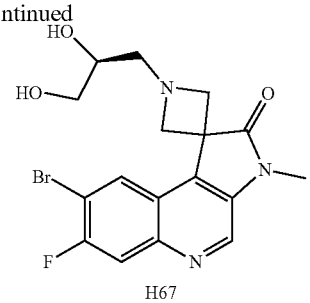

(S)-8'-Bromo-1-(2,3-dihydroxypropyl)-7'-fluoro-3'-methylspiro[azetidine-3,1'-pyrrolo[2,3-c]quinolin]-2'(3'H)-one To a stirred mixture of 8-bromo-7-fluoro-3-methyl-2,3-dihydrospiro[azetidine-3,1'-pyrrolo[2,3-c]quinolin]-2-one (40.0 mg, 0.12 mmol) and (4R)-2,2-dimethyl-1,3-dioxolane-4-carbaldehyde (93.0 mg, 0.71 mmol) in methanol (1.50 mL) and ethanol (1.50 mL) was added sodium cyanoborohydride (15.0 mg, 0.24 mmol) in portions at ambient temperature. The resulting mixture was stirred for 1 hour at 50° C. The resulting mixture was concentrated under reduced pressure. The residue was dissolved in methanol (1.00 mL) and hydrochloric acid (4.00 mL, 1 N) and stirred for 30 min at ambient temperature. The resulting mixture was concentrated under reduced pressure to give crude product which was used in the next step without further purification: MS: [(M+1)]$^+$=410.20, 412.20.

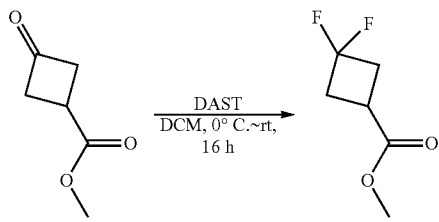

Methyl 3,3-difluorocyclobutane-1-carboxylate: To a stirred solution of methyl 3-oxocyclobutane-1-carboxylate (5.00 g, 39.0 mmol) in dichloromethane (230 mL) was added diethylaminosulfurtrifluoride (6.29 g, 39.0 mmol) dropwise at 0° C. under nitrogen atmosphere. After stirring for 16 hours at ambient temperature, the reaction was quenched by saturated aqueous sodium bicarbonate at 0° C. The resulting mixture was extracted with dichloromethane (8×100 mL). The combined organic layers was washed with brine (2×100 mL) and dried over anhydrous magnesium sulfate. After filtration, the filtrate was concentrated under reduced pressure to afford the title compound as a brown oil (5.50 g, 94%).

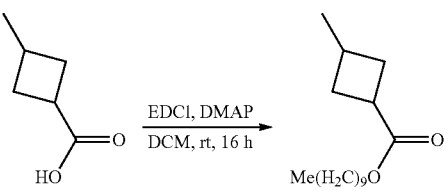

Decyl 3-methylcyclobutane-1-carboxylate: To a stirred solution of 3-methylcyclobutane-1-carboxylic acid (1.00 g, 8.76 mmol) and 1-decanol (2.08 g, 13.1 mmol) in dichloromethane (30.0 mL) were added 1-ethyl-3-(3-dimethylaminopropyl)carbodiimide hydrochloride (2.52 g, 13.1 mmol) and 4-dimethylaminopyridine (107 mg, 0.88 mmol) at ambient temperature. The resulting mixture was stirred for 16 hours at 25° C. and quenched by water (30.0 mL). The resulting mixture was extracted with dichloromethane (3×30.0 mL). The combined organic layers was washed with brine (2×30.0 mL) and dried over anhydrous sodium sulfate. After filtration, the filtrate was concentrated under reduced pressure. The residue was purified by silica gel column chromatography, eluted with 1%~8% ethyl acetate in petroleum ether. The desired fractions were collected and concentrated under reduced pressure to afford the title compound as a light yellow oil (1.82 g, 82%): $^1$H NMR (400 MHz, CDCl$_3$) δ 4.10-4.02 (m, 2H), 3.15-2.85 (m, 1H), 2.52-2.36 (m, 1H), 2.35-2.26 (m, 2H), 1.90-1.78 (m, 2H), 1.67-1.58 (m, 2H), 1.37-1.21 (m, 14H), 1.12 (d, J=6.5 Hz, 1H), 1.05 (d, J=6.5 Hz, 2H), 0.88 (t, J=6.7 Hz, 3H).

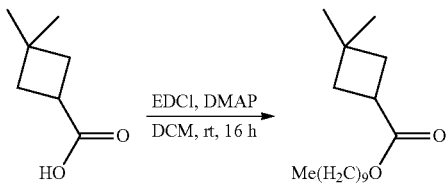

Decyl 3,3-dimethylcyclobutane-1-carboxylate: The title compound was prepared according to the procedure described above as a light yellow oil: $^1$H NMR (400 MHz, CDCl$_3$) δ 4.05 (t, J=6.7 Hz, 2H), 3.04 (p, J=8.9 Hz, 1H), 2.11-2.01 (m, 2H), 2.01-1.90 (m, 2H), 1.66-1.57 (m, 2H), 1.37-1.21 (m, 14H), 1.15 (s, 3H), 1.09 (s, 3H), 0.88 (t, J=6.7 Hz, 3H).

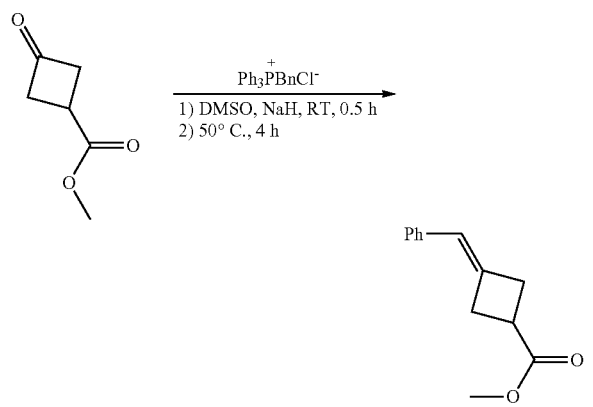

Methyl 3-benzylidenecyclobutane carboxylate: A solution of benzyltriphenylphosphonium chloride (15.2 g, 39.0 mmol) in dimethyl sulfoxide (80.0 mL) was treated with sodium hydride (1.72 g, 42.9 mmol, 60% w/w dispersed in mineral oil) for 0.5 hours at 25° C. under nitrogen atmosphere followed by the addition of methyl 3-oxocyclobutane-1-carboxylate (5.00 g, 39.0 mmol) dropwise over 2 min at ambient temperature. After stirring for 4 hours at 50° C., the resulting mixture was cooled down to ambient temperature. The reaction was quenched by saturated aqueous ammonium chloride (20.0 mL) at 0° C. and diluted with water (150 mL). The resulting mixture was extracted with ethyl acetate (3×100 mL). The combined organic layers was washed with brine (2×100 mL) and dried over anhydrous sodium sulfate. After filtration, the filtrate was concentrated under reduced pressure. The residue was purified by silica gel column chromatography, eluted with 1%~6% ethyl acetate in petroleum ether. The desired fractions were collected and concentrated under reduced pressure to afford the title compound as a light yellow oil (2.00 g, 26%): $^1$H NMR (400 MHz, CDCl$_3$) δ 7.33-7.27 (m, 2H), 7.20-7.15 (m, 3H), 6.16 (q, J=2.3 Hz, 1H), 3.73 (s, 3H), 3.44-3.06 (m, 5H); MS: [(M+1)]$^+$=203.20.

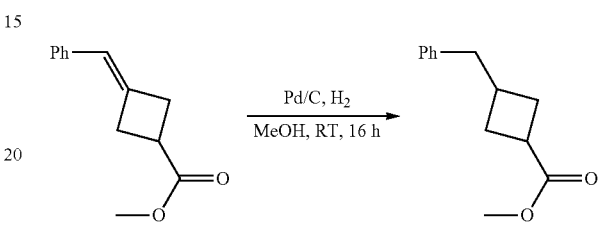

Methyl 3-benzylcyclobutanecarboxylate: To a stirred solution of methyl 3-(phenylmethylidene)cyclobutane-1-carboxylate (1.00 g, 4.94 mmol) in methanol (10.0 mL) was added anhydrous Pd/C (100 mg, 10% palladium on charcoal) at ambient temperature under nitrogen atmosphere. After stirring for 16 hours at ambient temperature under hydrogen atmosphere, the resulting mixture was filtered. The filtered cake was washed with methanol (3×20.0 mL). The filtrate was concentrated under reduced pressure to afford the title compound as a light yellow oil (913 mg, 91%): $^1$H NMR (400 MHz, CDCl$_3$) δ 7.30-7.24 (m, 2H), 7.21-7.11 (m, 3H), 3.67 (d, J=1.9 Hz, 3H), 3.15-2.90 (m, 1H), 2.79-2.67 (m, 2H), 2.56-2.42 (m, 1H), 2.41-2.24 (m, 2H), 2.06-1.97 (m, 2H); MS: [(M+1)]$^+$=205.10.

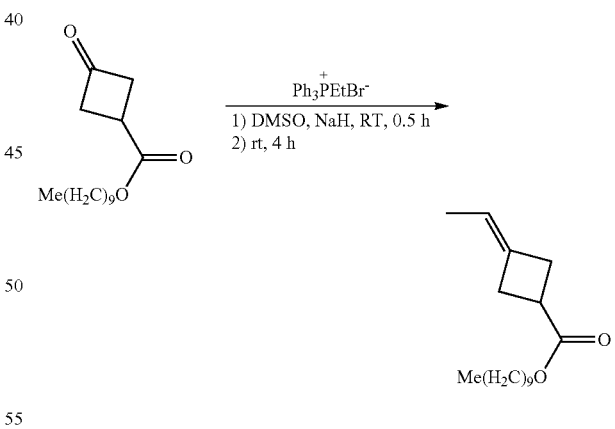

Decyl 3-ethylidenecyclobutane-1-carboxylate: To a solution of ethyltriphenylphosphonium bromide (17.3 g, 46.5 mmol) in dimethyl sulfoxide (300 mL) was added potassium t-butoxide (4.94 g, 44.1 mmol) in portions at 14° C. The resulting mixture was stirred for 0.5 hours at 25° C. under nitrogen atmosphere followed by the addition of decyl 3-oxocyclobutane-1-carboxylate (8.00 g, 31.5 mmol) dropwise over 2 min at 14° C. After stirring for 4 hours at 25° C., the reaction was quenched by saturated aqueous ammonium chloride (20.0 mL) at 0° C. The resulting mixture was diluted with water (1.00 L) and extracted with ethyl acetate (3×200 mL). The combined organic layers was washed with brine (2×100 mL) and dried over anhydrous sodium sulfate. After filtration, the filtrate was concentrated under reduced pressure. The residue was purified by silica gel column chromatography, eluted with 1%~5% ethyl acetate in petroleum ether. The desired fractions were collected and concentrated under reduced pressure to afford the title compound as a colorless oil (1.70 g, 21%): ¹H NMR (400 MHz, CDCl₃) δ 5.18 (qp, J=7.2, 2.6 Hz, 1H), 4.09 (t, J=6.7 Hz, 2H), 3.10 (tt, J=9.2, 7.2 Hz, 1H), 2.96-2.79 (m, 4H), 1.67-1.58 (m, 2H), 1.49 (dq, J=6.0, 2.0 Hz, 3H), 1.39-1.20 (m, 14H), 0.88 (t, J=6.7 Hz, 3H).

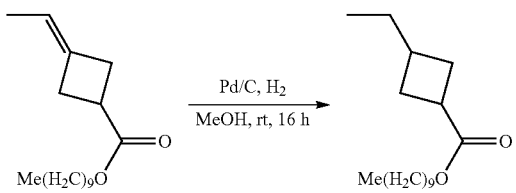

Decyl 3-ethylcyclobutane-1-carboxylate: To a stirred solution of decyl 3-ethylidenecyclobutane-1-carboxylate (700 mg, 4.94 mmol) in methanol (10.0 mL) was added anhydrous Pd/C (70.0 mg, 10% palladium on charcoal) at ambient temperature under nitrogen atmosphere. After stirring for 16 hours at ambient temperature under hydrogen atmosphere, the resulting mixture was filtered. The filtered cake was washed with methanol (3×20.0 mL). The filtrate was concentrated under reduced pressure to afford the title compound as a light yellow oil (666 mg, 95%): ¹H NMR (400 MHz, CDCl₃) δ 4.10-4.02 (m, 2H), 3.10-2.87 (m, 1H), 2.40-2.22 (m, 2H), 2.16-2.03 (m, 1H), 1.91-1.76 (m, 2H), 1.67-1.56 (m, 2H), 1.48-1.21 (m, 16H), 0.92-0.75 (m, 6H).

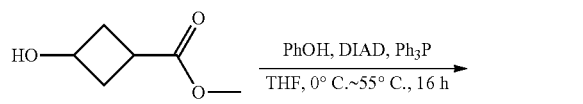

Methyl 3-phenoxycyclobutane-1-carboxylate: To a solution of methyl 3-hydroxycyclobutane-1-carboxylate (4.00 g, 30.7 mmol), triphenylphosphine (6.45 g, 24.6 mmol) and phenol (2.31 g, 24.6 mmol) in anhydrous tetrahydrofuran (50.0 mL) was added diisopropyl azodiformate (4.97 g, 24.6 mmol) dropwise at 0° C. After stirring for 16 hours at 55° C. under nitrogen atmosphere, the resulting mixture was concentrated under reduced pressure. The residue was purified by silica gel column chromatography, eluted with 2%~20% ethyl acetate in petroleum ether. The desired fractions were collected and concentrated under reduced pressure to afford the title compound as a colorless oil (3.80 g, 60%): ¹H NMR (400 MHz, CDCl₃) δ 7.27 (t, J=7.9 Hz, 2H), 6.94 (t, J=7.3 Hz, 1H), 6.79 (d, J=7.9 Hz, 2H), 4.90 (p, J=6.6 Hz, 1H), 3.74 (s, 3H), 3.23-3.13 (m, 1H), 2.79-2.68 (m, 2H), 2.52-2.41 (m, 2H).

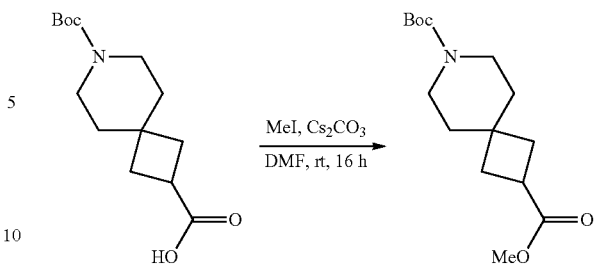

7-(tert-Butyl) 2-methyl 7-azaspiro[3.5]nonane-2,7-dicarboxylate: To a mixture of 7-(tert-butoxycarbonyl)-7-azaspiro[3.5]nonane-2-carboxylic acid (1.50, 5.57 mmol) and cesium carbonate (2.72 g, 8.35 mmol) in N,N-dimethylformamide (50.0 mL) was added iodomethane (1.03 g, 7.26 mmol) at ambient temperature under nitrogen atmosphere. The resulting mixture was stirred for 16 hours at 25° C. under nitrogen atmosphere. The resulting mixture was diluted with water (400 mL). The resulting mixture was extracted with ethyl acetate (3×100 mL). The combined organic layers was washed with brine (2×100 mL) and dried over anhydrous sodium sulfate. After filtration, the filtrate was concentrated under reduced pressure to afford the title compound as a light yellow oil (1.44 g, 91%): ¹H NMR (400 MHz, CDCl₃) δ 3.68 (s, 3H), 3.39-3.32 (m, 2H), 3.32-3.24 (m, 2H), 3.09 (p, J=8.8 Hz, 1H), 2.06 (d, J=8.9 Hz, 4H), 1.60-1.55 (m, 2H), 1.55-1.49 (m, 2H), 1.45 (s, 9H); MS: [(M+1)]⁺=284.20.

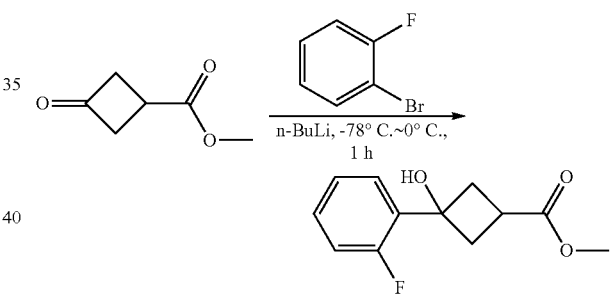

Methyl 3-(2-fluorophenyl)-3-hydroxycyclobutane-1-carboxylate: A solution of 1-bromo-2-fluorobenzene (6.83 g, 39.0 mmol) in anhydrous tetrahydrofuran (390 mL) was treated with n-butyl lithium (15.6 mL, 39.0 mmol, 2.50M in hexane) for 1 h at −78° C. followed by the addition of ethyl 3-oxocyclobutane-1-carboxylate (5.00 g, 39.0 mmol). The resulting mixture was stirred for additional hour under nitrogen atmosphere until the internal temperature was warmed to −10° C. The reaction was quenched by saturated aqueous ammonium chloride (30.0 mL) at −10° C. The resulting mixture was diluted with water (500 mL) and separated. The aqueous layer was extracted with ethyl acetate (3×100 mL). The combined organic layers was washed with brine (2×100 mL) and dried over anhydrous sodium sulfate. After filtration, the filtrate was concentrated under reduced pressure. The residue was purified by silica gel column chromatography, eluted with 3%~7% ethyl acetate in petroleum ether. The desired fractions were collected and concentrated under reduced pressure to afford the title compound as colorless oil (2.00 g, 23%): ¹H NMR (400 MHz, CDCl₃) δ7.43 (td, J=7.9, 1.8 Hz, 1H), 7.33-7.28 (m, 1H) 7.17-7.04 (m, 2H), 3.75 (s, 3H), 3.07-2.88 (m, 3H), 2.68-2.62 (m, 2H).

The following intermediates were prepared according to the procedure described above:

| Intermediates | Structure | Name | ¹H-NMR |
|---|---|---|---|
| 1 | 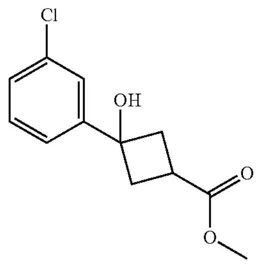 [SMILES: COC(=O)C1CC(O)(c2cccc(Cl)c2)C1] | Methyl 3-(3-chlorophenyl)-3-hydroxycyclobutane-1-carboxylate | ¹H NMR (400 MHz, CDCl₃) δ 7.49 (t, J = 1.9 Hz, 1H), 7.41-7.25 (m, 3H), 3.74 (s, 3H), 2.94-2.80 (m, 3H), 2.69-2.58 (m, 2H). |
| 2 | 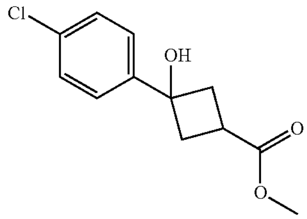 [SMILES: COC(=O)C1CC(O)(c2ccc(Cl)cc2)C1] | Methyl 3-(4-chlorophenyl)-3-hydroxycyclobutane-1-carboxylate | ¹H NMR (400 MHz, CDCl₃) δ 7.48-7.40 (m, 2H), 7.41-7.31 (m, 2H), 3.75 (s, 3H), 2.94-2.79 (m, 3H), 2.69-2.55 (m, 2H). |
| 3 | 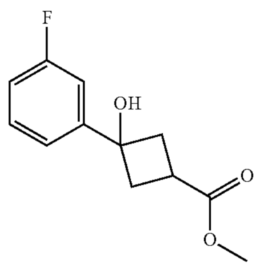 [SMILES: COC(=O)C1CC(O)(c2cccc(F)c2)C1] | Methyl 3-(3-fluorophenyl)-3-hydroxycyclobutane-1-carboxylate | ¹H NMR (400 MHz, CDCl₃) δ 7.37-7.30 (m, 2H), 7.29-7.22 (m, 2H), 3.75 (s, 3H), 2.92-2.81 (m, 3H), 2.66-2.59 (m, 2H). |
| 4 | 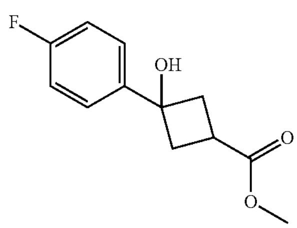 [SMILES: COC(=O)C1CC(O)(c2ccc(F)cc2)C1] | Methyl 3-(4-fluorophenyl)-3-hydroxycyclobutane-1-carboxylate | ¹H NMR (400 MHz, DMSO-d₆) δ 7.57-7.52 (m, 2H), 7.19-7.14 (m, 2H), 3.63 (s, 3H), 2.86-2.74 (m, 1H), 2.68-2.60 (m, 2H), 2.56-2.51 (m, 2H). |
| 5 | 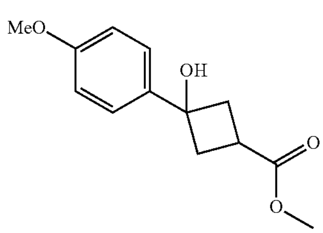 [SMILES: COC(=O)C1CC(O)(c2ccc(OC)cc2)C1] | Methyl 3-hydroxy-3-(4-methoxyphenyl)cyclobutane-1-carboxylate | ¹H NMR (400 MHz, CDCl₃) δ 7.46-7.40 (m, 2H), 6.94-6.88 (m, 2H), 3.82 (s, 3H), 3.73 (s, 3H), 2.90-2.74 (m, 3H), 2.65-2.58 (m, 2H). |

The following intermediates were prepared according to the procedure described above:

| Intermediate | Structure | Name | MS: [(M + 1)]⁺ | ¹H-NMR |
|---|---|---|---|---|
| 6 | 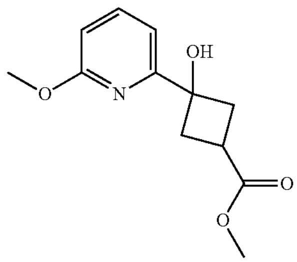 [SMILES: COC(=O)C1CC(O)(c2cccc(OC)n2)C1] | Methyl 3-hydroxy-3-(6-methoxypyridin-2-yl)cyclobutane-1-carboxylate | 238.15 | ¹H NMR (400 MHz, CDCl$_3$) δ 7.63 (dd, J = 8.2, 7.4 Hz, 1H), 7.10 (d, J = 7.4 Hz, 1H), 6.67 (d, J = 8.2 Hz, 1H), 3.96 (s, 3H), 3.74 (s, 3H), 3.09 (p, J = 8.6 Hz, 1H), 2.85-2.68 (m, 4H). |
| 7 | 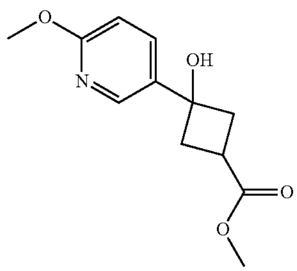 [SMILES: COC(=O)C1CC(O)(c2ccc(OC)nc2)C1] | Methyl 3-hydroxy-3-(6-methoxypyridin-3-yl)cyclobutane-1-carboxylate | 238.20 | ¹H NMR (400 MHz, CDCl$_3$) δ 8.29 (d, J = 2.5 Hz, 1H), 7.74 (dd, J = 8.6, 2.4 Hz, 1H), 6.78 (d, J = 8.6 Hz, 1H), 3.95 (s, 3H), 3.75 (s, 3H), 3.13 (br, 1H), 2.92-2.80 (m, J = 4.8 Hz, 3H), 2.68-2.57 (m, 2H). |
| 8 | 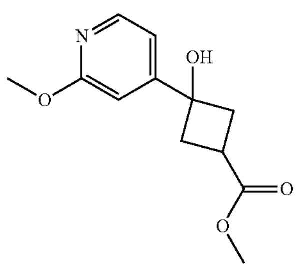 [SMILES: COC(=O)C1CC(O)(c2ccnc(OC)c2)C1] | Methyl 3-hydroxy-3-(2-methoxypyridin-4-yl)cyclobutane-1-carboxylate | 238.10 | ¹H NMR (400 MHz, CDCl$_3$) δ 8.15 (d, J = 5.4 Hz, 1H), 7.01 (dd, J = 5.4, 1.6 Hz, 1H), 6.87-6.84 (m, 1H), 3.94 (s, 3H), 3.75 (s, 3H), 3.59 (br, 1H), 2.98-2.89 (m, 1H), 2.85-2.76 (m, 2H), 2.66-2.58 (m, 2H). |
| 9 | 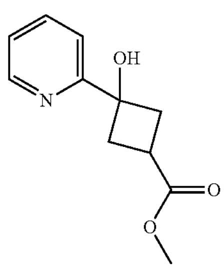 | Methyl 3-hydroxy-3-(pyridin-2-yl)cyclobutane-1-carboxylate | 208.20 | ¹H NMR (400 MHz, CDCl$_3$) δ 8.56-8.53 (m, 1H), 7.75 (td, J = 7.7, 1.8 Hz, 1H), 7.56 (dt, J = 7.9, 1.1 Hz, 1H), 7.25-7.21 (m, 1H), 5.08 (s, 1H), 3.75 (s, 3H), 3.09 (p, J = 8.5 Hz, 1H), 2.88-2.80 (m, 2H), 2.79-2.72 (m, 2H). |
| 10 | 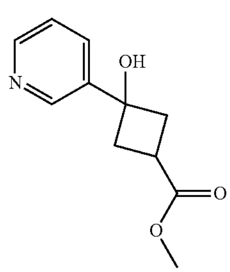 | Methyl 3-hydroxy-3-(pyridin-3-yl)cyclobutane-1-carboxylate | 208.10 | ¹H NMR (400 MHz, CDCl$_3$) δ 8.78 (s, 1H), 8.55 (d, J = 4.7 Hz, 1H), 7.91-7.83 (m, 1H), 7.34 (dd, J = 8.0, 4.8 Hz, 1H), 7.26 (s, 1H), 3.77 (d, J = 1.4 Hz, 3H), 3.00-2.87 (m, 3H), 2.70-2.62 (m, 2H). |

| Intermediate | Structure | Name | MS: [(M + 1)]+ | 1H-NMR |
|---|---|---|---|---|
| 11 | 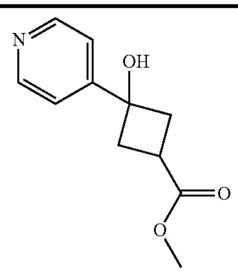 | Methyl 3-hydroxy-3-(pyridin-4-yl)cyclobutane-1-carboxylate | 208.20 | 1H NMR (400 MHz, CDCl3) δ 8.59 (d, J = 5.0 Hz, 2H), 7.48-7.42 (m, 2H), 3.76 (s, 3H), 3.03-2.93 (m, 1H), 2.88-2.79 (m, 2H), 2.70-2.62 (m, 2H). |

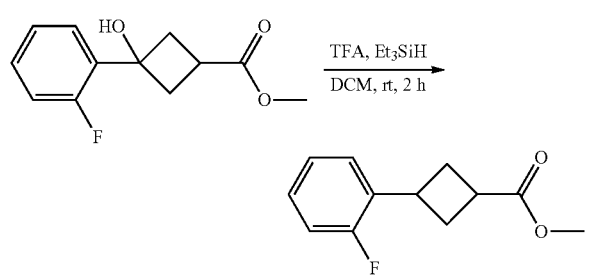

Methyl 3-(2-fluorophenyl)cyclobutane-1-carboxylate: To a solution of methyl 3-(2-fluorophenyl)-3-hydroxycyclobutane-1-carboxylate (2.00 g, 8.92 mmol) in trifluoroacetic acid (10.0 mL) and dichloromethane (10.0 mL) was added triethylsilane (5.19 g, 44.6 mmol) dropwise at 15° C. The resulting solution was stirred for 2 hours at ambient temperature. The resulting mixture was concentrated under reduced pressure. The residue was taken up with water (30.0 mL) and ethyl acetate (30.0 mL). The aqueous layer was extracted with ethyl acetate (3×50.0 mL). The combined organic layers was washed with brine (2×50.0 mL) and dried over anhydrous sodium sulfate. After filtration, the filtrate was concentrated under reduced pressure. The residue was purified by silica gel column chromatography, eluted with 1%~10% ethyl acetate in petroleum ether. The desired fractions were collected and concentrated under reduced pressure to afford the title compound as a light yellow oil (400 mg, 22%): 1H NMR (400 MHz, CDCl3) δ 7.43 (td, J=7.9, 1.8 Hz, 1H), 7.33-7.28 (m, 1H), 7.17-7.04 (m, 2H), 3.75 (s, 3H), 3.07-2.88 (m, 3H), 2.68-2.62 (m, 2H).

The following intermediates were prepared according to the procedure described above:

| Intermediate | Structure | Name | 1H-NMR |
|---|---|---|---|
| 1 | 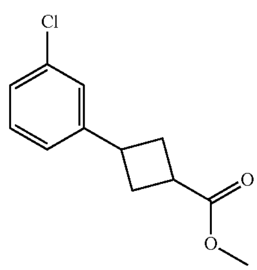 | Methyl 3-(3-chlorophenyl)cyclobutane-1-carboxylate | 1H NMR (400 MHz, CDCl3) δ 7.28-7.15 (m, 3H), 7.13-7.07 (m, 1H), 3.77 (s, 1H), 3.70 (s, 2H), 3.48-3.37 (m, 1H), 3.18-3.07 (m, 1H), 2.73-2.55 (m, 2H), 2.46-2.34 (m, 2H). |
| 2 | 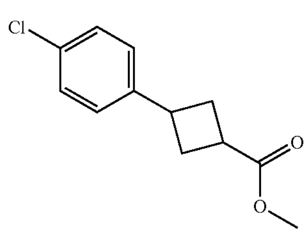 | Methyl 3-(4-chlorophenyl)cyclobutane-1-carboxylate | 1H NMR (400 MHz, CDCl3) δ 7.30-7.27 (m, 2H), 7.18-7.14 (m, 2H), 3.75 (s, 1H), 3.70 (s, 2H), 3.48-3.36 (m, 1H), 3.17-3.06 (m, 1H), 2.73-2.56 (m, 2H), 2.44-2.32 (m, 2H). |

| Intermediate | Structure | Name | ¹H-NMR |
|---|---|---|---|
| 3 | (structure: 3-fluorophenyl cyclobutane methyl carboxylate) | Methyl 3-(3-fluorophenyl)cyclobutane-1-carboxylate | ¹H NMR (400 MHz, CDCl₃) δ 7.29-7.22 (m, 1H), 7.01-6.85 (m, 3H), 3.70 (s, 3H), 3.50-3.39 (m, 1H), 3.18-3.07 (m, 1H), 2.66-2.57 (m, 2H), 2.45-2.35 (m, 2H). |
| 4 | (structure: 4-fluorophenyl cyclobutane methyl carboxylate) | Methyl 3-(4-fluorophenyl)cyclobutane-1-carboxylate | ¹H NMR (400 MHz, DMSO-d₆) δ 7.26 (dd, J = 8.4, 5.6 Hz, 2H), 7.13 (t, J = 8.7 Hz, 2H), 3.61 (s, 3H), 3.49-3.38 (m, 1H), 3.20-3.09 (m, 1H), 2.59-2.52 (m, 2H), 2.25-2.14 (m, 2H). |
| 5 | (structure: 4-methoxyphenyl cyclobutane methyl carboxylate) | Methyl 3-(4-methoxyphenyl)cyclobutane-1-carboxylate | ¹H NMR (400 MHz, CDCl₃) δ 7.20-7.13 (m, 2H), 6.89-6.82 (m, 2H), 3.79 (d, J = 1.8 Hz, 3H), 3.74 (s, 1.5H), 3.69 (s, 1.5H), 3.44-3.33 (m, 1H), 3.17-3.04 (m, 1H), 2.71-2.53 (m, 2H), 2.44-2.32 (m, 2H). |

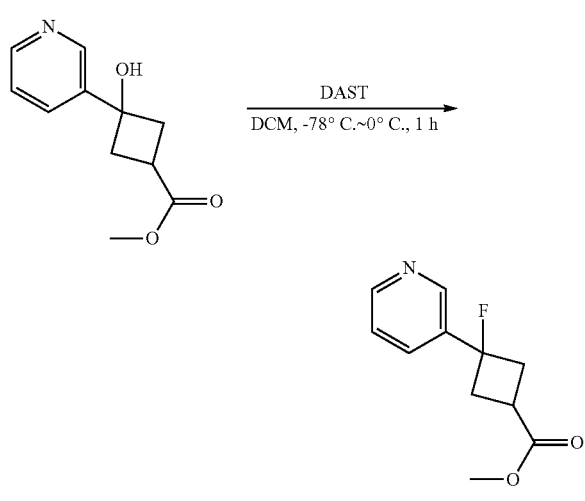

Methyl 3-fluoro-3-(pyridin-3-yl)cyclobutane-1-carboxylate: To a stirred solution of methyl 3-hydroxy-3-(pyridin-3-yl)cyclobutane-1-carboxylate (1.54 g, 7.43 mmol) in dichloromethane (22.0 mL) was added diethylaminosulfurtrifluoride (1.92 g, 11.9 mmol) dropwise at −78° C. under argon atmosphere. The mixture was stirred for 1 hour from −78° C. to 0° C. The reaction was quenched by saturated aqueous sodium bicarbonate (50.0 mL) at 0° C. The resulting mixture was extracted with ethyl acetate (3×100 mL). The combined organic layers was washed with brine (2×50.0 mL) and dried over anhydrous sodium sulfate. After filtration, the filtrate was concentrated under reduced pressure. The residue was purified by silica gel column chromatography, eluted with 1%~3% methanol in dichloromethane. The desired fractions were collected and concentrated under reduced pressure to afford the title compound to as a red oil (1.26 g, 82%): ¹H NMR (400 MHz, CDCl₃) δ 8.75 (d, J=9.9 Hz, 1H), 8.60 (d, J=4.8 Hz, 11H), 7.81 (d, J=8.0 Hz, 1H), 7.36 (dd, J=8.0, 4.9 Hz, 1H), 3.73 (s, 3H), 3.53 (p, J=8.8 Hz, 1H), 2.89 (dd, J=24.1, 8.7 Hz, 4H); MS: [(M+1)]⁺=210.20.

The following intermediates were prepared according to the procedure described above:

| Intermediate | Structure | Name | MS: [(M + 1)]+ | 1H-NMR |
|---|---|---|---|---|
| 1 | 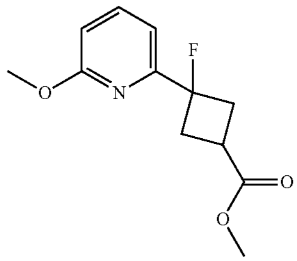 [SMILES: COC(=O)C1CC(F)(c2cccc(OC)n2)C1] | Methyl 3-fluoro-3-(6-methoxypyridin-2-yl)cyclobutane-1-carboxylate | 240.20 | 1H NMR (400 MHz, CDCl3) δ 7.61-7.54 (m, 1H), 7.07-6.99 (m. 1H), 6.69-6.63 (m, 1H), 3.95 (s, 0.7H), 3.94 (s, 2.3H), 3.75 (s, 0.7H), 3.72 (s, 2.3H), 3.50-3.40 (m, 1H), 3.28-3.07 (m, 2H), 2.89-2.65 (m, 2H). |
| 2 | 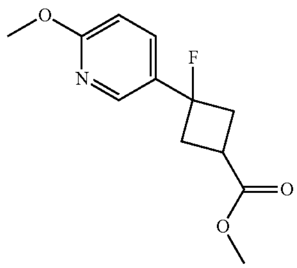 [SMILES: COC(=O)C1CC(F)(c2ccc(OC)nc2)C1] | Methyl 3-fluoro-3-(6-methoxypyridin-3-yl)cyclobutane-1-carboxylate | 240.20 | 1H NMR (400 MHz, CDCl3) δ 8.26 (d, J = 21.0 Hz, 1H), 7.72-7.62 (m, 1H), 6.83-6.74 (m, 1H), 3.97 (s, 0.5H), 3.96 (s, 2.5H), 3.74 (s, 0.5H), 3.71 (s, 2.5H), 3.49 (p, J = 8.7 Hz, 1H), 3.02-2.72 (m, 4H). |
| 3 | 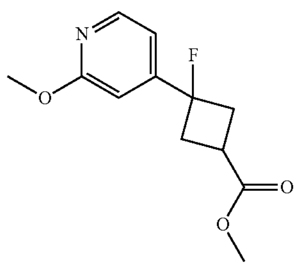 [SMILES: COC(=O)C1CC(F)(c2ccnc(OC)c2)C1] | Methyl 3-fluoro-3-(2-methoxypyridin-4-yl)cyclobutane-1-carboxylate | 240.20 | 1H NMR (400 MHz, CDCl3) δ 8.18 (d, J = 5.4 Hz, 1H), 6.97 (dd, J = 5.5, 1.5 Hz, 1H), 6.82 (d, J = 1.6 Hz, 1H), 3.95 (s, 3H), 3.74 (s, 3H), 3.49 (p, J = 8.8 Hz, 1H), 2.88-2.77 (m, 4H). |
| 4 | 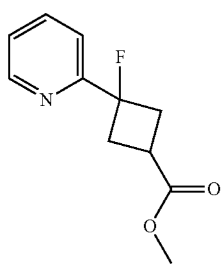 | Methyl 3-fluoro-3-(pyridin-2-yl)cyclobutane-1-carboxylate | 210.20 | 1H NMR (400 MHz, CDCl3) δ 8.65-8.59 (m, 1H), 7.71 (td, J = 7.7, 1.7 Hz, 1H), 7.50-7.45 (m, 1H), 7.24-7.20 (m, 1H), 3.73 (s, 3H), 3.50 (p, J = 8.9 Hz, 1H), 3.20-3.06 (m, 2H), 2.83-2.67 (m, 2H). |
| 5 | 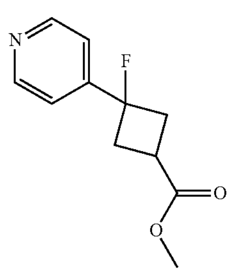 | Methyl 3-fluoro-3-(pyridin-4-yl)cyclobutane-1-carboxylate | 210.25 | 1H NMR (400 MHz, CDCl3) δ 8.67 (s, 2H), 7.41 (d, J = 4.8 Hz, 2H), 3.75 (s, 3H), 3.50 (p, J = 8.8 Hz, 1H), 2.85 (dd, J = 24.3, 8.8 Hz, 4H). |

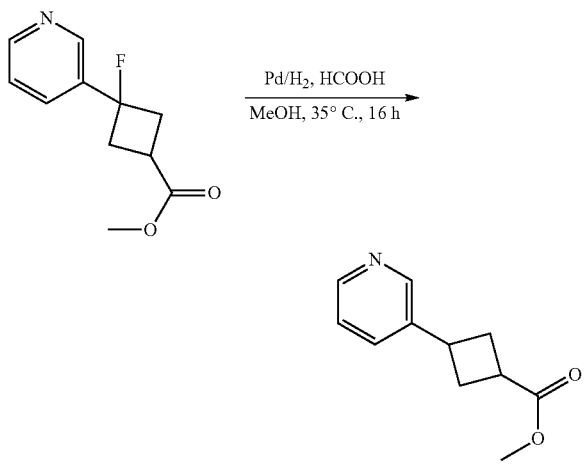

Methyl 3-(pyridin-3-yl)cyclobutane-1-carboxylate: To a stirred solution of methyl 3-fluoro-3-(pyridin-3-yl)cyclobutane-1-carboxylate (1.26 g, 6.02 mmol) in methanol (40.0 mL) and formic acid (2.00 mL) was added anhydrous Pd/C (1.26 g, 11.8 mol, 10% palladium on charcoal) at ambient temperature under nitrogen atmosphere. The resulting mixture was stirred for 16 hours at 35° C. under hydrogen atmosphere. The resulting mixture was filtered, the filtered cake was washed with methanol (4×20.0 mL). The filtrate was concentrated under reduced pressure. The residue was purified by silica gel column chromatography, eluted with 1%~3% methanol in dichloromethane. The desired fractions were collected and concentrated under reduced pressure to afford the title compound as a light yellow oil (1.05 g, 91%): $^1$H NMR (400 MHz, CDCl$_3$) δ 8.16 (s, 1H), 7.81 (d, J=7.9 Hz, 1H), 7.74 (d, J=7.9 Hz, 1H), 7.43 (s, 1H), 3.85 (p, J=8.8 Hz, 0.7H), 3.77 (s, 2H), 3.71 (s, 1H), 3.54 (p, J=9.2 Hz, 0.3H), 3.24-3.15 (m, 1H), 2.81-2.63 (m, 2H), 2.52-2.40 (m, 2H); MS: [(M+1)]$^+$=192.10.

The following intermediates were prepared according to the procedure described above:

| Intermediate | Structure | Name | MS: [(M + 1)]$^+$ | $^1$H-NMR |
|---|---|---|---|---|
| 1 | 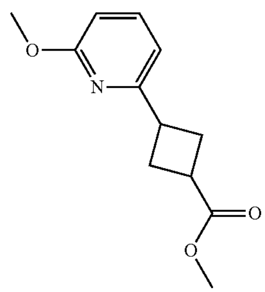 [SMILES: COC(=O)C1CC(c2cccc(OC)n2)C1] | Methyl 3-(6-methoxypyridin-2-yl)cyclobutane-1-carboxylate | 222.20 | $^1$H NMR (400 MHz, CDCl$_3$) δ 7.57-7.47 (m, 1H), 6.80-6.69 (m, 1H), 6.62-6.58 (m, 1H), 3.99 (s, 3H), 3.79-3.53 (m, 4H), 3.35 (p, J = 7.7 Hz, 0.7H), 3.15 (p, J = 9.2 Hz, 0.3H), 2.70-2.56 (m, 4H). |
| 2 | 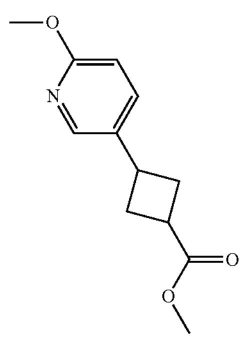 [SMILES: COC(=O)C1CC(c2ccc(OC)nc2)C1] | Methyl 3-(6-methoxypyridin-3-yl)cyclobutane-1-carboxylate | 222.10 | $^1$H NMR (400 MHz, CDCl$_3$) δ 8.01 (dd, J = 10.8, 2.4 Hz, 1H), 7.58-7.48 (m, 1H), 6.73 (d, J = 8.5 Hz, 1H), 3.93 (d, J = 2.0 Hz, 3H), 3.75 (s, 2H), 3.70 (s, 1H), 3.45-3.31 (m, 0.5H), 3.21-3.07 (m, 1H), 2.73-2.57 (m, 2.5H), 2.45-2.31 (m, 2H). |
| 3 | 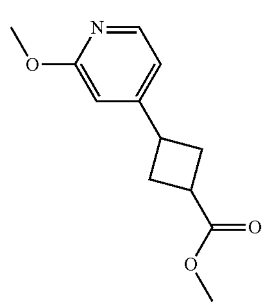 [SMILES: COC(=O)C1CC(c2ccnc(OC)c2)C1] | Methyl 3-(2-methoxypyridin-4-yl)cyclobutane-1-carboxylate | 222.20 | $^1$H NMR (400 MHz, CDCl$_3$) δ 8.10-8.06 (m, 1H), 6.76-6.72 (m, 1H), 6.59-6.57 (m, 1H), 3.94 (s, 2.2H), 3.93 (s, 0.8H), 3.74 (s, 2.2H), 3.72-3.65 (m, 1.5H), 3.45-3.34 (m, 0.3H), 3.19-3.09 (m, 1H), 2.73-2.56 (m, 2H), 2.46-2.35 (m, 2H). |

-continued

| Intermediate | Structure | Name | MS: [(M + 1)]⁺ | ¹H-NMR |
|---|---|---|---|---|
| 4 | 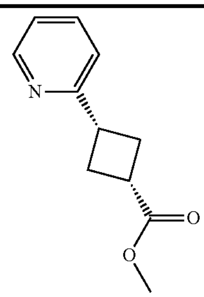 | cis-Methyl-3-(pyridin-2-yl)cyclobutane-1-carboxylate | 192.15 | ¹H NMR (400 MHz, CDCl₃) δ 8.60 (dt, J = 4.7, 1.5 Hz, 1H), 7.60 (td, J = 7.6, 1.9 Hz, 1H), 7.13 (dd, J = 7.6, 4.8 Hz, 2H), 3.88-3.77 (m, 1H), 3.75 (s, 3H), 3.29-3.20 (m, 1H), 2.69-2.63 (m, 4H). |
| 5 | 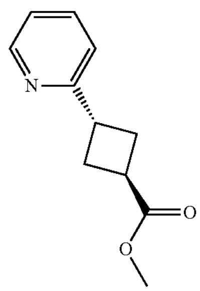 | trans-Methyl 3-(pyridin-2-yl)cyclobutane-1-carboxylate | 192.15 | ¹H NMR (400 MHz, CDCl₃) δ 8.56-8.54 (m, 1H), 7.62 (td, J = 7.7, 1.9 Hz, 1H), 7.21 (d, J = 7.8 Hz, 1H), 7.14-7.10 (m, 1H), 3.70 (s, 1H), 3.64-3.55 (m, 1H), 3.22-3.12 (m, 1H), 2.70-2.53 (m, 4H). |
| 6 | 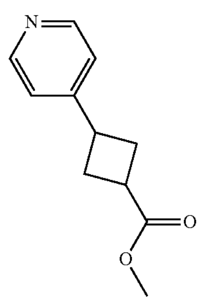 | Methyl 3-(pyridin-4-yl)cyclobutane-1-carboxylate | 192.10 | ¹H NMR (400 MHz, CDCl₃) δ 8.60 (s, 2H), 7.30 (s, 2H), 3.83 (p, J = 8.6 Hz, 1H), 3.76 (s, 2.4H), 3.71 (s, 0.6H), 3.21-3.13 (m, 1H), 2.81-2.64 (m, 2H), 2.51-2.40 (m, 2H). |

Note:
Compound 4 and 5 were separated by silica gel column chromatography, eluted with 1%~35% ethyl acetate in petroleum ether. compound 4: low polarity, compound 5: high polarity.

Intermediate I

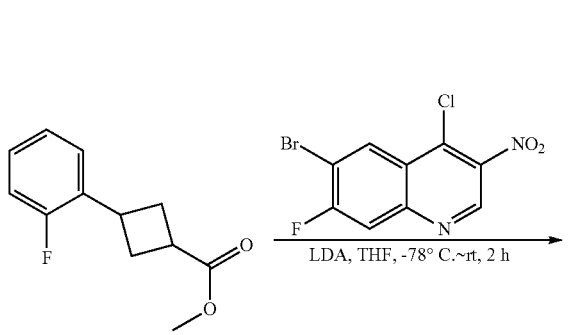

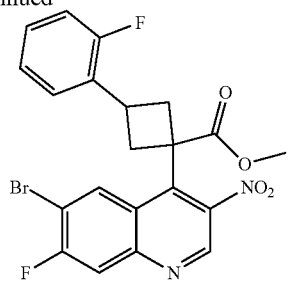

Methyl 1-(6-bromo-7-fluoro-3-nitroquinolin-4-yl)-3-(2-fluorophenyl)cyclobutane-1-carboxylate: To solution of diisopropylamine (302 mg, 2.98 mmol) in anhydrous tetrahydrofuran (25.0 mL) was added n-butyllithium (1.19 mL, 2.98 mmol, 2.50 M in hexane) at −78° C. under nitrogen atmosphere. The resulting mixture was stirred for 1 hour at −20° C.~−15° C. followed by) the addition of methyl 3-(2-fluorphenyl)cyclobutane-1-carboxylate (621 mg, 2.99 mmol) dropwise over 2 min at −78° C. After stirring for additional 1 hour at −78° C., 6-bromo-5-chloro-7-fluo-3-nitroquinoline (700 mg, 2.29 mmol) was added in portions to the reaction mixture. The resulting mixture was slowly warmed to ambient temperature. After stirring for 2 hours at ambient temperature, the reaction was quenched by saturated aqueous ammonium chloride (20.0 mL) at −30° C. The resulting mixture was diluted with water (150 mL) and separated. The aqueous layer was extracted with ethyl acetate (3×100 mL). The combined organic layers was washed with brine (2×50.0 mL) and dried over anhydrous sodium sulfate. After filtration, the filtrate was concentrated under reduced pressure, eluted with 1%~9% ethyl acetate in petroleum ether. The desired fractions were collected and concentrated under reduced pressure to afford the title compound as a yellow solid (270 mg, 25%): MS: $[(M+1)]^+$=477.10, 479.10.

The following intermediates were prepared according to the procedure described above:

| Intermediate | Structure | Name | MS: $[(M + 1)]^+$ | $^1$H-NMR |
|---|---|---|---|---|
| 1 | 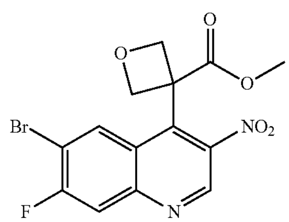 [SMILES: COC(=O)C1(c2c([N+](=O)[O-])cnc3cc(F)c(Br)cc23)COC1] | Methyl 3-(6-bromo-7-fluoro-3-nitroquinolin-4-yl)oxetane-3-carboxylate | 385.00 387.00 | $^1$H NMR (400 MHz, CDCl$_3$) δ 9.37 (s, 2H), 7.96 (d, J = 8.6 Hz, 2H), 7.52 (d, J = 6.8 Hz, 2H), 5.32 (d, J = 6.3 Hz, 4H), 4.88 (s, 3H). |
| 2 | 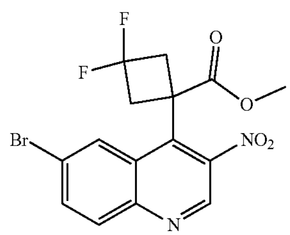 [SMILES: COC(=O)C1(c2c([N+](=O)[O-])cnc3ccc(Br)cc23)CC(F)(F)C1] | Methyl 1-(6-bromo-3-nitroquinolin-4-yl)-3,3-difluorocyclobutane-1-carboxylate | 401.00 403.00 | $^1$H NMR (400 MHz, CDCl$_3$) δ 9.20 (s, 1H), 8.12 (d, J = 8.8 Hz, 1H), 7.99-7.90 (m, 2H), 3.86 (s, 3H), 3.82-3.70 (m, 2H), 3.05 (s, 2H). |
| 3 | 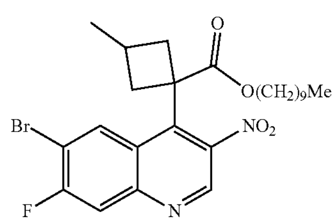 | Decyl 1-(6-bromo-7-fluoro-3-nitroquinolin-4-yl)-3-methylcyclobutane-1-carboxylate | 523.30 525.30 | Used directly in next step without further purification |
| 4 | 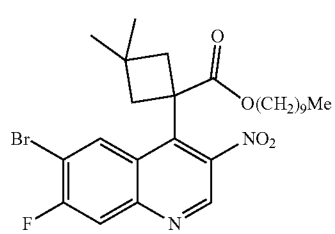 | Decyl 1-(6-bromo-7-fluoro-3-nitroquinolin-4-yl)-3,3-dimethylcyclobutane-1-carboxylate | 537.30 539.30 | Used directly in next step without further purification |
| 5 | 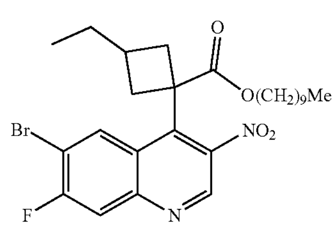 | Decyl 1-(6-bromo-7-fluoro-3-nitroquinolin-4-yl)-3-ethylcyclobutane-1-carboxylate | 537.25 539.25 | Used directly in next step without further purification |

-continued

| Intermediate | Structure | Name | MS: [(M + 1)]+ | 1H-NMR |
|---|---|---|---|---|
| 6 | 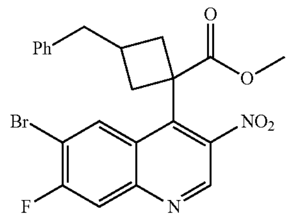 [SMILES: COC(=O)C1(c2c([N+](=O)[O-])cnc3cc(F)c(Br)cc23)CC(Cc2ccccc2)C1] | Methyl 3-benzyl-1-(6-bromo-7-fluoro-3-nitroquinolin-4-yl)cyclobutanecarboxylate | 473.10 475.10 | Used directly in next step without further purification |
| 7 | 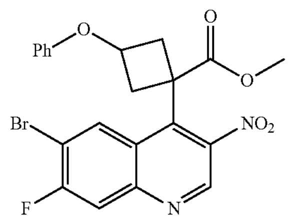 [SMILES: COC(=O)C1(c2c([N+](=O)[O-])cnc3cc(F)c(Br)cc23)CC(Oc2ccccc2)C1] | Methyl 1-(6-bromo-7-fluoro-3-nitroquinolin-4-yl)-3-phenoxycyclobutane-1-carboxylate | 475.10 477.10 | Used directly in next step without further purification |
| 8 | 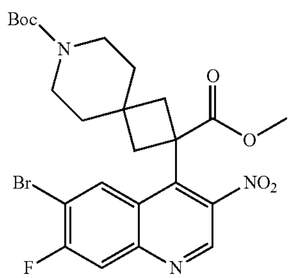 [SMILES: COC(=O)C1(c2c([N+](=O)[O-])cnc3cc(F)c(Br)cc23)CC2(CCN(C(=O)OC(C)(C)C)CC2)C1] | 7-(tert-Butyl) 2-methyl 2-(6-bromo-7-fluoro-3-nitroquinolin-4-yl)-7-azaspiro[3.5]nonane-2,7-dicarboxylate | 552.10 554.10 | Used directly in next step without further purification |
| 9 | 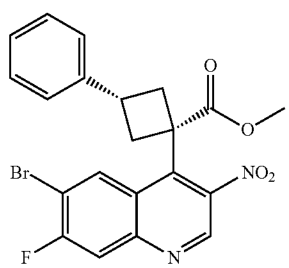 [SMILES: COC(=O)[C@]1(c2c([N+](=O)[O-])cnc3cc(F)c(Br)cc32)C[C@H](c2ccccc2)C1] | cis-Methyl-1-(6-bromo-7-fluoro-3-nitroquinolin-4-yl)-3-phenylcyclobutane-1-carboxylate | 459.05 461.00 | 1H NMR (400 MHz, CDCl3) δ 9.14 (s, 1H), 8.21 (d, J = 7.1 Hz, 1H), 7.90 (d, J = 8.7 Hz, 1H), 7.24 (d, J = 7.6 Hz, 2H), 7.16 (t, J = 7.3 Hz, 1H), 7.06 (d, J = 7.5 Hz, 2H), 4.07 (p, J = 9.6 Hz, 1H), 3.86 (s, 3H), 3.59-3.48 (m, 2H), 2.64 (br, 2H). |
| 10 | 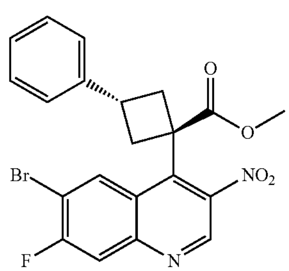 [SMILES: COC(=O)[C@]1(c2c([N+](=O)[O-])cnc3cc(F)c(Br)cc32)C[C@@H](c2ccccc2)C1] | trans-Methyl 1-(6-bromo-7-fluoro-3-nitroquinolin-4-yl)-3-phenylcyclobutane-1-carboxylate | 459.05 461.00 | 1H NMR (400 MHz, CDCl3) δ 9.21 (s, 1H), 8.19 (d, J = 7.1 Hz, 1H), 7.92 (d, J = 8.8 Hz, 1H), 7.39-7.32 (m, 4H), 7.25-7.22 (m, 1H), 3.71 (s, 3H), 3.52-3.37 (m, 3H), 3.10 (s, 2H). |
| 11 | 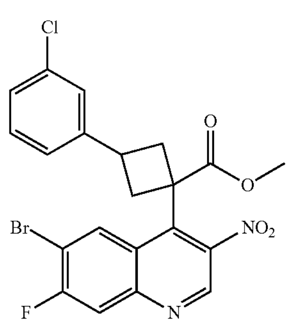 [SMILES: COC(=O)C1(c2c([N+](=O)[O-])cnc3cc(F)c(Br)cc23)CC(c2cccc(Cl)c2)C1] | Methyl 1-(6-bromo-7-fluoro-3-nitroquinolin-4-yl)-3-(3-chlorophenyl)cyclobutane-1-carboxydate | 493.10, 495.10, | Used directly in next step without further purification |

-continued

| Intermediate | Structure | Name | MS: [(M + 1)]+ | 1H-NMR |
|---|---|---|---|---|
| 12 | 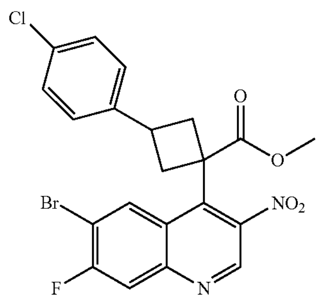 [SMILES: COC(=O)C1(c2c([N+](=O)[O-])cnc3cc(F)c(Br)cc23)CC(c2ccc(Cl)cc2)C1] | Methyl 1-(6-bromo-7-fluoro-3-nitroquinolin-4-yl)-3-(4-chlorophenyl)cyclobutane-1-carboxylate | 493.00<br>495.00 | Used directly in next step without further purification |
| 13 | 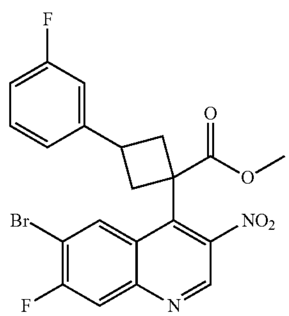 [SMILES: COC(=O)C1(c2c([N+](=O)[O-])cnc3cc(F)c(Br)cc23)CC(c2cccc(F)c2)C1] | Methyl 1-(6-bromo-7-fluoro-3-nitroquinolin-4-yl)-3-(3-fluorophenyl)cyclobutane-1-carboxylate | 477.10<br>479.10 | Used directly in next step without further purification |
| 14 | 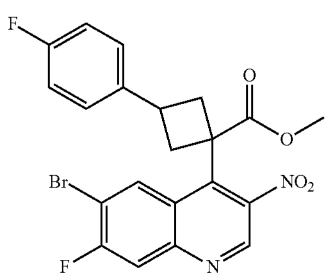 [SMILES: COC(=O)C1(c2c([N+](=O)[O-])cnc3cc(F)c(Br)cc23)CC(c2ccc(F)cc2)C1] | Methyl 1-(6-bromo-7-fluoro-3-nitroquinolin-4-yl)-3-(4-fluorophenyl)cyclobutane-1-carboxylate | 477.10<br>479.10 | Used directly in next step without further purification |
| 15 | 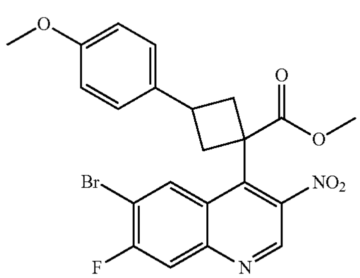 | Methyl 1-(6-bromo-7-fluoro-3-nitroquinolin-4-yl)-3-(4-methoxyphenyl)cyclobutane-1-carboxylate | 489.05<br>491.05 | Used directly in next step without further purification |
| 16 | 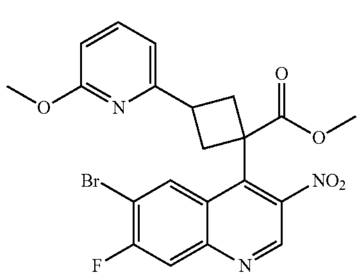 | Methyl 1-(6-bromo-7-fluoro-3-nitroquinolin-4-yl)-3-(6-methoxypyridin-2-yl)cyclobutane-1-carboxylate | 490.15<br>492.15 | Used directly in next step without further purification |

-continued

| Intermediate | Structure | Name | MS: [(M + 1)]⁺ | ¹H-NMR |
|---|---|---|---|---|
| 17 | 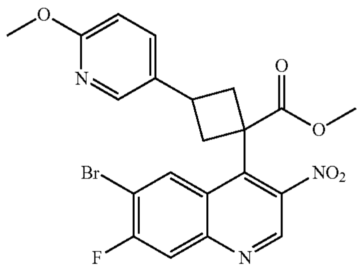 | Methyl 1-(6-bromo-7-fluoro-3-nitroquinolin-4-yl)-3-(6-methoxypyridin-3-yl)cyclobutane-1-carboxylate | 489.90 491.90 | Used directly in next step without further purification |
| 18 | 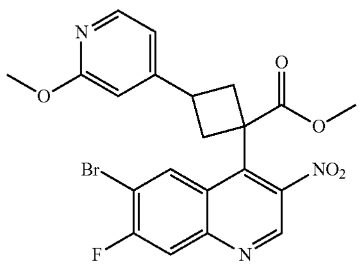 | Methyl 1-(6-bromo-7-fluoro-3-nitroquinolin-4-yl)-3-(2-methoxypyridin-4-yl)cyclobutane-1-carboxylate | 490.00 492.00 | Used directly in next step without further purification |
| 19 | 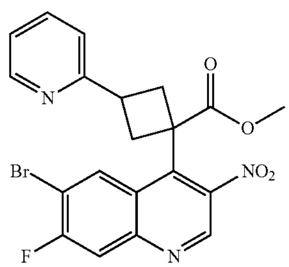 [SMILES: COC(=O)C1(c2c([N+](=O)[O-])cnc3cc(F)c(Br)cc23)CC(c2ccccn2)C1] | Methyl 1-(6-bromo-7-fluoro-3-nitroquinolin-4-yl)-3-(pyridin-2-yl)cyclobutane-1-carboxylate | 460.15 462.15 | Used directly in next step without further purification |
| 20 | 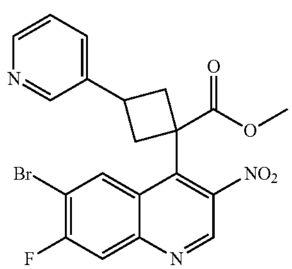 [SMILES: COC(=O)C1(c2c([N+](=O)[O-])cnc3cc(F)c(Br)cc23)CC(c2cccnc2)C1] | Methyl 1-(6-bromo-7-fluoro-3-nitroquinolin-4-yl)-3-(pyridin-3-yl)cyclobutane-1-carboxylate | 460.25 462.25 | Used directly in next step without further purification |
| 21 | 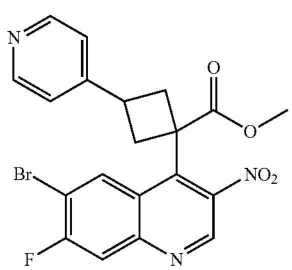 [SMILES: COC(=O)C1(c2c([N+](=O)[O-])cnc3cc(F)c(Br)cc23)CC(c2ccncc2)C1] | Methyl 1-(6-bromo-7-fluoro-3-nitroquinolin-4-yl)-3-(pyridin-4-yl)cyclobutane-1-carboxylate | 460.10 462.10 | Used directly in next step without further purification |

Note:

compound 9 and 10 were separated by Prep-Chiral-HPLC with the following conditions: Column: CHIRAL ART Cellulose-SB, 2 × 25 cm, 5 μm; Mobile Phase A: Hexane (plus 0.1% diethylamine); Mobile Phase B: i-PrOH; Flow rate: 20 mL/min; Gradient: 50 B to 50 B in 10 min; Detector: UV 220/254 nm; RT1: 6.79 min (compound 10); RT2: 8.25 min (compound 9).

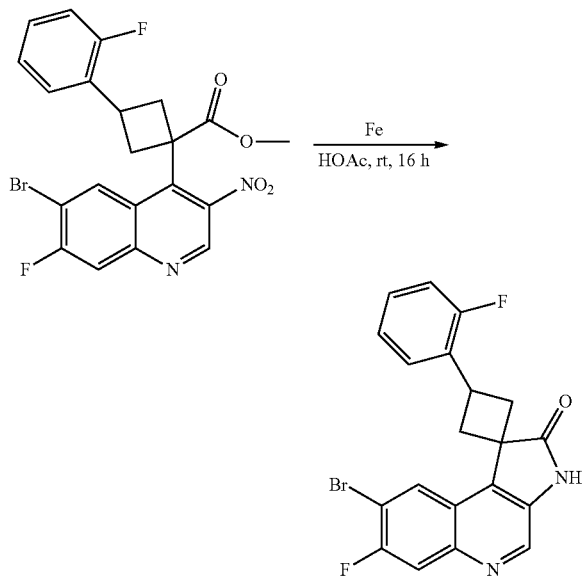

8-Bromo-7'-fluoro-3-(2-fluorophenyl)spiro[7-cyclobutane-1,1'-pyrrolo[2,3-c]quinolin]-2'(3'H)-one: To a solution of methyl 1-(6-bromo-7-fluoro-3-nitroquinolin 4-yl)-3-(2-fluorphenyl)cyclobutane-1-carboxylate (270 mg, 0.57 mol) in acetic acid (5.00 mL) was added iron powder (222 mg, 3.96 mmol) at ambient temperature. After stirring for 1 hour at 25° C., the resulting mixture was filtered and the filtered cake was washed with tetrahydrofuran (6×100 mL). The filtrate was concentrated under reduced pressure. The residue was purified by silica gel 8 column chromatography, eluted with 1%~6% methanol in dichloromethane. The desired fractions were collected and concentrated under reduced pressure to afford the title compound as a yellow solid (230 mg, 98%): MS: [(M+1)]$^+$=415.10, 417.10.

The following intermediates were prepared according to the procedure described above:

| Intermediate | Structure | Name | MS: [(M + 1)]$^+$ | $^1$H-NMR |
|---|---|---|---|---|
| 1 | 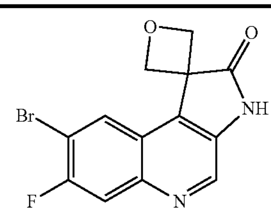 | 8'-Bromo-7'-fluorospiro[oxetane-3,1'-pyrrolo[2,3-c]quinolin]-2'(3'H)-one | 323.05 325.05 | $^1$H NMR (400 MHz, CD$_3$OD) δ 8.88 (d, J = 7.4 Hz, 1H), 8.67 (s, 1H), 7.86 (d, J = 9.8 Hz, 1H), 5.18 (d, J = 6.5 Hz, 2H), 4.96 (d, J = 6.4 Hz, 2H). |
| 2 | 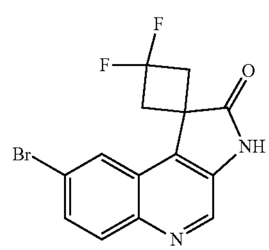 [SMILES: O=C1Nc2cnc3ccc(Br)cc3c2C12CC(F)(F)C2] | 8'-Bromo-3,3-difluorospiro[cyclobutane-1,1'-pyrrolo[2,3-c]quinolin]-2'(3'H)-one | 339.00 341.00 | $^1$H NMR (400 MHz, DMSO-d$_6$) δ 11.06 (s, 1H), 8.71 (s, 1H), 8.16 (t, J = 2.1 Hz, 1H), 8.01 (d, J = 9.0 Hz, 1H), 7.78 (dd, J = 9.0, 2.1 Hz, 1H), 3.55-3.40 (m, 2H), 3.30-3.12 (m, 2H). |
| 3 | 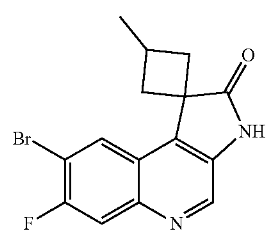 [SMILES: CC1CC2(C1)C(=O)Nc1cnc3cc(F)c(Br)cc3c12] | 8'-Bromo-7'-fluoro-3-methylspiro[cyclobutane-1,1'-pyrrolo[2,3-c]quinolin]-2'(3'H)-one | 335.00 337.00 | $^1$H NMR (400 MHz, DMSO-d$_6$) δ 10.75 (d, J = 3.1 Hz, 1H), 8.67 (d, J = 1.1 Hz, 1H), 8.49 (d, J = 7.5 Hz, 0.4H), 8.40 (d, J = 7.5 Hz, 0.6H), 7.98 (dd, J = 10.1, 1.4 Hz, 1H), 3.07-2.95 (m, 1H), 2.88-2.78 (m, 1H), 2.61-2.51 (m, 2H), 2.27-2.17 (m, 1H), 1.35 (dd, J = 6.8, 1.4 Hz, 3H). |
| 4 | 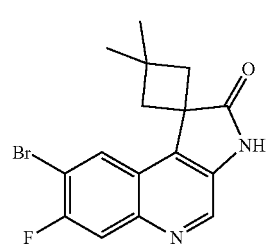 [SMILES: CC1(C)CC2(C1)C(=O)Nc1cnc3cc(F)c(Br)cc3c12] | 8'-Bromo-7'-fluoro-3,3-dimethylspiro[cyclobutane-1,1'-pyrrolo[2,3-c]quinolin]-2'(3'H)-one | 349.10 351.10 | $^1$H NMR (400 MHz, DMSO-d$_6$) δ 10.79 (s, 1H), 8.66 (s, 1H), 8.58 (d, J = 7.4 Hz, 1H), 7.99 (d, J = 10.1 Hz, 1H), 2.72-2.64 (m, 2H), 2.39-2.31 (m, 2H), 1.54 (s, 3H), 1.51 (s, 3H). |

-continued

| Intermediate | Structure | Name | MS: [(M + 1)]+ | 1H-NMR |
|---|---|---|---|---|
| 5 | 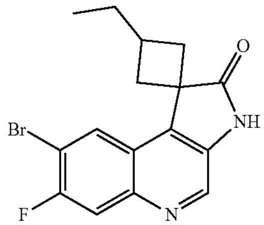 [SMILES: CCC1CC2(C1)C(=O)Nc1cnc3cc(F)c(Br)cc3c12] | 8'-Bromo-3-ethyl-7'-fluorospiro[cyclobutane-1,1'-pyrrolo[2,3-c]quinolin]-2'(3'H)-one | 349.05 351.05 | 1H NMR (400 MHz, DMSO-d6) δ 10.76 (d, J = 5.3 Hz, 1H), 8.67 (d, J = 1.7 Hz, 1H), 8.45 (d, J = 7.2 Hz, 0.4H), 8.39 (d, J = 7.4 Hz, 0.6H), 7.98 (dd, J = 10.1, 3.4 Hz, 1H), 2.88-2.73 (m, 2H), 2.55-2.51 (m, 2H), 2.29-2.19 (m, 1H), 1.78-1.64 (m, 2H), 0.99-0.88 (m, 3H). |
| 6 | 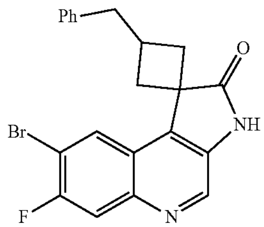 [SMILES: O=C1Nc2cnc3cc(F)c(Br)cc3c2C12CC(Cc1ccccc1)C2] | 3-Benzyl-8'-bromo-7'-fluorospiro[cyclobutane-1,1'-pyrrolo[2,3-c]quinolin]-2'(3'H)-one | 411.00 413.00 | 1H NMR (400 MHz, DMSO-d6) δ 10.81 (d, J = 12.1 Hz, 1H), 8.67 (d, J = 1.6 Hz, 1H), 8.42 (dd, J = 30.2, 7.4 Hz, 1H), 7.99 (dd, J = 10.1, 2.4 Hz, 1H), 7.38-7.27 (m, 4H), 7.27-7.19 (m, 1H), 3.28-3.13 (m, 1H), 3.10 (d, J = 7.6 Hz, 1H), 3.00 (d, J = 7.6 Hz, 1H), 2.81 (dd, J = 13.0, 9.2 Hz, 1H), 2.72-2.64 (m, 1H), 2.46 (d, J = 10.4 Hz, 1H), 2.36 (dd, J = 13.0, 5.9 Hz, 1H). |
| 7 | 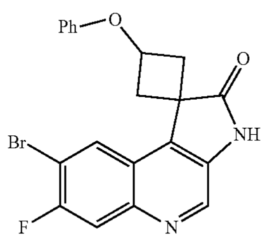 [SMILES: O=C1Nc2cnc3cc(F)c(Br)cc3c2C12CC(Oc1ccccc1)C2] | 8'-Bromo-7'-fluoro-3-phenoxyspiro[cyclobutane-1,1'-pyrrolo[2,3-c]quinolin]-2'(3'H)-one | 413.10 415.10 | 1H NMR (400 MHz, DMSO-d6) δ 10.91 (d, J = 9.1 Hz, 1H), 8.79 (d, J = 7.5 Hz, 0.5H), 8.70 (d, J = 1.8 Hz, 1H), 8.40 (d, J = 7.3 Hz, 0.5H), 8.00 (dd, J = 10.1, 7.8 Hz, 1H), 7.40-7.31 (m, 2H), 7.09-6.96 (m, 3H), 5.40 (p, J = 7.0 Hz, 0.5H), 5.19 (p, J = 6.5 Hz, 0.5H), 3.27 (dd, J = 14.4, 7.8 Hz, 1H), 3.11 (dd, J = 14.4, 7.4 Hz, 1H), 2.89 (dd, J = 14.5, 5.0 Hz, 1H), 2.75 (dd, J = 14.4, 5.9 Hz, 1H). |
| 8 | 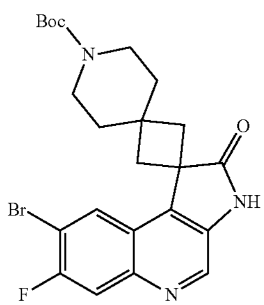 [SMILES: CC(C)(C)OC(=O)N1CCC2(CC1)CC1(C2)C(=O)Nc2cnc3cc(F)c(Br)cc3c21] | tert-Butyl 8''-bromo-7''-fluoro-2''-oxo-2'',3''-dihydrodispiro[piperidine-4,1'-cyclobutane-3',1''-pyrrolo[2,3-c]quinoline]-1-carboxylate | 490.20 492.20 | 1H NMR (400 MHz, CDCl3) δ 8.80 (s, 1H), 8.59 (d, J = 7.0 Hz, 1H), 8.21 (s, 1H), 7.96 (d, J = 9.3 Hz, 1H), 3.54-3.44 (m, 4H), 2.74 (d, J = 12.2 Hz, 2H), 2.60 (d, J = 12.0 Hz, 2H), 2.26 (s, 2H), 2.00 (s, 2H). |
| 9 | 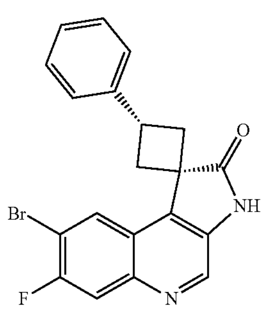 [SMILES: O=C1Nc2cnc3cc(F)c(Br)cc3c2[C@]12C[C@H](c1ccccc1)C2] | cis-8'-Bromo-7'-fluoro-3-phenylspiro[cyclobutane-1,1'-pyrrolo[2,3-c]quinolin]-2'(3'H)-one | 397.05 399.05 | 1H NMR (400 MHz, DMSO-d6) δ 10.90 (s, 1H), 8.71 (s, 1H), 8.56 (d, J = 7.4 Hz, 1H), 8.03 (d, J = 10.1 Hz, 1H), 7.67 (d, J = 7.5 Hz, 2H), 7.41 (t, J = 7.5 Hz, 2H), 7.28 (t, J = 7.2 Hz, 1H), 4.21 (p, J = 9.5 Hz, 1H), 3.14 (t, J = 11.7 Hz, 2H), 2.83 (dd, J = 13.2, 8.5 Hz, 2H). |

| Intermediate | Structure | Name | MS: [(M + 1)]+ | 1H-NMR |
|---|---|---|---|---|
| 10 | 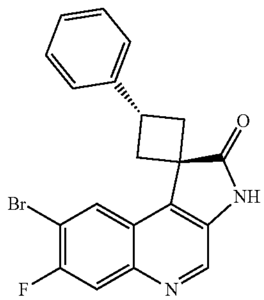 [SMILES: O=C1Nc2cnc3cc(F)c(Br)cc3c2[C@]12C[C@@H](c1ccccc1)C2] | trans-8'-Bromo-7'-fluoro-3-phenylspiro[cyclobutane-1,1'-pyrrolo[2,3-c]quinolin]-2'(3'H)-one | 397.05<br>399.05 | 1H NMR (400 MHz, DMSO-d6) δ 10.89 (s, 1H), 8.70 (s, 1H), 8.22 (d, J = 7.4 Hz, 1H), 7.98 (d, J = 10.1 Hz, 1H), 7.50-7.43 (m, 4H), 7.33 (s, 1H), 4.20 (p, J = 9.7 Hz, 1H), 3.03 (t, J = 11.1 Hz, 2H), 2.91 (t, J = 11.1 Hz, 2H). |
| 11 | 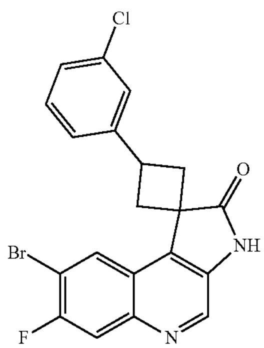 [SMILES: O=C1Nc2cnc3cc(F)c(Br)cc3c2C12CC(c1cccc(Cl)c1)C2] | 8'-Bromo-3-(3-chlorophenyl)-7'-fluorospiro[cyclobutane-1,1'-pyrrolo[2,3-c]quinolin]-2'(3'H)-one | 431.00<br>433.00<br>435.00 | 1H NMR (400 MHz, DMSO-d6) δ 10.91 (d, J = 10.1 Hz, 1H), 8.70 (d, J = 2.1 Hz, 1H), 8.53 (d, J = 7.3 Hz, 0.6H), 8.53 (d, J = 7.3 Hz, 0.4H), 8.05-7.95 (m, 1H), 7.79 (t, J = 1.9 Hz, 0.65H), 7.63 (dt, J = 7.7, 1.4 Hz, 0.65H), 7.56-7.31 (m, 2.7H), 4.32-4.14 (m, 1H), 3.21-3.09 (m, 1.35H), 3.07-2.99 (m, 0.65H), 2.92 (t, J = 11.3 Hz, 0.65H), 2.80 (dd, J = 13.5, 8.3 Hz, 1.35H). |
| 12 | 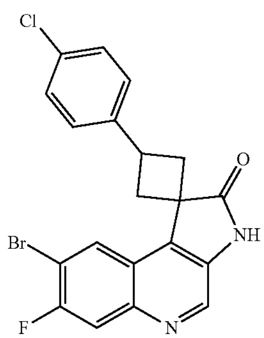 [SMILES: O=C1Nc2cnc3cc(F)c(Br)cc3c2C12CC(c1ccc(Cl)cc1)C2] | 8'-Bromo-3-(4-chlorophenyl)-7'-fluorospiro[cyclobutane-1,1'-pyrrolo[2,3-c]quinolin]-2'(3'H)-one | 431.00<br>433.00<br>435.00 | 1H NMR (400 MHz, CDCl3) δ 8.72 (d, J = 4.5 Hz, 1H), 8.51 (d, J = 7.1 Hz, 0.65H), 8.24 (d, J = 7.2 Hz, 0.35H), 7.91-7.81 (m, 1H), 7.67 (d, J = 8.4 Hz, 1.3H), 7.47-7.33 (m, 2.7H), 4.39 (p, J = 9.2 Hz, 0.35H) 4.16 (p, J = 9.1 Hz, 0.65H), 3.21-3.04 (m, 4H). |
| 13 | 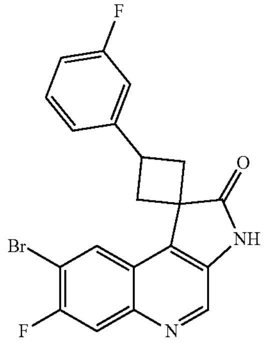 [SMILES: O=C1Nc2cnc3cc(F)c(Br)cc3c2C12CC(c1cccc(F)c1)C2] | 8'-Bromo-7'-fluoro-3-(3-fluorophenyl)spiro[cyclobutane-1,1'-pyrrolo[2,3-c]quinolin]-2'(3'H)-one | 415.10<br>417.20 | 1H NMR (400 MHz, CDCl3) δ 8.77 (s, 1H), 8.51 (d, J = 7.2 Hz, 0.6H), 8.43 (s, 1H), 8.25 (d, J = 7.2 Hz, 0.4H), 7.93-7.82 (m, 1H), 7.52-7.35 (m, 2H), 7.21-6.97 (m, 2H), 4.41 (p, J = 9.2 Hz, 0.4H), 4.19 (p, J = 9.2 Hz, 0.6H), 3.23-3.05 (m, 4H). |

| Intermediate | Structure | Name | MS: [(M + 1)]+ | 1H-NMR |
|---|---|---|---|---|
| 14 | 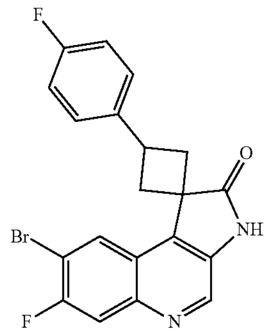 [SMILES: O=C1Nc2cnc3cc(F)c(Br)cc3c2C12CC(c1ccc(F)cc1)C2] | 8'-Bromo-7'-fluoro-3-(4-fluorophenyl)spiro[cyclobutane-1,1'-pyrrolo[2,3-c]quinolin]-2'(3'H)-one | 415.10 417.10 | 1H NMR (400 MHz, DMSO-$d_6$) δ 10.90 (d, J = 12.6 Hz, 1H), 8.70 (d, J = 2.2 Hz, 1H), 8.54 (d, J = 7.2 Hz, 0.6H), 8.54 (d, J = 7.2 Hz, 0.4H), 8.04-7.95 (m, 1H), 7.77-7.70 (m, 1.2H), 7.52-7.45 (m, 0.8H), 7.32-7.19 (m, 2H), 4.28-4.13 (m, 1H), 3.18-3.11 (m, 1.2H), 3.04-2.88 (m, 1.6H), 2.79 (dd, J = 13.5, 8.4 Hz, 1.2H). |
| 15 | 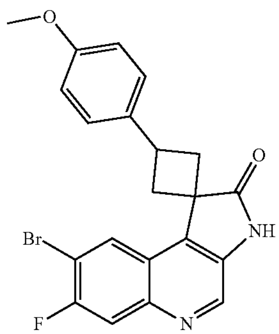 [SMILES: COc1ccc(C2CC3(C2)C(=O)Nc2cnc4cc(F)c(Br)cc4c23)cc1] | 8'-Bromo-7'-fluoro-3-(4-methoxyphenyl)spiro[cyclobutane-1,1'-pyrrolo[2,3-c]quinolin]-2'(3'H)-one | 427.15 429.15 | 1H NMR (400 MHz, DMSO-$d_6$) δ 10.88 (d, J = 8.3 Hz, 1H), 8.70 (d, J = 2.3 Hz, 1H), 8.54 (d, J = 7.2 Hz, 0.6H), 8.26 (d, J = 7.2 Hz, 0.4H), 8.04-8.95 (m, 1H), 7.61 (d, J = 8.5 Hz, 1H), 7.37 (d, J = 8.4 Hz, 1H), 7.05-6.94 (m, 2H), 4.14 (p, J = 9.3 Hz, 1H), 3.79 (s, 1.2H), 3.77 (s, 1.8H), 3.29-3.23 (m, 1H), 3.15-3.07 (m, 1H), 2.97 (t, J = 11.0 Hz, 1H), 2.91-2.85 (m, 1H). |
| 16 | 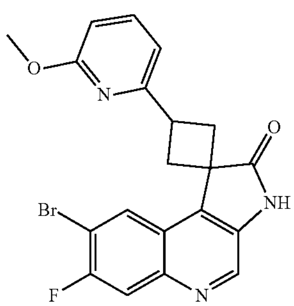 [SMILES: COc1cccc(C2CC3(C2)C(=O)Nc2cnc4cc(F)c(Br)cc4c23)n1] | 8'-Bromo-7'-fluoro-3-(6-methoxypyridin-2-yl)spiro[cyclobutane-1,1'-pyrrolo[2,3-c]quinolin]-2'(3'H)-one | 428.10 430.10 | 1H NMR (400 MHz, CDCl$_3$) δ 8.83-8.74 (m, 1.4H), 8.58 (d, J = 7.1 Hz, 0.6H), 8.26 (s, 0.4H), 8.17 (s, 0.6H), 7.93-7.86 (m, 1H), 7.67-7.56 (m, 1H), 7.20 (d, J = 7.3 Hz, 0.6H), 6.88 (d, J = 7.2 Hz, 0.4H), 6.63-6.65 (m, 1H), 4.45 (p, J = 9.3 Hz, 0.6H), 4.28 (p, J = 9.2 Hz, 0.4H), 4.17 (s, 1.3H), 4.05 (s, 1.7H), 3.55-3.44 (m, 1H), 3.31 (dd, J = 13.3, 8.5 Hz, 1H), 3.17-3.06 (m, 1H), 2.88 (dd, J = 11.9, 9.0 Hz, 1H). |
| 17 | 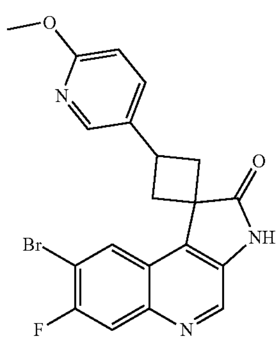 [SMILES: COc1ccc(C2CC3(C2)C(=O)Nc2cnc4cc(F)c(Br)cc4c23)cn1] | 8'-Bromo-7'-fluoro-3-(6-methoxypyridin-3-yl)spiro[cyclobutane-1,1'-pyrrolo[2,3-c]quinolin]-2'(3'H)-one | 428.10 430.10 | 1H NMR (400 MHz, CDCl$_3$) δ 8.73 (d, J = 3.1 Hz, 1H), 8.51 (d, J = 7.1 Hz, 0.54H), 8.32-8.19 (m, 1.7H), 7.91-7.81 (m, 1.46H), 7.67 (dd, J = 8.8, 2.4 Hz, 0.3H), 6.88 (dd, J = 9.1, 1.8 Hz, 1H), 4.39 (p, J = 9.3 Hz, 0.45H), 4.12 (p, J = 9.3 Hz, 0.55H), 3.98 (d, J = 8.7 Hz, 3H), 3.23-3.14 (m, 1H), 3.12-3.00 (m, 3H). |

| Intermediate | Structure | Name | MS: [(M + 1)]+ | 1H-NMR |
| --- | --- | --- | --- | --- |
| 18[a] | 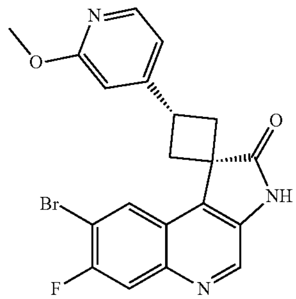 [SMILES: COc1cc([C@H]2C[C@]3(C2)C(=O)Nc2cnc4cc(F)c(Br)cc4c23)ccn1] | cis-8'-Bromo-7'-fluoro-3-(2-methoxypyridin-4-yl)spiro[cyclobutane-1,1'-pyrrolo[2,3-c]quinolin]-2'(3'H)-one | 428.00 430.00 | 1H NMR (400 MHz, DMSO-$d_6$) δ 10.91 (s, 1H), 8.70 (s, 1H), 8.51 (d, J = 7.3 Hz, 1H), 8.17 (d, J = 5.3 Hz, 1H), 8.02 (d, J = 10.0 Hz, 1H), 7.28 (dd, J = 5.4, 1.5 Hz, 1H), 7.10-7.06 (m, 1H), 5.76 (s, 0H), 4.22 (p, J = 9.2 Hz, 1H), 3.88 (s, 3H), 3.19-3.09 (m, 2H), 2.79 (dd, J = 13.6, 8.2 Hz, 2H). |
| 19[a] | 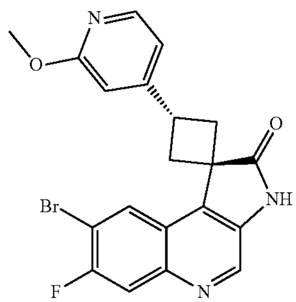 [SMILES: COc1cc([C@H]2C[C@@]3(C2)C(=O)Nc2cnc4cc(F)c(Br)cc4c23)ccn1] | trans-8'-Bromo-7'-fluoro-3-(2-methoxypyridin-4-yl)spiro[cyclobutane-1,1'-pyrrolo[2,3-c]quinolin]-2'(3'H)-one | 428.00 430.00 | 1H NMR (400 MHz, DMSO-$d_6$) δ 10.90 (s, 1H), 8.70 (s, 1H), 8.23 (d, J = 5.3 Hz, 1H), 8.10 (d, J = 7.4 Hz, 1H), 7.97 (d, J = 10.1 Hz, 1H), 7.06 (dd, J = 5.3, 1.5 Hz, 1H), 6.89 (s, 1H), 4.15 (p, J = 9.3 Hz, 1H), 3.91 (s, 3H), 3.08-2.98 (m, 2H), 2.92 (td, J = 10.0, 2.3 Hz, 2H). |
| 20[b] | 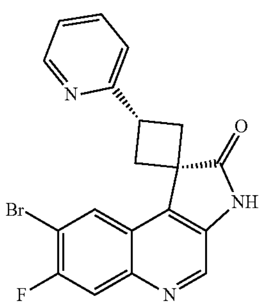 [SMILES: O=C1Nc2cnc3cc(F)c(Br)cc3c2[C@]12C[C@H](c1ccccn1)C2] | cis-8'-Bromo-7'-fluoro-3-(pyridin-2-yl)spiro[cyclobutane-1,1'-pyrrolo[2,3-c]quinolin]-2'(3'H)-one | 398.10 400.10 | 1H NMR (400 MHz, CDCl$_3$) δ 8.73 (s, 1H), 8.61 (d, J = 5.0 Hz, 1H), 8.56 (d, J = 7.1 Hz, 1H), 8.06 (s, 1H), 7.97-7.80 (m, 3H), 7.28-7.24 (m, 1H), 4.48 (p, J = 9.3 Hz, 1H), 3.23 (d, J = 9.3 Hz, 4H). |
| 21[b] | 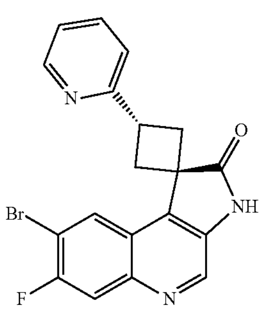 [SMILES: O=C1Nc2cnc3cc(F)c(Br)cc3c2[C@]12C[C@@H](c1ccccn1)C2] | trans-8'-Bromo-7'-fluoro-3-(pyridin-2-yl)spiro[cyclobutane-1,1'-pyrrolo[2,3-c]quinolin]-2'(3'H)-one | 398.10 400.10 | 1H NMR (400 MHz, CDCl$_3$) δ 10.15 (d, J = 7.5 Hz, 1H), 9.08-9.01 (m, 1H), 8.73 (s, 1H), 7.95 (s, 1H), 7.84 (d, J = 9.6 Hz, 1H), 7.66 (t, J = 7.6 Hz, 1H), 7.31-7.21 (m, 2H), 4.25 (p, J = 9.0 Hz, 1H), 3.47 (dd, J = 12.1, 9.0 Hz, 2H), 2.95 (dd, J = 12.4, 9.3 Hz, 2H). |

| Intermediate | Structure | Name | MS: [(M + 1)]+ | 1H-NMR |
|---|---|---|---|---|
| 22 | 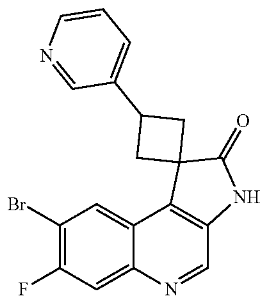 [SMILES: O=C1Nc2cnc3cc(F)c(Br)cc3c2C12CC(c1cccnc1)C2] | 8'-Bromo-7'-fluoro-3-(pyridin-3-yl)spiro[cyclobutane-1,1'-pyrrolo[2,3-c]quinolin]-2'(3'H)-one | 398.05 400.05 | 1H NMR (400 MHz, DMSO-$d_6$) δ 10.89 (d, J = 9.7 Hz, 1H), 8.85-8.68 (m, 2H), 8.57-8.48 (m, 1.6H), 8.26-8.15 (m, 1H), 8.07-7.88 (m, 1.4H), 7.51-7.44 (m, 1H), 4.29 (p, J = 9.1 Hz, 1H), 3.19 (dd, J = 12.9, 10.7 Hz, 1.2H), 3.10 (dd, J = 12.4, 9.9 Hz, 0.8H), 2.94 (t, J = 11.2 Hz, 0.8H), 2.82 (dd, J = 13.4, 8.2 Hz, 1.2H). |
| 23 | 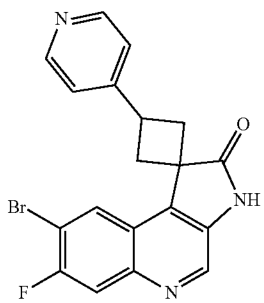 [SMILES: O=C1Nc2cnc3cc(F)c(Br)cc3c2C12CC(c1ccncc1)C2] | 8'-Bromo-7'-fluoro-3-(pyridin-4-yl)spiro[cyclobutane-1,1'-pyrrolo[2,3-c]quinolin]-2'(3'H)-one | 398.05 400.05 | 1H NMR (400 MHz, CDCl$_3$) δ 8.75 (s, 1H), 8.67 (d, J = 5.2 Hz, 2H), 8.47 (d, J = 7.0 Hz, 1H), 8.28 (s, 1H), 7.90 (d, J = 9.4 Hz, 1H), 7.68 (d, J = 5.3 Hz, 2H), 4.16 (p, J = 9.4 Hz, 1H), 3.28-3.16 (m, 2H), 3.16-3.06 (m, 2H). |

Note:
acompound 18 and 19 were separated by reversed phase chromatography with the following conditions: [Column: Spherical C18 Column, 20-40 μm, 330 g; Mobile Phase A: Water (plus 5 mM AcOH); Mobile Phase B: Acetonitrile; Flow rate: 80 mL/min; Gradient of mobile Phase B: 55% B to 75% B in 20 min; Detector: UV 254 nm]. cis-isomer: slower eluted isomer; trans-isomer: faster eluted isomer;
bcompound 20 and 21 were separated by reversed phase chromatography with the following conditions: [Column: Spherical C18 Column, 20-40 μm, 330 g; Mobile Phase A: Water (plus 5 mM AcOH); Mobile Phase B: Acetonitrile; Flow rate: 80 mL/min; Gradient of mobile Phase B: 5%~60%, 15 min, 60%~66%, 6 min, 66%, 5 min, 66%~69%, 3 min, 69%, 4 min, 69%~95% 3 min, 95%, 5 min; Detector: UV 254 nm]. cis-isomer: faster eluted isomer; trans-isomer: slower eluted isomer.

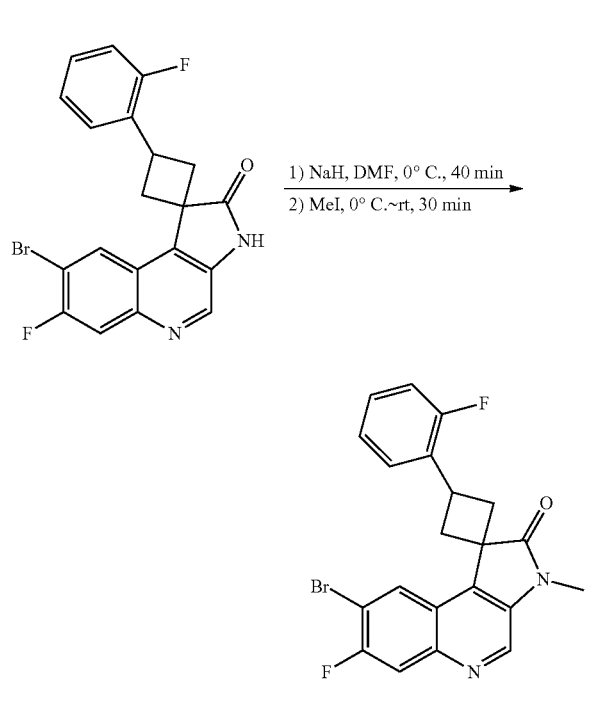

8'-Bromo-7'-fluoro-3-(2-fluorophenyl)-3'-methyl-spiro[cyclobutane-1,1'-pyrrolo[2,3-c]quinolin]-2'(3'H)-one To a solution of 8-bromo-7-fluoro-3-(2-fluorophenyl)-3H-spiro[cyclobutane-1,1-pyrrolo[2,3-c]quinolin]-2-one (156 mg, 0.38 mmol) in N,N-dimethylformamide (10.0 mL) was added sodium hydride (15.0 mg, 0.38 mmol, 60% w/w dispersed in mineral oil) at 0° C. under nitrogen atmosphere. The resulting mixture was stirred for 1 hour at 25° C. followed by the addition of iodomethane (64.0 mg, 0.45 mmol) over 2 min at 0° C. After stirring for additional 1.5 hours at 25° C., the reaction was quenched by saturated aqueous ammonium chloride (20.0 mL). The resulting mixture was diluted with water (150 mL) and extracted with ethyl acetate (3×100 mL). The combined organic layers was washed with brine (2×50.0 mL) and dried over anhydrous sodium sulfate. After filtration, the filtrate was concentrated under reduced pressure. The residue was purified by silica gel column chromatography, eluted with 1%~5% methanol in dichloromethane. The desired fractions were collected and concentrated under reduced pressure to afford the title compound as an off-white solid (70.0 mg, 44%): 1H NMR (400 MHz, CDCl$_3$) δ 8.78 (s, 1H), 8.58 (d, J=7.2 Hz, 0.6H), 8.50 (d, J=7.2 Hz, 0.4H), 7.94-7.84 (m, 1H), 7.46-7.28 (m, 3H), 7.18-7.04 (m, 1H), 4.56 (p, J=9.5 Hz, 1H), 3.42 (s, 1.2H), 3.44 (s, 1.8H), 3.28-3.06 (m, 4H); MS: [(M+1)]+=429.00, 431.00.

The following intermediates were prepared according to the procedure described above:

| Intermediate | Name | MS: [(M + 1)]+ | 1H-NMR |
|---|---|---|---|
| I1 | 8'-Bromo-7'-fluoro-3'-methylspiro[oxetane-3,1'-pyrrolo[2,3-c]quinolin]-2'(3'H)-one | 337.00<br>339.00 | 1H NMR (400 MHz, CDCl3)) δ 8.86 (d, J = 7.2 Hz, 1H), 8.70 (s, 1H), 7.89 (d, J = 9.4 Hz, 1H), 5.31 (d, J = 6.2 Hz, 2H), 4.97 (d, J = 6.1 Hz, 2H), 3.39 (s, 3H). |
| I2 | 8'-Bromo-3,3-difluoro-3'-methylspiro[cyclobutane-1,1'-pyrrolo[2,3-c]quinolin]-2'(3'H)-one | 353.00<br>355.00 | 1H NMR (400 MHz, DMSO-d) δ 8.96 (s, 1H), 8.19 (s, 1H), 8.09-8.01 (m, 1H), 7.81 (dd, J = 9.1, 2.1 Hz, 1H), 3.55-3.43 (m, 2H), 3.30-3.15 (m, 5H). |
| I3 | 8'-Bromo-7'-fluoro-3,3'-dimethylspiro[cyclobutane-1,1'-pyrrolo[2,3-c]quinolin]-2'(3'H)-one | 349.10<br>351.10 | 1H NMR (400 MHz, CDCl3) δ 8.65 (s, 1H), 8.56 (d, J = 7.3 Hz, 0.4H), 8.46 (d, J = 7.2 Hz, 0.6H), 7.88 (dd, J = 9.5, 5.6 Hz, 1H), 3.36 (d, J = 2.6 Hz, 3H), 3.25 (q, J = 8.5 Hz, 0.4H), 3.13-3.03 (m, 0.6H), 2.89-2.81 (m, 1.2H), 2.77-2.68 (m, 0.8H), 2.58 (t, J = 11.1 Hz, 0.8H), 2.46 (dd, J = 13.2, 7.0 Hz, 1.2H), 1.47 (d, J = 6.7 Hz, 1.8H), 1.43 (d, J = 6.8 Hz, 1.2H). |
| I4 | 8'-Bromo-7'-fluoro-3,3,3'-trimethylspiro[cyclobutane-1,1'-pyrrolo[2,3-c]quinolin]-2'(3'H)-one | 363.20<br>365.20 | 1H NMR (400 MHz, DMSO-d6) δ 8.90 (s, 1H), 8.62 (d, J = 7.5 Hz, 1H), 8.03 (d, J = 10.1 Hz, 1H), 3.29 (s, 3H), 2.75-2.67 (m, 2H), 2.40-2.31 (m, 2H), 1.57 (s, 3H), 1.52 (s, 3H). |
| I5 | 8'-Bromo-3-ethyl-7'-fluoro-3'-methylspiro[cyclobutane-1,1'-pyrrolo[2,3-c]quinolin]-2'(3'H)-one | 363.05<br>365.05 | 1H NMR (400 MHz, DMSO-d6) δ 8.90 (d, J = 2.9 Hz, 1H), 8.49 (d, J = 7.4 Hz, 0.4H), 8.42 (d, J = 7.4 Hz, 0.6H), 8.02 (dd, J = 10.1, 3.1 Hz, 1H), 3.29 (d, J = 4.5 Hz, 3H), 2.93-2.75 (m, 2H), 2.61-2.52 (m, 2H), 2.29-2.21 (m, 1H), 1.82-1.67 (m, 2H), 0.98-0.89 (m, 3H). |
| I6 | 3-Benzyl-8'-bromo-7'-fluoro-3'-methylspiro[cyclobutane-1,1'-pyrrolo[2,3-c]quinolin]-2'(3'H)-one | 425.10<br>427.10 | 1H NMR (400 MHz, DMSO-d6) δ 8.91 (s, 1H), 8.45 (dd, J = 30.3, 7.4 Hz, 1H), 8.03 (dd, J = 10.1, 3.1 Hz, 1H), 7.38-7.28 (m, 4H), 7.28-7.19 (m, 1H), 3.30 (d, J = 10.3 Hz, 3H), 3.28-3.15 (m, 1H), 3.12 (d, J = 7.4 Hz, 1H), 3.01 (d, J = 7.6 Hz, 1H), 2.83 (dd, J = 13.0, 9.0 Hz, 1H), 2.76-2.66 (m, 1H), 2.49-2.43 (m, 1H), 2.36 (dd, J = 13.2, 5.9 Hz, 1H). |

-continued

| Intermediate | Name | MS: [(M + 1)]+ | 1H-NMR |
|---|---|---|---|
| I7 | 8'-Bromo-7'-fluoro-3'-methyl-3-phenoxyspiro[cyclobutane-1,1'-pyrrolo[2,3-c]quinolin]-2'(3'H)-one | 427.00<br>429.00 | 1H NMR (400 MHz, DMSO-$d_6$) δ 8.94 (d, J = 1.7 Hz, 1H), 8.85 (dd, J = 7.5, 1.4 Hz, 0.5H), 8.43 (dd, J = 7.3, 1.2 Hz, 0.5H), 8.07-8.00 (m, 1 H), 7.42-7.29 (m, 2H), 7.13-6.95 (m, 3H), 5.42 (p, J = 6.5 Hz, 0.5H), 5.23 (p, J = 7.0, 1H), 3.33 (s, 1.5H), 3.31 (s, 1.5H), 3.30-3.25 (m, 1H), 3.16-3.08 (m, 1H), 2.94-2.87 (m, 1H), 2.81-2.72 (m, 1H). |
| I8 | tert-Butyl 8''-bromo-7''-fluoro-3''-methyl-2''-oxo-2'',3''-dihydrodispiro[piperidine-4,1'-cyclobutane-3',1''-pyrrolo[2,3-c]quinoline]-1-carboxylate | 504.20<br>506.20 | 1H NMR (400 MHz, CDCl$_3$) δ 8.72 (s, 1H), 8.60 (d, J = 7.1 Hz, 1H), 7.96 (d, J = 9.3 Hz, 1H), 3.54-3.44 (m, 4H), 3.39 (s, 3H), 2.73 (d, J = 13.1 Hz, 2H), 2.56 (d, J = 13.3 Hz, 2H), 2.34-2.28 (m, 2H), 2.00 (t, J = 5.7 Hz, 2H). |
| I9 | cis-8'-Bromo-7'-fluoro-3'-methyl-3-phenylspiro[cyclobutane-1,1'-pyrrolo[2,3-c]quinolin]-2'(3'H)-one | 411.00<br>413.00 | 1H NMR (400 MHz, DMSO-$d_6$) δ 8.95 (s, 1H), 8.60 (d, J = 7.4 Hz, 1H), 8.07 (d, J = 10.2 Hz, 1H), 7.70 (d, J = 7.6 Hz, 2H), 7.42 (t, J = 7.5 Hz, 2H), 7.29 (t, J = 7.3 Hz, 1H), 4.23 (p, J = 9.2 Hz, 1H), 3.33 (s, 3H), 3.22-3.12 (m. 2H), 2.85 (dd, J = 13.3, 8.4 Hz, 2H). |
| I10 | trans-8'-Bromo-7'-fluoro-3'-methyl-3-phenylspiro[cyclobutane-1,1'-pyrrolo[2,3-c]quinolin]-2'(3'H)-one | 411.00<br>413.00 | 1H NMR (400 MHz, DMSO-$d_6$) δ 8.94 (s, 1H), 8.24 (d, J = 7.3 Hz, 1H), 8.01 (d, J = 10.3 Hz, 1H), 7.47 (d, J = 4.4 Hz, 4H), 7.36-7.31 (m, 1H), 4.24 (p, J = 9.3 Hz, 1H), 3.34 (s, 3H), 3.05 (t, J = 11.2 Hz, 2H), 2.92 (t, J = 11.2 Hz, 2H). |
| I11 | 8'-Bromo-3-(3-chlorophenyl)-7'-fluoro-3'-methylspiro[cyclobutane-1,1'-pyrrolo[2,3-c]quinolin]-2'(3'H)-one | 445.00<br>447.00<br>449.00 | 1H NMR (400 MHz, DMSO-$d_6$) δ 8.95 (d, J = 3.3 Hz, 1H), 8.57 (d, J = 7.4 Hz, 0.7H), 8.19 (d, J = 7.5 Hz, 0.3H), 8.10-8.00 (m, 1H), 7.85 (t, J = 1.9 Hz, 0.7H), 7.65 (dt, J = 7.8, 1.4 Hz, 0.7H), 7.57-7.31 (m, 2.6H), 4.34-4.19 (m, 1H), 3.34 (s, 0.75H), 3.33 (s, 2.25 H), 3.24-3.13 (m, 1.5H), 3.07 (dd, J = 13.0, 9.5 Hz, 0.5H), 2.99-2.88 (m, 0.5H), 2.87-2.76 (m, 1.5H). |

| Intermediate | Structure | Name | MS: [(M + 1)]⁺ | ¹H-NMR |
|---|---|---|---|---|
| I12 | 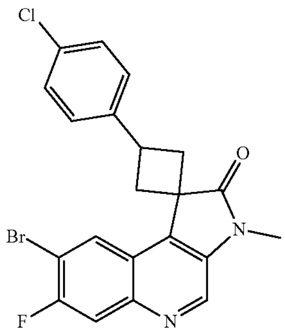 | 8'-Bromo-3-(4-chlorophenyl)-7'-fluoro-3'-methylspiro[cyclobutane-1,1'-pyrrolo[2,3-c]quinolin]-2'(3'H)-one | 445.10 447.10 449.10 | ¹H NMR (400 MHz, CDCl₃) δ 8.71 (d, J = 7.2 Hz, 1H), 8.54 (d, J = 7.2 Hz, 0.65H), 8.27 (d, J = 7.2 Hz, 0.35H), 7.94-7.83 (m, 1H), 7.76-7.72 (m, 1.3H), 7.49-7.35 (m, 2.7H), 4.43 (p, J = 9.2 Hz, 0.35H) 4.16 (p, J = 9.1 Hz, 0.65H), 3.43 (s, 1H), 3.42 (s, 2H), 3.22-3.02 (m, 4H). |
| I13 | 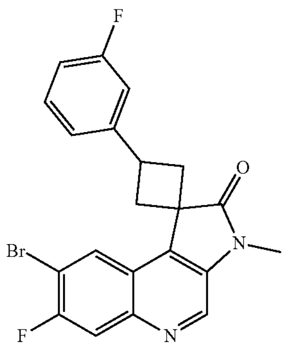 | 8'-Bromo-7'-fluor-3-(3-fluorophenyl)-3'-methylspiro[cyclobutane-1,1'-pyrrolo[2,3-c]quinolin]-2'(3'H)-one | 429.00 431.00 | ¹H NMR (400 MHz, CDCl₃) δ 8.71 (d, J = 7.0 Hz, 1H), 8.54 (d, J = 7.2 Hz, 0.6H), 8.28 (d, J = 7.0 Hz, 0.4H), 7.95-7.82 (m, 1H), 7.58-7.37 (m, 2.4H), 7.23-6.98 (m, 1.6H), 4.45 (p, J = 9.2 Hz, 0.4H) 4.19 (p, J = 9.2 Hz, 0.6H), 3.44 (s, 1.2H), 3.42 (s, 1.8H), 3.23-3.04 (m, 4H). |
| I14 | 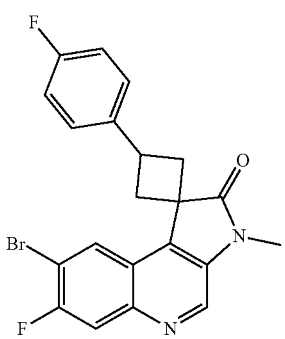 | 8'-Bromo-7'-fluoro-3-(4-fluorophenyl)-3'-methylspiro[cyclobutane-1,1'-pyrrolo[2,3-c]quinolin]-2'(3'H)-one | 429.00 431.00 | ¹H NMR (400 MHz, DMSO-d₆) δ 8.94 (d, J = 3.4 Hz, 1H), 8.57 (d, J = 7.3 Hz, 0.6H), 8.18 (d, J = 7.4 Hz, 0.4H), 8.08-8.00 (m, 1H), 7.80-7.72 (m, 1.2H), 7.50 (dd, J = 8.5, 5.5 Hz, 0.8H), 7.33-7.20 (m, 2H), 4.23 (h, J = 8.9 Hz, 1H), 3.34 (s, 1.2H), 3.32 (s, 1.8H), 3.21-3.13 (m, 1.2H), 3.07-2.99 (m, 0.8H), 2.9-2.89 (m, 0.8H), 2.80 (dd, J = 13.5, 8.3 Hz, 1.2H). |
| I15 | 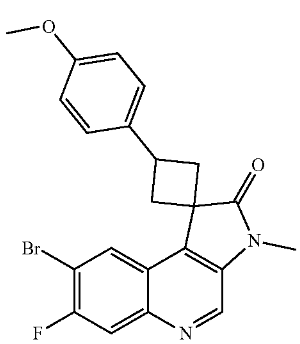 | 8'-Bromo-7'-fluoro-3-(4-methoxyphenyl)-3'-methylspiro[cyclobutane-1,1'-pyrrolo[2,3-c]quinolin]-2'(3'H)-one | 441.20 443.20 | ¹H NMR (400 MHz, CDCl₃) δ 8.70 (d, J = 6.4 Hz, 1H), 8.60 (d, J = 7.1 Hz, 0.6H), 8.38 (d, J = 7.2 Hz, 0.4H), 7.97-7.86 (m, 1H), 7.74-7.70 (m, 1H), 7.37 (d, J = 8.4 Hz, 1H), 7.07-6.97 (m, 2H), 4.39 (p, J = 9.2 Hz, 0.4H), 4.14 (p, J = 9.2 Hz, 0.6H), 3.89 (s, 1.2H), 3.87 (s, 1.8H), 3.43 (s, 1.2H), 3.42 (s, 1.8H), 3.20-3.01 (m, 4H). |

-continued

| Intermediate | Structure | Name | MS: [(M + 1)]⁺ | ¹H-NMR |
|---|---|---|---|---|
| I16 | 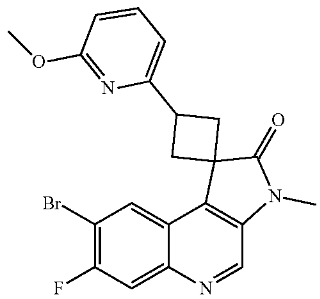 | 8'-Bromo-7'-fluoro-3-(6-methoxypyridin-2-yl)-3'-methylspiro[cyclobutane-1,1'-pyrrolo[2,3-c]quinolin]-2'(3'H)-one | 442.00<br>444.00 | ¹H NMR (400 MHz, CDCl₃) δ 8.34 (d, J = 7.2 Hz, 0.46H), 8.69 (s, 1H), 8.61 (d, J = 7.1 Hz, 0.54H), 7.99-7.94 (m, 1H), 7.68-7.55 (m, 1H), 6.87 (d, J = 7.2 Hz, 0.54H ), 6.73-6.65 (m, 1H), 4.54-4.43 (m, 0.54 H), 4.35-4.26 (m, 0.46 H), 4.29 (s, 1.3H), 4.16 (s, 1.7H), 4.05 (s, 2H), 3.51-3.46 (m, 1H), 3.42 (s, 1.3H), 3.38 (s, 1.7H), 3.29 (dd, J = 13.0, 8.1 Hz, 1H), 3.15-3.06 (m 1H), 2.85 (td, J = 9.1, 2.7 Hz, 1H). |
| I17 | 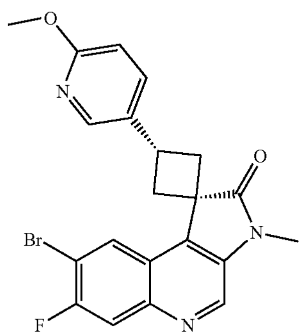 | cis-8'-Bromo-7'-fluoro-3-(6-methoxypyridin-3-yl)-3'-methylspiro[cyclobutane-1,1'-pyrrolo[2,3-c]quinolin]-2'(3'H)-one | 442.00<br>444.00 | ¹H NMR (400 MHz, CDCl₃) δ 8.68 (s, 1H), 8.31 (d, J = 7.2 Hz, 1H), 8.21 (d, J = 2.5 Hz, 1H), 7.86 (d, J = 9.5 Hz, 1H), 7.67 (dd, J = 8.6, 2.5 Hz, 1H), 6.88 (d, J = 8.5 Hz, 1H), 4.42 (p, J = 9.6 Hz, 1H), 3.99 (s, 3H), 3.41 (s, 3H), 3.05 (dd, J = 9.5, 4.1 Hz, 4H). |
| I18 | 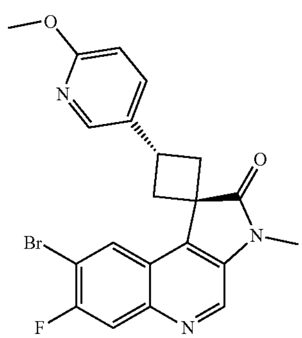 | trans-8'-Bromo-7'-fluoro-3-(6-methoxypyridin-3-yl)-3 methylspiro[cyclobutane-1,1'-pyrrolo[2,3-c]quinolin]-2'(3'H)-one | 442.00<br>444.00 | ¹H NMR (400 MHz, CDCl₃) δ 8.69 (s, 1H), 8.52 (d, J = 7.1 Hz, 1H), 8.42 (dd, J = 8.8, 2.4 Hz, 1H), 8.25 (d, J = 2.5 Hz, 1H), 7.91 (d, J = 9.5 Hz, 1H), 6.90 (d, J = 8.6 Hz, 1H), 4.12 (p, J = 9.1 Hz, 1H), 3.98 (s, 3H), 3.40 (s, 3H), 3.17 (dd, J = 13.8, 10.2 Hz, 2H), 3.02 (dd, J = 13.9, 8.3 Hz, 2H). |
| I19 | 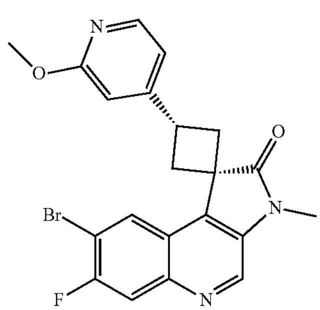 | cis-8'-Bromo-7'-fluoro-3-(2-methoxypyridin-4-yl)-3'-methylspiro[cyclobutane-1,1'-pyrrolo[2,3-c]quinolin]-2'(3'H)-one | 442.10<br>444.10 | ¹H NMR (400 MHz, DMSO-d₆) δ 8.94 (s, 1H), 8.54 (d, J = 7.3 Hz, 1H), 8.18 (d, J = 5.3 Hz, 1H), 8.05 (d, J = 10.1 Hz, 1H), 7.30 (dd, J = 5.4, 1.5 Hz, 1H), 7.09 (s, 1H), 4.23 (p, J = 9.2 Hz, 1H), 3.88 (s, 3H), 3.32 (s, 3H), 3.21-3.11 (m, 2H), 2.80 (dd, J = 13.7, 8.0 Hz, 2H). |
| I20 | 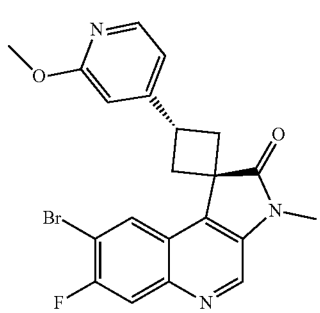 | trans-8'-bromo-7'-fluoro-3-(2-methoxypyridin-4-yl)-3' methylspiro[cyclobutane-1,1'-pyrrolo[2,3-c]quinolin]-2'(3'H)-one | 442.10<br>444.10 | ¹H NMR (400 MHz, DMSO-d₆) δ 8.93 (s, 1H), 8.23 (d, J = 5.2 Hz, 1H), 8.13 (d, J = 7.4 Hz, 1H), 8.00 (d, J = 10.1 Hz, 1H), 7.06 (dd, J = 5.6, 1.6 Hz, 1H), 6.89 (s, 1H), 4.18 (p, J = 9.6 Hz, 1H), 3.90 (s, 3H), 3.32 (s, 3H), 3.10-3.00 (m, 2H), 2.92 (td, J = 10.0, 2.4 Hz, 2H). |

| Intermediate | Structure | Name | MS: [(M + 1)]+ | 1H-NMR |
|---|---|---|---|---|
| I21 | 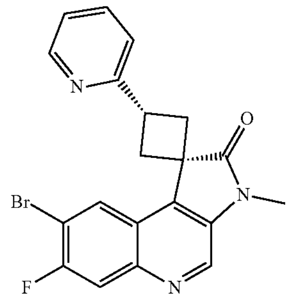 [SMILES: CN1c2cnc3cc(F)c(Br)cc3c2[C@]2(C[C@H](c3ccccn3)C2)C1=O] | cis-8'-Bromo-7'-fluoro-3'-methyl-3-(pyridin-2-yl)spiro[cyclobutane-1,1'-pyrrolo[2,3-c]quinolin]-2'(3'H)-one | 412.00 414.00 | 1H NMR (400 MHz, CDCl3) δ 8.69 (s, 1H), 8.60 (d, J = 5.3 Hz, 1H), 8.56 (d, J = 7.1 Hz, 1H), 8.03 (s, 1H), 7.88 (d, J = 9.5 Hz, 1H), 7.85 (s, 1H), 7.24 (s, 1H), 4.47 (s, 1H), 3.39 (s, 3H), 3.28-3.13 (m, 4H). |
| I22 | 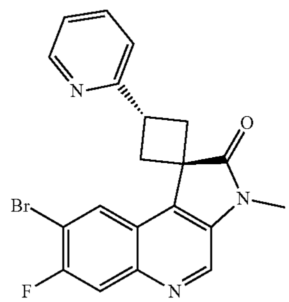 [SMILES: CN1c2cnc3cc(F)c(Br)cc3c2[C@]2(C[C@@H](c3ccccn3)C2)C1=O] | trans-8'-Bromo-7'-fluoro-3'-methyl-3-(pyridin-2-yl)spiro[cyclobutane-1,1'-pyrrolo[2,3-c]quinolin]-2'(3'H)-one | 412.10 414.10 | 1H NMR (400 MHz, CDCl3) δ 10.14 (d, J = 7.5 Hz, 1H), 9.07-9.00 (m, 1H), 8.66 (s, 1H), 7.83 (d, J = 9.7 Hz, 1H), 7.65 (td, J = 7.6, 1.8 Hz, 1H), 7.30-7.20 (m, 2H), 5.30 (s, 1H), 4.27 (p, J = 9.2 Hz, 1H), 3.49-3.38 (m, 2H), 2.94-2.86 (m, 2H). |
| I23 | 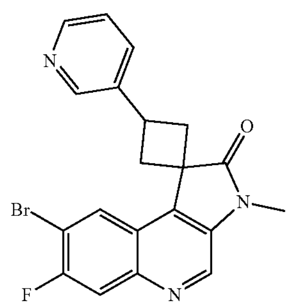 [SMILES: CN1C(=O)C2(CC(c3cccnc3)C2)c2c1cnc1cc(F)c(Br)cc21] | 8'-Bromo-7'-Fluoro-3'-methyl-3-(pyridin-3-yl)spiro[cyclobutane-1,1'-pyrrolo[2,3-c]quinolin]-2'(3'H)-one | 412.10 414.10 | 1H NMR (400 MHz, DMSO-d6) δ 8.94 (d, J = 3.0 Hz, 1H), 8.84 (s, 0.6H), 8.70 (s, 0.4H), 8.65-8.47 (m, 1.6H), 8.22 (dd, J = 16.5, 7.7 Hz, 1H), 8.11-7.88 (m, 1.4H), 7.53-7.42 (m, 1H), 4.38-4.19 (m, 1H), 3.45 (s, 1.2H), 3.33 (s, 1.8H), 3.21 (dd, J = 13.5, 10.4 Hz, 1.2H), 3.17-3.08 (m, 0.8H), 2.94 (t, J = 11.2 Hz, 0.8H), 2.83 (dd, J = 13.6, 8.1 Hz, 1.2H). |
| I24 | 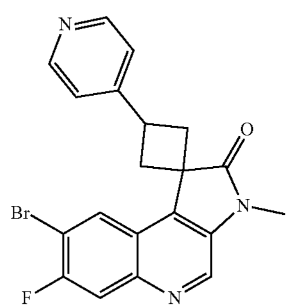 | 8'-Bromo-7'-fluoro-3'-methyl-3-(pyridin-4-yl)spiro[cyclobutane-1,1'-pyrrolo[2,3-c]quinolin]-2'(3'H)-one | 412.10 414.10 | H NMR (400 MHz, CDCl3) δ 8.70 (d, J = 9.4 Hz, 3H), 8.45 (d, J = 7.1 Hz, 0.5H), 8.15 (d, J = 7.1 Hz, 0.5H), 7.93-7.81 (m, 2H), 7.38-7.34 (m, 1H), 4.44 (p, J = 9.6 Hz, 0.5H), 4.20 (p, J = 8.7 Hz, 0.5H), 3.41 (d, J = 6.8 Hz, 3H), 3.28-3.18 (m, 1H), 3.10 (d, J = 9.7 Hz, 3H). |

Intermediate J

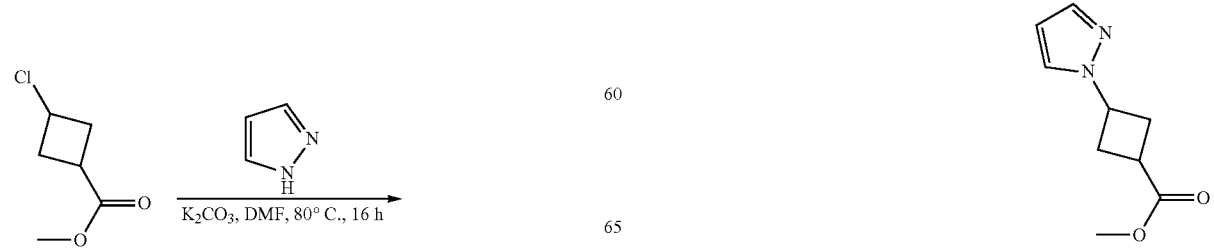

Methyl 3-(1H-pyrazol-1-yl)cyclobutane-1-carboxylate: To a solution of 1H-pyrazole (2.34 g, 34.3 mmol) in N,N-dimethylformamide (34.0 mL) were added methyl 3-chlorocyclobutane-1-carboxylate (1.70 g, 11.4 mmol) and potassium carbonate (6.32 g, 45.8 mmol) at ambient temperature. The resulting mixture was stirred for 16 hours at 80° C. After cooling down to ambient temperature, the resulting mixture was filtered. The filtered cake was washed with ethyl acetate (3×10 mL). The filtrate was condensed under reduced pressure. The residue was purified by reversed phase flash chromatography with the following conditions: [Column: Spherical C18, 20-40 μm, 330 g; Mobile Phase A: water (plus 10 mmol $NH_4HCO_3$); Mobile Phase B: Acetonitrile; Flow rate: 80 mL/min; Gradient: 35% B to 60% B in 20 min; Detector UV 220 n]. The fractions containing desired product were collected at 45% B and concentrated under reduced pressure to afford the title compound as light yellow oil (1.00 g, 49%): $^1$H NMR (400 MHz, $CDCl_3$) δ 7.57 (m, 0.3H), 7.55-7.48 (m, 1H), 7.41 (m, 0.3H), 6.26 (dd, J=11.5, 2.1 Hz, 1H), 5.04 (m, 0.3H), 4.75 (m, 0.7H), 3.74 (d, J=11.4 Hz, 3H), 3.22 (m, 0.3H), 3.03-2.83 (m, 1.7H), 2.85-2.70 (m, 4H); MS: $[(M+1)]^+$=181.20.

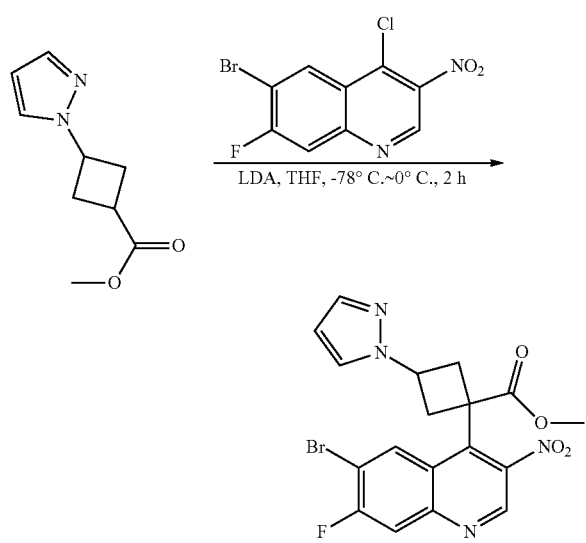

Methyl 1-(6-bromo-7-fluoro-3-nitroquinolin-4-yl)-3-(1H-pyrazol-1-yl)cyclobutane-1-carboxylate: A solution of methyl 3-(1H-pyrazol-1-yl)cyclobutane-1-carboxylate (600 mg, 3.33 mmol) in tetrahydrofuran (23.0 mL) was treated with lithium diisopropylamide (3.30 mL, 3.33 mmol, M in tetrahydrofuran) at −78° C. for 1 hour followed by the addition of 6-bromo-4-chloro-7-fluoro-3-nitroquinoline (1.12 g, 3.66 mmol). After stirring for additional 1 hour at 0° C., The reaction was quenched by saturated aqueous ammonium chloride (30.0 mL) and extracted with ethyl acetate (3×100 mL). The combined organic layers was concentrated under reduced pressure. The residue was purified by reverse phase flash chromatography with the following conditions: Column: C18 Column, 20-40 μm, 120 g; Mobile Phase A: Water (plus 5 mM $NH_4HCO_3$); Mobile Phase B: Acetonitrile; Flow rate: 60 mL/min; Gradient: 60% B to 80% B in 30 min; Detector UV 254 nm. The fractions containing desired product were collected at 75% B and concentrated under reduced pressure to afford the title compound as a yellow solid (25.0 mg, 2%): MS: $[(M+1)]^+$=449.20, 451.20.

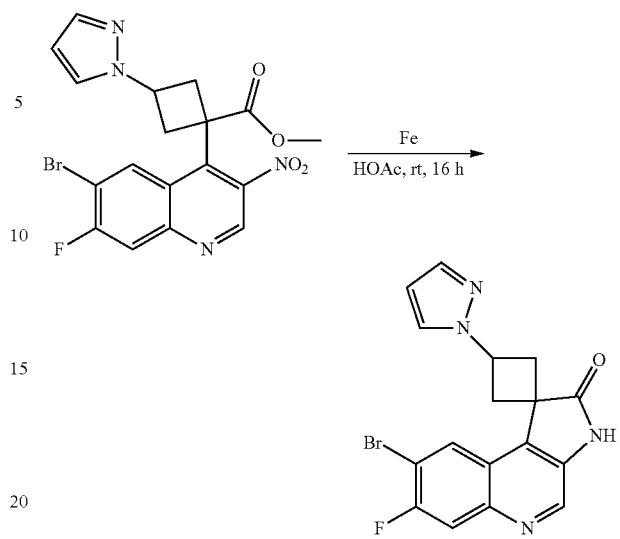

8'-Bromo-7'-fluoro-3-(1H-pyrazol-1-yl)spiro[cyclobutane-1,1'-pyrrolo[2,3-c]quinolin]-2'(3'H)-one: To a solution of methyl 1-(6-bromo-7-fluoro-3-nitroquinolin-4-yl)-3-(1H-pyrazol-1-yl)cyclobutane-1-carboxylate (25.0 mg, 0.056 mmol) in acetic acid (10.0 mL) was added iron powder (31.1 mg, 0.56 mmol). The reaction was stirred for 16 hours at ambient temperature. The resulting mixture was concentrated under reduced pressure and the residue was purified by reversed phase flash chromatography with the following conditions: Column: C18 Column, 20-40 μm, 120 g; Mobile Phase A: Water (plus 5 mM $NH_4HCO_3$); Mobile Phase B: Acetonitrile; Flow rate: 60 mL/min; Gradient: 60% B to 80% B in 30 min; Detector UV 254 nm. The fractions containing the desired product were collected at 75% B and concentrated under reduced pressure to afford the title compound as yellow solid (20.0 mg, 93%): $^1$H NMR (400 MHz, $CDCl_3$) δ 10.00 (s, 1H), 8.89 (s, 1H), 7.97 (s, 1H), 7.86 (d, J=1.7 Hz, 1H), 6.35 (t, J=1.9 Hz, 1H), 5.42 (s, 1H), 3.77 (s, 2H), 3.16 (s, 2H); MS: $[(M+1)]^+$=387.00, 389.00.

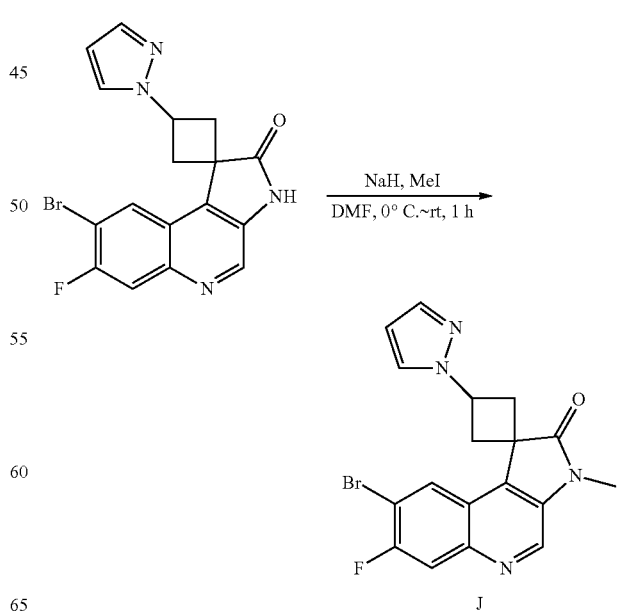

8'-Bromo-7'-fluoro-3'-methyl-3-(1H-pyrazol-1-yl)spiro[cyclobutane-1,1'-pyrrolo[2,3-c]quinolin]-2'(3'H)-one A solution of 8-bromo-7-fluoro-3-(1H-pyrazol-1-yl)-2,3-dihydrospiro[cyclobutane-1,1-pyrrolo[2,3-c]quinolin]-2-one (20.0 mg, 0.052 mmol) in N,N-dimethylformamide (5.00 mL) was treated with sodium hydride (2.69 mg, 0.067 mmol, 60% dispersed in mineral oil) at 0° C. for 30 min followed by the addition of iodomethane (11.0 mg, 0.077 mmol). The resulting mixture was stirred for 1 hour at ambient temperature and then quenched by saturated aqueous ammonium chloride (2.00 mL). The resulting mixture was concentrated under reduced pressure and the residue was purified by reversed phase flash chromatography with the following conditions: Column: C18 Column, 20-40 μm, 120 g; Mobile Phase A: Water (plus 10 mM NH$_4$HCO$_3$); Mobile Phase B: Acetonitrile; Flow rate: 60 mL/min; Gradient: 90% B to 95% B in 30 min; Detector: UV 254 nm. The fractions containing desired product were collected at 95% B and concentrated under reduced pressure to afford the title compound as yellow solid (17.0 mg, 82%): $^1$H NMR (400 MHz, CDCl$_3$) δ 10.10 (s, 1H), 8.71 (s, 1H), 8.13 (s, 1H), 7.85 (d, J=1.8 Hz, 1H), 7.53 (d, J=2.2 Hz, 1H), 6.33 (t, J=2.0 Hz, 1H), 5.42 (s, 1H), 3.75 (s, 2H), 3.43 (s, 3H), 3.14 (s, 2H); MS: [(M+1)]$^+$=400.95, 402.95.

Intermediate K

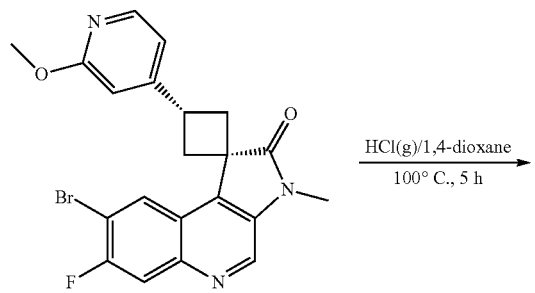

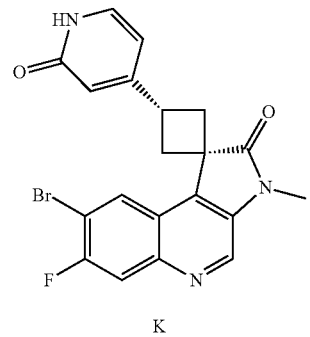

K cis-8'-Bromo-7'-fluoro-3'-methyl-3-(2-oxo-1,2-dihydropyridin-4-yl)spiro[cyclobutane-1,1'-pyrrolo[2,3-c]quinolin]-2'(3'H)-one: cis-8'-Bromo-7'-fluoro-3-(2-methoxypyridin-4-yl)-3'-methylspiro[cyclobutane-1,1'-pyrrolo[2,3-c]quinolin]-2'(3'H)-one (100 mg, 0.23 mmol) was treated with hydrogen chloride (50.0 mL, 4 M in 1,4-dioxane) for 5 hours at 100° C. After cooling down to ambient temperature, the reaction mixture was concentrated under reduced pressure. The residue was re-dissolved in dichloromethane and methanol (100 mL, v/v=10/1). The resulting mixture was neutralized to with ammonium hydroxide. The resulting mixture was concentrated under reduced pressure. The residue was purified by silica gel column chromatography, eluted with 1%~25% methanol in dichloromethane to afford the title compound as a light yellow solid (70.0 mg, 73%): $^1$H NMR (400 MHz, DMSO-d$_6$) δ 11.46 (s, 1H), 8.94 (d, J=2.7 Hz, 1H), 8.52 (d, J=7.4 Hz, 1H), 8.06 (dd, J=10.0, 2.6 Hz, 1H), 7.40 (d, J=6.8 Hz, 1H), 6.57 (dd, J=6.8, 1.7 Hz, 1H), 6.44 (s, 1H), 4.07 (p, J=9.2 Hz, 1H), 3.32 (s, 3H), 3.08 (dd, J=13.3, 10.3 Hz, 2H), 2.79-2.72 (m, 2H); MS: [(M+1)]$^+$=428.00, 430.00.

The following intermediates were prepared according to the procedure described above:

| Intermediate | Structure | Name | MS: [(M + 1)]$^+$ | $^1$H-NMR |
|---|---|---|---|---|
| K1 | 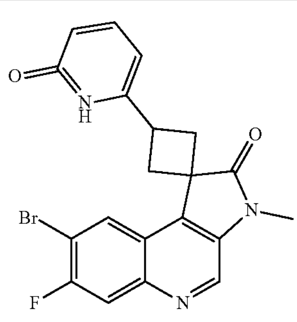 | 8'-Bromo-7'-fluoro-3'-methyl-3-(6-oxo-1,6-dihydropyridin-2-yl)spiro[cyclobutane-1,1'-pyrrolo[2,3-c]quinolin]-2'(3'H)-one | 428.00<br>430.00 | $^1$H NMR (400 MHz, DMSO-d$_6$) δ 11.71 (d, J = 25.2 Hz, 1H), 8.95 (d, J = 7.9 Hz, 1H), 8.49 (d, J = 7.6 Hz, 0.4H), 8.36 (s, 0.6H), 8.10-8.01 (m, 1H), 7.58-7.47 (m, 1H), 6.43 (s, 1H), 6.32-6.22 (m, 1H), 4.24-4.15 (m, 0.4H), 4.05-3.97 (m, 0.6H), 3.33 (s, 3H), 3.13-3.00 (m, 2H), 2.90-2.75 (m, 2H). |

| Intermediate | Structure | Name | MS: [(M + 1)]+ | 1H-NMR |
|---|---|---|---|---|
| K2 | 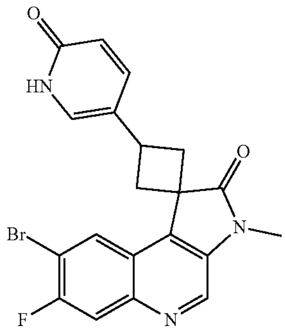 [SMILES: CN1C(=O)C2(CC(c3ccc(=O)[nH]c3)C2)c2c1cnc1cc(F)c(Br)cc21] | 8'-Bromo-7'-fluoro-3'-methyl-3-(6-oxo-1,6-dihydropyridin-3-yl)spiro[cyclobutane-1,1'-pyrrolo[2,3-c]quinolin]-2'(3'H)-one | 428.10 430.10 | Crude to next step |
| K3 | 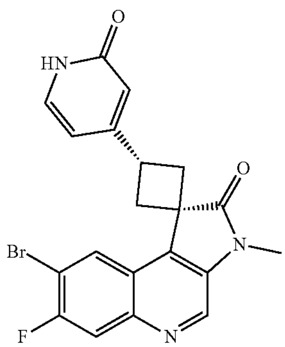 [SMILES: CN1c2cnc3cc(F)c(Br)cc3c2[C@]2(C[C@H](c3cc[nH]c(=O)c3)C2)C1=O] | cis-8'-Bromo-7'-fluoro-3'-methyl-3-(2-oxo-1,2-dihydropyridin-4-yl)spiro[cyclobutane-1,1'-pyrrolo[2,3-c]quinolin]-2'(3'H)-one | 428.00 430.00 | $^1$H NMR (400 MHz, DMSO-$d_6$) δ 11.46 (s, 1H), 8.94 (d, J = 2.7 Hz, 1H), 8.52 (d, J = 7.4 Hz, 1H), 8.06 (dd, J = 10.0, 2.6 Hz, 1H), 7.40 (d, J = 6.8 Hz, 1H), 6.57 (dd, J = 6.8, 1.7 Hz, 1H), 6.44 (s, 1H), 4.07 (p, J = 9.2 Hz, 1H), 3.32 (s, 3H), 3.08 (dd, J = 13.3, 10.3 Hz, 2H), 2.79-2.72 (m, 2H). |
| K4 | 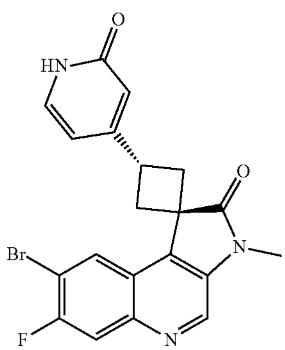 [SMILES: CN1c2cnc3cc(F)c(Br)cc3c2[C@]2(C[C@@H](c3cc[nH]c(=O)c3)C2)C1=O] | trans-8'-Bromo-7'-fluoro-3'-methyl-3-(2-oxo-1,2-dihydropyridin-4-yl)spiro[cyclobutane-1,1'-pyrrolo[2,3-c]quinolin]-2'(3'H)-one | 428.00 430.00 | $^1$H NMR (400 MHz, DMSO-$d_6$) δ 11.51 (s, 1H), 8.93 (s, 1H), 8.20 (d, J = 7.3 Hz, 1H), 8.01 (d, J = 10.1 Hz, 1H), 7.42 (d, J = 6.7 Hz, 1H), 6.37 (s, 1H), 6.18 (dd, J = 6.6, 1.7 Hz, 1H), 4.01 (p, J = 9.5 Hz, 1H), 3.32 (s, 3H), 2.97 (t, J = 11.0 Hz, 2H), 2.86 (t, J = 11.2 Hz, 2H). |

Intermediate L

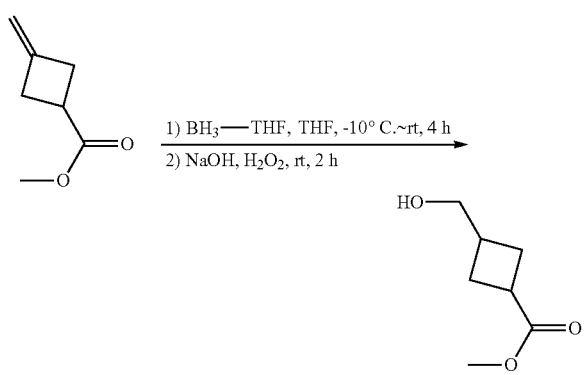

Methyl 3-(hydroxymethyl)cyclobutane-1-carboxylate: To a solution of methyl 3-methylidenecyclobutane-1-carboxylate (12.0 g, 95.1 mmol) (Prepared according to the procedure reported by PCT Int. Appl., 2017127430, 27 Jul. 2017) in anhydrous tetrahydrofuran (65.0 mL) was added borane (35.2 mL, 35.2 mmol, 1 M in tetrahydrofuran) dropwise at −10° C. The resulting mixture was stirred for 4 hours at 25° C. followed by the addition of methanol (2.00 mL). After stirring for 15 min at −10° C., sodium hydroxide solution (13.6 mL, 40.9 mmol, 3 M) and hydrogen peroxide solution (10.0 g, 100 mmol, 34% w/w) were added in sequence at 0° C. The resulting mixture was stirred for 2 hours at 25° C. The reaction was quenched by saturated aqueous sodium sulfite solution (50.0 mL) and diluted with water (150 mL). The resulting mixture was extracted with ethyl acetate (3×100 mL). The combined organic layers was washed with brine (2×100 mL), dried over anhydrous sodium sulfate and filtered. The filtrate was concentrated under reduced pressure. The residue was purified by silica gel column chromatography, eluted with 1%~20% ethyl acetate in petroleum ether. The desired fractions were collected and concentrated under reduced pressure to afford the title compound as a light yellow oil (8.6 g, 63%): $^1$H NMR (400 MHz, CDCl$_3$)

δ 3.75-3.63 (m, 4H), 3.59 (d, J=6.2 Hz, 1H), 3.17-2.97 (m, 1H), 2.62-2.24 (m, 3H), 2.11-2.01 (m, 2H).

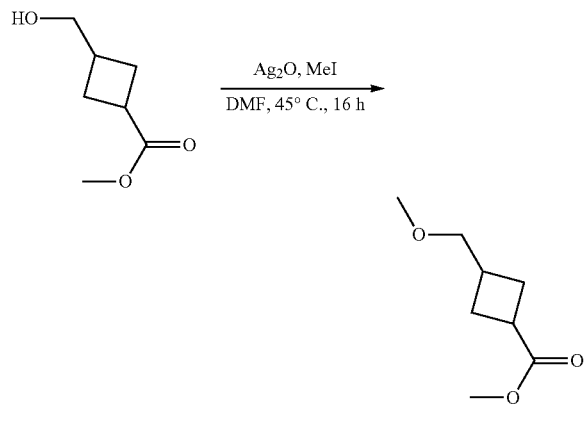

Methyl 3-(methoxymethyl)cyclobutane-1-carboxylate: A mixture of methyl 3-(hydroxymethyl)cyclobutane-1-carboxylate (2.50 g, 17.3 mmol), iodomethane (4.90 g, 34.7 mmol) and silver oxide (6.10 g, 26.0 mmol) in N-dimethylformamide (25.0 mL) was stirred for 16 hours at 45° C. The resulting mixture was cooled down to ambient temperature and filtered under reduced pressure. The filtered cake was washed with tetrahydrofuran (3×20.0 mL). The filtrate was diluted with water (250 mL) and extracted with diethyl ether (6×50.0 mL). The combined organic layers was washed with brine (2×100 mL) and dried over anhydrous sodium sulfate. After filtration, the filtrate was concentrated under reduced pressure to afford the title compound as a yellow oil (2.50 g, 90%): $^1$H NMR (400 MHz, DMSO-$d_6$) δ 3.59 (d, J=8.9 Hz, 3H), 3.37-3.31 (m, 1H), 3.26-3.19 (m, 4H), 3.17-3.00 (m, 1H), 2.48-2.38 (m, 1H), 2.25-2.13 (m, 2H), 1.99-1.84 (m, 2H).

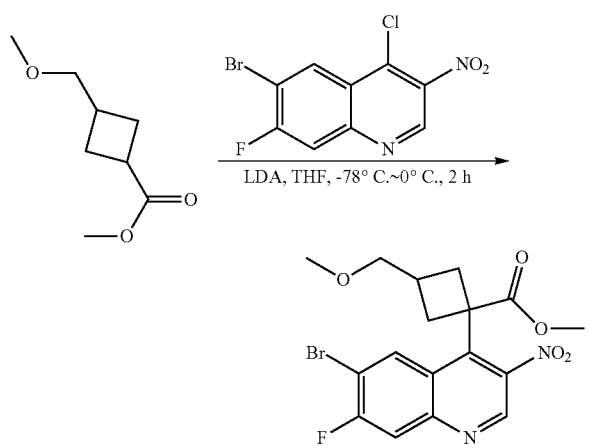

Methyl 1-(6-bromo-7-fluoro-3-nitroquinolin-4-yl)-3-(methoxymethyl)cyclobutane-1-carboxylate A solution of methyl 3-(methoxymethyl)cyclobutane-1-carboxylate (2.42 g, 15.3 mmol) in tetrahydrofuran (4.00 mL) was treated with freshly prepared lithium diisopropylamide (15.3 mmol) in anhydrous tetrahydrofuran (150 mL) for 1 hour at −78° C. followed by the addition of 6-bromo-4-chloro-7-fluoro-3-nitroquinoline (3.60 g, 11.8 mmol). The resulting mixture was slowly warmed to 0° C. After stirring for 1 hour at 0° C., the reaction was quenched by saturated ammonium chloride (30.0 mL) and diluted with water (800 mL). The resulting mixture was extracted with ethyl acetate (3×150 mL). The combined organic layers was washed with brine (2×100 mL) and dried over anhydrous sodium sulfate. After filtration, the filtrate was concentrated under reduced pressure. The residue was purified by silica gel column chromatography, eluted with 3%~20% ethyl acetate in petroleum ether to afford the title compound as a yellow oil (901 mg, 18%): $^1$H NMR (400 MHz, DMSO-$d_6$) δ 9.34-9.22 (m, 1H), 8.31 (dd, J=7.3, 1.9 Hz, 1H), 8.16 (dd, J=9.3, 2.1 Hz, 1H), 3.72 (s, 2H), 3.69 (s, 3H), 3.67-3.59 (m, 3H), 3.25 (s, 3H), 2.75-2.58 (m, 2H); MS: [(M+1)]$^+$=427.20, 429.20.

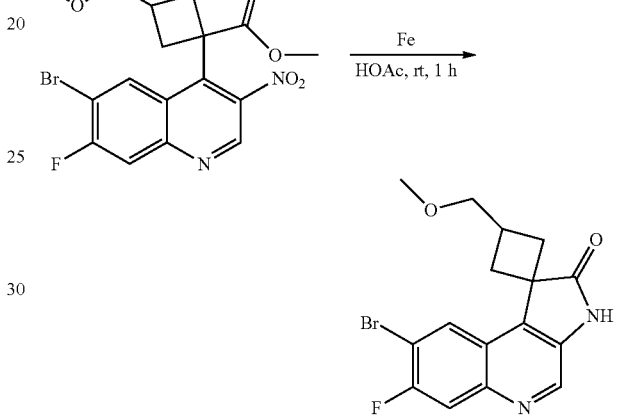

8'-Bromo-7'-fluoro-3-(methoxymethyl)spiro[cyclobutane-1,1'-pyrrolo[2,3-c]quinolin]-2'(3'H)-one To a solution of methyl 1-(6-bromo-7-fluoro-3-nitroquinolin-4-yl)-3-(methoxymethyl)cyclobutane-1-carboxylate (0.90 g, 2.11 mmol) in acetic acid (20.0 mL) was added iron powder (1.17 g, 21.1 mmol) at ambient temperature. After stirring for 1 hour at ambient temperature, the resulting mixture was filtered and the filtered cake was washed with tetrahydrofuran (6×50.0 mL). The filtrate was concentrated under reduced pressure. The residue was purified by silica gel column chromatography, eluted with 1%~5% methanol in dichloromethane to afford the title compound as a yellow solid (721 mg, 94%): $^1$H NMR (400 MHz, DMSO-$d_6$) δ 10.79 (br, 1H), 9.04 (d, J=7.5 Hz, 0.4H), 8.70-8.65 (m, 1H), 8.38 (d, J=7.5, 0.6H), 7.95-7.88 (m, 1H), 3.71-3.62 (m, 3H), 3.46 (s, 0.8H), 3.29 (s, 1.2H), 3.13-3.02 (m, 1H), 2.92-2.72 (m, 2H), 2.33-2.16 (m, 2H); MS: [(M+1)]$^+$=365.20, 367.20.

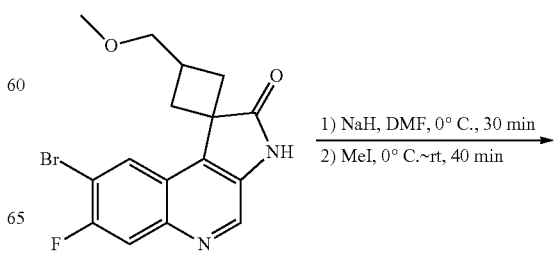

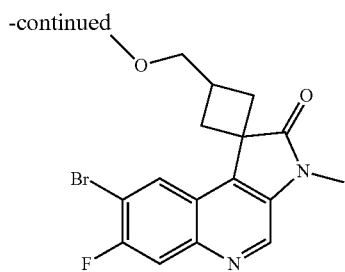

8'-Bromo-7'-fluoro-3-(methoxymethyl)-3'-methyl-spiro[cyclobutane-1,1'-pyrrolo[2,3-c]quinolin]-2'(3'H)-one A solution of 8-bromo-7-fluoro-3-(methoxymethyl)-2,3-dihydrospiro[cyclobutane-1,1-pyrrolo[2,3-c]quinolin]-2-one (400 mg, 1.10 mmol) in N,N-dimethylformamide (10.0 mL) was treated with sodium hydride (65.7 mg, 1.64 mmol, 60% dispersed in mineral oil) for 0.5 hours at 0° C. under nitrogen atmosphere followed by the addition of iodomethane (202 mg, 1.42 mmol). After stirring for additional 40 min at ambient temperature, the reaction was quenched by saturated ammonium chloride (30.0 mL) and diluted with water (100 mL). The resulting mixture was extracted with ethyl acetate (3×50.0 mL). The combined organic layers was washed with brine (2×50.0 mL) and dried over anhydrous sodium sulfate. After filtration, the filtrate was concentrated under reduced pressure. The residue was purified by silica gel column chromatography, eluted with 1-2% methanol in dichloromethane to afford the title compound as a yellow solid (402 mg, 97%): $^1$H NMR (400 MHz, CDCl$_3$) δ 9.18 (d, J=7.4 Hz, 0.5H), 8.70-8.65 (m, 1H), 8.42 (d, J=7.4 Hz, 0.5H), 7.90-7.83 (m, 1H), 3.83 (s, 1.5H), 3.69 (s, 1.5H), 3.46 (s, 1H), 3.29 (s, 1H), 3.10-3.06 (m, 1H), 2.92-2.72 (m, 2H), 2.63-2.46 (m, 2H); MS: [(M+1)]$^+$=379.20, 381.20.

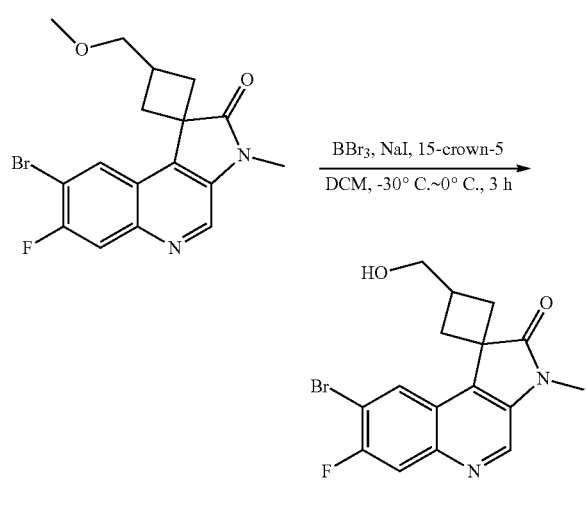

8'-Bromo-7'-fluoro-3-(hydroxymethyl)-3'-methyl-spiro[cyclobutane-1,1'-pyrrolo[2,3-c]quinolin]-2'(3'H)-one To a stirred mixture of 8'-bromo-7'-fluoro-3-(methoxymethyl)-3'-methylspiro[cyclobutane-1,1'-pyrrolo[2,3-c]quinolin]-2'(3'H)-one (0.41 g, 1.08 mmol), 15-crown-5 (1.43 g, 6.49 mmol) and sodium iodide (325 mg, 2.16 mmol) in anhydrous dichloromethane (20.0 mL) was added boron tribromide (10.8 mL, 10.8 mmol, 1M in dichloromethane) dropwise at −30° C. under nitrogen atmosphere. After stirring for 3 hours at 0° C. under nitrogen atmosphere, the mixture was quenched with saturated aqueous sodium bicarbonate (100 mL). The aqueous layer was extracted with ethyl acetate (3×100 mL). The combined organic layers was washed with brine (2×100 mL) and dried over anhydrous sodium sulfate. After filtration, the filtrate was concentrated under reduced pressure. The residue was purified by silica gel column chromatography, eluted with 1%~3% methanol in dichloromethane. The desired fractions were collected and concentrated under reduced pressure to afford the title compound as a colorless solid (0.27 g, 69%): $^1$H NMR (400 MHz, CDCl$_3$) δ 9.22 (d, J=7.2 Hz, 0.4H), 8.66 (d, J=10.3 Hz, 1H), 8.40 (d, J=7.2 Hz, 0.6H), 7.87 (t, J=9.2 Hz, 1H), 4.04 (d, J=5.8 Hz, 1.2H), 3.90-3.83 (m, 0.8H), 3.37 (d, J=2.8 Hz, 3H), 3.24-3.15 (m, 1H), 3.14-3.06 (m, 0.8H), 2.89 (dd, J=13.4, 10.0 Hz, 1.2H), 2.67 (dd, J=13.9, 6.3 Hz, 1.2H), 2.51 (td, J=9.4, 2.7 Hz, 0.8H); MS: [(M+1)]$^+$=365.00, 367.00.

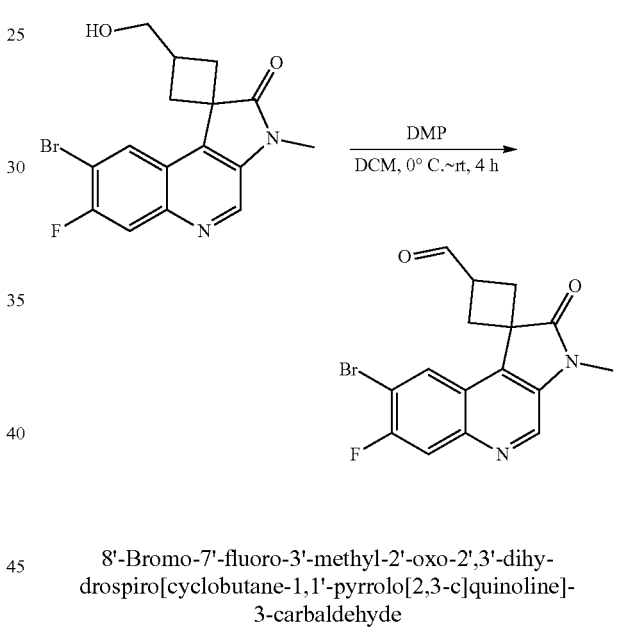

8'-Bromo-7'-fluoro-3'-methyl-2'-oxo-2',3'-dihydrospiro[cyclobutane-1,1'-pyrrolo[2,3-c]quinoline]-3-carbaldehyde To a solution of 8'-bromo-7'-fluoro-3-(hydroxymethyl)-3'-methylspiro[cyclobutane-1,1'-pyrrolo[2,3-c]quinolin]-2'(3'H)-one (200 mg, 0.55 mmol) in dichloromethane (5.00 mL) was added Dess-Martin periodinane (465 mg, 1.10 mmol) at 0° C. After stirring for 4 hours at 25° C., the reaction was quenched by a mixture of saturated aqueous sodium thiosulfate solution and saturated aqueous sodium bicarbonate (50 mL, v/v=1/1). The resulting mixture was extracted with ethyl acetate (3×50.0 mL). The combined organic layers was washed with brine (2×50.0 mL) and dried over anhydrous sodium sulfate. After filtration, the filtrate was concentrated under reduced pressure. The residue was purified by silica gel column chromatography, eluted with 5% methanol in dichloromethane. The desired fractions were collected and concentrated under reduced pressure to afford the title compound as a light yellow solid (110 mg, 56%) which was used in the next step without further purification: MS: [(M+1)]$^+$=363.00, 365.00.

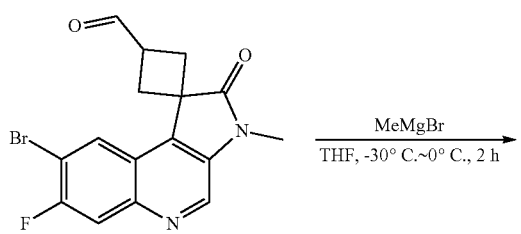

8'-Bromo-7'-fluoro-3-(1-hydroxyethyl)-3'-methyl-spiro[cyclobutane-1,1'-pyrrolo[2,3-c]quinolin]-2'(3'H)-one

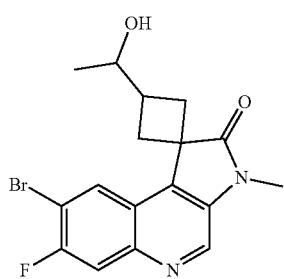

To a solution of 8'-bromo-7'-fluoro-3'-methyl-2'-oxo-2', 3'-dihydrospiro[cyclobutane-1,1'-pyrrolo[2,3-c]quinoline]-3-carbaldehyde (110 mg, 0.30 mmol) in tetrahydrofuran (5.00 mL) was added bromo(methyl)magnesium (0.90 mL, 0.90 mmol, 1M in ethyl ether) dropwise at −30° C. under nitrogen atmosphere. The resulting mixture was stirred for 2 hours at 0° C. under nitrogen atmosphere. The reaction was quenched by saturated aqueous ammonium chloride (5.00 mL) at 0° C. and diluted with water (20.0 mL). The resulting mixture was extracted with ethyl acetate (3×20.0 mL). The combined organic layers was washed with brine (2×20.0 mL) and dried over anhydrous sodium sulfate. After filtration, the filtrate was concentrated under reduced pressure. The residue was purified by Prep-TLC (5% methanol in dichloromethane) to afford the title compound as a yellow solid (57.0 mg, 50%): $^1$H NMR (400 MHz, CDCl$_3$) δ 9.22 (d, J=7.2 Hz, 0.6H), 8.65 (d, J=10.9 Hz, 1H), 8.37 (d, J=7.2 Hz, 0.4H), 7.89-7.90 (m, 1H), 4.10-4.00 (m, 1H), 3.37 (d, J=2.9 Hz, 3H), 3.20-3.11 (m, 1H), 3.05 (td, J=10.5, 3.7 Hz, 1H), 2.92-2.82 (m, 1H), 2.65-2.55 (m, 1H), 2.53-2.41 (m, 1H), 1.28-1.23 (m, 3H); MS: [(M+1)]$^+$=379.20, 381.20.

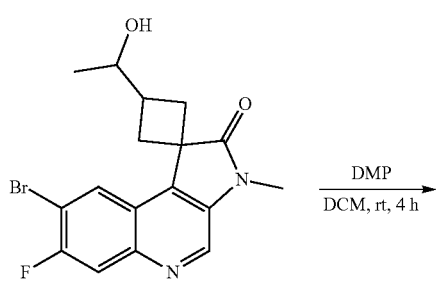

3-Acetyl-8'-bromo-7'-fluoro-3'-methylspiro[cyclobutane-1,1'-pyrrolo[2,3-c]quinolin]-2'(3'H)-one: To a solution of 8'-bromo-7'-fluoro-3-(1-hydroxyethyl)-3'-methylspiro[cyclobutane-1,1'-pyrrolo[2,3-c]quinolin]-2'(3'H)-one (57.0 mg, 0.15 mmol) in dichloromethane (5.00 mL) was added Dess-Martin periodinane (128 mg, 0.30 mmol) at 0° C. After stirring for 4 hours at 25° C., the reaction was quenched by a mixture of saturated sodium thiosulfate solution and saturated aqueous sodium bicarbonate (50 mL, v/v=1/1). The resulting mixture was extracted with ethyl acetate (3×50.0 mL). The combined organic layers was washed with brine (2×50.0 mL) and dried over anhydrous sodium sulfate. After filtration, the filtrate was concentrated under reduced pressure. The residue was purified by silica gel column chromatography, eluted with 5% methanol in dichloromethane. The desired fractions were collected and concentrated under reduced pressure to afford the title compound as a light yellow solid (50.0 mg, 88%): $^1$H NMR (400 MHz, CDCl$_3$) δ 8.74 (d, J=7.2 Hz, 0.6H), 8.67 (d, J=5.0 Hz, 1H), 8.31 (d, J=7.2 Hz, 0.4H), 7.85 (dd, J=21.0, 9.5 Hz, 1H), 4.16-3.98 (m, 1H), 3.37 (d, J=13.1 Hz, 3H), 3.19-3.05 (m, 2H), 3.01-2.91 (m, 1H), 2.75-2.67 (m, 1H), 2.34 (d, J=23.6 Hz, 3H); MS: [(M+1)]$^+$=377.10, 379.10.

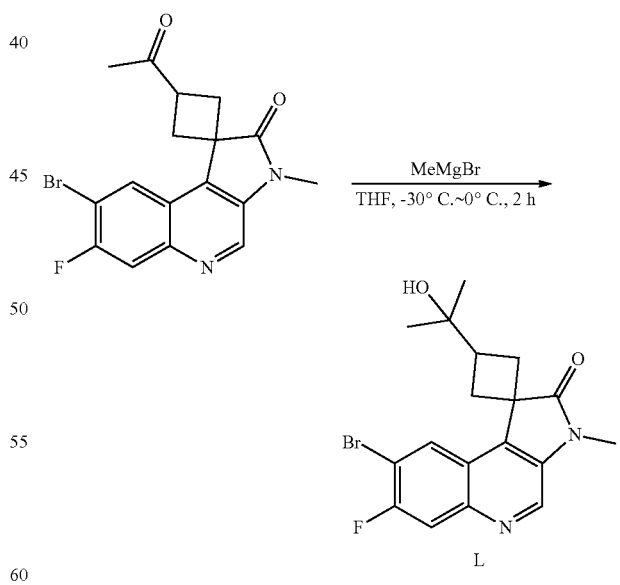

8'-Bromo-7'-fluoro-3-(2-hydroxypropan-2-yl)-3'-methylspiro[cyclobutane-1,1'-pyrrolo[2,3-c]quinolin]-2'(3'H)-one: To a solution of 3-acetyl-8'-bromo-7'-fluoro-3'-methylspiro[cyclobutane-1,1'-pyrrolo[2,3-c]quinolin]-2'(3'H)-one (50.0 mg, 0.13 mmol) in anhydrous tetrahydrofuran (5.00 mL) was added bromo(methyl)magnesium (0.40 mL, 0.40 mmol, 1M in diethyl ether) dropwise at −30° C. under nitrogen atmosphere. The resulting mixture was stirred for 2 hours at 0° C. under nitrogen atmosphere. The reaction was quenched by saturated aqueous ammonium chloride (5.00 mL) at 0° C. and diluted with water (20.0 mL). The resulting mixture was extracted with ethyl acetate (3×20.0 mL). The combined organic layers was washed with brine (2×20.0 mL) and dried over anhydrous sodium sulfate. After filtration, the filtrate was concentrated under reduced pressure. The residue was purified by Prep-TLC (5% methanol in dichloromethane) to afford the title compound as a yellow solid (25.0 mg, 48%): $^1$H NMR (400 MHz, CDCl$_3$) δ 9.29 (d, J=7.5 Hz, 0.7H), 8.65 (d, J=15.0 Hz, 1H), 8.35 (d, J=6.8 Hz, 0.3H), 7.90-7.77 (m, 1H), 3.38 (d, J=2.8 Hz, 3H), 3.11-2.75 (m, 4H), 2.50-2.41 (m, 1H), 1.28 (d, J=8.8 Hz, 6H); MS: [(M+1)]$^+$=393.20, 395.20.

Intermediate M

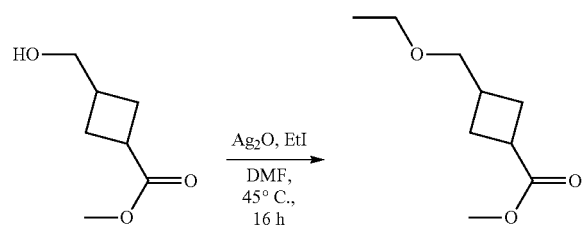

Methyl 3-(ethoxymethyl)cyclobutane-1-carboxylate: A mixture of methyl 3-(hydroxymethyl)cyclobutane-1-carboxylate (0.92 g, 6.38 mmol), iodoethane (2.99 g, 19.1 mmol) and silver oxide (2.22 g, 9.58 mmol) in N,N-dimethylformamide (10.0 mL) was stirred for 16 hours at 45° C. The resulting mixture was cooled down to ambient temperature and filtered. The filtered cake was washed with tetrahydrofuran (3×20.0 mL). The filtrate was diluted with water (150 mL) and extracted with diethyl ether (6×50.0 mL). The combined organic layers was washed with brine (2×100 mL) and dried over anhydrous sodium sulfate. After filtration, the filtrate was concentrated under reduced pressure to afford the title compound as a yellow oil (1.00 g, 91%): $^1$H NMR (400 MHz, CDCl$_3$) δ 4.19-4.01 (m, 2H), 3.76-3.58 (m, 5H), 3.10-2.99 (m, 1H), 2.64-2.25 (m, 5H), 2.15-2.00 (m, 3H).

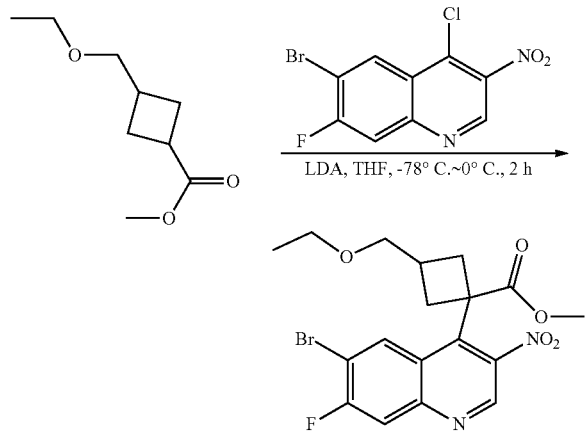

Methyl 1-(6-bromo-7-fluoro-3-nitroquinolin-4-yl)-3-(ethoxymethyl)cyclobutane-1-carboxylate: A solution of methyl 3-(ethoxymethyl)cyclobutane-1-carboxylate (660 mg, 3.83 mmol) in tetrahydrofuran (5.00 mL) was treated with freshly prepared lithium diisopropylamide (3.83 mmol) in anhydrous tetrahydrofuran (38.0 mL) for 1 hour at −78° C. followed by the addition of 6-bromo-4-chloro-7-fluoro-3-nitroquinoline (900 mg, 2.95 mmol). After stirring for additional 1 hour at 0° C., the reaction was quenched by saturated aqueous ammonium chloride (20.0 mL) and diluted with water (100 mL). The resulting mixture was extracted with ethyl acetate (3×50.0 mL). The combined organic layers was washed with brine (2×100 mL) and dried over anhydrous sodium sulfate. After filtration, the filtrate was concentrated under reduced pressure. The residue was purified by silica gel column chromatography, eluted with 2%~10% ethyl acetate in petroleum ether to afford the title compound as a yellow oil (174 mg, 14%): MS: [(M+1)]$^+$=441.20, 443.20.

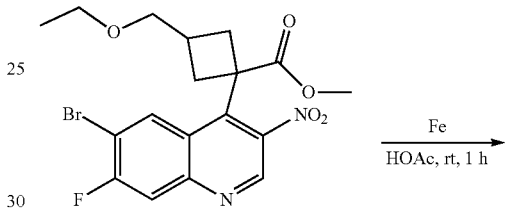

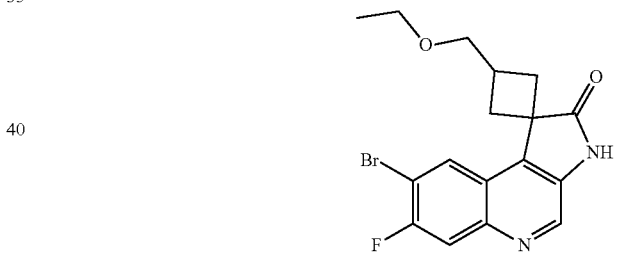

8'-Bromo-3-(ethoxymethyl)-7'-fluorospiro[cyclobutane-1,1'-pyrrolo[2,3-c]quinolin]-2'(3'H)-one: To a solution of methyl 1-(6-bromo-7-fluoro-3-nitroquinolin-4-yl)-3-(ethoxymethyl)cyclobutane-1-carboxylate (174 mg, 0.39 mmol) in acetic acid (8.00 mL) was added iron powder (220 mg, 3.94 mmol) at ambient temperature. After stirring for 1 hour at ambient temperature, the resulting mixture was filtered and the filtered cake was washed with tetrahydrofuran (6×50.0 mL). The filtrate was concentrated under reduced pressure. The residue was purified by silica gel column chromatography, eluted with 1%~5% methanol in dichloromethane to afford the title compound as a yellow solid (116 mg, 78%): $^1$H NMR (400 MHz, CDCl$_3$) δ 9.05 (d, J=7.3 Hz, 0.25H), 8.76 (d, J=7.4 Hz, 0.75H), 8.44 (d, J=7.1 Hz, 0.5H), 8.31 (br, 0.25H), 8.16 (br, 0.5H), 7.89 (dd, J=9.4, 3.1 Hz, 0.75H), 3.94-3.89 (m, 2H), 3.61-3.55 (m, 2H), 3.47-3.11 (m, 1H), 2.83-2.75 (m, 2H), 2.61-2.54 (m, 2H), 1.43-1.39 (m, 3H); MS: [(M+1)]$^+$=379.20, 381.20.

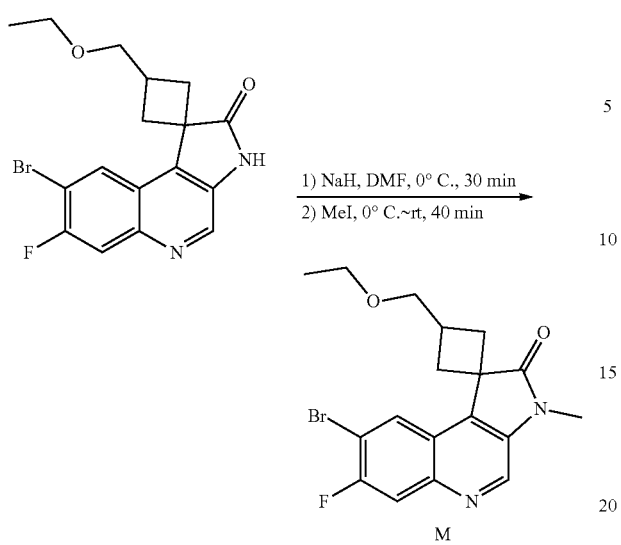

8'-Bromo-3-(ethoxymethyl)-7'-fluoro-3'-methylspiro[cyclobutane-1,1'-pyrrolo[2,3-c]quinolin]-2'(3'H)-one A solution of 8-bromo-3-(ethoxymethyl)-7-fluoro-2,3-dihydrospiro[cyclobutane-1,1-pyrrolo[2,3-c]quinolin]-2-one (116 mg, 0.31 mmol) in N,N-dimethylformamide (5.00 mL) was treated with sodium hydride (18.4 mg, 0.46 mmol, 60% dispersed in mineral oil) for 0.5 hours at 0° C. under nitrogen atmosphere followed by the addition of iodomethane (56.5 mg, 0.39 mmol) over 2 min After stirring for additional 40 min at ambient temperature, the reaction was quenched by saturated ammonium chloride (5.00 mL) and diluted with water (50.0 mL). The resulting mixture was extracted with ethyl acetate (3×50.0 mL). The combined organic layers was washed with brine (2×50.0 mL) and dried over anhydrous sodium sulfate. After filtration, the filtrate was concentrated under reduced pressure. The residue was purified by silica gel column chromatography, eluted with 1%~2% methanol in dichloromethane to afford the title compound as a yellow oil (120 mg, 99%): $^1$H NMR (400 MHz, CDCl$_3$) δ 9.03 (d, J=7.1 Hz, 0.4H), 8.67 (d, J=5.9 Hz, 1H), 8.44 (d, J=7.1 Hz, 0.6H), 7.90-7.83 (m, 1H), 3.90-3.80 (m, 2H), 3.68-3.57 (m, 2H), 3.39 (d, J=4.6 Hz, 3H), 3.23 (p, J=9.1 Hz, 1H), 3.14-3.06 (m, 0.8H), 2.88 (dd, J=13.3, 9.7 Hz, 1.2H), 2.56 (dd, J=13.4, 6.6 Hz, 1.2H), 2.48 (dd, J=12.2, 9.11 Hz, 0.8H), 1.43 (t, J=7.0 Hz, 1.2H), 1.29 (t, J=7.0 Hz, 1.8H); MS: [(M+1)]$^+$=393.10, 395.10.

Intermediate M1

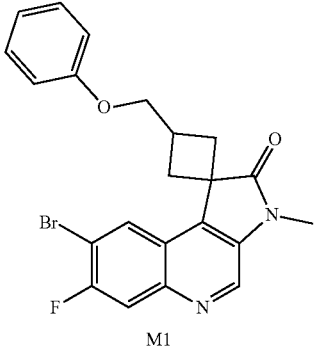

8'-Bromo-7'-fluoro-3'-methyl-3-(phenoxymethyl)spiro[cyclobutane-1,1'-pyrrolo[2,3-c]quinolin]-2'(3'H)-one To a solution of 8'-bromo-7'-fluoro-3-(hydroxymethyl)-3'-methylspiro[cyclobutane-1,1'-pyrrolo[2,3-c]quinolin]-2'(3'H)-one (50.0 mg, 0.14 mmol), triphenylphosphine (72.0 mg, 0.28 mmol) and phenol (20.0 mg, 0.21 mmol) in anhydrous tetrahydrofuran (3.00 mL) was added diisopropyl azodiformate (56.0 mg, 0.28 mmol) dropwise at 0° C. After stirring for 16 hours at ambient temperature, the resulting mixture was concentrated under reduced pressure. The residue was purified by silica gel column chromatography, eluted with 1%~4% methanol in dichloromethane. The desired fractions were collected and concentrated under reduced pressure to afford the title compound as an off-white solid (40.0 mg, 67%): $^1$H NMR (400 MHz, CDCl$_3$) δ 8.94 (d, J=7.1 Hz, 0.4H), 8.67 (s, 1H), 8.45 (d, J=7.1 Hz, 0.6H), 7.95-7.89 (m, 1H), 7.39-7.29 (m, 2H), 7.06-6.95 (m, 3H), 4.43 (d, J=7.5 Hz, 1.2H), 4.14 (d, J=2.9 Hz, 0.8H), 3.47-3.30 (m, 4H), 3.26 (t, J=6.4 Hz, 0.8H), 2.97 (t, J=11.4 Hz, 1.2H), 2.71-2.53 (m, 2H); MS: [(M+1)]$^+$=441.20, 443.20.

Intermediate M2

8'-Bromo-7'-fluoro-3-(isopropoxymethyl)-3'-methyl-spiro[cyclobutane-1,1'-pyrrolo[2,3-c]quinolin]-2'(3'H)-one A solution of 8'-bromo-7'-fluoro-3-(hydroxymethyl)-3'-methylspiro[cyclobutane-1,1'-pyrrolo[2,3-c]quinolin]-2'(3'H)-one (70.0 mg, 0.19 mmol) in anhydrous N,N-dimethylformamide (3.00 mL) was treated with sodium hydride (23.0 mg, 0.56 mmol, 60% w/w dispersed in mineral oil) for 1 hour at 0° C. under nitrogen atmosphere followed by the addition of 2-iodopropane (326 mg, 1.92 mmol) in portions over 2 min at 0° C. After additional 2 hours at 25° C., to the above mixture was added sodium hydride (23.0 mg, 0.56 mmol, 60% w/w dispersed in mineral oil) in portions over 2 min at 0° C. The resulting mixture was stirred for additional 16 hours at ambient temperature. The reaction was quenched by saturated aqueous ammonium chloride (5.00 mL) and diluted with water (50.0 mL). The resulting mixture was extracted with ethyl acetate (3×50.0 mL). The combined organic layers was washed with brine (2×50.0 mL) and dried over anhydrous sodium sulfate. After filtration, the filtrate was concentrated under reduced pressure. The residue was purified by Prep-TLC (6% methanol in dichloromethane) to afford the title compound as a yellow oil (16.0 mg, 21%): $^1$H NMR (400 MHz, DMSO-$d_6$) δ 8.91 (s, 1H), 8.75 (d, J=7.4 Hz, 0.5H), 8.43 (d, J=7.4 Hz, 0.5H), 8.03 (t, J=9.0 Hz, 1H), 3.80-3.70 (m, 1.5H), 3.63 (p, J=6.0 Hz, 0.5H), 3.53 (d, J=3.4 Hz, 1H), 3.30 (d, J=6.5 Hz, 3H), 3.27-3.19 (m, 0.5H), 3.10-2.98 (m, 0.5H), 2.90 (t, J=10.8 Hz, 1H), 2.80 (dd, J=13.0, 9.5 Hz, 1H), 2.37-2.25 (m, 2H), 1.31 (d, J=6.2 Hz, 3H), 1.15 (d, J=6.1 Hz, 3H); MS: [(M+1)]$^+$=407.10, 409.10.

Intermediate N

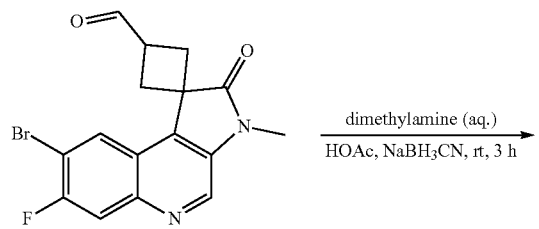

dimethylamine (aq.)
——————————→
HOAc, NaBH$_3$CN, rt, 3 h

8'-Bromo-3-((dimethylamino)methyl)-7'-fluoro-3'-methylspiro[cyclobutane-1,1'-pyrrolo[2,3-c]quinolin]-2'(3'H)-one: To a stirred solution of 8'-bromo-7'-fluoro-3'-methyl-2'-oxo-2',3'-dihydrospiro[cyclobutane-1,1'-pyrrolo[2,3-c]quinoline]-3-carbaldehyde (60.0 mg, 0.17 mmol) in dimethylamine (5.00 mL, 33% w/w in water) was added acetic acid (10.0 mg, 0.17 mmol). The resulting mixture was stirred for 2 hours at ambient temperature followed by the addition of sodium cyanoborohydride (42.0 mg, 0.66 mmol) at ambient temperature. After stirring for additional 3 hours, the resulting mixture was concentrated under reduced pressure. The residue was purified by Prep-TLC (10% methanol in dichloromethane) to afford the title compound as a yellow solid (40.0 mg, 62%): $^1$H NMR (400 MHz, CDCl$_3$) δ 8.66 (d, J=3.1 Hz, 1.5H), 8.33 (d, J=7.2 Hz, 0.5H), 7.85 (dd, J=9.5, 8.0 Hz, 1H), 3.45 (s, 2H), 3.37 (d, J=3.8 Hz, 3H), 3.13 (s, 1H), 3.03-2.64 (m, 6H), 2.65-2.46 (m, 4H); MS: [(M+1)]$^+$=392.10, 394.10.

Intermediate O

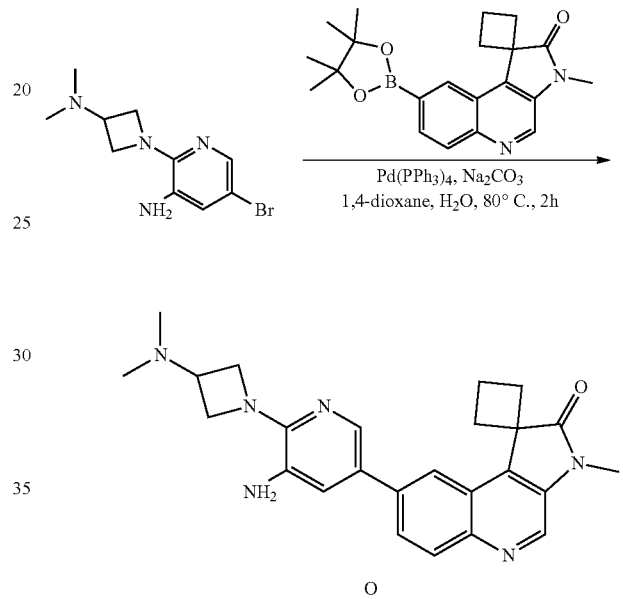

Pd(PPh$_3$)$_4$, Na$_2$CO$_3$
1,4-dioxane, H$_2$O, 80° C., 2h

8'-(5-Amino-6-(3-(dimethylamino)azetidin-1-yl)pyridin-3-yl)-3'-methylspiro[cyclobutane-1,1'-pyrrolo[2,3-c]quinolin]-2'(3'H)-one: To a solution of 3-methyl-8-(4,4,5,5-tetramethyl-1,3,2-dioxaborolan-2-yl)-2,3-dihydrospiro[cyclobutane-1,1-pyrrolo[2,3-c]quinolin]-2-one (262 mg, 0.72 mmol) in 1,4-dioxane (8.00 mL) were added water (2.00 mL), 5-bromo-2-[3-(dimethylamino)azetidin-1-yl]pyridin-3-amine (150 mg, 0.55 mmol), sodium carbonate (70.4 mg, 0.66 mmol) and tetrakis (triphenylphosphine) palladium (0) (Pd(PPh$_3$)$_4$, 96.0 mg, 0.08 mmol). After stirring for 2 hours at 80° C. under nitrogen atmosphere, the resulting mixture was concentrated under reduced pressure. The residue was purified by silica gel column chromatography, eluted with 1%~10% methanol in dichloromethane. The desired fractions were collected and concentrated under reduced pressure to afford the title compound as a yellow solid (143 mg, 61%): $^1$H NMR (400 MHz, CD$_3$OD) δ 8.68 (s, 1H), 8.40 (d, J=2.0 Hz, 1H), 8.10 (d, J=8.9 Hz, 1H), 7.99 (d, J=2.0 Hz, 1H), 7.89 (dd, J=9.1, 1.9 Hz, 1H), 7.73-7.51 (m, 1H), 7.40 (d, J=2.0 Hz, 1H), 4.25 (t, J=7.6 Hz, 2H), 3.96 (t, J=7.1 Hz, 2H), 3.38 (s, 3H), 3.29-3.19 (m, J=6.4 Hz, 1H), 3.04-2.87 (m, 2H), 2.74-2.57 (m, J=26.9, 17.6, 7.9 Hz, 4H), 2.26 (s, 6H); MS: [(M+1)]$^+$=429.35.

The following intermediates were prepared according to the procedure described above:

| Intermediate | Structure | Name | MS: [(M + 1)]+ | 1H NMR |
|---|---|---|---|---|
| O1 | 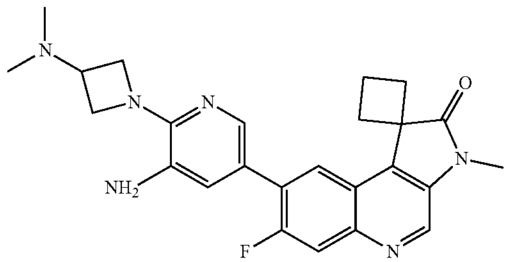 | 8'-(5-Amino-6-(3-(dimethylamino)azetidin-1-yl)pyridin-3-yl)-7'-fluoro-3 methylspiro[cyclobutane-1,1'-pyrrolo[2,3-c]quinolin]-2'(3'H)-one | 447.3 | 1H NMR (400 MHz, CD3OD) δ 8.73 (s, 1H), 8.34 (d, J = 8.1 Hz, 1H), 7.90 (s, 1H), 7.82 (d, J = 11.9 Hz, 1H), 7.34 (s, 1H), 4.26 (t, J = 7.6 Hz, 2H), 3.96 (t, J = 7.6 Hz, 2H), 3.37 (s, 3H), 3.25-3.16 (m, 1H), 3.02-2.89 (m, 2H), 2.76-2.47 (m, 4H), 2.26 (s, 6H). |

Intermediate P

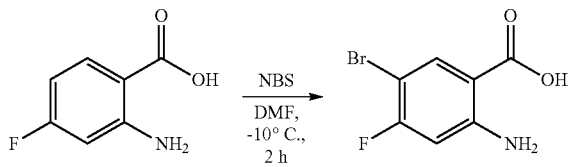

2-Amino-5-bromo-4-fluorobenzoic acid: To a solution of 2-amino-4-fluorobenzoic acid (200 g, 1.29 mol) in N-dimethylformamide (2.00 L) was added a solution of N-bromosuccinimide (230 g, 1.29 mol) in N,N-dimethylformamide (1.00 L) over 1 hour at −10° C. After stirring for additional 1 hour, the mixture was quenched by saturated aqueous sodium hydrogen sulfite (300 mL) and diluted with water (10.0 L). The precipitated solid was collected by filtration and washed with water (3×1.00 L). The filtered cake was dried under infrared light to afford the title compound as a light yellow solid (227 g, 76%): 1H NMR (400 MHz, DMSO-d6) δ 7.86 (d, J=8.2 Hz, 1H), 6.67 (d, J=11.5 Hz, 1H); MS: [(M+1)]+=234.05, 236.05

The following intermediates were prepared according to the procedure described above:

| Intermediate | Structure | Name | MS: [(M + 1)]+ | 1H NMR |
|---|---|---|---|---|
| P-1-1 | 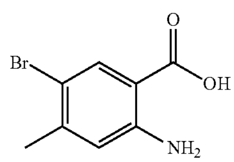 | 2-Amino-5-bromo-4-methylbenzoic acid | 229.95 231.95 | 1H NMR (400 MHz, DMSO-d6) δ 7.80 (s, 1H), 6.50 (d, J = 3.2 Hz, 1H), 6.16 (s, 2H). 2.16 (s, 3H). |
| P-1-2 | 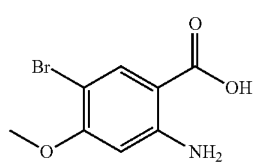 | 2-Amino-5-bromo-4-methoxybenzoic acid | 246.05 248.05 | 1H NMR (300 MHz, DMSO-d6) δ 7.76 (s, 1H), 6.42 (s, 1H), 3.79 (s, 3H). |
| P-1-3 | 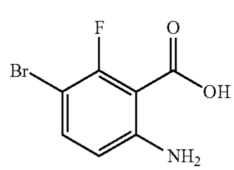 | 6-Amino-3-bromo-2-fluorobenzoic acid | 234.00 236.00 | 1H NMR (400 MHz, DMSO-d6) δ 8.76 (br, 2H), 7.40 (dd, J = 9.0, 7.5 Hz, 1H), 6.57 (dd, J = 9.0, 1.3 Hz, 1H). |

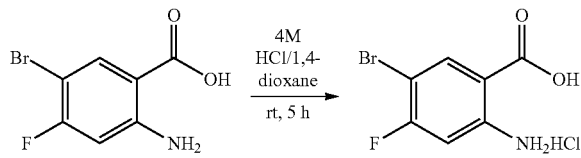

2-Amino-5-bromo-4-fluorobenzoic acid hydrochloride: 2-Amino-5-bromo-4-fluorobenzoic acid (227 g, 970 mmol) was treated with hydrogen chloride (2.50 L, 4 M in 1,4-dioxane) for 5 hours at ambient temperature. The mixture was filtered, the filtered cake was washed with diethyl ether (2×1.00 L) and dried under vacuum to afford the title compound as a colorless solid (250 g, 96%): MS: $[(M+1)]^+$=234.05, 236.05.

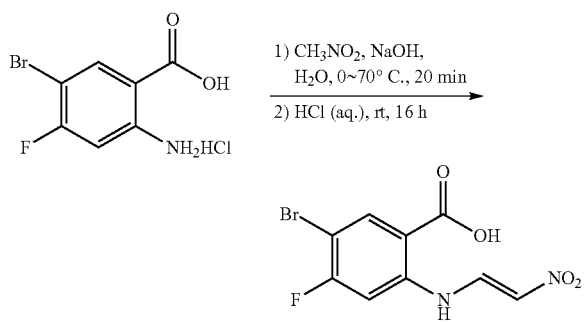

5-Bromo-4-fluoro-2-((2-nitrovinyl) amino) benzoic acid: Part-A: To a stirred solution of sodium hydroxide (141 g, 3.51 mol) in water (500 mL) was added nitromethane (113 mL, 1.85 mol) dropwise so as to maintain an internal temperature at 25-30° C. After the addition was completed, the cooling bath was removed and the temperature was increased to 70° C.-80° C. spontaneously and a red color solution was obtained. The mixture was then cooled down to 25° C. The resulting red solution was carefully poured into a mixture of ice (288 g) and concentrated hydrochloric acid (288 mL) to afford part-A.

Part-B: To a suspension of 2-amino-5-bromo-4-fluorobenzoic acid hydrochloride (190 g, 703 mmol) in concentrated hydrochloric acid (614 mL) and water (3.50 L) was added (Part-A). The resulting mixture was stirred for 16 hours at ambient temperature. The precipitated solid was collected by filtration, washed with water (500 mL) and methanol (500 mL). The resulting solid was dried under infrared light for 16 hours to afford the title compound as a yellow solid (197 g, 92%): $^1$H NMR (400 MHz, DMSO-$d_6$) δ 14.14 (br, 1H), 13.01 (d, J=13.2 Hz, 1H), 8.22 (d, J=7.9 Hz, 1H), 8.02 (dd, J=13.3, 6.5 Hz, 1H), 7.92 (d, J=11.4 Hz, 1H), 6.82 (d, J=6.4 Hz, 1H); MS: $[(M+1)]^+$=305.00, 307.00.

The following intermediates were prepared according to the procedure described above:

| Intermediate | Structure | Name | MS: $[(M + 1)]^+$ | $^1$H NMR |
|---|---|---|---|---|
| P-2-1 | 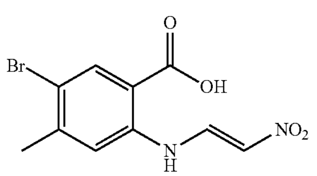 [SMILES: Cc1cc(N/C=C/[N+](=O)[O-])c(C(=O)O)cc1Br] | (E)-5-Bromo-4-methyl-2-((2-nitrovinyl)amino)benzoic acid | 301.00<br>303.00 | $^1$H NMR (400 MHz, DMSO-$d_6$) δ 13.97 (s, 1H), 12.92 (d, J = 13.5 Hz, 1H), 8.12-8.01 (m, 2H), 7.84 (s, 1H), 6.84-6.78 (m, 1H), 2.42 (s, 3H). |
| P-2-2 | 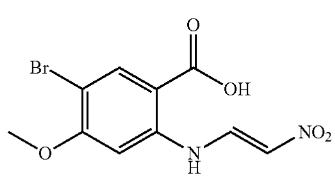 [SMILES: COc1cc(N/C=C/[N+](=O)[O-])c(C(=O)O)cc1Br] | (E)-5-Bromo-4-methoxy-2-((2-nitrovinyl)amino)benzoic acid | 317.00<br>319.00 | $^1$H NMR. (300 MHz, CD$_3$OD) δ 8.21 (s, 1H), 7.89 (d, J = 6.5 Hz, 1H), 7.16 (s, 1H), 6.72 (d, J = 6.4 Hz, 1H), 4.01 (s, 3H) |
| P-2-3 | 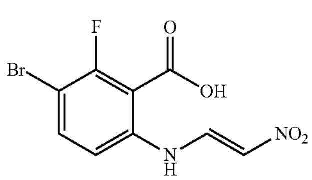 [SMILES: O=C(O)c1c(N/C=C/[N+](=O)[O-])ccc(Br)c1F] | (E)-3-Bromo-2-fluoro-6-((2-nitrovinyl)amino)benzoic acid | 305.00<br>307.00 | $^1$H NMR (400 MHz, DMSO-$d_6$) δ 12.34 (d, J = 13.2 Hz, 1H), 8.06-7.90 (m, 2H), 7.53 (d, J = 9.1 Hz, 1H), 7.43-7.35 (m, 1H), 6.80 (d, J = 6.2 Hz, 1H). |

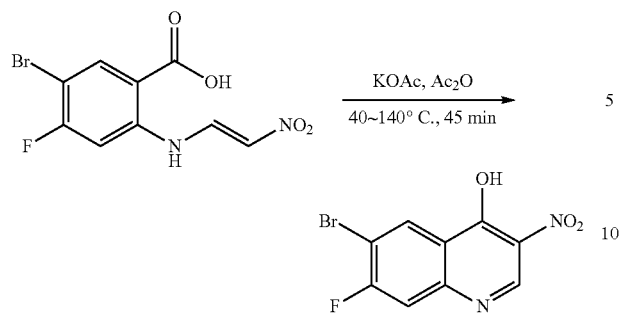

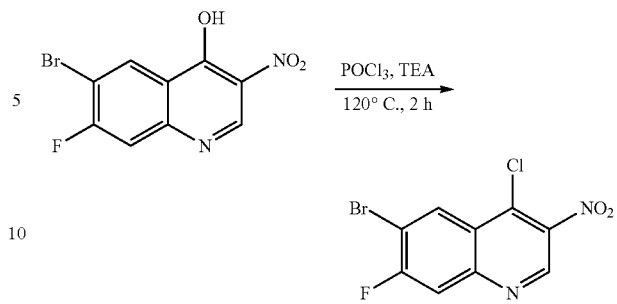

6-Bromo-7-fluoro-3-nitroquinolin-4-ol: A mixture of 5-bromo-4-fluoro-2-[[(E)-2-nitroethenyl]amino]benzoic acid (139 g, 456 mmol) in acetic anhydride (700 mL) was slowly heated to 70° C. until dissolution was accomplished. The resulting mixture was cooled down to 40° C. followed by the addition of potassium acetate (53.7 g, 547 mmol). The resulting mixture was slowly heated to 140° C. in 30 min After stirring for additional 45 min at 140° C., the reaction mixture was cooled down to ambient temperature. The resulting mixture was concentrated under reduced pressure and the residue was triturated with acetic acid (100 mL). The precipitated solid was collected by filtration and washed with acetic acid (125 mL), water (100 mL) and methanol (150 mL). The solid was dried under infrared light for 16 hours to afford the title compound as a brown solid (68 g, 53%): $^1$H NMR (400 MHz, DMSO-$d_6$) δ 13.12 (s, 1H), 9.25 (s, 1H), 8.45 (d, J=7.5 Hz, 1H), 7.64 (d, J=9.3 Hz, 1H); MS: [(M+1)]$^+$=287.00, 289.00.

The following intermediates were prepared according to the procedure described above:

6-Bromo-4-chloro-7-fluoro-3-nitroquinoline: To a mixture of 6-bromo-7-fluoro-3-nitroquinolin-4-ol (68.0 g, 237 mmol) in phosphoroyl trichloride (600 mL) was added triethylamine (30.5 mL, 390 mmol) dropwised at ambient temperature. The resulting mixture was stirred for 2 hours at 120° C. After cooling down to ambient temperature, the resulting mixture was concentrated under reduced pressure. The residue was taken up between dichloromethane (300 mL) and ice/water (300 g). The aqueous layer was extracted with dichloromethane (5×200 mL). The combined organic layers was washed with brine (100 mL) and dried over anhydrous sodium sulfate. After filtration, the filtrate was concentrated under reduced pressure. The residue was purified by silica gel column chromatography, eluted with 5%~20% ethyl acetate in petroleum ether. The desired fractions were collected and concentrated under reduced pressure to afford the title compound as a light yellow solid (65 g, 91%): $^1$H NMR (400 MHz, DMSO-$d_6$) δ 9.45 (s, 1H), 8.77 (d, J=7.3 Hz, 1H), 8.25 (d, J=9.4 Hz, 1H); MS: [(M+1)]$^+$=305.00, 307.00.

| Intermediate | Structure | Name | MS: [(M + 1)]$^+$ | $^1$H NMR |
|---|---|---|---|---|
| P-3-1 | 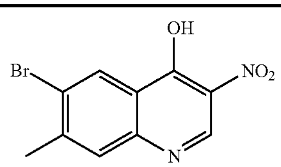 | 6-Bromo-7-methyl-3-nitroquinolin-4-ol | 282.95<br>284.95 | $^1$H NMR (400 MHz, DMSO-$d_6$) δ 13.05 (s, 1H), 9.18 (d, J = 1.8 Hz, 1H), 8.33 (s, 1H), 7.66 (s, 1H), 2.49 (s, 3H). |
| P-3-2 | 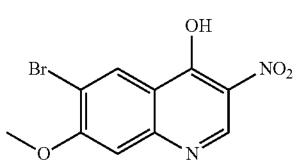 [SMILES: COc1cc2ncc([N+](=O)[O-])c(O)c2cc1Br] | 6-Bromo-7-methoxy-3-nitroquinolin-4-ol | 298.95<br>300.95 | $^1$H NMR (300 MHz, DMSO-$d_6$) δ 12.00 (br, 1H), 9.18 (s, 1H), 8.33 (s, 1H), 7.25 (s, 1H), 3.98 (s, 3H). |
| P-3-3 | 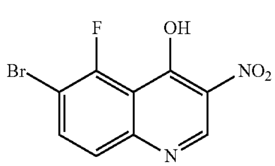 [SMILES: O=[N+]([O-])c1cnc2ccc(Br)c(F)c2c1O] | 6-Bromo-5-fluoro-3-nitroquinolin-4-ol | 287.00<br>289.00 | $^1$H NMR (400 MHz, DMSO-$d_6$) δ 12.66 (br, 1H), 9.16 (d, J = 1.7 Hz, 1H), 8.02 (dd, J = 9.1, 6.5 Hz, 1H), 7.47 (d, J = 8.9 Hz, 1H). |

The following intermediates were prepared according to the procedure described above:

| Intermediate | Structure | Name | MS: [(M + 1)]+ | 1H NMR |
|---|---|---|---|---|
| P-4-1 | 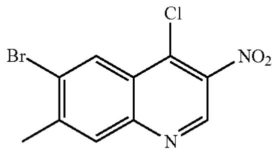 | 6-Bromo-4-chloro-7-methyl-3-nitroquinoline | 301.00<br>303.00 | 1H NMR (400 MHz, CDCl3) δ 9.24 (s, 1H), 8.62 (s, 1H), 8.07 (s, 1H), 2.68 (s, 3H). |
| P-4-2 | 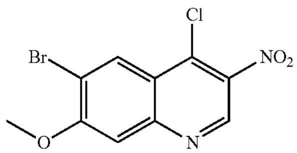 [SMILES: COc1cc2ncc([N+](=O)[O-])c(Cl)c2cc1Br] | 6-Bromo-4-chloro-7-methoxy-3-nitroquinoline | 316.95<br>318.95 | 1H NMR (300 MHz, CDCl3) δ 9.27 (s, 1H), 8.65 (s, 1H), 7.55 (s, 1H), 4.12 (s, 3H). |
| P-4-3 | 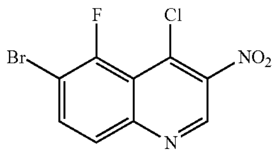 [SMILES: O=[N+]([O-])c1cnc2ccc(Br)c(F)c2c1Cl] | 6-Bromo-4-chloro-5-fluoro-3-nitroquinoline | 305.00<br>307.00 | 1H NMR (400 MHz, CDCl3) δ 9.09 (s, 1H), 8.03 (dd, J = 9.1, 6.5 Hz, 1H), 7.94 (dd, J = 9.1, 1.5 Hz, 1H). |

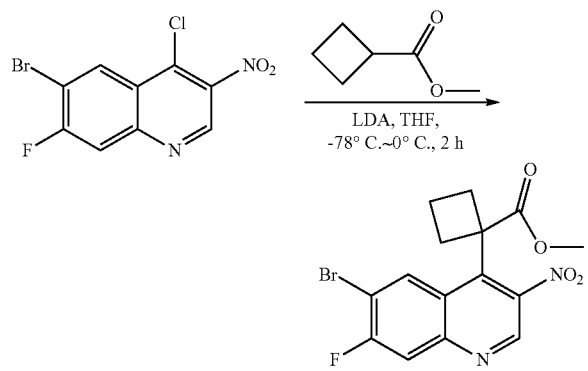

Methyl 1-(6-bromo-7-fluoro-3-nitroquinolin-4-yl)cyclobutane-1-carboxylate: A solution of methyl cyclobutanecarboxylate (0.73 g, 6.38 mmol) in tetrahydrofuran (5.00 mL) was treated with freshly prepared lithium diisopropylamide (6.38 mmol) in tetrahydrofuran (45.0 mL) for 1 hour at −78° C. under nitrogen atmosphere followed by the addition of 6-bromo-4-chloro-7-fluoro-3-nitroquinoline (1.50 g, 4.91 mmol) in portions over 2 min After stirring for additional 1 hour at ambient temperature, the reaction was quenched by saturated aqueous ammonium chloride (60.0 mL) and diluted with water (120 mL). The resulting mixture was extracted with ethyl acetate (3×60.0 mL). The combined organic layers was washed with brine (2×50.0 mL) and dried over anhydrous sodium sulfate. After filtration, the filtrate was concentrated under reduced pressure. The residue was purified by silica gel column chromatography, eluted with 1%~2% ethyl acetate in petroleum ether to afford the title compound as a colorless solid (240 mg, 13%): 1H NMR (400 MHz, CDCl3) δ 9.14 (s, 1H), 8.20 (d, J=7.2 Hz, 1H), 7.90 (d, J=8.8 Hz, 1H), 3.84 (s, 3H), 3.12-2.99 (m, 1H), 2.58-2.48 (m, 3H), 1.91-1.83 (m, 1H), 1.45-1.27 (m, 1H); MS: [(M+1)]+=383.17, 385.17.

The following intermediates were prepared according to the procedure described above:

| Intermediate | Structure | Name | MS: [(M + 1)]+ | 1H NMR |
|---|---|---|---|---|
| P-5-1 | 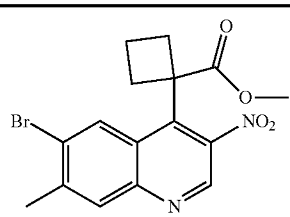 | Methyl 1-(6-bromo-7-methyl-3-nitroquinolin-4-yl)cyclobutane-1-carboxylate | 379.21<br>381.21 | 1H NMR (400 MHz, CD3Cl) δ 9.11 (s, 1H), 8.14-8.06 (m, 2H), 3.83 (s, 3H), 3.08-2.99 (m, 2H), 2.66 (s, 3H), 2.53-2.45 (m, 3H), 1.88-1.81 (m, 1H). |
| P-5-2 | 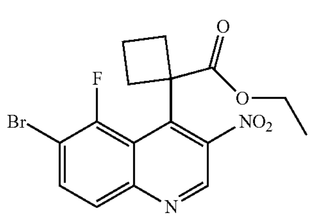 [SMILES: CCOC(=O)C1(c2c([N+](=O)[O-])cnc3ccc(Br)c(F)c23)CCC1] | Ethyl 1-(6-bromo-5-fluoro-3-nitroquinolin-4-yl)cyclobutane-1-carboxylate | 397.20<br>399.20 | 1H NMR (400 MHz, CDCl3) δ 9.15 (s, 1H), 8.01-7.89 (m, 2H), 4.35-4.21 (m, 2H), 3.08-2.99 (m, 2H), 2.53-2.45 (m, 3H), 1.88-1.81 (m, 1H), 1.26 (t, J = 7.6 Hz, 3H). |

-continued

| Intermediate | Structure | Name | MS: [(M + 1)]⁺ | ¹H NMR |
|---|---|---|---|---|
| P-5-3 | (structure) | Methyl 1-(6-bromo-3-nitroquinolin-4-yl)cyclopentane-1-carboxylate | 379.10 381.10 | ¹H NMR (300 MHz, DMSO-$d_6$) δ 9.13 (s, 1H), 8.27 (d, J = 1.8 Hz, 1H), 8.11-8.07 (m, 2H), 3.63 (s, 3H), 2.72-2.65 (m, 2H), 2.11-1.95 (m, 2H), 1.84-1.63 (m, 4H). |
| P-5-4 | (structure) | Methyl 1-(6-bromo-3-nitroquinolin-4-yl)cyclohexane-1-carboxylate | 393.10 395.10 | ¹H NMR (400 MHz, CDCl$_3$) δ 8.71 (s, 1H), 8.54 (d, J = 2.0 Hz, 1H), 8.04 (d, J = 8.9 Hz, 1H), 7.86 (dd, J = 8.9, 2.0 Hz, 1H), 3.61 (s, 3H), 2.57-2.53 (m, 2H), 2.03 (td, J = 12.8, 4.0 Hz, 2H), 1.95-1.64 (m, 4H), 1.37-1.23 (m, 2H). |
| P-5-5 | (structure) | Methyl 4-(6-bromo-3-nitroquinolin-4-yl)tetrahydro-2H-pyran-4-carboxylate | 395.10 397.10 | ¹H NMR (300 MHz, CDCl$_3$) δ 8.76 (s, 1H), 8.53 (d, J = 1.9 Hz, 1H), 8.06 (d, J = 8.9 Hz, 1H), 7.89 (d, J = 1.9 Hz, 1H), 4.03-3.86 (m, 4H), 3.69 (s, 3H), 2.49 (d, J = 13.4 Hz, 2H), 2.43-2.31 (m, 2H). |
| P-5-6 | (structure) | Ethyl 1-(6-bromo-3-nitroquinolin-4-yl)-3-((tetrahydro-2H-pyran-2-yl)oxy)cyclobutane-1-carboxylate | 479.10 481.10 | ¹H NMR (400 MHz, CDCl$_3$) δ 9.12 (s, 1H), 8.07 (d, J = 8.9 Hz, 1H), 8.02 (d, J = 2.0 Hz, 1H), 7.90 (dd, J = 9.0, 2.1 Hz, 1H), 4.66-4.56 (m, 2H), 4.26 (t, J = 7.1 Hz, 2H), 3.79 (t, J = 9.5 Hz, 1H), 3.53-3.36 (m 3H), 1.77-1.42 (m, 8H), 1.22 (t, J = 7.1 Hz, 3H). |
| P-5-7 | (structure) | Methyl 3-(6-bromo-3-nitroquinolin-4-yl)oxetane-3-carboxylate | 367.10 369.10 | ¹H NMR (300 MHz, CDCl$_3$) δ 9.35 (s, 1H), 8.13 (d, J = 9.0 Hz, 1H), 7.96 (dd, J = 9.0, 2.0 Hz, 1H), 7.41 (d, J = 2.1 Hz, 1H), 5.32 (d, J = 6.4 Hz, 2H), 4.88 (d, J = 6.3 Hz, 2H), 3.91 (s, 3H). |

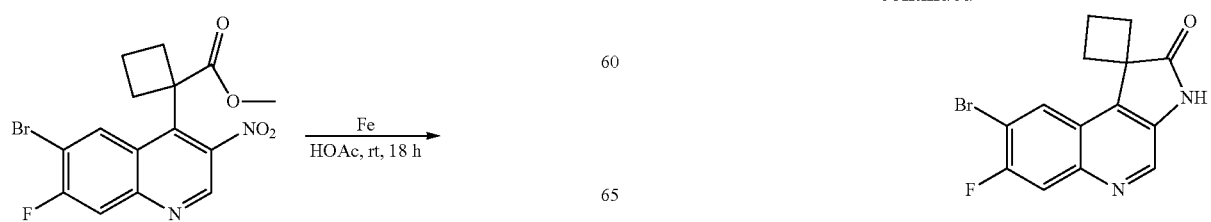

8'-Bromo-7'-fluorospiro[cyclobutane-1,1'-pyrrolo[2,3-c]quinolin]-2'(3'H)-one: A mixture of methyl 1-(6-bromo-7-fluor-3-nitroquinolin-4-yl)cyclobutane-1-carboxylate (240 mg, 0.63 mmol) and iron powder (350 mg, 6.26 mmol) in acetic acid (10.0 mL) was stirred for 18 hours at ambient temperature. The resulting mixture was filtered and the filtered cake was washed with ethyl acetate (5×100 mL). The filtrate was concentrated under reduced pressure. The residue was purified by silica gel column chromatography, eluted with 1%~2% methanol in dichloromethane to afford the title compound as a light yellow solid (100 mg, 50%): $^1$H NMR (400 MHz, DMSO-$d_6$) δ 10.75 (s, 1H), 8.68 (s, 1H), 8.52 (d, J=7.5 Hz, 1H), 7.98 (d, J=10.1 Hz, 1H), 2.90-2.75 (m, 2H), 2.50-2.37 (m, 4H); MS: [(M+1)]$^+$=321.15, 323.15.

The following intermediates were prepared according to the procedure described above:

| Intermediate | Structure | Name | MS: [(M + 1)]$^+$ | $^1$H NMR |
|---|---|---|---|---|
| P-6-1 | 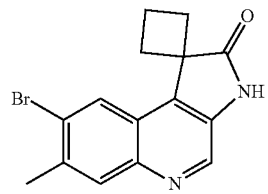 | 8'-Bromo-7'-methylspiro[cyclobutane-1,1'-pyrrolo[2,3-c]quinolin]-2' (3'H)-one | 317.19 319.19 | $^1$H NMR (400 MHz, DMSO-$d_6$) δ 11.95 (s, 1H), 10.68 (s, 1H), 8.61 (s, 1H), 8.41 (s, 1H), 8.02 (s, 1H), 2.98-2.65 (m, 4H), 2.40-2.20 (m, 2H), 1.91 (s, 3H). |
| P-6-2 | 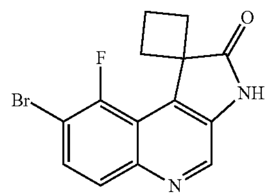 | 8'-Bromo-9'-fluorospiro[cyclobutane-1,1'-pyrrolo[2,3-c]quinolin]-2'(3'H)-one | 321.15 323.15 | $^1$H NMR (400 MHz, CDCl$_3$) δ 8.81 (s, 1H), 8.47 (br, 1 H), 7.89 (d, J = 9.1 Hz, 1H), 7.78-7.68 (m, 1H), 3.03-2.96 (m, 2H), 2.70-2.56 (m, 4H). |
| P-6-3 | 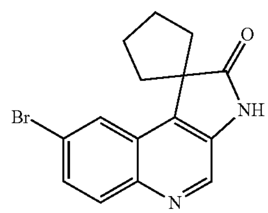 | 8'-Bromospiro[cyclopentane-1,1'-pyrrolo[2,3-c]quinolin]-2'(3'H)-one | 317.00 319.00 | $^1$H NMR (300 MHz, DMSO-$d_6$) δ 10.76 (s, 1H), 8.67 (s, 1H), 7.98 (d, J = 9.0 Hz, 1H), 7.90 (d, J = 2.1 Hz, 1H), 7.73 (dd, J = 9.0, 2.2 Hz, 1H), 2.18-2.09 (m, 8H). |
| P-6-4 | 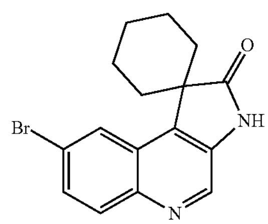 | 8'-Bromospiro[cyclohexane-1,1'-pyrrolo[2,3-c]quinolin]-2'(3'H)-one | 331.10 333.10 | $^1$H NMR (400 MHz, DMSO-$d_6$) δ 10.78 (s, 1H), 8.68 (s, 1H), 8.21 (d, J = 2.2 Hz, 1H), 7.96 (d, J = 9.0 Hz, 1H), 7.72 (dd, J = 9.0, 2.1 Hz, 1H), 2.29-2.11 (m, 4H), 1.82 (d, J = 12.1 Hz, 1H), 1.80-1.57 (m, 5H). |
| P-6-5 | 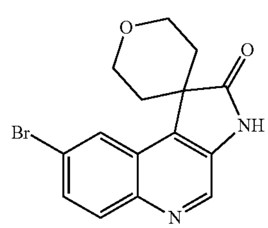 | 8'-Bromo-2,3,5,6-tetrahydrospiro[pyran-4,1'-pyrrolo[2,3-c]quinolin]-2'(3'H)-one | 333.00 335.00 | $^1$H NMR (300 MHz, DMSO-$d_6$) δ 10.88 (s, 1H), 8.67 (s, 1H), 8.10 (d, J = 2.1 Hz, 1H), 7.96 (d, J = 9.0 Hz, 1H), 7.71 (dd, J = 9.0, 2.1 Hz, 1H), 4.20 (t, J = 11.7 Hz, 2H), 3.83 (dd, J = 11.4, 4.9 Hz, 2H), 2.45-2.38 (m, 2H), 1.65 (d, J = 14.0 Hz, 2H). |
| P-6-6 | 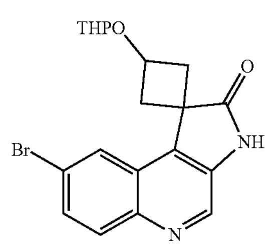 | 8'-Bromo-3-((tetrahydro-2H-pyran-2-yl)oxy)spiro[cyclobutane-1,1'-pyrrolo[2,3-c]quinolin]-2'(3'H)-one | 403.10 405.10 | $^1$H NMR (400 MHz, DMSO-$d_6$) δ 10.84 (s, 1H), 8.65 (d, J = 10.9 Hz, 2H), 7.99 (d, J = 8.9 Hz, 1H), 7.76 (d, J = 9.3 Hz, 1H), 4.80 (s, 1H), 4.66 (s, 1H), 3.87 (s, 1H), 3.32 (s, 1H), 2.83 (d, J = 16.0 Hz, 4H), 1.91 (s, 1H), 1.76 (s, 1H), 1.70 (s, 1H), 1.54 (s, 3H). |

| Intermediate | Structure | Name | MS: [(M + 1)]+ | 1H NMR |
|---|---|---|---|---|
| P-6-7 | 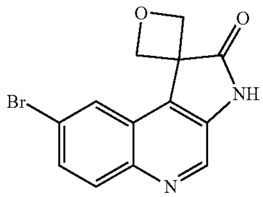 [SMILES: O=C1Nc2cnc3ccc(Br)cc3c2C12COC2] | 8'-Bromospiro[oxetane-3,1'-pyrrolo[2,3-c]quinolin]-2'(3'H)-one | 305.00<br>307.00 | 1H NMR (400 MHz, CDCl3) δ 8.74 (d, J = 1.4 Hz, 2H), 8.04 (d, J = 9.0 Hz, 1H), 7.89 (s, 1H), 7.77 (dd, J = 9.0, 2.1 Hz, 1H), 5.33-5.26 (m, 2H), 5.04 (d, J = 6.2 Hz, 2H). |

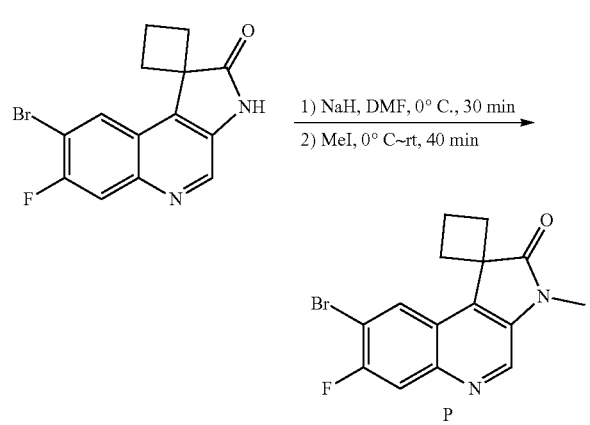

8'-Bromo-7'-fluoro-3'-methylspiro[cyclobutane-1,1'-pyrrolo-[2,3-c]quinolin]-2'(3'H)-one: A solution of 8-bromo-7-fluoro-2,3-dihydrospiro[cyclobutane-1,1-pyrrolo[2,3-c]quinoline]-2-one (100 mg, 0.31 mmol) in N,N-dimethylfomamide (10.0 mL) was treated with sodium hydride (19.9 mg, 0.50 mmol, 60% dispersed in mineral oil) at 0° C. for 30 min under nitrogen atmosphere followed by the addition of iodomethane (66.3 mg, 0.47 mmol). After stirring for additional 40 min at ambient temperature, the reaction was quenched by saturated aqueous ammonium chloride (10.0 mL). The resulting mixture was diluted with water (100 mL) and extracted with ethyl acetate (3×30.0 mL). The combined organic layers was washed with brine (2×20.0 mL) and dried over anhydrous sodium sulfate. After filtration, the filtrate was concentrated under reduced pressure. The residue was purified by Prep-TLC (DCM/MeOH=20/1, v/v) to afford the title compound as a colorless solid (102 mg, 98%): 1H NMR (400 MHz, CD3OD) δ 8.78 (s, 1H), 8.61 (d, J=7.4 Hz, 1H), 7.85 (d, J=9.8 Hz, 1H), 3.36 (s, 3H), 2.94-2.85 (m, 2H), 2.72-2.61 (m, 3H), 2.56-2.48 (m, 1H); MS: [(M+1)]+=335.00, 337.00.

The following intermediates were prepared according to the procedure described above:

| Intermediate | Structure | Name | MS: [(M + 1)]+ | 1H NMR |
|---|---|---|---|---|
| P1 | | 8'-Bromo-3',7'-dimethylspiro[cyclobutane-1,1'-pyrrolo[2,3-c]quinolin]-2'(3'H)-one | 331.21<br>333.21 | 1H NMR (400 MHz, CDCl3) δ 8.64 (s, 1H), 8.48 (s, 1H), 8.07 (s, 1H), 3.38 (s, 3H), 2.94-2.81 (m, 2H), 2.80-2.62 (m, 3H), 2.61 (s, 3H), 2.56-2.48 (m, 1H). |
| P2 | 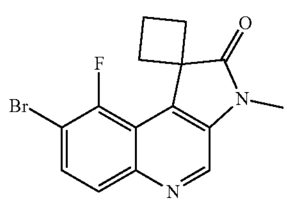 [SMILES: CN1C(=O)C2(CCC2)c2c1cnc1ccc(Br)c(F)c21] | 8'-Bromo-9'-fluoro-3'-methyispiro[cyclobutane-1,1'-pyrrolo[2,3-c]quinolin]-2'(3'H)-one | 335.18<br>337.18 | 1H NMR (400 MHz, CDCl3) δ 8.68 (s, 1H), 7.90-7.85 (m, 1 H), 7.71 (dd, J = 9.1, 7.2 Hz, 1H), 3.39 (s, 3H), 3.03-2.92 (m, 2H), 2.66 (q, J = 10.5, 9.8 Hz, 1H), 2.55 (td, J = 10.7, 9.8, 6.1 Hz, 2H), 2.38 (dt, J = 10.8, 5.8 Hz. 1H). |
| P3 | 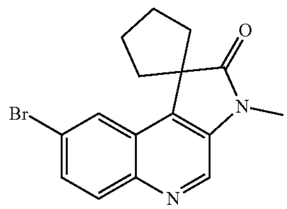 [SMILES: CN1C(=O)C2(CCCC2)c2c1cnc1ccc(Br)cc21] | 8'-Bromo-3'-methylspiro[cyclopentane-1,1'-pyrrolo[2,3-c]quinolin]-2'(3'H)-one | 331.0<br>333.0 | 1H NMR (400 MHz, CDCl3) δ 8.67 (s, 1H), 8.03 (d, J = 9.0 Hz, 1H), 7.95 (d, J = 2.1 Hz, 1H), 7.67 (dd, J = 9.1, 2.1 Hz, 1H), 3.47 (s, 3H), 2.31-2.16 (m, 8H). |

-continued

| Intermediate | Structure | Name | MS: [(M + 1)]⁺ | ¹H NMR |
|---|---|---|---|---|
| P4 | 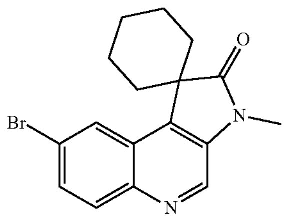 [SMILES: CN1C(=O)C2(CCCCC2)c2c1cnc1ccc(Br)cc21] | 8'-Bromo-3'-methylspiro[cyclohexane-1,1'-pyrrolo[2,3-c]quinolin]-2'(3'H)-one | 345.1<br>347.1 | ¹H NMR (400 MHz, CDCl₃) δ 8.69 (s, 1H), 8.19 (d, J = 2.1 Hz, 1H), 8.08 (d, J = 9.0 Hz, 1H), 7.69 (dd, J = 9.1, 2.1 Hz, 1H), 3.36 (s, 3H), 2.38-2.22 (m, 4H), 2.02 (d, J = 13.3 Hz, 1H), 1.82-1.70 (m, 5H). |
| P5 | 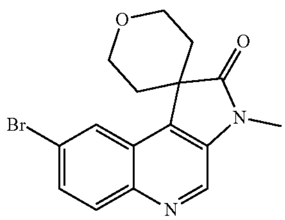 [SMILES: CN1C(=O)C2(CCOCC2)c2c1cnc1ccc(Br)cc21] | 8'-Bromo-3'-methyl-2,3,5,6-tetrahydrospiro[pyran-4,1'-pyrrolo[2,3-c]quinolin]-2'(3'H)-one | 347.05<br>349.05 | ¹H NMR (300 MHz, DMSO-d₆) δ 8.96 (s, 1H), 8.17 (d, J = 2.1 Hz, 1H), 8.03 (d, J = 9.0 Hz, 1H), 7.77 (dd, J = 9.0, 2.1 Hz, 1H), 4.25 (t, J = 11.5 Hz, 2H), 3.87 (dd, J = 11.5, 5.0 Hz, 2H), 3.32 (s, 3H), 2.57-2.43 (m, 2H), 1.66 (d, J = 14.0 Hz, 2H). |
| P6 | 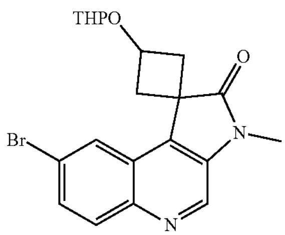 | 8'-Bromo-3'-methyl-3-((tetrahydro-2H-pyran-2-yl)oxy)spiro[cyclobutane-1,1'-pyrrolo[2,3-c]quinolin]-2'(3'H)-one | 417.1<br>419.1 | ¹H NMR (400 MHz, DMSO-d₆) δ 8.89 (s, 1H), 8.69 (d, J = 2.1 Hz, 1H), 8.03 (d, J = 9.0 Hz, 1H), 7.78 (dd, J = 9.2, 2.0 Hz, 1H), 4.81 (t, J = 3.8 Hz, 1H), 4.69 (p, J = 7.0 Hz, 1H), 3.91-3.83 (m, 1H), 3.56-3.48 (m, 1H), 3.31 (s, 3H), 2.90-2.79 (m, 4H), 1.91 (s, 1H), 1.82-1.65 (m, 2H), 1.63-1.49 (m, 3H). |
| P7 | 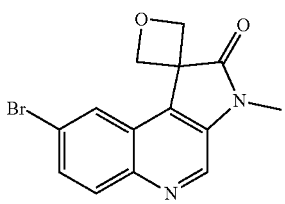 [SMILES: CN1C(=O)C2(COC2)c2c1cnc1ccc(Br)cc21] | 8'-Bromo-3'-methylspiro[oxetane-3,1'-pyrrolo[2,3-c]quinolin]-2'(3'H)-one | 318.9<br>320.9 | ¹H NMR (300 MHz, CDCl₃) δ 9.35 (s, 1H), 8.13 (d, J = 9.0 Hz, 1H), 7.96 (dd, J = 9.0, 2.0 Hz, 1H), 7.41 (d, J = 2.1 Hz, 1H), 5.32 (d, J = 6.4 Hz, 2H), 4.88 (d, J = 6.3 Hz, 2H), 3.91 (s. 3H). |
| P8 | 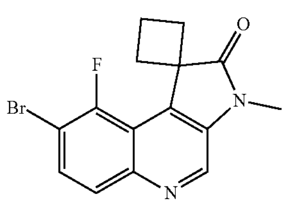 [SMILES: CN1C(=O)C2(CCC2)c2c1cnc1ccc(Br)c(F)c21] | 8'-Bromo-9'-fluoro-3 methylspiro[cyclobutane-1,1'-pyrrolo[2,3-c]quinolin]-2'(3'H)-one | 335.0<br>337.0 | ¹H NMR (400 MHz, CDCl₃) δ 8.68 (s, 1H), 7.87 (d, J = 9.2 Hz, 1H), 7.71 (dd, J = 9.2, 7.2 Hz, 1H), 3.39 (s, 3H), 3.02-2.91 (m, 2H), 2.72-2.51 (m, 3H), 2.43-2.32 (m, 1H). |

Intermediate Q

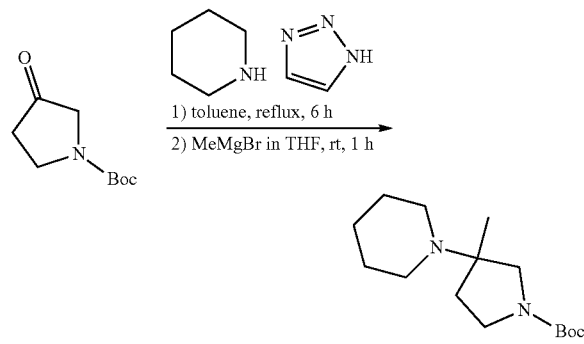

tert-Butyl 3-methyl-3-(piperidin-1-yl)pyrrolidine-1-carboxylate: To a solution of tert-butyl 3-oxopyrrolidine-1-carboxylate (5.00 g, 27.0 mmol) in toluene (50.0 mL) were added piperidine (2.50 g, 29.7 mmol) and 1H-1,2,3-triazole (2.20 g, 32.4 mmol) at ambient temperature under nitrogen atmosphere. The resulting mixture was reflux for 6 hours while collecting water via a Dean-Stark trap. The resulting mixture was cooled to ambient temperature followed by the addition of methylmagnesium bromide (108 mL, 108 mmol, 1 M in tetrahydrofuran) over 30 minutes at 0° C. The reaction mixture was stirred for additional 1 hour at ambient temperature. The reaction was quenched by saturated aqueous ammonium chloride (30.0 mL) and diluted with water (200 mL). The resulting mixture was extracted with ethyl acetate (3×100 mL). The combined organic layers was washed with brine (2×100 mL), dried over anhydrous sodium sulfate and filtered. The filtrate was concentrated under reduced pressure. The residue was purified by silica gel column chromatography, eluted with 1%~5% methanol in dichloromethane. The desired fractions were collected and concentrated under reduced pressure to afford the title compound as a light yellow oil (2.30 g, 32%): $^1$H NMR (400 MHz, CD$_3$OD) δ 3.55-3.45 (m, 1H), 3.35 (d, J=10.0 Hz, 4H), 3.15 (t, J=9.6 Hz, 1H), 2.59 (q, J=5.8, 5.3 Hz, 2H), 2.45 (t, J=7.0 Hz, 2H), 1.92-1.82 (m, 2H), 1.61 (p, J=5.6 Hz, 4H), 1.45 (s, 12H); MS: [(M+1)]$^+$=269.40.

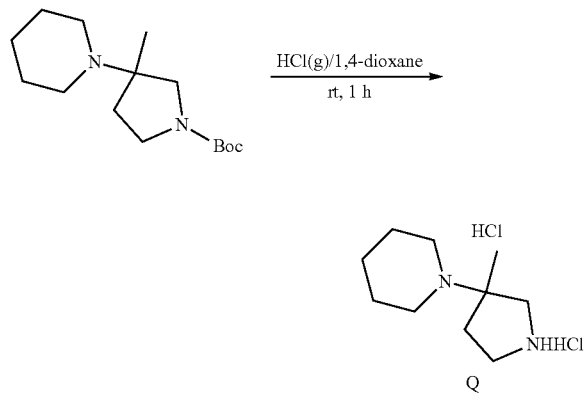

1-(3-Methylpyrrolidin-3-yl)piperidine dihydrochloride: tert-Butyl 3-methyl-3-(piperidin-1-yl)pyrrolidine-1-carboxylate (2.44 g, 9.09 mmol) was treated with hydrogen chloride (50.0 mL, 4M in 1,4-dioxane) for 1 hour at ambient temperature under nitrogen atmosphere. The resulting mixture was concentrated under reduced pressure to afford the title compound as a red solid (2.12 g, 97%): $^1$H NMR (400 MHz, CD$_3$OD) δ 3.87 (d, J=12.5 Hz, 1H), 3.76-3.67 (m, 1H), 3.57-3.44 (m, 3H), 3.37 (d, J=12.3 Hz, 1H), 3.28-3.16 (m, 2H), 2.65 (q, J=10.6 Hz, 1H), 2.38-2.29 (m, 1H), 2.17-1.92 (m, 4H), 1.87 (d, J=14.0 Hz, 1H), 1.62-1.48 (m, 4H); MS: [(M+1)]$^+$=169.20.

Intermediate R

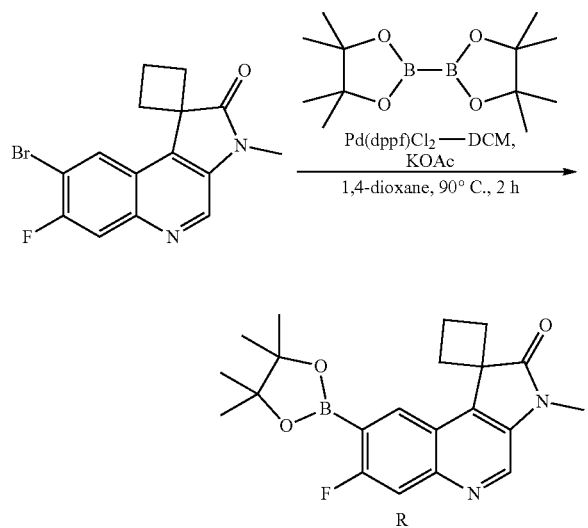

7'-Fluoro-3'-methyl-8'-(4,4,5,5-tetramethyl-1,3,2-dioxaborolan-2-yl)spiro[cyclobutane-1,1'-pyrrolo[2,3-c]quinolin]-2'(3'H)-one: To a solution of 8-bromo-7-fluoro-3-methyl-2,3-dihydrospiro[cyclobutane-1,1-pyrrolo[2,3-c]quinolin]-2-one (500 mg, 1.49 mmol) and bis(pinacolato)diboron (758 mg, 2.98 mmol) in 1,4-dioxane (20.0 mL) were added potassium acetate (586 mg, 5.97 mmol) and 1,1'-bis(diphenylphosphino)ferrocene-palladium (II) dichloride dichloromethane complex (Pd(dppf)Cl$_2$—CH$_2$Cl$_2$, 183 mg, 0.22 mmol) at ambient temperature. The resulting mixture was stirred for 2 hours at 90° C. under nitrogen atmosphere. The resulting mixture was concentrated under reduced pressure. The residue was purified by silica gel column chromatography, eluted with 1%~2% methanol in dichloromethane. The desired fractions were collected and concentrated under reduced pressure to afford the title compound as a brown solid (510 mg, 90%): $^1$H NMR (400 MHz, CDCl$_3$) δ 8.76 (d, J=6.2 Hz, 1H), 8.66 (s, 1H), 7.77 (d, J=10.5 Hz, 1H), 3.36 (s, 3H), 2.94-2.74 (m, 4H), 2.74-2.55 (m, 2H), 1.27 (s, 12H); MS: [(M+1)]$^+$=383.20.

Intermediate S

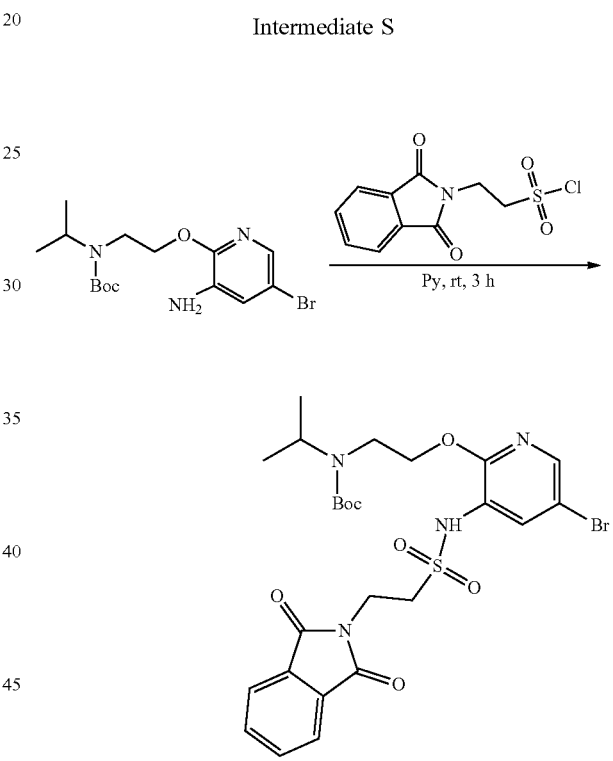

tert-Butyl (2-((5-bromo-3-((2-(1,3-dioxoisoindolin-2-yl)ethyl)sulfonamido)pyridin-2-yl)oxy)ethyl)(isopropyl)carbamate: To a stirred solution of tert-butyl (2-((3-amino-5-bromopyridin-2-yl)oxy)ethyl)(isopropyl)carbamate (1.00 g, 2.67 mmol) in pyridine (40.0 mL) was added 2-(1,3-dioxo-2,3-dihydro-1H-isoindol-2-yl)ethane-1-sulfonyl chloride (1.10 g, 4.01 mmol) in portions at ambient temperature. The resulting mixture was stirred for 3 hours at ambient temperature. The resulting mixture was concentrated under reduced pressure. The resulting mixture was diluted with saturated aqueous sodium bicarbonate (30.0 mL). The resulting mixture was extracted with ethyl acetate (3×50.0 mL). The combined organic layers was washed with brine (3×30.0 mL) and dried over anhydrous sodium sulfate. After filtration, the filtrate was concentrated under reduced pressure to give the crude product as an off-white solid (1.30 g, crude): MS: [(M+1)]$^+$=611.20, 613.20.

247

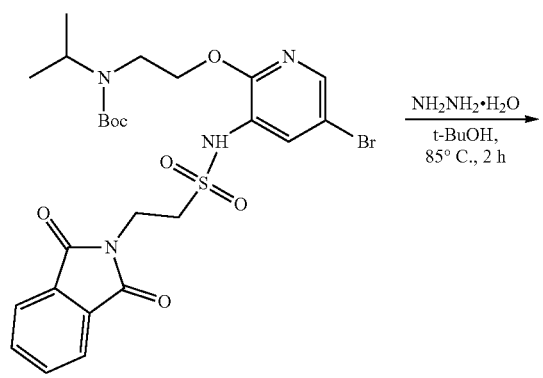 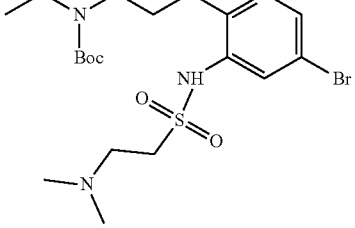

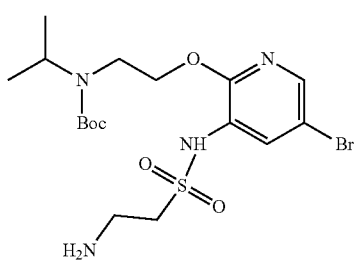

tert-Butyl (2-((3-((2-aminoethyl)sulfonamido)-5-bromopyridin-2-yl)oxy)ethyl)(isopropyl)carbamate: To a stirred solution of tert-butyl (2-((3-((2-(1,3-dioxoisoindolin-2-yl)ethyl)sulfonamido)-5-(3'-methyl-2'-oxo-2',3'-dihydrospiro[cyclobutane-1,1'-pyrrolo[2,3-c]quinolin]-8'-yl)pyridin-2-yl)oxy)ethyl)(isopropyl)carbamate (1.30 g, 2.13 mmol) in tert-butanol (50.0 mL) was added hydrazine hydrate (665 mg, 10.6 mmol, 80% w/w in water) dropwise at ambient temperature. The resulting mixture was stirred for 2 hours at 85° C. The resulting mixture was concentrated under reduced pressure. The residue was purified by silica gel column chromatography, eluted with 2%~20% methanol in dichloromethane. The desired fractions were collected and concentrated under reduced pressure to afford the title compound as an off-white solid (800 mg, 79%): $^1$H NMR (400 MHz, DMSO-d$_6$) δ 7.38 (d, J=2.1 Hz, 1H), 7.29 (d, J=2.1 Hz, 1H), 4.16 (s, 2H), 4.00 (s, 1H), 3.34 (s, 2H), 3.19 (t, J=5.9 Hz, 2H), 3.03 (t, J=6.0 Hz, 2H), 1.40 (s, 9H), 1.10 (d, J=6.7 Hz, 6H); MS: [(M+1)]$^+$=481.00, 483.00.

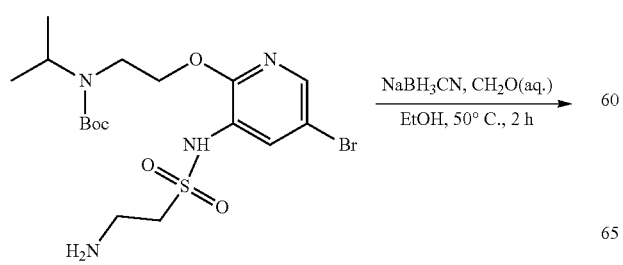

248

-continued

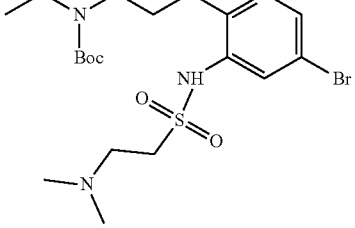

tert-Butyl (2-((5-bromo-3-((2-(dimethylamino)ethyl)sulfonamido)pyridin-2-yl)oxy)ethyl)(isopropyl)carbamate To a stirred mixture of tert-Butyl (2-((3-((2-aminoethyl)sulfonamido)-5-bromopyridin-2-yl)oxy)ethyl)(isopropyl)carbamat (800 mg, 1.66 mmol) in formalin (5.00 mL, 38%) and ethanol (5.00 mL) was added sodium cyanoborohydride (209 mg, 3.32 mmol) in portions at ambient temperature. The resulting mixture was stirred for 2 hours at 50° C. The resulting mixture was concentrated under reduced pressure. The residue was purified by silica gel column chromatography, eluted with 3%~20% methanol in dichloromethane. The desired fractions were collected and concentrated under reduced pressure to afford the title compound an off-white solid (500 mg, 59%): $^1$H NMR (400 MHz, DMSO-d$_6$) δ 8.26 (s, 1H), 7.78 (d, J=2.2 Hz, 1H), 7.61 (d, J=2.2 Hz, 1H), 4.35 (s, 2H), 4.17 (s, 1H), 3.32 (d, J=12.8 Hz, 4H), 2.91 (t, J=6.5 Hz, 2H), 2.37 (s, 6H), 1.39 (s, 9H), 1.06 (d, J=6.7 Hz, 6H); MS: [(M+1)]$^+$=509.15, 511.15.

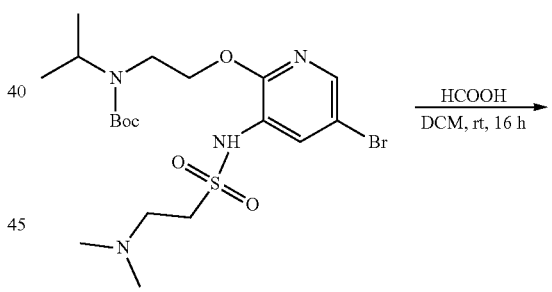

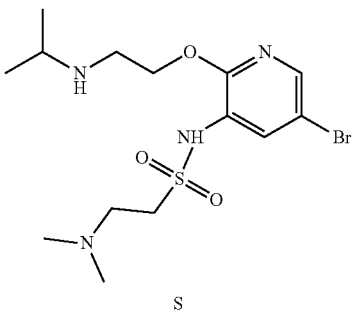

N-(5-Bromo-2-(2-(isopropylamino)ethoxy)pyridin-3-yl)-2-(dimethylamino)ethane-1-sulfonamide A solution of tert-butyl (2-((5-bromo-3-((2-(dimethylamino)ethyl)sulfonamido)pyridin-2-yl)oxy)ethyl)(isopopyl)carbamate (500 mg, 0.98 mmol) in formic acid (10.0 mL)

and dichloromethane (10.0 mL) was stirred for 16 hours at ambient temperature. The resulting mixture was concentrated under reduced pressure. The residue was purified by Prep-HPLC with the following conditions: [Column: Spherical C18, 20~40 µm, 330 g; Mobile Phase A: Water (plus 10 mM NH$_4$HCO$_3$ and 0.05% NH$_3$·H$_2$O); Mobile Phase B: acetonitrile; Flow rate: 65 mL/min; Gradient (B %): 5%~20%, 10 min; 20%~37%, 22 min; 37%~95%; 2 min; 95%, 5 min; Detector: UV 254 nm; Rt: 32 min]. The desired fractions were collected and concentrated under reduced pressure to afford the title compound as an off-white solid (300 mg, 75%): $^1$H NMR (400 MHz, DMSO-d$_6$) δ 7.59 (d, J=6.8 Hz, 2H), 4.36 (t, J=5.2 Hz, 2H), 3.22-3.12 (m, 1H), 3.08 (t, J=6.6 Hz, 4H), 2.68 (t, J=7.4 Hz, 2H), 2.18 (s, 6H), 1.16 (d, J=6.3 Hz, 6H); MS: [(M+1)]$^+$=409.10, 411.10.

Intermediate T and T1

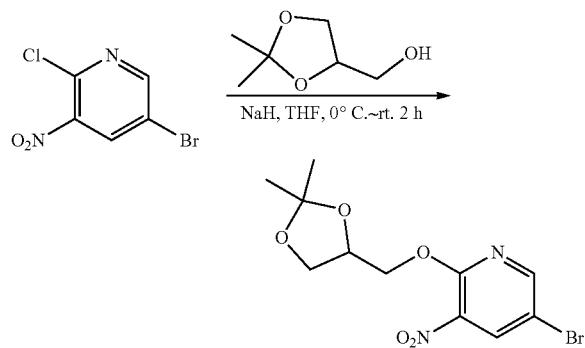

5-Bromo-2-((2,2-dimethyl-1,3-dioxolan-4-yl)methoxy)-3-nitropyridine: To a solution of (2,2-dimethyl-1,3-dioxolan-4-yl)methanol (6.60 g, 49.9 mmol) in anhydrous tetrahydrofuran (200 mL) was added sodium hydride (2.02 g, 50.6 mmol, 60% w/w dispersed in mineral oil) at 0° C. under nitrogen atmosphere. The resulting mixture was stirred for 1 hour at 25° C. followed by the addition of 5-bromo-2-chloro-3-nitropyridine (10.0 g, 42.1 mmol) at 0° C. After stirring for additional 2 hours at 25° C., the reaction was quenched by saturated aqueous ammonium chloride (20.0 mL). The resulting mixture was diluted with water (150 mL) and extracted with ethyl acetate (3×100 mL). The combined organic layers was washed with brine (2×50.0 mL) and dried over anhydrous sodium sulfate. After filtration, the filtrate was concentrated under reduced pressure. The residue was purified by silica gel column chromatography, eluted with 2%~5% ethyl acetate in petroleum ether. The desired fractions were collected and concentrated under reduced pressure to afford the title compound as a yellow oil (8.60 g, 62%): $^1$H NMR (400 MHz, DMSO-d$_6$) δ 8.71 (d, J=2.3 Hz, 1H), 8.66 (d, J=2.3 Hz, 1H), 4.56-4.48 (m, 1H), 4.48-4.36 (m, 2H), 4.07 (dd, J=8.5, 6.3 Hz, 1H), 3.81 (dd, J=8.4, 6.0 Hz, 1H), 1.30 (d, J=10.8 Hz, 6H); MS: [(M+1)]$^+$=333.00, 335.00.

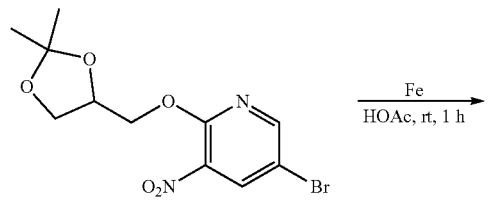

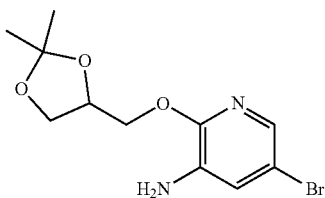

5-Bromo-2-((2,2-dimethyl-1,3-dioxolan-4-yl)methoxy)pyridin-3-amine: To a solution of 5-bromo-2-[(2,2-dimethyl-1,3-dioxolan-4-yl)methoxy]-3-nitropyridine (8.60 g, 25.8 mmol) in acetic acid (290 mL) was added iron powder (14.4 g, 258 mmol) at ambient temperature. After stirring for 1 hour at 25° C., the resulting mixture was filtered and the filtered cake was washed with tetrahydrofuran (6×100 mL). The filtrate was concentrated under reduced pressure. The residue was purified by silica gel column chromatography, eluted with 5%~30% ethyl acetate in petroleum ether. The desired fractions were collected and concentrated under reduced pressure to afford the title compound as an off-white solid (7.20 g, 92%): $^1$H NMR (400 MHz, DMSO-d$_6$) δ 7.37 (d, J=2.2 Hz, 1H), 7.02 (d, J=2.2 Hz, 1H), 5.28 (s, 2H), 4.40 (p, J=5.8 Hz, 1H), 4.25 (dd, J=5.5, 1.7 Hz, 2H), 4.08 (dd, J=8.5, 6.5 Hz, 1H), 3.80 (dd, J=8.5, 6.1 Hz, 1H), 1.34 (s, 3H), 1.29 (s, 3H); MS: [(M+1)]$^+$=303.00, 305.00.

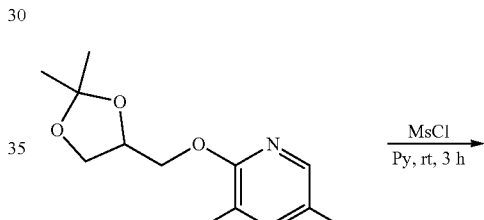

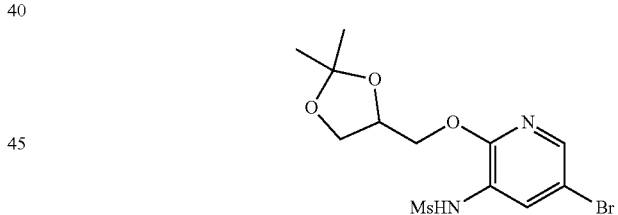

N-(5-Bromo-2-((2,2-dimethyl-1,3-dioxolan-4-yl)methoxy)pyridin-3-yl)methanesulfonamide: To a stirred solution of 5-bromo-2-[(2,2-dimethyl-1,3-dioxolan-4-yl)methoxy]pyridin-3-amine (2.00 g, 6.60 mmol) in pyridine (55.0 mL) was added methanesulfonyl chloride (1.13 g, 9.90 mmol) dropwise at ambient temperature. The resulting mixture was stirred at 25° C. for 3 hours. The resulting mixture was concentrated under reduced pressure. The residue was purified by silica gel column chromatography, eluted with 5%~30% ethyl acetate in petroleum ether. The desired fractions were collected and concentrated under reduced pressure to afford the title compound as a colorless solid (1.88 g, 75%): $^1$H NMR (400 MHz, DMSO-d$_6$) δ 9.45 (s, 1H), 8.09 (d, J=2.2 Hz, 1H), 7.78 (d, J=2.3 Hz, 1H), 4.44 (p, J=5.9 Hz, 1H), 4.30 (d, J=5.7 Hz, 2H), 4.08 (dd, J=8.5, 6.4 Hz, 1H), 3.85 (dd, J=8.6, 5.7 Hz, 1H), 3.10 (s, 3H), 1.34 (s, 3H), 1.29 (s, 3H); MS: [(M+1)]$^+$=381.00, 383.00.

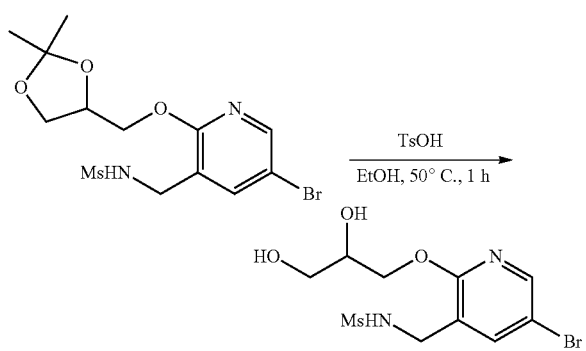

N-(5-Bromo-2-(2,3-dihydroxypropoxy)pyridin-3-yl)methanesulfonamide: To a solution of N-(5-bromo-2-((2,2-dimethyl-1,3-dioxolan-4-yl)methoxy)pyridin-3-yl)methanesulfonamide (2.50 g, 6.56 mmol) in ethanol (20.0 mL) was added 4-methylbenzene-1-sulfonic acid (1.10 g, 6.39 mmol) at ambient temperature. The resulting mixture was stirred for 1 hour at 50° C. The resulting mixture was concentrated under reduced pressure. The residue was purified by silica gel column chromatography, eluted with 1%-2% methanol in dichloromethane. The desired fractions were collected and concentrated under reduced pressure to afford the title compound as a colorless solid (2.00 g, 90%): $^1$H NMR (400 MHz, DMSO-$d_6$) δ 7.76 (s, 1H), 7.63 (d, J=2.3 Hz, 1H), 5.07 (s, 1H), 4.26 (dd, J=10.8, 3.9 Hz, 1H), 4.11 (dd, J=10.8, 6.6 Hz, 2H), 3.87-3.80 (m, 1H), 3.46 (dd, J=5.8, 2.9 Hz, 2H), 2.93 (s, 3H); MS: [(M+1)]$^+$=341.00, 343.00.

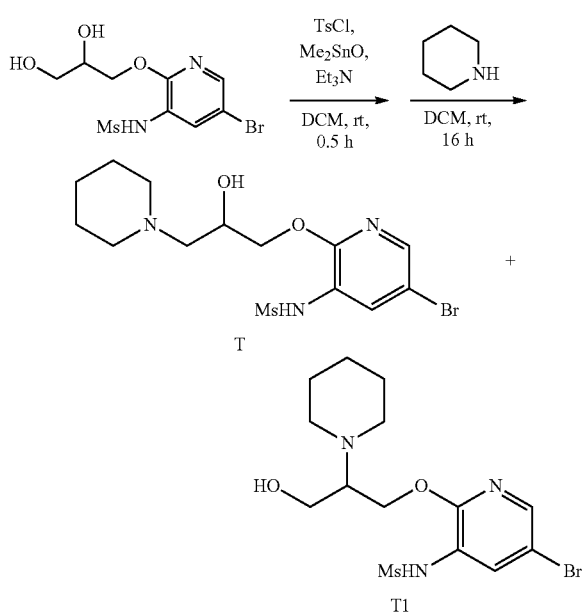

N-(5-Bromo-2-(2-hydroxy-3-(piperidin-1-yl)propoxy)pyridin-3-yl)methanesulfonamide and N-(5-bromo-2-(3-hydroxy-2-(piperidin-1-yl)propoxy)pyridin-3-yl)methanesulfonamide: To a solution of N-(5-bromo-2-(2,3-dihydroxypropoxy)pyridin-3-yl)methanesulfonamide (500 mg, 1.47 mmol) in dichloromethane (15.0 mL) were added dibutylstannanone (73.0 mg, 0.29 mmol), triethylamine (297 mg, 2.93 mmol) and 4-methylbenzenesulfonyl chloride (280 mg, 1.47 mmol) at 0° C. The resulting mixture was stirred for 1 hour at 25° C. followed by the addition of piperidine (430 mg, 5.05 mmol) at ambient temperature. After stirring for 16 hours at 25° C., the resulting mixture was concentrated under reduced pressure. The residue was purified by reversed phase flash chromatography with the following conditions: [Column: Spherical C18, 20~40 μm; 120 g; Mobile Phase A: Water (plus 10 mM trifluoroacetic acid); Mobile Phase B: acetonitrile; Flow rate: 45 mL/min; Gradient (B %): 5%~23%, 16 min; 23%, 4 min; 23%~26%, 3 min; 26%, 2 min; 26%~95%; 5 min; 95%, 5 min; Detector UV 254 nm; Rt1: 15 min; Rt2: 20 min] to afford N-(5-bromo-2-(2-hydroxy-3-(piperidin-1-yl)propoxy)pyridin-3-yl)methanesulfonamide (Rt1: 15 min) (66.5 mg, 17%): $^1$H NMR (400 MHz, DMSO-$d_6$) δ 7.86 (s, 1H), 7.68 (d, J=2.3 Hz, 1H), 4.27 (dd, J=10.2, 2.6 Hz, 1H), 4.08-3.96 (m, 2H), 2.98 (s, 3H), 2.49-2.31 (m, 6H), 1.48 (p, J=5.4 Hz, 4H), 1.41-1.32 (m, 2H); MS: [(M+1)]$^+$=408.00, 410.00; and N-(5-bromo-2-(3-hydroxy-2-(piperidin-1-yl)propoxy)pyridin-3-yl)methanesulfonamide (Rt2: 20 min) (94 mg, 23%): $^1$H NMR (400 MHz, DMSO-$d_6$) δ 7.64 (d, J=2.6 Hz, 1H), 7.37 (d, J=2.5 Hz, 1H), 4.31 (dd, J=12.9, 3.5 Hz, 1H), 3.95 (dt, J=6.7, 3.3 Hz, 1H), 3.56 (dd, J=13.0, 8.7 Hz, 1H), 3.09 (s, 3H), 2.41 (s, 2H), 2.35-2.26 (m, 4H), 1.48 (q, J=4.7 Hz, 4H), 1.36 (q, J=5.7 Hz, 2H); MS: [(M+1)]$^+$=408.00, 410.00.

Intermediate U

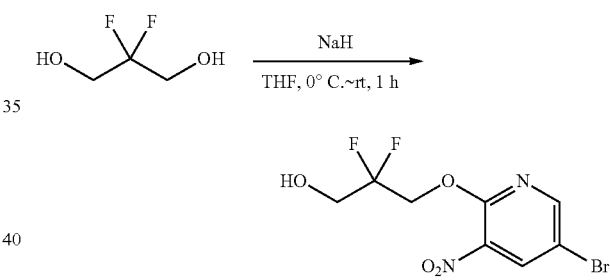

3-((5-Bromo-3-nitropyridin-2-yl)oxy)-2,2-difluoropropan-1-ol: To a stirred solution of 2,2-difluoropropane-1,3-diol (1.70 g, 15.2 mol) (Prepared according to the reported procedure by PCT Int. Appl., 2011071716, 16 Jun. 2011.) in anhydrous tetrahydrofuran (170 mL) was added sodium hydride (688 mg, 17.2 mmol, 60% w/w dispersed in mineral oil) in portions at 0° C. under nitrogen atmosphere. The resulting mixture was stirred for 2 hours at 25° C. followed by the addition of 5-bromo-2-chloro-3-nitropyridine (3.40 g, 14.3 mmol) at 0° C. After stirring for 1 hour at 25° C., the resulting solution was quenched by saturated aqueous ammonium chloride (25.0 mL) at 0° C. The resulting mixture was extracted with ethyl acetate (3×100 mL). The combined organic layers was washed with brine (100 mL) and dried over anhydrous sodium sulfate. After filtration, the filtrate was concentrated under reduced pressure. The residue was purified by silica gel column chromatography, eluted with 1%~20% ethyl acetate in petroleum ether. The desired fractions were collected and concentrated under reduced pressure to afford the title compound as a yellow oil (2.71 g, 61%): $^1$H NMR (400 MHz, CDCl$_3$) δ 8.49 (p, J=2.1 Hz, 1H), 4.80 (t, J=11.6 Hz, 1H), 4.05 (t, J=12.5 Hz, 1H); MS: [(M+1)]$^+$=312.95 314.95.

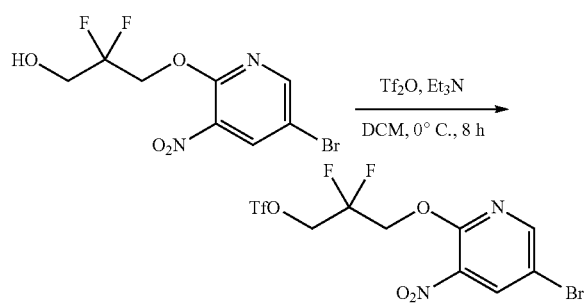

3-((5-Bromo-3-nitropyridin-2-yl)oxy)-2,2-difluoropropyl trifluoromethanesulfonate: To a solution of 3-((5-bromo-3-nitropyridin-2-yl)oxy)-2,2-difluoropropan-1-ol (1.20 g, 3.83 mmol) and triethylamine (194 mg, 1.92 mmol) in dichloromethane (40.0 mL) was added trifluoromethanesulfonic anhydride (10.8 g, 38.3 mmol) dropwise at 0° C. and stirred for 8 hours at 0° C. The resulting mixture was concentrated under reduced pressure. The residue was purified by silica gel column chromatography, eluted with 1%~3% ethyl acetate in petroleum ether. The desired fractions were collected and concentrated under reduced pressure to afford the title compound as a yellow oil (1.33 g, 78%): $^1$H NMR (400 MHz, CDCl$_3$) δ 8.52 (d, J=2.3 Hz, 1H), 8.48 (d, J=2.3 Hz, 1H), 4.83 (dt, J=22.5, 11.2 Hz, 4H).

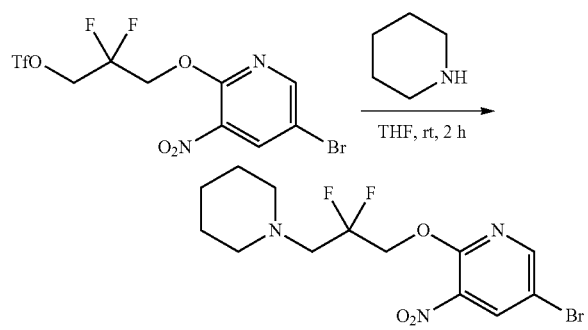

5-Bromo-2-(2,2-difluoro-3-(piperidin-1-yl)propoxy)-3-nitropyridine: To a stirred solution of 3-((5-bromo-3-nitropyridin-2-yl)oxy)-2,2-difluoropropyl trifluoromethanesulfonate (600 mg, 1.35 mmol) in tetrahydrofuran (20.0 mL) was added piperidine (230 mg, 2.70 mmol) dropwise at ambient temperature. After stirring for 2 hours at 25° C., the resulting mixture was concentrated under reduced pressure. The residue was purified by silica gel column chromatography, eluted with 1%~5% ethyl acetate in petroleum ether. The desired fractions were collected and concentrated under reduced pressure to afford the title compound as a yellow oil (434 mg, 85%): $^1$H NMR (400 MHz, CDCl$_3$) δ 8.46 (d, J=2.1 Hz, 1H), 8.44 (d, J=2.5 Hz, 1H), 4.78 (t, J=11.6 Hz, 2H), 2.91 (t, J=13.2 Hz, 2H), 2.56 (s, 4H), 1.50 (s, 4H), 1.43-1.34 (m, 2H); MS: [(M+1)]$^+$=380.05 382.05.

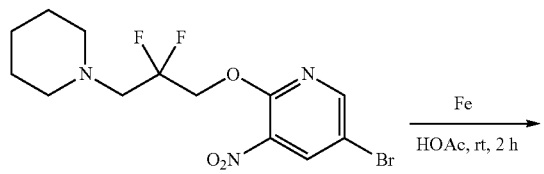

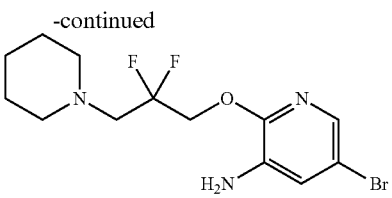

5-Bromo-2-(2,2-difluoro-3-(piperidin-1-yl)propoxy)pyridin-3-amine: To a solution of 3-((5-bromo-3-nitropyridin-2-yl)oxy)-2,2-difluoropropyl trifluoromethanesulfonate (450 mg, 1.18 mmol) in acetic acid (20.0 mL) was added iron powder (661 mg, 11.8 mmol) at ambient temperature. After stirring for 2 hours at 25° C., the resulting mixture was filtered and the filtered cake was washed with tetrahydrofuran (5×100 mL). The filtrate was concentrated under reduced pressure. The residue was basified to pH=8 with saturated sodium carbonate (50.0 mL). The resulting mixture was extracted with ethyl acetate (4×200 mL). The combined organic layers was washed with brine (100 mL) and dried over anhydrous sodium sulfate. After filtration, the filtrate was concentrated under reduced pressure. The residue was purified by silica gel column chromatography, eluted with 1%~5% ethyl acetate in petroleum ether. The desired fractions were collected and concentrated under reduced pressure to afford the title compound as a yellow oil (409 mg, 99%): $^1$H NMR (400 MHz, CDCl$_3$) δ 7.56 (d. J=1.9 Hz, 1H), 7.01 (s, 1H), 4.63 (t, J=12.9 Hz, 2H), 3.90 (s, 2H), 2.84 (t, J=14.0 Hz, 2H), 2.55 (s, 4H), 1.55 (s, 4H), 1.42-1.35 (m, 2H); MS: [(M+1)]$^+$=350.05, 352.05.

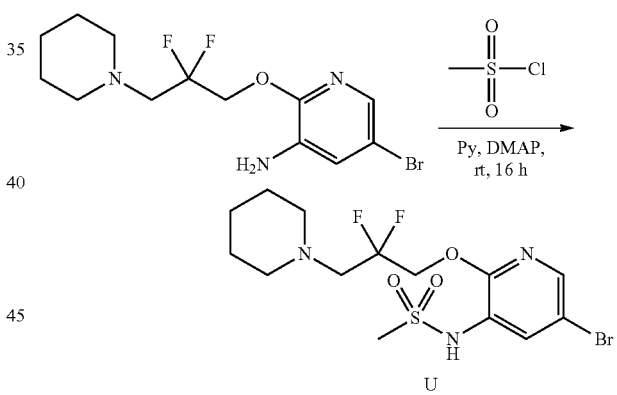

N-(5-Bromo-2-(2,2-difluoro-3-(piperidin-1-yl)propoxy)pyridin-3-yl)methanesulfonamide: To a stirred solution of 5-bromo-2-(2,2-difluoro-3-(piperidin-1-yl)propoxy)pyridin-3-amine (409 mg, 1.09 mmol) and N,N-dimethylpyridin-4-amine (13.3 mg, 0.11 mmol,) in pyridine (10.0 mL) was added methanesulfonyl chloride (241 mg, 2.10 mol) dropwise at ambient temperature. The resulting mixture was stirred under nitrogen atmosphere at 25° C. for 16 hours. The resulting mixture was concentrated under reduced pressure. The residue was purified by reversed phase flash chromatography with the following conditions: [Column: Spherical C18, 20~40 μm; 330 g; Mobile Phase A: Water (plus 10 mM trifluoracetic acid); Mobile Phase B: acetonitrile; Flow rate: 65 mL/min; Gradient (B %): 5%~5, 5 min; 5%~25%, 3 min; 25%~41%, 20 min; 41%~95%; 2 min; 95%, 5 min; Detector: 254 nm; Rt: 18.5 min]. The desired fractions were collected and concentrated under reduced pressure. The residue was basified to pH=8 with saturated aqueous sodium bicarbonate (50.0 mL) and extracted with ethyl acetate (3×100 mL). The combined organic layers was washed with brine (30.0 mL) and dried over anhydrous sodium sulfate. After filtration, the filtrate was concentrated under reduced pressure to afford the title compound as a yellow oil (224 mg, 45%): ¹H NMR (400 MHz, CDCl₃) δ 7.99 (s, 1H), 7.95 (d, J=1.8 Hz, 1H), 4.72 (t, J=13.4 Hz, 2H), 3.05 (s, 3H), 2.83 (s, 2H), 2.54 (s, 4H), 1.56 (s, 4H), 1.42 (s, 2H); MS: [(M+1)]⁺=428.05, 430.05.

Intermediate V

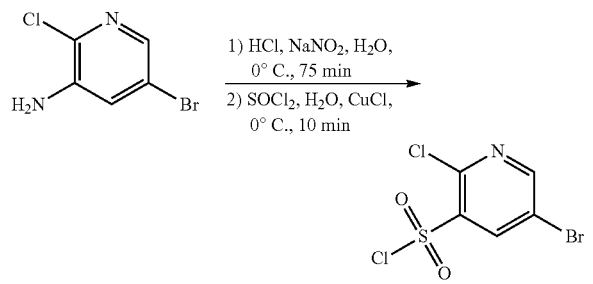

5-Bromo-2-chloropyridine-3-sulfonyl chloride: Step a. Thionyl chloride (3.90 mL, 53.8 mmol) was added dropwise over 10 min to water (23.0 mL) with stirring and maintaining the temperature of the mixture at 0-7° C. The resulting solution was stirred for 1 hour before copper (1) chloride (14.3 mg, 0.11 mmol) was added to the mixture. The resulting yellow-green solution was cooled to −3° C. Step b. To a solution of 5-bromo-2-chloropyridin-3-amine (2.60 g, 12.5 mmol) in hydrochloric acid (12.6 mL, 37% w/w in water) was added a solution of sodium nitrite (930 mg, 13.5 mmol) in water (3.60 mL) over 10 min at −5~0° C. The resulting slurry was stirred for 10 minutes at −2° C. Step c. The slurry from step b was cooled down to −5° C. and added to the solution obtained from step a over 20 min, maintaining the temperature of the reaction mixture between −3 to 0° C. (the slurry from step b was maintained at −5° C. throughout the addition). After stirring for additional 75 min at 0° C., the precipitated solid was collected by filtration and washed with ice-water. The filtered cake was dried under vacuum to afford the title compound as light orange solid (2.78 g, 77%): ¹H NMR (400 MHz, CDCl₃) δ 8.77 (d, J=2.3 Hz, 1H), 8.55 (d, J=2.3 Hz, 1H).

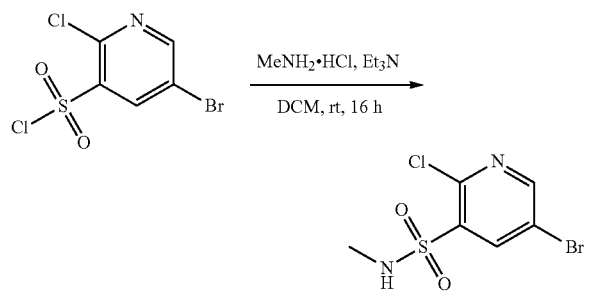

5-Bromo-2-chloro-N-methylpyridine-3-sulfonamide: To a solution of 5-bromo-2-chloropyridine-3-sulfonyl chloride (1.00 g, 3.44 mmol) and methanamine hydrochloride (279 mg, 4.13 mmol) in dichloromethane (20.0 mL) was added triethylamine (1.67 g, 16.5 mmol). The resulting solution was stirred at ambient temperature for 16 hours. The reaction mixture was washed with saturated aqueous sodium bicarbonate (10.0 mL), water (10.0 mL) and brine (10.0 mL), dried over anhydrous sodium sulfate. After filtration, the filtrate was concentrated under reduced pressure. The residue was purified by silica gel column chromatography, eluted with 3%~11% ethyl acetate in petroleum ether. The desired fractions were collected and concentrated under reduced pressure to afford the title compound as a light yellow solid (471 mg, 48%): ¹H NMR (400 MHz, CDCl₃) δ 8.64 (d, J=2.4 Hz, 1H), 8.53 (d, J=2.4 Hz, 1H), 5.11 (s, 1H), 2.73 (d, J=5.3 Hz, 3H); MS: [M+1)]⁺=584.95, 286.95

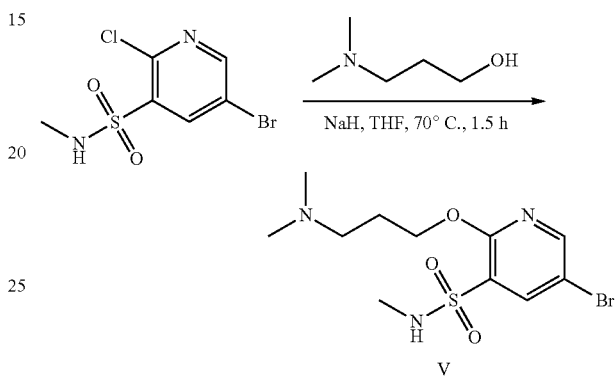

5-Bromo-2-(3-(dimethylamino)propoxy)-N-methylpyridine-3-sulfonamide: To a solution of 3-(dimethylamino) propan-1-ol (71.0 mg, 0.68 mmol) in anhydrous tetrahydrofuran (8.00 mL) was added sodium hydride (28.0 mg, 0.68 mmol, 60% w/w dispersed in mineral oil) at 0° C. under nitrogen atmosphere. The resulting mixture was stirred for 0.5 hours at 25° C. followed by the addition of 5-bromo-2-chloro-N-methylpyridine-3-sulfonamide (150 mg, 0.53 mmol) at 0° C. After stirring for additional 2 hours at 70° C. in a sealed tube, the reaction was quenched by citric acid (2 mL, 1 M in water). The resulting mixture was diluted with water (50.0 mL) and extracted with ethyl acetate (3×20.0 mL). The combined organic layers was washed with brine (2×20.0 mL), water (2×20.0 mL) and dried over anhydrous sodium sulfate. After filtration, the filtrate was concentrated under reduced pressure to afford the title compound as a light yellow solid (150 mg, 82%): ¹H NMR (400 MHz, CDCl₃) δ 8.32 (d, J=2.6 Hz, 1H), 8.26 (d, J=2.6 Hz, 1H), 4.47 (d, J=6.1 Hz, 2H), 2.64 (s, 2H), 2.53 (s, 3H), 2.34 (s, 6H), 2.04 (s, 2H); MS: [(M+1)]⁺=352.10, 354.10.

Intermediate W

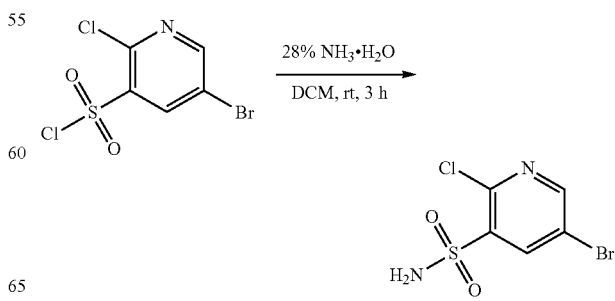

5-Bromo-2-chloropyridine-3-sulfonamide: To a stirring solution of 5-bromo-2-chloropyridine-3-sulfonyl chloride (4.46 g, 15.3 mol) in dichloromethane (25.0 mL) was added amine hydrate (25.0 mL, 28% $NH_3$ in water) dropwise at 0° C. The resulting mixture was stirred at ambient temperature for 3 hours. The resulting mixture was extracted with ethyl acetate (3×50.0 mL). The combined organic layers was washed with brine (2×50.0 mL), dried over anhydrous sodium sulfate and filtered. The filtrate was concentrated under reduced pressure. The residue was purified by silica gel column chromatography, eluted with 2%~20% ethyl acetate in petroleum ether. The desired fractions were collected and concentrated under reduced pressure to afford the title compound as an orange solid (2.61 g, 63%): $^1$H NMR (400 MHz, $CDCl_3$) δ 8.65 (d, J=2.7 Hz, 1H), 8.54 (d, J=2.6 Hz, 1H), 5.31 (s, 2H); MS: $[(M+1)]^+$=270.95, 272.95.

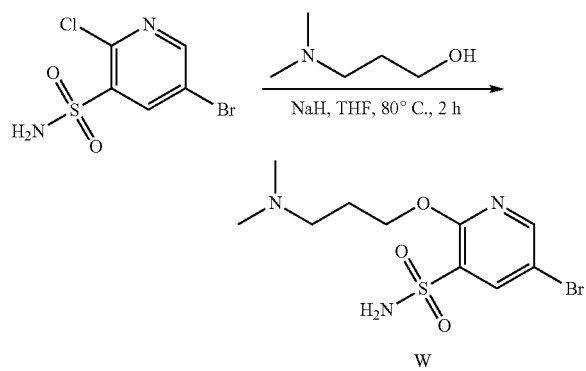

5-Bromo-2-(3-(dimethylamino)propoxy)pyridine-3-sulfonamide: A solution of 5-bromo-2-chloropyridine-3-sulfonamide (780 mg, 2.87 mmol) in anhydrous tetrahydrofuran (50.0 mL) was treated with sodium hydride (173 mg, 4.31 mmol, 60% w/w dispersed in mineral oil) for 0.5 hours at 0° C. under nitrogen atmosphere followed by the addition of 3-(dimethylamino)propan-1-ol (386 mg, 3.73 mmol) at 0° C. The resulting mixture was stirred for 2 hours at 80° C. in a sealed tube. After cooling down to ambient temperature, the reaction was quenched by citric acid (5.00 mL, 2M in water) at 0° C. The resulting mixture was concentrated under reduced pressure. The residue was purified by reversed phase flash chromatography with the following conditions: [Column: Spherical C18, 20~40 μm; 120 g; Mobile Phase A: Water (plus 10 mM $NH_4HCO_3$); Mobile Phase B: acetonitrile; Flow rate: 45 mL/min; Gradient (B %): 5%~27%, 3 min; 27%~30%, 2.5 min; 30%; 6.5 min; 95%, 5 min; Detector UV 254 nm; Rt: 5.5 min]. The desired fractions were collected and concentrated under reduced pressure to afford the title compound as a light brown solid (380 mg, 40%): $^1$H NMR (400 MHz, $CD_3OD$) δ 8.39 (d, J=2.4 Hz, 1H), 8.23 (d, J=2.5 Hz, 1H), 4.53 (t, J=5.9 Hz, 2H), 2.59 (t, J=7.0 Hz, 2H), 2.29 (s, 6H), 2.09-1.95 (m, 2H); MS: $[(M+1)]^+$=338.00, 340.00.

Intermediate X

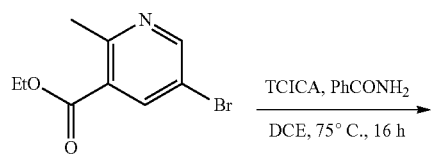

Ethyl 5-bromo-2-(chloromethyl)nicotinate: To a solution of ethyl 5-bromo-2-methylpyridine-3-carboxylate (2.00 g, 8.19 mmol) and benzamide (50.0 mg, 0.41 mmol) in trichloromethane (8.00 mL) was added trichloro-1,3,5-triazinane-2,4,6-trione (5.20 g, 22.4 mmol). After stirring for 16 hours at 75° C., the resulting mixture was cooled down to ambient temperature. The reaction was quenched by 10% aqueous sodium carbonate (10.0 mL). The resulting mixture was extracted with trichloromethane (4×30.0 mL). The organic layer was washed with saturated aqueous sodium bicarbonate (2×20.0 mL), water (2×20.0 mL) and brine (3×20.0 mL), dried over anhydrous sodium sulfate. After filtration and concentration, the residue was purified by silica gel column chromatography, eluted with 1%~2% ethyl acetate in petroleum ether. The desired fractions were collected and concentrated under reduced pressure to afford the title compound as a yellow solid (1.80 g, 79%): MS: $[(M+1)]^+$=277.95, 279.95.

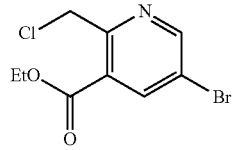

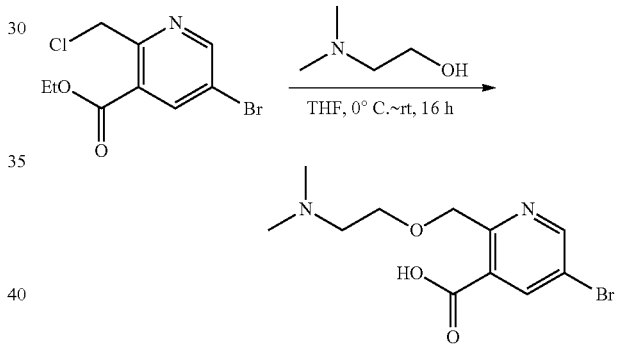

5-Bromo-2-((2-(dimethylamino)ethoxy)methyl)nicotinic acid: To a solution of 2-(dimethylamino)ethan-1-ol (606 mg, 6.80 mmol) in anhydrous tetrahydrofuran (10.0 mL) was added sodium hydride (248 mg, 6.20 mmol, 60% w/w dispersed in mineral oil) at 0° C. under nitrogen atmosphere. The resulting mixture was stirred for 30 minutes at 25° C. followed by the addition of ethyl 5-bromo-2-(chloromethyl)nicotinate (574 mg, 2.06 mmol) over 20 minutes at 0° C. After stirring for additional 16 hours at 25° C., the reaction was quenched by saturated aqueous ammonium chloride (2.00 mL). The resulting mixture was concentrated under reduced pressure. The residue was purified by reversed phase flash chromatography with the following conditions: [Column: Spherical C18, 20~40 μm; 120 g; Mobile Phase A: Water (plus 10 mM $NH_4HCO_3$); Mobile Phase B: acetonitrile; Flow rate: 45 mL/min; Gradient (B %): 2%~2%, 3 min; 2%~5%, 3 min; 5%~15%; 10 min, 15%~95%, 5 min; 95%, 5 min Detector: UV 254 nm; Rt: 12 min]. The desired fractions were collected and concentrated under reduced pressure to afford the title compound as a yellow solid (128 mg, 21%): $^1$H NMR (400 MHz, DMSO-$d_6$) δ 8.50 (d, J=2.3 Hz, 1H), 7.99 (d, J=2.2 Hz, 1H), 4.82 (s, 2H), 3.51 (t, J=6.0 Hz, 2H), 2.42 (t, J=6.0 Hz, 2H), 2.15 (s, 6H); MS: $[(M+1)]^+$=303.00, 305.00.

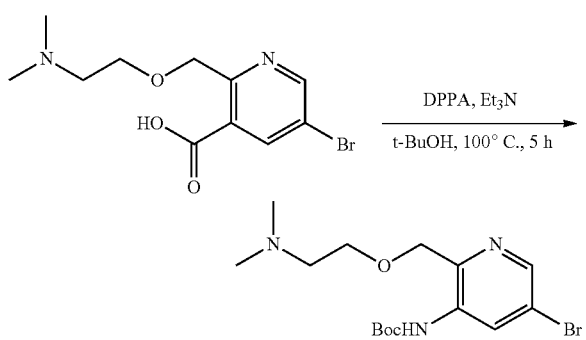

tert-Butyl (5-bromo-2-((2-(dimethylamino)ethoxy)methyl)pyridin-3-yl)carbamate: To a solution of 5-bromo-2-((2-(dimethylamino)ethoxy)methyl)nicotinic acid (600 mg, 1.98 mmol) and triethylamine (601 mg, 5.94 mmol) in tert-butanol (10.0 mL) was added diphenylphosphoryl azide (diphenylphosphorazidate) (1.09 g, 3.96 mmol) at ambient temperature. The resulting mixture was stirred for 1 hour at 25° C. After stirring for 5 hours at 100° C., the resulting mixture was concentrated under reduced pressure. The residue was purified by reversed phase flash chromatography with the following conditions: [Column: Spherical C18, 20~40 μm; 330 g; Mobile Phase A: Water (plus 10 mM NH$_4$HCO$_3$, and 0.05% NH$_3$·H$_2$O); Mobile Phase B: acetonitrile; Flow rate: 65 mL/min, Gradient (B %): 5%~40%, 8 min, 40%~56%, 15 min; 56%~72, 10 min; 72%~95%; 2 min; 95%, 5 min; Detector UV 254 nm; Rt: 33.5 min]. The desired fractions were collected and concentrated under reduced pressure to afford the title compound as a colorless oil (580 mg, 79%): $^1$H NMR (400 MHz, DMSO-d$_6$) δ 9.04 (s, 1H), 8.43 (d, J=2.1 Hz, 1H), 8.31 (d, J=2.1 Hz, 1H), 4.59 (s, 2H), 3.55 (t, J=5.6 Hz, 2H), 2.46 (t, J=5.6 Hz, 2H), 2.19 (s, 6H), 1.49 (s, 9H): MS: [(M+1)]$^+$=374.10, 376.10.

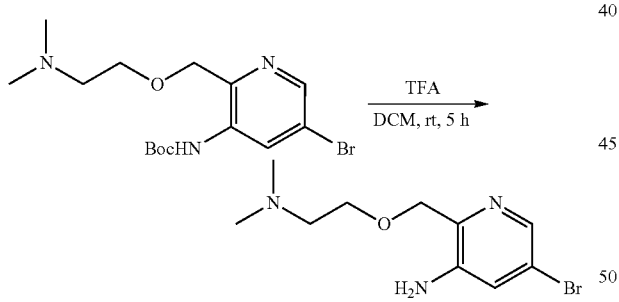

5-Bromo-2-((2-(dimethylamino)ethoxy)methyl)pyridin-3-amine: A solution of tert-butyl (5-bromo-2-((2-(dimethylamino)ethoxy)methyl)pyridin-3-yl)carbamate (580 mg, 1.55 mol) in trifluoroacetic acid (1.00 mL) and dichloromethane (7.00 mL) was stirred for 5 hours at ambient temperature. The resulting mixture was concentrated under reduced pressure. The residue was basified to pH=8 with saturated aqueous sodium bicarbonate (2.00 mL). The resulting mixture was concentrated under reduced pressure. The residue was purified by reversed phase flash chromatography with the following conditions: [Column: Spherical C18, 20~40 μm; 330 g; Mobile Phase A: Water (plus 10 mM NH$_4$HCO$_3$ and 0.05% NH$_3$·H$_2$O); Mobile Phase B: acetonitrile; Flow rate: 65 mL/min; Gradient (B %): 5%~25%, 5 min; 25%~40%, 15 min; 40%~95%; 2 min; 95%; 3 min; Detector UV 254 nm; Rt: 18 min]. The desired fractions were collected and concentrated under reduced pressure to afford the title compound as a colorless solid (360 mg, 85%): $^1$H NMR (400 MHz, DMSO-d$_6$) δ 7.74 (d, J=2.1 Hz, 1H), 7.19 (d, J=2.1 Hz, 1H), 4.44 (s, 2H), 3.51 (t, J=5.7 Hz, 2H), 2.43 (t, J=5.7 Hz, 2H), 2.15 (s, 6H); MS: [(M+1)]$^+$=274.00, 276.00.

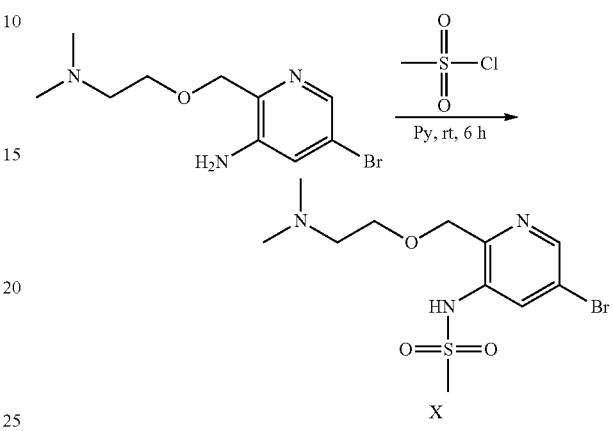

N-(5-Bromo-2-((2-(dimethylamino)ethoxy)methyl)pyridin-3-yl)methanesulfonamide: To a stirred solution of 5-bromo-2-((2-(dimethylamino)ethoxy)methyl)pyridin-3-amine (192 mg, 0.70 mmol) in pyridine (5.00 mL) was added methanesulfonyl chloride (121 mg, 1.05 mmol) at ambient temperature. The resulting mixture was stirred for 6 hours at ambient temperature. The resulting mixture was concentrated under reduced pressure. The residue was purified by reversed phase flash chromatography with the following conditions: [Column: Spherical C18, 20~40 μm; 120 g; Mobile Phase A: Water (plus 10 mM NH$_4$HCO$_3$ and 0.05% NH$_3$·H$_2$O); Mobile Phase B: acetonitrile; Flow rate: 45 mL/min; Gradient (B %): 5%~20%, 10 min; 20%~40%, 8 min; 40%~95%; 2 min; 95%, 5 min Detector: 254 nm; Rt: 10 min]. The desired fractions were collected and concentrated under reduced pressure to afford the title compound as a colorless solid (131 mg, 53%): $^1$H NMR (400 MHz, DMSO-d$_6$) δ 7.87 (d, J=2.1 Hz, 1H), 7.81 (d, J=2.1 Hz, 1H), 4.47 (s, 2H), 3.78 (t, J=5.4 Hz, 2H), 3.29 (t, J=5.4 Hz, 2H), 2.79 (s, 6H), 2.74 (s, 3H); MS: [(M+1)]$^+$=351.95, 353.95.

Intermediate Y

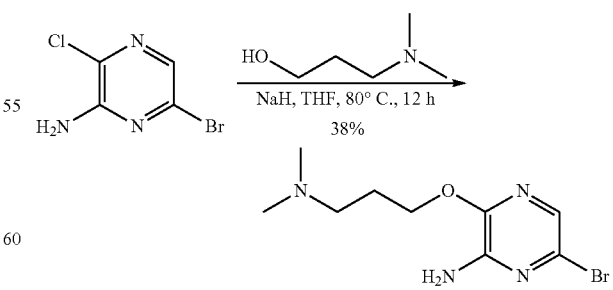

6-Bromo-3-(3-(dimethylamino)propoxy)pyrazin-2-amine. A solution of 3-(dimethylamino)propan-1-ol (0.70 g, 7.20 mmol) in tetrahydrofuran (20.0 mL) was treated with sodium hydrid (0.30 g, 7.20 mmol, 60% w/w dispersed in mineral oil) for 0.5 hours at 0° C. under nitrogen atmosphere followed by the addition of 6-bromo-3-chloropyrazin-2-amine (1.00 g, 4.80 mmol). After stirring for additional 12 hours at 80° C. in a sealed tube, the reaction was quenched with saturated aqueous ammonium chloride (3.00 mL) and diluted with water (20.0 mL). The resulting mixture was extracted with ethyl acetate (5×100 mL). The combined organic layers was washed with brine (2×20.0 mL) and dried over anhydrous sodium sulfate. After filtration, the filtrate was concentrated under reduced pressure. The residue was purified by silica gel column chromatography, eluted with 30% methanol in dichloromethane to afford the title compound as a yellow oil (500 mg, 38%). $^1$H NMR (400 MHz, CDCl$_3$) δ 7.46 (s, 1H), 5.04 (br, 2H), 4.39 (t, J=5.4 Hz, 2H), 2.45 (t, J=5.4 Hz, 2H), 2.28 (s, 6H), 1.97 (m, 2H); MS: [(M+1)]$^+$=275.15, 277.15.

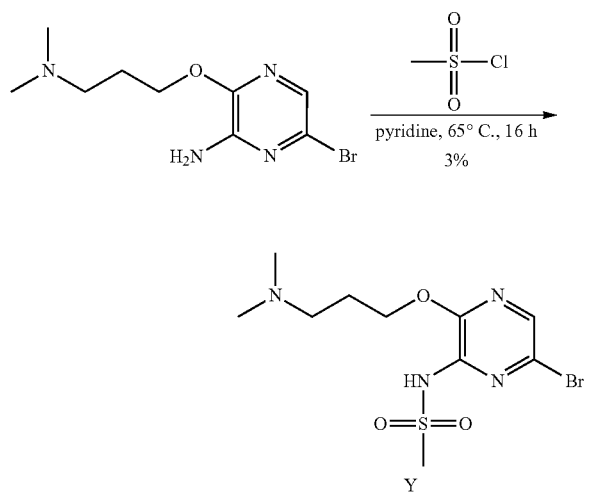

N-(6-Bromo-3-(3-(dimethylamino)propoxy)pyrazin-2-yl)methanesulfonamide. To a stirred mixture of 6-bromo-3-[3-(dimethylamino)propoxy]pyrazin-2-amine (500 mg, 1.82 mmol) in pyridine (20.0 mL) was added methanesulfonyl chloride (625 mg, 5.45 mmol) at ambient temperature. The mixture was stirred for 16 hours at 65° C. The resulting mixture was concentrated under reduced pressure. The residue was purified by reversed phase flash chromatography with the following conditions: [Column: Spherical C18, 20~40 μm; 330 g; Mobile Phase A: Water (plus 10 mM trifluoroacetic acid); Mobile Phase B: acetonitrile; Flow rate: 70 mL/min; Gradient (B %): 5%, 3 min; 5%~19%, 15 min; 19%, 10 min; 19~95%; 3 min; 95%, 5 min; Detector: UV 254 nm; Rt: 19 min]. Desired fractions were collected to afford the title compound as a light brown solid (20 mg, 3%): MS: [(M+1)]$^+$=353.00, 355.00.

Intermediate AA

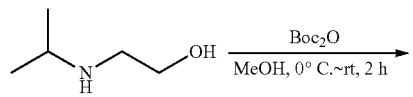

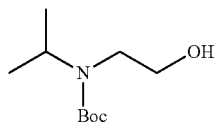

tert-Butyl N-(2-hydroxyethyl)-N-(propan-2-yl)carbamate: To a solution of 2-[(propan-2-yl)amino]ethan-1-ol (40.0 g, 388 mmol) in methanol (300 mL) was added di-tert-butyl dicarbonate (127 g, 586 mmol) dropwise at 0° C. The resulting mixture was stirred for 2 hours at ambient temperature and concentrated under reduced pressure. The residue was purified by silica gel column chromatography, eluted with 0%~4% ethyl acetate in petroleum ether. The desired fractions were collected and concentrated under reduced pressure to afford the title compound as a colorless oil (65.0 g, 82%): $^1$H NMR (400 MHz, CDCl$_3$) δ 4.17 (m, 1H), 3.71 (t, J=5.4 Hz, 2H), 3.30 (t, J=5.4 Hz, 2H), 1.47 (s, 9H), 1.12 (d, J=6.8 Hz, 6H).

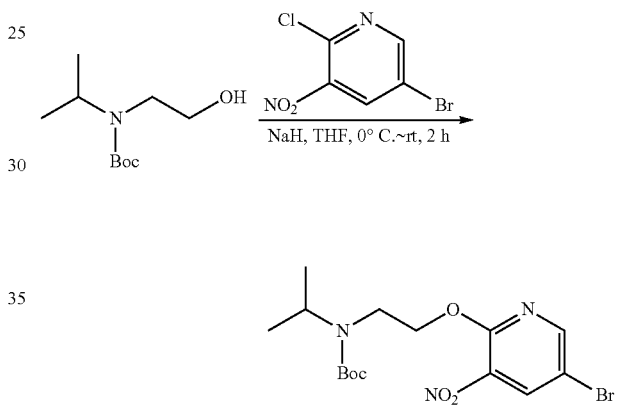

tert-Butyl N-[2-[(5-bromo-3-nitropyridin-2-yl)oxy]ethyl]-N-(propan-2-yl)carbamate: A solution of tert-butyl N-(2-hydroxyethyl)-N-(propan-2-yl)carbamate (15.4 g, 75.8 mmol) in anhydrous tetrahydrofuran (250 mL) was treated with sodium hydride (3.30 g, 82.1 mmol, 60% w/w dispersed in mineral oil) for hour at 0° C. under nitrogen atmosphere followed by the addition of 5-bromo-2-chloro-3-nitropyridine (15.0 g, 63.2 mmol) over 2 min at 0° C. After additional 2 hours at 25° C., the reaction was quenched by saturated aqueous ammonium chloride (50.0 mL) and diluted with water (500 mL). The aqueous layer was extracted with ethyl acetate (3×150 mL). The combined organic layers was washed with brine (2×100 mL) and dried over anhydrous sodium sulfate. After filtration, the filtrate was concentrated under reduced pressure. The residue was purified by silica gel column chromatography, eluted with 1%~18% ethyl acetate in petroleum ether. The desired fractions were collected and concentrated under reduced pressure to afford the title compound as alight yellow oil (18.0 g, 71%): $^1$H NMR (400 MHz, CDCl$_3$) δ8.42 (d, J=2.4 Hz, 1H), 8.37 (d, J=2.4 Hz, 1H), 4.57 (t, J=6.3 Hz, 2H), 4.32 (m, 1H), 3.51 (t, J=6.3 Hz, 2H), 1.47 (s, 9H), 1.15 (d, J=6.9 Hz, 6H); MS: [(M+1)]$^+$=404.00, 406.00.

The following intermediates were prepared according to the procedure described above:

| Intermediate | Structure | Name | MS: [(M + 1)]+ | 1H-NMR |
|---|---|---|---|---|
| AA-2-1 | 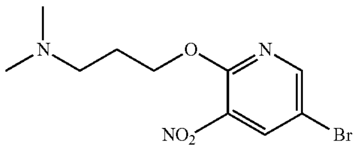 | 3-((5-bromo-3-nitropyridin-2-yl)oxy)-N,N-dimethylpropan-1-amine | 303.90 305.90 | 1H NMR (300 MHz, DMSO-d6) δ 8.68 (d, J = 2.3 Hz, 1H), 8.64 (d, J = 2.4 Hz, 1H), 4.45 (t, J = 6.5 Hz, 2H), 2.34 (t, J = 7.0 Hz, 2H), 2.13 (s, 6H), 1.87 (p, J = 6.7 Hz, 2H). |
| AA-2-2 | 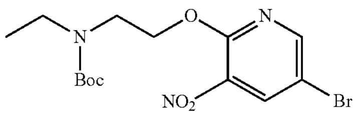 [SMILES: CCN(CCOc1ncc(Br)cc1[N+](=O)[O-])C(=O)OC(C)(C)C] | tert-Butyl (2-((5-bromo-3-nitropyridin-2-yl)oxy)ethyl)(ethyl)carbamate | 390.00 392.00 | 1H NMR (400 MHz, CDCl3) δ 8.42 (d, J = 2.3 Hz, 1H), 8.39 (d, J = 2.3 Hz, 1H), 4.58 (s, 2H), 3.62 (s, 2H), 3.36 (s, 2H), 1.45 (s, 9H), 1.12 (t, J = 7.1 Hz, 3H). |
| AA-2-3 | 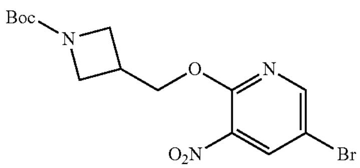 [SMILES: CC(C)(C)OC(=O)N1CC(COc2ncc(Br)cc2[N+](=O)[O-])C1] | tert-Butyl 3-(((5-Bromo-3-nitropyridin-2-yl)oxy)methyl)azetidine-1-carboxylate | 388.10, 390.10 | 1H NMR (400 MHz, CD3OD) δ 8.55 (d, J = 2.3 Hz, 1H), 8.52 (d, J = 2.3 Hz, 1H), 4.59 (d, J = 5.6 Hz, 2H), 4.04 (t, J = 8.6 Hz, 2H), 3.86 (s, 2H), 3.11-3.00 (m, 1H), 1.44 (s, 9H). |
| AA-2-4 | 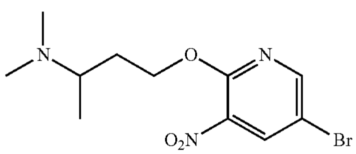 | 4-((5-Bromo-3-nitropyridin-2-yl)oxy)-N,N-dimethylbutan-2-amine | 318.05 320.05 | 1H NMR (400 MHz, CDCl3) δ 8.41 (d, J = 2.4 Hz, 1H), 8.36 (d, J = 2.4 Hz, 1H), 4.60-4.49 (m, 2H), 2.96-2.86 (m, 1H), 2.29 (s, 6H), 2.12-2.01 (m, 1H), 1.84-1.73 (m, 1H), 1.05 (d, J = 6.6 Hz, 3H). |
| AA-2-5 | 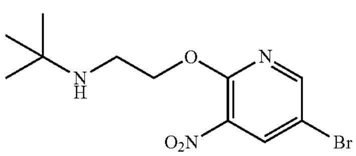 | N-(2-((5-Bromo-3-nitropyridin-2-yl)oxy)ethyl)-2-methylpropan-2-amine | 318.10 320.10 | 1H NMR (400 MHz, CD3OD) δ 8.58 (d, J = 2.3 Hz, 1H), 8.54 (d, J = 2.3 Hz, 1H), 4.62 (t, J = 5.4 Hz, 2H), 3.12 (t, J = 5.5 Hz, 2H), 1.22 (s, 9H). |
| AA-2-6 | 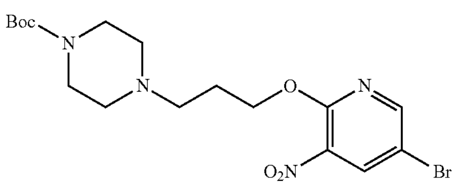 [SMILES: CC(C)(C)OC(=O)N1CCN(CCCOc2ncc(Br)cc2[N+](=O)[O-])CC1] | tert-Butyl 4-(3-((5-bromo-3-nitropyridin-2-yl)oxy)propyl)piperazine-1-carboxylate | 445.20 447.20 | 1H NMR (400 MHz, CDCl3) δ 8.42 (d, J = 2.4 Hz, 1H), 8.37 (d, J = 2.4 Hz, 1H), 4.54 (t, J = 6.4 Hz, 2H), 3.44 (s, 4H), 2.57 (s, 2H), 2.43 (s, 4H), 2.03 (s, 2H), 1.46 (s, 9H). |
| AA-2-7 | 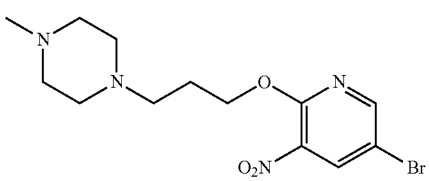 [SMILES: CN1CCN(CCCOc2ncc(Br)cc2[N+](=O)[O-])CC1] | 1-(3-((5-Bromo-3-nitropyridin-2-yl)oxy)propyl)-4-methylpiperazine | 359.00 361.00 | 1H NMR (400 MHz, CDCl3) δ 8.42 (d, J = 2.3 Hz, 1H), 8.37 (d, J = 2.4 Hz, 1H), 4.53 (t, J = 6.4 Hz, 2H), 2.70-2.53 (m, 6H), 2.52-2.42 (m, 4H), 2.31 (s, 3H), 2.01 (p, J = 6.7 Hz, 2H). |
| AA-2-8 | 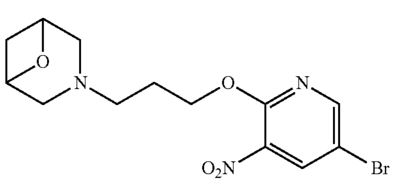 | 3-(3-((5-Bromo-3-nitropyridin-2-yl)oxy)propyl)-6-oxa-3-azabicyclo[3.1.1]heptane | 358.20 360.20 | 1H NMR (400 MHz, CD3OD) δ 8.54 (t, J = 2.2 Hz, 1H), 8.40 (d, J = 2.2 Hz, 1H), 4.84 (s, 1H), 4.51 (d, J = 6.2 Hz, 2H), 4.20 (t, J = 6.8 Hz, 2H), 3.13 (d, J = 11.5 Hz, 2H), 3.00 (q, J = 7.0 Hz, 1H), 2.71-2.60 (m, 4H), 2.30 (d, J = 8.1 Hz, 1H), 2.02 (p, J = 6.9 Hz, 2H). |

| Intermediate | Structure | Name | MS: [(M + 1)]+ | 1H-NMR |
|---|---|---|---|---|
| AA-2-9 | 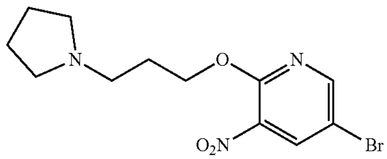 | 5-Bromo-3-nitro-2-(3-(pyrrolidin-1-yl)propoxy)pyridine | 330.0 332.0 | 1H NMR (300 MHz, CDCl3) δ 8.41 (d, J = 2.4 Hz, 1H), 8.37 (d, J = 2.4 Hz, 1H), 4.55 (t, J = 6.4 Hz, 2H), 2.68 (t, J = 7.4 Hz, 2H), 2.58 (t, J = 6.3 Hz, 4H), 2.12-2.01 (m, 2H), 1.86-1.75 (m, 4H). |
| AA-2-10 | 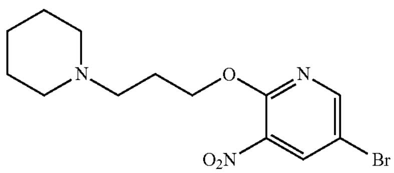 | 5-Bromo-3-nitro-2-(3-(piperidin-1-yl)propoxy)pyridine | 344.10, 346.10 | 1H NMR (300 MHz, CDCl3) δ 8.43 (d, J = 2.3 Hz, 1H), 8.40 (d, J = 2.3 Hz, 1H), 4.55 (t, J = 5.9 Hz, 2H), 3.03-2.75 (m, 6H), 2.33-2.22 (m, 2H), 1.90-1.80 (m, 4H), 1.63-1.53 (m, 2H). |
| AA-2-11 | 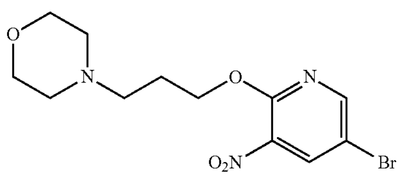 [SMILES: O=[N+]([O-])c1cc(Br)cnc1OCCCN1CCOCC1] | 4-[3-[(5-Bromo-3-nitropyridin-2-yl)oxy]propyl]morpholine | 346.00 348.00 | 1H NMR (300 MHz, DMSO-d6) δ 8.67 (dd, J = 10.6, 2.3 Hz, 2H), 4.47 (t, J = 6.4 Hz, 2H), 3.55 (t, J = 4.6 Hz, 4H), 2.45-2.32 (m, 6H), 1.90 (p, J = 6.8 Hz, 2H). |
| AA-2-12 | 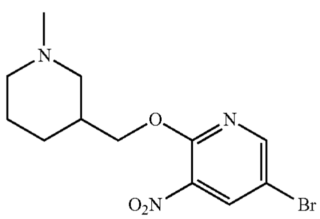 [SMILES: CN1CCCC(COc2ncc(Br)cc2[N+](=O)[O-])C1] | 5-Bromo-2-((1-methylpiperidin-3-yl)methoxy)-3-nitropyridine | 331.90 333.90 | 1H NMR (400 MHz, CDCl3) δ 8.44-8.40 (m, 2H), 4.42 (t, J = 5.4 Hz, 2H), 3.16 (br, 1H), 2.55 (br, 6H), 1.87 (s, 2H), 1.56 (br, 3H). |
| AA-2-13 | 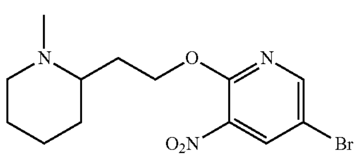 | 5-Bromo-2-(2-(1-methylpiperidin-2-yl)ethoxy)-3-nitropyridine | 344.05 346.05 | 1H NMR (400 MHz, DMSO-d6) δ 8.69 (d, J = 2.3 Hz, 1H), 8.66 (d, J = 2.3 Hz, 1H), 4.57-4.42 (m, 2H), 2.83 (s, 1H), 2.27 (s, 3H), 2.15 (br, 1H), 2.01 (s, 1H), 1.94-1.83 m, 1H), 1.65 (d, J = 11.6 Hz, 2H), 1.58-1.12 (m, 5H) |
| AA-2-14 | 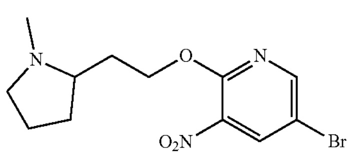 [SMILES: CN1CCCC1CCOc1ncc(Br)cc1[N+](=O)[O-]] | 5-Bromo-2-(2-(1-methylpyrrolidin-2-yl)ethoxy)-3-nitropyridine | 330.0 332.0 | 1H NMR (300 MHz, DMSO-d6) δ 8.72 (d, J = 2.3 Hz, 1H), 8.68 (d, J = 2.3 Hz, 1H), 4.56-4.49 (m, 2H), 3.41 (s, 1H), 3.17 (s, 1H), 2.89 (s, 1H), 2.70 (s, 3H), 2.40-2.25(m,1H), 2.25-2.12(m,1H), 2.06-1.81(m,3H), 1.71 (dt, J= 12.2, 8.2 Hz, 1H). |
| AA-2-15 | 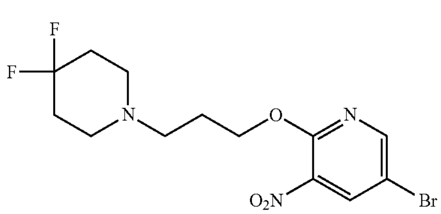 | 5-Bromo-2-[3-(4,4-difluoropiperidin-1-yl)propoxy]-3-nitropyridine | 379.95, 381.95 | 1H NMR (400 MHz, CDCl3) δ 8.39 (dd, J = 19.2, 2.3 Hz, 2H), 4.55 (t, J = 6.28 Hz, 2H), 2.65-2.54 (m, 6H), 2.00 (m, 6H). |

| Intermediate | Structure | Name | MS: [(M + 1)]+ | 1H-NMR |
|---|---|---|---|---|
| AA-2-16 | 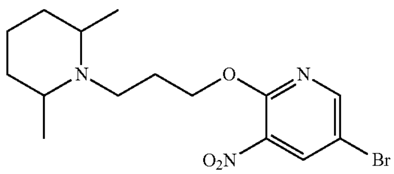 | 5-Bromo-2-[3-(2,6-dimethylpiperidin-1-yl)propoxy]-3-nitropyridine | 372.2, 374.2 | 1H NMR (400 MHz, DMSO-$d_6$) δ 8.68 (d, J = 2.4 Hz, 1H), 8.68 (dd, J = 2.4 Hz, 1H), 4.42 (t, J = 6.0 Hz, 2H), 2.83 (s, 2H), 2.40 (s, 2H), 1.82 (d, J = 10.3 Hz, 2H), 1.25 (d, J = 13.0 Hz, 2H), 1.12 (s, 2H), 1.05 (d, J = 6.4 Hz, 6H). |
| AA-2-17 | 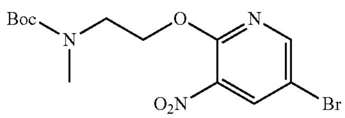 [SMILES: CN(CCOc1ncc(Br)cc1[N+](=O)[O-])C(=O)OC(C)(C)C] | tert-Butyl (2-((5-bromo-3-nitropyridin-2-yl)oxy)ethyl)(methyl)carbamate | 376.2 378.2 | 1H NMR (400 MHz, DMSO-$d_6$) δ 8.71 (d, J = 10.1 Hz, 1H), 8.66 (d, J = 2.3 Hz, 1H), 4.59-4.54 (m, 2H), 3.62-3.51 (m, 2H), 2.85 (d, J = 10.2 Hz, 3H), 1.31 (d, J = 25.8 Hz, 9H). |
| AA-2-18 | 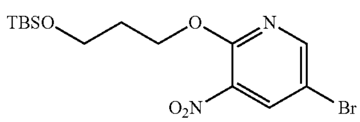 | 5-Bromo-2-(3-((tert-butyldimethylsilyl)oxy)propoxy)-3-nitropyridine | 391.20 393.20 | 1H NMR (400 MHz, $CDCl_3$) δ 8.42 (d, J = 2.4 Hz, 1H), 8.36 (d, J = 2.4 Hz, 1H), 4.56 (t, J = 6.2 Hz, 2H), 3.81 (t, J = 5.9 Hz, 3H), 2.01 (p, J = 6.2 Hz, 2H), 0.88 (s, 9H), 0.03 (s, 6H) |
| AA-2-19 | 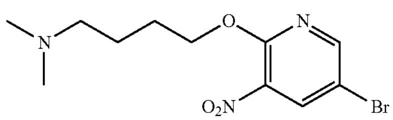 | 4-((5-Bromo-3-nitropyridin-2-yl) oxy)-N,N-dimethylbutan-1-amine | 318.05 320.05 | 1H NMR (300 MHz, DMSO-$d_6$) δ 8.71 (d, J = 2.3 Hz, 1H), 8.67 (d, J = 2.3 Hz, 1H), 4.45 (t, J = 5.8 Hz, 2H), 3.48-3.42 (m, 2H), 2.93 (t, J = 7.4 Hz, 2H), 2.61 (s, 6H), 2.10 (td, J = 5.5, 5.0, 2.6 Hz, 2H). |
| AA-2-20 | 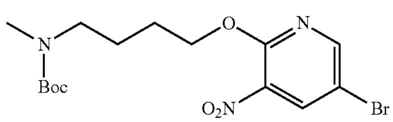 [SMILES: CN(CCCCOc1ncc(Br)cc1[N+](=O)[O-])C(=O)OC(C)(C)C] | tert-Butyl (4-((5-bromo-3-nitropyridin-2-yl)oxy)butyl)(methyl)carbamate | 404.00 406.00 | 1H NMR (400 MHz, $CDCl_3$) δ 8.38 (d, J = 2.4 Hz, 1H), 8.34 (d, J = 2.3 Hz, 1H), 4.46 (t, J = 6.3 Hz, 2H), 3.26 (t, J = 7.0 Hz, 2H), 2.83 (s, 3H), 1.83-1.74 (m, 2H), 1.72-1.63 (m, 2H), 1.42 (s, 9H). |

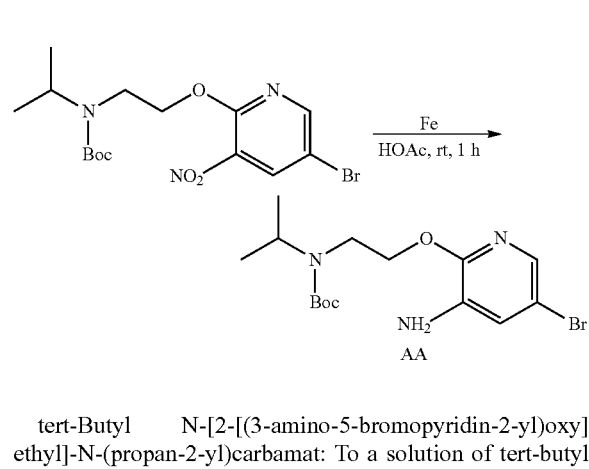

tert-Butyl N-[2-[(3-amino-5-bromopyridin-2-yl)oxy]ethyl]-N-(propan-2-yl)carbamat: To a solution of tert-butyl N-[2-[(5-bromo-3-nitropyridin-2-yl)oxy]ethyl]-N-(propan-2-yl)carbamat (15.0 g, 37.1 mmol) in acetic acid (150 mL) was added iron powder (20.7 g, 371 mmol) at ambient temperature. After stirring for additional 1 hour at ambient temperature, the resulting mixture was filtered and the filtered cake was washed with tetrahydrofuran (4×100 mL). The filtrate was concentrated under reduced pressure. The residue was purified by silica gel column chromatography, eluted with 20% ethyl acetate in petroleum ether. The desired fractions were collected and concentrated under reduced pressure to afford the title compound as a colorless solid (12.0 g, 86%): 1H NMR (400 MHz, $CD_3OD$) δ 7.40 (d, J=2.2 Hz, 1H), 7.04 (d, J=2.2 Hz, 1H), 4.40 (t, J=6.3 Hz, 2H), 4.25-3.99 (m, 1H), 3.52 (t, J=6.3 Hz, 2H), 1.46 (s, 9H), 1.17 (d, J=6.8 Hz, 6H), MS: [(M+1)]+=374.10, 376.10.

The following intermediates were prepared according to the procedure described above:

| Intermediate | Structure | Name | MS: [(M + 1)]⁺ | ¹H-NMR |
|---|---|---|---|---|
| AA1 | | 5-Bromo-2-(3-(dimethylamino)propoxy)pyridin-3-amine | 274.20 276.20 | ¹H NMR (300 MHz, DMSO-d₆) δ 7.36 (d, J = 2.3 Hz, 1H), 6.99 (d, J = 2.3 Hz, 1H), 5.25 (s, 2H), 4.23 (t, J = 6.6 Hz, 2H), 2.35 (t, J = 7.1 Hz, 2H), 2.13 (s, 6H), 1.99-1.75 (m, 2H). |
| AA2 | 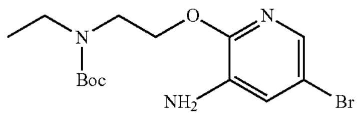 | tert-Butyl (2-((3-amino-5-bromopyridin-2-yl)oxy)ethyl)(ethyl)carbamate | 360.10 362.10 | ¹H NMR (400 MHz, CDCl₃) δ 7.54 (s, 1H), 6.98 (s, 1H), 4.42 (t, J = 5.7 Hz, 2H), 3.60 (s, 2H), 3.30 (d, J = 26.3 Hz, 2H), 1.45 (s, 9H), 1.12 (t, J = 6.9 Hz, 3H). |
| AA3 | 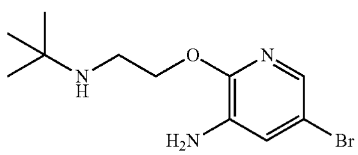 | 5-Bromo-2-(2-(tert-butylamino)ethoxy)pyridin-3-amine | 288.10 290.10 | ¹H NMR (400 MHz, CD₃OD) δ 7.42 (d, J = 2.1 Hz, 1H), 7.07 (d, J = 2.1 Hz, 1H), 4.45 (t, J = 5.3 Hz, 2H), 3.15 (t, J - 5.3 Hz, 2H), 1.25 (s, 9H). |
| AA4 | 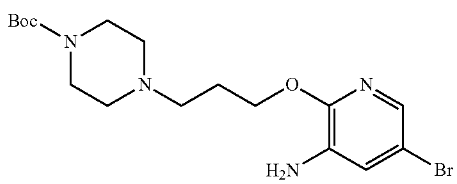 | tert-Butyl 4-(3-((3-amino-5-bromopyridin-2-yl)oxy)propyl)piperazine-1-carboxylate | 415.10 417.10 | ¹H NMR (400 MHz, DMSO-d₆) δ 7.37 (d, J = 2.2 Hz, 1H), 6.99 (d, J = 2.2 Hz, 1H), 5.25 (s, 2H), 4.25 (t, J = 6.5 Hz, 2H), 3.29 (t, J = 4.8 Hz, 4H), 2.44 (t, J = 7.2 Hz, 2H), 2.32 (t, J = 5.0 Hz, 4H), 1.87 (p, J = 6.9 Hz, 2H), 1.40 (s, 9H). |
| AA5 | 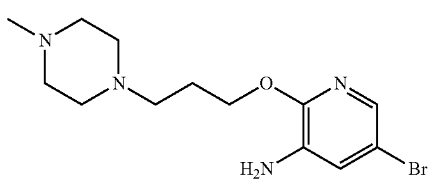 | 5-Bromo-2-(3-(4-methylpiperazin-1-yl)propoxy)pyridin-3-amine | 329.10 331.10 | ¹H NMR (400 MHz, CDCl₃) δ 7.55 (d, J = 2.1 Hz, 1H), 6.97 (d, J = 2.1 Hz, 1H), 4.36 (t, J = 6.4 Hz, 2H), 3.86 (s, 1H), 3.48 (s, 1H),2.67-2.43 (m, 8H), 2.31 (s, 3H), 1.99 (p, J = 7.1 Hz, 2H). |

| Intermediate | Structure | Name | MS: [(M + 1)]+ | 1H-NMR |
|---|---|---|---|---|
| AA6 | 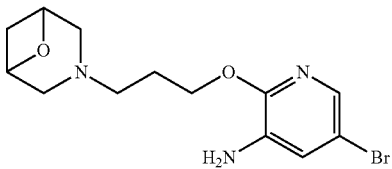 [SMILES: Nc1cc(Br)cnc1OCCCN1CC2CC(C1)O2] | 2-(3-(6-Oxa-3-azabicyclo[3.1.1]heptan-3-yl)propoxy)-5-Bromopyridin-3-amine | 328.10 330.10 | 1H NMR (400 MHz, CD3OD) δ 7.11 (d, J = 2.4 Hz, 1H), 6.66 (d, J = 2.4 Hz, 1H), 4.51 (d, J = 6.2 Hz, 2H), 4.04 (t, J = 7.0 Hz, 2H), 3.13 (d, J = 11.6 Hz, 2H), 3.00 (q, J = 6.5 Hz, 1H), 2.67 (d, J = 11.5 Hz, 2H), 2.60 (t, J = 6.8 Hz, 2H), 2.33 (d, J = 8.1 Hz, 1H), 1.97 (p, J = 6.6 Hz, 2H). |
| AA7 | 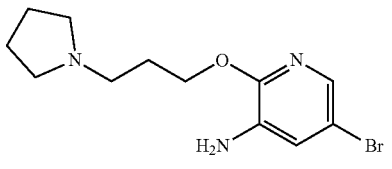 [SMILES: Nc1cc(Br)cnc1OCCCN1CCCC1] | 5-Bromo-2-(3-(pyrrolidin-1-yl)propoxy)pyridin-3-amine | 299.90 301.90 | 1H NMR. (400 MHz, CDCl3) δ 7.55 (d, J = 2.1 Hz, 1H), 6.97 (d, J = 2.2 Hz, 1H), 4.36 (t, J = 6.4 Hz, 2H), 3.88 (s, 2H), 2.67-2.61 (m, 2H), 2.59-2.54 (m, 4H), 2.08-2.00 (m, 2H), 1.83-1.78 (m, 4H). |
| AA8 | 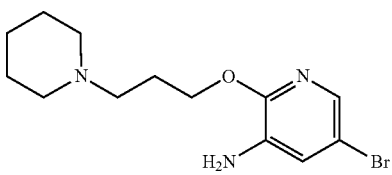 [SMILES: Nc1cc(Br)cnc1OCCCN1CCCCC1] | 5-Bromo-2-(3-(piperidin-1-yl)propoxy)pyridin-3-amine | 314.00 316.00 | 1H NMR (300 MHz, CDCl3) δ 7.54 (d, J = 2.2 Hz, 1H), 6.97 (d, J = 2.1 Hz, 1H), 4.35 (t, J = 6.3 Hz, 2H), 3.89 (s, 2H), 2.62-2.44 (m, 6H), 2.12-2.01 (m, 2H), 1.77-1.58 (m, 4H), 1.53-1.43 (m, 2H). |
| AA9 | 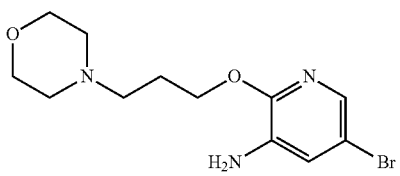 | 5-Bromo-2-(3-morpholinopropoxy)pyridin-3-amine | 316.05 318.05 | 1H NMR (400 MHz, CDCl3) δ 7.55 (d, J = 2.2 Hz, 1H), 6.98 (d, J = 2.2 Hz, 1H), 4.37 (t, J = 6.4 Hz, 2H), 3.86 (s, 2H), 3.74 (t, J = 4.7 Hz, 4H), 2.65-2.32 (m, 6H), 2.01 (p, J = 6.7 Hz, 2H). |
| AA10 | 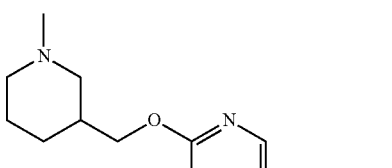 | 5-Bromo-2-((1-methylpiperidin-3-yl)methoxy)pyridin-3-amine | 300.05 302.05 | H NMR (400 MHz, CDCl3) δ 7.54 (d, J = 2.1 Hz, 1H), 6.98 (d, J = 2.2 Hz, 1H), 4.25-4.10(m, 2H), 3.84 (s, 2H), 3.06 (d, J = 10.9 Hz, 1H), 2.89 (s, 1H), 2.35 (s, 3H), 2.31-2.20 (m, 1H), 2.01 (s, 1H), 1.94-1.80 (m, 2H), 1.75 (s, 2H), 1.15-1.01 (m, 1H). |

-continued

| Intermediate | Structure | Name | MS: [(M + 1)]+ | 1H-NMR |
|---|---|---|---|---|
| AA11 | 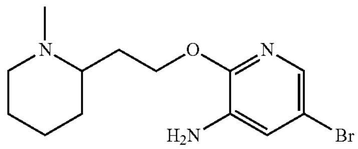 [SMILES: CN1CCCCC1CCOc1ncc(Br)cc1N] | 5-Bromo-2-(2-(1-methylpiperidin-2-yl)ethoxy)pyridin-3-amine | 314.15 316.15 | 1H NMR. (400 MHz, DMSO-$d_6$) δ 7.37 (d, J = 2.2 Hz, 1H), 6.99 (d, J = 2.2 Hz, 1H), 5.24 (s, 2H), 4.38-4.19 (m, 2H), 2.80 (s, 1H), 2.25 (s, 3H), 2.13 (d, J = 2.8 Hz, 1H), 1.98 (d, J = 9.7 Hz, 1H), 1.90-1.75 (m 1H), 1.71-1.57 (m, 2H), 1.57-1.39 (m, 2H), 1.39-1.13 (m, 3H). |
| AA12 | 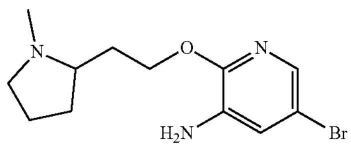 | 5-Bromo-2-(2-(1-methylpyrrolidin-2-yl)ethoxy)pyridin-3-amine | 300.00 302.00 | 1H NMR (300 MHz, DMSO-$d_6$) δ 7.38 (d, J = 2.2 Hz, 1H), 7.00 (d, J = 2.3 Hz, 1H), 5.23 (s, 2H), 4.36-4.19 (m, 2H), 3.41 (s, 1H), 3.01-2.91 (m, 1H), 2.24 (s, 3H), 2.14-2.00 (m, 2H), 1.99-1.85 (m, 1H), 1.73-1.56 (m, 3H), 1.55-1.42 (m, 1H). |
| AA13 | 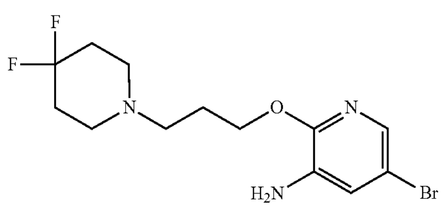 [SMILES: Nc1cc(Br)cnc1OCCCN1CCC(F)(F)CC1] | 5-Bromo-2-[3-(4,4-difluoropiperidin-1-yl)propoxy]pyridin-3-amine | 350.00 352.00 | 1H NMR (400 MHz, CDCl$_3$) δ 7.55 (d, J = 2.1 Hz, 1H), 6.98 (d, J = 2.1 Hz, 1H), 4.36 (t, J = 6.5 Hz, 2H), 3.85 (s, 2H), 2.62-2.53 (m, 6H), 2.09-1.93 (m, 6H). |
| AA14 | 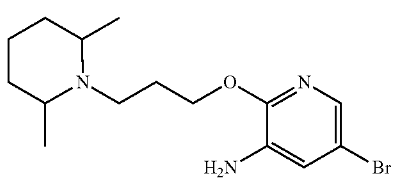 [SMILES: CC1CCCC(C)N1CCCOc1ncc(Br)cc1N] | 5-Bromo-2-[3-(2,6-dimethylpiperidin-1-yl)propoxy]pyridin-3-amine | 342.10 342.20 | 1H NMR (400 MHz, DMSO-$d_6$) δ 7.37 (d, J = 2.0 Hz, 1H), 7.00 (d, J = 2.4 Hz, 1H), 5.20 (s, 2H), 4.22 (t, J = 6.3 Hz, 2H), 2.77 (s, 2H), 2.36 (s, 2H), 1.78 (q, J = 8.4, 7.3 Hz, 2H), 1.35-1.09 (m, 4H), 1.02 (d, J = 6.2 Hz, 6H). |
| AA15 | 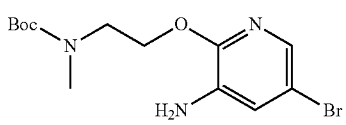 | tert-Butyl (2-((3-amino-5-bromopyridin-2-yl)oxy)ethyl(methyl)carbamate | 346.10 348.10 | 1H NMR (400 MHz, DMSO-$d_6$) δ 7.41-7.36 (m, 1H), 7.00 (d, J = 2.2 Hz, 1H), 5.22 (s, 2H), 4.33 (d, J = 20.2 Hz, 2H), 3.53 (s, 2H), 2.83 (t, J = 6.9 Hz, 3H), 1.42-1.27 (m, 9H). |

| Intermediate | Structure | Name | MS: [(M + 1)]+ | 1H-NMR |
|---|---|---|---|---|
| AA16 | Boc–N⟨azetidine⟩–CH2–O–pyridine(3-NH2, 5-Br) | tert-Butyl 3-(((3-amino-5-bromopyridin-2-yl)oxy)methyl)azetidine-1-carboxylate | 358.05 360.05 | Crude to the next step. |
| AA17 | (CH3)2N–CH(CH3)CH2CH2–O–pyridine(3-NH2, 5-Br) | 5-Bromo-2-(3-(dimethylamino)butoxy)pyridin-3-amine | 288.05 290.05 | 1H NMR (400 MHz, CDCl3) δ 7.55 (d, J = 2.1 Hz, 1H), 6.97 (d, J = 2.1 Hz, 1H), 4.44-4.31 (m, 2H), 3.93 (s, 2H), 3.00-2.89 (m, 1H), 2.35 (s, 6H), 2.21-2.10 (m, 1H), 1.80-1.70 (m, 1H), 1.10 (d, J = 6.6 Hz, 3H). |
| AA18 | TBSO–CH2CH2CH2–O–pyridine(3-NH2, 5-Br) | 5-Bromo-2-(3-((tert-butyldimethylsilyl)oxy)propoxy)pyridin-3-amine | 361.10 363.10 | 1H NMR (400 MHz, CDCl3) δ 7.55 (d, J = 2.2 Hz, 1H), 6.96 (d, J = 2.1 Hz, 1H), 4.40 (t, J = 6.3 Hz, 2H), 3.77 (t, J = 6.2 Hz, 2H), 1.99 (p, J = 6.2 Hz, 2H), 0.88 (s, 9H), 0.04 (s, 6H) |

Intermediate AA19

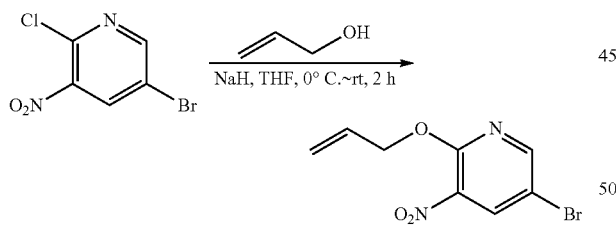

5-Bromo-3-nitro-2-(prop-2-en-1-yloxy)pyridine: To a solution of prop-2-en-1-ol (3.20 g, 55.2 mmol) in anhydrous tetrahydrofuran (200 mL) was added sodium hydride (2.28 g, 56.9 mmol, 60% w/w dispersed in mineral oil) at 0° C. under nitrogen atmosphere. The resulting mixture was stirred for 1 hour at ambient temperature followed by the addition of 5-bromo-2-chloro-3-nitropyridine (10.0 g, 42.1 mmol) over 2 minutes at 0° C. After stirring for additional 2 hours at ambient temperature, the reaction was quenched by saturated aqueous ammonium chloride (50.0 mL) and diluted with water (500 mL). The resulting mixture was extracted with ethyl acetate (3×150 mL). The combined organic layers was washed with brine (2×100 mL) and dried over anhydrous sodium sulfate. After filtration, the filtrate was concentrated under reduced pressure. The residue was purified by silica gel column chromatography, eluted with 1%~18% ethyl acetate in petroleum ether. The desired fractions were collected and concentrated under reduced pressure to afford the title compound as alight yellow oil (7.10 g, 66%): 1H NMR (400 MHz, CDCl3) δ 8.43 (d, J=2.4 Hz, 1H), 8.40 (d, J=2.4 Hz, 1H), 6.14-6.00 (m, 1H), 5.49 (dt, J=17.2, 1.6 Hz, 1H), 5.32 (dt, J=10.6, 1.5 Hz, 1H), 5.01 (dd, J=5.4, 1.5 Hz, 2H); MS: [(M+1)]+=259.00, 261.00.

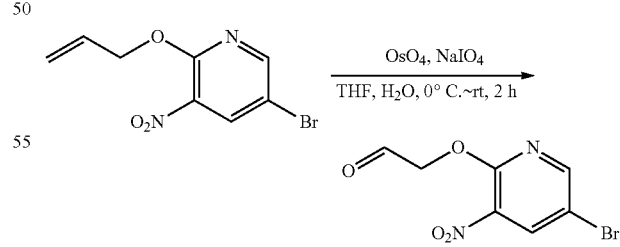

2-((5-Bromo-3-nitropyridin-2-yl)oxy)acetaldehyde: To a stirred mixture of 5-bromo-3-nitro-2-(prop-2-en-1-yloxy)pyridine (10.0 g, 38.6 mmol) and sodium periodate (20.6 g, 96.5 mmol) in tetrahydrofuran (200 mL) and water (200 mL) was added osmium(VIII) oxide (10.0 mL, 0.39 mmol, 1.00 g in 100 mL water) at 0° C. The resulting mixture was stirred for 2 hours at ambient temperature. The reaction was quenched by saturated aqueous sodium thiosulfate solution (10.0 mL) and diluted with water (300 mL). The resulting mixture was extracted with ethyl acetate (3×100 mL). The combined organic layers was washed with brine (2×100 mL) and dried over anhydrous sodium sulfate. After filtration, the filtrate was concentrated under reduced pressure. The residue was purified by silica gel column chromatography, eluted with 50% ethyl acetate in petroleum ether quickly within 10 minutes. The desired fractions were collected and concentrated under reduced pressure to afford the title compound as a light yellow solid (9.50 g, 95%): $^1$H NMR (400 MHz, CDCl$_3$) δ 9.74 (s, 1H), 8.48 (d, J=2.3 Hz, 1H), 8.39 (d, J=2.3 Hz, 1H), 5.07 (s, 2H); MS: [(M+1)]$^+$=260.90, 262.90.

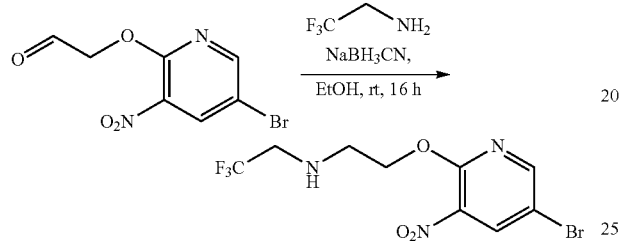

N-(2-((5-Bromo-3-nitropyridin-2-yl)oxy)ethyl)-2,2,2-trifluoroethan-1-amine: To a stirred solution of 2-((5-bromo-3-nitropyridin-2-yl)oxy)acetaldehyde (2.00 g, 7.66 mmol) and 2,2,2-trifluoroethan-1-amine (1.52 g, 15.2 mmol) in ethanol (25.0 mL) was added sodium cyanoborohydride (%~3 mg, 15.3 mmol) at ambient temperature. The resulting mixture was stirred under nitrogen atmosphere at ambient temperature for 16 hours. The resulting mixture was concentrated under reduced pressure. The residue was purified by silica gel column chromatography, eluted with 3%~35% ethyl acetate in petroleum ether. The desired fractions were collected and concentrated under reduced pressure to afford the title compound as a brown oil (406 mg, 16%): $^1$H NMR (400 MHz, CDCl$_3$) δ 8.49-8.39 (m, 2H), 4.58 (t, J=5.1 Hz, 2H), 3.33 (q, J=9.3 Hz, 2H), 3.20 (t, J=5.1 Hz, 2H); MS: [(M+1)]$^+$=344.00, 346.00.

The following intermediates were prepared according to the procedure described above:

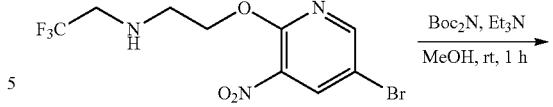

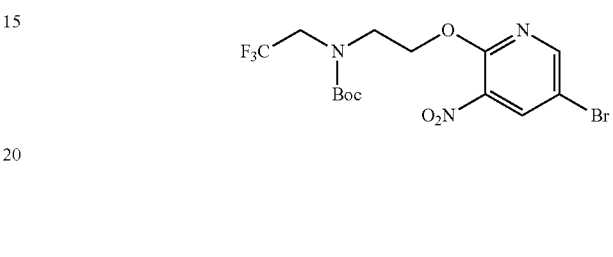

tert-Butyl (2-((5-bromo-3-nitropyridin-2-yl)oxy)ethyl(2,2,2-trifluoroethyl)carbamate: To stirred solution of N-(2-((5-bromo-3-nitropyridin-2-yl)oxy)ethyl)-2,2,2-trifluoroethan-1-amine (400 mg, 1.16 mmol) and di-tert-butyl pyrocarbonate (376 mg, 1.74 mmol) in methanol (10 mL) was added triethylamine (118 mg, 1.16 mmol) dropwise at ambient temperature. The resulting mixture was stirred at ambient temperature for 2 hours. The resulting mixture was concentrated under reduced pressure. The residue was purified by silica gel column chromatography, eluted with 3%~20% ethylacetate in petroleum ether. The desired fractions were collected and concentrated under reduced pressure to afford the title compound as a yellow oil (330 mg, 54%): $^1$H NMR (400 MHz, CDCl$_3$) δ 8.44 (d, J=2.9 Hz, 2H), 4.59 (dt, J=9.8, 5.0 Hz, 2H), 4.14-4.03 (m, 2H), 3.78 (dt, J=9.6, 5.0 Hz, 2H), 1.46 (s, 9H); MS: [(M+1)]$^+$=444.00, 446.00.

The following intermediates were prepared according to the procedure described above:

| Intermediate | Structure | Name | Ms: [(M + 1)]$^+$ | $^1$H NMR |
|---|---|---|---|---|
| AA19-1-1 | ![structure] | N-(2-((5-bromo-3-nitropyridin-2-yl)oxy)ethyl)-2,2-difluoroethan-1-amine | 326.00<br>328.00 | $^1$H NMR (400 MHz, CDCl$_3$) δ 8.43 (d, J = 2.3 Hz, 1H), 8.41 (d, J = 2.3 Hz, 1H), 5.88 (tt, J = 56.2, 4.3 Hz, 1H), 4.58 (t, J = 52 Hz, 2H), 3.18-3.04 (m, 4H). |
| AA19-1-2 | ![structure] | 2-((5-Bromo-3-nitropyridin-2-yl)oxy)-N-(2-fluoroethyl)ethan-1-amine | 308.00<br>310.00 | $^1$H NMR (400 MHz, DMSO-d$_6$) δ 8.70 (d, J = 2.3 Hz, 1H), 8.65 (d, J = 2.4 Hz, 1H), 4.54-4.46 (m, 3H), 4.39 (t, J = 5.0 Hz, 1H), 2.95 (t, J = 5.7 Hz, 2H), 2.90 (t, J = 5.0 Hz, 1H), 2.83 (t, J = 5.0 Hz, 1H). |

| Intermediate | Structure | Name | Ms: [(M + 1)]+ | 1H NMR |
| --- | --- | --- | --- | --- |
| AA19-2-1 | ![structure] | tert-Butyl (2-((5-bromo-3-nitropyridin-2-yl)oxy)ethyl)(2,2-difluoroethyl)carbamate | 426.05<br>428.05 | 1H NMR (400 MHz, CDCl3) δ 8.43 (d, J = 1.6 Hz, 2H), 5.92 (td, J = 56.3, 29.2 Hz, 1H), 4.59 (dt, J = 14.7, 5.2 Hz, 2H), 3.84-3.59 (m, 4H), 1.46 (s, J = 2.0 Hz, 9H). |
| AA19-2-2 | ![structure] | tert-Butyl (2-((5-bromo-3-nitropyridin-2-yl)oxy)ethyl)(2-fluoroethyl)carbamat | 408.0<br>410.0 | 1HNMR (400 MHz, DMSO-d6) δ 8.71 (d, J = 9.4 Hz, 1H), 8.65 (d, J = 2.3 Hz, 1H), 4.56 (q, J = 5.0 Hz, 3H), 4.45 (t, J = 5.1 Hz, 1H), 3.66-3.54 (m, 3H), 3.53-3.47 (m, 1H), 1.33 (d, J = 13.6 Hz, 9H). |

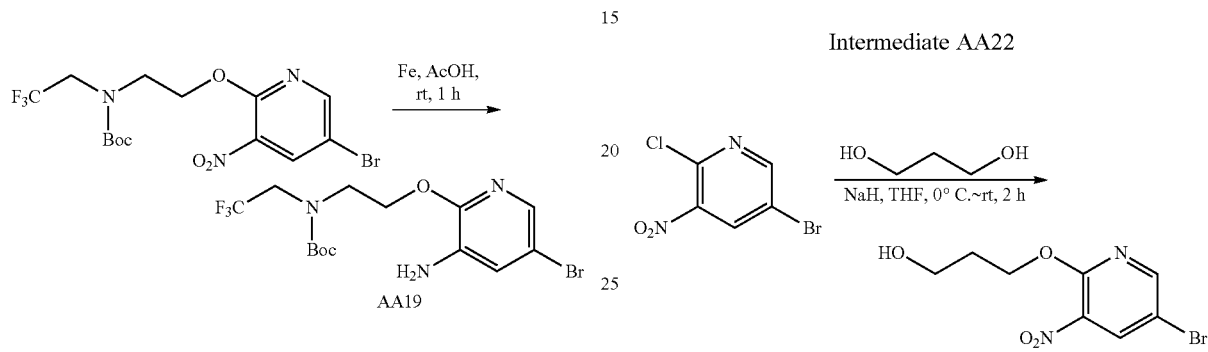

Intermediate AA22 tert-Butyl (2-((3-amino-5-bromopyridin-2-yl)oxy)ethyl)(2,2,2-trifluoroethyl)carbamate: To a solution of tert-butyl N-[2-[(5-bromo-3-nitropyridin-2-yl)oxy]ethyl]-N-(2,2,2-trifluromethyl)carbamate (330 mg, 0.74 mmol) in acetic acid (5 mL) was added iron powder (415 mg, 7.43 mmol) at ambient temperature. After stirring for 1 hour, the resulting mixture was filtered and the filtered cake was washed with tetrahydrofuran (6×80 mL). The filtrate was concentrated under reduced pressure. The residue was taken up with saturated aqueous sodium bicarbonate (20 mL). The resulting mixture was extracted with ethyl acetate (3×100 mL). The combined organic layers was washed with brine (3×100 mL) and dried over anhydrous sodium sulfate. After filtration, the filtrate was concentrated under reduced pressure. The residue was purified by silica gel column chromatography, eluted with 2%~10% ethyl acetate in petroleum ether to afford the title compound as a yellow oil (202 mg, 66%): 1H NMR (400 MHz, CDCl3) δ 7.59 (d, J=2.1 Hz, 1H), 7.06 (d, J=2.1 Hz, 1H), 4.55 (3, J=5.5 Hz, 2H), 4.16-3.96 (m, 2H), 3.93-3.84 (m, 2H), 1.46 (s, 9H): MS: [(M+1)]+=414.15, 416.15.

The following intermediates were prepared according to the procedure described above:

3-((5-Bromo-3-nitropyridin-2-yl)oxy)propan-1-ol: To a solution of 3-(dimethylamino)propan-1-ol (107 mg, 1.03 mmol) in anhydrous tetrahydrofuran (340 mL) was added sodium hydride (1.40 g, 35.0 mmol, 60% w/w dispersed in mineral oil) at 0° C. under nitrogen atmosphere. The resulting mixture was stirred for 30 minutes at 25° C. followed by the addition of 5-bromo-2-chloro-3-nitropyridine (6.78 g, 28.6 mmol) over 20 min at 0° C. After stirring for additional 2 hours at 25° C., the reaction was quenched by saturated aqueous ammonium chloride (50.0 mL) and diluted with water (150 mL). The resulting mixture was extracted with ethyl acetate (6×200 mL). The combined organic layers was washed with brine (100 mL) and dried over anhydrous sodium sulfate. After filtration, the filtrate was concentrated under reduced pressure. The residue was purified by silica gel column chromatography, eluted with 5%~20% ethyl acetate in petroleum ether. The desired fractions were collected and concentrated under reduced pressure to afford the title compound as a brown oil (4.70 g, 60%): 1H NMR (400 MHz, CDCl3) δ 8.44 (d, J=2.4 Hz, 1H), 8.41 (d, J=2.3 Hz, 1H), 4.65 (t, J=5.9 Hz, 2H), 3.87 (t, J=5.7 Hz, 2H), 2.09 (p, J=5.8 Hz, 2H); MS: [(M+1)]+=276.90, 278.90

| Intermediate | Structure | Name | Ms: [(M + 1)]+ | 1H NMR |
| --- | --- | --- | --- | --- |
| AA20 | ![structure] | tert-Butyl (2-((3-amino-5-bromopyridin-2-yl)oxy)ethyl)(2,2-difluoroethyl)carbamate | 396.15<br>398.15 | 1H NMR (400 MHz, CDCl3) δ 7.54 (s, 1H), 6.98 (s, 1H), 6.13-5.66 (m, 1H), 4.45 (t, J = 5.6 Hz, 2H), 3.91-3.49 (m, 4H), 1.44 (s, 9H). |
| AA21 | ![structure] | tert-Butyl (2-((3-amino-5-bromopyridin-2-yl)oxy)ethyl)(2-fluoroethyl)carbamate | 378.00<br>380.00 | 1H NMR (400 MHz, DMSO-d6) δ 7.37 (d, J = 2.1 Hz, 1H), 7.01 (s, 1H), 5.26 (s, 2H), 4.57 (t, J = 5.0 Hz, 1H), 4.45 (t, J = 5.1 Hz, 1H), 4.36 (s, 1H), 4.30 (s, 1H), 3.58 (s, 3H), 3.52 (t, J = 5.6 Hz, 1H), 1.36 (d, J= 22.4 Hz, 9H). |

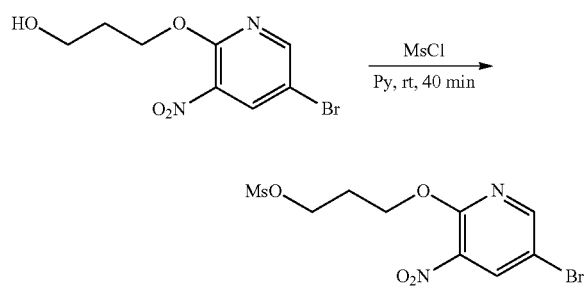

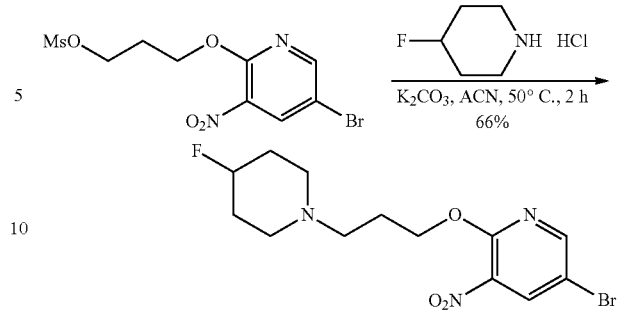

3-((5-Bromo-3-nitropyridin-2-yl)oxy)propyl methanesulfonate: To solution of 3-[(5-bromo-3-nitropyridin-2-yl)oxy]propan-1-ol (2.00 g, 7.22 mmol) in pyridine (25.0 mL) was added methanesulfonyl chloride (1.24 g, 10.8 mmol) at ambient temperature. The resulting mixture was stirred for 40 minutes at 25° C. under nitrogen atmosphere. The resulting mixture was concentrated under reduced pressure. The residue was purified by silica gel column chromatography, eluted with 5%~20% ethyl acetate in petroleum ether. The desired fractions were collected and concentrated under reduced pressure to afford the title compound as an orange solid (1.80 g, 71%): $^1$H NMR (400 MHz, CDCl$_3$) δ 8.44 (d, J=2.0 Hz, 1H), 8.40 (d, J=2.0 Hz, 1H), 4.61 (t, J=5.9 Hz, 2H), 4.47 (t, J=6.0 Hz, 2H), 3.03 (s, 3H), 2.28 (p, J=6.0 Hz, 2H); MS: [(M+1)]$^+$=354.95, 356.95.

5-Bromo-2-(3-(4-fluoropiperidin-1-yl)propoxy)-3-nitropyridine: To a solution of 4-fluoropiperidine hydrochloride (308 mg, 2.21 mmol) in acetonitrile (10.0 mL) were added 5-bromo-2-(3-bromopropoxy)-3-nitropyridine (500 mg, 1.47 mmol) and potassium carbonate (366 mg, 2.65 mmol). The resulting mixture was stirred for 2 hours at 50° C. The resulting mixture was concentrated under reduced pressure. The residue was purified by silica gel column chromatography, eluted with 20%~50% ethyl acetate in petroleum ether to afford the title compound as a light brown oil (350 mg, 66%): $^1$H NMR (400 MHz, CD$_3$OD) δ 8.52 (d, J=2.3 Hz, 1H), 8.51 (d, J=2.4 Hz, 1H), 4.74-4.57 (m, 1H), 4.53 (t, J=6.2 Hz, 2H), 2.68-2.56 (m, 4H), 2.46 (s, 2H), 2.06-1.99 (m, 2H), 1.96-1.78 (m, 4H); MS: [(M+1)]$^+$=362.05, 364.05

The following intermediates were prepared according to the procedure described above:

| Intermediate | Structure | Name | Ms: [(M + 1)]$^+$ | $^1$H-NMR |
| --- | --- | --- | --- | --- |
| AA22-1-1 | 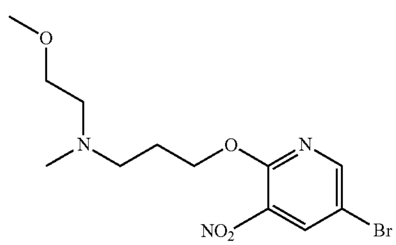 | 3-((5-Bromo-3-nitropyridin-2-yl)oxy)-N-(2-methoxyethyl)-N-methylpropan-1-amine | 348.10 350.10 | $^1$H NMR (400 MHz, CDCl$_3$) δ 8.42 (d, J = 2.3 Hz, 1H), 8.37 (d, J = 2.5 Hz, 1H), 4.54 (t, J = 6.2 Hz, 2H), 3.54 (s, 2H), 3.34 (s, 3H), 2.67 (s, 4H), 2.37 (s, 3H), 2.12-1.99 (m, 2H). |
| AA22-1-2 | 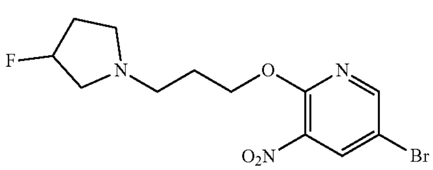 [SMILES: O=[N+]([O-])c1cc(Br)cnc1OCCCN1CCC(F)C1] | 5-Bromo-2-(3-(3-fluoropyrrolidin-1-yl)propoxy)-3-nitropyridine | 347.95 349.95 | $^1$H NMR (400 MHz, CDCl$_3$) δ 8.43 (d, J = 2.3 Hz, 1H), 8.38 (d, J = 2.4 Hz, 1H), 5.30-5.07 (m, 1H), 4.56 (t, J = 6.3 Hz, 2H), 3.03-2.38 (m, 6H), 2.25-2.01 (m, 4H). |
| AA22-1-3 | 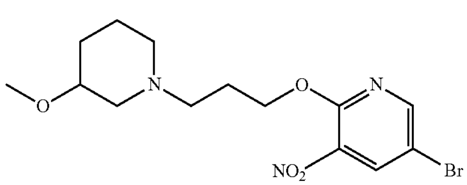 [SMILES: COC1CCCN(CCCOc2ncc(Br)cc2[N+](=O)[O-])C1] | 5-Bromo-2-(3-(3-methoxypiperidin-1-yl)propoxy)-3-nitropyridine | 374.10 376.10 | $^1$H NMR (400 MHz, CDCl$_3$) δ 8.45-8.39 (m, 1H), 8.39-8.34 (m, 1H), 4.52 (t, J = 6.4 Hz, 2H), 3.36 (s, 3H), 3.33-3.23 (m, 1H), 2.90 (d, J = 10.9 Hz, 1H), 2.72-2.59 (m, 1H), 2.55 (t, J = 7.3 Hz, 2H), 2.16-1.97 (m, 4H), 1.92 (d, J = 12.2 Hz, 1H), 1.80-1.69 (m, 1H), 1.57-1.40 (m, 1H), 1.33-1.21 (m, 1H). |

-continued

| Intermediate | Structure | Name | Ms: [(M + 1)]+ | 1H-NMR |
| --- | --- | --- | --- | --- |
| AA22-1-4 | 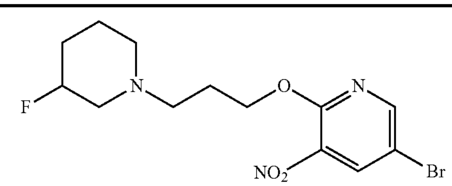 | 5-Bromo-2-(3-(3-fluoropiperidin-1-yl)propoxy)-3-nitropyridine | 362.00<br>364.00 | 1H NMR (400 MHz, DMSO-d6) δ 8.69 (d, J = 2.4 Hz, 1H), 8.65 (d, J = 2.3 Hz, 1H), 4.69-4.49 (m, 1H), 4.45 (t, J = 6.4 Hz, 2H), 2.76-2.63 (m, 1H), 2.48-2.37 (m, 3H), 2.37-2.26 (m, 1H), 2.25-2.16 (m, 1H), 1.89 (p, J = 6.8 Hz, 2H), 1.85-1.74 (m, 1H), 1.74-1.62 (m, 1H), 1.58-1.36 (m, 2H). |
| AA22-1-5 | 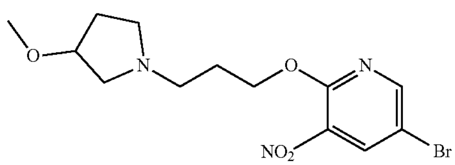 | 5-Bromo-2-(3-(3-methoxypyrrolidin-1-yl)propoxy)-3-nitropyridine | 360.05<br>362.05 | 1H NMR (400 MHz, CDCl3) δ 8.41 (d, J = 2.3 Hz, 1H), 8.37 (d, J = 2.4 Hz, 1H), 4.54 (t, J = 6.3 Hz, 2H), 3.93 (s, 1H), 3.29 (s, 3H), 2.84-2.25 (m, 6H), 2.14-2.01 (m, 3H), 1.84 (s, 1 H). |
| AA22-1-6 | 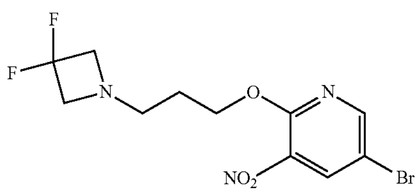 [SMILES: O=[N+]([O-])c1cc(Br)cnc1OCCCN1CC(F)(F)C1] | 5-Bromo-2-(3-(3,3-difluoroazetidin-1-yl)propoxy)-3-nitropyridine | 352.00<br>354.00 | 1H NMR (400 MHz, CDCl3)) δ 8.44 (d, J = 2.6 Hz, 1H), 8.40 (d, J = 2.0 Hz, 1H), 4.58-4.51 (m, 2H), 3.65-3.59 (m, 4H), 2.81-2.77 (m, 2H), 1.96-1.74 (m, 2H). |
| AA22-1-7 | 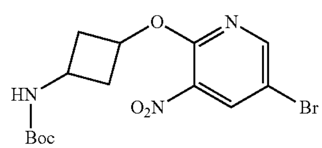 [SMILES: CC(C)(C)OC(=O)NC1CC(Oc2ncc(Br)cc2[N+](=O)[O-])C1] | tert-Butyl (3-((5-bromo-3-nitropyridin-2-yl)oxy)cyclobutyl)carbamate | 388.00<br>390.00 | used to next step without further purification |
| AA22-1-8 | 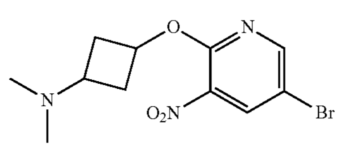 [SMILES: CN(C)C1CC(Oc2ncc(Br)cc2[N+](=O)[O-])C1] | 3-((5-Bromo-3-nitropyridin-2-yl)oxy)-N,N-dimethylcyclobutan-1-amine | 316.05<br>318.05 | used to next step without further purification |

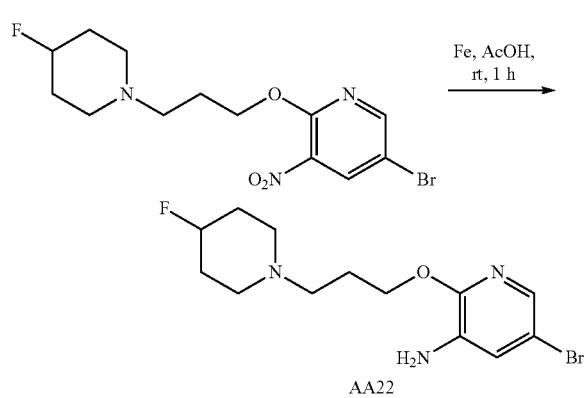

AA22

5-Bromo-2-(3-(4-fluoropiperidin-1-yl)propoxy)pyridin-3-amine: A mixture of 5-bromo-2-[3-(4-fluoropiperidin-1-yl)propoxy]-3-nitropyridin (350 mg, 0.97 mmol) and iron powder (270 mg, 4.83 mmol) in acetic acid (2.00 mL) was stirred for 1 hour at ambient temperature. The resulting mixture was filtered and the filtered cake was washed with ethyl acetate (3×40.0 mL). The filtrate was concentrated under reduced pressure. The residue was taken up with saturated aqueous sodium bicarbonate (20.0 mL). The resulting mixture was extracted with ethyl acetate (5×20.0 mL). The combined organic layers was washed with brine (10.0 mL) and dried over anhydrous sodium sulfate. After filtration, the filtrate was concentrated under reduced pressure. The residue was purified by silica gel column chromatography, eluted with 1%~2% methanol in dichloromethane to afford the title compound as alight brown solid (280 mg, 87%): 1H NMR (400 MHz, CDCl3) δ 7.54 (d, J=2.0 Hz, 1) 6.97 (d, J=2.1 Hz, 1H), 4.73 (d, J=48.8 Hz, 1H), 4.35 (t, J=6.3 Hz, 2H), 2.61 (dt, J=21.0, 12.4 Hz, 6H), 2.05-1.82 (m, 6H); MS: [(M+1)]+=332.10, 334.05

The following intermediates were prepared according to the procedure described above:

| Intermediate | Structure | Name | MS: [(M + 1)]+ | 1H-NMR |
|---|---|---|---|---|
| AA23 | 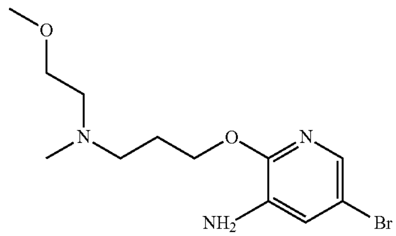 | 5-Bromo-2-(3-((2-methoxyethyl)(methyl)amino)propoxy)pyridin-3-amine | 318.10<br>320.10 | 1H NMR (400 MHz, CDCl3) δ 7.55 (d, J = 2.1 Hz, 1H), 6.97 (d, J = 2.1 Hz, 1H), 4.36 (t, J = 6.4 Hz, 2H), 3.87 (s, 2H), 3.53 (s, 2H), 3.35 (s, 3H), 2.66 (s, 4H), 2.36 (s, 3H), 2.03 (s, 2H). |
| AA24 | 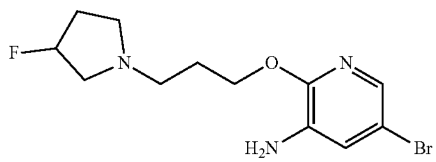 | 5-Bromo-2-(3-(3-fluoropyrrolidin-1-yl)propoxy)pyridin-3-amine | 318.05<br>320.05 | 1H NMR (400 MHz, CDCl3) δ 7.62-7.53 (m, 1H), 7.03-6.94 (m, 1H), 5.18 (d, J = 55.3 Hz, 1H), 4.38 (t, J = 6.4 Hz, 2H), 3.86 (s, 2H), 3.01-2.43 (m, 6H), 2.23-1.97(m, 4H). |
| AA25 | 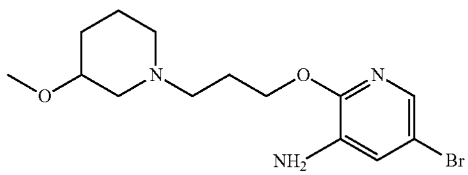 | 5-Bromo-2-(3-(3-methoxypiperidin-1-yl)propoxy)pyridin-3-amine | 344.10<br>346.10 | 1H NMR (400 MHz, CDCl3) δ 7.55 (s, 1H), 6.97 (s, 1H), 4.35 (t, J = 6.5 Hz, 2H), 3.86 (s, 2H), 3.37 (s, 4H), 2.97 (d, J = 25.7 Hz, 1H), 2.68 (s, 1H), 2.55 (s, 3H), 2.21-1.87 (m, 5H), 1.76 (s, 1H), 1.55 (s, 1 H), 1.39-1.29 (m, 1 H). |
| AA26 | 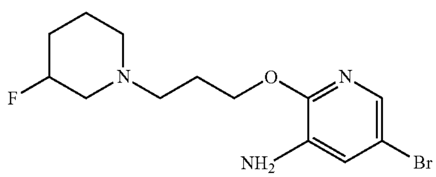 | 5-Bromo-2-(3-(3-fluoropiperidin-1-yl)propoxy)pyridin-3-amine | 331.95<br>333.95 | 1H NMR (400 MHz, DMSO-d6) δ 7.36 (d, J = 2.2 Hz, 1H), 6.98 (d, J = 2.2 Hz, 1H), 5.26 (s, 2H), 4.74-4.48 (m, 1H), 4 23 (t, J = 6.5 Hz, 2H), 2.81-2.64 (m, 1H), 2.46 (t, J = 7.1 Hz, 3H), 2.37-2.27 (m, 1H), 2.19 (t, J = 10.0 Hz, 1H), 1.86 (p, J = 6.9 Hz, 2H), 1.82-1.75 (m, 1H), 1.74-1.62 (m, 1H), 1.56-1.36 (m, 2H). |
| AA27 | 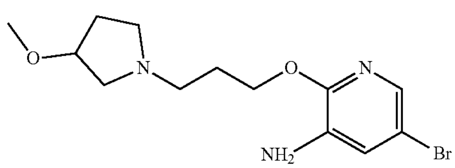 | 5-Bromo-2-(3-(3-methoxypyrrolidin-1-yl)propoxy)pyridin-3-amine | 330.05<br>332.05 | 1H NMR (400 MHz, CDCl3) δ 7.54 (d, J = 2.0Hz, 1H), 6.96 (d, J = 2.0 Hz, 1H), 4.36 (t, J = 6.4 Hz, 2H), 4.02-3.85 (m, 3H), 3.29 (s, 3H), 2.79-2.67 (m, 2H), 2.63 (dd, J = 9.7, 4.9 Hz, 3H), 2.51 (q, J = 7.9 Hz, 1H), 2.13-1.97 (m, 3H), 1.88-1.78 (m, 1H). |
| AA29 | 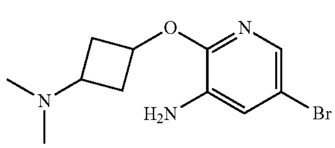 | 5-Bromo-2-(3-(dimethylamino)cyclobutoxy)pyridin-3-amine | 286.00<br>288.00 | used to next step without further purification |
| AA30 | 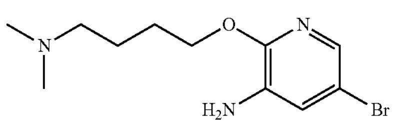 [SMILES: CN(C)CCCCOc1ncc(Br)cc1N] | 5-Bromo-2-(4-(dimethylamino)butoxy)pyridin-3-amine | 288.00<br>290.00 | 1H NMR (300 MHz, CD3OD) δ 7.40 (d, J = 2.2 Hz, 1H), 7.04 (d, J = 2.2 Hz, 1H), 4.33 (t, J = 6.1 Hz, 2H), 2.69-2.60 (m, 2H), 2.45 (s, 6H), 1.86-1.69 (m, 4H). |
| AA31 | 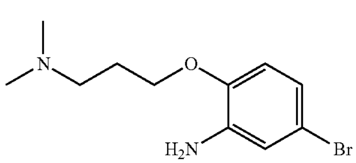 | 5-Bromo-2-(3-(dimethylamino)propoxy)aniline | 273.10<br>275.10 | 1H NMR (400 MHz, CD3OD) δ 6.85 (dd, J = 1.7, 0.8 Hz, 1H), 6.71 (d, J = 1.8 Hz, 2H), 4.86 (s, 7H), 4.01 (t, J = 6.1 Hz, 2H), 2.61-2.52 (m, 2H), 2.30 (s, 6H), 2.05-1.93 |

| Intermediate | Structure | Name | MS: [(M + 1)]+ | 1H-NMR |
|---|---|---|---|---|
| | | | | (m, 2H). |
| AA32 | 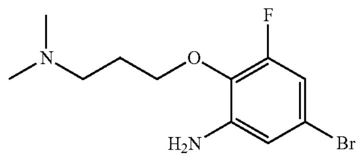 [SMILES: CN(C)CCCOc1c(N)cc(Br)cc1F] | 5-Bromo-2-(3-(dimethylamino)propoxy)-3-fluoroaniline | 291.10<br>293.10 | 1H NMR (400 MHz, CDCl3) δ 6.63-6.53 (m, 2H), 4.58 (s, 2H), 4.02 (t, J = 5.9 Hz, 2H), 2.56 (t, J = 6.8 Hz, 2H), 2.29 (s, 6H), 1.97 (p, J = 5.6 Hz, 2H). |

Intermediate AA28

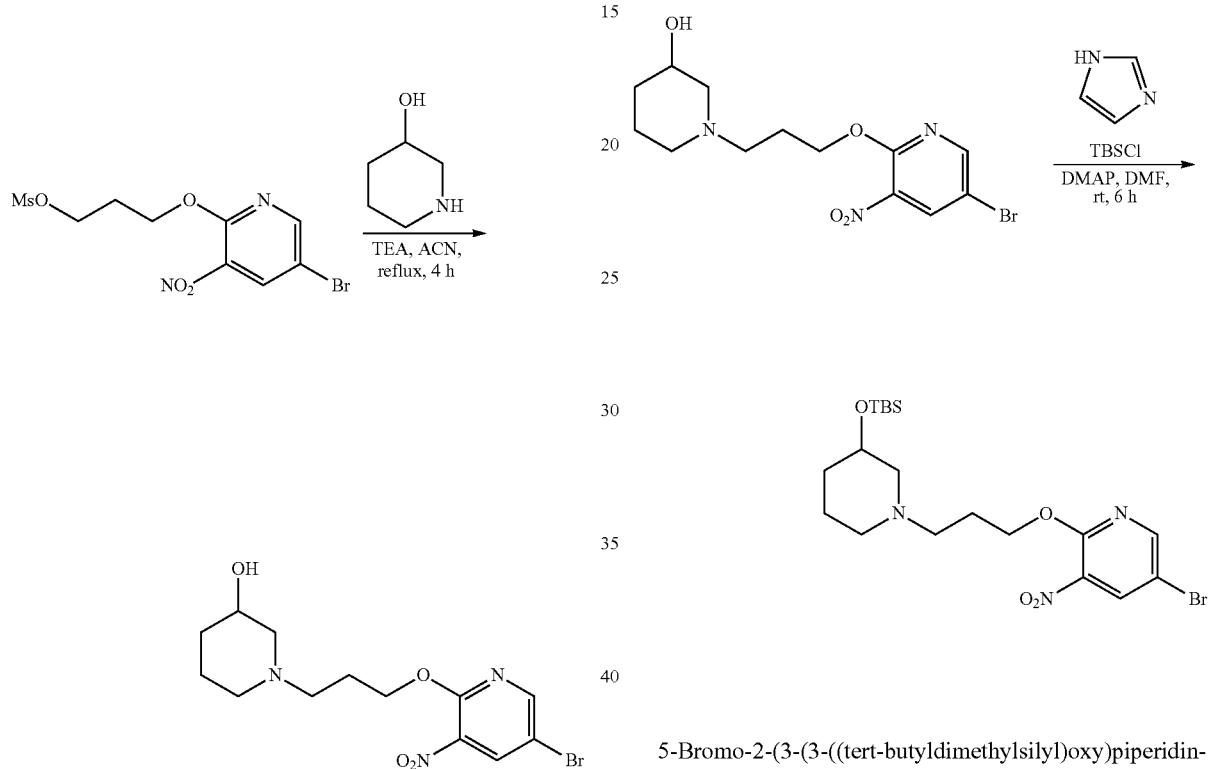

1-(3-((5-Bromo-3-nitropyridin-2-yl)oxy)piperidin-2-yl)oxy)piperidin-3-ol: To a stirred solution of 3-((5-bromo-3-nitropyridin-2-yl)oxy)propyl methanesulfonate (900 mg, 2.53 mmol) and triethylamine (513 mg, 5.07 mmol) in acetonitrile (12.0 mL) was added piperidin-3-(769 mg, 7.60 mmol) at ambient temperature. After stirring for 4 hours at 80° C. under nitrogen atmosphere, the resulting mixture was concentrated under reduced pressure. The residue was purified by silica gel column chromatography, eluted with 1%~3% methanol in dichlormethane. The desired fractions were collected and concentrated under reduced pressure to afford the title compound as a brown oil (568 mg, 66%): 1H NMR (400 MHz, CDCl3) δ 8.42 (d, J J=2.4 Hz, 1H), 8.37 (d, J=2.4 Hz, 1H), 4.54 (td, J=6.3, 2.0 Hz, 2H), 3.89 (s, 1H), 2.66 (s, 5H), 2.38 (s, 1H), 2.15-2.00 (m, 2H), 1.90 (s, 1H), 1.62 (s, 3H); MS: [(M+1)]+=360.00, 362.00.

5-Bromo-2-(3-(3-((tert-butyldimethylsilyl)oxy)piperidin-1-yl)propoxy)-3-nitropyridine: To a solution of 1-(3-((5-bromo-3-nitropyridin-2-yl)oxy)propyl)piperidin-3-ol (650 mg, 1.80 mmol) and N,N-4-dimethylaminopyridine (66.1 mg, 0.54 mmol) in N,N-dimethylformamide (17.0 mL) were added 1H-imidazole (246 mg, 3.61 mmol) and tert-butyldimethylsilyl chloride (1.09 g, 7.22 mmol). The resulting mixture was stirred for 16 hours h at 25° C. The resulting solution was diluted with water (300 mL). The resulting mixture was extracted with ethyl acetate (4×100 mL). The combined organic layers was washed with brine (150 mL), dried over anhydrous sodium sulfate. After filtration, the filtrate was concentrated under reduced pressure. The residue was purified by silica gel column chromatography, eluted with 5%~20% ethyl acetate in petroleum ether. The desired fractions were collected and concentrated under reduced pressure to afford the title compound as a brown oil (731 mg, 86%): 1H NMR (400 MHz, CDCl3) δ 8.41 (d, J=2.4 Hz, 1H), 8.36 (d, J=2.4 Hz, 1H), 4.52 (t, J=6.4 Hz, 2H), 3.68 (s, 1H), 2.89 (d, J=10.6 Hz, 1H), 2.76 (d, J=11.1 Hz, 1H), 2.54 (t, J=6.3 Hz, 2H), 2.06-1.%~6 (m, 2H), 1.92-1.80 (m, 3H), 1.68 (d, J=13.4 Hz, 1H), 1.50 (d, J=13.6 Hz, 1H), 1.29-1.14 (m, 1H), 0.88 (s, 9H), 0.06 (s, 6H); MS: [(M+1)]+=473.80, 475.80.

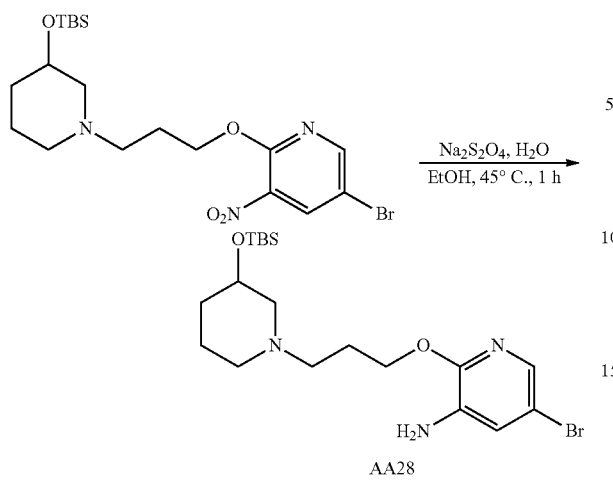

AA28

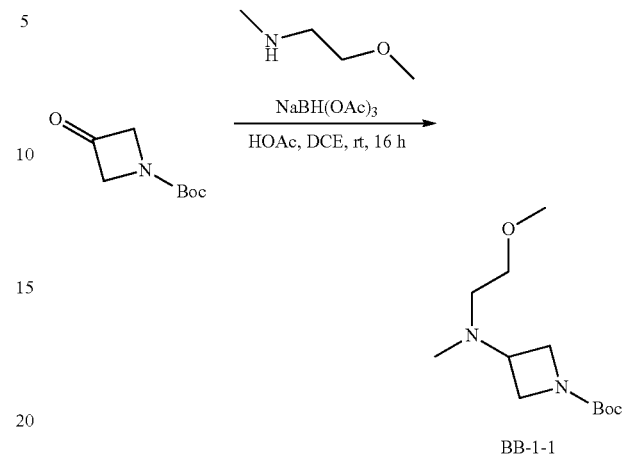

Intermediate BB

BB-1-1

5-Bromo-2-(3-(3-((tert-butyldimethylsilyl)oxy)piperidin-1-yl)propoxy)pyridin-3-amine: To a solution of 5-bromo-2-(3-(3-((tert-butyldimethylsilyl)oxy)piperidin-1-yl)propoxy)-3-nitropyridine (731 mg, 1.54 mmol) in ethanol (8.00 mL) and water (2.00 mL) was added sodium hyposulfite (1.34 g, 7.70 mmol) at ambient temperature. The resulting mixture was stirred for 1 hour at 45° C. The resulting mixture was concentrated under reduced pressure. The residue was purified by reverse phase flash chromatography with the following conditions: Column: Spherical C18, 20~40 μm, 120 g; Mobile Phase A: Water (plus 10 mM NH$_4$HCO$_3$ and 0.05% NH$_3$·H$_2$O); Mobile Phase B: acetonitrile; Flow rate: 45 mL/min; Gradient (B %): 5%~20%, 4 min; 20%~25%, 5 min; 25%, 3 min; 25%~95%; 3 min; 95%, 5 min; Detector: UV 254 nm; Rt: 15 min. The desired fractions were collected and concentrated under reduced pressure to afford the title compound as a colorless solid (646 mg, 95%): $^1$H NMR (400 MHz, CDCl$_3$) δ 7.55 (d, J=2.4 Hz, 1H), 6.98 (d, J=2.4 Hz, 1H), 4.73 (s, 2H), 4.35 (t, J=6.6 Hz, 2H), 3.91 (s, 1H), 2.91 (d, J=10.5 Hz, 1H), 2.78 (d, J=10.9 Hz, 1H), 2.56 (s, 2H), 2.06-1.97 (m, 6H), 1.77-1.70 (m, 1H), 1.30-1.19 (m, 1H), 0.90 (s, 9H), 0.08 (s, 6H); MS: [(M+1)]$^+$=444.15, 446.15.

tert-Butyl 3-((2-methoxyethyl)(methyl)amino)azetidine-1-carboxylate: To a stirred solution of (2-methoxyethyl)(methyl)amine (1.00 g, 11.2 mmol), tert-butyl 3-oxoazetidine-1-carboxylate (1.60 g, 9.35 mmol) and acetic acid (562 mg, 9.35 mmol) in 1,2-dichloroethane (35.0 mL) was added triacetoxyborohydride (2.97 g, 14.0 mmol) in portions at ambient temperature. The resulting mixture was stirred for 16 hours at 25° C. under nitrogen atmosphere. The resulting mixture was concentrated under reduced pressure. The residue was purified by silica gel column chromatography, 1%~5% methanol in dichloromethane. The desired fractions were collected and concentrated under reduced pressure to afford the title compound as a light yellow solid (2.20 g, 9%: $^1$H NMR (400 MHz, CDCl$_3$) δ 3.96-3.87 (m, 2H), 3.82 (dd, J=8.8, 5.5 Hz, 2H), 3.47 (t, J=5.5 Hz, 2H), 3.35 (s, 3H), 3.29-3.12 (m, 1H), 2.50 (t, J=5.5 Hz, 2H), 2.21 (s, 3H), 1.43 (s, 9H); MS: [(M+1)]$^+$=245.40.

The following intermediates were prepared according to the procedure described above (BB-1-1):

| Intermediate | Structure | Name | Ms: [(M + 1)]$^+$ | $^1$H NMR |
|---|---|---|---|---|
| BB-1-2 | ![structure] | tert-Butyl 3-(ethyl(methyl)amino)azetidine-1-carboxylate | 215.20 | $^1$H NMR (400 MHz, CDCl$_3$) δ 4.09-3.91 (m, 4H), 3.51-3.43 (m, 1H), 2.61 (q, J = 7.3 Hz, 2H), 2.34 (s, 3H), 1.16 (t, J = 7.3 Hz, 3H). |
| BB-1-3 | ![structure] | ter-Butyl 3-(isopropylamino)azetidine-1-carboxylate | 215.20 | $^1$H NMR (400 MHz, DMSO-d$_6$) δ 3.97-3.85 (m, 2H), 3.52 (d, J = 6.8 Hz, 3H), 2.70 (hept, J = 6.2 Hz, 1H), 1.37 (s, 9H), 0.93 (d, J = 6.2 Hz, 6H). |
| BB-1-4 | ![structure] | tert-Butyl 3-(ethyl(4-methoxybenzyl)amino)azetidine-1-carboxylate | 321.20 | $^1$H NMR (400 MHz, CDCl$_3$) δ 7.18 (d, J = 8.4 Hz, 2H), 6.85 (d, J = 8.4 Hz, 2H), 4.17-4.07 (m, 2H), 3.89 (t, J = 8.1 Hz, 2H), 3.80 (s, 3H), 3.56 (s, 2H), 3.54-3.45 (m, 1H), 2.49 (q, J = 7.1 Hz, 2H), 1.43 (s, 9H), 1.03 (t, J = 7.1 Hz, 3H). |

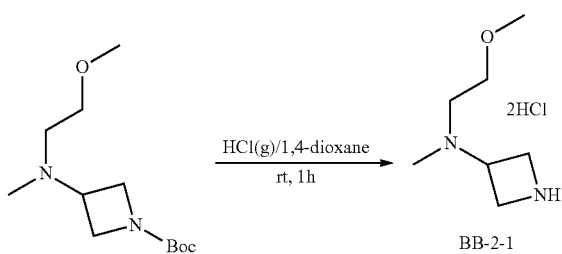

N-(2-Methoxyethyl)-N-methylazetidin-3-amine hydrochloride: tert-Butyl-3-[(2-methylethyl)(methyl)amino]azetidine-1-carboxylate (2.50 g, 10.2 mmol) was treated with hydrogen chloride (10 mL, 4 M in 1,4-dioxane) for 1 hour at 25° C. The resulting mixture was concentrated under reduced pressure to afford the title compound as light yellow solid (1.40 g, 95%): $^1$H NMR (400 MHz, CDCl$_3$) δ 3.96-3.87 (m, 2H), 3.82 (dd J=8.8, 5.5 Hz, 2H), 3.47 (t, J=5.5 Hz, 2H), 3.35 (s, 3H), 3.29-3.12 (m, 1H), 2.50 (t, J=5.5H, 2H), 2.21 (s, 3H), 1.43 (s, 9H); MS: [(M+1)]$^+$=145.10.

The following intermediates were prepared according to the procedure described above:

tert-Butyl 3,3-difluoro-[1,4'-bipiperidine]-1'-carboxylate: A solution of 3,3-difluoropiperidine hydrochloride (1.00 g, 6.35 mmol) and tert-butyl 4-oxopiperidine-1-carboxylate (1.26 g, 6.35 mmol) in N,N-dimethylformamide (20 mL) was added diisopropylethylamine (0.082 g, 0.63 mmol) at ambient temperature. The reaction mixture was stirred at 50° C. under nitrogen for 2 hours. The reaction mixture was cooled down to ambient temperature, followed by the additions of acetic acid (0.38 g, 6.35 mmol) and sodium triacetoxyborohydride (3.36 g, 15.9 mmol) and the reaction mixture was stirred at 50° C. under nitrogen for 5 hours. The above solution was diluted with saturated sodium bicarbonate (30.0 mL) and extracted with ethyl acetate (3×30.0 mL). The combined organic phases was dried over anhydrous sodium sulphate and filtered. The filtrate was concentrated under reduced pressure. The residue was purified by silica gel column chromatography, eluted with 2%~9% methanol in dichloromethane. The desired fractions were collected and concentrated under reduced pressure to afford the title compound as a light yellow oil (0.70 g, 36%): MS: [(M+1)]$^+$=305.3.

| Intermediate | Structure | Name | Ms: [(M + 1)]$^+$ | $^1$H NMR |
|---|---|---|---|---|
| BB-2-2 | 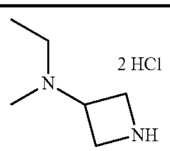 | N-Ethyl-N-methylazetidin-3-amine hydrochloride | 115.10 | crude |
| BB-2-3 | 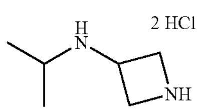 | N-Isopropylazetidin-3-amine hydrochloride | 115.10 | $^1$H NMR (400 MHz, DMSO-d$_6$) δ 10.31 (s, 2H), 9.77 (s, 1H), 9.28 (s, 1H), 4.41-4.21 (m, 3H), 4.18-4.08 (m, 2H), 3.36-3.23 (m, 1H), 1.21 (d, J = 6.5 Hz, 6H). |
| BB-2-4 | 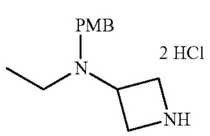 | N-Ethyl-N-(4-methoxybenzyl)azetidin-3-amine hydrochloride | 221.20 | $^1$H NMR (400 MHz, CD$_3$OD) δ 7.59-7.55 (m, 2H), 7.06-7.01 (m, 2H), 4.70 (s, 1H), 4.57 (p, J = 8.0 Hz, 1H), 4.50-4.09 (m, 4H), 3.87-3.73 (m, 4H), 3.20 (q, J = 7.2 Hz, 2H), 1.41 (t, J = 7.3 Hz, 3H). |

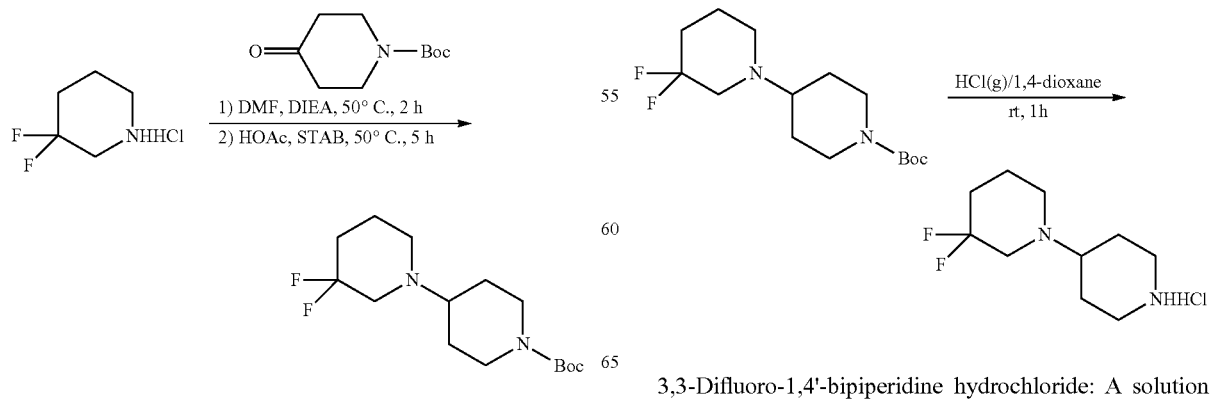

3,3-Difluoro-1,4'-bipiperidine hydrochloride: A solution of tert-butyl 3,3-difluoro-[1,4-bipiperidine]-1-carboxylate (0.70 g) in HCl (g)/1,4-dioxane solution (15.0 mL) was stirred for 1 hour at ambient temperature. The precipitated solid was collected by filtration and washed with 1,4-dioxane (3×20.0 mL) to afford the title compound as a colorless solid (0.50 g, 90%): MS: $[(M+1)]^+=205.2$.

1'-(5-Bromo-3-nitropyridin-2-yl)-3,3-difluoro-1,4'-bipiperidine (BB-1): To a stirred solution of 3,3-difluoro-1,4-bipiperdine hydrochloride (0.50 g, 2.08%) and 5-bromo-2-chloro-3-nitropyridine (0.49 g, 2.08 mmol) in tetrahydrofuran (40.0 mL) was added diisopropylethylamine (0.67 g, 5.19 mmol) at ambient temperature. The resulting mixture was stirred for 3 hours and concentrated under reduced pressure. The residue was purified by silica gel column chromatography, eluted with 3%~9% ethyl acetate in petroleum ether. The desired fractions were collected and concentrated under reduced pressure to afford the title compound as a yellow solid (0.50 g, 59%): MS: $[(M+1)]^+=405.10, 407.10$ The following intermediates were prepared according to the above procedure for the preparation of intermediate BB-1:

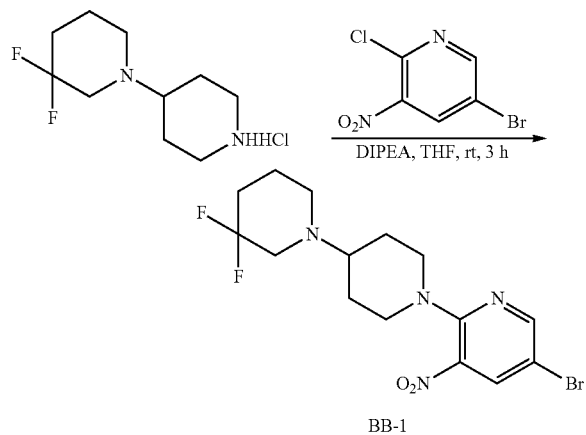

BB-1

| Intermediate | Structure | Name | Ms: $[(M + 1)]^+$ | $^1$H-NMR |
|---|---|---|---|---|
| BB-1-1 | 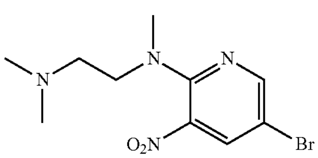 [SMILES: CN(C)CCN(C)c1ncc(Br)cc1[N+](=O)[O-]] | $N^1$-(5-Bromo-3-nitropyridin-2-yl)-$N^1,N^2,N^2$-trimethylethane-1,2-diamine | 303.00 305.00 | $^1$H NMR (400 MHz, CD$_3$OD) δ 8.38 (d, J = 2.2 Hz, 1H), 8.31 (d, J = 2.2 Hz, 1H), 3.85-3.77 (m, 2H), 2.88 (s, 3H), 2.71-2.62 (m, 2H), 2.33 (s, 6H). |
| BB-1-2 | 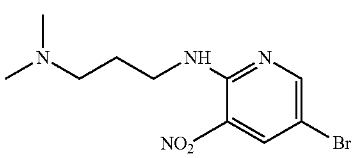 | $N^1$-(5-Bromo-3-nitropyridin-2-yl)-$N^3,N^3$-dimethylpropane-1,3-diamine | 303.00 305.00 | $^1$H NMR (400 MHz, CDCl$_3$) δ 8.93 (s, 1H), 8.53 (d, J = 2.3 Hz, 1H), 8.41 (d, J = 2.3 Hz, 1H), 3.71 (q, J = 6.1 Hz, 2H), 2.60 (s, 2H), 2.40 (s, 6H), 1.97-1.89 (m, 2H). |
| BB-1-3 | 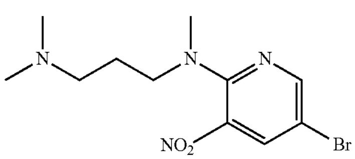 | $N^1$-(5-Bromo-3-nitropyridin-2-yl)-$N^1,N^3,N^3$-trimethylpropane-1,3-diamine | 317.10 319.10 | $^1$H NMR (400 MHz, DMSO-d$_6$) δ 8.45 (d, J = 2.3 Hz, 1H), 8.39 (d, J = 2.3 Hz, 1H), 3.59 (t, J = 7.2 Hz, 2H), 2.82-2.77 (m, 3H), 2.18 (t, J = 6.9 Hz, 2H), 2.09 (t, J = 1.3 Hz, 6H), 1.76-1.69 (m, 2H). |
| BB-1-4 | 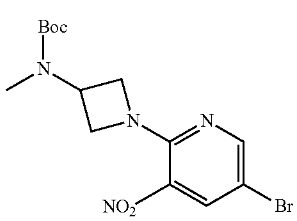 [SMILES: CN(C(=O)OC(C)(C)C)C1CN(c2ncc(Br)cc2[N+](=O)[O-])C1] | tert-Butyl (1-(5-bromo-3-nitropyridin-2-yl)azetidin-3-yl)(methyl)carbamate | 387.20 389.20 | $^1$H NMR (400 MHz, CD$_3$OD) δ 8.43 (d, J = 2.2 Hz, 1H), 8.38 (d, J = 2.2 Hz, 1H), 4.82-4.65 (m, 1H), 4.32 (t, J = 6.2 Hz, 2H), 4.24-4.12 (m, 2H), 2.96 (s, 3H), 1.45 (s, 9H). |
| BB-1-5 | 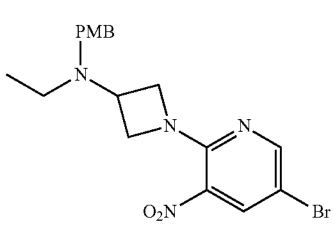 | 1-(5-Bromo-3-nitropyridin-2-yl)-N-ethyl-N-(4-methoxybenzyl)azetidin-3-amine | 421.20 423.20 | $^1$H NMR (400 MHz, CDCl$_3$) δ 8.36 (d, J = 2.2 Hz, 1H), 8.27 (d, J = 2.2 Hz, 1H), 7.18 (d, J = 8.8 Hz, 2H), 6.85 (d, J = 8.8 Hz, 2H), 4.17 (dd, J = 9.9, 7.4 Hz, 2H), 3.95 (dd, J = 10.0, 5.7 Hz, 2H), 3.80 (s, 3H), 3.70-3.61 (m, 1H), 3.56 (s, 2H), 2.50 (q, J = 7.1Hz, 2H), 1.02 (t, J = 7.1 Hz, 3H). |

-continued

| Intermediate | Structure | Name | Ms: [(M + 1)]+ | 1H-NMR |
|---|---|---|---|---|
| BB-1-6 | 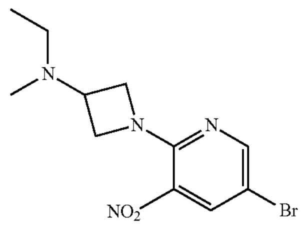 [SMILES: CCN(C)C1CN(c2ncc(Br)cc2[N+](=O)[O-])C1] | 1-(5-Bromo-3-nitropyridin-2-yl)-N-ethyl-N-methylazetidin-3-amine | 331.00<br>333.00 | 1H NMR (400 MHz, CDCl$_3$) δ 8.36 (d, J = 2.3 Hz, 1H), 8.28 (d, J = 2.2 Hz, 1H), 4.21 (ddd, J = 9.8, 7.1, 1.2 Hz, 2H), 3.94 (dd, J = 10.2, 5.4 Hz, 2H), 3.31 (tt, J = 7.1, 5.4 Hz, 1H), 2.36 (q, J = 7.1 Hz, 2H), 1.08 (t, J = 7.2 Hz, 3H). |
| BB-1-7 | 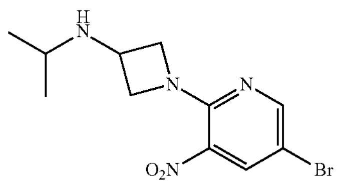 | 1-(5-Bromo-3-nitropyridin-2-yl)-N-isopropylazetidin-3-amine | 315.00<br>317.00 | 1H NMR (400 MHz, DMSO-d$_6$) δ 8.52 (d, J = 2.2 Hz, 1H), 8.43 (d, J = 2.2 Hz, 1H), 4.20 (t, J = 8.4 Hz, 2H), 3.75-3.63 (m, 2H), 2.72 (p, J = 6.3 Hz, 1H), 2.34 (s, 1H), 0.94 (d, J = 6.2 Hz, 6H). |
| BB-1-8 | 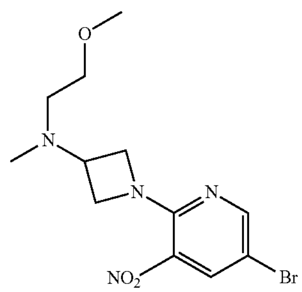 [SMILES: COCCN(C)C1CN(c2ncc(Br)cc2[N+](=O)[O-])C1] | 1-(5-Bromo-3-nitropyridin-2-yl)-N-(2-methoxyethyl)-N-methylazetidin-3-amine | 345.05<br>347.05 | 1H NMR (400 MHz, CDCl$_3$) δ 8.37 (d, J = 2.3 Hz, 1H), 8.28 (d, J = 2.3 Hz, 1H), 4.26-4.16 (m, 2H), 3.99 (s, 2H), 3.53-3.39 (m, 3H), 3.35 (s, 3H), 2.56 (s, 2H), 2.27 (s, 3H). |
| BB-1-9 | 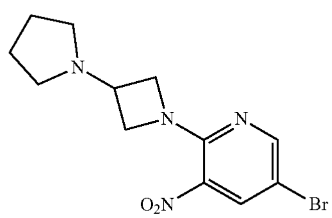 [SMILES: O=[N+]([O-])c1cc(Br)cnc1N1CC(N2CCCC2)C1] | 5-Bromo-3-nitro-2-(3-(pyrrolidin-1-yl)azetidin-1-yl)pyridine | 327.10<br>329.10 | 1H NMR (400 MHz, CDCl$_3$) δ 8.36 (d, J = 2.2 Hz, 1H), 8.28 (d, J = 2.2 Hz, 1H), 4.29-4.20 (m, 2H), 4.02 (s, 2H), 3.38 (s, 1H), 2.53 (s, 4H), 1.84 (s, 4H). |
| BB-1-10 | 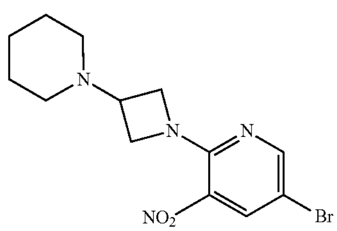 | 5-Bromo-3-nitro-2-(3-(piperidin-1-yl)azetidin-1-yl)pyridine | 341.20<br>343.20 | 1H NMR (400 MHz, CDCl$_3$) δ 8.36 (s, 1H), 8.27 (s, 1H), 4.21 (t, J = 8.5 Hz, 2H), 4.02-3.87 (m, 2H), 3.18 (p, J = 6.1 Hz, 1H), 2.31 (s, 4H), 1.60 (t, J = 5.7 Hz, 4H), 1.48 (q, J = 6.3, 5.8 Hz, 2H). |
| BB-1-11 | 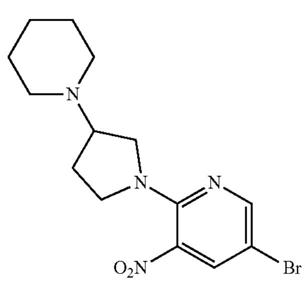 | 5-Bromo-3-nitro-2-(3-(piperidin-1-yl)pyrrolidin-1-yl)pyridine | 355.05<br>357.05 | 1H NMR (400 MHz, DMSO-d$_6$) δ 8.49 (d, J = 2.2 Hz, 1H), 8.42 (d, J = 2.2 Hz, 1H), 3.50-3.36 (m, 1H), 3.32-3.26 (m, 2H), 3.21 (t, J = 9.8 Hz, 1H), 2.90-2.76 (m, 1H), 2.44-2.38 (m, 2H), 2.36-2.26 (m, 2H), 2.22-2.10 (m, 1H), 1.82-1.67 (m, 1H), 1.50 (q, J = 5.7, 5.2 Hz, 4H), 1.44-1.33 (m, 2H). |

-continued

| Intermediate | Structure | Name | Ms: [(M + 1)]+ | 1H-NMR |
|---|---|---|---|---|
| BB-1-12 | 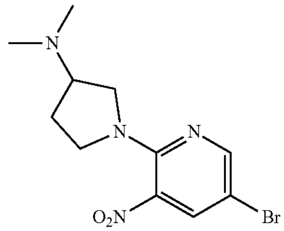 [SMILES: CN(C)C1CCN(c2ncc(Br)cc2[N+](=O)[O-])C1] | 1-(5-Bromo-3-nitropyridin-2-yl)-N,N-dimethylpyrrolidin-3-amine | 315.00<br>317.00 | 1H NMR (400 MHz, CDCl3) δ 8.34 (d, J = 2.1 Hz, 1H), 8.20 (d, J = 2.2 Hz, 1H), 3.64-3.54 (m, 1H), 3.47-3.30 (m, 3H), 2.84-2.72 (m, 1H), 2.30 (s, 6H), 2.24-2.16 (m, 1H), 1.89 (p, J = 10.4 Hz, 1H). |
| BB-1-13 | 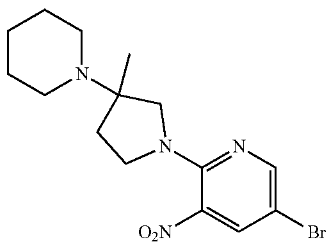 | 5-Bromo-2-(3-methyl-3-(piperidin-1-yl)pyrrolidin-1-yl)-3-nitropyridine | 369.10<br>371.10 | 1H NMR (400 MHz, CD3OD) δ 8.39 (d, J = 2.2 Hz, 1H), 8.30 (d, J = 2.1 Hz, 1H), 3.78-3.62 (m, 1H), 3.50 (d, J = 10.8 Hz, 1H), 3.40-3.32 (m, 1H), 3.11 (d, J = 10.8 Hz, 1H), 2.68-2.58 (m, 2H), 2.55-2.41 (m, 2H), 2.08-1.90 (m, 2H), 1.64 (p, J = 5.6 Hz, 4H), 1.49 (p, J = 6.3 Hz, 2H), 1.09 (s, 3H). |
| BB-1-14 | 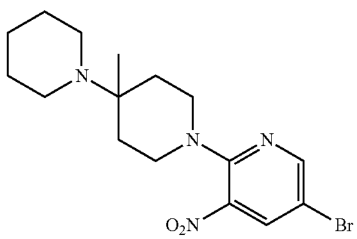 [SMILES: CC1(N2CCCCC2)CCN(c2ncc(Br)cc2[N+](=O)[O-])CC1] | 1'-(5-Bromo-3-nitropyridin-2-yl)-4'-methyl-1,4'-bipiperidine | 383.10<br>385.10 | 1H NMR (400 MHz, DMSO-d6) δ 8.46 (d, J = 2.4 Hz, 1H), 8.42 (d, J = 2.4 Hz, 1H), 3.40-3.29 (m, 4H), 2.43 (s, 4H), 1.88 (d, J = 13.9 Hz, 2H), 1.57-1.46 (m, 4H), 1.45-1.31 (m, 4H), 0.87 (s, 3H). |
| BB-1-15 | 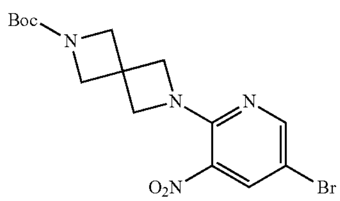 | tert-Butyl 6-(5-Bromo-3-nitropyridin-2-yl)-2,6-diazaspiro[3.3]heptane-2-carboxylate | 399.05<br>401.05 | 1H NMR (400 MHz, DMSO-d6) δ 8.53 (s, 1H), 8.43 (s, 1H), 4.18 (s, 4H), 4.01 (s, 4H), 1.37 (s, 9H). |
| BB-1-16 | 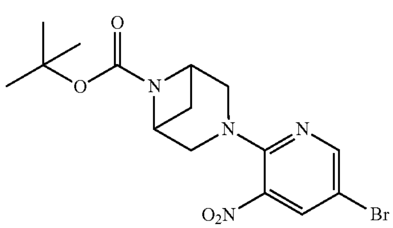 [SMILES: CC(C)(C)OC(=O)N1C2CC1CN(c1ncc(Br)cc1[N+](=O)[O-])C2] | tert-Butyl 3-(5-bromo-3-nitropyridin-2-yl)-3,6-diazabicyclo[3.1.1]heptane-6-carboxylate | 399.00<br>401.00 | 1H NMR (400 MHz, CDCl3) δ 8.35 (d, J = 2.3 Hz, 1H), 8.13 (d, J = 2.2 Hz, 1H), 4.24-4.08 (m, 4H), 3.51 (s, 2H), 2.68-2.62 (m, 1H) 1.50 (d, J = 8.8 Hz, 1H), 1.34 (s, 9H). |
| BB-1-17 | 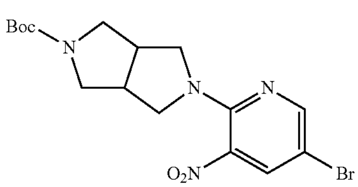 [SMILES: CC(C)(C)OC(=O)N1CC2CN(c3ncc(Br)cc3[N+](=O)[O-])CC2C1] | tert-Butyl 5-(5-Bromo-3-nitropyridin-2-yl)hexahydropyrrolo[3,4-c]pyrrole-2(1H)-carboxylate | 413.10<br>415.10 | 1H NMR (400 MHz, CDCl3) δ 8.35 (t, J = 1.7 Hz, 1H), 8.18 (d, J = 2.5 Hz, 1H), 3.69-3.57 (m, 4H), 3.28 (t, J = 14.6 Hz, 4H), 2.97 (s, 2H), 1.46 (s, 9H). |
| BB-1-18 | 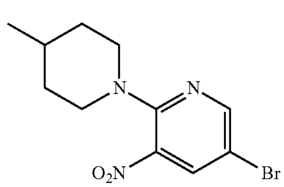 [SMILES: CC1CCN(c2ncc(Br)cc2[N+](=O)[O-])CC1] | 5-Bromo-2-(4-methylpiperidin-1-yl)-3-nitropyridine | 300.00<br>302.00 | 1H NMR (400 MHz, DMSO-d6) δ 8.47 (d, J = 2.2 Hz, 1H), 8.42 (d, J = 2.4 Hz, 1H), 3.68 (d, J = 13.1 Hz, 2H), 2.99 (t, J = 12.1 Hz, 2H), 1.72-1.59 (m, 3H), 1.22-1.08 (m, 2H), 0.92 (d, J = 6.0 Hz, 3H). |

-continued

| Intermediate | Structure | Name | Ms: [(M + 1)]⁺ | ¹H-NMR |
|---|---|---|---|---|
| BB-1-19 | 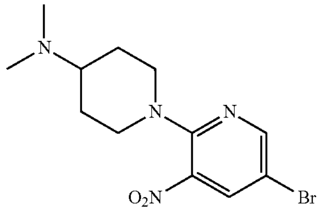 [SMILES: CN(C)C1CCN(c2ncc(Br)cc2[N+](=O)[O-])CC1] | 1-(5-Bromo-3-nitropyridin-2-yl)-N,N-dimethylpiperidin-4-amine | 329.05 331.05 | ¹H NMR (300 MHz, DMSO-$d_6$) δ 8.48 (d, J = 2.3 Hz, 1H), 8.43 (d, J = 2.3 Hz, 1H), 3.71 (d, J = 13.3 Hz, 2H), 3.08-2.93 (m, 2H), 2.40 (td, J = 10.9, 5.5 Hz, 1H), 2.19 (s, 6H), 1.81 (d, J = 11.1 Hz, 2H), 1.42 (qd, J = 11.8, 4.0 Hz, 2H). |
| BB-1-20 | 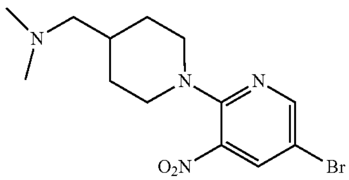 [SMILES: CN(C)CC1CCN(c2ncc(Br)cc2[N+](=O)[O-])CC1] | 1-(1-(5-Bromo-3-nitropyridin-2-yl)piperidin-4-yl)-N,N-dimethylmethanamine | 343.05 345.05 | ¹H NMR (300 MHz, DMSO-$d_6$) δ 8.48 (d, J = 2.3 Hz, 1H), 8.42 (d, J = 2.3 Hz, 1H), 3.69 (d, J = 13.4 Hz, 2H), 3.17 (d, J = 5.1 Hz, 1H), 3.07-2.92 (m, 2H), 2.17 (s, 6H). |
| BB-1-21 | 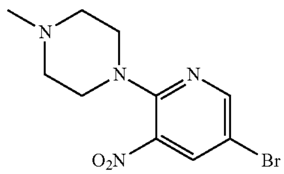 | 1-(5-Bromo-3-nitropyridin-2-yl)-4-methylpiperazine | 301.00 303.00 | ¹H NMR (300 MHz, CDCl₃) δ 8.35 (d, J = 2.2 Hz, 1H), 8.26 (s, 1H), 3.52 (s, 3H), 2.49 (d, J = 51.7 Hz, 8H). |
| BB-1-22 | 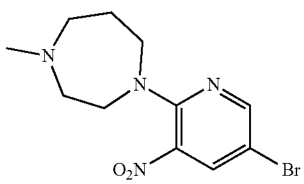 [SMILES: CN1CCCN(c2ncc(Br)cc2[N+](=O)[O-])CC1] | 1-(5-Bromo-3-nitropyridin-2-yl)-4-methyl-1,4-diazepane | 315.00 317.00 | ¹H NMR (300 MHz, DMSO-$d_6$) δ 8.51 (d, J = 2.2 Hz, 1H), 8.47 (d, J = 2.2 Hz, 1H), 3.76 (s, 2H), 3.27-3.07 (m, 4H), 2.94 (s, 2H), 2.55 (s, 3H), 2.10 (s, 2H). |
| BB-1-23 | 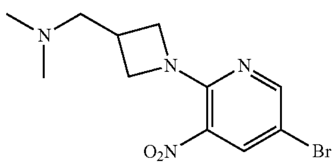 | 1-(1-(5-Bromo-3-nitropyridin-2-yl)azetidin-3-yl)-N,N-dimethylmethanamine | 315.00 317.00 | ¹H NMR(400 MHz, CDCl₃) δ 8.39 (d, J = 2.2 Hz, 1H), 8.31 (d, J = 2.2 Hz, 1H), 4.40 (dd, J = 10.0, 8.2 Hz, 2H), 4.01 (dd, J = 10.1, 5.2 Hz, 2H), 3.54-3.43 (m, 1H), 3.40 (d, J = 6.6 Hz, 2H), 2.83 (s, 6H). |
| BB-1-24 | 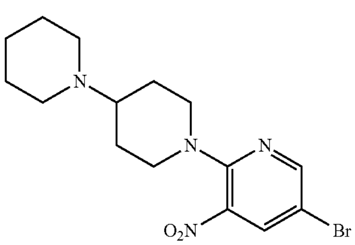 [SMILES: O=[N+]([O-])c1cc(Br)cnc1N1CCC(N2CCCCC2)CC1] | 1'-(5-Bromo-3-nitropyridin-2-yl)-1,4'-bipiperidine | 369.00 371.00 | ¹H NMR (300 MHz, CDCl₃) δ 8.32 (d, J = 2.3 Hz, 1H), 8.24 (d, J = 2.3 Hz, 1H), 3.86 (d, J = 13.2 Hz, 2H), 3.02 (t, J = 12.2 Hz, 2H), 2.57 (s, 5H), 1.94 (d, J = 12.8 Hz, 2H), 1.74-1.52 (m, 6H), 1.51-1.43 (m, 2H). |
| BB-1-25 | 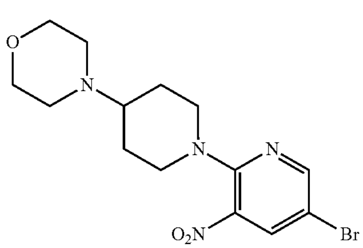 | 4-(1-(5-Bromo-3-nitropyridin-2-yl)piperidin-4-yl)morpholine | 371.10 373.10 | ¹H NMR (300 MHz, CDCl₃) δ 8.32 (d, J = 2.3 Hz, 1H), 8.24 (d, J = 2.3 Hz, 1H), 3.85 (d, J = 13.3 Hz, 2H), 3.74 (t, J = 4.6 Hz, 4H), 3.04 (td, J = 12.8, 2.6 Hz, 2H), 2.58 (t, J = 4.6 Hz, 4H), 2.54-2.41 (m, 1H), 1.93 (d, J = 12.9 Hz, 2H), 1.61 (qd, J = 12.0, 4.0 Hz, 2H). |

-continued

| Intermediate | Structure | Name | Ms: [(M + 1)]+ | 1H-NMR |
|---|---|---|---|---|
| BB-1-26 | 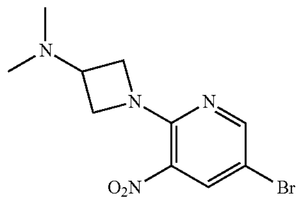 [SMILES: CN(C)C1CN(c2ncc(Br)cc2[N+](=O)[O-])C1] | 1-(5-Bromo-3-nitropyridin-2-yl)-N,N-dimethylazetidin-3-amine | 301.00<br>303.00 | 1H NMR (400 MHz, CDCl3) δ 8.37 (d, J = 2.2 Hz, 1H), 8.29 (d, J = 2.2 Hz, 1H), 4.20 (ddd, J = 10.0, 7.0, 1.2 Hz, 2H), 3.93 (ddd, J = 9.9, 5.1, 1.2 Hz, 2H), 3.16 (tt, J = 7.0, 5.1 Hz, 1H), 2.20 (s, 6H). |
| BB-1-27 | 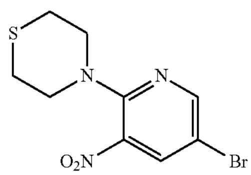 | 4-(5-Bromo-3-nitropyridin-2-yl)thiomorpholine | 303.95<br>305.95 | 1H NMR (400 MHz, CDCl3) δ 8.36 (dd, J = 4.7, 2.3 Hz, 1H), 8.25 (d, J = 2.2 Hz, 1H), 3.74-3.62 (m, 4H), 2.78-2.67 (m, 4H). |
| BB-1-28 | 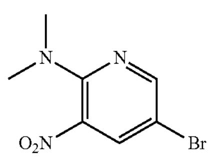 | 5-Bromo-N,N-dimethyl-3-nitropyridin-2-amine | 245.80<br>247.80 | 1H NMR (300 MHz, CDCl3) δ 8.32 (d, J = 2.3 Hz, 1H), 8.23 (d, J = 2.2 Hz, 1H), 3.04 (s, 6H). |
| BB-1-29 | 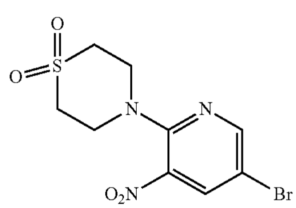 [SMILES: O=[N+]([O-])c1cc(Br)cnc1N1CCS(=O)(=O)CC1] | 4-(5-Bromo-3-nitropyridin-2-yl)thiomorpholine 1,1-dioxide | 335.90<br>337.90 | 1H NMR (400 MHz, DMSO-d6) δ δ 8.61 (d, J = 2.2 Hz, 1H), 8.56 (d, J = 2.2 Hz, 1H), 3.82-3.74 (m, 4H), 3.29-3.23 (m, 4H). |

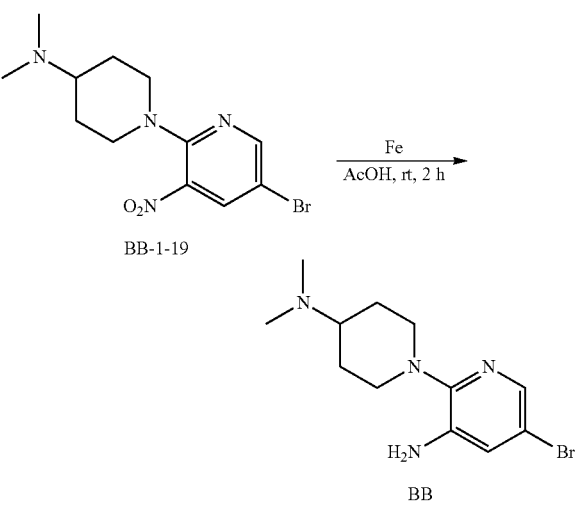

5-Bromo-2-(4-(dimethylamino)piperidin-1-yl)pyridin-3-amine: To a solution of 1-(5-bromo-3-nitropyridin-2-yl)-N,N-dimethylpiperidin-4-amine (6.80 g, 20.7 mmol) in acetic acid (92.1 mL) was added iron powder (11.5 g, 206 mmol) at ambient temperature. The resulting mixture was stirred for 2 hours at ambient temperature. The resulting mixture was filtered and the filtered cake was washed with tetrahydrofuran (3×100 mL). The filtrate was concentrated under reduced pressure. The residue was taken up with saturated aqueous sodium carbonate (100 mL) and extracted with ethyl acetate (3×100 mL). The combined organic layers was washed with brine (3×100 mL) and dried over anhydrous sodium sulfate. After filtration, the filtrate was concentrated under reduced pressure. The residue was purified by silica gel column chromatography, eluted with 2%~4% methanol in dichloromethane to afford the tile compound as a grey solid (5.68 g, 92%): 1H NMR (300 MHz, DMSO-d6) δ 7.56 (d, J=2.2 Hz, 1H), 7.08 (d, J=2.2 Hz, 1H), 5.09 (s, 2H), 3.35 (d, J=13.3 Hz, 1H), 2.56 (dd, J=12.3, 2.3 Hz, 1H), 2.20 (s, 6H), 1.79 (d, J=12.4 Hz, 2H), 1.58 (qd, J=11.9, 3.7 Hz, 2H); MS: [(M+1)]+=299.10, 301.10.

The following intermediates were prepared according to the procedure described above:

| Intermediate | Structure | Name | Ms: [(M + 1)]⁺ | ¹H-NMR |
|---|---|---|---|---|
| BB1 | 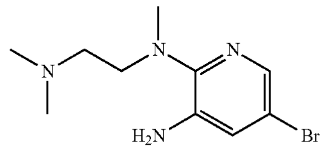 | 5-Bromo-N²-(2-(dimethylamino)ethyl)-N²-methylpyridine-2,3-diamine | 273.00<br>275.00 | ¹H NMR (400 MHz, CD$_3$OD) δ 7.57 (d, J = 2.2 Hz, 1H), 7.12 (d, J = 2.2 Hz, 1H), 3.17 (t, J = 6.4 Hz, 2H), 2.70 (s, 3H), 2.53 (t, J = 6.4 Hz, 2H), 2.28 (s, 6H). |
| BB2 | 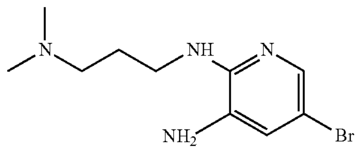 | 5-Bromo-N²-(3-(dimethylamino)propyl) pyridine-2,3-diamine | 273.00<br>275.00 | ¹H NMR (400 MHz, CDCl$_3$) δ 7.71 (d, J = 2.1 Hz, 1H), 6.90 (d, J = 2.1 Hz, 1H), 3.52-3.45 (m, 2H), 3.35 (s, 2H), 2.53 (t, J = 6.3 Hz, 2H), 2.33 (s, 6H), 1.85 (p, J = 6.3 Hz, 2H). |
| BB3 | 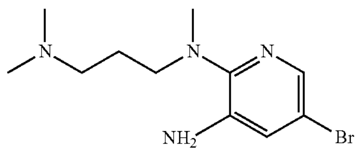 | 5-Bromo-N²-(3-(dimethylamino)propyl)-N²-methylpyridine-2,3-diamine | 287.10<br>289.10 | ¹H NMR (400 MHz, CD$_3$OD) δ 7.60 (t, J = 1.7 Hz, 1H), 7.14 (t, J = 1.8 Hz, 1H), 3.06 (t, J = 7.0 Hz, 2H), 2.71 (s, 3H), 2.40 (t, J = 7.5 Hz, 2H), 2.24 (s, 6H), 1.77-1.69 (m, 2H). |
| BB4 | 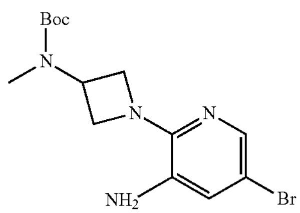 | tert-Butyl (1-(3-amino-5-Bromopyridin-2-yl)azetidin-3-yl)(methyl)carbamate | 357.10<br>359.10 | ¹H NMR (400 MHz, CD$_3$OD) δ 7.55 (d, J = 2.0 Hz, 1H), 7.04 (d, J = 2.0 Hz, 1H), 4.80-4.70 (m, 1H), 4.21 (t, J = 6.2 Hz, 2H), 4.02-3.92 (m, 2H), 2.92 (s, 3H), 1.46 (s, 9H). |
| BB5 | 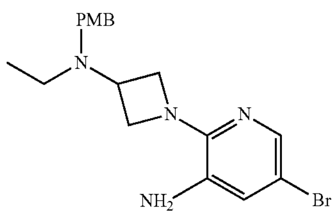 | 5-Bromo-2-(3-(ethyl(4-methoxybenzyl)amino) azetidin-1-yl)pyridin-3-amine | 391.20<br>393.20 | ¹H NMR (400 MHz, CDCl$_3$) δ 7.74 (d, J = 2.0 Hz, 1H), 7.22 (d, J = 8.4 Hz, 2H), 6.85 (d, J = 8.4 Hz, 2H), 4.03 (dd, J = 8.1, 6.9 Hz, 2H), 3.91 (t, J = 7.3 Hz, 2H), 3.80 (s, 3H), 3.64 (p, J = 6.8 Hz, 1H), 3.58 (s, 2H), 3.43 (s, 2H), 2.52 (q, J = 7.2 Hz, 2H), 1.04 (t, J = 7.2 Hz, 3H). |
| BB6 | 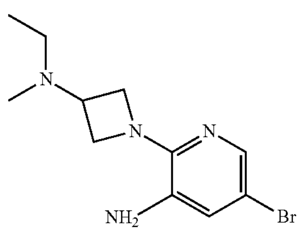 | 5-Bromo-2-(3-(ethyl(methyl)amino) azetidin-1-yl)pyridin-3-amine | 285.30<br>287.30 | ¹H NMR (400 MHz, CDCl$_3$) δ 7.75 (d, J = 2.1 Hz, 1H), 6.93 (d, J = 2.0 Hz, 1H), 4.07 (td, J = 7.0, 1.2 Hz, 2H), 3.94-3.86 (m, 2H), 3.30 (p, J = 6.5 Hz, 1H), 2.38 (q, J = 7.2 Hz, 2H), 2.18 (s, 3H), 1.08 (t, J = 7.2 Hz, 3H). |
| BB7 | 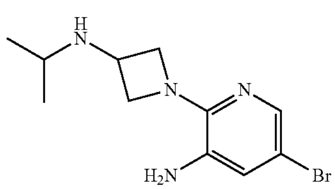 | 5-Bromo-2-(3-(isopropylamino) azetidin-1-yl)pyridin-3-amine | 285.05<br>287.05 | ¹H NMR (400 MHz, DMSO-d$_6$) δ 7.48 (d, J = 2.1 Hz, 1H), 6.93 (d, J = 2.1 Hz, 1H), 4.85 (s, 2H), 4.13 (t, J = 7.5 Hz, 2H), 3.65-3.75 (m, 1H), 3.55 (t, J = 7.0 Hz, 2H), 2.75 (p, J = 6.3 Hz, 1H), 0.95 (d, J = 6.2 Hz, 6H). |
| BB8 | 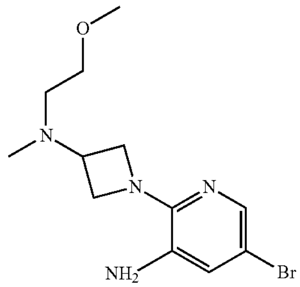 | 5-Bromo-2-(3-((2-methoxyethyl)(methyl) amino)azetidin-1-yl)pyridin-3-amine | 315.10<br>317.10 | ¹H NMR (400 MHz, CDCl$_3$) δ 7.73 (d, J = 2.0 Hz, 1H), 6.93 (d, J = 2.1 Hz, 1H), 4.06 (dd, J = 8.2, 6.8 Hz, 2H), 3.92 (dd, J = 8.1, 6.2 Hz, 2H), 3.52-3.38 (m, 5H), 3.35 (s, 3H), 2.57 (t, J = 5.7 Hz, 2H), 2.26 (s, 3H). |

-continued

| Intermediate | Structure | Name | Ms: [(M + 1)]⁺ | ¹H-NMR |
|---|---|---|---|---|
| BB9 | 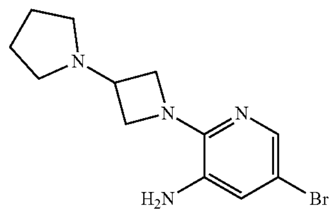 | 5-Bromo-2-(3-(pyrrolidin-1-yl)azetidin-1-yl)pyridin-3-amine | 297.20 299.20 | ¹H NMR (400 MHz, CDCl$_3$) δ 7.76 (d, J = 2.0 Hz, 1H), 6.94 (d, J = 2.0 Hz, 1H), 4.11 (dd, J = 8.2, 6.9 Hz, 2H), 3.97 (dd, J = 8.2, 5.3 Hz, 2H), 3.46 (s, 2H), 3.40-3.32 (m, 1H), 2.61-2.53 (m, 4H), 1.91-1.79 (m, 4H). |
| BB10 | 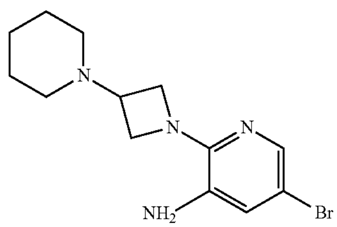 | 5-Bromo-2-(3-(piperidin-1-yl)azetidin-1-yl)pyridin-3-amine | 311.10 313.10 | ¹H NMR (400 MHz, CDCl$_3$) δ 7.73 (t, J = 1.6 Hz, 1H), 6.92 (t, J = 1.5 Hz, 1H), 4.07 (t J = 7.5 Hz, 2H), 3.94 (t, J = 7.0 Hz, 2H), 3.44 (s, 2H), 3.19 (t, J = 6.6 Hz, 1H), 2.35 (s, 4H), 1.72-1.55 (m, 4H), 1.54-1.40 (m, 2H). |
| BB11 | 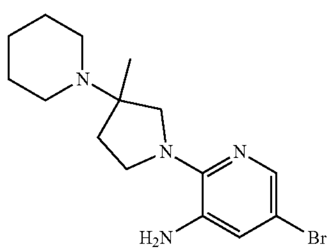 [SMILES: CC1(N2CCCCC2)CCN(c2ncc(Br)cc2N)C1] | 5-Bromo-2-(3-methyl-3-(piperidin-1-yl)pyrrolidin-1-yl)pyridin-3-amine | 339.10 341.10 | ¹H NMR (400 MHz, CD$_3$OD) δ 7.53 (d, J = 2.1 Hz, 1H), 7.09 (d, J = 2.0 Hz, 1H), 3.69 (q, J = 9.3 Hz, 1H), 3.52 (d, J = 9.7 Hz, 1H), 3.30-3.26 (m, 1H), 3.13 (d, J = 9.7 Hz, 1H), 2.73-2.61 (m, 2H), 2.60-2.50 (m, 2H), 2.05-1.83 (m, 2H), 1.65 (q, J = 5.8 Hz, 4H), 1.55-1.45 (m, 2H), 1.18 (s, 3H) |
| BB12 | 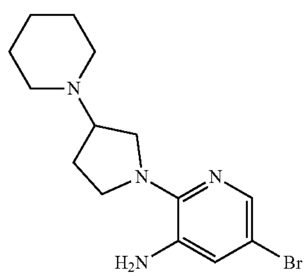 [SMILES: Nc1cc(Br)cnc1N1CCC(N2CCCCC2)C1] | 5-Bromo-2-(3-(piperidin-1-yl)pyrrolidin-1-yl)pyridin-3-amine | 325.05 327.05 | ¹H NMR (400 MHz, DMSO-d$_6$) δ 7.49 (d, J = 2.2 Hz, 1H), 7.01 (d, J = 2.2 Hz, 1H), 4.94 (s, 2H), 3.53-3.37 (m, 2H), 3.29-3.18 (m, 2H), 2.76 (p, J = 7.8 Hz, 1H), 2.45-2.39 (m, 2H), 2.37-2.28 (m, 2H), 2.10-1.96 (m, 1H), 1.74-1.60 (m, 1H), 1.55-1.46 (m, 4H), 1.44-1.33 (m, 2H). |
| BB13 | 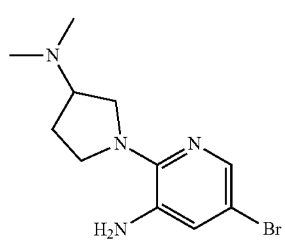 | 5-Bromo-2-(3-(dimethylamino)pyrrolidin-1-yl)pyridin-3-amine | 284.95 286.95 | ¹H NMR (400 MHz, CDCl$_3$) δ 7.74 (d, J = 2.1 Hz, 1H), 6.99 (s, 1H), 3.66 (s, 2H), 3.54-3.41 (m, 2H), 3.41-3.28 (m, 2H), 2.79 (p, J = 7.6 Hz,1H), 2.30 (s, 6H), 2.18-2.09 (m, 1H), 1.92-1.80 (m, 1H). |
| BB14 | 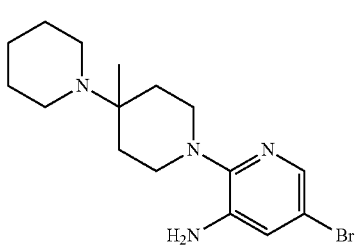 | 5-Bromo-2-(4'-methyl-[1,4'-bipiperidin]-1'-yl)pyridin-3-amine | 353.20 355.20 | ¹H NMR (400 MHz, DMSO-d$_6$) δ 7.56 (d, J = 2.3 Hz, 1H), 7.07 (d, J = 2.3 Hz, 1H), 5.07 (s, 2H), 3.14-3.04 (m, 2H), 2.88-2.75 (m, 2H), 2.48-2.38 (m, 4H), 1.90-1.78 (m, 2H), 1.64-1.53 (m, 2H), 1.52-1.43 (m, 4H), 1.42-1.33 (m, 2H), 0.89 (s, 3H). |

| Intermediate | Name | Ms: [(M + 1)]+ | ¹H-NMR |
|---|---|---|---|
| BB15 | 5-Bromo-2-(4-methylpiperidin-1-yl)pyridin-3-amine | 270.20<br>272.20 | ¹H NMR (400 MHz, DMSO-d₆) δ 7.56 (d, J = 2.2 Hz, 1H), 7.09 (d, J = 2.3 Hz, 1H), 5.04 (s, 2H), 3.28 (dd, J = 9.5, 6.3 Hz, 2H), 2.61-2.50 (m, 2H), 1.66 (dd, J = 13.0, 3.4 Hz, 2H), 1.54-1.42 (m, 1H) 1.33 (qd, J = 12.0, 3.8 Hz, 2H), 0.95 (d, J = 6.4 Hz, 3H). |
| BB16 | 5-Bromo-2-(4-((dimethylamino)methyl)piperidin-1-yl)pyridin-3-amine | 313.15<br>315.10 | ¹H NMR (300 MHz, CDCl₃) δ 7.79 (d, J = 2.2 Hz, 1H), 7.04 (d, J = 2.2 Hz, 1H), 3.84 (s, 2H), 3.44-3.26 (m 2H), 2.72 (td, J = 12.2, 2.4 Hz, 2H), 2.28 (s, 6H), 1.98-1.82 (m, 2H), 1.67 (ddq, J = 11.2, 7.6, 3.8 Hz, 1H), 1.39-1.25 (m, 2H). |
| BB17 | 5-Bromo-2-(4-methylpiperazin-1-yl)pyridin-3-amine | 271.10<br>273.10 | ¹H NMR (300 MHz, DMSO-d₆) δ 7.58 (d, J = 2.2 Hz, 1H), 7.11 (d, J = 2.2 Hz, 1H), 5.08 (s, 2H), 3.00-2.94 (m, 4H) 2.23 (s, 4H), 1.91 (s, 3H). |
| BB18 | 5-Bromo-2-(4-methyl-1,4-diazepan-1-yl)pyridin-3-amine | 285.05<br>287.05 | ¹H NMR (400 MHz, DMSO-d₆) δ 7.55 (d, J = 2.2 Hz, 1H), 7.09 (d, J = 2.2 Hz, 1H), 4.99 (s, 2H), 3.32-3.24 (m, 4H), 2.70 (t, J = 5.2 Hz, 4H), 2.34 (s, 3H), 1.89-1.81 (m, 2H). |
| BB19 | 5-Bromo-2-(3-((dimethylamino)methyl)azetidin-1-yl)pyridin-3-amine | 284.9<br>286.9 | ¹H NMR (400 MHz, CDCl₃) δ 7.73 (d, J = 2.0 Hz, 1H), 6.92 (d, J = 2.1 Hz, 1H), 4.14 (t, J = 8.0 Hz, 2H), 3.73 (dd, J = 8.0, 6.3 Hz, 2H), 2.97-2.87 (m, 1H), 2.68 (d. J = 7.2 Hz, 2H), 2.31 (s, 6H). |
| BB20 | 2-([1,4'-Bipiperidin]-1'-yl)-5-bromopyridin-3-amine | 339.2<br>341.2 | ¹H NMR (300 MHz, CDCl₃) δ 7.78 (d, J = 2.2 Hz, 1H), 7.05 (d, J = 2.2 Hz, 1H), 3.84 (s, 2H), 3.46-3.37 (m, 2H), 2.71 (td, J = 12.4, 2.2 Hz, 2H), 2.58 (t, J = 5.4 Hz, 4H), 2.43 (t, J = 11.5, 3.7 Hz, 1H), 1.98 (d, J = 12.5 Hz, 2H), 1.75-1.59 (m, 6H), 1.52-1.42 (m, 2H). |
| BB21 | 5-Bromo-2-(4-morpholinopiperidin-1-yl)pyridin-3-amine | 340.95<br>342.95 | ¹H NMR (400 MHz, CDCl₃) δ 7.79 (d, J = 2.2 Hz, 1H), 7.05 (d, J = 2.1 Hz, 1H), 3.84 (s, 2H), 3.80-3.72 (m, 4H), 3.45-3.36 (m, 2H), 2.73 (td, J = 12.4, 2.2 Hz, 2H), 2.65-2.55 (m, 4H), 2.40-2.29 (m, 1H), 2.03-1.94 (m, 2H), 1.61 (qd, J = 12.3, 3.9 Hz, 2H). |
| BB22 | 5-Bromo-2-(3-(dimethylamino)azetidin-1-yl)pyridin-3-amine | 271.0<br>273.0 | ¹H NMR (400 MHz, CDCl₃) δ 7.74 (d, J = 2.0 Hz, 1H), 6.93 (d, J = 2.0 Hz, 1H), 4.19-4.04 (m, 2H), 3.93-3.88 (m, 2H), 3.21-3.14 (m, 1H), 2.24 (s, 6H). |

-continued

| Intermediate | Structure | Name | Ms: [(M + 1)]⁺ | ¹H-NMR |
|---|---|---|---|---|
| BB23 | 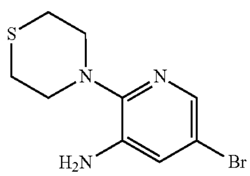 [SMILES: Nc1cc(Br)cnc1N1CCSCC1] | 5-Bromo-2-thiomorpholinopyridin-3-amine | 274.00<br>276.00 | ¹H NMR (400 MHz, CDCl$_3$) δ 7.80 (d, J = 2.2 Hz, 1H), 7.07 (d, J = 2.2 Hz, 1H), 3.83 (s, 2H), 3.37-3.21 (m 4H), 2.79 (t, J = 5.0 Hz, 4H) |
| BB24 | 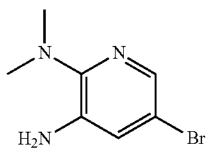 | 5-Bromo-N²,N²-dimethylpyridine-2,3-diamine | 216.00<br>218.00 | ¹H NMR (300 MHz, CDCl$_3$) δ 7.79 (d, J = 2.2 Hz, 1H), 7.04 (d, J = 2.1 Hz, 1H), 2.75 (s, 6H). |
| BB25 | 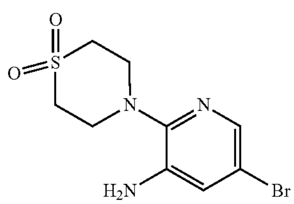 | 4-(3-Amino-5-bromopyridin-2-yl)thiomorpholine 1,1-dioxide | 306.00<br>308.00 | ¹H NMR (300 MHz, DMSO-d$_6$) δ 7.61 (d, J = 2.2 Hz, 1H), 7.15 (d, J = 2.3 Hz, 1H), 5.37 (s, 2H), 3.45-3.36 (m, 4H), 3.32-3.25 (m, 4H). |

Intermediate CC

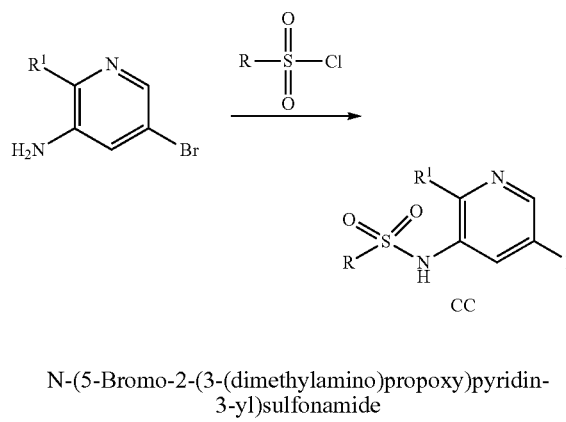

N-(5-Bromo-2-(3-(dimethylamino)propoxy)pyridin-3-yl)sulfonamide

General procedure A: To a solution of amine (1.0 mmol) in pyridine (10 mL) were added 4-dimethylaminopyridine (0.1 mmol) and the corresponding sulfonyl chloride (1.2 mmol) at ambient temperature. The resulting solution was stirred for 16 hours at 65° C. After cooling down to ambient temperature, the resulting mixture was concentrated under reduced pressure. The residue was purified by silica gel column chromatography, eluted with 1~20% methanol in dichloromethane. Desired fractions were collected and concentrated under reduced pressure afford the sulfonamide.

General procedure B: To a solution of amine (1.0 mmol) in pyridine (10 mL) was added the corresponding sulfonyl chloride (1.2 mmol) at ambient temperature. The resulting solution was stirred for 16 hours at ambient temperature. The resulting mixture was concentrated under reduced pressure. The residue was purified by silica gel column chromatography, eluted with 1~20% methanol in dichloromethane. Desired fractions were collected and concentrated under reduced pressure to afford the sulfonamide.

The following intermediates were prepared according to the above procedure A:

| Intermediate | Structure | Name | Ms: [(M +1)]⁺ | ¹H-NMR |
|---|---|---|---|---|
| CC1 | 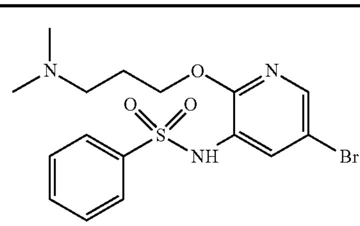 | N-(5-Bromo-2-(3-(dimethylamino)propoxy)pyridin-3-yl)benzenesulfonamide | 414.20<br>416.20 | ¹H NMR (300 MHz, CDCl$_3$) δ 7.91-7.81 (m, 2H), 7.77 (s, 2H), 7.56-7.44 (m, 3H), 4.29 (t, J = 5.9 Hz, 2H), 2.84 (t, J = 6.6 Hz, 2H), 2.66 (s, 6H), 2.11-2.04 (m, 2H). |

-continued

| Intermediate | Structure | Name | Ms: [(M +1)]⁺ | ¹H-NMR |
|---|---|---|---|---|
| CC2 | 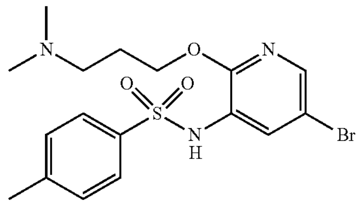 | N-(5-Bromo-2-(3-(dimethylamino)propoxy)pyridin-3-yl)-4-methylbenzene-sulfonamide | 428.10<br>430.10 | ¹H NMR (300 MHz, DMSO-$d_6$) δ 7.67-7.58 (m, 2H), 7.39 (d, J = 2.2 Hz, 1H), 7.25 (d, J = 7.9 Hz, 2H), 7.19 (d, J = 2.3 Hz, 1H), 4.23 (t, J = 5.5 Hz, 2H), 3.28 (t, J = 5.4 Hz, 2H), 2.89 (s, 6H), 2.32 (s, 3H), 2.13 (p, J = 5.9 Hz, 2H). |
| CC3 | 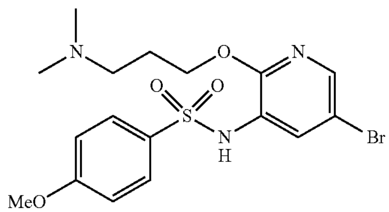 | N-(5-Bromo-2-(3-(dimethylamino)propoxy)pyridin-3-yl)-4-methoxybenzene-sulfonamide | 444.00<br>446.00 | ¹H NMR (400 MHz, CDCl$_3$) δ 7.82-7.72 (m, 4H), 6.91 (d, J = 8.9 Hz, 2H), 4.27 (t, J = 6.1 Hz, 2H), 3.83 (s, 3H), 2.56 (t, J = 6.4 Hz, 2H), 2.45 (s, 6H), 1.96-1.89 (m, 2H). |
| CC4 | 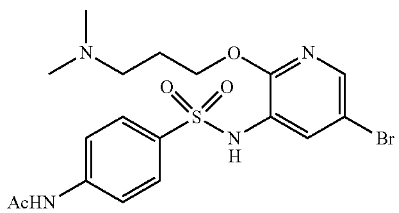 | N-(4-(N-(5-Bromo-2-(3-(dimethylamino)propoxy)pyridin-3-yl)sulfamoyl)phenyl)acetamide | 471.10<br>473.10 | ¹H NMR (300 MHz, CDCl$_3$) δ 10.15 (s, 1H), 7.71-7.59 (m, 5H), 7.40 (d, J = 2.2 Hz, 1H), 7.16 (d, J = 2.3 Hz, 1H), 4.22 (t, J = 5.5 Hz, 2H), 3.28 (t, J = 5.4 Hz, 2H), 2.89 (s, 6H), 2.15-2.08 (m, 2H), 2.04 (s, 3H). |
| CC5 | 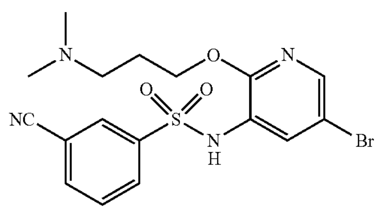 | N-(5-Bromo-2-(3-(dimethylamino)propoxy)pyridin-3-yl)-3-cyanobenzene-sulfonamide | 439.00<br>441.00 | ¹H NMR (400 MHz, DMSO-$d_6$) δ 8.05-7.95 (m, 2H), 7.87 (dt, J = 7.7, 1.4 Hz, 1H), 7.63 (t, J = 7.8 Hz, 1H), 7.36 (d, J = 2.3 Hz, 1H), 7.23 (d, J = 2.3 Hz, 1H), 4.17 (t, J = 6.5 Hz, 2H), 2.59 (t, J = 6.6 Hz, 2H), 2.35 (s, 6H), 1.90 (p, J = 6.6 Hz, 2H). |
| CC6 | 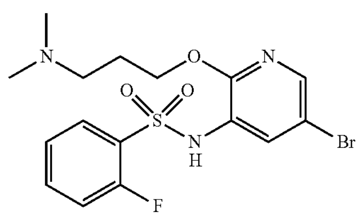 | N-(5-Bromo-2-(3-(dimethylamino)propoxy)pyridin-3-yl)-2-fluorobenzene-sulfonamide | 432.00<br>434.00 | ¹H NMR (400 MHz, CDCl$_3$) δ 8.01 (td, J = 7.6, 1.8 Hz, 1H), 7.59 (q, J = 2.2 Hz, 2H), 7.51-7.40 (m, 1H), 7.23 (td, J = 7.6, 1.1 Hz, 1H), 7.08 (td, J = 8.4, 1.2 Hz, 1H), 4.33 (t, J = 5.7 Hz, 2H), 3.08 (t, J = 5.9 Hz, 2H), 2.91 (s, 6H), 2.21-2.14 (m, 2H). |
| CC7 | 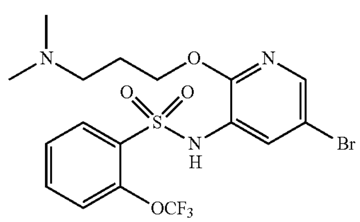 | N-(5-Bromo-2-(3-(dimethylamino)propoxy)pyridin-3-yl)-2-(trifluoromethoxy)benzenesulfonamide | 497.90<br>499.90 | ¹H NMR (300 MHz, CDCl$_3$) δ 8.14 (dd, J = 7.8, 1.8 Hz, 1H), 7.59 (d, J = 2.2 Hz, 1H), 7.56-7.51 (m, 1H), 7.49 (t, J = 1.8 Hz, 1H), 7.43-7.28 (m, 2H), 4.35 (t, J = 5.8 Hz, 2H), 3.11-2.97 (m, 2H), 2.85 (s, 6H), 2.19-2.10 (m, 2H). |
| CC8 | 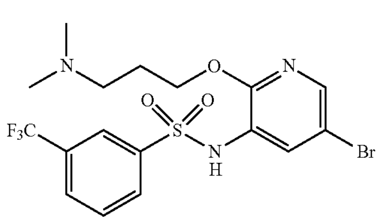 | N-(5-Bromo-2-(3-(dimethylamino)propoxy)pyridin-3-yl)-3-(trifluoromethyl)benzenesulfonamide | 481.90<br>483.90 | ¹H NMR (400 MHz, CDCl$_3$) δ 8.12 (s, 1H), 8.06 (d, J = 7.8 Hz, 1H), 7.71 (d, J = 7.8 Hz, 1H), 7.65-7.52 (m, 3H), 4.34 (t, J = 5.6 Hz, 2H), 3.10 (t, J = 5.7 Hz, 2H), 2.93 (s, 6H), 2.21-2.14 (m, 2H). |

-continued

| Intermediate | Structure | Name | Ms: [(M +1)]⁺ | ¹H-NMR |
|---|---|---|---|---|
| CC9 | 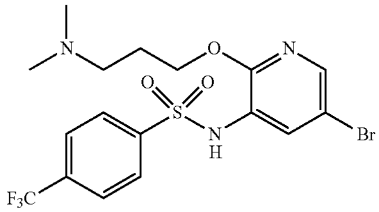 | N-(5-Bromo-2-(3-(dimethylamino)propoxy)pyridin-3-yl)-4-(trifluoromethyl)benzenesulfonamide | 481.90<br>483.90 | ¹H NMR (300 MHz, DMSO-$d_6$) δ 7.91 (d, J = 8.1 Hz, 2H), 7.80 (d, J = 8.1 Hz, 2H), 7.37 (d, J = 2.3 Hz, 1H), 7.24 (d, J = 2.3 Hz, 1H), 4.21 (t, J = 6.0 Hz, 2H), 2.64 (s, 6H), 2.97 (t, J = 6.0 Hz, 2H), 2.06-1.97 (m, 2H). |
| CC10 | 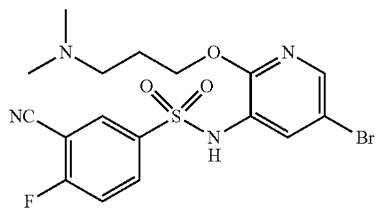 | N-(5-Bromo-2-(3-(dimethylamino)propoxy)pyridin-3-yl)-3-cyano-4-fluorobenzene-sulfonamide | 457.00<br>459.00 | ¹H NMR (300 MHz, CD$_3$OD) δ 8.24-8.09 (m, 2H), 7.54-7.42 (m, 2H), 7.32 (d, J = 2.2 Hz, 1H), 4.39 (t, J = 5.6 Hz, 2H), 3.39 (q, J = 5.5 Hz, 3H), 3.04 (s, 6H), 2.27 (p, J = 5.5 Hz, 2H). |
| CC11 | 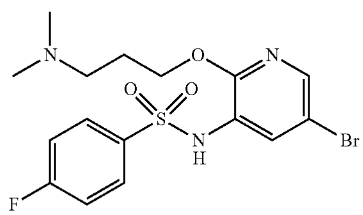 | N-(5-Bromo-2-(3-(dimethylamino)propoxy)pyridin-3-yl)-4-fluorobenzene-sulfonamide | 432.00<br>434.00 | ¹H NMR (400 MHz, CDCl$_3$) δ 7.85 (m, 2H), 7.68 (m, 2H), 7.10 (t, J = 8.5 Hz, 2H), 4.32 (t, J = 5.8 Hz, 2H), 2.86 (t, J = 6.0 Hz, 2H), 2.72 (s, 6H), 2.10-2.03 (m, 2H). |
| CC12 | 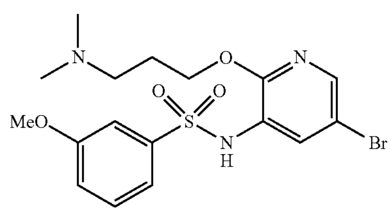 | N-(5-Bromo-2-(3-(dimethylamino)propoxy)pyridin-3-yl)-3-methoxybenzene-sulfonamide | 444.00<br>446.00 | ¹H NMR (400 MHz, DMSO-$d_6$) δ 7.43-7.26 (m, 3H), 7.26-7.20 (m, 2H), 7.02 (ddd, J = 8.1, 2.6, 1.1 Hz, 1H), 4.23 (t, J = 5.6 Hz, 2H), 3.77 (s, 3H), 3.35-3.28 (m, 2H), 2.91 (s, 6H), 2.16-2.09 (m, 2H). |
| CC13 | 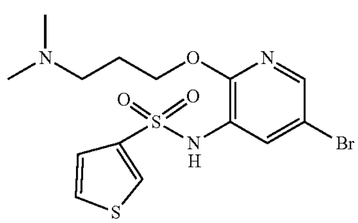 | N-(5-Bromo-2-(3-(dimethylamino)propoxy)pyridin-3-yl)thiophene-3-sulfonamide | 420.00<br>422.00 | ¹H NMR (300 MHz, CDCl$_3$) δ 7.91 (dd, J = 3.1, 1.3 Hz, 1H), 7.77 (d, J = 2.2 Hz, 1H), 7.71 (d, J = 2.3 Hz, 1H), 7.32 (dd, J= 5.1, 3.1 Hz, 1H), 7.25 (d, J = 1.3 Hz, 1H), 4.31 (t, J = 5.9 Hz, 2H), 2.79 (t, J = 6.0 Hz, 2H), 2.65 (s, 6H), 2.09-1.98 (m, 2H). |
| CC14 | 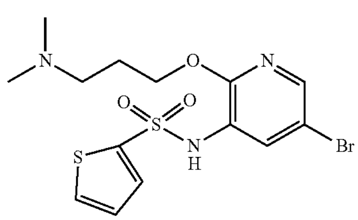 | N-(5-Bromo-2-(3-(dimethylamino)propoxy)pyridin-3-yl)thiophene-2-sulfonamide | 420.00<br>422.00 | ¹H NMR (300 MHz, DMSO-$d_6$) δ 7.62 (dd, J = 5.0, 1.3 Hz, 1H), 7.43 (d, J = 2.3 Hz, 1H), 7.39-7.34 (m, 2H), 7.01 (dd, J = 5.0, 3.6 Hz, 1H), 4.24 (t, J = 5.5 Hz, 2H), 3.40-3.30 (m, 2H), 2.93 (s, 6H), 2.19-2.08 (m, 2H). |
| CC15 | 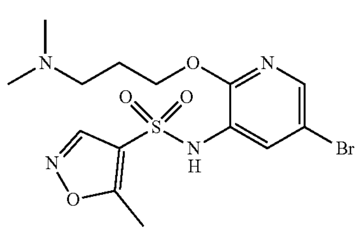 | N-(5-Bromo-2-(3-(dimethylamino)propoxy)pyridin-3-yl)-5-methylisoxazole-4-sulfonamide | 419.00<br>421.00 | ¹H NMR (300 MHz, DMSO-$d_6$) δ 9.30 (s, 1H), 7.89 (d, J = 2.3 Hz, 1H), 7.75 (d, J = 2.3 Hz, 1H), 4.33 (t, J = 5.7 Hz, 2H), 3.29 (t, J = 5.7 Hz, 2H), 2.83 (s, 6H), 2.14-2.04 (m, 2H), 1.83 (s, 3H). |

-continued

| Intermediate | Structure | Name | Ms: [(M +1)]⁺ | ¹H-NMR |
|---|---|---|---|---|
| CC16 | 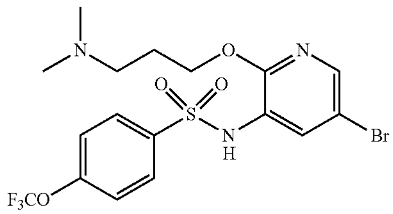 | N-(5-Bromo-2-(3-(dimethylamino)propoxy)pyridin-3-yl)-4-(trifluoromethoxy)benzenesulfonamide | 497.90 499.90 | ¹H NMR (300 MHz, CDCl₃) δ 7.97-7.89 (m, 2H), 7.73-7.62 (m, 2H), 7.30-7.25 (m, 1H), 7.24-7.23 (m, 1H), 4.32 (t, J = 5.6 Hz, 2H), 3.07 (t, J = 6.2 Hz, 2H), 2.85 (s, 6H), 2.21-2.11 (m, 2H). |
| CC17 | 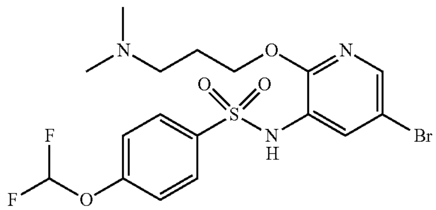 | N-(5-Bromo-2-(3-(dimethylamino)propoxy)pyridin-3-yl)-4-(difluoromethoxy)benzenesulfonamide | 479.90 481.90 | ¹H NMR (400 MHz, DMSO-d₆) δ 7.82-7.74 (m, 2H), 7.41 (d, J = 2.3 Hz, 1H), 7.31 (t, J = 73.6 Hz, 1H), 7.26-7.18 (m, 3H), 4.24 (t, J = 5.5 Hz, 2H), 3.34 (t, J = 5.2 Hz, 2H), 2.93 (s, 6H), 2.52-2.49 (m, 2H). |
| CC18 | 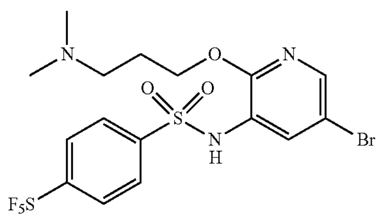 | N-(5-Bromo-2-(3-(dimethylamino)propoxy)pyridin-3-yl)-4-(pentafluoro-16-sulfaneyl)benzenesulfonamide | 540.00 542.00 | ¹H NMR (300 MHz, DMSO-d₆) δ 8.04-7.88 (m, 4H), 7.44 (d, J = 2.3 Hz, 1H), 7.26 (d, J = 2.3 Hz, 1H), 4.26 (t, J = 5.5 Hz, 2H), 3.36 (t, J = 5.3 Hz, 2H), 2.94 (s, 6H), 2.19-2.10 (m, 2H). |
| CC19 | 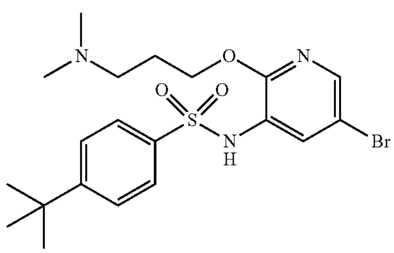 | N-(5-Bromo-2-(3-(dimethylamino)propoxy)pyridin-3-yl)-4-(tert-butyl)benzenesulfonamide | 470.10 472.10 | ¹H NMR (400 MHz, DMSO-d₆) δ 7.70-7.62 (m, 2H), 7.49-7.44 (m, 2H), 7.41 (d, J = 2.3 Hz, 1H), 7.28 (d, J = 2.3 Hz, 1H), 4.22 (t, J = 5.5 Hz, 2H), 3.30 (t, J = 5.0 Hz, 2H), 2.90 (s, 6H), 2.51 (s, 9H), 2.15-2.07 (m, 2H). |
| CC20 | 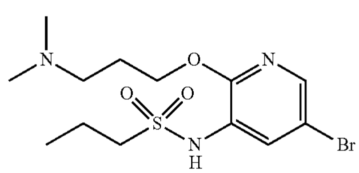 | N-(5-Bromo-2-(3-(dimethylamino)propoxy)pyridin-3-yl)propane-1-sulfonamide | 380.00 382.00 | ¹H NMR (300 MHz, CDCl₃) δ 7.89 (d, J = 2.2 Hz, 1H), 7.87 (d, J = 2.3 Hz, 1H), 4.40 (t, J = 6.0 Hz, 2H), 3.13-3.01 (m, 2H), 2.64-2.54 (m, 2H), 2.39 (s, 6H), 2.08-1.93 (m, 2H), 1.94-1.75 (m, 2H), 1.03 (t, J = 7.5 Hz, 3H). |
| CC21 | 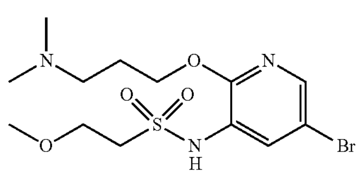 | N-(5-Bromo-2-(3-(dimethylamino)propoxy)pyridin-3-yl)-2-methoxyethane-1-sulfonamide | 396.00 398.00 | ¹H NMR (400 MHz, DMSO-d₆) δ 7.88 (d, J = 2.2 Hz, 1H), 7.86 (d, J = 2.3 Hz, 1H), 4.43 (t, J = 5.7 Hz, 2H), 3.80 (t, J = 5.9 Hz, 2H), 3.46 (t, J = 6.0 Hz, 2H), 3.28 (s, 3H), 3.20 (t, J = 7.5 Hz, 2H), 2.84 (s, 6H), 2.35-2.26 (m, 2H). |
| CC22 | 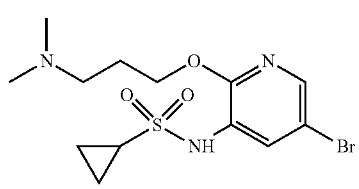 [SMILES: CN(C)CCCOc1ncc(Br)cc1NS(=O)(=O)C1CC1] | N-(5-Bromo-2-(3-(dimethylamino)propoxy)pyridin-3-yl)cyclopropanesulfonamide | 378.00 380.00 | ¹H NMR (300 MHz, CDCl₃) δ 7.93 (d, J = 0.6 Hz, 2H), 4.50 (t, J = 5.7 Hz, 2H), 3.23-3.06 (m, 2H), 2.82 (s, 6H), 2.72-2.63 (m, 1H), 2.34-2.19 (m, 2H), 1.33-1.25 (m, 2H), 1.09-1.01 (m, 2H). |

-continued

| Intermediate | Structure | Name | Ms: [(M +1)]⁺ | ¹H-NMR |
|---|---|---|---|---|
| CC23 | 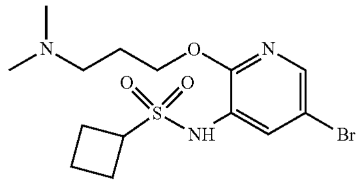 [SMILES: CN(C)CCCOc1ncc(Br)cc1NS(=O)(=O)C1CCC1] | N-(5-Bromo-2-(3-(dimethylamino)propoxy)pyridin-3-yl)cyclobutane-sulfonamide | 392.00 394.00 | $^1$H NMR (400 MHz, CDCl$_3$) δ 7.89-7.87 (m, 2H), 4.40 (t, J = 6.1 Hz, 2H), 3.91 (p, J = 8.2 Hz, 1H), 2.62-2.49 (m, 4H), 2.41 (s, 6H), 2.32-2.21 (m, 2H), 2.05-1.93 (m, 4H). |
| CC24 | 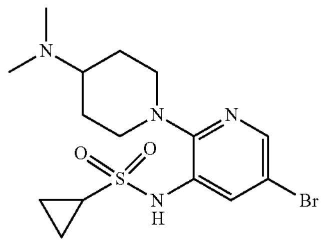 | N-(5-Bromo-2-(4-(dimethylamino)piperidin-1-yl)pyridin-3-yl)cyclopropane-sulfonamide | 402.95 404.95 | $^1$H NMR (400 MHz, CDCl$_3$) δ 8.13 (d, J = 2.2 Hz, 1H), 8.00 (d, J = 2.2 Hz, 1H), 3.18 (dq, J = 12.0, 2.3 Hz, 2H), 2.86 (td, J = 12.4, 2.3 Hz, 2H), 2.57 (tt, J = 7.9, 4.8 Hz, 1H), 2.35 (s, 6H), 2.03-1.95 (m, 2H), 1.65 (qd, J = 12.3, 3.9 Hz, 2H), 1.33-1.29 (m, 2H), 1.10-1.03 (m, 2H). |
| CC25 | 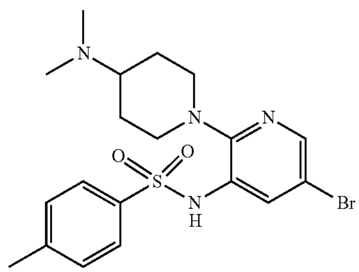 | N-(5-Bromo-2-(4-(dimethylamino)piperidin-1-yl)pyridin-3-yl)-4-methylbenzene-sulfonamide | 453.10 455.10 | $^1$H NMR (300 MHz, CDCl$_3$) δ 8.06 (d, J = 2.2 Hz, 1H), 7.98 (d, J = 2.2 Hz, 1H), 7.74 (d, J = 1.9 Hz, 1H), 7.72 (d, J = 1.9 Hz, 1H), 7.30 (s, 1H), 7.28 (s, 1H), 2.84-2.63 (m, 5H), 2.40 (s, 3H), 2.33 (s, 6H), 1.88 (d, 13.0 Hz, 2H), 1.56 (qd, J = 11.9, 4.3 Hz, 2H). |
| CC26 | 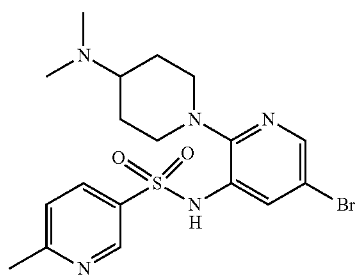 | N-(5-Bromo-2-(4-(dimethylamino)piperidin-1-yl)pyridin-3-yl)-6-methylpyridine-3-sulfonamide | 454.05 456.05 | $^1$H NMR (300 MHz, DMSO-d$_6$) δ 8.68 (d, J = 2.3 Hz, 1H), 7.88 (dd, J = 8.0, 2.3 Hz, 1H), 7.47 (d, J = 2.3 Hz, 1H), 7.32 (d, J = 2.3 Hz, 1H), 7.28 (d, J = 8.0 Hz, 1H), 4.34 (d, J = 12.6 Hz, 2H), 3.25-3.12 (m, 2H), 2.71 (s, 6H), 2.58-2.53 (m, 1H), 2.47 (s, 3H), 1.97 (d, J = 11.7 Hz, 2H), 1.72-1.55 (m, 2H). |
| CC27 | 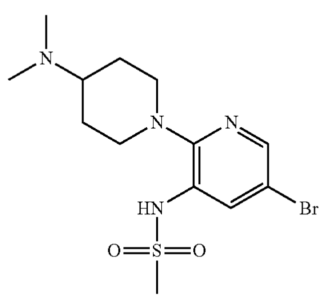 [SMILES: CN(C)C1CCN(c2ncc(Br)cc2NS(C)(=O)=O)CC1] | N-(5-Bromo-2-(4-(dimethylamino)piperidin-1-yl)pyridin-3-yl)methane-sulfonamide | 377.10 379.10 | $^1$H NMR (400 MHz, DMSO-d$_6$) δ 7.20 (s, 1H), 6.99 (d, J = 2.2 Hz, 1H), 3.09 (d, J = 12.5 Hz, 2H), 2.55-2.52 (m, 1H), 2.30 (s, 3H), 1.99 (t, J = 12.2 Hz, 2H), 1.87-1.80 (m, 4H), 1.72 (s, 6H). |
| CC28 | 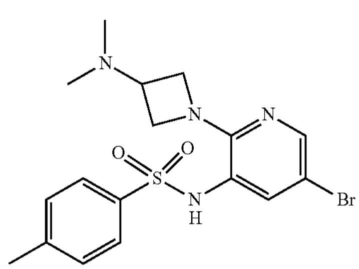 | N-(5-Bromo-2-(3-(dimethylamino)azetidin-1-yl)pyridin-3-yl)-4-methylbenzene-sulfonamide | 425.15 427.15 | $^1$H NMR (400 MHz, CDCl$_3$) δ 7.98 (d, J = 2.0 Hz, 1H), 7.65 (d, J = 7.9 Hz, 2H), 7.30 (d, J = 8.0 Hz, 2H), 7.20 (d, J = 2.0 Hz, 1H), 4.06 (t, J = 7.7 Hz, 2H), 3.74-3.68 (m, 2H), 3.06 (p, J = 6.4 Hz, 1H), 2.43 (s, 3H), 2.15 (s, 6H). |

-continued

| Intermediate | Structure | Name | Ms: [(M +1)]⁺ | ¹H-NMR |
|---|---|---|---|---|
| CC29 | 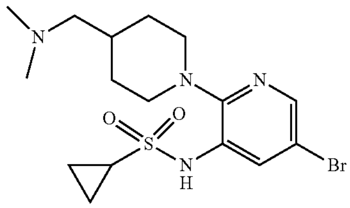 | N-(5-Bromo-2-(4-((dimethylamino)methyl)piperidin-1-yl)pyridin-3-yl)cyclopropane-sulfonamide | 416.95<br>419.00 | ¹H NMR (300 MHz, CDCl₃) δ 8.13 (d, J = 2.2 Hz, 1H), 8.00 (d, J = 2.2 Hz, 1H), 3.16 (d, J = 12.5 Hz, 2H), 2.88 (dd, J = 12.7, 10.4 Hz, 2H), 2.68 (s, 6H), 2.56 (dd, J = 8.1, 4.7 Hz, 1H), 2.06 (d, J = 13.2 Hz, 2H), 1.57-1.44 (m, 2H), 1.32-1.28 (m, 2H). |
| CC30 | 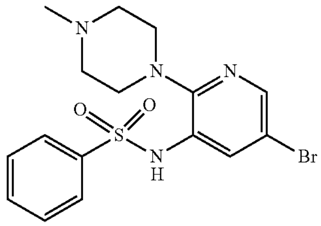 | N-(5-Bromo-2-(4-methylpiperazin-1-yl)pyridin-3-yl)benzene-sulfonamide | 411.00<br>413.00 | ¹H NMR (300 MHz, DMSO-d₆) δ 7.77-7.68 (m, 3H), 7.53-7.45 (m, 3H), 7.33 (d, J = 2.3 Hz, 1H), 3.57 (s, 4H), 2.96 (s, 4H), 2.61 (s, 3H). |
| CC31 | 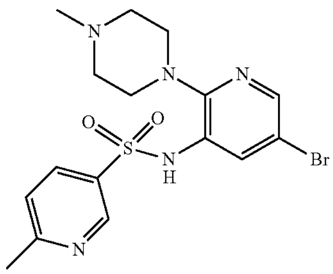 | N-(5-Bromo-2-(4-methylpiperazin-1-yl)pyridin-3-yl)-6-methylpyridine-3-sulfonamide | 426.0<br>428.0 | ¹H NMR (400 MHz, CD₃OD) δ 8.79 (d, J = 2.2 Hz, 1H), 8.06 (dd, J = 8.2, 2.4 Hz, 1H), 7.80 (d, J = 2.2 Hz, 1H), 7.52 (d, J = 2.2 Hz, 1H), 7.41 (d, J = 8.2 Hz, 1H), 3.05 (s, 4H), 2.70 (s, 4H), 2.58 (s, 3H). |
| CC32 | 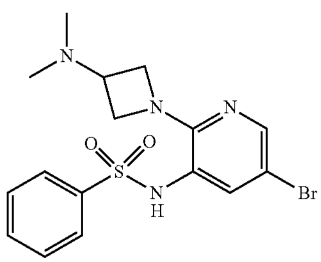 | N-(5-Bromo-2-(3-(dimethylamino)azetidin-1-yl)pyridin-3-yl)benzene-sulfonamide | 411.05<br>413.05 | ¹H NMR (400 MHz, CDCl₃) δ 7.97 (d, J = 2.1 Hz, 1H), 7.76 (d, J = 7.7 Hz, 2H), 7.62 (t, J = 7.5 Hz, 1H), 7.53 (d, J = 7.6 Hz, 2H), 7.10 (d, J = 2.1 Hz, 1H), 4.06 (q, J = 7.5 Hz, 2H), 3.71 (dd, J = 8.5, 5.5 Hz, 2H), 3.04 (p, J = 6.1 Hz, 1H), 2.16 (s, 6H). |
| CC33 | 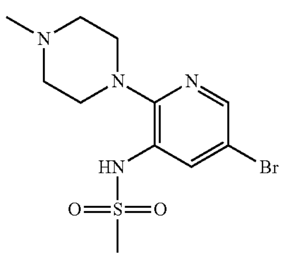 [SMILES: CN1CCN(c2ncc(Br)cc2NS(C)(=O)=O)CC1] | N-(5-Bromo-2-(4-methylpiperazin-1-yl)pyridin-3-yl)methanesulfonamide | 351.00<br>349.00 | ¹H NMR (400 MHz, DMSO-d) δ 7.37 (d, J = 1.4 Hz, 2H), 6.05 (s, 4H), 2.56 (d, J = 1.3 Hz, 3H), 2.36 (t, J = 4.8 Hz, 4H), 2.17 (s, 3H). |
| CC34 | 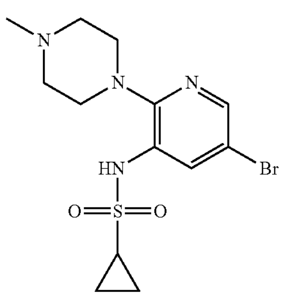 [SMILES: CN1CCN(c2ncc(Br)cc2NS(=O)(=O)C2CC2)CC1] | N-(5-Bromo-2-(4-methylpiperazin-1-yl)pyridin-3-yl)cyclopropane-sulfonamide | 374.95<br>376.95 | ¹H NMR (400 MHz, CD₃OD) δ 8.08 (d, J = 2.3 Hz, 1H), 7.88 (d, J = 2.3 Hz, 1H), 2.69 (s, 4H), 2.65 (s, 3H), 2.39 (s, 4H), 1.12-1.01 (m, 5H). |

| Intermediate | Structure | Name | Ms: [(M +1)]+ | 1H-NMR |
|---|---|---|---|---|
| CC35 | 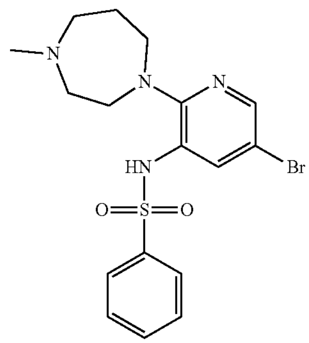 [SMILES: CN1CCCN(c2ncc(Br)cc2NS(=O)(=O)c2ccccc2)CC1] | N-(5-Bromo-2-(4-methyl-1,4-diazepan-1-yl)pyridin-3-yl)benzenesulfonamide | 425.00<br>427.00 | 1H NMR (300 MHz, DMSO-d6) δ 7.72-7.66 (m, 3H), 7.54-7.47 (m, 3H), 7.11 (s, 1H), 3.61-3.53 (m, 2H), 3.50-3.38 (m, 4H), 3.25 (t, J = 5.4 Hz, 2H), 2.83 (s, 3H), 2.08-1.97 (m, 2H). |
| CC36 | 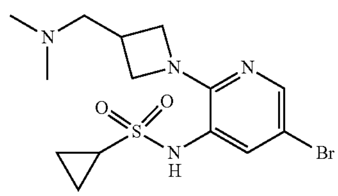 | N-(5-Bromo-2-(3-((dimethylamino)methyl)azetidin-1-yl)pyridin-3-yl)cyclopropanesulfonamide | 389.00<br>391.00 | 1H NMR (400 MHz, CDCl3) δ 8.08 (d, J = 2.2 Hz, 1H), 7.69 (d, J = 2.2 Hz, 1H), 4.27 (t, J = 8.1 Hz, 2H), 3.85 (dd, J = 8.2, 6.0 Hz, 2H), 2.93-2.85 (m, 1H), 2.59-2.52 (m, 3H), 2.24 (s, 6H), 1.22-1.18 (m, 2H), 1.07-1.02 (m, 2H). |
| CC37 | 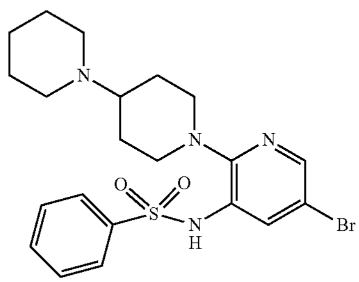 | N-(2-([1,4'-Bipiperidin]-1'-yl)-5-bromopyridin-3-yl)benzenesulfonamide | 479.10<br>481.10 | 1H NMR (300 MHz, DMSO-d6) δ 7.69 (dd, J = 6.9, 2.8 Hz, 2H), 7.50 (s, 1H), 7.44-7.40 (m, 3H), 7.28 (d, J = 2.3 Hz, 1H), 4.26 (d, J = 12.6 Hz, 2H), 3.17 (d, J = 5.1 Hz, 1H), 3.02 (s, 4H), 1.90 (d, J = 8.1 Hz, 2H), 1.74-1.58 (m, 8H), 1.51 (s, 2H). |
| CC38 | 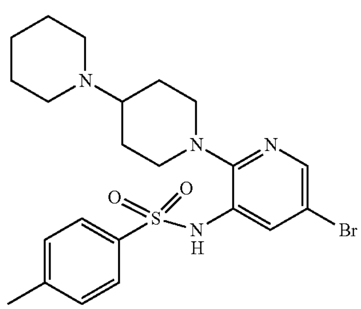 | N-(2-([1,4'-Bipiperidin]-'1'-yl)-5-bromopyridin-3-yl)-4-methylbenzenesulfonamide | 493.20<br>495.20 | 1H NMR (400 MHz, CDCl3) δ 8.05 (d, J = 2.2 Hz, 1H), 7.99 (d, J = 2.2 Hz, 1H), 7.73 (d, J = 8.1 Hz, 2H), 7.29 (d, J = 7.9 Hz, 2H), 2.81-2.64 (m, 4H), 2.56 (s, 4H), 2.40 (s, 3H), 2.38-2.31 (m, 1H), 1.89 (d, J = 12.6 Hz, 2H), 1.68-1.56 (m, 6H), 1.51-1.43 (m, 2H). |
| CC39 | 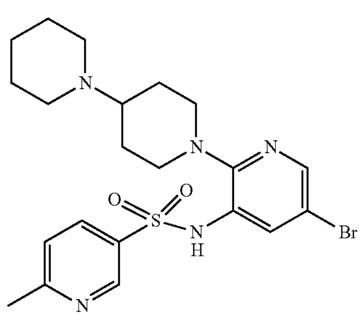 | N-(2-([1,4'-Bipiperidin]-1'-yl)-5-bromopyridin-3-yl)-6-methylpyridine-3-sulfonamide | 494.20<br>496.20 | 1H NMR (400 MHz, CDCl3) δ 8.94 (d, J = 2.4 Hz, 1H), 8.02-7.98 (m, 2H), 7.87 (d, J = 2.2 Hz, 1H), 7.26 (d, J = 8.6 Hz, 1H), 3.07 (d, J = 12.2 Hz, 2H), 2.73-2.64 (m, 3H), 2.61 (s, 7H), 1.94 (d, J = 12.5 Hz, 2H), 1.71-1.62 (m, 6H), 1.52-1.44 (m, 2H). |

| Intermediate | Structure | Name | Ms: [(M +1)]$^+$ | $^1$H-NMR |
|---|---|---|---|---|
| CC40 | 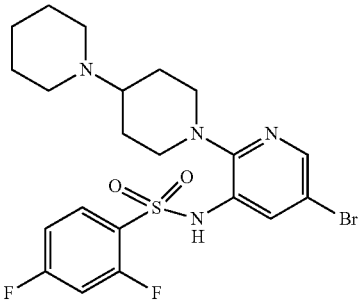 | N-(2-([1,4'-Bipiperidin]-1'-yl)-5-bromopyridin-3-yl)-2,4-difluorobenzene-sulfonamide | 515.10<br>517.10 | $^1$H NMR (400 MHz, DMSO-d$_6$) δ 9.23 (s, 1H), 7.78 (q, J = 7.9 Hz, 1H), 7.55 (s, 1H), 7.34 (s, 1H), 7.27 (t, J = 9.9 Hz, 1H), 7.11 (t, J = 8.6 Hz, 1H), 4.34 (d, J = 12.4 Hz, 2H), 3.31-2.79 (m, 5H), 2.56 (d, J = 11.8 Hz, 2H), 1.98 (d, J = 11.8 Hz, 2H), 1.78-1.61 (m, 6H), 1.61-1.40 (m, 2H). |
| CC41 | 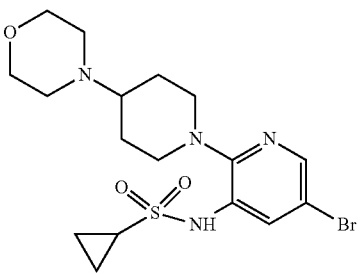 [SMILES: O=S(=O)(Nc1cc(Br)cnc1N1CCC(N2CCOCC2)CC1)C1CC1] | N-(5-Bromo-2-(4-morpholinopiperidin-1-yl)pyridin-3-yl)cyclopropane-sulfonamide<br>Molecular Weight: 445.38 | 445.10<br>497.10 | $^1$H NMR (400 MHz, DMSO-d$_6$) δ 9.11 (s, 1H), 8.14 (d, J = 2.3 Hz, 1H), 7.74 (d, J = 2.3 Hz, 1H), 3.73 (d, J = 12.7 Hz, 2H), 3.58 (t, J = 4.5 Hz, 4H), 2.88-2.80 (m, 1H), 2.73 (td, J = 12.3, 2.3 Hz, 2H), 2.56-2.44 (m, 4H), 2.33 (s, 1H), 1.86-1.78 (m, 2H), 1.60 (qd, J = 12.0, 3.4 Hz, 2H), 1.05-0.90 (m, 4H). |
| CC42 | 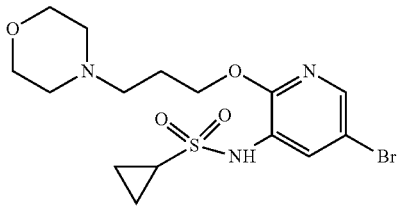 [SMILES: O=S(=O)(Nc1cc(Br)cnc1OCCCN1CCOCC1)C1CC1] | N-(5-Bromo-2-(3-morpholinopropoxy)pyridin-3-yl)cyclopropane-sulfonamide | 420.00<br>422.00 | $^1$H NMR (400 MHz, CDCl$_3$) δ 7.93 (t, J = 1.6 Hz, 2H), 4.44 (t, J = 6.3 Hz, 2H), 3.83 (s, 4H), 2.85-2.32 (m, 7H), 2.21-1.99 (m, 2H), 1.28-1.22 (m, 2H), 1.05-0.98 (m, 2H). |
| CC43 | 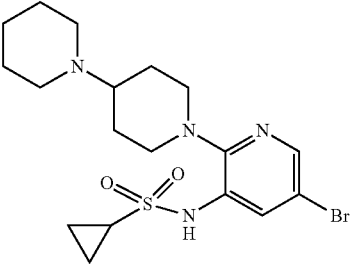 | N-(2-([1,4'-Bipiperidin]-1'-yl)-5-bromopyridin-3-yl)cyclopropane-sulfonamide | 443.15<br>445.15 | $^1$H NMR (400 MHz, DMSO-d$_6$) δ 7.82 (s, 1H), 7.63 (s, 1H), 3.98 (d, J = 12.3 Hz, 2H), 2.70-2.54 (m, 8H), 1.84-1.74 (m, 2H), 1.70-1.61 (m, 2H), 1.60-1.48 (m, 4H), 1.42 (s, 2H), 0.91-0.81 (m, 4H). |
| CC44 | 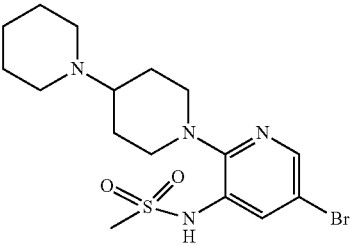 | N-(2-([1,4'-Bipiperidin]-1'-yl)-5-bromopyridin-3-yl)methane-sulfonamide | 417.00<br>419.00 | $^1$H NMR (400 MHz, CDCl$_3$) δ 8.13 (d, J = 2.2 Hz, 1H), 7.91 (d, J = 2.2 Hz, 1H), 3.17 (d, J = 12.2 Hz, 2H), 3.11 (s, 3H), 2.85 (td, J = 12.8, 2.4 Hz, 2H), 2.62 (s, 4H), 2.55-2.46 (m, 1H), 2.02 (d, J = 12.1 Hz, 2H), 1.81-1.72 (m, 2H), 1.71-1.63 (m, 4H), 1.52-1.45 (m, 2H). |

-continued

| Intermediate | Structure | Name | Ms: [(M +1)]⁺ | ¹H-NMR |
|---|---|---|---|---|
| CC45 | 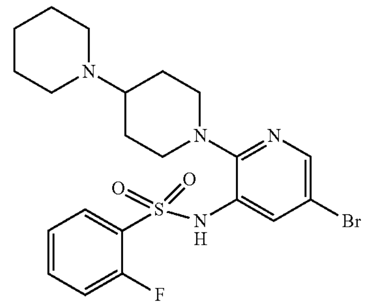 | N-(2-([1,4'-Bipiperidin]-1'-yl)-5-bromopyridin-3-yl)-2-fluorobenzene-sulfonamide | 497.20<br>499.20 | ¹H NMR (400 MHz, DMSO-d₆) δ 7.85 (s, 1H), 7.74 (t, J = 7.6 Hz, 1H), 7.60 (q, J = 7.0 Hz, 1H), 7.44-7.27 (m, 3H), 4.04 (d, J = 12.5 Hz, 2H), 3.45-2.82 (m, 5H), 2.59 (t, J 12.3 Hz, 2H), 1.98 (d, J = 11.7 Hz, 2H), 1.86-1.73 (m, 4H), 1.67 (qd, J = 12.1, 3.7 Hz, 3H), 1.55 (s, 1H). |
| CC46 | 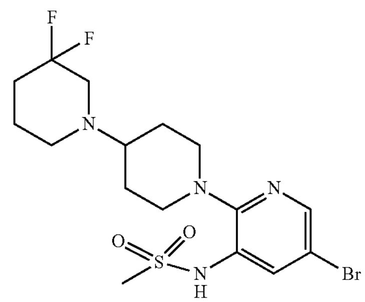 | N-(5-Bromo-2-(3,3-difluoro-[1,4'-bipiperidin]-1'-yl)pyridin-3-yl)methane-sulfonamide | 453.00<br>455.00 | ¹H NMR (400 MHz, CD₃OD) δ 8.04 (d, J = 2.1 Hz, 1H), 7.84 (d, J = 2.2 Hz, 1H), 3.58 (d, J = 12.7 Hz, 2H), 3.12 (s, 3H), 2.86-2.73 (m, 4H), 2.63 (d, J = 5.7 Hz, 2H), 2.55 (t, J = 12.0 Hz, 1H), 1.97-1.83 (m, 4H), 1.83-1.71 (m, 4H). |
| CC47 | 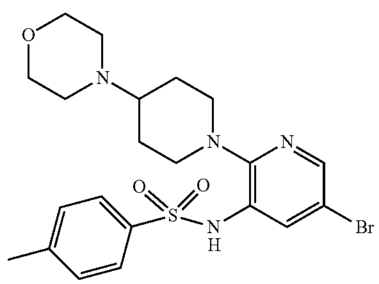 | N-(5-Bromo-2-(4-morpholinopiperidin-1-yl)pyridin-3-yl)-4-methylbenzene-sulfonamide | 495.10<br>497.10 | ¹H NMR (400 MHz, CDCl₃) δ 8.06 (d, J = 2.3 Hz, 1H), 7.98 (d, J = 2.2 Hz, 1H), 7.76-7.69 (m, 2H), 7.29 (d, J = 8.1 Hz, 2H), 3.79-3.72 (m, 4H), 2.82-2.74 (m, 2H), 2.69 (td, J = 12.2, 2.3 Hz, 2H), 2.62-2.55 (m, 4H), 2.40 (s, 3H), 2.29 (tt, J = 11.1, 3.9 Hz, 1JH), 1.91 (d, J = 12.2 Hz, 2H), 1.58 (qd, J = 12.0, 4.2 Hz, 2H). |
| CC48 | 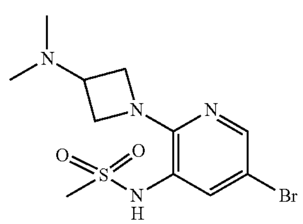 | N-(5-Bromo-2-(3-(dimethylamino)azetidin-1-yl)pyridin-3-yl)methane-sulfonamide | 349.00<br>351.00 | ¹H NMR (400 MHz, CD₃OD) δ 7.92 (d, J = 2.2 Hz, 1H), 7.61 (d, J = 2.2 Hz, 1H), 4.27 (dd, J = 8.8, 7.2 Hz, 2H), 3.96 (dd, J = 9.0, 5.6 Hz, 2H), 3.20 (p, J = 6.4 Hz, 1H), 3.00 (s, 3H), 2.20 (s, 6H). |

The following intermediates were prepared according to the procedure B:

| Intermediate | Structure | Name | MS: [(M + 1)]⁺ | ¹H-NMR |
|---|---|---|---|---|
| CC49 | 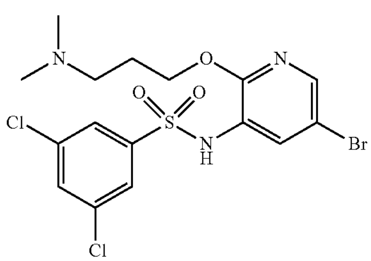 [SMILES: CN(C)CCCOc1ncc(Br)cc1NS(=O)(=O)c1cc(Cl)cc(Cl)c1] | N-(5-Bromo-2-(3-(dimethylamino)propoxy)pyridin-3-yl)-3,5-dichlorobenzenesulfonamide | 482.00<br>484.00<br>486.00 | ¹H NMR (400 MHz, DMSO-d₆) δ 7.68 (t, J = 1.9 Hz, 1H), 7.61 (d, J = 1.9 Hz, 2H), 7.40 (d, J = 2.3 Hz, 1H), 7.25 (d, J = 2.3 Hz, 1H), 4.18 (t, J = 6.3 Hz, 2H), 2.69 (t, J = 6.7 Hz, 2H), 2.42 (s, 6H), 1.98-1.90 (m, 2H). |

| Intermediate | Structure | Name | MS: [(M + 1)]⁺ | ¹H-NMR |
|---|---|---|---|---|
| CC50 | 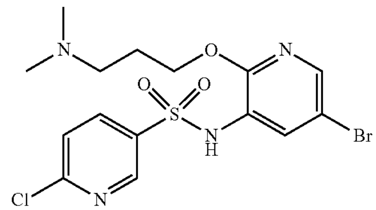 [SMILES: CN(C)CCCOc1ncc(Br)cc1NS(=O)(=O)c1ccc(Cl)nc1] | N-(5-Bromo-2-(3-(dimethylamino)propoxy)pyridin-3-yl)-6-chloropyridine-3-sulfonamide | 448.80 450.80 452.80 | ¹H NMR (300 MHz, CD₃OD) δ 8.75 (d, J = 2.4 Hz, 1H), 8.17 (dd, J = 8.3, 2.5 Hz, 1H), 7.60-7.47 (m, 2H), 7.37 (d, J = 2.3 Hz, 1H), 4.39 (t, J = 5.6 Hz, 2H), 3.45-3.35 (m, 2H), 3.04 (s, 6H), 2.26 (p, J = 5.5 Hz, 2H). |
| CC51 | 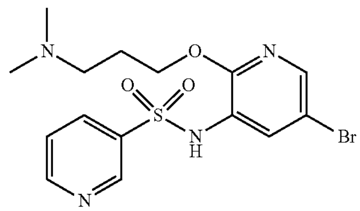 [SMILES: CN(C)CCCOc1ncc(Br)cc1NS(=O)(=O)c1cccnc1] | N-(5-Bromo-2-(3-(dimethylamino)propoxy)pyridin-3-yl)pyridine-3-sulfonamide | 415.00 417.00 | ¹H NMR (300 MHz, CD₃OD) δ 8.93 (dd, J = 2.3, 0.9 Hz, 1H), 8.63 (dd, J = 5.0, 1.6 Hz, 1H), 8.21 (dt, J = 8.0, 1.8 Hz, 1H), 7.58-7.46 (m, 2H), 7.36 (d, J = 2.2 Hz, 1H), 4.36 (t, J = 5.6 Hz, 2H), 3.40-3.34 (m, 2H), 3.03 (s, 6H), 2.28-2.19 (m, 2H). |
| CC52 | 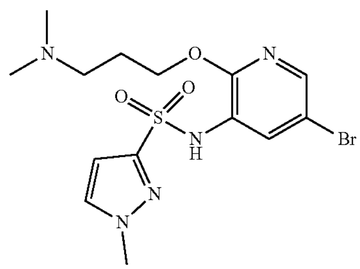 [SMILES: CN(C)CCCOc1ncc(Br)cc1NS(=O)(=O)c1ccn(C)n1] | N-(5-Bromo-2-(3-(dimethylamino)propoxy)pyridin-3-yl)-1-methyl-1H-pyrazole-3-sulfonamide | 417.90 419.90 | ¹H NMR (300 MHz, CD₃OD) δ 7.63 (d, J = 2.3 Hz, 1H), 7.50 (dd, J = 17.6, 2.2 Hz, 2H), 6.61 (d, J = 2.3 Hz, 1H), 4.36 (t, J = 5.6 Hz, 2H), 3.91 (s, 3H), 3.36 (t, J = 3.8 Hz, 2H), 3.01 (s, 6H), 2.24 (p, J = 5.5 Hz, 2H). |
| CC53 | 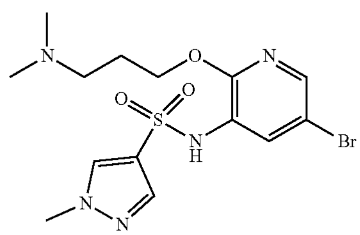 [SMILES: CN(C)CCCOc1ncc(Br)cc1NS(=O)(=O)c1cnn(C)c1] | N-(5-Bromo-2-(3-(dimethylamino)propoxy)pyridin-3-yl)-1-methyl-1H-pyrazole-4-sulfonamide | 418.00 420.00 | ¹H NMR (300 MHz, CD₃OD) δ 8.02 (s, 1H), 7.86-7.83 (m, 1H), 7.71 (d, J = 0.8 Hz, 1H), 7.69 (d, J = 2.3 Hz, 1H), 4.36 (t, J = 5.9 Hz, 2H), 3.88 (s, 3H), 3.26 (t, J = 7.2 Hz, 2H), 2.93 (s, 6H), 2.22-2.11 (m, 2H). |
| CC54 | 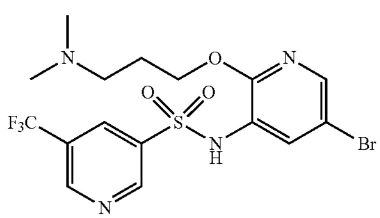 [SMILES: CN(C)CCCOc1ncc(Br)cc1NS(=O)(=O)c1cncc(C(F)(F)F)c1] | N-(5-Bromo-2-(3-(dimethylamino)propoxy)pyridin-3-yl)-5-(trifluoromethyl)pyridine-3-sulfonamide | 483.10 485.10 | ¹H NMR (400 MHz, CDCl₃) δ 9.19 (d, J = 2.0 Hz, 1H), 8.90 (d, J = 2.1 Hz, 1H), 8.42 (d, J = 2.2 Hz, 1H), 7.61-7.52 (m, 2H), 4.38 (t, J = 5.6 Hz, 2H), 3.26 (t, J = 5.6 Hz, 2H), 3.07 (s, 6H), 2.29-2.21 (m, 2H). |
| CC55 | 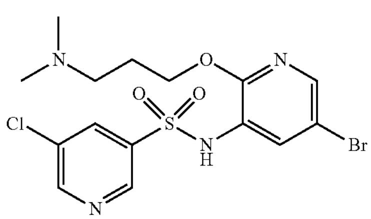 [SMILES: CN(C)CCCOc1ncc(Br)cc1NS(=O)(=O)c1cncc(Cl)c1] | N-(5-Bromo-2-(3-(dimethylamino)propoxy)pyridin-3-yl)-5-chloropyridine-3-sulfonamide | 448.90 450.90 452.90 | ¹H NMR (400 MHz, CDCl₃) δ 8.87 (d, J = 1.9 Hz, 1H), 8.58 (d, J = 2.3 Hz, 1H), 8.13 (t, J = 2.1 Hz, 1H), 7.55 (d, J = 2.2 Hz, 1H), 7.51 (d, J = 2.2 Hz, 1H), 6.88 (s, 2H), 4.37 (t, J = 5.6 Hz, 2H), 3.26-3.21 (m, 2H), 3.06 (s, 6H), 2.26-2.19 (m, 2H). |
| CC56 | 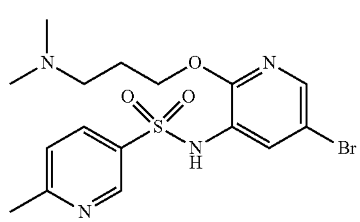 [SMILES: Cc1ccc(S(=O)(=O)Nc2cc(Br)cnc2OCCCN(C)C)cn1] | N-(5-Bromo-2-(3-(dimethylamino)propoxy)pyridin-3-yl)-6-methylpyridine-3-sulfonamide | 428.90 430.90 | ¹H NMR (400 MHz, DMSO-d₆) δ 8.74 (d, J = 2.3 Hz, 1H), 7.95 (dd, J = 8.1, 2.4 Hz, 1H), 7.41 (d, J = 2.2 Hz, 1H), 7.32 (d, J = 8.1 Hz, 1H), 7.20 (d, J = 2.3 Hz, 1H), 4.24 (t, J = 5.6 Hz, 2H), 3.34 (t, J = 5.2 Hz, 2H), 2.93 (s, 6H), 2.48 (s, 3H), 2.19-2.10 (m, 2H). |

| Intermediate | Name | MS: [(M + 1)]+ | 1H-NMR |
|---|---|---|---|
| CC57 | N-(5-Bromo-2-(3-(dimethylamino)propoxy)pyridin-3-yl)methanesulfonamide | 352.00 354.00 | 1H NMR (300 MHz, DMSO-d6) δ 7.79 (d, J = 2.3 Hz, 1H), 7.62 (d, J = 2.3 Hz, 1H), 4.30 (t, J = 5.8 Hz, 2H), 3.14 (t, J = 6.6 Hz, 2H), 2.93 (s, 3H), 2.71 (s, 6H), 2.15-2.04 (m, 2H). |
| CC58 | N-(5-Bromo-2-(3-(dimethylamino)propoxy)pyridin-3-yl)ethanesulfonamide | 366.00 368.00 | 1H NMR (300 MHz, CD3OD) δ 8.02 (d, J = 2.3 Hz, 1H), 7.88 (d, J = 2.2 Hz, 1H), 4.50 (t, J = 5.9 Hz, 2H), 3.43-3.31 (m, 2H), 3.19 (q, J = 7.3 Hz, 2H), 2.93 (s, 6H), 2.29-2.18 (m, 2H), 1.36 (t, J = 7.3 Hz, 3H) |
| CC59 | N-(5-Bromo-2-(3-(dimethylamino)propoxy)pyridin-3-yl)-1-phenylmethanesulfonamide | 428.00 430.00 | 1H NMR (300 MHz, CDCl3) 7.76 (d, J = 2.2 Hz, 1H), 7.46 (s, 1H), 7.31 (s, 5H), 4.42 (s, 2H), 4.35 (t, J = 5.7 Hz, 2H), 2.90 (s, 2H), 2.55 (s, 6H), 2.16-2.07 (m, 2H). |
| CC60 | tert-Butyl (2-((5-bromo-3-(methylsulfonamido)pyridin-2-yl)oxy)ethyl)(isopropyl)carbamate | 452.00 454.00 | 1H NMR (400 MHz, DMSO-d6) δ 9.41 (s, 1H), 8.05 (d, J = 2.2 Hz, 1H), 7.79 (d, J = 2.2 Hz, 1H), 4.35 (t, J = 6.3 Hz, 2H), 4.15 (m, 1H), 3.43 (t, J = 6.3 Hz, 2H), 3.11 (s, 3H), 1.39 (s, 9H), 1.09 (d, J = 6.8 Hz, 6H). |
| CC61 | tert-Butyl (2-((5-bromo-3-(ethylsulfonamido)pyridin-2-yl)oxy)ethyl)(isopropyl)carbamate | 466.10 468.10 | 1H NMR (400 MHz, CD3OD) δ 7.92 (s, 1H), 7.87 (s, 1H), 4.48 (t, J = 6.6 Hz, 2H), 4.25-4.20 (m, 1H), 3.54 (t, J = 6.6 Hz, 2H), 3.13 (t, J = 7.3 Hz, 2H), 1.49 (s, 9H), 1.35 (t, J = 7.4 Hz, 3H), 1.19 (d, J = 6.8 Hz, 6H). |
| CC62 | tert-Butyl (2-((5-bromo-3-(methylsulfonamido)pyridin-2-yl)oxy)ethyl)(ethyl)carbamate | 438.00 440.00 | 1H NMR (400 MHz, CDCl3) δ 7.95-7.90 (m, 2H), 4.45 (s, 2H), 3.58 (t, J = 5.5 Hz, 2H), 3.25 (s, 3H), 3.04 (s, 2H), 1.46 (s, 9H), 1.12 (t, J = 7.0 Hz, 3H). |
| CC63 | N-(5-Bromo-2-(3-(dimethylamino)butoxy)pyridin-3-yl)methanesulfonamide | 366.15 368.15 | 1H NMR (400 MHz, CDCl3) δ 7.83 (d, J = 2.2 Hz, 1H), 7.79 (d, J = 2.2 Hz, 1H), 4.50-4.43 (m, 1H), 4.34-4.31 (m, 1H), 3.05-2.96 (m, 4H), 2.54 (s, 6H), 2.09-1.89 (m, 2H), 1.15 (d, J = 6.7 Hz, 3H). |

-continued

| Intermediate | Name | MS: [(M + 1)]+ | 1H-NMR |
|---|---|---|---|
| CC64 | N-(5-Bromo-2-(2-(tert-butylamino)ethoxy)pyridin-3-yl)methanesulfonamide | 366.10<br>368.10 | 1H NMR (400 MHz, DMSO-d6) δ 7.65 (d, J = 2.3 Hz, 1H), 7.59 (d, J = 2.3 Hz, 1H), 4.30 (t, J = 5.4 Hz, 2H), 3.02 (t, J = 5.5 Hz, 2H), 2.80 (s, 3H), 1.19 (s, 9H). |
| CC65 | tert-Butyl 4-(3-((5-bromo-3-(methylsulfonamido)pyridin-2-yl)oxy)propyl)piperazine-1-carboxylate | 493.10<br>495.10 | 1H NMR (400 MHz, CDCl3) δ 8.06 (d, J = 2.2 Hz, 1H), 7.76 (d, J = 2.3 Hz, 1H), 4.31 (t, J = 6.4 Hz, 2H), 3.30 (s, 4H), 3.09 (s, 3H), 2.45 (t, J = 6.9 Hz, 2H), 2.32 (s, 4H), 1.90 (p, J = 6.9 Hz, 2H), 1.39 (s, 9H). |
| CC66 | N-(5-Bromo-2-(3-(4-methylpiperazin-1-yl)propoxy)pyridin-3-yl)methanesulfonamide | 407.10<br>409.10 | 1H NMR (400 MHz, CDCl3) δ 7.95 (d, J = 2.2 Hz, 1H), 7.89 (d, J = 2.2 Hz, 1H), 4.42 (t, J = 6.5 Hz, 2H), 3.06 (s, 3H), 2.80-2.45 (m, 10H), 2.37 (s, 3H), 1.99 (p, J = 7.1 Hz, 2H). |
| CC67 | N-(5-Bromo-2-(3-morpholinopropoxy)pyridin-3-yl)methanesulfonamide | 394.10<br>396.10 | 1H NMR (400 MHz, CD3OD) δ 7.98 (d, J = 2.3 Hz, 1H), 7.85 (d, J = 2.3 Hz, 1H), 4.44 (t, J = 6.4 Hz, 2H), 3.70 (t, J = 4.7 Hz, 4H), 3.02 (s, 3H), 2.59-2.45 (m, 6H), 2.08-1.95 (m, 2H). |
| CC68 | N-(2-(3-(6-Oxa-3-azabicyclo[3.1.1]heptan-3-yl)propoxy)-5-Bromopyridin-3-yl)methanesulfonamide | 406.20<br>408.20 | 1H NMR (400 MHz, CD3OD) δ 7.63 (s, 1H), 7.55 (d, J = 2.5 Hz, 1H), 4.54 (d, J = 6.2 Hz, 2H), 4.11 (t, J = 6.9 Hz, 2H), 3.15 (d, J = 11.6 Hz, 2H), 3.07 (s, 3H), 3.02 (q, J = 6.6 Hz, 1H), 2.68 (d, J = 11.6 Hz, 2H), 2.63 (t, J = 6.7 Hz, 2H), 2.34 (d, J = 8.0 Hz, 1H), 2.01 (p, J = 6.6 Hz, 2H). |
| CC69 | N-(5-Bromo-2-(3-((2-cyanoethyl)(methyl)amino)propoxy)pyridin-3-yl)methanesulfonamide | 391.15<br>393.15 | 1H NMR (400 MHz, CDCl3) δ 7.59 (s, 1H), 7.54 (d, J = 2.4 Hz, 1H), 7.35 (d, J = 2.2 Hz, 1H), 4.09 (t, J = 7.0 Hz, 2H), 3.06 (s, 3H), 2.69 (t, J = 6.6 Hz, 2H), 2.53 (t, J = 6.5 Hz, 2H), 2.43 (t, J = 6.4 Hz, 2H), 2.28 (s, 3H), 1.94 (p, J = 6.7 Hz, 2H). |
| CC70 | N-(5-Bromo-2-(3-((tert-butyldimethylsilyloxy)propoxy)pyridin-3-yl)methanesulfonamide | 439.10<br>441.10 | 1H NMR (400 MHz, CDCl3) δ 7.95 (d, J = 2.2 Hz, 1H), 7.89 (d, J = 2.2 Hz, 1H), 6.71 (s, 1H), 4.47 (t, J = 6.5 Hz, 2H), 3.75 (t, J = 5.9 Hz, 2H), 3.04 (s, 3H), 1.99 (p, J = 6.2 Hz, 2H), 0.89 (s, 9H), 0.05 (s, 6H). |

| Intermediate | Name | MS: [(M + 1)]+ | 1H-NMR |
|---|---|---|---|
| CC71 | N-(5-Bromo-2-((2-(dimethylamino)ethyl)(methyl)amino)pyridin-3-yl)methanesulfonamide | 351.05 353.05 | 1H NMR (400 MHz, CDCl3) δ 7.96 (d, J = 5.6 Hz, 2H), 3.00 (s, 2H), 2.92 (s, 3H), 2.84 (s, 3H), 2.76 (s, 2H), 2.60 (s, 6H). |
| CC72 | N-(5-Bromo-2-((3-(dimethylamino)propyl)amino)pyridin-3-yl)methanesulfonamide | 351.00 353.00 | 1H NMR (400 MHz, DMSO-d6) δ 7.61 (d, J = 2.2 Hz, 1H), 7.26 (d, J = 2.2 Hz, 1H), 6.25 (s, 1H), 3.35-3.29 (m, 2H), 2.79 (s, 3H), 2.65 (t, J = 7.3 Hz, 2H), 2.45 (s, 6H), 1.76 (p, J = 6.9 Hz, 2H). |
| CC73 | N-(5-Bromo-2-((3-(dimethylamino)propyl)(methyl)amino)pyridin-3-yl)metlianesulfonamide | 365.10 367.10 | 1H NMR (400 MHz, CDCl3) δ 7.96 (d, J = 2.1 Hz, 1H), 7.86 (d, J = 2.0 Hz, 1H), 3.11 (t, J = 6.3 Hz, 2H), 2.95 (s, 5H), 2.74 (d, J = 2.2 Hz, 9H), 2.00-1.94 (m, J = 6.1 Hz, 2H). |
| CC74 | tert-Butyl (1-(5-Bromo-3-(methylsulfonamido)pyridin-2-yl)azetidin-3-yl(methyl)carbamate | 435.20 437.20 | 1H NMR (400 MHz, CD3OD) δ 8.06 (d, J = 2.2 Hz, 1H), 7.65 (d, J = 2.2 Hz, 1H), 4.83-4.64 (m, 1H), 4.38 (t, J = 8.5 Hz, 2H), 4.19 (dd, J = 9.2, 6.0 Hz, 2H), 3.06 (s, 3H), 2.94 (s, 3H), 1.46 (s, 9H). |
| CC75 | N-(5-Bromo-2-(3-(ethyl(4-methoxybenzyl)amino)azetidin-1-yl)pyridin-3-yl)methanesulfonamide | 469.30 471.30 | 1H NMR (400 MHz, CDCl3) δ 8.10 (d, J = 2.2 Hz, 1H), 7.68 (d, J = 2.2 Hz, 1H), 7.22 (d, J = 8.4, 2H), 6.85 (d, J = 8.4, 2H), 4.09 (t, J = 7.5 Hz, 2H), 3.96 (t, J = 7.2 Hz, 2H), 3.81 (s, 3H), 3.65 (p, J = 6.6 Hz, 1H), 3.59 (s, 2H), 3.00 (s, 3H), 2.54 (q, J = 7.1 Hz, 2H), 1.08 (t, J = 7.1 Hz, 3H). |
| CC76 | N-(5-Bromo-2-(3-(dimethylamino)azetidin-1-yl)pyridin-3-yl)ethanesulfonamide | 363.00 365.00 | 1H NMR (400 MHz, DMSO-d6) δ 7.63 (d, J = 2.0 Hz, 1H), 7.35 (d, J = 2.3 Hz, 1H), 4.07 (t, J = 7.8 Hz, 2H), 3.76 (dd, J = 8.8, 5.8 Hz, 2H), 2.99 (p, J = 6.5 Hz, 1H), 2.90 (q, J = 7.5 Hz, 2H), 1.18 (t, J = 7.3 Hz, 3H). |
| CC77 | N-(5-Bromo-2-(3-(dimethylamino)azetidin-1-yl)pyridin-3-yl)-2-methylthiazole-5-sulfonamide | 432.00 434.00 | 1H NMR (400 MHz, CD3OD) δ 7.86 (s, 1H), 7.78 (d, J = 2.2 Hz, 1H), 7.28 (d, J = 2.2 Hz, 1H), 4.32-4.23 (m, 2H), 3.96 (dd, J = 9.4, 5.2 Hz, 2H), 3.48-3.42 (m, 1H), 2.72 (s, 3H), 2.43 (s, 6H). |

-continued

| Intermediate | Structure | Name | MS: [(M + 1)]+ | 1H-NMR |
|---|---|---|---|---|
| CC78 | 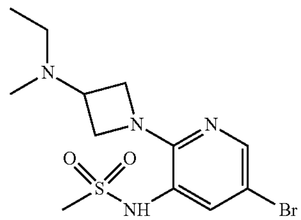 [SMILES: CCN(C)C1CN(c2ncc(Br)cc2NS(C)(=O)=O)C1] | N-(5-Bromo-2-(3-(ethyl(methylamino)azetidin-1-yl)pyridin-3-yl)methanesulfonamide | 363.30 365.30 | 1H NMR (400 MHz, CDCl3) δ 8.09 (d, J = 2.2 Hz, 1H), 7.63 (d, J = 2.2 Hz, 1H), 4.26-4.17 (m, 2H), 3.98-3.94 (m, J = 8.3, 5.9 Hz, 2H), 3.36-3.29 (m, 1H), 3.07 (s, 3H), 2.41 (q, J = 7.2 Hz, 2H), 2.19 (s, 3H), 1.10 (t, J = 7.2 Hz, 3H). |
| CC79 | 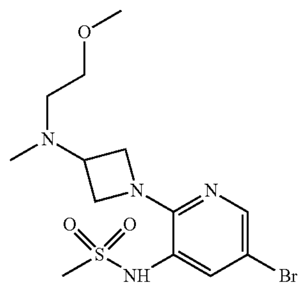 [SMILES: COCCN(C)C1CN(c2ncc(Br)cc2NS(C)(=O)=O)C1] | N-(5-Bromo-2-(3-((2-methoxyethyl)(methyl)amino)azetidin-1-yl)pyridin-3-yl)methanesulfonamide | 393.10 395.10 | 1H NMR (400 MHz, DMSO-d6) δ 9.12 (s, 1H), 8.08 (d, J = 2.2 Hz, 1H), 7.60 (d, J = 2.3 Hz, 1H), 4.14 (dd, J = 8.9, 7.0 Hz, 2H), 3.86 (dd, J = 8.9, 5.6 Hz, 2H), 3.40 (t, J = 5.7 Hz, 2H), 3.36-3.28 (m, 1H), 3.23 (s, 3H), 3.08 (s, 3H), 2.46 (t, J = 5.8 Hz, 2H), 2.15 (s, 3H). |
| CC80 | 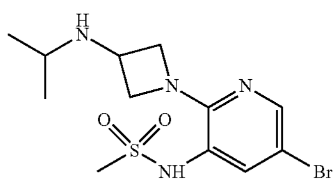 [SMILES: CC(C)NC1CN(c2ncc(Br)cc2NS(C)(=O)=O)C1] | N-(5-Bromo-2-(3-(isopropylamino)azetidin-1-yl)pyridin-3-yl)methanesulfonamide | 363.05 365.05 | 1H NMR (400 MHz, DMSO-d6) δ 7.85 (d, J = 2.2 Hz, 1H), 7.49 (d, J = 2.2 Hz, 1H), 4.26 (t, J = 6.3 Hz, 2H), 3.85-3.78 (m, 2H), 3.77-3.71 (m, 1H), 2.92 (s, 3H), 2.90-2.85 (m, 1H), 1.03 (d, J = 6.3 Hz, 6H). |
| CC81 | 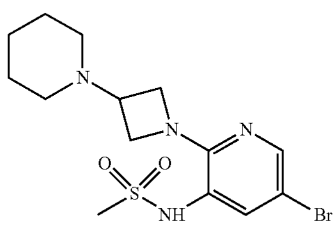 [SMILES: CS(=O)(=O)Nc1cc(Br)cnc1N1CC(N2CCCCC2)C1] | N-(5-Bromo-2-(3-(piperidin-1-yl)azetidin-1-yl)pyridin-3-yl)methanesulfonamide | 389.20 391.20 | 1H NMR (400 MHz, CD3OD) δ 8.02-7.93 (m, 1H), 7.62 (q, J = 2.1 Hz, 1H), 4.27 (t, J = 6.2 Hz, 2H), 4.01 (dt, J = 8.2, 3.7 Hz, 2H), 3.28-3.16 (m, 1H), 3.08-2.98 (m, 3H), 2.41 (s, 4H), 1.65 (p, J = 5.8 Hz, 4H), 1.51 (s, 2H). |
| CC82 | 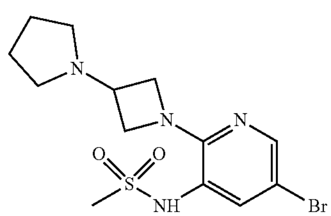 [SMILES: CS(=O)(=O)Nc1cc(Br)cnc1N1CC(N2CCCC2)C1] | N-(5-Bromo-2-(3-(pyrrolidin-1-yl)azetidin-1-yl)pyridin-3-yl)methanesulfonamide | 375.00 377.00 | 1H NMR (400 MHz, CDCl3) δ 8.26 (s, 1H), 7.34 (d, J = 2.2 Hz, 1H), 4.65 (s, 1H), 4.24 (s, 2H), 4.00 (s, 1H), 3.73 (s, 1H), 3.45 (s, 3H), 2.55 (s, 2H), 2.37-2.01 (m, 4H), 1.85 (s, 2H). |
| CC83 | 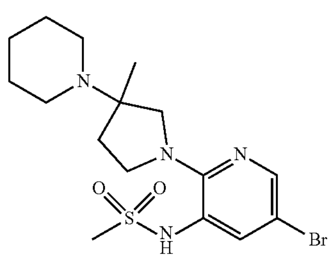 [SMILES: CC1(N2CCCCC2)CCN(c2ncc(Br)cc2NS(C)(=O)=O)C1] | N-(5-Bromo-2-(3-methyl-3-(piperidin-1-yl)pyrrolidin-1-yl)pyridin-3-yl)methanesulfonamide | 417.20 419.20 | 1H NMR (400 MHz, CD3OD) δ 7.96 (d, J = 2.3 Hz, 1H), 7.60 (d, J = 2.2 Hz, 1H), 3.88-3.75 (m, 1H), 3.74-3.64 (m, 2H), 3.55 (d, J = 10.5 Hz, 1H), 2.96 (s, 3H), 2.86-2.74 (m, 2H), 2.73-2.67 (m, 2H), 2.05-1.96 (m, 2H), 1.71 (p, J = 5.7 Hz, 4H), 1.58-1.48 (m, 2H), 1.20 (s, 3H). |

-continued

| Intermediate | Name | MS: [(M + 1)]+ | 1H-NMR |
|---|---|---|---|
| CC84 | N-(5-Bromo-2-(3-(piperidin-1-yl)pyrrolidin-1-yl)pyridin-3-yl)methanesulfonamide | 403.10 405.10 | 1H NMR (400 MHz, DMSO-d6) δ 8.05 (d, J = 2.2 Hz, 1H), 7.59 (d, J = 2.3 Hz, 1H), 3.75 (dd, J = 10.6, 7.1 Hz, 1H), 3.68-3.60 (m, 1H), 3.58-3.48 (m, 1H), 3.47-3.38 (m, 1H), 3.00 (s, 3H), 2.79 (q, J = 7.8 Hz, 1H), 2.49-2.45 (m, 2H), 2.43-2.34 (m, 2H), 2.15-2.06 (m, 1H), 1.74-1.61 (m, 1H), 1.52 (q, J = 5.7 Hz, 4H), 1.41 (q, J = 5.8 Hz, 2H). |
| CC85 | N-(5-Bromo-2-(3-(dimethylamino)pyrrolidin-1-yl)pyridin-3-yl)methanesulfonamide | 362.95 364.95 | 1H NMR (400 MHz, CDCl3) δ 8.11 (d, J = 2.2 Hz, 1H), 7.72 (d, J = 2.2 Hz, 1H), 3.60-3.51 (m, 3H), 3.44 (dd, J = 10.2, 7.5 Hz, 1H), 3.07 (s, 3H), 2.83 (p, J = 7.2 Hz, 1H), 2.33 (s, 6H), 2.21-2.13 (m, 1H), 1.96-1.85 (m, 1H). |
| CC86 | N-(5-Bromo-2-(4'-methyl-[1,4'-bipiperidin]-1'-yl)pyridin-3-yl)methanesulfonamide Molecular Weight: 431.39 | 431.10 433.10 | 1H NMR (400 MHz, DMSO-d6) δ 7.35 (s, 2H), 3.26-3.13 (m, 4H), 2.55 (s, 3H), 2.47-2.40 (m, 4H), 1.69 (t, J = 10.0 Hz, 2H), 1.55-1.44 (m, 6H), 1.42-1.32 (m, 2H), 0.87 (s, 3H). |
| CC87 | N-(5-Bromo-2-(4-morpholinopiperidin-1-yl)pyridin-3-yl)methanesulfonamide | 419.10 421.10 | 1H NMR (400 MHz, DMSO-d6) δ 9.02 (s, 1H), 8.13 (d, J = 2.3 Hz, 1H), 7.73 (d, J = 2.3 Hz, 1H), 3.66 (d, J = 12.4 Hz, 2H), 3.58 (t, J = 4.5 Hz, 4H), 3.16 (s, 3H), 2.76-2.65 (m, 2H), 2.52-2.47 (m, 4H), 2.38-2.26 (m, 1H), 1.88-1.76 (m, 2H), 1.66-1.52 (m, 2H). |
| CC88 | N-(5-Bromo-2-(4-methylpiperidin-1-yl)pyridin-3-yl)methanesulfonamide | 348.10 350.10 | 1H NMR (400 MHz, DMSO-d6) δ 8.91 (s, 1H), 8.15 (s, 1H), 7.73 (s, 1H), 3.55 (d, J = 12.3 Hz, 2H), 3.17 (s, 3H), 2.71 (t, J = 12.5 Hz, 2H), 1.65 (d, J = 12.4 Hz, 2H), 1.51 (s, 1H), 1.40-1.26 (m, 2H), 0.94 (d, J = 6.4 Hz, 3H). |
| CC89 | tert-Butyl (2-((5-bromo-3-(methylsulfonamido)pyridin-2-yl)oxy)ethyl)(2,2,2-trifluoroethyl)carbamate | 492.00 494.00 | 1H NMR (400 MHz, CD3OD) δ 7.98 (s, 1H), 7.88 (s, 1H), 4.57 (t, J = 7.2 Hz, 2H), 4.05 (q, J = 9.1 Hz, 2H), 3.75 (t, J = 5.5 Hz, 2H), 3.03 (s, 3H), 1.42 (s, 9H). |

-continued

| Inter-mediate | Name | MS: [(M + 1)]+ | 1H-NMR |
|---|---|---|---|
| CC90 | tert-Butyl (2-((5-bromo-3-(methylsulfonamido)pyridin-2-yl)oxy)ethyl)(2,2-difluoroethyl)carbamate | 474.15<br>476.15 | Crude to the next step without further purification. |
| CC91 | tert-Butyl (2-((5-bromo-3-(methylsulfonamido)pyridin-2-yl)oxy)ethyl)(2-fluoroethyl)carbamate | 456.10<br>458.10 | $^1$H NMR (400 MHz, DMSO-d$_6$) δ 9.39 (d, J = 46.4 Hz, 1H), 8.05 (s, 1H), 7.79 (s, 1H), 4.57 (t, J = 5.0 Hz, 1H), 4.48-4.36 (m, 3H), 3.64-3.55 (m, 3H), 3.51 (t, J = 5.0 Hz, 1H), 3.10 (s, 3H), 1.36 (d, J = 14.0 Hz, 9H). |
| CC92 | N-(5-Bromo-2-(3-(4-fluoropiperidin-1-yl)propoxy)pyridin-3-yl)methanesulfonamide | 410.00<br>412.00 | $^1$H NMR (400 MHz, CD$_3$OD) δ 7.94 (d, J = 2.2 Hz, 1H), 7.83 (d, J = 2.3 Hz, 1H), 4.67 (d, J = 49.2 Hz, 1H), 4.41 (t, J = 6.4 Hz, 2H), 3.01 (s, 3H), 2.66 (d, J = 9.9 Hz, 2H), 2.60 (t, J = 7.6 Hz, 2H), 2.52 (d, J = 8.3 Hz, 2H), 2.04 (q, J = 7.0 Hz, 2H), 1.98-1.78 (m, 4H). |
| CC93 | N-(5-Bromo-2-(3-((2-methoxyethyl)(methyl)amino)propoxy)pyridin-3-yl)methanesulfonamide | 396.10<br>398.10 | $^1$H NMR (400 MHz, CDCl$_3$) δ 7.92 (d, J = 2.2 Hz, 1H), 7.88 (d, J = 2.3 Hz, 1H), 4.42 (t, J = 6.2 Hz, 2H), 3.59 (s, 2H), 3.35 (s, 3H), 3.05 (s, 3H), 2.82-2.68 (m, 4H), 2.44 (s, 3H), 2.09-2.00 (m, 2H). |
| CC94 | N-(5-Bromo-2-(3-(3-fluoropyrrolidin-1-yl)propoxy)pyridin-3-yl)methanesulfonamide | 396.00<br>398.00 | $^1$H NMR (400 MHz, CDCl$_3$) δ 7.94 (d, J = 2.2 Hz, 1H), 7.89 (d, J = 2.2 Hz, 1H), 5.31-5.09 (m, 1H), 4.50-4.40 (m, 2H), 3.06 (s, 3H), 2.95-2.65 (m, 6H), 2.20-1.98 (m, 3H). |
| CC95 | N-(5-Bromo-2-(3-(3-methoxypiperidin-1-yl)propoxy)pyridin-3-yl)methanesulfonamide | 442.00<br>444.00 | $^1$H NMR (400 MHz, CDCl$_3$) δ 7.97 (d, J = 2.2 Hz, 1H), 7.92 (d, J = 2.3 Hz, 1H), 4.44 (t, J = 6.5 Hz, 2H), 3.40 (s, 3H), 3.38-3.30 (m, 1H), 3.06 (s, 3H), 2.91 (d, J = 10.9 Hz, 1H), 2.71-2.61 (m, 1H), 2.52 (t, J = 7.3 Hz, 2H), 2.18-2.06 (m, 2H), 2.02 (p, J = 6.9 Hz, 2H), 1.97-1.90 (m, 1H), 1.87-1.75 (m, 1H), 1.61-1.48 (m, 1H), 1.38-1.29 (m, 1H). |

-continued

| Intermediate | Name | MS: [(M + 1)]⁺ | ¹H-NMR |
|---|---|---|---|
| CC96 | N-(5-Bromo-2-(3-(3-fluoropiperidin-1-yl)propoxy)pyridin-3-yl)methanesulfonamide | 409.95 411.95 | ¹H NMR (400 MHz, DMSO-$d_6$) δ 1.11 (d, J = 2.0 Hz, 1H), 7.61 (d, J = 2.0 Hz, 1H), 4.61 (ddd, J = 47.6, 8.2, 4.2 Hz, 1H), 4.23 (t, J = 6.6 Hz, 2H), 2.90 (s, 3H), 2.79-2.65 (m, 1H), 2.44 (q, J = 10.6, 8.9 Hz, 3H), 2.32 (q, J = 8.5, 7.9 Hz, 1H), 2.20 (t, J = 9.6 Hz, 1H), 1.87 (p, J = 6.8 Hz, 2H), 1.80 (d, J = 14.0 Hz, 1H), 1.69 (d, J = 9.8 Hz, 1H), 1.55-1.37 (m, 2H). |
| CC97 | N-(5-Bromo-2-(3-(3-methoxypyrrolidin-1-yl)propoxy)pyridin-3-yl)methanesulfonamide | 408.05 410.05 | ¹H NMR (400 MHz, CDCl$_3$) δ 7.54 (d, J = 2.0 Hz, 1H), 6.96 (d, J = 2.0 Hz, 1H), 4.36 (t, J = 6.4 Hz, 2H), 4.02-3.85 (m, 3H), 3.29 (s, 3H), 2.79-2.67 (m, 2H), 2.63 (dd, J = 9.7, 4.9 Hz, 3H), 2.51 (q, J = 7.9 Hz, 1H), 2.13-1.97 (m, 3H), 1.88-1.78 (m, 1H). |
| CC98 | N-(5-Bromo-2-(3-(3-((tert-butyldimethylsilyl)oxy)piperidin-1-yl)propoxy)pyridin-3-yl)methanesulfonamide | 522.05 524.05 | ¹H NMR (400 MHz, CDCl$_3$) δ 7.93 (d, J = 2.4 Hz, 1H), 7.89 (d, J = 2.4 Hz, 1H), 4.43 (t, J = 6.5 Hz, 2H), 3.78 (s, 1H), 3.08 (s, 3H), 2.97-2.80 (m, 2H), 2.64-2.45 (m, 2H), 2.10-1.42 (m, 8H), 0.91 (s, 9H), 0.09 (s, 6H). |
| CC99 | N-(5-Bromo-2-(3-((tert-butyldimethylsilyl)oxy)propoxy)pyridin-3-yl)methanesulfonamide | 439.10 441.10 | ¹H NMR (400 MHz, CDCl$_3$) δ 7.95 (d, J = 2.2 Hz, 1H), 7.89 (d, J = 2.2 Hz, 1H), 6.71 (s, 1H), 4.47 (t, J = 6.5 Hz, 2H), 3.75 (t, J = 5.9 Hz, 2H), 3.04 (s, 3H), 1.99 (p, J = 6.2 Hz, 2H), 0.89 (s, 9H), 0.05 (s, 6H). |
| CC100 | tert-Butyl (2-((5-bromo-3-(cyclopropanesulfonamido)pyridin-2-yl)oxy)ethyl)(isopropyl)carbamate | 478.00 480.00 | ¹H NMR (400 MHz, CDCl$_3$) δ 7.99-7.92 (m, 2H), 7.21 (s, 1H), 4.46 (t, J = 6.2 Hz, 2H), 4.15-4.10 (m, 1H), 3.52-3.48 (m, 3H), 2.56-2.50 (m, 2H), 1.49 (s, 9H), 1.31-1.22 (m, 2H), 1.17 (d, J = 6.8 Hz, 6H). |
| CC101 | N-(5-Bromo-2-(3-(dimethylamino)azetidin-1-yl)pyridin-3-yl)cyclopropanesulfonamide | 375.10 377.10 | ¹H NMR (400 MHz, DMSO-$d_6$) δ 8.10 (s, 1H), 7.61 (s, 1H), 4.18 (t, J = 8.1 Hz, 2H), 3.97-3.88 (m, 2H), 3.22 (s, 1H), 2.83-2.75 (m, 1H), 2.18 (s, 6H), 1.04-0.97 (m, 2H), 0.92-0.83 (m, 2H). |

-continued

| Intermediate | Structure | Name | MS: [(M + 1)]+ | 1H-NMR |
|---|---|---|---|---|
| CC102 | 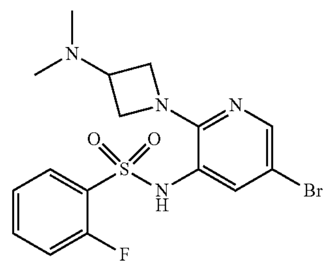 [SMILES: CN(C)C1CN(c2ncc(Br)cc2NS(=O)(=O)c2ccccc2F)C1] | N-(5-Bromo-2-(3-(dimethylamino)azetidin-1-yl)pyridin-3-yl)-2-fluorobenzenesulfonamide | 429.05 431.05 | $^1$H NMR (400 MHz, DMSO-d$_6$) δ 7.68 (td, J = 7.6, 1.9 Hz, 1H), 7.41-7.34 (m, 1H), 7.27 (d, J = 2.2 Hz, 1H), 7.19-7.11 (m, 3H), 3.99 (dd, J = 9.0, 6.7 Hz, 2H), 3.58 (dd, J = 8.9, 5.9 Hz, 2H), 2.87 (p, J = 6.3 Hz, 1H), 2.02 (s, 6H). |
| CC103 | 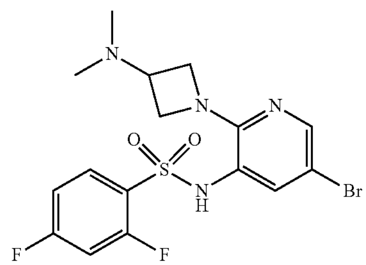 [SMILES: CN(C)C1CN(c2ncc(Br)cc2NS(=O)(=O)c2ccc(F)cc2F)C1] | N-(5-Bromo-2-(3-(dimethylamino)azetidin-1-yl)pyridin-3-yl)-2,4-difluorobenzenesulfonamide | 447.20 449.20 | $^1$H NMR (400 MHz, DMSO-d$_6$) δ 10.03 (s, 1H), 7.76 (td, J = 8.5, 6.6 Hz, 1H), 7.66 (s, 1H), 7.38 (t, J = 9.4 Hz, 1H), 7.22-7.11 (m, 1H), 7.09 (d, J = 2.2 Hz, 1H), 4.15 (dd, J = 9.6, 7.1 Hz, 2H), 3.94-3.85 (m, 2H), 3.59 (s, 1H), 2.46 (s, 6H). |
| CC114 | 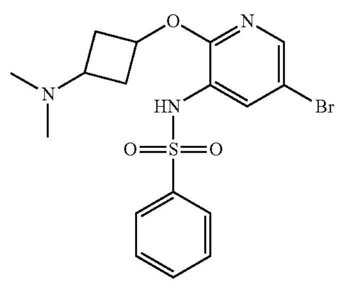 [SMILES: CN(C)C1CC(Oc2ncc(Br)cc2NS(=O)(=O)c2ccccc2)C1] | N-(5-Bromo-2-(3-(dimethylamino)cyclobutoxy)pyridin-3-yl)benzenesulfonamide | 426.00 428.00 | used to next step without further purification |
| CC115 | 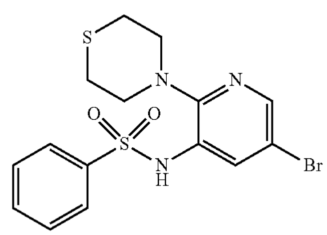 [SMILES: O=S(=O)(Nc1cc(Br)cnc1N1CCSCC1)c1ccccc1] | N-(5-Bromo-2-thiomorpholinopyridin-3-yl)benzenesulfonamide | 413.70 415.70 | $^1$H NMR (400 MHz, DMSO-d$_6$) δ 9.74 (s, 1H), 8.16 (d, J = 2.2 Hz, 1H), 7.78 (dd, J = 7.2, 1.8 Hz, 2H), 7.74-7.65 (m, 1H), 7.62 (dd, J = 8.3, 6.7 Hz, 2H), 7.43 (d, J = 2.3 Hz, 1H), 3.23-3.16 (m, 4H), 2.63-2.56 (m, 4H). |
| CC116 | 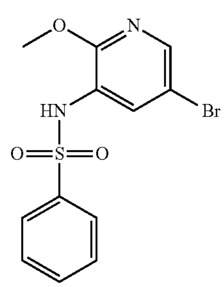 [SMILES: COc1ncc(Br)cc1NS(=O)(=O)c1ccccc1] | N-(5-Bromo-2-methoxypyridin-3-yl)benzenesulfonamide | 342.80 344.80 | $^1$H NMR (300 MHz, CDCl$_3$) δ 7.93-7.86 (m, 2H), 7.86-7.77 (m, 2H), 7.64-7.53 (m, 1H), 7.48 (dd, J = 8.3, 6.7 Hz, 2H), 6.92 (s, 1H), 3.80 (s, 3H). |

-continued

| Intermediate | Structure | Name | MS: [(M + 1)]+ | 1H-NMR |
|---|---|---|---|---|
| CC117 | 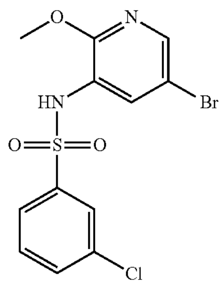 [SMILES: COc1ncc(Br)cc1NS(=O)(=O)c1cccc(Cl)c1] | N-(5-Bromo-2-methoxypyridin-3-yl)-3-chlorobenzenesulfonamide | 376.80 378.80 | 1H NMR (300 MHz, DMSO-d6) δ 10.33 (s, 1H), 8.10 (d, J = 2.3 Hz, 1H), 7.83-7.56 (m, 5H), 3.62 (s, 3H). |
| CC118 | 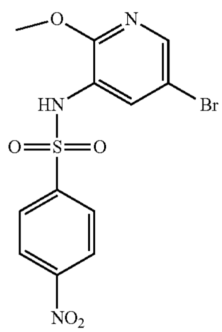 [SMILES: COc1ncc(Br)cc1NS(=O)(=O)c1ccc([N+](=O)[O-])cc1] | N-(5-Bromo-2-methoxypyridin-3-yl)-4-nitrobenzenesulfonamide | 388.10 390.10 | 1H NMR (300 MHz, CDCl3) δ 8.36-8.25 (m, 2H), 8.03-7.87 (m, 4H), 6.92 (s, 1H), 3.79 (s, 3H). |
| CC119 | 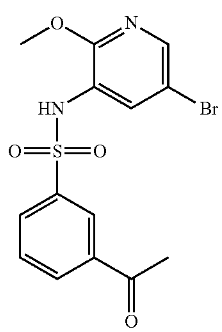 [SMILES: COc1ncc(Br)cc1NS(=O)(=O)c1cccc(C(C)=O)c1] | 3-Acetyl-N-(5-bromo-2-methoxypyridin-3-yl)benzenesulfonamide | 385.00 387.00 | 1H NMR (400 MHz, DMSO-d6) δ 10.33 (s, 1H), 8.29-8.17 (m, 2H), 8.06 (d, J = 2.2 Hz, 1H), 7.99-7.91 (m, 1H), 7.76-7.67 (m, 2H), 3.57 (s, 3H), 2.60 (s, 3H). |
| CC120 | 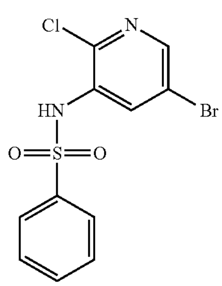 [SMILES: O=S(=O)(Nc1cc(Br)cnc1Cl)c1ccccc1] | N-(5-Bromo-2-chloropyridin-3-yl)benzenesulfonamide | 347.00 349.00 | 1H NMR (300 MHz, DMSO-d6) δ 10.56 (s, 1H), 8.37 (d, J = 2.3 Hz, 1H), 7.86 (d, J = 2.3 Hz, 1H), 7.77-7.49 (m, 5H). |
| CC121 | 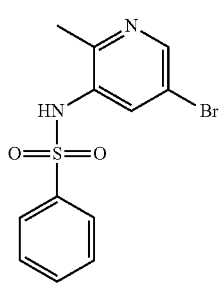 [SMILES: Cc1ncc(Br)cc1NS(=O)(=O)c1ccccc1] | N-(5-Bromo-2-methylpyridin-3-yl)benzenesulfonamide | 327.00 329.00 | 1H NMR (300 MHz, DMSO-d6) δ 10.13 (s, 1H), 8.41 (d, J = 2.2 Hz, 1H), 7.75-7.64 (m, 3H), 7.64-7.54 (m, 3H), 2.07 (s, 3H). |

-continued

| Inter-mediate | Structure | Name | MS: [(M + 1)]+ | 1H-NMR |
|---|---|---|---|---|
| CC122 | 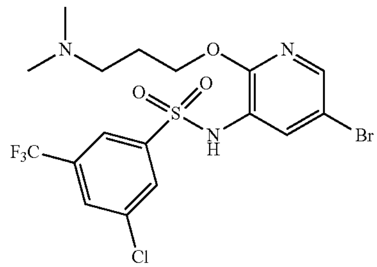 [SMILES: CN(C)CCCOc1ncc(Br)cc1NS(=O)(=O)c1cc(Cl)cc(C(F)(F)F)c1] | N-(5-Bromo-2-(3-(dimethylamino)propoxy) pyridin-3-yl)-3-chloro-5-(trifluoromethyl) benzenesulfonamide | 516.00 518.00 | 1H NMR (300 MHz, CD3OD) δ 8.05-7.94 (m, 2H), 7.84 (s, 1H), 7.52 (d, J = 2.2 Hz, 1H), 7.32 (d, J = 2.2 Hz, 1H), 4.37 (t, J = 5.5 Hz, 2H), 3.44-3.35 (m, 2H), 3.03 (s, 6H), 2.24 (p, J = 5.5 Hz, 2H). |
| CC123 | 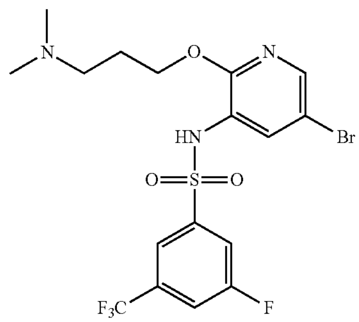 [SMILES: CN(C)CCCOc1ncc(Br)cc1NS(=O)(=O)c1cc(F)cc(C(F)(F)F)c1] | N-(5-Bromo-2-(3-(dimethylamino)propoxy) pyridin-3-yl)-3-fluoro-5-(trifluoromethyl) benzenesulfonamide | 500.05 502.05 | 1H NMR (400 MHz, CDCl3) δ 7.93 (s, 1H), 7.71 (dt, J = 7.9, 2.0 Hz, 1H), 7.55 (d, J = 2.2 Hz, 1H), 7.48 (d, J = 2.2 Hz, 1H), 7.37 (dt, J = 8.4, 2.1 Hz, 1H), 4.38 (t, J = 5.6 Hz, 2H), 3.26-3.19 (m, 2H), 3.05 (s, 6H), 2.23 (p, J = 5.6 Hz, 2H). |
| CC124 | 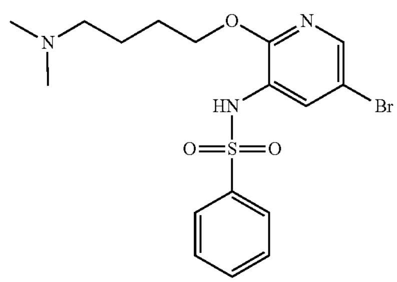 [SMILES: CN(C)CCCCOc1ncc(Br)cc1NS(=O)(=O)c1ccccc1] | N-(5-Bromo-2-(4-(dimethylamino)butoxy) pyridin-3-yl)benzenesulfonamide | 428.00 430.00 | 1H NMR (400 MHz, DMSO-d6) 8.05 (d, J = 2.3 Hz, 1H), 7.78-7.72 (m, 2H), 7.69 (d, J = 2.3 Hz, 1H), 7.68-7.62 (m, 1H), 7.61-7.55 (m, 2H), 4.03 (t, J = 6.4 Hz, 2H), 3.08-3.00 (m, 2H), 2.77 (s, 6H), 1.69-1.59 (m, 2H), 1.57-1.48 (m, 2H). |
| CC125 | 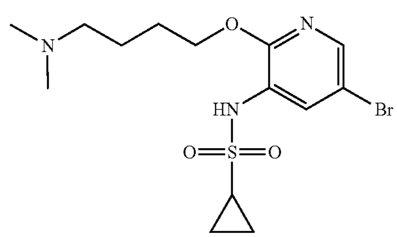 [SMILES: CN(C)CCCCOc1ncc(Br)cc1NS(=O)(=O)C1CC1] | N-(5-Bromo-2-(4-(dimethylamino)butoxy) pyridin-3-yl) cyclopropanesulfonamide | 392.05 394.05 | 1H NMR (300 MHz, CDCl3) δ 7.92 (d, J = 2.2 Hz, 1H), 7.87 (d, J = 2.2 Hz, 1H), 4.39 (t, J = 5.6 Hz, 2H), 3.14 (s, 2H), 2.85 (d, J = 4.6 Hz, 6H), 2.71-2.57 (m, 1H), 2.06-1.86 (m, 4H), 1.31-1.22 (m, 2H), 1.05 (q, J = 6.8 Hz, 2H). |
| CC126 | 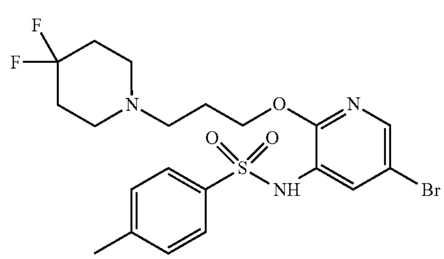 [SMILES: Cc1ccc(S(=O)(=O)Nc2cc(Br)cnc2OCCCN2CCC(F)(F)CC2)cc1] | N-(5-Bromo-2-(3-(4,4-difluoropiperidin-1-yl)propoxy)pyridin-3-yl)-4-methylbenzenesulfonamide | 503.95 505.95 | 1H NMR (400 MHz, CDCl3) δ 7.89 (s, 1H), 7.89-7.82 (m, 1H), 7.70 (d, J = 8.1 Hz, 2H), 7.27 (d, J = 8.1 Hz, 2H), 4.25 (t, J = 6.5 Hz, 2H), 2.54 (t, J = 5.8 Hz, 4H), 2.43 (t, J = 7.2 Hz, 2H), 2.40 (s, 3H), 2.01 (tt, J = 13.3, 5.5 Hz, 4H), 1.85 (p, J = 6.8 Hz, 2H). |
| CC127 | 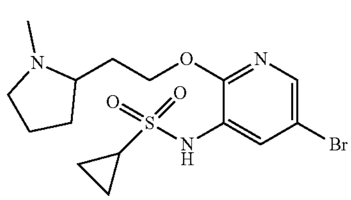 [SMILES: CN1CCCC1CCOc1ncc(Br)cc1NS(=O)(=O)C1CC1] | N-(5-Bromo-2-(2-(1-methylpyrrolidin-2-yl)ethoxy)pyridin-3-yl) cyclopropanesulfonamide | 404.00 406.00 | 1H NMR (300 MHz, DMSO-d6) δ 7.90 (s, 1H), 7.73 (d, J = 2.3 Hz, 1H), 4.39-4.31 (m, 2H), 3.60-3.48 (m, 2H), 2.98-2.82 (m, 1H), 2.73 (s, 3H), 2.66 (t, J = 6.6 Hz, 1H), 2.30-1.96 (m, 3H), 1.95-1.78 (m, 2H), 1.77-1.62 (m, 1H), 0.93-0.87 (m, 4H). |

| Intermediate | Name | MS: [(M + 1)]+ | 1H-NMR |
|---|---|---|---|
| CC128 | N-(5-Bromo-2-(2-(1-methylpiperidin-2-yl)ethoxy)pyridin-3-yl)cyclopropanesulfonamide | 418.00 420.00 | 1H NMR (400 MHz, CD3OD) δ 7.73 (d, J = 2.2 Hz, 1H), 7.64 (d, J = 2.2 Hz, 1H), 4.50-4.30 (m, 1H), 4.34 (td, J = 10.2, 4.8 Hz, 1H), 3.64 (d, J = 12.4 Hz, 1H), 3.17-3.07 (m, 1H), 2.89-2.76 (m, 4H), 2.58-2.40 (m, 2H), 2.09-2.00 (m, 1H), 1.93-1.74 (m, 4H), 1.68-1.48 (m, 2H), 1.08-0.81 (m, 4H). |
| CC129 | N-(5-Bromo-2-(2-(1-methylpiperidin-2-yl)ethoxy)pyridin-3-yl)benzenesulfonamide | 454.10 456.10 | 1H NMR (400 MHz, DMSO-d6) δ 7.75-7.69 (m, 2H), 7.51-7.42 (m, 4H), 7.24 (s, 1H), 4.38-4.23 (m, 1H), 4.20-4.09 (m, 1H), ), 3.88-3.70 (m, 1 H), 3.21-3.12 (m, 1H), 3.04-2.92 (m, 1H), 2.90 (s, 3H), 2.01-1.88 (m, 1H), 1.87-1.67 (m, 5H), 1.58-1.40 (m, 2H). |
| CC130 | N-(5-Bromo-2-((1-methylpiperidin-3-yl)methoxy)pyridin-3-yl)benzenesulfonamide | 440.00 442.00 | 1H NMR (400 MHz, CDCl3) δ 7.89-7.86 (m, 2H), 7.84 (t, J = 2.4 Hz, 2H), 7.58 (t, J = 7.4 Hz, 1H), 7.51 (t, J = 7.6 Hz, 2H), 4.10 (d, J = 27.1 Hz, 2H), 2.67 (s, 3H), 2.51 (s, 2H), 2.27 (s, 2H), 2.05 (s, 3H), 1.90 (s, 2H). |
| CC131 | N-(5-Bromo-2-((1-methylpiperidin-3-yl)methoxy)pyridin-3-yl)cyclopropanesulfonamide | 403.95 405.95 | 1H NMR (400 MHz, CDCl3) δ 7.94 (d, J = 2.2 Hz, 1H), 7.90 (d, J = 2.2 Hz, 1H), 4.37 (dd, J = 11.0, 4.3 Hz, 1H), 4.16 (dd, J = 11.0, 8.2 Hz, 1H), 3.94 (d, J = 11.2 Hz, 1H), 3.61 (d, J = 12.3 Hz, 1H), 2.83 (d, J = 3.8 Hz, 3H), 2.79-2.70 (m, 1H), 2.70-2.59 (m, 2H), 2.54-2.42 (m, 1H), 2.26-2.13 (m, 1H), 1.31-1.21 (m, 5H), 1.05 (d, J = 7.8 Hz, 2H). |
| CC132 | N-(5-Bomo-2-(3-(dimethylamino)propoxy)phenyl)-3-fluorobenzenesulfonamide | 431.05 433.05 | 1H NMR (400 MHz, DMSO-d6) δ 9.51 (s, 1H), 7.70-7.59 (m, 1H), 7.57-7.45 (m, 3H), 7.39-7.32 (m, 2H), 6.92-6.87 (m, 1H), 3.77 (t, J = 5.8 Hz, 2H), 3.22-3.12 (m, 2H), 2.80 (d, J = 4.4 Hz, 6H), 1.96-1.83 (m, 2H). |

-continued

| Intermediate | Name | MS: [(M + 1)]+ | ¹H-NMR |
|---|---|---|---|
| CC133 | N-(5-Bromo-2-(3-(dimethylamino)propoxy)phenyl)-3-chlorobenzenesulfonamide | 446.90 448.90 | ¹H NMR (400 MHz, CDCl₃) δ 7.81 (t, J = 1.9 Hz, 1H), 7.68 (dt, J = 7.9, 1.3 Hz, 1H), 7.60 (d, J = 2.4 Hz, 1H), 7.46 (ddd, J = 8.0, 2.1, 1.1 Hz, 1H), 7.36 (t, J = 7.9 Hz, 1H), 7.05 (dd, J = 8.6, 2.4 Hz, 1H), 6.69 (d, J = 8.6 Hz, 1H), 3.97 (t, J = 5.7 Hz, 2H), 2.68 (t, J = 6.8 Hz, 2H), 2.53 (s, 6H), 2.01-1.93 (m, 2H). |
| CC134 | N-(5-Bromo-2-(3-(dimethylamino)propoxy)-3-fluorophenyl)benzenesulfonamide | 430.90 432.90 | ¹H NMR (400 MHz, CDCl₃) δ 7.87-7.79 (m, 2H), 7.52-7.39 (m, 3H), 7.37 (t, J = 2.0 Hz, 1H), 6.75 (dd, J = 9.8, 2.3 Hz, 1H), 4.04 (t, J = 5.5 Hz, 2H), 2.93-2.84 (m, 2H), 2.70 (s, 6H), 2.04 (p, J = 5.6 Hz, 2H). |
| CC135 | N-(5-Bromo-2-(3-(piperidin-1-yl)propoxy)pyridin-3-yl)benzenesulfonamide | 453.90 455.90 | ¹H NMR (300 MHz, DMSO-d₆) δ 7.74-7.70 (m, 2H), 7.57 (d, J = 2.3 Hz, 1H), 7.52-7.45 (m, 3H), 7.40 (d, J = 2.3 Hz, 1H), 4.16 (t, J = 6.0 Hz, 2H), 2.99 (t, J = 5.5 Hz, 6H), 2.02-1.90 (m, 2H), 1.76-1.64 (m, 4H), 1.55-1.44 (m, 2H). |
| CC136 | N-(5-Bromo-2-(3-(piperidin-1-yl)propoxy)pyridin-3-yl)-4-methoxybenzenesulfonamide | 484.00 486.00 | ¹H NMR (400 MHz, CDCl₃) δ 7.86 (d, J = 2.3 Hz, 1H), 7.82 (d, J = 2.2 Hz, 1H), 7.78-7.71 (m, 2H), 6.95-6.88 (m, 2H), 4.23 (t, J = 6.4 Hz, 2H), 3.84 (s, 3H), 2.53-2.42 (m, 6H), 1.91 (p, J = 6.7 Hz, 2H), 1.64 (p, J = 5.7 Hz, 4H), 1.48 (p, J = 6.0 Hz, 2H). |
| CC137 | N-(5-Bromo-2-(3-morpholinopropoxy)pyridin-3-yl)benzenesulfonamide | 456.05 458.05 | ¹H NMR (400 MHz, DMSO-d₆) δ 7.95 (d, J = 2.3 Hz, 1H), 7.72 (dd, J = 7.2, 1.7 Hz, 2H), 7.67 (d, J = 2.4 Hz, 1H), 7.65-7.59 (m, 1H), 7.57-7.52 (m, 2H), 4.04 (t, J = 6.5 Hz, 2H), 3.57 (t, J = 4.6 Hz, 4H), 2.39-2.29 (m, 6H), 1.67 (p, J = 6.8 Hz, 2H). |

-continued

| Intermediate | Structure | Name | MS: [(M + 1)]+ | 1H-NMR |
|---|---|---|---|---|
| CC138 | 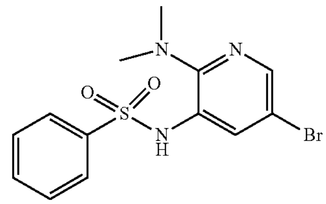 [SMILES: CN(C)c1ncc(Br)cc1NS(=O)(=O)c1ccccc1] | N-(5-Bromo-2-(dimethylamino)pyridin-3-yl)benzenesulfonamide | 356.10 358.10 | 1H NMR (300 MHz, CDCl3) δ 8.06 (d, J = 2.2 Hz, 1H), 7.94 (d, J = 2.2 Hz, 1H), 7.90-7.85 (m, 2H), 7.63-7.56 (m, 1H), 7.54-7.46 (m, 2H), 2.53 (s, 6H). |
| CC139 | 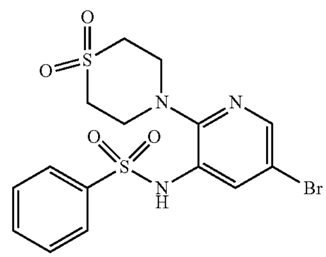 [SMILES: O=S1(=O)CCN(c2ncc(Br)cc2NS(=O)(=O)c2ccccc2)CC1] | N-(5-Bromo-2-(1,1-dioxidothiomorpholino)pyridin-3-yl)benzenesulfonamide | 446.10 448.10 | 1H NMR (300 MHz, DMSO-d6) δ 10.11 (s, 1H), 8.26-8.10 (m, 1H), 7.85-7.74 (m, 2H), 7.75-7.55 (m, 3H), 7.51 (d, J = 2.2 Hz, 1H), 3.46-3.36 (m, 4H), 3.22-3.12 (m, 4H). |
| CC140 | 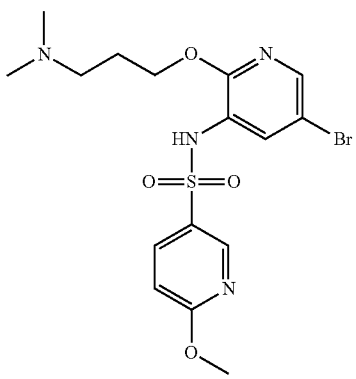 [SMILES: COc1ccc(S(=O)(=O)Nc2cc(Br)cnc2OCCCN(C)C)cn1] | N-(5-Bromo-2-(3-(dimethylamino)propoxy)pyridin-3-yl)-6-methoxypyridine-3-sulfonamide | 445.00 447.00 | 1H NMR (300 MHz, DMSO-d6) δ 8.50 (d, J = 2.5 Hz, 1H), 7.95 (dd, J = 8.7, 2.5 Hz, 1H), 7.42 (d, J = 2.3 Hz, 1H), 7.21 (d, J = 2.3 Hz, 1H), 6.91-6.82 (m, 1H), 4.24 (t, J = 5.4 Hz, 2H), 3.39-3.30 (m, 2H), 2.93 (s, 6H), 2.14 (p, J = 5.3 Hz, 2H). |
| CC141 | 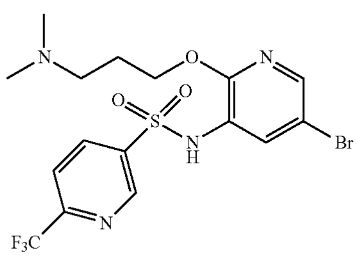 [SMILES: CN(C)CCCOc1ncc(Br)cc1NS(=O)(=O)c1ccc(C(F)(F)F)nc1] | N-(5-Bromo-2-(3-(dimethylamino)propoxy)pyridin-3-yl)-6-(trifluoromethyl)pyridine-3-sulfonamide | 483.00 485.00 | 1H NMR (300 MHz, CDCl3) δ 9.14 (s, 1H), 8.41 (d, J = 8.5 Hz, 1H), 7.75 (d, J = 8.2 Hz, 1H), 7.63 (d, J = 1.7 Hz, 2H), 4.36 (t, J = 5.6 Hz, 2H), 3.27-3.18 (m, 2H), 3.05 (s, 6H), 2.25 (p, J = 5.4 Hz, 2H). |
| CC142 | 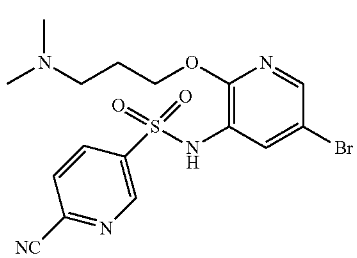 [SMILES: CN(C)CCCOc1ncc(Br)cc1NS(=O)(=O)c1ccc(C#N)nc1] | N-(5-Bromo-2-(3-(dimethylamino)propoxy)pyridin-3-yl)-6-cyanopyridine-3-sulfonamide | 440.05 442.05 | 1H NMR (300 MHz, CDCl3) δ 9.06 (dd, J = 2.2, 1.0 Hz, 1H), 8.30 (dd, J = 8.0, 2.1 Hz, 1H), 7.77-7.70 (m, 1H), 7.52 (dd, J = 16.2, 2.1 Hz, 2H), 5.67 (s, 1H), 4.39 (t, J = 5.6 Hz, 2H), 3.30-3.23 (m, 2H), 3.10 (s, 6H), 2.25 (p, J = 5.5 Hz, 2H). |

| Inter-mediate | Structure | Name | MS: [(M + 1)]+ | 1H-NMR |
|---|---|---|---|---|
| CC143 | 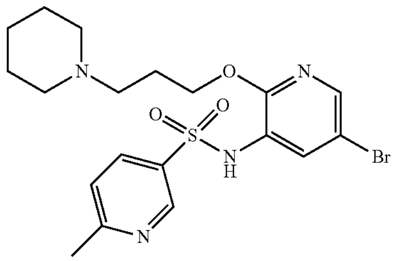 [SMILES: Cc1ccc(S(=O)(=O)Nc2cc(Br)cnc2OCCCN2CCCCC2)cn1] | N-(5-Bromo-2-(3-(piperidin-1-yl)propoxy)pyridin-3-yl)-6-methylpyridine-3-sulfonamide | 469.10 471.10 | 1H NMR (300 MHz, DMSO-d6) δ 8.72 (d, J = 2.3 Hz, 1H), 7.92 (dd, J = 8.1, 2.4 Hz, 1H), 7.47 (d, J = 2.3 Hz, 1H), 7.37-7.28 (m, 2H), 4.20 (t, J = 5.8 Hz, 2H), 3.24-3.13 (m, 6H), 2.49 (s, 3H), 2.12-1.99 (m, 2H), 1.83-1.72 (m, 4H), 1.59-1.47 (m, 2H). |
| CC144 | 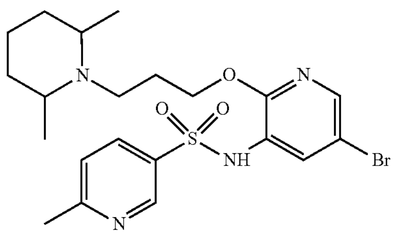 [SMILES: Cc1ccc(S(=O)(=O)Nc2cc(Br)cnc2OCCCN2C(C)CCCC2C)cn1] | N-(5-Bromo-2-(3-(2,6-dimethylpiperidin-1-yl)propoxy)pyridin-3-yl)-6-methylpyridine-3-sulfonamide | 497.10 499.10 | 1H NMR (400 MHz, DMSO-d6) δ 8.67 (d, J = 2.4 Hz, 1H), 7.86 (dd, J = 8.0, 2.3 Hz, 1H), 7.32-7.29 (m, 2H), 7.26 (d, J = 8.1 Hz, 1H), 4.18-4.12 (m, 2H), 2.92 (s, 2H), 2.74 (s, 2H), 2.45 (s, 3H), 1.85-1.77 (m, 2H), 1.57 (d, J = 13.0 Hz, 3H), 1.39-1.19 (m, 3H), 1.08 (s, 3H), 1.07 (s, 3H). |
| CC145 | 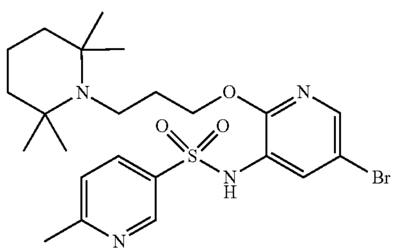 [SMILES: Cc1ccc(S(=O)(=O)Nc2cc(Br)cnc2OCCCN2C(C)(C)CCCC2(C)C)cn1] | N-(5-Bromo-2-(3-(2,2,6,6-tetramethylpiperidin-1-yl)propoxy)pyridin-3-yl)-6-methylpyridine-3-sulfonamide | 525.20 527.20 | 1H NMR (400 MHz, DMSO-d6) δ 8.68 (d, J = 2.4 Hz, 1H), 7.86 (dd, J = 8.1, 2.3 Hz, 1H), 7.29-7.26 (m, 2H), 4.08 (t, J = 6.5 Hz, 2H), 2.54-2.53 (m, 2H), 2.45 (s, 3H), 1.78-1.69 (m, 2H), 1.53-1.45 (m, 2H), 1.34 (t, J = 5.9 Hz, 4H), 0.98 (s, 12H). |

Note:
CC100~CC103, CC114~CC139, Reaction conditions: sulfonyl chloride (1.5 eq.), DMAP, Py, 60° C., 16 h.

Intermediate CC104

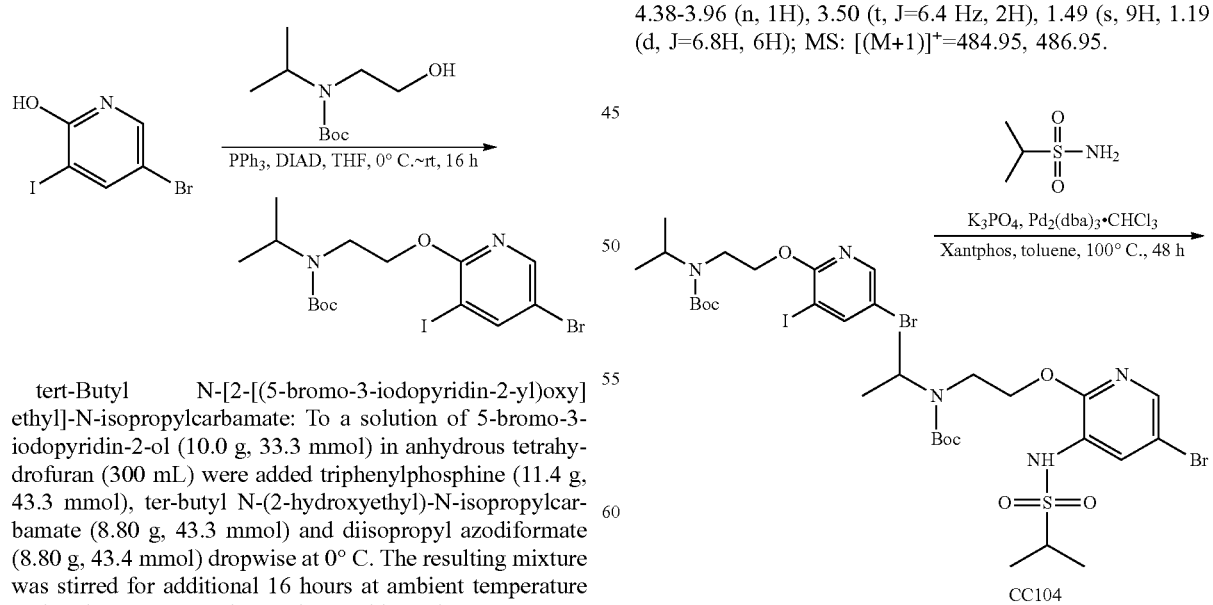

tert-Butyl N-[2-[(5-bromo-3-iodopyridin-2-yl)oxy]ethyl]-N-isopropylcarbamate: To a solution of 5-bromo-3-iodopyridin-2-ol (10.0 g, 33.3 mmol) in anhydrous tetrahydrofuran (300 mL) were added triphenylphosphine (11.4 g, 43.3 mmol), ter-butyl N-(2-hydroxyethyl)-N-isopropylcarbamate (8.80 g, 43.3 mmol) and diisopropyl azodiformate (8.80 g, 43.4 mmol) dropwise at 0° C. The resulting mixture was stirred for additional 16 hours at ambient temperature under nitrogen atmosphere. The resulting mixture was concentrated under reduced pressure. The residue was purified by silica gel column chromatography, eluted with 2%~10% ethyl acetate in petroleum ether. The desired fractions were collected and concentrated under reduced pressure to afford the title compound as a colorless oil (14.0 g, 87%): 1H NMR (400 MHz, CDCl3) δ 8.14 (s, 2H), 4.43 (t, J=6.4 Hz, 2H), 4.38-3.96 (n, 1H), 3.50 (t, J=6.4 Hz, 2H), 1.49 (s, 9H), 1.19 (d, J=6.8H, 6H); MS: [(M+1)]+=484.95, 486.95.

tert-Butyl (2-((5-bromo-3-(((1-methylethyl)sulfonamido)pyridin-2-yl)oxy)ethyl)(isopropyl)carbamate: To a mixture of tert-butyl(2-((5-bromo-3-iodopyridin-2-yl)oxy)ethyl(isopropyl)carbamate (5.00 g, 10.3 mol), 4,5-bis(diphenylphosphino)-9,9-dimethyxanthene (1.80 g, 3.10 mmol) and propane-2-sulfonamide (1.50 g, 12.4 mmol) in toluene (125 mL) were added tripotassium phosphate (10.9 g, 51.5 mmol) and tris(dibenzylideneacetone)dipalladium-chloroform adduct (1.10 g, 1.10 mmol) at ambient temperature. The resulting mixture was stirred for 48 hours at 100° C. under argon atmosphere. After cooling down to ambient temperature, the resulting mixture was filtered. The filtered cake was washed with ethyl acetate (3×20.0 mL). The filtrate was concentrated under reduced pressure. The residue was purified by silica gel column chromatography, eluted with 1%~20% ethyl acetate in petroleum ether. The desired fractions were collected and concentrated under reduced pressure to afford the title compound as a colorless solid (1.90 g, 39%): $^1$H NMR (400 MHz, CDCl$_3$) δ 7.94 (d, J=2.1 Hz, 1H), 7.89 (d, J=2.2 Hz, 1H), 4.44 (t, J=6.3 Hz, 2H), 4.11 (m, 1H), 3.48 (t, J=6.3 Hz, 2H), 3.27 (p, J=6.8 Hz, 1), 1.48 (s, 9H), 1.41 (d, J=6.8 Hz, 6H), 1.14 (d, J=6.8 Hz, 6H), MS: [(M+1)]$^+$=480.20, 482.20.

The following intermediates were prepared according to the procedure described above:

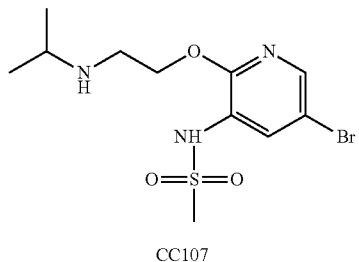

CC107

N-(5-Bromo-2-[2-[(propan-2-yl)amino]ethoxy]pyridin-3-yl)methanesulfonamide: To a solution of tert-butyl N-[2-[(5-bromo-3-methanesulfonamidopyridin-2-yl)oxy]ethyl]-N-(propan-2-yl)carbamate (3.00 g, 6.63 mmol) in dichloromethane (5.00 mL) was treated with hydrogen chloride (20.0 mL, 4 M in 1,4-dioxane) for 40 min at ambient temperature. The resulting mixture was concentrated under reduced pressure. The residue was basified to pH=8 with

| Intermediate | Structure | Name | Ms: [(M + 1)]$^+$ | $^1$H NMR |
|---|---|---|---|---|
| CC105 | 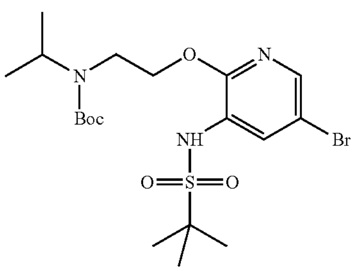 [SMILES: CC(C)N(CCOc1ncc(Br)cc1NS(=O)(=O)C(C)(C)C)C(=O)OC(C)(C)C] | tert-Butyl (2-((5-bromo-3-((1,1-dimethylethyl)sulfonamido)pyridin-2-yl)oxy)ethyl)(isopropyl)carbamate | 494.20 496.20 | $^1$H NMR (400 MHz, CDCl$_3$) δ 8.02 (d, J = 2.2 Hz, 1H), 7.87 (d, J = 2.2 Hz, 1H), 4.45 (t, J = 6.3 Hz, 2H), 4.12 (m, 1 H), 3.49 (t, J = 6.3 Hz, 2H), 1.48 (s, 9H), 1.42 (s, 9H), 1.14 (d, J = 6.8 Hz, 6H). |
| CC106 | 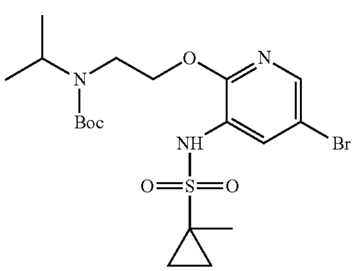 [SMILES: CC(C)N(CCOc1ncc(Br)cc1NS(=O)(=O)C1(C)CC1)C(=O)OC(C)(C)C] | tert-Butyl (2-((5-bromo-3-((1-methylcyclopropane)-1-sulfonamido)pyridin-2-yl)oxy)ethyl)(isopropyl)carbamate | 492.20 494.40 | $^1$H NMR (400 MHz, CDCl$_3$) δ 7.94 (s, 1H), 7.91 (s, 1H), 4.45 (t, J = 6.4 Hz, 2H), 4.11 (m, 1H), 3.51 (t, J = 6.4 Hz, 2H), 1.51 (s, 3H), 1.48 (s, 9H), 1.43-1.48 (m, 2H), 1.15 (d, J = 6.8 Hz, 6H), 0.80-0.75 (m, 2H). |

Intermediate CC107

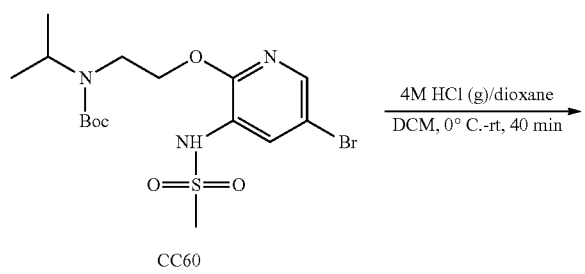

saturated aqueous sodium bicarbonate (30.0 mL). The resulting mixture was extracted with ethyl acetate (6×200 mL). The combined organic layers was dried over anhydrous sodium sulfate and filtered. The filtrate was concentrated under reduced pressure. The residue was purified by silica gel column chromatography, eluted with 1%~10% methanol in dichloromethane. The desired fractions were collected and concentrated under reduced pressure to afford the title compound as a colorless solid (1.20 g, 50%): $^1$H NMR (400 MHz, DMSO-d$_6$) δ 7.68 (d, J=2.3 Hz, 1H), 7.61 (d, J=2.3 Hz, 1H), 5.75 (s, 1H), 4.36 (t, J=5.2 Hz, 2H), 3.15 (p, J=6.5 Hz, 1H), 3.07 (t, J=5.1 Hz, 2H), 2.84 (s, 3H), 1.15 (d, J=6.4 Hz, 6H); MS: [(M+1)]$^+$=352.10, 354.10.

The following intermediates were prepared according to the procedure described above:

| Intermediate | Name | Ms: [(M + 1)]+ | 1H NMR |
|---|---|---|---|
| CC108 | N-(5-Bromos-2-(2-(isopropylamino)ethoxy)pyridin-3-yl)ethanesulfonamide | 366.10 368.10 | 1H NMR (400 MHz, CDCl$_3$) δ 7.92 (s, 2H), 4.50 (t, J = 5.3 Hz, 2H), 3.15 (q, J = 7.4 Hz, 2H), 3.07 (t, J = 5.3 Hz, 2H), 2.97 (hept, J = 6.4 Hz, 1H), 1.40 (t, J = 7.4 Hz, 3H), 1.16 (d, J = 6.3 Hz, 6H). |
| CC109 | N-(5-Bromo-2-(2-(isopropylamino)ethoxy)pyridin-3-yl)cyclopropanesulfonamide | 378.00 380.00 | 1H NMR (400 MHz, CDCl$_3$) δ 7.96-7.87 (m, 2H), 4.50 (t, J = 5.1 Hz, 2H), 3.09 (t, J = 5.1 Hz, 2H), 3.00 (p, J = 6.3 Hz, 1H), 2.61-2.53 (m, 1H), 1.25-1.21 (m, 2H), 1.18 (d, J = 6.2 Hz, 6H), 1.01-0.95 (m, 2H). |
| CC110 | N-(5-Bromo-2-(2-(isopropylamino)ethoxy)pyridin-3-yl)propane-2-sulfonamide | 380.15 382.15 | 1H NMR (400 MHz, CDCl$_3$) δ 7.95 (d, J = 2.2 Hz, 1H), 7.91 (d, J = 2.3 Hz, 1H), 4.48 (t, J = 5.4 Hz, 2H), 3.27 (p, J = 6.8 Hz, 1H), 3.02 (t, J = 5.4 Hz, 2H), 2.91 (p, J = 6.3 Hz, 1H), 1.40 (d, J = 6.8 Hz, 6H), 1.11 (d, J = 6.2 Hz, 6H). |
| CC111 | N-(5-Bromo-2-(2-(isopropylamino)ethoxy)pyridin-3-yl)-2-methylpropane-2-sulfonamide | 394.20 396.20 | 1H NMR (400 MHz, CDCl$_3$) δ 7.99 (d, J = 2.3 Hz, 1H), 7.90 (d, J = 2.3 Hz, 1H), 4.52 (t, J = 5.2 Hz, 2H), 3.07 (t, J = 5.2 Hz, 2H), 3.03-2.94 (m, 1H), 1.41 (s, 9H), 1.15 (d, J = 6.3 Hz, 6H). |
| CC112 | N-(5-Bromo-2-(2-(isopropylamino)ethoxy)pyridin-3-yl)-1-methylcyclopropane-1-sulfonamide | 392.20 394.20 | 1H NMR (400 MHz, CDCl$_3$) δ 7.92 (q, J = 2.3 Hz, 2H), 4.51 (t, J = 5.3 Hz, 2H), 3.07 (t, J = 5.3 Hz, 2H), 2.97 (p, J = 6.3 Hz, 1H), 1.51 (s, 3H), 1.41-1.36 (m, 2H), 1.15 (d, J = 6.3 Hz, 6H), 0.79-0.73 (m, 2H). |
| CC113 | [2-({5-Bromo-3-[(dimethylsulfamoyl)amino]pyridin-2-yl}oxy)ethyl](propan-2-yl)amine | 381.05 383.05 | 1H NMR (400 MHz, DMSO-d$_6$) δ 7.69 (d, J = 2.2 Hz, 1H), 7.65 (d, J = 2.3 Hz, 1H), 4.34 (t, J = 5.2 Hz, 2H), 3.21-3.12 (m, 1H), 3.08 (t, J = 5.3 Hz, 2H), 2.59 (s, 6H), 1.16 (d, J = 6.4 Hz, 6H). |

Intermediate DD

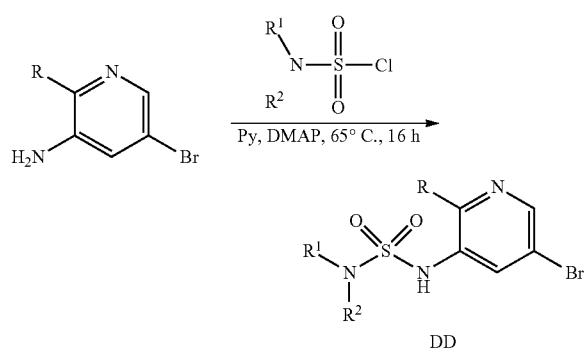

General Procedure: To a solution of amine (1.0 mmol) in pyridine (10 mL) were added 4-dimethylaminopyridine (0.1 mmol) and the corresponding sulfamoyl chloride (5.0 mmol) at ambient temperature. The resulting solution was stirred for 16 hours at 65° C. After cooling down to ambient temperature, the resulting mixture was concentrated under reduced pressure. The residue was purified by silica gel column chromatography, eluted with 1~20% methanol in dichloromethane. Desired fractions were collected and concentrated under reduced pressure to afford the title compound.

The following intermediates were prepared according to the above procedure:

| Intermediate | Structure | Name | Ms: [(M + 1)]+ | 1H NMR |
|---|---|---|---|---|
| DD1 | 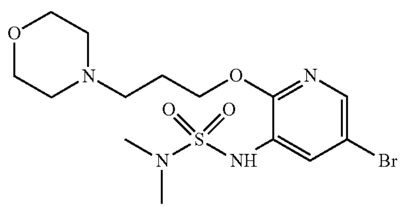 [SMILES: CN(C)S(=O)(=O)Nc1cc(Br)cnc1OCCCN1CCOCC1] | ({5-Bromo-2-[3-(morpholin-4-yl)propoxy]pyridin-3-yl}sulfamoyl)dimethylamine. | 423.10 425.10 | 1H NMR (400 MHz, DMSO-d6) δ 8.04 (d, J = 2.3 Hz, 1H), 7.74 (d, J = 2.3 Hz, 1H), 4.33 (t, J = 6.4 Hz, 2H), 3.58 (t, J = 4.6 Hz, 4H), 2.70 (s, 6H), 2.50-2.46 (m, 2H), 2.44-2.35 (m, 4H), 1.93 (p, J = 6.7 Hz, 2H). |
| DD2 | 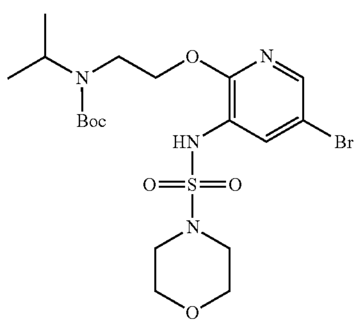 [SMILES: CC(C)N(CCOc1ncc(Br)cc1NS(=O)(=O)N1CCOCC1)C(=O)OC(C)(C)C] | tert-Butyl (2-((5-Bromo-3-(morpholine-4-sulfonamido)pyridin-2-yl)oxy)ethyl)(isopropyl)carbamate | 523.30 525.30 | 1H NMR (400 MHz, CDCl3) δ 7.90 (s, 1H), 7.83 (s, 1H), 7.44 (s, 1H), 7.28 (s, 1H), 4.50-4.43 (m, 2H), 3.80-3.71 (m, 1H), 3.71-3.66 (m, 4H), 3.58-3.42 (m, 2H), 3.25 (t, J = 4.7 Hz, 4H), 1.48 (s, 9H), 1.15 (d, J = 6.8 Hz, 6H). |
| DD3 | 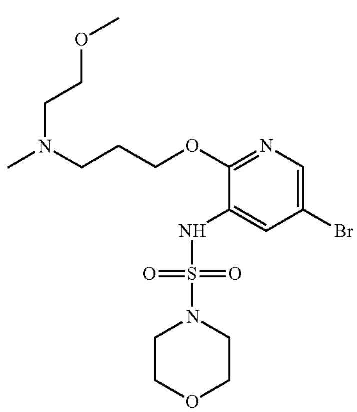 [SMILES: COCCN(C)CCCOc1ncc(Br)cc1NS(=O)(=O)N1CCOCC1] | N-(5-Bromo-2-(3-((2-methoxyethyl)(methyl)amino)propoxy)pyridin-3-yl)morpholine-4-sulfonamide | 467.15 469.15 | 1H NMR (400 MHz, DMSO-d6) δ 7.78 (s, 1H), 7.67 (d, J = 2.3 Hz, 1H), 4.29 (t, J = 5.9 Hz, 2H), 3.56 (t, J = 4.5 Hz, 6H), 3.23 (s, 3H), 3.03-2.93 (m, 8H), 2.54 (s, 3H), 2.01 (q, J = 6.3 Hz, 2H). |

-continued

| Intermediate | Structure | Name | Ms: [(M + 1)]+ | 1H NMR |
|---|---|---|---|---|
| DD4 | 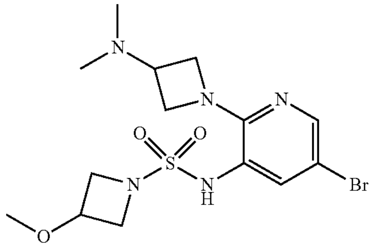 [SMILES: COC1CN(S(=O)(=O)Nc2cc(Br)cnc2N2CC(N(C)C)C2)C1] | N-(5-Bromo-2-(3-(dimethylamino)azetidin-1-yl)pyridin-3-yl)-3-methoxyazetidine-1-sulfonamide | 420.10 422.10 | 1H NMR (400 MHz, CD3OD) δ 8.05 (d, J = 2.2 Hz, 1H), 7.72 (d, J = 2.2 Hz, 1H), 4.40-4.26 (m, 3H), 4.21 (q, J = 5.4 Hz, 1H), 4.13-4.02 (m, 4H), 3.89-3.78 (m, 2H), 3.63 (s, 3H), 2.52 (s, 6H). |
| DD5 | 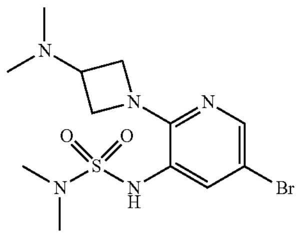 [SMILES: CN(C)C1CN(c2ncc(Br)cc2NS(=O)(=O)N(C)C)C1] | 1-{5-Bromo-3-[(dimethylsulfamoyl)amino]pyridin-2-yl}-N,N-dimethylazetidin-3-amine | 378.10 380.10 | 1H NMR (400 MHz, DMSO-d6) δ 9.18 (s, 1H), 8.03 (s, 1H), 7.48 (d, J = 2.0 Hz, 1H), 4.15 (t, J = 8.0 Hz, 2H), 3.89 (dd, J = 8.9, 5.6 Hz, 2H), 3.14 (s, 1H), 2.75 (s, 6H), 2.13 (s, 6H). |
| DD6 | 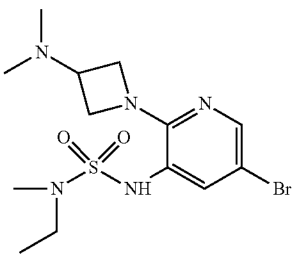 [SMILES: CCN(C)S(=O)(=O)Nc1cc(Br)cnc1N1CC(N(C)C)C1] | 1-(5-Bromo-3-{[ethyl(methyl)sulfamoyl]amino}pyridin-2-yl)-N,N-dimethylazetidin-3-amine | 392.05 394.05 | 1H NMR (400 MHz, DMSO-d6) δ 9.08 (s, 1H), 8.04 (d, J = 2.3 Hz, 1H), 7.45 (d, J = 2.3 Hz, 1H), 4.15 (dd, J = 8.9, 7.0 Hz, 2H), 3.88 (dd, J = 8.9, 5.5 Hz, 2H), 3.21-3.09 (m, 3H), 2.76 (s, 3H), 2.12 (s, 6H), 1.06 (t, J = 7.1 Hz, 3H). |
| DD7 | 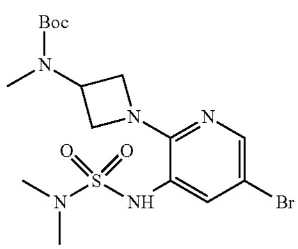 [SMILES: CN(C(=O)OC(C)(C)C)C1CN(c2ncc(Br)cc2NS(=O)(=O)N(C)C)C1] | tert-Butyl (1-(5-bromo-3-((N,N-dimethylsulfamoyl)amino)pyridin-2-yl)azetidin-3-yl)(methyl)carbamate | 464.10 466.10 | 1H NMR (400 MHz, DMSO-d6) δ 9.14 (s, 1H), 8.09 (d, J = 2.2 Hz, 1H), 7.50 (d, J = 2.2 Hz, 1H), 4.29 (t, J = 8.5 Hz, 2H), 4.25-4.17 (m, 1H), 4.10 (dd, J = 8.9, 6.3 Hz, 2H), 2.84 (d, J = 8.8 Hz, 3H), 2.76 (s, 5H), 1.39 (s, 9H). |
| DD8 | 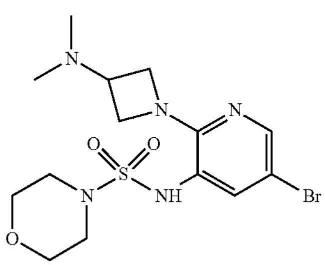 [SMILES: CN(C)C1CN(c2ncc(Br)cc2NS(=O)(=O)N2CCOCC2)C1] | N-(5-Bromo-2-(3-(dimethylamino)azetidin-1-yl)pyridin-3-yl)morpholine-4-sulfonamide | 420.10 422.10 | 1H NMR (400 MHz, CDCl3) δ 8.08-8.04 (m, 1H), 7.67-7.62 (m, 1H), 4.17 (t, J = 7.6 Hz, 2H), 4.04-3.94 (m, 2H), 3.73 (t, J = 4.7 Hz, 4H), 3.27 (t, J = 4.6 Hz, 4H), 3.24-3.14 (m, 1H), 2.25 (s, 6H). |
| DD9 | 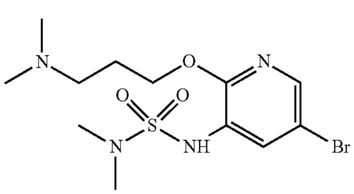 [SMILES: CN(C)CCCOc1ncc(Br)cc1NS(=O)(=O)N(C)C] | [3-({5-Bromo-3-[(dimethylsulfamoyl)amino]pyridine-2-yl}oxy)propyl]dimethylamine | 380.90 382.90 | 1H NMR (300 MHz, CDCl3) δ 7.89 (d, J = 2.2 Hz, 1H), 7.75 (d, J = 2.1 Hz, 1H), 7.54 (s, 1H), 4.48 (t, J = 5.7 Hz, 2H), 3.32 (s, 8H), 2.91 (s, 6H), 2.34-2.21 (m, 2H). |

-continued

| Intermediate | Structure | Name | Ms: [(M + 1)]+ | 1H NMR |
|---|---|---|---|---|
| DD10 | 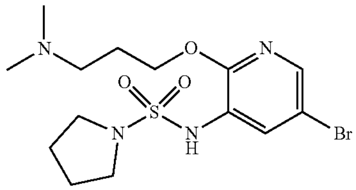 [SMILES: CN(C)CCCOc1ncc(Br)cc1NS(=O)(=O)N1CCCC1] | N-(5-Bromo-2-(3-(dimethylamino)propoxy)pyridin-3-yl)pyrrolidine-1-sulfonamide | 407.00 409.00 | 1H NMR (300 MHz, DMSO-d6) δ 7.76 (d, J = 2.3 Hz, 1H), 7.65 (d, J = 2.3 Hz, 1H), 4.28 (t, J = 5.8 Hz, 2H), 3.12-3.04 (m, 6H), 2.66 (s, 6H), 2.10-2.00 (m, 2H), 1.79-1.72 (m, 4H). |
| DD11 | 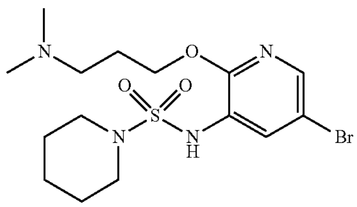 [SMILES: CN(C)CCCOc1ncc(Br)cc1NS(=O)(=O)N1CCCCC1] | N-(5-Bromo-2-(3-(dimethylamino)propoxy)pyridin-3-yl)piperidine-1-sulfonamide | 421.10 423.10 | 1H NMR (400 MHz, DMSO-d6) δ 7.58 (d, J = 2.3 Hz, 1H), 7.55 (d, J = 2.3 Hz, 1H), 4.26 (t, J = 5.8 Hz, 2H), 3.07 (t, J = 5.8 Hz, 2H), 2.97 (t, J = 5.7 Hz, 4H), 2.67 (s, 6H), 2.10-2.02 (m, 2H), 1.50-1.37 (m, 6H). |
| DD12 | 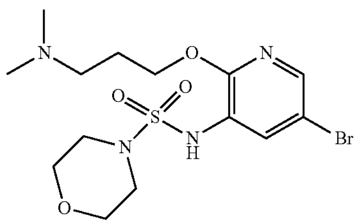 [SMILES: CN(C)CCCOc1ncc(Br)cc1NS(=O)(=O)N1CCOCC1] | N-(5-Bromo-2-(3-(dimethylamino)propoxy)pyridin-3-yl)morpholine-4-sulfonamide | 423.10 425.10 | 1H NMR (300 MHz, CDCl3) δ 7.82 (s, 2H), 4.42 (t, J = 5.9 Hz, 2H), 3.72-3.67 (m, 4H), 3.24-3.20 (m, 4H), 2.77 (t, J = 6.3 Hz, 2H), 2.56 (s, 6H), 2.14-2.04 (m, 2H). |
| DD13 | 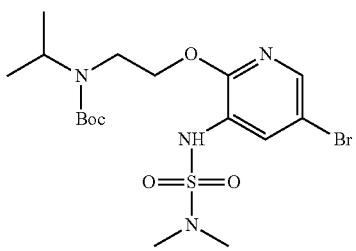 [SMILES: CC(C)N(CCOc1ncc(Br)cc1NS(=O)(=O)N(C)C)C(=O)OC(C)(C)C] | tert-Butyl (2-((5-bromo-3-((N,N-dimethylsulfamoyl)amino)pyridin-2-yl)oxy)ethyl)(isopropyl)carbamate | 481.05 483.05 | 1H NMR (400 MHz, CDCl3) δ 7.88 (s, 1H), 7.81 (s, 1H), 4.43 (t, J = 6.3 Hz, 2H), 4.13-4.10 (m, 1H), 3.55-3.45 (m, 2H), 2.88 (s, 6H), 1.46 (s, 9H), 1.17 (d, J = 6.4 Hz, 6H). |
| DD14 | 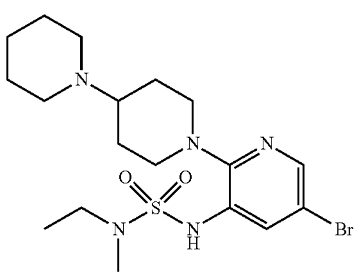 [SMILES: CCN(C)S(=O)(=O)Nc1cc(Br)cnc1N1CCC(N2CCCCC2)CC1] | (2-{[1,4'-Bipiperidine]-1'-yl}-5-bromopyridin-3-yl)sulfamoyl](ethyl)methylamine | 445.12 447.12 | 1H NMR (400 MHz, DMSO-d6) δ 9.21 (s, 1H), 8.06 (d, J = 2.2 Hz, 1H), 7.63 (d, J = 2.3 Hz, 1H), 3.81 (d, J = 12.7 Hz, 2H), 3.14 (q, J = 7.1 Hz, 4H), 3.06 (s, 3H), 2.79-2.69 (m, 5H), 1.98 (d, J = 11.3 Hz, 2H), 1.82 (dt, J = 12.2, 6.5 Hz, 2H), 1.72 (t, J = 5.7 Hz, 4H), 1.53 (s, 2H), 1.05 (t, J = 7.1 Hz, 3H). |
| DD15 | 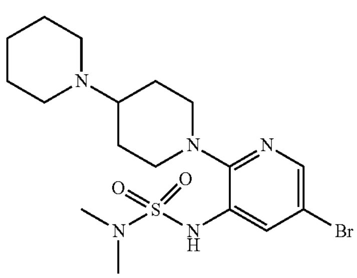 [SMILES: CN(C)S(=O)(=O)Nc1cc(Br)cnc1N1CCC(N2CCCCC2)CC1] | 2-{[1,4'-Bipiperidine]-1'-yl}-5-bromopyridin-3-yl)sulfamoyl]dimethylamine | 446.10 448.10 | 1H NMR (400 MHz, CD3OD) δ 7.99 (d, J = 2.2 H, 1H), 7.78 (d, J = 2.2 H, 1H), 3.75 (d, J = 12.2 Hz, 2H), 3.19-3.08 (m, 5H), 2.83 (s, 6H), 2.64 (t, J = 3.8 Hz, 2H), 2.07 (d, J = 11.5 Hz, 2H), 2.02-1.91 (m, 2H), 1.83 (s, 4H), 1.65 (s, 2H). |

-continued

| Intermediate | Structure | Name | Ms: [(M + 1)]+ | 1H NMR |
|---|---|---|---|---|
| DD16 | 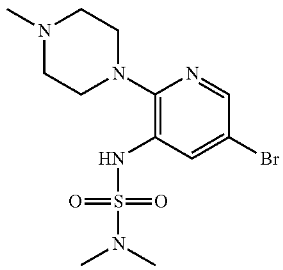 [SMILES: CN1CCN(c2ncc(Br)cc2NS(=O)(=O)N(C)C)CC1] | [5-Bromo-2-(4-methylpiperazin-1-yl)pyridin-3-yl]sulfamoyl} dimethylamine | 378.05 380.05 | 1H NMR (400 MHz, CD3OD) δ 8.13 (d, J = 2.0 Hz, 1H), 7.82 (d, J = 2.0 Hz, 1H), 3.43 (s, 4H), 2.86 (s, 6H), 2.83 (s, 3H), 2.63 (s, 4H). |
| DD17 | 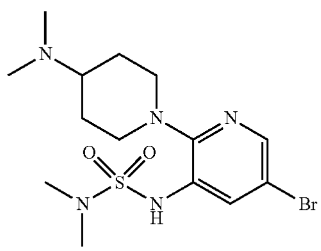 [SMILES: CN(C)C1CCN(c2ncc(Br)cc2NS(=O)(=O)N(C)C)CC1] | 1-{5-Bromo-3-[(dimethylsulfamoyl)amino]pyridin-2-yl}-N,N-dimethylpiperidin-4-amine | 406.10 408.10 | 1H NMR (400 MHz, CDCl3) δ 8.09 (d, J = 2.1 Hz, 1H), 7.78 (d, J = 2.1 Hz, 1H), 3.36 (d, J = 12.7 Hz, 2H), 3.18 (s, 2H), 2.92 (d, J = 1.8 Hz, 6H), 2.88 (d, J = 5.3 Hz, 1H), 2.85 (s, 6H), 2.30-2.22 (m, 2H), 2.08 (d, J = 12.4 Hz, 2H). |

Intermediate EE

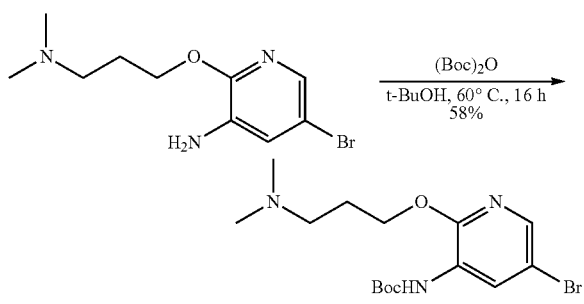

tert-Butyl (5-bromo-2-(3-(dimethylamino)propoxy)pyridin-3-yl)carbamate: To a solution of 5-bromo-2-(3-(dimethylamino)propoxy)pyridin-3-amine (2.00 g, 7.30 mmol) in tert-butanol (60.0 mL) was added di-tert-butyl dicarbonate (2.40 g, 10.9 mmol) at ambient temperature. The resulting mixture was stirred for 16 hours at 60° C. under nitrogen atmosphere. The mixture was cooled down to ambient temperature. The resulting mixture was concentrated under reduced pressure. The residue was purified by silica gel column chromatography, eluted with 2%~7% methanol in dichloromethane to afford the title compound (1.59 g, 57%) as a light brown oil: 1H NMR (400 MHz, CDCl3) δ 8.48 (s, 1H), 7.78 (d, J=2.3 Hz, 1H), 7.18 (s, 1H), 4.39 (t, J=6.4 Hz, 2H), 2.45 (t, J=7.2 Hz, 2H), 2.28 (s, 6H), 1.99 (p, J=6.7 Hz, 2H), 1.54 (s, 9H); MS: [(M+1)]+=373.6, 375.6.

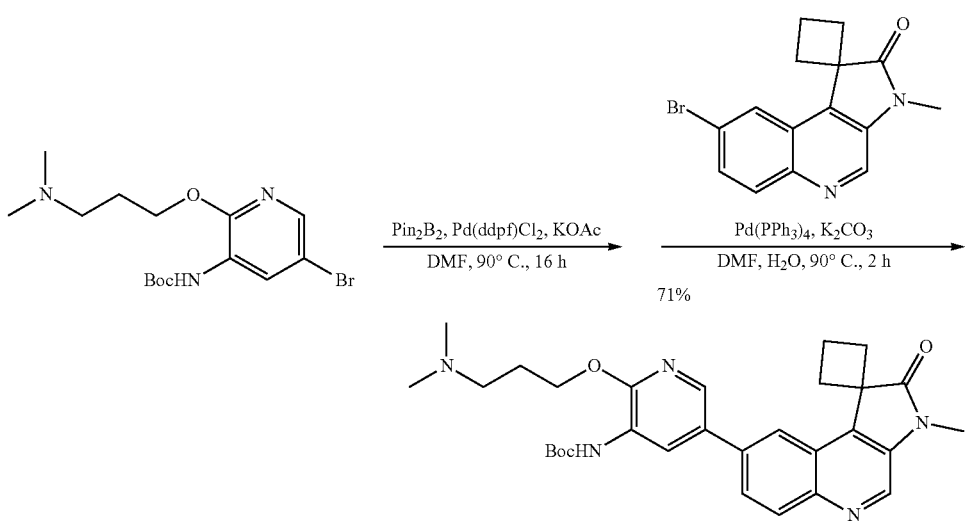

tert-Butyl (2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)carbamate: To a solution of tert-butyl (5-bromo-2-(3-(dimethylamino)propoxy)pyridin-3-yl)carbamate (0.96 g, 2.57 mmol) and 4,4,5,5-tetramethyl-2-(tetramethyl-1,3,2-dioxaborolan-2-yl)-1,3,2-dioxaborolane (1.31 g, 5.14 mmol) in N,N-dimethylformamide (70.0 mL) were added potassium acetate (1.01 g, 10.3 mmol) and 1,1'-bis(diphenylphosphino)ferrocene-palladium (II) dichloride (0.38 g, 0.51 mmol) at ambient temperature. The resulting mixture was stirred for 2 hours at 90° C. under nitrogen atmosphere, then cooled down to ambient temperature.

To the above mixture were added water (10.0 mL), potassium carbonate (0.56 g, 4.11 mmol), 8'-bromo-3'-methylspiro[cyclobutane-1,1'-pyrrolo[2,3-c]quinolin]-2'(3'H)-one (0.65 g, 2.05 mmol) and tetrakis (triphenylphosphine) palladium (0.36 g, 0.31 mmol). After stirring for 2 hours at 90° C. under nitrogen atmosphere, the resulting mixture was concentrated under reduced pressure. The residue was purified by silica gel column chromatography, eluted with 1%~10% methanol in dichloromethane to afford the title compound (0.97 g, 71%) as a brown solid: $^1$H NMR (300 MHz, CDCl$_3$) δ 8.82 (s, 1H), 8.64 (s, 1H), 8.43 (d, J=2.0 Hz, 1H), 8.22-8.15 (m, 2H), 7.89 (dd, J=8.9, 2.0 Hz, 1H), 7.24 (s, 1H), 4.54 (t, J=6.4 Hz, 2H), 3.38 (s, 3H), 3.02-2.85 (m, 2H), 2.82-2.58 (m, 6H), 2.43 (s, 6H), 2.19-2.12 (m, 2H), 1.57 (s, 9H); MS: [(M+1)]$^+$=532.2.

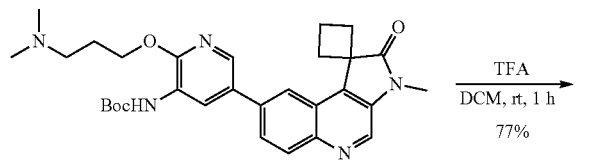

8'-(5-Amino-6-(3-(dimethylamino)propoxy)pyridin-3-yl)-3'-methylspiro[cyclobutane-1,1'-pyrrolo[2,3-c]quinolin]-2'(3'H)-one: A solution of tert-butyl (2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)carbamate (0.97 g, 1.82 mmol) in trifluoroacetic acid (10.0 mL) and dichloromethane (60.0 mL) was stirred for 1 hour at ambient temperature. The resulting mixture was concentrated under reduced pressure. The residue was basified to pH=8 with saturated aqueous of sodium bicarbonate. The resulting mixture was extracted with ethyl acetate (4×100 mL). The combined organic layers was washed with brine (2×100 mL), dried over anhydrous sodium sulfate. After filtration, the filtrate was concentrated under reduced pressure to afford the title compound (0.60 g, 77%) as a brown solid: $^1$H NMR (400 MHz, CDCl$_3$) δ 8.63 (s, 1H), 8.35 (d, J=2.0 Hz, 1H), 8.18 (d, J=8.8 Hz, 1H), 7.95 (d, J=2.2 Hz, 1H), 7.79 (dd, J=8.9, 2.0 Hz, 1H), 7.25 (d, J=2.2 Hz, 1H), 4.49 (t, J=6.5 Hz, 2H), 4.01 (s, 2H), 3.38 (s, 3H), 2.99-2.85 (m, 2H), 2.81-2.60 (m, 3H), 2.60-2.40 (m, 3H), 2.30 (s, 6H), 2.11-1.99 (m, 2H) MS: [(M+1)]$^+$=432.2.

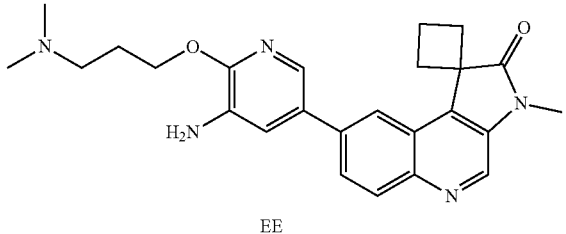

EE

Intermediate EE1

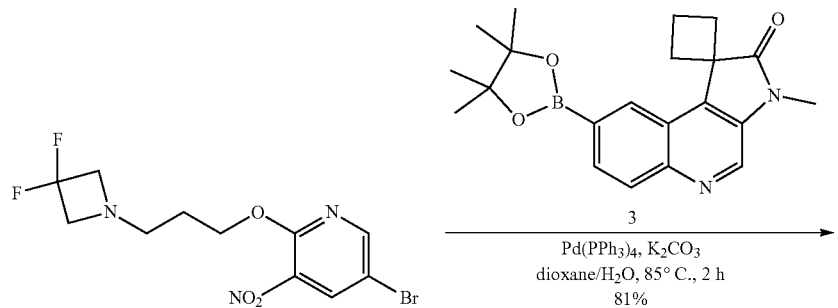

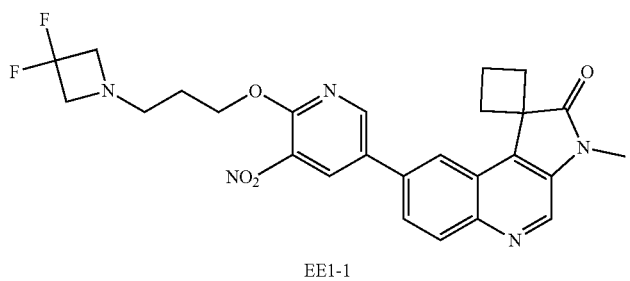

EE1-1

8'-(6-(3-(3,3-Difluoroazetidin-1-yl)propoxy)-5-nitropyridin-3-yl)-3'-methylspiro[cyclobutane-1,1'-pyrrolo[2,3-c]quinolin]-2'(3'H)-one: To a solution of 5-bromo-2-[3-(3,3-difluoroazetidin-1-yl)propoxy]-3-nitropyridine (300 mg, 0.85 mmol) in 1,4-dioxane (15.0 mL) were added water (1.50 mL), 3-methyl-8-(4,4,5,5-tetramethyl-1,3,2-dioxaborolan-2-yl)-2,3-dihydrospiro[cyclobutane-1,1-pyrrolo[2,3-c]quinolin]-2-one (404 mg, 1.11 mmol), potassium carbonate (118 mg, 0.85 mmol) and tetrakis(triphenylphosphine)palladium (0) (Pd(PPh$_3$)$_4$. 197 mg, 0.17 mmol). After stirring for 2 hours at 85° C. under nitrogen atmosphere, the resulting mixture was concentrated under reduced pressure. The residue was purified by Prep-TLC (CH$_2$Cl$_2$/MeOH=18/1, v/v) to afford the title compound as a yellow solid (350 mg, 81%): $^1$H NMR (400 MHz, CDCl$_3$) δ 8.74 (d, J=2.6 Hz, 1H), 8.69 (s, 1H), 8.25 (d, J=9.4 Hz, 2H), 8.19 (s, 1H), 7.68 (d, J=8.8 Hz, 1H), 4.31 (t, J=6.6 Hz, 2H), 3.58 (t, J=11.7 Hz, 4H), 3.39 (s, 3H), 2.95-2.73 (m, 5H), 2.69 (t, J=6.3 Hz, 2H), 2.58-2.47 (m, 1H), 2.01 (p, J=6.1 Hz, 2H); MS: [(M+1)]$^+$=509.50, 511.50.

The following intermediates were prepared according to the procedure described above:

| Intermediate | Structure | Name | MS: [(M+1)]$^+$ | $^1$H NMR |
| --- | --- | --- | --- | --- |
| EE1-2 | 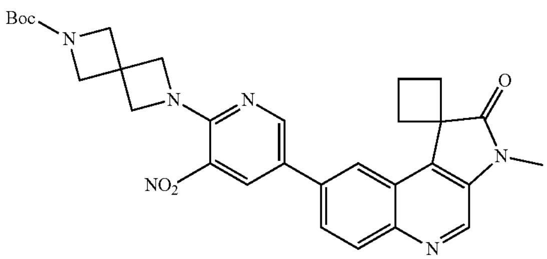 | tert-Butyl 6-(5-(3'-methyl-2'-oxo-2',3'-dihydrospiro[cyclobutane-1,1'-pyrrolo[2,3-c]quinolin]-8'-yl)-3-nitropyridin-2-yl)-2,6-diazaspiro[3.3]heptane-2-carboxylate | 557.30 | $^1$H NMR (400 MHz, DMSO-d$_6$) δ 9.03 (d, J = 2.3 Hz, 1H), 8.84 (s, 1H), 8.69 (d, J = 2.3 Hz, 1H), 8.41 (s, 1H), 8.16 (d, J = 8.8 Hz, 1H), 8.01 (d, J = 8.8 Hz, 1H), 4.29 (s, 4H), 4.06 (s, 4H), 1.39 (s, 9H) |
| EE1-3 | 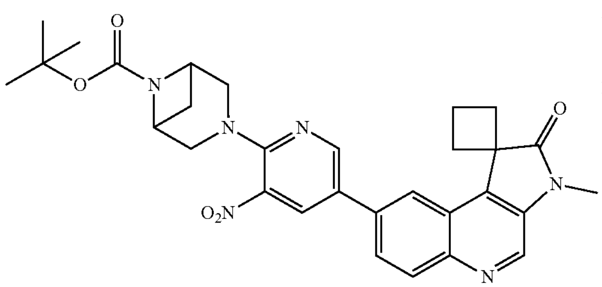 [SMILES: CN1C(=O)C2(CCC2)c2c1cnc1ccc(-c3cnc(N4CC5CC(C4)N5C(=O)OC(C)(C)C)c([N+](=O)[O-])c3)cc21] | tert-Butyl 3-(5-(3'-methyl-2'-oxo-2',3'-dihydrospiro[cyclobutane-1,1'-pyrrolo[2,3-c]quiriolin]-8'-yl)-3-nitropyridin-2-yl)-3,6-diazabicyclo[3.1.1]heptane-6-carboxylate | 557.20 | $^1$H NMR (400 MHz, CDCl$_3$) δ 8.78 (d, J = 2.1 Hz, 1H), 8.66 (s, 1H), 8.48 (s, 1H), 8.43-8.37 (m, 2H), 7.90 (d, J = 9.2 Hz, 1H), 4.25 (s, 6H), 3.40 (s, 3H), 3.02-2.51 (m, 7H), 1.56 (d, J = 8.8 Hz, 1H), 1.36 (s, 9H). |
| EE1-4 | 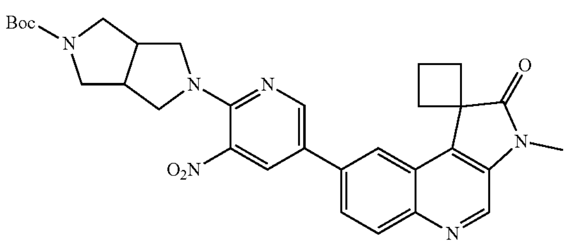 [SMILES: CN1C(=O)C2(CCC2)c2c1cnc1ccc(-c3cnc(N4CC5CN(C(=O)OC(C)(C)C)CC5C4)c([N+](=O)[O-])c3)cc21] | tert-Butyl 5-(5-(3'-methyl-2'-oxo-2',3'-dihydrospiro[cyclobutane-1,1'-pyrrolo[2,3-c]quinolin]-8'-yl)-3-nitropyridin-2-yl)hexahydropyrrolo[3,4-c]pyrrole-2(1H)-carboxylate | 571.30 | $^1$H NMR (400 MHz, CDCl$_3$) δ 8.78 (s, 1H), 8.66 (s, 1H), 8.45 (s, 1H), 8.40 (s, 1H), 8.34 (s, 1H), 7.86 (d, J = 8.3 Hz, 1H), 3.86-3.76 (m, 2H), 3.73-3.60 (m, 2H), 3.47-3.36 (m, 5H) δ .31 (d, J = 10.8 Hz, 2H), 3.03 (s, 2H), 2.97-2.88 (m, 2H), 2.86-2.68 (m, 3H) 2.62-2.51 (m, 1H), 1.47 (s, 9H). |
| EE1-5 | 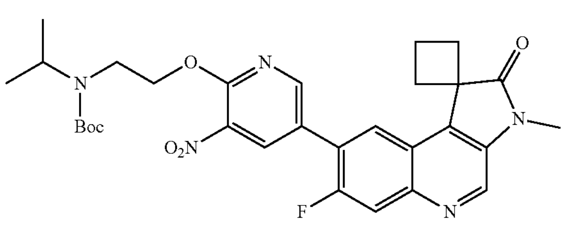 [SMILES: CC(C)N(CCOc1ncc(-c2cc3c4c(cnc3cc2F)N(C)C(=O)C42CCC2)cc1[N+](=O)[O-])C(=O)OC(C)(C)C] | tert-Butyl (2-((5-(7'-fluoro-3'-methyl-2'-oxo-2',3'-dihydrospiro[cyclobutane-1,1'-pyrrolo[2,3-c]quinolin]-8'-yl)-3-nitropyridin-2-yl)oxy)ethyl)(isopropyl)carbamate | 580.40 | $^1$H NMR (400 MHz, DMSO-d$_6$) δ 8.87 (s, 1H), 8.25 (d, J = 8.2 Hz, 1H), 7.94 (d, J = 12.0 Hz, 1H), 7.74 (s, 1H), 7.27 (s, 1H), 4.42 (s, 2H), 4.14 (s, 1H), 3.50 (s, 2H), 3.31 (s, 2H), 2.92-2.83 (m, 2H), 2.64-2.51 (m, 4H), 1.41 (s, 9H). |

| Intermediate | Structure | Name | MS: [(M + 1)]+ | 1H NMR |
|---|---|---|---|---|
| EE1-6 | 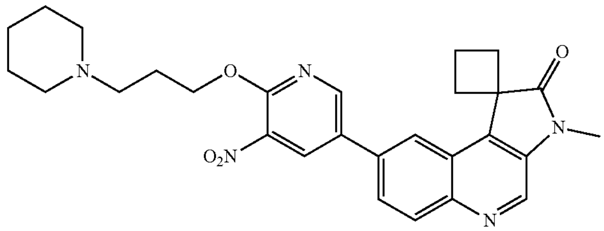 [SMILES: CN1C(=O)C2(CCC2)c2c1cnc1ccc(-c3cnc(OCCCN4CCCCC4)c([N+](=O)[O-])c3)cc21] | 3'-Methyl-8'-(5-nitro-6-(3-(piperidin-1-yl)propoxy)pyridin-3-yl)spiro[cyclobutane-1,1'-pyrrolo[2,3-c]quinolin]-2'(3'H)-one | 502.30 | 1H NMR (400 MHz, CDCl3) δ 8.77 (d, J = 2.4 Hz, 1H), 8.70 (s, 1H), 8.62 (d, J = 2.3 Hz, 1H), 8.40 (d, J = 2.0 Hz, 1H), 8.27 (d, J = 8.8 Hz, 1H), 7.81 (dd, J = 8.8, 2.1 Hz, 1H), 4.66 (t, J = 6.1 Hz, 2H), 3.34 (s, 3H), 2.96-2.87 (m, 2H), 2.87-2.35 (m, 10H), 2.23 (s, 2H), 1.73 (s, 4H), 1.52 (s, 2H). |
| EE1-7 | 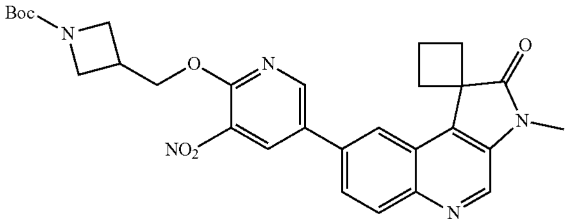 [SMILES: CN1C(=O)C2(CCC2)c2c1cnc1ccc(-c3cnc(OCC4CN(C(=O)OC(C)(C)C)C4)c([N+](=O)[O-])c3)cc21] | tert-Butyl 3-(((5-(3'-methyl-2'-oxo-2',3'-dihydrospiro[cyclobutane-1,1'-pyrrolo[2,3-c]quinolin]-8'-yl)-3-nitropyridin-2-yl)oxy)methyl)azetidine-1-carboxylate | 546.20 | 1H NMR (400 MHz, CD3OD) δ 8.89 (d, J = 2.3 Hz, 1H), 8.82-8.74 (m, 2H), 8.54 (s, 1H), 8.20 (d, J = 8.8 Hz, 1H), 7.99 (d, J = 8.8 Hz, 1H), 4.71 (d, J = 5.7 Hz, 2H), 4.09 (t, J = 8.6 Hz, 2H), 3.96-3.85 (m, 2H), 3.43-3.40 (m, 1H), 3.39 (s, 3H), 3.18-3.08 (m, 2H), 3.07-2.96 (m, 2H), 2.73-2.64 (m, 2H), 1.47 (s, 9H). |

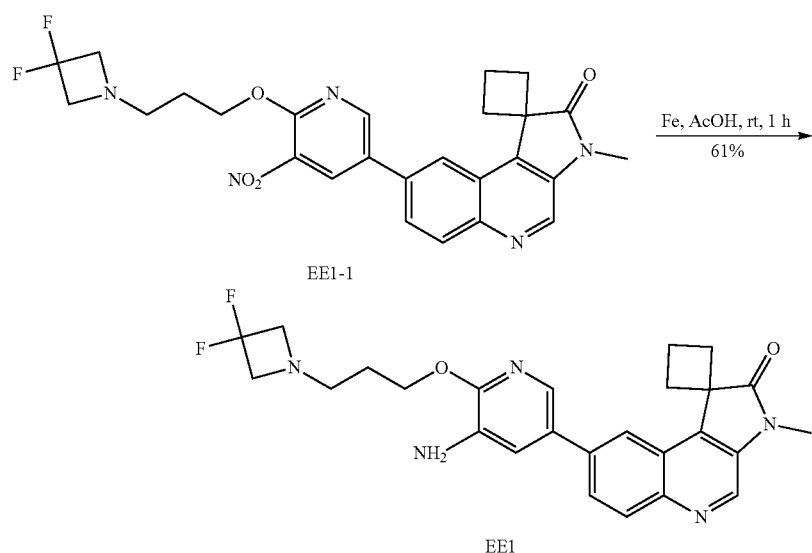

8'-(5-Amino-6-(3-(3,3-difluoroazetidin-1-yl)propoxy)pyridin-3-yl)-3'-methylspiro[cyclobutane-1,1'-pyrrolo[2,3-c]quinolin]-2'(3'H)-one: To a solution of 8-[6-[3-(3,3-difluoroazetidin-1-yl)propoxy]-5-nitropyridin-3-yl]-3-methyl-2,3-dihydrospiro[cyclobutane-1,1-pyrrolo[2,3-c]quinolin]-2-one (70.0 mg, 0.14 mmol) in acetic acid (3.00 mL) was added iron (76.7 mg, 1.37 mmol) at ambient temperature. After stirring for 1 hour at ambient temperature, the resulting mixture was filtered and the filtered cake was washed with tetrahydrofuran (6×10.0 mL). The filtrate was concentrated under reduced pressure. The residue was purified by silica gel column chromatography, eluted with 2%~5% methanol in dichloromethane to afford the title compound as a brown solid (40.0 mg, 61%): 1H NMR (400 MHz, CDCl3) δ 8.63 (s, 1H), 8.27-8.20 (m, 2H), 7.73 (d, J=9.2 Hz, 1H), 7.24 (s, 1H), 6.95 (d, J=2.2 Hz, 1H), 4.23 (t, J=6.8 Hz, 2H), 4.07-3.56 (m, 4H), 3.38 (s, 3H), 2.99-2.67 (m, 7H), 2.61-2.48 (m, 1H), 2.07-1.97 (m, 2H); MS: [(M+1)]⁺=479.53.

The following intermediates were prepared according to the procedure described above:

| Intermediate | Structure | Name | MS: [(M+1)]⁺ | ¹H NMR |
|---|---|---|---|---|
| EE2 | 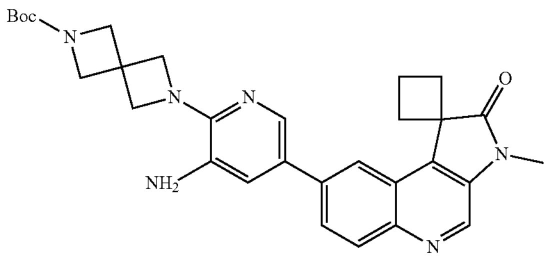 [SMILES: CN1C(=O)C2(CCC2)c2c1cnc1ccc(-c3cnc(N4CC5(CN(C(=O)OC(C)(C)C)C5)C4)c(N)c3)cc21] | tert-Butyl 6-(3-amino-5-(3'-methyl-2'-oxo-2',3'-dihydrospiro[cyclobutane-1,1'-pyrrolo[2,3-c]quinolin]-8'-yl)pyridin-2-yl)-2,6-diazaspiro[3.3]heptane-2-carboxylate | 527.30 | ¹H NMR (400 MHz, CD₃OD) δ 8.70 (d, J = 2.4 Hz, 1H), 8.43 (s, 1H), 8.15-8.06 (m, 1H), 7.99 (s, 1H), 7.91 (d, J = 8.9 Hz, 1H), 7.41 (s, 1H), 4.24 (s, 4H), 4.13 (s, 4H), 1.46 (s, 9H). |
| EE3 | 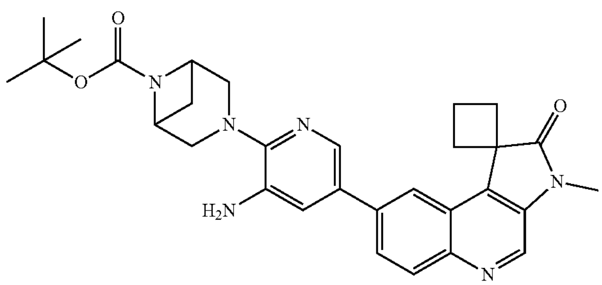 [SMILES: CN1C(=O)C2(CCC2)c2c1cnc1ccc(-c3cnc(N4CC5CC(C4)N5C(=O)OC(C)(C)C)c(N)c3)cc21] | tert-Butyl 3-(3-amino-5-(3'-methyl-2'-oxo-2',3'-dihydrospiro[cyclobutane-1,1'-pyrrolo[2,3-c]quinolin]-8'-yl)pyridin-2-yl)-3,6-diazabicyclo[3.1.1]heptane-6-carboxylate | 527.30 | ¹H NMR (400 MHz, CDCl₃) δ 8.66 (s, 1H), 8.39 (s, 1H), 8.33-8.19 (m, 2H), 7.82 (d, J = 9.0 Hz, 1H), 7.34 (s, 1H), 4.66 (s, 2H), 4.26 (s, 2H), 4.12-3.70 (m, 2H), 3.39 (s, 3H), 2.92 (s, 2H), 2.83-2.65 (m, 4H), 2.62-2.51 (m, 2H), 1.41 (s, 9H). |
| EE4 | 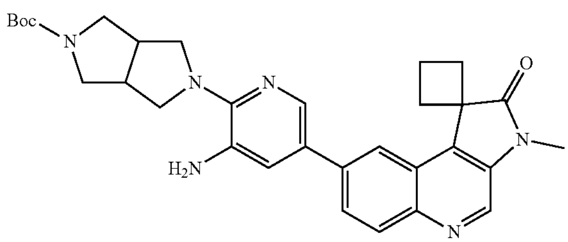 [SMILES: CN1C(=O)C2(CCC2)c2c1cnc1ccc(-c3cnc(N4CC5CN(C(=O)OC(C)(C)C)CC5C4)c(N)c3)cc21] | tert-Butyl 5-(3-amino-5-(3'-methyl-2'-oxo-2',3'-dihydrospiro[cyclobutane-1,1'-pyrrolo[2,3-c]quinolin]-8'-yl)pyridin-2-yl)hexahydropyrrolo[3,4-c]pyrrole-2(1H)-carboxylate | 541.30 | ¹H NMR (400 MHz, CDCl₃) δ 8.64 (s, 1H), 8.37 (s, 1H), 8.28-8.18 (m, 2H), 7.80 (d, J = 8.9 Hz, 1H), 7.33 (s, 1H), 7.26 (s, 2H), 3.93 (s, 2H), 3.64 (s, 4H), 3.46 (s, 2H), 3.38 (s, 3H), 3.04 (s, 2H), 2.98-2.85 (m, 2H), 2.84-2.66 (m, 3H), 2.60-2.49 (m, 1H). |
| EE5 | 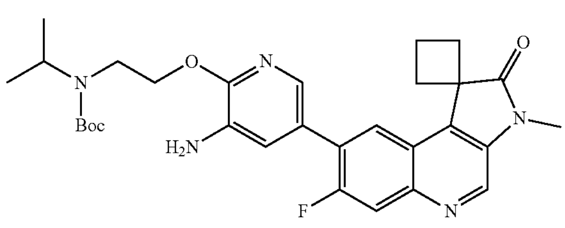 | tert-Butyl (2-((3-amino-5-(7'-fluoro-3'-methyl-2'-oxo-2',3'-dihydrospiro[cyclobutane-1,1'-pyrrolo[2,3-c]quinolin]-8'-yl)pyridin-2-yl)oxy)ethyl)(isopropyl)carbamate | 550.40 | ¹H NMR (400 MHz, CD₃OD) δ 8.75 (s, 1H), 8.36 (d, J = 8.1 Hz, 1H), 7.83 (d, J = 11.8 Hz, 1H), 7.77 (s, 1H), 7.34 (s, 1H), 4.53 (s, 2H), 4.23 (s, 1H), 3.61 (s, 2H), 3.38 (s, 3H), 3.00-2.90 (m, 2H), 2.74-2.58 (m, 3H), 2.58-2.45 (m, 1H), 1.48 (s, 9H), 1.22 (d, J = 6.8 Hz, 6H). |

| Intermediate | Structure | Name | MS: [(M + 1)]+ | 1H NMR |
|---|---|---|---|---|
| EE6 | 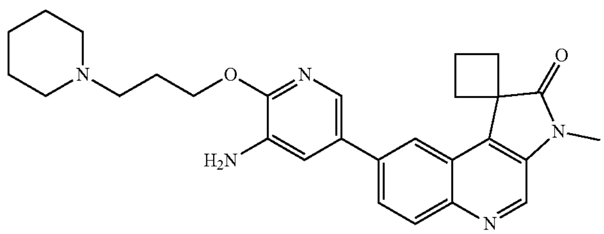 | 8'-(5-Amino-6-(3-(piperidin-1-yl)propoxy)pyridin-3-yl)-3'-methylspiro[cyclobutane-1,1'-pyrrolo[2,3-c]quinolin]-2'(3'-H)-one | 472.30 | 1H NMR (400 MHz, CDCl3) δ 8.66 (s, 1H), 8.37 (d, J = 1.9 Hz, 1H), 8.21 (d, J = 8.8 Hz, 1H), 7.96 (d, J = 2.2 Hz, 1H), 7.81 (dd, J = 8.9, 2.0 Hz, 1H), 7.27 (d, J = 2.2 Hz, 1H), 4.51 (t, J = 6.3 Hz, 2H), 3.01-2.91 (m, 2H), 2.85-2.48 (m, 10H), 2.20 (s, 2H), 1.90-1.81 (m, 4H), 1.81-1.70 (m, 2H). |
| EE7 | 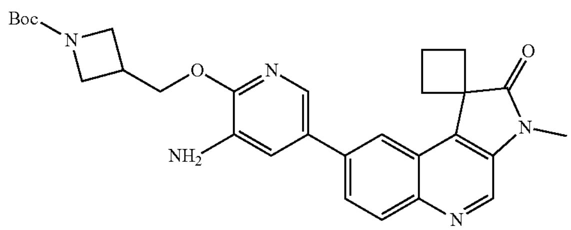 | tert-Butyl 3-(((3-amino-5-(3-methyl-2'-oxo-2',3'-dihydrospiro[cyclobutane-1,1'-pyrrolo[2,3-c]quinolin]-8'-yl)pyridin-2-yl)oxy)methyl)azetidine-1-carboxylate | 516.30 | 1H NMR (400 MHz, CD3OD) δ 8.69 (s, 1H), 8.42 (s, 1H), 8.11 (d, J = 2.1 Hz, 1H), 7.92-7.82 (m, 2H), 7.42 (s, 1H), 4.55 (d, J = 6.3 Hz, 2H), 4.11 (t, J = 8.5 Hz, 2H), 3.86 (dd, J = 8.7, 5.4 Hz, 2H), 3.40-3.38 (m, 1H), 3.37 (s, 3H), 3.15-3.03 (m, 2H), 3.02-2.92 (m, 2H), 2.70-2.64 (m, 2H), 1.46 (s, 9H). |
| EE8 | 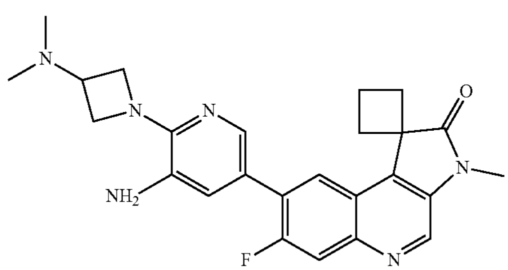 | 8'-(5-Amino-6-(3-(dimethylamino)azetidin-1-yl)pyridin-3-yl)-7'-fluoro-3 methylspiro[cyclobutane-1,1'-pyrrolo[2,3-c]quinolin]-2'(3'-H)-one | 447.53 | used directly in the next step |

Synthesis of Exemplary Compounds

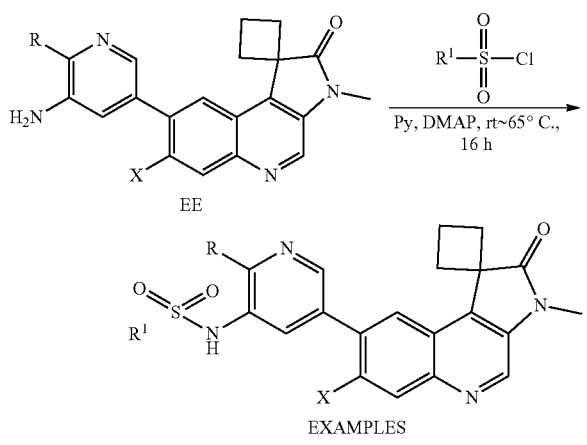

EXAMPLES

General Procedure: To a solution of amine (1.0 mmol) in pyridine (10 mL) were added 4-dimethylaminopyridine (0.1 mmol) and the corresponding sulphonyl chloride or sulfamoyl chloride (5.0 mmol) at ambient temperature. The resulting solution was stirred for 16 hours at 11-65° C. After cooling down to ambient temperature, the resulting mixture was concentrated under reduced pressure. The residue was purified by reversed phase flash chromatography with the following conditions: [Column: Spherical C18, 20~40 μm, 120 g; Mobile phase A: Water (plus 10 mM NH4HCO3 or HCOOH); Mobile phase B: acetonitrile; Flow rate: 45 mL/min; Gradient (B %): 5%~20%, 7 min; 20%~27%, 8 min; 27%~95%, 2 min; 95%, 5 min; Detector UV 254 nm. Desired fractions were collected and concentrated under reduced pressure to afford the desired Example compounds as free base or formate.

Preparation of HCl salt: A solution of the free amine (1.0 mmol) in diluted aqueous HCl solution (1.0 mmol, 0.008 M) and acetonitrile (3.0 mL) was lyophilized to afford the HCl salt:

The following Example compounds were synthesized according to the above procedure:

| EXAMPLES | Structure | Name | MS: [(M + 1)]+ | 1H NMR |
|---|---|---|---|---|
| 157 | 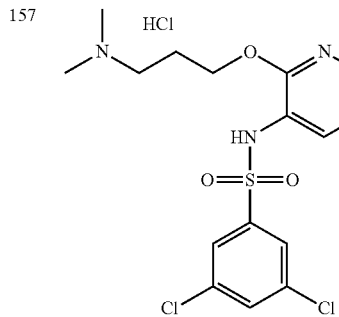 | 3,5-Dichloro-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride | 640.10 642.10 | 1H NMR (400 MHz, DMSO-$d_6$) δ 8.80 (s, 1H), 8.19 (d, J = 2.0 Hz, 1H), 8.10 (d, J = 8.9 Hz, 1H), 7.97 (d, J = 2.3 Hz, 1H), 7.82 (dd, J = 8.9, 2.0 Hz, 1H), 7.71 (s, 3H), 7.53 (d, J = 2.3 Hz, 1H), 4.38 (t, J = 5.5 Hz, 2H), 3.39 (t, J = 6.0 Hz, 2H), 3.30 (s, 3H), 2.96 (s, 6H), 2.82-2.70 (m, 2H), 2.67-2.55 (m, 2H), 2.49-2.44 (m, 2H), 2.21 (t, J = 5.7 Hz, 2H). |
| 159 | 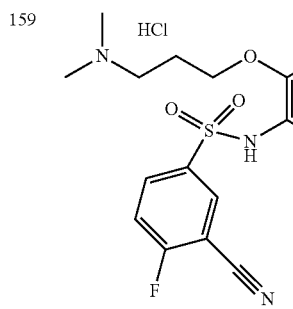 | 3-Cyano-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-fluorobenzenesulfonamide hydrochloride | 615.25 | 1H NMR (400 MHz, $CD_3OD$) δ 8.75 (s, 1H), 8.43 (s, 1H), 8.33 (s, 1H), 8.29 (dd, J = 5.9, 2.4 Hz, 1H), 8.19-8.12 (m, 2H), 8.03 (s, 1H), 7.90 (dd, J = 8.9, 2.0 Hz, 1H), 7.53 (t, J = 8.9 Hz, 1H), 4.44 (t, J = 6.0 Hz, 2H), 3.39 (s, 3H), 3.35 (t, J = 7.2 Hz, 2H), 2.99 (s, 6H), 2.98-2.89 (m, 2H), 2.78-2.58 (m, 4H), 2.27-2.18 (m, 2H). |
| 163 | 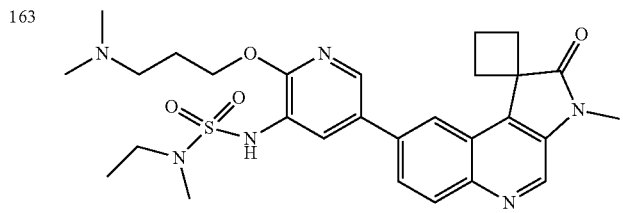 | 8'-{6-[3-(Dimethylamino)propoxy]5-{[ethyl(methyl)sulfamoyl]amino}pyridin-3-yl}-3'-Methyl-2',3'-dihydrospiro[cyclobutane-1,1'-pyrrolo[2,3-c]quinoline]-2'-one | 553.25 | 1H NMR (400 MHz, DMSO-$d_6$) δ 8.84 (s, 1H), 8.36 (d, J = 2.0 Hz, 1H), 8.32 (d, J = 2.4 Hz, 1H), 8.16 (d, J = 8.8 Hz, 1H), 8.06 (d, J = 2.4 Hz, 1H), 7.94 (dd, J = 8.9, 1.9 Hz, 1H), 4.39 (t, J = 6.2 Hz, 2H), 3.31 (s, 3H), 3.13 (q, J = 7.1 Hz, 2H), 2.93-2.83 (m, 2H), 2.71 (s, 3H), 2.67 (t, J = 6.6 Hz, 2H), 2.63-2.53 (m, 4H), 2.36 (s, 6H), 2.05-1.96 (m, 2H), 1.01 (t, J = 7.1 Hz, 3H). |
| 166 | 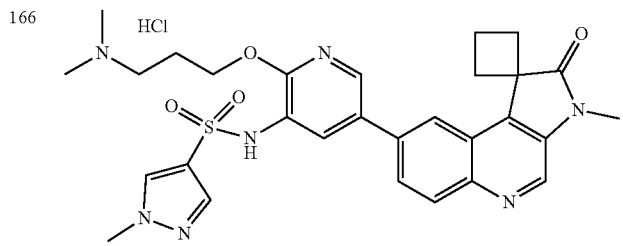 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1-methyl-1H-pyrazole-4-sulfonamide hydrochloride | 576.30 | 1H NMR (400 MHz, $CD_3OD$) δ 8.74 (s, 1H), 8.45 (d, J = 2.1 Hz, 1H), 8.38 (d, J = 2.3 Hz, 1H), 8.19-8.09 (m, 2H), 8.03 (s, 1H), 7.90 (dd, J = 8.9, 2.0 Hz, 1H), 7.77 (s, 1H), 4.47 (t, J = 5.9 Hz, 2H), 3.86 (s, 3H), 3.39 (s, 3H), 3.28 (s, 2H), 2.95 (s, 8H), 2.77-2.60 (m, 4H), 2.26-2.18 (m, 2H). |

| EXAMPLES | Structure | Name | MS: [(M + 1)]+ | 1H NMR |
|---|---|---|---|---|
| 169 | 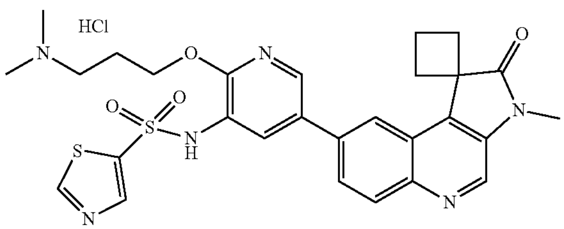 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)thiazole-5-sulfonamide hydrochloride | 579.20 | 1H NMR (300 MHz, CD3OD) δ 9.21 (s, 1H), 8.76 (s, 1H), 8.49-8.47 (m, 2H), 8.31 (s, 1H), 8.22-8.17 (m, 2H), 7.95 (dd, J = 8.8, 2.0 Hz, 1H), 4.42 (t, J = 5.6 Hz, 2H), 3.39 (s, 3H), 3.29-3.22 (m, 2H), 3.03-2.97 (m, 2H), 2.95 (s, 6H), 2.78-2.63 (m, 4H), 2.19-2.13 (m, 2H). |
| 170 | 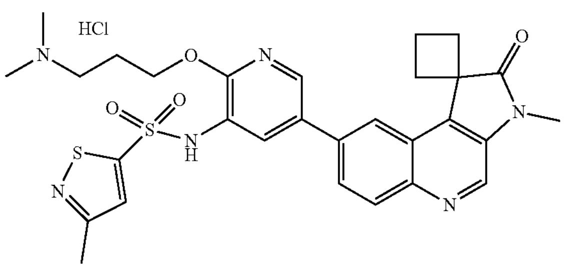 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3-methylisothiazole-5-sulfonamide hydrochloride | 593.50 | 1H NMR (400 MHz, DMSO-d6) δ 8.82 (s, 1H), 8.29 (d, J = 2.0 Hz, 1H), 8.13 (d, J = 8.8 Hz, 1H), 8.00 (d, J = 2.3 Hz, 1H), 7.91-7.83 (m, 2H), 7.35 (s, 1H), 4.37 (t, J = 5.5 Hz, 2H), 3.36-3.32 (m, 2H), 3.31 (s, 3H), 2.98 (s, 6H), 2.91-2.79 (m, 2H), 2.65-2.51 (m, 4H), 2.35 (s, 3H), 2.20 (m, 2H). |
| 188 | 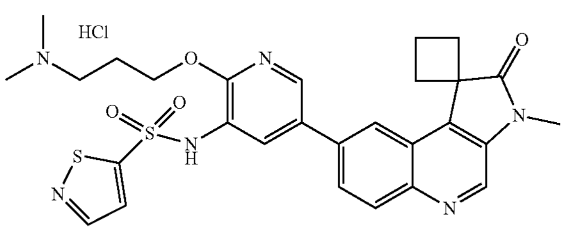 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)isothiazole-5-sulfonamide hydrochloride | 579.15 | 1H NMR (300 MHz, CD3OD) δ 8.77 (s, 1H), 8.55 (d, J = 1.8 Hz, 1H), 8.53-8.48 (m, 2H), 8.24-8.18 (m, 2H), 7.96 (d, J = 9.2 Hz, 1H), 7.66 (d, J = 1.8 Hz, 1H), 4.41 (t, J = 6.0 Hz, 2H), 3.40 (s, 3H), 3.27-3.19 (m, 2H), 3.9-2.96 (m, 2H), 2.95 (s, 6H), 2.80-2.57 (m, 4H), 2.18-2.05 (m, 2H). |
| 239 | 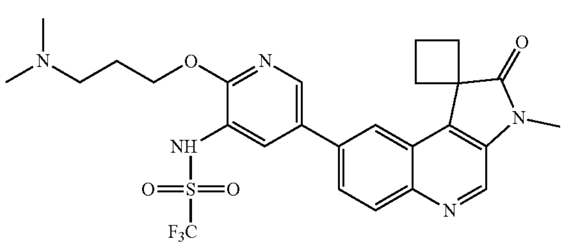 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1,1,1-trifluoromethane-sulfonamide | 564.20 | 1H NMR (400 MHz, DMSO-d6) δ 9.53 (s, 1H), 8.82 (s, 1H), 8.33 (d, J = 2.0 Hz, 1H), 8.16-8.13 (m, 2H), 8.08(d, J = 2.3 Hz, 1H), 7.91 (dd, J = 8.9, 2.0 Hz, 1H), 4.40 (t, J = 5.5 Hz, 2H), 3.43-3.37 (m, 2H), 3.31 (s, 3H), 2.91 (s, 6H), 2.90-2.81 (m, 2H), 2.65-2.50 (m, 4H), 2.23-2.16 (m, 2H). |

-continued

| EXAMPLES | Structure | Name | MS: [(M+1)]+ | 1H NMR |
|---|---|---|---|---|
| 245 | 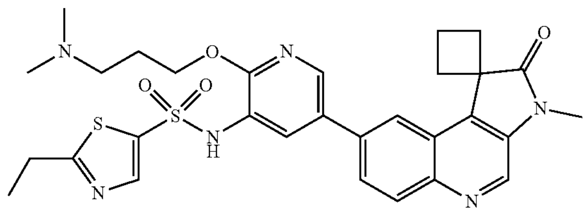 [SMILES: CCc1ncc(S(=O)(=O)Nc2cc(-c3ccc4ncc5c(c4c3)C3(CCC3)C(=O)N5C)cnc2OCCCN(C)C)s1] | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-ethylthiazole-5-sulfonamide | 607.20 | 1H NMR (400 MHz, DMSO-d6) δ 8.81 (s, 1H), 8.29 (d, J = 1.9 Hz, 1H), 8.13 (d, J = 8.9 Hz, 1H), 7.98 (d, J = 2.1 Hz, 1H), 7.87-7.83 (m, 3H), 4.36 (t, J = 5.4 Hz, 2H), 3.38 (t, J = 5.2 Hz, 2H), 3.31 (s, 3H), 2.96 (s, 6H), 2.94-2.80 (m, 4H), 2.64-2.51 (m, 4H), 2.23-2.15 (m, 2H), 1.21 (t, J = 7.5 Hz, 3H). |
| 247 | 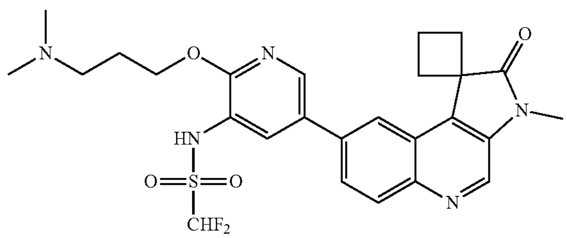 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1,1'-difluoromethanesulfonamide | 546.15 | 1H NMR (400 MHz, DMSO-d6) δ 8.82 (s, 1H), 8.34 (s, 1H), 8.14 (d, J = 8.9 Hz, 1H), 8.10 (d, J = 2.1 Hz, 1H), 8.04 (s, 1H), 7.91 (d, J = 8.6 Hz, 1H), 6.58 (t, J = 54.1 Hz, 1H), 4.38 (t, J = 5.6 Hz, 2H), 3.44-3.35 (m, 2H), 3.31 (s, 3H), 2.91 (s, 6H), 2.90-2.81 (m, 2H), 2.64-2.51 (m, 4H), 2.23-2.16 (m, 2H). |
| 307 | 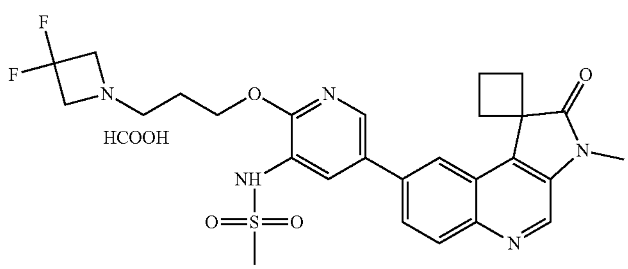 [SMILES: CN1C(=O)C2(CCC2)c2c1cnc1ccc(-c3cnc(OCCCN4CC(F)(F)C4)c(NS(C)(=O)=O)c3)cc21 ; "HCOOH"] | N-(2-(3-(3,3-Difluoroazetidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide formate | 558.30 | 1H NMR (400 MHz, CD3OD) δ 8.72 (s, 1H), 8.45-8.39 (m, 1H), 8.17-8.09 (m, 2H), 8.03 (d, J = 2.4 Hz, 1H), 7.93 (d, J = 9.0 Hz, 1H), 4.22 (t, J = 7.3 Hz, 2H), 3.62 (t, J = 12.1 Hz, 4H), 3.38 (s, 3H), 3.11 (s, 3H), 3.05-2.93 (m, 2H), 2.78-2.57 (m, 6H), 1.94 (p, J = 7.2 Hz, 2H). |
| 289 | 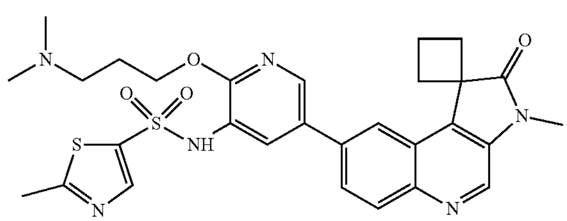 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-methylthiazole-5-sulfonamide | 593.25 | 1H NMR (400 MHz, DMSO-d6) δ 8.81 (s, 1H), 8.28 (d, J = 2.0 Hz, 1H), 8.13 (d, J = 8.9 Hz, 1H), 7.97 (d, J = 2.2 Hz, 1H), 7.89-7.80 (m, 3H), 4.36 (t, J = 5.5 Hz, 2H), 3.31 (s, 5H), 2.95 (s, 6H), 2.90-2.78 (m, 2H), 2.64-2.53 (m, 7H), 2.25-2.12 (m, 2H). |

| EXAMPLES | Structure | Name | MS: [(M + 1)]+ | 1H NMR |
|---|---|---|---|---|
| 301 | 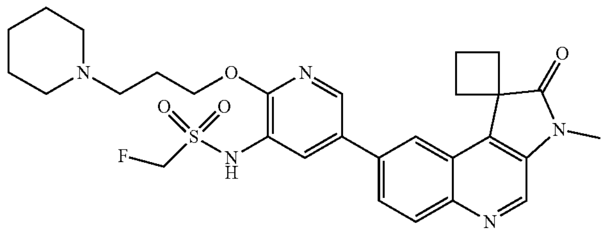 [SMILES: CN1C(=O)C2(CCC2)c2c1cnc1ccc(-c3cnc(OCCCN4CCCCC4)c(NS(=O)(=O)CF)c3)cc21] | 1-Fluoro-N-(5-(3'-methyl-2'-oxo-2',3'-dihydrospiro[cyclobutane-1,1'-pyrrolo[2,3-c]quinolin-8-yl)-2-(3-(piperidin-1-yl)propoxy)pyridin-3-yl)methanesulfonamide | 568.30 | 1H NMR (400 MHz, DMSO-d6) δ 8.85 (s, 1H), 8.66 (d, J = 2.3 Hz, 1H), 8.38 (d, J = 15.8 Hz, 2H), 8.17 (d, J = 8.9 Hz, 1H), 7.98 (d, J = 8.7 Hz, 1H), 4.43 (t, J = 6.2 Hz, 2H), 3.32 (s, 3H), 2.95 (d, J = 8.5 Hz, 2H), 2.61-2.32 (m, 12H), 1.97-1.87 (m, 2H), 1.57-1.45 (m, 4H), 1.43-1.34 (m, 2H). |
| 340 | 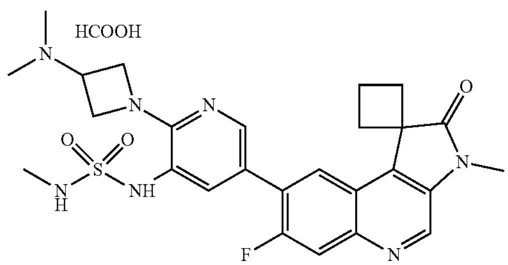 | 8'-{6-[3-(Dimethylamino)azetidin-1-yl]-5-[(methylsulfamoyl)amino]pyridin-3-yl}-7'-fluoro-3'-methyl-2',3'-dihydrospiro[cyclobutane-1,1'-pyrrolo[2,3-c]quinoline]-2'-one | 540.35 | 1H NMR (400 MHz, DMSO-d6) δ 8.85 (s, 2H), 8.43 (t, J = 2.2 Hz, 1H), 8.29 (d, J = 8.3 Hz, 1H), 7.95 (d, J = 12.3 Hz, 1H), 7.72 (d, J = 1.8 Hz, 1H), 7.23 (q, J = 4.9 Hz, 1H), 4.32 (t, J = 8.3 Hz, 2H), 4.16-4.07 (m, 2H), 3.30 (s, 3H), 2.96-2.87 (m, 2H), 2.64 (d, J = 4.9 Hz, 3H), 2.62-2.52 (m, 3H), 2.48-2.39 (m, 2H), 2.33 (s, 6H). |
| 302 | 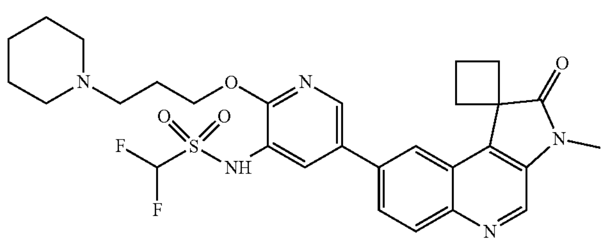 [SMILES: CN1C(=O)C2(CCC2)c2c1cnc1ccc(-c3cnc(OCCCN4CCCCC4)c(NS(=O)(=O)C(F)F)c3)cc21] | 1,1-Difluoro-N-(5-(3-methyl-2'-oxo-2',3'-dihydrospiro[cyclobutane-1,1'-pyrrolo[2,3-c]quinolin-8-yl)-2-(3-(piperidin-1-yl)propoxy)pyridin-3-yl)methanesulfonamide | 586.20 | 1H NMR (400 MHz, DMSO-d6) δ 8.81 (s, 1H), 8.34 (d, J = 1.9 Hz, 1H), 8.13 (d, J = 8.8 Hz, 1H), 8.04 (dd, J = 17.0, 2.3 Hz, 2H), 7.92 (dd, J = 8.9, 1.9 Hz, 1H), 6.44 (t, J = 54.4 Hz, 1H), 4.36 (t, J = 5.8 Hz, 2H), 3.31 (s, 9H), 2.92-2.82 (m, 2H), 2.63-2.52(m, 4H), 2.21-2.12 (m, 2H), 1.78 (s, 4H), 1.54 (s, 2H). |
| 341 | 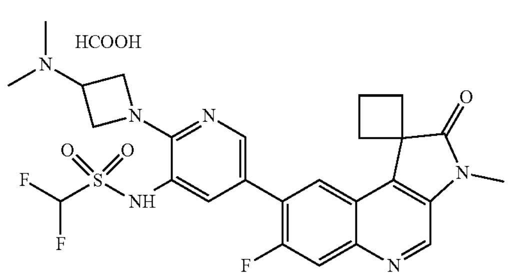 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin-8'-yl)pyridin-3-yl)-1,1-difluoromethanesulfonamide formate | 561.30 | 1H NMR (400 MHz, DMSO-d6) δ 8.82 (s, 1H), 8.22 (d, J = 8.4 Hz, 1H), 8.14 (s, 1H), 7.94 (s, 1H), 7.90 (d, J = 12.4 Hz, 1H), 7.76 (d, J = 1.9 Hz, 1H), 6.37 (t, J = 14.8 Hz, 1H), 4.31 (t, J = 8.7 Hz, 2H), 4.16-4.08 (m, 2H), 3.88-3.70 (m, 1H), 2.90-2.79 (m, 2H), 2.69-2.40 (m, 10H). |

| EX-AM-PLES | Structure | Name | MS: [(M + 1)]+ | 1H NMR |
|---|---|---|---|---|
| 342 | 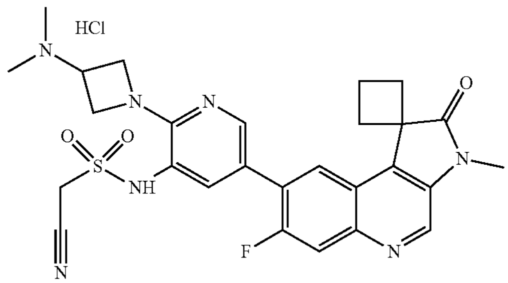 | 1-Cyano-N-(2-(3-(dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | 550.30 | 1H NMR (400 MHz, CD3OD) δ 8.78 (s, 1H), 8.53 (s, 1H), 8.41 (d, J = 8.1 Hz, 1H), 8.05 (s, 1H), 7.87 (d, J = 11.9 Hz, 1H), 4.66 (dd, J = 10.4, 7.5 Hz, 2H), 4.45 (dd, J = 10.4, 4.8 Hz, 2H), 4.32-4.19 (m, 1H), 3.38 (s, 3H), 3.30 (s, 2H), 3.04-2.92 (m, 8H), 2.72-7.58 (m, 3H), 2.57-2.46 (m, 1H) |
| 343 | 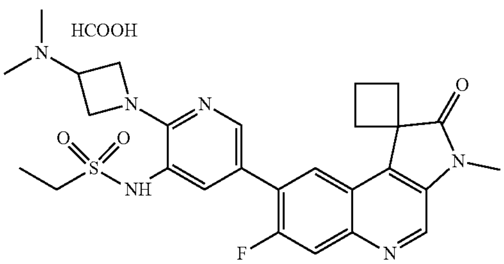 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)ethanesulfonamide formate | 539.35 | 1H NMR (400 MHz, CD3OD) δ 8.75 (s, 1H), 8.42 (t, J = 1.9 Hz, 1H), 8.37 (d, J = 8.2 Hz, 1H), 7.87-7.82 (m, 2H), 4.53-4.44 (m, 2H), 4.22 (dd, J = 9.4, 5.2 Hz, 2H), 3.58-3.50 (m, 1H), 3.37 (s, 3H), 3.25 (q, J = 7.4 Hz, 2H), 3.01-2.92 (m, 2H), 2.74-2.50 (m, 4H), 2.45 (s, 6H), 1.43 (t, J = 7.3 Hz, 3H). |
| 252 | 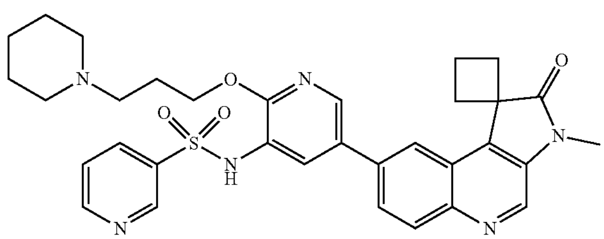 [SMILES: CN1C(=O)C2(CCC2)c2c1cnc1ccc(-c3cnc(OCCCN4CCCCC4)c(NS(=O)(=O)c4cccnc4)c3)cc21] | N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)pyridine-3-sulfonamide | 613.35 | 1H NMR (400 MHz, DMSO-d6) δ 8.92 (s, 1H), 8.81 (s, 1H), 8.63 (s, 1H), 8.27 (s, 1H), 8.14-8.07 (m, 3H), 7.84 (d, J = 9.3 Hz, 2H), 7.49 (s, 1H), 4.26 (s, 2H), 3.31 (s, 3H), 2.95 (s, 6H), 2.88-2.79 (m, 2H), 2.64-2.52 (m, 4H), 2.01-1.94 (m, 2H), 1.75-1.66 (m, 4H), 1.54-1.46 (m, 2H). |

The following intermediates were synthesized according to the above procedure:

| Intermediate | Structure | Name | MS: [(M + 1)]+ | 1H NMR |
|---|---|---|---|---|
| EE5 | 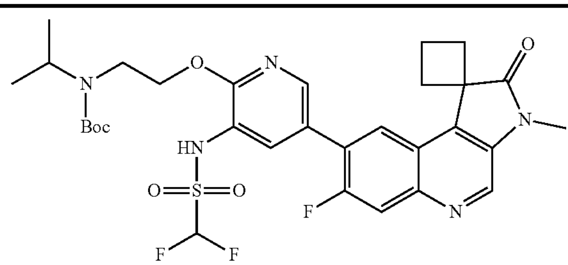 | tert-Butyl (2-((3-((difluoromethyl)sulfonamido)-5-(7'-fluoro-3'-methyl-2'-oxo-2',3'-dihydrospiro[cyclobutane-1,1'-pyrrolo[2,3-c]quinolin]-8'-yl)pyridin-2-yl)oxy)ethyl)(isopropyl)carbamate | 664.30 | used in the next step without further purification |

-continued

| Intermediate | Structure | Name | MS: [(M + 1)]+ | 1H NMR |
|---|---|---|---|---|
| EE6 | 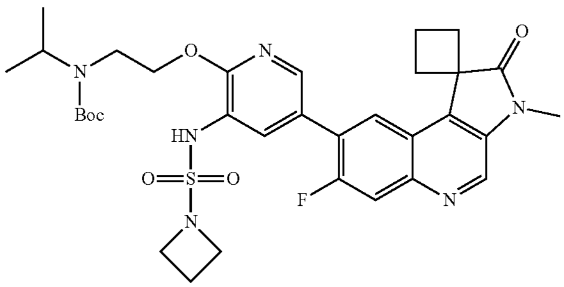 [SMILES: CC(C)N(CCOc1ncc(-c2cc3c4c(cnc3cc2F)N(C)C(=O)C42CCC2)cc1NS(=O)(=O)N1CCC1)C(=O)OC(C)(C)C] | tert-Butyl (2-((3-(azetidine-1-sulfonamido)-5-(7'-fluoro-3'-methyl-2'-oxo-2',3'-dihydrospiro[cyclobutane-1,1'-pyrrolo[2,3-c]quinolin]-8'-yl)pyridin-2-yl)oxy)ethyl)(isopropyl)carbamate | 669.30 | used in the next step without further purification |
| EE7 | 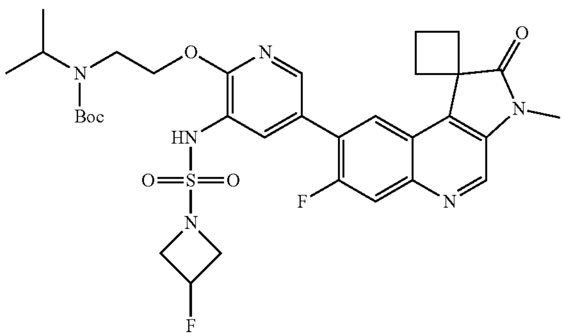 [SMILES: CC(C)N(CCOc1ncc(-c2cc3c4c(cnc3cc2F)N(C)C(=O)C42CCC2)cc1NS(=O)(=O)N1CC(F)C1)C(=O)OC(C)(C)C] | tert-Butyl (2-((5-(7'-fluoro-3methyl-2'-oxo-2',3'-dihydrospiro[cyclobutane-1,1'-pyrrolo[2,3-c]quinolin]-8'-yl)-3-((3-fluoroazetidine)-1-sulfonamido)pyridin-2-yl)oxy)ethyl)(isopropyl)carbamate | 687.40 | used in the next step without further purification |
| EE8 | 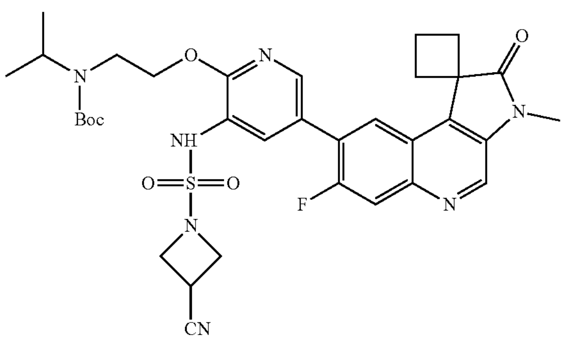 [SMILES: CC(C)N(CCOc1ncc(-c2cc3c4c(cnc3cc2F)N(C)C(=O)C42CCC2)cc1NS(=O)(=O)N1CC(C#N)C1)C(=O)OC(C)(C)C] | ter-Butyl (2-((3-((3-cyanoazetidine)-1-sulfonamido)-5-(7'-fluoro-3'-methyl-2'-oxo-2',3'-dihydrospiro[cyclobutane-1,1'-pyrrolo[2,3-c]quinolin]-8'-yl)pyridin-2-yl)oxy)ethyl)(isopropyl))carbamate | 694.40 | 1H NMR (400 MHz, CDCl3) δ 8.66 (s, 1H), 8.23 (d, J = 8.1 Hz, 1H), 8.18 (s, 1H), 8.09 (s, 1H), 7.82 (d, J = 11.5 Hz, 1H), 6.02 (d, J = 31.5 Hz, 2H), 4.55 (t, J = 6.3 Hz, 2H), 4.16 (s, 1H), 3.94 (d, J = 6.0 Hz, 2H), 3.60 (s, 3H), 3.36 (s, 3H), 2.88-2.61 (m, 5H), 2.48 (s, 1H), 1.21 (d, J = 6.7 Hz, 6H). |
| EE9 | 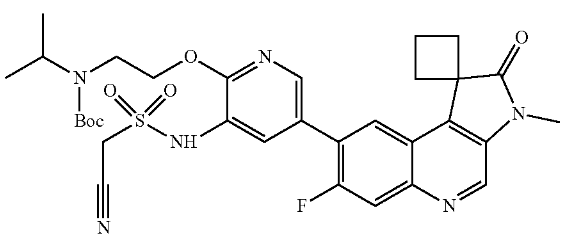 [SMILES: CC(C)N(CCOc1ncc(-c2cc3c4c(cnc3cc2F)N(C)C(=O)C42CCC2)cc1NS(=O)(=O)CC#N)C(=O)OC(C)(C)C] | tert-Butyl (2-((3-((cyanomethyl)sulfonamido)-5-(7'-fluoro-3'-methyl-2'-oxo-2',3'-dihydrospiro[cyclobutane-1,1'-pyrrolo[2,3-c]quinolin]-8'-yl)pyridin-2-yl)oxy)ethyl)(isopropyl)carbamate | 653.30 | 1H NMR (400 MHz, CDCl3) δ 8.69 (s, 1H), 8.39 (s, 1H), 8.32 (d, J = 7.7 Hz, 1H), 8.19 (s, 1H), 7.97 (d, J = 10.9 Hz, 1H), 4.64 (t, J = 5.3 Hz, 2H), 4.34-431 (m, 3H), 3.63 (s, 2H), 3.41 (s, 3H), 2.95-2.64 (m, 5H), 2.55 (s, 1H), 1.51(s, 9H), 1.23 (d, J = 6.7 Hz, 6H). |
| EE10 | 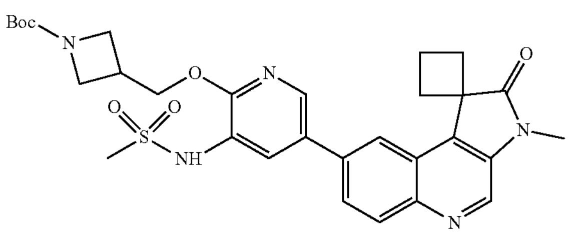 [SMILES: CN1C(=O)C2(CCC2)c2c1cnc1ccc(-c3cnc(OCC4CN(C(=O)OC(C)(C)C)C4)c(NS(C)(=O)=O)c3)cc21] | tert-Butyl 3-(((5-(3'-methyl-2'-oxo-2',3'-dihydrospiro[cyclobutane-1,1'-pyrrolo[2,3-c]quinolin]-8'-yl)-3-(methylsulfonamido)pyridin-2-yl)oxy)methyl)azetidine-1-carboxylate | 594.30 | 1H NMR (400 MHz, CDCl3)) δ 8.67 (s, 1H), 8.41 (d, J = 2.0 Hz, 1H), 8.35 (d, J = 2.2 Hz, 1H), 8.28-8.21 (m, 2H), 7.85 (dd, J = 8.8, 1.9 Hz, 1H), 4.67 (d, J = 6.8 Hz, 2H), 4.14 (t, J = 8.5 Hz, 2H), 3.80 (dd, J = 8.8, 5.0 Hz, 2H), 3.41 (s, 3H), 3.09 (s, 3H), 3.07-3.02 (m, 1H), 2.97-2.87 (m, 2H), |

-continued

| Intermediate | Structure | Name | MS: [(M + 1)]+ | 1H NMR |
|---|---|---|---|---|
| | | | | 2.86-2.74 (m, 2H), 2.73-2.53 (m, 2H), 1.46 (s, 9H). |
| EE11 | 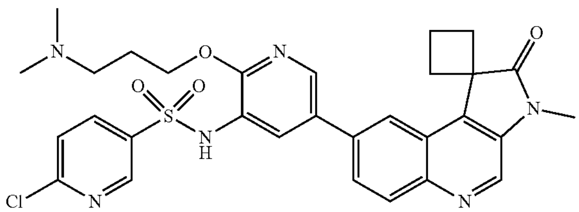 | 6-Chloro-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyridine-3-sulfonamide | 607.20 | 1H NMR (400 MHz, CDCl3) δ 8.81 (s, 1H), 8.76 (d, J = 2.4 Hz, 1H), 8.19 (d, J = 2.0 Hz, 1H), 8.15 (dd, J = 8.3, 2.5 Hz, 1H), 8.11 (d, J = 8.8 Hz, 1H), 7.95 (d, J = 2.3 Hz, 1H), 7.80 (dd, J = 8.9, 2.0 Hz, 1H), 7.63 (d, J = 2.2 Hz, 1H), 7.58 (d, J = 8.3 Hz, 1H), 4.36 (t, J = 5.5 Hz, 2H), 3.30 (s, 5H), 2.96 (s, 6H), 2.82-2.71 (m, 2H), 2.64-2.54 (m, 2H), 2.48-2.35 (m, 2H), 2.23-2.15 (m, 2H). |
| EE12 | 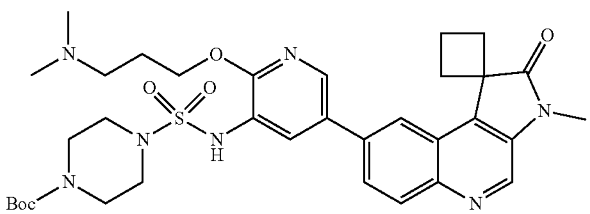 | tert-Butyl 4-(N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)sulfamoyl)piperazine-1-carboxylate | 680.30 | 1H NMR (400 MHz, CDCl3) δ 8.65 (s, 1H), 8.39 (d, J = 2.0 Hz, 1H), 8.24-8.19 (m, 2H), 8.15 (d, J = 2.3 Hz, 1H), 7.81 (dd, J = 8.9, 2.0 Hz, 1H), 4.51 (t, J = 6.0 Hz, 2H), 3.46-3.40 (m, 4H), 3.38 (s, 3H), 3.23 (t, J = 5.1 Hz, 4H), 2.96-2.86 (m, 2H), 2.83-2.46 (m, 6H), 2.43 (s, 6H), 2.06 (p, J = 6.0 Hz, 2H), 1.42 (s, 9H) |

The following examples were synthesized according to the above procedure:

| Examples | Structure | Name | MS: [(M + 1)]+ | 1H NMR |
|---|---|---|---|---|
| 347 | 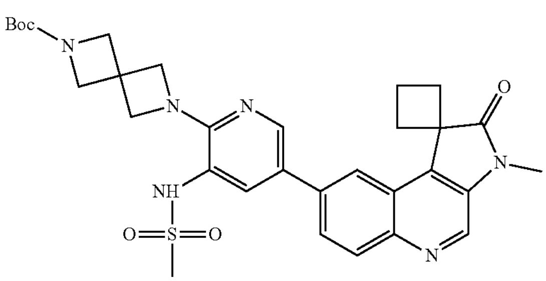 [SMILES: CN1C(=O)C2(CCC2)c2c1cnc1ccc(-c3cnc(N4CC5(CN(C(=O)OC(C)(C)C)C5)C4)c(NS(C)(=O)=O)c3)cc21] | tert-Butyl 6-(5-(3'-methyl-2'-oxo-2',3'-dihydrospiro[cyclobutane-1,1'-pyrrolo[2,3-c]quinolin]-8'-yl)-3-(methylsulfonamido)pyridin-2-yl)-2,6-diazaspiro[3.3]heptane-2-carboxylate | 605.35 | 1H NMR (400 MHz, DMSO-d6) δ 9.12 (s, 1H), 8.81 (s, 1H), 8.56 (s, 1H), 8.32 (d, J = 1.9 Hz, 1H), 8.13 (d, J = 8.8 Hz, 1H), 7.98-7.88 (m, 2H), 4.32 (s, 4H), 4.05 (s, 4H), 3.30 (s, 3H), 3.14 (s, 3H), 2.98-2.88 (m, 2H), 2.61-2.50 (m, 4H), 1.39 (s, 9H). |

-continued

| Examples | Structure | Name | MS: [(M + 1)]+ | 1H NMR |
|---|---|---|---|---|
| 359 | 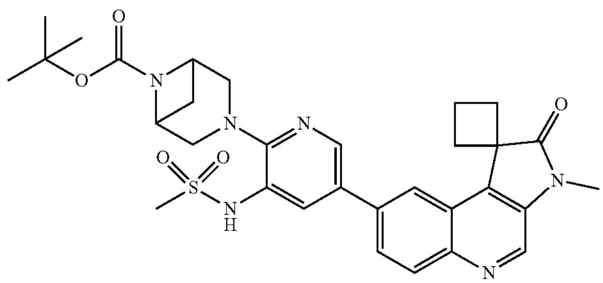 [SMILES: CN1C(=O)C2(CCC2)c2c1cnc1ccc(-c3cnc(N4CC5CC(C4)N5C(=O)OC(C)(C)C)c(NS(C)(=O)=O)c3)cc21] | tert-Butyl 3-(5-(3'-methyl-2'-oxo-2',3'-dihydrospiro[cyclobutane-1,1'-pyrrolo[2,3-c]quinolin]-8'-yl)-3-(methylsulfonamido)pyridin-2-yl)-3,6-diazabicydo[3.1.1]heptane-6-carboxylate | 605.25 | 1H NMR (400 MHz, DMSO-d6) δ 9.17 (s, 1H), 8.81 (s, 1H), 8.68 (d, J = 2.2 Hz, 1H), 8.35 (d, J = 1.8 Hz, 1H), 8.14 (d, J = 8.9 Hz, 1H), 7.96 (dd, J = 12.4, 2.2 Hz, 2H), 4.25 (d, J = 12.6 Hz, 2H), 4.18 (d, J = 6.1 Hz, 2H), 3.88 (d, J = 12.2 Hz, 2H), 3.31 (s, 3H), 3.07 (s, 3H), 3.00-2.89 (m, 2H), 2.61-2.51 (m, 5H), 1.50 (d, J = 8.5 Hz, 1H), 1.33 (s, 9H). |
| 348 | 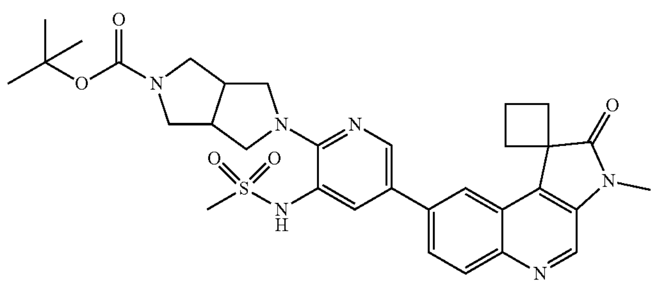 [SMILES: CN1C(=O)C2(CCC2)c2c1cnc1ccc(-c3cnc(N4CC5CN(C(=O)OC(C)(C)C)CC5C4)c(NS(C)(=O)=O)c3)cc21] | tert-Butyl 5-(5-(3'-methyl-2'-oxo-2',3'-dihydrospiro[cyclobutane-1,1'-pyrrolo[2,3-c]quinolin]-8'-yl)-3-(methylsulfonamido)pyridin-2-yl)hexahydropyrrolo[3,4-c]pyrrole-2(1H)-carboxylate | 619.20 | 1H NMR (400 MHz, DMSO-d6) δ 9.13 (s, 1H), 8.80 (s, 1H), 8.61 (s, 1H), 8.33 (s, 1H), 8.13 (d, J = 8.9 Hz, 1H), 7.98-7.92 (m, 2H), 3.88 (s, 2H), 3.67-3.50 (m, 4H), 3.18 (d, J = 11.1 Hz, 2H), 3.09 (s, 3H), 2.99-2.88 (m, 4H), 2.62-2.51 (m, 7H), 1.40 (s, 9H). |

Example 368

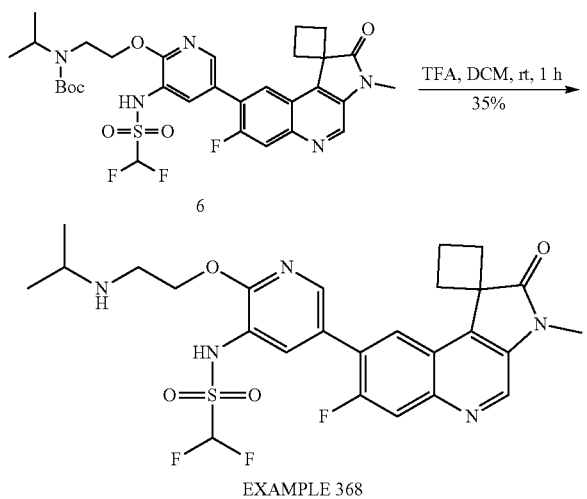

EXAMPLE 368

1,1-Difluoro-N-(5-(7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide: A solution of tert-butyl N-(2-[[3-(difluoromethanesulfonamido)-5-[7-fluoro-3-methyl-2-oxo-2,3-dihydrospiro[cyclobutane-1,1-pyrrolo[2,3-c]quinolin]-8-yl]pyridin-2-yl]oxy]ethyl)-N-(propan-2-yl)carbamate (10.0 mg, 0.015 mmol) in dichloromethane (6.00 mL) was treated with trifluoracetic acid (1.00 mL) for 1 hour at ambient temperature under nitrogen atmosphere. The resulting mixture was concentrated under reduced pressure. The residue was purified by reversed phase flash chromatography with the following conditions: (Column: Spherical C18, 20~40 μm, 120 g; Mobile phase A: Water (plus 0.05% formic acid); Mobile phase B: acetonitrile; Flow rate: 45 mL/min; Gradient (B %): 5%~28%, 5 min; 28%~45%, 15 min; 45%~95%; 2 min; 95%, 5 min; Detector: UV 254 nm). Desired fractions were collected and concentrated under reduced pressure to afford the title compound as a colorless solid (3.00 mg, 35%): 1H NMR (400 MHz, DMSO-d6) δ 8.87 (s, 1H), 8.64 (s, 1H), 8.27 (d, J=8.2 Hz, 1H), 7.96 (d, J=12.1 Hz, 1H), 7.90 (s, 1H), 6.37 (t, J=14.8 Hz, 1H), 4.59-4.51 (m, 2H), 3.49-3.42 (m, 2H), 3.31 (s, 3H), 2.91-2.82 (m, 2H), 2.60-2.52 (m, 4H) 2.47-2.40 (m, 1H), 1.28 (d, J=6.4 Hz, 6H): MS: [(M+1)]+=564.30.

Prep-HPLC purification with the following conditions: [Column: Spherical C18, 20~40 μm, 120 g; Mobile phase A: Water (plus 10 mM NH4HCO3 or HCOOH); Mobile phase B: acetonitrile; Flow rate: 45 mL/min; Gradient (B %): 5%~20%, 7 min; 20%~27%, 8 min; 27%~95%, 2 min; 95%, 5 min; Detector UV 254 nm. Desired fractions were collected and concentrated under reduced pressure to afford the desired example compounds as free base or formate.

Preparation of HCl salt or mesylate: A solution of the free amine (1.0 mmol) in diluted aqueous HCl (Methanesulfonic acid) solution (1.0 mmol, 0.008 M) and acetonitrile (3.0 mL) was lyophilized to afford the corresponding salt:

The following examples were prepared according to the procedure described above:

| Example | Structure | Name | MS: [(M+1)]+ | 1H NMR |
|---|---|---|---|---|
| 346 | 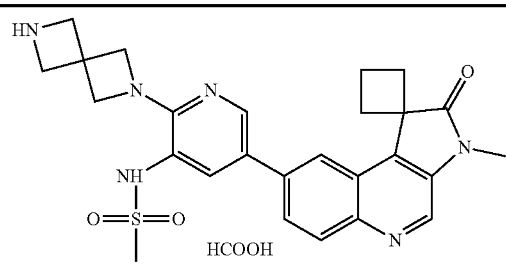 | N-(5-(3'-Methyl-2'-oxo-2',3'-dihydrospiro[cyclobutane-1,1 pyrrole[2,3-c]quinolin]-8'-yl)-2-(2,6-diazaspiro[3.3]heptan-2-yl)pyridin-3-yl)methanesulfonamide formate | 505.25 | 1H NMR (400 MHz, DMSO-d6) δ 8.78 (s, 1H), 8.38 (s, 2H), 8.31 (s, 1H), 8.25 (s, 1H), 8.10 (d, J = 8.8 Hz, 1H), 7.91 (dd, J = 8.9, 2.0 Hz, 1H), 7.83 (d, J = 2.3 Hz, 1H), 4.27 (s, 4H), 4.04 (s, 4H), 3.30 (s, 3H), 2.96-2.76 (m, 5H), 2.61-2.51 (m, 4H). |
| 360 | 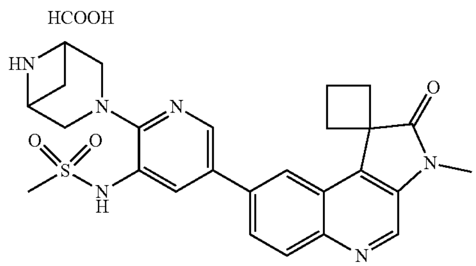 [SMILES: "HCOOH" ; CN1C(=O)C2(CCC2)c2c1cnc1ccc(-c3cnc(N4CC5CC(C4)N5)c(NS(C)(=O)=O)c3)cc21] | N-(2-(3,6-Diazabicyclo[3.1.1]heptan-3-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide formate | 505.25 | 1H NMR (400 MHz, CD3OD) δ 8.74 (s, 1H), 8.65 (s, 1H), 8.52 (s, 1H), 8.50 (s, 1H), 8.18 (d, J = 8.9 Hz, 1H), 8.06 (d, J = 1.5 Hz, 1H), 8.00 (d, J = 9.2 Hz, 1H), 4.54-4.48 (m, 2H), 4.44 (d, J = 6.3 Hz, 2H), 4.16 (d, J = 13.4 Hz, 2H), 3.39 (s, 3H), 3.09 (s, 3H), 3.07-2.94 (m, 3H), 2.77-2.58 (m, 4H), 2.14 (d, J = 10.2 Hz, 1H). |
| 349 | 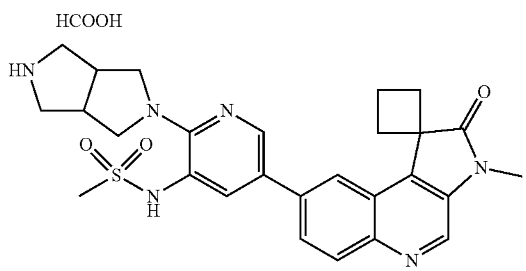 [SMILES: "HCOOH" ; CN1C(=O)C2(CCC2)c2c1cnc1ccc(-c3cnc(N4CC5CNCC5C4)c(NS(C)(=O)=O)c3)cc21] | N-(2-(Hexahydropyrrolo[3,4-c]pyrrol-2(1H)-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide formate | 519.35 | 1H NMR (400 MHz, CD3OD) δ 8.73 (s, 1H), 8.56 (d, J = 2.3 Hz, 1H), 8.48 (s, 1H), 8.17 (d, J = 8.9 Hz, 1H), 8.03 (d, J = 2.3 Hz, 1H), 7.97 (dd, J = 9.0, 2.0 Hz, 1H), 4.11-4.03 (m, 2H), 3.55 (dd, J = 11.5, 7.0 Hz, 2H), 3.47 (dd, J = 11.3, 5.8 Hz, 2H), 3.40-3.33 (m, 5H), 3.20 (s, 2H), 3.11 (s, 3H), 3.06-2.97 (m, 2H), 2.75-2.59 (m, 4H). |
| 370 | 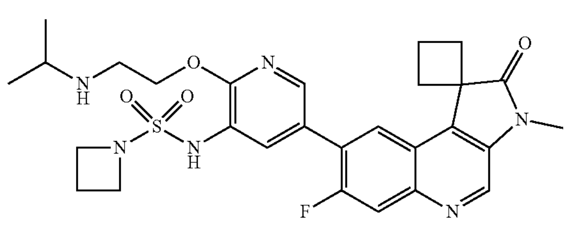 [SMILES: CC(C)NCCOc1ncc(-c2cc3c4c(cnc3cc2F)N(C)C(=O)C42CCC2)cc1NS(=O)(=O)N1CCC1] | N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)azetidine-1-sulfonamide | 569.35 | 1H NMR (400 MHz, DMSO-d6) δ 8.87 (s, 1H), 8.30 (d, J = 8.3 Hz, 1H), 8.08 (s, 1H), 8.02 (d, J = 1.8 Hz, 1H), 7.96 (d, J = 12.2 Hz, 1H), 4.44 (t, J = 5.2 Hz, 2H), 3.69 (t, J = 7.6 Hz, 4H), 3.31 |

| Example | Structure | Name | MS: [(M + 1)]+ | 1H NMR |
|---|---|---|---|---|
| | | | | (s, 3H), 3.12-3.02 (m, 3H), 2.93-2.81 (m, 2H), 2.62-2.44 (m, 4H), 2.04 (p, J = 1.1 Hz, 2H), 1.15 (d, J = 6.3 Hz, 6H). |
| 371 | 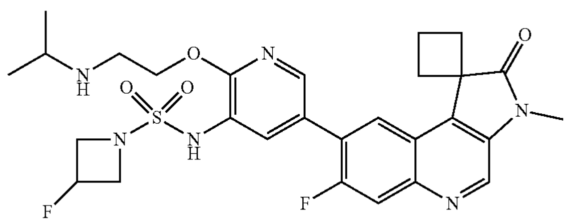 [SMILES: CC(C)NCCOc1ncc(-c2cc3c4c(cnc3cc2F)N(C)C(=O)C42CCC2)cc1NS(=O)(=O)N1CC(F)C1] | 3-Fluoro-N-(5-(7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)azetidine-1-sulfonamide | 587.30 | 1H NMR (400 MHz, DMSO-d6) δ 8.87 (s, 1H), 8.29 (d, J = 8.3 Hz, 1H), 8.03-7.93 (m, 3H), 5.35-5.11 (m, 1H), 4.46 (s, 2H), 3.94-3.71 (m, 4H), 3.30 (s, 3H), 3.29-3.21 (m, 1H), 3.18 (t, J = 5.6 Hz, 2H), 2.91-2.80 (m, 2H), 2.62-2.53 (m, 2H), 2.49-2.42 (m, 2H), 1.23 (d, J = 6.3 Hz, 6H). |
| 372 | 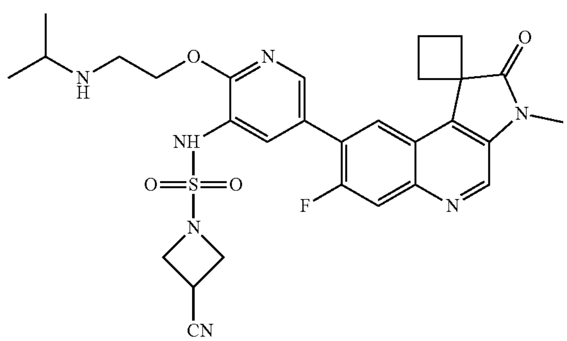 [SMILES: CC(C)NCCOc1ncc(-c2cc3c4c(cnc3cc2F)N(C)C(=O)C42CCC2)cc1NS(=O)(=O)N1CC(C#N)C1] | 3-Cyano-N-(5-(7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)azetidine-1-sulfonamide | 594.30 | 1H NMR (400 MHz, DMSO-d6) δ 8.88 (s, 1H), 8.30 (d, J = 8.3 Hz, 1H), 8.25 (s, 1H), 8.03 (s, 1H), 7.98 (d, J = 12.1 Hz, 1H), 6.08 (d, J = 2.9 Hz, 2H), 4.44 (t, J = 5.1 Hz, 2H), 3.77 (s, 2H), 3.52-3.50 (m, 1H), 3.31 (s, 3H), 3.04-2.96 (m, 2H), 2.95-2.86 (m, 3H), 2.59-2.52 (m, 2H), 2.49-2.40 (m, 2H), 1.08 (d, J = 6.3 Hz, 6H). |
| 374 | 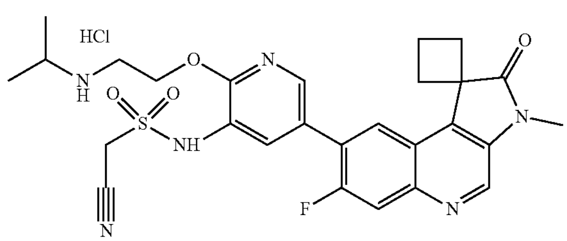 [SMILES: CC(C)NCCOc1ncc(-c2cc3c4c(cnc3cc2F)N(C)C(=O)C42CCC2)cc1NS(=O)(=O)CCN ; Cl] | 1-Cyano-N'-(5-(7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | 553.20 | 1H NMR (400 MHz, CD3OD) δ 8.89 (s, 1H), 8.51-8.48 (m, 2H), 8.30 (d, J = 1.8 Hz, 1H), 7.93 (d, J = 11.5 Hz, 1H), 4.79 (t, J = 5.2 Hz, 2H), 4.72 (d, J = 5.1 Hz, 2H), 3.61 (t, J = 5.2 Hz, 2H), 3.54 (p, J = 6.4 Hz, 1H), 3.39 (s, 3H), 3.04-2.92 (m, 2H), 2.78-2.66 (m, 2H), 2.66-2.53 (m, 2H), 1.43 (d, J = 6.5 Hz, 6H). |

| Example | Structure | Name | MS: [(M+1)]+ | 1H NMR |
|---|---|---|---|---|
| 310 | HCl (structure) | N-(2-(Azetidin-3-ylmethoxy)-5-(3'-methyl-2'-oxo-2',3'-dihydrospiro[cyclobutane-1,1'-pyrrole[2,3-c]quinolin]-8'-yl)pyridin-3-yl)methanesulfonamide hydrochloride | 494.15 | 1H NMR (400 MHz, CD3OD) δ 8.90 (s, 1H), 8.56 (d, J = 2.0 Hz, 1H), 8.46 (d, J = 2.0 Hz, 1H), 8.37 (d, J = 2.0 Hz, 1H), 8.26 (d, J = 8.9 Hz, 1H), 8.07 (dd, J = 8.9, 2.0 Hz, 1H), 4.66 (dd, J = 13.4, 3.6 Hz, 1H), 4.39 (dd, J = 13.5, 8.9 Hz, 1H), 3.77 (dd, J = 11.1, 5.7 Hz, 2H), 3.70 (dd, J = 11.2, 6.3 Hz, 1H), 3.49 (dd, J = 13.4, 8.6 Hz, 1H), 3.41 (s, 3H), 3.23 (s, 3H), 3.10-3.01 (m, 2H), 2.78-2.61 (m, 4H), 2.58-2.48 (m, 1H). |
| 329 | HCOOH (structure) | N-(5-(3'-Methyl-2'-oxo-2',3'-dihydrospiro[cyclobutane-1,1'-pyrrolo[2,3-c]quinolin]-8'-yl)-2-(3-(methylamino)azetidin-1-yl)pyridin-3-yl)methanesulfonamide formate | 493.30 | 1H NMR (400 MHz, DMSO-d6) δ 8.80 (s, 1H), 8.56 (d, J = 2.1 Hz, 1H), 8.32 (s, 1H), 8.20 (s, 1H), 8.13 (d, J = 8.8 Hz, 1H), 7.94 (d, J = 8.9 Hz, 1H), 7.89 (d, J = 2.1 Hz, 1H), 4.35 (t, J = 8.0 Hz, 2H), 3.94 (dd, J = 9.0, 5.3 Hz, 2H), 3.67-3.59 (m, 1H), 3.31 (s, 3H), 3.12 (s, 3H), 2.98-2.89 (m, 2H), 2.61-2.50 (m, 3H), 2.49-2.44 (m, 1H), 2.32 (s, 3H). |
| 240 | HCOOH (structure) | N-(5-(3'-Methyl-2'-oxo-2',3'-dihydrospiro[cyclobutane-1,1'-pyrrolo[2,3-c]quinolin]-8'-yl)-2-(3-(methylamino)propoxy)pyridin-3-yl)methanesulfonamide formate | 496.25 | 1H NMR (400 MHz, DMSO-d6) δ 8.82 (s, 1H), 8.37 (d, J = 2.0 Hz, 1H), 8.25 (s, 1H), 8.14 (d, J = 8.9 Hz, 1H), 8.03 (s, 1H), 7.96-7.92 (m, 2H), 4.36 (t, J = 5.5 Hz, 2H), 3.31 (s, 3H), 3.12 (t, J = 5.4 Hz, 2H), 2.93-2.86 (m, 2H), 2.85 (s, 3H), 2.66 (s, 3H), 2.63-2.51 (m, 4H), 2.11-2.04 (m, 2H). |

-continued

| Example | Structure | Name | MS: [(M+1)]+ | 1H NMR |
|---|---|---|---|---|
| 332 | 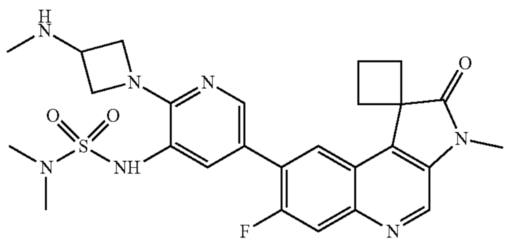 | 8'-{5-[(Dimethylsulfamoyl)amino]-6-[3-(methylamino)azetidin-1-yl]pyridin-3-yl}-7'-fluoro-3'-methyl-2',3'-dihydrospiro[cyclobutane-1,1'-pyrrolo[2,3-c]quinoline]-2'-one | 540.35 | 1H NMR (400 MHz, CD3OD) δ 8.76 (s, 1H), 8.36 (d, J = 8.8 Hz, 2H), 7.92-7.82 (m, 2H), 4.60-4.50 (m, 2H), 4.16 (dd, J = 9.6, 4.9 Hz, 2H), 3.86-3.80 (m, 1H), 3.38 (s, 3H), 2.99-2.91 (m, 2H), 2.89 (s, 6H), 2.76-2.55 (m, 4H) 2.53 (s, 3H). |
| 333 | 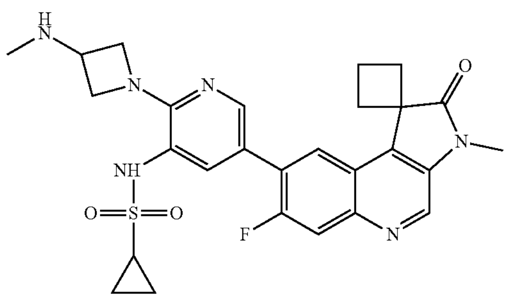 | N-(5-(7'-Fluoro-3'-methyl-2'-oxo-2',3'-dihydrospiro[cyclobutane-1,1'-pyrrolo[2,3-c]quinolin]-8'-yl)-2-(3-(methylamino)azetidin-1-yl)pyridin-3-yl)cyclopropanesulfonamide | 537.35 | 1H NMR (400 MHz, DMSO-d6) δ 8.85 (s, 1H), 8.40 (s, 1H), 8.26 (d, J = 8.3 Hz, 1H), 7.95 (d, J = 12.4 Hz, 1H), 7.80 (s, 1H), 4.36 (t, J = 8.3 Hz, 2H), 3.91 (s, 2H), 3.56 (s, 1H), 3.30 (s, 3H), 2.98-2.83 (m, 2H), 2.76 (s, 1H), 2.47-2.31 (m, 3H), 2.27 (s, 3H), 1.09-0.96 (m, 3H), 0.94 (s, 2H). |
| 334 | 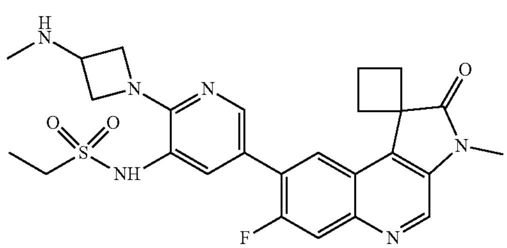 | N-(5-(7'-Fluoro-3'-methyl-2'-oxo-2',3'-dihydrospiro[cyclobutane-1,1'-pyrrolo[2,3-c]quinolin-8'-yl)-2-(3-(methylamino)azetidin-1-yl)pyridin-3-yl)ethanesulfonamide | 525.30 | 1H NMR (400 MHz, DMSO-d6) δ 8.85 (s, 1H), 8.41 (s, 1H), 8.25 (d, J = 8.4 Hz, 1H), 7.94 (d, J = 12.2 Hz, 1H), 7.71 (d, J = 2.1 Hz, 1H), 4.41-4.32 (m, 2H), 3.94 (dd, J = 9.1, 5.4 Hz, 2H), 3.64-3.57 (m, 1H), 3.30 (s, 3H), 3.19 (d, J = 7.4 Hz, 2H), 2.97-2.88 (m, 2H), 2.58-2.37 (m, 4H), 2.29 (s, 3H), 1.30 (t, J = 7.3 Hz, 3H). |
| 373 | 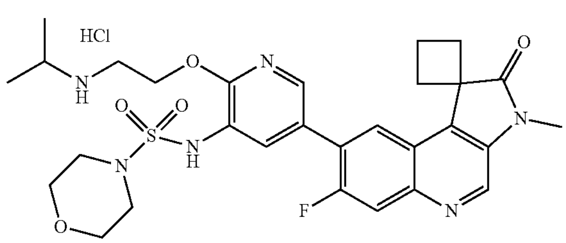 [SMILES: CC(C)NCCOc1ncc(-c2cc3c4c(cnc3cc2F)N(C)C(=O)C42CCC2)cc1NS(=O)(=O)N1CCOCC1 ; Cl] | N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)morpholine-4-sulfonamide hydrochloride | 599.25 | 1H NMR (400 MHz, CD3OD) δ 8.95 (s, 1H), 8.51 (d, J = 7.8 Hz, 1H), 8.34 (t, J = 2.0 Hz, 1H), 8.20 (t, J = 1.9 Hz, 1H), 7.97 (d, J = 11.4 Hz, 1H), 4.79 (t, J = 5.2 Hz, 2H), 3.71-3.66 (m, 4H), 3.63-3.50 |

| Example | Structure | Name | MS: [(M + 1)]+ | 1H NMR |
|---|---|---|---|---|
| | | | | (m, 3H), 3.40 (s, 3H), 3.32-3.22 (m, 4H), 3.05-2.93 (m, 2H), 2.82-2.70 (m, 2H), 2.68-2.52 (m, 2H), 1.43 (d, J = 6.5 Hz, 6H). |
| 300 | 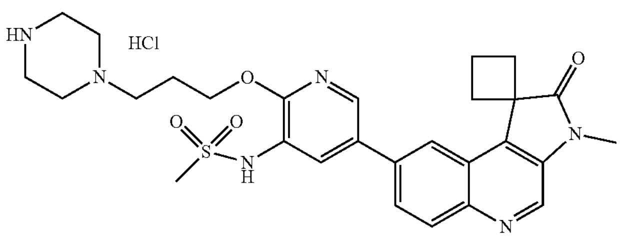 [SMILES: CN1C(=O)C2(CCC2)c2c1cnc1ccc(-c3cnc(OCCCN4CCNCC4)c(NS(C)(=O)=O)c3)cc21 ; Cl] | N-(5-(3'-Methyl-2'-oxo-2',3'-dihydrospiro[cyclobutane-1,1'-pyrrole[2,3-c]quinolin]-8'-yl)-2-(3-(piperazin-1-yl)propoxy)pyridin-3-yl)methanesulfonamide | 551.35 | 1H NMR (400 MHz, CD3OD) δ 8.75 (s, 1H), 8.50 (s, 1H), 8.42 (s, 1H), 8.24 (s, 1H), 8.18 (d, J = 8.9 Hz, 1H), 7.99 (d, J = 9.0 Hz, 1H), 4.58 (t, J = 6.4 Hz, 2H), 3.39 (s, 3H), 3.24 (t, J = 5.2 Hz, 4H), 3.10 (s, 3H), 2.99 (q, J = 9.5, 8.6 Hz, 2H), 2.79-2.67 (m, 10H), 2.14-2.06 (m, 2H). |
| 249 | 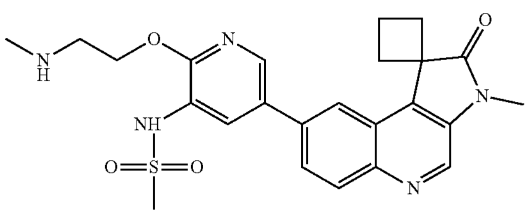 | N-(5-(3'-Methyl-2'-oxo-2',3'-dihydrospiro[cyclobutane-1,1'-pyrrolo[2,3-c]quinolin]-8'-yl)-2-(2-(methylamino)ethoxy)pyridin-3-yl)methanesulfonamide | 482.20 | 1H NMR (400 MHz, DMSO-d6) δ 8.82 (s, 1H), 8.38 (s, 1H), 8.27 (s, 1H), 8.14 (d, J = 8.8 Hz, 1H), 8.06 (s, 1H), 7.96 (d, J = 8.9 Hz, 1H), 4.45 (t, J = 5.0 Hz, 2H), 3.31 (s, 3H), 3.04 (t, J = 4.9 Hz, 2H), 3.00 (s, 3H), 2.94-2.85 (m, 2H), 2.61-2.52 (m, 4H), 2.48 (s, 3H). |
| 308 | 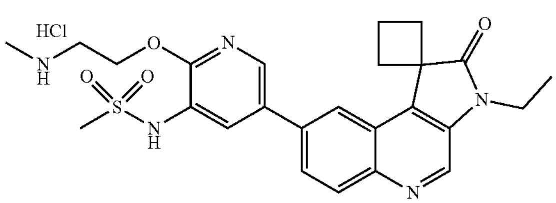 [SMILES: CCN1C(=O)C2(CCC2)c2c1cnc1ccc(-c3cnc(OCCNC)c(NS(C)(=O)=O)c3)cc21 ; Cl] | N-(5-(3'-Ethyl-2'-oxo-2',3'-dihydrospiro[cyclobutane-1,1'-pyrrolo[2,3-c]quinolin]-8'-yl)-2-(2-(methylamino)ethoxy)pyridin-3-yl)methanesulfonamide hydrochloride | 496.15 | 1H NMR (400 MHz, CD3OD) δ 8.76 (d, J = 1.4 Hz, 1H), 8.51 (s, 1H), 8.27 (d, J = 9.7 Hz, 2H), 8.17 (d, J = 8.9 Hz, 1H), 7.99 (d, J = 9.0 Hz, 1H), 4.59 (t, J = 4.8 Hz, 2H), 3.96 (q, J = 7.3 Hz, 2H), 3.24 (t, J = 4.8 Hz, 2H), 3.05 (s, 3H), 3.04-2.94 (m, 2H), 2.76-2.60 (m, 7H), 1.33 (t, J = 7.2 Hz, 3H). |

| Example | Structure | Name | MS: [(M + 1)]+ | 1H NMR |
|---|---|---|---|---|
| 250 | 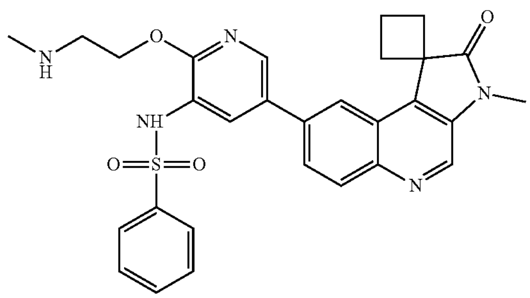 | N-(5-(3'-Methyl-2'-oxo-2',3'-dihydrospiro[cyclobutane-1,1'-pyrrolo[2,3-c]quinolin]-8'-yl)-2-(2-(methylamino)ethoxy)pyridin-3-yl)benzenesulfonamide | 544.15 | 1H NMR (400 MHz, DMSO-$d_6$) δ 8.82 (s, 1H), 8.26 (s, 1H), 8.14-8.05 (m, 2H), 7.86-7.78 (m, 4H), 7.48-7.44 (m, 3H), 4.38 (t, J = 5.0 Hz, 2H), 3.31 (s, 3H), 3.12 (t, J = 5.0 Hz, 2H), 2.88-2.79 (m, 2H), 2.61 (s, 3H), 2.60-2.52 (m, 4H). |
| 248 | 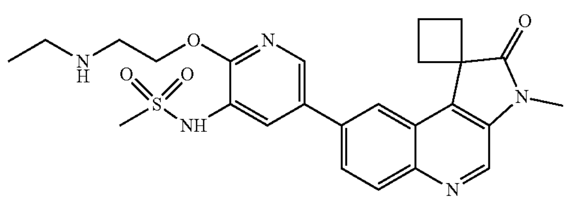 [SMILES: CCNCCOc1ncc(-c2ccc3ncc4c(c3c2)C2(CCC2)C(=O)N4C)cc1NS(C)(=O)=O] | N-(2-(2-(Ethylamino)ethoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 496.15 | 1H NMR (400 MHz, DMSO-$d_6$) δ 8.83 (s, 1H), 8.38 (s, 1H), 8.28 (s, 1H), 8.14 (d, J = 8.8 Hz, 1H), 8.07 (s, 1H), 7.96 (d, J = 8.9 Hz, 1H), 4.45 (t, J = 5.7 Hz, 2H), 3.30 (s, 3H), 3.08-3.02 (m, 2H), 3.00 (s, 3H), 2.96-2.85 (m, 2H), 2.81-2.72 (m, 2H), 2.64-2.53 (m, 4H), 1.14 (t, J = 7.1 Hz, 3H). |
| 520 | 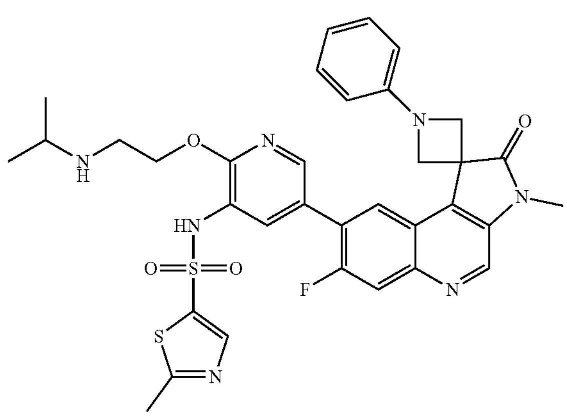 [SMILES: Cc1ncc(S(=O)(=O)Nc2cc(-c3cc4c5c(cnc4cc3F)N(C)C(=O)C53CN(c4ccccc4)C3)cnc2OCCNC(C)C)s1] | N-(5-(7'-Fluoro-3'-methyl-2'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)-2-methylthiazole-5-sulfonamide | 688.40 | 1H NMR (400 MHz, DMSO-$d_6$) δ 8.94 (s, 1H), 8.61 (d, J = 8.9 Hz, 1H), 7.96 (d, J = 12.0 Hz, 1H), 7.71 (d, J = 9.1 Hz, 2H), 7.59 (s, 1H), 7.26 (t, J = 8.0 Hz, 2H), 6.81 (t, J = 8.0 Hz, 1H), 6.66 (d, J = 8.0 Hz, 2H), 4.46 (d, J = 7.8 Hz, 2H), 4.34 (t, J = 5.0 Hz, 2H), 4.10 (d, J = 7.7 Hz, 2H), 3.33 (s, 3H), 3.28-3.16 (m, 3 H), 2.58 (s, 3H), 1.21 (d, J = 6.3 Hz, 6H). |

| Example | Structure | Name | MS: [(M+1)]+ | 1H NMR |
|---|---|---|---|---|
| 521 | 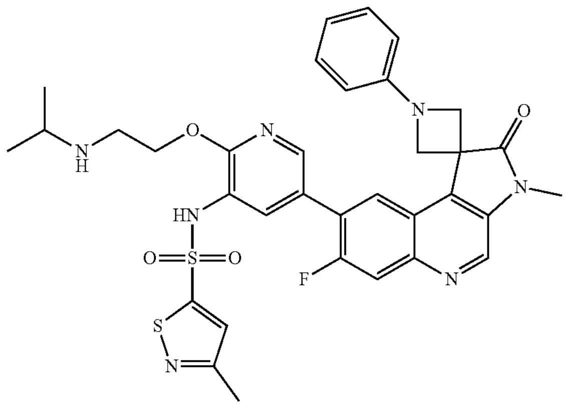 [SMILES: Cc1cc(S(=O)(=O)Nc2cc(-c3cc4c5c(cnc4cc3F)N(C)C(=O)C53CN(c4ccccc4)C3)cnc2OCCNC(C)C)sn1] | N-(5-(7'-Fluoro-3'-methyl-2'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)-3-methylisothiazole-5-sulfonamide | 688.35 | 1H NMR (400 MHz, DMSO-$d_6$) δ 8.93 (s, 1H), 8.60 (d, J = 8.4 Hz, 1H), 7.96 (d, J = 12.0 Hz, 1H), 7.72 (d, J = 2.6 Hz, 1H), 7.59 (s, 1H), 7.30-7.23 (m, 3H), 6.81 (t, J = 7.3 Hz, 1H), 6.66 (d, J = 8.0 Hz, 2H), 4.46 (d, J = 7.9 Hz, 2H), 4.34 (t, J = 5.0 Hz, 2H), 4.10 (d, J = 7.9 Hz, 2H), 3.33 (s, 3H), 3.31-3.20 (m, 3H), 2.36 (s, 3H), 1.22 (d, J = 6.5 Hz, 6H). |
| 458 | 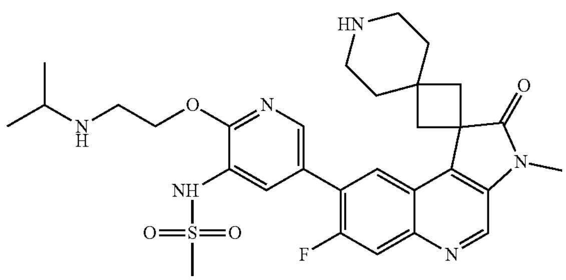 [SMILES: CC(C)NCCOc1ncc(-c2cc3c4c(cnc3cc2F)N(C)C(=O)C42CC3(CCNCC3)C2)cc1NS(C)(=O)=O] | N-(5-(7''-Fluoro-3''-methyl-2''-oxo-2'',3''-dihydrodispiro[piperidine-4,1'-cyclobutane-31''-pyrrolo[2,3-c]quinolin]-8''-yl)-2-(2-(isopropylamino)ethoxy)pyridin-3-yl)methanesulfonamide | 597.30 | 1H NMR (400 MHz, DMSO-$d_6$) δ 8.87 (s, 1H), 8.31 (d, J = 8.2 Hz, 1H), 8.02-7.93 (m, 2H), 7.84 (s, 1H), 4.39 (t, J = 5.5 Hz, 2H), 3.30 (s, 3H), 2.94 (t, J = 5.6 Hz, 2H), 2.91-2.72 (m, 10H), 2.36 (d, J = 12.7 Hz, 2H), 2.20 (s, 2H), 1.90 (d, J = 6.0 Hz, 2H), 1.05 (d, J = 6.3 Hz, 6H). |
| 330 | 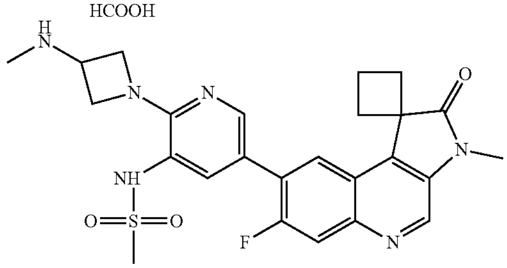 | N-(5-(7'-Fluor-3'-methyl-2'-oxo-2',3'-dihydrospiro[cyclobutane-1,1-pyrrolo[2,3-c]quinolin]-8'-yl)-2-(3-(methylamino)azetidin-1-yl)pyridin-3-yl)methanesulfonamide formate | 493.30 | 1H NMR (400 MHz, DMSO-$d_6$) δ 8.80 (s, 1H), 8.56 (d, J = 2.1 Hz, 1H), 8.32 (s, 1H), 8.20 (s, 1H), 8.13 (d, J = 8.8 Hz, 1H), 7.94 (d, J = 8.9 Hz, 1H), 7.89 (d, J = 2.1 Hz, 1H), 4.35 (t, J = 8.0 Hz, 2H), 3.94 (dd, J = 9.0, 5.3 Hz, 2H), 3.67-3.59 (m, 1H), 3.31 (s, 3H), 3.12 (s, 3H), 2.98-2.89 (m, 2H), 2.61-2.50 (m, 3H), 2.49-2.44 (m, 1H), 2.32 (s, 3H). |

-continued

| Example | Structure | Name | MS: [(M + 1)]+ | 1H NMR |
|---|---|---|---|---|
| 331 | 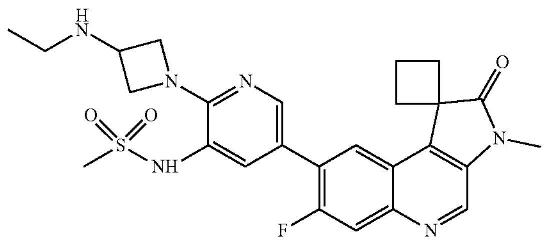 [SMILES: CCNC1CN(c2ncc(-c3cc4c5c(cnc4cc3F)N(C)C(=O)C53CCC3)cc2NS(C)(=O)=O)C1] | N-(2-(3-(Ethylamino)azetidin-1-yl)-5-(7'-fluoro-3'-methyl-2'-oxo-2',3'-dihydrospiro[cyclobutane-1,1'-pyrrolo[2,3-c]quinolin-8'-yl)pyridin-3-yl)methanesulfonamide | 525.25 | 1H NMR (400 MHz, CD3OD) δ 8.76 (s, 1H), 8.44 (s, 1H), 8.38 (d, J = 8.1 Hz, 1H), 7.92 (s, 1H), 7.85 (d, J = 11.8 Hz, 1H), 4.60 (t, J = 9.3 Hz, 2H), 4.31-4.22 (m, 2H), 4.08-4.01 (m, 1H), 3.38 (s, 3H), 3.12 (s, 3H), 3.05-2.93 (m, 4H), 2.76-2.48 (m, 4H), 1.30 (t, J = 7.2 Hz, 3H). |
| 378 | 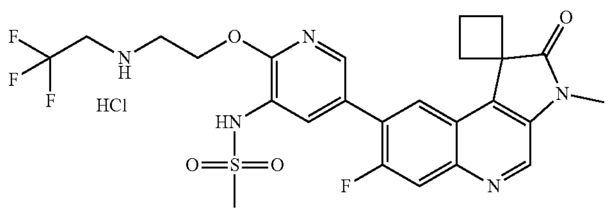 [SMILES: CN1C(=O)C2(CCC2)c2c1cnc1cc(F)c(-c3cnc(OCCNCC(F)(F)F)c(NS(C)(=O)=O)c3)cc21 ; Cl] | N-(5-(7'-Fluoro-3'-methyl-2'-oxo-2',3'-dihydrospiro[cyclobutane-1,1'-pyrrolo[2,3-c]quinolin]-8'-yl)-2-(2-((2,2,2-trifluoroethyl)amino)ethoxy)pyridin-3-yl)methanesulfonamide hydrochloride | 568.25 | 1H NMR (400 MHz, CD3OD) δ 8.85 (s, 1H), 8.47 (d, J = 7.9 Hz, 1H), 8.37 (s, 1H), 8.26 (s, 1H), 7.95-7.90 (m, 1H), 4.80 (t, J = 4.9 Hz, 2H), 4.14 (q, J = 9.1 Hz, 2H), 3.70-3.65 (m, 2H), 3.39 (s, 3H), 3.14 (s, 3H), 3.01-2.92 (m, 2H), 2.77-2.67 (m, 2H), 2.67-2.52 (m, 2H). |
| 379 | 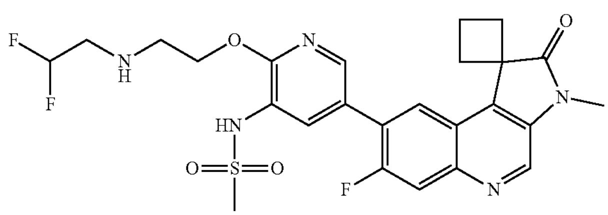 [SMILES: CN1C(=O)C2(CCC2)c2c1cnc1cc(F)c(-c3cnc(OCCNCC(F)F)c(NS(C)(=O)=O)c3)cc21] | N-(2-(2-((2,2-Difluoroethyl)amino)ethoxy)-5-(7fluoro-3'-methyl-2'-oxo-2',3'-dihydrospiro[cyclobutane-1,1'-pyrrole[2,3-c]quinolin]-8'-yl)pyridin-3-yl)methanesulfonamide | 550.30 | 1H NMR (400 MHz, CD3OD) δ 8.77 (s, 1H), 8.42 (d, J = 8.1 Hz, 1H), 8.33 (t, J = 2.2 Hz, 1H), 8.18 (d, J = 2.1 Hz, 1H), 7.87 (d, J = 12.0 Hz, 1H), 6.00 (tt, J = 56.0, 4.1 Hz, 1H), 4.57 (t, J = 5.1 Hz, 2H), 3.38 (s, 3H), 3.16-3.11 (m, 3H), 3.10-3.02 (m, 4H), 3.00-2.91 (m, 2H), 2.75-2.52 (m, 6H). |
| 380 | 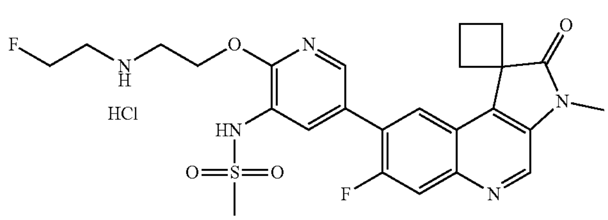 [SMILES: CN1C(=O)C2(CCC2)c2c1cnc1cc(F)c(-c3cnc(OCCNCCF)c(NS(C)(=O)=O)c3)cc21 ; Cl] | N-(5-(7'-Fluoro-3'-methyl-2'-oxo-2',3'-dihydrospiro[cyclobutane-1,1'-pyrrolo[2,3-c]quinolin]-8'-yl)-2-(2-((2-fluoroethyl)amino)ethoxy)pyridin-3-yl)methanesulfonamide hydrochloride | 532.25 | 1H NMR (400 MHz, CD3OD) δ 8.80 (s, 1H), 8.43 (d, J = 8.1 Hz, 1H), 8.37 (t, J = 2.1 Hz, 1H), 8.28-8.22 (m, 1H), 7.89 (d, J = 11.9 Hz, 1H), 4.90-4.88 (m, 1H), 4.83-4.75 (m, 3H), 3.68-3.63 (m, 2H), 3.62-3.58 (m, 1H), 3.55- |

| Example | Structure | Name | MS: [(M+1)]+ | 1H NMR |
|---|---|---|---|---|
| | | | | 3.51 (m, 1H), 3.39 (s, 3H), 3.15 (s, 3H), 3.00-2.91 (m, 2H), 2.77-2.67 (m, 2H), 2.65-2.50 (m, 2H). |
| 177 | 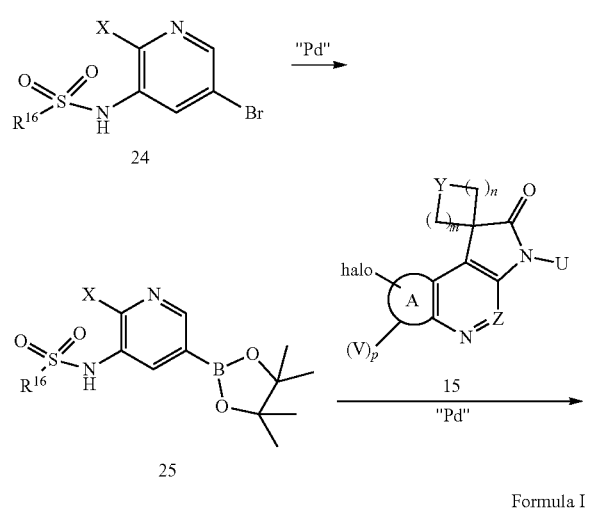 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)piperazine-1-sulfonamide | 580.10 | 1H NMR (400 MHz, CD3OD) δ 8.73 (s, 1H), 8.50 (d, J = 2.0 Hz, 1H), 8.21 (d, J = 2.3 Hz, 1H), 8.18-8.14 (m, 2H), 7.97 (dd, J = 8.9, 1.9 Hz, 1H), 4.50 (t, J = 5.9 Hz, 2H), 3.39 (s, 3H), 3.19 (t, J = 10.2 Hz, 4H), 3.05-2.94 (m, 4H), 2.82-2.76 (m, 4H), 2.75-2.61 (m, 10H), 2.24-2.15 (m, 2H). |

General Procedure: To a solution of INTERMEDIATE 24 (1.0 equiv.) and 4,4,5,5-tetramethyl-2-(tetramethyl-1,3,2-dioxaborolan-2-yl)-1,3,2-dioxaborolane (2.0 equiv.) in 1,4-dioxane (20 mL) were added 1,1'-bis(diphenylphosphino)ferrocene-palladium (II) dichloride (0.1 equiv.) and potassium acetate (4 equiv.). The resulting mixture was stirred for 2 hours at 90° C. under nitrogen atmosphere and then cooled down to ambient temperature. To the reaction mixture was added water (5.0 mL), INTERMEDIATE 15 (0.7 equiv.), potassium carbonate (2.0 equiv.) and tetrakis(triphenylphosphine) palladium (0) (0.1 equiv.) under nitrogen atmosphere. The resulting mixture was stirred for 2 h at 80° C. under nitrogen atmosphere. After cooling down to ambient temperature, the resulting mixture was concentrated under reduced pressure. The residue was purified by silica gel column chromatography, eluted with 1%~10% methanol in dichloromethane with 0.1% ammonia. Desired fractions were collected and concentrated under reduced pressure to afford the desired compound.

For the compounds purified by reversed phase flash chromatography with the following conditions: [Column: Spherical C18, 20~40 μm, 120 g; Mobile phase A: Water (plus 10 mM NH4HCO3 or HCOOH or CF3COOH); Mobile phase B: acetonitrile; Flow rate: 45 mL/min; Gradient (B %): 5%~20%, 7 min; 20%~27%, 8 min; 27%~95%, 2 min; 95%, 5 min; Detector: UV 254 nm. Desired fractions were collected and concentrated under reduced pressure to afford the desired Example compounds as free base or formate or trifluoroacetic acid salt.

Preparation of HCl salt: A solution of the free amine (1.0 mmol) in diluted aqueous HCl solution (1.0 mmol, 0.008 M) and acetonitrile (3.0 mL) was lyophilized to afford the HCl salt:

The following Example compounds were synthesized according to the above procedure:

| Examples | Structure | Name | MS: [(M + 1)]+ | 1H NMR |
|---|---|---|---|---|
| 1 | 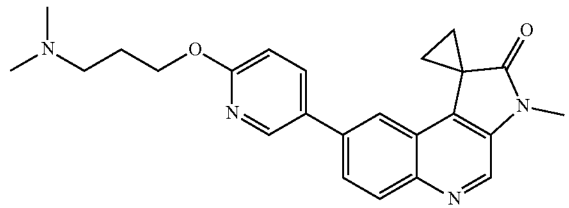 | 8'-(6-(3-(Dimethylamino) propoxy)pyridin-3-yl)-3'-methylspiro [cyclopropane-1,1'-pyrrolo[2, 3-c]quinolin]-2'(3'H)-one | 403.20 | $^1$H NMR (400 MHz, DMSO-$d_6$) δ 8.90 (s, 1H), 8.64 (d, J = 2.5 Hz, 1H), 8.18 (dd, J = 8.7, 2.7 Hz, 1H), 8.12 (d, J = 8.9 Hz, 1H), 7.91 (dd, J = 8.9, 2.0 Hz, 1H), 7.57 (d, J = 2.0 Hz, 1H), 6.94 (d, J = 8.6 Hz, 1H), 4.35 (t, J = 6.6 Hz, 2H), 3.42 (s, 3H), 2.56-2.51 (m, 2H), 2.38 (t, J = 7.1 Hz, 2H), 2.17 (s, 6H), 1.93-1.85 (m, 2H), 1.76 (q, J = 4.3 Hz, 2H). |
| 2 | 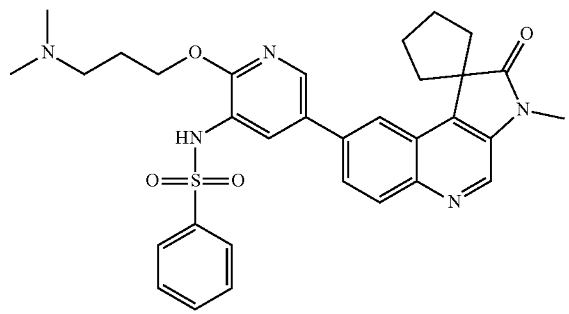 | N-(2-(3-(Dimethylamino) propoxy)-5-(3'-methyl-2'-oxo-2',3'-dihydrospiro[cyclopentane-1,1'-pyrrolo[2,3-c]quinolin]-8'-yl)pyridin-3-yl) benzenesulfonamide | 586.40 | $^1$H NMR (400 MHz, DMSO-$d_6$) δ 8.83 (s, 1H), 8.09 (d, J = 8.8 Hz, 1H), 7.93 (d, J = 2.3 Hz, 1H), 7.83-7.73 (m, 4H), 7.65 (d, J = 2.3 Hz, 1H), 7.45-7.42 (m, 3H), 4.30 (t, J = 5.6 Hz, 2H), 3.51 (s, 3H), 3.16 (t, J = 5.6 Hz, 2H), 2.82 (s, 6H), 2.26-2.04 (m, 10H). |
| 3 | 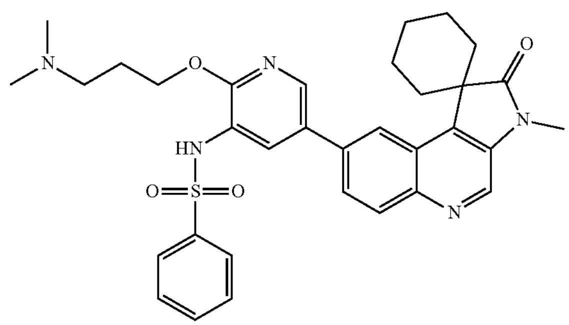 | N-(2-(3-(Dimethylamino) propoxy)-5-(3'-methyl-2'-oxo-2',3'-dihydrospiro[cyclohexane-1,1'-pyrrolo[2,3-c]quinolin]-8'-yl)pyridin-3-yl) benzenesulfonamide | 600.40 | $^1$H NMR (300 MHz, DMSO-$d_6$) δ 8.85 (s, 1H), 8.07 (t, J = 7.2 Hz, 2H), 7.97 (d, J = 2.1 Hz, 1H), 7.82 (dd, J = 6.7, 2.9 Hz, 2H), 7.75 (d, J = 9.6 Hz, 1H), 7.66 (d, J = 2.2 Hz, 1H), 7.47-7.40 (m, 3H), 4.31 (t, J = 5.7 Hz, 2H), 3.30 (s, 3H), 3.16 (t, J = 4.5 Hz, 2H), 2.81 (s, 6H), 2.31-2.16 (m, 4H), 2.11-2.01 (m, 2H), 1.91-1.84 (m, 1H), 1.79-1.63 (m, 5H). |

| Examples | Structure | Name | MS: [(M + 1)]+ | 1H NMR |
|---|---|---|---|---|
| 4 | 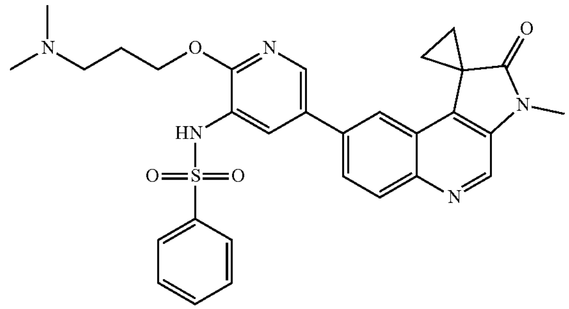 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | 558.30 | 1H NMR (400 MHz, DMSO-$d_6$) δ 8.88 (s, 1H), 8.08 (d, J = 8.9 Hz, 1H), 7.95 (d, J = 2.3 Hz, 1H), 7.82 (dd, J = 6.6, 3.1 Hz, 2H), 7.70 (dd, J = 8.9, 1.9 Hz, 1H), 7.58 (d, J = 2.3 Hz, 1H), 7.52-7.48 (m, 3H), 7.31 (d, J = 2.0 Hz, 1H), 4.28 (t, J = 5.7 Hz, 2H), 3.41 (s, 3H), 3.11 (t, J = 5.7 Hz, 2H), 2.78 (s, 6H), 2.28 (q, J = 4.5 Hz, 2H), 2.09-2.02 (m, 2H), 1.81 (q, J = 4.3 Hz, 2H). |
| 5 | 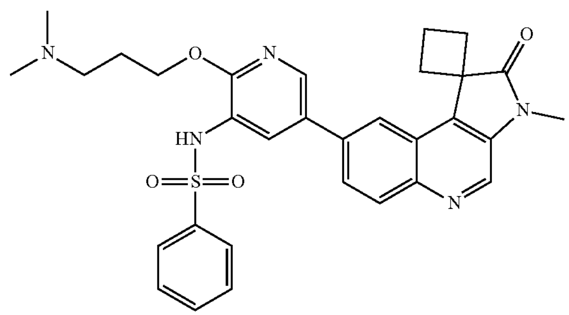 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)benzenesulfonamide | 572.30 | 1H NMR (300 MHz, DMSO-$d_6$) δ 8.77 (s, 1H), 8.18 (d, J = 1.9 Hz, 1H), 8.06 (d, J = 8.9 Hz, 1H), 7.96 (d, J = 2.2 Hz, 1H), 7.77 (m, 3H), 7.66 (d, J = 2.3 Hz, 1H), 7.39 (dd, J = 6.9, 3.2 Hz, 3H), 4.28 (t, J = 5.7 Hz, 2H), 3.27 (s, 3H), 3.10 (t, J = 5.5 Hz, 2H), 2.75 (s, 8H), 2.60-2.49 (m, 4H), 2.07-2.01 (m, 2H). |
| 6 | 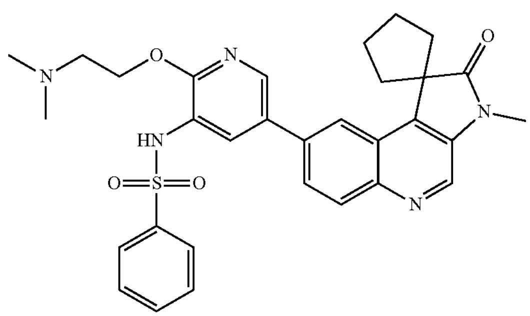 | N-(2-(2-(Dimethylamino)ethoxy)-5-(3'-methyl-2'-oxo-2',3'-dihydrospiro[cyclopentane-1,1'-pyrrolo[2,3-c]quinolin]-8'-yl)pyridin-3-yl)benzenesulfonamide | 572.40 | 1H NMR (300 MHz, DMSO-$d_6$) δ 8.86 (s, 1H), 8.31 (d, J = 2.3 Hz, 1H), 8.14 (d, J = 8.7 Hz, 1H), 7.96 (d, J = 2.3 Hz, 1H), 7.86 (d, J = 8.9 Hz, 2H), 7.83-7.74 (m, 2H), 7.60-7.51 (m, 3H), 4.27 (t, J = 6.1 Hz, 2H), 3.32 (s, 3H), 2.64 (t, J = 6.1 Hz, 2H), 2.31 (s, 6H), 2.31-2.04 (m, 8H). |

| Examples | Structure | Name | MS: [(M + 1)]+ | ¹H NMR |
|---|---|---|---|---|
| 8 | 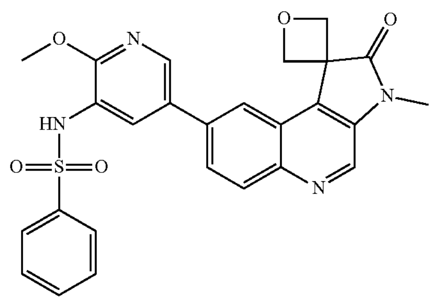 [SMILES: COc1ncc(-c2ccc3ncc4c(c3c2)C2(COC2)C(=O)N4C)cc1NS(=O)(=O)c1ccccc1] | N-(2-Methoxy-5-(3'-methyl-2'-oxo-2',3'-dihydrospiro[oxetane-3,1'-pyrrolo[2,3-c]quinolin]-8'-yl)pyridin-3-yl)benzenesulfonamide | 503.00 | ¹H NMR (300 MHz, CDCl₃) δ 8.72 (d, J = 2.0 Hz, 1H), 8.70 (s, 1H), 8.28-8.23 (m, 2H), 8.19 (d, J = 2.3 Hz, 1H), 7.90 (dd, J = 7.2, 1.8 Hz, 2H), 7.85 (dd, J = 8.9, 2.0 Hz, 1H), 7.57 (t, J = 7.4 Hz, 1H), 7.52-7.44 (m, 2H), 7.04 (s, 1H), 5.34 (d, J = 5.9 Hz, 2H), 5.08 (d, J = 5.9 Hz, 2H), 3.91 (s, 3H), 3.41 (s, 3H). |
| 9 | 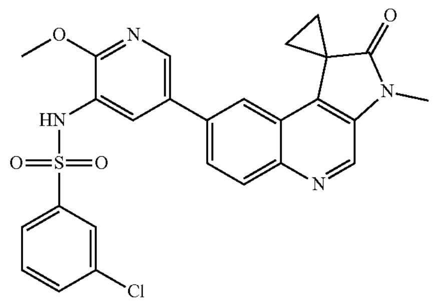 [SMILES: COc1ncc(-c2ccc3ncc4c(c3c2)C2(CC2)C(=O)N4C)cc1NS(=O)(=O)c1cccc(Cl)c1] | 3-Chloro-N-(2-methoxy-5-(3'-methyl-2'-oxo-2',3'-dihydrospiro[cyclopropane-1,1'-pyrrolo[2,3-c]quinolin]-8'-yl)pyridin-3-yl)benzenesulfonamide | 521.00 | ¹H NMR (300 MHz, DMSO-d₆) δ 10.25 (s, 1H), 8.91 (s, 1H), 8.47 (d, J = 2.3 Hz, 1H), 8.12 (d, J = 8.9 Hz, 1H), 7.95 (d, J = 2.3 Hz, 1H), 7.86-7.81 (m, 2H), 7.78-7.69 (m, 2H), 7.62 (t, J = 7.9 Hz, 1H), 7.51 (d, J = 2.0 Hz, 1H), 3.70 (s, 3H), 3.42 (s, 3H), 2.46 (q, J = 4.1 Hz, 2H), 1.78 (q, J = 4.3 Hz, 2H). |
| 10 | 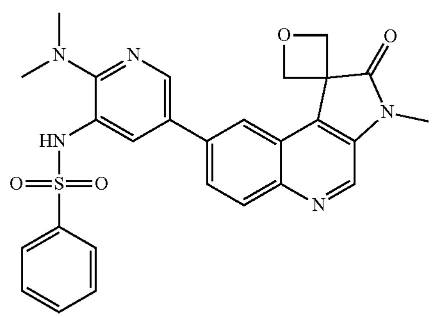 [SMILES: CN(C)c1ncc(-c2ccc3ncc4c(c3c2)C2(COC2)C(=O)N4C)cc1NS(=O)(=O)c1ccccc1] | N-(2-(Dimethylamino)-5-(3'-methyl-2'-oxo-2',3'-dihydrospiro[cyclobutane-1,1'-pyrrolo[2,3-c]quinolin]-8'-yl)pyridin-3-yl)benzenesulfonamide | 514.30 | ¹H NMR (400 MHz, CDCl₃) δ 8.66 (s, 1H), 8.46 (d, J = 2.2 Hz, 1H), 8.41 (s, 1H), 8.32 (d, J = 8.7 Hz, 1H), 8.16 (d, J = 2.3 Hz, 1H), 7.92 (d, J = 7.7 Hz, 2H), 7.81 (d, J = 8.8 Hz, 1H), 7.58 (t, J = 7.4 Hz, 1H), 7.50 (t, J = 7.7 Hz, 2H), 3.39 (s, 3H), 2.98-2.87 (m, 2H), 2.84-2.74 (m, 3H), 2.69 (s, 6H), 2.64-2.53 (m, 1H). |

-continued

| Examples | Structure | Name | MS: [(M + 1)]+ | 1H NMR |
|---|---|---|---|---|
| 11 | 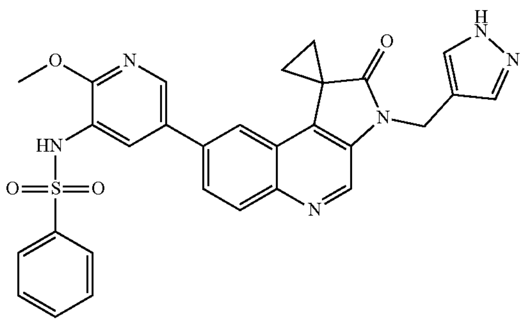 [SMILES: COc1ncc(-c2ccc3ncc4c(c3c2)C2(CC2)C(=O)N4Cc2cn[nH]c2)cc1NS(=O)(=O)c1ccccc1] | N-(5-(3'-((1H-Pyrazol-4-yl)methyl)-2'-oxo-2',3'-dihydrospiro[cyclopropane-1,1'-pyrrolo[2,3-c]quinolin]-8'-yl)-2-methoxypyridin-3-yl)benzenesulfonamide | 553.20 | 1H NMR (400 MHz, DMSO-d6) δ 12.79 (s, 1H), 8.96 (s, 1H), 8.30 (s, 1H), 8.08 (d, J = 8.8 Hz, 1H), 7.87-7.75 (m, 5H), 7.65-7.49 (m, 4H), 7.45 (s, 1H), 5.03 (s, 2H), 3.71 (s, 3H), 2.44 (q, J = 3.2 Hz, 2H), 1.83 (q, J = 3.6 Hz, 2H). |
| 12 | 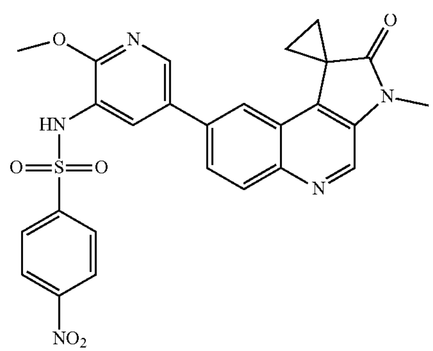 [SMILES: COc1ncc(-c2ccc3ncc4c(c3c2)C2(CC2)C(=O)N4C)cc1NS(=O)(=O)c1ccc([N+](=O)[O-])cc1] | N-(2-Methoxy-5-(3'-methyl-2'-oxo-2',3'-dihydrospiro[cyclopropane-1,1'-pyrrolo[2,3-c]quinolin]-8'-yl)pyridin-3-yl)-4-nitrobenzenesulfonamide | 532.20 | 1H NMR (300 MHz, DMSO-d6) δ 10.48 (s, 1H), 8.91 (s, 1H), 8.53-8.38 (m, 3H), 8.17-7.97 (m, 4H), 7.86 (d, J = 9.1 Hz, 1H), 7.51 (s, 1H), 3.65 (s, 3H), 3.42 (s, 3H), 3.17 (s, 2H), 1.88-1.67 (m, 2H). |
| 13 | 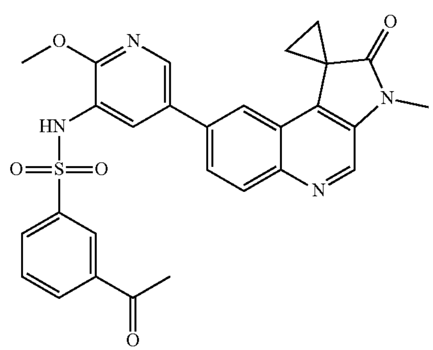 [SMILES: COc1ncc(-c2ccc3ncc4c(c3c2)C2(CC2)C(=O)N4C)cc1NS(=O)(=O)c1cccc(C(C)=O)c1] | 3-Acetyl-N-(2-methoxy-5-(3'-methyl-2'-oxo-2',3'-dihydrospiro[cyclopropane-1,1'-pyrrolo[2,3-c]quinolin]-8'-yl)pyridin-3-yl)benzenesulfonamide | 529.20 | 1H NMR (400 MHz, DMSO-d6) δ 10.26 (s, 1H), 8.92 (s, 1H), 8.45 (d, J = 2.3 Hz, 1H), 8.33 (s, 1H), 8.24 (d, J = 7.8 Hz, 1H), 8.13 (d, J = 8.8 Hz, 1H), 8.05-7.99 (m, 1H), 7.95 (d, J = 2.4 Hz, 1H), 7.82 (dd, J = 8.9, 1.8 Hz, 1H), 7.75 (t, J = 7.8 Hz, 1H), 7.51 (s, 1H), 3.66 (s, 3H), 3.42 (s, 3H), 2.61 (s, 3H), 2.48-2.44 (m, 2H), 1.81-1.74 (m, 2H). |

| Examples | Structure | Name | MS: [(M + 1)]+ | 1H NMR |
|---|---|---|---|---|
| 14 | 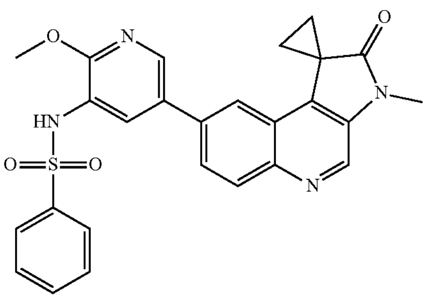 [SMILES: COc1ncc(-c2ccc3ncc4c(c3c2)C2(CC2)C(=O)N4C)cc1NS(=O)(=O)c1ccccc1] | N-(2-Methoxy-5-(3'-methyl-2'-oxo-2',3'-dihydrospiro[cyclopropane-1,1'-pyrrolo[2,3-c]quinolin]-8'-yl)pyridin-3-yl)benzenesulfonamide | 487.00 | 1H NMR (300 MHz, DMSO-d6) δ 10.03 (s, 1H), 8.87 (s, 1H), 8.37 (d, J = 2.3 Hz, 1H), 8.09 (d, J = 8.9 Hz, 1H), 7.87 (d, J = 2.3 Hz, 1H), 7.81-7.72 (m, 3H), 7.66-7.51 (m, 3H), 7.44 (d, J = 1.9 Hz, 1H), 3.67 (s, 3H), 3.42 (s, 3H), 2.42-2.25 (q, J = 4.2 Hz, 2H), 1.75 (q, J = 4.2 Hz, 2H). |
| 15 | 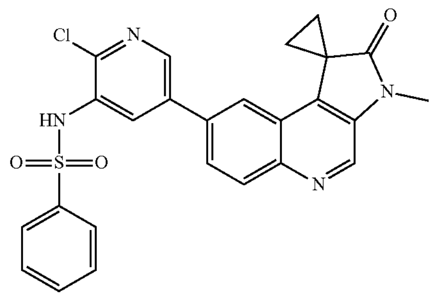 | N-(2-Chloro-5-(3'-methyl-2'-oxo-2',3'-dihydrospiro[cyclopropane-1,1'-pyrrolo[2,3-c]quinolin]-8'-yl)pyridin-3-yl)benzenesulfonamide | 490.90 | 1H NMR (400 MHz, DMSO-d6) δ 8.91 (s, 1H), 8.11 (d, J = 8.9 Hz, 2H), 7.85-7.68 (m, 4H), 7.50 (s, 3H), 7.44 (s, 1H), 3.40 (s, 3H), 2.36 (s, 2H), 1.79 (q, J = 4.4 Hz, 2H). |
| 16 | 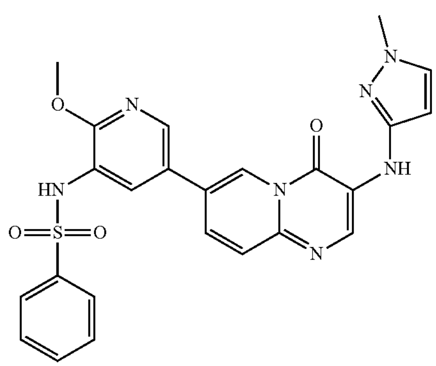 [SMILES: COc1ncc(-c2ccc3ncc(Nc4ccn(C)n4)c(=O)n3c2)cc1NS(=O)(=O)c1ccccc1] | N-(2-Methoxy-5-(3-((1-methyl-1H-pyrazol-3-yl)amino)-4-oxo-4H-pyrido[1,2-a]pyrimidin-7-yl)pyridin-3-yl)benzenesulfonamide | 504.00 | 1H NMR (300 MHz, CDCl3) δ 9.21 (s, 1H), 8.97 (s, 1H), 8.13 (d, J = 2.3 Hz, 1H), 8.01 (d, J = 2.3 Hz, 1H), 7.85 (d, J = 7.3 Hz, 2H), 7.70-7.47 (m, 5H), 7.00 (s, 2H), 5.93 (d, J = 2.3 Hz, 1H), 3.89 (s, 3H), 3.86 (s, 3H). |

-continued

| Examples | Structure | Name | MS: [(M + 1)]+ | 1H NMR |
|---|---|---|---|---|
| 17 | 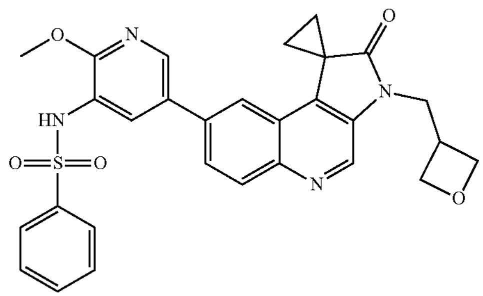 [SMILES: COc1ncc(-c2ccc3ncc4c(c3c2)C2(CC2)C(=O)N4CC2COC2)cc1NS(=O)(=O)c1ccccc1] | N-(2-Methoxy-5-(3 (oxetan-3-ylmethyl)-2'-oxo-2',3'-dihydrospiro[cyclopropane-1,1'-pyrrolo[2,3-c]quinolin]-8'-yl)pyridin-3-yl)benzenesulfonamide | 543.20 | 1H NMR (300 MHz, DMSO-d6) δ 10.04 (s, 1H), 8.96 (s, 1H), 8.36 (d, J = 2.3 Hz, 1H), 8.08 (d, J = 8.8 Hz, 1H), 7.85 (d, J = 2.3 Hz, 1H), 7.83-7.79 (m, 3H), 7.65-7.55 (m, 3H), 7.44 (d, J = 1.9 Hz, 1H), 4.63 (dd, J = 7.7, 6.0 Hz, 2H), 4.40 (t, J = 6.0 Hz, 2H), 4.24 (d, J = 7.2 Hz, 2H), 3.67 (s, 3H), 3.44-3.55 (m, 1H), 2.45 (q, J = 4.2 Hz, 2H), 1.78 (q, J = 4.3 Hz, 2H). |
| 18 | 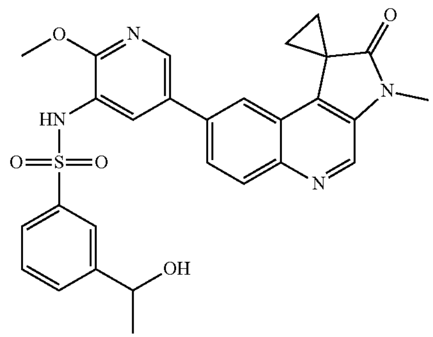 [SMILES: COc1ncc(-c2ccc3ncc4c(c3c2)C2(CC2)C(=O)N4C)cc1NS(=O)(=O)c1cccc(C(C)O)c1] | 3-(1-Hydroxyethyl)-N-(2-methoxy-5-(3'-methyl-2'-oxo-2',3'-dihydrospiro[cyclopropane-1,1'-pyrrolo[2,3-c]quinolin]-8'-yl)pyridin-3-yl)benzenesulfonamide | 531.10 | 1H NMR (400 MHz, DMSO-d6) δ 8.90 (s, 1H), 8.26 (s, 1H), 8.10 (d, J = 8.9 Hz, 1H), 7.94-7.71 (m, 3H), 7.64 (d, J = 7.6 Hz, 1H), 7.52-7.46 (m, 3H), 5.34 (d, J = 4.0 Hz, 1H), 4.84-4.71 (m, 1H), 3.73 (s, 3H), 3.42 (s, 3H), 2.46-2.39 (m, 2H), 1.81-1.76 (m, 2H), 1.26 (d, J = 6.5 Hz, 3H). |
| 19 | 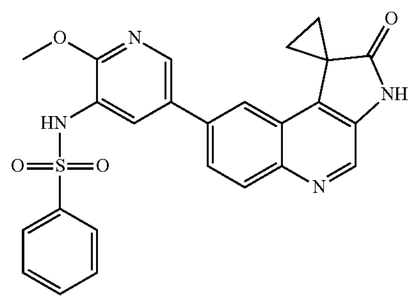 [SMILES: COc1ncc(-c2ccc3ncc4c(c3c2)C2(CC2)C(=O)N4)cc1NS(=O)(=O)c1ccccc1] | N-(2-Methoxy-5-(2'-oxo-2',3'-dihydrospiro[cyclopropane-1,1'-pyrrolo[2,3-c]quinolin]-8'-yl)pyridin-3-yl)benzenesulfonamide | 473.30 | 1H NMR (400 MHz, DMSO-d6) δ 11.03 (s, 1H), 10.08 (s, 1H), 8.68 (s, 1H), 8.39 (d, J = 2.2 Hz, 1H), 8.08 (d, J = 8.8 Hz, 1H), 7.88 (d, J = 2.1 Hz, 1H), 7.79 (t, J = 9.5 Hz, 3H), 7.69-7.55 (m, 3H), 7.45 (s, 1H), 3.70 (s, 3H), 2.39 (q, J = 3.9 Hz, 2H), 1.73 (q, J = 4.4 Hz, 2H). |

-continued

| Examples | Structure | Name | MS: [M + 1]+ | 1H NMR |
|---|---|---|---|---|
| 20 | 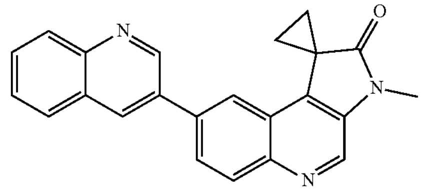 [SMILES: CN1C(=O)C2(CC2)c2c1cnc1ccc(-c3cnc4ccccc4c3)cc21] | 3'-Methyl-8'-(quinolin-3-yl)spiro[cyclopropane-1,1'-pyrrolo[2,3-c]quinolin]-2'(3'H)-one | 351.90 | 1H NMR (400 MHz, DMSO-d6) δ 9.40 (d, J = 2.3 Hz, 1H), 8.96 (s, 1H), 8.83 (d, J = 2.3 Hz, 1H), 8.21 (d, J = 8.8 Hz, 1H), 8.15-8.07 (m, 3H), 7.85-7.78 (m, 2H), 7.69 (t, J = 7.5 Hz, 1H), 3.44 (s, 3H), 2.61 (q, J = 4.4 Hz, 2H), 1.80 (q, J = 4.4 Hz, 2H). |
| 22 | 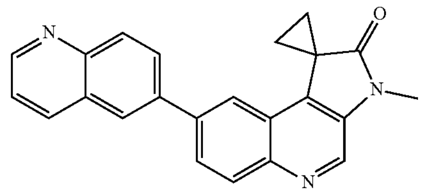 | 3'-Methyl-8'-(quinolin-6-yl)spiro[cyclopropane-1,1'-pyrrolo[2,3-c]quinolin]-2'(3'H)-one | 352.10 | 1H NMR (400 MHz, CDCl3) δ 8.97 (dd, J = 4.3, 1.6 Hz, 1H), 8.76 (s, 1H), 8.27 (t, J = 8.9 Hz, 3H), 8.07 (d, J = 2.0 Hz, 1H), 8.02 (dd, J = 8.7, 2.1 Hz, 1H), 7.96 (dd, J = 8.8, 1.9 Hz, 1H), 7.66 (d, J = 1.9 Hz, 1H), 7.49 (dd, J = 8.3, 4.2 Hz, 1H), 3.51 (s, 3H), 2.37 (q, J = 4.5 Hz, 2H), 2.05 (q, J = 4.4 Hz, 2H). |
| 23 | 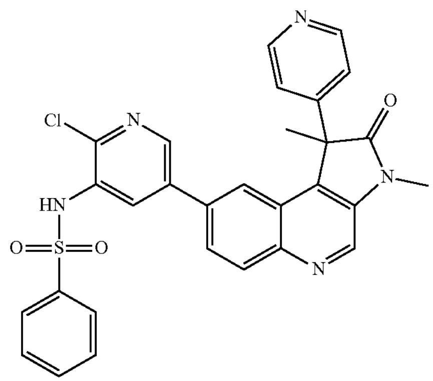 [SMILES: CN1C(=O)C(C)(c2ccncc2)c2c1cnc1ccc(-c3cnc(Cl)c(NS(=O)(=O)c4ccccc4)c3)cc21] | N-(2-Chloro-5-(1,3-dimethyl-2-oxo-1-(pyridin-4-yl)-2,3-dihydro-1H-pyrrolo[2,3-c]quinolin-8-yl)pyridin-3-yl)benzenesulfonamide | 556.10 | 1H NMR (400 MHz, DMSO-d6) δ 10.49 (s, 1H), 9.10 (s, 1H), 8.55-8.49 (m, 2H), 8.20 (d, J = 8.9 Hz, 1H), 7.85 (d, J = 7.5 Hz, 2H), 7.71 (d, J = 7.7 Hz, 2H), 7.65 (s, 1H), 7.59-7.50 (m, 3H), 7.30-7.23 (m, 2H), 3.40 (s, 3H), 2.00 (s, 3H). |

-continued

| Examples | Structure | Name | MS: [(M + 1)]+ | 1H NMR |
|---|---|---|---|---|
| 24 | 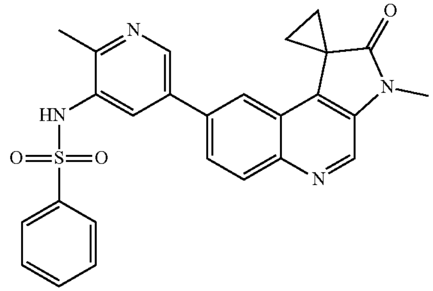 [SMILES: Cc1ncc(-c2ccc3ncc4c(c3c2)C2(CC2)C(=O)N4C)cc1NS(=O)(=O)c1ccccc1] | N-(2-Methyl-5-(3'-methyl-2'-oxo-2',3'-dihydrospiro[cyclopropane-1,1'-pyrrolo[2,3-c]quinolin]-8'-yl)pyridin-3-yl)benzenesulfonamide | 471.10 | 1H NMR (400 MHz, DMSO-d6) δ 10.05 (s, 1H), 8.93 (s, 1H), 8.77-8.71 (m, 1H), 8.13 (d, J = 8.9 Hz, 1H), 7.80-7.65 (m, 5H), 7.60 (t, J = 7.6 Hz, 2H), 7.50 (s, 1H), 3.42 (s, 3H), 2.41 (q, J = 4.5 Hz, 2H), 2.23 (s, 3H), 1.80 (q, J = 4.3 Hz, 2H). |
| 25 | 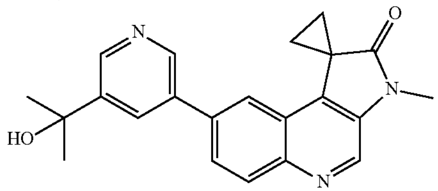 [SMILES: CN1C(=O)C2(CC2)c2c1cnc1ccc(-c3cncc(C(C)(C)O)c3)cc21] | 8'-(5-(2-Hydroxypropan-2-yl)pyridin-3-yl)-3-methylspiro[cyclopropane-1,1'-pyrrolo[2,3-c]quinolin]-2(3'-H)-one | 360.20 | 1H NMR (300 MHz, DMSO-d6) δ 8.94 (s, 1H), 8.90 (d, J = 2.2 Hz, 1H), 8.75 (d, J = 2.1 Hz, 1H), 8.21-8.15 (m, 2H), 7.95 (dd, J = 8.7, 1.8 Hz, 1H), 7.65 (s, 1H), 5.33 (s, 1H), 3.43 (s, 3H), 2.55 (q, J = 4.2 Hz, 2H), 1.78 (q, J = 4.2 Hz, 2H), 1.54 (s, 6H). |
| 26 | 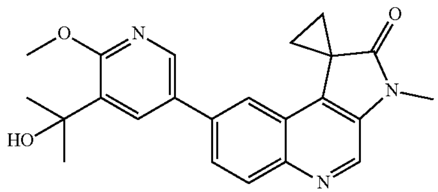 | 8'-(5-(2-Hydroxypropan-2-yl)-6-methoxypyridin-3-yl)-3'-methylspiro[cyclopropane-1,1'-pyrrolo[2,3-c]quinolin]-2(3'-H)-one | 390.20 | 1H NMR (300 MHz, DMSO-d6) δ 8.91 (s, 1H), 8.53 (d, J = 2.5 Hz, 1H), 8.25 (d, J = 2.6 Hz, 1H), 8.14 (d, J = 8.8 Hz, 1H), 7.88 (dd, J = 8.9, 1.9 Hz, 1H), 7.58 (d, J = 1.8 Hz, 1H), 5.30 (s, 1H), 3.97 (s, 3H), 3.42 (s, 3H), 2.48 (q, J = 4.2 Hz, 2H), 1.79 (q, J = 4.2 Hz, 2H), 1.54 (s, 6H). |
| 28 | 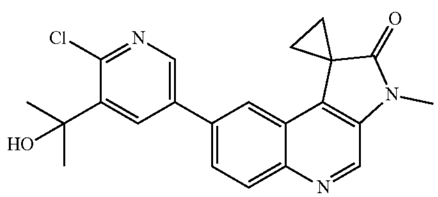 [SMILES: CN1C(=O)C2(CC2)c2c1cnc1ccc(-c3cnc(Cl)c(C(C)(C)O)c3)cc21] | 8'-(6-Chloro-5-(2-hydroxypropan-2-yl)pyridin-3-yl)-3'-methylspiro[cyclopropane-1,1'-pyrrolo[2,3-c]quinolin]-2(3'-H)-one | 394.10 | 1H NMR (300 MHz, DMSO-d6) δ 8.95 (s, 1H), 8.78 (d, J = 2.5 Hz, 1H), 8.51 (d, J = 2.5 Hz, 1H), 8.18 (d, J = 8.8 Hz, 1H), 7.92 (dd, J = 8.9, 1.9 Hz, 1H), 7.67 (d, J = 2.0 Hz, 1H), 5.62 (s, 1H), 3.43 (s, 3H), 2.52 (q, J = 4.2 Hz, 2H), 1.79 (q, J = 4.2 Hz, 2H), 1.68 (s, 6H). |

-continued

| Examples | Structure | Name | MS: [(M + 1)]+ | 1H NMR |
|---|---|---|---|---|
| 29 | 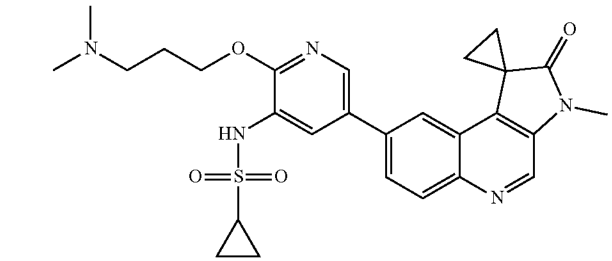 | N-(2-(3-(Dimethylamino) propoxy)-5-(3'-methyl-2'-oxo-2',3'-dihydrospiro [cyclopropane-1,1'-pyrrolo[2,3-c]quinolin]-8'-yl)pyridin-3-yl) cyclopropanesulfonamide | 522.20 | 1H NMR (300 MHz, CD3OD) δ 8.79 (s, 1H), 8.22 (d, J = 2.4 Hz, 1H), 8.13 (d, J = 9.0 Hz, 1H), 8.08 (d, J = 2.3 Hz, 1H), 7.88 (dd, J = 9.0, 2.0 Hz, 1H), 7.60 (d, J = 1.9 Hz, 1H), 4.51 (t, J = 6.2 Hz, 2H), 3.49 (s, 3H), 2.76 (t, J = 7.1 Hz, 2H), 2.47 (s, 6H), 2.52-2.41 (m, 1H), 2.17-2.06 (m, 2H), 1.95 (q, J = 4.5 Hz, 2H), 1.11-1.03 (m, 2H), 1.02-0.94 (m, 2H). |
| 30 | 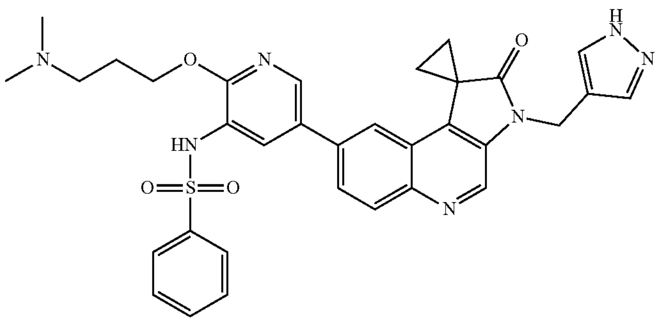 [SMILES: CN(C)CCCOc1ncc(-c2ccc3ncc4c(c3c2)C2(CC2)C(=O)N4Cc2cn[nH]c2)cc1NS(=O)(=O)c1ccccc1] | N-(5-(3'-((1H-Pyrazol-4-yl)methyl)-2'-oxo-2',3'-dihydrospiro[cyclopropane-1,1'-pyrrolo[2,3-c]quinolin]-8'-yl)-2-(3-(dimethylamino) propoxy)pyridin-3-yl)benzenesulfonamide | 624.20 | 1H NMR (300 MHz, DMSO-d6) 12.73 (br, 1H), 8 8.93 (s, 1H), 8.04 (d, J = 8.9 Hz, 1H), 7.91 (d, J = 2.3 Hz, 1H), 7.84-7.79 (m, 2H), 7.68 (dd, J = 8.8, 1.8 Hz, 2H), 7.55 (d, J = 2.3 Hz, 1H), 7.52-7.46 (m, 4H), 7.30 (d, J = 1.9 Hz, 1H), 5.02 (s, 2H), 4.28 (t, J = 5.8 Hz, 2H), 3.09 (s, 2H), 2.76 (s, 6H), 2.33-2.26 (m, 2H), 2.10-2.01 (m, 2H), 1.85 (q, J = 4.3 Hz, 2H). |
| 31 | 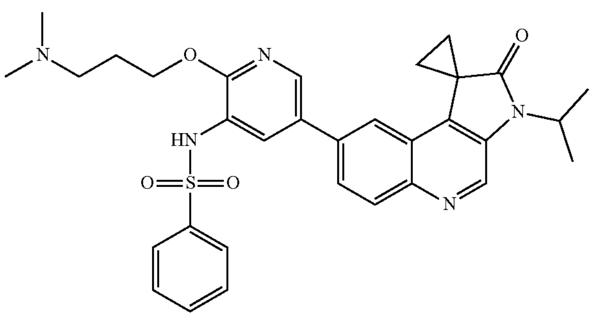 [SMILES: CC(C)N1C(=O)C2(CC2)c2c1cnc1ccc(-c3cnc(OCCCN(C)C)c(NS(=O)(=O)c4ccccc4)c3)cc21] | N-(2-(3-(Dimethylamino) propoxy)-5-(3'-isopropyl-2'-oxo-2',3'-dihydrospiro [cyclopropane-1,1'-pyrrolo[2,3-c]quinolin]-8'-yl)pyridin-3-yl)benzenesulfonamide | 586.20 | 1H NMR (300 MHz, DMSO-d6) δ 9.04 (s, 1H), 8.07 (d, J = 8.8 Hz, 1H), 7.93 (d, J = 2.3 Hz, 1H), 7.87-7.80 (m, 2H), 7.70 (dd, J = 8.9, 1.8 Hz, 1H), 7.60-7.45 (m, 4H), 7.31 (d, J = 1.9 Hz, 1H), 4.82-4.75 (m, 1H), 4.29 (t, J = 5.7Hz, 2H), 3.11 (m, 2H), 2.78 (s, 6H), 2.35-2.26 (m, 2H), 2.10-2.01(m, 2H), 1.85-1.78 (m, 2H), 1.53 (d, J = 7.0 Hz, 6H). |

| Examples | Structure | Name | MS: [M + 1]+ | 1H NMR |
|---|---|---|---|---|
| 32 | 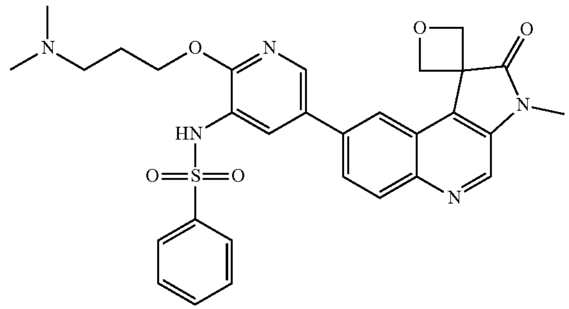 | N-(2-(3-(Dimethylamino) propoxy)-5-(3'-methyl-2'-oxo-2',3'-dihydrospiro[oxetane-3,1'-pyrrolo[2,3-c]quinolin]-8'-yl)benzenesulfonamide | 574.20 | 1H NMR (300 MHz, DMSO-$d_6$) δ 8.85 (s, 1H), 8.51 (d, J = 2.0 Hz, 1H), 8.14 (d, J = 8.9 Hz, 1H), 7.97 (d, J = 2.3 Hz, 1H), 7.84 (dd, J = 6.6, 3.0 Hz, 2H), 7.76 (dd, J = 8.9, 2.0 Hz, 1H), 7.72 (d, J = 2.3 Hz, 1H), 7.49-7.42 (m, 3H), 5.08-4.94 (m, 4H), 4.29 (t, J = 5.7 Hz, 2H), 3.31 (s, 3H), 3.09 (t, J = 5.7 Hz, 2H), 2.77 (s, 6H), 2.11-2.00 (m, 2H). |
| 33 | 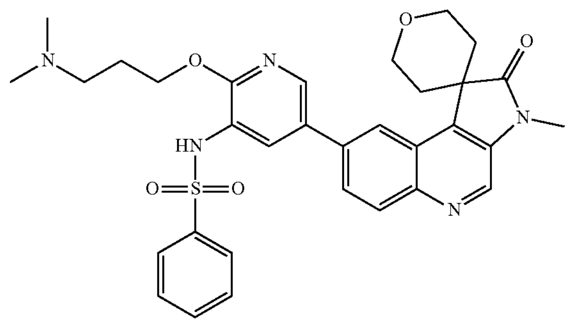 | N-(2-(3-(Dimethylamino) propoxy)-5-(3'-methyl-2'-oxo-2',3',5',6'-hexahydrospiro[pyran-4,1'-pyrrolo[2,3-c]quinolin]-8'-yl)benzenesulfonamide | 602.20 | 1H NMR (300 MHz, DMSO-$d_6$) δ 8.90 (s, 1H), 8.13 (d, J = 8.8 Hz, 1H), 8.01 (s, 1H), 7.95 (d, J = 2.3 Hz, 1H), 7.85 (dd, J = 6.5, 3.0 Hz, 2H), 7.73-7.66 (m, 2H), 7.50-7.45 (m, 3H), 4.39-4.23 (m, 4H), 4.00-3.84 (m, 2H), 3.33 (s, 3H), 3.13 (t, J = 5.7 Hz, 2H), 2.81 (s, 6H), 2.60 (t, J = 10.4 Hz, 2H), 2.09 (d, J = 4.6 Hz, 2H), 1.72 (d, J = 14.1 Hz, 2H). |
| 34 | 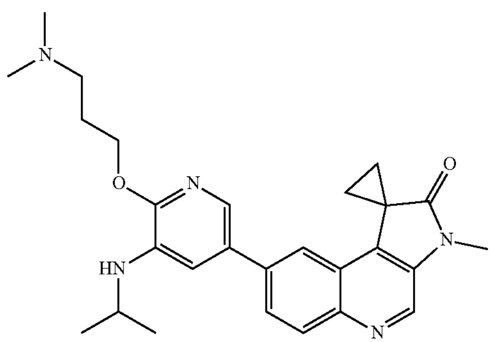 | 8'-(6-(3-Dimethylamino) propoxy)-5-(isopropylamino) pyridin-3-yl)-3'-methylspiro[cyclopropane-1,1'-pyrrolo[2,3-c]quinolin]-2'(3'-H)-one | 460.50 | 1H NMR (400 MHz, DMSO-$d_6$) δ 8.89 (s, 1H), 8.09 (d, J = 8.9 Hz, 1H), 7.88 (dd, J = 8.9, 1.9 Hz, 1H), 7.76 (d, J = 2.1 Hz, 1H), 7.51 (d, J = 1.9 Hz, 1H), 7.13 (d, J = 2.1 Hz, 1H), 4.67 (d, J = 8.5 Hz, 1H), 4.37 (t, J = 6.7 Hz, 2H), 3.87-3.73 (m, 1H), 3.42 (s, 3H), 2.36 (t, J = 7.0 Hz, 2H), 2.16 (s, 6H), 1.91 (p, J = 6.9 Hz, 2H), 1.76 (q, J = 4.3 Hz, 2H), 1.22 (d, J = 6.3 Hz, 6H). |

| Examples | Structure | Name | MS: [(M + 1)]+ | 1H NMR |
|---|---|---|---|---|
| 35 | 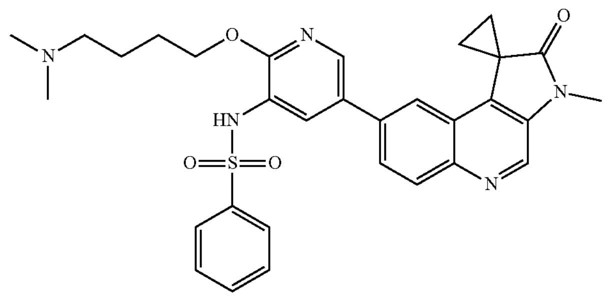 | N-(2-(4-(Dimethylamino)butoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | 572.50 | 1H NMR (300 MHz, DMSO-$d_6$) δ 8.89 (s, 1H), 8.17 (d, J = 2.3 Hz, 1H), 8.10 (d, J = 8.9 Hz, 1H), 7.83-7.72 (m, 4H), 7.60-7.46 (m, 3H), 7.41 (s, 1H), 4.18 (t, J = 6.1 Hz, 2H), 3.41 (s, 3H), 2.49 (s, 2H), 2.41-2.36 (m, 2H), 2.35 (s, 6H), 1.80 (q, J = 4.0 Hz, 2H), 1.68-1.51 (m, 4H). |
| 36 | 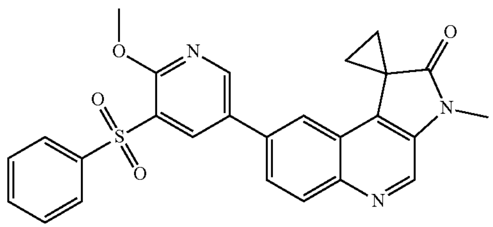 [SMILES: COc1ncc(-c2ccc3ncc4c(c3c2)C2(CC2)C(=O)N4C)cc1S(=O)(=O)c1ccccc1] | 8'-(6-Methoxy-5-(phenylsulfonyl)pyridin-3-yl)-3'-methylspirocyclopropane-1,1'-pyrrolo[2,3-c]quinolin]-2'(3'-H)-one | 472.50 | 1H NMR (300 MHz, CDCl$_3$) δ 8.77 (s, 1H), 8.68 (d, J = 2.5 Hz, 1H), 8.60 (d, J = 2.5 Hz, 1H), 8.40 (d, J = 8.8 Hz, 1H), 8.08-8.03 (m, 2H), 7.84 (d, J = 8.7 Hz, 1H), 7.65 (t, J = 7.3 Hz, 1H), 7.59-7.51 (m, 3H), 4.01 (s, 3H), 3.51 (s, 3H), 2.38 (q, J = 3.9 Hz, 2H), 2.12 (q, J = 3.7 Hz, 2H). |
| 37 | 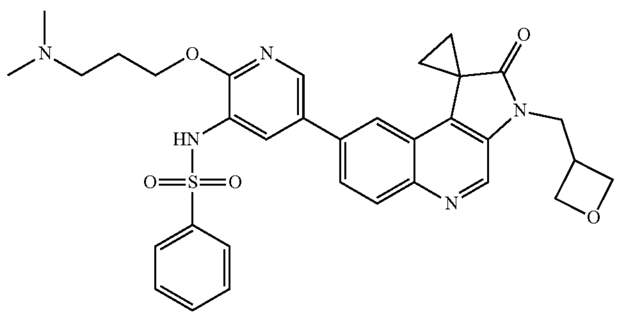 [SMILES: CN(C)CCCOc1ncc(-c2ccc3ncc4c(c3c2)C2(CC2)C(=O)N4CC2COC2)cc1NS(=O)(=O)c1ccccc1] | N-(2-(3-(Dimethylamino)propoxy)-5-(3'-(oxetan-3-ylmethyl)-2'-oxo-2',3'-dihydrospiro[cyclopropane-1,1'-pyrrolo[2,3-c]quinolin]-8'-yl)pyridin-3-yl)benzenesulfonamide | 614.20 | 1H NMR (400 MHz, DMSO-$d_6$) δ 8.97 (s, 1H), 8.09 (d, J = 8.8 Hz, 1H), 8.03 (s, 1H), 7.82 (dd, J = 7.4, 2.2 Hz, 2H), 7.73 (d, J = 8.9 Hz, 1H), 7.64 (s, 1H), 7.57-7.49 (m, 3H), 7.35 (s, 1H), 4.67 (dd, J = 7.7, 6.0 Hz, 2H), 4.44 (t, J = 6.1 Hz, 2H), 4.28 (d, J = 6.9 Hz, 4H), 3.52-3.45 (m, 1H), 3.19 (t, J = 6.1 Hz, 2H), 2.83 (s, 5H), 2.34 (s, 2H), 2.07 (d, J = 7.3 Hz, 2H), 1.85 (q, J = 4.3 Hz, 2H). |

-continued

| Examples | Structure | Name | MS: [(M + 1)]+ | 1H NMR |
|---|---|---|---|---|
| 38 | 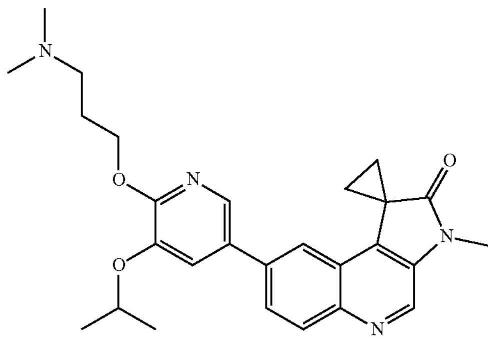 | 8'-(6-(3-(Dimethylamino) propoxy)-5-isopropoxypyridin-3-yl)-3'-methylspiro[cyclopropane-1,1'-pyrrolo[2,3-c]quinolin]-2'(3'-H)-one | 461.20 | 1H NMR (300 MHz, DMSO-d6) δ 8.90 (s, 1H), 8.20-8.06 (m, 2H), 7.92 (dd, J = 8.9, 1.9 Hz, 1H), 7.69 (d, J = 2.1 Hz, 1H), 7.54 (d, J = 1.9 Hz, 1H), 4.76 (p, J = 6.1 Hz, 1H), 4.36 (t, J = 6.7 Hz, 2H), 2.55 (q, J = 4.4 Hz, 2H), 2.36 (t, J = 7.1 Hz, 2H), 2.15 (s, 6H), 1.88 (p, J = 6.8 Hz, 2H), 1.75 (q, J = 4.3 Hz, 2H), 1.32 (d, J = 6.0 Hz, 6H). |
| 39 | 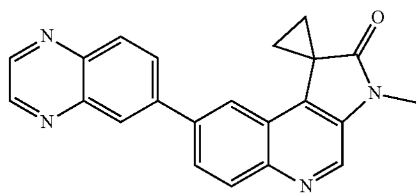 [SMILES: CN1C(=O)C2(CC2)c2c1cnc1ccc(-c3ccc4nccnc4c3)cc21] | 3'-Methyl-8'-(quinoxalin-6-yl)spiro[cyclopropane-1,1'-pyrrolo[2,3-c]quinolin]-2'(3'-H)-one | 353.40 | 1H NMR (300 MHz, DMSO-d6) δ 9.03 (d, J = 1.8 Hz, 1H), 8.99 (d, J = 1.8 Hz, 1H), 8.96 (s, 1H), 8.55 (d, J = 2.0 Hz, 1H), 8.39 (dd, J = 8.8, 2.1 Hz, 1H), 8.22 (t, J = 9.0 Hz, 2H), 8.13 (dd, J = 6.0 Hz, 1H), 7.81 (s, 1H), 3.44 (s, 3H), 2.60 (q, J = 4.4 Hz, 2H), 1.81 (q, J = 4.5 Hz, 2H). |
| 40 | 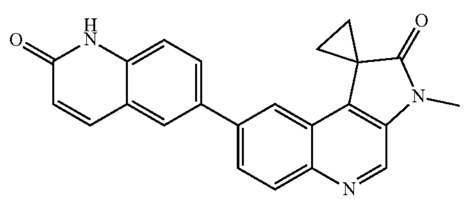 [SMILES: CN1C(=O)C2(CC2)c2c1cnc1ccc(-c3ccc4[nH]c(=O)ccc4c3)cc21] | 3'-Methyl-8'-(2-oxo-1,2,4a,8a-tetrahydroquinolin-6-yl)spiro[cyclopropane-1,1'-pyrrolo[2,3-c]quinolin]-2'(3'-H)-one | 368.10 | 1H NMR (300 MHz, DMSO-d6) δ 8.91(s, 1H), 8.20-8.09 (m, 2H), 8.08-7.91(m, 3H), 7.62 (s, 1H), 7.45 (d, J = 8.7 Hz, 1H), 6.57 (d, J = 9.5 Hz, 1H), 3.42 (s, 3H), 1.79 (q, J = 4.2 Hz, 2H), 1.24 (q, J = 4.5 Hz, 2H) |
| 41 | 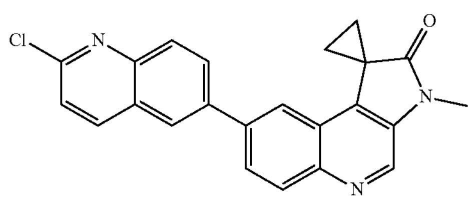 [SMILES: CN1C(=O)C2(CC2)c2c1cnc1ccc(-c3ccc4nc(Cl)ccc4c3)cc21] | 8'-(2-Chloroquinolin-6-yl)-3'-methylspiro [cyclopropane-1,1'-pyrrolo [2,3-c]quinolin]-2'(3'-H)-one | 386.10 | 1H NMR (300 MHz, CDCl3) δ 8.76 (s, 1H), 8.31-8.12 (m, 3H), 8.06 (s, 2H), 7.93 (d, J = 9.3 Hz, 1H), 7.64 (s, 1H), 7.47 (d, J = 8.6 Hz, 1H), 3.51 (s, 3H), 2.37 (s, 2H), 2.06 (s, 2H). |

-continued

| Examples | Structure | Name | MS: [(M + 1)]+ | ¹H NMR |
|---|---|---|---|---|
| 42 | 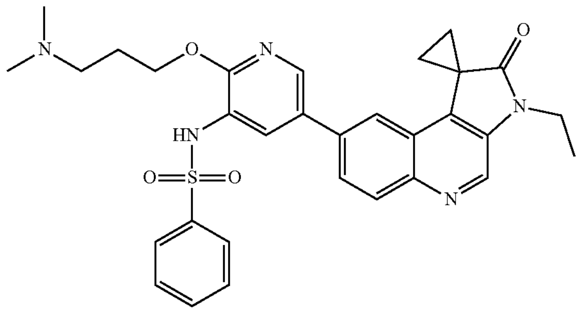 [SMILES: CCN1C(=O)C2(CC2)c2c1cnc1ccc(-c3cnc(OCCCN(C)C)c(NS(=O)(=O)c4ccccc4)c3)cc21] | N-(2-(3-(Dimethylamino) propoxy)-5-(3'-ethyl-2'-oxo-2',3'-dihydrospiro [cyclopropane-1,1'-pyrrolo[2,3-c]quinolin]-8'-yl)pyridin-3-yl)benzenesulfonamide | 572.20 | ¹H NMR (300 MHz, DMSO-d₆) δ 8.92 (s, 1H), 8.06 (d, J = 8.9 Hz, 1H), 7.87-7.77 (m, 3H), 7.68 (dd, J = 8.8, 1.9 Hz, 1H), 7.53 (d, J = 2.3 Hz, 1H), 7.51-7.42 (m, 3H), 7.29 (d, J = 1.9 Hz, 1H), 4.27 (t, J = 6.1 Hz, 2H), 3.98 (q, J = 7.1 Hz, 2H), 2.76-2.54 (m, 8H), 2.28 (t, J = 4.7 Hz, 2H), 2.01 (t, J = 5.9 Hz, 2H), 1.82 (q, J = 4.3 Hz, 2H), 1.27 (t, J = 7.1 Hz, 3H). |
| 43 | 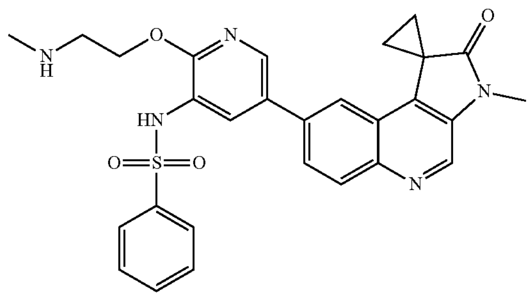 | N-(5-(3'-Methyl-2'-oxo-2',3'-dihydrospiro [cyclopropane-1,1'-pyrrolo[2,3-c]quinolin]-8'-yl)-2-(2-(methylamino)ethoxy) pyridin-3-yl)benzenesulfonamide | 530.20 | ¹H NMR (400 MHz, CDCl₃) δ 8.68 (s, 1H), 8.13-7.99 (m, 3H), 7.90 (d, J = 1.7 Hz, 1H), 7.63-7.40 (m, 4H), 7.29 (d, J = 1.9 Hz, 1H), 4.61 (s, 2H), 3.50 (s, 3H), 3.27 (s, 2H), 2.80 (s, 3H), 2.21 (q, J = 4.5 Hz, 2H), 1.98 (q, J = 4.3 Hz, 2H). |
| 44 | 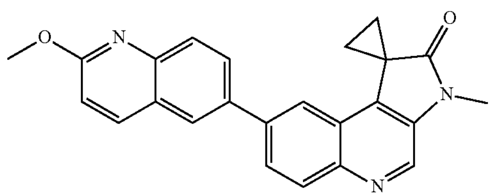 | 8'-(2-Methoxyquinolin-6-yl)-3'-methylspiro [cyclopropane-1,1'-pyrrolo[2,3-c]quinolin]-2'(3'-H)-one | 382.20 | ¹H NMR (300 MHz, CDCl₃) δ 8.73 (s, 1H), 8.28 (d, J = 8.9 Hz, 1H), 8.08 (d, J = 8.8 Hz, 1H), 8.00-7.88 (m, 4H), 7.63 (d, J = 2.0 Hz, 1H), 6.98 (d, J = 8.8 Hz, 1H), 4.12 (s, 3H), 3.50 (s, 3H), 2.40 (q, J = 4.4 Hz, 2H), 2.07 (q, J = 4.4 Hz, 2H). |
| 45 | 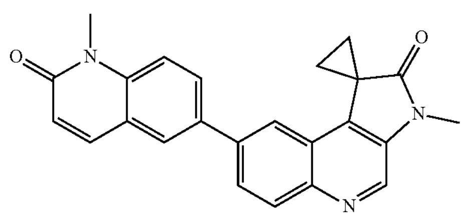 [SMILES: CN1C(=O)C2(CC2)c2c1cnc1ccc(-c3ccc4c(ccc(=O)n4C)c3)cc21] | 3'-Methyl-8'-(1-methyl-2-oxo-1,2-dihydroquinolin-6-yl)spiro[cyclopropane-1,1'-pyrrolo[2,3-c]quinolin]-2'(3'-H)-one | 382.10 | ¹H NMR (400 MHz, CDCl₃) δ 8.74 (s, 1H), 8.28 (s, 1H), 7.95-7.83 (m, 2H), 7.82-7.68 (m, 2H), 7.65-7.40 (m, 2H), 6.80 (d, J = 9.4 Hz, 1H), 3.79 (s, 3H), 3.51 (s, 3H), 2.37 (q, J = 3.8 Hz, 2H), 2.16-1.91 (m, 2H). |

-continued

| Examples | Structure | Name | MS: [(M + 1)]+ | ¹H NMR |
|---|---|---|---|---|
| 46 | 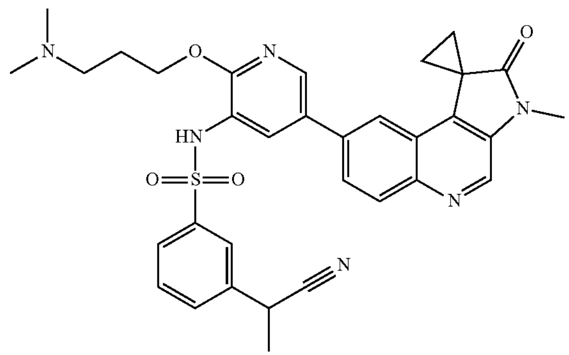 | 3-(1-Cyanoethyl)-N-((2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | 611.30 | ¹H NMR (300 MHz, DMSO-d₆) δ 8.88 (s, 1H), 8.07 (d, J = 8.8 Hz, 1H), 7.91 (d, J = 2.3 Hz, 2H), 7.87-7.71 (m, 2H), 7.63 (dd, J = 8.9, 1.8 Hz, 1H), 7.54 (dd, J = 6.0, 3.5 Hz, 3H), 7.34 (d, J = 1.9 Hz, 1H), 4.43 (q, J = 7.2 Hz, 1H), 4.30 (t, J = 5.6 Hz, 2H), 3.41 (s, 3H), 3.19 (t, J = 5.4 Hz, 2H), 2.84 (s, 6H), 2.30 (q, J = 4.5 Hz, 2H), 2.14-2.04 (m, 2H), 1.79 (q, J = 4.3 Hz, 2H), 1.50 (d, J = 7.2 Hz, 3H). |
| 47 | 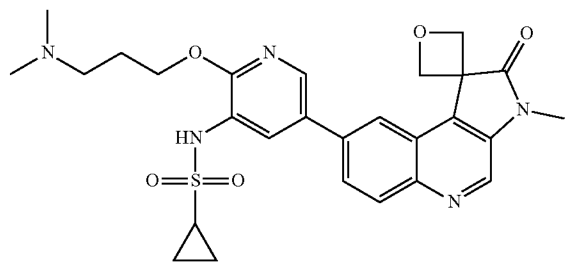 | N-(2-(3-(Dimethylamino)propoxy)-5-(3'-methyl-2'-oxo-2',3'-dihydrospiro[oxetane-3,1'-pyrrolo[2,3-c]quinolin]-8'-yl)pyridin-3-yl)cyclopropanesulfonamide | 538.00 | ¹H NMR (300 MHz, DMSO-d₆) δ 8.88 (s, 1H), 8.63 (d, J = 1.9 Hz, 1H), 8.34 (d, J = 2.3 Hz, 1H), 8.19 (d, J = 8.9 Hz, 1H), 8.01 (d, J = 2.3 Hz, 1H), 7.96 (dd, J = 8.9, 2.0 Hz, 1H), 5.02 (s, 4H), 4.40 (t, J = 6.3 Hz, 2H), 3.31 (s, 3H), 2.76-2.65 (m, 1H), 2.58 (t, J = 6.7 Hz, 2H), 2.29 (s, 6H), 1.96 (p, J = 6.5 Hz, 2H), 0.96-0.90 (m, 4H). |
| 48 | 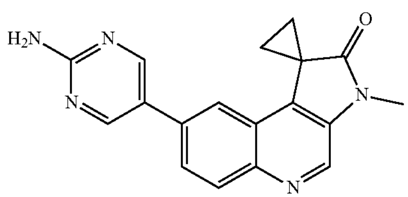 [SMILES: CN1C(=O)C2(CC2)c2c1cnc1ccc(-c3cnc(N)nc3)cc21] | 8'-(2-Aminopyrimidin-5-yl)-3'-methylspiro[cyclopropane-1,1'-pyrrolo[2,3-c]quinolin]-2'(3'-H)-one | 318.20 | ¹H NMR (300 MHz, DMSO-d₆) δ 8.88 (s, 1H), 8.74 (s, 2H), 8.09 (d, J = 8.9 Hz, 1H), 7.89 (dd, J = 8.9, 1.9 Hz, 1H), 7.53 (d, J = 1.9 Hz, 1H), 6.90 (s, 2H), 3.42 (s, 3H), 2.56 (q, J = 4.2 Hz, 2H), 1.75 (q, J = 4.2 Hz, 2H). |

| Examples | Structure | Name | MS: [(M + 1)]+ | 1H NMR |
|---|---|---|---|---|
| 50 | 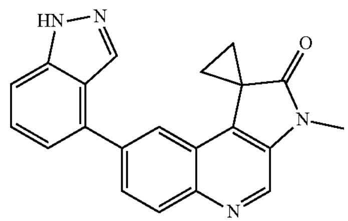 [SMILES: CN1C(=O)C2(CC2)c2c1cnc1ccc(-c3cccc4[nH]ncc34)cc21] | 8'-(1H-indazol-4-yl)-3'-methylspiro[cyclopropane-1,1'-pyrrolo[2,3-c]quinolin]-2'(3'-H)-one | 341.20 | 1H NMR (300 MHz, DMSO-d6) δ 13.33 (s, 1H), 8.95 (s, 1H), 8.26 (s, 1H), 8.20 (d, J = 8.8 Hz, 1H), 7.99 (dd, J = 8.8, 1.8 Hz, 1H), 7.70 (d, J = 1.9 Hz, 1H), 7.62 (d, J = 8.2 Hz, 1H), 7.50 (t, J = 7.6 Hz, 1H), 7.42 (d, J = 7.2 Hz, 1H), 3.44 (s, 3H), 2.43 (q, J = 4.5 Hz, 2H), 1.79 (q, J = 4.5 Hz, 2H). |
| 51 | 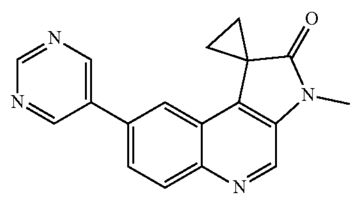 [SMILES: CN1C(=O)C2(CC2)c2c1cnc1ccc(-c3cncnc3)cc21] | 3'-Methyl-8'-(pyrimidin-5-yl)spiro[cyclopropane-1,1'-pyrrolo[2,3-c]quinolin]-2'(3'-H)-one | 303.00 | 1H NMR(400 MHz, DMSO-d6) δ 9.31 (s, 2H), 9.25 (s, 1H), 8.96 (s, 1H), 8.19 (d, J = 8.8 Hz, 1H), 8.02 (dd, J = 8.9, 2.0 Hz, 1H), 7.75 (d, J = 2.0 Hz, 1H), 3.43 (s, 3H), 2.61 (q, J = 4.4 Hz, 2H), 1.77 (q, J = 4.3 Hz, 2H). |
| 52 | 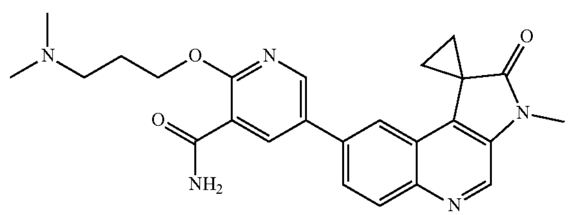 | 2-(3-(Dimethylamino)propoxy)-5-(3'-methyl-2'-oxo-2',3'-dihydrospiro[cyclopropane-1,1'-pyrrolo[2,3-c]quinolin]-8'-yl)nicotinamide | 446.30 | 1H NMR (400 MHz, CD3OD) δ 8.82 (s, 1H), 8.70 (d, J = 2.6 Hz, 1H), 8.63 (d, J = 2.6 Hz, 1H), 8.17 (d, J = 8.9 Hz, 1H), 7.93 (dd, J = 8.9, 2.0 Hz, 1H), 7.68 (d, J = 1.9 Hz, 1H), 4.65 (t, J = 6.2 Hz, 2H), 3.50 (s, 3H), 2.65 (t, J = 7.3 Hz, 2H), 2.51 (q, J = 4.5 Hz, 2H), 2.38 (s, 6H), 2.12 (p, J = 6.6 Hz, 2H), 1.96 (q, J = 4.4 Hz, 2H). |
| 54 | 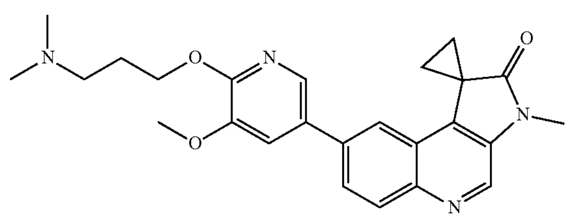 | 8'-(6-(3-(Dimethylamino)propoxy)-5-methoxypyridin-3-yl)-3'-methylspiro[cyclopropane-1,1'-pyrrolo[2,3-c]quinolin]-2'(3'-H)-one | 433.30 | 1H NMR (300 MHz, DMSO-d6) δ 8.91 (s, 1H), 8.18-8.08 (m, 2H), 7.94 (dd, J = 8.9, 1.9 Hz, 1H), 7.67 (d, J = 2.1 Hz, 1H), 7.57 (d, J = 1.9 Hz, 1H), 4.36 (t, J = 6.7 Hz, 2H), 3.92 (s, 3H), 3.42 (s, 3H), 2.55 (t, J = 3.1 Hz, 2H), 2.35 (t, J = 7.0 Hz, 2H), 2.15 (s, 6H), 1.89 (p, J = 7.0 Hz, 2H), 1.76 (q, J = 4.3 Hz, 2H). |

| Examples | Structure | Name | MS: [(M + 1)]+ | 1H NMR |
|---|---|---|---|---|
| 55 | 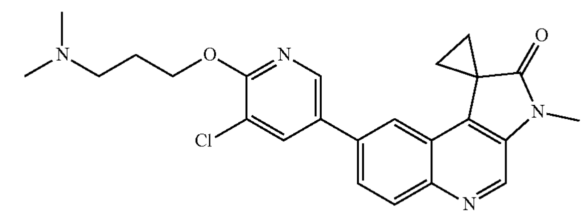 | 8'-(5-Chloro-6-(3-(dimethylamino)propoxy)pyridin-3-yl)-3'-methylspiro[cyclopropane-1,1'-pyrrolo[2,3-c]quinolin]-2'(3'H)-one | 437.10 | 1H NMR (300 MHz, DMSO-d6) δ 8.92 (s, 1H), 8.60 (d, J = 2.2 Hz, 1H), 8.43 (d, J = 2.2 Hz, 1H), 8.12 (d, J = 8.9 Hz, 1H), 7.94 (d, J = 10.8 Hz, 1H), 7.60 (s, 1H), 4.45 (t, J = 6.5 Hz, 2H), 3.43 (s, 3H), 2.59 (t, J = 3.7 Hz, 2H), 2.39 (t, J = 7.1 Hz, 2H), 2.17 (s, 6H), 1.92-1.87 (m, 2H), 1.79-1.75 (m, 2H). |
| 56 | 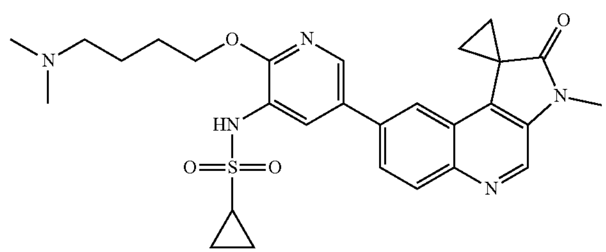 | N-(2-(4-(Dimethylamino)butoxy)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide | 536.30 | 1H NMR (300 MHz, CDCl3) δ 8.73 (s, 1H), 8.23-8.17 (m 2H), 8.08 (d, J = 2.3 Hz, 1H), 7.75 (dd, J = 8.9, 2.0 Hz, 1H), 7.47 (d, J = 2.0 Hz, 1H), 4.50 (t, J = 6.0 Hz, 2H), 3.49 (s, 3H), 2.85-2.42 (m, 9H), 2.31 (q, J = 4.4 Hz, 2H), 2.01 (q, J = 4.4 Hz, 2H), 1.99-1.80 (m, 4H), 1.32-1.23 (m, 2H), 1.10-1.01 (m, 2H). |
| 57 | 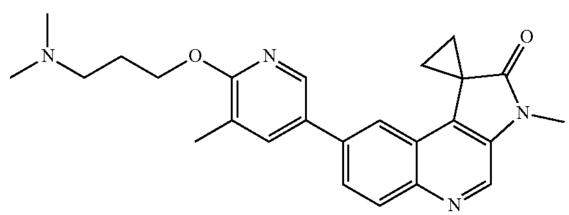 | 8'-(6-(3-(Dimethylamino)propoxy)-5-methylpyridin-3-yl)-3'-methylspiro[cyclopropane-1,1'-pyrrolo[2,3-c]quinolin]-2'(3'H)-one | 417.20 | 1H NMR (300 MHz, DMSO-d6) δ 8.90 (s, 1H), 8.45 (d, J = 2.4 Hz, 1H), 8.11 (d, J = 8.9 Hz, 1H), 8.03 (s, 1H), 7.90 (d, J = 8.9 Hz, 1H), 7.55 (s, 1H), 4.37 (t, J = 6.6 Hz, 2H), 3.42 (s, 3H), 2.56-2.51 (m, 2H), 2.38 (t, J = 7.1 Hz, 2H), 2.25 (s, 3H), 2.16 (s, 6H), 1.89 (q, J = 4.2 Hz, 2H), 1.76 (q, J = 4.2 Hz, 2H). |

| Examples | Structure | Name | MS: [(M + 1)]+ | ¹H NMR |
|---|---|---|---|---|
| 58 | 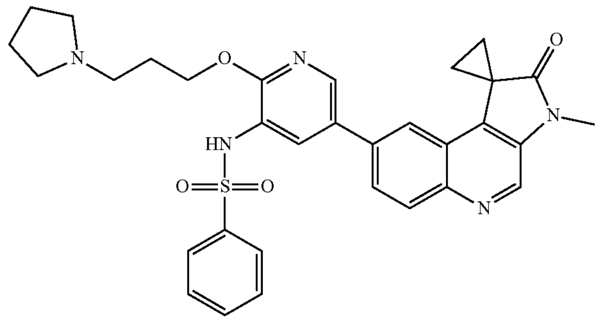 [SMILES: CN1C(=O)C2(CC2)c2c1cnc1ccc(-c3cnc(OCCCN4CCCC4)c(NS(=O)(=O)c4ccccc4)c3)cc21] | N-(5-(3'-Methyl-2'-oxo-2',3'-dihydrospiro[cyclopropane-1,1'-pyrrolo[2,3-c]quinolin]-8'-yl)-2-(3-(pyrrolidin-1-yl)propoxy)pyridin-3-yl)benzenesulfonamide | 584.30 | ¹H NMR (300 MHz, DMSO-d₆) δ 8.88 (s, 1H), 8.07 (d, J = 8.8 Hz, 1H), 7.95 (d, J = 2.3 Hz, 1H), 7.84-7.76 (m, 2H), 7.70 (dd, J = 8.9, 1.9 Hz, 1H), 7.62 (d, J = 2.3 Hz, 1H), 7.56-7.47 (m, 3H), 7.32 (d, J = 1.9 Hz, 1H), 4.28 (t, J = 5.9 Hz, 2H), 3.41 (s, 3H), 3.20-2.98 (m, 6H), 2.33-2.24 (m, 2H), 2.01 (t, J = 6.0 Hz, 2H), 1.93 (s, 4H), 1.81 (q, J = 4.3 Hz, 2H). |
| 59 | 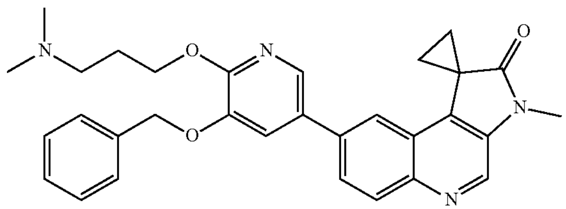 | 8'-(5-(Benzyloxy)-6-(3-(dimethylamino)propoxy)pyridin-3-yl)-3methylspiro[cycloproane-1,1'-pyrrolo[2,3-c]quinolin]-2'(3'-)-one | 509.20 | ¹H NMR (400 MHz, CD₃OD) δ 8.77 (d, J = 5.6 Hz, 1H), 8.12-8.07 (m, 1H), 8.03 (d, J = 2.4 Hz, 1H), 7.84 (d, J = 8.9 Hz, 1H), 7.57 (s, 1H), 7.50 (d, J = 7.7 Hz, 3H), 7.41 (t, J = 7.1 Hz, 2H), 7.34 (t, J = 7.5 Hz, 1H), 5.27 (s, 2H), 4.46 (t, J = 6.4 Hz, 2H), 3.45 (s, 3H), 2.65-2.56 (m, 2H), 2.43-2.37 (m, 2H), 2.30 (s, 6H), 2.10-2.01 (m, 2H), 1.96-1.91(m, 2H). |
| 60 | 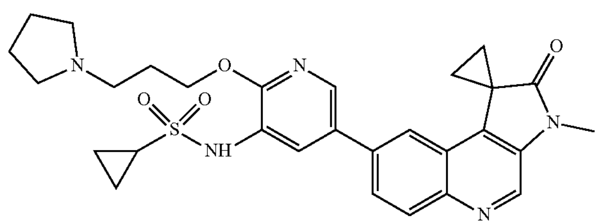 [SMILES: CN1C(=O)C2(CC2)c2c1cnc1ccc(-c3cnc(OCCCN4CCCC4)c(NS(=O)(=O)C4CC4)c3)cc21] | N-(5-(3-Methyl-2'-oxo-2,3'-dihydrospiro[cyclopropane-1,1'-pyrrolo[2,3-c]quinolin]-8'-yl)-2-(3-(pyrrolidin-1-yl)propoxy)pyridin-3-yl)cyclopropanesulfonamide | 548.00 | ¹H NMR (300 MHz, DMSO-d₆) δ 8.92 (s, 1H), 8.38 (d, J = 2.3 Hz, 1H), 8.14 (d, J = 8.8 Hz, 1H), 8.00 (d, J = 2.3 Hz, 1H), 7.87 (dd, J = 8.9, 1.9 Hz, 1H), 7.56 (d, J = 1.9 Hz, 1H), 4.42 (t, J = 6.4 Hz, 2H), 3.43 (s, 3H), 2.77-2.64 (m, 3H), 2.62-2.51 (m, 5H), 1.98 (q, J = 6.7 Hz, 2H), 1.82-1.70 (m, 6H), 0.94 (d, J = 6.3 Hz, 4H). |

| Examples | Structure | Name | MS: [(M + 1)]+ | 1H NMR |
|---|---|---|---|---|
| 61 | 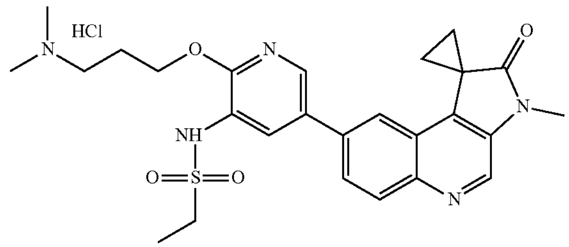 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)ethanesulfonamide hydrochloride | 510.10 | 1H NMR (300 MHz, DMSO-d6) δ 9.71(br, 1H), 8.93 (s, 1H), 8.49 (d, J = 2.3 Hz, 1H), 8.15 (d, J = 8.9 Hz, 1H), 8.05 (d, J = 2.3 Hz, 1H), 7.89 (dd, J = 8.9, 1.9 Hz, 1H), 7.56 (d, J = 1.9 Hz, 1H), 4.46 (t, J = 6.0 Hz, 2H), 3.42(s, 3H), 3.20(q, J = 6.0 Hz, 4H), 2.79 (s, 6H), 2.48 (s, 2H), 2.17 (q, J = 4.4 Hz, 2H), 1.79 (q, J = 4.4 Hz, 2H), 1.30 (t, J = 7.5 Hz, 3H). |
| 62 | 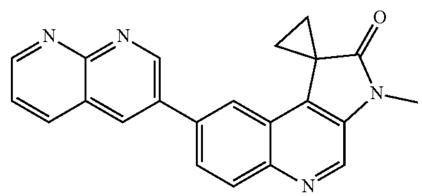 [SMILES: CN1C(=O)C2(CC2)c2c1cnc1ccc(-c3cnc4ncccc4c3)cc21] | 3'-Methyl-8'-(1,8-naphthyridin-3-yl)spiro[cyclopropane-1,1'-pyrrolo[2,3-c]quinolin]-2'(3'-H)-one | 353.20 | 1H NMR (400 MHz, DMSO-d6) δ 9.60 (d, J = 2.6 Hz, 1H), 9.13 (dd, J = 4.4, 1.9 Hz, 1H), 8.97 (s, 1H), 8.93 (d, J = 2.6 Hz, 1H), 8.59 (dd, J = 8.1, 1.9 Hz, 1H), 8.22 (d, J = 8.8 Hz, 1H), 8.13 (dd, J = 8.9, 1.9 Hz, 1H), 7.85 (dd, J = 1.9 Hz, 1H), 7.73 (dd, J = 8.2, 4.2 Hz, 1H), 3.44 (s, 3H), 2.62 (q, J = 4.5 Hz, 2H), 1.81 (q, J = 4.4 Hz, 2H). |
| 63 | 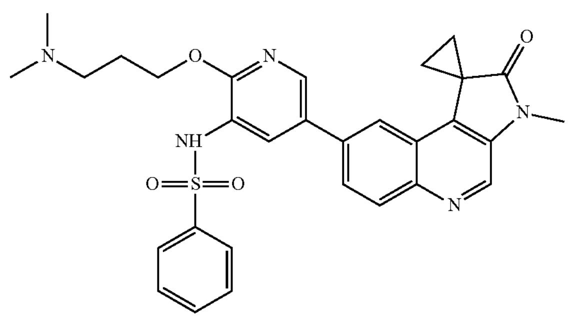 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)phenyl)benzenesulfonamide | 557.30 | 1H NMR (300 MHz, CDCl3) δ 8.70 (d, J = 1.6 Hz, 1H), 8.22-8.08 (m, 1H), 7.85 (dd, J = 7.7, 1.9 Hz, 3H), 7.74 (dd, J = 9.0, 2.0 Hz, 1H), 7.64-7.35 (m, 4H), 7.26-7.24 (m, 1H), 6.98-6.87 (m, 1H), 4.01 (t, J = 5.8 Hz, 2H), 3.48 (s, 3H), 2.52 (t, J = 6.1 Hz, 2H), 2.38 (s, 6H), 2.30 (q, J = 4.0 Hz, 2H), 2.01 (q, J = 4.4 Hz, 2H), 1.95-1.86 (m, 2H). |

| Examples | Structure | Name | MS: [(M + 1)]+ | 1H NMR |
|---|---|---|---|---|
| 64 | 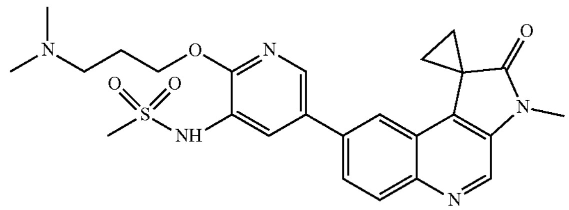 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)methanesulfonamide | 496.20 | 1H NMR (300 MHz, CDCl$_3$) δ 8.76 (s, 1H), 8.22-8.17 (m, 2H), 8.10 (d, J = 2.3 Hz, 1H), 7.79 (dd, J = 8.9, 2.0 Hz, 1H), 7.51 (d, J = 2.0 Hz, 1H), 4.54 (t, J = 6.2 Hz, 2H), 3.52 (s, 3H), 3.07 (s, 3H), 2.58 (t, J = 6.5 Hz, 2H), 2.33 (q, J = 4.4 Hz, 2H), 2.13-1.98 (m, 4H). |
| 65 | 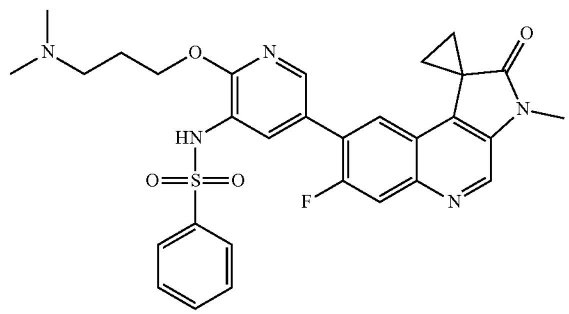 | N-(2-(3-(Dimethylamino)propoxy)-5-(7'-fluoro-3'-methyl-2'-oxo-2',3'-dihydrospiro[cyclopropane-1,1'-pyrrolo[2,3-c]quinolin]-8'-yl)pyridin-3-yl)benzenesulfonamide | 576.20 | 1H NMR (300 MHz, DMSO-d$_6$) δ 8.91 (s, 1H), 7.91-7.76 (m, 4H), 7.55-7.44 (m, 4H), 7.26 (d, J = 8.1 Hz, 1H), 4.30 (t, J = 5.7 Hz, 2H), 3.40 (s, 3H) δ .18-3.11 (m, 2H), 2.79 (s, 6H), 2.29 (q, J = 4.5 Hz, 2H), 2.11-2.04 (m, 2H), 1.78 (q, J = 4.4 Hz, 2H). |
| 66 | 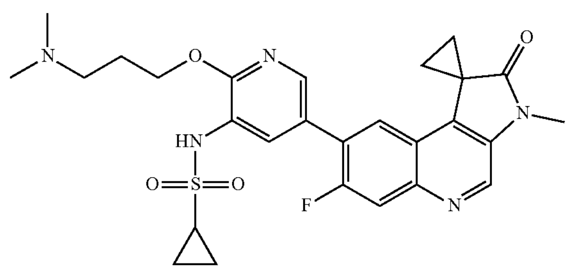 | N-(2-(3-(Dimethylamino)propoxy)-5-(7'-fluoro-3'-methyl-2'-oxo-2',3'-dihydrospiro[cyclopropane-1,1'-pyrrolo[2,3-c]quinolin]-8'-yl)pyridin-3-yl)cyclopropanesulfonamide | 540.20 | 1H NMR (400 MHz, DMSO-d$_6$) δ 8.94 (s, 1H), 8.20 (s, 1H), 7.97-7.88 (m, 2H), 7.49 (t, J = 8.2 Hz, 1H), 4.39 (t, J = 6.3 Hz, 2H), 3.41 (s, 3H), 2.70-2.62 (m, 1H), 2.59 (t, J = 6.7 Hz, 2H), 2.47 (q, J = 4.3 Hz, 2H), 2.30 (s, 6H), 1.97 (p, J = 6.5 Hz, 2H), 1.76 (q, J = 4.3 Hz, 2H), 0.98-0.89 (m, 4H). |

| Examples | Structure | Name | MS: [(M + 1)]+ | ¹H NMR |
|---|---|---|---|---|
| 67 | 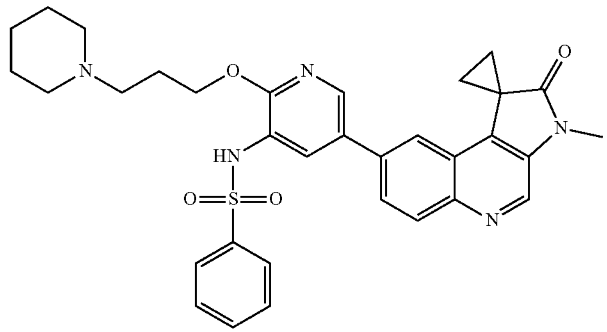 [SMILES: CN1C(=O)C2(CC2)c2c1cnc1ccc(-c3cnc(OCCCN4CCCCC4)c(NS(=O)(=O)c4ccccc4)c3)cc21] | N-(5-(3'-Methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)benzenesulfonamide | 597.90 | ¹H NMR (300 MHz, DMSO-$d_6$) δ 8.90 (s, 1H), 8.25 (d, J = 2.3 Hz, 1H), 8.11 (d, J = 8.8 Hz, 1H), 7.84 (d, J = 2.3 Hz, 1H), 7.81-7.75 (m, 3H), 7.64-7.50 (m, 3H), 7.44 (d, J = 1.9 Hz, 1H), 4.16 (t, J = 6.4 Hz, 2H), 3.41 (s, 3H), 2.57-2.51 (m, 6H), 2.40 (q, J = 4.4 Hz, 2H), 1.86-1.74 (m, 4H), 1.63-1.52 (m, 4H), 1.48-1.38 (m, 2H). |
| 68 | 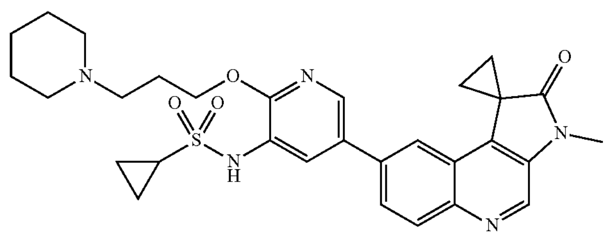 [SMILES: CN1C(=O)C2(CC2)c2c1cnc1ccc(-c3cnc(OCCCN4CCCCC4)c(NS(=O)(=O)C4CC4)c3)cc21] | N-(5-(3'-Methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)cyclopropanesulfonamide | 562.00 | ¹H NMR (300 MHz, DMSO-$d_6$) δ 8.91 (s, 1H), 8.46 (d, J = 2.3 Hz, 1H), 8.13 (d, J = 8.8 Hz, 1H), 8.01 (d, J = 2.3 Hz, 1H), 7.87 (dd, J = 8.9, 1.9 Hz, 1H), 7.55 (d, J = 2.0 Hz, 1H), 4.40 (t, J = 6.4 Hz, 2H), 3.42 (s, 3H), 2.83-2.71 (m, 1H), 2.49-2.47 (m, 4H), 2.40 (s, 4H), 1.96 (p, J = 6.6 Hz, 2H), 1.77 (q, J = 4.3 Hz, 2H), 1.58-1.44 (m, 4H), 1.45-1.34 (m, 2H), 1.00-0.91 (m, 4H). |
| 69 | 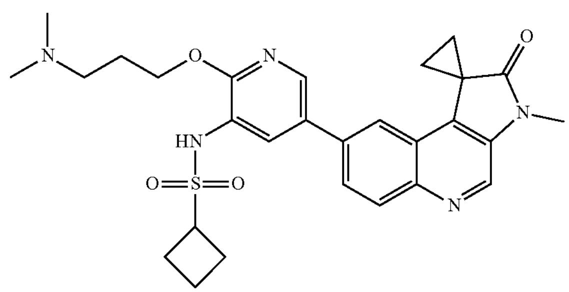 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)cyclobutanesulfonamide | 536.20 | ¹H NMR (300 MHz, DMSO-$d_6$) δ 8.91 (s, 1H), 8.37 (d, J = 2.3 Hz, 1H), 8.13 (d, J = 8.9 Hz, 1H), 7.96 (d, J = 2.4 Hz, 1H), 7.86 (dd, J = 8.9, 1.9 Hz, 1H), 7.54 (d, J = 1.9 Hz, 1H), 4.38 (t, J = 6.3 Hz, 2H), 3.98 (p, J = 8.1 Hz, 1H), 3.42 (s, 3H), 2.54-2.52 (m, 2H), 2.49-2.45 (m, 2H), 2.42-2.30 (m, 2H), 2.29-2.16 (m, 8H), 2.00-1.82 (m, 4H), 1.77 (q, J = 4.3 Hz, 2H). |

-continued

| Examples | Structure | Name | MS: [(M + 1)]+ | 1H NMR |
|---|---|---|---|---|
| 70 | 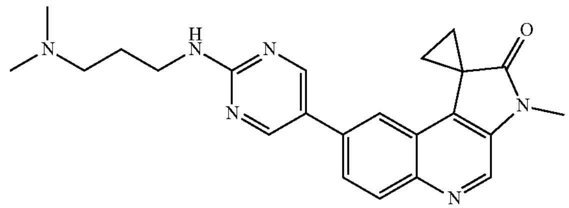 | 8'-(2-((3-(Dimethylamino)propyl)aminopyrimidin-5-yl)-3'-methylspiro[cyclopropane-1,1'-pyrrolo[2,3-c]quinolin]-2'(3'-H)-one | 403.20 | 1H NMR (400 MHz, DMSO-d6) δ 8.87 (s, 1H), 8.77 (s, 2H), 8.08 (d, J = 8.8 Hz, 1H), 7.88 (dd, J = 9.0, 1.9 Hz, 1H), 7.52 (d, J = 2.0 Hz, 1H), 7.47 (t, J = 5.9 Hz, 1H), 3.41 (s, 3H), 3.35 (d, J = 6.8 Hz, 2H), 2.57-2.53 (m, 2H), 2.27 (t, J = 7.1 Hz, 2H), 2.14 (s, 6H), 1.79-1.61 (m, 4H). |
| 71 | 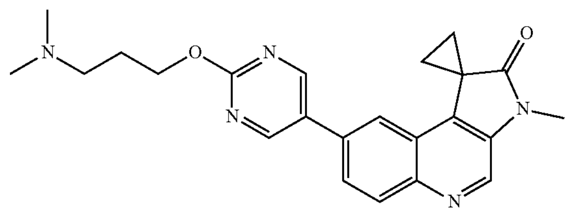 | 8'-(2-(3-(Dimethylamino)propoxy)pyrimidin-5-yl)-3'-methylspiro[cyclopropane-1,1'-pyrrolo[2,3-c]quinolin]-2'(3'-H)-one | 404.50 | 1H NMR (300 MHz, DMSO-d6) δ 9.08 (s, 2H), 8.93 (s, 1H), 8.14 (d, J = 8.9 Hz, 1H), 7.94 (dd, J = 8.9, 3.0 Hz, 1H), 7.65 (s, 1H), 4.41 (t, J = 6.6 Hz, 2H), 3.42 (s, 3H), 2.58 (q, J = 3.9 Hz, 2H), 2.37(t, J = 6.9 Hz, 2H), 2.16 (s, 6H), 1.91 (p, J = 6.9 Hz, 2H), 1.76 (q, J = 4.2 Hz, 2H). |
| 72 | 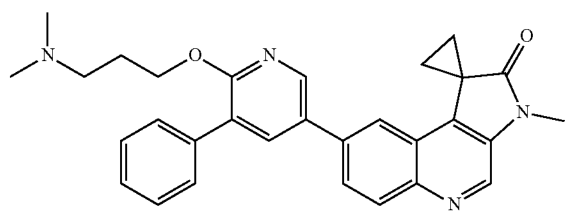 | 8'-(6-(3-(Dimethylamino)propoxy)-5-phenylpyridin-3-yl)-3'-methylspiro[cyclopropane-1,1'-pyrrolo[2,3-c]quinolin]-2'(3'-H)-one | 479.30 | 1H NMR (300 MHz, DMSO-d6) δ 8.91 (s, 1H), 8.64 (d, J = 2.5 Hz, 1H), 8.18-8.09 (m, 2H), 8.00 (dd, J = 8.9, 1.9 Hz, 1H), 7.74-7.67 (m, 2H), 7.64 (d, J = 2.0 Hz, 1H), 7.53-7.45 (m, 2H), 7.44-7.37 (m, 1H), 4.41 (t, J = 6.4 Hz, 2H), 3.42 (s, 3H), 2.56 (q, J = 4.2 Hz, 2H), 2.34 (t, J = 7.1 Hz, 2H), 2.13 (s, 6H), 1.85 (p, J = 6.8 Hz, 2H), 1.75 (q, J = 4.2 Hz, 2H). |

-continued

| Examples | Structure | Name | MS: [(M + 1)]+ | 1H NMR |
|---|---|---|---|---|
| 73 | 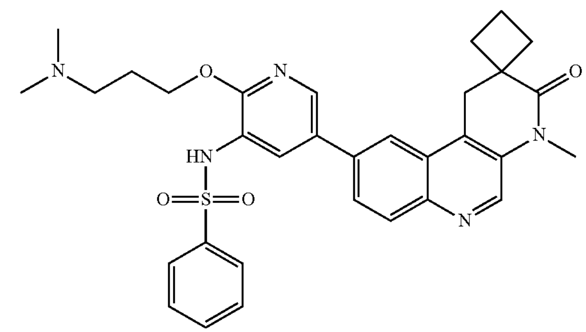 [SMILES: CN(C)CCCOc1ncc(-c2ccc3ncc4c(c3c2)CC2(CCC2)C(=O)N4C)cc1NS(=O)(=O)c1ccccc1] | N-(2-(3-(Dimethylamino)propoxy)-5-(4-methyl-3-oxo-3,4-dihydro-1H-spiro[benzo[f][1,7]naphthyridine-2,1'-cyclobutan]-9-yl)pyridin-3-yl)benzenesulfonamide | 586.40 | 1H NMR (300 MHz, DMSO-d6) δ 8.83 (s, 1H), 8.08-8.01 (m, 3H), 7.83 (dd, J = 6.7, 2.9 Hz, 2H), 7.73 (dd, J = 9.0, 1.5 Hz, 1H), 7.65 (d, J = 2.2 Hz, 1H), 7.52 (d, J = 2.3 Hz, 1H), 7.50 (d, J = 1.4 Hz, 1H), 4.27 (t, J = 5.8 Hz, 2H), 3.52 (s, 2H), 3.47 (s, 3H), 3.05 (t, J = 6.0 Hz, 2H), 2.74 (s, 6H), 2.45-2.25 (m, 2H), 2.13-1.75 (m, 6H). |
| 74 | 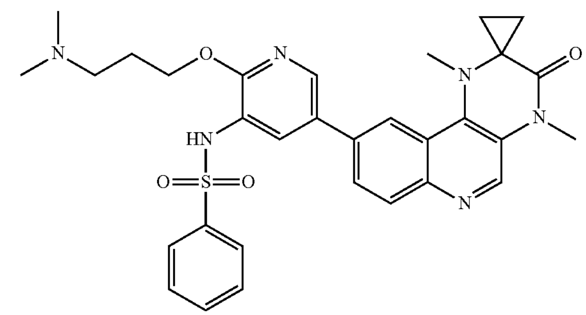 [SMILES: CN(C)CCCOc1ncc(-c2ccc3ncc4c(c3c2)N(C)C2(CC2)C(=O)N4C)cc1NS(=O)(=O)c1ccccc1] | N-(5-(1',4'-Dimethyl-3'-oxo-3'4'-dihydro-1'H-spiro[cyclopropane-1,2'-pyrazino[2,3-c]quinolin]-9'-yl)-2-(3-(dimethylamino)propoxy)pyridin-3-yl)benzenesulfonamide | 587.30 | 1H NMR (300 MHz, DMSO-d6) δ 8.07 (d, J = 2.2 Hz, 1H), 7.83-7.70 (m, 3H), 7.58 (dd, J = 8.9, 2.3 Hz, 1H), 7.54-7.41 (m, 4H), 7.33 (d, J = 8.9 Hz, 1H), 6.95 (s, 1H), 4.23 (t, J = 5.7 Hz, 2H), 3.59 (s, 3H), 3.11 (s, 3H), 3.03 (t, J = 5.4 Hz, 2H), 2.72 (s, 6H), 2.04-1.98 (m, 2H), 1.61 (q, J = 3.9 Hz, 2H), 1.08 (q, J = 3.9 Hz, 2H). |
| 75 | 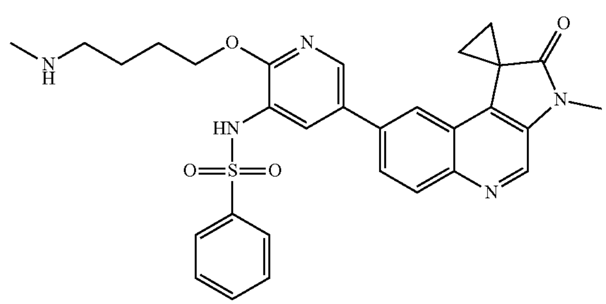 | N-(5-(3-Methyl-2'-oxo-2',3'-dihydrospiro[cyclopropane-1,1'-pyrrolo[2,3-c]quinolin]-8'-yl)-2-(4-(methylamino)butoxy)pyridin-3-yl)benzenesulfonamide | 558.30 | 1H NMR (300 MHz, DMSO-d6) δ 8.87 (s, 1H), 8.07 (d, J = 8.9 Hz, 1H), 7.82 (dd, J = 6.8, 2.4 Hz, 3H), 7.66 (dd, J = 8.9, 1.8 Hz, 1H), 7.51-7.46 (m, 4H), 7.27 (d, J = 1.9 Hz, 1H), 4.29 (t, J = 5.4 Hz, 2H), 3.45 (s, 3H), 3.11 (t, J = 5.8 Hz, 2H), 2.76 (s, 3H), 2.24 (q, J = 4.5 Hz, 2H), 1.94-1.84 (m, 3H), 1.84-1.78 (m, 3H). |

| Examples | Structure | Name | MS: [(M + 1)]+ | 1H NMR |
|---|---|---|---|---|
| 76 | 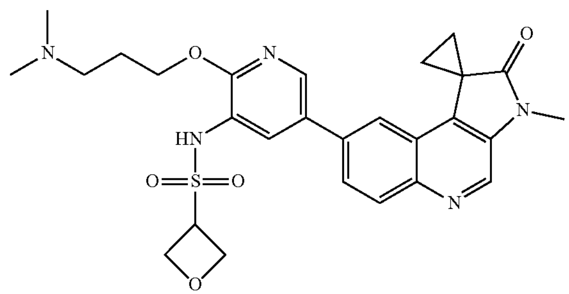 | N-(2-(3-(Dimethylamino) propoxy)-5-(3'-methyl-2'-oxo-2',3'-dihydrospiro [cyclopropane-1,1'-pyrrolo[2,3-c]quinolin]-8'-yl)pyridin-3-yl)oxetane-3-sulfonamide | 538.30 | 1H NMR (400 MHz, DMSO-$d_6$) δ 8.89 (s, 1H), 8.11 (d, J = 8.7 Hz, 1H), 8.05 (s, 1H), 7.88–7.80 (m, 2H), 7.50 (s, 1H), 4.72 (d, J=7.2 Hz, 4H), 4.58-4.49 (m, 1H), 4.32 (t, J = 6.6 Hz, 2H), 3.42 (s, 3H), 2.81-2.70 (m, 2H), 2.48-2.32 (m, 8H), 2.04-1.92 (m, 2H), 1.80-1.73 (m, 2H). |
| 77 | 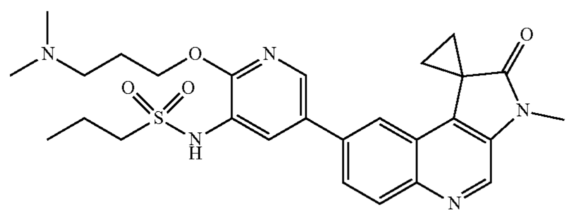 | N-(2-(3-(Dimethylamino)propoxy)-5-(3'-methyl-2'-oxo-2',3'-dihydrospiro [cyclopropane-1,1'-pyrrolo [2,3-c]quinolin]-8'-yl)pyridin-3-yl)propane-1-sulfonamide | 523.80 | 1H NMR (300 MHz, CD$_3$OD) δ 8.80 (s, 1H), 8.19 (d, J = 2.3 Hz, 1H), 8.14 (d, J = 8.8 Hz, 1H), 8.05 (d, J = 2.3 Hz, 1H), 7.89 (dd, J = 9.0, 2.0 Hz, 1H), 7.61 (d, J = 1.9 Hz, 1H), 4.51 (t, J = 6.2 Hz, 2H), 3.49 (s, 3H), 3.18-3.06 (m, 2H), 2.80 (t, J = 7.0 Hz, 2H), 2.51 (s, 6H), 2.47 (t, J = 4.0 Hz, 2H), 2.12 (p, J = 6.6 Hz, 2H), 1.96 (q, J = 4.4 Hz, 2H), 1.92-1.82 (m, 2H), 1.05 (t, J = 7.5 Hz, 3H). |
| 78 | 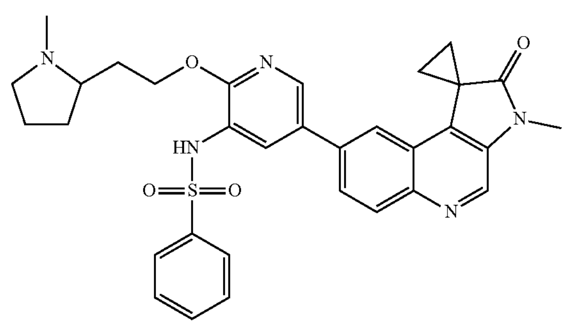 [SMILES: CN1C(=O)C2(CC2)c2c1cnc1ccc(-c3cnc(OCCC4CCCN4C)c(NS(=O)(=O)c4ccccc4)c3)cc21] | N-(5-(3'-Methyl-2'-oxo-2',3'-dihydrospiro[cyclopropane-1,1'-pyrrolo[2,3-c]quinolin]-8'-yl)-2-(2-(1-methylpyrrolidin-2-yl)ethoxy)pyridin-3-yl)benzenesulfonamide | 584.30 | 1H NMR (300 MHz, DMSO-$d_6$) A 8.90 (s, 1H), 8.09 (d, J = 8.9 Hz, 1H), 7.99 (d, J = 2.2 Hz, 1H), 7.81 (dd, J = 6.5, 3.0 Hz, 2H), 7.75-7.68 (m, 1H), 7.62 (d, J = 2.3 Hz, 1H), 7.55-7.49 (m, 3H), 7.34 (s, 1H), 4.36 (s, 2H), 3.42 (s, 3H), 2.87 (d, J = 9.9 Hz, 1H), 2.80 (s, 3H), 2.35-2.26 (m, 3H), 2.22-2.12 (m, 1H), 2.21-1.91 (m, 4H), 1.85-1.77 (m, 3H). |

-continued

| Examples | Structure | Name | MS: [(M + 1)]+ | 1H NMR |
|---|---|---|---|---|
| 79 | 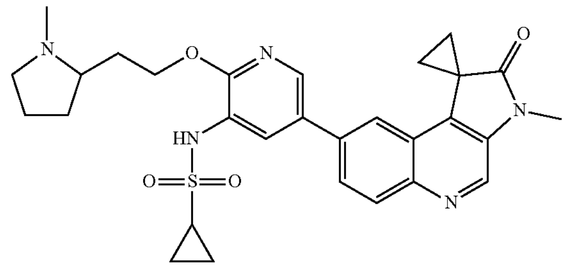 [SMILES: CN1C(=O)C2(CC2)c2c1cnc1ccc(-c3cnc(OCCC4CCCN4C)c(NS(=O)(=O)C4CC4)c3)cc21] | N-(5-(3'-Methyl-2'-oxo-2',3'-dihydrospiro[cyclopropane-1,1'-pyrrolo[2,3-c]quinolin]-8'-yl)-2-(2-(1-methylpyrrolidin-2-yl)ethoxy)pyridin-3-yl)cyclopropanesulfonamide | 548.30 | 1H NMR (300 MHz, CD3OD) δ 8.83 (s, 1H), 8.23 (d, J = 2.3 Hz, 1H), 8.17 (d, J = 8.9 Hz, 1H), 8.11 (d, J = 2.3 Hz, 1H), 7.92 (dd, J = 8.9, 1.9 Hz, 1H), 7.64 (d, J = 2.0 Hz, 1H), 4.57 (t, J = 6.4 Hz, 2H), 3.52 (s, 3H), 3.41 (d, J = 5.3 Hz, 1H), 2.85-2.75 (m, 1H), 2.73-2.65 (m, 1H), 2.60 (s, 3H), 2.59-2.54 (m, 1H), 2.53-2.48 (m, 2H), 2.36-2.26 (m, 1H), 2.09-1.85 (m, 1H), 2.05-1.88 (m, 5H), 1.81-1.66 (m, 1H), 1.18-1.08 (m, 2H), 1.01 (d, J = 81 Hz, 2H). |
| 80 | 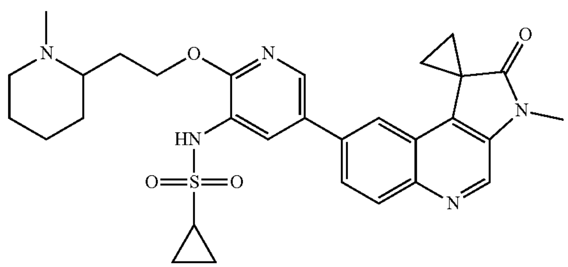 [SMILES: CN1C(=O)C2(CC2)c2c1cnc1ccc(-c3cnc(OCCC4CCCCN4C)c(NS(=O)(=O)C4CC4)c3)cc21] | N-(5-(3'-Methyl-2'-oxo-2',3'-dihydrospiro[cyclopropane-1,1'-pyrrolo[2,3-c]quinolin]-8'-yl)-2-(1-methylpiperidin-2-yl)ethoxy)pyridin-3-yl)cyclopropanesulfonamide | 562.20 | 1H NMR (400 MHz, CD3OD) δ 8.79 (s, 1H), 8.12 (dd, J = 5.6, 3.3 Hz, 2H), 8.04 (d, J = 2.3 Hz, 1H), 7.87 (dd, J = 8.9, 1.9 Hz, 1H), 7.59 (d, J = 1.9 Hz, 1H), 4.62-4.45 (m, 2H), 3.48 (s, 3H), 3.46-3.41 (m, 1H), 2.96 (br, 1H), 2.76 (s, 3H), 2.74-2.60 (m, 2H), 2.46 (q, J = 4.5 Hz, 2H), 2.40-2.26 (m, 1H), 2.24-2.12 (m, 1H), 1.98-1.89 (m, 3H), 1.89-1.76 (m, 3H), 2.41-2.27 (m, 2H), 1.15-1.03 (m, 2H), 1.03-0.90 (m, 2H). |
| 81 | 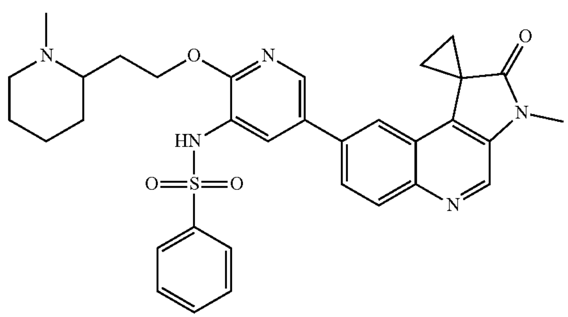 [SMILES: CN1C(=O)C2(CC2)c2c1cnc1ccc(-c3cnc(OCCC4CCCCN4C)c(NS(=O)(=O)c4ccccc4)c3)cc21] | N-(5-(3'-Methyl-2'-oxo-2',3'-dihydrospiro[cyclopropane-1,1'-pyrrolo[2,3-c]quinolin]-8'-yl)-2-(2-(1-methylpiperidin-2-yl)ethoxy)pyridin-3-yl)benzenesulfonamide | 598.20 | 1H NMR (400 MHz, CD3OD) δ 8.74 (s, 1H), 8.04 (d, J = 8.9 Hz, 1H), 7.94-7.87 (m, 2H), 7.84 (d, J = 2.2 Hz, 1H), 7.71 (dd, J = 8.9, 1.9 Hz, 1H), 7.58 (d, J = 2.2 Hz, 1H), 7.55-7.45 (m, 3H), 7.33 (d, J = 1.9 Hz, 1H), 4.59-4.53 (m, 1H), 4.38 (td, J = 10.6, 4.4 Hz, 1H), 3.89 (d, J = 12.2 Hz, 1H), 3.46 (s, 3H), 3.30-3.24 (m, 1H), 3.01 (s, 3H), 2.93 (t, J = 11.6 Hz, 1H), 2.64 (s, 1H), 2.27 (qd, J = 10.5, 4.1 Hz, 2H), 2.08-1.82 (m, 7H), 1.80-1.57 (m, 2H). |

-continued

| Examples | Structure | Name | MS: [M + 1]+ | 1H NMR |
|---|---|---|---|---|
| 82 | 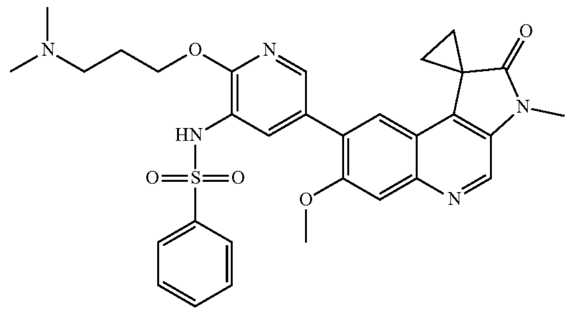 | N-(2-(3-(Dimethylamino)propoxy)-5-(7-methoxy-3'-methyl-2'-oxo-2',3'-dihydrospiro[cyclopropane-1,1'-pyrrolo[2,3-c]quinolin]-8'-yl)pyridin-3-yl)benzenesulfonamide | 588.30 | 1H NMR (300 MHz, CD3OD) δ 8.68 (s, 1H), 7.84 (dd, J = 8.4, 1.8 Hz, 3H), 7.70 (d, J = 2.1 Hz, 1H), 7.53 (dd, J = 10.6, 7.2 Hz, 3H), 7.46 (s, 1H), 7.24 (s, 1H), 4.34 (t, J = 5.8 Hz, 2H), 3.88 (s, 3H), 3.45 (s, 3H), 2.96 (t, J = 6.4 Hz, 2H), 2.72 (s, 6H), 2.26 (q, J = 4.5 Hz, 2H), 2.08 (t, J = 6.0 Hz, 2H), 1.90 (q, J = 4.4 Hz, 2H). |
| 83 | 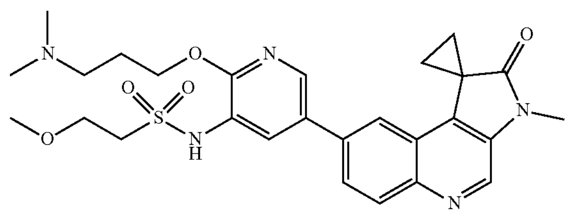 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-2-methoxyethane-1-sulfonamide | 540.30 | 1H NMR (300 MHz, DMSO-d6) δ 8.91 (s, 1H), 8.26 (d, J = 2.1 Hz, 1H), 8.14 (d, J = 8.9 Hz, 1H), 7.93 (d, J = 2.3 Hz, 1H), 7.86 (dd, J = 8.9, 1.9 Hz, 1H), 7.54 (d, J = 1.9 Hz, 1H), 4.39 (t, J = 6.1 Hz, 2H), 3.73 (s, 2H), 3.50-3.40 (s, 3H), 3.37 (d, J = 6.7 Hz, 2H), 3.30-3.20 (m, 3H), 2.70 (d, J = 6.4 Hz, 2H), 2.47 (t, J = 4.0 Hz, 2H), 2.40 (s, 6H), 2.01 (t, J = 6.4 Hz, 2H), 1.78 (q, J = 4.3 Hz, 2H). |
| 84 | 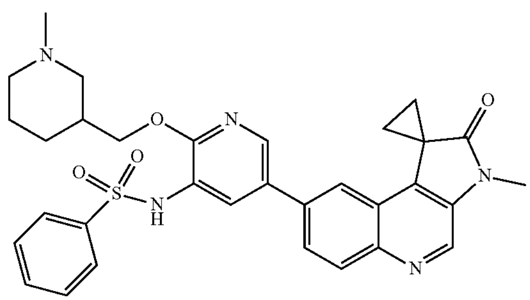 [SMILES: CN1CCCC(COc2ncc(-c3ccc4ncc5c(c4c3)C3(CC3)C(=O)N5C)cc2NS(=O)(=O)c2ccccc2)C1] | N-(5-(3'-Methyl-2'-oxo-2',3'-dihydrospiro[cyclopropane-1,1'-pyrrolo[2,3-c]quinolin]-8'-yl)-2-((1-methylpiperidin-3-yl)methoxy)pyridin-3-yl)benzenesulfonamide | 584.30 | 1H NMR (300 MHz, DMSO-d6) δ 8.90 (s, 1H), 8.20 (d, J = 2.3 Hz, 1H), 8.11 (d, J = 8.9 Hz, 1H), 7.84-7.74 (m, 4H), 7.63-7.49 (m, 3H), 7.42 (d, J = 1.9 Hz, 1H), 4.14-4.00 (m, 2H), 3.41 (s, 3H), 2.93-2.82 (m, 1H), 2.77-2.66 (m, 1H), 2.39 (q, J = 4.2 Hz, 2H), 2.36 (s, 3H), 2.30-2.20 (m, 1H), 2.19-1.91 (m, 2H), 1.80 (q, J = 4.2 Hz, 2H), 1.76-1.44 (m, 3H), 1.19-1.03 (m, 1H). |

| Examples | Structure | Name | MS: [(M + 1)]+ | 1H NMR |
|---|---|---|---|---|
| 85 | 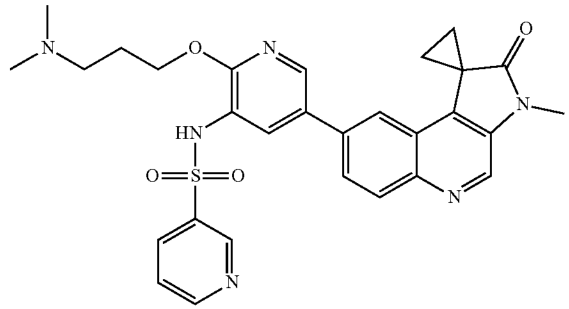 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridine-3-sulfonamide | 559.20 | 1H NMR (300 MHz, DMSO-d6) δ 8.96 (d, J = 2.2 Hz, 1H), 8.87 (s, 1H), 8.65 (dd, J = 4.8, 1.6 Hz, 1H), 8.16 (dt, J = 7.9, 2.0 Hz, 1H), 8.07 (d, J = 8.9 Hz, 1H), 7.86 (d, J = 2.2 Hz, 1H), 7.67 (dd, J = 8.9, 1.9 Hz, 1H), 7.58-7.46 (m, 2H), 7.28 (d, J = 1.9 Hz, 1H), 4.33 (t, J = 5.5 Hz, 2H), 3.41 (s, 3H), 3.37-3.25 (m, 2H), 2.92 (s, 6H), 2.26 (q, J = 4.5 Hz, 2H), 2.21-2.10 (m, 2H), 1.80 (q, J = 4.3 Hz, 2H). |
| 86 | 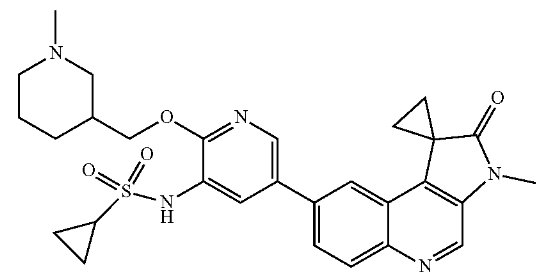 [SMILES: CN1CCCC(COc2ncc(-c3ccc4ncc5c(c4c3)C3(CC3)C(=O)N5C)cc2NS(=O)(=O)C2CC2)C1] | N-(5-(3'-Methyl-2'-oxo-2',3'-dihydrospiro[cyclopropane-1,1'-pyrrolo[2,3-c]quinolin]-8'-yl)-2-((1-methylpiperidin-3-yl)methoxy)pyridin-3-yl)cyclopropanesulfonamide | 548.30 | 1H NMR (300 MHz, DMSO-d6) δ 8.91 (s, 1H), 8.43 (d, J = 2.3 Hz, 1H), 8.13 (d, J = 8.9 Hz, 1H), 8.02 (d, J = 2.3 Hz, 1H), 7.87 (dd, J = 8.9, 1.9 Hz, 1H), 7.55 (d, J = 1.9 Hz, 1H), 4.33-4.25 (m, 1H), 4.24-4.15 (m, 1H), 3.42 (s, 3 H), 2.93 (d, J = 11.0 Hz, 1H), 2.82-2.70 (m, 2H), 2.69-2.59 (m, 2H), 2.18 (s, 4H), 1.95 (t, J = 10.6 Hz, 1H), 1.90-1.72 (m, 4H), 1.73-1.60 (m, 1H), 1.59-1.42 (m, 1H), 1.19-1.01 (m, 1H), 1.00-0.92 (m, 4H). |
| 87 | 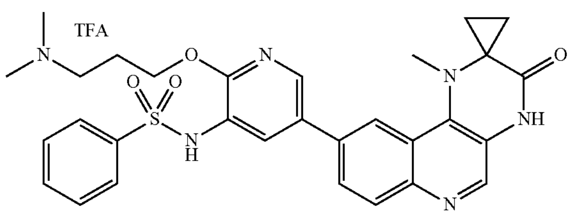 [SMILES: CN(C)CCCOc1ncc(-c2ccc3ncc4c(c3c2)N(C)C2(CC2)C(=O)N4)cc1NS(=O)(=O)c1ccccc1] | N-(2-(3-(Dimethylamino)propoxy)-5-(1'-methyl-3'-oxo-3',4'-dihydro-1'H-spiro[cyclopropane-1,2'-pyrazino[2,3-c]quinolin]-9'-yl)benzenesulfonamide | 573.10 | 1H NMR (400 MHz, CD3OD) δ 8.57 (d, J = 1.3 Hz, 1H), 8.40 (d, J = 2.3 Hz, 1H), 8.12 (dd, J = 3.4, 1.8 Hz, 2H), 8.06 (s, 1H), 7.58-7.50 (m, 2H), 7.68-7.62 (m, 1H), 7.58-7.51 (m, 3H), 4.25 (t, J = 6.0 Hz, 2H), 4.21 (s, 3H), 3.21 (t, J = 8.0 Hz, 2H), 2.92 (s, 6H), 2.10-2.02 (m, 2H), 1.78-1.72 (m, 2H), 1.43-1.36 (m, 2H). |

| Examples | Structure | Name | MS: [(M + 1)]+ | 1H NMR |
|---|---|---|---|---|
| 88 | 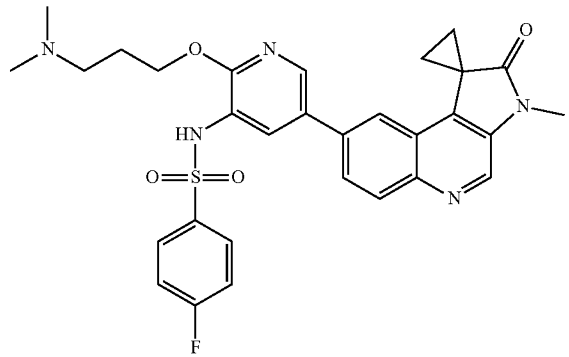 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-fluorobenzenesulfonamide | 576.30 | 1H NMR (300 MHz, DMSO-d6) δ 8.89 (s, 1H), 8.08 (d, J = 8.8 Hz, 1H), 7.93-7.80 (m, 3H), 7.70 (dd, J = 8.8, 1.8 Hz, 1H), 7.50 (d, J = 2.3 Hz, 1H), 7.39-7.25 (m, 3H), 4.31 (t, J = 5.7 Hz, 2H), 3.42 (s, 3H), 3.13 (t, J = 5.8 Hz, 2H), 2.79 (s, 6H), 2.25 (q, J = 3.9 Hz, 2H), 2.15-2.03 (m, 2H), 1.81 (q, J = 4.4 Hz, 2H). |
| 89 | 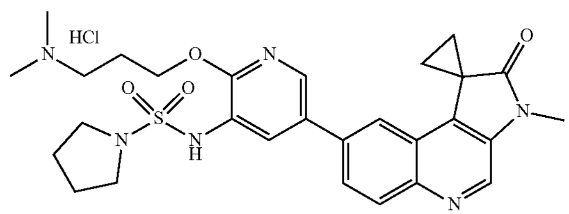 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)pyrrolidine-1-sulfonamide hydrochloride | 551.20 | 1H NMR (300 MHz, DMSO-d6) δ 9.96 (br, 1H), 9.38 (br, 1H), 8.92 (s, 1H), 8.44 (d, J = 2.3 Hz, 1H), 8.15 (d, J = 8.9 Hz, 1H), 8.07 (d, J = 2.3 Hz, 1H), 7.86 (dd, J = 8.9, 1.9 Hz, 1H), 7.54 (d, J = 1.9 Hz, 1H), 4.45 (t, J = 5.9 Hz, 2H), 3.42 (s, 3H), 3.37 (s, 2H), 3.27-3.19 (m, 4H), 2.81 (s, 6H), 2.49 (q, J = 3.6 Hz, 2H), 2.17 (t, J = 7.5 Hz, 2H), 1.85-1.72 (m, 6H). |
| 90 | 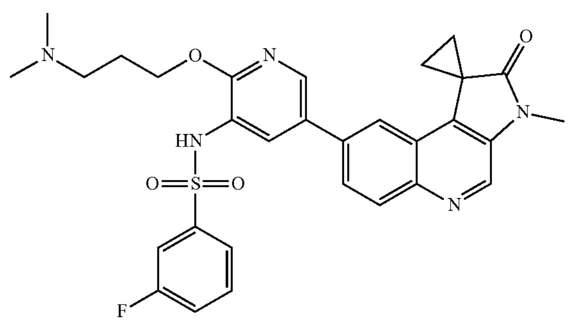 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)phenyl)-3-fluorobenzenesulfonamide | 575.30 | 1H NMR (300 MHz, DMSO-d6) δ 8.86 (s, 1H), 8.05 (d, J = 8.9 Hz, 1H), 7.72-7.61 (m, 2H), 7.59-7.49 (m, 2H), 7.44 (d, J = 2.2 Hz, 1H), 7.36 (t, J = 7.7 Hz, 1H), 7.30 (d, J = 1.8 Hz, 1H), 7.17 (dd, J = 8.2, 2.3 Hz, 1H), 6.98 (d, J = 8.3 Hz, 1H), 4.06 (t, J = 5.6 Hz, 2H), 3.41 (s, 3H), 3.08 (t, J = 5.8 Hz, 2H), 2.76 (s, 6H), 2.23 (q, J = 3.9 Hz, 2H), 2.09-2.00 (m, 2H), 1.79 (q, J = 3.6 Hz, 2H). |

| Examples | Structure | Name | MS: [M + 1]+ | 1H NMR |
|---|---|---|---|---|
| 91 | 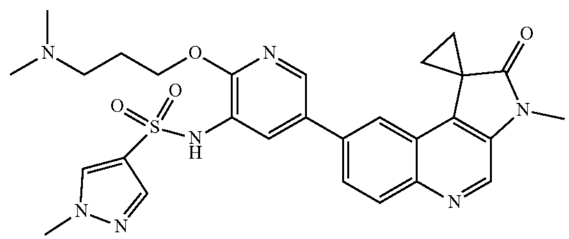 | N-(2-(3-(Dimethylamino) propoxy)-5-(3'-methyl-2'-oxo-2',3'-dihydrospiro [cyclopropane-1,1'-pyrrolo[2,3-c]quinolin]-8'-yl)pyridin-3-yl)-1-methyl-1H-pyrazole-4-sulfonamide | 562.30 | 1H NMR (300 MHz, DMSO-d6) δ 8.90 (s, 1H), 8.16-8.07 (m, 2H), 8.03 (d, J = 2.3 Hz, 1H), 7.83-7.70 (m, 2H), 7.64 (d, J = 0.7Hz, 1H), 7.43 (d, J = 1.9 Hz, 1H), 3.83 (s, 3H), 3.42 (s, 3H), 4.29 (t, J = 5.9 Hz, 2H), 2.92 (t, J = 6.0 Hz, 2H), 2.62 (s, 6H), 2.40 (q, J = 4.4 Hz, 2H), 2.01 (p, J = 6.0 Hz, 2H), 1.81 (q, J = 4.3 Hz, 2H). |
| 92 | 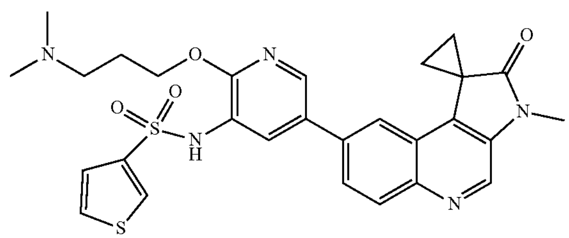 | N-(2-(3-(Dimethylamino) propoxy)-5-(3'-methyl-2'-oxo-2',3'-dihydrospiro [cyclopropane-1,1'-pyrrolo[2,3-c]quinolin]-8'-yl)pyridin-3-yl)thiophene-3-sulfonamide | 564.10 | 1H NMR (400 MHz, CDCl3) δ 8.72 (s, 1H), 8.18 (d, J = 8.8 Hz, 1H), 8.07 (d, J = 2.3 Hz, 1H), 8.00 (d, J = 2.3 Hz, 1H), 7.97 (dd, J = 3.1, 1.3 Hz, 1H), 7.71 (dd, J = 8.9, 1.9 Hz, 1H), 7.41 (d, J = 1.9 Hz, 1H), 7.38 (dd, J = 5.1, 3.1 Hz, 1H), 7.34 (dd, J = 5.2, 1.4 Hz, 1H), 4.42 (t, J = 6.0 Hz, 2H), 3.49 (s, 3H), 2.74 (t, J = 6.5 Hz, 2H), 2.57 (s, 6H), 2.28 (q, J = 4.5 Hz, 2H), 2.07 (p, J = 6.3 Hz, 2H), 2.01 (q, J = 4.3 Hz, 2H). |
| 93 | 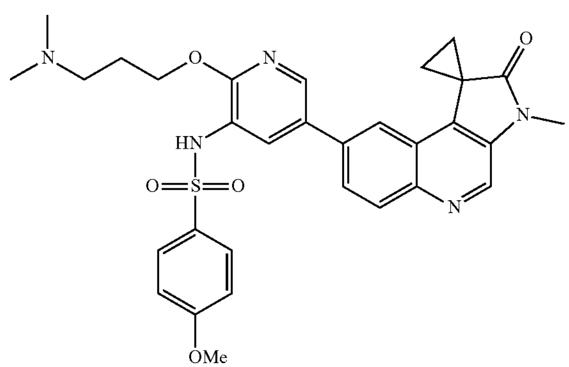 | N-(2-(3-(Dimethylamino) propoxy)-5-(3'-methyl-2'-oxo-2',3'-dihydrospiro [cyclopropane-1,1'-pyrrolo[2,3-c]quinolin]-8'-yl)pyridin-3-yl)-4-methoxybenzenesulfonamide | 588.20 | 1H NMR (400 MHz, DMSO-d6) δ 8.89 (s, 1H), 8.09 (d, J = 8.8 Hz, 1H), 8.01 (d, J = 2.2 Hz, 1H), 7.73 (dd, J = 8.9, 2.1 Hz, 3H), 7.64 (d, J = 2.3 Hz, 1H), 7.35 (d, J = 1.9 Hz, 1H), 7.02 (d, J = 8.8 Hz, 2H), 4.26 (t, J = 5.9 Hz, 2H), 3.78 (s, 3H), 3.41 (s, 3H), 2.90 (t, J = 6.1 Hz, 2H), 2.62 (s, 6H), 2.33 (q, J = 3.6 Hz, 2H), 2.02-1.94 (m, 2H), 1.81 (q, J = 4.3 Hz, 2H). |

| Examples | Structure | Name | MS: [(M + 1)]+ | 1H NMR |
|---|---|---|---|---|
| 94 | 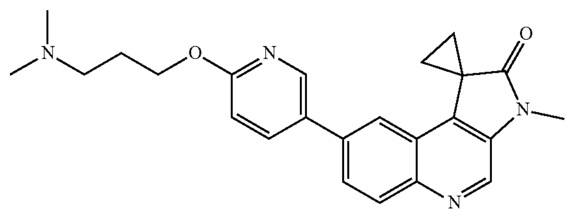 | 8'-(6-((3-(Dimethylamino)propyl)amino)pyridin-3-yl)-3'-methylspiro[cyclopropane-1,1'-pyrrolo[2,3-c]quinolin]-2'(3'-H)-one | 402.20 | 1H NMR (300 MHz, DMSO-d6) δ 8.84 (s, 1H), 8.47 (d, J = 2.5 Hz, 1H), 8.05 (d, J = 8.9 Hz, 1H), 7.86 (dd, J = 8.8, 2.2 Hz, 2H), 7.46 (d, J = 1.9 Hz, 1H), 6.81 (t, J = 5.7 Hz, 1H), 6.59 (d, J = 8.7 Hz, 1H), 3.31-3.27 (m, 2H), 2.48-2.46 (m, 2H), 2.28 (t, J = 7.1 Hz, 2H), 2.14 (s, 6H), 1.75 (q, J = 4.3 Hz, 2H), 1.72-1.62 (m, 2H). |
| 95 | 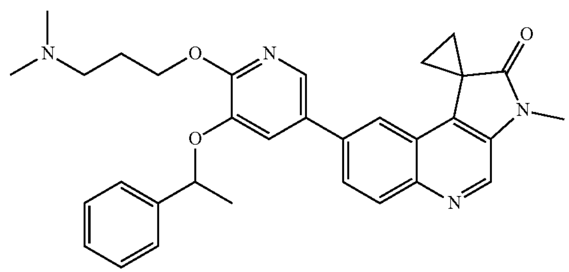 | 8'-(6-(3-(Dimethylamino)propoxy)-5-(1-phenylethoxy)pyridin-3-yl)-3'-methylspiro[cyclopropane-1,1'-pyrrolo[2,3-c]quinolin]-2'(3'-H)-one | 523.20 | 1H NMR (300 MHz, DMSO-d6) δ 8.88 (s, 1H), 8.12-8.04 (m, 2H), 7.81 (dd, J = 8.9, 1.9 Hz, 1H), 7.58 (d, J = 2.1 Hz, 1H), 7.52-7.44 (m, 2H), 7.39 (t, J = 7.5 Hz, 2H), 7.33-7.24 (m, 2H), 5.76 (q, J = 6.4 Hz, 1H), 4.47-4.33 (m, 2H), 3.41 (s, 3H), 2.41 (t, J = 7.1 Hz, 2H), 2.30-2.22 (m, 2H), 2.18 (s, 6H), 1.92 (p, J = 6.8 Hz, 2H), 1.79 (q, J = 3.0 Hz, 2H), 1.62 (d, J = 6.3 Hz, 3H). |
| 96 | 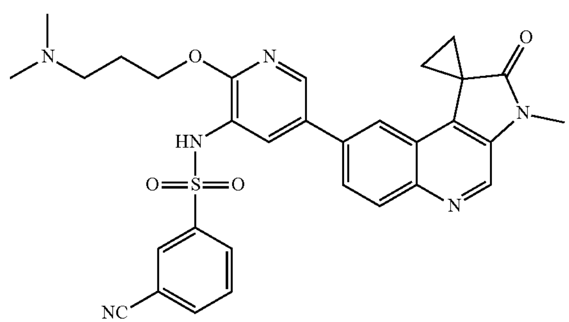 | 3-Cyano-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | 583.20 | 1H NMR (300 MHz, DMSO-d6) δ 8.87 (s, 1H), 8.19-8.00 (m, 3H), 7.95 (d, J = 7.6 Hz, 1H), 7.85 (d, J = 2.2 Hz, 1H), 7.76-7.62 (m, 2H), 7.42 (d, J = 2.2 Hz, 1H), 7.25 (d, J = 1.9 Hz, 1H), 4.33 (t, J = 5.7 Hz, 2H), 3.40 (s, 3H), 3.24-3.14 (m, 2H), 2.73 (s, 6H), 2.21 (q, J = 4.4 Hz, 2H), 2.17-2.08 (m, 2H), 1.79 (q, J = 4.3 Hz, 2H). |

| Examples | Structure | Name | MS: [(M + 1)]+ | ¹H NMR |
|---|---|---|---|---|
| 97 | 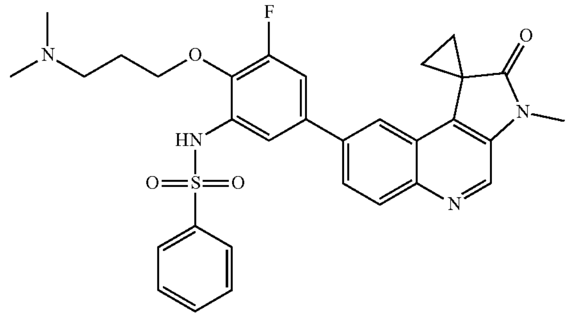 | N-(2-(3-(Dimethylamino) propoxy)-3-fluoro-5-(3'-methyl-2'-oxo-2',3'-dihydrospiro[cyclopropane-1,1'-pyrrolo[2,3-c]quinolin]-8'-yl)phenyl)benzenesulfonamide | 575.20 | ¹H NMR (300 MHz, DMSO-d₆) δ 8.86 (s, 1H), 8.04 (d, J = 8.9 Hz, 1H), 7.85 (dd, J = 6.6, 2.9 Hz, 2H), 7.58 (dd, J = 8.9, 1.8 Hz, 1H), 7.48 (dd, J 5.1, 1.9 Hz, 3H), 7.26 (t, J = 2.2 Hz, 2H), 6.96 (dd, J = 11.7, 2.1 Hz, 1H), 4.10 (t, J = 5.6 Hz, 2H), 3.40 (s, 3H), 3.36 (t, J = 5.5 Hz, 2H), 2.97 (s, 6H), 2.25 (q, J = 4.5 Hz, 2H), 2.16 (p, J = 5.8 Hz, 2H), 1.80 (q, J = 4.3 Hz, 2H). |
| 98 | 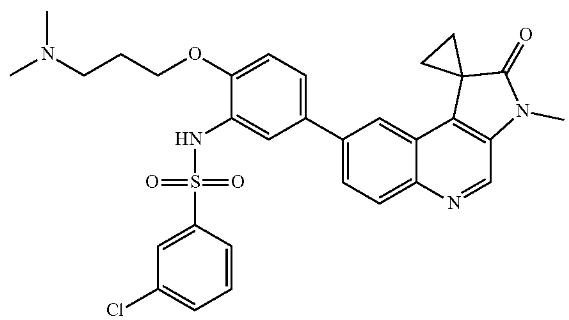 | 3-Chloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)phenyl) benzenesulfonamide | 591.20 | ¹H NMR (300 MHz, DMSO-d₆) δ 8.85 (d, J = 1.3 Hz, 1H), 8.05 (d, J = 8.9 Hz, 1H), 7.81-7.69 (m, 2H), 7.67 (dd, J = 8.9, 1.9 Hz, 1H), 7.62-7.46 (m, 2H), 7.42 (d, J = 2.2 Hz, 1H), 7.34-7.27 (m, 1H), 7.17 (dd, J = 8.3, 2.3 Hz, 1H), 6.98 (d, J = 8.3 Hz, 1H), 4.07 (t, J = 5.6 Hz, 2H), 3.40 (s, 3H), 3.11 (t, J = 6.1 Hz, 2H), 2.77 (s, 6H), 2.24 (q, J = 4.5 Hz, 2H), 2.11-2.02 (m, 2H), 1.79 (q, J = 4.4 Hz, 2H). |
| 99 | 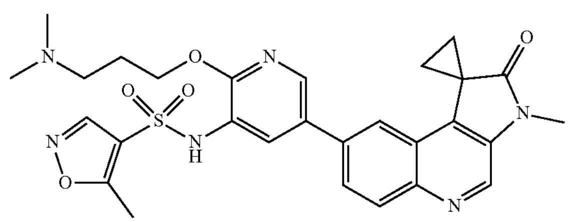 | N-(2-(3-(Dimethylamino) propoxy)-5-(3'-methyl-2'-oxo-2',3'-dihydrospiro [cyclopropane-1,1'-pyrrolo[2,3-c]quinolin]-8'-yl)pyridin-3-yl)-5-methylisoxazole-4-sulfonamide | 563.10 | ¹H NMR (300 MHz, DMSO-d₆) δ 8.91 (s, 1H), 8.25 (d, J = 2.2 Hz, 1H), 8.12 (d, J = 8.8 Hz, 1H), 8.02 (d, J = 2.2 Hz, 1H), 7.89 (d, J = 8.8 Hz, 1H), 7.58 (s, 1H), 4.38 (t, J = 6.3 Hz, 2H), 3.42 (s, 3H), 2.67-2.54 (m, 4H), 2.32 (s, 6H), 2.04-1.90 (m, 2H), 1.80 (s, 3H), 1.75 (q, J = 3.9 Hz, 2H). |

| Examples | Structure | Name | MS: [(M + 1)]+ | 1H NMR |
|---|---|---|---|---|
| 100 | 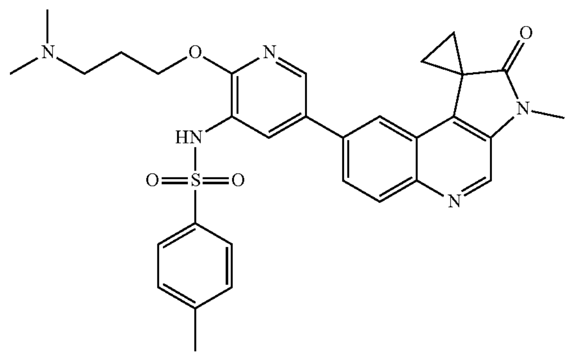 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-methylbenzenesulfonamide | 571.80 | 1H NMR (300 MHz, DMSO-d6) δ 8.89 (s, 1H), 8.09 (d, J = 8.8 Hz, 1H), 7.97 (d, J = 2.2 Hz, 1H), 7.77-7.66 (m, 3H), 7.60 (d, J = 2.3 Hz, 1H), 7.36-7.26 (m, 3H), 4.28 (t, J = 5.9 Hz, 2H), 2.99 (t, J = 5.9 Hz, 2H), 2.69 (s, 6H), 2.34 (s, 3H), 2.30 (q, J = 4.2 Hz, 2H), 2.07-2.00 (m, 2H), 1.82 (q, J = 4.3 Hz, 2H) |
| 101 | 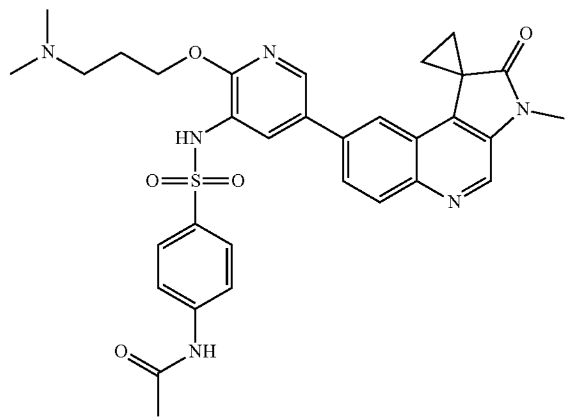 | N-(4-(N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)sulfamoyl)phenyl)acetamide | 615.20 | 1H NMR (300 MHz, DMSO-d6) δ 10.16 (s, 1H), 8.87 (s, 1H), 8.07 (d, J = 8.9 Hz, 1H), 7.91 (s, 1H), 7.74-7.64 (m, 5H), 7.55 (d, J = 2.1 Hz, 1H), 7.31 (d, J = 1.8 Hz, 1H), 4.26 (t, J = 6.0 Hz, 2H), 3.41 (s, 3H), 2.91-2.81 (m, 2H), 2.58 (s, 6H), 2.30-2.26(m, 2H), 2.03 (s, 3H), 2.02-1.96 (m, 2H), 1.81 (q, J = 3.9 Hz, 2H). |

| Examples | Structure | Name | MS: [(M + 1)]+ | ¹H NMR |
|---|---|---|---|---|
| 102 | 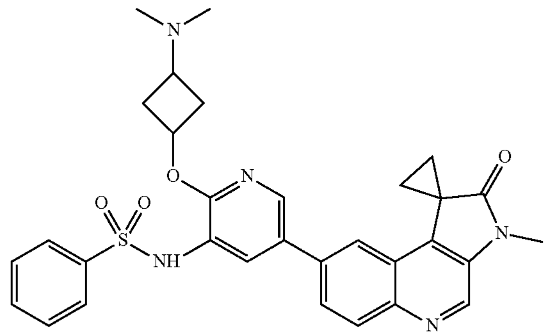 [SMILES: CN1C(=O)C2(CC2)c2c1cnc1ccc(-c3cnc(OC4CC(N(C)C)C4)c(NS(=O)(=O)c4ccccc4)c3)cc21] | N-(2-(3-(Dimethylamino)cyclobutoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | 570.10 | ¹H NMR (300 MHz, DMSO-d₆) δ 8.90 (s, 1H), 8.25 (s, 1H), 8.11 (d, J = 8.8 Hz, 1H), 7.89 (s, 1H), 7.86-7.76 (m, 3H), 7.65-7.52 (m, 3H), 7.47 (s, 1H), 5.11-4.98 (m, 1H), 3.42 (s, 3H), 2.78-2.65 (m, 1H), 2.44 (q, J = 4.5 Hz, 2H), 2.21 (d, J = 5.8 Hz, 2H), 2.07 (s, 6H), 2.00-1.88 (m, 2H), 1.80 (q, J = 4.2 Hz, 2H). |
| 103 | 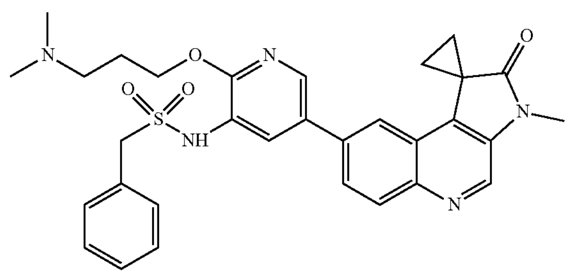 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-1-phenylmethanesulfonamide | 572.20 | ¹H NMR (300 MHz, DMSO-d₆) δ 8.91 (s, 1H), 8.1-8.10 (m, 2H), 7.85-7.77 (m, 2H), 7.52 (d, J = 1.9 Hz, 1H), 7.35-7.24 (m, 5H), 4.40 (s, 2H), 4.37 (t, J = 6.0 Hz, 2H), 3.42 (s, 3H), 2.73 (t, J = 6.1 Hz, 2H), 2.47 (q, J = 3.9 Hz, 2H), 2.31 (s, 6H), 2.00 (p, J = 6.2 Hz, 2H), 1.79 (q, J = 4.3 Hz, 2H). |
| 104 | 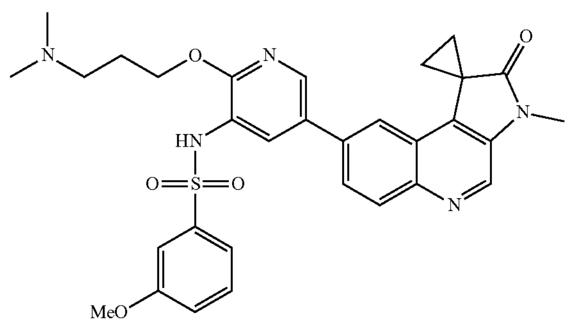 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-3-methoxybenzenesulfonamide | 588.20 | ¹H NMR (300 MHz, DMSO-d₆) δ 8.88 (s, 1H), 8.07 (d, J = 8.9 Hz, 1H), 7.91 (d, J = 2.2 Hz, 1H), 7.69 (dd, J = 8.9, 1.9 Hz, 1H), 7.56 (d, J = 2.3 Hz, 1H), 7.43-7.35 (m, 2H), 7.34-7.28 (m, 2H), 7.10-7.01 (m, 1H), 4.29 (t, J = 5.8 Hz, 2H), 3.75 (s, 3H), 3.41 (s, 3H), 3.04 (br, 2H), 2.71 (s, 6H), 2.29 (q, J = 4.5 Hz, 2H), 2.10-1.98 (m, 2H), 1.79 (q, J = 4.3 Hz, 2H). |

| Examples | Structure | Name | MS: [(M + 1)]+ | 1H NMR |
|---|---|---|---|---|
| 105 | 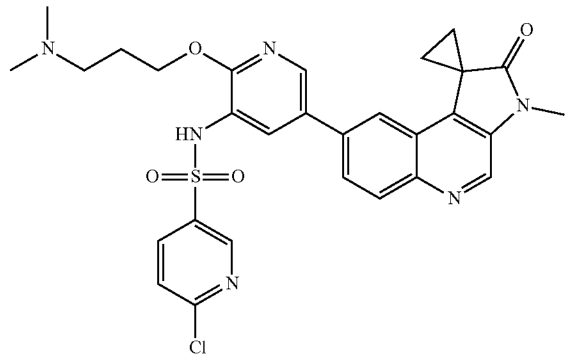 | 6-Chloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)pyridine-3-sulfonamide | 593.10 | 1H NMR (300 MHz, DMSO-d6) δ 8.88 (s, 1H), 8.09 (d, J = 8.9 Hz, 1H), 7.85 (d, J = 2.3 Hz, 1H), 7.73 (dd, J = 8.8, 1.9 Hz, 1H), 7.68-7.57 (m, 2H), 7.49-7.39 (m, 1H), 7.35 (s, 1H), 7.04 (dd, J = 5.0, 3.6 Hz, 1H), 4.32 (t, J = 5.6 Hz, 2H), 3.41 (s, 3H), 3.34-3.15 (m, 2H), 2.86 (s, 6H), 2.31 (q, J = 3.9 Hz, 2H), 2.19-2.09 (m, 2H), 1.83 (q, J = 4.4 Hz, 2H). |
| 106 | 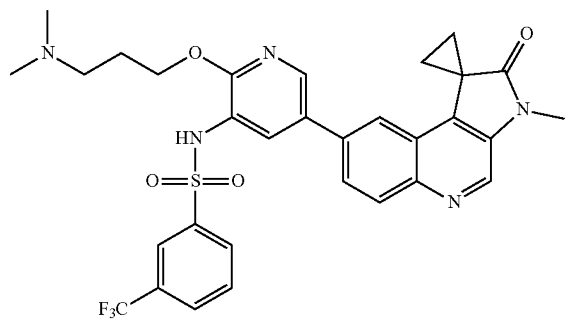 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-3-(trifluoromethyl)benzenesulfonamide | 626.20 | 1H NMR (400 MHz, CDCl3) δ 8.71 (s, 1H), 8.21-8.09 (m, 3H), 7.97 (d, J = 2.2 Hz, 1H), 7.84 (d, J = 2.2 Hz, 1H), 7.76 (d, J = 7.8 Hz, 1H), 7.69-7.56 (m, 2H), 7.36 (d, J = 1.9 Hz, 1H), 4.43 (t, J = 5.7 Hz, 2H), 3.48 (s, 3H), 3.02 (t, J = 5.9 Hz, 2H), 2.83 (s, 6H), 2.26-2.12 (m, 4H), 1.98 (q, J = 4.4Hz, 2H). |
| 107 | 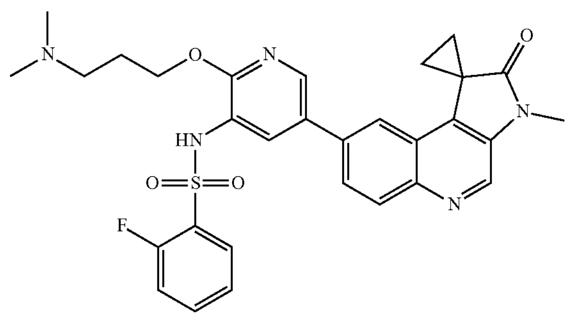 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-2-fluorobenzenesulfonamide | 576.20 | 1H NMR (400 MHz, CDCl3) δ 8.71 (s, 1H), 8.14(d, J = 8.8 Hz, 1H), 8.05 (td, J = 7.6, 1.8 Hz, 1H), 7.89 (dd, J = 14.9, 2.2 Hz, 2H), 7.65 (dd, J = 8.8, 1.9 Hz, 1H), 7.54-7.43 (m, 1H), 7.35 (d, J = 1.9 Hz, 1H), 7.30-7.20 (m, 1H), 7.17-7.07 (m, 1H), 4.43 (t, J = 5.9 Hz, 2H), 3.49 (s, 3H), 2.93 (t, J = 6.0 Hz, 2H), 2.77 (s, 6H), 2.26 (q, J = 4.4 Hz, 2H), 2.14 (p, J = 5.9 Hz, 2H), 2.00 (q, J = 4.3 Hz, 2H). |

| Examples | Structure | Name | MS: [(M + 1)]+ | 1H NMR |
|---|---|---|---|---|
| 108 | 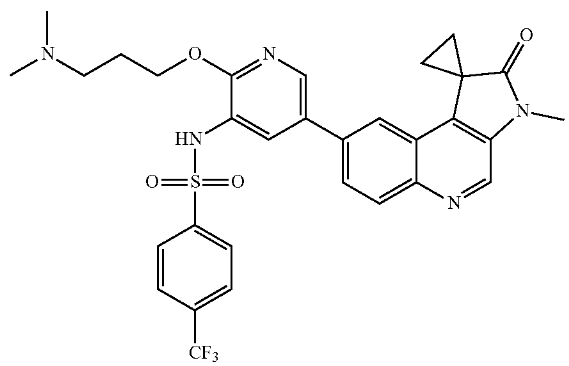 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-(trifluoromethyl)benzenesulfonamide | 626.10 | 1H NMR (300 MHz, DMSO-d6) δ 8.89 (s, 1H), 8.06 (dd, J = 16.7, 8.5 Hz, 3H), 7.88 (d, J = 8.2 Hz, 3H), 7.70 (dd, J = 8.1, 1.5 Hz, 1H), 7.52 (s, 1H), 7.26 (s, 1H), 4.34 (t, J = 4.8 Hz, 2H), 3.41 (s, 3H), 3.21-3.16 (m, 2H), 2.95 (s, 6H), 2.31-2.10 (m, 4H), 1.78 (q, J = 3.3, 2H). |
| 109 | 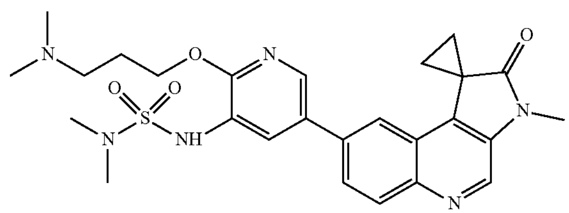 | 8'-[6-[3-(Dimethylamino)propoxy]-5-[(dimethylsulfamoyl)amino]pyridine-3-yl]-3'-methyl-2',3'-dihydrospiro[cyclopropane-1,1'-pyrrolo[2,3-c]quinoline]-2'-one | 525.20 | 1H NMR (300 MHz, CD3OD) δ 8.80 (s, 1H), 8.16-8.11 (m, 2H), 8.07 (d, J = 2.3 Hz, 1H), 7.89 (dd, J = 9.0, 1.9 Hz, 1H), 7.61 (d, J = 2.0 Hz, 1H), 4.50 (t, J = 6.0 Hz, 2H), 3.49 (s, 3H), 2.88 (t, J = 6.8 Hz, 2H), 2.81 (s, 6H), 2.57 (s, 6H), 2.51-2.42 (m, 2H), 2.16 (q, J = 6.4 Hz, 2H), 1.97 (q, J = 4.5 Hz, 2H). |
| 110 | 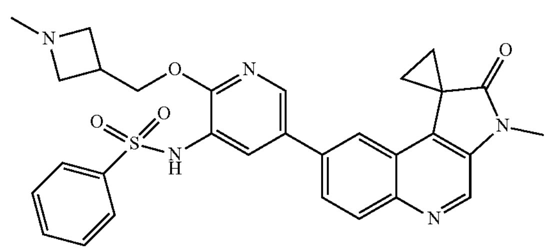 | N-(5-(3'-Methyl-2'-oxo-2',3'-dihydrospiro[cyclopropane-1,1'-pyrrolo[2,3-c]quinolin]-8'-yl)-2-((1-methylazetidin-3-yl)methoxy)pyridin-3-yl)benzenesulfonamide | 556.20 | 1H NMR (300 MHz, CDCl3) δ 8.64 (s, 1H), 8.03 (dd, J = 6.6, 3.0 Hz, 2H), 7.96 (d, J = 8.9 Hz, 1H), 7.61-7.42 (m, 4H), 7.39 (d, J = 1.6 Hz, 1H), 7.14 (d, J = 1.9 Hz, 1H), 6.95 (d, J = 1.7 Hz, 1H), 4.49-4.29 (m, 1H), 4.20 (dd, J = 13.3, 9.2 Hz, 1H), 3.73 (dd, J = 12.8, 4.90 Hz, 1H), 3.59 (dd, J = 9.60, 5.40 Hz, 1H), 3.50-3.43 (m, 5H), 3.41 (s, 3H), 2.76-2.63 (m, 1H), 2.18 (q, J = 3.90, 2H), 2.01 (q, J = 3.90 Hz, 2H). |

-continued

| Examples | Structure | Name | MS: [(M + 1)]+ | 1H NMR |
|---|---|---|---|---|
| 111 | 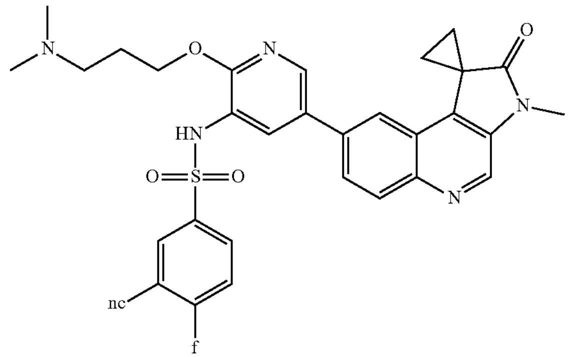 | 3-Cyano-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-fluorobenzenesulfonamide | 601.20 | 1H NMR (300 MHz, CDCl3) δ 8.73 (s, 1H), 8.33-8.22 (m, 1H), 8.17 (d, J = 8.7 Hz, 2H), 7.90 (d, J = 2.2 Hz, 1H), 7.75-7.58 (m, 2H), 7.40-7.29 (m, 2H), 4.53 (t, J = 5.5 Hz, 2H), 3.51 (s, 3H), 3.32-3.17 (m, 2H), 3.07 (s, 6H), 2.32 (p, J = 5.4 Hz, 2H), 2.24 (q, J = 4.3 Hz, 2H), 2.02 (q, J = 4.3 Hz, 2H). |
| 112 | 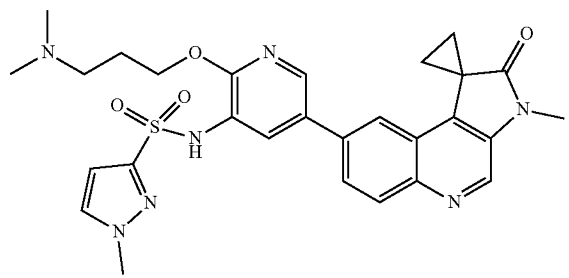 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-1-methyl-1H-pyrazole-3-sulfonamide | 562.20 | 1H NMR (300 MHz, CD3OD) δ 8.80 (s, 1H), 8.11 (d, J = 8.8 Hz, 1H), 7.89-7.80 (m 3H), 7.67 (d, J = 2.3 Hz, 1H), 7.51 (s, 1H), 6.70 (d, J = 2.3 Hz, 1H), 4.46 (t, J = 5.6 Hz, 2H), 3.90 (s, 3H), 3.51 (s, 3H), 3.27(t, J = 6.0 Hz, 2H), 2.98 (s, 6H), 2.43 (q, J = 4.4 Hz, 2H), 2.29-2.22 (m, 2H), 1.99 (q, J = 4.5 Hz, 2H). |
| 113 | 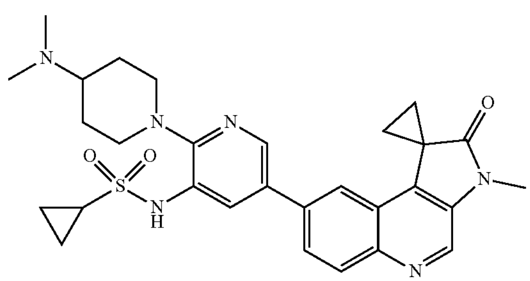 | N-(2-(4-(Dimethylamino)piperidin-1-yl)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide | 547.25 | 1H NMR (300 MHz, CDCl3) δ 8.75 (s, 1H), 8.38 (d, J = 2.3 Hz, 1H), 8.27-8.10 (m, 2H), 7.76 (d, J = 9.4 Hz, 1H), 7.51 (s, 1H), 3.50 (s, 3H), 3.40 (s, 2H), 3.01 (t, J = 12.0 Hz, 2H), 2.70-2.62 (m, 7H), 2.34-2.24 (m, 4H), 2.06-1.96 (m, 5H), 1.35 (s, 2H), 1.12-1.04 (m, 2H). |

| Examples | Structure | Name | MS: [(M + 1)]+ | 1H NMR |
|---|---|---|---|---|
| 114 | 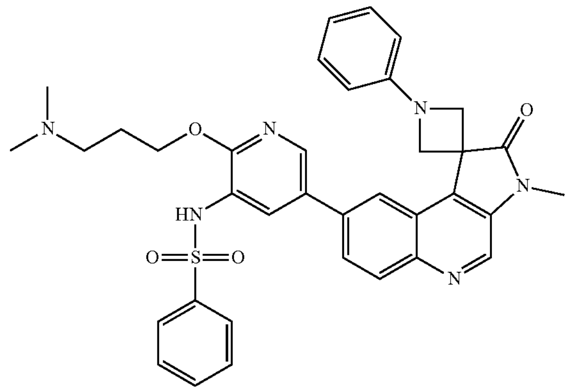 | N-(2-(3-(Dimethylamino)propoxy)-5-(3'-methyl-2'-oxo-1-phenyl-2',3'-dihydrospiro[azetidine-3,1'-pyrrolo[2,3-c]quinolin]-8'-yl)pyridin-3-yl)benzenesulfonamide | 649.30 | 1H NMR (300 MHz, DMSO-d6) δ 8.90 (s, 1H), 8.64 (d, J = 1.9 Hz, 1H), 8.16 (d, J = 8.9 Hz, 1H), 7.80-7.69 (m, 3H), 7.60 (dd, J = 9.6, 2.1 Hz, 2H), 7.49-7.37 (m, 3H), 7.27 (t, J = 7.8 Hz, 2H), 6.82 (t, J = 7.3 Hz, 1H), 6.68 (d, J = 7.9 Hz, 2H), 4.46 (d, J = 7.8 Hz, 2H), 4.19 (t, J = 5.8 Hz, 2H), 4.12 (d, J = 7.8 Hz, 2H), 3.33 (s, 3H), 3.01 (t, J = 5.8 Hz, 2H), 2.71 (s, 6H), 2.01-1.95 (m, 2H). |
| 115 | 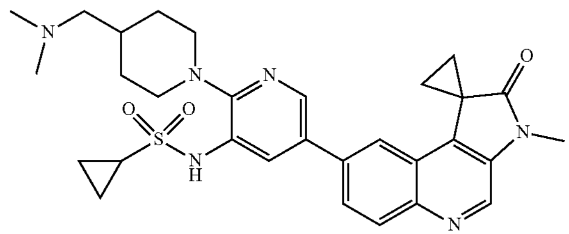 | N-(2-(4-((Dimethylamino)methyl)piperidin-1-yl)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide | 561.30 | 1H NMR (400 MHz, CDCl3) δ 8.74 (s, 1H), 8.39 (d, J = 2.2 Hz, 1H), 8.21 (d, J = 8.9 Hz, 1H), 8.16 (d, J = 2.1 Hz, 1H), 7.77 (dd, J = 8.8, 1.9 Hz, 1H), 7.51 (d, J = 2.1 Hz, 1H), 3.50 (s, 3H), 3.30-3.21 (m, 2H), 2.98 (t, J = 12.1 Hz, 2H), 2.78 (s, 6H), 2.64-2.56 (m, 2H), 2.31 (q, J = 4.5 Hz, 2H), 2.23-1.98 (m, 4H), 1.36-1.30 (m, 2H), 1.12-1.07 (m, 2H), 0.93-0.69 (m, 4H). |
| 116 | 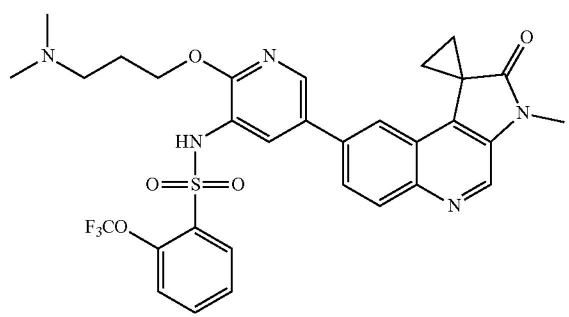 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-2-(trifluoromethoxy)benzenesulfonamide | 642.20 | 1H NMR (300 MHz, CD3OD) δ 8.76 (s, 1H), 8.07 (dd, J = 8.6, 4.8 Hz, 2H), 7.85 (d, J = 2.2 Hz, 1H), 7.79-7.68 (m, 1H), 7.65-7.53 (m, 2H), 7.48-7.35 (m, 3H), 4.43 (t, J = 5.8 Hz, 2H), 3.47 (s, 3H), 3.19-3.12 (m, 2H), 2.80 (s, 6H), 2.28 (q, J = 4.5 Hz, 2H), 2.19 (t, J = 6.2 Hz, 2H), 1.92 (q, J = 4.3 Hz, 2H). |

| Examples | Structure | Name | MS: [(M + 1)]+ | 1H NMR |
|---|---|---|---|---|
| 117 | 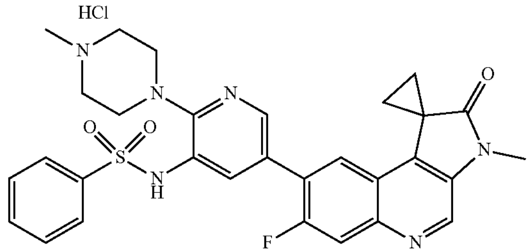 [SMILES: Cl ; CN1CCN(c2ncc(-c3cc4c5c(cnc4cc3F)N(C)C(=O)C53CC3)cc2NS(=O)(=O)c2ccccc2)CC1] | N-(5-(7'-Fluoro-3'-methyl-2'-oxo-2',3'-dihydrospiro[cyclopropane-1,1'-pyrrolo[2,3-c]quinolin]-8'-yl)-2-(4-methylpiperazin-1-yl)Pyridin-3-yl)benzenesulfonamide hydrochloride | 573.30 | 1H NMR (300 MHz, DMSO-$d_6$) δ 10.17 (s, 2H), 8.95 (s, 1H), 8.47 (t, J = 1.5 Hz, 1H), 7.90 (d, J = 12.2 Hz, 1H), 7.85-7.78 (m, 2H), 7.75-7.56 (m, 4H), 7.41 (t, J = 8.8 Hz, 1H), 3.77 (t, J = 7.2 Hz, 4H), 3.41 (s, 3H), 3.22 (t, J = 7.5 Hz, 4H), 2.82 (s, 3H), 2.41 (q, J = 4.5 Hz, 2H), 1.79 (q, J = 4.3 Hz, 2H). |
| 118 | 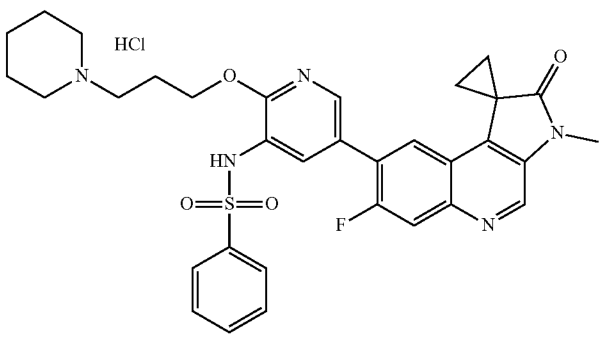 [SMILES: CN1C(=O)C2(CC2)c2c1cnc1cc(F)c(-c3cnc(OCCCN4CCCCC4)c(NS(=O)(=O)c4ccccc4)c3)cc21 ; Cl] | N-(5-(7'-Fluoro-3'-methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)benzenesulfonamide hydrochloride | 616.20 | 1H NMR (400 MHz, DMSO-$d_6$) δ 10.00 (s, 1H), 9.72 (br, 1H), 8.96 (s, 1H), 8.31 (d, J = 2.0 Hz, 1H), 7.98-7.89 (m, 2H), 7.83-7.76 (m, 2H), 7.71-7.65 (m, 1H), 7.65-7.57 (m, 2H), 7.45 (d, J = 8.4 Hz, 1H), 4.17 (t, J = 5.8 Hz, 2H), 3.42 (s, 5H), 3.19-3.12 (m, 2H), 2.94-2.81 (m, 2H), 2.49-2.43 (m, 2H), 2.06-1.96 (m, 2H), 1.90-1.65 (m, 7H), 1.52-1.35 (m, 1H). |
| 119 | 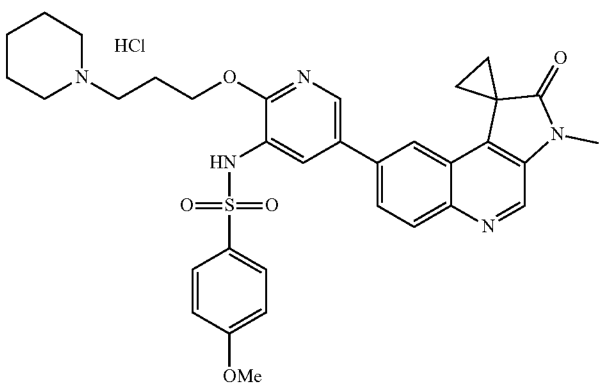 [SMILES: COc1ccc(S(=O)(=O)Nc2cc(-c3ccc4ncc5c(c4c3)C3(CC3)C(=O)N5C)cnc2OCCCN2CCCCC2)cc1 ; Cl] | 4-Methoxy-N-(5-(3'-methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)benzenesulfonamide hydrochloride | 628.10 | 1H NMR (400 MHz, DMSO-$d_6$) δ 9.86 (s, 2H), 8.92 (s, 1H), 8.41 (d, J = 2.3 Hz, 1H), 8.14 (d, J = 8.9 Hz, 1H), 7.96 (d, J = 2.3 Hz, 1H), 7.82 (dd, J = 8.9, 1.9 Hz, 1H), 7.73 (d, J = 8.7 Hz, 2H), 7.49 (d, J = 2.0 Hz, 1H), 7.13 (d, J = 8.8 Hz, 2H), 4.19 (t, J = 5.9 Hz, 2H), 3.82 (s, 3H), 3.42 (s, 5H), 3.17 (t, J = 7.2 Hz, 2H), 2.86 (br, 2H), 2.45-2.44 (m, 2H), 2.04-2.00 (m, 2H), 1.81-1.80 (m, 2H), 1.49-1.40 (m, 1H). |

| Examples | Structure | Name | MS: [(M + 1)]+ | ¹H NMR |
|---|---|---|---|---|
| 120 | 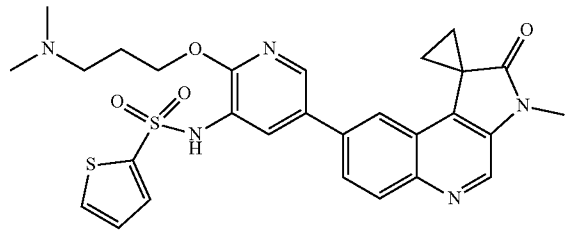 | N-(2-(3-(Dimethylamino)propoxy)-5-(3'-methyl-2-oxo-2',3'-dihydrospiro[cyclopropane-1,1'-pyrrolo[2,3-c]quinolin]-8'-yl)pyridin-3-yl)thiophene-2-sulfonamide | 564.10 | ¹H NMR (300 MHz, DMSO-$d_6$) δ 8.89 (s, 1H), 8.10 (d, J = 8.9 Hz, 1H), 7.88 (d, J = 2.2 Hz, 1H), 7.74 (dd, J = 8.8, 1.9 Hz, 1H), 7.68-7.64 (m, 2H), 7.45 (dd, J = 3.6, 1.3 Hz, 1H), 7.36 (d, J = 1.9 Hz, 1H), 7.05 (dd, J = 5.0, 3.6 Hz, 1H), 4.33 (t, J = 5.6 Hz, 2H), 3.42 (s, 3H), 3.35-3.31 (m, 2H), 2.32 (q, J = 4.4 Hz, 2H), 2.20-2.11 (m, 2H), 1.84 (q, J = 4.4 Hz, 2H). |
| 121 | 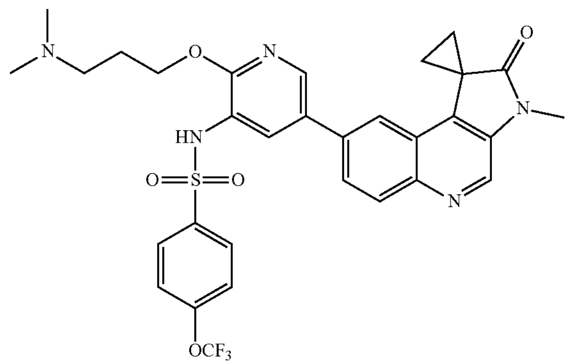 | N-(2-(3-(Dimethylamino)propoxy)-5-(3'-methyl-2-oxo-2',3'-dihydrospiro[cyclopropane-1,1'-pyrrolo[2,3-c]quinolin]-8'-yl)pyridin-3-yl)-4-(trifluoromethoxy)benzenesulfonamide | 642.10 | ¹H NMR (400 MHz, DMSO-$d_6$) δ 10.15 (s, 1H), 8.93 (s, 1H), 8.46 (s, 1H), 8.13 (d, J = 8.8 Hz, 1H), 8.00 (s, 1H), 7.90 (d, J = 8.8 Hz, 2H), 7.83 (d, J = 9.2 Hz, 1H), 7.62 (d, J = 8.3 Hz, 2H), 7.52 (s, 1H), 4.11 (t, J = 5.6 Hz, 2H), 3.42 (s, 3H), 3.21 (t, J = 7.7 Hz, 2H), 2.80 (s, 6H), 2.48 (q, J = 4.2 Hz, 2H ), 2.00-1.89 (m, 2H), 1.79 (q, J = 4 2 Hz, 2H). |
| 122 | 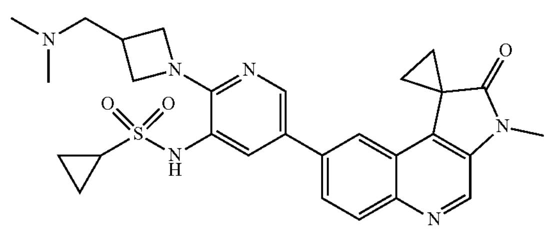 | N-(2-((3-((Dimethylamino)methyl)azetidin-1-yl)-5-(3'-methyl-2-oxo-2',3'-dihydrospiro[cyclopropane-1,1'-pyrrolo[2,3-c]quinolin]-8'-yl)pyridin-3-yl)cyclopropanesulfonamide | 533.20 | ¹H NMR (300 MHz, DMSO-$d_6$) δ 8.87 (s, 1H), 8.48 (d, J = 2.2 Hz, 1H), 8.09 (d, J = 8.8 Hz, 1H), 7.90-7.76 (m, 2H), 7.48 (d, J = 1.9 Hz, 1H), 4.28 (t, J = 8.3 Hz, 2H), 3.85 (dd, J = 8.8, 5.6 Hz, 2H), 3.41 (s, 3H), 2.89-2.76 (m, 2H), 2.51 (m, 4H), 2.15 (s, 6H), 1.75 (q, J = 4.3 Hz, 2H), 1.02 (dd, J = 7.4, 4.8 Hz, 2H), 0.96-0.85 (m, 2H). |

| Examples | Structure | Name | MS: [(M + 1)]+ | 1H NMR |
|---|---|---|---|---|
| 123 | 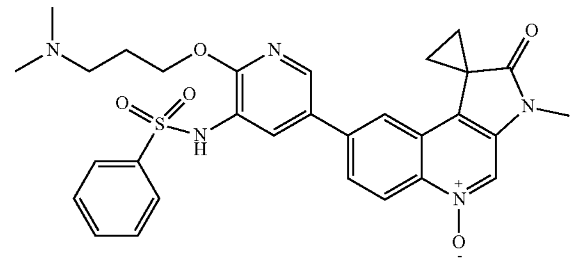 | 8'-(6-(3-(Dimethylamino)propoxy)-5-(phenylsulfonamido)pyridin-3-yl)-3'-methyl-2'-oxo-2',3'-dihydrospiro[cyclopropane-1,1'-pyrrolo[2,3-c]quinoline]5'-oxide | 574.20 | 1H NMR (300 MHz, DMSO-d6) δ 8.87 (s, 1H), 8.58 (d, J = 9.2 Hz, 1H), 7.94 (d, J = 2.3 Hz, 1H), 7.88-7.77 (m, 2H), 7.72 (dd, J = 9.2, 1.7 Hz, 1H), 7.55 (d, J = 2.3 Hz, 1H), 7.53-7.45 (m, 3H), 7.28 (d, J = 1.8 Hz, 1H), 4.30 (t, J = 5.7 Hz, 2H), 3.40-3.30 (s, 3H), 3.17 (t, J = 5.6 Hz, 2H), 2.82 (s, 6H), 2.61 (s, 1H), 2.34-2.16 (m, 2H), 2.09 (s, 2H), 1.78 (q, J = 4.4 Hz, 2H). |
| 124 | 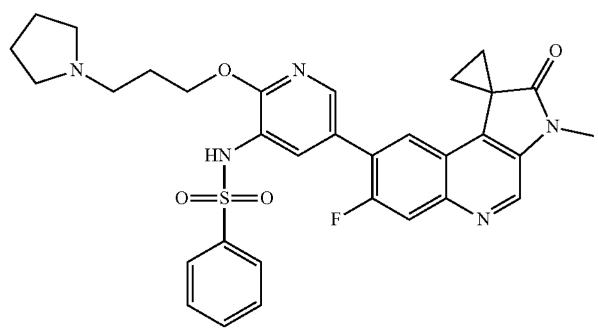 [SMILES: CN1C(=O)C2(CC2)c2c1cnc1cc(F)c(-c3cnc(OCCCN4CCCC4)c(NS(=O)(=O)c4ccccc4)c3)cc21] | N-(5-(7'-Fluoro-3'-methyl-2'-oxo-2',3'-dihydrospiro[cyclopropane-1,1'-pyrrolo[2,3-c]quinolin]-8'-yl)-2-(3-(pyrrolidin-1-yl)propoxy)pyridin-3-yl)benzenesulfonamide | 602.20 | 1H NMR (400 MHz, DMSO-d6) δ 8.92 (s, 1H), 7.98-7.84 (m, 2H), 7.79-7.75 (m, 2H), 7.62 (s, 1H), 7.58-7.44 (m, 3H), 7.30 (d, J = 8.1 Hz, 1H), 4.28 (t, J = 5.8 Hz, 2H), 3.40 (s, 3H), 3.25-3.10 (m, 6H), 2.10-1.92 (m, 6H), 1.78 (q, J = 4.4 Hz, 2H). |
| 125 | 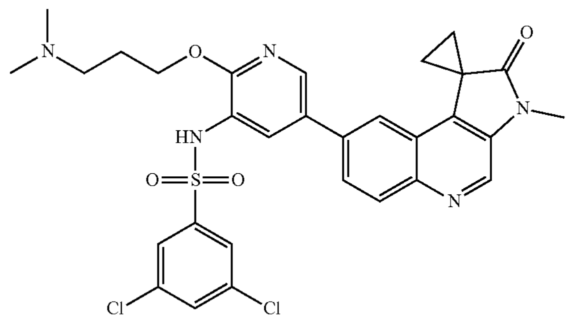 | 3,5-Dichloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | 626.10 | 1H NMR (400 MHz, DMSO-d6) δ 8.87 (s, 1H), 8.07 (d, J = 8.8 Hz, 1H), 7.90 (d, J = 2.2 Hz, 1H), 7.79 (t, J = 1.9 Hz, 1H), 7.74 (d, J = 1.9 Hz, 2H), 7.67 (dd, J = 8.8, 1.9 Hz, 1H), 7.40 (d, J = 2.2 Hz, 1H), 7.27 (d, J = 1.9 Hz, 1H), 4.36 (t, J = 5.5 Hz, 2H), 3.40 (s, 3H), 3.37 (t, J = 5.2 Hz, 2H) 2.95 (s, 6H), 2.24-2.16 (m, 4H), 1.78 (q, J = 4.3 Hz, 2H). |

| Examples | Structure | Name | MS: [(M + 1)]+ | 1H NMR |
|---|---|---|---|---|
| 126 | 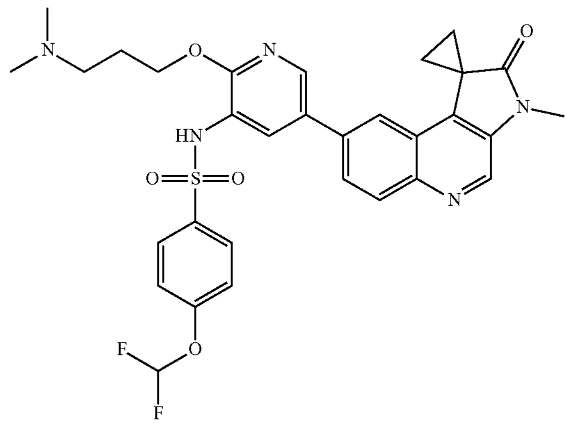 | 4-(Difluoromethoxy)-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | 624.10 | 1H NMR (300 MHz, DMSO-d6) δ 8.88 (s, 1H), 8.08 (d, J = 8.9 Hz, 1H), 7.93-7.81 (m, 3H), 7.70 (dd, J = 8.9, 1.8 Hz, 1H), 7.31 (t, J = 73.5 Hz, 1H), 7.53 (d, J = 2.3 Hz, 1H), 7.30-7.22 (m, 3H), 4.31 (t, J = 5.6 Hz, 2H), 3.40 (s, 3H), 3.21-3.14 (m, 2H), 2.83 (s, 6H), 2.27 (q, J = 4.5 Hz, 2H), 2.14-2.06 (m, 2H), 1.81 (q, J = 4.3 Hz, 2H). |
| 127 | 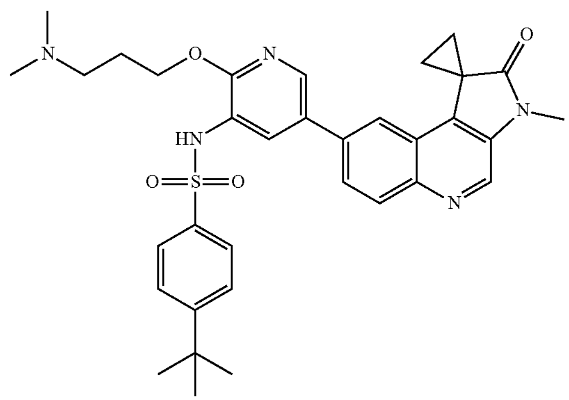 | 4-(tert-Butyl)-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | 614.10 | 1H NMR (300 MHz, DMSO-d6) δ 8.89 (s, 1H), 8.14-8.00 (m, 2H), 7.78-7.65 (m, 4H), 7.53 (d, J = 8.4 Hz, 2H), 7.39 (s, 1H), 4.24 (t, J = 5.7 Hz, 2H), 3.42 (s, 3H), 3.04 (t, J = 6.0 Hz 2H), 2.72 (s, 6H), 2.37 (q, J = 4.2 Hz, 2H), 2.05-1.95 (m, 2H), 1.81 (q, J = 4.3 Hz, 2H), 1.27 (s, 9H). |

| Examples | Structure | Name | MS: [(M + 1)]+ | 1H NMR |
|---|---|---|---|---|
| 128 | 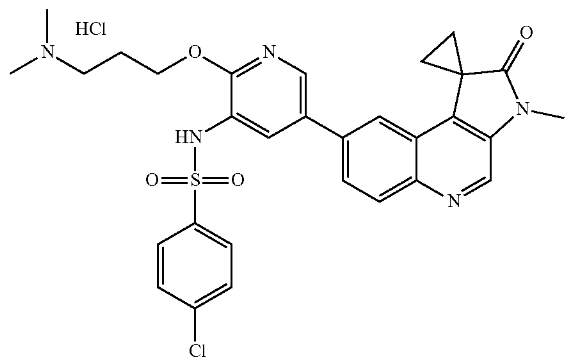 | 4-Chloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)benzenesulfonamide hydrochloride | 592.20 | 1H NMR (400 MHz, DMSO-d6) δ 10.02 (s, 2H), 8.92 (s, 1H), 8.39 (s, 1H), 8.13 (d, J = 8.8 Hz, 1H), 7.93 (s, 1H), 7.86-7.75 (m, 3H), 7.68 (d, J = 8.4 Hz, 2H), 7.47 (s, 1H), 4.18 (t, J = 5.8 Hz, 2H), 3.60 (s, 3H), 3.21 (t, J = 7.5 Hz, 2H), 2.81 (s, 6H), 2.47-2.39 (m, 2H), 1.99 (t, J = 7.5 Hz, 2H), 1.80 (q, J = 4.3 Hz, 2H). |
| 129 | 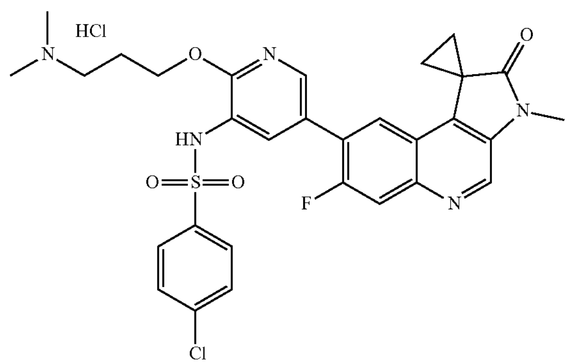 | 4-Chloro-N-(2-(3-(dimethylamino)propoxy)-5-(7-fluoro-3'-methyl-2'-oxo-2',3'-dihydrospiro[cyclopropane-1,1'-pyrrolo[2,3-c]quinolin]-8'-yl)pyridin-3-yl)benzenesulfonamide hydrochloride | 610.20 | 1H NMR (400 MHz, DMSO-d6) δ 10.12 (s, 2H), 8.94 (s, 1H), 8.36-8.14 (m, 1H), 7.98-7.83 (m, 2H), 7.81-7.73 (m, 2H), 7.72-7.61 (m, 2H), 7.44 (d, J = 8.4 Hz, 1H), 4.16 (t, J = 5.9 Hz, 2H), 3.45 (s, 3H), 3.19 (t, J = 7.7 Hz, 2H), 2.78 (s, 6H), 2.46-2.41 (m, 2H), 2.02-1.92 (m, 2H), 1.76 (q, J = 4.4 Hz, 2H). |
| 130 | 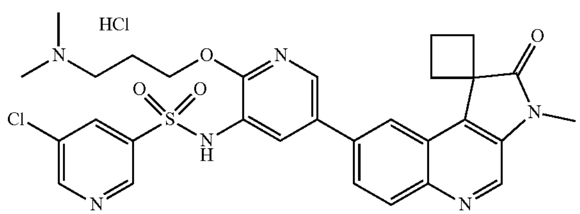 | 5-Chloro-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyridine-3-sulfonamide hydrochloride | 607.10 | 1H NMR (400 MHz, DMSO-d6) δ 10.54 (s, 1H), 9.86 (d, J = 2.2 Hz, 1H), 8.95 (d, J = 2.0 Hz, 1H), 8.91 (d, J = 2.0 Hz, 1H), 8.87 (s, 1H), 8.58 (s, 1H), 8.38 (d, J = 2.0 Hz, 1H), 8.27 (t, J = 2.1 Hz, 1H), 8.18 (t, J = 7.2 Hz, 2H), 7.98 (dd, J = 9.0, 1.9 Hz, 1H), 4.19 (t, J = 6.0 Hz, 2H), 3.33 (s, 3H), 3.22 (t, J = 6.8 Hz, 2H), 2.98-2.89 (m, 2H), 2.82 (s, 6H), 2.65-2.58 (m, 4H), 2.02-1.92 (m, 2H). |

| Examples | Structure | Name | MS: [(M + 1)]+ | 1H NMR |
|---|---|---|---|---|
| 131 | 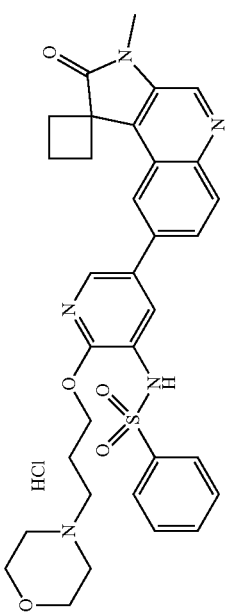 | N-(5-(3'-Methyl-2'-oxo-2',3'-dihydrospiro[cyclobutane-1,1'-pyrrolo[2,3-c]quinolin]-8'-yl)-2-(3-morpholinopropoxy)pyridin-3-yl)benzenesulfonamide hydrochloride | 613.90 | 1H NMR (400 MHz, CDCl₃) δ 12.82 (s, 1H), 8.65 (s, 1H), 8.55 (s, 1H), 8.32 (d, J = 2.0 Hz, 1H), 8.23-8.18 (m, 2H), 8.05 (d, J = 2.2 Hz, 1H), 8.01 (d, J = 7.6 Hz, 2H), 7.73 (dd, J = 8.8, 2.0 Hz, 1H), 7.57 (t, J = 7.2 Hz, 1H), 7.50 (t, J = 7.5 Hz, 2H), 4.43 (t, J = 5.6 Hz, 2H), 4.36 (s, 2H), 4.03 (s, 2H), 3.39 (s, 3H), 3.63 (s, 2H), 3.28 (s, 2H), 2.98-2.84 (m, 4H), 2.83-2.72 (m, 2H), 2.72-2.62 (m, 1H), 2.62-2.51 (m, 1H), 2.46 (s, 2H). |
| 132 | 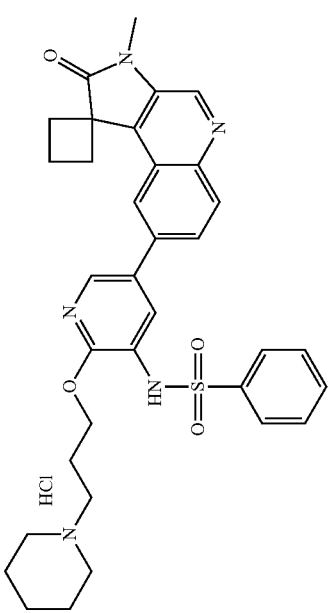 | N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)benzenesulfonamide hydrochloride | 612.30 | 1H NMR (300 MHz, CDCl₃) δ 11.85 (s, 1H), 8.68 (s, 1H), 8.34 (s, 1H), 8.27 (d, J = 8.8 Hz, 1H), 8.20 (d, J = 2.1 Hz, 1H), 8.08 (d, J = 2.1 Hz, 1H), 8.04-7.96 (m, 2H), 7.83-7.72 (m, 1H), 7.60-7.44 (m, 3H), 4.38 (s, 2H), 3.69 (s, 2H), 3.39 (s, 3H), 3.23 (s, 2H), 2.98-2.53 (m, 8H), 2.50-2.26 (m, 4H), 2.01-1.84 (m, 4H), 1.55-1.36 (m, 1H). |
| 133 | 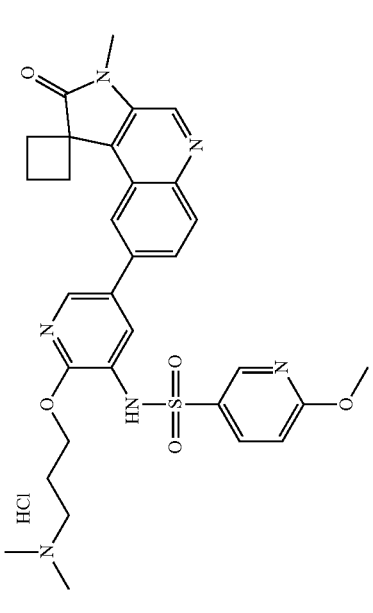 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-6-methoxypyridine-3-sulfonamide hydrochloride | 603.10 | 1H NMR (300 MHz, DMSO-d₆) δ 10.13 (s, 2H), 8.87 (s, 1H), 8.53 (d, J = 2.6 Hz, 1H), 8.37 (d, J = 1.8 Hz, 1H), 8.19 (d, J = 8.1 Hz, 1H), 8.13 (s, 1H), 8.06 (t, J = 2.7, 3.9 Hz, 1H), 7.97 (d, J = 9.6 Hz, 1H), 7.06 (d, J = 8.8 Hz, 1H), 4.21 (t, J = 5.7 Hz, 2H), 3.91 (s, 3H), 3.33 (s, 3H), 3.25 (t, J = 7.7 Hz, 2H), 2.98-2.87 (m, 2H), 2.82 (s, 6H), 2.64-2.53 (m, 4H), 2.06-1.98 (m, 2H). |

| Examples | Structure | Name | MS: [(M + 1)]+ | 1H NMR |
|---|---|---|---|---|
| 134 | 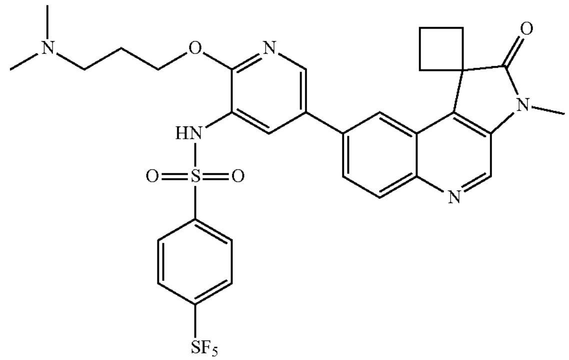 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-(pentafluoro-16-sulfaneyl)benzenesulfonamide | 698.10 | 1H NMR (300 MHz, CDCl3) δ 8.63 (s, 1H), 8.34 (d, J = 2.0 Hz, 1H), 8.17 (d, J = 8.9 Hz, 1H), 8.11-7.95 (m, 4H), 7.84-7.69 (m, 3H), 4.47 (t, J = 5.6 Hz, 2H), 3.38 (s, 3H), 3.04 (t, J = 5.7 Hz, 2H), 2.88 (s, 6H), 2.83-2.51 (m, 6H), 2.23-2.14 (m, 2H). |
| 135 | 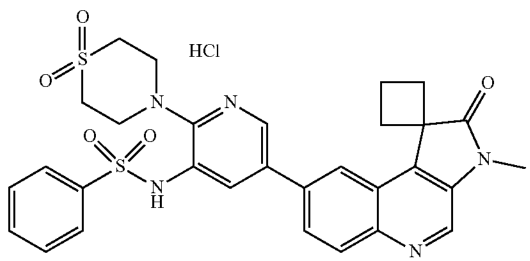 [SMILES: CN1C(=O)C2(CCC2)c2c1cnc1ccc(-c3cnc(N4CCS(=O)(=O)CC4)c(NS(=O)(=O)c4ccccc4)c3)cc21 ; Cl] | N-(2-(1,1-Dioxidothiomorpholino)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride | 604.20 | 1H NMR (400 MHz, DMSO-d6) δ 9.97 (s, 1H), 8.92 (s, 1H), 8.67 (d, J = 2.2 Hz, 1H), 8.31 (d, J = 2.0 Hz, 1H), 8.19 (d, J = 8.9 Hz, 1H), 7.92-7.79 (m, 4H), 7.71-7.56 (m, 3H), 3.60-3.51 (m, 6H), 3.32 (s, 3H), 3.26-3.24 (m, 4H), 2.92-2.82 (m, 2H), 2.64-2.54 (m, 2H). |
| 136 | 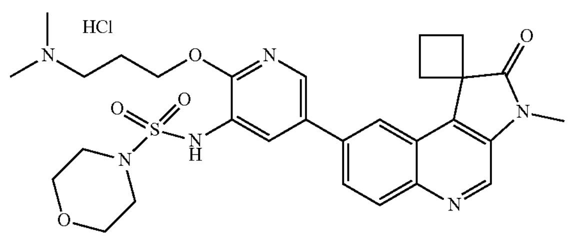 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)morpholine-4-sulfonamide hydrochloride | 581.30 | 1H NMR (400 MHz, DMSO-d6) δ 10.20 (s, 1H), 9.70 (s, 1H), 8.86 (s, 1H), 8.54 (d, J = 2.3 Hz, 1H), 8.38 (d, J = 2.0 Hz, 1H), 8.23-8.16 (m, 2H), 7.98 (dd, J = 8.9, 2.0 Hz, 1H), 4.49 (t, J = 5.9 Hz, 2H), 3.60 (t, J = 4.6 Hz, 4H), 3.41-3.37 (m, 2H), 3.32 (s, 3H), 3.10 (t, J = 4.7 Hz, 4H), 2.96-2.86 (m, 2H), 2.81 (s, 6H), 2.63-2.52 (m, 4H), 2.26-2.17 (m, 2H). |

| Examples | Structure | Name | MS: [(M + 1)]+ | 1H NMR |
|---|---|---|---|---|
| 137 | 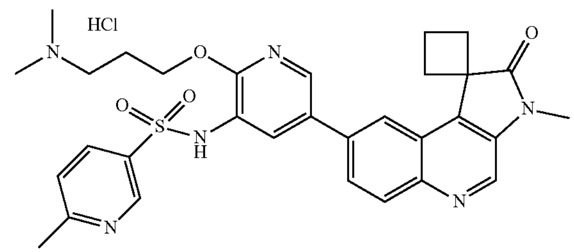 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide hydrochloride | 587.20 | 1H NMR (400 MHz, DMSO-d6) δ 10.27 (s, 1H), 10.16 (br, 1H), 8.88 (s, 1H), 8.80 (d, J = 2.4 Hz, 1H), 8.54 (d, J = 2.3 Hz, 1H), 8.38 (s, 1H), 8.22-8.13 (m, 2H), 8.04-7.95 (m, 2H), 7.50 (d, J = 8.2 Hz, 1H), 4.16 (t, J = 5.9 Hz, 2H), 3.32 (s, 3H), 3.23-3.15 (m, 2H), 2.98-2.87 (m, 2H), 2.80 (d, J = 4.7 Hz, 6H), 2.64-2.52 (m, 7H), 2.02-1.92 (m, 2H). |
| 139 | 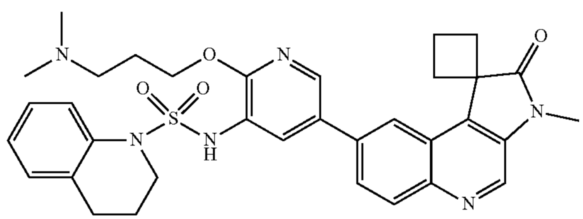 [SMILES: CN(C)CCCOc1ncc(-c2ccc3ncc4c(c3c2)C2(CCC2)C(=O)N4C)cc1NS(=O)(=O)N1CCCc2ccccc21] | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3,4-dihydroquinoline-1(2H)-sulfonamide | 627.20 | 1H NMR (400 MHz, DMSO-d6) δ 8.84 (s, 1H), 8.30 (d, J = 8.8 Hz, 2H), 8.15 (d, J = 8.8 Hz, 1H), 8.00-7.85 (m, 2H), 7.27 (d, J = 5.4 Hz, 2H), 6.54 (s, 1H), 6.38 (d, J = 9.2 Hz, 1H), 4.28 (t, J = 6.3 Hz, 2H), 3.31 (s, 3H), 3.16 (s, 2H), 2.87 (q, J = 9.5 Hz, 2H), 2.64-2.52 (m, 6H), 2.33 (s, 6H), 2.06-1.84 (m, 4H), 1.72 (t, J = 6.0 Hz, 2H). |
| 141 | 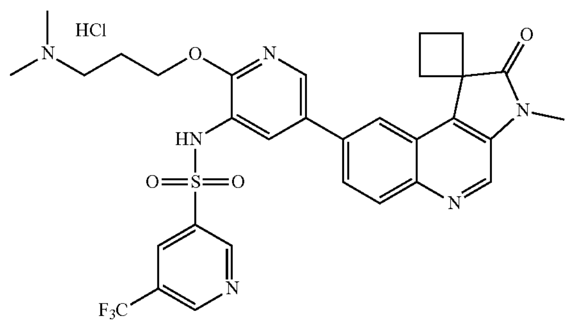 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-5-(trifluoromethyl)pyridine-3-sulfonamide hydrochloride | 641.10 | 1H NMR (400 MHz, DMSO-d6) δ 10.65 (br, 1H), 10.04 (br, 1H), 9.25 (d, J = 2.1 Hz, 1H), 8.85 (s, 1H), 8.42 (s, 1H), 8.32 (s, 1H), 8.15 (d, J = 8.9 Hz, 1H), 8.02 (s, 1H), 7.91 (d, J = 8.8 Hz, 1H), 4.22 (s, 2H), 3.31 (s, 3H), 3.28-3.19 (m, 2H), 2.85 (s, 8H), 2.64-2.52 (m, 4H), 2.01 (s, 2H). |

-continued

| Examples | Structure | Name | MS: [(M + 1)]+ | 1H NMR |
|---|---|---|---|---|
| 142 | 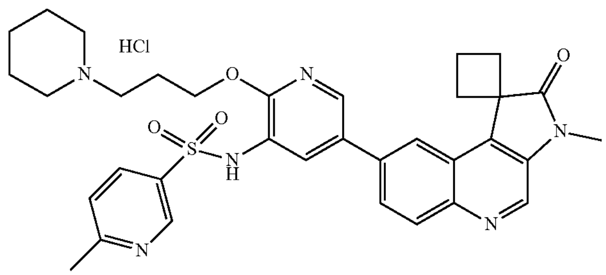 [SMILES: Cc1ccc(S(=O)(=O)Nc2cc(-c3ccc4ncc5c(c4c3)C3(CCC3)C(=O)N5C)cnc2OCCCN2CCCCC2)cn1 ; Cl] | 6-Methyl-N-(5-(3-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)pyridine-3-sulfonamide hydrochloride | 627.10 | 1H NMR (400 MHz, DMSO-d6) δ 8.85 (s, 2H), 8.79 (d, J = 1.6 Hz, 1H), 8.47 (s, 1H), 8.35 (s, 1H), 8.16 (d, J = 8.8 Hz, 1H), 8.10 (dd, J = 8, 2 Hz, 1H), 7.94 (d, J = 8.8 Hz, 1H), 7.48 (d, J = 8.4 Hz, 1H), 4.18 (t, J = 5.6 Hz, 2H), 3.32 (s, 3H), 3.13-3.09 (m, 6H), 2.94-2.88 (m, 2H), 2.69-2.60 (m, 7H), 2.02-1.99 (m, 2H), 1.81-1.79 (m, 4H), 1.57 (br, 2H). |
| 143 | 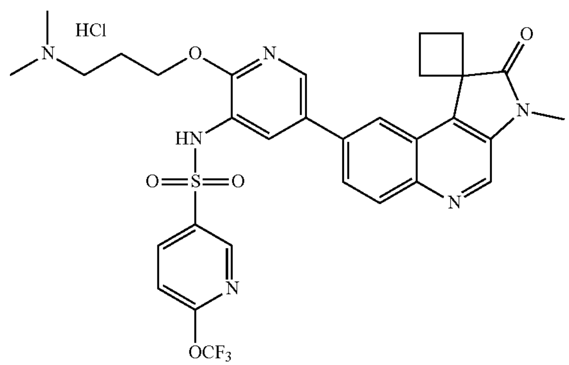 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-(trifluoromethoxy)benzenesulfonamide hydrochloride | 656.10 | 1H NMR (400 MHz, DMSO-d6) δ 10.12 (br, 1H), 8.85 (s, 1H), 8.41 (s, 1H), 8.33 (s, 1H), 8.15 (d, J = 8.9 Hz, 1H), 8.03 (s, 1H), 7.94-7.87 (m, 3H), 7.58 (d, J = 8.3 Hz, 2H), 4.17 (s, 2H), 3.32 (s, 3H), 3.24 (t, J = 7.4 Hz, 2H), 2.94-2.84 (m, 2H), 2.82 (s, 6H), 2.64-2.52 (m, 4H), 2.06-1.96 (m, 2H). |
| 144 | 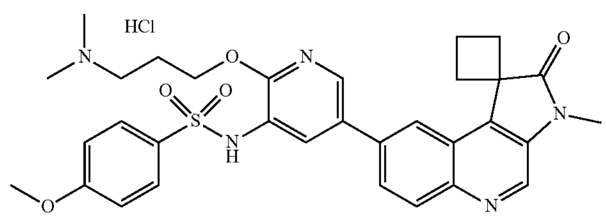 | N-(2-(3-(Dimethylamino)propoxy)-5-(3'-methyl-2'-oxo-2',3'-dihydrospiro[cyclobutane]-1,1'-pyrrolo[2,3-c]quinolin]-8'-yl)pyridin-3-yl)-4-methoxybenzenesulfonamide hydrochloride | 602.20 | 1HNMR(400 MHz, DMSO-d6) δ 8.85 (s, 1H), 8.40(s, 1H), 8.32(s, 1H), 8.15(d, J = 8.8 Hz, 1H), 8.02 (s, 1H), 7.91 (d, J = 8.8 Hz, 1H), 7.73 (d, J = 8.8 Hz, 2H), 7.08 (d, J = 8.8 Hz, 2H), 4.23 (t, J = 5.6 Hz, 2H), 3.81 (s, 3H), 3.32 (s, 3H), 3.20-3.17 (m, 2H), 2.97-2.85 (m, 2H), 2.77 (s, 6H), 2.67-2.55 (m, 4H), 2.08-2.02 (m, 2H). |

-continued

| Examples | Structure | Name | MS: [(M + 1)]+ | 1H NMR |
|---|---|---|---|---|
| 145 | 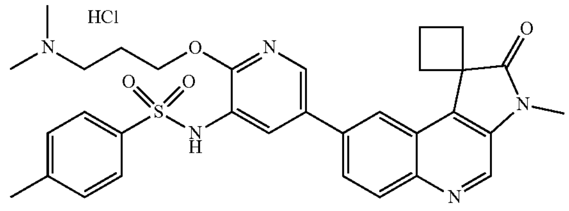 | N-(2-(3-(Dimethylamino)propoxy)-5-(3'-methyl-2'-oxo-2',3'-dihydrospiro[cyclobutane-1,1'-pyrrolo[2,3-c]quinolin]-8-yl)pyridin-3-yl)-4-methylbenzenesulfonamide hydrochloride | 586.20 | 1H NMR (400 MHz, DMSO-$d_6$) δ 9.97 (br, 1H), 8.85 (s, 1H), 8.41 (s, 1H), 8.31 (s, 1H), 8.16 (d, J = 8.8 Hz, 1H), 8.01 (s, 1H), 7.90 (d, J = 9.2 Hz, 1H), 7.68 (d, J = 8.4 Hz, 2H), 7.36 (d, J = 8.0 Hz, 2H), 4.22 (t, J = 5.6 Hz, 2H), 3.32 (s, 3H), 3.20-3.18 (m, 2H), 2.97-2.84 (m, 2H), 2.80 (s, 6H), 2.67-2.57 (m, 4H), 2.34 (s, 3H), 2.04-2.02 (m, 2H). |
| 146 | 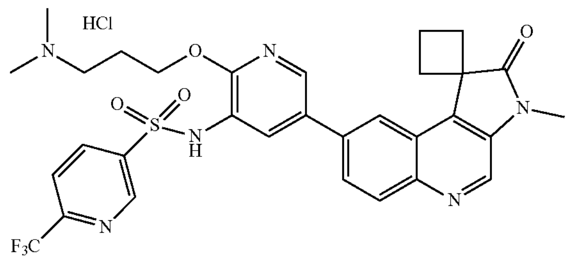 | N-(2-(3-(Dimethylamino)propoxy)-5-(3'-methyl-2'-oxo-2',3'-dihydrospiro[cyclobutane-1,1'-pyrrolo[2,3-c]quinolin]-8-yl)pyridin-3-yl)-6-(trifluoromethyl)pyridine-3-sulfonamide hydrochloride | 641.10 | 1H NMR (300 MHz, DMSO-$d_6$) δ 9.16 (s, 1H), 8.85 (s, 1H), 8.55 (s, 1H), 8.44-8.34 (m, 2H), 8.21-8.11 (m, 3H), 7.95 (d, J = 8.6 Hz, 1H), 4.14 (t, J = 5.7 Hz, 2H), 3.32 (s, 3H), 3.27-3.14 (m, 2H), 2.95-2.88 (m, 2H), 2.83 (s, 6H), 2.64-2.52 (m, 4H), 2.00-1.83 (m, 2H). |
| 147 | 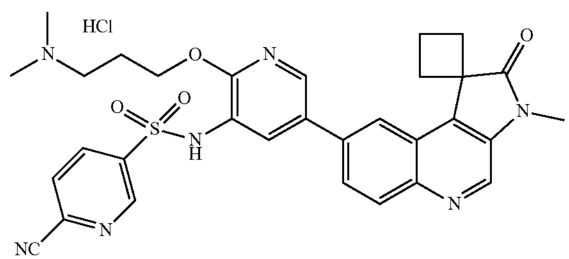 | 6-Cyano-N-(2-(3-(dimethylamino)propoxy)-5-(3'-methyl-2'-oxo-2',3'-dihydrospiro[cyclobulane-1,1'-pyrrolo[2,3-c]quinolin]-8-yl)pyridin-3-yl)pyridine-3-sulfonamide hydrochloride | 598.10 | 1H NMR (300 MHz, DMSO-$d_6$) δ 9.10 (d, J = 2.2 Hz, 1H), 8.85 (s, 1H), 8.47 (s, 1H), 8.40 (dd, J = 8.1, 2.3 Hz, 1H), 8.34 (s, 1H), 8.27 (d, J = 8.0 Hz, 1H), 8.16 (d, J = 8.9 Hz, 1H), 8.08 (s, 1H), 7.95 (d, J = 8.5 Hz, 1H), 4.19 (t, J = 5.7 Hz, 2H), 3.32 (s, 3H), 3.28-3.18 (m, 2H), 2.99-2.87 (m, 2H), 2.84 (s, 6H), 2.66-2.52 (m, 4H), 2.06-1.94 (m, 2H). |

| Examples | Structure | Name | MS: [(M + 1)]+ | 1H NMR |
|---|---|---|---|---|
| 148 | (structure with HCl, pyridine sulfonamide) | N-(2-(3-(Dimethylamino)propoxy)-5-(3'-methyl-2-oxo-2',3'-dihydrospiro[cyclobutane-1,1'-pyrrolo[2,3-c]quinolin]-8'-yl)pyridin-3-yl)pyridine-2-sulfonamide hydrochloride | 573.10 | 1H NMR (300 MHz, DMSO-d6) δ 8.84 (s, 1H), 8.69 (d, J = 4.6 Hz, 1H), 8.39 (s, 1H), 8.35 (s, 1H), 8.23-8.13 (m, 2H), 8.07 (d, J = 7.9 Hz, 1H), 8.03-7.97 (m, 1H), 7.92 (dd, J = 9.0, 1.9 Hz, 1H), 7.64 (t, J = 6.2 Hz, 1H), 4.28 (t, J = 5.7 Hz, 2H), 3.31 (s, 3H), 3.21 (t, J = 7.4 Hz, 2H), 2.94-2.82 (m, 2H), 2.81 (s, 6H), 2.65-2.53 (m, 4H), 2.10-1.97 (m, 2H). |
| 149 | (structure with HCl, dimethylsulfamoyl) | 8'-{6-[3-(Dimethylamino)propoxy]-5-[(dimethylsulfamoyl)amino]pyridine-3-yl}-3'-methyl-2',3'-dihydrospiro[cyclobutane-1,1'-pyrrolo[2,3-c]quinoline]-2'-one hydrochloride | 539.25 | 1H NMR (300 MHz, DMSO-d6) δ 8.85 (s, 1H), 8.48 (d, J = 2.3 Hz, 1H), 8.37 (d, J = 1.9 Hz, 1H), 8.21-8.15 (m, 2H), 7.97 (dd, J = 8.9, 1.9 Hz, 1H), 4.48 (t, J = 5.9 Hz, 2H), 3.32 (s, 3H), 3.30-3.27 (m, 2H), 2.97-2.83 (m, 2H), 2.78 (s, 6H), 2.75 (s, 6H), 2.67-2.52 (m, 4H), 2.26-2.14 (m, 2H). |
| 150 | (structure with CF3 benzenesulfonamide) | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3-(trifluoromethyl)benzenesulfonamide | 640.30 | 1H NMR (400 MHz, DMSO-d6) δ 8.80 (s, 1H), 8.21 (d, J = 2.0 Hz, 1H), 8.11-8.04 (m, 3H), 7.96 (d, J = 2.2 Hz, 1H), 7.85-7.73 (m, 2H), 7.72-7.61 (m, 2H), 4.37 (t, J = 5.5 Hz, 2H), 3.35 (t, J = 5.4 Hz, 2H), 3.30 (s, 3H), 2.95 (s, 6H), 2.83-2.70 (m, 2H), 2.64-2.56 (m, 2H), 2.51-2.42 (m, 2H), 2.18 (p, J = 5.5 Hz, 2H). |

| Examples | Structure | Name | MS: [(M + 1)]+ | 1H NMR |
|---|---|---|---|---|
| 152 | 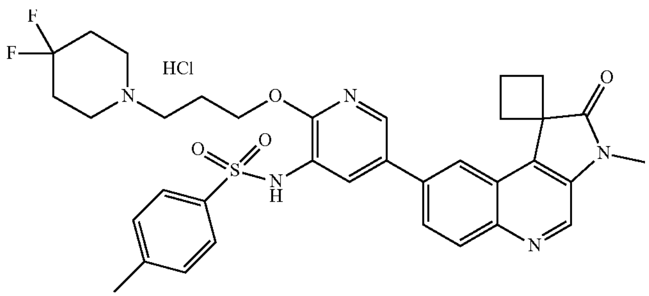 [SMILES: Cc1ccc(S(=O)(=O)Nc2cc(-c3ccc4ncc5c(c4c3)C3(CCC3)C(=O)N5C)cnc2OCCCN2CCC(F)(F)CC2)cc1 ; Cl] | N-(2-(3-(4,4-Difluoropiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride | 662.25 | 1H NMR (400 MHz, DMSO-d6) δ 11.24 (br, 1H), 9.97 (s, 1H), 8.85 (s, 1H), 8.47 (d, J = 2.3 Hz, 1H), 8.33 (d, J = 2.0 Hz, 1H), 8.17 (d, J = 8.9 Hz, 1H), 8.07 (d, J = 2.3 Hz, 1H), 7.93 (dd, J = 8.9, 2.0 Hz, 1H), 7.72-7.66 (m, 2H), 7.40 (d, J = 8.0 Hz, 2H), 4.20 (t, J = 5.9 Hz, 2H), 3.71-3.58 (m, 2H), 3.32 (s, 7 H), 3.32-3.09 (m, 2H), 2.96-2.84 (m, 2H), 2.66-2.51 (m, 4H), 2.46-2.37 (m, 2H), 2.35 (s, 3H), 2.16-2.05 (m, 2H). |
| 153 | 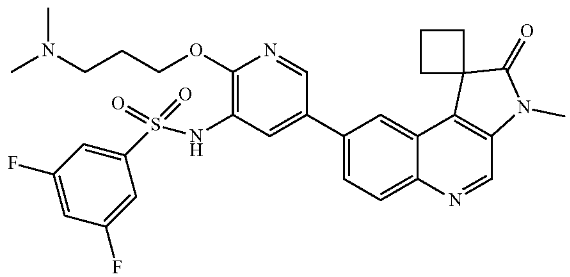 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3,5-difluorobenzenesulfonamide | 608.30 | 1H NMR (300 MHz, DMSO-d6) δ 8.81 (s, 1H), 8.18 (d, J = 1.9 Hz, 1H), 8.10 (d, J = 8.9 Hz, 1H), 7.97 (d, J = 2.3 Hz, 1H), 7.81 (dd, J = 8.9, 1.9 Hz, 1H), 7.55 (d, J = 2.3 Hz, 1H), 7.47-7.31 (m, 3H), 4.38 (t, J = 5.5 Hz, 2H), 3.40 (t, J = 10.3 Hz, 2H), 3.31 (s, 3H), 2.97 (s, 6H), 2.83-2.69 (m, 2H), 2.67-2.46 (m, 4H), 2.26-2.16 (m, 2H). |
| 154 | 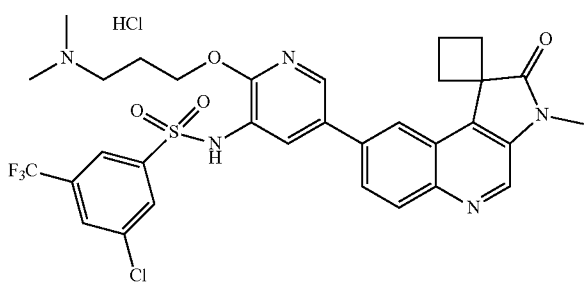 | 3-Chloro-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-5-(trifluoromethyl)benzenesulfonamide hydrochloride | 674.15 | 1H NMR (300 MHz, DMSO-d6) δ 10.52 (s, 1H), 9.92 (br, 1H), 8.86 (s, 1H), 8.55 (s, 1H), 8.34 (d, J = 2.0 Hz, 1H), 8.28 (s, 1H), 8.00-8.21 (m, 3H), 8.00-7.91 (m, 2H), 4.22 (t, J = 6.0 Hz, 2H), 3.32 (s, 3H), 3.23 (t, J = 7.2 Hz, 2H), 2.96-2.84 (m, 2H), 2.80 (s, 6H), 2.66-2.52 (m, 4H), 2.07-1.93 (m, 2H). |

| Examples | Structure | Name | MS: [(M + 1)]+ | 1H NMR |
|---|---|---|---|---|
| 155 | 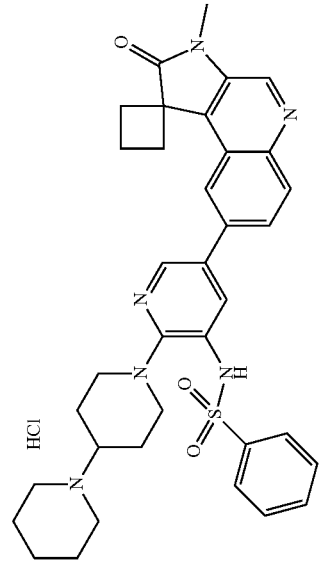 | N-(2-([1,4-Bipiperidin]-1'-yl)-5-(3'-methyl-2'-oxo-2',3'-dihydrospiro[cyclobulane-1,1'-pyrrolo[2,3-c]quinolin]-8'-yl)pyridin-3-yl)benzenesulfonamide hydrochloride | 637.30 | 1H NMR (400 MHz, CD3OD) δ 8.75 (s, 1H), 8.54 (d, J = 2.3 Hz, 1H), 8.37 (d, J = 2.0 Hz, 1H), 8.14 (d, J = 9.0 Hz, 1H), 7.88 (s, 1H), 7.86 (d, J = 1.5 Hz, 1H), 7.82-7.78 (m, 2H), 7.63 (t, J = 7.3 Hz, 1H), 7.56-7.53 (m, 2H), 3.80 (d, J = 13.1 Hz, 2H), 3.56 (d, J = 12.2 Hz, 2H), 3.34 (s, 4H), 3.07 (t, J = 12.0 Hz, 2H), 2.98-2.87 (m, 4H), 2.78-2.70 (m, 2H), 2.66-2.52 (m, 2H), 2.14-1.94 (m, 6H), 2.66-2.52 (m, 3H), 1.62-1.50 (m, 1H). |
| 156 | 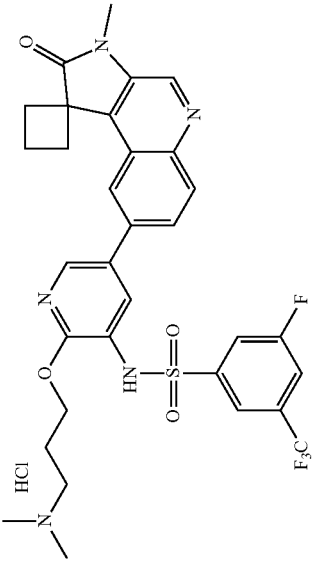 | N-(2-(3-(Dimethylamino)propoxy)-5-(3'-methyl-2'-oxo-2',3'-dihydrospiro[cyclobulane-1,1'-pyrrolo[2,3-c]quinolin]-8'-yl)pyridin-3-yl)-3-fluoro-5-(trifluoromethyl)benzenesulfonamide hydrochloride | 658.20 | 1H NMR (400 MHz, DMSO-d6) δ 10.48 (s, 1H), 8.86 (s, 1H), 8.56 (s, 1H), 8.34 (s, 1H), 8.19-8.05 (m, 3H), 8.01-7.91 (m, 2H), 7.88 (s, 1H), 4.21 (t, J = 6.4Hz, 2H), 3.32 (s, 3H), 3.23 (t, J = 6.8Hz, 2H), 2.97-2.84 (m, 2H), 2.80 (s, 6H), 2.64-2.51 (m, 4H), 2.04-1.93 (m, 2H). |
| 158 | 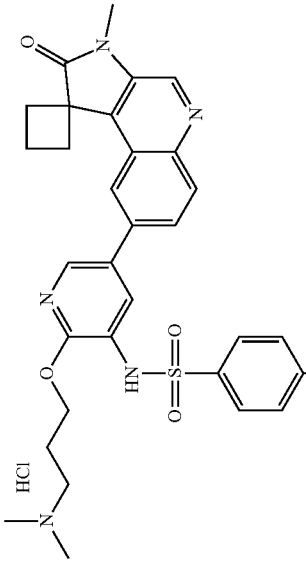 | N-(2-(3-(Dimethylamino)propoxy)-5-(3'-methyl-2'-oxo-2',3'-dihydrospiro[cyclobulane-1,1'-pyrrolo[2,3-c]quinolin]-8'-yl)pyridin-3-yl)-4-fluorobenzenesulfonamide hydrochloride | 590.20 | 1H NMR (400 MHz, CD3OD) δ 8.76 (s, 1H), 8.48-8.41 (m 2H), 8.18 (d, J = 9.0 Hz, 1H), 8.09 (d, J = 1.9 Hz, 1H), 7.93-7.86 (m, 3H), 7.30 (t, J = 8.7 Hz, 2H), 4.41 (t, J = 6.3 Hz, 2H), 3.39 (s, 3H), 3.01-3.92 (m, 8H), 2.78-2.58 (m, 4H), 2.21-2.12 (m, 2H). |

| Examples | Structure | Name | MS: [(M + 1)]+ | 1H NMR |
|---|---|---|---|---|
| 160 | (structure) | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)thiazole-4-sulfonamide hydrochloride | 579.15 | 1H NMR (400 MHz, CD3OD) δ 9.11 (d, J = 2.0 Hz, 1H), 8.75 (s, 1H), 8.49 (d, J = 2.0 Hz, 1H), 8.38 (d, J = 2.3 Hz, 1H), 8.35 (d, J = 2.0 Hz, 1H), 8.33 (d, J = 2.3 Hz, 1H), 8.17 (d, J = 8.9 Hz, 1H), 7.92 (dd, J = 8.9, 2.0 Hz, 1H), 4.47 (t, J = 5.7 Hz, 2H), 3.42 (t, J = 7.5 Hz, 2H), 3.39 (s, 3H), 2.99 (s, 8H), 2.77-2.59 (m, 4H), 2.29-2.20 (m, 2H). |
| 161 | (structure) | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-oxo-1,2-dihydropyridine-4-sulfonamide | 589.20 | 1H NMR (400 MHz, DMSO-d6) δ 12.15 (br, 1H), 10.16 (br, 1H), 8.85 (s, 1H), 8.50 (s, 1H), 8.37 (d, J = 1.9 Hz, 1H), 8.17 (d, J = 8.8 Hz, 1H), 8.09 (s, 1H), 7.96 (d, J = 8.4 Hz, 1H), 7.74 (s, 1H), 7.68 (dd, J = 9.7, 2.8 Hz, 1H), 6.50 (d, J = 9.7 Hz, 1H), 4.28 0.J = 5.9 Hz, 2H), 3.32 (s, 3H), 3.26 (t, J = 7.9 Hz, 2H), 2.91 (q, J = 9.2, 7.9 Hz, 2H), 2.81 (s, 6H), 2.64-2.51 (m, 4H), 2.13-2.04 (m, 2H). |
| 162 | (structure) | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methylpiperazine-1-sulfonamide hydrochloride | 594.25 | 1H NMR (400 MHz, CDCl3) δ 8.66 (s, 1H), 8.38 (d, J = 2.0 Hz, 1H), 8.25 (d, J = 2.2 Hz, 1H), 8.22 (d, J = 8.8 Hz, 1H), 8.14 (d, J = 2.2 Hz, 1H), 7.80 (dd, J = 8.9, 2.0 Hz, 1H), 4.61 (t, J = 5.7 Hz, 2H), 3.44 (s, 4H), 3.39 (s, 3H), 3.25 (t, J = 7.3 Hz, 2H), 2.96-2.88 (m, 2H), 2.84 (s, 6H), 2.82-2.67 (m, 4H), 2.57 (s, 4H), 2.46-2.37 (m, 2H), 2.34 (s, 3H). |
| 164 | (structure) | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)azetidine-1-sulfonamide | 551.30 | 1H NMR (400 MHz, DMSO-d6) δ 8.83 (s, 1H), 8.37 (d, J = 2 Hz, 1H), 8.20 (d, J = 2.4 Hz, 1H), 8.15 (d, J = 8.8 Hz, 1H), 8.10 (d, J = 2.4 Hz, 1H), 7.94 (dd, J = 8.8, 2 Hz, 1H), 4.38 (t, J = 6.0 Hz, 2H), 3.77-3.66 (m, 4H), 3.31 (s, 3H), 2.92-2.82 (m, 4H), 2.68-2.57 (m, 4H), 2.54 (s, 6H), 2.09-2.01 (m, 4H). |

| Examples | Structure | Name | MS: [(M + 1)]+ | 1H NMR |
|---|---|---|---|---|
| 165 | 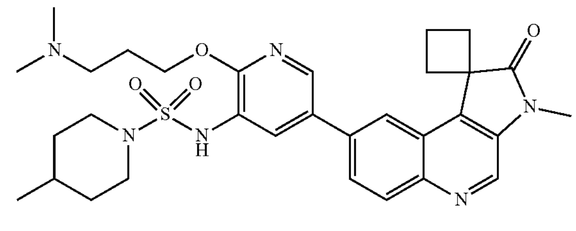 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methylpiperidine-1-sulfonamide | 593.30 | 1H NMR (400 MHz, DMSO-d6) δ 8.84 (s, 1H), 8.37 (d, J = 2.0 Hz, 1H), 8.31 (d, J = 2.4 Hz, 1H), 8.16 (d, J = 8.8 Hz, 1H), 8.10 (d, J = 2.4 Hz, 1H), 7.95 (dd, J = 8.8, 2.0 Hz, 1H), 4.40 (t, J = 6.4 Hz, 2H), 3.56 (d, J = 12Hz, 2H), 3.32 (s, 3H), 2.93-2.83 (m, 2H), 2.74-2.52 (m, 8H), 2.38 (s, 6H), 2.04-1.98 (m, 2H), 1.60 (d, J = 11.8 Hz, 2H), 1.40-1.37 (m, 1H), 1.08-0.93 (m, 2H), 0.82 (d, J = 6.4 Hz, 3H). |
| 166 | 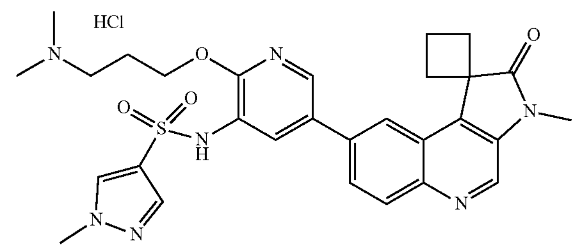 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1-methyl-1H-pyrazole-4-sulfonamide hydrochloride | 576.30 | 1H NMR (400 MHz, CD3OD) δ 8.74 (s, 1H), 8.45 (d, J = 2.1 Hz, 1H), 8.38 (d, J = 2.3 Hz, 1H), 8.19-8.09 (m, 2H), 8.03 (s, 1H), 7.90 (dd, J = 8.9, 2.0 Hz, 1H), 7.77 (s, 1H), 4.47 (t, J = 5.9 Hz, 2H), 3.86 (s, 3H), 3.39 (s, 3H), 3.28 (s, 2H), 2.95 (s, 8H), 2.77-2.60 (m, 4H), 2.26-2.18 (m, 2H). |
| 167 | 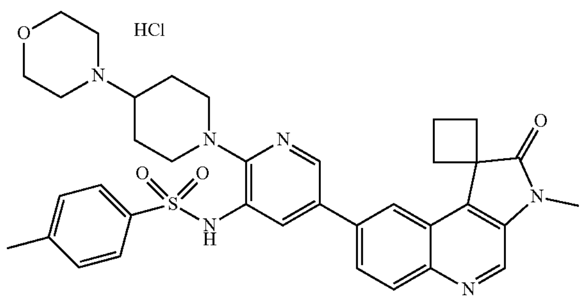 | 4-Methyl-N-(5-(3'-methyl-2'-oxo-2',3'-dihydrospiro[cyclobutane-1,1'-pyrrolo[2,3-c]quinolin]-8'-yl)-2-(4-morpholinopiperidin-1-yl)pyridin-3-yl)benzenesulfonamide hydrochloride | 653.30 | 1H NMR (400 MHz, CD3OD) δ 8.76 (s, 1H), 8.54 (d, J = 2.3 Hz, 1H), 8.39 (d, J = 2.0 Hz, 1H), 8.16 (d, J = 8.9 Hz, 1H), 7.84-7.72 (m, 4H), 7.38 (d, J = 8.1 Hz, 2H), 3.96 (br, 4H), 3.85 (d, J = 13.0 Hz, 2H), 3.41 (s, 8H), 3.00-2.88 (m, 4H), 2.80-2.53 (m, 4H), 2.39 (s, 3H), 2.19 (d, J = 11.8 Hz, 2H), 2.08-1.92 (m, 2H). |

| Examples | Structure | Name | MS: [(M + 1)]+ | 1H NMR |
|---|---|---|---|---|
| 168 | 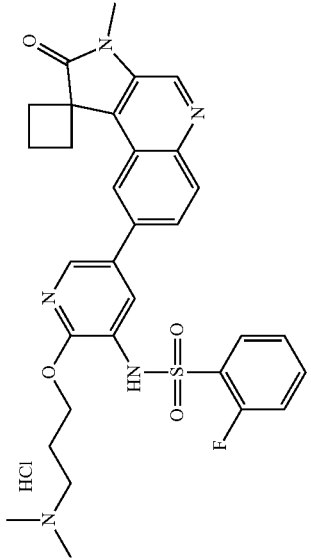 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-fluorobenzenesulfonamide hydrochloride | 590.50 | 1H NMR (400 MHz, CD3OD) δ 8.75 (s, 1H), 8.43 (d, J = 2.0 Hz, 1H), 8.39 (d, J = 2.3 Hz, 1H), 8.20-8.10 (m, 2H), 7.92-7.82 (m, 2H), 7.72-7.62 (m, 1H), 7.40-7.26 (m, 2H), 4.43 (t, J = 5.9 Hz, 2H), 3.39 (s, 3H), 3.38-3.35 (m, 2H), 2.97 (s, 6H), 3.03-2.91 (m, 2H), 2.84-2.45 (m, 4H), 2.25-2.16 (m, 2H). |
| 171 | 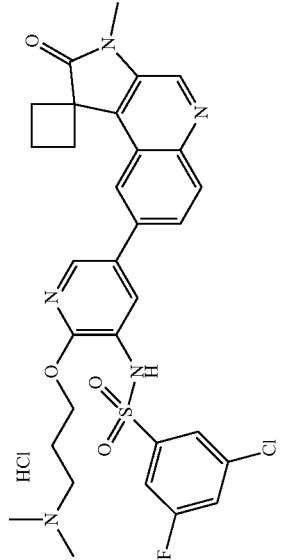 | 3-Chloro-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-5-fluorobenzenesulfonamide hydrochloride | 624.15 | 1H NMR (300 MHz, CD3OD) δ 8.74 (s, 1H), 8.42 (s, 1H), 8.30 (s, 1H), 8.16 (d, J = 9.0 Hz, 1H), 7.97 (s, 1H), 7.90 (d, J = 8.7 Hz, 1H), 7.68 (s, 1H), 7.54 (d, J = 8.0 Hz, 1H), 7.48 (d, J = 8.5 Hz, 1H), 4.45 (t, J = 5.8 Hz, 2H), 3.39 (s, 3H), 3.35 (s, 2H), 2.99 (s, 6H), 2.97-2.89 (m, 2H), 2.78-2.56 (m, 4H), 2.27-2.18 (m, 2H). |
| 172 | 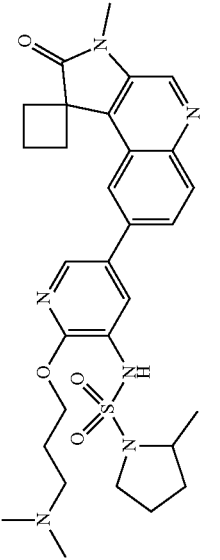 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-methylpyrrolidine-1-sulfonamide | 579.35 | 1H NMR (400 MHz, CD3OD) δ 8.73 (s, 1H), 8.49 (d, J = 1.9 Hz, 1H), 8.30-8.26 (m, 2H), 8.17 (d, J = 8.9 Hz, 1H), 7.96 (dd, J = 9.0, 2.0 Hz, 1H), 4.51 (t, J = 6.2 Hz, 2H), 3.93-3.84 (m, 1H), 3.45-3.38 (m, 2H), 3.39 (s, 3H), 3.03-2.94 (m, 2H), 2.79-2.62 (m, 6H), 2.47 (s, 6H), 2.12 (p, J = 6.7 Hz, 2H), 2.02-1.75 (m, 3H), 1.59-1.50 (m, 1H), 1.16 (d, J = 6.3 Hz, 3H). |

| Examples | Structure | Name | MS: [(M + 1)]+ | 1H NMR |
|---|---|---|---|---|
| 174 | 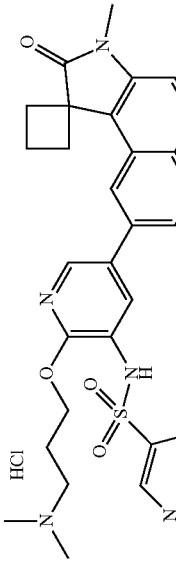 | 5-Cyano-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyridine-3-sulfonamide hydrochloride | 598.20 | 1H NMR (400 MHz, CD3OD) δ 9.20 (d, J = 2.1 Hz, 1H), 9.12 (s, 1H), 8.76 (s, 1H), 8.59 (d, J = 2.1 Hz, 1H), 8.48 (s, 1H), 8.44 (s, 1H), 8.19 (d, J = 9.1 Hz, 2H), 7.94 (dd, J = 9.3, 1.9 Hz, 1H), 4.38 (t, J = 6.1 Hz, 2H), 3.39 (s, 3H), 3.29-3.26 (m, 2 H), 2.98 (s, 8H), 2.78-2.60 (m, 4H), 2.19-2.13 (m, 2H). |
| 175 | 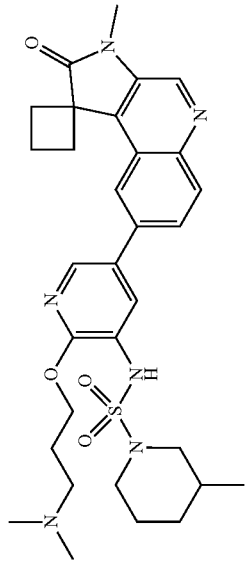 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3-methylpiperidine-1-sulfonamide | 593.40 | 1H NMR (400 MHz, DMSO-d6) δ 8.84 (s, 1H), 8.36 (d, J = 1.9 Hz, 1H), 8.32 (d, J = 2.3 Hz, 1H), 8.16 (d, J = 8.9 Hz, 1H), 8.09 (d, J = 2.3 Hz, 1H), 7.95 (dd, J = 9.0, 1.9 Hz, 1H), 4.40 (t, J = 6.1 Hz, 2H), 3.49 (d, J = 11.2 Hz, 2H), 3.31 (s, 3H), 2.87 (t, J = 8.9 Hz, 2H), 2.77 (t, J = 6.6 Hz, 2H), 2.65-2.54 (m, 4H), 2.43 (s, 6H), 2.33 (t, J = 11.0 Hz, 2H), 2.07-1.98 (m, 2H), 1.61 (d, J = 11.8 Hz, 2H), 1.48 (s, 1H), 1.39-1.27 (m, 1H), 0.98-0.85 (m, 1H), 0.79 (d, J = 6.6 Hz, 3H). |
| 176 | 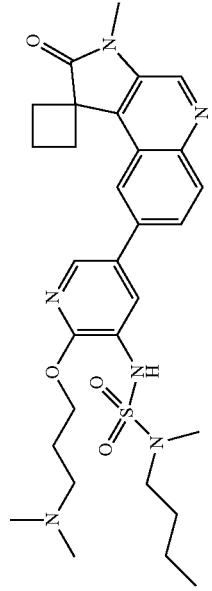 | 8'-(5-{[Butyl(methyl)sulfamoyl]amino}-6-[3-(dimethylamino)propoxy]pyridin-3-yl)-3-methyl-2',3'-dihydrospiro[cyclobutane-1,1'-pyrrolo[2,3-c]quinoline]-2'-one | 581.35 | 1H NMR (400 MHz, CD3OD) δ 8.59 (s, 1H), 8.34 (s, 1H), 8.10 (s, 1H), 8.06-8.00 (m, 2H), 7.81 (d, J = 8.8 Hz, 1H), 4.37 (t, J = 6.1 Hz, 2H), 3.24 (s, 3H), 3.01 (t, J = 7.3 Hz, 2H), 2.88-2.79 (m, 2H), 2.71-2.63 (m, 5H), 2.61-2.46 (m, 4H), 2.38 (s, 6H), 2.03-1.94 (m, 2H), 1.36-1.26 (m, 2H), 1.10-1.01 (m, 2H), 0.63 (t, J = 7.4Hz, 3H). |
| 177 | 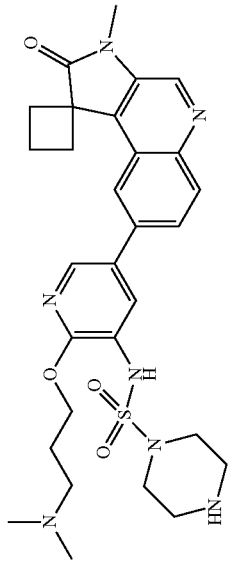 | N-(2-(3-(Dimethylamino)propoxy)-5-(3'-methyl-2'-oxo-2',3'-dihydrospiro[cyclobutane-1,1'-pyrrolo[2,3-c]pyridin-8'-yl)pyridin-3-yl)piperazine-1-sulfonamide | 580.25 | 1H NMR (400 MHz, CD3OD) δ 8.73 (s, 1H), 8.50 (d, J = 2.0 Hz, 1H), 8.21 (d, J = 2.3 Hz, 1H), 8.18-8.14 (m, 2H), 7.97 (dd, J = 8.9, 1.9 Hz, 1H), 4.50 (t, J = 5.9 Hz, 2H), 3.39 (s, 3H), 3.19 (t, J = 10.2 Hz, 4H), 3.05-2.94 (m, 4H), 2.82-2.76 (m, 4H), 2.75-2.61 (m, 10H), 2.24- 2.15 (m, 2H). |

-continued

| Examples | Structure | Name | MS: [(M + 1)]⁺ | ¹H NMR |
|---|---|---|---|---|
| 179 | 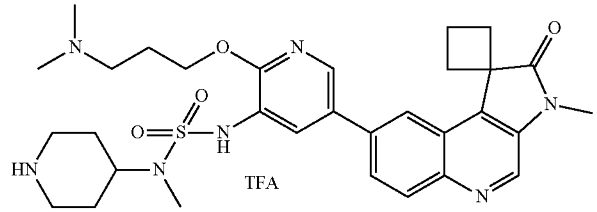 [SMILES: CN(C)CCCOc1ncc(-c2ccc3ncc4c(c3c2)C2(CCC2)C(=O)N4C)cc1NS(=O)(=O)N(C)C1CCNCC1] | N-Methyl-N-(piperidin-4-yl){2-[3-(dimethylamino)propoxy]-5-{3'-methyl-2'-oxo-2',3'-dihydrospiro[cyclobutane-1,1'-pyrrolo[2,3-c]quinoline]-8'-yl}pyridin-3-yl}aminosulfonamide 2,2,2-trifluoroacetate | 608.10 | ¹H NMR (300 MHz, CD₃OD) δ 8.80 (s, 1H), 8.50 (d, J = 1.8 Hz, 1H), 8.41 (d, J = 2.3 Hz, 1H), 8.26-8.13 (m, 2H), 8.02-7.93 (m, 1H), 4.62 (t, J = 6.0 Hz, 2H), 4.13-3.97 (m, 1H), 3.49-3.37 (m, 7H), 3.10-2.91 (m 10H), 2.86 (s, 3H), 2.80-2.58 (m, 4H), 2.38-2.22 (m, 2H), 2.07-1.79 (m, 4H). |
| 180 | 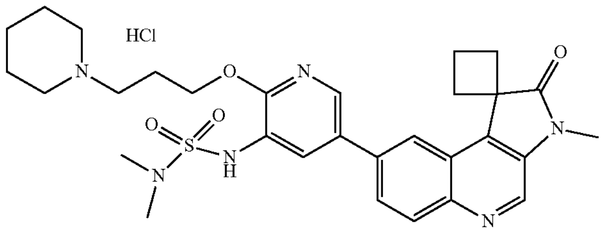 [SMILES: CN1C(=O)C2(CCC2)c2c1cnc1ccc(-c3cnc(OCCCN4CCCCC4)c(NS(=O)(=O)N(C)C)c3)cc21 ; Cl] | 8'-{5-[(Dimethylsulfamoyl)amino]-6-[3-(piperidin-1-yl)propoxy]pyridine-3-yl}-3'-methyl-2',3'-dihydrospiro[cyclobutane-1,1'-pyrrolo[2,3-c]quinoline]-2'-one hydrochloride | 579.35 | ¹H NMR (400 MHz, CD₃OD) δ 8.82 (s, 1H), 8.53 (d, J = 1.9 Hz, 1H), 8.42 (d, J = 2.3 Hz, 1H), 8.26-8.21 (m, 2H), 8.03 (dd, J = 9.0, 1.9 Hz, 1H), 4.65 (t, J = 5.9 Hz, 2H), 3.63 (d, J = 12.5 Hz, 2H), 3.45-3.40 (m, 5H), 3.06-3.97 (m, 4H), 2.89 (s, 6H), 2.82-2.63 (m, 4H), 2.40-2.30 (m, 2H), 2.06-1.97 (m, 2H), 1.93-1.74 (m, 3H), 1.64-1.52 (m, 1H). |
| 181 | 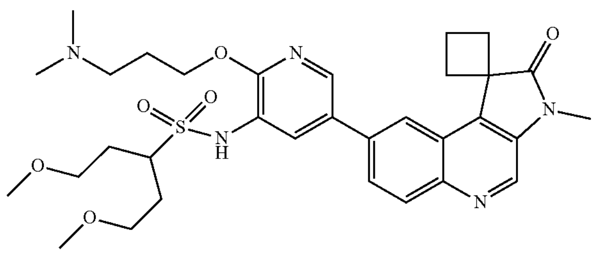 | 8'-(5-{[Bis(2-methoxyethyl)sulfamoyl]amino}-6-[3-(dimethylamino)propoxy]pyridine-3-yl)-3'-methyl-2',3'-dihydrospiro[cyclobutane-1,1'-pyrrolo[2,3-c]quinoline]-2'-one | 627.25 | ¹H NMR (300 MHz, CD₃OD) δ 8.72 (s, 1H), 8.49 (d, J = 1.9 Hz, 1H), 8.28-8.19 (m, 2H), 8.16 (d, J = 8.9 Hz, 1H), 7.97 (dd, J = 9.0, 2.0 Hz, 1H), 4.53 (t, J = 6.2 Hz, 2H), 3.50 (s, 8H), 3.38 (s, 3H), 3.21 (s, 6H), 3.07-2.92 (m, 2H), 2.81-2.57 (m, 6H), 2.46 (s, 6H), 2.12 (p, J = 6.6 Hz, 2H). |
| 182 | 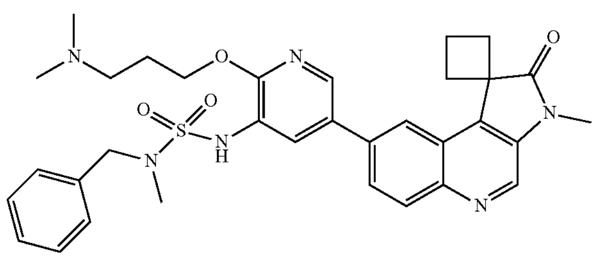 [SMILES: CN(C)CCCOc1ncc(-c2ccc3ncc4c(c3c2)C2(CCC2)C(=O)N4C)cc1NS(=O)(=O)N(C)Cc1ccccc1] | N-Benzyl-N-methyl({2-[3-(dimethylamino)propoxy]-5-{3'-methyl-2'-oxo-2',3'-dihydrospiro[cyclobutane-1,1'-pyrrolo[2,3-c]quinoline]-8'-yl}pyridin-3-yl})aminosulfonamide | 615.35 | ¹H NMR (400 MHz, CD₃OD) δ 8.75 (d, J = 2.0 Hz, 1H), 8.46 (d, J = 2.0 Hz, 1H), 8.41 (d, J = 2.3 Hz, 1H), 8.25 (d, J = 8.9 Hz, 1H), 8.19 (d, J = 8.9 Hz, 1H), 7.96 (dd, J = 8.9, 2.0 Hz, 1H), 7.22-7.14 (m, 5H), 4.59 (t, J = 5.9 Hz, 2H), 4.37 (s, 2H), 3.38 (s, 3H), 3.35 (t, J = 7.6 Hz, 2H), 2.95-2.86 (m, 8H), 2.77 (s, 3H), 2.71-2.61 (m, 2H), 2.60-2.50 (m, 2H), 2.32-2.22 (m, 2H). |

| Examples | Structure | Name | MS: [(M + 1)]+ | ¹H NMR |
|---|---|---|---|---|
| 183 | 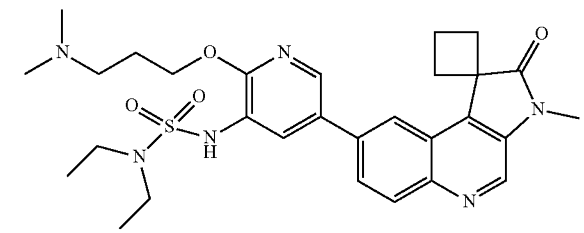 | 8'-{5-[(Diethylsulfamoyl)amino]-6-[3-(dimethylamino)propoxy]pyridine-3-yl]-3'-methyl-2',3'-dihydrospiro[cyclobutane-1,1'-pyrrolo[2,3-c]quinoline]-2'-one | 567.35 | ¹H NMR (400 MHz, CD₃OD) δ 8.79 (s, 1H), 8.50 (d, J = 1.9 Hz, 1H), 8.40 (d, J = 2.3 Hz, 1H), 8.21 (d, J = 8.9 Hz, 1H), 8.17 (d, J = 2.3 Hz, 1H), 7.99 (dd, J = 8.9, 2.0 Hz, 1H), 4.62 (t, J = 5.9 Hz, 2H), 3.47-3.32 (m, 9H), 3.03-2.96 (m, 2H), 2.97 (s, 6H), 2.80-2.61 (m, 4H), 2.35-2.27 (m, 2H), 1.11 (t, J = 7.1 Hz, 6H). |
| 184 | 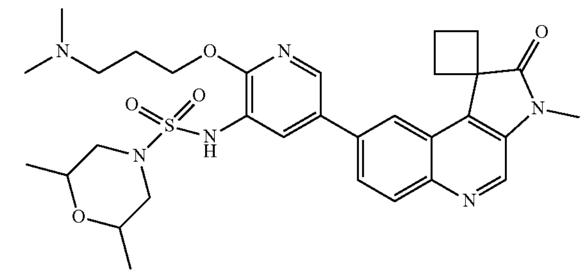 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2,6-dimethylmorpholine-4-sulfonamide | 609.25 | ¹H NMR (300 MHz, CD₃OD) δ 8.72 (s, 1H), 8.49 (d, J = 1.8 Hz, 1H), 8.21-8.14 (m, 3H), 7.96 (dd, J = 8.9, 1.9 Hz, 1H), 4.51 (t, J = 6.0 Hz, 2H), 3.60-3.45 (m, 4H), 3.39 (s, 3H), 3.11-2.93 (m, 4H), 2.72 (s, 10H), 2.42 (t, J = 11.1 Hz, 2H), 2.27-2.16 (m, 2H), 1.11 (d, J = 6.2 Hz, 6H). |
| 186 | 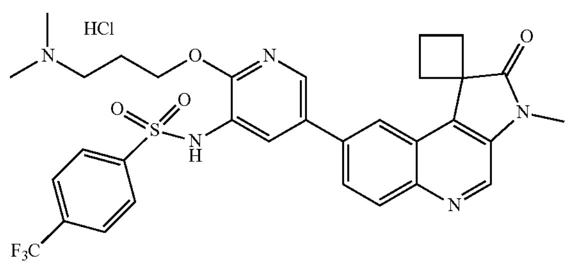 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-(trifluoromethyl)benzenesulfonamide hydrochloride | 640.30 | ¹H NMR (300 MHz, CD₃OD) δ 8.83 (s, 1H), 8.52 (s, 1H), 8.49 (d, J = 2.3 Hz, 1H), 8.22 (d, J = 8.8 Hz, 1H), 8.16 (d, J = 2.3 Hz, 1H), 8.05 (d, J = 8.4 Hz, 2H), 7.97 (d, J = 10.5 Hz, 1H), 7.92 (d, J = 8.5 Hz, 2H), 4.40 (t, J = 6.0 Hz, 2H), 3.42 (s, 3H), 3.31-3.28 (m, 2H), 2.97 (s, 3H), 2.83-2.59 (m, 4H), 2.22-2.11 (m, 2H). |
| 187 | 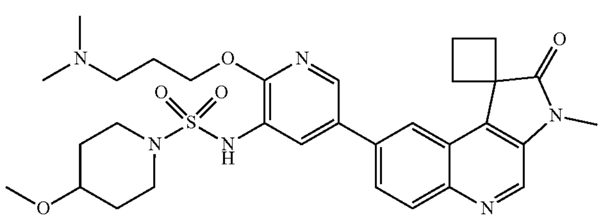 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methoxypiperidine-1-sulfonamide | 609.35 | ¹H NMR (300 MHz, CD₃OD) δ 8.73 (s, 1H), 8.49 (d, J = 1.9 Hz, 1H), 8.20 (d, J = 0.8 Hz, 2H), 8.17 (d, J = 8.9 Hz, 1H), 7.96 (dd, J = 9.0, 1.9 Hz, 1H), 4.51 (t, J = 6.1 Hz, 2H), 3.52-3.42 (m, 2H), 3.39 (s, 3H), 3.28 (s, 3H), 3.12-2.96 (m, 4H), 2.87 (t, J = 6.8 Hz, 2H), 2.78-2.62 (m, 4H), 2.56 (s, 6H), 2.21-2.10 (m, 2H), 1.90-1.78 (m, 2H), 1.61-1.46 (m, 3H). |

| Examples | Structure | Name | MS: [(M + 1)]+ | 1H NMR |
|---|---|---|---|---|
| 189 | 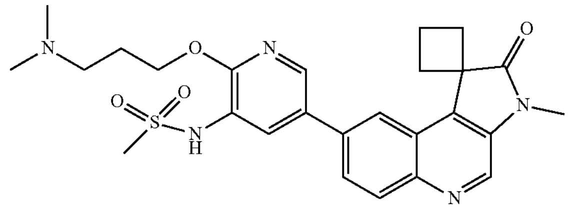 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 510.20 | 1H NMR (300 MHz, DMSO-d6) δ 8.84 (s, 1H), 8.38 (d, J = 1.9 Hz, 1H), 8.32 (d, J = 2.3 Hz, 1H), 8.16 (d, J = 8.9 Hz, 1H), 8.04 (d, J = 2.3 Hz, 1H), 7.97 (dd, J = 8.9, 1.9 Hz, 1H), 4.40 (t, J = 6.3 Hz, 2H), 3.32 (s, 3H), 3.01 (s, 3H), 2.97-2.85 (m, 2H), 2.67-2.53 (m, 6H), 2.34 (s, 6H), 2.04-1.94 (m, 2H). |
| 190 | 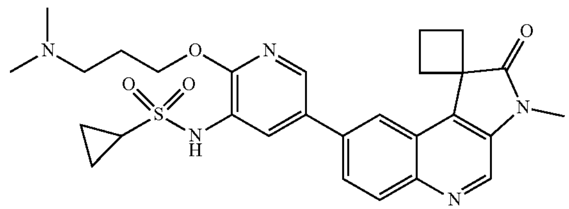 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide | 536.30 | 1H NMR (300 MHz, CD3OD) δ 8.74 (s, 1H), 8.50 (d, J = 1.7 Hz, 1H), 8.33 (d, J = 2.3 Hz, 1H), 8.24 (d, J = 2.3 Hz, 1H), 8.18 (d, J = 8.9 Hz, 1H), 7.98 (dd, J = 9.0, 1.8 Hz, 1H), 4.53 (t, J = 6.2 Hz, 2H), 3.39 (s, 3H), 3.05-2.95 (m, 2H), 2.82-2.73 (m, 3H), 2.73-2.60 (m, 4H), 2.49 (s, 6H), 2.13 (t, J = 6.9 Hz, 2H), 1.12-1.04 (m, 2H), 1.03-0.95 (m, 2H). |
| 191 | 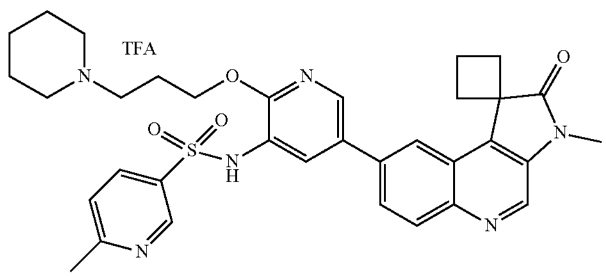 [SMILES: Cc1ccc(S(=O)(=O)Nc2cc(-c3ccc4ncc5c(c4c3)C3(CCC3)C(=O)N5C)cnc2OCCCN2CCCCC2)cn1 ; "TFA"] | N,6-Dimethyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)sulfonamide 2,2,2-trifluoroacetate | 641.40 | 1H NMR (300 MHz, CD3OD) δ 8.83 (s, 1H), 8.79 (d, J = 2.3 Hz, 1H), 8.65 (d, J = 2.4 Hz, 1H), 8.51 (d, J = 1.9 Hz, 1H), 8.21 (d, J = 9.0 Hz, 1H), 8.06 (dt, J = 5.5, 2.6 Hz, 2H), 7.97 (dd, J = 9.0, 2.0 Hz, 1H), 7.53 (d, J = 8.2 Hz, 1H), 4.40 (t J = 5.9 Hz, 2H), 3.58 (d, J = 12.7 Hz, 2H), 3.40 (s, 3H), 3.32 (s, 3H), 3.29-3.24 (m, 2H), 3.09-2.91 (m, 4H), 2.83-2.52 (m, 7H), 2.18-2.06 (m, 2H), 2.00 (d, J = 14.7 Hz, 2H), 1.92-1.67 (m, 3H), 1.64-1.48 (m, 1H). |

-continued-

| Examples | Structure | Name | MS: [(M + 1)]+ | 1H NMR |
|---|---|---|---|---|
| 192 | 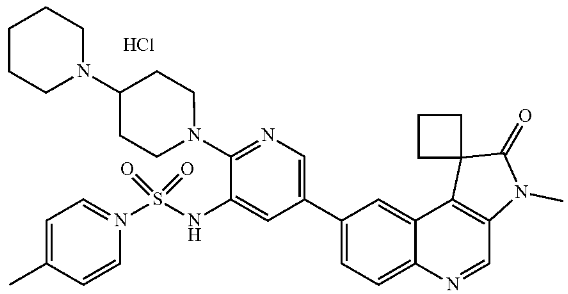 | N-(2-(1,4-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-4-methylbenzenesulfonamide hydrochloride | 651.35 | 1H NMR (400 MHz, CD3OD) δ 8.83 (s, 1H), 8.54 (d, J = 2.3 Hz, 1H), 8.42 (d, J = 1.9 Hz, 1H), 8.18 (d, J = 9.0 Hz, 1H), 7.89 (dd, J = 9.0, 2.0 Hz, 1H), 7.82 (d, J = 2.3 Hz, 1H), 7.77-7.73 (m, 2H), 7.36 (d, J = 8.1 Hz, 2H), 3.82 (d, J = 13.1 Hz, 2H), 3.56 (d, J = 11.8 Hz, 2H), 3.40 (s, 4H), 3.08 (t, J = 12.3 Hz, 2H), 3.00-2.87 (m, 3H), 2.80-2.52 (m, 4H), 2.37 (s, 3H), 2.15-1.95 (m, 6H), 1.92-1.74 (m, 3H), 1.63-1.48 (m, 1H). |
| 193 | 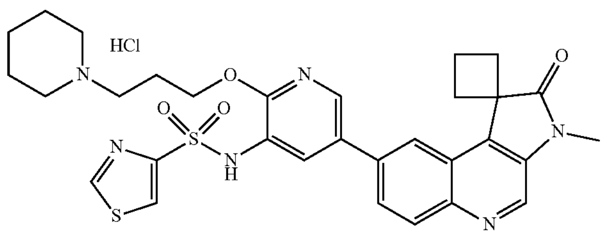 [SMILES: CN1C(=O)C2(CCC2)c2c1cnc1ccc(-c3cnc(OCCCN4CCCCC4)c(NS(=O)(=O)c4cscn4)c3)cc21 ; Cl] | N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)thiazole-4-sulfonamide hydrochloride | 618.95 | 1H NMR (300 MHz, CD3OD) δ 9.12 (d, J = 2.0 Hz, 1H), 8.75 (s, 1H), 8.50 (d, J = 1.9 Hz, 1H), 8.41-8.34 (m, 3H), 8.17 (d, J = 8.9 Hz, 1H), 7.93 (dd, J = 8.9, 1.9 Hz, 1H), 4.46 (t, J = 5.7 Hz, 2H), 3.62 (br, 2H), 3.39 (s, 5H), 3.08-2.93 (m, 4H), 2.78-2.58 (m, 4H), 2.32-2.19 (m, 2H), 1.98 (br, 2H), 1.85 (br, 3H), 1.58 (br, 1H). |
| 194 | 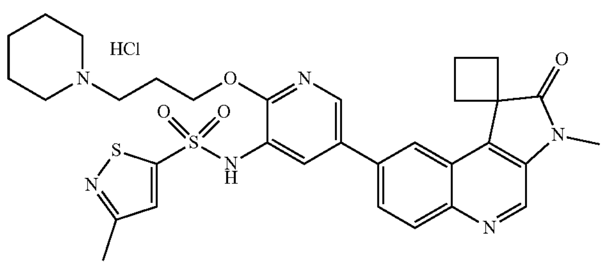 [SMILES: Cc1cc(S(=O)(=O)Nc2cc(-c3ccc4ncc5c(c4c3)C3(CCC3)C(=O)N5C)cnc2OCCCN2CCCCC2)sn1 ; Cl] | 3-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)isothiazole-5-sulfonamide hydrochloride | 633.20 | 1H NMR (300 MHz, CD3OD) δ 8.80 (s, 1H), 8.51 (d, J = 2.3 Hz, 2H), 8.27-8.16 (m, 2H), 7.99 (dd, J = 9.0, 2.0 Hz, 1H), 7.47 (s, 1H), 4.43 (t, J = 6.0 Hz, 2H), 3.57 (d, J = 12.8 Hz, 2H), 3.40 (s, 3H), 3.29-3.17 (m, 2H), 3.07-2.90 (m, 4H), 2.81-2.60 (m, 4H), 2.47 (s, 3H), 2.22-2.11 (m, 2H), 2.00 (d, J = 15.0 Hz 2H), 1.92-1.70 (m, 3H), 1.65-1.50 (m, 1H). |

| Examples | Structure | Name | MS: [(M + 1)]+ | ¹H NMR |
|---|---|---|---|---|
| 195 | 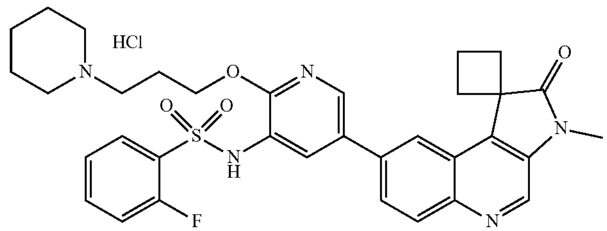 [SMILES: CN1C(=O)C2(CCC2)c2c1cnc1ccc(-c3cnc(OCCCN4CCCCC4)c(NS(=O)(=O)c4ccccc4F)c3)cc21 ; Cl] | 2-Fluoro-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)benzenesulfonamide hydrochloride | 630.20 | ¹H NMR (400 MHz, CD₃OD) δ 8.83 (s, 1H), 8.50 (d, J = 1.9 Hz, 1H), 8.43 (d, J = 2.3 Hz, 1H), 8.22 (d, J = 8.9 Hz, 1H), 8.19 (d, J = 2.3 Hz, 1H), 7.97 (dd, J = 8.9, 1.9 Hz, 1H), 7.89 (td, J = 7.6, 1.8 Hz, 1H), 7.73-7.67 (m, 1H), 7.42-7.31 (m, 2H), 4.45 (t, J = 5.9 Hz, 2H), 3.62 (d, J = 12.5 Hz, 2H), 3.42 (s, 3H), 3.39-3.33 (m, 2H), 3.07-2.95 (m, 4H), 2.84-2.63 (m, 4H), 2.29-2.20 (m, 2H), 2.04 (d, J = 14.9 Hz, 2H), 1.95-1.76 (m, 3H), 1.66-1.53 (m, 1H). |
| 196 | 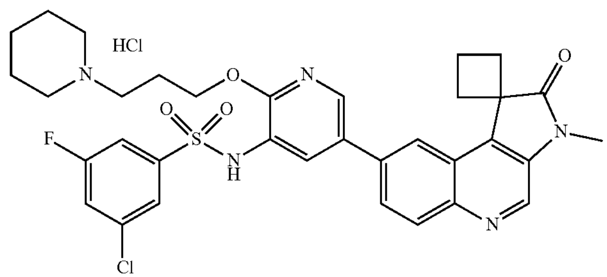 [SMILES: CN1C(=O)C2(CCC2)c2c1cnc1ccc(-c3cnc(OCCCN4CCCCC4)c(NS(=O)(=O)c4cc(F)cc(Cl)c4)c3)cc21 ; Cl] | 3-Chloro-5-fluoro-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)benzenesulfonamide hydrochloride | 664.25 | ¹H NMR (400 MHz, CD₃OD) δ 8.83 (s, 1H), 8.51 (s, 1H), 8.48 (d, J = 2.4 Hz, 1H), 8.22 (d, J = 9.0 Hz, 1H), 8.17 (d, J = 2.2 Hz, 1H), 8.01 (dd, J = 8.8 Hz, 2.0 Hz, 1H), 7.67 (s, 1H), 7.59-7.53 (m, 2H), 4.42 (t, J = 6.0 Hz, 2H), 3.58 (d, J = 12.4 Hz, 2H), 3.40 (s, 3H), 3.28-3.25 (m, 2H), 3.05-2.92 (m, 4H), 2.81-2.62 (m, 4H), 2.23-2.14 (m, 2H), 2.00 (d, J = 14.9 Hz, 2H), 1.90-1.74 (m, 3H), 1.63-1.51 (m, 1H). |
| 197 | 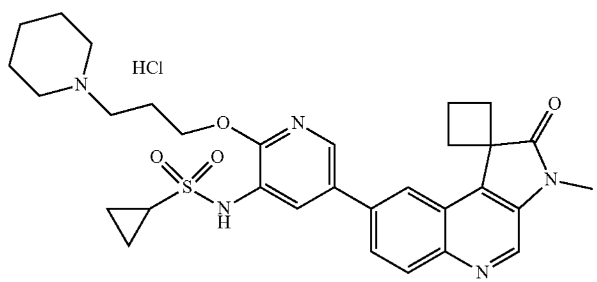 [SMILES: CN1C(=O)C2(CCC2)c2c1cnc1ccc(-c3cnc(OCCCN4CCCCC4)c(NS(=O)(=O)C4CC4)c3)cc21 ; Cl] | N-(5-(3-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)cyclopropanesulfonamide hydrochloride | 576.35 | ¹H NMR (400 MHz, CD₃OD) δ 8.81 (s, 1H), 8.53 (d, J = 1.9 Hz, 1H), 8.46 (d, J = 2.3 Hz, 1H), 8.28 (d, J = 2.3 Hz, 1H), 8.21 (d, J = 8.9 Hz, 1H), 8.04 (dd, J = 8.9, 1.9 Hz, 1H), 4.62 (t, J = 5.9 Hz, 2H), 3.61 (d, J = 12.5 Hz, 2H), 3.44-3.37 (m, 5H), 3.06-2.94 (m, 4H), 2.80-2.70 (m, 3H), 2.69-2.60 (m, 2H), 2.38-2.29 (m, 2H), 1.99 (d, J = 14.5 Hz, 2H), 1.91-1.74 (m, 3H), 1.61-1.51 (m, 1H), 1.14-1.07 (m, 2H), 1.07-1.00 (m, 2H). |

| Examples | Structure | Name | MS: [(M + 1)]+ | 1H NMR |
|---|---|---|---|---|
| 199 | 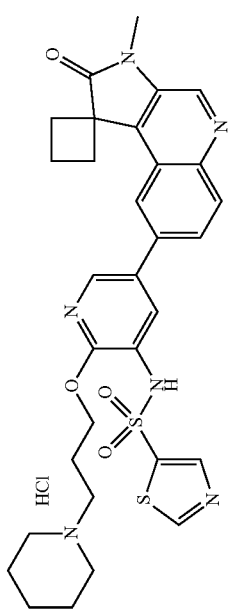 | N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)thiazole-5-sulfonamide hydrochloride | 619.15 | 1H NMR (300 MHz, CD3OD) δ 9.22 (d, J = 0.8 Hz, 1H), 8.79 (s, 1H), 8.50 (d, J = 2.7 Hz, 2H), 8.32 (d, J = 0.8 Hz, 1H), 8.25 (d, J = 2.3 Hz, 1H), 8.21 (d, J = 9.0 Hz, 1H), 7.98 (dd, J = 9.0, 1.9 Hz, 1H), 4.41 (t, J = 5.9 Hz, 2H), 3.58 (d, J = 12.5 Hz, 2H), 3.40 (s, 3H), 3.24-3.14 (m, 2H), 3.07-2.90 (m, 4H), 2.81-2.57 (m, 4H), 2.21-2.10 (m, 2H), 2.01 (d, J = 14.6 Hz, 2H), 1.93-1.70 (m, 3H), 1.64-1.50 (m, 1H). |
| 200 | 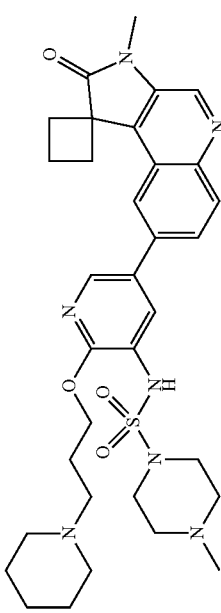 | 4-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)piperazine-1-sulfonamide | 634.30 | 1H NMR (300 MHz, DMSO-d6) δ 8.84 (s, 1H), 8.46 (d, J = 2.3 Hz, 1H), 8.38 (d, J = 2.0 Hz, 1H), 8.20-8.12 (m, 1H), 7.97 (dd, J = 8.9, 1.9 Hz, 1H), 4.41 (t, J = 6.3 Hz, 2H), 3.31 (s, 3H), 3.12 (t, J = 5.2 Hz, 4H), 2.97-2.84 (m, 2H), 2.63-2.53 (m, 5H), 2.49-2.38 (m, 5H), 2.28 (t, J = 5.2 Hz, 4H), 2.12 (s, 3H), 2.05-1.94 (m, 2H), 1.58-1.47 (m, 4H), 1.45-1.32 (m, 2H). |
| 201 | 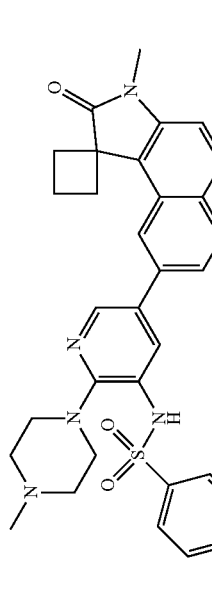 | 6-Methyl-N-(5-(3'-methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)pyridine-3-sulfonamide | 584.2 | 1H NMR (400 MHz, CD3OD) δ 8.73 (s, 1H), 8.40 (dd, J = 11.0, 1.6 Hz, 2H), 8.14 (d, J = 8.9 Hz, 1H), 8.10 (dd, J = 8.2, 2.3 Hz, 1H), 7.89 (d, J = 2.2 Hz, 1H), 7.86 (dd, J = 9.0, 1.5 Hz, 1H), 7.41 (d, J = 8.3 Hz, 1H), 3.49-3.42 (m, 4H), 3.38 (s, 3H), 2.99-2.87 (m, 6H), 2.77-2.67 (m, 2H), 2.66-2.61 (m, 2H), 2.60 (s, 3H), 2.54 (s, 3H). |
| 202 | 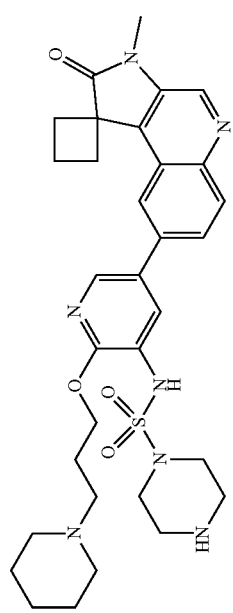 | N-(5-(3'-Methyl-2'-oxo-2',3'-dihydrospiro[cyclobutane-1,1'-pyrrolo[2,3-c]quinolin]-8'-yl)-2-(3-(piperidin-3-yl)propoxy)pyridin-3-yl)piperazine-1-sulfonamide | 620.30 | 1H NMR (400 MHz, CD3OD) δ 8.76 (s, 1H), 8.52 (s, 1H), 8.32 (d, J = 2.3 Hz, 1H), 8.29 (d, J = 2.3 Hz, 1H), 8.20 (d, J = 8.9 Hz, 1H), 8.00 (d, J = 8.9 Hz, 1H), 4.55 (t, J = 6.3 Hz, 2H), 3.41 (s, 3H), 3.24 (t, J = 5.1 Hz, 4H), 3.07-2.97 (m, 2H), 2.83-2.77 (m, 6H), 2.76-2.65 (m, 8H), 2.21-2.13 (m, 2H), 1.77-1.69 (m, 4H), 1.61-1.54 (m, 2H). |

-continued

| Examples | Structure | Name | MS: [(M + 1)]+ | 1H NMR |
|---|---|---|---|---|
| 203 | 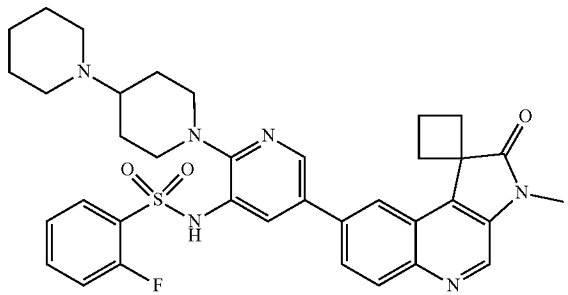 [SMILES: CN1C(=O)C2(CCC2)c2c1cnc1ccc(-c3cnc(N4CCC(N5CCCCC5)CC4)c(NS(=O)(=O)c4ccccc4F)c3)cc21] | N-(2-(1,4-Bipiperidin]-1'-yl)-5-(3'-methyl-2'-oxo-2'3'-dihydrospiro[cyclobutane-1,1'-pyrrolo[2,3-c]quinolin]-8'-yl)pyridin-3-yl)-2-fluorobenzenesulfonamide | 655.25 | 1H NMR (400 MHz, DMSO-$d_6$) δ 8.78 (s, 1H), 8.23 (d, J = 1.9 Hz, 1H), 8.08 (d, J = 8.9 Hz, 2H), 7.84-7.77 (m, 2H), 7.72 (d, J = 2.3 Hz, 1H), 7.43 (s, 1H), 7.26-7.14 (m, 2H), 4.51 (s, 2H), 3.30 (s, 5H), 3.17-2.90 (br, 3H), 2.85-2.75 (m, 2H), 2.69-2.53 (m, 5H), 2.49-2.42 (m, 1H), 1.95 (s, 2H), 1.70 (s, 6H), 1.52 (s, 2H). |
| 204 | 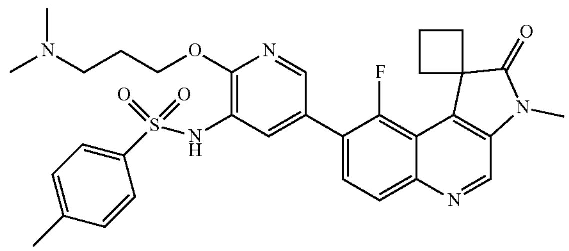 | N-(2-(3-(Dimethylamino)propoxy)-5-(9'-fluoro-3'-methyl-2'-oxo-2',3'-dihydrospiro[cyclobutane-1,1'-pyrrolo[2,3-c]quinolin]-8'-yl)pyridin-3-yl)-4-methylbenzenesulfonamide | 604.20 | 1H NMR (400 MHz, CD$_3$OD) δ 8.80 (s, 1H), 7.96 (d, J = 9.8 Hz, 2H), 7.81 (s, 1H), 7.75 (d, J = 8.0 Hz, 2H), 7.66-7.60 (m, 1H), 7.29 (d, J = 7.9 Hz, 2H), 4.39 (t, J = 5.7 Hz, 2H), 3.40 (s, 3H), 3.02-2.92 (m, 4H), 2.74 (s, 6H), 2.54 (s, 3H), 2.60-2.47 (m, 3H), 2.30-2.22 (m, 1H), 2.12 (p, J = 6.3 Hz, 2H). |
| 205 | 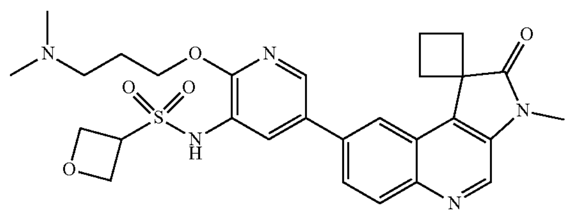 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)oxetane-3-sulfonamide | 552.25 | 1H NMR (400 MHz, DMSO-$d_6$) δ 8.83 (s, 1H), 8.35 (s, 1H), 8.18 (d, J = 2.0 Hz, 1H), 8.15 (d, J = 8.8 Hz, 1H), 7.99 (d, J = 2.3 Hz, 1H), 7.95 (d, J = 8.9 Hz, 1H), 4.74 (s, 2H), 4.72 (s, 2H), 4.66-4.58 (m, 1H), 4.36 (t, J = 5.9 Hz, 2H), 3.31 (s, 3H), 3.01-2.95 (m, 2H), 2.94-2.84 (m, 2H), 2.63 (s, 6H), 2.62-2.52 (m, 4H), 2.10-2.03 (m, 2H). |

| Examples | Structure | Name | MS: [(M + 1)]⁺ | ¹H NMR |
|---|---|---|---|---|
| 207 | 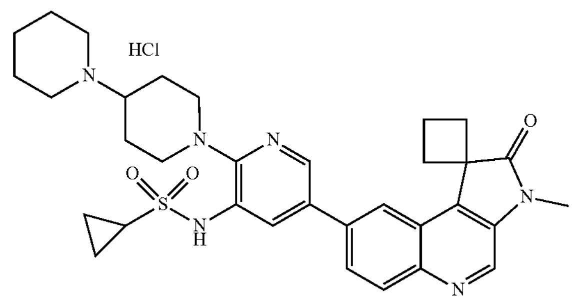 [SMILES: CN1C(=O)C2(CCC2)c2c1cnc1ccc(-c3cnc(N4CCC(N5CCCCC5)CC4)c(NS(=O)(=O)C4CC4)c3)cc21 ; Cl] | N-(2-([1,4-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide hydrochloride | 601.30 | ¹H NMR (400 MHz, CD₃OD) δ 8.84 (s, 1H), 8.59 (d, J = 2.1 Hz, 1H), 8.56 (s, 1H), 8.26 (d, J = 2.1 Hz, 1H), 8.23 (d, J = 8.8 Hz, 1H), 8.09 (d, J = 9.1 Hz, 1H), 4.02 (d, J = 13.1 Hz, 2H), 3.57 (d, J = 12.3 Hz, 2H), 3.40 (s, 4H), 3.15-2.98 (m, 6 H), 2.86-2.81 (m, 1 H), 2.79-2.70 (m, 2H), 2.70-2.61 (m, 2H), 2.19 (d, J = 11.7 Hz, 2H), 2.12-1.98 (m, 4H), 1.92-1.74 (m, 3H), 1.61-1.50 (m, 1H), 1.19-1.13 (m, 2H), 1.11-1.05 (m, 2H). |
| 209 | 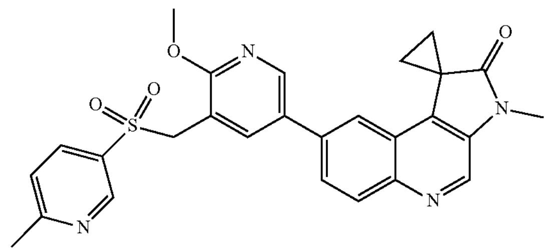 | 8'-(6-Methoxy-5-((((6-methylpyridin-3-yl)sulfonyl)methyl)pyridin-3-yl)-3'-methylspiro[cyclopropane-1,1'-pyrrolo[2,3-c]quinolin]-2'(3'H)-one | 501.15 | ¹H NMR (400 MHz, DMSO-d₆) δ 8.93 (s, 1H), 8.65 (d, J = 3.0 Hz, 2H), 8.19-8.10 (m 2H), 7.95 (dd, J = 8.1, 2.3 Hz, 1H), 7.81 (d, J = 9.0 Hz, 1H), 7.57 (s, 1H), 7.51 (d, J = 8.1 Hz, 1H), 4.78 (s, 2H), 3.53 (s, 3H), 3.42 (s, 3H), 2.59 (s, 3H), 2.57-2.53 (m, 2H), 1.82-1.77 (m, 2H). |
| 210 | 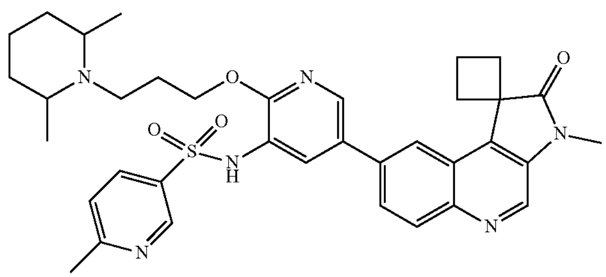 [SMILES: Cc1ccc(S(=O)(=O)Nc2cc(-c3ccc4ncc5c(c4c3)C3(CCC3)C(=O)N5C)cnc2OCCCN2C(C)CCCC2C)cn1] | N-(2-(3-(2,6-Dimethylpiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide | 655.25 | ¹H NMR (400 MHz, DMSO-d₆) δ 8.82 (s, 1H), 8.76 (d, J = 2.3 Hz, 1H), 8.29 (d, J = 2.0 Hz, 1H), 8.13 (d, J = 8.8 Hz, 1H), 8.08 (s, 1H), 7.94 (dd, J = 8.1, 2.4 Hz, 1H), 7.92-7.84 (m, 2H), 7.31 (d, J = 8.2 Hz, 1H), 4.38-4.30 (m, 2H), 3.31 (s, 3H), 3.17 (s, 2H), 2.90-2.81 (m, 2 H), 2.65-2.52 (m, 6H), 2.45 (s, 3H), 1.97-1.89 (m, 2H), 1.68 (d, J = 8.0 Hz, 3H), 1.45 (s, 3H), 1.24 (s, 3H), 1.32 (s, 3H). |

-continued

| Examples | Structure | Name | MS: [(M + 1)]+ | 1H NMR |
|---|---|---|---|---|
| 211 | 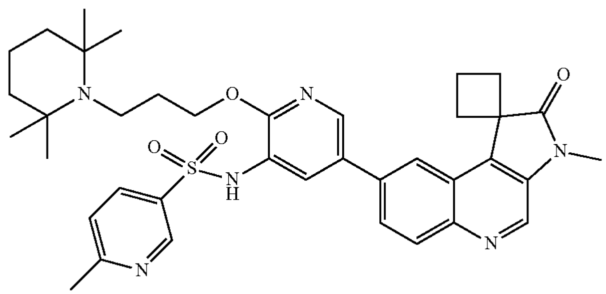 [SMILES: Cc1ccc(S(=O)(=O)Nc2cc(-c3ccc4ncc5c(c4c3)C3(CCC3)C(=O)N5C)cnc2OCCCN2C(C)(C)CCCC2(C)C)cn1] | 6-Methyl-N-(5-(3'-methyl-2'-oxo-2',3'-dihydrospiro[cyclobutane-1,1'-pyrrolo[2,3-c]quinolin]-8'-yl)-2-(3-(2,2,6,6-tetramethylpiperidin-1-yl)propoxy)pyridin-3-yl)pyridine-3-sulfonamide | 683.45 | 1H NMR (400 MHz, DMSO-d6) δ 8.83 (s, 1H), 8.76 (d, J = 2.4 Hz, 1H), 8.33 (d, J = 1.9 Hz, 1H), 8.14 (d, J = 8.9 Hz, 1H), 7.99 (s, 1H), 7.97-7.88 (m, 2H), 7.35 (d, J = 8.4 Hz, 1H), 4.16 (s, 2H), 3.31 (s, 3H), 2.94-2.84 (m, 2H), 2.64-2.52 (m, 9H), 1.77 (s, 2H), 1.60-1.40 (m, 6H), 1.11 (s, 12H). |
| 215 | 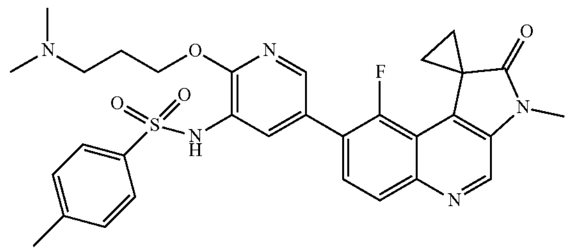 | N-(2-(3-(Dimethylamino)propoxy)-5-(9'-fluoro-3'-methyl-2'-oxo-2',3'-dihydrospiro[cyclopropane-1,1'-pyrrolo[2,3-c]quinolin]-8'-yl)pyridin-3-yl)-4-methylbenzenesulfonamide | 590.30 | 1H NMR (400 MHz, DMSO-L) δ 8.98 (s, 1H), 7.95 (d, J = 8.8 Hz, 1H), 7.84 (s, 1H), 7.69 (d, J = 8.0 Hz, 2H), 7.62-7.53 (m, 2H), 7.31 (d, J = 8.0 Hz, 2H), 4.28 (t, J = 5.8 Hz, 2H), 3.44 (s, 3H), 3.09 (s, 2H), 2.76 (s, 6H), 2.35 (s, 3H), 2.19-2.14 (m, 2H), 2.07-2.01 (m, 2H), 1.70-1.65 (m, 2H). |
| 216 | 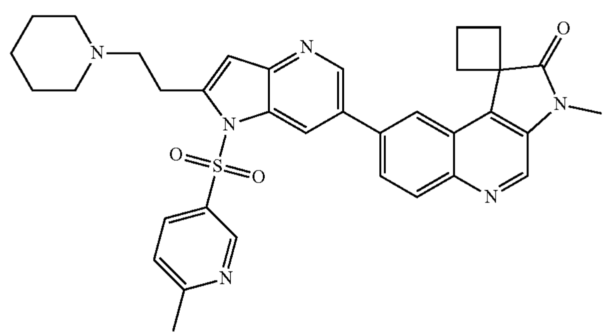 [SMILES: Cc1ccc(S(=O)(=O)n2c(CCN3CCCCC3)cc3ncc(-c4ccc5ncc6c(c5c4)C4(CCC4)C(=O)N6C)cc32)cn1] | 3'-Methyl-8'-(1-((6-methylpyridin-3-yl)sulfonyl)-2-(2-(piperidin-1-yl)ethyl)-1H-pyrrolo[3,2-b]pyridin-6-yl)spiro[cyclobutane-1,1'-pyrrolo[2,3-c]quinolin]-2'(3'H)-one | 621.20 | 1H NMR (400 MHz, DMSO-L) δ 9.03 (dd, J = 9.8, 2.3 Hz, 2H), 8.88 (s, 1H), 8.75 (d, J = 2.0 Hz, 1H), 8.53 (d, J = 1.9 Hz, 1H), 8.23 (td, J = 5.5, 2.9 Hz, 2H), 8.11 (dd, J 8.9, 2.0 Hz, 1H), 7.48 (d, J = 8.4 Hz, 1H), 6.94 (s, 1H), 3.33 (s, 3H), 3.24 (t, J = 7.3 Hz, 2H), 3.05-2.95 (m, 2H), 2.71 (t, J = 7.4 Hz, 2H), 2.65-2.52 (m, 7H), 2.43 (s, 4H), 1.54-1.47 (m, 4H), 1.43-1.36 (m, 2H). |

| Examples | Structure | Name | MS: [(M + 1)]+ | ¹H NMR |
|---|---|---|---|---|
| 217 | 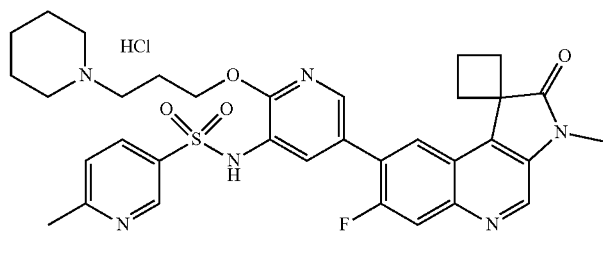 [SMILES: Cc1ccc(S(=O)(=O)Nc2cc(-c3cc4c5c(cnc4cc3F)N(C)C(=O)C53CCC3)cnc2OCCCN2CCCCC2)cn1 ; Cl] | N-(5-(7'-Fluoro-3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)-6-methylpyridine-3-sulfonamide hydrochloride | 645.20 | ¹H NMR (400 MHz, CD₃OD) δ 8.86 (s, 1H), 8.80 (s, 1H), 8.39 (d, J = 8.1 Hz, 1H), 8.34 (s, 1H), 8.09 (s, 1H), 8.04 (dd, J = 8.1, 2.4 Hz, 1H), 7.88 (d, J = 12.0 Hz, 1H), 7.45 (d, J = 8.2 Hz, 1H), 4.39 (t, J = 6.0 Hz, 2H), 3.60 (d, J = 12.6 Hz, 2H), 3.39 (s, 3H), 3.27 (d, J = 8.3 Hz, 2H), 3.04-2.90 (m, 4H), 2.78-2.62 (m, 3H), 2.61 (s, 3H), 2.60-2.50 (m, 1H), 2.22-2.13 (m, 2H), 2.01 (d, J = 14.8 Hz, 2H), 1.93-1.73 (m, 3H), 1.63-1.51 (m, 1H). |
| 218 | 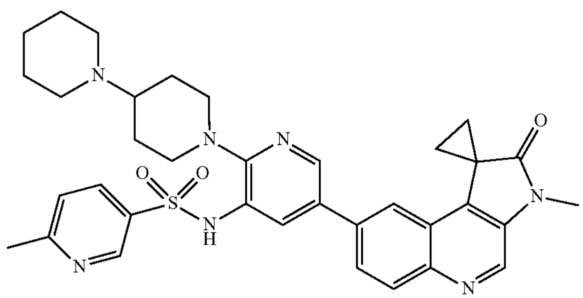 | N-(2-(1,4-Bipiperidin]-1'-yl)-5-(3'-methyl-2'-oxo-2',3'-dihydrospiro[cyclopropane-1,1'-pyrrolo[2,3-c]quinolin]-8'-yl)pyridin-3-yl)-6-methylpyridine-3-sulfonamide | 638.35 | ¹H NMR (400 MHz, DMSO-d₆) δ 8.86 (s, 1H), 8.75 (d, J = 2.4 Hz, 1H), 8.06 (d, J = 8.9 Hz, 2H), 7.96 (dd, J = 8.1, 2.4 Hz, 1H), 7.69 (dd, J = 8.9, 1.9 Hz, 1H), 7.58 (d, J = 2.3 Hz, 1H), 7.38-7.31 (m, 2H), 4.37 (s, 2H), 3.41 (s, 3H), 3.15-2.74 (br, 5H), 2.63 (t, J = 12.5 Hz, 2H), 2.47 (s, 3H), 2.34-2.28 (m, 2H), 1.91 (s, 2H), 1.79 (q, J = 4.3 Hz, 2H), 1.75-1.56 (m, 6H), 1.51 (s, 2H). |
| 219 | 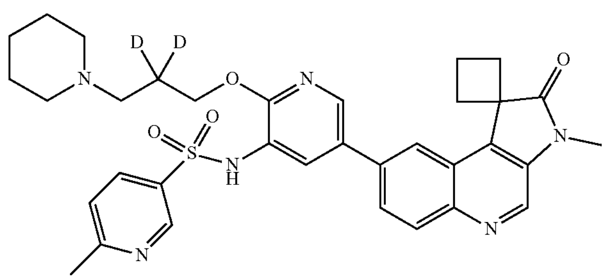 [SMILES: [2H]C([2H])(COc1ncc(-c2ccc3ncc4c(c3c2)C2(CCC2)C(=O)N4C)cc1NS(=O)(=O)c1ccc(C)nc1)CN1CCCCC1] | 6-Methyl-N-(5-(3'-methyl-2'-oxo-2',3'-dihydrospiro[cyclobutane-1,1'-pyrrolo[2,3-c]quinolin]-8'-yl)-2-(3-(piperidin-3-yl)propoxy-2,2-d2)pyridin-3-yl)pyridine-3-sulfonamide | 629.20 | ¹H NMR (400 MHz, CD₃OD) δ 8.87 (s, 1H), 8.70 (s, 1H), 8.36 (s, 1H), 8.18 (d, J = 9.2 Hz, 1H), 8.09 (d, J = 9.1 Hz, 1H), 8.04 (s, 1H), 7.91 (s, 1H), 7.86 (d, J = 9.1 Hz, 1H), 7.40 (d, J = 8.3 Hz, 1H), 4.09 (s, 2H), 3.39 (s, 3H), 2.99 (d, J = 9.0 Hz, 2H), 2.77-2.55 (m, 8H), 2.54 (s, 3H), 2.50 (s, 2H), 1.67-1.60 (m, 4H), 1.53-1.47 (m, 2H), |

-continued

| Examples | Structure | Name | MS: [(M + 1)]+ | 1H NMR |
|---|---|---|---|---|
| 220 | 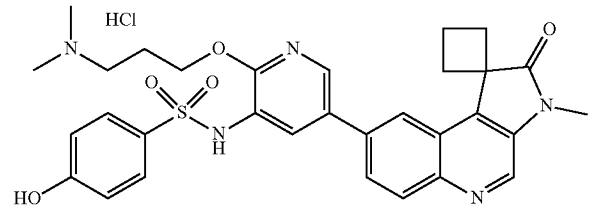 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-hydroxybenzenesulfonamide hydrochloride | 588.30 | 1H NMR (400 MHz, CD3OD) δ 8.79 (s, 1H), 8.46-8.41 (m, 2H), 8.18 (d, J = 8.9 Hz, 1H), 8.02 (d, J = 2.3 Hz, 1H), 7.92 (d, J = 9.0 Hz, 1H), 7.66 (d, J = 8.7 Hz, 2H), 4.44 (t, J = 5.8 Hz, 2H), 3.40 (s, 3H), 3.28 (s, 2H), 2.96 (s, 8H), 2.79-2.69 (m, 2H), 2.68-2.57 (m, 2H), 2.23-2.14 (m, 2H). |
| 221 | 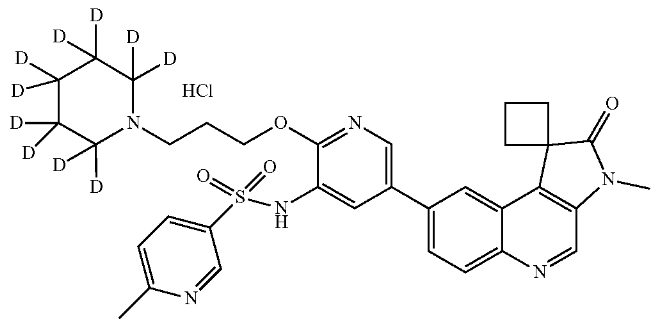 [SMILES: [2H]C1([2H])N(CCCOc2ncc(-c3ccc4ncc5c(c4c3)C3(CCC3)C(=O)N5C)cc2NS(=O)(=O)c2ccc(C)nc2)C([2H])([2H])C([2H])([2H])C([2H])([2H])C1([2H])[2H] ; Cl] | 6-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl-d10)propoxy)pyridin-3-yl)pyridine-3-sulfonamide hydrochloride | 637.35 | 1H NMR (400 MHz, DMSO-d6) δ 10.24 (s, 1H), 9.50 (s, 1H), 8.86 (s, 1H), 8.81 (d, J = 2.2 Hz, 1H), 8.54 (d, J = 2.2 Hz, 1H), 8.36 (s, 1H), 8.20-8.13 (m, 2H), 8.03-7.94 (m, 2H), 7.48 (d, J = 8.6 Hz, 1H), 4.17 (t, J = 6.0 Hz, 2H), 3.32 (s, 3H), 3.21-3.13 (m, 2H), 2.96-2.87 (m, 2H), 2.64-2.53 (m, 7H), 2.04-1.95 (m, 2H). |
| 222 | 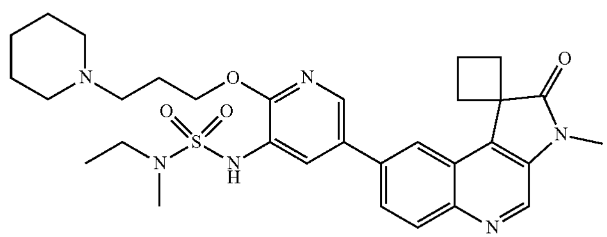 [SMILES: CCN(C)S(=O)(=O)Nc1cc(-c2ccc3ncc4c(c3c2)C2(CCC2)C(=O)N4C)cnc1OCCCN1CCCCC1] | 8'-(5-{[Ethyl(methyl)sulfamoyl]amino}-6-[3-(piperidin-1-yl)propoxy]pyridin-3-yl)-3'-methyl-2',3'-dihydrospiro[cyclobutane-1,1'-pyrrolo[2,3-c]quinoline]-2'-one | 593.55 | 1H NMR (400 MHz, CD3OD) δ 8.74 (s, 1H), 8.49 (d, J = 1.8 Hz, 1H), 8.32 (d, J = 2.2 Hz, 1H), 8.22 (d, J = 2.2 Hz, 1H), 8.18 (d, J = 9.0 Hz, 1H), 7.97 (d, J = 8.9 Hz, 1H), 4.52 (t, J = 6.3 Hz, 2H), 3.39 (s, 3H), 3.25 (q, J = 7.1 Hz, 2H), 3.04-2.94 (m, 2H), 2.83 (s, 3H), 2.78-2.54 (m, 10H), 2.17-2.07 (m, 2H), 1.72-1.64 (m, 4H), 1.57-1.49 (m, 2H), 1.09 (t, J = 7.1 Hz, 3H). |
| 225 | 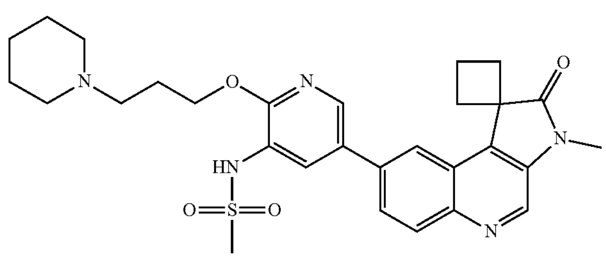 [SMILES: CN1C(=O)C2(CCC2)c2c1cnc1ccc(-c3cnc(OCCCN4CCCCC4)c(NS(C)(=O)=O)c3)cc21] | N-(5-(3'-Methyl-2'-oxo-2',3'-dihydrospiro[cyclobutane-1,1'-pyrrolo[2,3-c]quinolin]-8'-yl)-2-(3-(piperidin-3-yl)propoxy)pyridin-3-yl)methanesulfonamide | 550.25 | 1H NMR (400 MHz, CDCl3) δ 8.66 (s, 1H), 8.40 (d, J = 1.9 Hz, 1H), 8.33 (d, J = 2.2 Hz, 1H), 8.24-8.20 (m, 2H), 7.84 (dd, J = 9.0, 2.0 Hz, 1H), 4.53 (t, J = 6.3 Hz, 2H), 3.39 (s, 3H), 3.11 (s, 3H), 2.98-2.87 (m, 2H), 2.83-2.74 (m, 2H), 2.73-2.50 (m, 8H), 2.19-2.09 (m, 2H), 1.76-1.66 (m, 4H), 1.55-1.47 (m, 2H). |

| Examples | Structure | Name | MS: [(M + 1)]+ | 1H NMR |
|---|---|---|---|---|
| 231 | 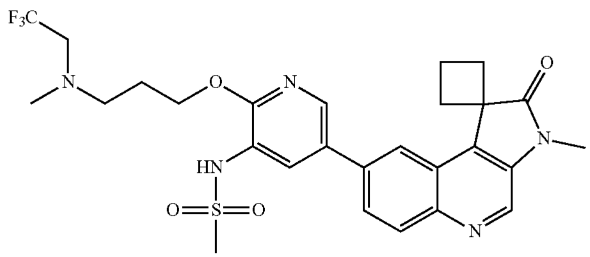 | N-(2-(3-Methyl(2,2,2-trifluoroethyl)amino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 578.20 | 1H NMR (400 MHz, CDCl3) δ 8.66 (s, 1H), 8.42 (s, 1H), 8.34 (s, 2H), 8.21 (s, 1H), 7.89 (d, J = 8.0 Hz, 1H), 6.93 (s, 1H), 4.57 (t, J = 6.3 Hz, 2H), 3.40 (s, 3H), 3.09 (s, 5H), 2.99-2.98 (m, 2H), 2.85-2.76 (m, 4H), 2.76-2.66 (m, 1H), 2.66-2.56 (m, 1H), 2.52 (s, 3H), 2.09-2.02 (m, 2H). |
| 232 | 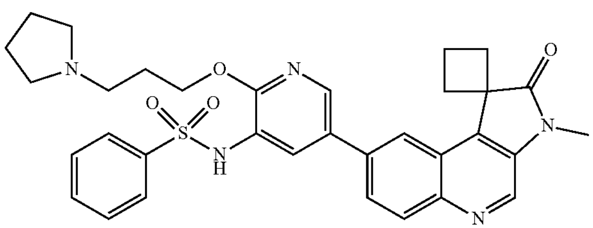 [SMILES: CN1C(=O)C2(CCC2)c2c1cnc1ccc(-c3cnc(OCCCN4CCCC4)c(NS(=O)(=O)c4ccccc4)c3)cc21] | N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)propoxy)pyridin-3-yl)benzenesulfonamide | 598.15 | 1H NMR (400 MHz, DMSO-d6) δ 8.80 (s, 1H), 8.23 (s, 1H), 8.10 (d, J = 8.9 Hz, 1H), 8.03 (d, J = 2.1 Hz, 1H), 7.80-7.75 (m, 4H), 7.44(s, 2H), 7.42 (s, 1H), 4.31 (t, J = 5.9 Hz, 2H), 3.30 (s, 3H), 3.17-3.06 (m, 6H), 2.87-2.76 (m, 2H), 2.63-2.51 (m, 4H), 2.09-2.00 (m, 2H), 1.97-1.91 (m, 4H). |
| 233 | 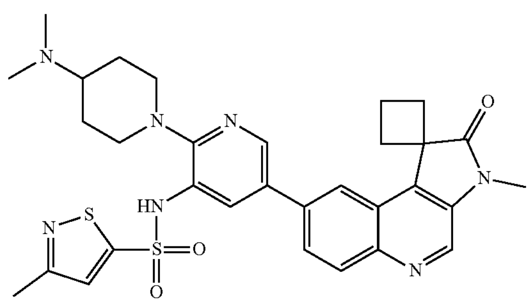 | N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)-3-methylisothiazole-5-sulfonamide | 618.15 | 1H NMR (400 MHz, CD3OD) δ 8.70 (s, 1H), 8.44 (d, J = 1.8 Hz, 1H), 8.17 (d, J = 2.0 Hz, 1H), 8.13 (d, J = 9.1 Hz, 1H), 8.01 (d, J = 2.2 Hz, 1H), 7.91 (dd, J = 8.8, 1.8 Hz, 1H), 7.29 (s, 1H), 4.26 (d, J = 12.6 Hz, 2H), 3.38 (s, 3H), 3.02-2.93 (m, 2H), 2.87 (s, 6H), 2.81-2.59 (m, 7H), 2.39 (s, 3H), 2.06 (d, J = 8.7 Hz, 2H), 1.91 (d, J = 12.3 Hz, 2H). |
| 234 | 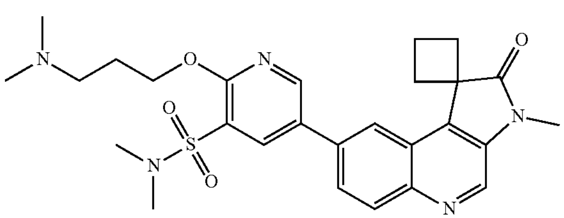 | 2-(3-(Dimethylamino)propoxy)-N,N-dimethyl-5-(3'-methyl-2'-oxo-2',3'-dihydrospiro[cyclobutane-1,1'-pyrrolo[2,3-c]quinolin]-8'-yl)pyridine-3-sulfonamide | 524.15 | 1H NMR (400 MHz, CD3OD) δ 8.84 (d, J = 2.6 Hz, 1H), 8.77 (s, 1H), 8.57 (d, J = 2.4 Hz, 1H), 8.53 (s, 1H), 8.22 (d, J = 8.9 Hz, 1H), 8.00 (d, J = 8.7 Hz, 1H), 4.62 (t, J = 6.2 Hz, 2H), 3.39 (s, 3H), 3.07-2.97 (m, 2H), 2.94 (s, 6H), 2.77-2.52 (m, 6H), 2.34 (s, 6H), 2.13-2.04 (m, 2H). |

| Examples | Structure | Name | MS: [(M + 1)]+ | 1H NMR |
|---|---|---|---|---|
| 235 | 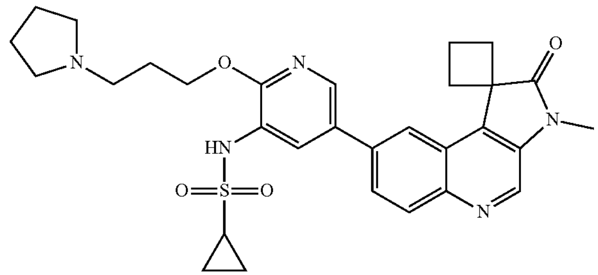 [SMILES: CN1C(=O)C2(CCC2)c2c1cnc1ccc(-c3cnc(OCCCN4CCCC4)c(NS(=O)(=O)C4CC4)c3)cc21] | N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)propoxy)pyridin-3-yl)cyclopropanesulfonamide | 562.25 | 1H NMR (400 MHz, DMSO-d6) δ 8.84(s, 1H), 8.43(s, 1H), 8.38(s, 1H), 8.16(d, J = 8.8 Hz, 1H), 8.13 (s, 1H), 7.97 (d, J = 9.2 Hz, 1H), 4.43 (t, J = 6.4 Hz, 2H), 3.31 (s, 3H), 2.96-2.87 (m, 2H), 2.78-2.66 (m, 3H), 2.62-2.51 (m, 8H), 2.04-1.96 (m, 2H), 1.74 (s, 4H), 0.93 (d, J = 8.5 Hz, 4H). |
| 236 | 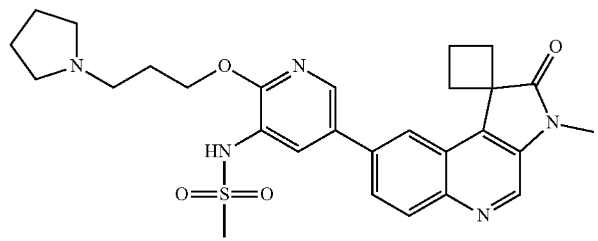 [SMILES: CN1C(=O)C2(CCC2)c2c1cnc1ccc(-c3cnc(OCCCN4CCCC4)c(NS(C)(=O)=O)c3)cc21] | N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)propoxy)pyridin-3-yl)methanesulfonamide | 536.15 | 1H NMR (400 MHz, DMSO-d6) δ 8.83 (s, 1H), 8.39 (d, J = 2.3 Hz, 1H), 8.38 (d, J = 2.0 Hz, 1H), 8.16 (d, J = 2.3 Hz, 1H), 8.9 Hz, 1H), 8.08 (d, J = 2.3 Hz, 1H), 7.97 (dd, J = 8.9, 2.0 Hz, 1H), 4.43 (t, J = 6.3 Hz, 2H), 3.31 (s, 3H), 3.05 (s, 3H), 2.96-2.86 (m, 2H), 2.74 (t, J = 6.8 Hz, 2H), 2.68-2.62 (m, 4H), 2.62-2.52 (m, 4H), 2.04-1.96 (m, 2H), 1.79-1.73 (m, 4H). |
| 237 | 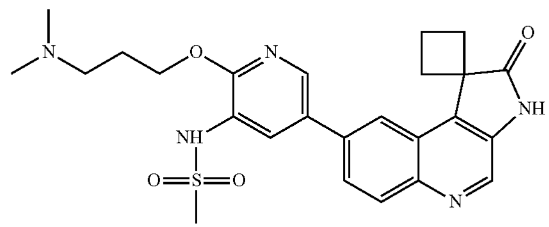 [SMILES: CN(C)CCCOc1ncc(-c2ccc3ncc4c(c3c2)C2(CCC2)C(=O)N4)cc1NS(C)(=O)=O] | N-(2-(3-(Dimethylamino)propoxy)-5-(2'-oxo-2',3'-dihydrospiro[cyclobutane-1,1'-pyrrolo[2,3-c]quinolin]-8'-yl)pyridin-3-yl)methanesulfonamide | 496.20 | 1H NMR (400 MHz, DMSO-d6) δ 10.68 (s, 1H), 8.62 (s, 1H), 8.35 (s, 1H), 8.34 (d, J = 2.3 Hz, 1H), 8.12 (d, J = 8.8 Hz, 1H), 8.04 (d, J = 2.3 Hz, 1H), 7.94 (dd, J = 8.8, 2.0 Hz, 1H), 4.40 (t, J = 6.2 Hz, 2H), 3.03 (s, 3H), 2.94-2.84 (m, 2H), 2.64 (t, J = 6.6 Hz, 2H), 2.61-2.51 (m, 2H), 2.49-2.41 (m, 2H), 2.35 (s, 6H), 2.02-1.95 (m, 2H). |
| 238 | 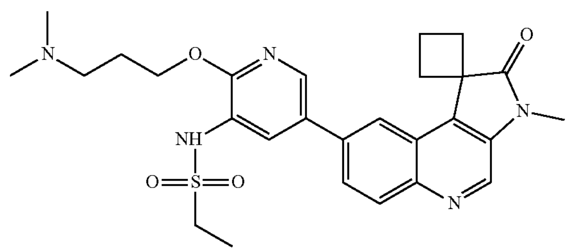 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)ethanesulfonamide | 524.25 | 1H NMR (400 MHz, DMSO-d6) δ 8.84 (s, 1H), 8.40 (d, J = 2.3 Hz, 1H), 8.38 (d, J = 2.1 Hz, 1H), 8.16 (d, J = 8.8 Hz, 1H), 8.09 (d, J = 2.3 Hz, 1H), 7.97 (dd, J = 8.9, 2.0 Hz, 1H), 4.41 (t, J = 6.3 Hz, 2H), 3.31 (s, 3H), 3.14 (q, J = 7.3 Hz, 2H), 2.96-2.86 (m, 2H), 2.63-2.51 (m, 5H), 2.50-2.45 (m, 1H), 2.31 (s, 6H), 2.02-1.93 (m, 2H), 1.28 (t, J = 7.3 Hz, 3H). |

| Examples | Structure | Name | MS: [(M + 1)]+ | 1H NMR |
|---|---|---|---|---|
| 240 | 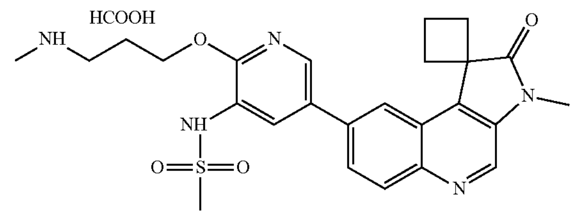 | N-(5-(3'-Methyl-2'-oxo-2',3'-dihydrospiro[cyclobutane-1,1'-pyrrolo[2,3-c]quinolin]-8'-yl)-2-(3-(methylamino)propoxy)pyridin-3-yl)methanesulfonamide formate | 496.25 | 1H NMR (400 MHz, DMSO-d6) δ 8.82 (s, 1H), 8.37 (d, J = 2.0 Hz, 1H), 8.25 (s, 1H), 8.14 (d, J = 8.9 Hz, 1H), 8.03 (s, 1H), 7.96-7.92 (m, 2H), 4.36 (t, J = 5.5 Hz, 2H), 3.31 (s, 3H), 3.12 (t, J = 5.4 Hz, 2H), 2.93-2.86 (m, 2H), 2.85 (s, 3H), 2.66 (s, 3H), 2.63-2.51 (m, 4H), 2.11-2.04 (m, 2H) |
| 241 | 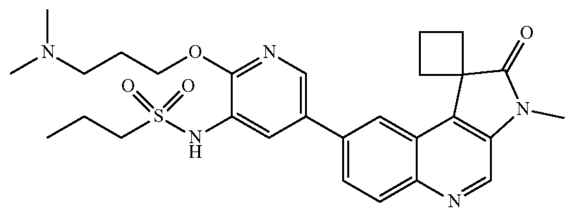 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)propane-1-sulfonamide | 538.20 | 1H NMR (400 MHz, DMSO-d6) δ 8.84 (s, 1H), 8.39 (dd, J = 9.2, 2.1 Hz, 2H), 8.16 (d, J = 8.9 Hz, 1H), 8.09 (d, J = 2.3 Hz, 1H), 7.97 (dd, J = 8.9, 2.0 Hz, 1H), 4.41 (t, J = 6.3 Hz, 2H), 3.15-3.09 (m, 2H), 2.95-2.86 (m, 2H), 2.63-2.51 (m, 6H), 2.30 (s, 6H), 2.01-1.93 (m, 2H), 1.82-1.71 (m, 2H), 0.97 (t, J = 7.4 Hz, 3H). |
| 242 | 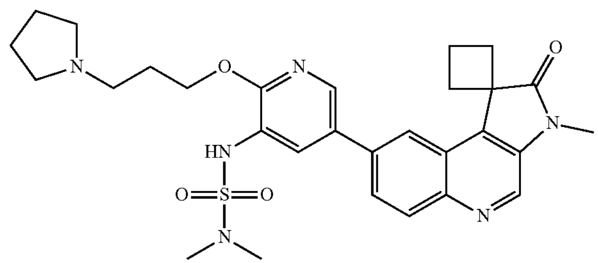 [SMILES: CN1C(=O)C2(CCC2)c2c1cnc1ccc(-c3cnc(OCCCN4CCCC4)c(NS(=O)(=O)N(C)C)c3)cc21] | 8'-(5-[(Dimethylsulfamoyl)amino]-6-[3-(pyrrolidin-1-yl)propoxy]pyridin-3-yl)-3'-methyl-2',3'-dihydrospiro[cyclobutane-1,1'-pyrrolo[2,3-c]quinoline]-2'-one | 565.20 | 1H NMR (400 MHz, DMSO-d6) δ 8.83 (s, 1H), 8.36 (d, J = 2.0 Hz, 1H), 8.30 (d, J = 2.3 Hz, 1H), 8.16 (d, J = 8.9 Hz, 1H), 8.11 (d, J = 2.3 Hz, 1H), 7.95 (dd, J = 8.8, 2.0 Hz, 1H), 4.42 (t, J = 6.2 Hz, 2H), 3.31 (s, 3H), 2.93-2.84 (m, 2H), 2.82 (t, J = 6.6 Hz, 2H), 2.75-2.70 (m, 4H), 2.69 (s, 6H), 2.64-2.51 (m, 4H), 2.06-1.99 (m 2H), 1.82-1.76 (m, 4H). |
| 243 | 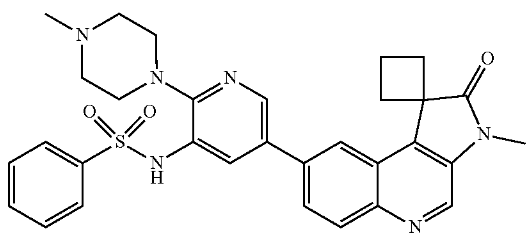 [SMILES: CN1CCN(c2ncc(-c3ccc4ncc5c(c4c3)C3(CCC3)C(=O)N5C)cc2NS(=O)(=O)c2ccccc2)CC1] | N-(5-(3'-Methyl-2'-oxo-2',3'-dihydrospiro[cyclobutane-1,1'-pyrrolo[2,3-c]quinolin]-8'-yl)-2-(4-methylpiperazin-1-yl)Pyridin-3-yl)benzenesulfonamide | 569.25 | 1H NMR (400 MHz, DMSO-d6) δ 9.66 (s, 1H), 8.81 (s, 1H), 8.48 (s, 1H), 8.22 (d, J = 2.0 Hz, 1H), 8.10 (d, J = 8.9 Hz, 1H), 7.82-7.75 (m, 3H), 7.63 (d, J = 2.3 Hz, 1H), 7.60-7.50 (m, 3H), 3.34 (s, 4H), 3.30 (s, 3H), 2.88-2.76 (m, 2H), 2.62-2.51 (m, 8H), 2.32 (s, 3H). |

-continued

| Examples | Structure | Name | MS: [(M + 1)]+ | 1H NMR |
|---|---|---|---|---|
| 244 | 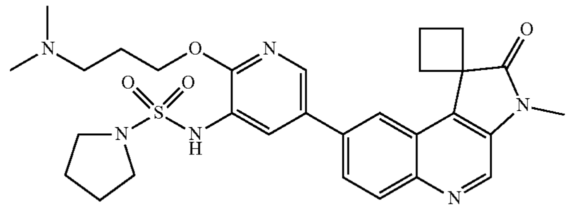 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyrrolidine-1-sulfonamide | 565.35 | 1H NMR (400 MHz, CD3OD) δ 8.73 (s, 1H), 8.50 (d, J = 1.9 Hz, 1H), 8.25 (s, 2H), 8.17 (d, J = 8.9 Hz, 1H), 7.97 (d, J = 9.1 Hz, 1H), 4.52 (t, J = 6.1 Hz, 2H), 3.39 (s, 3H), 3.30-3.26 (m, 4H), 2.04-2.94 (m, 2H), 2.80 (t, J = 7.0 Hz, 2H), 2.77-2.62 (m, 4H), 2.51 (s, 6H), 2.17-2.09 (m, 2H), 1.88-1.82 (m, 4H). |
| 246 | 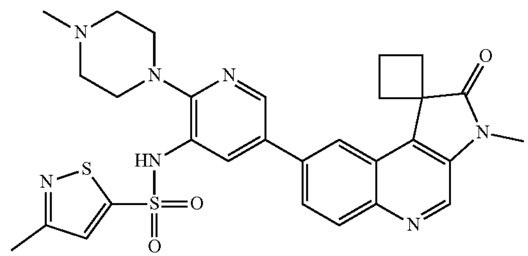 | 3-Methyl-N-(5-(3'-methyl-2'-oxo-2',3'-dihydrospiro[cyclobutane-1,1'-pyrrolo[2,3-c]quinolin]-8'-yl)pyridin-3-yl)-2-(4-methylpiperazin-1-yl)pyridin-3-yl)isothiazole-5-sulfonamide | 590.15 | 1H NMR (400 MHz, DMSO-d6) δ 8.79 (s, 1H), 8.31 (s, 1H), 8.13-8.07 (m, 2H), 7.93 (s, 1H), 7.87 (d, J = 8.8 Hz, 1H), 7.22 (s, 1H), 3.30 (s, 3H), 3.06 (br, 4H), 2.89-2.80 (m, 2H), 2.74-2.63 (m, 2H), 2.62-2.51 (m, 9H), 2.32 (s, 3H). |
| 253 | 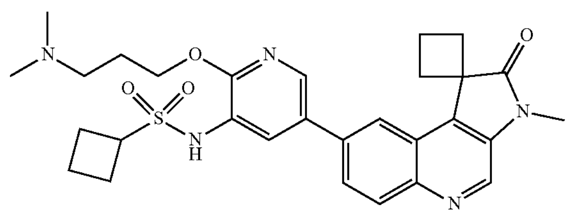 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)cyclobutanesulfonamide | 550.20 | 1H NMR (400 MHz, DMSO-d6) δ 8.84 (d, J = 1.8 Hz, 1H), 8.43 (s, 1H), 8.38 (s, 1H), 8.17 (d, J = 8.9 Hz, 1H), 8.10 (s, 1H), 7.97 (d, J = 9.0 Hz, 1H), 4.41 (t, J = 6.5 Hz, 2H), 4.05-3.96 (m, 1H), 2.97-2.86 (m, 2H), 2.62-2.50 (m, 4H), 2.44-2.30 (m, 3H), 2.28 (s, 6H), 2.26-2.15 (m, 3H), 2.01-1.83 (m, 4H). |
| 254 | 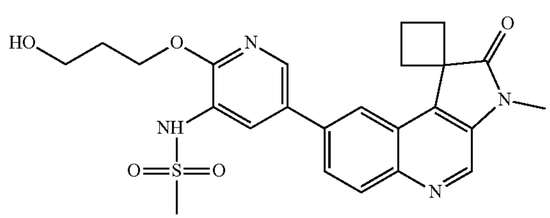 [SMILES: CN1C(=O)C2(CCC2)c2c1cnc1ccc(-c3cnc(OCCCO)c(NS(C)(=O)=O)c3)cc21] | N-(2-(3-Hydroxypropoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 483.20 | 1H NMR (400 MHz, DMSO-d6) δ 9.39 (s, 1H), 8.84 (d, J = 2.1 Hz, 1H), 8.52 (s, 1H), 8.39 (s, 1H), 8.19-8.11 (m, 2H), 7.99 (d, J = 9.0 Hz, 1H), 4.54 (s, 1H), 4.47 (t, J = 6.5 Hz, 2H), 3.66-3.60 (m, 2H), 3.31 (s, 3H), 3.12 (s, 3H), 2.92 (d, J = 9.6 Hz, 2H), 2.62-2.52 (m, 4H), 1.99-1.92 (m, 2H). |

| Examples | Structure | Name | MS: [(M + 1)]+ | 1H NMR |
|---|---|---|---|---|
| 255 | 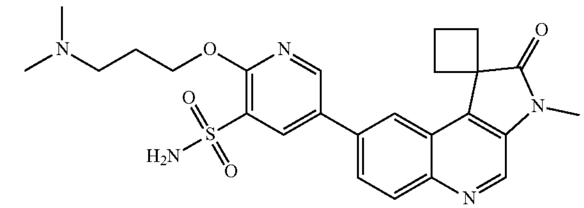 | 2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridine-3-sulfonamide | 496.20 | 1H NMR (400 MHz, DMSO-d6) δ 8.93 (d, J = 2.4 Hz, 1H), 8.87 (s, 1H), 8.49 (d, J = 2.5 Hz, 1H), 8.43 (d, J = 2.0 Hz, 1H), 8.20 (d, J = 8.8 Hz, 1H), 7.99 (dd, J = 8.8, 2.0 Hz, 1H), 7.62 (s, 2H), 4.55 (t, J = 6.2 Hz, 2H), 3.31 (s, 3H), 3.00-2.90 (m, 2H), 2.60-2.51 (m, 6H), 2.25 (s, 6H), 2.05-1.97 (m, 2H). |
| 256 | 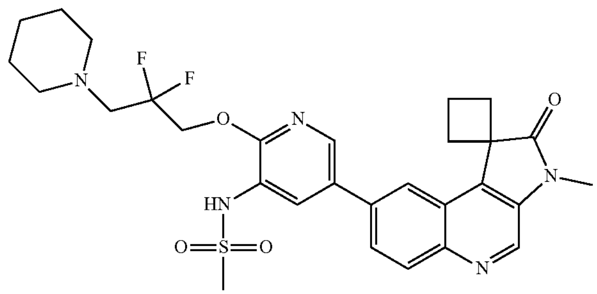 [SMILES: CN1C(=O)C2(CCC2)c2c1cnc1ccc(-c3cnc(OCC(F)(F)CN4CCCCC4)c(NS(C)(=O)=O)c3)cc21] | N-(2-(2,2-Difluoro-3-(piperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 586.25 | 1H NMR (400 MHz, CD3OD) δ 8.74 (s, 1H), 8.51 (d, J = 2.0 Hz, 1H), 8.48 (d, J = 2.3 Hz, 1H), 8.24 (d, J = 2.3 Hz, 1H), 8.18 (d, J = 8.9 Hz, 1H), 7.99 (dd, J = 8.9, 2.0 Hz, 1H), 4.85 (t, J = 7.2 Hz, 2H), 3.39 (s, 3H), 3.08 (s, 3H), 3.05-2.90 (m, 4H), 2.76-2.61 (m, 4H), 2.59 (t, J = 5.3 Hz, 4H), 1.61-1.53 (m, 4H), 1.47-1.39 (m, 2H). |
| 257 | 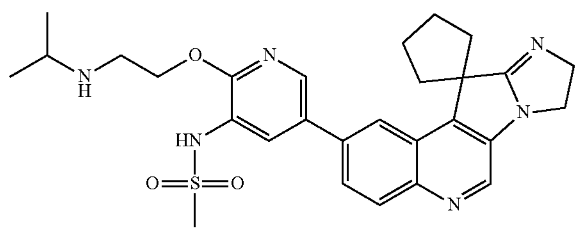 [SMILES: CC(C)NCCOc1ncc(-c2ccc3ncc4c(c3c2)C2(CCCC2)C2=NCCN24)cc1NS(C)(=O)=O] | N-(5-(8',9'-Dihydrospiro[cyclopentane-1,11'-imidazo[1',2':1,5]pyrrolo[2,3-c]quinolin]-2'-yl)-2-(2-(isopropylamino)ethoxy)pyridin-3-yl)methanesulfonamide | 535.20 | 1H NMR (400 MHz, DMSO-d6) δ 8.61 (s, 1H), 8.32 (d, J = 2.3 Hz, 1H), 8.08 (d, J = 8.8 Hz, 1H), 7.98 (d, J = 2.3 Hz, 1H), 7.89 (d, J = 1.9 Hz, 1H), 7.85 (dd, J = 8.8, 1.9 Hz, 1H), 4.41 (t, J = 5.3 Hz, 2H), 4.16 (t, J = 8.7 Hz, 2H), 3.75 (t, J = 8.6 Hz, 2H), 3.05 (s, 3H), 2.96 (t, J = 5.4 Hz, 2H), 2.89 (p, J = 6.1 Hz, 1H), 2.44-2.35 (m, 2H), 2.16-2.04 (m, 6H), 1.06 (d, J = 6.2 Hz, 6H). |
| 258 | 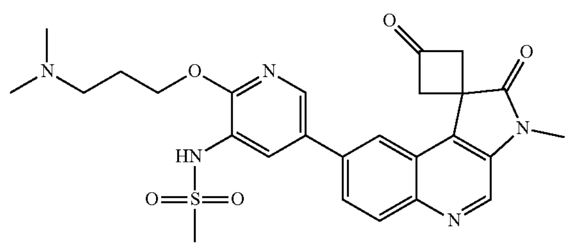 | N-(2-(3-(Dimethylamino)propoxy)-5-(3'-methyl-2',3'-dioxo-2',3'-dihydrospiro[cyclobutane-1,1'-pyrrolo[2,3-c]quinolin]-8'-yl)pyridin-3-yl)methanesulfonamide | 524.15 | 1H NMR (400 MHz, DMSO-d6) δ 8.95 (s, 1H), 8.30 (s, 1H), 8.19 (d, J = 8.9 Hz, 1H), 7.94-7.86 (m, 3H), 4.40 (t, J = 6.8 Hz, 2H), 4.06 (d, J = 18.2 Hz, 2H), 3.66 (d, J = 18.1 Hz, 2H), 3.40 (s, 3H), 3.04 (s, 3H), 2.62 (t, J = 7.3 Hz, 2H), 2.33 (s, 6H), 2.02-1.93 (m, 2H). |

| Examples | Structure | Name | MS: [(M + 1)]+ | 1H NMR |
|---|---|---|---|---|
| 259 | 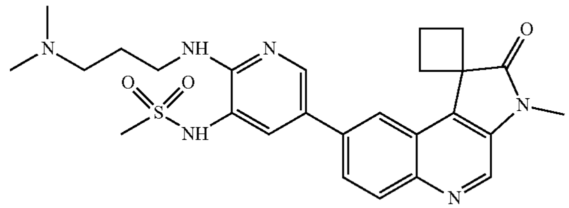 | N-(2-((3-(Dimethylamino)propyl) amino)-5-(3'-methyl-2'-oxo-2',3'-dihydrospiro[cyclobutane-1,1'-pyrrolo[2,3-c]quinolin]-8'-yl) pyridin-3-yl)methanesulfonamide | 509.25 | 1H NMR (400 MHz, DMSO-d6) δ 8.78 (s, 1H), 8.39 (s, 1H), 8.31 (s, 1H), 8.11 (d, J = 8.9 Hz, 1H), 7.93 (d, J = 9.2 Hz, 1H), 7.83 (s, 1H), 6.53 (s, 1H), 3.48-3.41 (m, 2H), 3.30 (s, 3H), 2.99 (s, 3H), 2.95-2.86 (m, 2H), 2.62-2.51 (m, 4H), 2.44 (t, J = 7.1 Hz, 2H), 2.26 (s, 6H), 1.81-1.71 (m, 2H). |
| 260 | 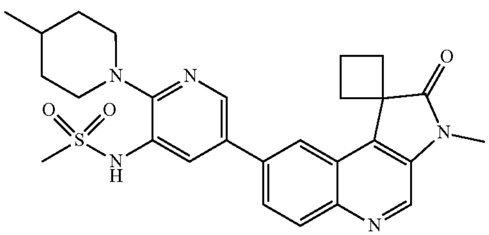 | N-(5-(3'-Methyl-2'-oxo-2',3'-dihydrospiro[cyclobutane-1,1'-pyrrolo[2,3-c]quinolin]-8'-yl)-2-(4-methylpiperidin-1-yl)Pyridin-3-yl)methanesulfonamide | 506.2 | 1H NMR (400 MHz, DMSO-d6) δ 8.91 (s, 1H), 8.84 (s, 1H), 8.63 (s, 1H), 8.39 (s, 1H), 8.16 (d, J = 8.8 Hz, 1H), 8.05 (s, 1H), 7.99 (d, J = 8.9 Hz, 1H), 3.75 (d, J = 12.3 Hz, 2H), 3.30 (s, 3H), 3.21 (s, 3H), 2.99-2.89 (m, 2H), 2.82 (t, J = 12.1 Hz, 2H), 2.63-2.52 (m, 4H), 1.71 (d, J = 12.6 Hz, 2H), 1.57 (br, 1H), 1.45-1.33 (m, 2H), 0.98 (d, J = 6.3Hz, 3H). |
| 261 | 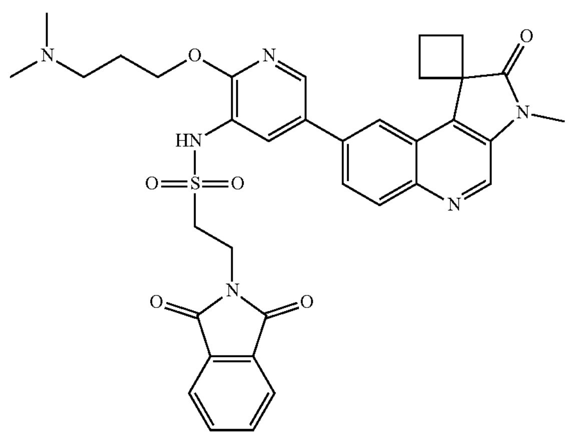 | N-(2-(3-(Dimethylamino)propoxy)-5-(3'-methyl-2'-oxo-2',3'-dihydrospiro [cyclobutane-1,1'-pyrrolo[2,3-c]quinolin]-8'-yl)pyridin-3-yl)-2-(1,3-dioxoisoindolin-2-yl)ethane-1-sulfonamide | 669.20 | 1H NMR (400 MHz, DMSO-d6) δ 8.83 (s, 1H), 8.34 (s, 1H), 8.14 (d, J = 9.0 Hz, 1H), 7.87 (d, J = 10.8 Hz, 2H), 7.77-7.72 (m, 3H), 7.72-7.67 (m, 2H), 4.24 (t, J = 6.6 Hz, 2H), 3.96 (t, J = 6.6 Hz, 2H), 3.53 (t, J = 6.6 Hz, 2H), 3.32 (s, 3H), 3.10(t, J = 6.6 Hz, 2H), 3.00-2.90 (m, 2H), 2.71 (s, 6H), 2.61-2.52 (m, 4H), 2.13-2.05 (m, 2H). |

| Examples | Structure | Name | MS: [(M + 1)]+ | 1H NMR |
|---|---|---|---|---|
| 262 | 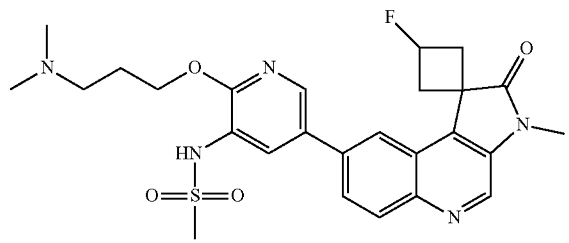 | N-(2-(3-(Dimethylamino)propoxy)-5-(3'-fluoro-3'-methyl-2'-oxo-2',3'-dihydrospiro[cyclobutane-1,1'-pyrrolo[2,3-c]quinolin]-8'-yl)pyridin-3-yl)methanesulfonamide | 528.20 | 1H NMR(400MHz, DMSO-$d_6$) δ 8.88(s, 1H), 8.41(s, 1H), 8.29(s, 1H), 8.18(d, J = 8.8 Hz, 1H), 7.97-7.92 (m, 2H), 5.72-5.50 (m, 1H), 4.39 (t, J = 6.3 Hz, 2H), 3.32 (s, 3H), 3.28-3.18 (m, 2H), 3.01 (s, 3H), 2.99-2.89 (m, 2H), 2.65 (t, J = 6.6 Hz, 2H), 2.36 (s, 6H), 2.03-1.94 (m, 2H). |
| 263 | 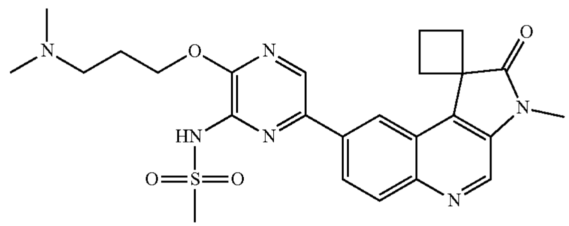 | N-(3-(3-(Dimethylamino)propoxy)-6-(3'-methyl-2'-oxo-2',3'-dihydrospiro[cyclobutane-1,1'-pyrrolo[2,3-c]quinolin]-8'-yl)pyrazin-2-yl)methanesulfonamide | 511.15 | 1H NMR (400 MHz, DMSO-$d_6$) δ 9.01 (d, J = 1.8 Hz, 1H), 8.79 (s, 1H), 8.22 (dd, J = 9.0, 1.8 Hz, 1H), 8.11 (s, 1H), 8.09 (d, J = 9.0 Hz, 1H), 4.38 (t, J = 5.5 Hz, 2H), 3.31 (s, 3H), 3.13 (s, 3H), 2.88 (s, 8H), 2.76 (d, J = 14.4 Hz, 1H), 2.56-2.51 (m, 5H), 2.21-2.13 (m, 2H). |
| 265 | 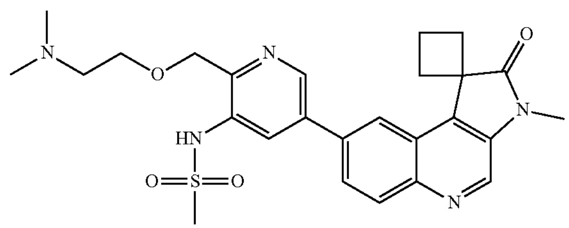 | N-(2-((2-(Dimethylamino)ethoxy)methyl)-5-(3'-methyl-2'-oxo-2',3'-dihydrospiro[cyclobutane-1,1'-pyrrolo[2,3-c]quinolin]-8'-yl)pyridin-3-yl)methanesulfonamide | 510.20 | 1H NMR (400 MHz, DMSO-$d_6$) δ 8.87(s, 1H), 8.65(s, 1H), 8.47(s, 1H), 8.26(s, 1H), 8.20(d, J = 8.9 Hz, 1H), 8.06-7.98 (m, 1H), 4.69 (s, 2H), 3.78 (t, J = 5.3 Hz, 2H), 3.32 (s, 3H), 3.02-2.98 (m, 5H), 2.96-2.87 (m, 2H), 2.60 (s, 6H), 2.59-2.52 (m, 4 H). |
| 266 | 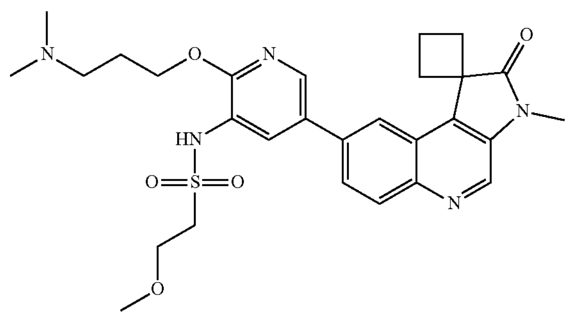 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-methoxyethane-1-sulfonamide | 554.20 | 1H NMR (400 MHz, DMSO-$d_6$) δ 8.83 (s, 1H), 8.37 (d, J = 2.0 Hz, 1H), 8.27 (d, J = 2.3 Hz, 1H), 8.15 (d, J = 8.9 Hz, 1H), 8.04 (d, J = 2.3 Hz, 1H), 7.96 (dd, J = 8.8, 1.9 Hz, 1H), 4.39 (t, J = 6.1 Hz, 2H), 3.70 (t, J = 6.7 Hz, 2H), 3.37 (t, J = 6.7 Hz, 2H), 3.31 (s, 3H), 3.20 (s, 3H), 2.95-2.85 (m, 2H), 2.75 (t, J = 6.4 Hz, 2H), 2.62-2.52 (m, 4H), 2.43 (s, 6H), 2.06-1.97 (m, 2H). |

-continued

| Examples | Structure | Name | MS: [(M + 1)]+ | ¹H NMR |
|---|---|---|---|---|
| 267 | 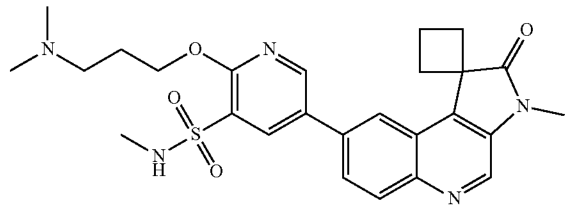 | 2-(3-(Dimethylamino)propoxy)-N-methyl-5-(3'-methyl-2'-oxo-2',3'-dihydrospiro[cyclobutane-1,1'-pyrrolo[2,3-c]quinolin]-8'-yl)pyridine-3-sulfonamide | 510.25 | ¹H NMR (400 MHz, CDCl3) δ 8.68 (d, J = 2.2 Hz, 2H), 8.56 (d, J = 2.5 Hz, 1H), 8.39 (d, J = 2.0 Hz, 1H), 8.25 (d, J = 8.9 Hz, 1H), 7.83 (dd, J = 8.9, 2.0 Hz, 1H), 4.66 (s, 2H), 3.39 (s, 3H), 2.97-2.85 (m, 3H), 2.84-2.66 (m, 4H), 2.62 (s, 3H), 2.59-2.38 (m, 7H), 2.18 (s, 2H). |
| 268 | 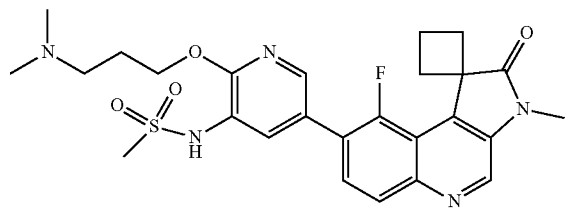 | N-(2-(3-(Dimethylamino)propoxy)-5-(9'-fluoro-3'-methyl-2'-oxo-2',3'-dihydrospiro[cyclobutane-1,1'-pyrrolo[2,3-c]quinolin]-8'-yl)pyridin-3-yl)methanesulfonamide | 528.15 | ¹H NMR (400 MHz, DMSO-d₆) δ 8.92 (s, 1H), 8.27 (s, 1H), 8.01 (d, J = 8.8 Hz, 1H), 7.94 (d, J = 2.3 Hz, 1H), 7.78 (t, J = 8.5 Hz, 1H), 4.42 (t, J = 6.1 Hz, 2H), 3.33 (s, 3H), 3.05 (s, 3H), 2.97-2.87 (m, 2H), 2.84-2.75 (m, 2H), 2.45 (s, 6H), 2.44-2.38 (m, 3H), 2.24-2.14 (m, 1H), 2.07-1.99 (m, 2H). |
| 270 | 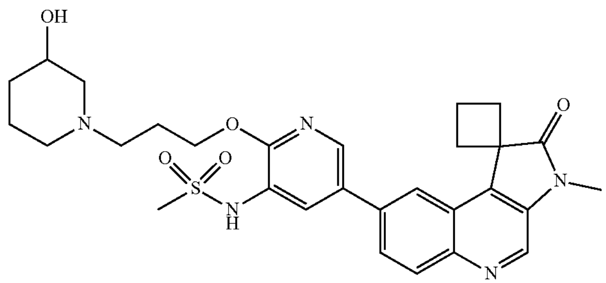 [SMILES: CN1C(=O)C2(CCC2)c2c1cnc1ccc(-c3cnc(OCCCN4CCCC(O)C4)c(NS(C)(=O)=O)c3)cc21] | N-(2-(3-(3-Hydroxypiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 566.20 | ¹H NMR (400 MHz, DMSO-d₆) δ 8.84 (s, 1H), 8.50 (d, J = 1.7 Hz, 1H), 8.38 (d, J = 1.9 Hz, 1H), 8.16 (d, J = 8.9 Hz, 1H), 8.11 (d, J = 2.4 Hz, 1H), 7.98 (dd, J = 8.8, 2.0 Hz, 1H), 4.59 (s, 1H), 4.41 (t, J = 6.4 Hz, 2H), 3.50-3.42 (m, 1H), 3.31 (s, 3H), 3.11 (s, 3H), 2.97-2.84 (m, 3H), 2.73-2.66 (m, 1H), 2.62-2.52 (m, 5H), 1.98-1.90 (m, 2H), 1.88-1.69 (m, 3H), 1.62 (d, J = 13.3 Hz, 1H), 1.47-1.35 (m, 1H), 1.12-1.01 (m, 1H). |
| 272 | 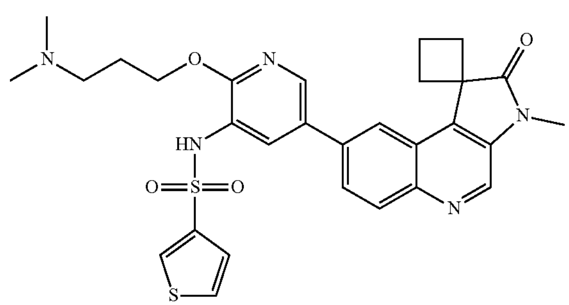 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)thiophene-3-sulfonamide | 578.25 | ¹H NMR (400 MHz, DMSO-d₆) δ 8.82 (s, 1H), 8.27 (s, 1H), 8.13 (d, J = 8.8 Hz, 1H), 8.02 (s, 1H), 7.95 (d, J = 2.8 Hz, 1H), 7.85-7.76 (m, 2H), 7.61-7.54 (m, 1H), 7.26 (d, J = 5.3 Hz, 1H), 4.33 (t, J = 5.6 Hz, 2H), 3.31 (s, 3H), 3.20-3.12 (m, 2H), 2.90-2.83 (m, 2H), 2.81 (s, 6H), 2.68-2.51 (m, 4H), 2.15-2.02 (m, 2H). |

-continued

| Examples | Structure | Name | MS: [(M + 1)]+ | 1H NMR |
|---|---|---|---|---|
| 273 | 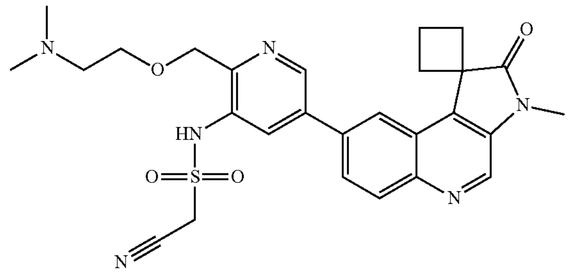 | 1-Cyano-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 535.15 | 1H NMR (400 MHz, DMSO-$d_6$) δ 8.82 (s, 1H), 8.39 (d, J = 2.0 Hz, 1H), 8.14 (d, J = 8.9 Hz, 1H), 8.05-7.93 (m, 3H), 4.38 (t, J = 5.5 Hz, 2H), 4.31 (s, 2H), 3.42-3.33 (m, 2H), 3.31 (s, 3H), 2.91 (s, 6H), 2.90-2.79 (m, 2H), 2.63-2.51 (m, 4H), 2.19 (d, J = 5.6 Hz, 2H). |
| 274 | 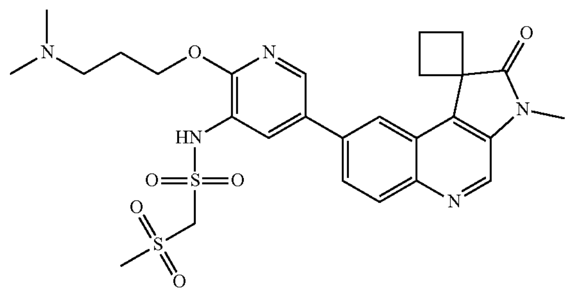 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1-(methylsulfonyl)methanesulfonamide | 588.15 | 1H NMR (400 MHz, DMSO-$d_6$) d 8.82 (s, 1H), 8.38 (d, J = 2.1 Hz, 1H), 8.14 (d, J = 8.9 Hz, 1H), 8.03-7.94 (m, 3H), 4.67 (s, 2H), 4.36 (t, J = 5.6 Hz, 2H), 3.31 (s, 3H), 3.30-3.23 (m, 2H), 3.15 (s, 3H), 2.96-2.80 (m, 8H), 2.64-2.51 (m, 4H), 2.16 (s, 2H). |
| 275 | 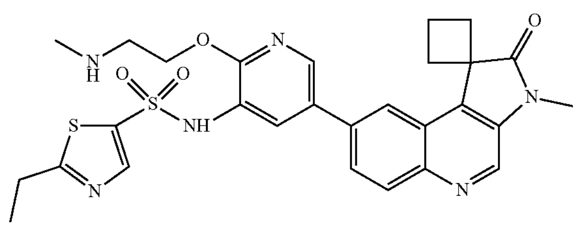 [SMILES: CCc1ncc(S(=O)(=O)Nc2cc(-c3ccc4ncc5c(c4c3)C3(CCC3)C(=O)N5C)cnc2OCCNC)s1] | 2-Ethyl-N-(5-(3'-methyl-2'-oxo-2',3'-dihydrospiro[cyclobutane-1,1'-pyrrolo[2,3-c]quinolin]-8'-yl)-2-(2-(methylamino)ethoxy)pyridin-3-yl)thiazole-5-sulfonamide | 579.15 | 1H NMR (400 MHz, DMSO-$d_6$) δ 8.82 (s, 1H), 8.32 (s, 1H), 8.13 (d, J = 8.8 Hz, 1H), 8.05 (s, 1H), 7.95 (m, 1H), 7.90-7.82 (m, 2H), 4.48 (s, 2H), 3.3l (s, 3H), 3.30-3.26 (m, 2H), 2.94-2.81 (m, 4H), 2.69 (s, 3H), 2.61-2.53 (m, 4H), 1.21 (t, J = 7.5 Hz, 3H). |

| Examples | Structure | Name | MS: [(M + 1)]+ | 1H NMR |
|---|---|---|---|---|
| 277 | 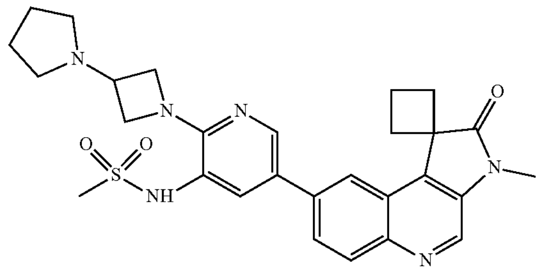 [SMILES: CN1C(=O)C2(CCC2)c2c1cnc1ccc(-c3cnc(N4CC(N5CCCC5)C4)c(NS(C)(=O)=O)c3)cc21] | N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)azetidin-1-yl)pyridin-3-yl)methanesulfonamide | 533.30 | 1H NMR (400 MHz, DMSO-$d_6$) δ 9.10 (s, 1H), 8.81 (s, 1H), 8.58 (d, J = 2.2 Hz, 1H), 8.33 (d, J = 2.0 Hz, 1H), 8.13 (d, J = 8.9 Hz, 1H), 7.96 (dd, J = 8.8, 1.9 Hz, 1H), 7.91 (d, J = 2.3 Hz, 1H), 4.28 (t, J = 7.9 Hz, 2H), 4.07 (dd, J = 8.9, 5.0 Hz, 2H), 3.38-3.33 (m, 1H), 3.31, 3.15 (s, 3H), 2.98-2.86 (m, 2H), 2.61-2.51 (m, 4H), 2.49-2.42 (m, 4H), 1.73 (s, 4H). |
| 278 | 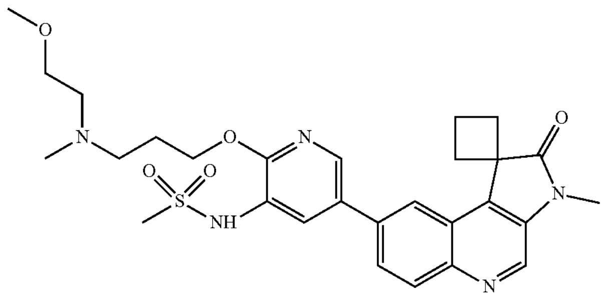 | N-(2-(2-Methoxyethyl)(methyl)amino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 554.20 | 1H NMR (400 MHz, CDCl$_3$) δ 8.66 (s, 1H), 8.40 (s, 1H), 8.33 (d, J = 2.1 Hz, 1H), 8.24-8.20 (m, 2H), 7.86-7.82 (m, 1H), 4.55 (t, J = 6.3 Hz, 2H), 3.59 (s, 2H), 3.38 (d, J = 6.6 Hz, 6H), 3.10 (s, 3H), 2.99-2.86 (m, 2H), 2.84-2.65 (m, 8H), 2.64-2.53 (m, 1H), 2.42 (s, 2H), 2.10 (s, 2H). |
| 279 | 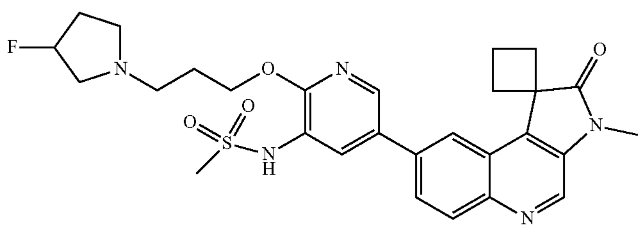 [SMILES: CN1C(=O)C2(CCC2)c2c1cnc1ccc(-c3cnc(OCCCN4CCC(F)C4)c(NS(C)(=O)=O)c3)cc21] | N-(2-(3-(3-Fluoropyrrolidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 554.30 | 1H NMR (400 MHz, CDCl$_3$) δ 8.66 (s, 1H), 8.40 (s, 1H), 8.32 (s, 1H), 8.23 (d, J = 8.9 Hz, 1H), 8.19 (s, 1H), 7.83 (d, J = 9.2 Hz, 1H), 5.42-5.16 (m, 1H), 4.61 (s, 2H), 3.39 (s, 3H), 3.16 (s, 4H), 3.08-2.85 (m, 5H), 2.85-2.52 (m, 6H), 2.50-2.07 (br, 4H). |
| 280 | 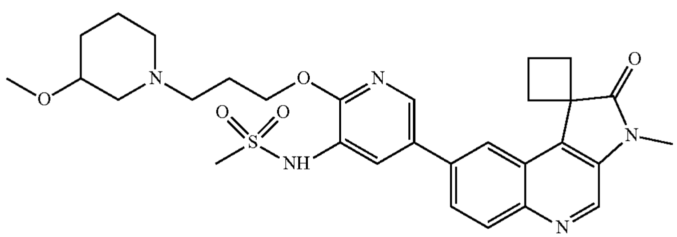 | N-(2-(3-(3-Methoxypiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 566.30 | 1HNMR(400 MHz, DMSO-$d_6$) δ 8.84 (s, 1H), 8.51 (s, 1H), 8.38(s, 1H), 8.17(d, J = 8.8 Hz, 1H), 8.11 (s, 1H), 7.98 (d, J = 9.1 Hz, 1H), 4.42 (t, J = 6.3 Hz, 2H), 3.31 (s, 3H), 3.25 (s, 3H), 3.24-3.16 (m, 1H), 3.12 (s, 3H), 3.00-2.86 (m, 3H), 2.68 (d, J = 10.0 Hz, 1H), 2.63-2.51 (m, 6H), 2.20-1.87 (m, 4H), 1.83 (t, J = 9.6 Hz, 1H), 1.69-1.61(m, 1H), 1.46-1.33 (m, 1H), 1.15-1.04 (m, 1H). |

| Examples | Structure | Name | MS: [(M + 1)]+ | 1H NMR |
|---|---|---|---|---|
| 281 | 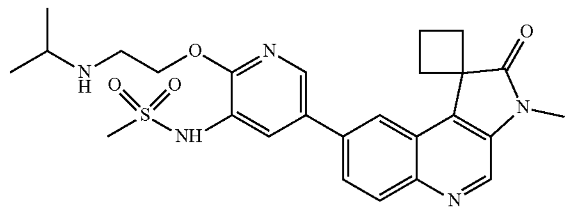 [SMILES: CC(C)NCCOc1ncc(-c2ccc3ncc4c(c3c2)C2(CCC2)C(=O)N4C)cc1NS(C)(=O)=O] | N-(2-(2-(Isopropylamino)ethoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 510.15 | 1H NMR (400 MHz, CD3OD) δ 8.72 (s, 1H), 8.50 (s, 1H), 8.20 (d, J = 6.0 Hz, 2H), 8.16 (d, J = 8.9 Hz, 1H), 7.98 (d, J = 8.9 Hz, 1H), 4.56 (t, J = 4.8 Hz, 2H), 3.38 (s, 3H), 3.26 (t, J = 5.1 Hz, 2H), 3.23-3.15 (m, 1H), 3.05-2.94 (m, 5H), 2.77-2.60 (m, 4H), 1.29 (d, J = 6.3 Hz, 6H). |
| 282 | 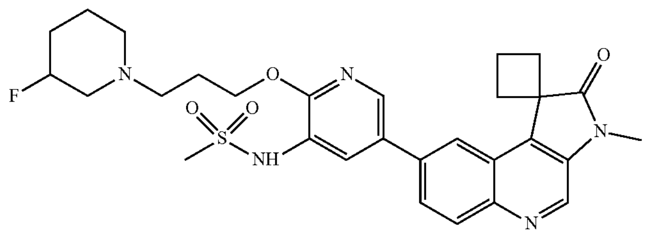 [SMILES: CN1C(=O)C2(CCC2)c2c1cnc1ccc(-c3cnc(OCCCN4CCCC(F)C4)c(NS(C)(=O)=O)c3)cc21] | N-(2-(3-(3-Fluoropiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 568.15 | 1H NMR (400 MHz, DMSO-d6) δ 9.39(s, 1H), 8.84(s, 1H), 8.52(s, 1H), 8.38(s, 1H), 8.17(d, J = 8.9 Hz, 1H), 8.12 (s, 1H), 7.99 (d, J = 9.0 Hz, 1H), 4.63 (d, J = 49.5 Hz, 1H), 4.47-4.38 (m, 2H), 3.12 (s, 3H), 3.32 (s, 3H), 2.97-2.87 (m, 2H), 2.80-2.66 (m, 1H), 2.62-2.52 (m, 5H), 2.48-2.41 (m, 2 H), 2.41-2.31 (m, 1H), 2.30-2.20 (m, 1H), 2.25 (s, 1H), 1.96 (t, J = 6.9 Hz, 2H), 1.90-1.77 (m, 1H), 1.71 (s, 1H), 1.59-1.41 (m, 2H). |
| 283 | 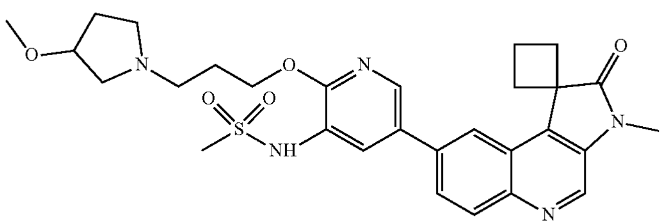 | N-(2-(3-Methoxypyrrolidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 566.30 | 1H NMR (400 MHz, DMSO-d6) δ 8.84 (s, 1H), 8.49 (s, 1H), 8.39 (d, J = 2.7 Hz, 1H), 8.17 (d, J = 9.1 Hz, 1H), 8.11 (s, 1H), 7.98 (d, J = 8.9 Hz, 1H), 4.43 (s, 2H), 3.88 (s, 1H), 3.31 (s, 3H), 3.17 (d, J = 4.0 Hz, 3H), 3.10 (s, 3H), 2.96-2.81 (m, 2H), 2.77-2.69 (m, 1H), 2.65-2.52 (m, 9H), 2.02-1.92 (m, 3H), 1.67 (s, 1H). |
| 284 | 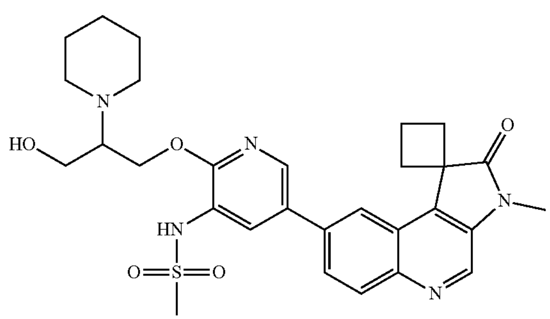 [SMILES: CN1C(=O)C2(CCC2)c2c1cnc1ccc(-c3cnc(OCC(CO)N4CCCCC4)c(NS(C)(=O)=O)c3)cc21] | N-(2-(3-Hydroxy-2-(piperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 566.20 | 1H NMR (400 MHz, DMSO-d6) δ 8.84 (s, 1H), 8.47 (s, 1H), 8.39 (d, J = 1.9 Hz, 1H), 8.19-8.14 (m, 2H), 7.99 (dd, J = 8.8, 1.9 Hz, 1H), 5.05 (s, 1H), 4.44 (dd, J = 10.8, 3.0 Hz, 1H), 4.18 (dd, J = 10.7, 7.0 Hz, 1H), 4.06 (s, 1H), 3.13 (s, 3H), 3.31 (s, 3H), 2.92 (q, J = 9.1 Hz, 2H), 2.63-2.52 (m, 4H), 2.49-2.32 (m, 6H), 1.53-1.46 (m, 4H), 1.42-1.33 (m, 2H). |

| Examples | Structure | Name | MS: [(M + 1)]+ | 1H NMR |
|---|---|---|---|---|
| 286 | 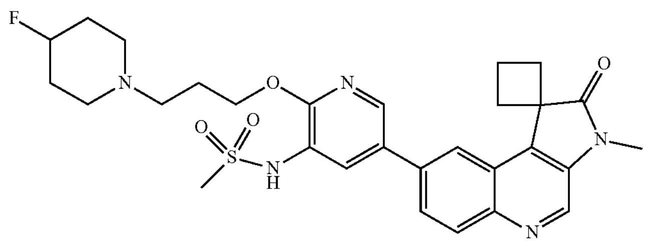 [SMILES: CN1C(=O)C2(CCC2)c2c1cnc1ccc(-c3cnc(OCCCN4CCC(F)CC4)c(NS(C)(=O)=O)c3)cc21] | N-(2-(3-(4-Fluoropiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 568.20 | 1H NMR (400 MHz, CD3OD) δ 8.74 (s, 1H), 8.50 (s, 1H), 8.42 (s, 1H), 8.24 (s, 1H), 8.18 (d, J = 9.0 Hz, 1H), 7.99 (d, J = 8.8 Hz, 1H), 4.69 (d, J = 48 Hz, 1 H), 4.55 (t, J = 6.4 Hz, 2H), 3.39 (s, 3H), 3.08 (s, 3H), 3.05-2.95 (m, 2H), 2.77-2.60 (m, 8H), 2.54 (s, 2H), 2.15-2.06 (m, 2H), 2.04-1.95 (m, 1H), 1.88 (br, 3H). |
| 287 | 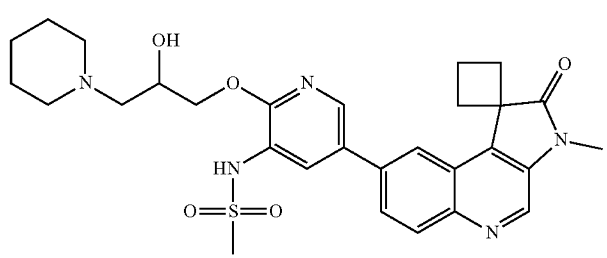 [SMILES: CN1C(=O)C2(CCC2)c2c1cnc1ccc(-c3cnc(OCC(O)CN4CCCCC4)c(NS(C)(=O)=O)c3)cc21] | N-(2-(2-Hydroxy-3-(piperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 566.25 | 1H NMR (400 MHz, DMSO-d6) δ 8.85 (d, J = 1.4 Hz, 1H), 8.49 (s, 1H), 8.40 (s, 1H), 8.18 (d, J = 10.5 Hz, 2H), 8.00 (d, J = 9.0 Hz, 1H), 5.06 (s, 1 H), 4.45 (d, J = 11.4 Hz, 1H), 4.23-4.13 (m, 1H), 4.07 (s, 1H), 3.32 (s, 3H), 3.14 (s, 3H), 2.97-2.87 (m, 2H), 2.62-2.52 (m, 4H), 2.49-2.31 (m, 6H), 1.54-1.47 (m, 4H), 1.38 (s, 2H). |
| 288 | 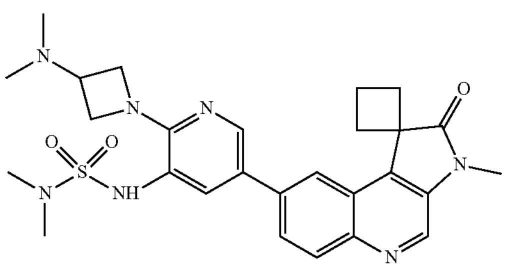 | 8'-(6-[3-(Dimethylamino)azetidin-1-yl]-5-[(dimethylsulfamoyl)amino]pyridin-3-yl}-3'-methyl-2',3'-dihydrospiro[cyclobutane-1,1'-pyrrolo[2,3-c]quinoline]-2'-one | 536.25 | 1H NMR (400 MHz, DMSO-d6) δ 9.11(s, 1H), 8.81(s, 1H), 8.55(s, 1H), 8.30(s, 1H), 8.14(d, J = 8.9 Hz, 1H), 7.92 (d, J = 9.0 Hz, 1H), 7.86 (s, 1H), 4.25 (t, J = 7.9 Hz, 2H), 3.99 (t, J = 7.2 Hz, 2H), 3.31 (s, 3H), 3.18-3.11 (m, 1H), 2.96-2.86 (m, 2H), 2.80 (s, 6H), 2.63-2.53 (m, 4H), 2.13 (s, 6H). |
| 290 | 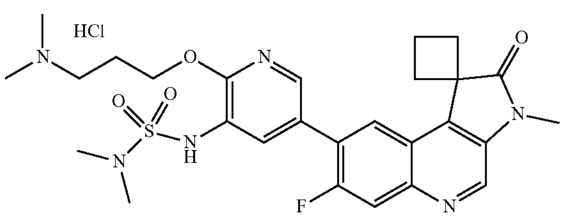 | 8'-{6-[3-(Dimethylamino)propoxy]-5-[(dimethylsulfamoyl)amino]pyridin-3-yl}-7'-fluoro-3'-methyl-2',3'-dihydrospiro[cyclobutane-1,1'-pyrrolo[2,3-c]quinoline]-2'-one hydrochloride | 557.25 | 1H NMR (400 MHz, CD3OD) δ 8.85 (s, 1H), 8.44 (d, J = 8.0 Hz, 1H), 8.33 (s, 1H), 8.12 (s, 1H), 7.91 (d, J = 11.7 Hz, 1H), 4.64 (t, J = 5.8 Hz, 2H), 3.49-3.42 (m, 2H), 3.39 (s, 3H), 3.01-2.92 (m, 8H), 2.87 (s, 6H), 2.80-2.68 (m, 2H), 2.68-2.52 (m, 2H), 2.33 (p, J = 6.2 Hz, 2H). |

-continued

| Examples | Structure | Name | MS: [M + 1]+ | 1H NMR |
|---|---|---|---|---|
| 291 | 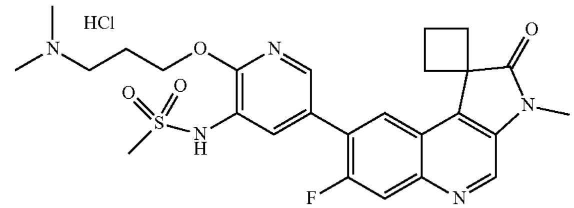 | N-(2-(3-(Dimethylamino)propoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | 528.30 | 1H NMR (400 MHz, CD3OD) δ 8.78 (s, 1H), 8.44-8.35 (m, 2H), 8.15 (s, 1H), 7.87 (d, J = 11.9 Hz, 1H), 4.64 (t, J = 5.9 Hz, 2H), 3.41 (t, J = 7.7 Hz, 2H), 3.38 (s, 3H), 3.12 (s, 3H), 3.00-2.91 (m, 8H), 2.75-2.52 (m, 4H), 2.32 (p, J = 6.3 Hz, 2H). |
| 292 | 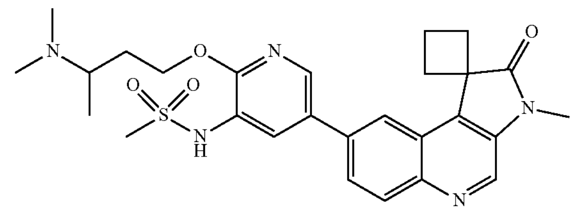 | N-(2-(3-(Dimethylamino)butoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 524.20 | 1H NMR (400 MHz, DMSO-d6) δ 8.84 (s, 1H), 8.37 (d, J = 10.8 Hz, 2H), 8.16 (d, J = 8.8 Hz, 1H), 8.06 (s, 1H), 7.98 (d, J = 9.0 Hz, 1H), 4.48-4.35 (m, 2H), 3.31 (s, 3H), 3.11-3.00 (m, 4H), 2.96-2.87 (m, 2H), 2.64-2.51 (m, 4H), 2.35 (s, 6H), 2.07-1.96 (m, 1H), 1.88-1.79 (m, 1H), 1.03 (d, J = 6.6 Hz, 3H). |
| 293 | 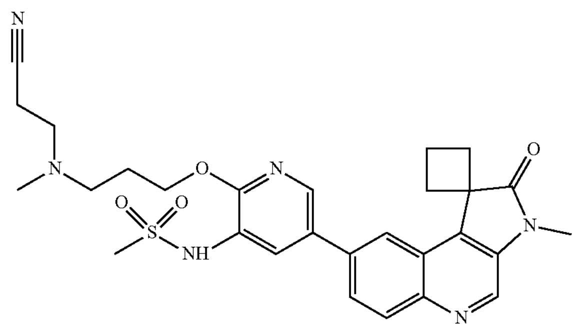 | N-(2-(3-((2-Cyanoethyl)(methyl)amino)propoxy)-5-(3'-methyl-2'-oxo-2',3'-dihydrospiro[cyclobutane-1,1'-pyrrolo[2,3-c]pyridin-3-yl)methanesulfonamide | 549.20 | 1H NMR (400 MHz, DMSO-d6) δ 9.01 (s, 1H), 8.81 (s, 1H), 8.28 (d, J = 2.0 Hz, 1H), 8.17 (d, J = 2.5 Hz, 1H), 8.13 (d, J = 8.9 Hz, 1H), 7.97-7.91 (m, 2H), 4.13 (t, J = 7.4 Hz, 2H), 3.31 (s, 3H), 3.17 (s, 3H), 2.89 (t, J = 9.1 Hz, 2H), 2.69-2.52 (m, 8H), 2.45 (t, J = 6.7 Hz, 2H), 2.22 (s, 3H), 1.92 (p, J = 7.0 Hz, 2H). |

| Examples | Structure | Name | MS: [(M + 1)]+ | 1H NMR |
|---|---|---|---|---|
| 294 | 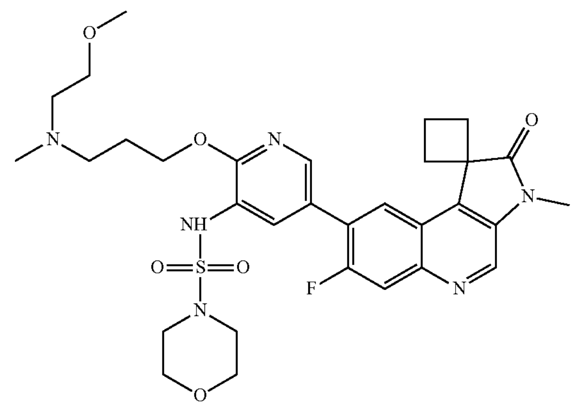 | N-(5-(7'-Fluoro-3'-methyl-2'-oxo-2',3'-dihydrospiro[cyclobutane-1,1'-pyrrolo[2,3-c]quinolin]-8'-yl)-2-(3-((2-methoxyethyl)(methyl)amino)propoxy)pyridin-3-yl)morpholine-4-sulfonamide | 643.25 | 1H NMR (400 MHz, CD3OD) δ 8.78 (s, 1H), 8.40 (d, J = 8.2 Hz, 1H), 8.29 (t, J = 2.0 Hz, 1H), 8.16 (t, J = 1.9 Hz, 1H), 7.88 (d, J = 12.0 Hz, 1H), 4.62 (t, J = 6.0 Hz, 2H), 3.72-3.65 (m, 6H) δ .39 (d, J = 5.6 Hz, 6H), 3.29-3.19 (m, 8H), 3.01-2.89 (m, 2H), 2.80 (s, 3H), 2.77-2.66 (m, 2H), 2.66-2.50 (m, 2H), 2.27 (p, J = 6.2 Hz, 2H). |
| 297 | 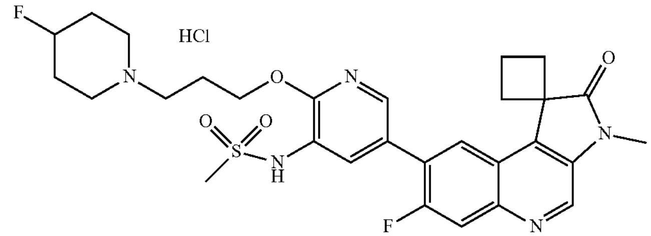 [SMILES: CN1C(=O)C2(CCC2)c2c1cnc1cc(F)c(-c3cnc(OCCCN4CCC(F)CC4)c(NS(C)(=O)=O)c3)cc21 ; Cl] | N-(5-(7'-Fluoro-3'-methyl-2'-oxo-2',3'-dihydrospiro[cyclobutane-1,1'-pyrrolo[2,3-c]quinolin]-8'-yl)-2-(3-(4-fluoropiperidin-1-yl)propoxy)pyridin-3-yl)methanesulfonamide hydrochloride | 568.20 | 1H NMR (400 MHz, CD3OD) δ 8.74 (s, 1H), 8.50 (s, 1H), 8.42 (s, 1H), 8.24 (s, 1H), 8.18 (d, J = 9.0 Hz, 1H), 7.99 (d, J = 8.8 Hz, 1H), 4.69 (d, J = 48 Hz, 1H ), 4.55 (t, J = 6.4 Hz, 2H), 3.39 (s, 3H), 3.08 (s, 3H), 3.05-2.95 (m, 2H), 2.77-2.60 (m, 8H), 2.54 (s, 2H), 2.15-2.06 (m, 2H), 2.04-1.95 (m, 1H), 1.88 (br, 3H). |
| 298 | 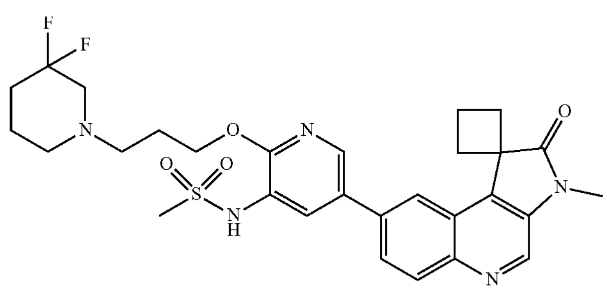 [SMILES: CN1C(=O)C2(CCC2)c2c1cnc1ccc(-c3cnc(OCCCN4CCCC(F)(F)C4)c(NS(C)(=O)=O)c3)cc21] | N-(2-(3-(3,3-Difluoropiperidin-1-yl)propoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide | 586.20 | 1H NMR (400 MHz, CD3OD) δ 8.72 (s, 1H), 8.43 (s, 1H), 8.14 (d, J = 8.9 Hz, 1H), 8.10 (s, 1H), 8.00 (s, 1H), 7.94 (dd, J = 8.9, 2.0 Hz, 1H), 4.23 (t, J = 6.8 Hz, 2H), 3.38(s, 3H), 3.11 (s, 3H), 3.00 (q, J = 9.4, 8.6 Hz, 2H), 2.75-2.58 (m, 6H), 2.50 (t, J = 6.8 Hz, 2H), 2.47-2.40 (m, 2H), 2.08 (p, J = 6.9 Hz, 2H), 1.92-1.79 (m, 2H), 1.75-1.67 (m, 2H). |

-continued

| Examples | Structure | Name | MS: [(M + 1)]+ | ¹H NMR |
|---|---|---|---|---|
| 299 | 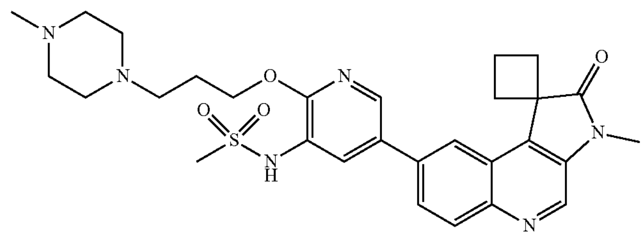 | N-(5-(3'-Methyl-2'-oxo-2',3'-dihydrospiro[cyclobutane-1,1'-pyrrolo[2,3-c]quinolin]-8'-yl)-2-(3-(4-methylpiperazin-1-yl)propoxy)pyridin-3-yl)methanesulfonamide | 565.25 | ¹H NMR (400 MHz, DMSO-d₆) δ 8.84(s, 1H), 8.49(s, 1H), 8.38(s, 1H), 8.16(d, J = 8.9 Hz, 1H), 8.10 (s, 1H), 7.98 (d, J = 8.8 Hz, 1H), 4.41 (t, J = 6.5 Hz, 2H), 3.31 (s, 3H), 3.10 (s, 3H), 2.97-2.87 (m, 2H), 2.63-2.44 (m, 8H), 2.44-2.20 (m, 6H), 2.15 (s, 3H), 2.00-1.90 (m, 2H). |
| 303 | 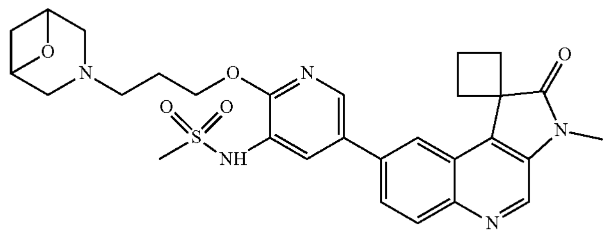 [SMILES: CN1C(=O)C2(CCC2)c2c1cnc1ccc(-c3cnc(OCCCN4CC5CC(C4)O5)c(NS(C)(=O)=O)c3)cc21] | N-(2-(3-(6-Oxa-3-azabicyclo[3.1.1]heptan-3-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | 564.30 | ¹H NMR (400 MHz, DMSO-d₆) δ 9.03 (s, 1H), 8.81 (s, 1H), 8.27 (d, J = 2.0 Hz, 1H), 8.19 (d, J = 2.4 Hz, 1H), 8.13 (d, J = 8.9 Hz, 1H), 7.98-7.90 (m, 2H), 4.41 (d, J = 6.1 Hz, 2H), 4.17 (t, J = 7.2 Hz, 2H), 3.30 (s, 3H), 3.17 (s, 3H), 3.11-3.03 (m, 2H), 2.93-2.79 (m, 3H), 2.66-2.51 (m, 8H), 2.21 (d, J = 7.7 Hz, 1H), 1.99 (p, J = 7.1 Hz, 2H). |
| 304 | 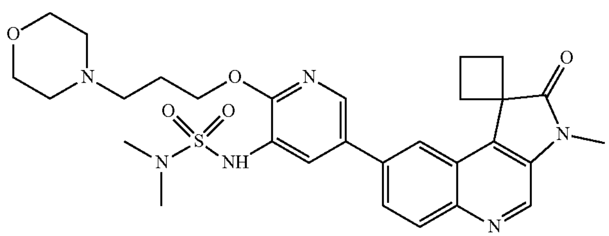 [SMILES: CN1C(=O)C2(CCC2)c2c1cnc1ccc(-c3cnc(OCCCN4CCOCC4)c(NS(=O)(=O)N(C)C)c3)cc21] | 8'-[5-[(Dimethylsulfamoyl)amino]-6-[3-(morpholin-4-yl)propoxy]pyridin-3-yl]-3'-methyl-2',3'-dihydrospiro[cyclobutane-1,1'-pyrrolo[2,3-c]quinoline]-2'-one | 581.30 | ¹H NMR (400 MHz, DMSO-d₆) δ 8.84 (s, 1H), 8.47 (s, 1H), 8.37 (d, J = 1.9 Hz, 1H), 8.17 (d, J = 8.8 Hz, 1H), 8.14 (d, J = 2.3 Hz, 1H), 7.96 (dd, J = 8.8, 1.9 Hz, 1H), 4.44 (t, J = 6.4 Hz, 2H), 3.59 (t, J = 4.6 Hz, 4H), 3.31 (s, 3H), 2.97-2.87 (m, 2H), 2.73 (s, 6H), 2.62-2.52 (m, 6H), 2.39 (s, 4H), 1.98 (p, J = 6.7 Hz, 2H). |
| 305 | 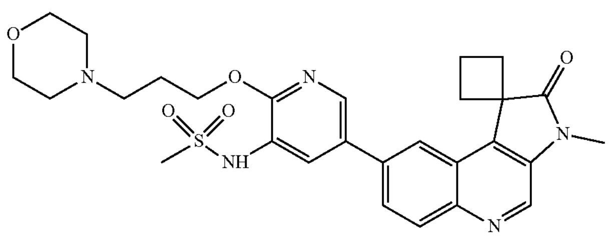 [SMILES: CN1C(=O)C2(CCC2)c2c1cnc1ccc(-c3cnc(OCCCN4CCOCC4)c(NS(C)(=O)=O)c3)cc21] | N-(5-(3'-Methyl-2'-oxo-2',3'-dihydrospiro[cyclobutane-1,1'-pyrrolo[2,3-c]quinolin]-8'-yl)-2-(3-morpholinopropoxy)pyridin-3-yl)methanesulfonamide | 552.30 | ¹H NMR (400 MHz, DMSO-d₆) δ 8.84 (s, 1H), 8.51 (d, J = 2.3 Hz, 1H), 8.39 (d, J = 2.0 Hz, 1H), 8.16 (d, J = 8.9 Hz, 1H), 8.12 (d, J = 2.3 Hz, 1H), 7.98 (dd, J = 8.9, 2.0 Hz, 1H), 4.44 (t, J = 6.4 Hz, 2H), 3.58 (t, J = 4.6 Hz, 4H), 3.30 (s, 3H), 3.12 (s, 3H), 2.97-2.85 (m, 2H), 2.63-2.53 (m, 6H), 2.39 (s, 4H), 1.96 (p, J = 6.6 Hz, 2H). |

-continued

| Examples | Structure | Name | MS: [(M + 1)]+ | 1H NMR |
|---|---|---|---|---|
| 306 | 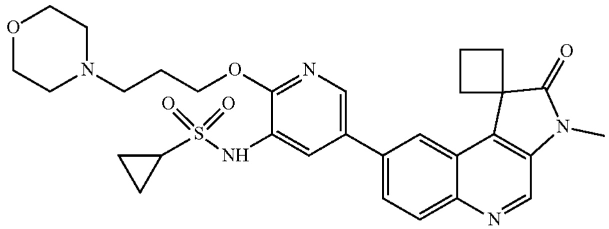 [SMILES: CN1C(=O)C2(CCC2)c2c1cnc1ccc(-c3cnc(OCCCN4CCOCC4)c(NS(=O)(=O)C4CC4)c3)cc21] | N-(5-(3'-Methyl-2'-oxo-2',3'-dihydrospiro[cyclobutane-1,1'-pyrrolo[2,3-c]quinolin]-8'-yl)-2-(3-morpholinopropoxy)pyridin-3-yl)cyclopropanesulfonamide | 578.20 | 1H NMR (400 MHz, DMSO-$d_6$) δ 8.84 (s, 1H), 8.52 (d, J = 2.0 Hz, 1H), 8.38 (d, J = 1.6 Hz, 1H), 8.17 (d, J = 8.9 Hz, 1H), 8.14 (d, J = 2.2 Hz, 1H), 7.98 (d, J = 8.8 Hz, 1H), 4.43 (t, J = 6.5 Hz, 2H), 3.59 (t, J = 4.8 Hz, 4H), 3.31 (s, 3H), 2.97-2.88 (m, 2H), 2.82-2.74 (m, 1H), 2.63-2.52 (m, 6H ) 2.41-2.36 (m, 4H), 2.01-1.93 (m, 2H), 0.96 (d, J = 6.3 Hz, 4H). |
| 309 | 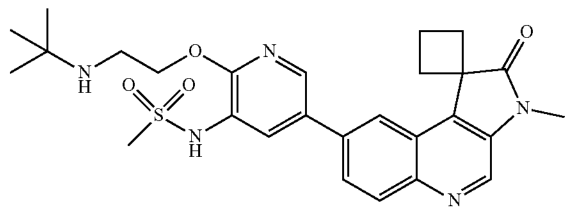 [SMILES: CN1C(=O)C2(CCC2)c2c1cnc1ccc(-c3cnc(OCCNC(C)(C)C)c(NS(C)(=O)=O)c3)cc21] | N-(2-(2-(tert-Butylamino)ethoxy)-5-(3'-methyl-2'-oxo-2',3'-dihydrospirocyclobulane-1,1'-pyrrolo[2,3-c]quinolin]-8'-yl)pyridin-3-yl)methanesulfonamide | 524.35 | 1H NMR (400 MHz, DMSO-$d_6$) δ 8.84 (s, 1H), 8.43-8.37 (m, 2H), 8.16 (d, J = 8.9 Hz, 1H), 8.09 (d, J = 2.2 Hz, 1H), 7.98 (d, J = 8.6 Hz, 1H), 4.42 (t, J = 5.5 Hz, 2H), 3.04 (s, 3H), 3.31 (s, 3H), 3.00-2.86 (m, 4H), 2.62-2.53 (m, 4H), 1.13 (s, 9H). |
| 311 | 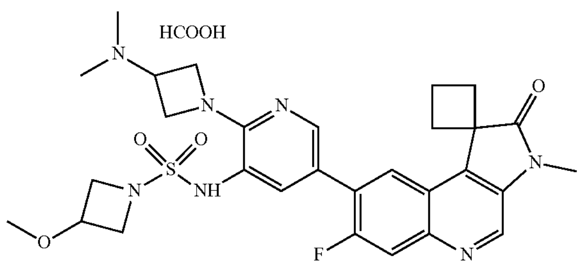 | N-(2-(3-(Dimethylamino)azetidin-1-yl)-5-(7'-fluoro-3'-methyl-2'-oxo-2',3'-dihydrospiro[cyclobulane-1,1'-pyrrolo[2,3-c]quinolin]-8'-yl)pyridin-3-yl)-3-methoxyazetidine-1-sulfonamide formate | 596.35 | 1H NMR (400 MHz, CD$_3$OD) δ 8.76 (s, 1H), 8.43-8.34 (m, 2H), 8.01 (d, J = 1.8 Hz, 1H), 7.85 (d, J = 12.1 Hz, 1H), 4.50-4.41 (m, 2H), 4.23-4.15 (m, 3H), 4.11-4.03 (m, 2H), 3.86 (dd, J = 8.7, 4.9 Hz, 2H), 3.58-3.51 (m, 1H), 3.38 (s, 3H), 3.24 (s, 3H), 3.01-2.92 (m, 2H), 2.78-2.53 (m, 4H), 2.46 (s, 6H). |
| 312 | 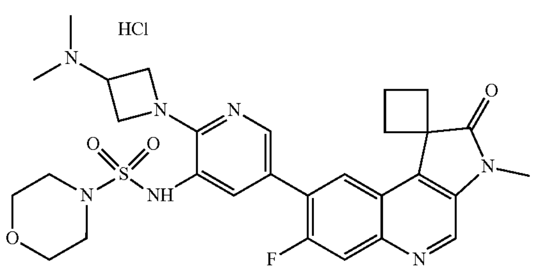 [SMILES: CN1C(=O)C2(CCC2)c2c1cnc1cc(F)c(-c3cnc(N4CC(N(C)C)C4)c(NS(=O)(=O)N4CCOCC4)c3)cc21 ; Cl] | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)morpholine-4-sulfonamide hydrochloride | 596.35 | 1H NMR (400 MHz, CD$_3$OD) δ 8.84 (s, 1H), 8.48 (s, 1H), 8.41 (d, J = 8.2 Hz, 1H), 7.98 (s, 1H), 7.91 (d, J = 11.8 Hz, 1H), 4.69-4.60 (m, 2H), 4.44 (dd, J = 10.4, 5.0 Hz, 2H), 4.30-4.23 (m, 1H), 3.72 (t, J = 5.1 Hz, 4H), 3.39 (s, 3H), 3.29-3.27 (m, 4H), 3.02-2.92 (m, 8H), 2.75-2.67 (m, 2H), 2.68-2.50 (m, 2H). |

| Examples | Structure | Name | MS: [(M + 1)]+ | 1H NMR |
|---|---|---|---|---|
| 313 | 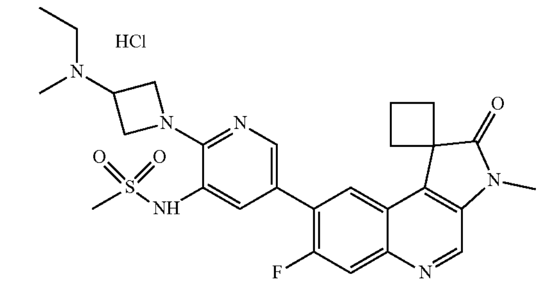 | N-(2-(3-(Ethyl(methyl)amino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | 539.30 | 1H NMR (400 MHz, CD3OD) δ 8.85 (s, 1H), 8.52 (s, 1H), 8.44 (d, J = 8.1 Hz, 1H), 7.99 (s, 1H), 7.92 (d, J = 11.8 Hz, 1H), 4.73-4.63 (m, 2H), 4.50 (dd, J = 10.5, 5.0 Hz, 2H), 4.40-4.29 (m, 1H), 3.41 (s, 4H), 3.17 (s, 4H), 3.08-2.93 (m, 5H), 2.78-2.53 (m, 4H), 1.43 (t, J = 7.2 Hz, 3H). |
| 314 | 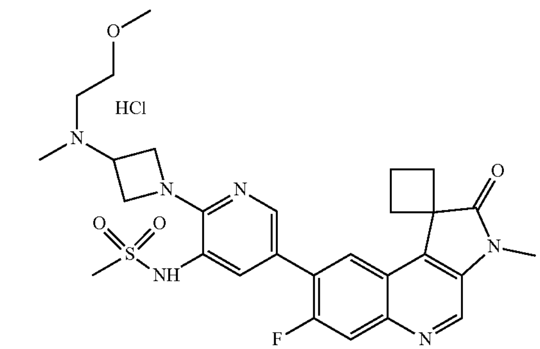 | N-(5-(7'-Fluoro-3'-methyl-2'-oxo-2',3'-dihydrospiro[cyclobutane-1,1'-pyrrolo[2,3-c]quinolin]-8'-yl)-2-(3((2-methoxyethyl)(methyl)amino)azetidin-1-yl)pyridin-3-yl)methanesulfonamide hydrochloride | 569.30 | 1H NMR (400 MHz, CD3OD) δ 8.77 (s, 1H), 8.49 (s, 1H), 8.38 (d, J = 8.2 Hz, 1H), 7.94 (s, 1H), 7.86 (d, J = 12.0 Hz, 1H), 4.64 (t, J = 9.1 Hz, 2H), 4.45 (dd, J = 10.4, 4.9 Hz, 2H), 4.33-4.27 (m, 1H), 3.74 (t, J = 5.8 Hz, 2H), 3.46 (s, 4H), 3.38 (s, 4H), 3.14 (s, 3H), 3.03-2.93 (m, 5H), 2.75-2.58 (m, 3H), 2.56-2.46 (m, 1H). |
| 315 | 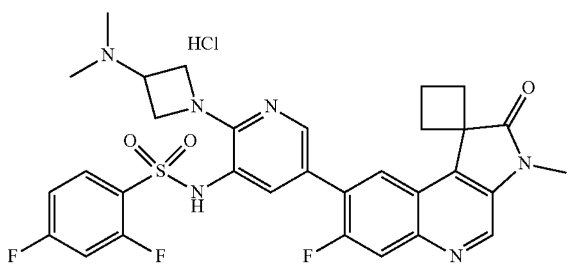 [SMILES: CN1C(=O)C2(CCC2)c2c1cnc1cc(F)c(-c3cnc(N4CC(N(C)C)C4)c(NS(=O)(=O)c4ccc(F)cc4F)c3)cc21 ; Cl] | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)-2,4-difluorobenzenesulfonamide hydrochloride | 623.35 | 1H NMR (400 MHz, CD3OD) δ 8.79 (s, 1H), 8.44 (s, 1H), 8.23 (d, J = 8.1 Hz, 1H), 7.90-7.76 (m, 1H), 7.77 (d, J = 11.9 Hz, 1H), 7.33-7.27 (m, 1H), 7.25 (s, 1H), 7.16-7.08 (m, 1H), 4.73-4.64 (m, 2H), 4.50 (dd, J = 10.5, 4.7 Hz, 2H), 4.34-4.23 (m, 1H), 3.37 (s, 3H), 3.01 (s, 6H), 2.89-2.81 (m, 2H), 2.75-2.56 (m, 3H), 2.46-2.36 (m, 1H). |

| Examples | Structure | Name | MS: [(M + 1)]+ | 1H NMR |
|---|---|---|---|---|
| 316 | 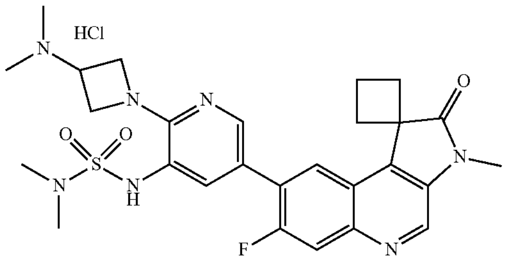 | 8'-{6-[3-(Dimethylamino)azetidin-1-yl]-5-[(dimethylsulfamoyl) amino]pyridin-3-yl]-7'-fluoro-3'-methyl-2',3'-dihydrospiro[cyclobutane-1,1'-pyrrolo[2,3-c]quinoline]-2'-one hydrochloride | 554.30 | 1H NMR (400 MHz, CD3OD) δ 8.79 (s, 1H), 8.46 (t, J = 1.9 Hz, 1H), 8.38 (d, J = 8.2 Hz, 1H), 7.94-7.84 (m, 2H), 4.69-4.59 (m, 2H), 4.49-4.40 (m, 2H), 1.29-4.22 (m, 1H), 3.38 (s, 3H), 2.99 (s, 6H), 2.97-2.91 (m, 2H), 2.90 (s, 6H), 2.76-2.57 (m, 3H), 2.56-2.46 (m, 1H). |
| 317 | 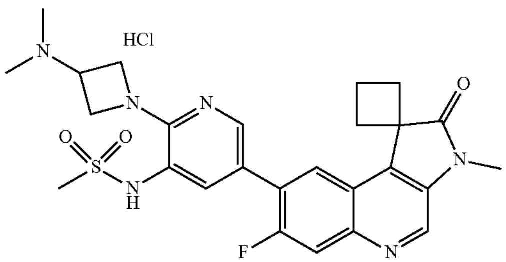 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | 525.15 | 1H NMR (400 MHz, CD3OD) δ 8.77 (s, 1H), 8.48 (s, 1H), 8.38 (d, J = 8.2 Hz, 1H), 7.94 (s, 1H), 7.86 (d, J = 12.0 Hz, 1H), 4.64-4.56 (m, 2H), 4.39 (dd, J = 10.4, 4.8 Hz, 2H), 4.11-4.04 (m, 1H), 3.38 (s, 3H), 3.14 (s, 3H), 3.02-2.93 (m, 2H), 2.86 (s, 6H), 2.74-2.60 (m, 3H), 2.55-2.45 (m, 1H). |
| 318 | 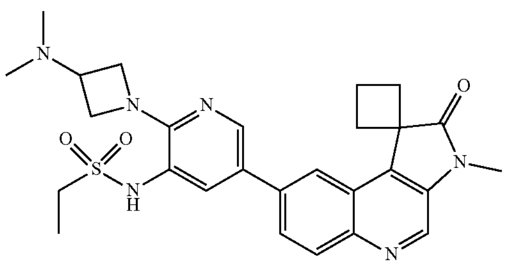 | N-(2-(3-(Dimethylamino)azetidin-1-yl)-5-(3'-methyl-2'-oxo-2',3'-dihydrospiro [cyclobutane-1,1'-pyrrolo[2,3-c]quinolin]-8'-yl)pyridin-3-yl)ethanesulfonamide | 521.35 | 1H NMR (400 MHz, DMSO-d6) δ 9.09(s, 1H), 8.81(s, 1H), 8.58(s, 1H), 8.32(s, 1H), 8.13(d, J = 8.8 Hz, 1H), 7.95 (d, J = 9.0 Hz, 1H), 7.82 (s, 1H), 4.26 (L J = 7.9 Hz, 2H), 4.04-3.96 (m, 2H), 3.31 (s, 3H), 3.26 (q, J = 7.4 Hz, 2H), 3.18-3.10 (m, 1H), 2.99-2.90 (m, 2H), 2.61-2.45 (m, 4H), 2.13 (s, 6H), 1.32 (t, J = 7.3 Hz, 3H). |

| Examples | Structure | Name | MS: [(M + 1)]+ | 1H NMR |
|---|---|---|---|---|
| 319 | 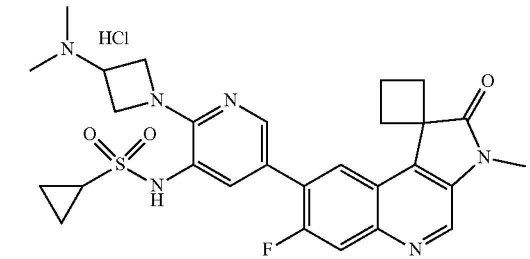 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)cyclopropanesulfonamide hydrochloride | 551.20 | 1H NMR (400 MHz, CD3OD) δ 8.77 (s, 1H), 8.48 (t, J = 1.6 Hz, 1H), 8.37 (d, J = 8.2 Hz, 1H), 7.98 (t, J = 2.0 Hz, 1H), 7.86 (d, J = 12.1 Hz, 1H), 4.64 (dd, J = 10.5, 7.4 Hz, 2H), 4.44 (dd, J = 10.6, 4.8 Hz, 2H), 4.22-4.14 (m, 1H), 3.38 (s, 3H), 3.08-2.91 (m, 8H), 2.80-2.59 (m, 4H), 2.53-2.45 (m, 1H), 1.10 (d, J = 6.3 Hz, 4H). |
| 320 | 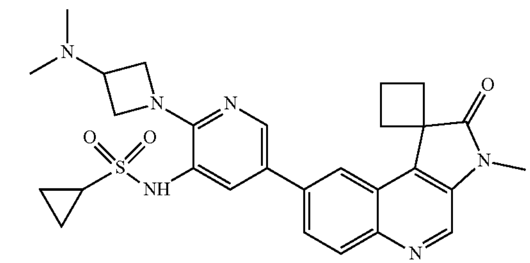 | N-(2-(3-(Dimethylamino)azetidin-1-yl)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide | 533.20 | 1H NMR (400 MHz, DMSO-d6) δ 9.14 (s, 1H), 8.81 (s, 1H), 8.60 (d, J = 2.2 Hz, 1H), 8.32 (d, J = 1.9 Hz, 1H), 8.13 (d, J = 8.9 Hz, 1H), 7.98-7.90 (m, 2H), 4.26 (t, J = 7.9 Hz, 2H), 4.03-3.94 (m, 2H), 3.31 (s, 3H), 3.17-3.08 (m, 1H), 2.99-2.81 (m, 3H), 2.62-2.52 (m, 4H), 2.13 (s, 6H), 1.05-0.99 (m, 2H), 0.98-0.90 (m, 2H). |
| 321 | 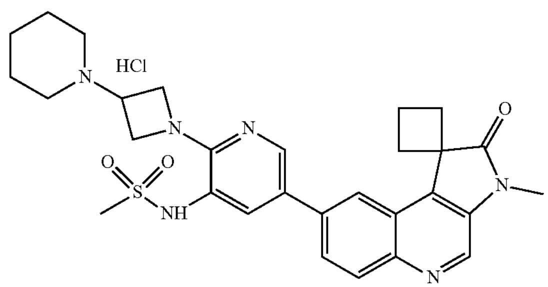 [SMILES: CN1C(=O)C2(CCC2)c2c1cnc1ccc(-c3cnc(N4CC(N5CCCCC5)C4)c(NS(C)(=O)=O)c3)cc21 ; Cl] | N-(5-(3'-Methyl-2'-oxo-2',3'-dihydrospiro[cyclobutane-1,1'-pyrrolo[2,3-c]quinolin]-8'-yl)-2-(3-(piperidin-1-yl)azetidin-1-yl)pyridin-3-yl)methanesulfonamide hydrochloride | 547.30 | 1H NMR (400 MHz, CD3OD) δ 8.84 (s, 1H), 8.61 (d, J = 2.3 Hz, 1H), 8.52 (d, J = 1.9 Hz, 1H), 8.22 (d, J = 9.0 Hz, 1H), 8.12-8.06 (m, 1H), 8.04 (d, J = 2.2 Hz, 1H), 4.63 (dd, J = 10.2, 7.5 Hz, 2H), 4.47 (dd, J = 10.3, 5.2 Hz, 2H), 4.25-4.18 (m, 1H), 3.62 (d, J = 12.3 Hz, 2H), 3.39 (s, 3H), 3.18 (s, 3H), 3.10-2.90 (m, 4H), 2.80-2.56 (m, 4H), 2.10-1.99 (m, 2H), 1.95-1.71 (m, 3H), 1.65-1.51 (m, 1H). |

| Examples | Structure | Name | MS: [(M + 1)]+ | 1H NMR |
|---|---|---|---|---|
| 322 | 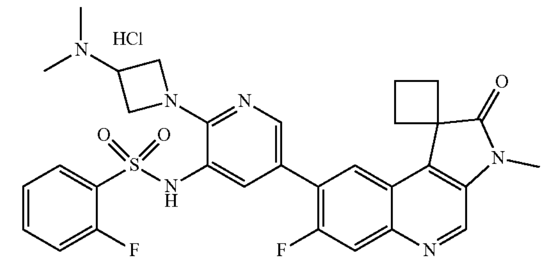 [SMILES: CN1C(=O)C2(CCC2)c2c1cnc1cc(F)c(-c3cnc(N4CC(N(C)C)C4)c(NS(=O)(=O)c4ccccc4F)c3)cc21 ; Cl] | N-(2-(3-(Dimethylamino)azetidin-1-yl)-5-(7-fluoro-3'-methyl-2'-oxo-2',3'-dihydrospiro[cyclobutane-1,1'-pyrrolo[2,3-c]quinolin]-8'-yl)pyridin-3-yl)-2-fluorobenzenesulfonamide hydrochloride | 605.30 | 1H NMR (400 MHz, CD3OD) δ 8.73 (s, 1H), 8.37 (s, 1H), 8.20 (d, J = 8.2 Hz, 1H), 7.80 (t, J = 7.6 Hz, 1H), 7.74 (d, J = 12.1 Hz, 1H), 7.67 (d, J = 6.4 Hz, 1H), 7.41-7.27 (m, 3H), 4.54-4.45 (m, 2H), 4.23 (dd, J = 9.7, 5.2 Hz, 2H), 3.68-3.60 (m, 1H), 3.36 (s, 3H), 2.91-2.81 (m, 2H), 2.72-2.57 (m, 3H), 2.53 (s, 6H), 2.50-2.39 (m, 1H). |
| 323 | 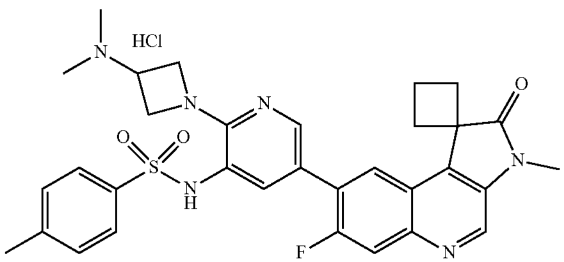 | N-(2-(3-(Dimethylamino)azetidin-1-yl)-5-(7-fluoro-3'-methyl-2'-oxo-2',3'-dihydrospiro[cyclobutane-1,1'-pyrrolo[2,3-c]quinolin]-8'-yl)pyridin-3-yl)-4-methylbenzenesulfonamide hydrochloride | 601.30 | 1H NMR (400 MHz, CD3OD) δ 8.83 (s, 1H), 8.44 (t, J = 1.7 Hz, 1H), 8.24 (d, J = 8.0 Hz, 1H), 7.81 (d, J = 11.8 Hz, 1H), 7.70 (d, J = 8.3 Hz, 2H), 7.37 (d, J = 8.2 Hz, 2H), 7.12 (t, J = 1.9 Hz, 1H), 4.66 (dd, J = 10.5, 7.5 Hz, 2H), 4.46 (dd, J = 10.6, 4.7 Hz, 2H), 4.29-4.21 (m, 1H), 3.37 (s, 3H), 2.99 (s, 6H), 2.86 (q, J = 10.4, 9.6 Hz, 2H), 2.76-2.57 (m, 3H), 2.46-2.38 (m, 1H), 2.36 (s, 3H). |
| 324 | 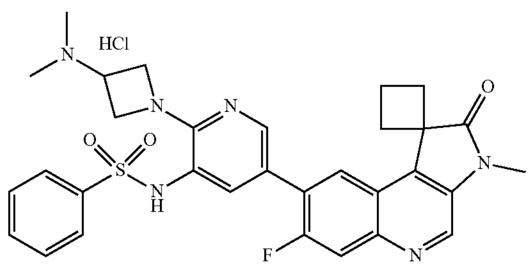 [SMILES: CN1C(=O)C2(CCC2)c2c1cnc1cc(F)c(-c3cnc(N4CC(N(C)C)C4)c(NS(=O)(=O)c4ccccc4)c3)cc21 ; Cl] | N-(2-(3-(Dimethylamino)azetidin-1-yl)-5-(7-fluoro-3'-methyl-2'-oxo-2',3'-dihydrospiro[cyclobutane-1,1'-pyrrolo[2,3-c]quinolin]-8'-yl)pyridin-3-yl)benzenesulfonamide hydrochloride | 587.35 | 1H NMR (400 MHz, CD3OD) δ 8.75 (s, 1H), 8.46-8.40 (m, 1H), 8.17 (d, J = 8.2 Hz, 1H), 7.86-7.78 (m, 2H), 7.76 (d, J = 12.0 Hz, 1H), 7.67-7.58 (m, 1H), 7.56 (dd, J = 8.3, 6.7 Hz, 2H), 7.07 (t, J = 2.0 Hz, 1H), 4.65 (dd, J = 10.5, 7.4 Hz, 2H), 4.45 (dd, J = 10.6, 4.7 Hz, 2H), 4.23-4.20 (m, 1H), 3.36 (s, 3H), 2.99 (s, 6H), 2.90-2.77 (m, 2H), 2.74-2.54 (m, 3H), 2.46-2.36 (m, 1H). |

| Examples | Structure | Name | MS: [(M + 1)]+ | 1H NMR |
|---|---|---|---|---|
| 325 | (structure with HCOOH salt) | N-(5-(2,3'-Dimethyl-2'-oxo-2',3'-dihydrospiro[cyclobutane-1,1'-pyrrolo[2,3-c]quinolin]-8'-yl)-2-(3-(dimethylamino)azetidin-1-yl)pyridin-3-yl)methanesulfonamideformate | 521.30 | 1H NMR (400 MHz, CD3OD) δ 8.73 (d, J = 16.8 Hz, 1H), 8.49 (t, J = 2.4 Hz, 1H), 8.41 (d, J = 2.1 Hz, 1H), 8.15 (dd, J = 8.9, 6.2 Hz, 1H), 8.01-7.91 (m, 2H), 4.45-4.36 (m, 2H), 4.12 (dd, J = 9.0, 5.5 Hz, 2H), 3.38 (d, J = 2.7 Hz, 3H), 3.35-3.32 (m, 2H), 3.13 (d, J = 3.6 Hz, 3H), 2.87-2.76 (m, 1H), 2.74-2.44 (m, 3H), 2.30 (s, 6H), 1.05 (d, J = 6.8 Hz, 0.5H), 0.91 (d, J = 7.3 Hz, 2.5H). |
| 326 | (structure with HCl salt) | N-(2-(3-(Ethyl(methyl)amino)azetidin-1-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide hydrochloride | 521.30 | 1H NMR (400 MHz, CD3OD) δ 8.96 (s, 1H), 8.65 (d, J = 2.2 Hz, 1H), 8.60 (d, J = 1.9 Hz, 1H), 8.29 (d, J = 9.0 Hz, 1H), 8.22 (dd, J = 9.0, 1.8 Hz, 1H), 8.10 (d, J = 2.3 Hz, 1H), 4.75-4.64 (m, 2H), 4.51 (dd, J = 10.4, 5.1 Hz, 2H), 4.41-4.27 (m, 1H), 3.43 (s, 4H), 3.21 (s, 4H), 3.11-3.03 (m, 2H), 2.97 (s, 3H), 2.86-2.76 (m, 2H), 2.74-2.59 (m, 2H), 1.43 (t, J = 7.3 Hz, 3H). |
| 327 | (structure with HCl salt) | N-(5-(4'-Amino-3'-methyl-2'-oxo-2',3'-dihydrospiro[cyclobutane-1,1'-pyrrolo[2,3-c]quinolin]-8'-yl)-2-(3-(dimethylamino)azetidin-1-yl)pyridin-3-yl)methanesulfonamide hydrochloride | 522.30 | 1H NMR (400 MHz, CD3OD) δ 8.52 (d, J = 2.2 Hz, 1H), 8.36 (s, 1H), 7.99-7.91 (m, 2H), 7.82 (d, J = 8.6 Hz, 1H), 4.64-4.56 (m, 2H), 4.41 (dd, J = 10.2, 4.8 Hz, 2H), 4.25-4.18 (m, 1H), 3.60 (s, 3H), 3.16 (s, 3H), 3.07-2.94 (m, 8H), 2.73-2.61 (m, 3H), 2.61-2.48 (m, 1H). |

| Examples | Structure | Name | MS: [(M + 1)]+ | 1H NMR |
|---|---|---|---|---|
| 328 | 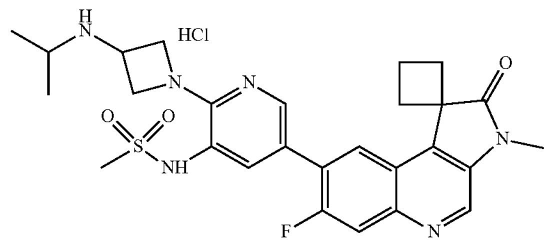 [SMILES: CC(C)NC1CN(c2ncc(-c3cc4c5c(cnc4cc3F)N(C)C(=O)C53CCC3)cc2NS(C)(=O)=O)C1 ; Cl] | N-(5-(7'-Fluoro-3'-methyl-2'-oxo-2',3'-dihydrospiro[cyclobutane-1,1'-pyrrolo[2,3-c]quinolin]-8'-yl)-2-(3-(isopropylamino)azetidin-1-yl)pyridin-3-yl)methanesulfonamide hydrochloride | 539.35 | 1H NMR (400 MHz, CD3OD) δ 8.84 (s, 1H), 8.49 (d, J = 1.9 Hz, 1H), 8.42 (d, J = 8.1 Hz, 1H), 7.98-7.85 (m, 2H), 4.71 (dd, J = 10.2, 7.1 Hz, 2H), 4.45-4.32 (m, 3H), 3.55-3.46 (m, 1H), 3.39 (s, 3H), 3.14 (s, 3H), 3.04-2.94 (m, 2H), 2.75-2.59 (m, 3H), 2.57-2.45 (m, 1H) |
| 335 | 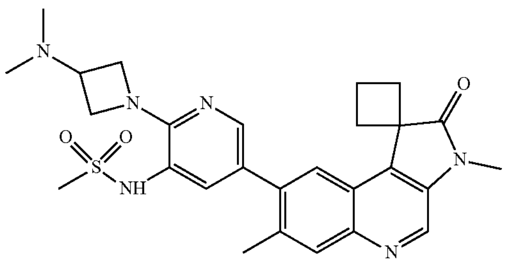 | N-(5-(3',7'-Dimethyl-2'-oxo-2',3'-dihydrospiro[cyclobutane-1,1'-pyrrolo[2,3-c]quinolin]-8'-yl)-2-(3-(dimethylamino)azetidin-1-yl)pyridin-3-yl)methanesulfonamide | 521.20 | 1H NMR (400 MHz, DMSO-d6) δ 9.04 (s, 1H), 8.79 (s, 1H), 8.21 (s, 1H), 8.02 (d, J = 19.5 Hz, 2H), 7.65 (d, J = 2.2 Hz, 1H), 4.25-4.19 (m, 2H), 3.96 (dd, J = 8.9, 5.4 Hz, 2H), 3.30 (s, 3H), 3.14-3.04 (m, 4H), 2.91-2.82 (m, 2H), 2.51-2.45 (m, 6H), 2.34-2.30 (m, 1H), 2.12(s, 6H). |
| 336 | 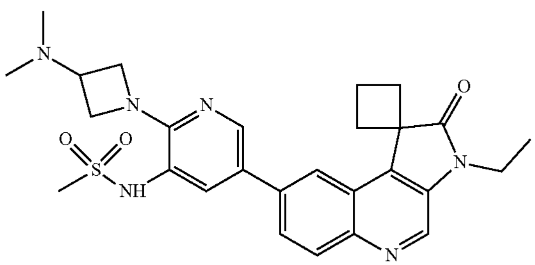 [SMILES: CCN1C(=O)C2(CCC2)c2c1cnc1ccc(-c3cnc(N4CC(N(C)C)C4)c(NS(C)(=O)=O)c3)cc21] | N-(2-(3-(Dimethylamino)azetidin-1-yl)-5-(3'-ethyl-2'-oxo-2',3'-dihydrospiro[cyclobutane-1,1'-pyrrolo[2,3-c]quinolin]-8'-yl)pyridin-3-yl)methanesulfonamide | 521.30 | 1H NMR (400 MHz, DMSO-d6) δ 9.09 (s, 1H), 8.86 (s, 1H), 8.58 (d, J = 2.2 Hz, 1H), 8.33 (d, J = 2.1 Hz, 1H), 8.13 (d, J = 8.9 Hz, 1H), 7.99-7.93 (m, 1H), 7.91 (d, J = 2.3 Hz, 1H), 4.30-4.21 (m, 2H), 4.08-3.95 (m, 2H), 3.92-3.82 (m, 2H), 3.20-3.08 (m, 4H), 3.00-2.89 (m, 2H), 2.62-2.52 (m, 41-1), 2.12 (s, 6H), 1.24 (t, J = 7.1 Hz, 3H). |
| 337 | 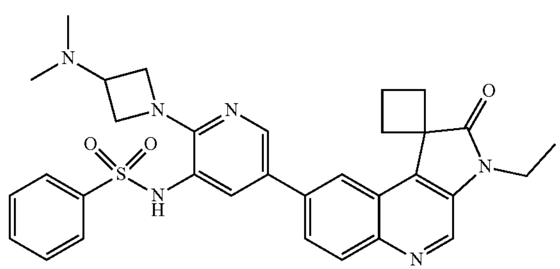 [SMILES: CCN1C(=O)C2(CCC2)c2c1cnc1ccc(-c3cnc(N4CC(N(C)C)C4)c(NS(=O)(=O)c4ccccc4)c3)cc21] | N-(2-(3-(Dimethylamino)azetidin-1-yl)-5-(3'-ethyl-2'-oxo-2',3'-dihydrospiro[cyclobutane-1,1'-pyrrolo[2,3-c]quinolin]-8'-yl)pyridin-3-yl)benzenesulfonamide | 583.35 | 1H NMR (400 MHz, DMSO-d6) δ 9.65 (s, 1H), 8.83 (s, 1H), 8.54 (s, 1H), 8.12-8.02 (m, 2H), 7.81-7.74 (m, 2H), 7.70-7.60 (m, 2H), 7.58 (t, J = 7.5 Hz, 2H), 7.20 (s, 1H), 4.17 (t, J = 7.9 Hz, 2H), 3.91-3.81 (m, 4H), 3.11 (s, 1H), 2.74 (q, J = 8.8 Hz, 2H), 2.60-2.41 (m, 3H), 2.40-2.31 (m, 2H), 2.10 (s, 6H), 1.22 (t, J = 7.0 Hz, 3H). |

| Examples | Structure | Name | MS: [(M + 1)]+ | 1H NMR |
|---|---|---|---|---|
| 338 | 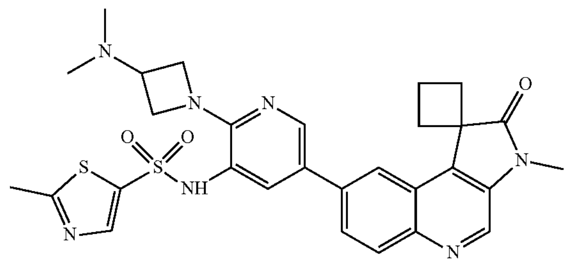 | N-(2-(3-(Dimethylamino)azetidin-1-yl)-5-(3'-methyl-2'-oxo-2',3'-dihydrospiro[cyclobutane-1,1'-pyrrolo[2,3-c]quinolin]-8'-yl)pyridin-3-yl)-2-methylthiazole-5-sulfonamide | 599.20 | 1H NMR (400 MHz, DMSO-d6) δ 8.78 (s, 1H), 8.23 (d, J = 1.9 Hz, 2H), 8.08 (d, J = 8.9 Hz, 1H), 7.85-7.77 (m, 2H), 7.64-7.53 (m, 1H), 4.23 (t, J = 8.2 Hz, 2H), 3.93 (s, 2H), 3.30 (s, 3H), 2.84 (q, J = 8.6, 7.6 Hz, 2H), 2.61 (s, 3H), 2.59-2.52 (m, 4H), 2.29 (s, 6H). |
| 339 | 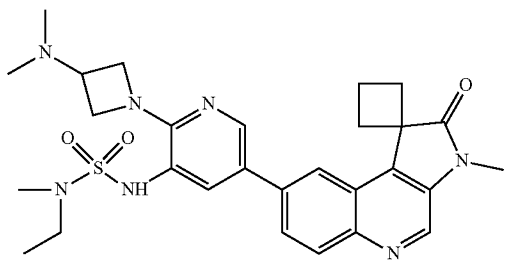 | 8'-[6-[3-(Dimethylamino)azetidin-1-yl]-5-{[ethyl(methyl)sulfamoyl]amino}pyridin-3-yl]-3'-methyl-2',3'-dihydrospiro[cyclobutane-1,1'-pyrrolo[2,3-c]quinoline]-2'-one | 550.35 | 1H NMR (400 MHz, DMSO-d6) δ 9.03 (s, 1H), 8.81 (s, 1H), 8.56 (d, J = 2.2 Hz, 1H), 8.30 (d, J = 2.0 Hz, 1H), 8.14 (d, J = 8.9 Hz, 1H), 7.91 (dd, J = 9.0, 1.9 Hz, 1H), 7.83 (d, J = 2.2 Hz, 1H), 4.25 (dd, J = 8.7, 7.1Hz, 2H), 3.99 (dd, J = 8.9, 5.5 Hz, 2H), 3.31 (s, 3H), 3.23-3.11 (m, 3H), 2.96-2.87 (m, 2H), 2.81 (s, 3H), 2.61-2.51 (m, 4H), 2.13 (s, 6H), 1.06 (t, J = 7.1 Hz, 3H). |
| 344 | 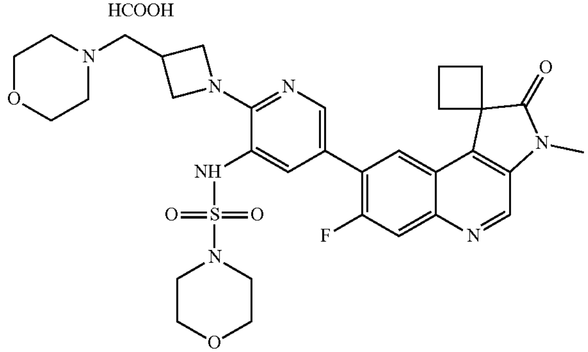 [SMILES: "HCOOH" ; CN1C(=O)C2(CCC2)c2c1cnc1cc(F)c(-c3cnc(N4CC(CN5CCOCC5)C4)c(NS(=O)(=O)N4CCOCC4)c3)cc21] | N-(5-(7'-Fluoro-3'-methyl-2'-oxo-2',3'-dihydrospiro[cyclobutane-1,1'-pyrrolo[2,3-c]quinolin]-8'-yl)-2-(3-(morpholinomethyl)azetidin-1-yl)pyridin-3-yl)methanesulfonamideformate | 581.35 | 1H NMR (400 MHz, DMSO-d6) δ 8.84 (s, 1H), 8.38 (t, J = 2.2 Hz, 1H), 8.25 (d, J = 8.4 Hz, 1H), 8.20 (s, 1H), 7.93 (d, J = 12.2 Hz, 1H), 7.78 (t, J = 2.0 Hz, 1H), 4.30 (t, J = 8.4 Hz, 2H), 3.87 (dd, J = 8.8, 5.7 Hz, 2H), 3.58 (t, J = 4.6 Hz, 4H), 3.30 (s, 3H), 3.07 (s, 3H), 2.96-2.85 (m, 3H), 2.61-2.50 (m, 4H), 2.49-2.34 (m, 6H), |

| Examples | Structure | Name | MS: [(M + 1)]+ | ¹H NMR |
|---|---|---|---|---|
| 351 | 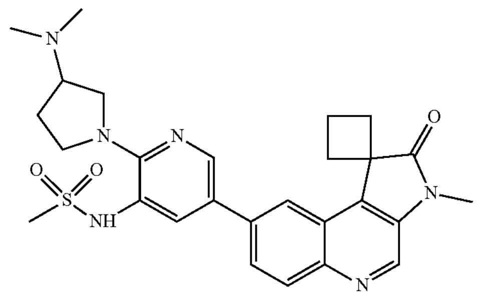 | (rac)-N-(2-(3-(Dimethylamino)pyrrolidin-1-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide | 521.30 | ¹H NMR (400 MHz, CDCl₃) δ 8.65 (s, 1H), 8.53 (d, J = 2.2 Hz, 1H), 8.39 (d, J = 2.0 Hz, 1H), 8.21 (d, J = 8.8 Hz, 1H), 8.05 (d, J = 2.2 Hz, 1H), 7.82 (dd, J = 8.9, 1.9 Hz, 1H), 3.84-3.56 (m, 4H), 3.39 (s, 3H), 3.18 (s, 3H), 2.97-2.88 (m, 2H), 2.81-2.63 (m, 3H), 2.62-2.44 (m, 7H), 2.29 (s, 2H), 2.11 (s, 1H). |
| 352 | 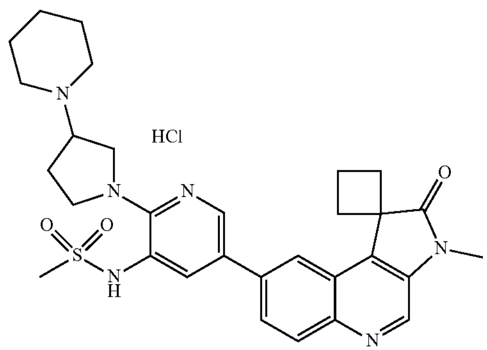 [SMILES: CN1C(=O)C2(CCC2)c2c1cnc1ccc(-c3cnc(N4CCC(N5CCCCC5)C4)c(NS(C)(=O)=O)c3)cc21 ; Cl] | (rac)-N-(5-(3'-Methyl-2'-oxo-2',3'-dihydrospiro[cyclobutane-1,1'-pyrrolo[2,3-c]quinolin]-8'-yl)-2-(3-(piperidin-1-yl)pyrrolidin-1-yl)pyridin-3-yl)methanesulfonamide hydrochloride | 561.35 | ¹H NMR (400 MHz, CD₃OD) δ 8.76 (d, J = 1.8 Hz, 1H), 8.62 (d, J = 2.3 Hz, 1H), 8.49 (s, 1H), 8.19 (d, J = 8.9 Hz, 1H), 8.04-7.98 (m, 2H), 4.19-4.05 (m, 3H), 4.00 (p, J = 7.1 Hz, 1H), 3.86-3.77 (m 1H), 3.67 (d, J = 12.4 Hz, 1H), 3.56 (d, J = 12.4 Hz, 1H), 3.39 (s, 3H), 3.21-2.97 (m, 7H), 2.78-2.52 (m, 5H), 2.33-2.20 (m, 1H), 2.08-1.98 (m, 2H), 1.93-1.74 (m, 3H), 1.65-1.51 (m, 1H). |
| 353 | 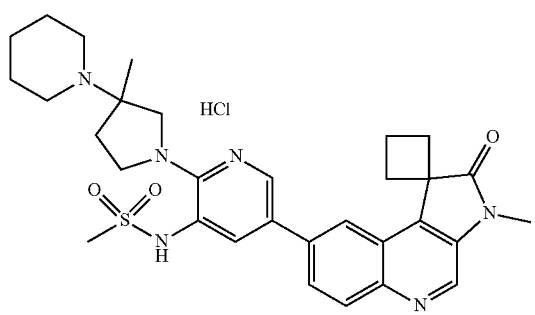 [SMILES: CN1C(=O)C2(CCC2)c2c1cnc1ccc(-c3cnc(N4CCC(C)(N5CCCCC5)C4)c(NS(C)(=O)=O)c3)cc21 ; Cl] | (rac)-N-(5-(3'-Methyl-2'-oxo-2',3'-dihydrospiro[cyclobutane-1,1'-pyrrolo[2,3-c]quinolin]-8'-yl)-2-(3-methyl-3-(piperidin-1-yl)pyrrolidin-1-yl)pyridin-3-yl)methanesulfonamide hydrochloride | 575.35 | ¹H NMR (400 MHz, CD₃OD) δ 8.70 (s, 1H), 8.48(d, J = 19.1 Hz, 2H), 8.14 (d, J = 8.9 Hz, 1H), 7.96 (d, J = 10.4 Hz, 2H), 3.96 (q, J = 9.5 Hz, 1H), 2.87-3.72 (m, 3H), 3.38 (s, 3H), 3.06 (s, 3H), 3.05-2.97 (m, 2H), 2.85-2.76 (m, 2H), 2.76-2.59 (m, 6H), 2.09-2.02 (m, 2H), 1.77-1.69 (m, 4H), 1.59-1.51 (m, 2H), 1.23 (s, 3H). |

| Examples | Structure | Name | MS: [(M + 1)]+ | 1H NMR |
|---|---|---|---|---|
| 354 | 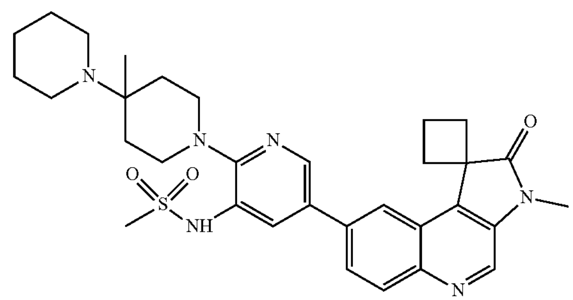 [SMILES: CN1C(=O)C2(CCC2)c2c1cnc1ccc(-c3cnc(N4CCC(C)(N5CCCCC5)CC4)c(NS(C)(=O)=O)c3)cc21] | N-(5-(3'-Methyl-2'-oxo-2',3'-dihydrospiro[cyclobutane-1,1'-pyrrolo[2,3-c]quinolin]-8'-yl)-2-(4'-methyl-[1,4'-bipiperidin]-1'-yl)pyridin-3-yl)methanesulfonamide MolecularWeight: 588.77 | 589.40 | 1H NMR (400 MHz, DMSO-d6) δ 8.93 (s, 1H), 8.83 (s, 1H), 8.55 (s, 1H), 8.38 (s, 1H), 8.15 (d, J = 8.9 Hz, 1H), 8.06-7.95 (m, 2H), 3.58-3.45 (m, 2H), 3.31 (s, 3H), 3.21-3.12 (m, 5H), 2.98-2.87 (m, 2H), 2.61-2.52 (m, 8H), 1.92-1.85 (m, 2H), 1.69-1.59 (m, 2H), 1.53 (s, 4H), 1.46-1.37 (m, 2H), 0.96 (s, 3H). |
| 355 | 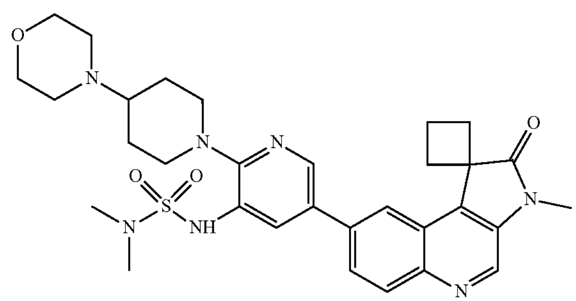 [SMILES: CN1C(=O)C2(CCC2)c2c1cnc1ccc(-c3cnc(N4CCC(N5CCOCC5)CC4)c(NS(=O)(=O)N(C)C)c3)cc21] | 8'-{5-[(Dimethylsulfamoyl)amino]-6-[4-(morpholin-4-yl)piperidin-1-yl]pyridin-3-yl}-3'-methyl-2',3'-dihydrospiro[cyclobutane-1,1'-pyrrolo[2,3-c]quinoline]-2'-one | 606.30 | 1H NMR (400 MHz, DMSO-d6) δ 8.99 (s, 1H), 8.84 (s, 1H), 8.60 (s, 1H), 8.37 (s, 1H), 8.17 (d, J = 8.9 Hz, 1H), 8.04 (s, 1H), 7.96 (d, J = 9.1 Hz, 1H), 3.79 (d, J = 12.8 Hz, 2H), 3.60 (s, 4H), 3.32 (s, 3H), 2.95-2.77 (m, 10H), 2.62-2.52 (m, 8H), 2.41-2.30 (m, 1H), 1.88 (d, J = 12.2 Hz, 2H), 1.74-1.62 (m, 2H). |
| 356 | 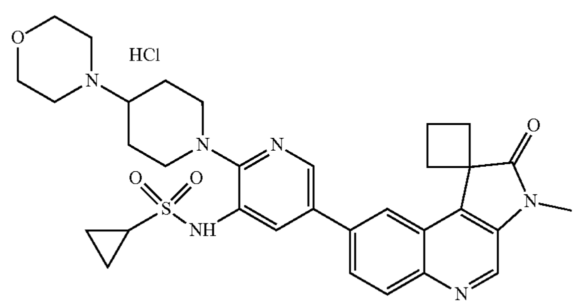 [SMILES: CN1C(=O)C2(CCC2)c2c1cnc1ccc(-c3cnc(N4CCC(N5CCOCC5)CC4)c(NS(=O)(=O)C4CC4)c3)cc21 ; Cl] | N-(5-(3'-Methyl-2'-oxo-2',3'-dihydrospiro[cyclobutane-1,1'-pyrrolo[2,3-c]quinolin]-8'-yl)-2-(4-morpholinopiperidin-1-yl)pyridin-3-yl)cyclopropanesulfonamide hydrochloride | 603.35 | 1H NMR (400 MHz, CD3OD) δ 8.76 (s, 1H), 8.58 (d, J = 2.2 Hz, 1H), 8.51 (s, 1H), 8.24 (d, J = 2.3 Hz, 1H), 8.20 (d, J = 8.8 Hz, 1H), 8.03-7.96 (m, 1H), 4.12 (d, J = 10.8 Hz, 2H), 4.04 (d, J = 13.2 Hz, 2H), 3.88-3.73 (m 2H), 3.62-3.41 (m, 4H), 3.39 (s, 3H), 3.28-3.20 (m, 1H), 3.08-2.94 (m, 4H), 2.87-2.78 (m, 1H), 2.77 2.59 (m, 4H), 2.26 (d, J = 12.0 Hz, 2H), 2.10-1.97 (m, 2H), 1.19-1.12 (m, 2H), 1.12-1.05 (m, 2H). |

-continued

| Examples | Structure | Name | MS: [(M + 1)]+ | ¹H NMR |
|---|---|---|---|---|
| 357 | 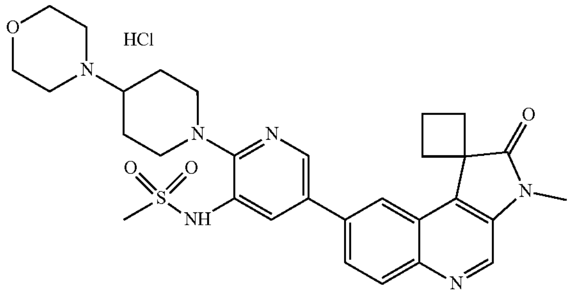 [SMILES: CN1C(=O)C2(CCC2)c2c1cnc1ccc(-c3cnc(N4CCC(N5CCOCC5)CC4)c(NS(C)(=O)=O)c3)cc21 ; Cl] | N-(5-(3'-Methyl-2'-oxo-2',3'-dihydrospiro[cyclobutane-1,1'-pyrrolo[2,3-c]quinolin]-8'-yl)-2-(4-morpholinopiperidin-1-yl)Pyridin-3-yl)methanesulfonamide hydrochloride | 577.30 | ¹H NMR (400 MHz, CD₃OD) δ 8.76 (s, 1H), 8.57 (d, J = 2.2 Hz, 1H), 8.52 (s, 1H), 8.22-8.17 (m, 2H), 8.05-7.97 (m, 1H), 4.13 (d, J = 12.5 Hz, 2H), 3.95 (d, J = 13.0 Hz, 2H), 3.81 (t, J = 12.2 Hz, 2H), 3.57 (d, J = 12.0 Hz, 2H), 3.50-3.42 (m, 1H), 3.39 (s, 3H), 3.26 (s, 2H), 3.22 (s, 3H), 3.08-2.95 (m, 4H), 2.77-2.59 (m, 4H), 2.26 (d, J = 11.8 Hz, 2H), 2.11-1.98 (m, 2H). |
| 358 | 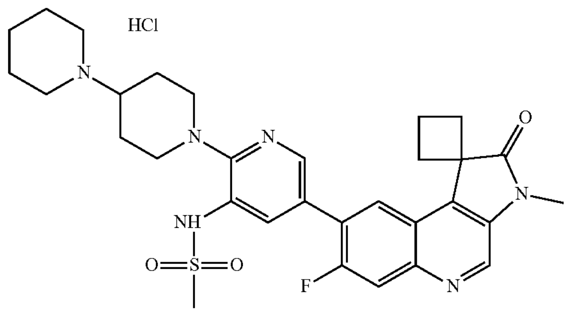 [SMILES: CN1C(=O)C2(CCC2)c2c1cnc1cc(F)c(-c3cnc(N4CCC(N5CCCCC5)CC4)c(NS(C)(=O)=O)c3)cc21 ; Cl] | N-(2-([1,4-Bipiperidin]-1'-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | 593.20 | ¹H NMR (400 MHz, CD₃OD) δ 8.86 (s, 1H), 8.51-8.42 (m, 2H), 8.16-8.10 (m, 1H), 7.92 (d, J = 11.7 Hz, 1H), 4.04 (d, J = 12.9 Hz, 2H), 3.60 (d, J = 12.2 Hz, 2H), 3.48-3.43 (m, 1H), 3.41 (s, 3H), 3.22 (s, 3H), 3.14-2.91 (m, 6H), 2.76-2.48 (m, 4H), 2.21 (d, J = 11.8 Hz, 2H), 2.14-1.97 (m, 4H), 1.92-1.73 (m, 3H), 1.63-1.48 (m, 1H). |
| 362 | 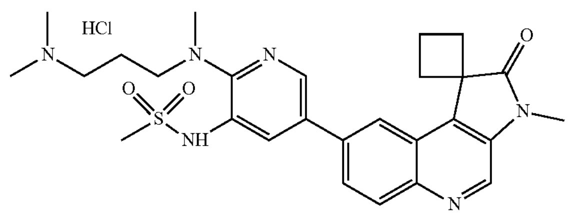 | N-(2-((3-(Dimethylamino)propyl)(methyl)amino)-5-(3'-methyl-2'-oxo-2',3'-dihydrospiro[cyclobutane-1,1'-pyrrolo[2,3-c]quinolin]-8'-yl)pyridin-3-yl)methanesulfonamide hydrochloride | 523.35 | ¹H NMR (400 MHz, CD₃OD) δ 8.81 (s, 1H), 8.63 (d, J = 2.3 Hz, 1H), 8.52 (d, J = 2.0 Hz, 1H), 8.21 (d, J = 8.9 Hz, 1H), 8.13 (d, J = 2.3 Hz, 1H), 8.05 (dd, J = 8.9, 1.9 Hz, 1H), 3.65 (t, J = 6.5 Hz, 2H), 3.41 (s, 3H), 3.31-3.26 (m, 2H), 3.18 (d, J = 2.9 Hz, 6H), 3.09-2.98 (m, 2H), 2.93 (s, 6H), 2.80-2.70 (m, 2H), 2.70-2.60 (m, 2H), 2.13 (p, J = 6.8 Hz, 2H). |

| Examples | Structure | Name | MS: [(M + 1)]+ | 1H NMR |
|---|---|---|---|---|
| 363 | 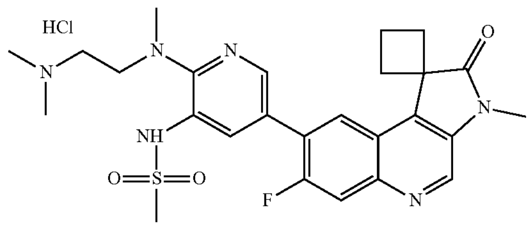 | N-(2-((2-(Dimethylamino)ethyl)(methyl)amino)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | 527.20 | 1H NMR (400 MHz, CD3OD) δ 8.79 (s, 1H), 8.54 (s, 1H), 8.42 (d, J = 8.1 Hz, 1H), 8.09 (t, J = 1.9 Hz, 1H), 7.87 (d, J = 12.0 Hz, 1H), 3.85 (t, J = 5.6 Hz, 2H), 3.46 (t, J = 5.7 Hz, 2H), 3.38 (s, 3H), 3.17 (s, 3H), 3.14 (s, 3H), 2.98 (s, 6H), 2.97-2.92 (m, 1H), 2.75-2.46 (m, 5H). |
| 364 | 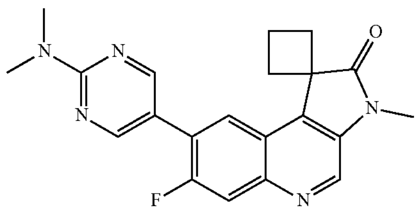 | 8'-(2-(Dimethylamino)pyrimidin-5-yl)-7'-fluoro-3'-methylspiro[cyclobutane-1,1'-pyrrolo[2,3-c]quinolin]-2'(3'-H)-one | 378.30 | 1H NMR (400 MHz, CDCl3) δ 8.71 (s, 2H), 8.63 (s, 1H), 8.28 (d, J = 7.5 Hz, 1H), 8.14 (s, 1H), 3.39 (s, 3H), 3.33 (s, 6H), 2.95-2.67 (m, 5H) 2.57-2.45 (m, 1H). |
| 365 | 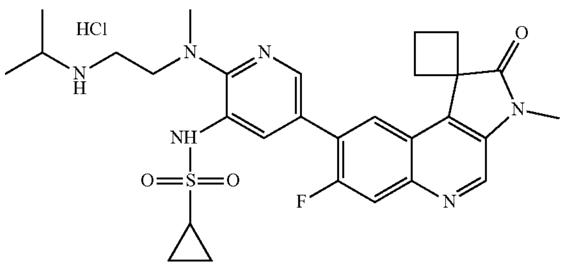 [SMILES: CC(C)NCCN(C)c1ncc(-c2cc3c4c(cnc3cc2F)N(C)C(=O)C42CCC2)cc1NS(=O)(=O)C1CC1 ; Cl] | N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)cyclopropanesulfonamide hydrochloride | 554.20 | 1H NMR (400 MHz, DMSO-d6) δ 9.40 (s, 1H), 8.90 (s, 1H), 8.85 (s, 2H), 8.43 (d, J = 2.1 Hz, 1H), 8.31 (d, J = 8.3 Hz, 1H), 8.14 (s, 1H), 8.01 (d, J = 12.1 Hz, 1H), 4.63 (t, J = 5.3 Hz, 2H), 3.51-3.44 (m, 3H), 3.31 (s, 3H), 2.96-2.87 (m, 2H), 2.81 (p, J = 6.6 Hz, 1H), 2.61-2.53 (m, 3H), 2.49-2.38 (m, 1H), 1.33 (d, J = 6.4 Hz, 6H), 1.03-0.97 (m, 4H). |
| 366 | 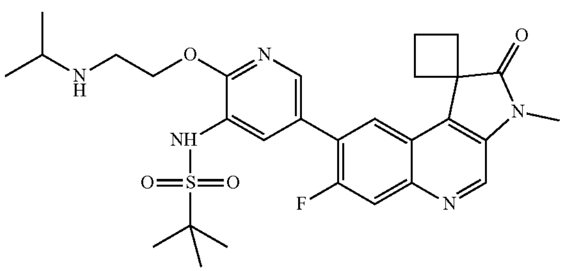 [SMILES: CC(C)NCCOc1ncc(-c2cc3c4c(cnc3cc2F)N(C)C(=O)C42CCC2)cc1NS(=O)(=O)C(C)(C)C] | N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)-2-methylpropane-2-sulfonamide | 570.30 | 1H NMR (400 MHz, DMSO-d6) δ 8.89 (s, 1H), 8.37-8.29 (m, 2H), 8.16 (s, 1H), 7.98 (d, J = 12.1 Hz, 1H), 4.44 (t, J = 5.2 Hz, 2H), 3.31 (s, 3H), 2.98-2.81 (m, 5H), 2.63-2.56 (m, 2H), 2.48-2.39 (m, 2H), 1.32 (s, 9H), 1.05 (d, J = 6.2 Hz, 6H). |

-continued

| Examples | Structure | Name | MS: [(M + 1)]+ | 1H NMR |
|---|---|---|---|---|
| 367 | 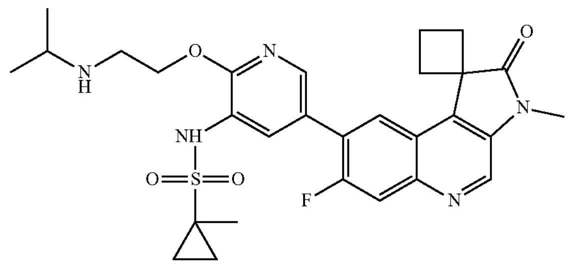 [SMILES: CC(C)NCCOc1ncc(-c2cc3c4c(cnc3cc2F)N(C)C(=O)C42CCC2)cc1NS(=O)(=O)C1(C)CC1] | N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)-1-methylcyclopropane-1-sulfonamide | 568.30 | 1H NMR (400 MHz, DMSO-$d_6$) δ 8.88 (s, 1H), 8.34 (s, 1H), 8.30 (d, J = 8.2 Hz, 1H), 8.05 (t, J = 1.9 Hz, 1H), 7.98 (d, J = 12.1 Hz, 1H), 4.44 (t, J = 5.3 Hz, 2H), 3.31 (s, 3H), 2.95 (t, J = 5.4 Hz, 2H), 2.94-2.79 (m, 3H), 2.60-2.53 (m, 2H), 2.49-2.40 (m, 2H), 1.50 (s, 3H), 1.05 (d, J = 6.3 Hz, 8H), 0.75 (q, J = 3.6 Hz, 2H). |
| 369 | 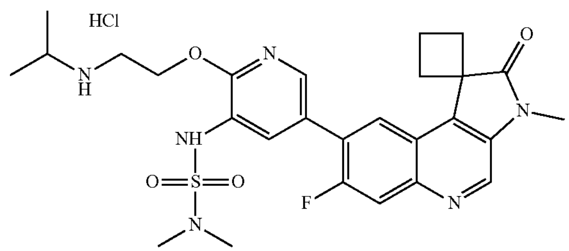 [SMILES: CC(C)NCCOc1ncc(-c2cc3c4c(cnc3cc2F)N(C)C(=O)C42CCC2)cc1NS(=O)(=O)N(C)C ; Cl] | 8'-{5-[(Dimethylsulfamoyl)amino]-6-{[(propan-2-ylamino]ethoxy'}pyridin-3-yl}-7'-fluoro-3'-methyl-2',3'-dihydrospiro[cyclobutane-1,1'-pyrrolo[2,3-c]quinoline]-2'-one hydrochloride | 557.25 | 1H NMR (400 MHz, CD$_3$OD) δ 8.85 (s, 1H), 8.44 (d, J = 8.0 Hz, 1H), 8.30 (s, 1H), 8.14 (s, 1H), 7.91 (d, J = 11.8 Hz, 1H), 4.78 (t, J = 5.1 Hz, 2H), 3.61-3.49 (m, 3H), 3.39 (s, 3H), 3.02-2.92 (m, 2H), 2.88 (s, 6H), 2.79-2.49 (m, 4H), 1.43 (d, J = 6.5 Hz, 6H). |
| 375 | 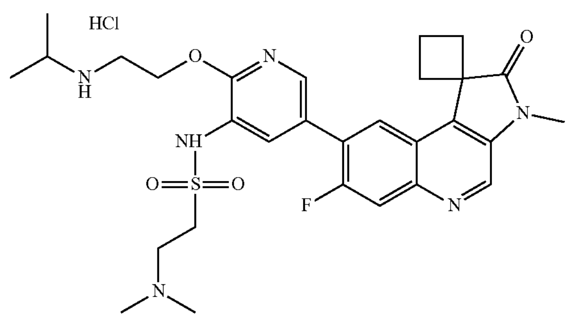 [SMILES: CC(C)NCCOc1ncc(-c2cc3c4c(cnc3cc2F)N(C)C(=O)C42CCC2)cc1NS(=O)(=O)CCN(C)C ; Cl] | 2-(Dimethylamino)-N-(5-(7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)ethane-1-sulfonamide hydrochloride | 585.40 | 1H NMR (400 MHz, CD$_3$OD) δ 9.00 (s, 1H), 8.56 (d, J = 7.6 Hz, 1H), 8.43 (t, J = 2.1 Hz, 1H), 8.27 (s, 1H), 8.00 (d, J = 11.1 Hz, 1H), 4.84 (t, J = 5.0 Hz, 2H), 3.89 (t, J = 6.9 Hz, 2H), 3.76 (t, J = 6.9 Hz, 2H), 3.65-3.57 (m, 2H), 3.56-3.53 (m, 1H), 3.41 (s, 3H), 3.08-3.01 (m, 2H), 3.00 (s, 6H), 2.83-2.72 (m, 2H), 2.67-2.53 (m, 2H), 1.46 (d, J = 6.5 Hz, 6H). |

| Examples | Structure | Name | MS: [(M + 1)]+ | ¹H NMR |
|---|---|---|---|---|
| 381 | 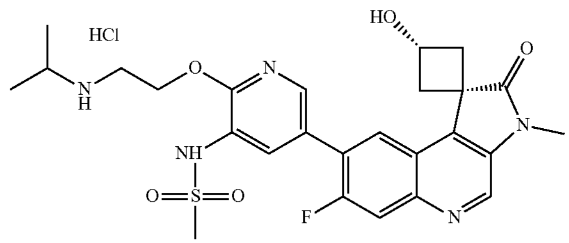 [SMILES: CC(C)NCCOc1ncc(-c2cc3c(cc2F)ncc2c3[C@]3(C[C@H](O)C3)C(=O)N2C)cc1NS(C)(=O)=O ; Cl] | cis-N-(5-(7'-Fluoro-3-hydroxy-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | 544.30 | ¹H NMR (400 MHz, CD₃OD) δ 8.91 (s, 1H), 8.36 (t, J = 2.1 Hz, 1H), 8.29 (d, J = 7.9 Hz, 1H), 8.26-8.24 (m, 1H), 7.94 (d, J = 11.4 Hz, 1H), 5.04 (p, J = 7.3 Hz, 1H), 4.81-4.73 (m, 2H), 3.60-3.50 (m, 3H), 3.41 (s, 3H), 3.19-3.12 (m, 5H), 2.80 (dd, J = 14.4, 6.2 Hz, 2H), 1.43 (d, J = 6.6 Hz, 6H). |
| 382 | 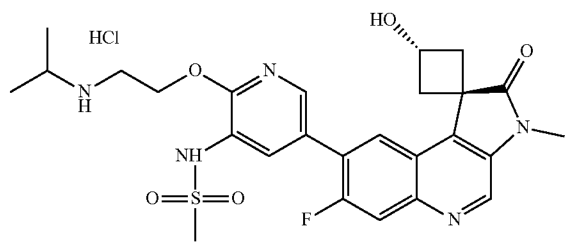 [SMILES: CC(C)NCCOc1ncc(-c2cc3c(cc2F)ncc2c3[C@]3(C[C@@H](O)C3)C(=O)N2C)cc1NS(C)(=O)=O ; Cl] | trans-N-(5-(7'-Fluoro-3-hydroxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 544.30 | ¹H NMR (400 MHz, CD₃OD) δ 8.85-8.81 (m, 2H), 8.35 (s, 1H), 8.19 (s, 1H), 7.88 (d, J = 11.8 Hz, 1H), 4.76 (t, J = 5.0 Hz, 2H), 3.59-3.51 (m, 3H), 3.38 (s, 3H), 3.17 (s, 3H), 2.92 (d, J = 7.0 Hz, 4H), 1.42 (d, J = 6.6 Hz, 6H). |
| 383 | 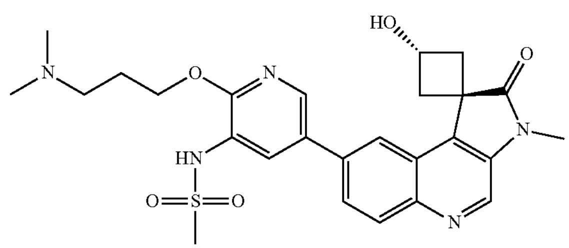 | trans-N-(2-(3-(Dimethylamino)propoxy)-5-(3-hydroxy-3'-methyl-2'-oxo-2',3'-dihydrospiro[cyclobutane-1,1'-pyrrolo[2,3-c]quinolin]-8'-yl)pyridin-3-yl)methanesulfonamide | 526.20 | ¹H NMR (400 MHz, DMSO-d₆) δ 8.84 (s, 1H), 8.76 (s, 1H), 8.34 (s, 1H), 8.16 (d, J = 8.9 Hz, 1H), 7.97 (s, 1H), 7.90 (d, J = 9.2 Hz, 1H), 5.85 (s, 1H), 4.78-4.70 (m, 1H), 4.40 (t, J = 6.2 Hz, 2H), 3.31 (s, 3H), 3.04 (s, 3H), 2.89-2.74 (m, 4H), 2.64 (t, J = 6.6 Hz, 2H), 2.34 (s, 6H), 2.03-1.94 (m, 2H). |
| 384 | 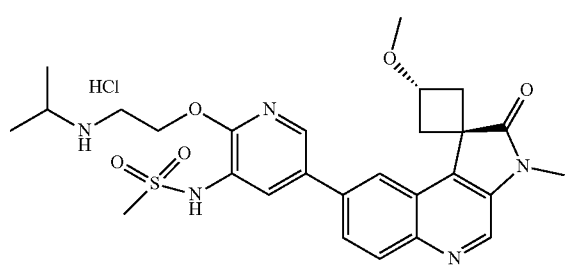 [SMILES: CO[C@H]1C[C@@]2(C1)C(=O)N(C)c1cnc3ccc(-c4cnc(OCCNC(C)C)c(NS(C)(=O)=O)c4)cc3c12 ; Cl] | trans-N-(2-(2-(Isopropylamino)ethoxy)-5-(3-methoxy-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | 540.30 | ¹H NMR (400 MHz, CD₃OD) δ 8.91 (d, J = 1.9 Hz, 1H), 8.83 (s, 1H), 8.47 (d, J = 2.2 Hz, 1H), 8.28 (d, J = 2.2 Hz, 1H), 8.21 (d, J = 8.9 Hz, 1H), 8.02 (dd, J = 8.9, 2.0 Hz, 1H), 4.78-4.75 (m, 2H), 4.48 (p, J = 6.6 Hz, 1H), 3.60-3.50 (m, 3H), 3.44 (s, 3H), 3.40 (s, 3H), 3.17 (s, 3H), 3.02-2.91 (m, 4H), 1.42 (d, J = 6.5 Hz, 6H). |

-continued

| Examples | Structure | Name | MS: [(M + 1)]+ | 1H NMR |
|---|---|---|---|---|
| 385 | 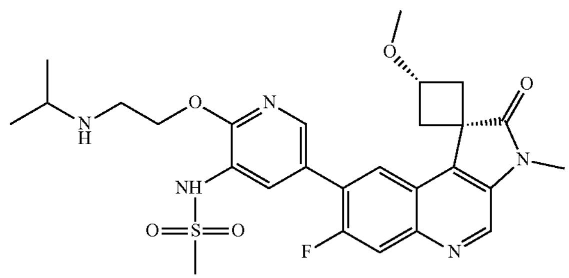 [SMILES: CO[C@H]1C[C@]2(C1)C(=O)N(C)c1cnc3cc(F)c(-c4cnc(OCCNC(C)C)c(NS(C)(=O)=O)c4)cc3c12] | cis-N-(5-(7'-Fluoro-3-methoxy-3-methyl-2'-oxo-2',3'-dihydrospiro[cyclobutane-1,1'-pyrrolo[2,3-c]quinolin]-8'-yl)-2-(isopropylamino)ethoxy)pyridin-3-yl)methanesulfonamide | 558.15 | 1H NMR (400 MHz, DMSO-d6) δ 8.90 (s, 1H), 8.33 (d, J = 2.8 Hz, 1H), 8.09 (d, J = 8.2 Hz, 1H), 8.05-7.95 (m, 2H), 4.62 (p, J = 7.6 Hz, 1H), 4.45 (t, J = 5.3 Hz, 2H), 3.32 (s, 3H), 3.27 (s, 3H), 3.06 (s, 3H), 3.04-2.90 (m, 5H), 2.61 (dd, J = 13.0, 6.0 Hz, 2H), 1.08 (d, J = 6.2 Hz, 6H). |
| 386 | 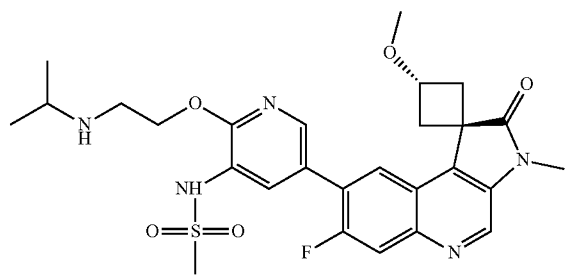 | trans-N-(5-(7'-Fluoro-3-methoxy-3-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 558.20 | 1H NMR (400 MHz, DMSO-d6) δ 8.90 (s, 1H), 8.64 (d, J = 8.3 Hz, 1H), 8.26 (s, 1H), 8.01-7.94 (m, 2H), 4.45 (t, J = 5.2 Hz, 2H), 4.36 (p, J = 6.4 Hz, 1H), 3.31 (s, 3H), 3.30 (s, 3H), 3.05 (s, 3H), 3.01 (t, J = 5.5 Hz, 2H), 2.98-2.89 (m, 1H), 2.89-2.76 (m, 4H), 1.08 (d, J = 6.2 Hz, 6H). |
| 387 | 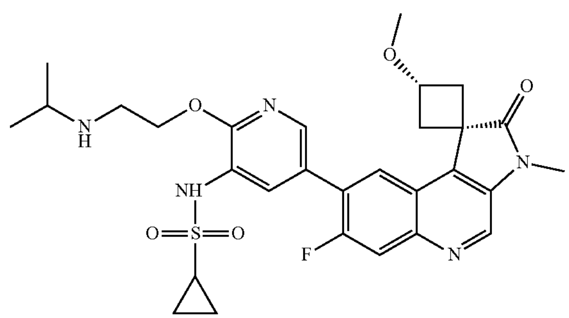 [SMILES: CO[C@H]1C[C@]2(C1)C(=O)N(C)c1cnc3cc(F)c(-c4cnc(OCCNC(C)C)c(NS(=O)(=O)C5CC5)c4)cc3c12] | cis-N-(5-(7'-Fluoro-3-methoxy-3-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)cyclopropanesulfonamid | 584.35 | 1H NMR (400 MHz, DMSO-d6) δ 8.91 (s, 1H), 8.34 (s, 1H), 8.09 (d, J = 8.4 Hz, 1H), 8.05 (s, 1H), 7.99 (d, J = 12.1 Hz, 1H), 4.64 (s, 1H), 4.43 (t, J = 5.2 Hz, 2H), 3.32 (s, 3H), 3.27 (s, 3H), 3.05-2.95 (m, 4H), 2.93-2.83 (m, 1H), 2.79-2.71 (m, 1H), 2.61 (dd, J = 13.4, 6.0 Hz, 2H), 1.06 (d, J = 6.2 Hz, 6H), 0.97-0.90 (m, 4H). |

| Examples | Structure | Name | MS: [(M + 1)]+ | 1H NMR |
|---|---|---|---|---|
| 388 | 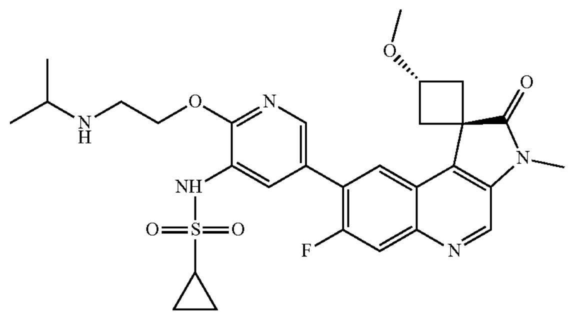 [SMILES: CO[C@H]1C[C@@]2(C1)C(=O)N(C)c1cnc3cc(F)c(-c4cnc(OCCNC(C)C)c(NS(=O)(=O)C5CC5)c4)cc3c12] | trans-N-{5-(7'-Fluoro-3-methoxy-3 methyl-2'-oxo-2',3'-dihydrospiro [cyclobutane-1,1'-pyrrolo[2,3-c]quinolin]-8'-yl)-2-(2-(isopropylamino)ethoxy)pyridin-3-yl)cyclopropanesulfonamide | 584.35 | 1H NMR (400 MHz, DMSO-d6) δ 8.90 (s, 1H), 8.66 (d, J = 8.1 Hz, 1H), 8.29 (s, 1H), 7.98 (d, J = 13.1 Hz, 2H), 4.43 (t, J = 5.2 Hz, 2H), 4.40-4.31 (m, 1H), 3.33(d, 6H), 2.98 (t, J = 5.1 Hz, 2H), 2.93-2.77 (m, 5H), 2.73 (t, J = 6.5 Hz, 1H), 1.06 (d, J = 6.2 Hz, 6H), 0.94 (d, J = 6.4 Hz, 4H). |
| 389 | 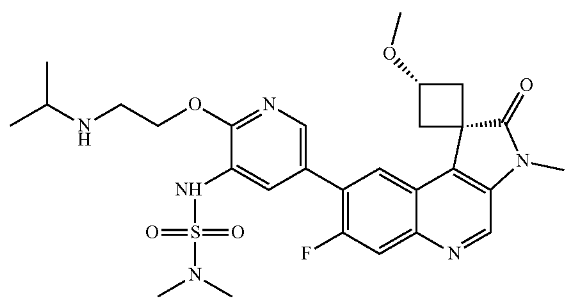 [SMILES: CO[C@H]1C[C@]2(C1)C(=O)N(C)c1cnc3cc(F)c(-c4cnc(OCCNC(C)C)c(NS(=O)(=O)N(C)C)c4)cc3c12] | cis-8'-{5-[(Dimethylsulfamoyl)amino]-6-{2-[(propan-2-yl)amino]ethoxy}pyridine-3-yl}-7-fluoro-3-Methoxy-3'-methyl-2',3'-dihydrospiro[cyclobutane-1,1'-pyrrolo[2,3-c]quinoline]-2'-one | 587.10 | 1H NMR (400 MHz, DMSO-d6) δ 8.90 (s, 1H), 8.23 (s, 1H), 8.08 (d, J = 8.4 Hz, 1H), 8.03 (s, 1H), 7.98 (d, J = 12.2 Hz, 1H), 4.69-4.60 (m, 1H), 4.43 (t, J = 5.9 Hz, 2H)' 3.32 (s, 3H), 3.28 (s, 3H), 3.04-2.90 (m, 5H), 2.69 (s, 6H), 2.62 (dd, J = 14.0, 5.8 Hz, 2H), 1.09 (d, J = 6.3 Hz, 6H). |
| 390 | 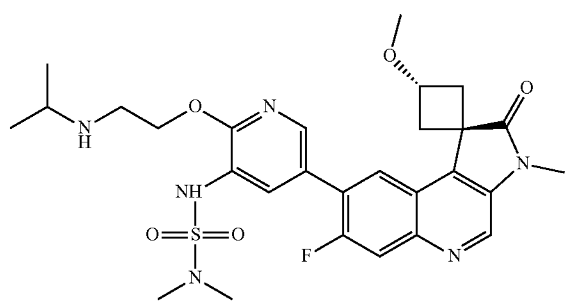 [SMILES: CO[C@H]1C[C@@]2(C1)C(=O)N(C)c1cnc3cc(F)c(-c4cnc(OCCNC(C)C)c(NS(=O)(=O)N(C)C)c4)cc3c12] | trans-3'-{5-[(Dimethylsulfamoyl)amino]-6-{2-[(propan-2-yl)amino]ethoxy}pyridine-3-yl}-7-fluoro-3-Methoxy-3'-methyl-2',3'-dihydrospiro[cyclobutane-1,1'-pyrrolo[2,3-c]quinoline]-2'-one | 587.40 | 1H NMR (400 MHz, DMSO-d6) δ 8.90 (s, 1H), 8.62 (d, J = 8.3 Hz, 1H), 8.19 (s, 1H), 8.01-7.95 (m, 2H), 4.43 (t, J = 5.2 Hz, 2H), 4.36 (p, J = 6.5 Hz, 1H), 3.31 (s, 3H), 3.30 (s, 3 H), 2.98 (t, J = 5.1 Hz, 2H), 2.94-2.84 (m, 1H), 2.85-2.79 (m, 4H), 2.69 (s, 6H), 1.07 (d, J = 6.2 Hz, 6H). |

| Examples | Name | MS: [(M + 1)]+ | 1H NMR |
|---|---|---|---|
| 391 | cis-N-(2-([1,4-Bipiperidin]-1'-yl)-5-(7'-fluoro-3'-methoxy-3'-methyl-2'-oxo-2',3'-dihydrospiro[cyclobutane-1,1'-pyrrolo[2,3-c]quinolin]-8'-yl)pyridin-3-yl)methanesulfonamide | 623.40 | 1H NMR (400 MHz, DMSO-d6) δ 9.08(s, 1H), 8.89(s, 1H), 8.41(s, 1H), 8.08(d, J = 8.3 Hz, 1H), 7.97 (d, J = 12.2 Hz, 1H), 7.92 (t, J = 1.8 Hz, 1H), 4.63 (p, J = 7.1 Hz, 1H), 4.00 (d, J = 12.2 Hz, 2H), 3.31 (s, 3H), 3.27 (s, 3H), 3.11 (s, 3H), 3.00 (dd, J = 13.4, 8.1 Hz, 2H), 2.78 (t, J = 12.1 Hz, 2H), 2.65-2.54 (m, 7H), 1.82 (d, J = 11.9 Hz, 2H), 1.74-1.62 (m, 2H), 1.57-1.49 (m, 4H), 1.45-1.37 (m, 2H). |
| 392 | Bipiperidin]-1'-yl)-5-(7'-fluoro-3'-methoxy-3'-methyl-2'-oxo-2',3'-dihydrospiro[cyclobutane-1,1'-pyrrolo[2,3-c]quinolin]-8'-yl)pyridin-3-yl)methanesulfonamide | 623.40 | 1H NMR (400 MHz, DMSO-d6) δ 9.08 (s, 1H), 8.88 (s, 1H), 8.59 (d, J = 8.4 Hz, 1H), 8.37 (s, 1H), 7.96 (d, J = 12.2 Hz, 1H), 7.88 (t, J = 2.1 Hz, 1H), 4.36 (p, J = 6.6 Hz, 1H), 4.01 (d, J = 12.4 Hz, 2H), 3.31 (s, 3H), 3.30 (s, 3H), 3.11 (s, 3H), 2.91-2.74 (m, 6H), 2.56 (s, 5H), 1.81 (d, J = 11.8 Hz, 2H), 1.74-1.61 (m, 2H), 1.58-1.47 (m, 4H), 1.45-1.37 (m, 2H). |
| 393 | cis-N-(5-(3-Ethoxy-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 572.30 | 1H NMR (400 MHz, DMSO-d6) δ 8.89 (s, 1H), 8.29 (d, J = 2.3 Hz, 1H), 8.11 (d, J = 8.2 Hz, 1H), 8.02 (d, J = 1.9 Hz, 1H), 7.98 (d, J = 12.1 Hz, 1H), 4.71 (p, J = 7.1 Hz, 1H), 4.48 (d, J = 5.1 Hz, 2H), 3.32 (s, 3H), 3.15-2.95 (m, 8H), 2.68-2.58 (m, 2H), 1.20-1.11 (m, 9H). |

| Examples | Structure | Name | MS: [(M + 1)]+ | 1H NMR |
|---|---|---|---|---|
| 394 | 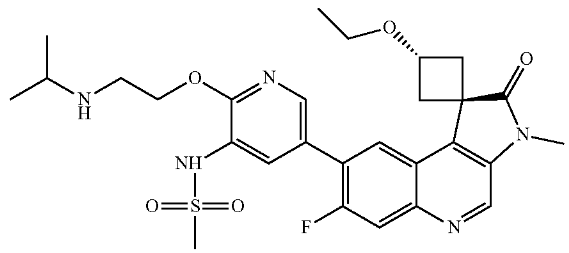 [SMILES: CCO[C@H]1C[C@@]2(C1)C(=O)N(C)c1cnc3cc(F)c(-c4cnc(OCCNC(C)C)c(NS(C)(=O)=O)c4)cc3c12] | trans-N-(5-(3-Ethoxy-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 572.30 | 1H NMR (400 MHz, DMSO-d6) δ 8.88 (s, 1H), 8.64 (d, J = 8.4 Hz, 1H), 8.21 (s, 1H), 7.99-7.92 (m, 2H), 4.48-4.38 (m, 3H), 3.31 (s, 3H), 3.07-2.92 (m, 6H), 2.90-2.76 (m, 4H), 1.14-1.06 (m, 9H). |
| 395 | 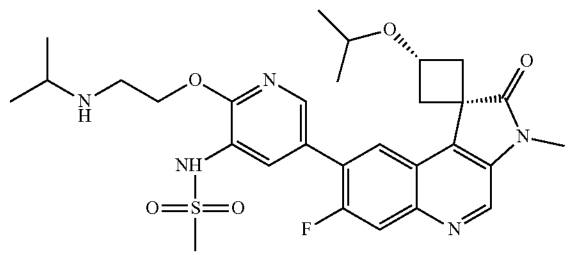 | cis-N-(5-(7'-Fluoro-3-isopropoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 586.20 | 1H NMR (400 MHz, DMSO-d6) δ 8.90 (s, 1H), 8.32 (d, J = 2.3 Hz, 1H), 8.14 (d, J = 8.3 Hz, 1H), 8.03 (d, J = 1.9 Hz, 1H), 7.98 (d, J = 12.1 Hz, 1H), 4.76 (p, J = 7.2 Hz, 1H), 4.48 (t, J = 5.2 Hz, 2H), 3.74 (p, J = 6.1 Hz, 1H), 3.32 (s, 3H), 3.11 (t, J = 5.3 Hz, 2H), 3.06 (s, 3H), 3.05-2.98 (m, 3H), 2.67-2.59 (m, 2H), 1.14 (d, J = 6.1 Hz, 12H). |
| 396 | 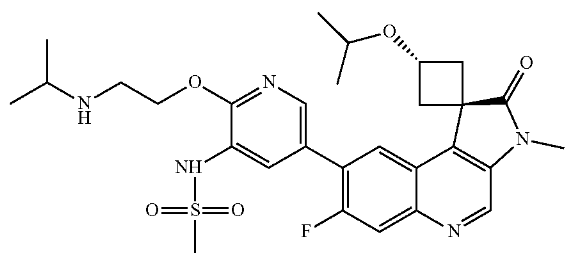 [SMILES: CC(C)NCCOc1ncc(-c2cc3c(cc2F)ncc2c3[C@]3(C[C@@H](OC(C)C)C3)C(=O)N2C)cc1NS(C)(=O)=O] | trans-N-(5-(7'-Fluoro-3-isopropoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 586.20 | 1H NMR (400 MHz, DMSO-d6) δ 8.88 (d, J = 2.3 Hz, 1H), 8.63 (d, J = 8.3 Hz, 1H), 8.23 (d, J = 3.6 Hz, 1H), 8.01-7.91 (m, 2H), 4.56-4.40 (m, 3H), 3.70 (p, J = 6.1 Hz, 1H), 3.31 (s, H), 3.08-3.94 (m, 6H), 2.83 (d, J = 6.8 Hz, 4H), 1.14-1.05 (m, 12H). |

| Examples | Structure | Name | MS: [(M + 1)]+ | 1H NMR |
|---|---|---|---|---|
| 397 | 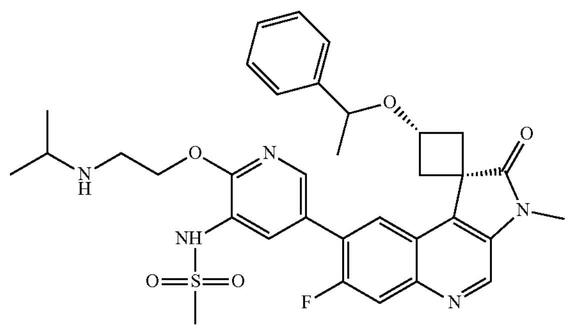 [SMILES: CC(C)NCCOc1ncc(-c2cc3c(cc2F)ncc2c3[C@]3(C[C@H](OC(C)c4ccccc4)C3)C(=O)N2C)cc1NS(C)(=O)=O] | cis-N-(5-(7'-Fluoro-3'-methyl-2'-oxo-3-(1-phenylethoxy)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 648.30 | 1H NMR (400 MHz, DMSO-d6) δ 8.87 (s, 1H), 8.15 (s, 1H), 7.97-7.91 (m, 3H), 7.39 (d, J = 7.1 Hz, 2H), 7.30 (t, J = 7.5 Hz, 2H), 7.21 (t, J = 7.3 Hz, 1H), 4.69 (p, J = 7.2 Hz, 1H), 4.61 (q, J = 6.5 Hz, 1H), 4.50 (t, J = 5.4 Hz, 2H), 3.30 (s, 3H), 3.06 (s, 3H), 3.05-2.89 (m, 3H), 2.69 (dd, J = 15.1, 9.4 Hz, 2H), 2.03-1.94 (m, 1H), 1.44 (d, J = 6.4 Hz, 3H), 1.09 (d, J = 6.2 Hz, 6H). |
| 398 | 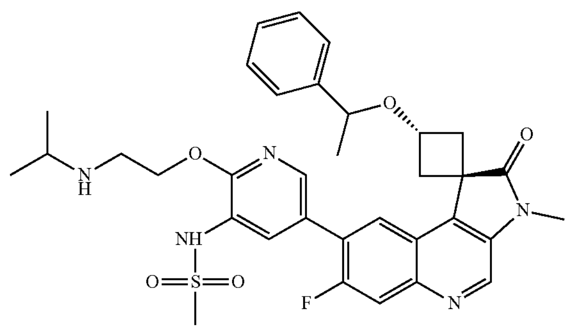 [SMILES: CC(C)NCCOc1ncc(-c2cc3c(cc2F)ncc2c3[C@]3(C[C@@H](OC(C)c4ccccc4)C3)C(=O)N2C)cc1NS(C)(=O)=O] | trans-N-(5-(7'-Fluoro-3'-methyl-2'-oxo-3-(1-phenylethoxy)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 648.25 | 1H NMR (400 MHz, DMSO-d6) δ 8.88 (s, 1H), 8.59 (d, J = 8.3 Hz, 1H), 8.33 (s, 1H), 8.02-7.94 (m, 2H), 7.34-7.22 (m, 5H), 4.58 (q, J = 6.3 Hz, 1H), 4.44 (t, J = 5.4 Hz, 2H), 4.37 (p, J = 6.9 Hz, 1H), 3.28 (s, 3H), 3.05 (s, 3H), 2.97 (q, J = 5.5 Hz, 3H), 2.88 (p, J = 6.2 Hz, 1H), 2.84-2.74 (m, 1H), 2.69 (dd, J = 13.1, 5.8 Hz, 1H), 2.59-2.54 (m, 1H), 1.35 (d, J = 6.4 Hz, 3H), 1.05 (d, J = 6.3 Hz, 6H). |
| 400 | 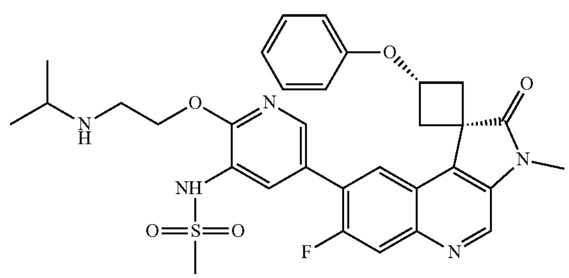 [SMILES: CC(C)NCCOc1ncc(-c2cc3c(cc2F)ncc2c3[C@]3(C[C@H](Oc4ccccc4)C3)C(=O)N2C)cc1NS(C)(=O)=O] | cis-N-(5-(7'-Fluoro-3'-methyl-2'-oxo-3-phenoxy-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 620.40 | 1H NMR (400 MHz, DMSO-d6) δ 8.92 (s, 1H), 8.39 (d, J = 2.0 Hz, 1H), 8.22 (d, J = 8.2 Hz, 1H), 8.07 (d, J = 2.0 Hz, 1H), 8.01 (d, J = 12.1 Hz, 1H), 7.34-7.28 (m, 2H), 7.00-6.94 (m, 3H), 5.40 (p, J = 6.6 Hz, 1H), 4.43 (t, J = 5.3 Hz, 2H), 3.41-3.34 (m, 2H), 3.33 (s, 3H), 3.02 (t, J = 5.2 Hz, 2H), 2.97 (s, 3H), 2.97-2.90 (m, 1H), 2.78 (dd, J = 14.3, 5.7 Hz, 2H), 1.08 (d, J = 6.3 Hz, 6H). |

| Examples | Structure | Name | MS: [(M + 1)]+ | 1H NMR |
|---|---|---|---|---|
| 401 | 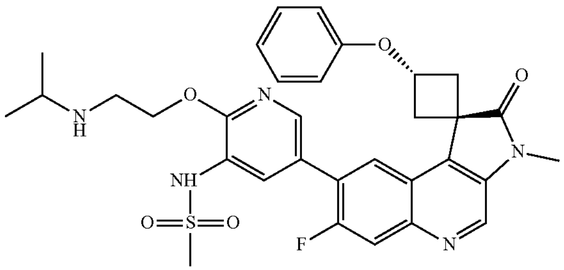 [SMILES: CC(C)NCCOc1ncc(-c2cc3c(cc2F)ncc2c3[C@]3(C[C@@H](Oc4ccccc4)C3)C(=O)N2C)cc1NS(C)(=O)=O] | trans-N-(5-(7'-Fluoro-3'-methyl-2'-oxo-3-phenoxy-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 620.40 | 1H NMR (400 MHz, DMSO-d6) δ 8.93 (s, 1H), 8.59 (d, J = 8.4 Hz, 1H), 8.28 (d, J = 2.2 Hz, 1H), 7.99 (d, J = 12.3 Hz, 2H), 7.32-7.23 (m, 2H), 6.95 (t, J = 7.3 Hz, 1H), 6.86 (d, J = 8.1 Hz, 2H), 5.21 (p, J = 6.4 Hz, 1H), 4.53 (t, J = 5.3 Hz, 2H), 3.34 (s, 3H), 3.17-2.99 (m, 10H), 1.14 (d, J = 6.3 Hz, 6H). |
| 402 | 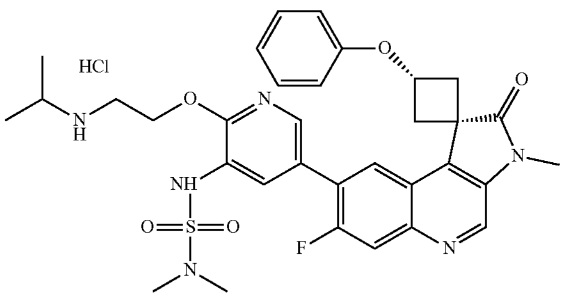 [SMILES: CC(C)NCCOc1ncc(-c2cc3c(cc2F)ncc2c3[C@]3(C[C@H](Oc4ccccc4)C3)C(=O)N2C)cc1NS(=O)(=O)N(C)C ; Cl] | cis-8'-{5-[(Dimethylsulfamoyl)amino]-6-{2-[(propan-2-ylamino)ethoxy]pyridine-3-yl}-7'-fluoro-3'-methyl-3-phenoxy-2',3'-dihydrospiro[cyclobutane-1,1'-pyrrolo[2,3-c]quinoline]-2'-one hydrochloride | 649.45 | 1H NMR (400 MHz, DMSO-d6) δ 9.45(s, 1H), 8.94(s, 1H), 8.92(s, 2H), 8.44(t, J = 1.8 Hz, 1H), 8.22 (d, J = 8.2 Hz, 1H), 8.13 (t, J = 2.0 Hz, 1H), 8.03 (d, J = 12.1 Hz, 1H), 7.33-7.27 (m, 2H), 7.00-6.94 (m, 3H), 5.37 (p, J = 7.0 Hz, 1H), 4.62 (t, J = 4.9 Hz, 2H), 3.50-3.37 (m, 5H), 3.33 (s, 3H) 2.80 (dd, J = 14.2, 5.9 Hz, 2H), 2.71 (s, 6H), 1.31 (d, J = 6.5 Hz, 6H). |
| 403 | 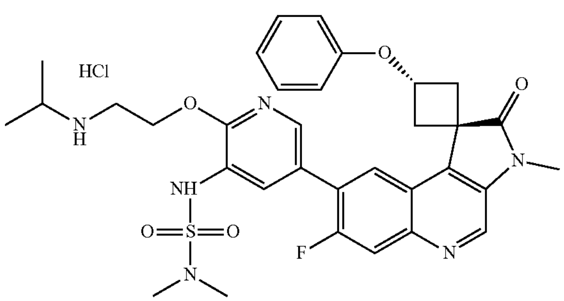 [SMILES: CC(C)NCCOc1ncc(-c2cc3c(cc2F)ncc2c3[C@]3(C[C@@H](Oc4ccccc4)C3)C(=O)N2C)cc1NS(=O)(=O)N(C)C ; Cl] | trans-S'-{5-[(Dimethylsulfamoyl)amino]-6-{2-[(propan-2-ylamino)ethoxy]pyridine-3-yl}-7'-fluoro-3'-methyl-3-phenoxy-2',3'-dihydrospiro[cyclobutane-1,1'-pyrrolo[2,3-c]quinoline]-2'-one hydrochloride | 649.45 | 1H NMR (400 MHz, DMSO-d6) δ 9.43 (s, 1H), 8.94 (s, 1H), 8.85 (s, 2H), 8.60 (d, J = 8.3 Hz, 1H), 8.29 (d, J = 2.1 Hz, 1H), 8.08 (d, J = 12.1 Hz, 2.2 Hz, 1H), 8.01 (d, J = 12.1 Hz, 1H), 7.29 (t, J = 7.8 Hz, 2H), 6.96 (t, J = 7.4 Hz, 1H), 6.87 (d, J = 8.1 Hz, 2H), 5.25-5.17 (m, 1H), 4.69 (t, J = 4.9 Hz, 2H), 3.54-3.48 (m, 3H), 3.35 (s, 3H), 3.13 (dd, J = 13.9, 7.5 Hz, 2H), 3.03 (dd, J = 14.3, 5.3 Hz, 2H), 2.75 (s, 6H), 1.34 (d, J = 6.5 Hz, 6H). |

| Examples | Structure | Name | MS: [(M + 1)]+ | 1H NMR |
|---|---|---|---|---|
| 404 | 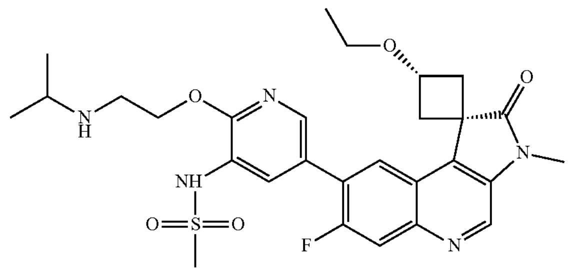 [SMILES: CCO[C@H]1C[C@]2(C1)C(=O)N(C)c1cnc3cc(F)c(-c4cnc(OCCNC(C)C)c(NS(C)(=O)=O)c4)cc3c12] | cis-N-(5-(7'-Fluoro-3-(methoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 572.25 | 1H NMR (400 MHz, DMSO-d6) δ 8.88 (s, 1H), 8.30 (d, J = 2.2 Hz, 1H), 8.24 (d, J = 8.3 Hz, 1H), 8.02-7.96 (m, 2H), 4.44 (t, J = 5.4 Hz, 2H), 3.69 (d, J = 7.6 Hz, 2H), 3.31 (s, 3H), 3.30 (s, 3H), 3.16-3.06 (m, 1H), 3.04 (s, 3H), 2.99 (t, J = 5.5 Hz, 2H), 2.97-2.83 (m, 3H), 2.31 (dd, J = 13.2, 6.3 Hz, 2H), 1.08 (d, J = 6.3 Hz, 6H). |
| 405 | 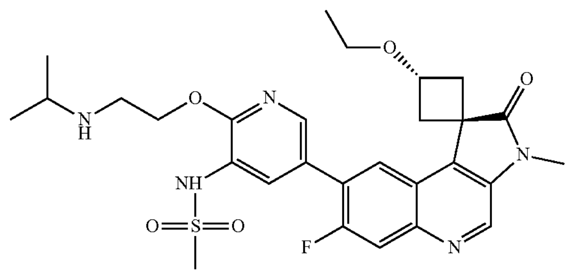 [SMILES: CCO[C@H]1C[C@@]2(C1)C(=O)N(C)c1cnc3cc(F)c(-c4cnc(OCCNC(C)C)c(NS(C)(=O)=O)c4)cc3c12] | trans-N-(5-(7'-Fluoro-3-(methoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 572.25 | 1H NMR (400 MHz, DMSO-d6) δ 8.88 (s, 1H), 8.67 (d, J = 8.4 Hz, 1H), 8.23 (d, J = 2.1 Hz, 1H), 7.95 (d, J = 12.3 Hz, 2H), 4.43 (t, J = 5.4 Hz, 2H), 3.43 (d, J = 3.0 Hz, 2H), 3.32 (s, 3H), 3.24 (s, 3H), 3.23-3.14 (m, 1H), 3.04 (s, 3H), 3.03-2.95 (m, 4H), 2.91 (p, J = 6.2 Hz, 1H), 2.35 (dd, J = 11.7, 8.6 Hz, 2H), 1.07 (d, J = 6.2 Hz, 6H). |
| 406 | 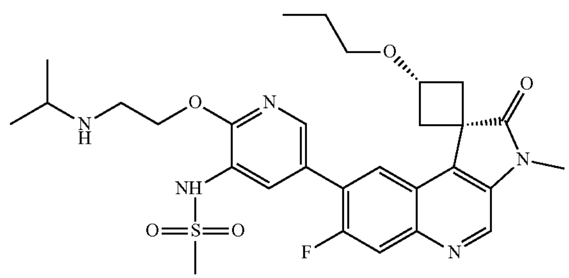 [SMILES: CCCO[C@H]1C[C@]2(C1)C(=O)N(C)c1cnc3cc(F)c(-c4cnc(OCCNC(C)C)c(NS(C)(=O)=O)c4)cc3c12] | cis-N-(5-(3-(Ethoxymethyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 586.25 | 1H NMR (400 MHz, DMSO-d6) δ 8.87 (s, 1H), 8.23 (d, J = 8.2 Hz, 1H), 8.17 (s, 1H), 7.99-7.94 (m, 2H), 4.46 (t, J = 5.2 Hz, 2H), 3.72 (d, J = 7.4 Hz, 2H), 3.50 (q, J = 7.0 Hz, 2H), 3.30 (s, 3H), 3.13-3.02 (m, 4H), 2.96 (s, 3H), 2.93-2.82 (m, 2H), 2.31 (dd, J = 13.1, 6.2 Hz, 2H), 1.17-1.11 (m, 9H). |

-continued

| Examples | Structure | Name | MS: [(M + 1)]+ | 1H NMR |
|---|---|---|---|---|
| 407 | 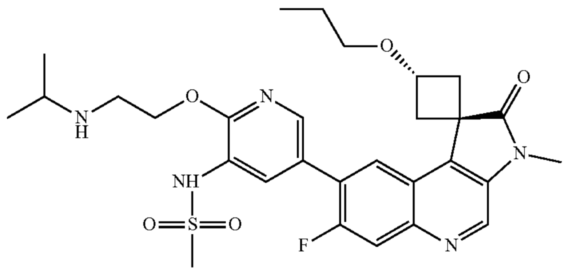 [SMILES: CCCO[C@H]1C[C@@]2(C1)C(=O)N(C)c1cnc3cc(F)c(-c4cnc(OCCNC(C)C)c(NS(C)(=O)=O)c4)cc3c12] | trans-N-(5-(3-(Ethoxymethyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 586.20 | 1H NMR (400 MHz, DMSO-$d_6$) δ 8.87 (s, 1H), 8.59 (d, J = 8.3 Hz, 1H), 8.12 (s, 1H), 7.98-7.88 (m, 2H), 4.47 (s, 2H), 3.48 (d, J = 3.7 Hz, 2H), 3.41 (q, J = 6.9 Hz, 2H), 3.32 (s, 3H), 3.26-3.07 (m, 4H), 3.02-2.91 (m, 5H), 2.38 (t, J = 10.1 Hz, 2H), 1.17 (d, J = 6.4 Hz, 6H), 0.89 (t, J = 7.0 Hz, 3H). |
| 408 | 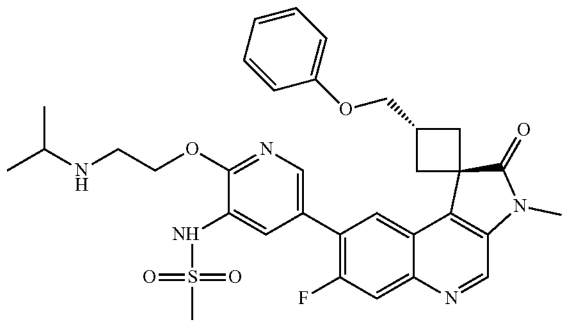 [SMILES: CC(C)NCCOc1ncc(-c2cc3c(cc2F)ncc2c3[C@]3(C[C@@H](COc4ccccc4)C3)C(=O)N2C)cc1NS(C)(=O)=O] | trans-N-(5-(7'-Fluoro-3'-methyl-2'-oxo-3-(phenoxymethyl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 634.25 | 1H NMR (400 MHz, DMSO-$d_6$) δ 8.91 (s, 1H), 8.59 (d, J = 8.2 Hz, 1H), 8.17 (s, 1H), 7.97 (d, J = 11.7 Hz, 1H), 7.92 (s, 1H), 7.10 (t, J = 7.8 Hz, 2H), 6.85 (t, J = 7.3 Hz, 1H), 6.60 (d, J = 8.1 Hz, 2H), 4.33 (t, J = 5.4 Hz, 2H), 4.09 (d, J = 3.9 Hz, 2H), 3.46 (s, 1H), 3.34 (s, 3H), 3.12 (t, J = 11.0 Hz, 2H), 3.00-2.86 (m, 6H), 2.58-2.44 (m, 2H), 1.07 (d, J = 6.2 Hz, 6H). |
| 409 | 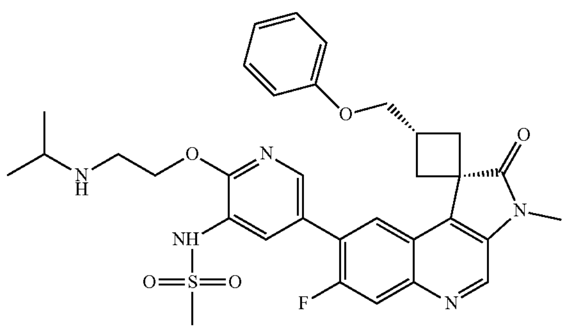 [SMILES: CC(C)NCCOc1ncc(-c2cc3c(cc2F)ncc2c3[C@]3(C[C@H](COc4ccccc4)C3)C(=O)N2C)cc1NS(C)(=O)=O] | cis-N-(5-(7'-Fluoro-3'-methyl-2'-oxo-3-(phenoxymethyl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 634.45 | 1H NMR (400 MHz, DMSO-$d_6$) δ 8.89 (s, 1H), 8.32 (d, J = 2.3 Hz, 1H), 8.28 (d, J = 8.3 Hz, 1H), 7.99 (d, J = 12.0 Hz, 2H), 7.31 (t, J = 7.8 Hz, 2H), 7.00 (d, J = 8.1 Hz, 2H), 6.95 (t, J = 7.3 Hz, 1H), 4.44 (t, J = 5.4 Hz, 2H), 4.35 (d, J = 7.5 Hz, 2H), 3.31 (s, 4H), 3.08-2.96 (m, 7H), 2.91 (p, J = 6.3 Hz, 1H), 2.43 (dd, J = 13.4, 6.1 Hz, 2H), 1.07 (d, J = 6.2 Hz, 6H). |

| Examples | Structure | Name | MS: [(M + 1)]+ | 1H NMR |
|---|---|---|---|---|
| 410 | 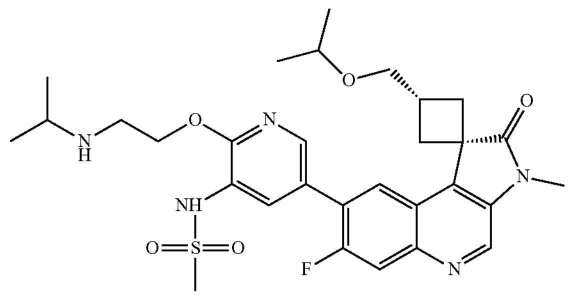 [SMILES: CC(C)NCCOc1ncc(-c2cc3c(cc2F)ncc2c3[C@]3(C[C@H](COC(C)C)C3)C(=O)N2C)cc1NS(C)(=O)=O] | cis-N-(5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 600.30 | 1H NMR (400 MHz, DMSO-d6) δ 8.88 (s, 1H), 8.33 (s, 1H), 8.28-8.20 (m, 1H), 8.03-7.94 (m, 2H), 4.45 (t, J = 5.3 Hz, 2H), 3.73 (d, J = 7.4 Hz, 2H), 3.67-3.57 (m, 2H), 3.05 (s, 3H), 3.30 (s, 3H), 3.01 (t, J = 5.2 Hz, 2H), 2.97-2.84 (m, 3H), 2.29 (dd, J = 13.1, 6.1 Hz, 2H), 1.10 (dd, J = 17.6, 6.2 Hz, 12H). |
| 411 | 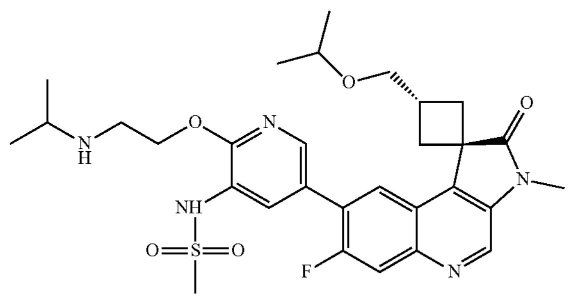 [SMILES: CC(C)NCCOc1ncc(-c2cc3c(cc2F)ncc2c3[C@]3(C[C@@H](COC(C)C)C3)C(=O)N2C)cc1NS(C)(=O)=O] | trans-N-{5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 600.25 | 1H NMR (400 MHz, DMSO-d6) δ 8.89 (s, 1H), 8.47 (d, J = 8.2 Hz, 1H), 8.20 (s, 1H), 7.95 (d, J = 11.8 Hz, 1H), 7.90 (s, 1H), 4.43 (t, J = 5.0 Hz, 2H), 3.49 (t, J = 5.2 Hz, 3H), 3.32 (s, 3H), 3.20 (s, 1H), 3.05-2.88 (m, 8H), 2.40-2.30 (m, 2H), 1.07 (d, J = 6.3 Hz, 6H), 0.88 (d, J = 6.1 Hz, 6H). |
| 412 | 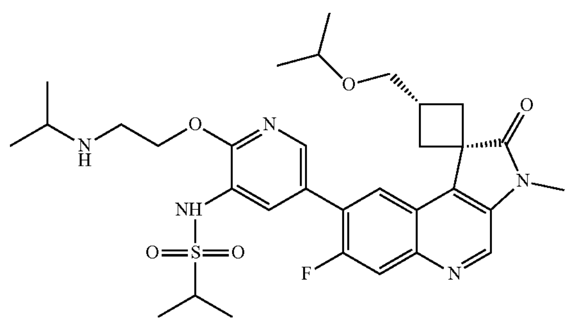 [SMILES: CC(C)NCCOc1ncc(-c2cc3c(cc2F)ncc2c3[C@]3(C[C@H](COC(C)C)C3)C(=O)N2C)cc1NS(=O)(=O)C(C)C] | cis-N-(5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)propane-2-sulfonamide | 628.15 | 1H NMR (400 MHz, DMSO) δ 8.88 (s, 1H), 8.37 (t, J = 2.0 Hz, 1H), 8.23 (d, J = 8.4 Hz, 1H), 8.08 (t, J = 2.0 Hz, 1H), 7.99 (d, J = 12.1 Hz, 1H), 4.48 (t, J = 5.4 Hz, 2H), 3.73 (d, J = 7.4 Hz, 2H), 3.62 (p, J = 6.1 Hz, 1H), 3.35-3.27 (m, 4H), 3.09-2.94 (m, 4H), 2.92-2.83 (m, 2H), 2.29 (dd, J = 13.2, 6.2 Hz, 2H), 1.30 (d, J = 6.8 Hz, 6H), 1.11 (dd, J = 7.9, 6.0 Hz, 12H). |

| Examples | Structure | Name | MS: [(M + 1)]+ | 1H NMR |
|---|---|---|---|---|
| 413 | 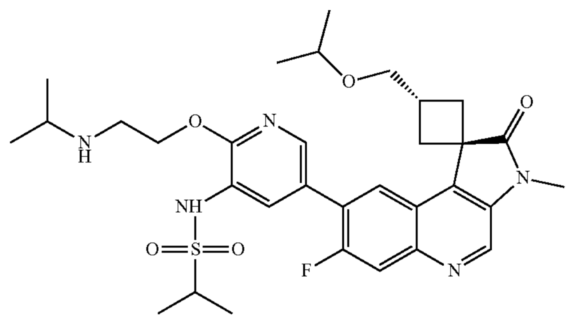 [SMILES: CC(C)NCCOc1ncc(-c2cc3c(cc2F)ncc2c3[C@]3(C[C@@H](COC(C)C)C3)C(=O)N2C)cc1NS(=O)(=O)C(C)C] | trans-N-{5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)propane-2-sulfonamide | 628.25 | 1H NMR (400 MHz, DMSO-d6) δ 8.89 (s, 1H), 8.47 (d, J = 8.3 Hz, 1H), 8.22 (d, J = 2.2 Hz, 1H), 7.99-7.91 (m, 2H), 4.42 (t, J = 5.3 Hz, 2H), 3.52-3.45 (m, 3H), 3.32 (s, 3H), 3.29-3.16 (m, 2H), 2.98-2.89 (m, 4H), 2.88-2.80 (m, 1H), 2.40-2.32 (m, 2H), 1.28 (d, J = 6.8 Hz, 6H), 1.04 (d, J = 6.2 Hz, 6H), 0.87 (d, J = 6.2 Hz, 6H). |
| 414 | 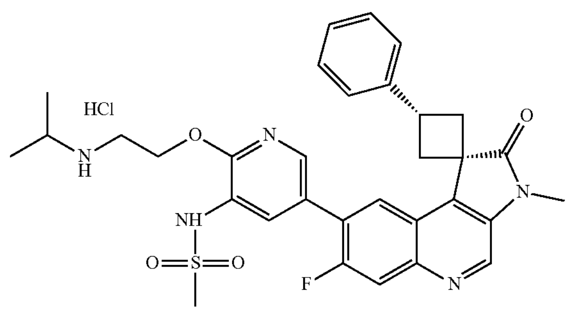 [SMILES: CC(C)NCCOc1ncc(-c2cc3c(cc2F)ncc2c3[C@]3(C[C@H](c4ccccc4)C3)C(=O)N2C)cc1NS(C)(=O)=O ; Cl] | cis-N-(5-(7'-Fluoro-3'-methyl-2'-oxo-3-phenyl-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | 604.35 | 1H NMR (400 MHz, CD3OD) δ 8.97 (s, 1H), 8.64 (s, 1H), 8.44 (s, 1H), 8.34 (s, 1H), 8.00 (d, J = 11.9 Hz, 1H), 7.73 (s, 1H), 7.38 (t, J = 7.5 Hz, 2H), 7.27 (d, J = 7.4 Hz, 2H), 4.79 (t, J = 5.2 Hz, 1H), 4.33-4.27 (m, 1H), 3.60-3.50 (m, 3H), 3.42 (s, 3H), 3.28-3.26 (m, 1H), 3.14-3.03 (m, 6H), 1.42 (d, J = 6.5 Hz, 6H). |
| 415 | 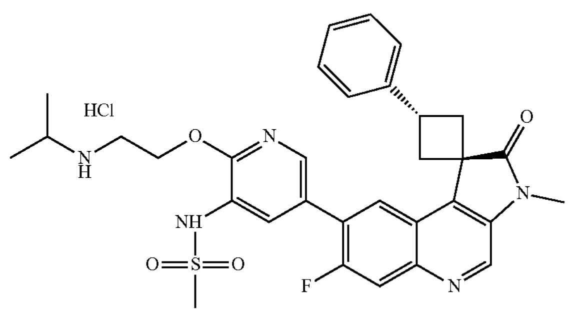 [SMILES: CC(C)NCCOc1ncc(-c2cc3c(cc2F)ncc2c3[C@]3(C[C@@H](c4ccccc4)C3)C(=O)N2C)cc1NS(C)(=O)=O ; Cl] | trans-N-(5-(7'-Fluoro-3'-methyl-2'-oxo-3-phenyl-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | 604.30 | 1H NMR (400 MHz, CD3OD) δ 8.97 (s, 1H), 8.25 (d, J = 7.7 Hz, 1H), 8.04 (s, 1H), 7.98 (s, 1H), 7.93 (d, J = 11.2 Hz, 1H), 7.38 (d, J = 10.4 Hz, 4H), 7.21 (s, 1H), 4.79 (t, J = 5.2 Hz, 2H), 4.41-4.32 (m, 1H), 3.65-3.51 (m, 4H), 3.45 (s, 3H), 3.29-3.21 (m, 1H), 3.14-3.05 (m, 5H), 1.45 (d, J = 6.5 Hz, 6H). |

| Examples | Structure | Name | MS: [(M + 1)]+ | 1H NMR |
|---|---|---|---|---|
| 416 | 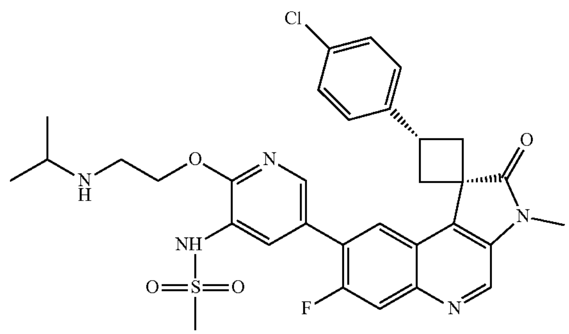 [SMILES: CC(C)NCCOc1ncc(-c2cc3c(cc2F)ncc2c3[C@]3(C[C@H](c4ccc(Cl)cc4)C3)C(=O)N2C)cc1NS(C)(=O)=O] | cis-N-(5-(4-(Chlorophenyl)-7-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 638.15, 640.15 | 1H NMR (400 MHz, DMSO-$d_6$) δ 8.92 (s, 1H), 8.39-8.34 (m, 2H), 8.08 (t, J = 1.7 Hz, 1H), 8.01 (d, J = 12.1 Hz, 1H), 7.75 (d, J = 8.3 Hz, 2H), 7.46 (d, J = 8.2 Hz, 2H), 4.45 (t, J = 5.3 Hz, 2H), 4.22 (p, J = 9.1 Hz, 1H), 3.34 (s, 3H), 3.26 (dd, J = 13.0, 10.2 Hz, 2H), 3.04 (s, 3H), 3.00 (t, J = 5.3 Hz, 2H), 2.98-2.89 (m, 1H), 2.81 (dd, J = 13.2, 8.2 Hz, 2H), 1.08 (d, J = 6.2 Hz, 6H). |
| 417 | 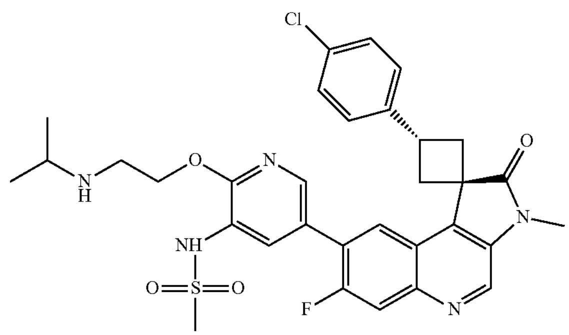 [SMILES: CC(C)NCCOc1ncc(-c2cc3c(cc2F)ncc2c3[C@]3(C[C@@H](c4ccc(Cl)cc4)C3)C(=O)N2C)cc1NS(C)(=O)=O] | trans-N-(5-(4-(Chlorophenyl)-7-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 638.10, 640.10 | 1H NMR (400 MHz, DMSO-$d_6$) δ 8.92 (s, 1H), 8.13-8.06 (m, 2H), 7.97 (d, J = 12.0 Hz, 1H), 7.88 (d, J = 2.4 Hz, 1H), 7.50 (d, J = 8.1 Hz, 2H), 7.39 (d, J = 8.1 Hz, 2H), 4.51 (1J = 5.3 Hz, 2H), 4.22 (p, J = 9.5 Hz, 1H), 3.35 (s, 3H), 3.17 (dd, J = 12.6, 9.4 Hz, 2H), 3.06-2.98 (m, 5H), 2.98-2.84 (m, 3H), 1.08 (d, J = 6.2 Hz, 6H). |
| 418 | 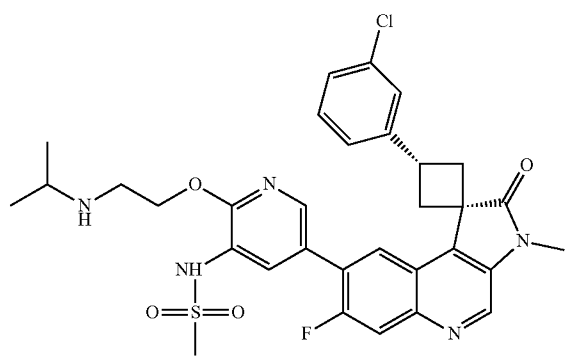 | cis-N-(5-(3-(Chlorophenyl)-7-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 638.35, 640.35 | 1H NMR (400 MHz, DMSO-$d_6$) δ 8.92 (s, 1H), 8.36 (d, J = 8.2 Hz, 1H), 8.32 (s, 1H), 8.07 (s, 1H), 8.01 (d, J = 12.2 Hz, 1H), 7.86 (d, J = 2.0 Hz, 1H), 7.68 (d, J = 7.8 Hz, 1H), 7.42 (t, J = 7.8 Hz, 1H), 7.35-7.31 (m, 1H), 4.44 (t, J = 5.4 Hz, 2H), 4.29-4.19 (m, 1H), 3.34 (s, 3H), 3.26 (dd, J = 13.3, 10.2 Hz, 2H), 3.02 (s, 3H), 2.99(1J = 5.4 Hz, 2H), 2.96-2.87 (m, 1H), 2.82 (ddJ = 13.5, 8.1 Hz, 2H), 1.08 (dJ = 6.3 Hz, 6H). |

| Examples | Structure | Name | MS: [(M + 1)]+ | 1H NMR |
|---|---|---|---|---|
| 419 | 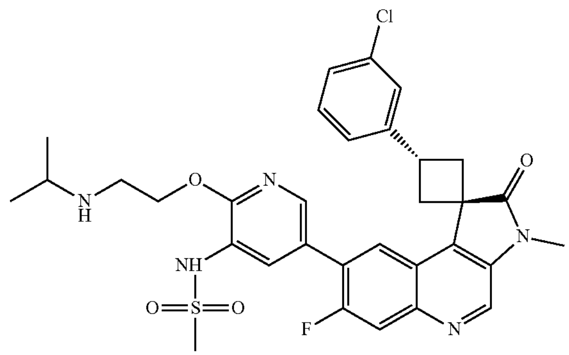 [SMILES: CC(C)NCCOc1ncc(-c2cc3c(cc2F)ncc2c3[C@]3(C[C@@H](c4cccc(Cl)c4)C3)C(=O)N2C)cc1NS(C)(=O)=O] | trans-N-(5-(3-(3-Chlorophenyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 638.35, 640.35 | 1H NMR (400 MHz, DMSO-d6) δ 8.91 (s, 1H), 8.06 (d, J = 8.3 Hz, 1H), 8.00-7.89 (m, 2H), 7.81 (d, J = 2.7 Hz, 1H), 7.48-7.34 (m, 3H), 7.26 (d, J = 7.9 Hz, 1H), 4.47 (t, J = 5.3 Hz, 2H), 4.25 (p, J = 9.7 Hz, 1H), 3.35 (s, 3H), 3.17 (dd, J = 12.5, 9.3 Hz, 2H), 2.98-2.84 (m, 6H), 1.10 (d, J = 6.3 Hz, 6H). |
| 420 | 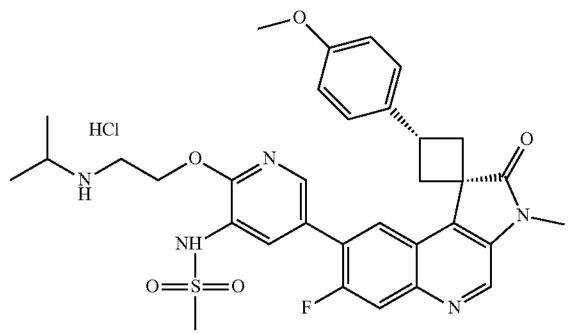 [SMILES: COc1ccc([C@H]2C[C@]3(C2)C(=O)N(C)c2cnc4cc(F)c(-c5cnc(OCCNC(C)C)c(NS(C)(=O)=O)c5)cc4c23)cc1 ; Cl] | cis-N-(5-(7'-Fluoro-3-(4-methoxyphenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | 634.30 | 1H NMR (400 MHz, CD3OD) δ 8.73 (s, 1H), 8.44 (d, J = 8.0 Hz, 1H), 8.32 (t, J = 2.3 Hz, 1H), 8.24-8.19 (m, 1H), 7.82 (d, J = 11.9 Hz, 1H), 7.57 (d, J = 8.4 Hz, 2H), 6.87-6.80 (m, 2H), 4.69 (t, J = 5.1 Hz, 2H), 4.13 (p, J = 9.3 Hz, 1H), 3.71 (s, 3H), 3.51-3.39 (m, 3H), 3.31 (s, 3H), 3.12 (dd, J = 13.3, 10.0 Hz, 2H), 3.04 (s, 3H), 2.90 (dd, J = 13.7, 8.4 Hz, 2H), 1.33 (d, J = 6.6 Hz, 6H). |
| 421 | 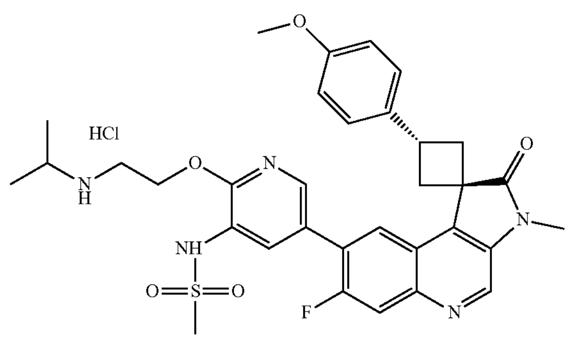 [SMILES: COc1ccc([C@H]2C[C@@]3(C2)C(=O)N(C)c2cnc4cc(F)c(-c5cnc(OCCNC(C)C)c(NS(C)(=O)=O)c5)cc4c23)cc1 ; Cl] | trans-N-(5-(7'-Fluoro-3-(4-methoxyphenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | 634.30 | 1H NMR (400 MHz, CD3OD) δ 8.73 (s, 1H), 8.11 (d, J = 8.1 Hz, 1H), 7.97 (t, J = 2.1 Hz, 1H), 7.86 (dd, J = 2.2, 1.0 Hz, 1H), 7.76 (d, J = 11.8 Hz, 1H), 7.22 (d, J = 8.4 Hz, 2H), 6.85-6.80 (m, 2H), 4.75-4.68 (m, 2H), 4.17 (p, J = 9.4 Hz, 1H), 3.69 (s, 3H), 3.57-3.41 (m, 3H), 3.33 (s, 3H), 3.13-3.03 (m, 2H), 3.00 (s, 3H), 2.93 (td, J = 9.9, 2.4 Hz, 2H), 1.34 (d, J = 6.6 Hz, 6H). |

| Examples | Structure | Name | MS: [(M + 1)]+ | 1H NMR |
|---|---|---|---|---|
| 422 | 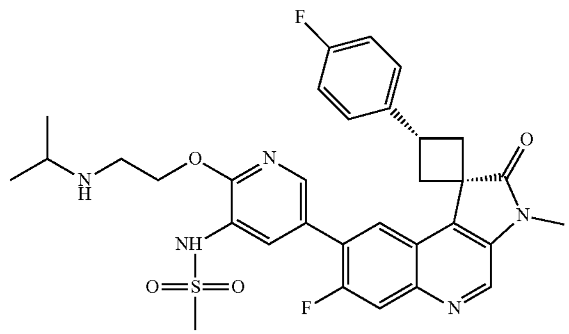 | cis-N-(5-(7'-Fluoro-3-(4-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 622.40 | 1H NMR (400 MHz, DMSO-$d_6$) δ 8.92 (s, 1H), 8.37 (d, J = 8.2 Hz, 1H), 8.34 (d, J = 2.4 Hz, 1H), 8.07 (t, J = 1.8 Hz, 1H), 8.01 (d, J = 12.1 Hz, 1H), 7.81-7.75 (m, 2H), 7.26-7.19 (m, 2H), 4.44 (t, J = 5.4 Hz, 2H), 4.22 (p, J = 9.2 Hz, 1H), 3.34 (s, 3H), 3.31-3.21 (m, 2H), 3.03 (s, 3H), 2.98 (t, J = 5.4 Hz, 2H), 2.91 (p, J = 6.3 Hz, 1H), 2.81 (dd, J = 13.3, 8.2 Hz, 2H), 1.07 (d, J = 6.3 Hz, 6H). |
| 423 | 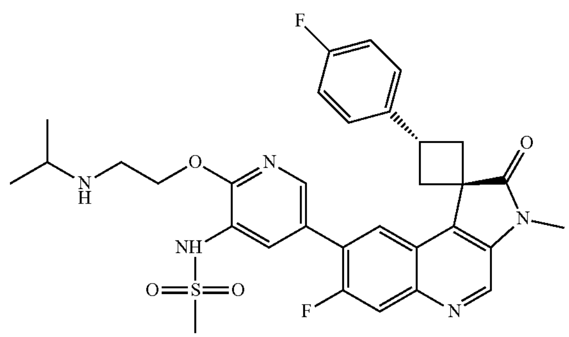 | trans-N-(5-(7'-Fluoro-3-(4-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 622.40 | 1H NMR (400 MHz, DMSO-$d_6$) δ 8.92 (s, 1H), 8.09 (d, J = 8.2 Hz, 1H), 8.03 (d, J = 2.1 Hz, 1H), 7.97 (d, J = 12.1 Hz, 1H), 7.88 (t, J = 2.3 Hz, 1H), 7.54-7.45 (m, 2H), 7.15 (t, J = 8.8Hz, 2H), 4.48 (t, J = 5.3 Hz, 2H), 4.28-4.16 (m, 1H), 3.36 (s, 3H), 3.16 (dd, J = 12.6, 9.6 Hz, 2H), 3.02 (s, 5H), 2.97-2.86 (m, 3H), 1.08 (d, J = 6.2 Hz, 6H). |
| 424 | 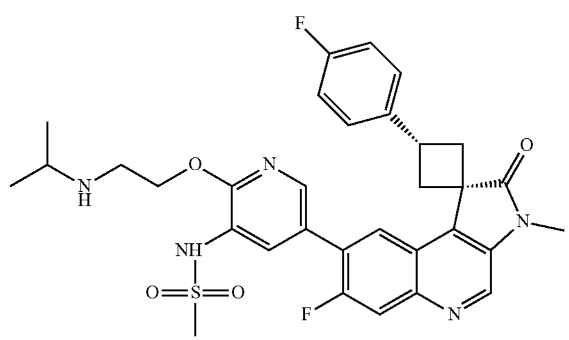 | cis-N-(5-(7'-Fluoro-3-(3-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 622.20 | 1H NMR (400 MHz, DMSO-$d_6$) δ 8.92 (s, 1H), 8.35 (t, J = 5.8 Hz, 2H), 8.08 (s, 1H), 8.01 (d, J = 12.1 Hz, 1H), 7.64 (d, J = 10.5 Hz, 1H), 7.53 (d, J = 7.7 Hz, 1H), 7.42 (q, J = 7.5 Hz, 1H), 7.09 (td, J = 8.6, 2.5 Hz, 1H), 4.45 (t, J = 5.4 Hz, 2H), 4.24 (p, J = 9.0 Hz, 1H), 3.32 (s, 3H), 3.26 (dd, J = 13.2, 10.1 Hz, 2H), 3.04 (s, 3H), 2.99 (t, J = 5.4 Hz, 2H), 2.97-2.89 (m, 1H), 2.83 (dd, J = 13.3, 8.1 Hz, 2H), 1.08 (d, J = 6.2 Hz, 6H). |

| Examples | Structure | Name | MS: [(M + 1)]+ | 1H NMR |
|---|---|---|---|---|
| 425 | 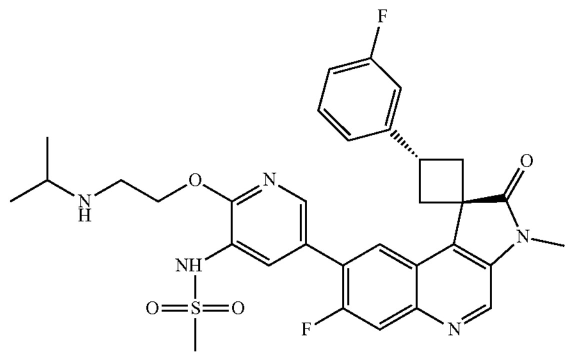 | trans-N-(5-(7'-Fluoro-3-(3-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 622.20 | 1H NMR (400 MHz, DMSO-d6) δ 8.91 (s, 1H), 8.07 (d, J = 8.2 Hz, 1H), 7.96 (d, J = 11.9 Hz, 2H), 7.82 (d, J = 2.5 Hz, 1H), 7.39 (q, J = 7.4 Hz, 1H), 7.31 (d, J = 7.8 Hz, 1H), 7.21 (d, J = 10.4 Hz, 1H), 7.01 (td, J = 8.5, 2.4 Hz, 1H), 4.48 (t, J = 5.3 Hz, 2H), 4.24 (p, J = 9.5 Hz, 1H), 3.35 (s, 3H), 3.18 (dd, J = 12.4, 9.5 Hz, 2H), 3.03 (t, J = 5.4 Hz, 2H), 3.00-2.84 (m, 6H), 1.10 (d, J = 6.3 Hz, 6H). |
| 426 | 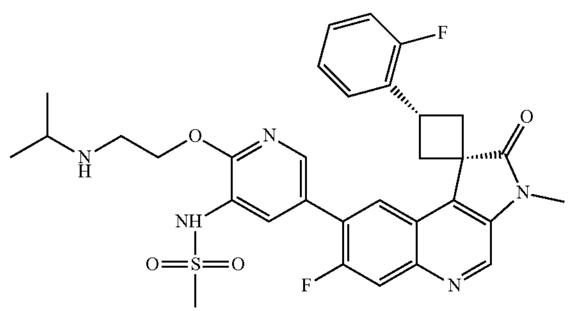 | cis-N-(5-(7'-Fluoro-3-(2-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 622.25 | 1H NMR (400 MHz, DMSO-d6) δ 8.93 (s, 1H), 8.39 (d, J = 8.3 Hz, 1H), 8.36 (d, J = 2.0 Hz, 1H), 8.06-8.00 (m, 2H), 7.88 (t, J = 8.6 Hz, 1H), 7.37-7.29 (m, 2H), 7.21-7.15 (m, 1H), 4.50-4.42 (m, 3H), 3.32 (s, 3H), 3.26 (t, J = 11.5 Hz, 2H), 3.01 (s, 5H), 2.98-2.84 (m, 3H), 1.08 (d, J = 6.3 Hz, 6H). |
| 427 | 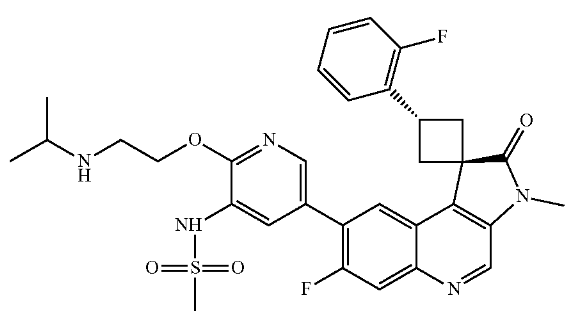 [SMILES: CC(C)NCCOc1ncc(-c2cc3c(cc2F)ncc2c3[C@]3(C[C@@H](c4ccccc4F)C3)C(=O)N2C)cc1NS(C)(=O)=O] | trans-N-(5-(7'-Fluoro-3-(2-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 622.25 | 1H NMR (400 MHz, DMSO-d6) δ 8.94 (s, 1H), 8.18 (s, 1H), 8.15 (d, J = 8.1 Hz, 1H), 7.99 (d, J = 12.0 Hz, 1H), 7.91 (t, J = 3.4 Hz, 1H), 7.70 (t, J = 7.5 Hz, 1H), 7.33-7.14 (m, 3H), 4.52 (t, J = 6.8 Hz, 2H), 4.40 (p, J = 9.5 Hz, 1H), 3.37 (s, 3H), 3.27 (t, J = 11.2 Hz, 2H), 3.16-3.10 (m, 3H), 3.06 (s, 3H), 2.88 (t, J = 10.6 Hz, 2H), 1.15 (d, J = 6.3 Hz, 6H). |

| Examples | Structure | Name | MS: [(M + 1)]+ | 1H NMR |
|---|---|---|---|---|
| 428 | 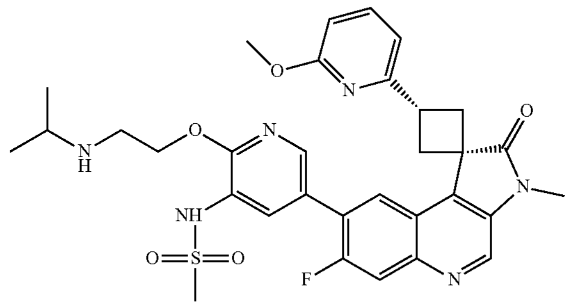 [SMILES: COc1cccc([C@H]2C[C@]3(C2)C(=O)N(C)c2cnc4cc(F)c(-c5cnc(OCCNC(C)C)c(NS(C)(=O)=O)c5)cc4c23)n1] | cis-N-(5-(7'-Fluoro-3-(6-methoxypyridin-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 635.40 | 1H NMR (400 MHz, DMSO-d6) δ 8.91 (s, 1H), 8.39 (d, J = 8.3 Hz, 1H), 8.34 (t, J = 2.1 Hz, 1H), 8.05-7.98 (m, 2H), 7.72 (dd, J = 8.2, 7.3 Hz, 1H), 7.20 (d, J = 7.2 Hz, 1H), 6.69 (d, J = 8.2 Hz, 1H), 4.44 (t, J = 5.4 Hz, 2H), 4.24 (p, J = 9.0 Hz, 1H), 3.93 (s, 3H), 3.31 (s, 3H), 3.16 (dd, J = 12.9, 9.9 Hz, 2H), 3.11-2.96 (m, 7H), 2.92 (p, J = 6.3 Hz, 1H), 1.07 (d, J = 6.2 Hz, 6H). |
| 429 | 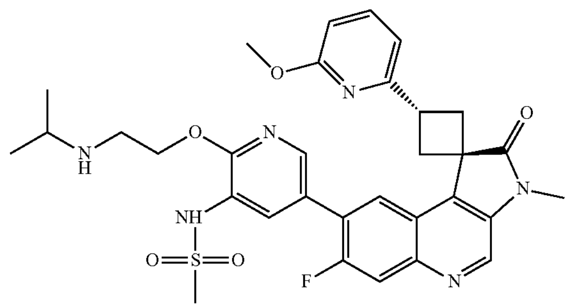 [SMILES: COc1cccc([C@H]2C[C@@]3(C2)C(=O)N(C)c2cnc4cc(F)c(-c5cnc(OCCNC(C)C)c(NS(C)(=O)=O)c5)cc4c23)n1] | trans-N-(5-(7'-Fluoro-3-(6-methoxypyridin-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 635.35 | 1H NMR (400 MHz, DMSO-d6) δ 8.92 (s, 1H), 8.48 (d, J = 8.3 Hz, 1H), 7.96 (d, J = 11.8 Hz, 1H), 7.92 (s, 1H), 7.79 (t, J = 2.2 Hz, 1H), 7.66 (dd, J = 8.2, 7.2 Hz, 1H), 7.02 (d, J = 7.1 Hz, 1H), 6.60 (d, J = 8.1 Hz, 1H), 4.45 (t, J = 5.4 Hz, 2H), 4.27 (p, J = 9.1 Hz, 1H), 3.45-3.39 (m, 2H), 3.36 (s, 3H), 3.34 (s, 3H), 3.02 (t, J = 5.4 Hz, 2H), 2.99-2.90 (m, 4H), 2.79-2.69 (m, 2H), 1.09 (d, J = 6.3 Hz, 6H). |
| 430 | 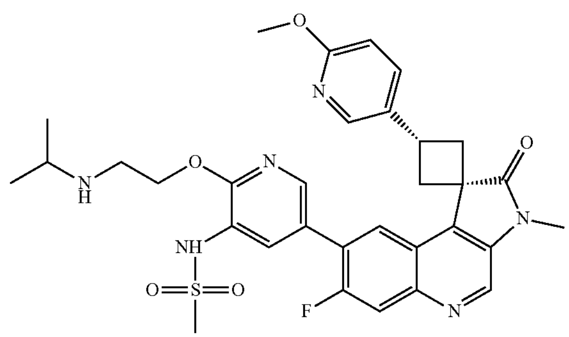 [SMILES: COc1ccc([C@H]2C[C@]3(C2)C(=O)N(C)c2cnc4cc(F)c(-c5cnc(OCCNC(C)C)c(NS(C)(=O)=O)c5)cc4c23)cn1] | cis-N-(5-(7'-Fluoro-3-(6-methoxypyridin-3-yl))-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 635.40 | 1H NMR (400 MHz, DMSO-d6) δ 8.92 (s, 1H), 8.20 (d, J = 1.7 Hz, 1H), 8.13 (d, J = 8.3 Hz, 1H), 8.10-8.06 (m, 1H), 7.98 (d, J = 12.1 Hz, 1H), 7.90 (t, J = 2.4 Hz, 1H), 7.86 (dd, J = 8.5, 2.5 Hz, 1H), 6.81 (d, J = 8.5 Hz, 1H), 4.47 (t, J = 5.0 Hz, 2H), 4.22 (p, J = 9.1 Hz, 1H), 3.82 (s, 3H), 3.36 (s, 3H), 3.20 (t, J = 11.1 Hz, 2H), 3.03 (s, 5H), 3.00-2.82 (m, 3H), 1.09 (d, J = 6.3 Hz, 6H). |

| Examples | Structure | Name | MS: [(M + 1)]+ | 1H NMR |
|---|---|---|---|---|
| 431 | 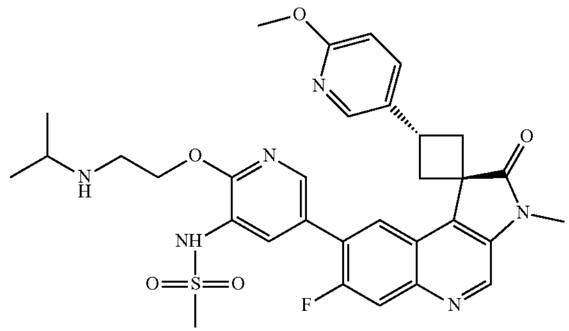 [SMILES: COc1ccc([C@H]2C[C@@]3(C2)C(=O)N(C)c2cnc4cc(F)c(-c5cnc(OCCNC(C)C)c(NS(C)(=O)=O)c5)cc4c23)cn1] | trans-N-(5-(7'-Fluoro-3-(6-methoxypyridin-3-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 635.40 | 1H NMR (400 MHz, DMSO-d6) δ 8.92 (s, 1H), 8.39-8.30 (m, 4H), 8.12-8.09 (m, 1H), 8.01 (d, J = 12.1 Hz, 1H), 6.91 (d, J = 8.5 Hz, 1H), 4.45 (t, J = 5.4 Hz, 2H), 4.19 (p, J = 9.1 Hz, 1H), 3.86 (s, 3H), 3.27 (t, J = 11.5 Hz, 2H), 3.34 (s, 3H), 3.06 (s, 3H), 2.99 (t, J = 5.2 Hz, 2H), 2.96-2.87 (m, 1H), 2.78 (dd, J = 13.3, 8.0Hz, 2H), 1.08 (d, J = 6.2 Hz, 6H). |
| 432 | 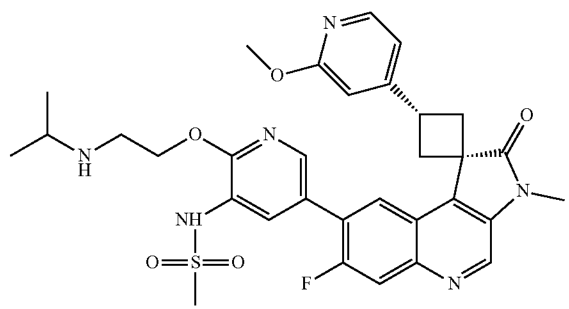 [SMILES: COc1cc([C@H]2C[C@]3(C2)C(=O)N(C)c2cnc4cc(F)c(-c5cnc(OCCNC(C)C)c(NS(C)(=O)=O)c5)cc4c23)ccn1] | cis-N-(5-(7'-Fluoro-3-(2-methoxypyridin-4-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 635.20 | 1H NMR (400 MHz, DMSO-d6) δ 8.92 (s, 1H), 8.13 (d, J = 5.2 Hz, 1H), 8.06 (d, J = 8.2 Hz, 2H), 7.97 (d, J = 12.0 Hz, 1H), 7.85 (t, J = 2.3 Hz, 1H), 7.10 (dd, J = 5.4, 1.4 Hz, 1H), 6.80 (s, 1H), 4.46 (t, J = 5.4 Hz, 2H), 4.19 (p, J = 9.5 Hz, 1H), 3.81 (s, 3H), 3.35 (s, 3H), 3.19 (dd, J = 12.7, 9.8 Hz, 2H), 3.05-2.99 (m, 5H), 2.97-2.81 (m, 3H), 1.08 (d, J = 6.3 Hz, 6H). |
| 433 | 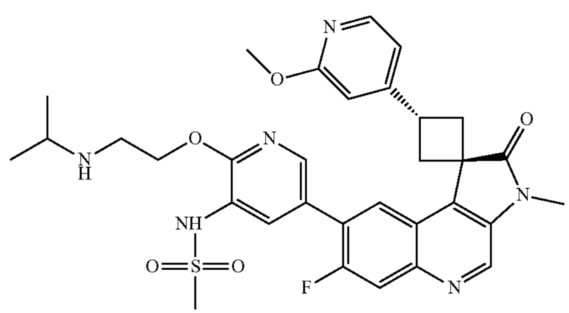 [SMILES: COc1cc([C@H]2C[C@@]3(C2)C(=O)N(C)c2cnc4cc(F)c(-c5cnc(OCCNC(C)C)c(NS(C)(=O)=O)c5)cc4c23)ccn1] | trans-N-(5-(7'-Fluoro-3-(2-methoxypyridin-4-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 635.25 | 1H NMR (400 MHz, DMSO-d6) δ 8.92 (s, 1H), 8.39-8.30 (m, 2H), 8.17 (d, J = 5.3 Hz, 1H), 8.09 (t, J = 1.7 Hz, 1H), 8.01 (d, J = 12.2 Hz, 1H), 7.33 (dd, J = 5.4, 1.4 Hz, 1H), 7.12 (s, 1H), 4.44 (t, J = 5.4 Hz, 2H), 4.19 (p, J = 9.2 Hz, 1H), 3.87 (s, 3H), 3.33 (s, 3H), 3.30-3.20 (m, 2H), 3.04 (s, 3H), 2.99 (t, J = 5.4 Hz, 2H), 2.91 (p, J = 6.1 Hz, 1H), 2.81 (dd, J = 13.3, 8.0 Hz, 2H), 1.07 (d, J = 6.2 Hz, 6H). |

| Examples | Structure | Name | MS: [(M + 1)]+ | 1H NMR |
|---|---|---|---|---|
| 434 | 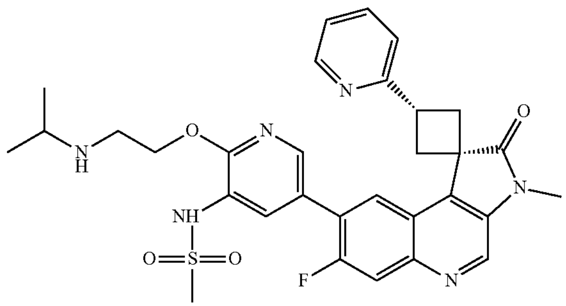 | cis-N-(5-(7'-Fluoro-3'-methyl-2'-oxo-3-(pyridin-2-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 605.25 | 1H NMR (400 MHz, DMSO-d6) δ 8.91 (s, 1H), 8.58-8.51 (m 1H), 8.40 (d, J = 8.2 Hz, 1H), 8.33 (d, J = 2.0 Hz, 1H), 8.05-7.99 (m, 2H), 7.84 (td, J = 7.7, 1.9 Hz, 1H), 7.69 (d, J = 7.9 Hz, 1H), 7.32-7.24 (m, 1H), 4.44 (t, J = 5.3 Hz, 2H), 4.33 (p, J = 9.1 Hz, 1H), 3.31 (s, 3H), 3.21 (dd, J = 13.0, 10.1 Hz, 2H), 3.06-2.97 (m, 7H), 2.92 (p, J = 6.2 Hz, 1H), 1.07 (d, J = 6.2 Hz, 6H). |
| 435 | 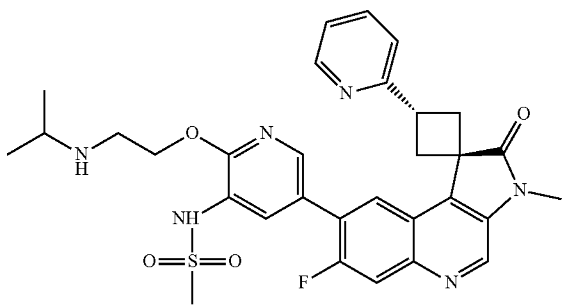 [SMILES: CC(C)NCCOc1ncc(-c2cc3c(cc2F)ncc2c3[C@]3(C[C@@H](c4ccccn4)C3)C(=O)N2C)cc1NS(C)(=O)=O] | trans-N-(5-(7'-Fluoro-3'-methyl-2'-oxo-3-(pyridin-2-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 605.20 | 1H NMR (400 MHz, DMSO-d6) δ 9.38 (d, J = 8.5 Hz, 1H), 8.91 (s, 1H), 8.54 (t, J = 2.8 Hz, 1H), 8.40 (d, J = 2.2 Hz, 1H), 8.00 (t, J = 2.3 Hz, 1H), 7.97 (d, J = 12.1 Hz, 1H), 7.74 (td, J = 7.5, 1.8 Hz, 1H), 7.43 (d, J = 7.7 Hz, 1H), 7.30-7.21 (m, 1H), 4.54 (t, J = 5.4 Hz, 2H), 4.25 (p, J = 9.2 Hz, 1H), 3.43-3.34 (m, 5H), 3.08-3.03 (m, 5H), 2.94 (p, J = 6.2 Hz, 1H), 2.74 (t, J = 10.4 Hz, 2H), 1.10 (d, J = 6.2 Hz, 6H). |
| 436 | 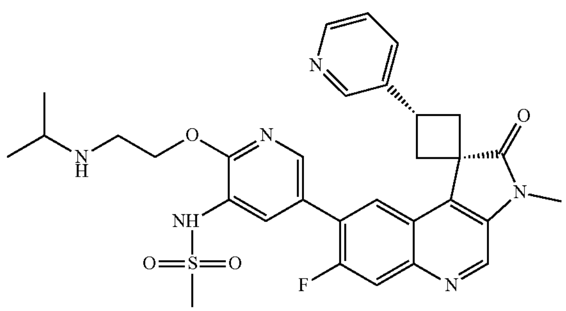 [SMILES: CC(C)NCCOc1ncc(-c2cc3c(cc2F)ncc2c3[C@]3(C[C@H](c4cccnc4)C3)C(=O)N2C)cc1NS(C)(=O)=O] | cis-N-(5-(7'-Fluoro-3'-methyl-2'-oxo-3-(pyridin-3-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 605.30 | 1H NMR (400 MHz, DMSO-d6) δ 8.92 (s, 1H), 8.83 (d, J = 2.3 Hz, 1H), 8.49 (dd, J = 4.8, 1.6 Hz, 1H), 8.42-8.35 (m, 2H), 8.32-8.24 (m, 1H), 8.12 (s, 1H), 8.02 (d, J = 12.2 Hz, 1H), 7.46 (dd, J = 7.9, 4.8 Hz, 1H), 4.46 (t, J = 5.4 Hz, 2H), 4.27 (p, J = 9.3 Hz, 1H), 3.36-3.25 (m, 5H), 3.07 (s, 3H), 3.01 (t, J = 5.4 Hz, 2H), 2.93 (p, J = 6.4 Hz, 1H), 2.84 (dd, J = 13.3, 8.0 Hz, 2H), 1.08 (d, J = 6.3 Hz, 6H). |

| Examples | Structure | Name | MS: [(M + 1)]+ | 1H NMR |
|---|---|---|---|---|
| 437 | 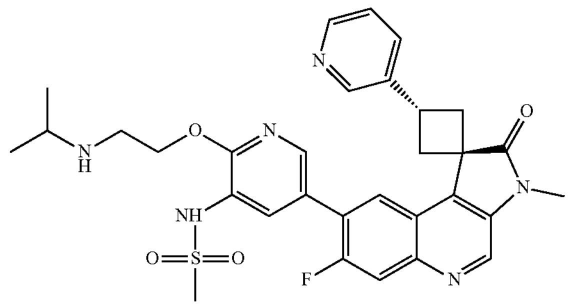 [SMILES: CC(C)NCCOc1ncc(-c2cc3c(cc2F)ncc2c3[C@]3(C[C@@H](c4cccnc4)C3)C(=O)N2C)cc1NS(C)(=O)=O] | trans-N-{5-(7'-Fluoro-3'-methyl-2'-oxo-3-(pyridin-3-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 605.30 | 1H NMR (400 MHz, DMSO-$d_6$) δ 8.92 (s, 1H), 8.62 (d, J = 2.4 Hz, 1H), 8.44 (d, J = 4.6 Hz, 1H), 8.08 (d, J = 8.1 Hz, 2H), 7.96 (t, J = 10.0 Hz, 2H), 7.87 (s, 1H), 7.38 (dd, J = 7.9, 5.0 Hz, 1H), 4.48 (t, J = 5.3 Hz, 2H), 4.30 (p, J = 9.2 Hz, 1H), 3.36 (s, 3H), 3.30-3.19 (m, 2H), 3.04 (s, 5H), 2.98-2.87 (m, 3H), 1.10 (d, J = 6.2 Hz, 6H). |
| 438 | 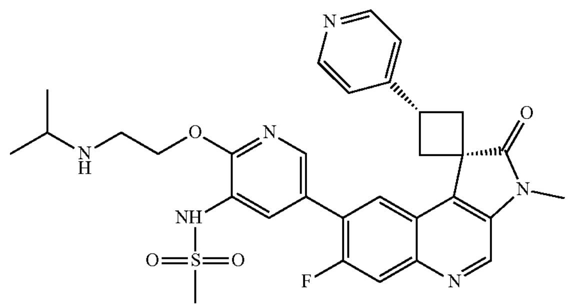 | cis-N-(5-(7'-Fluoro-3'-methyl-2'-oxo-3-(pyridin-4-yl)-2',3'-dihydrospirocyclobutane-1,1'-pyrrolo[2,3-c]quinolin]-8'-yl)-2-(2-(isopropylamino)ethoxy)pyridin-3-yl)methanesulfonamide | 605.35 | 1H NMR (400 MHz, DMSO-$d_6$) δ 8.92 (s, 1H), 8.55-8.49 (m, 2H), 8.12 (d, J = 2.2 Hz, 1H), 8.06 (d, J = 8.2 Hz, 1H), 7.96 (d, J = 12.0 Hz, 1H), 7.87 (t, J = 2.2 Hz, 1H), 7.51-7.45 (m, 2H), 4.48 (t, J = 5.4 Hz, 2H), 4.25 (p, J = 9.4 Hz, 1H), 3.36 (s, 3H), 3.28-3.17 (m, 2H), 3.05-2.98 (m, 5H), 2.98-2.84 (m, 3H), 1.10 (d, J = 6.3 Hz, 6H). |
| 439 | 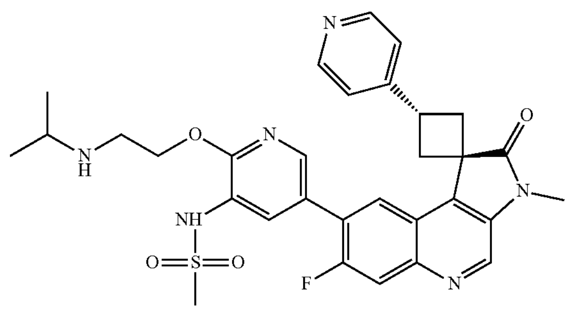 [SMILES: CC(C)NCCOc1ncc(-c2cc3c(cc2F)ncc2c3[C@]3(C[C@@H](c4ccncc4)C3)C(=O)N2C)cc1NS(C)(=O)=O] | trans-N-{5-(7'-Fluoro-3'-methyl-2'-oxo-3-(pyridin-4-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 605.25 | 1H NMR (400 MHz, DMSO-$d_6$) δ 8.91 (s, 1H), 8.61-8.54 (m, 2H), 8.39-8.29 (m, 2H), 8.07 (t, J = 1.8 Hz, 1H), 8.00 (d, J = 12.1 Hz, 1H), 7.73-7.66 (m, 2H), 4.45 (t, J = 5.4 Hz, 2H), 4.24 (p, J = 9.3 Hz, 1H), 3.33 (s, 3H), 3.28 (dd, J = 13.3, 10.3 Hz, 2H), 3.02 (s, 3H), 2.98 (t, J = 5.4 Hz, 2H), 2.83 (dd, J = 13.3, 8.0 Hz, 2H), 2.96-2.87 (m, 1H), 1.07 (d, J = 6.2 Hz, 6H) |

-continued

| Examples | Structure | Name | MS: [(M + 1)]+ | 1H NMR |
|---|---|---|---|---|
| 440 | 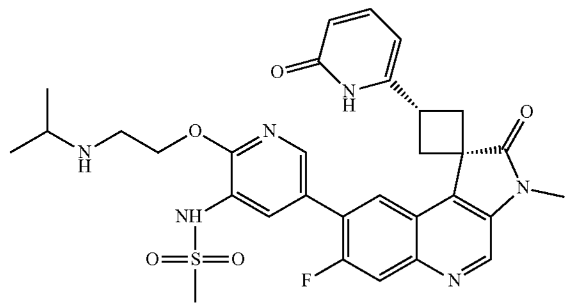 [SMILES: CC(C)NCCOc1ncc(-c2cc3c(cc2F)ncc2c3[C@]3(C[C@H](c4cccc(=O)[nH]4)C3)C(=O)N2C)cc1NS(C)(=O)=O] | cis-N-(5-(7'-Fluoro-3'-methyl-2'-oxo-3-(6-oxo-1,6-dihydropyridin-2-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 621.35 | 1H NMR (400 MHz, DMSO-d6) δ 11.67 (s, 1H), 8.93 (s, 1H), 8.39 (s, 1H), 8.29 (d, J = 8.2 Hz, 1H), 8.05-7.99 (m, 2H), 7.48 (dd, J = 9.1, 6.8 Hz, 1H), 6.38 (d, J = 6.7 Hz, 1H), 6.23 (d, J = 9.1 Hz, 1H), 4.45 (t, J = 5.4 Hz, 2H), 4.15 (p, J = 9.2 Hz, 1H), 3.34 (s, 3H), 3.04 (s, 3H), 2.99 (t, J = 5.3 Hz, 2H), 2.91 (p, J = 6.3 Hz, 1H), 2.79 (dd, J = 13.4, 8.0 Hz, 2H), 1.07 (d, J = 6.2 Hz, 6H). |
| 441 | 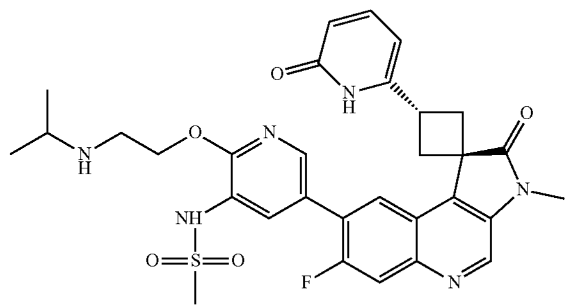 [SMILES: CC(C)NCCOc1ncc(-c2cc3c(cc2F)ncc2c3[C@]3(C[C@@H](c4cccc(=O)[nH]4)C3)C(=O)N2C)cc1NS(C)(=O)=O] | trans-N-(5-(7'-Fluoro-3'-methyl-2'-oxo-3-(6-oxo-1,6-dihydropyridin-2-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 621.35 | 1H NMR (400 MHz, DMSO-d6) δ 11.57(s, 1H), 8.91 (s, 1H), 8.20-8.14 (m, 2H), 7.97 (d, J = 12.0 Hz, 1H), 7.89 (t, J = 2.2 Hz, 1H), 7.38 (dd, J = 9.2, 6.8 Hz, 1H), 6.48 (d, J = 6.8 Hz, 1H), 6.15 (d, J = 9.1 Hz, 1H) 4.46 ft, J = 5.4 Hz, 2H), 4.00 (p, J = 9.3 Hz, 1H), 3.34 (s, 3H), 3.16 (dd, J = 12.7, 9.5 Hz, 2H), 3.04-2.98 (m, 5H), 2.92 (p, J = 6.3 Hz, 1H), 2.86-2.78 (m, 2H), 1.08 (d, J = 6.2 Hz, 6H). |
| 442 | 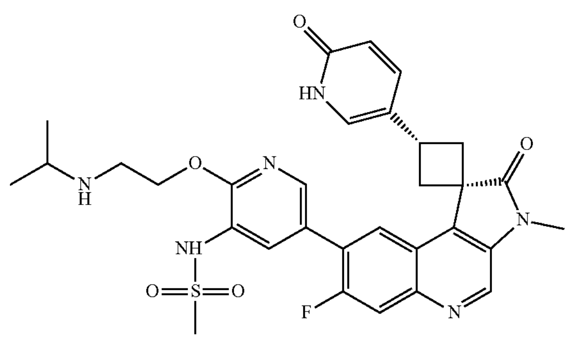 [SMILES: CC(C)NCCOc1ncc(-c2cc3c(cc2F)ncc2c3[C@]3(C[C@H](c4ccc(=O)[nH]c4)C3)C(=O)N2C)cc1NS(C)(=O)=O] | cis-N-(5-(7'-Fluoro-3'-methyl-2'-oxo-3-(6-oxo-1,6-dihydropyridin-3-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 621.25 | 1H NMR (400 MHz, CD3OD) δ 8.81 (s, 1H), 8.54-8.44 (m, 2H), 8.21 (d, J = 2.0 Hz, 2H), 7.90 (d, J = 12.1 Hz, 1H), 7.83 (d, J = 2.6 Hz, 1H), 6.69 (d, J = 9.4 Hz, 1H), 4.59 (t, J = 5.0 Hz, 2H), 4.23 (p, J = 9.0 Hz, 1H), 3.43 (s, 3H), 3.31-3.18 (m, 5H), 3.03 (s, 3H), 2.90 (dd, J = 13.7, 8.1 Hz, 2H), 1.32 (d, J = 6.4 Hz, 6H). |

| Examples | Structure | Name | MS: [(M + 1)]+ | 1H NMR |
|---|---|---|---|---|
| 443 | 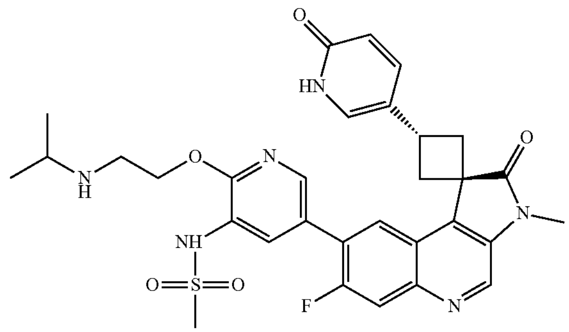 [SMILES: CC(C)NCCOc1ncc(-c2cc3c(cc2F)ncc2c3[C@]3(C[C@@H](c4ccc(=O)[nH]c4)C3)C(=O)N2C)cc1NS(C)(=O)=O] | trans-N-(5-(7'-Fluoro-3'-methyl-2'-oxo-3-(6-oxo-1,6-dihydropyridin-3-yl)-2',3'-dihydrospiro[cyclobutane-1,1'-pyrrolo[2,3-c]quinolin]-8'-yl)-2-(isopropylamino)ethoxy)pyridin-3-yl)methanesulfonamide | 621.20 | 1H NMR (400 MHz, CD3OD) δ 8.78 (s, 1H), 8.17 (d, J = 8.2 Hz, 1H), 7.92 (t, J = 2.3 Hz, 1H), 7.83 (d, J = 11.8 Hz, 1H), 7.70 (d, J = 2.1 Hz, 1H), 7.66 (dd, J = 9.4, 2.7 Hz, 1H), 7.43 (d, J = 2.4 Hz, 1H), 6.59 (d, J = 9.4 Hz, 1H), 4.63 (t, J = 5.0 Hz, 2H), 4.12 (p, J = 9.6 Hz, 1H), 3.41 (s, 3H), 3.36-3.32 (m, 3H), 3.19-3.08 (m, 2H), 3.05-2.96 (m, 2H), 2.95 (s, 3H), 1.35 (d, J = 6.5 Hz, 6H). |
| 444 | 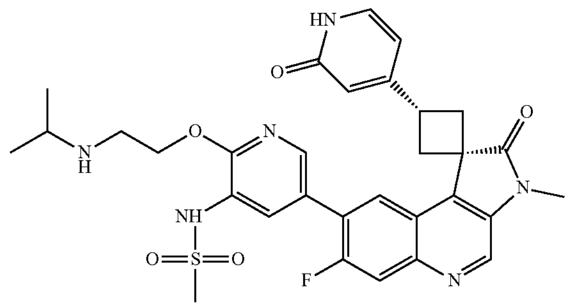 [SMILES: CC(C)NCCOc1ncc(-c2cc3c(cc2F)ncc2c3[C@]3(C[C@H](c4cc[nH]c(=O)c4)C3)C(=O)N2C)cc1NS(C)(=O)=O] | cis-N-(5-(7'-fluoro-3'-methyl-2'-oxo-3-(2-oxo-1,2-dihydropyridin-4-yl)-2',3'-dihydrospiro[cyclobutane-1,1'-pyrrolo[2,3-c]quinolin]-8'-yl)-2-(isopropylamino)ethoxy)pyridin-3-yl)methanesulfonamide | 621.25 | 1H NMR (400 MHz, DMSO-d6) δ 11.41 (s, 1H), 8.91 (s, 1H), 8.40-8.28 (m, 2H), 8.07 (t, J = 1.8 Hz, 1H), 8.00 (d, J = 12.1 Hz, 1H), 7.39 (d, J = 6.8 Hz, 1H), 6.61 (dd, J = 6.8, 1.7 Hz, 1H), 6.44 (d, J = 1.5 Hz, 1H), 4.45 (t, J = 5.3 Hz, 2H), 4.03 (p, J = 9.2 Hz, 1H), 3.32 (s, 3H), 3.16 (dd, J = 13.1, 10.1 Hz, 2H), 3.05 (s, 3H), 3.00 (t, J = 5.4 Hz, 2H), 2.93 (p, J = 6.3 Hz, 1H), 2.77 (dd, J = 13.2, 8.1 Hz, 2H), 1.08 (d, J = 6.2 Hz, 6H). |
| 445 | 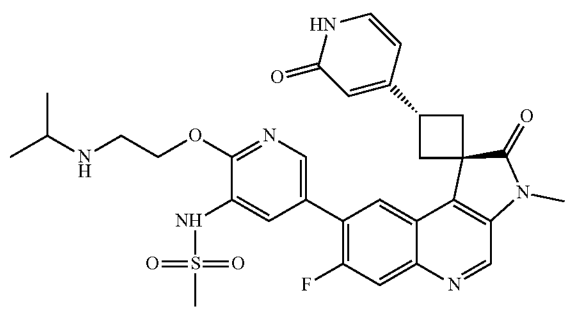 [SMILES: CC(C)NCCOc1ncc(-c2cc3c(cc2F)ncc2c3[C@]3(C[C@@H](c4cc[nH]c(=O)c4)C3)C(=O)N2C)cc1NS(C)(=O)=O] | trans-N-(5-(7'-Fluoro-3'-methyl-2'-oxo-3-(2-oxo-1,2-dihydropyridin-4-yl)-2',3'-dihydrospiro[cyclobutane-1,1'-pyrrolo[2,3-c]quinolin]-8'-yl)-2-(isopropylamino)ethoxy)pyridin-3-yl)methanesulfonamide | 621.20 | 1H NMR (400 MHz, DMSO-d6) δ 8.91 (s, 1H), 8.07 (d, J = 8.3 Hz, 1H), 8.04 (t, J = 1.6 Hz, 1H), 7.97 (d, J = 12.1 Hz, 1H), 7.91 (t, J = 2.2 Hz, 1H), 7.35 (d, J = 6.7 Hz, 1H), 6.33 (s, 1H), 6.25 (dd, J = 6.8, 1.7 Hz, 1H), 4.47 (t, J = 5.4 Hz, 2H), 4.03 (p, J = 9.4 Hz, 1H), 3.34 (s, 3H), 3.13 (dd, J = 12.6, 9.7 Hz, 2H), 3.04 (s, 3H), 2.99 (t, J = 5.3 Hz, 2H), 2.96-2.87 (m, 1H), 2.82 (td, J = 9.8, 2.4 Hz, 2H), 1.08 (d, J = 6.2 Hz, 6H). |

| Examples | Name | MS: [(M + 1)]+ | 1H NMR |
|---|---|---|---|
| 446 | N-(5-(7'-Fluoro-3,3,3'-trimethyl-2'-oxo-1,1'-pyrrolo[2,3-c]quinolin]-8'-yl)-2-(2-(isopropylamino)ethoxy)pyridin-3-yl)methanesulfonamide | 556.40 | 1H NMR (400 MHz, DMSO-d6) δ 8.87 (s, 1H), 8.41 (d, J = 8.2 Hz, 1H), 8.23 (t, J = 1.9 Hz, 1H), 8.01-7.93 (m, 2H), 4.44 (t, J = 5.3 Hz, 2H), 3.31 (s, 3H), 3.02 (s, 3H), 2.99 (t, J = 5.4 Hz, 2H), 2.93 (p, J = 6.3 Hz, 1H), 2.81 (d, J = 13.0 Hz, 2H), 2.39-2.30 (m, 2H), 1.57 (s, 3H), 1.45 (s, 3H), 1.08 (d, J = 6.2 Hz, 6H). |
| 447 | trans-N-(5-(7'-Fluoro-3,3'-dimethyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 542.30 | 1H NMR (400 MHz, DMSO-d6) δ 8.89 (s, 1H), 8.38-8.30 (m, 2H), 8.06-7.93 (m, 2H), 4.50 (t, J = 5.3 Hz, 2H), 3.31 (s, 3H), 3.17-3.08 (m, 2H), 3.09 (s, 3H), 3.06-2.97 (m, 2H), 2.71-2.63 (m, 2H), 2.57 (t, J = 10.3 Hz, 2H), 1.31 (d, J = 6.8 Hz, 3H), 1.24 (s, 2H), 1.14 (d, J = 6.3 Hz, 6H). |
| 448 | cis-N-(5-(7'-Fluoro-3,3'-dimethyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 542.30 | 1H NMR (400 MHz, DMSO-d6) δ 8.87 (s, 1H), 8.33-8.24 (m, 2H), 8.03-7.94 (m, 2H), 4.45 (t, J = 5.3 Hz, 2H), 3.31 (s, 3H), 3.05 (s, 3H), 3.04-2.89 (m, 5H), 2.25 (dd, J = 12.8, 6.6 Hz, 2H), 1.35 (d, J = 6.5 Hz, 3H), 1.24 (s, 1H), 1.09 (d, J = 6.2 Hz, 6H). |
| 450 | trans-N-(5-(3-Benzyl-7-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 618.30 | 1H NMR (400 MHz, DMSO-d6) δ 8.89 (s, 1H), 8.41-8.34 (m, 2H), 8.06 (d, J = 1.9 Hz, 1H), 7.99 (d, J = 12.0 Hz, 1H), 7.31-7.24 (m, 4H), 7.19-7.14 (m, 1H), 4.46 (t, J = 5.3 Hz, 2H), 3.30 (s, 3H), 3.27-3.16 (m, 1H), 3.07-3.00 (m, 5H), 2.96 (t, J = 7.7 Hz, 3H), 2.81 (t, J = 10.9 Hz, 2H), 2.46 (s, 2H), 1.07 (d, J = 6.2 Hz, 6H). |

-continued

| Examples | Structure | Name | MS: [(M + 1)]+ | 1H NMR |
|---|---|---|---|---|
| 451 | 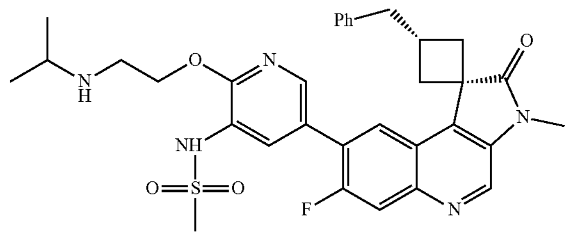 [SMILES: CC(C)NCCOc1ncc(-c2cc3c(cc2F)ncc2c3[C@]3(C[C@H](Cc4ccccc4)C3)C(=O)N2C)cc1NS(C)(=O)=O] | cis-N-(5-(3-Benzyl-7-fluoro-3'-methyl-2'-oxo-2',3'-pyrrolo[2,3-c]quinolin]-8'-yl)-2-(2-(isopropylamino)ethoxy)pyridin-3-yl)methanesulfonamide | 618.25 | 1H NMR (400 MHz, DMSO-d6) δ 8.88 (s, 1H), 8.29 (d, J = 2.3 Hz, 1H), 8.23 (d, J = 8.3 Hz, 1H), 8.02-7.93 (m, 2H), 7.32-7.26 (m, 4H), 7.21-7.15 (m, 1H), 4.44 (t, J = 5.3 Hz, 2H), 3.32 (s, 3H), 3.25-3.16 (m, 1H), 3.11 (d, J = 7.8 Hz, 2H), 3.03 (s, 3H), 3.00 (t, J = 5.4 Hz, 2H), 2.92 (dd, J = 12.8, 8.8 Hz, 3H), 2.35 (dd, J = 12.8, 5.7 Hz, 2H), 1.08 (d, J = 6.3 Hz, 6H). |
| 452 | 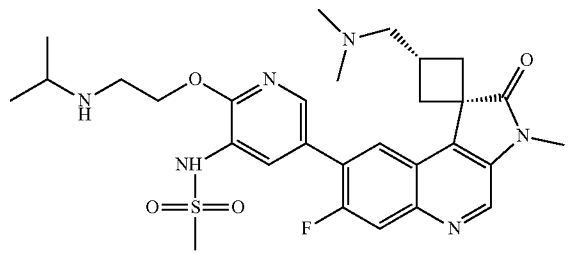 | cis-N-(5-((Dimethylamino)methyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 585.50 | 1H NMR (400 MHz, DMSO-d6) δ 8.87 (s, 1H), 8.29 (s, 1H), 8.26 (d, J = 8.2 Hz, 1H), 7.98 (d, J = 12.1 Hz, 2H), 4.43 (t, J = 5.4 Hz, 2H), 3.30 (s, 3H), 3.06-2.94 (m, 6H), 2.94-2.84 (m, 3H), 2.65 (d, J = 7.4 Hz, 2H), 2.28 (dd, J = 12.9, 6.0 Hz, 2H), 2.18 (s, 6H), 1.06 (d, J = 6.2 Hz, 6H). |
| 453 | 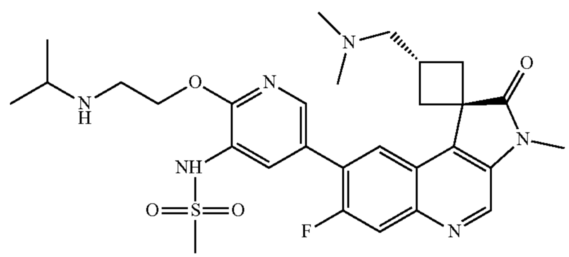 [SMILES: CC(C)NCCOc1ncc(-c2cc3c(cc2F)ncc2c3[C@]3(C[C@@H](CN(C)C)C3)C(=O)N2C)cc1NS(C)(=O)=O] | trans-N-(5-((Dimethylamino)methyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 585.45 | 1H NMR (400 MHz, DMSO-d6) δ 8.88 (s, 1H), 8.39 (s, 1H), 8.26 (d, J = 8.3 Hz, 1H), 8.27 (s, 1H), 7.97 (t, J = 6.0 Hz, 2H), 4.43 (J = 5.3 Hz, 2H), 3.31 (s, 3H), 3.15-3.04 (m, 1H), 3.03 (s, 3H), 2.97 (t, J = 5.5 Hz, 2H), 2.93-2.85 (m, 1H), 2.74 (t, J = 10.7 Hz, 2H), 2.57-2.52 (m, 4H), 2.16 (s, 6H), 1.06 (d, J = 6.2 Hz, 6H). |
| 454 | 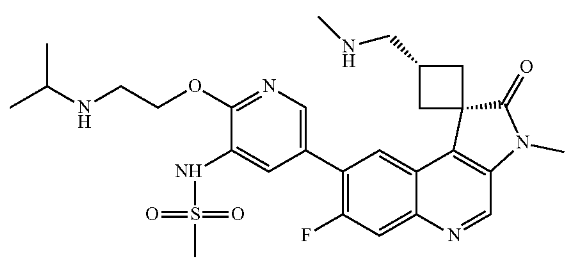 [SMILES: CNC[C@H]1C[C@]2(C1)C(=O)N(C)c1cnc3cc(F)c(-c4cnc(OCCNC(C)C)c(NS(C)(=O)=O)c4)cc3c12] | cis-N-(5-(7'-Fluoro-3'-methyl-3-((methylamino)methyl)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 571.25 | 1H NMR (400 MHz, DMSO-d6) δ 8.87 (s, 1H), 8.24 (d, J = 8.3 Hz, 1H), 8.17 (s, 1H), 7.93 (d, J = 12.1 Hz, 1H), 4.42 (t, J = 5.4 Hz, 2H), 3.30 (s, 3H), 3.10-2.92 (m, 8H), 2.92-2.83 (m, 3H), 2.40 (t, J = 5.4 Hz, 2H), 2.39-2.31 (m, 2H), 1.06 (d, J = 6.3 Hz, 6H). |

| Examples | Structure | Name | MS: [(M + 1)]+ | ¹H NMR |
|---|---|---|---|---|
| 455 | 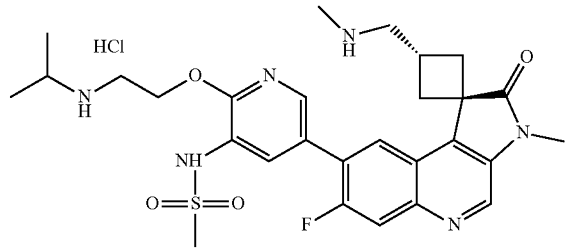 [SMILES: CNC[C@H]1C[C@@]2(C1)C(=O)N(C)c1cnc3cc(F)c(-c4cnc(OCCNC(C)C)c(NS(C)(=O)=O)c4)cc3c12 ; Cl] | trans-N-(5-(7'-Fluoro-3'-methyl-3-((methylamino)methyl)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | 571.25 | ¹H NMR (400 MHz, DMSO-$d_6$) δ 8.90 (s, 1H), 8.45-8.36 (m, 2H), 8.07 (s, 1H), 7.99 (d, J = 12.1 Hz, 1H), 4.53 (t, J = 5.2 Hz, 2H), 3.35-3.22 (m, 4H), 3.22-3.13 (m, 3H), 3.12 (s, 3H), 3.03 (d, J = 6.6 Hz, 2H), 2.92 (t, J = 11.0 Hz, 2H), 2.54-2.44 (m, 5H), 1.19 (d, J = 6.3 Hz, 6H). |
| 456 | 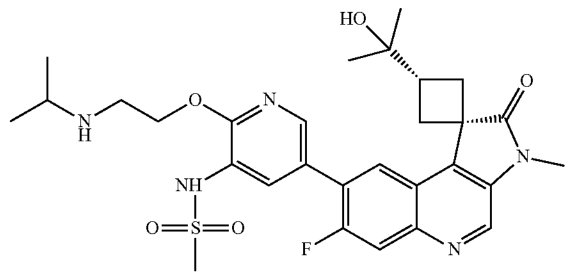 [SMILES: CC(C)NCCOc1ncc(-c2cc3c(cc2F)ncc2c3[C@]3(C[C@H](C(C)(C)O)C3)C(=O)N2C)cc1NS(C)(=O)=O] | cis-N-(5-(7'-Fluoro-3-(2-hydroxypropan-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 586.35 | ¹H NMR (400 MHz, DMSO-$d_6$) δ 8.88 (s, 1H), 8.29 (d, J = 7.9 Hz, 2H), 8.02-7.96 (m, 2H), 4.47 (t, J = 5.3 Hz, 2H), 3.30 (s, 3H), 3.11-2.94 (m, 7H), 2.71 (dd, J = 13.0, 8.7 Hz, 2H), 2.59 (dd, J = 12.9, 10.0 Hz, 2H), 1.17 (s, 6H), 1.12 (d, J = 6.3 Hz, 6H). |
| 457 | 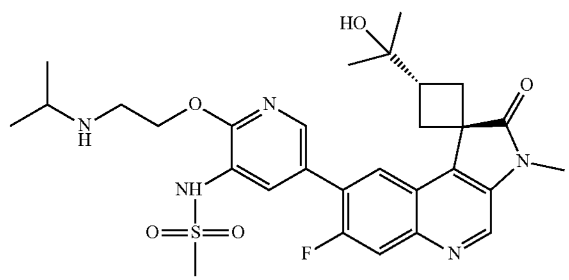 [SMILES: CC(C)NCCOc1ncc(-c2cc3c(cc2F)ncc2c3[C@]3(C[C@@H](C(C)(C)O)C3)C(=O)N2C)cc1NS(C)(=O)=O] | trans-N-(5-(7'-Fluoro-3-(2-hydroxypropan-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 586.25 | ¹H NMR (400 MHz, DMSO-$d_6$) δ 8.95 (d, J = 8.5 Hz, 1H), 8.87 (s, 1H), 8.29 (t, J = 2.0 Hz, 1H), 7.96-7.90 (m, 2H), 4.62 (s, 1H), 4.46 (t, J = 5.4 Hz, 2H), 3.32 (s, 3H), 3.10 (s, 3H), 3.06-2.85 (m, 6H), 2.24 (dd, J = 10.8, 7.9 Hz, 2H), 1.10 (d, J = 6.2 Hz, 12H). |

| Examples | Structure | Name | MS: [(M + 1)]+ | 1H NMR |
|---|---|---|---|---|
| 459 | 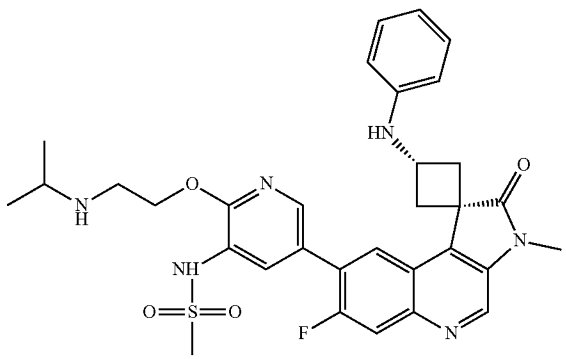 [SMILES: CC(C)NCCOc1ncc(-c2cc3c(cc2F)ncc2c3[C@]3(C[C@H](Nc4ccccc4)C3)C(=O)N2C)cc1NS(C)(=O)=O] | cis-N-(5-(7'-Fluoro-3'-methyl-2'-oxo-3-(phenylamino)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 619.20 | 1H NMR (400 MHz, DMSO-d6) δ 9.38(s, 1H), 8.93(s, 1H), 8.81(s, 2H), 8.48(t, J = 1.8 Hz, 1H), 8.34 (d, J = 8.3 Hz, 1H), 8.15 (d, J = 2.0 Hz, 1H), 8.03 (d, J = 12.1 Hz, 1H), 7.11 (t, J = 7.7 Hz, 2H), 6.63 (d, J = 8.0 Hz, 2H), 6.58 (t, J = 7.3 Hz, 1H), 6.26 (s, 1H), 4.61 (t, J = 4.9 Hz, 2H), 4.54 (p, J = 7.8 Hz, 1H), 3.45-3.40 (m, 3H), 3.33 (s, 3H), 3.24 (dd, J = 13.0, 8.4 Hz, 2H), 3.11 (s, 3H), 2.58 (dd, J = 13.3, 6.5 Hz, 2H), 1.31 (d, J = 6.5 Hz, 6H). |
| 460 | 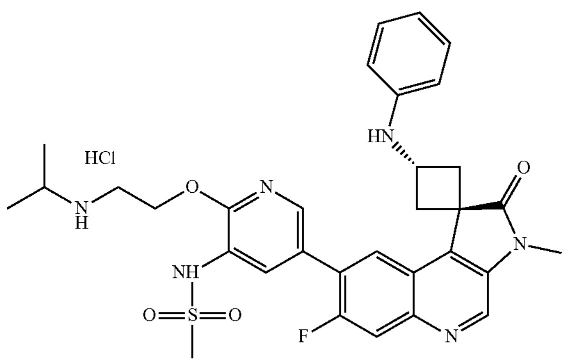 [SMILES: CC(C)NCCOc1ncc(-c2cc3c(cc2F)ncc2c3[C@]3(C[C@@H](Nc4ccccc4)C3)C(=O)N2C)cc1NS(C)(=O)=O ; Cl] | trans-N-(5-(7'-Fluoro-3'-methyl-2'-oxo-3-(phenylamino)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | 619.20 | 1H NMR (400 MHz, DMSO-d6) δ 9.40 (s, 1H), 8.92 (s, 1H), 8.86 (s, 2H), 8.73 (d, J = 8.3 Hz, 1H), 8.44 (s, 1H), 8.09 (d, J = 2.3 Hz, 1H), 7.99 (d, J = 12.1 Hz, 1H), 7.12 (t, J = 7.7 Hz, 2H), 6.62-6.53 (m, 3H), 6.42 (d, J = 4.2 Hz, 1H), 4.65 (t, J = 4.7 Hz, 2H), 4.35 (p, J = 7.8 Hz, 1H), 3.47 (s, 3H), 3.34 (s, 3H), 3.12 (s, 3H), 2.95 (dd, J = 12.2, 8.2 Hz, 2H), 2.87 (dd, J = 12.7, 7.1 Hz, 2H), 1.34 (d, J = 6.6, 6H). |

| Examples | Structure | Name | MS: [(M + 1)]+ | 1H NMR |
|---|---|---|---|---|
| 461 | 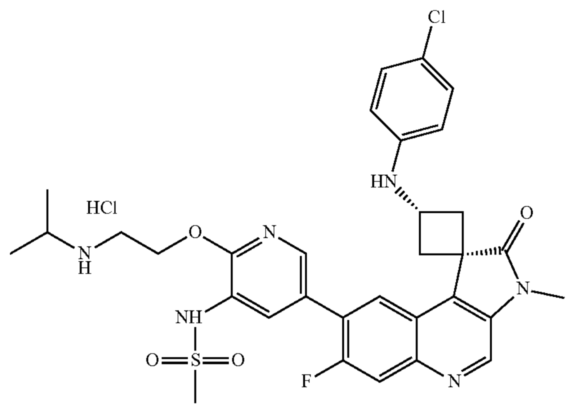 [SMILES: CC(C)NCCOc1ncc(-c2cc3c(cc2F)ncc2c3[C@]3(C[C@H](Nc4ccc(Cl)cc4)C3)C(=O)N2C)cc1NS(C)(=O)=O ; Cl] | cis-N-(5-(3-((4-Chlorophenyl)amino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 653.35, 655.35 | 1H NMR (400 MHz, DMSO-$d_6$) δ 9.40 (s, 1H), 8.93 (s, 1H), 8.85 (s, 2H), 8.47 (t, J = 1.9 Hz, 1H), 8.32 (d, J = 8.2 Hz, 1H), 8.15 (t, J = 1.9 Hz, 1H), 8.03 (d, J = 12.1 Hz, 1H), 7.14-7.10 (m, 2H), 6.67-6.62 (m, 2H), 4.62 (t, J = 4.9 Hz, 2H), 4.50 (p, J = 7.8 Hz, 1H), 3.49-3.38 (m, 3H), 3.33 (s, 3H), 3.24 (dd, J = 13.3, 8.4 Hz, 2H), 3.11 (s, 3H), 2.57 (dd, J = 13.4, 6.6 Hz, 2H), 1.31 (d, J = 6.5 Hz, 6H). |
| 462 | 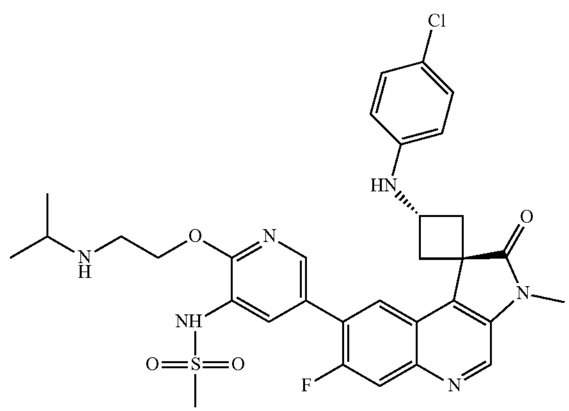 [SMILES: CC(C)NCCOc1ncc(-c2cc3c(cc2F)ncc2c3[C@]3(C[C@@H](Nc4ccc(Cl)cc4)C3)C(=O)N2C)cc1NS(C)(=O)=O] | trans-N-(5-(3-((4-Chlorophenyl)amino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 653.30, 655.30 | 1H NMR (400 MHz, DMSO-$d_6$) δ 8.90 (s, 1H), 8.67 (d, J = 8.4 Hz, 1H), 8.30 (s, 1H), 7.98-7.94 (m, 2H), 7.16-7.08 (m, 1H), 6.65 (d, J = 4.3 Hz, 1H), 6.60-6.52 (m, 2H), 4.48 (t, J = 5.3 Hz, 2H), 4.33 (s, 1H), 3.33 (s, 3H), 3.07-2.91 (m, 8H), 2.90-2.80 (m, 2H), 1.09(d, J = 6.2Hz, 6H). |

| Examples | Structure | Name | MS: [(M + 1)]+ | 1H NMR |
|---|---|---|---|---|
| 463 | 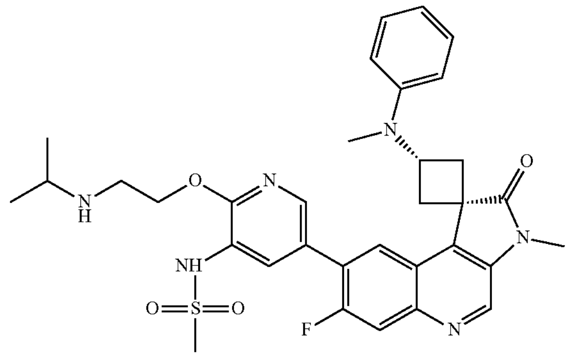 [SMILES: CC(C)NCCOc1ncc(-c2cc3c(cc2F)ncc2c3[C@]3(C[C@H](N(C)c4ccccc4)C3)C(=O)N2C)cc1NS(C)(=O)=O] | cis-N-(5-(7'-Fluoro-3'-methyl-3-(methyl)(phenyl)amino)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 633.25 | 1H NMR (400 MHz, DMSO-d6) δ 8.92 (s, 1H), 8.43 (s, 1H), 8.36 (d, J = 8.2 Hz, 1H), 8.06 (d, J = 2.5 Hz, 1H), 8.01 (d, J = 12.1 Hz, 1H), 7.22 (t, J = 7.7 Hz, 2H), 6.89 (d, J = 8.1 Hz, 2H), 6.73 (t, J = 7.2 Hz, 1H), 4.91 (p, J = 8.4 Hz, 1H), 4.46 (t, J = 5.3 Hz, 2H), 3.33 (s, 3H), 3.16-3.08 (m, 2H), 3.06 (s, 3H), 3.04-2.90 (m, 5H), 2.90-2.82(m, 3H), 1.08 (d, J = 6.3 Hz, 6H). |
| 464 | 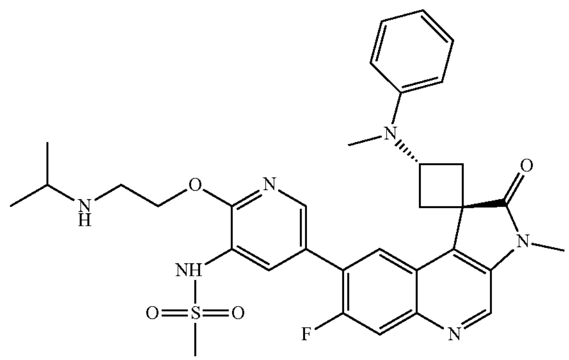 [SMILES: CC(C)NCCOc1ncc(-c2cc3c(cc2F)ncc2c3[C@]3(C[C@@H](N(C)c4ccccc4)C3)C(=O)N2C)cc1NS(C)(=O)=O] | trans-N-{5-(7'-Fluoro-3'-methyl-3-(methyl)(phenyl)amino)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 633.20 | 1H NMR (400 MHz, DMSO-d6) δ 8.90 (s, 1H), 8.72 (d, J = 8.4 Hz, 1H), 8.28 (s, 1H), 8.00-7.92 (m, 2H), 7.16 (t, J = 7.7 Hz, 2H), 6.76 (dd, J = 12.5, 7.6 Hz, 3H), 4.51 (t, J = 5.4 Hz, 2H), 4.32 (p, J = 7.5 Hz, 1H), 3.34 (s, 3H), 3.06-3.00 (m, 5H), 2.99-2.80 (m, 8H), 1.08 (d, J = 6.3 Hz, 6H). |
| 465 | 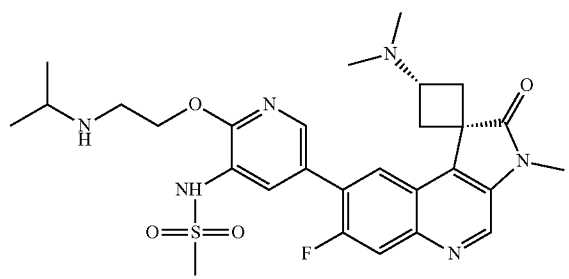 [SMILES: CC(C)NCCOc1ncc(-c2cc3c(cc2F)ncc2c3[C@]3(C[C@H](N(C)C)C3)C(=O)N2C)cc1NS(C)(=O)=O] | cis-N-(5-(3-(Dimethylamino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 571.35 | 1H NMR (400 MHz, DMSO-d6) δ 8.89 (s, 1H), 8.26 (d, J = 8.5 Hz, 1H), 8.00-7.96 (m, 2H), 4.42 (t, J = 5.4 Hz, 2H), 3.41 (p, J = 7.8 Hz, 1H), 3.31 (s, 3H), 3.02 (s, 3H), 2.96 (t, J = 5.4 Hz, 2H), 2.88 (p, J = 6.3 Hz, 1H), 2.80-2.71 (m, 2H), 2.58 (dd, J = 13.1, 7.4 Hz, 2H), 2.15 (s, 6H), 1.06 (d, J = 6.2 Hz, 6H). |

| Examples | Structure | Name | MS: [(M + 1)]+ | 1H NMR |
|---|---|---|---|---|
| 466 | 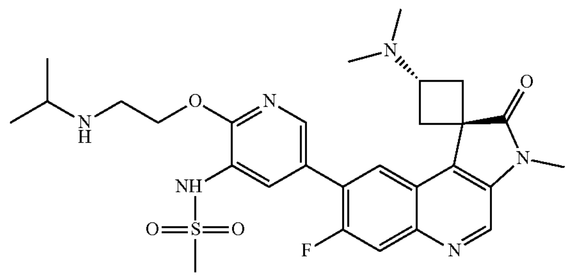 [SMILES: CC(C)NCCOc1ncc(-c2cc3c(cc2F)ncc2c3[C@]3(C[C@@H](N(C)C)C3)C(=O)N2C)cc1NS(C)(=O)=O] | trans-N-(5-(3-(Dimethylamino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 571.35 | 1H NMR (400 MHz, DMSO-d6) δ 9.23 (d, J = 8.6 Hz, 1H), 8.87 (s, 1H), 8.32 (t, J = 1.9 Hz, 1H), 7.99 (t, J = 1.9 Hz, 1H), 7.95 (d, J = 12.4 Hz, 1H), 4.43 (t, J = 5.4 Hz, 2H), 3.31 (s, 3H), 3.04 (s, 3H), 3.03-2.94 (m, 3H), 2.87 (p, J = 6.2Hz, 1H), 2.72 (dd, J = 13.0, 6.0 Hz, 2H), 2.62 (dd, J = 13.0, 8.1 Hz, 2H), 2.17 (s, 6H), 1.05 (d, J = 6.3 Hz, 6H). |
| 467 | 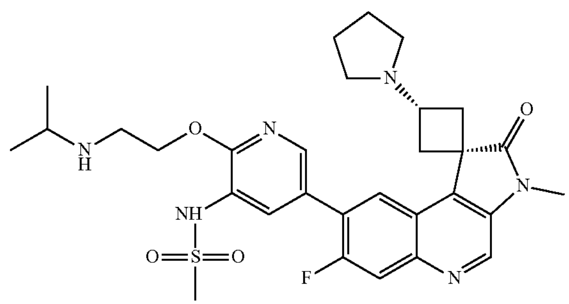 [SMILES: CC(C)NCCOc1ncc(-c2cc3c(cc2F)ncc2c3[C@]3(C[C@H](N4CCCC4)C3)C(=O)N2C)cc1NS(C)(=O)=O] | cis-N-(5-(7'-Fluoro-3'-methyl-2'-oxo-3-(pyrrolidin-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 597.40 | 1H NMR (400 MHz, DMSO-d6) δ 8.89 (s, 1H), 8.28 (d, J = 8.6 Hz, 2H), 8.02-7.94 (m, 2H), 4.43 (t, J = 5.4 Hz, 2H), 3.77-3.65 (m, 1H), 3.31 (s, 3H), 3.03 (s, 3H), 2.97 (t, J = 5.4 Hz, 2H), 2.90 (p, J = 6.2 Hz, 1H), 2.78 (dd, J = 13.0, 8.2 Hz, 2H), 2.67 (d, J = 13.0 Hz, 2H), 2.58-2.51 (m, 4H), 1.74 (s, 4H), 1.06 (d, J = 6.2 Hz, 6H). |
| 468 | 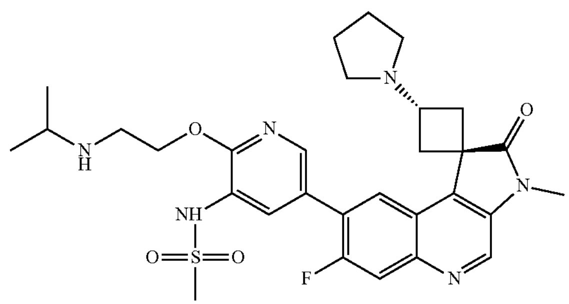 [SMILES: CC(C)NCCOc1ncc(-c2cc3c(cc2F)ncc2c3[C@]3(C[C@@H](N4CCCC4)C3)C(=O)N2C)cc1NS(C)(=O)=O] | trans-N-(5-(7'-Fluoro-3'-methyl-2'-oxo-3-(pyrrolidin-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 597.40 | 1H NMR (400 MHz, DMSO-d6) δ 9.30 (d, J = 8.6 Hz, 1H), 8.88 (s, 1H), 8.34 (s, 1H), 8.01 (s, 1H), 7.95 (d, J = 12.2 Hz, 1H), 4.47 (t, J = 5.2 Hz, 2H), 3.52-3.50 (m, 1H), 3.31 (s, 3H), 3.22-3.09 (m, 3H), 3.07 (s, 3H), 2.79 (dd, J = 13.1, 5.6 Hz, 2H), 2.65 (dd, J = 12.5, 6.1 Hz, 2H), 2.46-2.41 (m, 4 H), 1.69 (s, 4H), 1.13 (d, J = 6.1 Hz, 6H). |

| Examples | Structure | Name | MS: [(M + 1)]+ | 1H NMR |
|---|---|---|---|---|
| 469 | 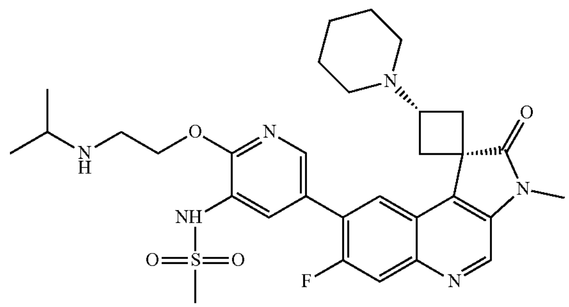 [SMILES: CC(C)NCCOc1ncc(-c2cc3c(cc2F)ncc2c3[C@]3(C[C@H](N4CCCCC4)C3)C(=O)N2C)cc1NS(C)(=O)=O] | cis-N-(5-(7'-Fluoro-3'-methyl-2'-oxo-3-(piperidin-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 611.30 | 1H NMR (400 MHz, DMSO-d6) δ 8.89 (s, 1H), 8.31-8.26 (m, 2H), 8.00-7.95 (m, 2H), 4.44 (t, J = 5.4 Hz, 2H), 3.43 (p, J = 8.2 Hz, 1H), 3.31 (s, 3H), 3.05 (s, 3H), 2.98 (t, J = 5.4 Hz, 2H), 2.91 (p, J = 6.4 Hz, 1H), 2.75 (dd, J = 13.0, 8.2 Hz, 2H), 2.61 (dd, J = 13.1, 7.7 Hz, 2H), 2.34 (s, 4H), 1.54 (s, 4H), 1.44 (s, 2H), 1.07 (d, J = 6.3 Hz, 6H). |
| 470 | 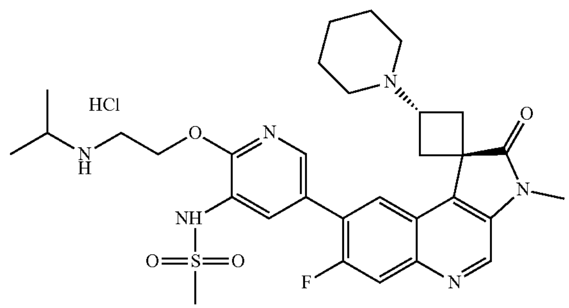 [SMILES: CC(C)NCCOc1ncc(-c2cc3c(cc2F)ncc2c3[C@]3(C[C@@H](N4CCCCC4)C3)C(=O)N2C)cc1NS(C)(=O)=O ; Cl] | trans-N-{5-(7'-Fluoro-3'-methyl-2'-oxo-3-(piperidin-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | 611.30 | 1H NMR (400 MHz, DMSO-d6) δ 9.02 (d, J = 8.5 Hz, 1H), 8.87 (s, 1H), 8.35 (d, J = 2.2 Hz, 1H), 7.99-7.91 (m, 2H), 4.42 (t, J = 5.4 Hz, 2H), 3.31 (s, 3H), 3.06-2.93 (m, 6H), 2.86 (p, J = 6.3 Hz, 1H), 2.75 (dd, J = 13.4, 6.2 Hz, 2H), 2.59 (dd, J = 12.8, 8.2 Hz, 2H), 2.28 (s, 4H), 1.48 (s, 4H), 1.40 (s, 2H), 1.05 (d, J = 6.2 Hz, 6H). |
| 471 | 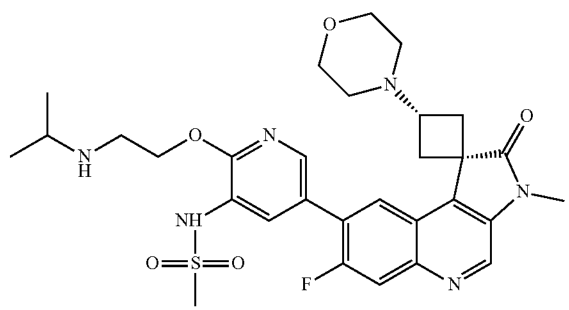 | cis-N-(5-(7'-Fluoro-3'-methyl-3-morpholino-2-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 613.30 | 1H NMR (400 MHz, DMSO-d6) δ 8.89 (s, 1H), 8.29-8.24 (m, 2H), 8.01-7.95 (m, 2H), 4.44 (t, J = 5.4 Hz, 2H), 3.64 (t, J = 4.4 Hz, 4H), 3.51 (t, J = 7.9 Hz, 1H), 3.31 (s, 3H), 3.04 (s, 3H), 2.98 (t, J = 5.4 Hz, 2H), 2.91 (p, J = 6.2 Hz, 1H), 2.77 (dd, J = 13.0, 8.3 Hz, 2H), 2.64 (dd, J = 13.0, 7.7 Hz, 2H), 2.41 (s, 4H), 1.07 (d, J = 6.3 Hz, 6H). |

| Examples | Structure | Name | MS: [(M + 1)]+ | 1H NMR |
|---|---|---|---|---|
| 472 | 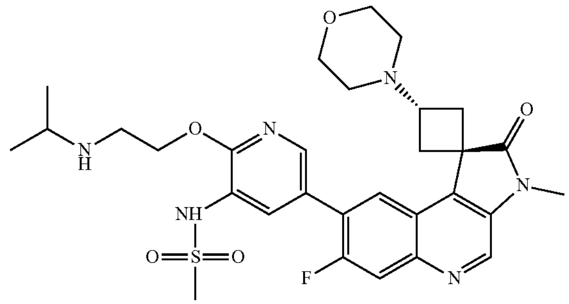 [SMILES: CC(C)NCCOc1ncc(-c2cc3c(cc2F)ncc2c3[C@]3(C[C@@H](N4CCOCC4)C3)C(=O)N2C)cc1NS(C)(=O)=O] | trans-N-(5-(7'-Fluoro-3'-methyl-3-morpholino-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 613.30 | 1H NMR (400 MHz, DMSO-d6) δ 8.96 (d, J = 8.5 Hz, 1H), 8.88 (s, 1H), 8.35 (d, J = 2.2 Hz, 1H), 7.98-7.93 (m, 2H), 4.43 (t, J = 5.3 Hz, 2H), 3.57 (LJ = 4.5 Hz, 4H), 3.31 (s, 3H), 3.09 (p, J = 7.3 Hz, 1H), 3.02 (s, 3H), 2.98 (LJ = 5.4 Hz, 2H), 2.89 (p, J = 6.2 Hz, 1H), 2.81 (dd, J = 13.2, 6.4 Hz, 2H), 2.59 (dd, J = 13.1, 8.2 Hz, 2H), 2.36 (s, 4H), 1.06 (d, J = 6.2 Hz, 6H). |
| 473 | 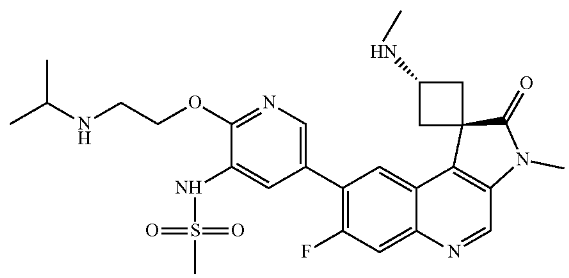 [SMILES: CN[C@H]1C[C@@]2(C1)C(=O)N(C)c1cnc3cc(F)c(-c4cnc(OCCNC(C)C)c(NS(C)(=O)=O)c4)cc3c12] | trans-N-(5-(7'-Fluoro-3'-methyl-3-(methylamino)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 557.45 | 1H NMR (400 MHz, DMSO-d6) δ 9.15 (d, J = 8.3 Hz, 1H), 8.88 (s, 1H), 8.36 (s, 1H), 8.04 (s, 1H), 7.95 (d, J = 12.3 Hz, 1H), 4.48 (s, 2H), 3.77-3.66 (m, 1H), 3.31 (s, 3H), 3.09 (s, 5H), 2.67-2.63 (m, 5H), 2.32 (s, 3H), 1.12 (d, J = 6.2 Hz, 6H). |
| 474 | 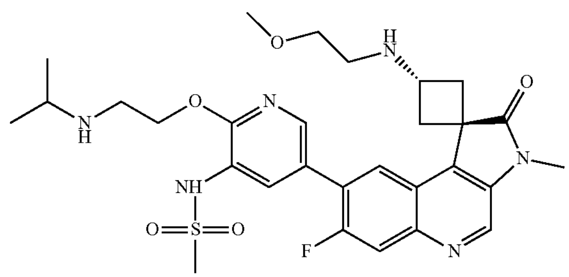 [SMILES: COCCN[C@H]1C[C@@]2(C1)C(=O)N(C)c1cnc3cc(F)c(-c4cnc(OCCNC(C)C)c(NS(C)(=O)=O)c4)cc3c12] | trans-N-{5-(7'-Fluoro-3-((2-methoxyethyl)amino)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 601.25 | 1H NMR (400 MHz, DMSO-d6) δ 9.08 (d, J = 8.5 Hz, 1H), 8.87 (s, 1H), 8.31 (d, J = 1.8 Hz, 1H), 7.97 (t, J = 2.2 Hz, 1H), 7.94 (d, J = 12.2 Hz, 1H), 4.44 (t, J = 5.4 Hz, 2H), 3.83-3.75 (m, 1H), 3.36 (t, J = 5.7 Hz, 2H), 3.30 (s, 3H), 3.20 (s, 3H), 3.05 (s, 3H), 2.98 (t, J = 5.4 Hz, 2H), 2.89 (p, J = 6.3 Hz, 1H), 2.71-2.64 (m, 6H), 1.06 (d, J = 6.2 Hz, 6H). |

| Examples | Structure | Name | MS: [(M + 1)]+ | 1H NMR |
|---|---|---|---|---|
| 475 | 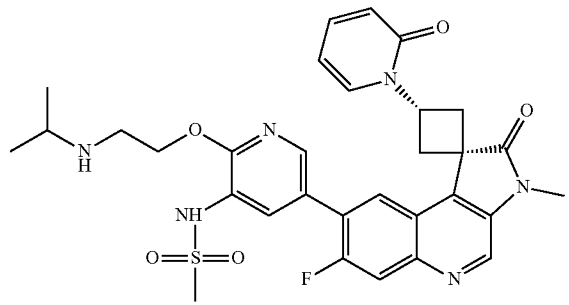 [SMILES: CC(C)NCCOc1ncc(-c2cc3c(cc2F)ncc2c3[C@]3(C[C@H](n4ccccc4=O)C3)C(=O)N2C)cc1NS(C)(=O)=O] | cis-N-(5-(7'-Fluoro-3'-methyl-2'-oxo-3-(2-oxopyridin-1(2H)-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 621.30 | 1H NMR (400 MHz, DMSO-d6) δ 9.04 (s, 1H), 8.26 (s, 1H), 8.19 (d, J = 8.6 Hz, 1H), 7.91 (t, J = 2.2 Hz, 1H), 7.85 (d, J = 12.6 Hz, 1H), 7.59 (dd, J = 7.0, 2.0 Hz, 1H), 7.45 (ddd, J = 8.9, 6.6, 2.0 Hz, 1H), 6.48 (dd, J = 9.3, 1.3 Hz, 1H), 6.24 (td, J = 6.8, 1.5 Hz, 1H), 5.46-5.39 (m, 1H), 4.66 (dd, J = 10.8, 6.9 Hz, 1H), 4.41 (t, J = 5.4 Hz, 2H), 3.82 (s, 3H), 3.66 (dd, J = 15.4, 6.5 Hz, 1H), 3.00 (s, 3H), 2.96 (t, J = 5.4 Hz, 2H), 2.89 (p, J = 6.2 Hz, 1H), 1.06 (d, J = 6.3 Hz, 6H). |
| 476 | 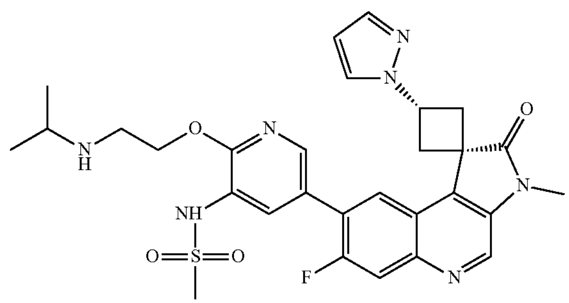 [SMILES: CC(C)NCCOc1ncc(-c2cc3c(cc2F)ncc2c3[C@]3(C[C@H](n4cccn4)C3)C(=O)N2C)cc1NS(C)(=O)=O] | cis-N-(5-(7'-Fluoro-3'-methyl-2'-oxo-3-(1H-pyrazol-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 594.20 | 1H NMR (400 MHz, DMSO-d6) δ 9.47 (d, J = 8.5 Hz, 1H), 8.92 (s, 1H), 8.55 (d, J = 2.0 Hz, 1H), 8.07 (t, J = 2.3 Hz, 1H), 7.99 (dd, J = 7.3, 5.0 Hz, 2H), 7.68 (d, J = 1.7 Hz, 1H), 6.28 (t, J = 2.0 Hz, 1H), 5.51 (p, J = 8.7 Hz, 1H), 4.51 (t, J = 5.4 Hz, 2H), 3.61 (t, J = 10.7 Hz, 2H), 3.36 (s, 3H), 3.04 (s, 3H), 3.06-2.85 (m, 5H), 1.08 (d, J = 6.3 Hz, 6H). |
| 477 | 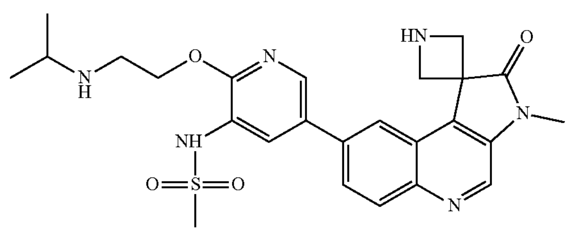 [SMILES: CC(C)NCCOc1ncc(-c2ccc3ncc4c(c3c2)C2(CNC2)C(=O)N4C)cc1NS(C)(=O)=O] | N-(2-(3-(Dimethylamino)propoxy)-5-(3'-methyl-2'-oxo-2',3'-dihydrospiro[azetidine-3,1'-pyrrolo[2,3-c]quinolin]-8'-yl)pyridin-3-yl)methanesulfonamide | 511.30 | 1H NMR (400 MHz, DMSO-d6) δ 9.40 (d, J = 2.0 Hz, 1H), 8.84 (s, 1H), 8.30 (d, J = 2.3 Hz, 1H), 8.15 (d, J = 8.9 Hz, 1H), 7.99-7.94 (m, 2H), 4.39 (t, J = 6.3 Hz, 2H), 4.21 (d, J = 7.6 Hz, 2H), 3.73 (d, J = 7.6 Hz, 2H), 3.31 (s, 3H), 3.03 (s, 3H), 2.62 (t, J = 6.6 Hz, 2H), 2.33 (s, 6H), 1.97 (p, J = 6.5 Hz, 2H). |

| Examples | Structure | Name | MS: [(M + 1)]+ | 1H NMR |
|---|---|---|---|---|
| 478 | 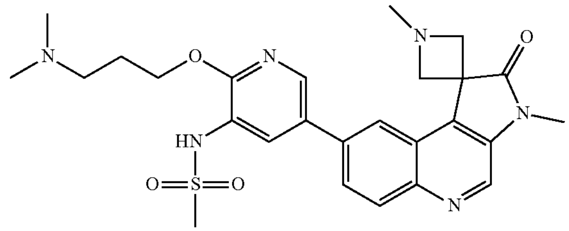 | N-(5-(1,3'-Dimethyl-2'-oxo-2',3'-dihydrospiro[azetidine-3,1'-pyrrolo[2,3-c]quinolin]-8'-yl)-2-(3-(dimethylamino)propoxy)pyridin-3-yl)methanesulfonamide | 525.15 | 1H NMR (400 MHz, DMSO-d6) δ 9.44 (d, J = 2.0 Hz, 1H), 8.85 (s, 1H), 8.29 (d, J = 2.2 Hz, 1H), 8.14 (d, J = 8.9 Hz, 1H), 8.01-7.94 (m, 2H), 4.39 (t, J = 6.2 Hz, 2H), 3.89 (d, J = 7.5 Hz, 2H), 3.47 (d, J = 7.5 Hz, 2H), 3.31 (s, 3H), 3.03 (s, 3H), 2.68 (t, J = 6.4 Hz, 2H), 2.38 (s, 6H), 1.99 (p, J = 6.3Hz, 2H). |
| 479 | 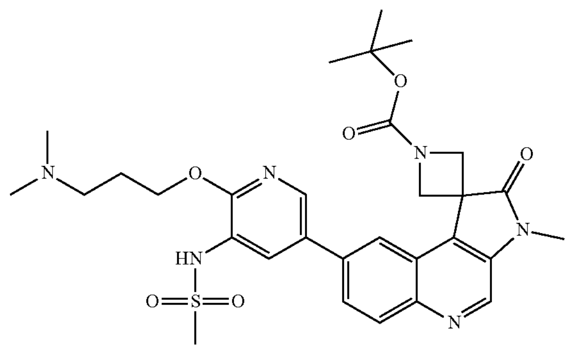 | tert-Butyl 8'-(6-(3-(dimethylamino)propoxy)-5-(methylsulfonamido)pyridin-3-yl)-3'-methyl-2'-oxo-2',3'-dihydrospiro[azetidine-3,1'-pyrrolo[2,3-c]quinoline]-1-carboxylate | 611.25 | 1H NMR (400 MHz, DMSO-d6) δ 8.91 (s, 1H), 8.23-8.16 (m, 3H), 7.97-7.89 (m, 2H), 4.43-4.36 (m, 4H), 4.25 (d, J = 8.9 Hz, 2H), 3.34 (s, 3H), 3.00 (s, 3H), 2.62 (t, J = 6.6 Hz, 2H), 2.33 (s, 6H), 1.97 (p, J = 6.5 Hz, 2H), 1.45 (s, 9H). |
| 480 | 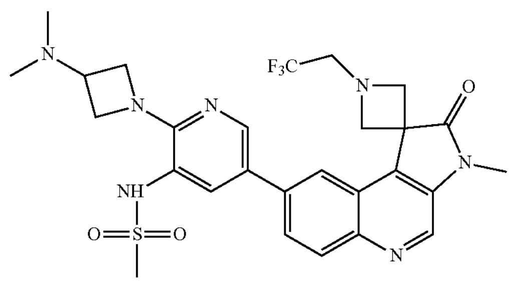 | N-2-(3-(Dimethylamino)azetidin-1-yl)-5-(3'-methyl-2'-oxo-1-(2,2,2-trifluoroethyl)-2',3'-dihydrospiro[azetidine-3,1'-pyrrolo[2,3-c]quinolin]-8'-yl)pyridin-3-yl)methanesulfonamide | 590.30 | 1H NMR (400 MHz, DMSO-d6) δ 9.32 (s, 1H), 9.06 (s, 1H), 8.84 (s, 1H), 8.52 (s, 1H), 8.13 (d, J = 8.9 Hz, 1H), 7.94 (d, J = 8.6 Hz, 1H), 7.85 (s, 1H), 4.23 (t, J = 7.9 Hz, 2H), 4.01-3.93 (m, 4H), 3.80 (d, J = 7.6 Hz, 2H), 3.58-3.46 (m, 2H), 3.30 (s, 3H), 3.17 (d, J = 5.2 Hz, 1H), 3.12 (s, 3H), 2.12 (s, 6H). |

-continued

| Examples | Structure | Name | MS: [(M + 1)]+ | 1H NMR |
|---|---|---|---|---|
| 481 | 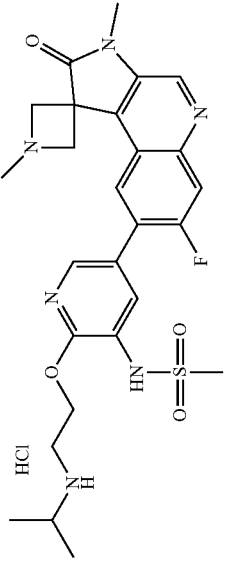 | N-(5-(7'-Fluoro-1,3'-dimethyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | 543.40 | 1H NMR (400 MHz, CD3OD) δ 8.84 (s, 2H), 8.37 (t, J = 2.1 Hz, 1H), 8.23 (s, 1H), 7.90 (d, J = 11.9 Hz, 1H), 4.82-4.73(m, 2H), 4.57 (s, 1H), 4.26-3.84 (m, 2H), 3.66-3.49 (m, 4H), 3.41 (s, 3H), 3.15 (s, 3H), 2.93 (s, 3H). |
| 482 | 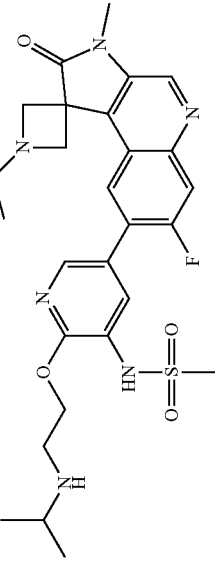 | N-(5-(1-Ethyl-7-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 557.30 | 1H NMR (400 MHz, DMSO-d6) δ 9.54 (d, J = 8.8 Hz, 1H), 8.89 (s, 1H), 8.26 (t, J = 1.9 Hz, 1H), 7.98 (t, J = 2.0 Hz, 1H), 7.95 (d, J = 12.3 Hz, 1H), 4.45 (t, J = 5.3 Hz, 2H), 3.82 (d, J = 7.4 Hz, 2H), 3.44 (d, J = 7.4 Hz, 2H), 3.31 (s, 3H), 3.02 (t, J = 5.3 Hz, 2H), 2.99-2.92 (m, 1H), 2.63 (q, J = 7.1 Hz, 2H), 1.09 (d, J = 6.3 Hz, 6H), 1.00 (t, J = 7.1 Hz, 3H). |
| 483 | 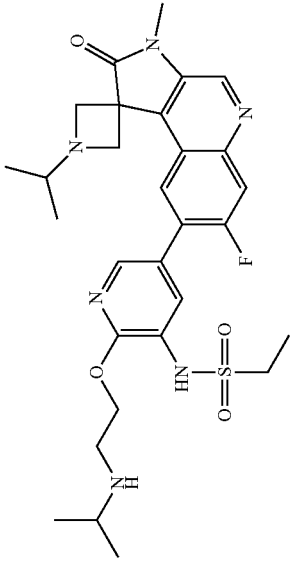 | N-(5-(7'-Fluoro-1-isopropyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)ethanesulfonamide | 585.30 | 1H NMR (400 MHz, DMSO-d6) δ 9.68 (d, J = 8.9 Hz, 1H), 8.90 (s, 1H), 8.32 (t, J = 2.0 Hz, 1H), 8.05 (s, 1H), 7.95 (d, J = 12.4 Hz, 1H), 4.45 (t, J = 5.2 Hz, 2H), 3.75 (d, J = 7.4 Hz, 2H), 3.48 (d, J = 7.4 Hz, 2H), 3.13 (q, J = 7.3 Hz, 2H), 3.04 (s, 2H), 2.63-2.55 (m, 2H), 1.28 (t, J = 7.3 Hz, 3H), 1.09 (d, J = 6.0 Hz, 6H), 0.98 (d, J = 6.1 Hz, 6H). |

| Examples | Structure | Name | MS: [(M + 1)]+ | 1H NMR |
|---|---|---|---|---|
| 484 | 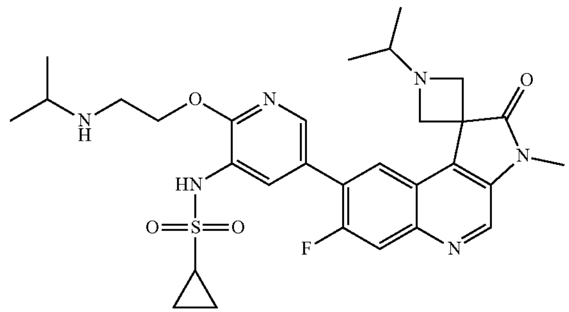 [SMILES: CC(C)NCCOc1ncc(-c2cc3c4c(cnc3cc2F)N(C)C(=O)C42CN(C(C)C)C2)cc1NS(=O)(=O)C1CC1] | N-(5-(7'-Fluoro-1-isopropyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)cyclopropanesulfonamide | 597.40 | 1H NMR (400 MHz, DMSO-d6) δ 9.70 (d, J = 8.9 Hz, 1H), 8.90 (s, 1H), 8.31 (t, J = 1.9 Hz, 1H), 8.02 (t, J = 2.0 Hz, 1H), 7.95 (d, J = 12.5 Hz, 1H), 4.42 (t, J = 5.3 Hz, 2H), 3.80-3.73 (m, 2H), 3.49 (d, J = 7.3 Hz, 2H), 3.32 (s, 3H), 2.96 (t, J = 5.4 Hz, 2H), 2.85 (p, J = 6.3 Hz, 1H), 2.74-2.66 (m, 1H), 2.64-2.55 (m 1H), 1.05 (d, J = 6.2 Hz, 6H), 0.98 (d, J = 6.1 Hz, 6H), 0.95-0.89 (m, 4H). |
| 485 | 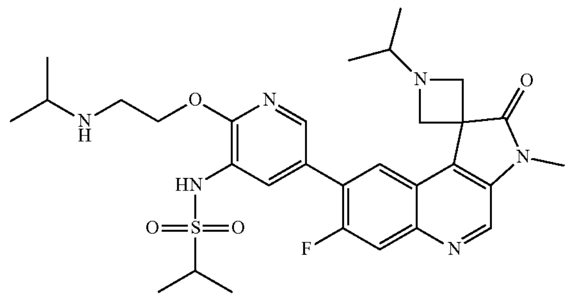 [SMILES: CC(C)NCCOc1ncc(-c2cc3c4c(cnc3cc2F)N(C)C(=O)C42CN(C(C)C)C2)cc1NS(=O)(=O)C(C)C] | N-(5-(7'-Fluoro-1-isopropyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)propane-2-sulfonamide | 599.40 | 1H NMR (400 MHz, DMSO-d6) δ 9.68 (d, J = 8.9 Hz, 1H), 8.89 (s, 1H), 8.28 (s, 1H), 8.05 (d, J = 1.9 Hz, 1H), 7.94 (d, J = 12.5 Hz, 1H), 4.40 (t, J = 5.3 Hz, 2H), 3.75 (d, J = 7.4 Hz, 2H), 3.31 (s, 3H), 3.49 (d, J = 7.6 Hz, 2H), 3.22 (p, J = 6.8 Hz, 1H), 2.92 (t, J = 5.4 Hz, 2H), 2.80 (p, J = 6.2 Hz, 1H), 2.58 (p, J = 6.0 Hz, 1H), 1.28 (d, J = 6.8 Hz, 6H), 1.03 (d, J = 6.2 Hz, 6H), 0.98 (d, J = 6.1 Hz, 6H). |
| 486 | 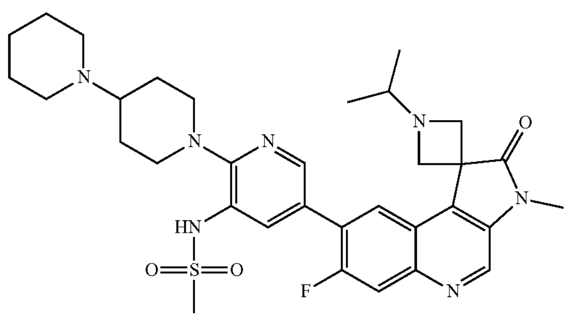 [SMILES: CC(C)N1CC2(C1)C(=O)N(C)c1cnc3cc(F)c(-c4cnc(N5CCC(N6CCCCC6)CC5)c(NS(C)(=O)=O)c4)cc3c12] | N-(2-(1,4-Bipiperidin]-1'-yl)-5-(7'-fluoro-1-isopropyl-3'-methyl-2'-oxo-2',3'-dihydrospiro[azetidine-3,1'-pyrrolo[2,3-c]quinolin]-8'-yl)pyridin-3-yl)methanesulfonamide | 636.30 | 1H NMR (400 MHz, DMSO-d6) δ 9.61 (d, J = 9.0 Hz, 1H), 8.88 (s, 1H), 8.38 (s, 1H), 7.96-7.89 (m, 2H), 3.95 (d, J = 12.3 Hz, 2H), 3.77 (d, J = 7.1 Hz, 2H), 3.47 (d, J = 7.2 Hz, 2H), 3.31 (s, 3H), 3.11 (s, 3H), 2.79 (t, J = 12.2 Hz, 2H), 2.63-2.52 (m, 6H), 1.79 (d, J = 12.4 Hz, 2H), 1.67 (q, J = 11.7 Hz, 2H), 1.51 (d, J = 6.3 Hz, 4H), 1.40 (s, 2H), 0.97 (d, J = 6.0 Hz, 6H). |

-continued

| Examples | Structure | Name | MS: [(M + 1)]+ | 1H NMR |
|---|---|---|---|---|
| 487 | 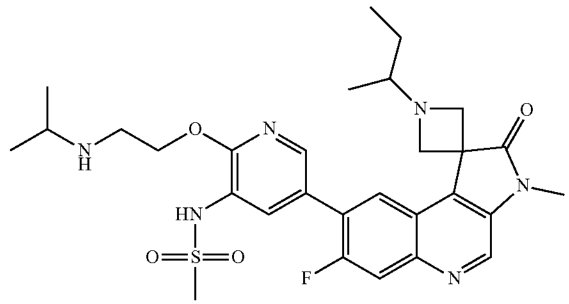 [SMILES: CCC(C)N1CC2(C1)C(=O)N(C)c1cnc3cc(F)c(-c4cnc(OCCNC(C)C)c(NS(C)(=O)=O)c4)cc3c12] | N-(5-(1-(sec-Butyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 585.35 | 1H NMR (400 MHz, DMSO-d6) δ 9.63 (d, J = 8.8 Hz, 1H), 8.90 (s, 1H), 8.24 (s, 1H), 7.98-7.90 (m, 2H), 4.41 (t, J = 5.5 Hz, 2H), 3.75 (d, J = 7.1 Hz, 2H), 3.48 (d, J = 7.1 Hz, 2H), 3.31 (s, 3H), 3.01 (s, 3H), 2.95 (t, J = 5.5 Hz, 2H), 2.90-2.80 (m, 1H), 2.62 (s, 3H), 2.48-2.42 (m, 1H), 1.44 (s, 1H), 1.30-1.19 (m, 1H), 1.04 (d, J = 6.2 Hz, 6H), 0.96 (d, J = 6.2 Hz, 3H), 0.81 (t, J = 7.4 Hz, 3H). |
| 488 | 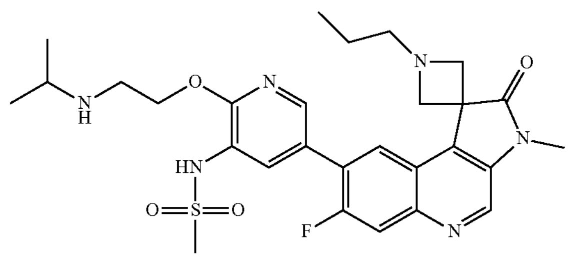 [SMILES: CCCN1CC2(C1)C(=O)N(C)c1cnc3cc(F)c(-c4cnc(OCCNC(C)C)c(NS(C)(=O)=O)c4)cc3c12] | N-(5-(7'-Fluoro-3'-methyl-2'-oxo-1-propyl-2',3'-dihydrospiro[azetidine-3,1'-pyrrolo[2,3-c]quinolin]-8'-yl)-2-(2-(isopropylamino)ethoxy)pyridin-3-yl)methanesulfonamide | 571.30 | 1H NMR (400 MHz, DMSO-d6) δ 9.53 (d, J = 8.8 Hz, 1H), 8.90 (s, 1H), 8.24 (s, 1H), 8.00-7.92 (m, 2H), 4.43 (t, J = 5.4 Hz, 2H), 3.83 (d, J = 7.4 Hz, 2H), 3.45 (d, J = 7.6 Hz, 2H), 3.32 (s, 3H), 3.04 (s, 3H), 2.97 (t, J = 5.5 Hz, 2H), 2.93-2.85 (m, 1H), 2.59 (t, J = 6.9 Hz, 2H), 1.40 (q, J = 7.1 Hz, 2H), 1.07 (d, J = 6.2 Hz, 6H), 0.89 (t, J = 7.3 Hz, 3H). |
| 489 | 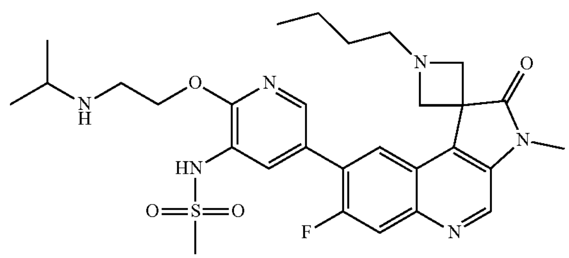 [SMILES: CCCCN1CC2(C1)C(=O)N(C)c1cnc3cc(F)c(-c4cnc(OCCNC(C)C)c(NS(C)(=O)=O)c4)cc3c12] | N-(5-(1-butyl-7-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 585.25 | 1H NMR (400 MHz, DMSO-d6) δ 9.50 (d, J = 8.7 Hz, 1H), 8.89 (s, 1H), 8.20 (s, 1H), 7.98-7.89 (m, 2H), 4.42 (t, J = 5.4 Hz, 2H), 3.81 (d, J = 7.4 Hz, 2H), 3.43 (d, J = 7.3 Hz, 2H), 3.30 (s, 3H), 3.01 (s, 3H), 2.96 (t, J = 5.4 Hz, 2H), 2.87 (p, J = 6.1 Hz, 1H), 2.60 (t, J = 6.2 Hz, 2H), 1.39-1.27 (m, 4H), 1.05 (d, J = 6.2 Hz, 6H), 0.83 (t, J = 6.9Hz, 3H). |

| Examples | Structure | Name | MS: [(M + 1)]+ | 1H NMR |
|---|---|---|---|---|
| 490 | 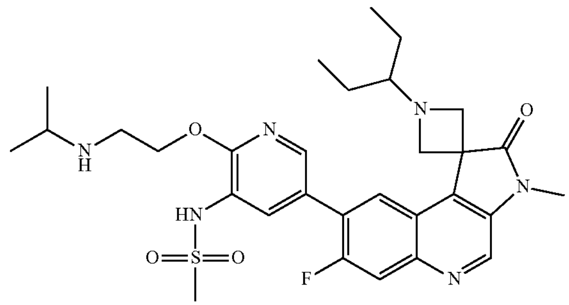 [SMILES: CCC(CC)N1CC2(C1)C(=O)N(C)c1cnc3cc(F)c(-c4cnc(OCCNC(C)C)c(NS(C)(=O)=O)c4)cc3c12] | N-(5-(7'-Fluoro-3'-methyl-2'-oxo-1-(pentan-3-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | 599.25 | 1H NMR (400 MHz, DMSO-$d_6$) δ 9.57 (d, J = 8.7 Hz, 1H), 8.84 (s, 1H), 7.96-7.86 (m, 2H), 7.82 (t, J = 2.2 Hz, 1H), 4.41 (t, J = 4.9 Hz, 2H), 3.73 (d, J = 7.1 Hz, 2H), 3.49 (d, J = 7.2 Hz, 2H), 3.31 (s, 3H), 3.21-3.06 (m, 3H), 2.85 (s, 3H), 2.34 (s, 1H), 1.49-1.29 (m, 4H), 1.20 (d, J = 6.4 Hz, 6H), 0.77 (t, J = 7.4 Hz, 6H). |
| 491 | 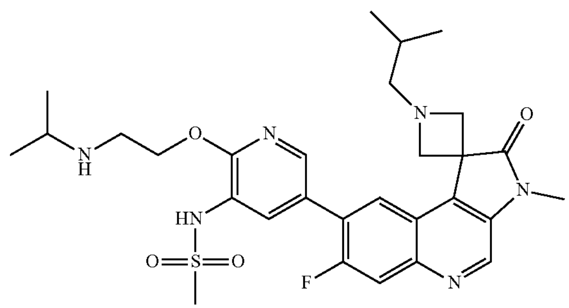 [SMILES: CC(C)CN1CC2(C1)C(=O)N(C)c1cnc3cc(F)c(-c4cnc(OCCNC(C)C)c(NS(C)(=O)=O)c4)cc3c12] | N-(5-(7'-Fluoro-1-isobutyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 585.40 | 1H NMR (400 MHz, DMSO-$d_6$) δ 9.50 (d, J = 8.7 Hz, 1H), 8.89 (s, 1H), 8.20 (d, J = 1.9 Hz, 1H), 7.95 (d, J = 12.1 Hz, 1H), 7.91 (t, J = 2.2 Hz, 1H), 4.40 (t, J = 5.4 Hz, 2H), 3.82 (d, J = 7.4 Hz, 2H), 3.45 (d, J = 7.4 Hz, 2H), 3.31 (s, 3H), 3.01 (s, 3H), 2.95 (t, J = 5.5 Hz, 2H), 2.86 (p, J = 6.1 Hz, 1H), 2.43 (d, J = 7.0 Hz, 2H), 1.61 (dt, J = 13.4, 6.7 Hz, 1H), 1.05 (d, J = 6.2 Hz, 6H), 0.86 (d, J = 6.6 Hz, 6H). |
| 492 | 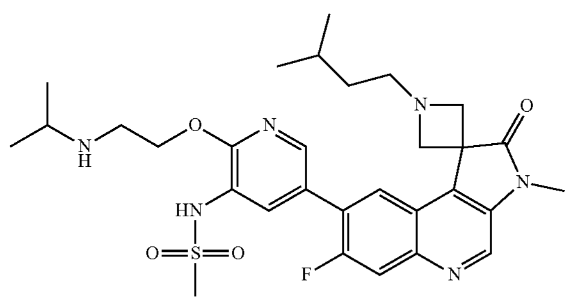 [SMILES: CC(C)CCN1CC2(C1)C(=O)N(C)c1cnc3cc(F)c(-c4cnc(OCCNC(C)C)c(NS(C)(=O)=O)c4)cc3c12] | N-(5-(7'-Fluoro-1-isopentyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 599.40 | 1H NMR (400 MHz, DMSO-$d_6$) δ 9.46 (d, J = 8.8 Hz, 1H), 8.89 (s, 1H), 8.18 (d, J = 1.9 Hz, 1H), 7.94 (d, J = 12.1 Hz, 1H), 7.91 (t, J = 2.1 Hz, 1H), 4.43 (t, J = 5.4 Hz, 2H), 3.81 (d, J = 7.2 Hz, 2H), 3.42 (d, J = 7.3 Hz, 2H), 3.31 (s, 3H), 3.01 (s, 3H), 2.97 (t, J = 5.4 Hz, 2H), 2.87 (p, J = 6.4 Hz, 1H), 2.60 (t, J = 7.0 Hz, 2H), 1.65 (dt, J = 13.3, 6.7 Hz, 1H), 1.29-1.22 (m, 2H), 1.05 (d, J = 6.2 Hz, 6H), 0.83 (d, J = 6.6 Hz, 6H). |

| Examples | Structure | Name | MS: [(M + 1)]+ | 1H NMR |
|---|---|---|---|---|
| 493 | 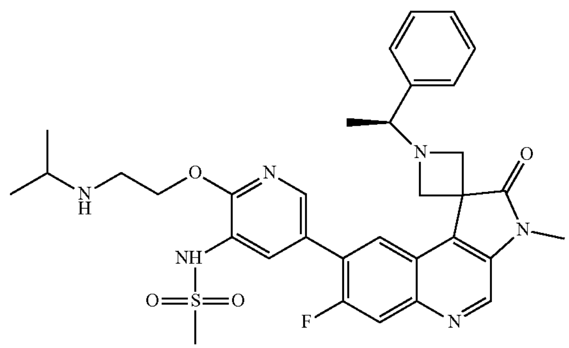 [SMILES: CC(C)NCCOc1ncc(-c2cc3c4c(cnc3cc2F)N(C)C(=O)C42CN([C@@H](C)c3ccccc3)C2)cc1NS(C)(=O)=O] | (S)-N-(5-(7'-Fluoro-3'-methyl-2'-oxo-1-(1-phenylethyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | 633.20 | 1H NMR (400 MHz, DMSO-d6) δ 9.63 (d, J = 8.8 Hz, 1H), 8.88 (s, 1H), 8.23-8.15 (m, 1H), 8.03 (t, J = 2.0 Hz, 1H), 7.95 (d, J = 12.1 Hz, 1H), 7.37 (d, J = 7.0 Hz, 2H), 7.30 (t, J = 7.5 Hz, 2H), 7.23 (dd, J = 8.4, 6.2 Hz, 1H), 4.54 (t, J = 5.1 Hz, 2H), 3.91 (d, J = 7.2 Hz, 2H), 3.65 (d, J = 7.6 Hz, 1H), 3.43 (d, J = 7.6 Hz, 1H), 3.34 (d, J = 7.5 Hz, 1H), 3.30 (s, 3H), 3.28-3.18 (m, 3H), 2.99 (s, 3H), 1.22 (dd, J = 8.1, 6.2 Hz, 9H). |
| 494 | 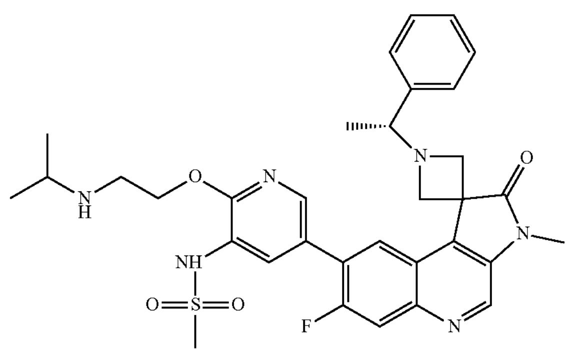 [SMILES: CC(C)NCCOc1ncc(-c2cc3c4c(cnc3cc2F)N(C)C(=O)C42CN([C@H](C)c3ccccc3)C2)cc1NS(C)(=O)=O] | (R)-N-(5-(7'-Fluoro-3'-methyl-2'-oxo-1-(1-phenylethyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | 633.20 | 1H NMR (400 MHz, DMSO-d6) δ 9.63 (d, J = 8.8 Hz, 1H), 8.88 (s, 1H), 8.23-8.15 (m, 1H), 8.03 (t, J = 2.0 Hz, 1H), 7.95 (d, J = 12.1 Hz, 1H), 7.37 (d, J = 7.0 Hz, 2H), 7.30 (t, J = 7.5 Hz, 2H), 7.23 (dd, J = 8.4, 6.2 Hz, 1H), 4.54 (t, J = 5.1 Hz, 2H), 3.91 (d, J = 7.2 Hz, 2H), 3.65 (d, J = 7.6 Hz, 1H), 3.43 (d, J = 7.6 Hz, 1H), 3.34 (d, J = 7.5 Hz, 1H), 3.30 (s, 3H), 3.28-3.18 (m, 3H), 2.99 (s, 3H), 1.22 (dd, J = 8.1, 6.2 Hz, 9H). |
| 495 | 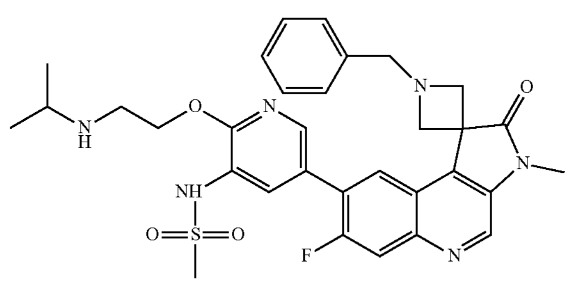 | N-(5-(1-Benzyl-7-fluoro-3'-methyl-2'-oxo-2,3'-dihydrospiro[azetidine-3,1'-pyrrolo[2,3-c]quinolin]-8'-yl)-2-(2-(isopropylamino)ethoxy)pyridin-3-yl)methanesulfonamide | 619.25 | 1H NMR (400 MHz, DMSO-d6) δ 9.54 (d, J = 8.8 Hz, 1H), 8.89 (s, 1H), 8.25 (s, 1H), 7.98 (d, J = 2.2 Hz, 1H), 7.94 (d, J = 12.1 Hz, 1H), 7.37 (d, J = 7.5 Hz, 2H), 7.32 (t, J = 7.4 Hz, 2H), 7.23 (t, J = 7.2 Hz, 1H), 4.49 (t, J = 5.4 Hz, 2H), 3.81 (s, 2H), 3.79 (d, J = 7.3 Hz, 2H), 3.56 (d, J = 7.4 Hz, 2H), 3.31 (s, 3H), 3.01 (d, J = 7.2 Hz, 5H), 2.89 (p, J = 6.3 Hz, 1H), 1.06 (d, J = 6.2 Hz, 6H). |

| Examples | Structure | Name | MS: [(M + 1)]+ | 1H NMR |
|---|---|---|---|---|
| 496 | 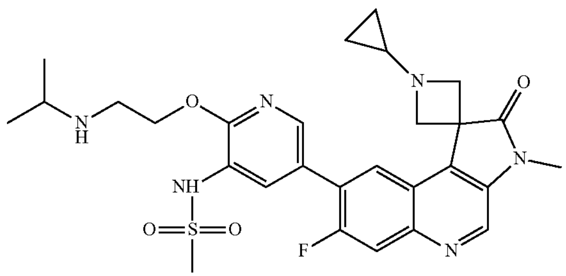 [SMILES: CC(C)NCCOc1ncc(-c2cc3c4c(cnc3cc2F)N(C)C(=O)C42CN(C3CC3)C2)cc1NS(C)(=O)=O] | N-(5-(1-Cyclopropyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 569.25 | 1H NMR (400 MHz, DMSO-d6) δ 9.31 (d, J = 8.8 Hz, 1H), 8.89 (s, 1H), 8.19 (s, 1H), 7.98-7.89 (m, 2H), 4.42 (t, J = 5.3 Hz, 2H), 3.80 (d, J = 7.2 Hz, 2H), 3.68 (d, J = 7.3 Hz, 2H), 3.31 (s, 3H), 3.02 (s, 3H), 2.97 (t, J = 5.1 Hz, 2H), 2.93-2.85 (m, 1H), 2.14 (s, 1H), 1.06 (d, J = 6.2 Hz, 7H), 0.46 (d, J = 6.4 Hz, 2H). |
| 497 | 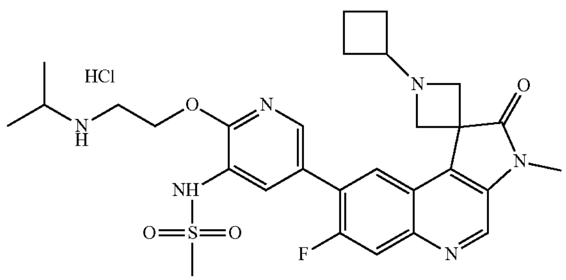 [SMILES: CC(C)NCCOc1ncc(-c2cc3c4c(cnc3cc2F)N(C)C(=O)C42CN(C3CCC3)C2)cc1NS(C)(=O)=O ; Cl] | N-(5-(1-Cyclobutyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | 583.40 | 1H NMR (400 MHz, CD3OD) δ 8.90 (s, 1H), 8.55 (d, J = 7.9 Hz, 1H), 8.40 (s, 1H), 8.18 (s, 1H), 7.95 (d, J = 11.4 Hz, 1H), δ 12 (d, J = 12.2 Hz, 2H), 4.78 (t, J = 5.2 Hz, 3H), 4.26 (d, J = 12.1 Hz, 2H), 3.63-3.50 (m, 4H), 3.43 (s, 3H), 3.18 (s, 3H), 2.53-2.42 (m, 2H), 2.36-2.31 (m, 2H), 2.07-1.91 (m, 2H). |
| 498 | 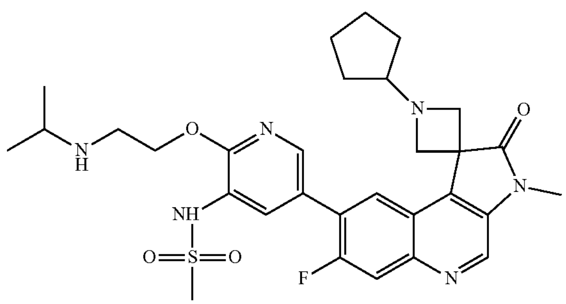 [SMILES: CC(C)NCCOc1ncc(-c2cc3c4c(cnc3cc2F)N(C)C(=O)C42CN(C3CCCC3)C2)cc1NS(C)(=O)=O] | N-(5-(1-Cyclopentyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 597.30 | 1H NMR (400 MHz, DMSO-d6) δ 9.51 (d, J = 8.9 Hz, 1H), 8.89 (s, 1H), 8.22 (d, J = 1.7 Hz, 1H), 7.98-7.90 (m, 2H), 4.41 (t, J = 5.4 Hz, 2H), 3.77 (d, J = 7.1 Hz, 2H), 3.40 (d, J = 7.2 Hz, 2H), 3.31 (s, 3H), 3.02 (s, 3H), 2.97 (q, J = 5.8 Hz, 3H), 2.87 (p, J = 6.2 Hz, 1H), 1.61 (d, J = 9.9 Hz, 2H), 1.50 (dd, J = 23.0, 7.1Hz, 6H), 1.05 (d, J = 6.2 Hz, 6H). |

| Examples | Structure | Name | MS: [(M + 1)]+ | 1H NMR |
|---|---|---|---|---|
| 499 | 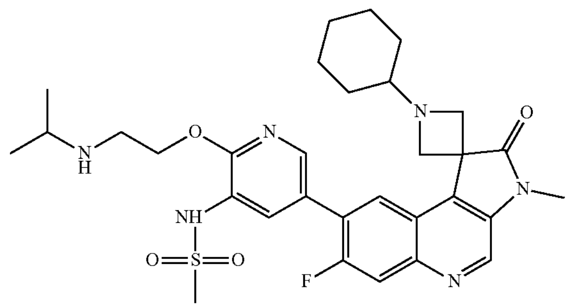 [SMILES: CC(C)NCCOc1ncc(-c2cc3c4c(cnc3cc2F)N(C)C(=O)C42CN(C3CCCCC3)C2)cc1NS(C)(=O)=O] | N-(5-(1-Cyclohexyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 611.60 | 1H NMR (400 MHz, DMSO-d6) δ 9.62 (d, J = 8.8 Hz, 1H), 8.90 (s, 1H), 8.27 (s, 1H), 7.95 (d, J = 11.6 Hz, 2H), 4.42 (t, J = 5.3 Hz, 2H), 3.75 (d, J = 7.0 Hz, 2H), 3.46 (d, J = 7.2 Hz, 2H), 3.3l(s, 3H), 3.03 (s, 3H), 2.98 (t, J = 5.3 Hz, 2H), 2.92-2.86 (m, 1H), 2.38 (s, 1H), 1.61 (d, J = 8.9 Hz, 4H), 1.51-1.18 (m, 6H), 1.06 (d, J = 6.2 Hz, 6H). |
| 500 | 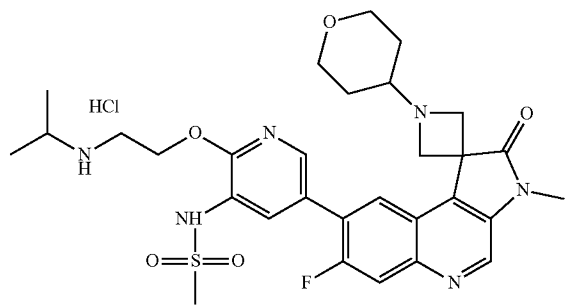 [SMILES: CC(C)NCCOc1ncc(-c2cc3c4c(cnc3cc2F)N(C)C(=O)C42CN(C3CCOCC3)C2)cc1NS(C)(=O)=O ; Cl] | N-(5-(7'-Fluoro-3'-methyl-2'-oxo-1-(tetrahydro-2H-pyran-4-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | 613.35 | 1H NMR (400 MHz, CD3OD) δ 9.64 (s, 1H), 8.83 (s, 1H), 8.34 (s, 1H), 8.21 (s, 1H), 7.87 (d, J = 11.8 Hz, 1H), 4.77 (t, J = 5.0 Hz, 2H), 3.93 (s, 3H), 3.71 (s, 2H), 3.63-3.45 (m, 6H), 3.40 (s, 3H), 3.13 (s, 3H), 2.75 (s, 1H), 1.86 (s, 2H), 1.42 (d, J = 6.6 Hz, 8H). |
| 501 | 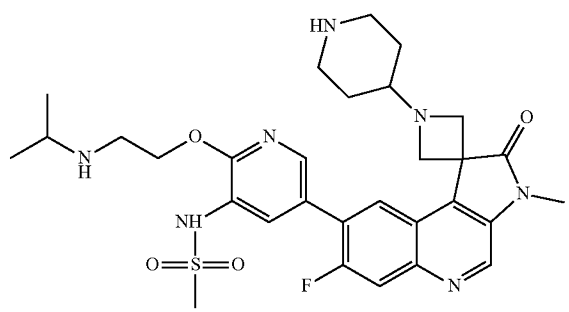 [SMILES: CC(C)NCCOc1ncc(-c2cc3c4c(cnc3cc2F)N(C)C(=O)C42CN(C3CCNCC3)C2)cc1NS(C)(=O)=O] | N-(5-(7'-Fluoro-3'-methyl-2'-oxo-1-(piperidin-4-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | 612.25 | 1H NMR (400 MHz, DMSO-d6) δ 9.40 (d, J = 8.9 Hz, 1H), 8.90 (s, 1H), 8.19 (d, J = 12.4 Hz, 1H), 7.96 (s, 1H), 7.72 (s, 1H), 4.40 (t, J = 5.2 Hz, 2H), 3.86 (d, J = 7.3 Hz, 2H), 3.57-3.46 (m, 4H), 3.32 (s, 3H), 3.17 (t, J = 11.1 Hz, 2H), 2.98-2.76 (m, 7H), 1.76-1.66 (m, 2H), 1.64-1.53 (m, 2H), 1.03 (d, J = 6.8 Hz, 6H). |

| Examples | Structure | Name | MS: [(M + 1)]+ | 1H NMR |
|---|---|---|---|---|
| 502 | 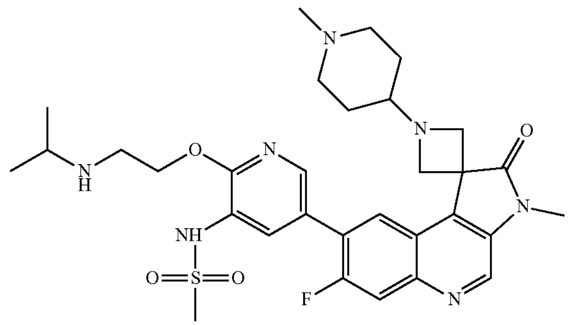 [SMILES: CC(C)NCCOc1ncc(-c2cc3c4c(cnc3cc2F)N(C)C(=O)C42CN(C3CCN(C)CC3)C2)cc1NS(C)(=O)=O] | N-(5-(7'-Fluoro-3'-methyl-1-(1-methylpiperidin-4-yl)-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 626.3 | 1H NMR (400 MHz, DMSO-d6) δ 9.44 (d, J = 8.7 Hz, 1H), 8.90 (s, 1H), 8.17 (d, J = 2.1 Hz, 1H), 7.94 (d, J = 12.1 Hz, 1H), 7.90 (d, J = 2.2 Hz, 1H), 4.40 (t, J = 5.3 Hz, 2H), 3.78 (d, J = 7.2 Hz, 2H), 3.47 (d, J = 7.3 Hz, 2H), 3.31 (s, 3H), 3.01 (s, 3H), 2.96 (t, J = 5.4 Hz, 2H), 2.88 (p, J = 6.2 Hz, 1H), 2.47-2.43 (m, 2H), 2.39 (s, 1H), 2.13-2.04 (m, 2H), 2.02 (s, 3H), 1.71-1.60 (m, 2H), 1.39-1.31 (m, 2H), 1.06 (d, J = 6.2 Hz, 6H). |
| 503 | 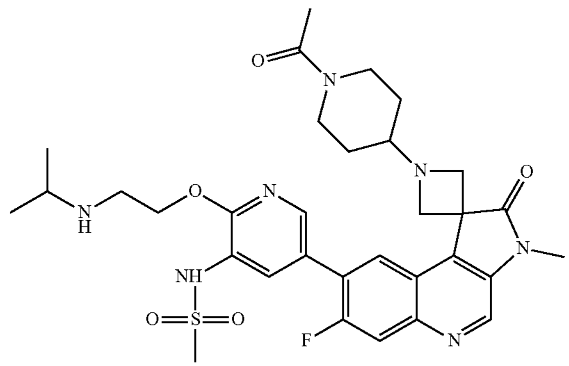 [SMILES: CC(=O)N1CCC(N2CC3(C2)C(=O)N(C)c2cnc4cc(F)c(-c5cnc(OCCNC(C)C)c(NS(C)(=O)=O)c5)cc4c23)CC1] | N-(5-(1-(1-Acetylpiperidin-4-yl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 654.20 | 1H NMR (400 MHz, DMSO-d6) δ 9.49 (d, J = 8.8 Hz, 1H), 8.91 (s, 1H), 8.18 (d, J = 2.1 Hz, 1H), 7.95 (d, J = 12.1 Hz, 1H), 7.92 (d, J = 2.3 Hz, 1H), 4.40 (q, J = 5.0 Hz, 2H), 3.81 (t, J = 5.6 Hz, 2H), 3.58-3.49 (m, 6H), 3.32 (s, 3H), 3.01 (s, 6H), 2.63 (s, 1H), 1.99 (s, 3H), 1.68 (s, 1H), 1.57 (s, 1H), 1.37 (s, 1H), 1.23 (s, 1H). |
| 504 | 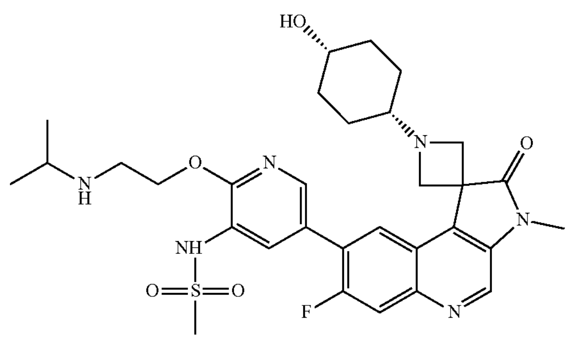 [SMILES: CC(C)NCCOc1ncc(-c2cc3c4c(cnc3cc2F)N(C)C(=O)C42CN([C@H]3CC[C@@H](O)CC3)C2)cc1NS(C)(=O)=O] | N-(5-(7'-Fluoro-1-(cis-4-hydroxycyclohexyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 627.40 | 1H NMR (400 MHz, DMSO-d6) δ 9.43 (d, J = 8.8 Hz, 1H), 8.90 (s, 1H), 8.20 (s, 1H), 7.95 (d, J = 12.2 Hz, 1H), 7.92 (t, J = 2.2 Hz, 1H), 4.40 (t, J = 5.4 Hz, 2H), 3.80 (d, J = 7.4 Hz, 2H), 3.55-3.50 (m, 3H), 3.31 (s, 3H), 3.00 (s, 3H), 2.96 (t, J = 5.3 Hz, 2H), 2.94-2.86 (m, 1H), 2.40 (s, 1H), 1.60-1.38 (m, 8H), 1.06 (d, J = 6.3 Hz, 6H). |

| Examples | Structure | Name | MS: [(M + 1)]+ | ¹H NMR |
|---|---|---|---|---|
| 505 | 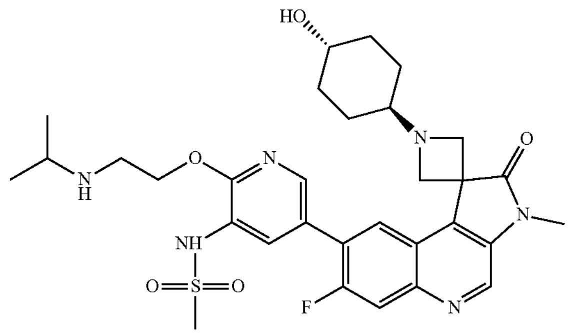 [SMILES: CC(C)NCCOc1ncc(-c2cc3c4c(cnc3cc2F)N(C)C(=O)C42CN([C@H]3CC[C@H](O)CC3)C2)cc1NS(C)(=O)=O] | N-(5-(7'-Fluoro-1-(trans-4-hydroxycyclohexyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 627.40 | ¹H NMR (400 MHz, DMSO-d₆) δ 9.59 (d, J = 8.9 Hz, 1H), 8.89 (s, 1H), 8.22 (s, 1H), 7.98-7.90 (m, 2H), 4.41 (t, J = 5.4 Hz, 2H), 3.74 (d, J = 7.2 Hz, 2H), 3.52-3.45 (m, 3H), 3.01 (s, 3H), 2.95 (t, J = 5.4 Hz, 2H), 2.87 (p, J = 6.3 Hz, 1H), 2.29 (s, 1H), 1.77 (d, J = 9.8 Hz, 4H), 1.26-1.07 (m, 4H), 1.05 (d, J = 6.2 Hz, 6H). |
| 506 | 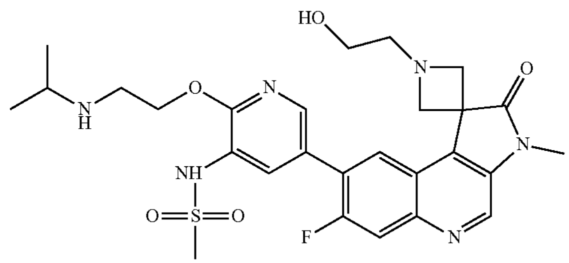 [SMILES: CC(C)NCCOc1ncc(-c2cc3c4c(cnc3cc2F)N(C)C(=O)C42CN(CCO)C2)cc1NS(C)(=O)=O] | N-(5-(7'-Fluoro-1-(2-hydroxyethyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 573.30 | ¹H NMR (400 MHz, DMSO-d₆) δ 9.55 (d, J = 8.8 Hz, 1H), 8.89 (s, 1H), 8.24 (t, J = 1.8 Hz, 1H), 7.99-7.91 (m, 2H), 4.44 (t, J = 5.3 Hz, 2H), 3.86 (d, J = 7.5 Hz, 2H), 3.57 (d, J = 7.6 Hz, 2H), 3.50 (t, J = 5.9 Hz, 2H), 3.45 (q, J = 7.0 Hz, 1H), 3.31 (s, 3H), 3.03 (s, 3H), 3.00 (t, J = 5.4 Hz, 2H), 2.93 (p, J = 6.2 Hz, 1H), 2.72 (t, J = 5.9 Hz, 2H), 1.08 (d, J = 6.3 Hz, 6H). |
| 507 | 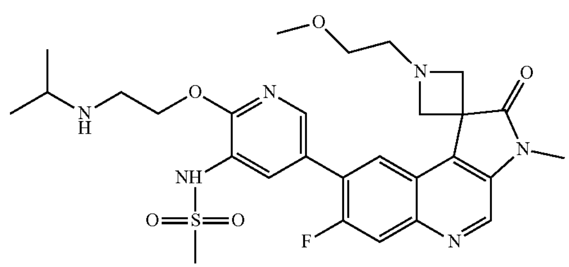 [SMILES: COCCN1CC2(C1)C(=O)N(C)c1cnc3cc(F)c(-c4cnc(OCCNC(C)C)c(NS(C)(=O)=O)c4)cc3c12] | N-(5-(7'-Fluoro-1-(2-methoxyethyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 587.25 | ¹H NMR (400 MHz, DMSO-d₆) δ 9.56 (d, J = 8.9 Hz, 1H), 8.90 (s, 1H), 8.26 (s, 1H), 7.99-7.91 (m, 2H), 4.43 (t, J = 5.4 Hz, 2H), 3.84 (d, J = 7.5 Hz, 2H), 3.55 (d, J = 7.5 Hz, 2H), 3.31 (s, 3H), 3.26 (s, 3H), 3.44 (d, J = 5.5 Hz, 2H), 3.04 (s, 3H), 2.97 (t, J = 5.4 Hz, 2H), 2.93-2.84 (m, 1H), 2.79 (t, J = 5.5 Hz, 2H), 1.06 (d, J = 6.2 Hz, 6H). |

| Examples | Name | MS: [(M + 1)]+ | 1H NMR |
|---|---|---|---|
| 508 | N-(5-(1-(2,2-Difluoroethyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 593.25 | 1H NMR (400 MHz, DMSO-d6) δ 9.41 (d, J = 8.8 Hz, 1H), 8.91 (s, 1H), 8.29-8.24 (m, 2H), 7.97 (dd, J = 7.2, 5.1 Hz, 2H), 6.04 (tt, J = 55.8, 3.8 Hz, 1H), 4.44 (t, J = 5.4 Hz, 2H), 3.91 (d, J = 7.6 Hz, 2H), 3.69 (d, J = 7.6 Hz, 2H), 3.31 (s, 3H), 3.16-2.92 (m, 8H), 1.09 (d, J = 6.3 Hz, 6H). |
| 509 | (R)-N-(5-(1-(2,3-Dihydroxypropyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 603.40 | 1H NMR (400 MHz, DMSO-d6) δ 9.47 (d, J = 8.8 Hz, 1H), 8.88 (s, 1H), 8.23 (t, J = 1.6 Hz, 1H), 7.97-7.91 (m, 2H), 4.43 (t, J = 5.4 Hz, 2H), 3.87 (dd, J = 16.7, 7.4 Hz, 2H), 3.56 (dd, J = 13.2, 7.6 Hz, 4H), 3.39-3.78 (m, 6H), 3.30 (s, 3H), 3.03 (s, 3H), 3.02-2.90 (m, 3H), 2.76 (dd, J = 12.1, 4.6 Hz, 1H), 2.57 (dd, J = 12.0, 6.5 Hz, 1H), 1.08 (d, J = 6.3 Hz, 6H). |
| 510 | (S)-N-(5-(1-(2,3-Dihydroxypropyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 603.40 | 1H NMR (400 MHz, DMSO-d6) δ 9.48 (d, J = 8.7 Hz, 1H), 8.89 (s, 1H), 8.28 (d, J = 1.8 Hz, 1H), 7.99-7.93 (m, 2H), 4.46 (t, J = 5.1 Hz, 3H), 3.87 (dd, J = 16.5, 7.4 Hz, 2H), 3.56 (dd, J = 13.1, 7.6 Hz, 4H), 3.30 (s, 3H), 3.06 (s, 7H), 2.76 (dd, J = 12.1, 4.6 Hz, 1H), 2.57 (dd, J = 12.1, 6.5 Hz, 1H), 1.11 (d, J = 6.2 Hz, 6H). |

-continued

| Examples | Structure | Name | MS: [(M + 1)]+ | 1H NMR |
|---|---|---|---|---|
| 511 | 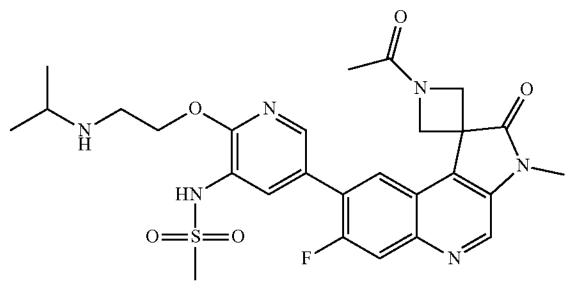 [SMILES: CC(=O)N1CC2(C1)C(=O)N(C)c1cnc3cc(F)c(-c4cnc(OCCNC(C)C)c(NS(C)(=O)=O)c4)cc3c12] | N-(5-(1-Acetyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 571.30 | 1H NMR (400 MHz, DMSO-d6) δ 8.95 (s, 1H), 8.20 (d, J = 2.1 Hz, 1H), 8.03 (s, 1H), 8.00 (d, J = 3.3 Hz, 1H), 7.92 (t, J = 2.1 Hz, 1H), 4.76 (d, J = 9.0 Hz, 1H), 4.50 (d, J = 9.0 Hz, 1H), 4.42 (t, J = 5.4 Hz, 2H), 4.33 (d, J = 9.9 Hz, 1H), 4.20 (d, J = 10.0 Hz, 1H), 3.33 (s, 3H), 3.01 (s, 3H), 2.98 (t, J = 5.4 Hz, 2H), 2.91 (p, J = 6.3 Hz, 1H), 1.96 (s, 3H), 1.07 (d, J = 6.3 Hz, 6H). |
| 512 | 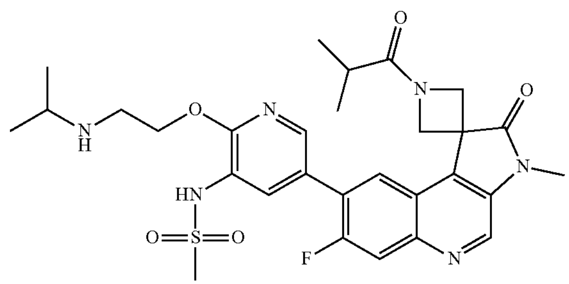 [SMILES: CC(C)NCCOc1ncc(-c2cc3c4c(cnc3cc2F)N(C)C(=O)C42CN(C(=O)C(C)C)C2)cc1NS(C)(=O)=O] | N-(5-(7'-Fluoro-1-isobutyryl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 599.20 | 1H NMR (400 MHz, DMSO-d6) δ 8.95 (s, 1H), 8.12 (d, J = 2.2 Hz, 1H), 8.01 (d, J = 12.0 Hz, 1H), 7.98 (d, J = 8.2 Hz, 1H), 7.89 (t, J = 2.3 Hz, 1H), 4.79 (d, J = 9.0 Hz, 1H), 4.54 (d, J = 9.1 Hz, 1H), 4.41 (t, J = 5.3 Hz, 2H), 4.33 (d, J = 9.9 Hz, 1H), 4.20 (d, J = 10.0 Hz, 1H), 3.34 (s, 3H), 3.00 (s, 3H), 2.97 (t, J = 5.6 Hz, 2H), 2.9 (p, J = 6.3 Hz, 1H), 2.64 (p, J = 6.6 Hz, 1H), 1.07 (d, J = 6.3 Hz, 6H), 1.03 (d, J = 6.7 Hz, 3H), 0.99 (d, J = 6.7 Hz, 3H). |
| 513 | 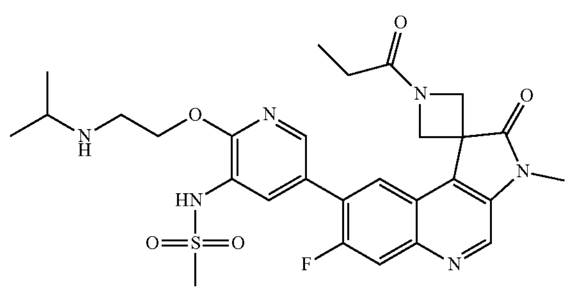 | Methyl 7'-fluoro-8'-(6-(2-(isopropylamino)ethoxy)-3-(methylsulfonamido)pyridin-3-yl)-3'-methyl-2'-oxo-2',3'-dihydrospiro[azetidine-3,1'-pyrrolo[2,3-c]quinoline]-1-carboxylate | 587.20 | 1H NMR (400 MHz, DMSO-d6) δ 8.94 (s, 1H), 8.14 (s, 1H), 8.11 (d, J = 8.3 Hz, 1H), 8.01 (d, J = 12.0 Hz, 1H), 7.88 (d, J = 2.2 Hz, 1H), 4.43 (t, J = 5.6 Hz, 4H), 4.29 (d, J = 8.8 Hz, 2H), 3.67(s, 3H), 3.32 (s, 3H), 2.98 (s, 3H), 2.98-2.86 (m, 3H), 1.08 (d, J = 6.3 Hz, 6H). |

| Examples | Structure | Name | MS: [(M + 1)]+ | 1H NMR |
|---|---|---|---|---|
| 514 | 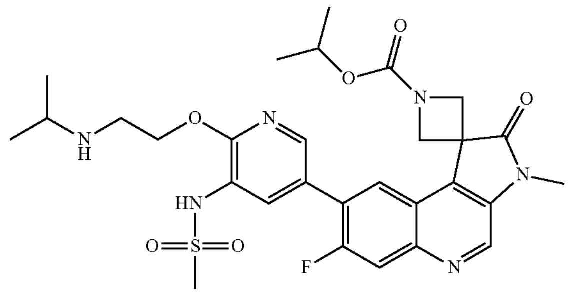 [SMILES: CC(C)NCCOc1ncc(-c2cc3c4c(cnc3cc2F)N(C)C(=O)C42CN(C(=O)OC(C)C)C2)cc1NS(C)(=O)=O] | Isopropyl 7'-fluoro-8'-(6-(2-(isopropylamino)ethoxy)-5-(methylsulfonamido)pyridin-3-yl)-3'-methyl-2'-oxo-2',3'-dihydrospiro[azetidine-3,1'-pyrrolo[2,3-c]quinoline]-1-carboxylate | 615.20 | 1H NMR (400 MHz, DMSO-$d_6$) δ 8.94 (s, 1H), 8.13 (s, 1H), 8.07 (d, J = 8.2 Hz, 1H), 8.01 (d, J = 12.0 Hz, 1H), 7.91 (t, J = 2.3 Hz, 1H), 4.89-4.78 (m, 1H), 4.43 (t, J = 5.4 Hz, 4H), 4.27 (d, J = 9.0 Hz, 2H), 3.32 (s, 3H), 3.06-2.88 (m, 6H), 1.17 (s, 6H), 1.08 (d, J = 6.3 Hz, 6H). |
| 515 | 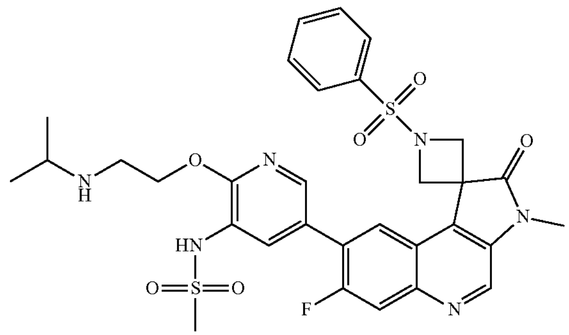 [SMILES: CC(C)NCCOc1ncc(-c2cc3c4c(cnc3cc2F)N(C)C(=O)C42CN(S(=O)(=O)c3ccccc3)C2)cc1NS(C)(=O)=O] | N-(5-(7'-Fluoro-3'-methyl-2'-oxo-1-(phenylsulfonyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | 669.35 | 1H NMR (400 MHz, DMSO-$d_6$) δ 8.90 (s, 1H), 8.59 (d, J = 8.4 Hz, 1H), 8.19 (d, J = 2.2 Hz, 1H), 8.00 (d, J = 12.0 Hz, 1H), 7.97-7.86 (m, 3H), 7.86-7.77 (m, 1H), 7.71 (t, J = 7.7 Hz, 2H), 4.48 (t, J = 5.3 Hz, 2H), 4.31 (d, J = 8.6 Hz, 2H), 4.11 (d, J = 8.7 Hz, 2H), 3.20 (s, 3H), 3.04 (s, 3H), 3.02 (t, J = 5.6 Hz, 2H), 2.95 (p, J = 6.2 Hz, 1H), 1.09 (d, J = 6.2 Hz, 6H). |
| 516 | 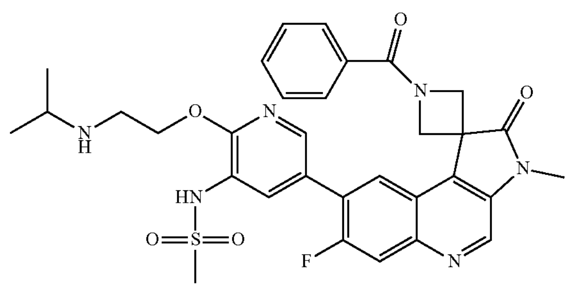 [SMILES: CC(C)NCCOc1ncc(-c2cc3c4c(cnc3cc2F)N(C)C(=O)C42CN(C(=O)c3ccccc3)C2)cc1NS(C)(=O)=O] | N-(5-(1'-Benzoyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 633.40 | 1H NMR (400 MHz, DMSO-$d_6$) δ 8.96 (s, 1H), 8.14 (s, 1H), 8.04 (d, J = 2.7 Hz, 1H), 8.02 (d, J = 6.4 Hz, 1H), 7.91 (t, J = 2.3 Hz, 1H), 7.78-7.70 (m, 2H), 7.56 (t, J = 7.3 Hz, 1H), 7.48 (dd, J = 8.2, 6.7 Hz, 2H), 4.89 (d, J = 8.8 Hz, 1H), 4.67-4.58 (m, 2H), 4.45 (t, J = 5.3 Hz, 3H), 3.02-2.87 (m, 7H), 1.07 (d, J = 6.2 Hz, 6H). |

| Examples | Structure | Name | MS: [(M + 1)]+ | 1H NMR |
|---|---|---|---|---|
| 517 | 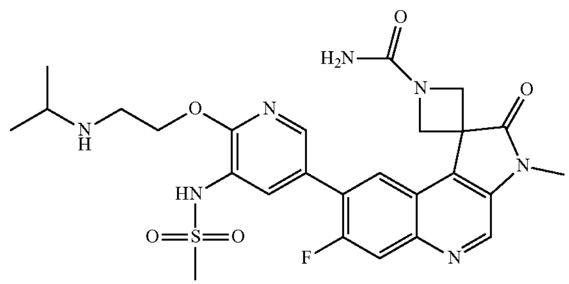 [SMILES: CC(C)NCCOc1ncc(-c2cc3c4c(cnc3cc2F)N(C)C(=O)C42CN(C(N)=O)C2)cc1NS(C)(=O)=O] | 7'-Fluoro-8'-(6-(2-(isopropylamino) ethoxy)-5-(methylsulfonamido) pyridin-3-yl)-3'-methyl-2'-oxo-2',3'-dihydrospiro[azetidine-3,1'-pyrrolo[2,3-c]quinoline]-1-carboxamide | 560.15 | 1H NMR (400 MHz, DMSO-d6) δ 8.93 (s, 1H), 8.35 (d, J = 8.4 Hz, 1H), 8.17-8.11 (m, 1H), 8.00 (d, J = 12.1 Hz, 1H), 7.90 (t, J = 2.3 Hz, 1H), 6.28 (s, 2H), 4.43 (t, J = 5.3 Hz, 2H), 4.28-4.17 (m, 4H), 3.32 (s, 3H), 3.00 (s, 3H), 2.99-2.89 (m, 3H), 1.08 (d, J = 6.3 Hz, 6H). |
| 518 | 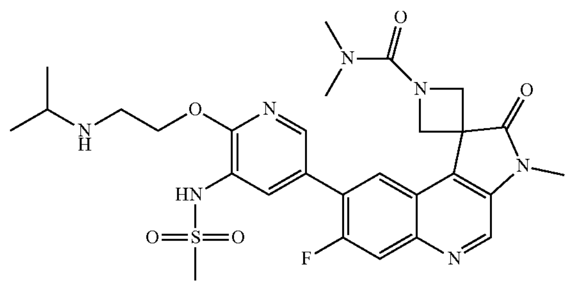 [SMILES: CC(C)NCCOc1ncc(-c2cc3c4c(cnc3cc2F)N(C)C(=O)C42CN(C(=O)N(C)C)C2)cc1NS(C)(=O)=O] | 7'-Fluoro-8'-(6-(2-(isopropylamino) ethoxy)-5-(methylsulfonamido)pyridin-3-yl)-N,N,3'-trimethyl-2'-oxo-2',3'-dihydrospiro[azetidine-3,1'-pyrrolo[2,3-c]quinoline]-1-carboxamide | 600.25 | 1H NMR (400 MHz, DMSO-d6) δ 8.93 (s, 1H), 8.39 (d, J = 8.4 Hz, 1H), 8.20 (d, 1H), 7.92 (t, J = 12.1 Hz, 1H), 4.43 (t, J = 5.4 Hz, 2H), 4.39-4.27 (m, 4H), 3.32 (s, 3H), 3.00 (s, 3H), 2.99-2.88 (m, 3H), 2.85 (s, 6H), 1.07 (d, J = 6.2 Hz, 6H). |
| 519 | 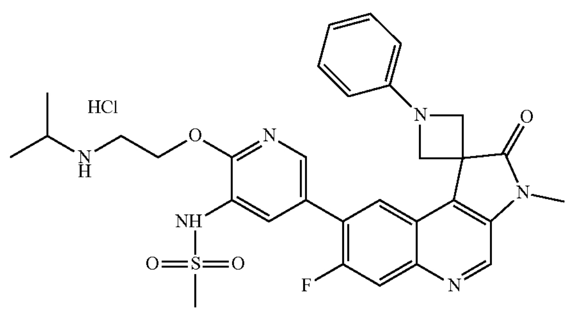 [SMILES: CC(C)NCCOc1ncc(-c2cc3c4c(cnc3cc2F)N(C)C(=O)C42CN(c3ccccc3)C2)cc1NS(C)(=O)=O ; Cl] | N-(5-(7'-Fluoro-3'-methyl-2'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | 605.25 | 1H NMR (400 MHz, CD3OD) δ 9.01 (d, J = 8.1 Hz, 1H), 8.97 (s, 1H), 8.21 (t, J = 2.3 Hz, 1H), 8.13 (t, J = 1.7 Hz, 1H), 7.96 (d, J = 11.5 Hz, 1H), 7.33-7.24 (m, 2H), 6.87 (t, J = 7.4 Hz, 1H), 6.74-6.67 (m, 2H), 4.68 (t, J = 5.0 Hz, 2H), 4.49 (d, J = 7.6 Hz, 2H), 4.30 (m, 3H), 3.42 (s, 3H), 3.53-3.44 (m, 3H), 2.70 (s, 3H), 1.37 (d, J = 6.5 Hz, 6H). |

-continued

| Examples | Structure | Name | MS: [(M + 1)]+ | 1H NMR |
|---|---|---|---|---|
| 522 | 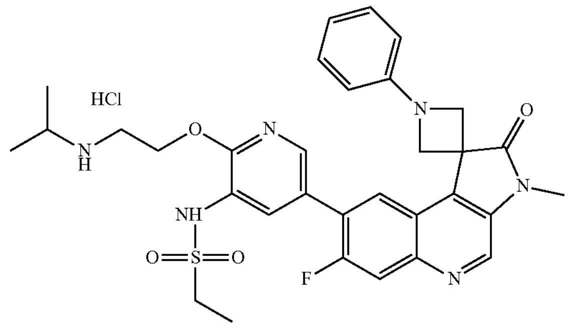 [SMILES: CCS(=O)(=O)Nc1cc(-c2cc3c4c(cnc3cc2F)N(C)C(=O)C42CN(c3ccccc3)C2)cnc1OCCNC(C)C ; Cl] | N-(5-(7'-Fluoro-3'-methyl-2'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)ethanesulfonamide hydrochloride | 619.3 | 1H NMR (400 MHz, CD3OD) δ 8.92 (d, J = 8.3 Hz, 1H), 8.89 (s, 1H), 8.19 (s, 1H), 8.13 (s, 1H), 7.93 (d, J = 12.0 Hz, 1H), 7.31 (t, J = 7.8 Hz, 2H), 6.88 (t, J = 7.4 Hz, 1H), 6.73 (d, J = 7.8 Hz, 2H), 4.70 (t, J = 5.0 Hz, 2H), 4.50 (d, J = 7.5 Hz, 2H), 4.31 (d, J = 7.6 Hz, 2H), 3.56-3.46 (m, 3H), 3.44 (s, 3H), 2.88 (q, J = 7.2 Hz, 2H), 1.39 (d, J = 6.5 Hz, 6H), 1.17 (t, J = 7.3 Hz, 3H). |
| 523 | 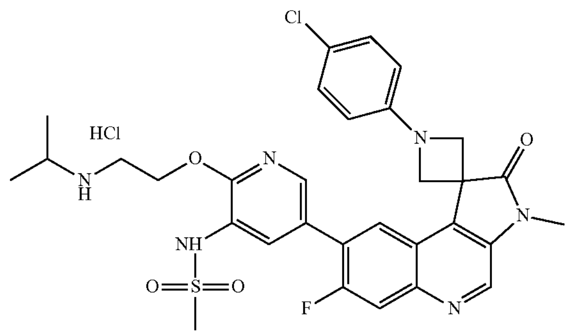 [SMILES: CC(C)NCCOc1ncc(-c2cc3c4c(cnc3cc2F)N(C)C(=O)C42CN(c3ccc(Cl)cc3)C2)cc1NS(C)(=O)=O ; Cl] | N-(5-(1-(4-Chlorophenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | 639.30, 641.30 | 1H NMR (400 MHz, CD3OD) δ 8.93 (s, 1H), 8.86 (d, J = 8.0 Hz, 1H), 8.17 (s, 1H), 8.12 (s, 1H), 7.94 (d, J = 11.7 Hz, 1H), 7.26 (d, J = 8.3 Hz, 2H), 6.68 (d, J = 8.4 Hz, 2H), 4.70 (t, J = 5.0 Hz, 2H), 4.48 (d, J = 7.7 Hz, 2H), 4.31 (d, J = 7.6 Hz, 2H), 3.54-3.46 (m, 3H), 3.42 (s, 3H), 2.84 (s, 3H), 1.38 (d, J = 6.5 Hz, 6H). |
| 524 | 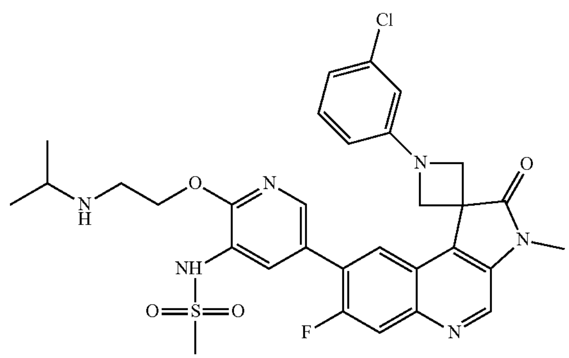 [SMILES: CC(C)NCCOc1ncc(-c2cc3c4c(cnc3cc2F)N(C)C(=O)C42CN(c3cccc(Cl)c3)C2)cc1NS(C)(=O)=O] | N-(5-(1-(3-Chlorophenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 639.15, 641.15 | 1H NMR (400 MHz, DMSO-d6) δ 8.96 (s, 1H), 8.54 (d, J = 8.4 Hz, 1H), 8.05 (s, 1H), 8.01 (d, J = 12.0 Hz, 1H), 7.84 (s, 1H), 7.27 (t, J = 8.0 Hz, 1H), 6.83 (d, J = 8.1 Hz, 1H), 6.72 (s, 1H), 6.62 (d, J = 8.4 Hz, 1H), 4.51 (d, J = 8.1 Hz, 2H), 4.36 (t, J = 5.3 Hz, 2H), 4.14 (d, J = 8.2 Hz, 2H), 3.34 (s, 3H), 2.92 (dt, J = 17.4, 5.7 Hz, 3H), 2.84 (s, 3H), 1.04 (d, J = 6.2 Hz, 7H). |

| Examples | Structure | Name | MS: [(M + 1)]+ | ¹H NMR |
|---|---|---|---|---|
| 525 | 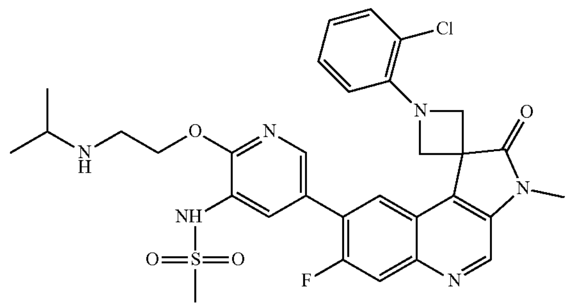 [SMILES: CC(C)NCCOc1ncc(-c2cc3c4c(cnc3cc2F)N(C)C(=O)C42CN(c3ccccc3Cl)C2)cc1NS(C)(=O)=O] | N-(5-(1-(2-Chlorophenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 639.35, 641.35 | ¹H NMR (400 MHz, DMSO-d₆) δ 8.97 (s, 1H), 8.87 (d, J = 8.4 Hz, 1H), 8.11 (s, 1H), 8.01 (d, J = 12.1 Hz, 1H), 7.88 (t, J = 2.2 Hz, 1H), 7.35 (dd, J = 8.0, 1.4 Hz, 1H), 7.29 (t, J = 7.5 Hz, 1H), 6.97-6.87 (m, 2H), 4.58 (d, J = 8.1 Hz, 2H), 4.36(t, J = 5.4 Hz, 2H), 4.29 (d, J = 8.2 Hz, 2H), 3.34 (s, 3H), 2.97-2.87 (m 3H), 2.85 (s, 3H), 1.04 (d, J = 6.3 Hz, 6H). |
| 526 | 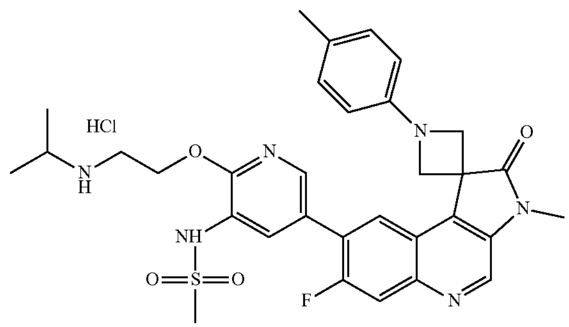 [SMILES: Cc1ccc(N2CC3(C2)C(=O)N(C)c2cnc4cc(F)c(-c5cnc(OCCNC(C)C)c(NS(C)(=O)=O)c5)cc4c23)cc1 ; Cl] | N-(5-(7'-Fluoro-3'-methyl-2'-oxo-1-(p-tolyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | 619.25 | ¹H NMR (400 MHz, CD₃OD) δ 9.01 (d, J = 8.2 Hz, 1H), 8.88 (s, 1H), 8.21 (t, J = 2.3 Hz, 1H), 8.11 (s, 1H), 7.91 (d, J = 11.9 Hz, 1H), 7.10 (d, J = 7.8 Hz, 2H), 6.61 (d, J = 7.9 Hz, 2H), 4.68 (t, J = 5.4 Hz, 2H), 4.44 (d, J = 7.5 Hz, 2H), 4.25 (d, J = 7.5 Hz, 2H), 3.52-3.44 (m, 3H), 3.41 (s, 3H), 2.71 (s, 3H), 2.28 (s, 3H), 1.37 (d, J = 6.5 Hz, 6H). |
| 527 | 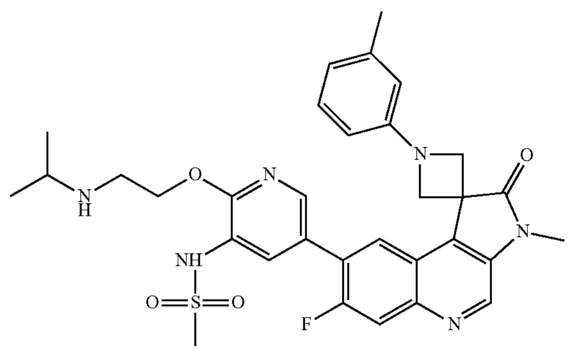 [SMILES: Cc1cccc(N2CC3(C2)C(=O)N(C)c2cnc4cc(F)c(-c5cnc(OCCNC(C)C)c(NS(C)(=O)=O)c5)cc4c23)c1] | N-(5-(7'-Fluoro-3'-methyl-2'-oxo-1-(m-tolyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | 619.40 | ¹H NMR (400 MHz, DMSO-d₆) δ 8.95 (s, 1H), 8.65 (d, J = 8.8 Hz, 1H), 8.00 (d, J = 12.3 Hz, 1H), 7.90 (s, 1H), 7.78 (s, 1H), 7.14 (t, J = 7.7 Hz, 1H), 6.64 (d, J = 8.1 Hz, 1H), 6.49-6.44 (m, 2H), 4.44 (d, J = 7.7 Hz, 2H), 4.36 (s, 2H), 4.10 (d, J = 7.8 Hz, 2H), 3.33 (s, 3H), 3.07-3.97 (m, 3H), 2.72 (s, 3H), 2.27 (s, 3H), 1.11 (d, J = 6.6 Hz, 6H). |

| Examples | Structure | Name | MS: [(M + 1)]+ | 1H NMR |
|---|---|---|---|---|
| 528 | 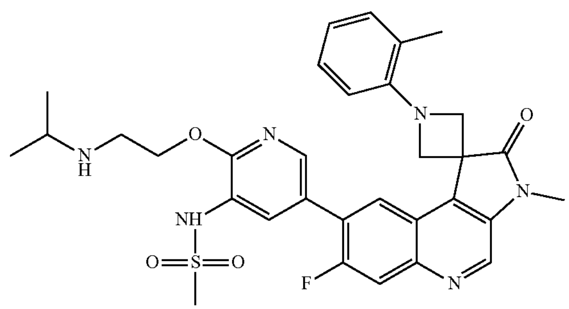 [SMILES: Cc1ccccc1N1CC2(C1)C(=O)N(C)c1cnc3cc(F)c(-c4cnc(OCCNC(C)C)c(NS(C)(=O)=O)c4)cc3c12] | N-(5-(7'-Fluoro-3'-methyl-2'-oxo-1-(o-tolyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | 619.25 | 1H NMR (400 MHz, DMSO-d6) δ 9.00 (d, J = 8.5 Hz, 1H), 8.97 (s, 1H), 8.07 (d, J = 1.8 Hz, 1H), 8.01 (d, J = 12.0 Hz, 1H), 7.85 (t, J = 2.2 Hz, 1H), 7.14 (t, J = 7.0 Hz, 1H), 7.09 (d, J = 7.2 Hz, 1H), 6.84 (t, J = 7.4 Hz, 1H), 6.71 (d, J = 7.9 Hz, 1H), 4.44 (d, J = 7.8 Hz, 2H), 4.36 (t, J = 5.3 Hz, 2H), 4 24 (d, J = 7.9 Hz, 2H), 3.34 (s, 3H), 3.00-2.87 (m, 3H), 2.79 (s, 3H), 2.22 (s, 3H), 1.06 (d, J = 6.3 Hz, 6H). |
| 529 | 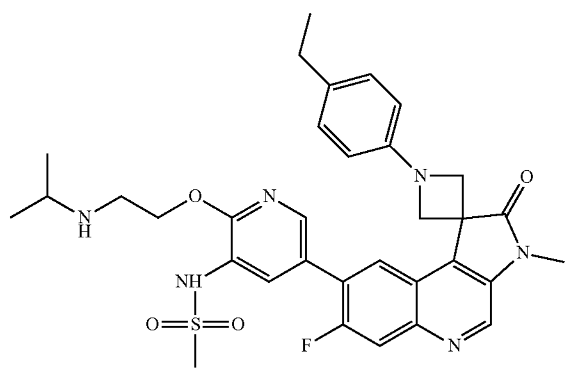 [SMILES: CCc1ccc(N2CC3(C2)C(=O)N(C)c2cnc4cc(F)c(-c5cnc(OCCNC(C)C)c(NS(C)(=O)=O)c5)cc4c23)cc1] | N-(5-(1-(4-Ethylphenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 633.20 | 1H NMR (400 MHz, DMSO-d6) δ 8.96 (s, 1H), 8.73 (d, J = 8.4 Hz, 1H), 8.06-7.97 (m, 2H), 7.84 (d, J = 2.3 Hz, 1H), 7.11 (d, J = 8.0 Hz, 2H), 6.60 (d, J = 8.0 Hz, 2H), 4.45 (d, J = 7.7 Hz, 2H), 4.35 (t, J = 5.3 Hz, 2H), 4.08 (d, J = 7.8 Hz, 2H), 3.34 (s, 3H), 2.97-2.87 (m, 3H), 2.80 (s, 3H), 2.56 (q, J = 7.5 Hz, 2H), 1.16 (t, J = 7.6 Hz, 3H), 1.05 (d, J = 6.3 Hz, 6H). |
| 530 | 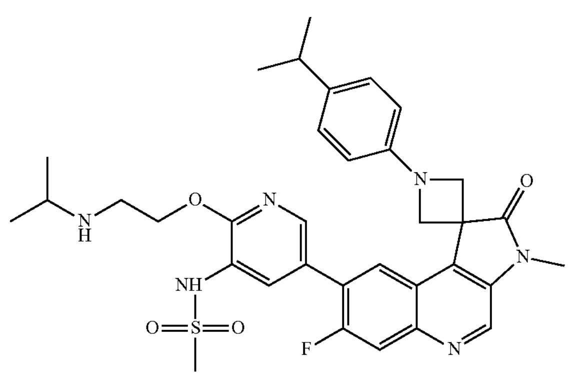 [SMILES: CC(C)NCCOc1ncc(-c2cc3c4c(cnc3cc2F)N(C)C(=O)C42CN(c3ccc(C(C)C)cc3)C2)cc1NS(C)(=O)=O] | N-(5-(7'-Fluoro-1-(4-isopropylphenyl)-3'methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 647.30 | 1H NMR (400 MHz, DMSO-d6) δ 8.97 (s, 1H), 8.74 (d, J = 8.5 Hz, 1H), 8.13 (s, 1H), 8.02 (d, J = 12.1 Hz, 1H), 7.90 (s, 1H), 7.14 (d, J = 8.2 Hz, 2H), 6.60 (d, J = 8.2 Hz, 2H), 4.45 (d, J = 7.7 Hz, 2H), 4.39 (t, J = 5.3 Hz, 2H), 4.07 (d, J = 7.7 Hz, 2H), 3.33 (s, 3H), 3.03 (s, 3H), 2.85 (s, 3H), 2.84-2.81 (m, 1H), 1.18 (d, J = 6.9 Hz, 6H), 1.08 (d, J = 6.3 Hz, 6H). |

| Examples | Structure | Name | MS: [(M + 1)]+ | 1H NMR |
|---|---|---|---|---|
| 531 | 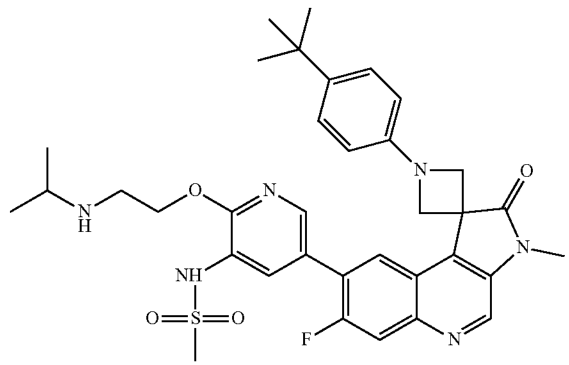 [SMILES: CC(C)NCCOc1ncc(-c2cc3c4c(cnc3cc2F)N(C)C(=O)C42CN(c3ccc(C(C)(C)C)cc3)C2)cc1NS(C)(=O)=O] | N-(5-(1-(4-(ter-Butyl)phenyl)-7′-fluoro-3′-methyl-2′-oxo-2′,3′-dihydrospiro[azetidine-3,1′-pyrrolo[2,3-c]quinolin]-8′-yl)-2-(2-(isopropylamino)ethoxy)pyridin-3-yl)methanesulfonamide | 661.50 | 1H NMR (400 MHz, DMSO-d6) δ 8.97 (s, 1H), 8.75 (d, J = 8.5 Hz, 1H), 8.07 (s, 1H), 8.01 (d, J = 12.1 Hz, 1H), 7.86 (d, J = 2.3 Hz, 1H), 7.29 (d, J = 8.6 Hz, 2H), 6.64-6.57 (m, 2H), 4.45 (d, J = 7.7 Hz, 2H), 4.35 (t, J = 5.3 Hz, 2H), 4.08 (d, J = 7.8 Hz, 2H), 3.34 (s, 3H), 2.96-2.85 (m, 3H), 2.79 (s, 3H), 1.27 (s, 9H), 1.04 (d, J = 6.2 Hz, 6H). |
| 532 | 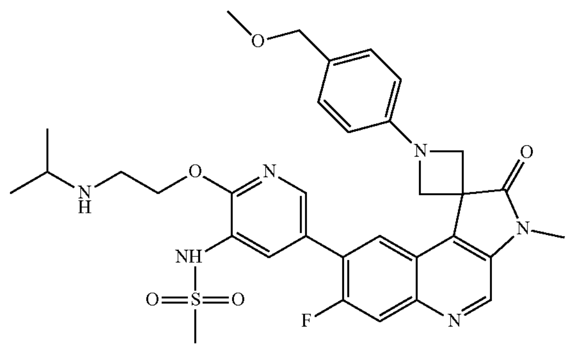 [SMILES: COCc1ccc(N2CC3(C2)C(=O)N(C)c2cnc4cc(F)c(-c5cnc(OCCNC(C)C)c(NS(C)(=O)=O)c5)cc4c23)cc1] | N-(5-(7′-Fluoro-1-(4-(methoxymethyl)phenyl)-3′-methyl-2′-oxo-2′,3′-dihydrospiro[azetidine-3,1′-pyrrolo[2,3-c]quinolin]-8′-yl)-2-(2-(isopropylamino)ethoxy)pyridin-3-yl)methanesulfonamide | 649.45 | 1H NMR (400 MHz, DMSO-d6) δ 8.96 (s, 1H), 8.66 (d, J = 8.4 Hz, 1H), 8.04-7.96 (m, 2H), 7.82 (t, J = 2.2 Hz, 1H), 7.21 (d, J = 8.4 Hz, 2H), 6.64 (d, J = 8.4 Hz, 2H), 4.48 (d, J = 7.9 Hz, 2H), 4.36-4.30 (m, 4H), 4.11 (d, J = 7.9 Hz, 2H), 3.33 (s, 3H), 3.25 (s, 3H), 2.99-2.88 (m, 3H), 2.78 (s, 3H), 1.05 (d, J = 6.3 Hz, 6H). |

| Examples | Structure | Name | MS: [(M + 1)]⁺ | ¹H NMR |
|---|---|---|---|---|
| 533 | 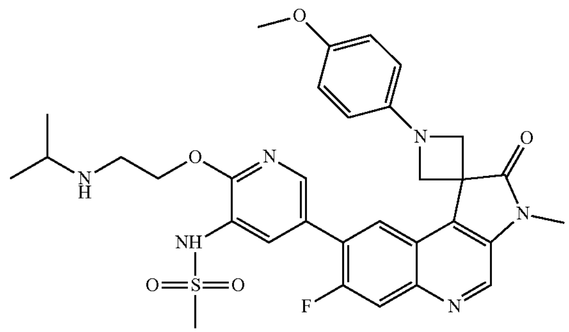 [SMILES: COc1ccc(N2CC3(C2)C(=O)N(C)c2cnc4cc(F)c(-c5cnc(OCCNC(C)C)c(NS(C)(=O)=O)c5)cc4c23)cc1] | N-(5-(7'-Fluoro-1-(4-methoxyphenyl)-3-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 635.40 | ¹H NMR (400 MHz, DMSO-d₆) δ 8.96 (s, 1H), 8.78 (d, J = 8.6 Hz, 1H), 8.05 (s, 1H), 8.00 (d, J = 12.0 Hz, 1H), 7.85 (s, 1H), 6.88 (d, J = 8.2 Hz, 2H), 6.63 (d, J = 8.6 Hz, 2H), 4.41 (d, J = 7.5 Hz, 2H), 4.35 (t, J = 5.3 Hz, 2H), 4.05 (d, J = 7.7 Hz, 2H), 3.70 (s, 3H), 3.33 (s, 3H), 2.96-2.87 (m, 3H), 2.84 (s, 3H), 1.04 (d, J = 6.2 Hz, 6H). |
| 534 | 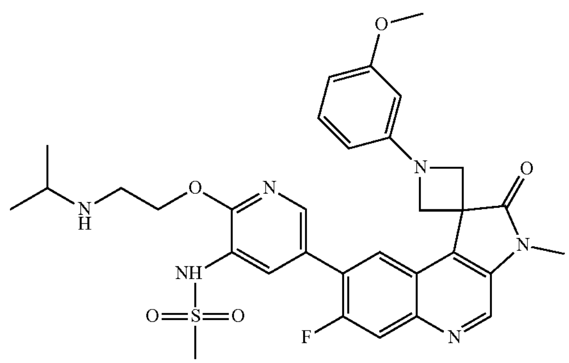 [SMILES: COc1cccc(N2CC3(C2)C(=O)N(C)c2cnc4cc(F)c(-c5cnc(OCCNC(C)C)c(NS(C)(=O)=O)c5)cc4c23)c1] | N-(5-(7'-Fluoro-1-(3-methoxyphenyl)-3-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 635.40 | ¹H NMR (400 MHz, DMSO-d₆) δ 8.96 (s, 1H), 8.63 (d, J = 8.5 Hz, 1H), 8.04 (s, 1H), 8.00 (d, J = 12.1 Hz, 1H), 7.84 (d, J = 2.3 Hz, 1H), 7.15 (t, J = 8.1 Hz, 1H), 6.40 (dd, J = 8.2, 2.2 Hz, 1H), 6.25 (d, J = 8.1 Hz, 1H), 6.20 (d, J = 2.2 Hz, 1H), 4.46 (d, J = 7.8 Hz, 2H), 4.36 (t, J = 5.3 Hz, 2H), 4.12 (d, J = 7.9 Hz, 2H), 3.73 (s, 3H), 3.33 (s, 3H), 2.98-2.86 (m, 3H), 2.82 (s, 3H), 1.04 (d, J = 6.3 Hz, 6H). |
| 535 | 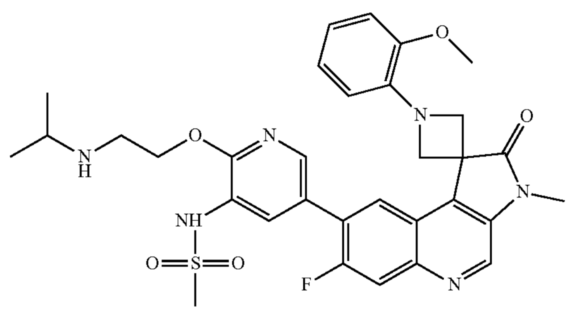 [SMILES: COc1ccccc1N1CC2(C1)C(=O)N(C)c1cnc3cc(F)c(-c4cnc(OCCNC(C)C)c(NS(C)(=O)=O)c4)cc3c12] | N-(5-(7'-Fluoro-1-(2-methoxyphenyl)-3-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 635.40 | ¹H NMR (400 MHz, DMSO-d₆) δ 8.91 (d, J = 8.5 Hz, 1H), 8.89 (s, 1H), 7.97 (d, J = 11.9 Hz, 1H), 7.67 (s, 2H), 6.95-6.84 (m, 3H), 6.66 (d, J = 7.3 Hz, 1H), 4.42 (d, J = 8.2 Hz, 2H), 4.35 (t, J = 5.3 Hz, 2H), 4.20 (d, J = 8.3 Hz, 2H), 3.86 (s, 3H), 3.73 (s, 3H), 3.33 (s, 3H), 3.18 (s, 3H), 1.20 (d, J = 6.4 Hz, 6H). |

| Examples | Structure | Name | MS: [(M + 1)]+ | 1H NMR |
|---|---|---|---|---|
| 536 | 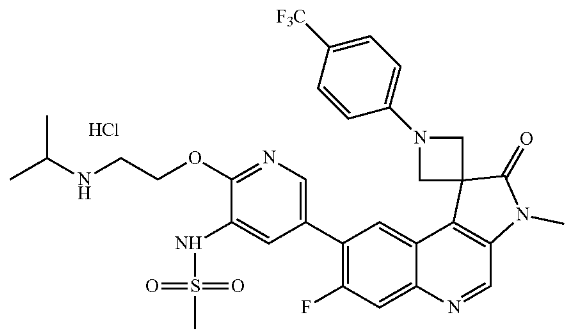 [SMILES: CC(C)NCCOc1ncc(-c2cc3c4c(cnc3cc2F)N(C)C(=O)C42CN(c3ccc(C(F)(F)F)cc3)C2)cc1NS(C)(=O)=O ; Cl] | N-(5-(7'-Fluoro-3'-methyl-2'-oxo-1-(4-(trifluoromethyl)phenyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | 673.4 | 1H NMR (400 MHz, CD3OD) δ 8.90 (s, 1H), 8.70(d, J = 8.1 Hz, 1H), 8.17 (d, J = 2.4 Hz, 1H), 8.11 (t, J = 1.9 Hz, 1H), 7.92 (d, J = 11.7 Hz, 1H), 7.55 (d, J = 8.2 Hz, 2H), 6.80 (d, J = 8.2 Hz, 2H), 4.67 (t, J = 4.9 Hz, 2H), 4.56 (d, J = 7.9 Hz, 2H), 4.39 (d, J = 7.9 Hz, 2H), 3.52-3.45 (m, 3H), 3.42 (s, 3H), 2.82 (s, 3H), 1.37 (d, J = 6.5 Hz, 6H). |
| 537 | 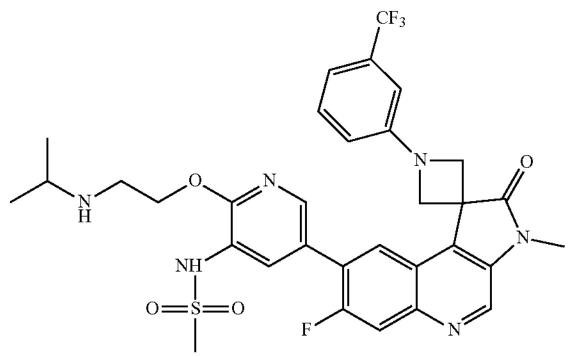 [SMILES: CC(C)NCCOc1ncc(-c2cc3c4c(cnc3cc2F)N(C)C(=O)C42CN(c3cccc(C(F)(F)F)c3)C2)cc1NS(C)(=O)=O] | N-(5-(7'-Fluoro-3'-methyl-2'-oxo-1-(3-(trifluoromethyl)phenyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | 673.15 | 1H NMR (400 MHz, DMSO-d6) δ 8.98 (s, 1H), 8.53 (d, J = 8.5 Hz, 1H), 8.07 (s, 1H), 8.02 (d, J = 12.1 Hz, 1H), 7.86 (t, J = 2.2 Hz, 1H), 7.49 (t, J = 7.9 Hz, 1H), 7.14 (d, J = 7.8 Hz, 1H), 6.96 (d, J = 8.8 Hz, 1H), 6.93 (s, 1H), 4.58 (d, J = 8.1 Hz, 2H), 4.36 (t, J = 5.3 Hz, 2H), 4.19 (d, J = 8.2 Hz, 2H), 3.35 (s, 3H), 2.97-2.87 (m, 3H), 2.82 (s, 3H), 1.05 (d, J = 6.3 Hz, 6H). |
| 538 | 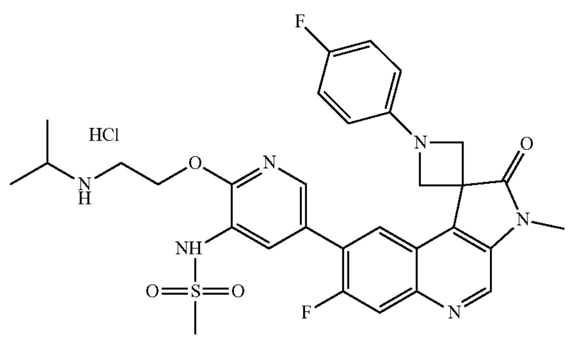 [SMILES: CC(C)NCCOc1ncc(-c2cc3c4c(cnc3cc2F)N(C)C(=O)C42CN(c3ccc(F)cc3)C2)cc1NS(C)(=O)=O ; Cl] | N-(5-(7'-Fluoro-1-(4-fluorophenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | 623.30 | 1H NMR (400 MHz, CD3OD) δ 8.95 (d, J = 6.9 Hz, 2H), 8.15 (dt, J = 18.0, 2.1 Hz, 2H), 7.94 (t, J = 11.6 Hz, 1H), 7.03 (t, J = 8.6 Hz, 2H), 6.73-6.65 (m, 2H), 4.69 (t, J = 4.9 Hz, 2H), 4.47 (d, J = 7.6 Hz, 2H), 4.29 (d, J = 7.6 Hz, 2H), 3.54-3.45 (m, 3H), 3.42 (s, 3H), 2.83 (s, 3H), 1.38 (d, J = 6.5 Hz, 6H). |

| Examples | Structure | Name | MS: [(M + 1)]+ | 1H NMR |
|---|---|---|---|---|
| 539 | 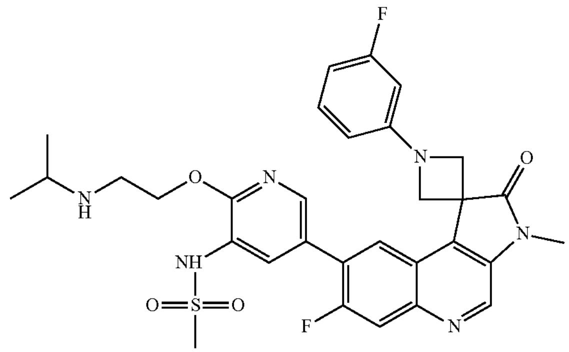 | N-(5-(7'-Fluoro-1-(3-fluorophenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 623.20 | 1H NMR (400 MHz, DMSO-d6) δ 8.97 (s, 1H), 8.54 (d, J = 8.4 Hz, 1H), 8.06 (s, 1H), 8.01 (d, J = 12.1 Hz, 1H), 7.85 (d, J = 2.3 Hz, 1H), 7.31-7.24 (m, 1H), 6.60 (t, J = 8.2 Hz, 1H), 6.54-6.47 (m, 2H), 4.49 (d, J = 8.1 Hz, 2H), 4.35 (t, J = 5.4 Hz, 2H), 4.14 (d, J = 8.1 Hz, 2H), 2.92 (d, J = 17.7 Hz, 3H), 2.85 (s, 3H), 1.04 (d, J = 6.3 Hz, 6H). |
| 540 | 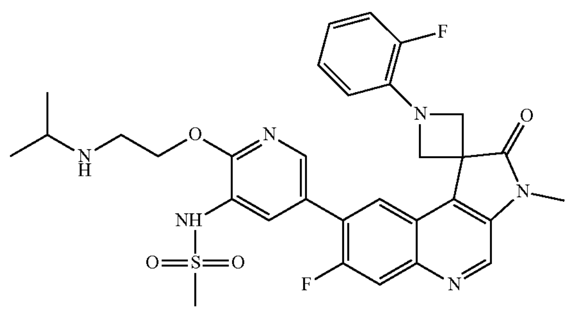 | N-(5-(7'-Fluoro-1-(2-fluorophenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 623.20 | 1H NMR (400 MHz, DMSO-d6) δ 8.97 (s, 1H), 8.78 (d, J = 8.4 Hz, 1H), 8.07 (s, 1H), 8.01 (d, J = 12.1 Hz, 1H), 7.86 (s, 1H), 7.13 (dt, J = 15.6, 7.9 Hz, 2H), 6.84 (dt, J = 28.3, 7.9 Hz, 2H), 4.50 (d, J = 5.4 Hz, 2H), 4.34 (t, J = 8.1 Hz, 2H), 3.34 (s, 3H), 2.95-2.85 (m, 3H), 2.82 (s, 3H), 1.04 (d, J = 6.2 Hz, 6H). |
| 541 | 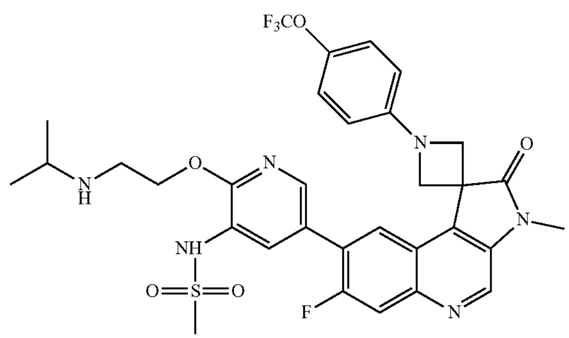 | N-(5-(7'-Fluoro-3'-methyl-2'-oxo-1-(4-(trifluoromethoxy)phenyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | 689.25 | 1H NMR (400 MHz, DMSO-d6) δ 8.97 (s, 1H), 8.59 (d, J = 8.4 Hz, 1H), 8.05 (s, 1H), 8.01 (d, J = 12.1 Hz, 1H), 7.85 (s, 1H), 7.26 (d, J = 8.5 Hz, 2H), 6.73 (d, J = 8.7 Hz, 2H), 4.51 (d, J = 8.0 Hz, 2H), 4.35 (t, J = 5.3 Hz, 2H), 4.14 (d, J = 8.0 Hz, 2H), 3.34 (s, 3H), 2.94-2.84 (m, 3H), 2.81 (s, 3H), 1.03 (d, J = 6.3 Hz, 6H). |

| Examples | Structure | Name | MS: [(M + 1)]+ | 1H NMR |
|---|---|---|---|---|
| 542 | 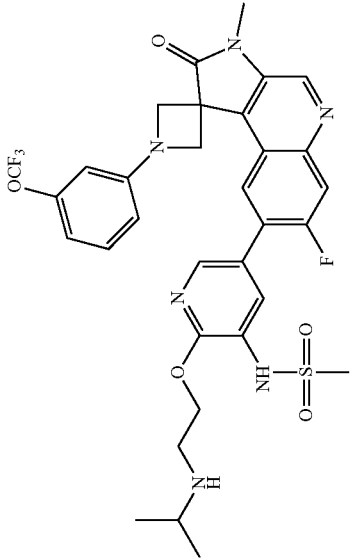 | N-(5-(7'-Fluoro-3'-methyl-2'-oxo-1-(3-(trifluoromethoxy)phenyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | 689.20 | 1H NMR (400 MHz, DMSO-d6) δ 8.97 (s, 1H), 8.51 (d, J = 8.4 Hz, 1H), 8.05 (s, 1H), 8.01 (d, J = 12.0 Hz, 1H), 7.85 (s, 1H), 7.37 (t, J = 8.2 Hz, 1H), 6.76 (d, J = 8.4 Hz, 1H), 6.72-6.65 (m, 1H), 6.61 (s, 1H), 4.53 (d, J = 8.1 Hz, 2H), 4.35 (t, J = 5.4 Hz, 2H), 4.16 (d, J = 8.1 Hz, 2H), 3.34 (s, 3H), 2.97-2.86 (m, 3H), 2.82 (s, 3H), 1.04 (d, J = 6.3 Hz, 6H). |
| 543 | 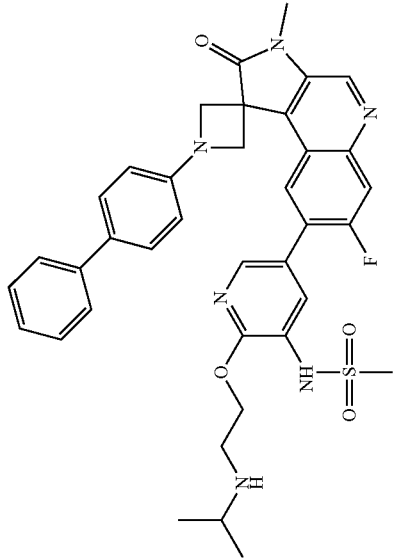 | N-(5-(1-([1,1'-Biphenyl]-4-yl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 681.50 | 1H NMR (400 MHz, CD3OD) δ 8.86 (d, J = 8.8 Hz, 2H), 8.14 (d, J = 12.0 Hz, 2H), 7.91 (d, J = 12.2 Hz, 1H), 7.62-7.55 (m, 4H), 7.41 (t, J = 7.7 Hz, 2H), 7.28 (t, J = 7.5 Hz, 1H), 6.79 (d, J = 8.5 Hz, 2H), 4.56 (d, J = 5.0 Hz, 2H), 4.52 (d, J = 7.6 Hz, 2H), 4.37 (d, J = 7.7 Hz, 2H), 3.45-3.38 (m, 6H), 2.77 (s, 3H), 1.33 (d, J = 6.6 Hz, 6H). |

| Examples | Structure | Name | MS: [(M + 1)]+ | 1H NMR |
|---|---|---|---|---|
| 544 | 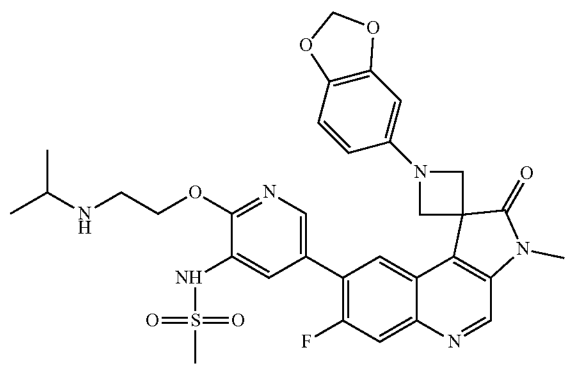 [SMILES: CC(C)NCCOc1ncc(-c2cc3c4c(cnc3cc2F)N(C)C(=O)C42CN(c3ccc4c(c3)OCO4)C2)cc1NS(C)(=O)=O] | N-(5-(1-(Benzo[d][1,3]dioxol-5-yl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 649.30 | 1H NMR (400 MHz, DMSO-d6) δ 8.96 (s, 1H), 8.69 (d, J = 8.6 Hz, 1H), 8.04 (s, 1H), 8.00 (d, J = 12.1 Hz, 1H), 7.85 (s, 1H), 6.82 (d, J = 8.2 Hz, 1H), 6.41 (d, J = 2.3 Hz, 1H), 6.07 (dd, J = 8.3, 2.2 Hz, 1H), 5.94 (s, 2H), 4.40 (d, J = 7.8 Hz, 2H), 4.36 (t, J = 5.3 Hz, 2H), 4.06 (d, J = 7.8 Hz, 2H), 3.33 (s, 3H), 2.96-2.88 (m, 3H), 2.87 (s, 3H), 1.05 (d, J = 6.3 Hz, 6H). |
| 545 | 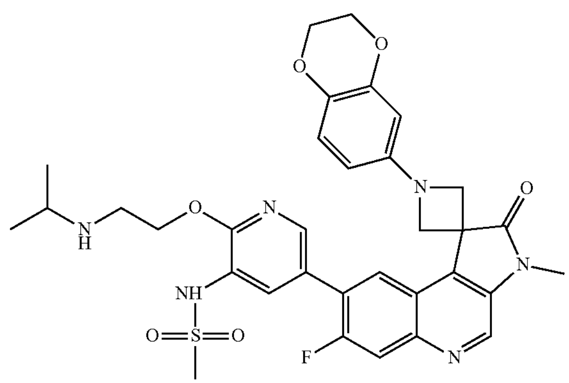 [SMILES: CC(C)NCCOc1ncc(-c2cc3c4c(cnc3cc2F)N(C)C(=O)C42CN(c3ccc4c(c3)OCCO4)C2)cc1NS(C)(=O)=O] | N-(5-(1-(2,3-Dihydrobenzo[b][1,4]dioxin-6-yl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 663.20 | 1H NMR (400 MHz, DMSO-d6) δ 8.95 (s, 1H), 8.70 (d, J = 8.4 Hz, 1H), 8.04 (s, 1H), 7.99 (d, J = 12.2 Hz, 1H), 7.85 (d, J = 2.3 Hz, 1H), 6.76 (d, J = 8.3 Hz, 1H), 6.21-6.12 (m, 2H), 4.41-4.33 (m, 4H), 4.19 (dd, J = 17.7, 4.7 Hz, 4H), 4.03 (d, J = 7.8 Hz, 2H), 3.33 (s, 3H), 2.97-2.89 (m, 3H), 2.87 (s, 3H), 1.05 (d, J = 6.2 Hz, 6H). |

-continued

| Examples | Structure | Name | MS: [(M + 1)]+ | 1H NMR |
|---|---|---|---|---|
| 546 | 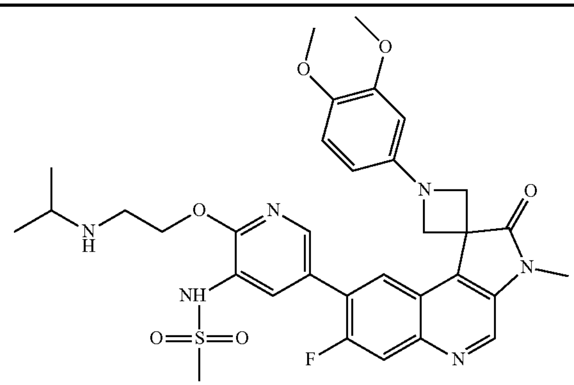 | N-(5-(1-(3,4-Dimethoxyphenyl)-7-fluoro-3'-methyl-2'-oxo-2',3'-dihydrospiro[azetidine-3,1'-pyrrolo[2,3-c]quinolin]-8-yl)-2-(2-(isopropylamino)ethoxy)pyridin-3-yl)methanesulfonamide | 665.25 | 1H NMR (400 MHz, DMSO-$d_6$) δ 8.96 (s, 1H), 8.76 (d, J = 8.4 Hz, 1H), 8.07 (s, 1H), 8.00 (d, J = 12.1 Hz, 1H), 7.86 (s, 1H), 6.87 (d, J = 8.5 Hz, 1H), 6.33 (d, J = 2.6 Hz, 1H), 6.15 (dd, J = 8.5, 2.6 Hz, 1H), 4.41 (d, J = 7.7 Hz, 2H), 4.35 (t, J = 5.4 Hz, 2H), 4.09 (d, J = 7.7 Hz, 2H), 3.75 (s, 3H), 3.69 (s, 3H), 3.33 (s, 3H), 2.96-2.86 (m, 3H), 2.83 (s, 3H), 1.04 (d, J = 6.2 Hz, 6H). |
| 547 | 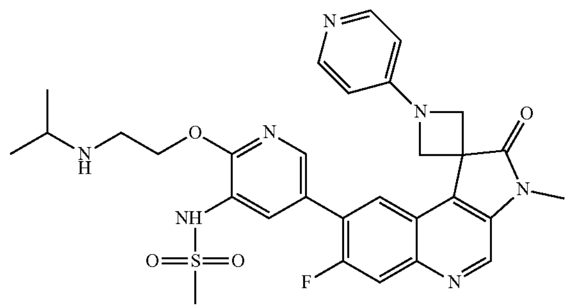 [SMILES: CC(C)NCCOc1ncc(-c2cc3c4c(cnc3cc2F)N(C)C(=O)C42CN(c3ccncc3)C2)cc1NS(C)(=O)=O] | N-(5-(7'-Fluoro-3'-methyl-2'-oxo-1-(pyridin-4-yl)-2',3'-dihydrospiro[azetidine-3,1'-pyrrolo[2,3-c]quinolin]-8-yl)-2-(2-(isopropylamino)ethoxy)pyridin-3-yl)methanesulfonamide | 606.30 | 1H NMR (400 MHz, DMSO-$d_6$) δ 8.97 (s, 1H), 8.32 (d, J = 8.3 Hz, 1H), 8.24 (d, J = 5.4 Hz, 2H), 8.06 (s, 1H), 8.02 (d, J = 12.1 Hz, 1H), 7.83 (s, 1H), 6.61 (d, J = 5.5 Hz, 2H), 4.57 (d, J = 8.4 Hz, 2H), 4.35 (t, J = 5.2 Hz, 2H), 4.22 (d, J = 8.5 Hz, 2H), 3.34 (s, 3H), 2.97-2.88 (m, 3H), 2.86 (s, 3H), 1.05 (d, J = 6.3 Hz, 6H). |
| 548 | 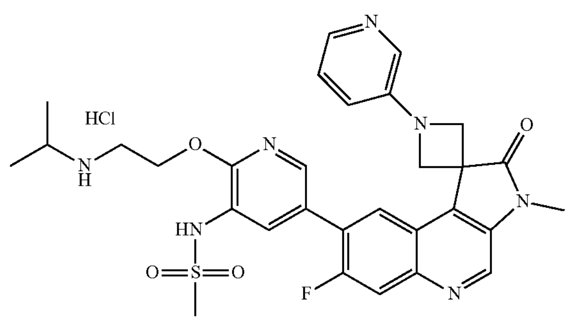 [SMILES: CC(C)NCCOc1ncc(-c2cc3c4c(cnc3cc2F)N(C)C(=O)C42CN(c3cccnc3)C2)cc1NS(C)(=O)=O ; Cl] | N-(5-(7'-Fluoro-3'-methyl-2'-oxo-1-(pyridin-3-yl)-2',3'-dihydrospiro[azetidine-3,1'-pyrrolo[2,3-c]quinolin]-8-yl)-2-(2-(isopropylamino)ethoxy)pyridin-3-yl)methanesulfonamide hydrochloride | 606.25 | 1H NMR (400 MHz, CD$_3$OD) δ 8.88 (s, 1H), 8.74 (d, J = 8.2 Hz, 1H), 8.25-8.18 (m, 1H), 8.12 (s, 1H), 8.07 (d, J = 10.4 Hz, 2H), 7.92 (d, J = 12.0 Hz, 1H), 7.44 (s, 1H), 7.28 (d, J = 7.8 Hz, 1H), 4.68 (t, J = 4.9 Hz, 2H), 4.60 (d, J = 7.9 Hz, 2H), 4.40 (d, J = 7.9 Hz, 2H), 3.54-3.45 (m, 3H), 3.42 (s, 3H), 2.84 (s, 3H), 1.38 (d, J = 6.5 Hz, 6H). |

-continued

| Examples | Structure | Name | MS: [(M + 1)]+ | ¹H NMR |
|---|---|---|---|---|
| 549 | 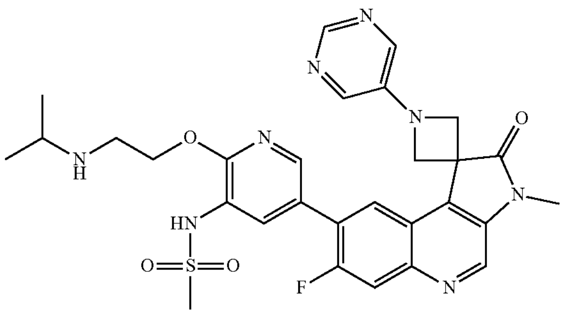 [SMILES: CC(C)NCCOc1ncc(-c2cc3c4c(cnc3cc2F)N(C)C(=O)C42CN(c3cncnc3)C2)cc1NS(C)(=O)=O] | N-(5-(7'-Fluoro-3'-methyl-2'-oxo-1-(pyrimidin-5-yl)-2',3'-dihydrospiro[azetidine-3,1'-pyrrolo[2,3-c]quinolin]-8'-yl)-2-(isopropylamino)ethoxy)pyridin-3-yl)methanesulfonamide | 607.35 | ¹H NMR (400 MHz, DMSO-d₆) δ 8.97 (s, 1H), 8.69 (s, 1H), 8.53 (d, J = 8.4 Hz, 1H), 8.29 (s, 2H), 8.10 (s, 1H), 8.01 (d, J = 12.1 Hz, 1H), 7.88 (d, J = 2.3 Hz, 1H), 4.61 (d, J = 8.3 Hz, 2H), 4.35 (t, J = 5.3 Hz, 2H), 4.28 (d, J = 8.3 Hz, 2H), 3.34(s, 3H), 2.96-2.86 (m, 3H), 2.85 (s, 3H), 1.03 (d, J = 6.2 Hz, 6H). |
| 550 | 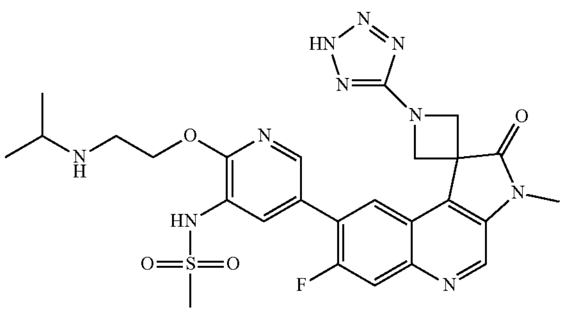 [SMILES: CC(C)NCCOc1ncc(-c2cc3c4c(cnc3cc2F)N(C)C(=O)C42CN(c3nn[nH]n3)C2)cc1NS(C)(=O)=O] | N-(5-(7'-Fluoro-3'-methyl-2'-oxo-1-(2H-tetrazol-5-yl)-2',3'-dihydrospiro[azetidine-3,1'-pyrrolo[2,3-c]quinolin]-8'-yl)-2-(isopropylamino)ethoxy)pyridin-3-yl)methanesulfonamide | 597.15 | ¹H NMR (400 MHz, DMSO-d₆) δ 8.95 (s, 1H), 8.92 (d, J = 8.5 Hz, 1H), 8.20 (d, J = 2.1 Hz, 1H), 8.00 (d, J = 12.1 Hz, 1H), 7.95 (d, J = 2.2 Hz, 1H), 4.55 (t, J = 5.0 Hz, 2H), 4.32 (d, J = 7.9 Hz, 2H), 4.24 (d, J = 8.0 Hz, 2H), 3.39-3.28 (m, 6H), 2.99 (s, 3H), 1.23 (d, J = 6.4 Hz, 6H). |
| 551 | 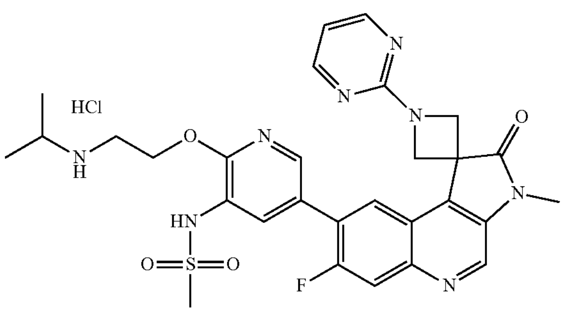 [SMILES: CC(C)NCCOc1ncc(-c2cc3c4c(cnc3cc2F)N(C)C(=O)C42CN(c3ncccn3)C2)cc1NS(C)(=O)=O ; Cl] | N-(5-(7'-Fluoro-3'-methyl-2'-oxo-1-(pyrimidin-2-yl)-2',3'-dihydrospiro[azetidine-3,1'-pyrrolo[2,3-c]quinolin]-8'-yl)-2-(isopropylamino)ethoxy)pyridin-3-yl)methanesulfonamide hydrochloride | 607.25 | ¹H NMR (400 MHz, CD₃OD) δ 8.88 (s, 1H), 8.49-8.43 (m, 3H), 8.17 (s, 1H), 8.08 (s, 1H), 7.93 (d, J = 11.9 Hz, 1H), 6.87 (t, J = 4.9 Hz, 1H), 4.69 (t, J = 5.3 Hz, 2H), 4.65-4.59 (m, 4H), 3.54-3.47 (m, 3H), 3.42 (s, 3H), 2.97 (s, 3H), 1.39 (d, J = 6.5 Hz, 6H). |

| Examples | Structure | Name | MS: [(M + 1)]+ | 1H NMR |
|---|---|---|---|---|
| 552 | 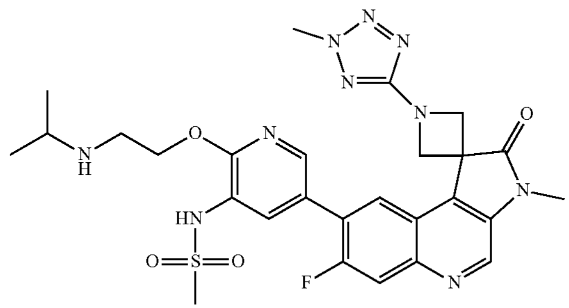 | N-(5-(7'-Fluoro-3'-methyl-1-(2-methyl-2H-tetrazol-5-yl)-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 611.35 | 1H NMR (400 MHz, DMSO-d6) δ 8.97 (s, 1H), 8.66 (d, J = 8.4 Hz, 1H), 8.25 (d, J = 2.2 Hz, 1H), 8.03 (d, J = 12.1 Hz, 1H), 7.96 (t, J = 1.9 Hz, 1H), 4.71 (d, J = 8.4 Hz, 2H), 4.63 (d, J = 8.4 Hz, 2H), 4.39 (t, J = 5.4 Hz, 2H), 3.89 (s, 3H), 3.34 (s, 3H), 2.98-2.89 (m, 3H), 2.89 (s, 3H), 1.05 (d, J = 6.3 Hz, 6H). |
| 553 | 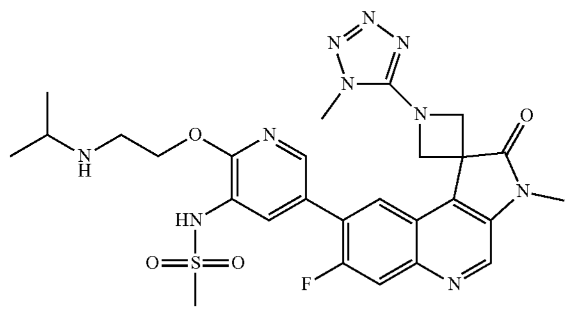 [SMILES: CC(C)NCCOc1ncc(-c2cc3c4c(cnc3cc2F)N(C)C(=O)C42CN(c3nnnn3C)C2)cc1NS(C)(=O)=O] | N-(5-(7'-Fluoro-3'-methyl-1-(1-methyl-1H-tetrazol-5-yl)-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | 611.30 | 1H NMR (400 MHz, DMSO-d6) δ 8.95 (s, 1H), 8.51 (d, J = 8.3 Hz, 1H), 8.04-7.96 (m, 2H), 7.85 (t, J = 2.2 Hz, 1H), 4.59 (d, J = 8.5 Hz, 2H), 4.43 (t, J = 5.2 Hz, 2H), 4.36 (d, J = 8.5 Hz, 2H), 4.25 (s, 3H), 3.32 (s, 3H), 3.06-2.94 (m, 3H), 2.87 (s, 3H), 1.09 (d, J = 6.3 Hz, 6H). |
| 554 | 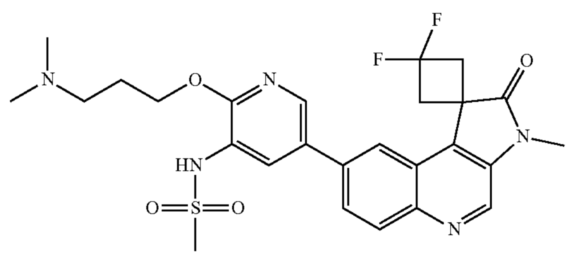 | N-(5-(3,3-Difluoro-3'-methyl-2'-oxo-2',3'-dihydrospiro[cyclobutane-1,1'-pyrrolo[2,3-c]quinolin]-8'-yl)-2-(3-(dimethylamino)propoxy)pyridin-3-yl)methanesulfonamide | 546.25 | 1H NMR (400 MHz, DMSO-d6) δ 8.91 (s, 1H), 8.30 (s, 1H), 8.23-8.16 (m, 2H), 7.98-7.92 (m, 2H), 4.39 (t, J = 6.3 Hz, 2H), 3.66-3.51 (m, 2H), 3.35 (s, 3H), 3.31-3.15 (s, 2H), 3.03 (s, 3H), 2.64 (t, J = 6.6 Hz, 2H), 2.35 (s, 6H), 1.98 (p, J = 6.4 Hz, 2H). |

-continued

| Examples | Structure | Name | MS: [(M + 1)]+ | 1H NMR |
|---|---|---|---|---|
| 555 | 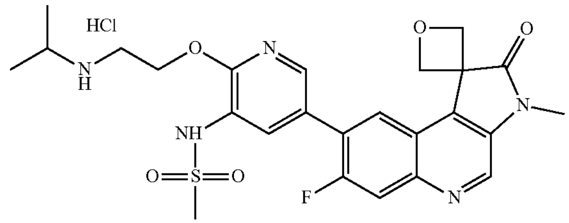 [SMILES: CC(C)NCCOc1ncc(-c2cc3c4c(cnc3cc2F)N(C)C(=O)C42COC2)cc1NS(C)(=O)=O ; Cl] | N-(5-(7'-Fluoro-3'-methyl-2'-oxo-2',3'-dihydrospiro[oxetane-3,1'-pyrrolo[2,3-c]quinolin]-8'-yl)-2-(2-(isopropylamino)ethoxy)pyridin-3-yl)methanesulfonamide hydrochloride | 530.35 | 1H NMR (400 MHz, CD3OD) δ 8.82 (s, 1H), 8.75 (d, J = 8.2 Hz, 1H), 8.32 (t, J = 1.8 Hz, 1H), 8.20 (t, J = 1.9 Hz, 1H), 7.91 (d, J = 11.9 Hz, 1H), 5.20 (d, J = 6.4 Hz, 2H), 5.03 (d, J = 6.4 Hz, 2H), 4.79-4.74 (m, 2H), 3.60-3.50 (m, 3H), 3.39 (s, 3H), 3.14 (s, 3H), 1.42 (d, J = 6.6 Hz, 6H). |
| 556 | 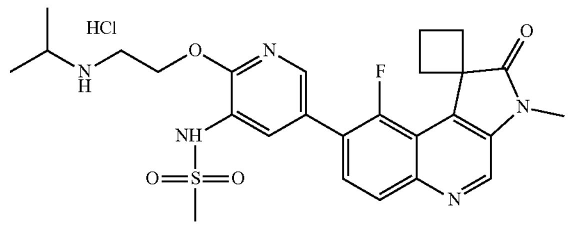 [SMILES: CC(C)NCCOc1ncc(-c2ccc3ncc4c(c3c2F)C2(CCC2)C(=O)N4C)cc1NS(C)(=O)=O ; Cl] | N-(5-(9'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | 527.61 | 1H NMR (400 MHz, CD3OD) δ 8.94 (s, 1H), 8.38 (s, 1H), 8.25 (s, 1H), 8.08 (d, J = 9.0 Hz, 1H), 7.90 (t, J = 8.5 Hz, 1H), 4.78 (s, 2H), 3.61-3.51 (m, 3H), 3.42 (s, 3H), 3.16 (s, 3H), 3.10-2.98 (m, 2H), 2.60-2.51 (m, 3H), 2.37-2.24 (m, 1H), 1.44 (d, J = 6.6 Hz, 6H). |
| 557 | 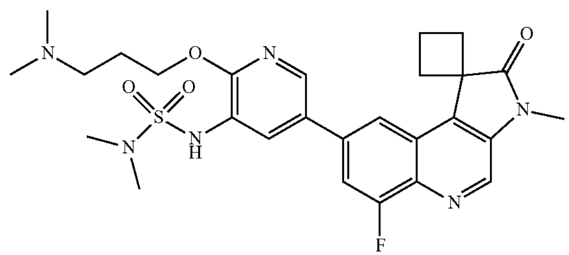 | 8'-[6-[3-(Dimethylamino)propoxy]-5-[(dimethylsulfamoyl)amino]pyridin-3-yl]-6'-fluoro-3'-methyl-2',3'-dihydrospiro[cyclobutane-1,1'-pyrrolo[2,3-c]quinoline]-2'-one | 557.35 | 1H NMR (400 MHz, DMSO-d6) δ 8.86 (s, 1H), 8.24 (s, 1H), 8.16 (s, 1H), 8.08 (s, 1H), 7.83 (d, J = 12.2 Hz, 1H), 4.39 (t, J = 6.1 Hz, 2H), 3.31 (s, 3H), 2.90-2.81 (m, 2H), 2.77 (t, J = 6.3 Hz, 2H), 2.66 (s, 6H), 2.63-2.51 (m, 4H), 2.44 (s, 6H), 2.07-1.98 (m, 2H). |
| 558 | 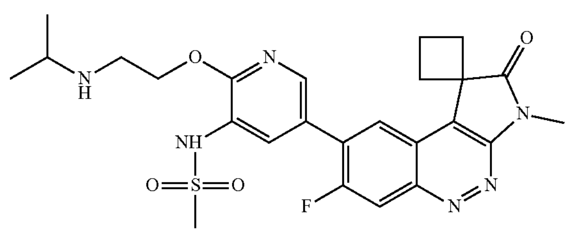 [SMILES: CC(C)NCCOc1ncc(-c2cc3c4c(nnc3cc2F)N(C)C(=O)C42CCC2)cc1NS(C)(=O)=O] | N-(5-(7'-Fluoro-3'-methyl-2'-oxo-2',3'-dihydrospiro[cyclobutane-1,1'-pyrrolo[2,3-c]cinnolin]-8'-yl)-2-(2-(isopropylamino)ethoxy)pyridin-3-yl)methanesulfonamide | 529.15 | 1H NMR (400 MHz, DMSO-d6) δ 8.39 (s, 1H), 8.35-8.24 (m, 2H), 8.06 (s, 1H), 4.51 (t, J = 6.3 Hz, 2H), 3.15 (s, 3H), 3.10 (s, 3H), 2.97-2.83 (m, 3H), 2.70-2.53 (m, 3H), 2.46-2.30 (m, 3H), 1.16 (d, J = 6.2 Hz, 6H). |

| Examples | Structure | Name | MS: [(M + 1)]+ | 1H NMR |
|---|---|---|---|---|
| 560 | 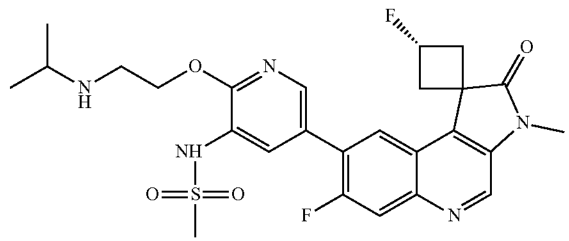 | cis-N-(5-(3,7'-Difluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | 546.25 | 1H NMR (400 MHz, DMSO-$d_6$) δ 8.93 (s, 1H), 8.34 (d, J = 8.2 Hz, 1H), 8.25 (s, 1H), 8.01 (d, J = 12.0 Hz, 1H), 7.94 (t, J = 2.2 Hz, 1H), 5.76-5.42 (m, 1H), 4.43 (t, J = 5.4 Hz, 2H), 3.32 (s, 3H), 3.06-3.03 (m, 1H), 3.03 (s, 3H), 3.02-2.86 (m, 6H), 1.07 (d, J = 6.2 Hz, 6H). |
| 561 | 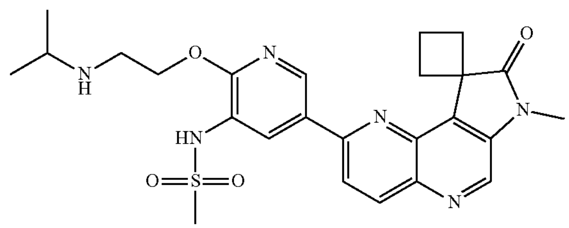 [SMILES: CC(C)NCCOc1ncc(-c2ccc3ncc4c(c3n2)C2(CCC2)C(=O)N4C)cc1NS(C)(=O)=O] | N-(5-[7-Methyl-8-oxo-7,8-dihydrospiro[cyclobutane-1,9-pyrrolo[2,3-c][1,5-naphthyridin]-2-yl]-2-[2-[(propan-2-yl)amino]ethoxy]pyridin-3-yl)methanesulfonamide | 511.30 | 1H NMR (400 MHz, DMSO-$d_6$) δ 8.97 (s, 1H), 8.81 (d, J = 2.2 Hz, 1H), 8.65 (d, J = 2.2 Hz, 1H), 8.36 (d, J = 8.8 Hz, 1H), 8.16 (d, J = 8.8 Hz, 1H), 4.56-4.48 (m, 2H), 4.44 (t, J = 5.4 Hz, 2H), 3.79 (s, 3H), 3.24 (t, J = 6.2 Hz, 2H), 3.08 (s, 3H), 2.97 (t, J = 5.4 Hz, 2H), 2.88 (p, J = 6.2 Hz, 1H), 2.15 (p, J = 5.6 Hz, 2H), 1.06 (d, J = 6.2 Hz, 6H). |
| 562 | 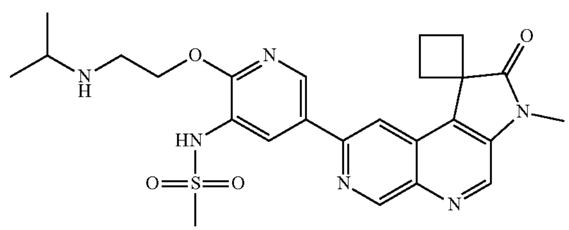 [SMILES: CC(C)NCCOc1ncc(-c2cc3c4c(cnc3cn2)N(C)C(=O)C42CCC2)cc1NS(C)(=O)=O] | N-(2-(2-(Isopropylamino)ethoxy)-5-(3'-methyl-2'-oxo-2',3'-dihydrospiro[cyclobutane-1,1'-pyrrolo[2,3-c][1,7]naphthyridin]-8'-yl)methanesulfonamide | 511.25 | 1H NMR (400 MHz, DMSO-$d_6$) δ 9.34 (s, 1H), 9.06 (s, 1H), 8.74 (d, J = 2.3 Hz, 1H), 8.41 (d, J = 2.2 Hz, 1H), 8.36 (s, 1H), 4.51 (t, J = 5.9 Hz, 2H), 4.43 (t, J = 5.4 Hz, 2H), 3.81 (s, 3H), 3.18 (t, J = 6.2 Hz, 2H), 3.05 (s, 3H), 2.95 (t, J = 5.4 Hz, 2H), 2.85 (p, J = 6.2 Hz, 1H), 2.15 (p, J = 6.2 Hz, 2H), 1.04 (d, J = 6.2 Hz, 6H). |

Note: 1. examples 385 and 386 were separated by Prep-Chiral HPLC with the following conditions: Column: CHIRALPAK IC, 2×25 cm, 5 μm; Mobile Phase A: methyl tert-butyl ether (plus 0.1% diethylamine); Mobile Phase B: EtOH; Flow rate: 20 mL/min; Gradient: 30% B in 13 min; Detector UV 220/254 nm; example 385, RT1: 8.78 min; example 386, RT2:11.34 min 2. examples 387 and 388 were separated by Prep-HPLC with the following conditions: Column: XBridge Prep OBD C18 Column 30×150 mm, 5 μm; Mobile Phase A: $H_2O$ (plus 10 mM $NH_4HCO_3$); Mobile Phase B: acetonitrile; Flow rate: 60 mL/min; Gradient: 25% B to 35% B in 11 min; Detector: UV 220 nm; example 387, RT1: 8.93 min; example 388, RT2: 9.98 min 3. examples 393 and 394 were separated by Prep-Chiral HPLC with the following conditions: Column: CHIRALPAK IC, 2×25 cm, 5 μm; Mobile Phase A: Hexane:dichloromethane=3:1 (plus 0.1% isopropyl alcohol); Mobile Phase B: EtOH Flow rate: 20 ml/min; Gradient: 30% B in 20 min; Detector: UV 254/220 nm; example 393, RT1: 13.28 min; example 394, RT2: 16.15 min 4. examples 395 and 3% were separated by Prep-Chiral HPLC with the following conditions: Column: CHIRALPAK IC, 2×25 cm, 5 μm; Mobile Phase A: Hexane:dichloromethane=3:1 (plus 0.1% isopropyl alcohol); Mobile Phase B: EtOH; Flow rate: 20 mL/min; Gradient: 30% B in 27 min; Detector UV 254/220 nm; example 395, RT1: 17.34 min; example 3%, RT2: 22.33 min 5. examples 456 and 457 were separated by Prep-Chiral-HPLC with the following conditions: Column: Chiralpak IC, 2×25 cm, 5 μm; Mobile Phase A: Hexane:dichloromethane=3:1 (plus 0.2% isopropyl alcohol); Mobile Phase B: EtOH; Flow rate: 20 mL/min; Gradient: 30% B in 10 min; Detector UV 220/254 nm; example 457, RT1: 5.35 min; example 456, RT2: 7.23 min 6. examples 400 and 401 were separated by Prep-Chiral HPLC with the following conditions: Column: CHIRALPAK IE, 2×25 cm, 5 μm; Mobile Phase A: methyl tert-butyl ether (plus 0.1% isopropyl alcohol); Mobile Phase B: EtOH; Flow rate: 20 mL/min; Gradient: 10% B in 19 min; Detector: UV 220/254 nm; example 400, RT1: 11.59 min; example 401, RT2: 15.89 min 7. examples 402 and 403 were separated by Prep-Chiral HPLC with the following conditions: Column: CHIRALPAK IE, 2×25 cm, 5 μm; Mobile Phase A: Hexane (plus 0.1% diethylamine); Mobile Phase B: EtOH; Flow rate: 20 mL/min; Gradient: 50% B in 19 min; Detector UV 220/254 nm; example 403, RT1: 11.68 min; example 402, RT2: 15.99 min 8. examples 416 and 417 were separated by Prep-HPLC with the following conditions: Column: Spherical C18, 20~40 μm, 120 g; Mobile Phase A: Water (plus 10 mM $NH_4HCO_3$); Mobile Phase B: acetonitrile; Flow rate: 45 mL/min; Gradient (B %): 5%~35%, 5 min; 35%~55%, 30 min; 55%~95%; 3 min; 95%, 5 min; Detector: UV 254 nm; example 416 as faster eluted isomer while example 417 as slower eluted isomer.

9. examples 420 and 421 were separated by Prep-Chiral-HPLC with the following conditions: Column: CHIRALPAK IC, 2×25 cm, 5 μm; Mobile Phase A: Hexane:dichloromethane=3:1 (plus 0.2% isopropyl alcohol); Mobile Phase B: EtOH. Flow rate: 20 mL/min; Gradient: 50% B in 23 min; Detector UV 254/220 nm; example 420, RT1: 13.96 min; example 421, RT2: 20.45 min 10. examples 422 and 423 were separated by Prep-Chiral-HPLC with the following conditions: Column: CHIRALPAK IE, 2×25 cm, 5 μm; Mobile Phase A: Hexane (plus 0.1% diethylamine); Mobile Phase B: EtOH; Flow rate: 20 mL/min; Gradient: 10% B in 19 min; Detector UV 220/254 nm; example 422, RT1: 11.59 min; example 423, RT2:15.89 min 11. examples 424 and 425 were separated by Prep-HPLC with the following conditions: Column: Spherical C18, 20~40 μm, 120 g; Mobile Phase A: Water (plus 10 mM $NH_4HCO_3$); Mobile Phase B: acetonitrile; Flow rate: 45 mL/min; Gradient (B %): 5%, 2 min; 5%~25%, 8 min; 25%~46%, 12 min; 46%, 8 min; 46%~95%; 3 min; 95%, 2 min; Detector UV 254 nm; example 424 as faster eluted isomer (RT1: 24 min); example 425 as slower eluted isomer (RT2: 28 min).

12. examples 428 and 429 were separated by Prep-HPLC with the following conditions: Column: Spherical C18, 20-40 μm, 120 g; Mobile Phase A: Water (plus 10 mM $NH_4HCO_3$); Mobile Phase B: acetonitrile; Flow rate: 45 mL/min; Gradient: 30% B-50% B in 20 min; Detector: UV 254 nm; example 429 as the faster eluted isomer: example 428 as the slower eluted isomer.

13. examples 436 and 437 were separated by Prep-Chiral-HPLC with the following conditions: Column: CHIRALPAK IC, 2×25 cm, 5 μm; Mobile Phase A: Hexane:dichloromethane=3:1 (plus 0.2% isopropyl alcohol); Mobile Phase B: EtOH; Flow rate: 20 mL/min; Gradient: 70% B in 15 min; Detector: UV 220/254 nm; example 436, RT1: 9.23 min; example 437, RT2: 12.34 min 14. examples 438 and 439 were separated by Prep-Chiral-HPLC with the following conditions: Column: CHIRALPAK IG, 20×250 mm, 5 μm; Mobile Phase A: Hexane:dichloromethane=3:1 (plus 0.2% isopropyl alcohol); Mobile Phase B: Methanol:dichloromethane=1:1; Flow rate: 20 mL/min; Gradient: 15% B in 15 min; Detector UV 220/254 nm; example 439. RT1: 9.59 min; example 438. RT2: 12.53 min 15. examples 440 and 441 were separated by Prep-HPLC with the following conditions: Column: Spherical C18, 20-40 μm, 120 g; Mobile Phase A: Water (plus 10 mM $NH_4HCO_3$); Mobile Phase B: acetonitrile; Flow rate: 45 mL/min; Gradient: 30% B-50% B in 20 min; Detector: UV 254 nm; example 441 as faster eluted isomer: example 440 as slower eluted isomer.

16. examples 442 and 443 were separated by Prep-HPLC with the following conditions: Column: XBridge Shield RP18 OBD Column, 30×150 mm, 5 μm; Mobile Phase A: Water (plus 10 mM $NH_4HCO_3$); Mobile Phase B: acetonitrile; Flow rate: 60 mL/min; Gradient: 15 B to 30 B in 17 min; Detector: UV 254/220 nm; example 443 as the faster eluted isomer, example 442 as the slower eluted isomer.

17. examples 418 and 419 were separated by Prep-HPLC with the following conditions: Column: Spherical C18, 20~40 μm, 120 g; Mobile Phase A: Water (plus 10 mM $NH_4HCO_3$); Mobile Phase B: acetonitrile; Flow rate: 45 mL/min, Gradient (B %): 5%~35%, 5 min 35%~55%, 30 min; 55%~95%; 3 min; 95%, 5 min; Detector: UV 254 nm; example 418 as faster eluted isomer while example 419 as slower eluted isomer.

18. examples 426 and 427 were separated by Prep-HPLC with the following conditions: Column: Spherical C18, 20~40 μm, 120 g; Mobile Phase A: Water (plus 10 mM $NH_4HCO_3$); Mobile Phase B: acetonitrile; Flow rate: 45 mL/min; Gradient (B %): 5%~35%, 5 min; 35%~55%, 30 min; 55195%; 3 min; 95%, 5 min; Detector UV 254 nm; example 426 as faster eluted isomer while example 427 as slower eluted isomer.

19. examples 459 and 460 were separated by Prep-Chiral-HPLC with the following conditions: Column: CHIRAL- PAK IG, 20×250 mm, 5 μm; Mobile Phase A: Hexane (plus 0.2% isopropyl alcohol); Mobile Phase B: EtOH; Flow rate: 18 mL/min; Gradient: 50% B in 27 min; Detector UV 220/254 nm; example 460, RT1: 12.27 min; example 459, RT2: 23.09 min 20. examples 461 and 462 were separated by Prep-Chiral-HPLC with the following conditions: CHIRALPAK IG, 2×25 cm, 5 μm; Mobile Phase A: Hexane:dichloromethane=3:1 (plus 0.2% isopropyl alcohol); Mobile Phase B: EtOH; Flow rate: 20 mL/min; Gradient: 30% B in 10 min; Detector UV 254/220 nm; example 462, RT1: 5.77 min; example 461, RT2: 8.94 min 21. examples 447 and 448 were separated by Prep-Chiral-HPLC with the following conditions: Column: Chiralpak IC, 2×25 cm, 5 μm; Mobile Phase A: Hexane:dichloromethane=3:1 (plus 0.2% isopropyl alcohol); Mobile Phase B: EtOH; Flow rate: 20 mL/min; Gradient: 40% B in 23 min; Detector: UV 220/254 nm; example 448, RT1: 13.44 min; example 447, RT2: 18.78 min 22. examples 454 and 455 were separated by Prep-Chiral-HPLC with the following conditions: Column: Chiralpak IC, 2×25 cm, 5 μm; Mobile Phase A: Hexane:dichloromethane=3:1 (plus 0.2% isopropyl alcohol); Mobile Phase B: EtOH; Flow rate: 20 ml/min; Gradient: 30% B in 25 min; Detector: UV 220/254 nm; example 454, RT1: 17.09 min; example 455, RT2:21.45 min 23. examples 450 and 451 were separated by Prep-Chiral-HPLC with the following conditions: Column: Chiralpak IC, 2×25 cm, 5 μm; Mobile Phase A: Hexane:dichloromethane=3:1 (plus 0.2% isopropyl alcohol); Mobile Phase B: EtOH; Flow rate: 20 mL/min; Gradient: 30% B in 17 min; Detector: UV 220/254 nm; example 451, RT1: 10.64 min; example 450, RT2: 14.72 min 24. examples 404 and 405 were separated by Prep-Chiral-HPLC with the following conditions: Column: CHIRALPAK IF, 2×25 cm, 5 μm; Mobile Phase A: Hexane (plus 0.2% isopropyl alcohol); Mobile Phase B: EtOH; Flow rate: 16 mL/min; Gradient: 50% B in 18 min; Detector UV 254/220 nm; example 405, RT1: 11.52 min; example 404, RT2:14.23 min 25. examples 406 and 407 were separated by Prep-Chiral-HPLC with the following conditions: Column: Chiralpak IC, 2×25 cm, 5 μm; Mobile Phase A: Hexane:dichloromethane=3:1 (plus 0.2% isopropyl alcohol); Mobile Phase B: EtOH; Flow rate: 20 mL/min; Gradient: 30% B in 20 min; Detector: UV 220/254 nm; example 406, RT1: 12.42 min; example 407, RT2: 18.15 min 26. examples 408 and 409 were separated by Prep-Chiral-HPLC with the following conditions: Column: CHIRALPAK IC, 2×25 cm, 5 μm; Mobile Phase A: Hexane:dichloromethane=3:1 (plus 0.2% isopropyl alcohol); Mobile Phase B: EtOH; Flow rate: 20 mL/min; Gradient: 30% B in 14 min; Detector: UV 220/254 nm; example 409, RT1: 12.08 min; example 408, RT2: 18.21 min 27. examples 410 and 411 were separated by Prep-Chiral-HPLC with the following conditions: Column: CHIRALPAK IC, 2×25 cm, 5 μm; Mobile Phase A: Hexane:dichloromethane=3:1 (plus 0.2% isopropyl alcohol); Mobile Phase B: EtOH; Flow rate: 20 mL/min; Gradient: 30% B in 14 min; Detector: UV 220/254 nm; example 410, RT1: 8.25 min; example 411, RT2: 12.65 min 28. examples 412 and 413 were separated by Prep-Chiral-HPLC with the following conditions: Column: CHIRALPAK IC, 2×25 cm, 5 μm; Mobile Phase A: Hexane:dichloromethane=3:1 (plus 0.2% isopropyl alcohol); Mobile Phase B: EtOH; Flow rate: 20 mL/min; Gradient: 30% B in 7.8 min; Detector: UV 220/254 nm; example 412, RT1: 6.00 min; example 413, RT2: 7.14 min 29. examples 452 and 453 were separated by Prep-Chiral-HPLC with the following conditions: Column: Chiralpak IC, 2×25 cm, 5 μm; Mobile Phase A: Hexane:dichloromethane=3:1 (plus 0.2% isopropyl alcohol); Mobile Phase B: EtOH; Flow rate: 20 ml/min; Gradient: 30% B in 21 min; Detector: UV 220/254 nm; example 452, RT1: 13.29 min; example 453, RT2: 18.16 min

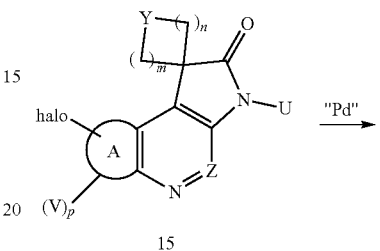

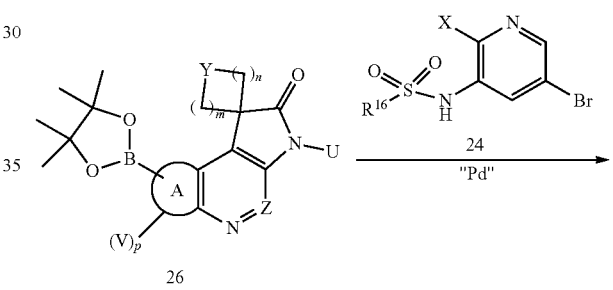

Formula I

General Procedure: To a solution of INTERMEDIATE 15 (1.0 equiv.) and 4,4,5,5-tetramethyl-2-(tetramethyl-1,3,2-dioxaborolan-2-yl)-1,3,2-dioxaborolane (2.0 equiv.) in 1,4-dioxane (20 mL) were added 1,1'-bis(diphenylphosphino)ferrocene-palladium (II) dichloride (0.1 equiv.) and potassium acetate (4.0 equiv.). The resulting mixture was stirred for 2 hours at 90° C. under nitrogen atmosphere and then cooled down to ambient temperature. To the reaction mixture was added water (5.0 mL), INTERMEDIATE 24 (0.7 equiv.), potassium carbonate (2.0 equiv.) and tetrakis(triphenylphosphine)palladium (0) (0.1 equiv.) under nitrogen atmosphere. The resulting mixture was stirred for 2 hours at 80° C. under nitrogen atmosphere. After cooling down to ambient temperature, the resulting mixture was concentrated under reduced pressure. The residue was purified by silica gel column chromatography, eluted with 1%~10% methanol in dichloromethane with 0.1% ammonia. Desired fractions were collected and concentrated under reduced pressure to afford the desired compound.

The following Example compounds were prepared according to the above procedure:

| EXAMPLES | Structure | Name | MS: [(M + 1)]+ | 1H NMR |
|---|---|---|---|---|
| 49 | 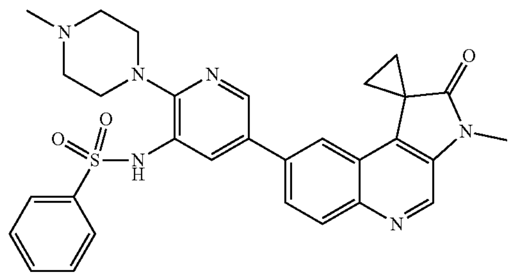 [SMILES: CN1CCN(c2ncc(-c3ccc4ncc5c(c4c3)C3(CC3)C(=O)N5C)cc2NS(=O)(=O)c2ccccc2)CC1] | N-(5-(3'-Methyl-2'-oxo-2',3'-dihydrospiro[cyclopropane-1,1'-pyrrolo[2,3-c]quinolin]-8'-yl)-2-(4-methylpiperazin-1-yl)pyridin-3-yl)benzenesulfonamide | 555.20 | 1H NMR (400 MHz, CDCl3) δ 8.75 (s, 1H), 8.35 (d, J = 2.3 Hz, 1H), 8.21 (d, J = 8.9 Hz, 1H), 8.06 (s, 1H), 7.94-7.87 (m, 2H), 7.70 (d, J = 8.8 Hz, 1H), 7.62 (t, J = 7.4 Hz, 1H), 7.53 (t, J = 7.7 Hz, 2H), 7.45 (s, 1H), 3.50 (s, 3H), 3.30-2.35 (br, 11H), 2.28 (q, J = 4.4 Hz, 2H), 2.03 (q, J = 4.6 Hz, 2H). |
| 53 | 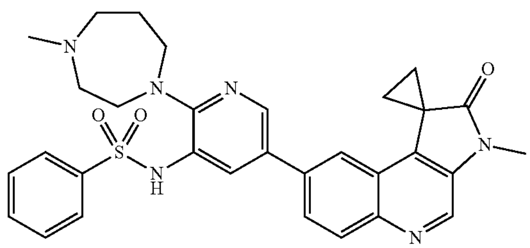 [SMILES: CN1CCCN(c2ncc(-c3ccc4ncc5c(c4c3)C3(CC3)C(=O)N5C)cc2NS(=O)(=O)c2ccccc2)CC1] | N-(2-(4-Methyl-1,4-diazepan-1-yl)-5-(3'-methyl-2'-oxo-2',3'-dihydrospiro[cyclopropane-1,1'-pyrrolo[2,3-c]quinolin]-8'-yl)pyridin-3-yl)benzenesulfonamide | 569.30 | 1H NMR (300 MHz, CDCl3) δ 8.72 (s, 1H), 8.26 (d, J = 2.3 Hz, 1H), 8.16 (d, J = 8.9 Hz, 1H), 8.00-7.87 (m, 3H), 7.67 (dd, J = 8.8, 1.9 Hz, 1H), 7.62-7.46 (m, 3H), 7.38 (d, J = 1.9 Hz, 1H), 3.49 (s, 4H), 3.45-3.38 (m, 3 H), 3.14-2.85 (m, 6H) 2.72 (s, 3H), 2.24 (q, J = 4.4 Hz, 2H), 2.00 (q, J = 4.3 Hz, 2H). |
| 113 | 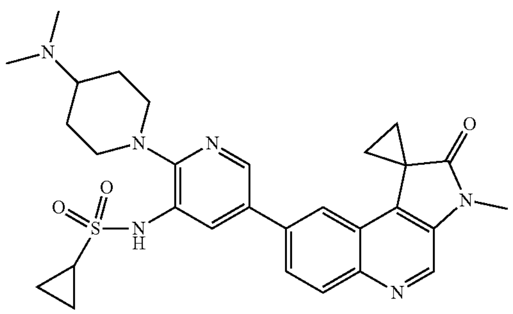 | N-(2-(4-(Dimethylamino)piperidin-1-yl)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide | 547.25 | 1H NMR (300 MHz, CDCl3) δ 8.75 (s, 1H), 8.38 (d, J = 2.3 Hz, 1H), 8.27-8.10 (m, 2H), 7.76 (d, J = 9.4 Hz, 1H), 7.51 (s, 1H), 3.50 (s, 3H), 3.40 (s, 2H), 3.01 (t, J = 12.0 Hz, 2H), 2.70-2.62 (m, 7H), 2.34-2.24 (m, 4H), 2.06-1.96 (m, 5H), 1.35 (s, 2H), 1.12-1.04 (m, 2H). |
| 115 | 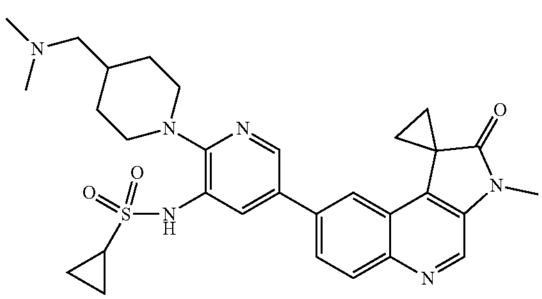 | N-(2-(4-(Dimethylamino)methyl)piperidin-1-yl)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide | 561.30 | 1H NMR (400 MHz, CDCl3) δ 8.74 (s, 1H), 8.39 (d, J = 2.2 Hz, 1H), 8.21 (d, J = 8.9 Hz, 1H), 8.16 (d, J = 2.1 Hz, 1H), 7.77 (dd, J = 8.8, 1.9 Hz, 1H), 7.51 (d, J = 2.1 Hz, 1H), 3.50 (s, 3H), 3.30-3.21 (m, 2H), 2.98 (t, J = 12.1 Hz, 2H), 2.78 (s, 6H), 2.64-2.56 (m, 2H), 2.31 (q, J = 4.5 Hz, 2H), 2.23-1.98 (m, 4H), 1.36-1.30 (m, 2H), 1.12-1.07 (m, 2H), 0.93-0.69 (m, 4H). |
| 173 | 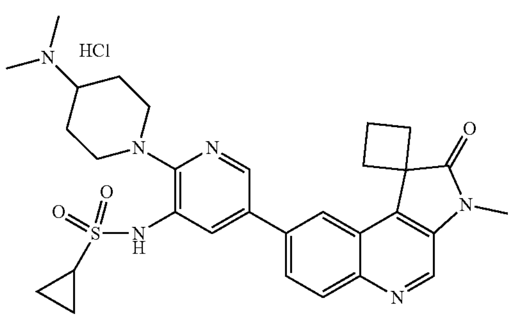 | N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide | 561.35 | 1H NMR (400 MHz, DMSO-d6) δ 10.44 (br, 1H), 9.24 (s, 1H), 8.85 (s, 1H), 8.67 (d, J = 2.3 Hz, 1H), 8.39 (d, J = 2.0 Hz, 1H), 8.18 (d, J = 8.9 Hz, 1H), 8.12 (d, J = 2.3 Hz, 1H), 7.99 (dd, J = 8.9, 2.0 Hz, 1H), 4.03 (d, J = 12.8 Hz, 2H), 3.32 (s, 3H), 2.98-2.84 (m, 5H), 2.77 (d, J = 4.7 Hz, 6H), 2.62-2.51 (m, 5H), 2.12 (d, J = 11.4 Hz, 2H), 1.95-1.83 (m, 2H), 1.06-0.98 (m, 4H). |

| EXAMPLES | Structure | Name | MS: [(M + 1)]+ | ¹H NMR |
|---|---|---|---|---|
| 178 | 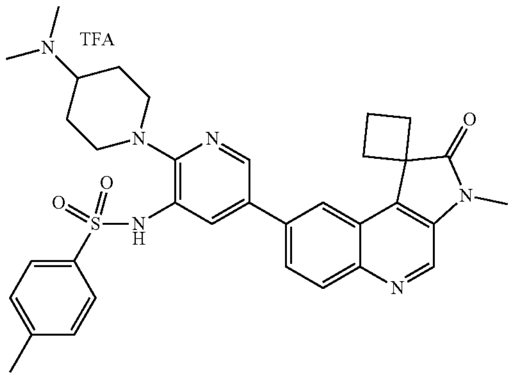 | N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)-4-methylbenzenesulfonamide 2,2,2-trifluoroacetate | 611.35 | ¹H NMR (300 MHz, CD₃OD) δ 8.83 (s, 1H), 8.54 (d, J = 2.3 Hz, 1H), 8.42 (d, J = 1.9 Hz, 1H), 8.19 (d, J = 9.0 Hz, 1H), 7.95-7.80 (m, 2H), 7.75 (d, J = 8.3 Hz, 2H), 7.36 (d, J = 8.1 Hz, 2H), 3.80 (d, J = 13.0 Hz, 2H), 3.47-3.34 (m, 4H), 3.01-2.85 (m, 10 H), 2.83-2.52 (m, 4H), 2.37 (s, 3H), 2.13-1.89 (m, 4H). |
| 185 | 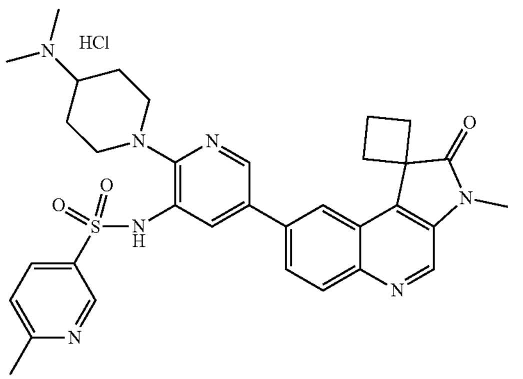 | N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide hydrochloride | 612.35 | ¹H NMR (300 MHz, CD₃OD) δ 8.85 (d, J = 2.0 Hz, 1H), 8.81 (s, 1H), 8.59 (d, J = 2.3 Hz, 1H), 8.44 (s, 1H), 8.19 (d, J = 8.9 Hz, 1H), 8.09 (dd, J = 8.4, 2.4 Hz, 1H), 7.90 (dd, J = 9.0, 2.0 Hz, 1H), 7.85 (d, J = 2.2 Hz, 1H), 7.47 (d, J = 8.3 Hz, 1H), 3.84 (d, J = 12.0 Hz, 2H), 3.40 (s, 4H), 3.03-2.87 (m, 10H), 2.82-2.62 (m, 4H), 2.57 (s, 3H), 2.14-2.05 (m, 2H), 2.01-1.90 (m, 2H). |
| 198 | 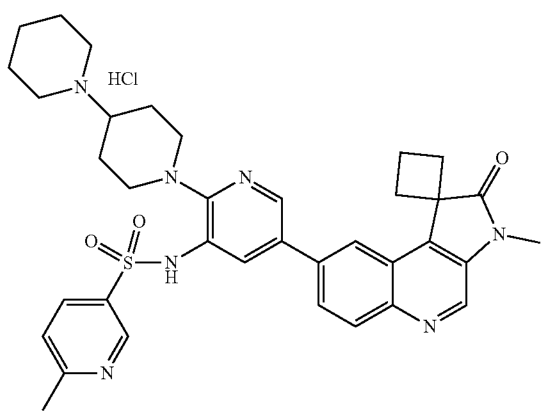 [SMILES: Cc1ccc(S(=O)(=O)Nc2cc(-c3ccc4ncc5c(c4c3)C3(CCC3)C(=O)N5C)cnc2N2CCC(N3CCCCC3)CC2)cn1 ; Cl] | N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide hydrochloride | 652.40 | ¹H NMR (300 MHz, CD₃OD) δ 8.84 (d, J = 2.4 Hz, 1H), 8.78 (s, 1H), 8.58 (d, J = 2.3 Hz, 1H), 8.42 (d, J = 1.9 Hz, 1H), 8.17 (d, J = 8.9 Hz, 1H), 8.09 (dd, J = 8.3, 2.4 Hz, 1H), 7.88-7.82 (m, 2H), 7.47 (d, J = 8.3 Hz, 1H), 3.84 (d, J = 13.1 Hz, 2H), 3.56 (d, J = 12.0 Hz, 2H), 3.39 (s, 4H), 3.07 (t, J = 12.0 Hz, 2H), 3.01-2.86 (m, 4H), 2.81-2.59 (m, 3H), 2.57 (s, 4H), 2.18-1.72 (m, 9H), 1.64-1.50 (m, 1H). |
| 206 | 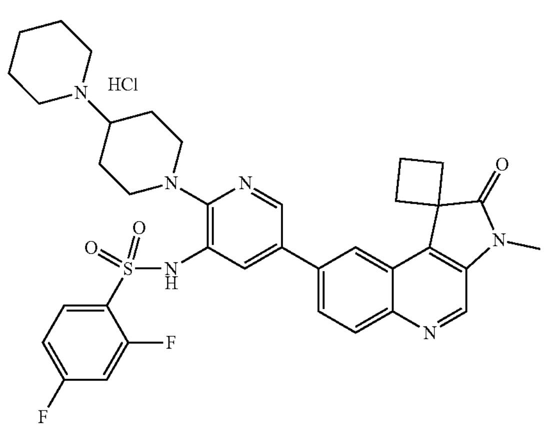 [SMILES: CN1C(=O)C2(CCC2)c2c1cnc1ccc(-c3cnc(N4CCC(N5CCCCC5)CC4)c(NS(=O)(=O)c4ccc(F)cc4F)c3)cc21 ; Cl] | N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-2,4-difluorobenzenesulfonamide hydrochloride | 673.35 | ¹H NMR (400 MHz, DMSO-d₆) δ 10.18 (s, 1H), 9.49 (s, 1H), 8.85 (s, 1H), 8.68 (d, J = 2.3 Hz, 1H), 8.27 (d, J = 2.0 Hz, 1H), 8.15 (d, J = 8.8 Hz, 1H), 7.93-7.78 (m, 2H), 7.76 (d, J = 2.3 Hz, 1H), 7.64 (t, J = 10.0 Hz, 1H), 7.26 (t, J = 8.6 Hz, 1H), 3.90 (d, J = 12.8 Hz, 2H), 3.31 (s, 3H), 3.01-2.89 (m, 2H), 2.89-2.73 (m, 4H), 2.63-2.52 (m, 6H), 2.48-2.37 (m, 1H), 2.06 (d, J = 11.9 Hz, 2H), 1.86 (d, J = 13.5 Hz, 2H), 1.82-1.66 (m, 5H), 1.50-1.38 (m, 1H). |

| EXAMPLES | Structure | Name | MS: [(M + 1)]+ | 1H NMR |
|---|---|---|---|---|
| 208 | 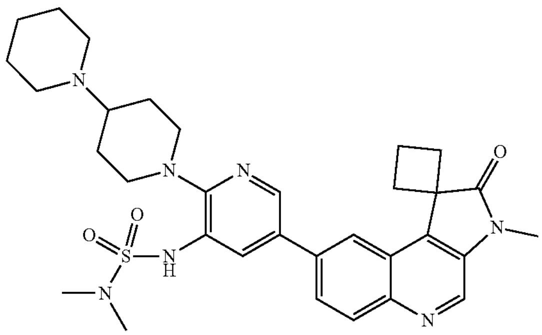 [SMILES: CN1C(=O)C2(CCC2)c2c1cnc1ccc(-c3cnc(N4CCC(N5CCCCC5)CC4)c(NS(=O)(=O)N(C)C)c3)cc21] | 8'-(6-{[1,4'-Bipiperidine]-1'-yl}-5-[(dimethylsulfamoyl)amino]pyridin-3-yl)-3'-methyl-2',3'-dihydrospiro[cyclobutane-1,1'-pyrrolo[2,3-c]quinoline]-2'-one | 604.35 | 1H NMR (400 MHz, CD3OD) δ 8.74 (s, 1H), 8.50 (s, 1H), 8.42 (s, 1H), 8.21-8.16 (m, 2H), 7.98 (d, J = 8.9 Hz, 1H), 3.83 (d, J = 12.6 Hz, 2H), 3.39 (s, 3 H), 3.04-2.89 (m, 4H), 2.87 (s, 9H), 2.79-2.62 (m, 6H), 2.06 (d, J = 12.2 Hz, 2H), 1.98-1.86 (m, 2H), 1.78-1.70 (m, 4H), 1.62-1.53 (m, 2H). |
| 212 | 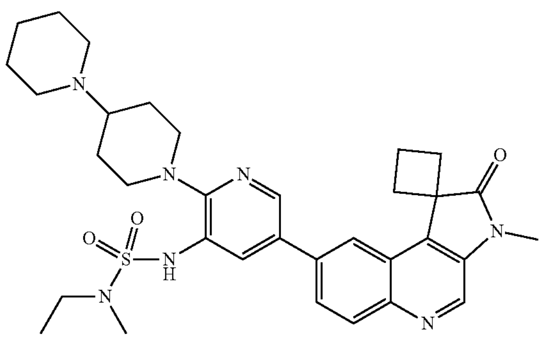 [SMILES: CCN(C)S(=O)(=O)Nc1cc(-c2ccc3ncc4c(c3c2)C2(CCC2)C(=O)N4C)cnc1N1CCC(N2CCCCC2)CC1] | 8'-(6-{[1,4'-Bipiperidine]-1'-yl}-5-[(ethyl(methyl)sulfamoyl)amino}pyridin-3-yl)-3'-methyl-2',3'-dihydrospiro[cyclobutane-1,1'-pyrrolo[2,3-c]quinoline]-2'-one | 618.35 | 1H NMR (400 MHz, DMSO-d6) δ 8.90 (s, 1H), 8.84 (s, 1H), 8.53 (s, 1H), 8.36 (d, J = 2.0 Hz, 1H), 8.16 (d, J = 8.9 Hz, 1H), 8.00 (d, J = 2.3 Hz, 1H), 7.95 (dd, J = 8.9, 1.9 Hz, 1H), 3.87 (d, J = 12.5 Hz, 2H), 3.31 (s, 3H), 3.19 (q, J = 7.2 Hz, 2H), 2.95-2.85 (m, 2H), 2.83-2.74 (m, 5H), 2.62-2.52 (m, 9H), 1.85-1.67 (m, 4 H), 1.57-1.49 (m, 4H), 1.45-1.38 (m, 2H), 1.05 (t, J = 7.1 Hz, 3H). |
| 213 | 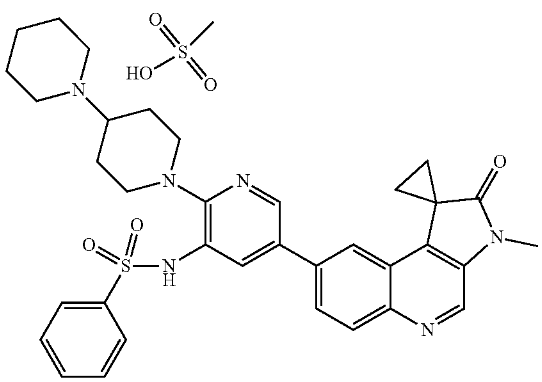 | N-(2-([1,4'-Bipiperidin]-1'-yl)-5-(3'-methyl-2'-oxo-2',3'-dihydrospiro[cyclopropane-1,1'-pyrrolo[2,3-c]quinolin]-8'-yl)pyridin-3-yl)benzenesulfonamide methanesulfonate | 623.30 | 1H NMR (400 MHz, CD3OD) δ 8.82 (s, 1H), 8.44 (d, J = 2.2 Hz, 1H), 8.11 (d, J = 8.9 Hz, 1H), 7.87 (d, J = 7.7 Hz, 2H), 7.73-7.65 (m, 2H), 7.64-7.55 (m, 3H), 7.46 (s, 1H), 3.84 (d, J = 12.9 Hz, 2H), 3.55 (d, J = 12.2 Hz, 2H), 3.49 (s, 3H), 3.42-3.34 (m, 1H), 3.07 (t, J = 12.1 Hz, 2H), 2.90 (t, J = 12.3 Hz, 2H), 2.70 (s, 3H), 2.37 (q, J = 4.6 Hz, 2H), 2.14-1.93 (m, 8H), 1.92-1.72 (m, 3H), 1,63-1.51 (m, 1H). |
| 214 | 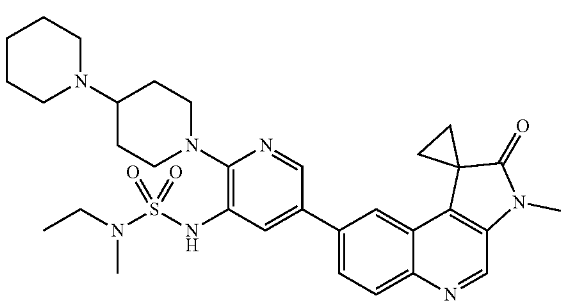 [SMILES: CCN(C)S(=O)(=O)Nc1cc(-c2ccc3ncc4c(c3c2)C2(CC2)C(=O)N4C)cnc1N1CCC(N2CCCCC2)CC1] | 8'-(6-{[1,4'-Bipiperidine]-1'-yl}-5-{[(ethyl(methyl)sulfamoyl]amino}pyridin-3-yl)-3'-methyl-2',3'-dihydrospiro[cyclopropane-1,1'-pyrrolo[2,3-c]quinoline]-2'-one | 604.35 | 1H NMR (400 MHz, DMSO-d6) δ 8.90 (s, 1H), 8.48 (d, J = 2.2 Hz, 1H), 8.13 (d, J = 9.0 Hz, 1H), 7.87 (d, J = 2.3 Hz, 1H), 7.84 (dd, J = 9.0, 1.9 Hz, 1H), 7.53 (d, J = 1.9 Hz, 1H), 3.85 (d, J = 12.1 Hz, 2H), 3.42 (s, 3H), 3.20 (q, J = 7.1 Hz, 2H), 2.79 (s, 3H), 2.78-2.72 (m, 2H), 2.61-2.52 (m, 5H), 2.47-2.43 (m, 2H), 1.84-1.66 (m, 6H), 1.57-1.49 (m, 4H), 1.41 (s, 2H), 1.07 (t, J = 7.1 Hz, 3H). |

-continued

| EXAMPLES | Structure | Name | MS: [(M + 1)]+ | 1H NMR |
|---|---|---|---|---|
| 224 | 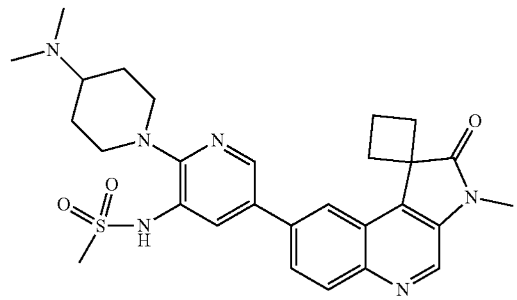 | N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide | 535.25 | 1H NMR (400 MHz, DMSO-d6) δ 9.04 (s, 1H), 8.83 (s, 1H), 8.56 (d, J = 2.3 Hz, 1H), 8.38 (d, J = 2.0 Hz, 1H), 8.16 (d, J = 8.8 Hz, 1H), 8.04 (d, J = 2.3 Hz, 1H), 7.99 (dd, J = 8.9, 1.9 Hz, 1H), 3.89 (d, J = 12.3 Hz, 2H), 3.31 (s, 3H), 3.16 (s, 3H), 2.98-2.89 (m, 2H), 2.79 (t, J = 12.0 Hz, 2H), 2.59-2.51 (m, 4H), 2.41-2.31 (m, 1H), 2.28 (s, 6H), 1.86 (d, J = 11.8 Hz, 2H), 1.70-1.59 (m, 2H). |
| 226 | 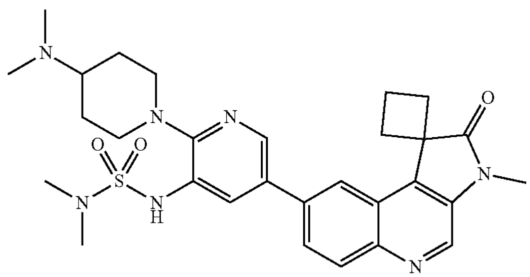 | 8'-{6-[4-(Dimethylamino)piperidin-1-yl]-5-[(dimethylsulfamoyl)amino]pyridin-3-yl}-3'-methyl-2',3'-dihydrospiro[cyclobutane-1,1'-pyrrolo[2,3-c]quinoline]-2'-one | 564.20 | 1H NMR (400 MHz, DMSO-d6) δ 8.83 (s, 1H), 8.48 (s, 1H), 8.36 (s. 1H), 8.16 (d, J = 8.8 Hz, 1H), 8.03 (d, J = 2.3 Hz, 1H), 7.96 (d, J = 9.0 Hz, 1H), 3.94 (d, J = 12.1 Hz, 2H), 3.31 (s, 3H), 2.95-2.84 (m, 2H), 2.83-2.76 (m, 2H), 2.75 (s, 8H), 2.65-2.54 (m, 4H), 2.46-2.35 (m, 1H), 2.31 (s, 6H), 1.87 (d, J = 12.3 Hz, 2H), 1.73-1.61 (m, 2H). |
| 227 | HCl | N-(5-(3'-Methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)cyclopropanesulfonamide hydrochloride | 533.25 | 1H NMR (400 MHz, CD3OD) δ 8.79 (s, 1H), 8.65 (d, J = 2.1 Hz, 1H), 8.54 (s, 1H), 8.30 (d, J = 2.2 Hz, 1H), 8.22 (d, J = 8.9 Hz, 1H), 8.02 (d, J = 8.9 Hz, 1H), 4.06 (d, J = 12.9 Hz, 2H), 3.65 (d, J = 9.8 Hz, 2H), 3.42 (s, 7H), 3.02 (s, 5H), 2.91-2.83 (m, 1H), 2.79-2.60 (m, 4H), 1.22-1.15 (m, 2H), 1.15-1.07 (m, 2H). |
| 228 | 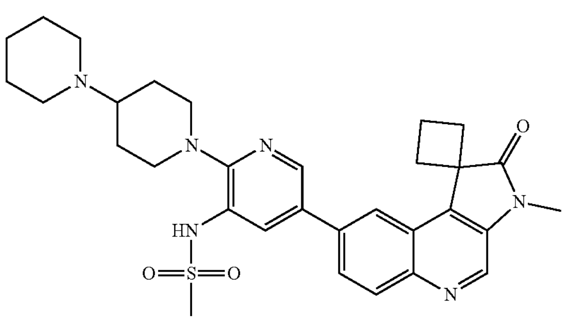 [SMILES: CN1C(=O)C2(CCC2)c2c1cnc1ccc(-c3cnc(N4CCC(N5CCCCC5)CC4)c(NS(C)(=O)=O)c3)cc21] | N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide | 575.25 | 1H NMR (400 MHz, CD3OD) δ 8.74 (s, 1H), 8.52 (s, 1H), 8.43 (s, 1H), 8.20-8.16 (m, 2H), 8.00 (d, J = 8.9 Hz, 1H), 3.88 (d, J = 12.5 Hz, 2H), 3.39 (s, 3H), 3.14 (s, 3H), 3.06-2.95 (m, 2H), 2.95-2.82 (m, 6H), 2.77-2.61 (m, 5H), 2.09-2.01 (m, 2H), 1.95-1.83 (m, 2H), 1.78-1.69 (m, 4H), 1.61-1.54 (m, 2H). |
| 229 | 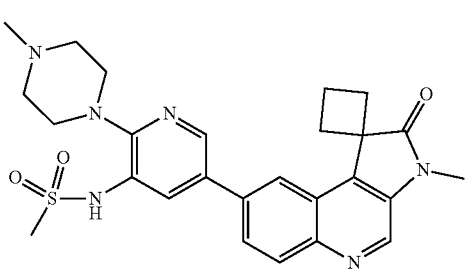 | N-(5-(3'-Methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)methanesulfonamide | 507.25 | 1H NMR (400 MHz, CD3OD) δ 8.75 (s, 1H), 8.53 (d, J = 11.8 Hz, 2H), 8.24-8.15 (m, 2H), 8.00 (d, J = 9.2 Hz, 1H), 3.40 (s, 7H), 3.19 (s, 3H), 3.06-2.96 (m, 2H), 2.78 (t, J = 4.8 Hz, 4H), 2.74-2.59 (m, 4H), 2.45 (s, 3H). |

-continued

| EXAMPLES | Structure | Name | MS: [(M + 1)]+ | 1H NMR |
|---|---|---|---|---|
| 230 | 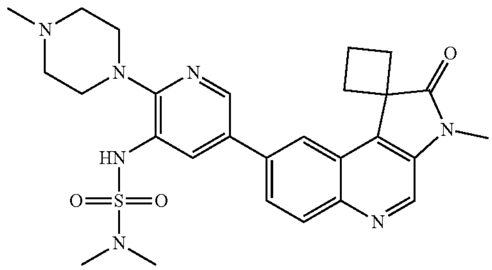 | 8'-{5-[(Dimethylsulfamoyl)amino]-6-(4-methylpiperazin-1-yl)pyridin-3-yl}-3'-methyl-2',3'-dihydrospiro[cyclobutane-1,1'-pyrrolo[2,3-c]quinoline]-2'-one | 536.25 | 1H NMR (400 MHz, DMSO-d6) δ 9.03 (s, 1H), 8.84 (s, 1H), 8.59 (s, 1H), 8.37 (s, 1H), 8.17 (d, J = 8.5 Hz, 1H), 8.05 (s, 1H), 7.96 (d, J = 8.9 Hz, 1H), 3.35 (s, 4H), 3.31 (s, 3H), 2.96-2.85 (m, 2H), 2.78 (s, 6H), 2.57 (s, 8H), 2.28 (s, 3H). |
| 251 | 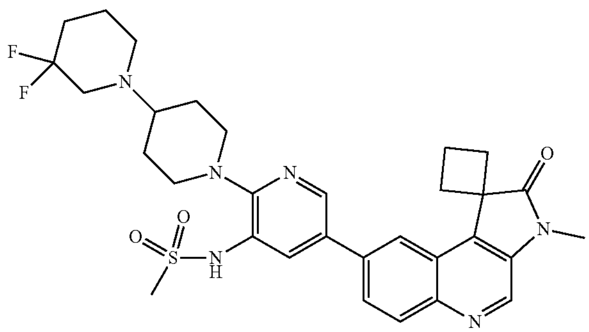 [SMILES: CN1C(=O)C2(CCC2)c2c1cnc1ccc(-c3cnc(N4CCC(N5CCCC(F)(F)C5)CC4)c(NS(C)(=O)=O)c3)cc21] | N-(2-(3,3-Difluoro-[1,4'-bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide | 611.20 | 1H NMR (400 MHz, DMSO-d6) δ 8.97 (s, 1H), 8.84 (s, 1H), 8.62 (s, 1H), 8.39 (s, 1H), 8.16 (d, J = 8.8 Hz, 1H), 8.07 (s, 1H), 7.99 (d, J = 9.2 Hz, 1H), 3.81 (d, J = 12.2 Hz, 2H), 3.32 (s, 3H), 2.98-2.88 (m, 2H), 2.86-2.74 (m, 4H), 2.62-2.52 (m, 10H), 1.95-1.60 (m, 8H). |

The following intermediates were prepared according to the procedure described above:

| Intermediate | Structure | Name | MS: [(M + 1)]+ | 1H NMR |
|---|---|---|---|---|
| EE11 | 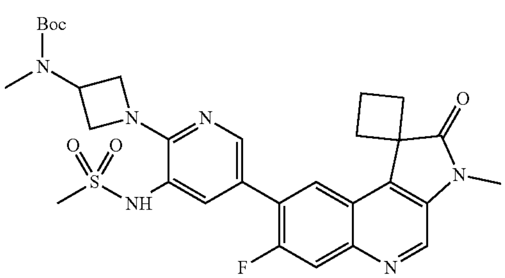 | tert-Butyl (1-(5-(7'-fluoro-3'-methyl-2'-oxo-2',3'-dihydrospiro[cyclobutane-1,1'-pyrrolo[2,3-c]quinolin]-8'-yl)-3-(methylsulfonamido)pyridin-2-yl)azetidin-3-yl)(methyl)carbamate | 611.40 | 1H NMR (400 MHz, CD3OD) δ 8.72 (s, 1H), 8.38 (d, J = 2.4 Hz, 1H), 8.34 (d, J = 8.2 Hz, 1H), 7.90 (d, J = 2.5 Hz, 1H), 7.81 (d, J = 12.1 Hz, 1H), 4.52 (t, J = 8.6 Hz, 2H), 4.33 (dd, J = 9.4, 5.8 Hz, 2H), 4.21-4.05 (m, 1H), 3.36 (s, 3H), 3.11 (s, 3H), 3.01-2.90 (m, 5H), 2.73-2.47 (m, 4H). |
| EE12 | 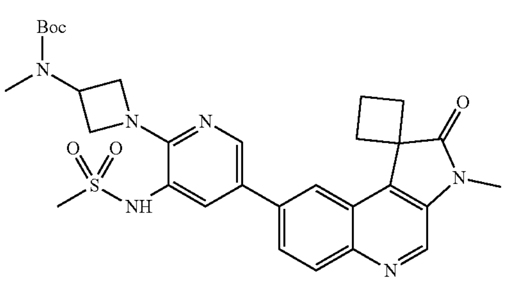 | tert-Butyl methyl(1-(5-(3'-methyl-2'-oxo-2',3'-dihydrospiro[cyclobutane-1,1'-pyrrolo[2,3-c]quinolin]-8'-yl)-3-(methylsulfonamido)pyridin-2-yl)azetidin-3-yl)carbamate Molecular Weight: 592.72 | 593.30 | 1H NMR (400 MHz, CD3OD) δ 8.71 (s, 1H), 8.50 (d, J = 1.7 Hz, 1H), 8.44 (d, J = 1.9 Hz, 1H), 8.15 (d, J = 8.9 Hz, 1H), 7.99 (d, J = 2.2 Hz, 1H), 7.95 (d, J = 8.7 Hz, 1H), 4.51 (t, J = 8.5 Hz, 2H), 4.32 (dd, J = 9.2, 6.0 Hz, 2H), 3.72-3.60 (m, 1H), 3.38 (s, 3H), 3.14 (s, 3H), 3.05-2.95 (m, 5H), 2.74-2.55 (m, 4H), 1.48 (s, 9H). |

| Intermediate | Structure | Name | MS: [(M + 1)]+ | 1H NMR |
|---|---|---|---|---|
| EE13 | 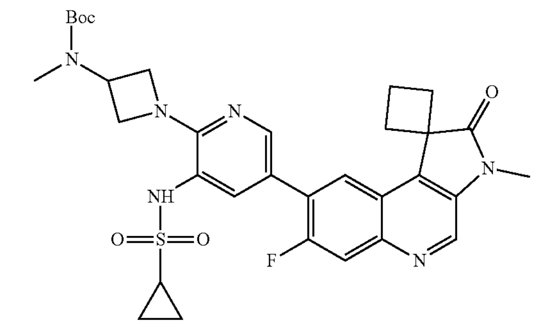 | tert-Butyl (1-(3-(cyclopropanesulfonamido)-5-(7'-fluoro-3'-methyl-2'-oxo-2',3'-dihydrospiro[cyclobutane-1,1'-pyrrolo[2,3-c]quinolin]-8'-yl)pyridin-2-yl)azetidin-3-yl)(methyl)carbamate Molecular Weight: 636.74 | 637.45 | 1H NMR (400 MHz, CDCl₃) δ 8.64 (s, 1H), 8.42 (d, J = 22.5 Hz, 1H), 8.26 (d, J = 7.7 Hz, 1H), 7.97-7.83 (m, 2H), 4.57-4.19 (m, 4H), 4.04 (s, 1H), 3.38 (s, 3H), 2.99 (d, J = 8.2 Hz, 3H), 2.92-2.81 (m, 2H), 2.81-2.55 (m, 4H), 2.55-2.43 (m, 1H), 1.63 (s, 9H), 1.29-1.25 (m, 2H), 1.16-1.05 (m, 2H). |
| EE14 | 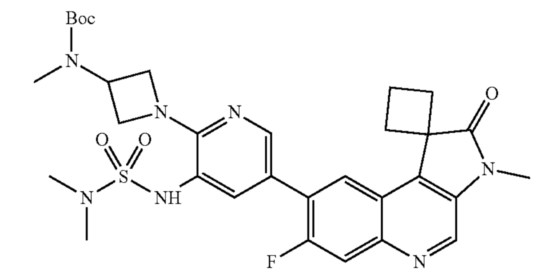 | tert-Butyl (1-(3-((N,N-dimethylsulfamoyl)amino)-5-(7'-fluoro-3'-methyl-2'-oxo-2',3'-dihydrospiro[cyclobutane-1,1'-pyrrolo[2,3-c]quinolin]-8'-yl)pyridin-2-yl)azetidin-3-yl)(methyl)carbamate | 640.45 | 1H NMR (400 MHz, DMSO-d₆) δ 9.15 (s, 1H), 8.86 (s, 1H), 8.44 (s, 1H), 8.24 (d, J = 8.4 Hz, 1H), 7.95 (d, J = 12.2 Hz, 1H), 7.77 (s, 1H), 4.42 (t, J = 8.6 Hz, 2H), 4.23 (dd, J = 9.3, 5.9 Hz, 2H), 4.12-4.05 (m 1H), 2.95-2.84 (m, 5H), 2.80 (s, 6H), 2.59-2.51 (m, 3H), 2.47-2.38 (m, 1H), 1.42 (s, 9H). |
| EE15 | 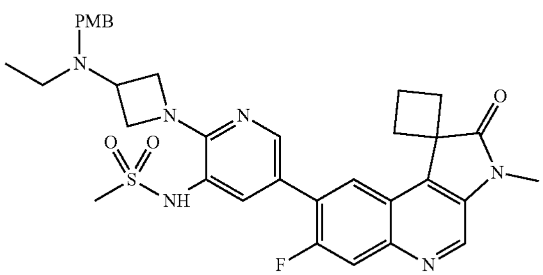 | N-(2-(3-(Ethyl(4-methoxybenzyl)amino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide | 645.30 | 1H NMR (400 MHz, CDCl₃) δ 8.64 (s, 1H), 8.44 (s, 1H), 8.26 (d, J = 8.1 Hz, 1H), 7.93-7.85 (m, 2H), 7.25 (d, J = 8.4 Hz, 1H), 6.87 (d, J = 8.4 Hz, 1H), 4.28 (t, J = 7.7 Hz, 2H), 4.15 (s, 2H), 3.82 (s, 3H), 3.79-3.70 (m, 1H), 3.65 (s, 2H), 3.37 (s, 3H), 3.07 (s, 3H), 2.86 (q, J = 9.7, 8.6 Hz, 2H), 2.79-2.63 (m, 3H), 2.63-2.45 (m, 3H). |
| EE16 | 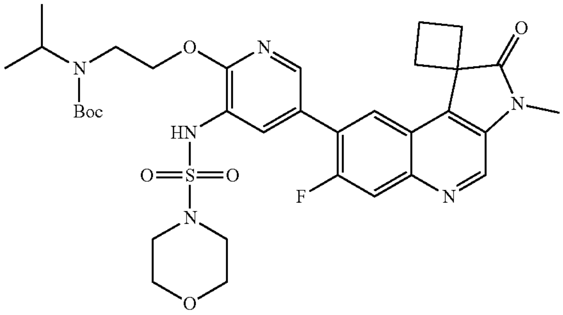 [SMILES: CC(C)N(CCOc1ncc(-c2cc3c4c(cnc3cc2F)N(C)C(=O)C42CCC2)cc1NS(=O)(=O)N1CCOCC1)C(=O)OC(C)(C)C] | tert-Butyl (2-((5-(7'-fluoro-3'-methyl-2'-oxo-2',3'-dihydrospiro[cyclobutane-1,1'-pyrrolo[2,3-c]quinolin]-8'-yl)-3-(morpholine-4-sulfonamido)pyridin-2-yl)oxy)ethyl)(isopropyl)carbamate | 700.30 | 1H NMR (400 MHz, CDCl₃) δ 8.66 (s, 1H), 8.30 (d, J = 7.9 Hz, 1H), 8.17 (s, 1H), 8.11 (s, 1H), 8.05-7.93 (m, 1H), 4.56 (s, 2H), 3.73 (q, J = 3.6, 2.6 Hz, 4H), 3.68-3.41 (m, 2H), 3.39 (s, 3H), 3.35-3.25 (m, 4H), 2.89-2.73 (m, 4H), 2.72-2.40 (m, 3H), 1.50 (s, 9H), 1.19 (d, J = 6.7 Hz, 6H). |

-continued

| Intermediate | Structure | Name | MS: [(M+1)]+ | 1H NMR |
|---|---|---|---|---|
| EE17 | 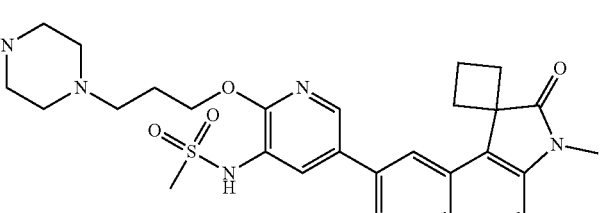 | tert-Butyl 4-(3-((5-(3'-methyl-2'-oxo-2',3'-dihydro-spiro[cyclobutane-1,1'-pyrrolo[2,3-c]quinolin]-8'-yl)-3-(methylsulfonamido)pyridin-2-yl)oxy)propyl)piperazine-1-carboxylate | 651.40 | 1H NMR (400 MHz, CDCl3) δ 8.65 (s, 1H), 8.39 (d, J = 2.0 Hz, 1H), 8.33 (d, J = 2.2 Hz, 1H), 8.24-8.18 (m, 2H), 7.82 (dd, J = 8.9, 2.0 Hz, 1H), 4.55 (t, J = 6.5 Hz, 2H), 3.48 (s, 4H), 3.38 (s, 3H), 3.09 (s, 3H), 2.95-2.86 (m, 2H), 2.82-2.63 (m, 3H), 2.62-2.52 (m, 3H), 2.47 (s, 4H), 2.08 (p, J = 6.9 Hz, 2H), 1.46 (s, 9H). |
| EE18 | 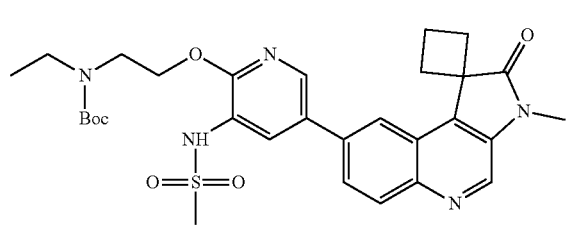 [SMILES: CCN(CCOc1ncc(-c2ccc3ncc4c(c3c2)C2(CCC2)C(=O)N4C)cc1NS(C)(=O)=O)C(=O)OC(C)(C)C] | tert-Butyl 4-(3-((5-(3'-methyl-2'-oxo-2',3'-dihydro-spiro[cyclobutane-1,1'-pyrrolo[2,3-c]quinolin]-8'-yl)-3-(methylsulfonamido)pyridin-2-yl)oxy)ethyl)carbamate | 596.20 | 1H NMR (400 MHz, CDCl3) δ 8.66 (s, 1H), 8.40 (s, 1H), 8.32 (s, 1H), 8.29-8.21 (m, 2H), 7.85 (d, J = 9.0 Hz, 1H), 4.57 (s, 2H), 3.65 (s, 2H), 3.39 (s, 3H), 3.31 (s, 2H), 2.98-2.86 (m, 2H), 2.85-2.50 (m, 4H), 1.49 (s, 9H), 1.16 (t, J = 7.0 Hz, 3H). |
| EE19 | 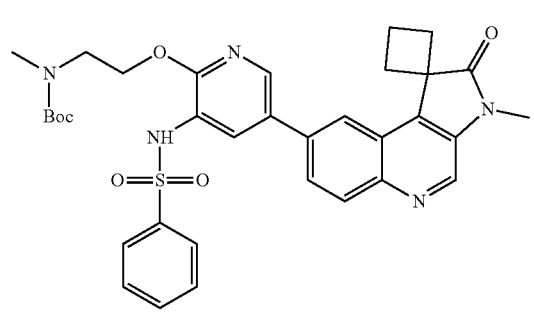 | tert-Butyl methyl(2-((5-(3'-methyl-2'-oxo-2',3'-dihydro-spiro[cyclobutane-1,1'-pyrrolo[2,3-c]quinolin]-8'-yl)-3-(phenylsulfonamido)pyridin-2-yl)oxy)ethyl)carbamate | 644.20 | 1H NMR (400 MHz, DMSO-d6) δ 8.85 (s, 1H), 8.45 (s, 1H), 8.32 (s, 1H), 8.16 (d, J = 8.8 Hz, 1H), 8.05 (s, 1H), 7.83 (d, J = 7.7 Hz, 2H), 7.67-7.49 (m, 4H), 4.30 (s, 2H), 3.93 (s, 3H), 3.47-3.40 (m, 2H), 2.95-2.83 (m, 2H), 2.80 (s, 3H), 2.65-2.52 (m, 4H), 1.35 (d, J = 36.0 Hz, 9H). |
| EE20 | 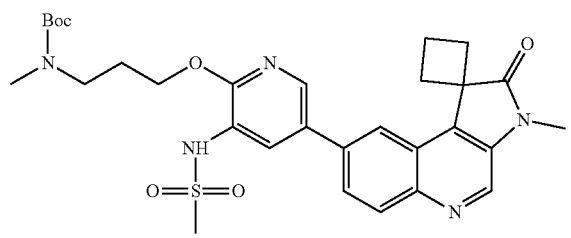 | tert-Butyl methyl(3-((5-(3'-methyl-2'-oxo-2',3'-dihydro-spiro[cyclobutane-1,1'-pyrrolo[2,3-c]quinolin]-8'-yl)-3-(methylsulfonamido)pyridin-2-yl)oxy)propyl)carbamate | 596.30 | 1H NMR (400 MHz, CD3OD) δ 8.74 (s, 1H), 8.49 (d, J = 2.0 Hz, 1H), 8.42 (d, J = 2.3 Hz, 1H), 8.25 (d, J = 2.3 Hz, 1H), 8.18 (d, J = 8.9 Hz, 1H), 7.98 (dd, J = 8.9, 2.0 Hz, 1H), 4.51 (s, 2H), 3.48 (t, J = 6.9 Hz, 2H), 3.39 (s, 3H), 3.09 (s, 3H), 3.04-2.94 (m, 2H), 2.91 (s, 3H), 2.77-2.60 (m, 4H), 2.10 (s, 2H), 1.44 (s, 9H). |
| EE21 | 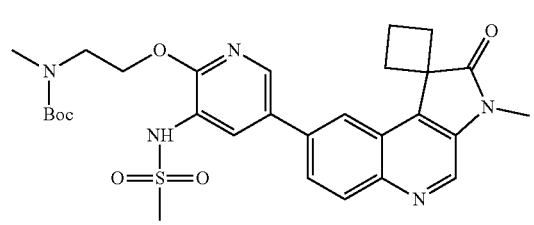 | tert-Butyl methyl(2-((5-(3'-methyl-2'-oxo-2',3'-dihydro-spiro[cyclobutane-1,1'-pyrrolo[2,3-c]quinolin]-8'-yl)-3-(methylsulfonamido)pyridin-2-yl)oxy)ethyl)carbamate | 582.20 | 1H NMR (400 MHz, DMSO-d6) δ 8.85 (s, 1H), 8.51 (s, 1H), 8.38 (s, 1H), 8.21-8.12 (m, 2H), 7.98 (d, J = 9.0 Hz, 1H), 4.53 (s, 2H), 3.64 (s, 2H), 3.32 (s, 3H), 3.13 (s, 3H), 2.96-2.85 (m, 5H), 2.62-2.51 (m, 4H), 1.35 (d, J = 27.8 Hz, 9H). |

-continued

| Intermediate | Structure | Name | MS: [(M + 1)]⁺ | ¹H NMR |
|---|---|---|---|---|
| EE22 | 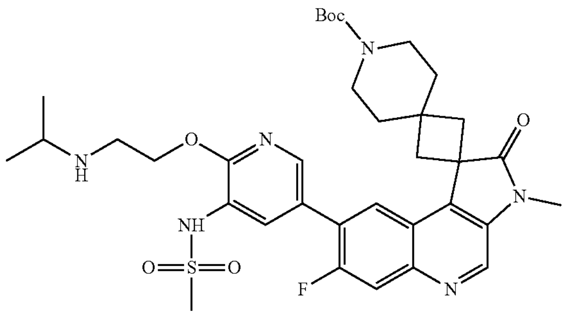 [SMILES: CC(C)NCCOc1ncc(-c2cc3c4c(cnc3cc2F)N(C)C(=O)C42CC3(CCN(C(=O)OC(C)(C)C)CC3)C2)cc1NS(C)(=O)=O] | tert-Butyl 7″-fluoro-8″-(6-(2-(isopropylamino)ethoxy)-5-(methylsulfonamido)pyridin-3-yl)-3″-methyl-2″-oxo-2″,3″-dihydro-dispiro[piperidine-4,1′-cyclobutane-3′,1″-pyrrolo[2,3-c]quinoline]-1-carboxylate | 697.30 | Crude to the next step directly. |
| EE23 | 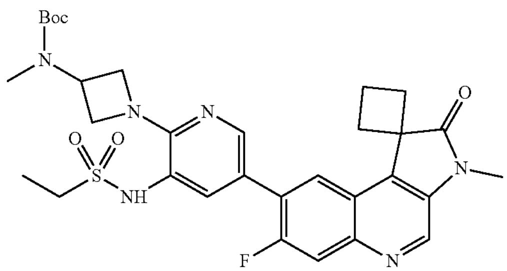 | tert-Butyl (1-(3-(ethylsulfonamido)-5-(7′-fluoro-3′-methyl-2′-oxo-2′,3′-dihydro-spiro[cyclobutane-1,1′-pyrrolo[2,3-c]quinolin]-8′-yl)pyridin-2-yl)azetidin-3-yl)(methyl)carbamate | 625.40 | ¹H NMR (400 MHz, DMSO-$d_6$) δ 9.17 (s, 1H), 8.86 (s, 1H), 8.46 (s, 1H), 8.26 (d, J = 8.2 Hz, 1H), 7.95 (d, J = 12.3 Hz, 1H), 7.75 (s, 1H), 4.42 (t, J = 8.6 Hz, 2H), 4.23 (dd, J = 9.5, 5.8 Hz, 2H), 3.30 (s, 3H), 3.28-3.20 (m, 1H), 2.96-2.84 (m, 7H), 2.60-2.51 (m, 2H), 2.48-2.37 (m, 2H), 1.41 (s, 9H), 1.30 (t, J = 7.3 Hz, 3H). |
| EE24 | 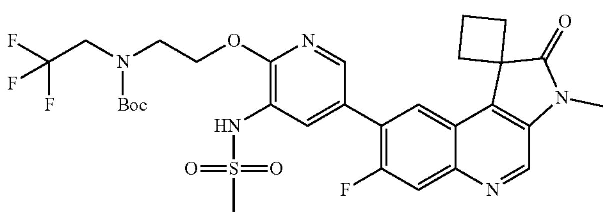 [SMILES: CN1C(=O)C2(CCC2)c2c1cnc1cc(F)c(-c3cnc(OCCN(CC(F)(F)F)C(=O)OC(C)(C)C)c(NS(C)(=O)=O)c3)cc21] | tert-Butyl (2-((5-(7′-fluoro-3′-methyl-2′-oxo-2′,3′-dihydro-spiro[cyclobutane-1,1′-pyrrolo[2,3-c]quinolin]-8′-yl)-3-(methylsulfonamido)pyridin-2-yl)oxy)ethyl)(2,2,2-trifluoroethyl)carbamate | 668.35 | ¹H NMR (400 MHz, CD₃OD) δ 8.78 (s, 1H), 8.42 (d, J = 8.2 Hz, 1H), 8.34 (s, 1H), 8.16 (s, 1H), 7.88 (d, J = 11.9 Hz, 1H), 4.70 (s, 2H), 4.11 (q, J = 9.2 Hz, 2H), 3.83 (s, 2H), 3.38 (s, 3H), 3.08 (s, 3H), 2.96 (q, J = 9.8, 9.1 Hz, 2H), 2.76-2.53 (m, 4H), 1.44 (s, 9H). |
| EE25 | 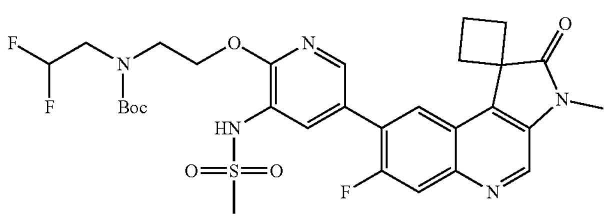 [SMILES: CN1C(=O)C2(CCC2)c2c1cnc1cc(F)c(-c3cnc(OCCN(CC(F)F)C(=O)OC(C)(C)C)c(NS(C)(=O)=O)c3)cc21] | tert-Butyl (2,2-difluoroethyl)(2-((5-(7′-fluoro-3′-methyl-2′-oxo-2′,3′-dihydro-spiro[cyclobutane-1,1′-pyrrolo[2,3-c]quinolin]-8′-yl)-3-(methylsulfonamido)pyridin-2-yl)oxy)ethyl)carbamate | 650.15 | Crude to the next step without further purification. |
| EE26 | 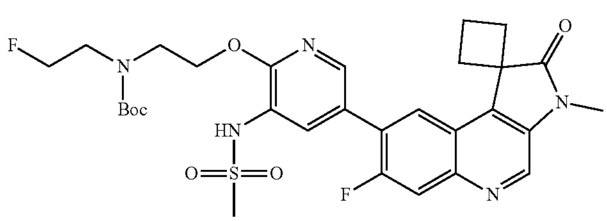 [SMILES: CN1C(=O)C2(CCC2)c2c1cnc1cc(F)c(-c3cnc(OCCN(CCF)C(=O)OC(C)(C)C)c(NS(C)(=O)=O)c3)cc21] | tert-Butyl (2-((5-(7′-fluoro-3′-methyl-2′-oxo-2′,3′-dihydro-spiro[cyclobutane-1,1′-pyrrolo[2,3-c]quinolin]-8′-yl)-3-(methylsulfonamido)pyridin-2-yl)oxy)ethyl)(2-fluoroethyl)carbamate | 632.20 | ¹H NMR (400 MHz, DMSO-$d_6$) δ 8.89 (s, 1H), 8.39 (s, 1H), 8.31 (s, 1H), 8.05 (s, 1H), 7.99 (d, J = 12.0 Hz, 1H), 4.64-4.39 (m, 4H), 3.72-3.53 (m, 4H), 3.31 (s, 3H), 3.12 (s, 3H), 2.96-2.84 (m, 4H), 2.61-2.41 (m, 4H), 1.37 (d, J = 14.0 Hz, 9H). |

Example 361

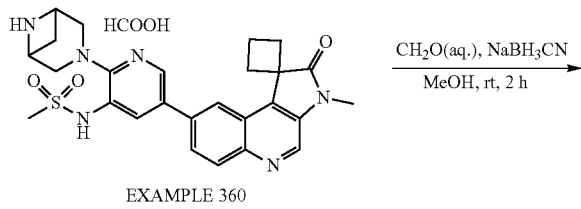

EXAMPLE 360

EXAMPLE 361

N-(5-(3'-Methyl-2'-oxo-2',3'-dihydrospiro[cyclobutane-1,1'-pyrrolo[2,3-c]quinolin]-8'-yl)-2-(6-methyl-3,6-diazabicyclo[3.1.1]heptan-3-yl)pyridin-3-yl)methanesulfonamide formate: To a solution of N-(2-(3,6-diazabicyclo[3.1.1]heptan-3-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide formate (30.0 mg, 0.05 mmol) in methanol (4.00 mL) was added formalin solution (21.5 mg, 0.27 mmol, 38% in water) at ambient temperature. The resulting mixture was stirred for 2 hours at 25° C. followed by the addition of sodium cyanoborohydride (6.80 mg, 0.11 mmol). After stirring for additional 2 hours at 25° C., the resulting mixture was purified by Prep-HPLC with the following conditions: [Column: Spherical C18, 20~40 μm, 120 g; Mobile Phase A: Water (plus 0.05% formic acid); Mobile phase B: acetonitrile; Flow rate: 45 mL/min Gradient (B %): 5%~16%, 4 min 16%~26%, 5 min; 26%, 5 min; 26%~95%; 3 min; 95%; 3 min Detector. UV 254 nm; Rt: 10 min]. The desired fractions were collected and concentrated under reduced pressure to afford the title compound as a yellow solid (22.0 mg, 72%): $^1$H NMR (400 MHz, DMSO-$d_6$) δ 8.81 (s, 1H), 8.66 (d, J=2.1 Hz, 1H), 8.35 (s, 1H), 8.18 (s, 1H), 8.14 (d, J=8.9 Hz, 1H), 7.97 (d, J=10.8 Hz, 2H), 3.99 (d, J=12.7 Hz, 4H), 3.67 (s, 2H), 3.31 (s, 3H), 3.06 (s, 3H), 2.95 (d, J=9.9 Hz, 2H), 2.61-2.52 (m, 5H), 2.19 (s, 3H), 1.58 (d, J=8.5 Hz, 1H); MS: [(M+1)]$^+$=519.15.

The following examples were prepared according to the procedure described above:

| Example | Structure | Name | MS: [(M + 1)]$^+$ | $^1$H NMR |
|---|---|---|---|---|
| 345 | 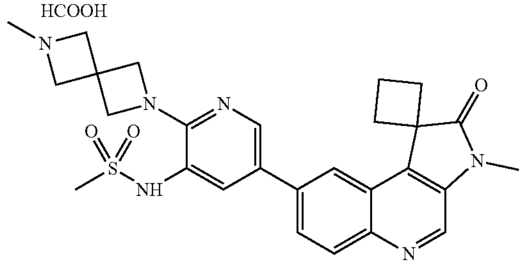 | N-(5-(3'-Methyl-2'-oxo-2',3'-dihydrospiro[cyclobutane-1,1'-pyrrolo[2,3-c]quinolin]-8'-yl)-2-(6-methyl-2,6-diazaspiro[3.3]heptan-2-yl)pyridin-3-yl)methanesulfonamide formate | 519.30 | $^1$H NMR (400 MHz, DMSO-$d_6$) δ 8.80 (s, 1H), 8.50 (s, 1H), 8.31 (d, J = 2.1 Hz, 1H), 8.21 (s, 1H), 8.12 (d, J = 8.9 Hz, 1H), 7.93 (dd, J = 9.0, 2.1 Hz, 1H), 7.88 (d, J = 2.3 Hz, 1H), 4.24 (s, 4H), 3.35 (s, 4H), 3.30 (s, 3H), 3.10 (s, 3H), 2.97-2.87 (m, 2H), 2.61-2.52 (m, 4H), 2.24 (s, 3H). |
| 350 | 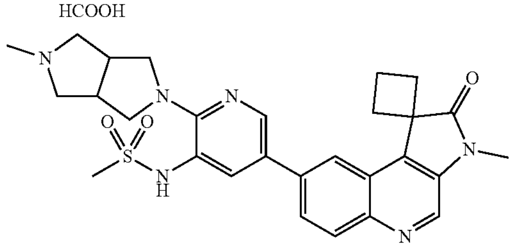 | N-(5-(3'-Methyl-2'-oxo-2',3'-dihydrospiro[cyclobutane-1,1'-pyrrolo[2,3-c]quinolin]-8'-yl)-2-(5-methylhexahydropyrrolo[3,4-c]pyrrol-2(1H)-yl)pyridin-3-yl)methanesulfonamide formate | 533.30 | $^1$H NMR (400 MHz, CD$_3$OD) δ 8.73 (s, 1H), 8.54 (d, J = 2.3 Hz, 1H), 8.48 (d, J = 2.1 Hz, 1H), 8.17 (d, J = 8.9 Hz, 1H), 8.06 (d, J = 2.3 Hz, 1H), 7.98 (dd, J = 9.0, 2.0 Hz, 1H), 4.06 (d, J = 11.0 Hz, 2H), 3.49-3.32 (m, 9H), 3.20 (s, 2H), 3.12 (s, 3H), 3.06-2.97 (m, 2H), 2.83 (s, 3H), 2.76-2.55 (m, 4H). |

Synthesis of Example 223 and 264

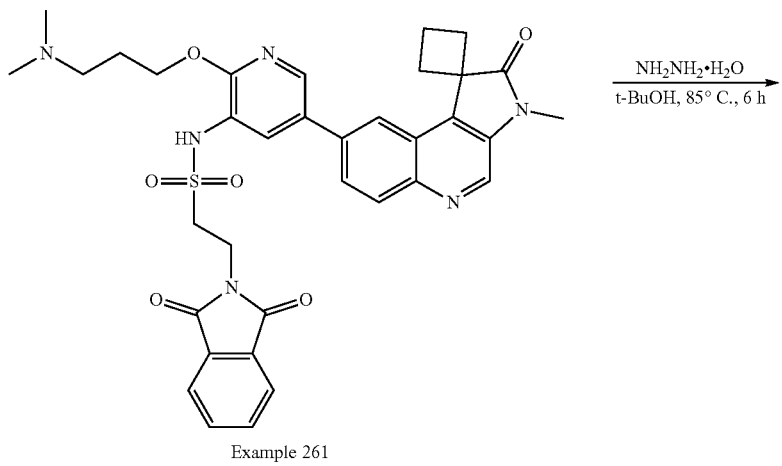

Example 261

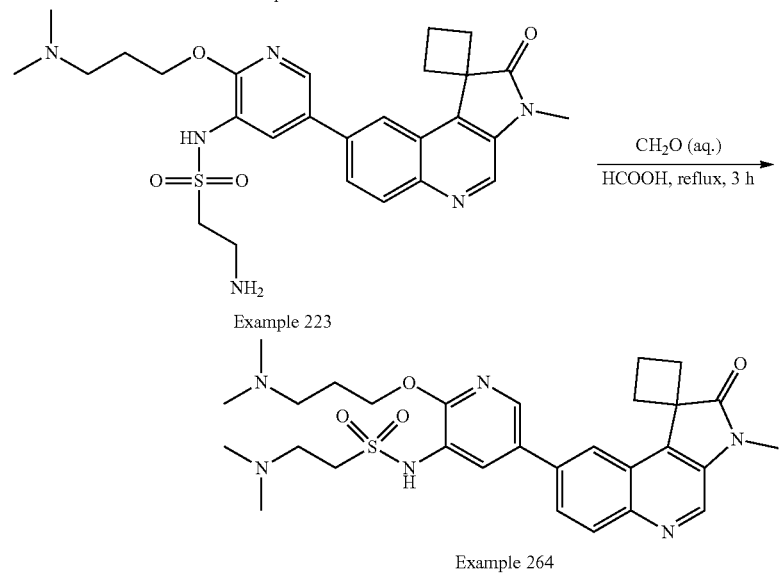

Example 223

Example 264

2-Amino-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)ethane-1-sulfonamide (EXAMPLE 223): To a stirred solution of N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-(1,3-dioxoisoindolin-2-yl)ethane-1-sulfonamide (EXAMPLE 261) (330 mg, 0.49 mmol) in tert-butanol (7.00 mL) was added hydrazine hydrate (7.00 mL, 80% w/w in water) dropwise at ambient temperature. The resulting mixture was stirred for 6 hours at 85° C. The resulting mixture was concentrated under reduced pressure. To the residue was added sodium hydroxide (7.00 mL, 1 N) dropwise at ambient temperature. The resulting mixture was stirred for 1 hour at ambient temperature. The resulting mixture was concentrated under reduced pressure. The residue was purified by Prep-HPLC with the following conditions: [Column: Spherical C18, 20~40 μm, 120 g; Mobile Phase A: Water (plus 10 mM NH$_4$HCO$_3$ and 0.05% NH$_3$·H$_2$O); Mobile Phase B: acetonitrile. Flow rate: 45 mL/min; Gradient (B %): 5%~25%, 10 min; 25%~40, 20 min; 40%~95%; 2 min; 95%, 5 min; Detector: UV 254 nm; Rt: 17 min]. The desired fractions were collected and concentrated under reduced pressure to afford the title compound as a yellow solid (90.0 mg, 34%): $^1$H NMR (400 MHz, DMSO-d$_6$) δ 8.81 (s, 1H), 8.35 (d, J=2.0 Hz, 1H), 8.14 (d, J=8.9 Hz, 1H), 8.01 (s, 1H), 7.92 (dd, J=8.9, 2.0 Hz, 1H), 7.87 (s, 1H), 4.31 (t, J=6.7 Hz, 2H), 3.31 (s, 3H), 3.19 (s, 2H), 3.11-3.06 (m, 2H), 2.90-2.82 (m, 2H), 2.64-2.52 (m, 4H), 2.48-2.42 (m, 2H), 2.26 (s, 6H), 1.98-1.89 (m, 2H); MS: [(M+1)]$^+$=539.25.

2-(Dimethylamino)-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)ethane-1-sulfonamide (EXAMPLE 264): To a stirred solution of 2-amino-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)ethane-1-sulfonamide (120 mg, 0.22 mmol) in formic acid (15.0 mL) was added formalin (15.0 mL, 37%) dropwise at ambient temperature under nitrogen atmosphere. The resulting mixture was refluxed for 3 hours under nitrogen atmosphere. The resulting mixture was concentrated under reduced pressure. The residue was purified by Prep-HPLC with the following conditions: [Column: Spherical C18, 20~40 μm, 120 g; Mobile Phase A: Water (plus 10 mM NH$_4$HCO$_3$ and 0.05% NH$_3$·H$_2$O); Mobile Phase B: acetonitrile; Flow rate: 45 mL/min; Gradient (B %): 5%~20%, 15 min; 20%~40%, 25 min; 40%~95%; 5 min; 95%, 5 min; Detector: UV 254 nm; Rt: 22 min]. The desired fractions were collected and concentrated under reduced pressure to afford the title compound as an off-white solid (58.0 mg, 46%): ¹H NMR (400 MHz, DMSO-d₆) δ 8.83 (s, 1H), 8.37 (d, J=2.0 Hz, 1H), 8.32 (d, J=2.3 Hz, 1H), 8.16 (d, J=8.8 Hz, 1H), 8.08 (d, J=2.3 Hz, 1H), 7.96 (dd, J=9.0, 1.9 Hz, 1H), 4.41 (t, J=6.3 Hz, 2H), 3.31 (s, 3H), 3.30 (t, J=7.2 Hz, 2H), 2.94-2.85 (m, 2H), 2.71 (t, J=7.3 Hz, 2H), 2.65 (t, J=6.6 Hz, 2H), 2.62-2.52 (m, 4H), 2.35 (s, 6H), 2.16 (s, 6H), 2.03-1.96 (m, 2H); MS: [(M+1)]⁺=567.25.

Example 269

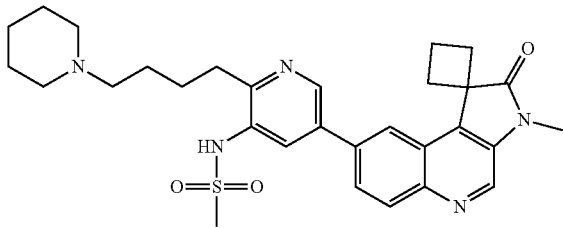 [SMILES: CN1C(=O)C2(CCC2)c2c1cnc1ccc(-c3cnc(CCCCN4CCCCC4)c(NS(C)(=O)=O)c3)cc21]

Example 269

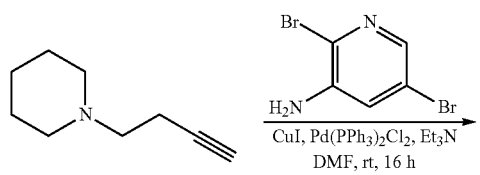

1-(But-3-yn-1-yl)piperidine: To a stirred solution of piperidine (5.00 g, 58.7 mmol) and 4-bromobut-1-yne (15.6 g, 118 mmol) in acetonitrile (150 mL) was added cesium carbonate (47.8 g, 147 mmol) at ambient temperature. The resulting mixture was refluxed for 16 hours. After cooling down to ambient temperature, the resulting mixture was filtered and the filtered cake was washed with acetonitrile (3×20.0 mL). The filtrate was concentrated under reduced pressure. The residue was re-dissolved into ethyl acetate (100 mL), washed with water (3×100 mL) and dried over anhydrous sodium sulfate. After filtration, the filtrate was concentrated under reduced pressure to afford the title compound as a brown oil 3.92 g, 49%): MS: [(M+1)]⁺=138.10.

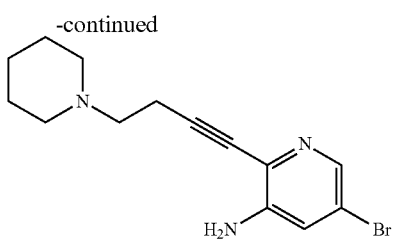

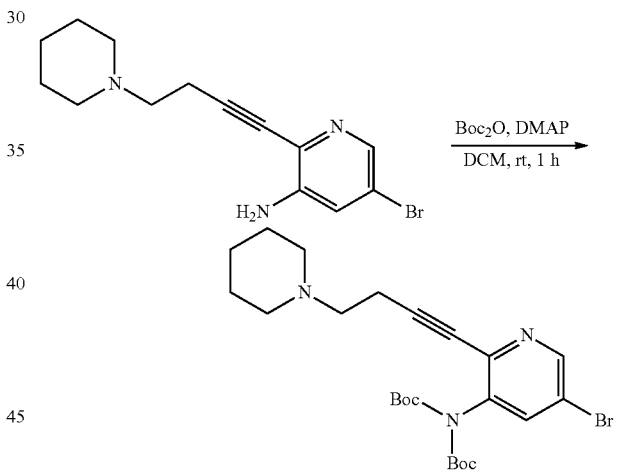

5-Bromo-2-(4-(piperidin-1-yl)but-1-yn-1-yl)pyridin-3-amine: To a stirred mixture of 1-(but-3-yn-1-yl)piperidine (1.09 g, 7.94 mmol) and 2,5-dibromopyridin-3-amine (2.00 g, 7.94 mmol) in N,N-dimethylformamide (40.0 mL) were added triethylamine (18.0 mL, 178 mmol), copper (I) iodide (76.0 mg, 0.40 mmol) and bis(triphenylphosphine)palladium(II) dichloride (279 mg, 0.40 mmol) at ambient temperature under nitrogen atmosphere. The resulting mixture was stirred for 16 hours at 25° C. The resulting mixture was concentrated under reduced pressure. The residue was purified by silica gel column chromatography, eluted with 2%~9% methanol in dichloromethane. The desired fractions were collected and concentrated under reduced pressure to afford the title compound as a brown solid (960 mg, 40%): ¹H NMR (400 MHz, CDCl₃) δ 7.95 (d, J=2.0 Hz, 1H), 7.14 (d, J=2.1 Hz, 1H), 4.61 (s, 2H), 2.81 (s, 4H), 2.64 (s, 4H), 1.71 (s, 4H), 1.43 (s, 2H); MS: [(M+1)]⁺=308.10, 310.10.

tert-Butyl N-[5-bromo-2-[4-(piperidin-1-yl)but-1-yn-1-yl]pyridin-3-yl]-N-[(tert-butoxy)carbonyl]carbamate A mixture of 5-bromo-2-[4-(piperidin-1-yl)but-1-yn-1-yl]pyridin-3-amine (900 mg, 2.92 mmol), 4-dimethylaminopyridine (179 mg, 1.46 mmol) and di-tert-butyl dicarbonate (6.37 g, 29.2 mmol) in dichloromethane (36.0 mL) was stirred for 1 hour at ambient temperature. The resulting mixture was concentrated under reduced pressure. The residue was purified by silica gel column chromatography, eluted with 2%~9% methanol in dichloromethane. The desired fractions were collected and concentrated under reduced pressure to afford the title compound as a light brown solid (1.05 g, 71%): ¹H NMR (400 MHz, CDCl₃) δ 8.54 (d, J=2.1 Hz, 1H), 7.64 (d, J=2.1 Hz, 1H), 2.67 (s, 4H), 2.45 (s, 4H), 1.57 (s, 6H), 1.41 (s, 18H); MS: [(M+1)]⁺=508.20, 510.20.

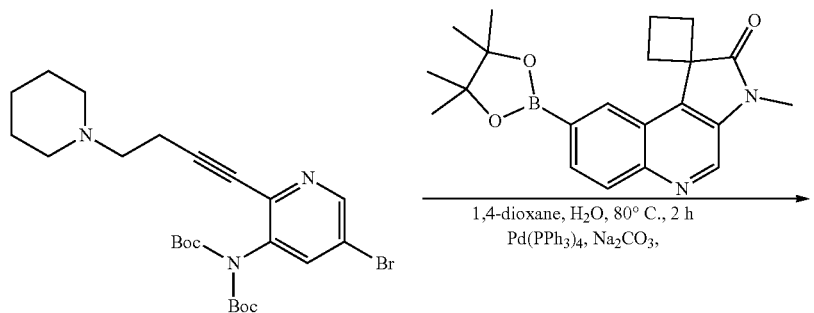

tert-Butyl N-[(tert-butoxy)carbonyl]-N-(5-{3'-methyl-2-oxo-2',3'-dihydrospiro[cyclobutane-1,1'-pyrrolo[2,3-c]quinoline]-8'-yl}-2-[4-(piperidin-1-yl)but-1-yn-1-yl]pyridin-3-yl)carbamate: To a solution of tert-butyl N-[5-bromo-2-[4-(piperidin-1-yl)but-1-yn-1-yl]pyridin-3-yl]-N-[(tert-butoxy)carbonyl]carbamate (200 mg, 0.39 mmol) and 3-methyl-8-(4,4,5,5-tetramethyl-1,3,2-dioxaborolan-2-yl)-2,3-dihydrospiro[cyclobutane-1,1-pyrrolo[2,3-c]quinolin]-2-one (215 mg, 0.59 mmol) in water (1.00 mL) and 1,4-dioxane (6.00 mL) were added sodium carbonate (84.0 mg, 0.79 mmol) and tetrakis(triphenylphosphine)palladium (0) (68.0 mg, 0.06 mmol). After stirring for 2 hours at 80° C. under nitrogen atmosphere, the resulting mixture was cooled down to ambient temperature. The resulting mixture was concentrated under reduced pressure. The residue was purified by silica gel column chromatography, eluted with 2%~9% methanol in dichloromethane. The desired fractions were collected and concentrated under reduced pressure to afford the title compound as a light brown solid (200 mg, 77%): $^1$H NMR (400 MHz, CD$_3$OD) δ 8.95 (d, J=2.1 Hz, 1H), 8.78 (s, 1H), 8.56 (d, J=2.0 Hz, 1H), 8.32 (d, J=2.1 Hz, 1H), 8.23 (d, J=8.9 Hz, 1H), 8.02 (dd, J=9.0, 2.0 Hz, 1H), 3.39 (s, 3H), 3.02 (q, J=9.9, 8.1 Hz, 2H), 2.83-2.48 (m, 12H), 1.66 (p, J=5.7 Hz, 4H), 1.55-1.48 (m, 2H), 1.44 (s, 18H); MS: [(M+1)]$^+$=666.40.

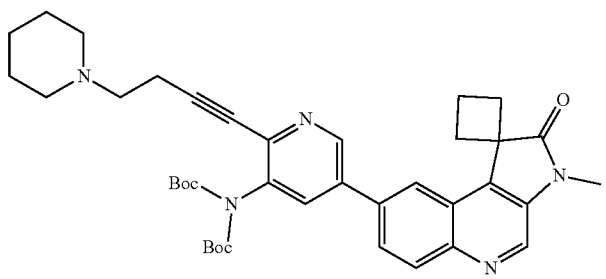

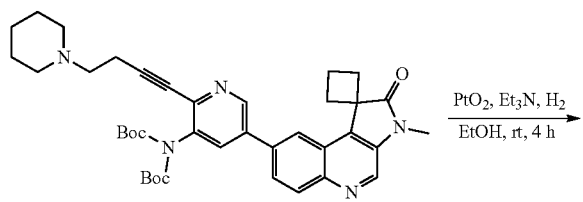

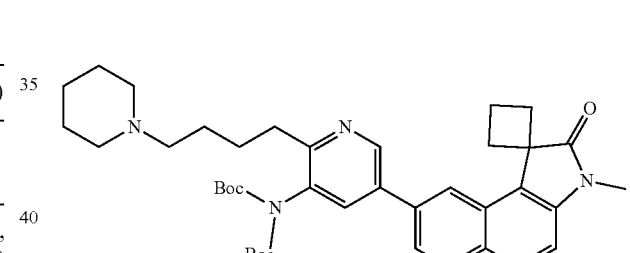

tert-Butyl N-[(tert-butoxy)carbonyl]-N-(5-(3'-methyl-2'-oxo-2',3'-dihydrospiro[cyclobutane-1,1'-pyrrolo[2,3-c]quinoline]-8'-yl)-2-[4-(piperidin-1-yl)butyl]pyridin-3-yl)carbamate: A mixture of tert-butyl N-[(tert-butoxy)carbonyl]-N-(5-[3-methyl-2-oxo-2,3-dihydrospiro[cyclobutane-1,1-pyrrolo[2,3-c]quinolin]-8-yl]-2-[4-(piperidin-1-yl)but-1-yn-1-yl]pyridin-3-yl)carbamate (50.0 mg, 0.08 mmol), triethylamine (0.10 mL) and platinum(IV) oxide (13.6 mg, 0.06 mmol) in ethanol (5.00 mL) was stirred for 4 hours at ambient temperature under hydrogen atmosphere. The resulting mixture was filtered and the filtered cake was washed with methanol (2×5.00 mL). The filtrate was concentrated under reduced pressure to give the crude product which was used in the next step directly without further purification; $^1$H NMR (400 MHz, CD$_3$OD) δ 8.96 (d, J=2.0 Hz, 1H), 8.78 (s, 1H), 8.54 (s, 1H), 8.23 (d, J=8.9 Hz, 1H), 8.18 (d, J=2.1 Hz, 1H), 8.01 (d, J=8.4 Hz, 1H), 3.39 (s, 3H), 3.12-2.92 (m, 6H), 2.83 (t, J=7.2 Hz, 2H), 2.77-2.50 (m, 4H), 1.91-1.75 (m, 8H), 1.64 (s, 2H), 1.47 (s, 18H); MS: [(M+1)]$^+$=670.40.

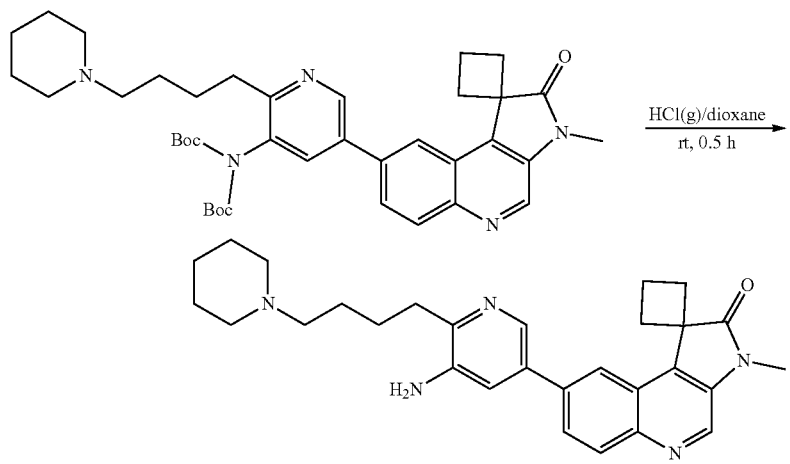

8'-(5-Amino-6-(4-(piperidin-1-yl)butyl)pyridin-3-yl)-3'-methylspiro[cyclobutan-1,1'-pyrrolo[2,3-c]quinolin]-2'(3'H)-one: tert-butyl N-[(tert-butoxy)carbonyl]-N-(5-[3-methyl-2-oxo-2,3-dihydrospiro[cyclobutane-1,1-pyrrolo[2,3-c]quinolin]-8-yl]-2-[4-(piperidin-1-yl)butyl]pyridin-3-yl) carbamate (150 mg, 0.22 mmol) was treated with hydrogen chloride (6.00 mL, 4 M in 1,4-dioxane) for 30 minutes at ambient temperature. The resulting mixture was concentrated under reduced pressure. The residue was purified by Prep-HPLC with the following conditions: [Column: Spherical C18, 20~40 μm, 120 g; Mobile Phase A: Water (plus 10 mM NH$_4$HCO$_3$ and 0.05% NH$_3$·H$_2$O); Mobile Phase B: acetonitrile; Flow rate: 45 mL/min; Gradient (B %): 5% 6 min; 5%~20%, 2 min; 20%~35%, 15 min 35%~95%; 2 min; 95%, 5 min Detector: UV 254 nm; Rt: 13.5 min]. The desired fractions were collected and concentrated under reduced pressure to afford the title compound as yellow solid (96.0 mg, 92%): MS: [(M+1)]$^+$=470.40.

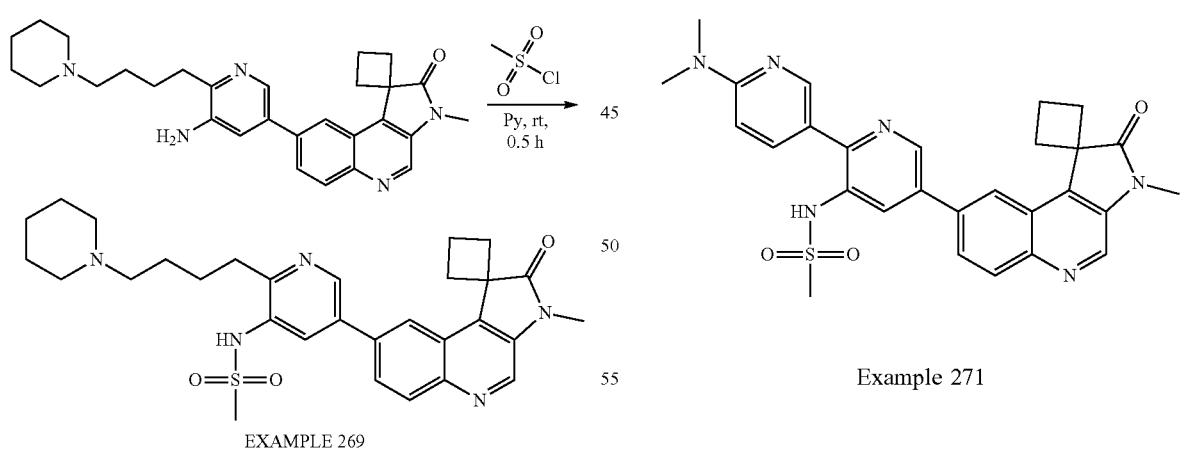

EXAMPLE 269

N-(5-(3'-Methyl-2'-oxo-2',3'-dihydrospiro[cyclobutane-1,1'-pyrrolo[2,3-c]quinolin]-8'-yl)-2-(4-(piperidin-1-yl)butyl)pyridin-3-yl)methanesulfonamide: A solution of 8'-(5-amino-6-(4-(piperidin-1-yl)butyl)pyridin-3-yl)-3'-methylspiro[cyclobutane-1,1'-pyrrolo[2,3-c]quinolin]-2'(3'H)-one (150 mg, 0.32 mmol) and methanesulfonyl chloride (73.0 mg, 0.64 mmol) in pyridine (6.00 mL) was stirred for 0.5 hours at ambient temperature. The resulting mixture was concentrated under reduced pressure. The residue was purified by Prep-HPLC with the following conditions: [Column: Spherical C18, 20~40 μm, 120 g; Mobile Phase A: Water (plus 10 mM NH$_4$HCO$_3$ and 0.05% NH$_3$·H$_2$O); Mobile Phase B: acetonitrile; Flow rate: 50 mL/min; Gradient (B %): 0%, 6 min; 0%~20%, 2 min; 20%~35%, 15 min; 35%~95%; 2 min 95%, 5 min Detector: UV 254 nm; Rt: 15.4 min]. The fractions containing desired product were collected and concentrated under reduced pressure to afford the title compound as light yellow solid (6.20 mg, 4%): $^1$H NMR (400 MHz, CD$_3$OD) δ 8.78 (d, J=2.0 Hz, 1H), 8.59 (d, J=2.0 Hz, 1H), 8.56 (d, J=1.9 Hz, 1H), 8.24-8.21 (m, 2H), 8.04 (d, J=9.1 Hz, 1H), 3.42 (s, 3H), 3.07-2.95 (m, 13H), 2.77-2.66 (m, 4H), 1.88 (t, J=7.3 Hz, 2H), 1.84-1.75 (m, 6H), 1.67-1.60 (m, 2H); MS: [(M+1)]$^+$=548.20.

Example 271

Example 271

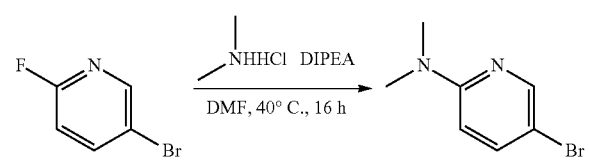

5-Bromo-N,N-dimethylpyridin-2-amine: A mixture of dimethylamine hydochloride (4.90 g, 60.1 mmol), 5-bromo- 2-fluoropyridine (7.00 g, 39.8 mmol) and diisopropylethylamine (12.3 g, 95.1 mmol,) in N,N-dimethylformamide (140 mL) was stirred for 16 hours at 40° C. The resulting mixture was diluted with water (500 mL) and extracted with ethyl acetate (3×150 mL). The combined organic layers was washed with brine (2×50.0 mL), dried over anhydrous sodium sulfate and filtered. The filtrate was concentrated under reduced pressure to afford the title compound as light yellow oil (7.60 g, 95%): $^1$H NMR (400 MHz, CDCl$_3$) δ 8.17 (d, J=2.5 Hz, 1H), 7.49 (dd, J=9.0, 2.5 Hz, 1H), 6.41 (d, J=9.0 Hz, 1H), 3.06 (s, 6H); MS: [(M+1)]$^+$=201.00, 203.00.

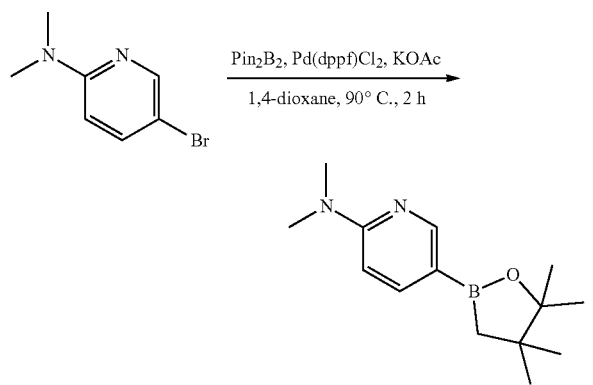

N,N-Dimethyl-5-(4,4,5,5-tetramethyl-1,3,2-dioxaborolan-2-yl)pyridin-2-amine: To a solution of 5-bromo-N,N-dimethylpyridin-2-amine (4.00 g, 19.9 mol) and 4,4,5,5-tetramethyl-2-(4,4,5,5-tetramethyl-1,3,2-dioxaborolan-2-yl)-1,3,2-dioxaborolane (10.1 g, 39.8 mmol) in 1,4-dioxane (200 mL) were added potassium acetate (7.81 g, 79.6 mmol) and 1,1'-bis(diphenylphosphino)ferrocene-paladium(II)dichloride dichloromethane complex (1.46 g, 1.99 mmol) at ambient temperature. The resulting mixture was stirred for 2 hours at 90° C. under nitrogen atmosphere. The resulting mixture was concentrated under reduced pressure. The residue was purified by silica gel column chromatography, eluted with 1%~8% methanol in dichloromethane. The desired fractions were collected and concentrated under reduced pressure to afford the title compound (crude) which was used directly in next step; MS: [(M+1)]$^+$=249.1

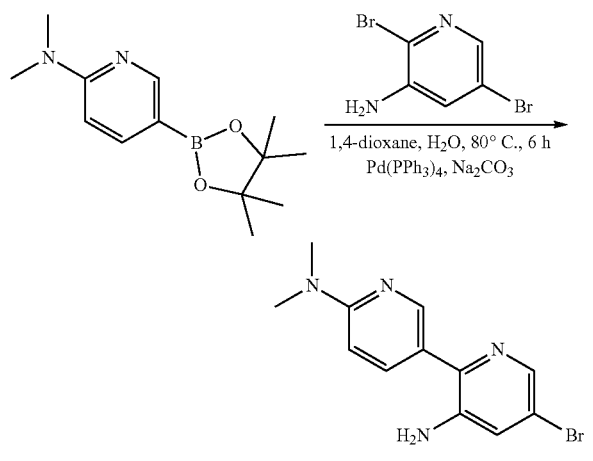

5-Bromo-N$^6$,N$^6$-dimethyl-[2,3-bipyridine]-3,6-diamine: To a solution of 2,5-dibromopyridin-3-amine (1.00 g, 3.97 mol) and N,N-dimethyl-5-(4,4,5,5-tetramethyl-1,3,2-dioxaborolan-2-yl)pyridin-2-amine (1.50 g, 6.03 mol) in water (1.00 mL) and 1,4-dioxane (5.00 mL) were added sodium carbonate (63.0 mg, 0.60 mmol) and tetrakis(triphenylphosphine) palladium (0) (46.0 mg, 0.04 mmol). The resulting mixture was stirred for 6 hours at 80° C. under nitrogen atmosphere. The resulting mixture was filtered and the filtered cake was washed with methanol (3×10.0 mL). The filtrate was concentrated under reduced pressure. The residue was purified by Prep-HPLC with the following conditions: [Column: Spherical C18, 20~40 μm, 120 g; Mobile Phase A: Water (plus 10 mM NH$_4$HCO$_3$ and 0.05% NH$_3$·H$_2$O); Mobile Phase B: acetonitrile; Flow rate: 45 mL/min; Gradient (B %): 5%, 5 min; 5%~22%, 2 min 22~4%, 20 min; 40%~95%; 2 min; 95%, 5 min; Detector: UV 254 nm; Rt: 14.7 min] to afford the title compound as light brown solid (150 mg, 13%): MS: [(M+1)]$^+$=293.00, 295.00.

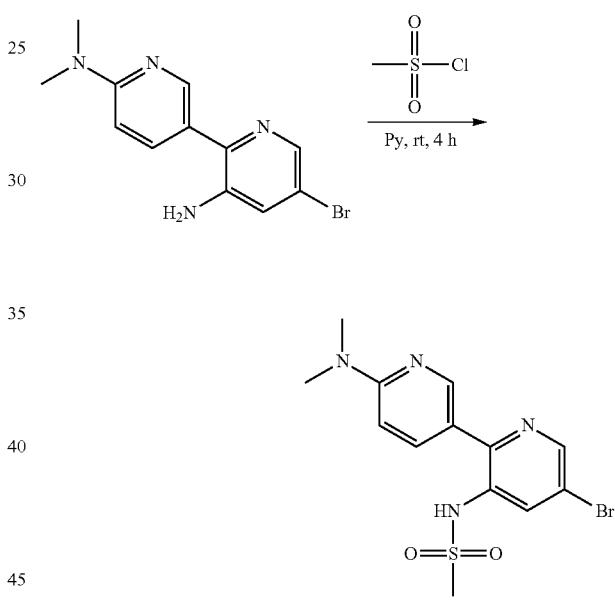

N-[5-Bromo-6-(dimethylamino)-[2,3-bipyridin]-3-yl]methanesulfonamide: A solution of 5-bromo-N$^6$,N$^6$-dimethyl-[2,3-bipyridine]-3,6-diamine (120 mg, 0.41 mmol) and methanesulfonyl chloride (93.8 mg, 0.82 mmol) in pyridine (6.00 mL) was stirred for 4 hours at ambient temperature. The resulting mixture was concentrated under reduced pressure. The residue was purified by Prep-HPLC with the following conditions: [Column: Spherical C18, 20~40 μm, 120 g; Mobile Phase A: Water (plus 10 mM NH$_4$HCO$_3$ and 0.05% NH$_3$·H$_2$O); Mobile Phase B: acetonitrile; Flow rate: 45 mL/min; Gradient (B %): 5% 22%, 6 min; 22%~40%, 20 min; 40%~95%; 2 min; 95%, 5 min; Detector: 254 nm; Rt: 12.5 min]. The desired fractions were collected and concentrated under reduced pressure to afford the title compound as a colorless solid (40.0 mg, 27%): $^1$H NMR (400 MHz, CD$_3$OD) δ 8.80 (d, J=2.1 Hz, 1H), 8.44 (d, J=2.5 Hz, 1H), 8.32-8.27 (m, 1H), 7.90 (dd, J=9.2, 2.5 Hz, 1H), 6.79 (d, J=8.9 Hz, 1H), 3.22 (s, 6H), 3.14 (s, 3H); MS: [(M+1)]$^+$=371.00, 373.00.

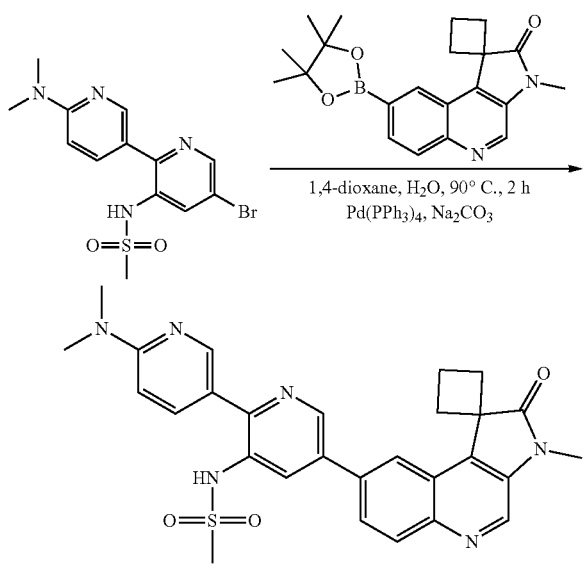

EXAMPLE 271

N-(6'-(Dimethylamino)-5-(3'-methyl-2'-oxo-2',3'-dihydrospiro[cyclobutane-1,1'-pyrrolo[2,3-c]quinolin]-8'-yl)-[2,3'-bipyridin]-3-yl)methanesulfonamide (EXAMPLE 271). To a solution of 3-methyl-8-(4,4,5,5-tetramethyl-1,3,2-dioxaborolan-2-yl)-2,3-dihydrospiro[cyclobutane-1,1'-pyrrolo[2,3-c]quinolin]-2-one (58.9 mg, 0.16 mmol) in 1,4-dioxane (2.00 mL) were added N-[5-bromo-6-(dimethylamino)-[2,3-bipyridin]-3-yl]methanesulfonamide (40.0 mg, 0.11 mmol), water (0.40 mL), sodium carbonate (17.1 mg, 0.16 mmol) and tetrakis (triphenylphosphine) palladium (0) (12.5 mg, 0.01 mmol). The resulting mixture was stirred for 2 hours at 90° C. under nitrogen atmosphere. The resulting mixture was concentrated under reduced pressure. The residue was purified by reversed phase flash chromatography with the following conditions: [Column: Spherical C18, 20~40 µm, 120 g; Mobile Phase A: Water (plus 10 mM $NH_4HCO_3$ and 0.05% $NH_3 \cdot H_2O$); Mobile Phase B: acetonitrile; Flow rate: 45 mL/min; Gradient (B %): 5%, 6 min; 5% 25%, 2 min; 25%~40%, 15 min; 40%~95%; 2 min; 95%, 5 min; Detector UV 254 nm; Rt: 14.4 min]. The fractions containing desired product was collected and concentrated under reduced pressure to afford the title compound as a yellow solid (37.4 mg, 66%): $^1$H NMR (400 MHz, DMSO-$d_6$) δ 9.58 (br, 1H), 9.02 (s, 1H), 8.88 (s, 1H), 8.70 (d, J=2.0 Hz, 1H), 8.51 (d, J=2.0 Hz, 1H), 8.23-8.21 (m, 2H), 8.09-8.06 (m, 2H), 6.77 (d, J=8.8 Hz, 1H), 3.33 (s, 3H), 3.12 (s, 6H), 3.07 (s, 3H), 3.03-2.99 (m, 2H), 2.59-2.40 (m, 4H); MS: $[(M+1)]^+=529.15$ Example 276 and 285

EXAMPLE 276

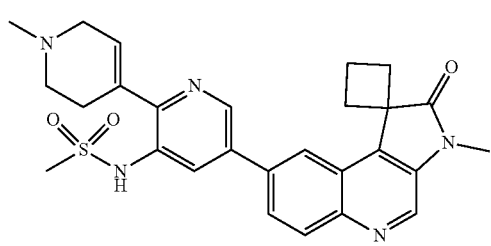

EXAMPLE 285

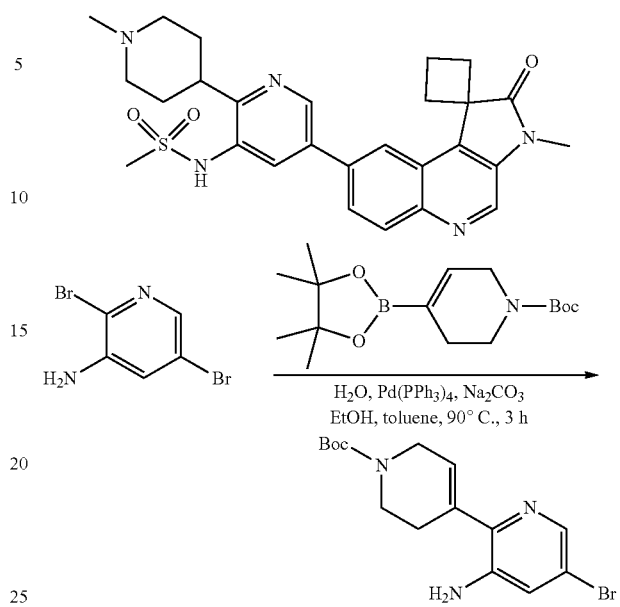

tert-Butyl 3-amino-5-bromo-3',6'-dihydro-[2,4'-bipyridine]-1'(2'H)-carboxylate: To a solution of 2,5-dibromopyridin-3-amine (2.00 g, 7.94 mmol) and tert-butyl 4-(4,4,5,5-tetramethyl-1,3,2-dioxaborolan-2-yl)-1,2,3,6-tetrahydropyridine-1-carboxylate (2.90 g, 9.38 mmol) in toluene (20.0 mL), ethanol (6.00 mL) and water (1.20 mL) were added sodium carbonate (3.40 g, 32.1 mmol) and tetrakis(triphenylphosphine)palladium (0) (900 mg, 0.78 mmol). After stirring for 3 hours at 90° C. under nitrogen atmosphere, the resulting mixture was concentrated under reduced pressure. The residue was purified by silica gel column chromatography, eluted with 5%~50% ethyl acetate in petroleum ether. The desired fractions were collected and concentrated under reduced pressure to afford the title compound as a yellow oil (1.60 g, 57%): $^1$H NMR (400 MHz, $CDCl_3$) δ 8.09 (s, 1H), 7.26 (s, 1H), 6.12 (s, 1H), 4.16-4.08 (m, 2H), 3.69 (t, J=5.6 Hz, 2H), 2.59 (s, 2H), 1.49 (s, 9H); MS: $[(M+1)]^+=354.00, 356.00$.

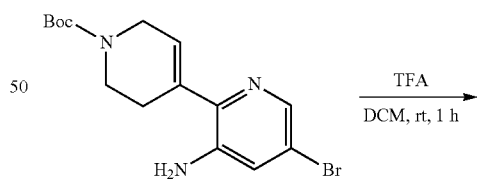

5-Bromo-1',2',3',6'-tetrahydro-[2,4'-bipyridin]-3-amine: To a solution of tert-butyl 3-amino-5-bromo-3',6'-dihydro-[2,4'-bipyridine]-1'(2'H)-carboxylate (1.60 g, 4.52 mmol) in dichloromethane (45.0 mL) was added trifluoroacetic acid (9.00 mL) at ambient temperature. The mixture was stirred at ambient temperature for 1 hour. The mixture was concentrated under reduced pressure. The residue was purified by reversed phase flash chromatography with the following conditions: [Column: Spherical C18, 20~40 μm, 330 g; Mobile Phase A: Water (plus 10 mM NH₄HCO₃ and 0.05% NH₃·H₂O); Mobile Phase B: acetonitrile; Flow rate: 65 mL/min; Gradient (B %): 5%~25%, 4 min; 25%~35%, 10 min; 35%~95%, 3 min; 95%, 5 min; Detector: UV 254 nm; Rt: 14 min] to afford the title compound as a light yellow solid (600 mg, 53%): $^1$H NMR (400 MHz, CD₃OD) δ 7.80 (d, J=2.0 Hz, 1H), 7.27 (d, J=2.0 Hz, 1H), 6.02-5.98 (m, 1H), 3.44 (q, J=3.0 Hz, 2H), 3.06 (t, J=5.8 Hz, 2H), 2.41-2.35 (m, 2H); MS: $[(M+1)]^+$=254.0, 256.0.

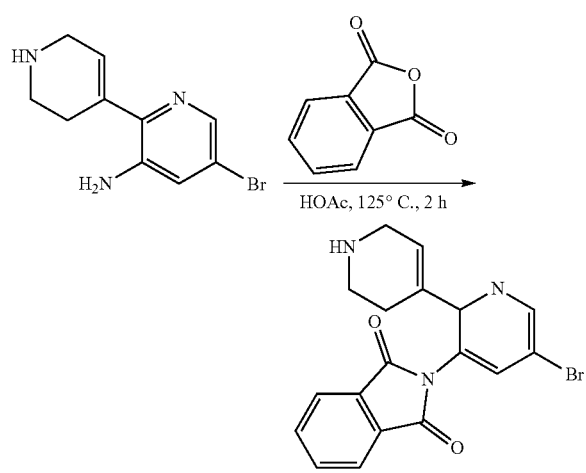

2-(5-Bromo-1',2',3',6'-tetrahydro-[2,4'-bipyridin]-3-yl)isoindoline-1,3-dione: A solution of 5-bromo-1',2',3',6'-tetrahydro-[2,4'-bipyridin]-3-amine (500 mg, 1.97 mmol) and 1,3-dihydro-2-benzofuran-1,3-dione (379 mg, 2.56 mmol) in acetic acid (20.0 mL) was stirred for 2 hours at 125° C. The resulting mixture was concentrated under reduced pressure. The residue was basified to pH=8 with saturated aqueous sodium bicarbonate (20.0 mL). The resulting mixture was extracted with ethyl acetate (6×50.0 mL). The combined organic layers was washed with brine (50.0 mL) and dried over anhydrous sodium sulfate. After filtration, the filtrate was concentrated under reduced pressure. The residue was purified by silica gel column chromatography, eluted with 2%~6% methanol in dichloromethane. The desired fractions were collected and concentrated under reduced pressure to afford the title compound as an off-white solid (300 mg, 40%): $^1$H NMR (400 MHz, CD₃OD) δ 8.73 (s, 1H), 8.09 (s, 1H), 7.97 (d, J=3.8 Hz, 2H), 7.90 (dd, J=5.5, 3.2 Hz, 2H), 5.72 (s, 1H), 3.15 (s, 2H), 2.97-2.90 (m, 2H), 2.48 (s, 2H); MS: $[(M+1)]^+$=384.00, 386.00.

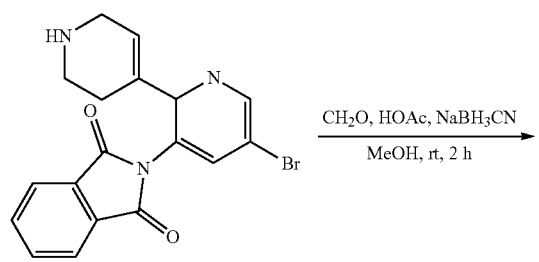

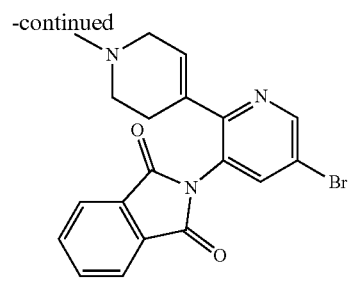

2-(5-Bromo-1'-methyl-1',2',3',6'-tetrahydro-[2,4'-bipyridin]-3-yl)isoindoline-1,3-dione: To solution of 2-(5-bromo-1',2',3',6'-tetrahydro-[2,4'-bipyridin]-3-yl)isoindoline-1,3-dione (400 mg, 1.04 mmol), acetic acid (0.10 mL) and formalin (101 mg, 1.25 mmol, 37% w/w) in methanol (15.0 mL) was added sodium cyanoborohydride (131 mg, 2.08 mmol) at 0° C. The resulting mixture was stirred for 2 hours at 25° C. The resulting mixture was concentrated under reduced pressure. The residue was purified by silica gel column chromatography, eluted with 3%~10% ethyl acetate in petroleum ether. The desired fractions were collected and concentrated under reduced pressure to afford the title compound as a yellow solid (300 mg, 73%): $^1$H NMR (400 MHz, DMSO-d₆) δ 8.87 (d, J=2.2 Hz, 1H), 8.36 (d, J=2.2 Hz, 1H), 8.05-8.00 (m, 2H), 8.00-7.95 (m, 2H), 5.80 (s, 1H), 2.86-2.57 (m, 9H); MS: $[(M+1)]^+$=398.00, 400.00.

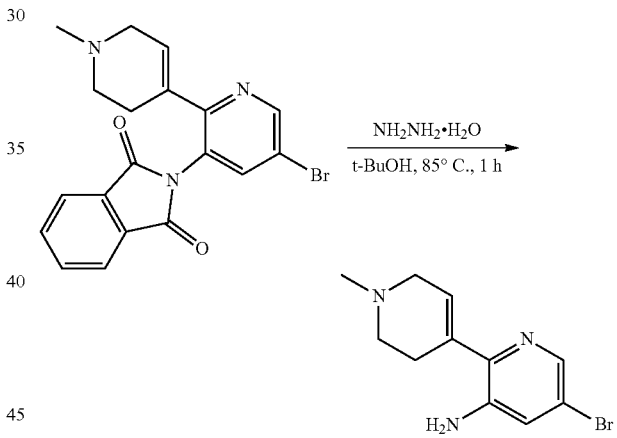

5-Bromo-1'-methyl-1',2',3',6'-tetrahydro-[2,4'-bipyridin]-3-amine: A solution of 2-[5-bromo-1-methyl-1,2,3,6-tetrahydro-[2,4-bipyridin]-3-yl]-2,3-dihydro-1H-isoindole-1,3-dione (300 mg, 0.75 mmol) in hydrazine hydrate (6.00 mL, 85% in water) and tert-butanol (6.00 mL) was stirred for 1 hour at 85° C. The resulting mixture was concentrated under reduced pressure. The residue was purified by reversed phase flash chromatography with the following conditions: [Column: Spherical C18, 20~40 μm, 330 g; Mobile Phase A: Water (plus 10 mM NH₄HCO₃ and 0.05% NH₃·H₂O); Mobile Phase B: acetonitrile; Flow rate: 65 mL/min; Gradient (B %): 5%~28%, 4 min; 28%~38%, 8 min; 38%~95%, 2 min; 95%, 5 min; Detector: UV 254 nm; Rt: 17 min]. The desired fractions were collected and concentrated under reduced pressure to afford the title compound as a light yellow solid (120 mg, 60%): $^1$H NMR (400 MHz, DMSO-d₆) δ 7.80 (d, J=2.0 Hz, 1H), 7.22 (d, J=1.9 Hz, 1H), 6.03 (s, 1H), 5.36 (s, 2H), 3.00 (d, J=3.2 Hz, 2H), 2.54 (t, J=5.7 Hz, 2H), 2.44 (s, 2H), 2.27 (s, 3H); MS: $[(M+1)]^+$=268.00, 270.00.

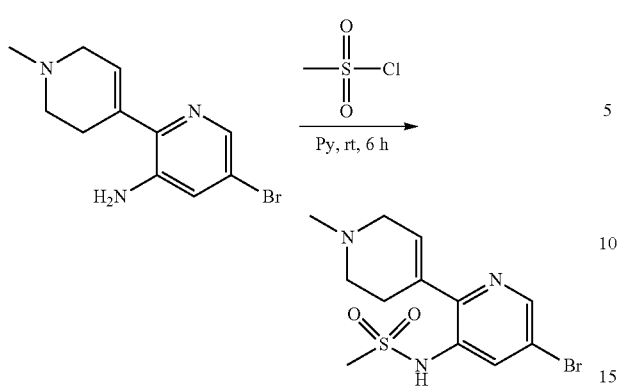

N-(5-Bromo-1'-methyl-1',2',3',6'-tetrahydro-[2,4'-bipyridin]-3-yl)methanesulfonamide: To a stirred solution of 5-bromo-1'-methyl-1',2',3',6'-tetrahydro-[2,4'-bipyridin]-3-amine (100 mg, 0.37 mmol) in pyridine (20.0 mL) was added methanesulfonyl chloride (64.1 mg, 0.56 mmol) dropwise at ambient temperature. The resulting mixture was stirred under nitrogen atmosphere at 25° C. for 6 hours. The resulting mixture was concentrated under reduced pressure. The residue was purified by reversed phase flash chromatography with the following conditions: [Column: Spherical C18, 20~40 μm, 120 g; Mobile Phase A: Water (plus 10 mM $NH_4HCO_3$ and 0.05% $NH_3 \cdot H_2O$); Mobile Phase B: acetonitrile; Flow rate: 45 mL/min; Gradient (B %): 5%~20%, 5 min; 20%~58%, 5 min; 58%~95%, 2 min; 95%, 5 min; Detector 254 nm; Rt: 13 min]. The desired fractions were collected and concentrated under reduced pressure to afford the title compound as a yellow solid (80.0 mg, 62%): $^1$H NMR (400 MHz, DMSO-$d_6$) δ 8.14 (d, J=3.9 Hz, 1H), 7.84 (s, 1H), 6.69 (s, 1H), 3.56 (s, 2H), 3.09 (s, 2H), 2.88 (s, 3H), 2.70 (s, 2H), 2.66 (s, 3H); MS: $[(M+1)]^+$=346.00, 348.00.

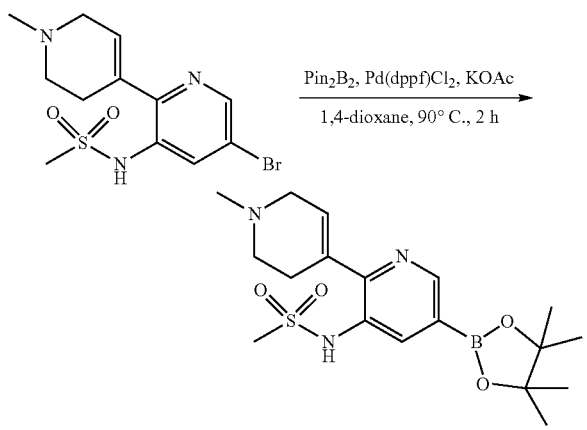

N-(1'-Methyl-5-(4,4,5,5-tetramethyl-1,3,2-dioxaborolan-2-yl)-1',2',3',6'-tetrahydro-[2,4'-bipyridin]-3-yl)methanesulfonamide: To a solution of N-(5-bromo-1'-methyl-1',2', 3',6'-tetrahydro-[2,4'-bipyridin]-3-yl)methanesulfonamide (200 mg, 0.58 mmol) and 4,4,5,5-tetramethyl-2-(4,4,5,5-tetramethyl-1,3,2-dioxaborolan-2-yl)-1,3,2-dioxaborolane (440 mg, 1.73 mmol) in 1,4-dioxane (15.0 mL) were added potassium acetate (227 mg, 2.31 mmol) and 1,1'-bis(diphenylphosphino)ferrocene-palladium(II)dichloride dichloromethane complex (94.3 mg, 0.12 mmol) at ambient temperature. The resulting mixture was stirred for 2 hours at 90° C. under nitrogen atmosphere. The resulting mixture was used for the next step without further purification. MS: $[(M+1)]^+$=394.20

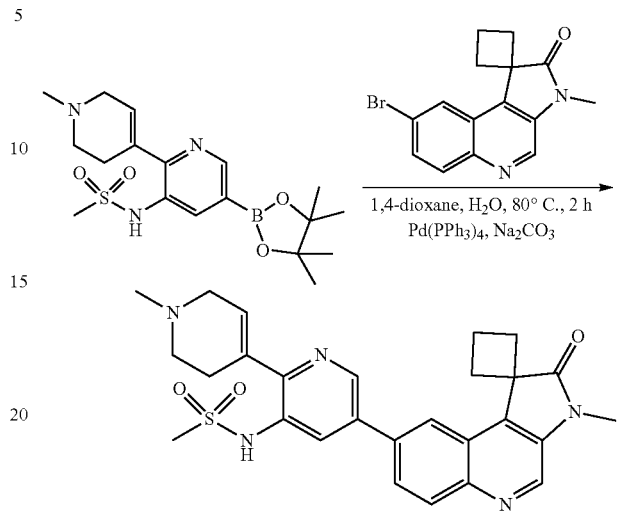

EXAMPLE 276

N-(1'-Methyl-5-(3'-methyl-2-oxo-2',3'-dihydrospiro[cyclobutane-1,1'-pyrrolo[2,3-c]quinolin]-8'-yl)-1',2',3',6'-tetrahydro-[2,4'-bipyridin]-3-yl)methanesulfonamide: To a solution of N-(1'-methyl-5-(4,4,5,5-tetramethyl-1,3,2-dioxaborolan-2-yl)-1',2',3',6'-tetrahydro-[2,4'-bipyridin]-3-yl)methanesulfonamide (57.0 mg, 0.14 mmol) and 8-bromo-3-methyl-2,3-dihydrospiro[cyclobutane-1,1-pyrrolo[2,3-c]quinolin]-2-one (36.8 mg, 0.12 mmol) in 1,4-dioxane (7.00 mL) and water (0.70 mL) were added sodium carbonate (18.4 mg, 0.17 mmol) and tetrakis(triphenylphosphine)-palladium (0) (34.0 mg, 0.03 mmol). After stirring for 2 hours at 80° C. under nitrogen atmosphere, the resulting mixture was concentrated under reduced pressure. The residue was purified by reversed phase flash chromatography with the following conditions: [Column: Spherical C18, 20~40 μm, 120 g; Mobile Phase A: Water (plus 10 mM $NH_4HCO_3$ and 0.05% $NH_3 \cdot H_2O$); Mobile Phase B: acetonitrile; Flow rate: 45 mL/min; Gradient (B %): 5%~24%, 4 min; 24%~35%, 10 min; 35%, 3 min; 35%~95%, 4 min; 95%, 5 min; Detector UV 254 nm; Rt: 18 min]. The desired fractions were collected and concentrated under reduced pressure to afford the title compound as an orange solid (12.2 mg, 17%): $^1$H NMR (400 MHz, DMSO-$d_6$) δ 9.38 (s, 1H), 8.86 (s, 1H), 8.81 (s, 1H), 8.45 (s, 1H), 8.18 (d, J=8.9 Hz, 1H), 8.08 (s, 1H), 8.00 (d, J=9.0 Hz, 1H), 3.33-3.24 (m, 1H), 3.03 (s, 3H), 3.02-2.89 (m, 4H), 2.68-2.55 (m, 2H), 2.51 (s, 3H), 2.30 (s, 3H), 2.16 (t, J=11.9 Hz, 2H), 1.91 (q, J=12.4 Hz, 2H), 1.74 (d, J=12.9 Hz, 2H); MS: $[(M+1)]^+$=504.30

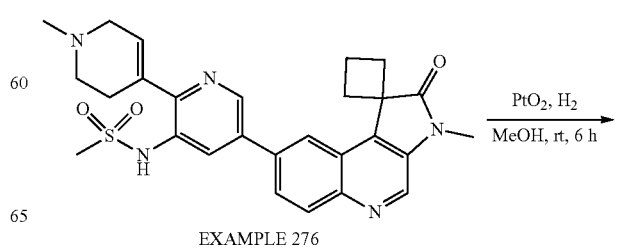

EXAMPLE 276

EXAMPLE 285

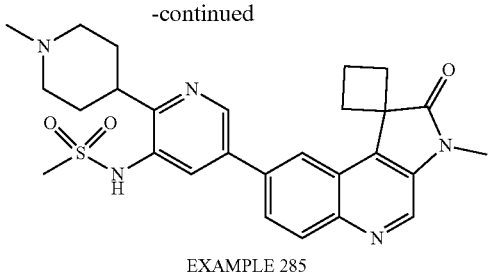

N-(5-(3'-Methyl-2'-oxo-2',3'-dihydrospiro[cyclobutane-1,1'-pyrrolo[2,3-c]quinolin]-8'-yl)-2-(1-methylpiperidin-4-yl)pyridin-3-yl)methanesulfonamide: To a stirred solution of N-(1'-methyl-5-(3'-methyl-2'-oxo-2',3'-dihydrospiro[cyclobutane-1,1'-pyrrolo[2,3-c]quinolin]-8'-yl)-1',2',3',6'-tetrahydro-[2,4'-bipyridin]-3-yl)methanesulfonamide (100 mg, 0.20 mmol) in methanol (5.00 mL) was added anhydrous platinum (IV) oxide (22.5 mg, 0.10 mmol) at ambient temperature under nitrogen atmosphere. The resulting mixture was stirred for 6 hours at ambient temperature under hydrogen atmosphere. The resulting mixture was filtered and the filtered cake was washed with methanol (3×20.0 mL). The filtrate was concentrated under reduced pressure. The residue was purified by reversed phase flash chromatography with the following conditions: [Column Spherical C18, 20~40 μm, 120 g; Mobile Phase A: Water (plus 10 mM NH₄HCO₃ and 0.05% NH₃·H₂O); Mobile Phase B: acetonitrile; Flow rate: 45 mL/min; Gradient (B %): 5%~24%, 5 min; 24%~30%, 5 min 30%~95%, 2 min; 95%, 5 min; Detector UV 254 nm; Rt: 15 min]. The desired fractions were collected and concentrated under reduced pressure to afford the title compound as an orange solid (54.6 mg, 55%): $^1$H NMR (400 MHz, DMSO-d₆) δ 9.39 (s, 1H), 8.86 (s, 1H), 8.82 (s, 1H), 8.45 (s, 1H), 8.18 (d, J=8.8 Hz, 1H), 8.08 (d, J=2.4 Hz, 1H), 8.00 (d, J=9.0 Hz, 1H), 3.03 (s, 3H), 2.95 (t, J=10.3 Hz, 4H), 2.59-2.51 (m, 5H), 2.55 (s, 3H), 2.30 (s, 3H), 2.16 (t, J=11.8 Hz, 2H), 1.98-1.84 (m, 2H), 1.78-1.66 (m, 2H); MS: [(M+1)]⁺=506.25

Synthesis of Example 376 and 377

EXAMPLE 376

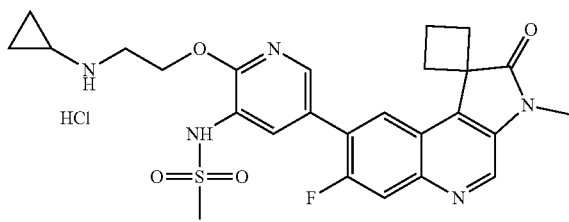

EXAMPLE 377

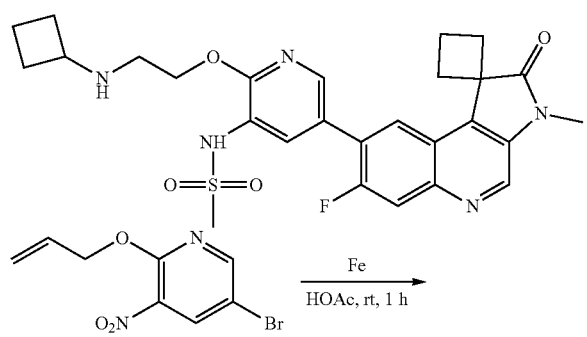

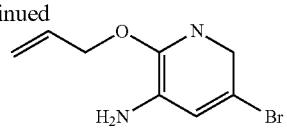

5-Bromo-2-(prop-2-en-1-yloxy)pyridin-3-amine: To a solution of 5-bromo-3-nitro-2-(prop-2-en-1-yloxy)pyridine (2.00 g, 7.72 mmol) in acetic acid (30.0 mL) was added iron powder (4.30 g, 77.2 mmol) at ambient temperature. The resulting mixture was stirred for 1 hour at ambient temperature. The resulting mixture was filtered and the filtered cake was washed with tetrahydrofuran (4×50.0 mL). The filtrate was concentrated under reduced pressure. The residue was purified by silica gel column chromatography, eluted with 20%, ethyl acetate in petroleum ether. The desired fractions were collected and concentrated under reduced pressure to afford the title compound as a colorless solid (1.56 g, 89%): $^1$H NMR (400 MHz, DMSO-d₆) δ 7.38 (d, J=2.0 Hz, 1H), 7.02 (d, J=2.0 Hz, 1H), 6.13-5.99 (m, 1H), 5.41 (dt, J=17.3, 1.8 Hz, 1H), 5.31 (s, 2H), 5.22 (dt, J=10.4, 1.7 Hz, 1H), 4.79 (dt, J=4.9, 1.7 Hz, 2H); MS: [(M+1)]⁺=229.10, 231.10.

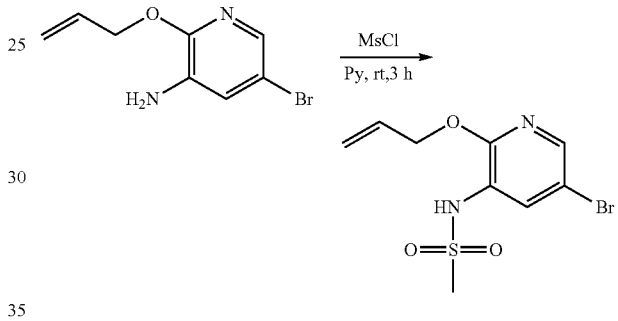

N-[5-Bromo-2-(prop-2-en-1-yloxy)pyridin-3-yl]methanesulfonamide: To a solution of 5-bromo-2-(prop-2-en-1-yloxy)pyridin-3-amine (1.00 g, 4.37 mmol) in pyridine (30.0 mL) was added methanesulfonyl chloride (700 mg, 6.11 mmol). The resulting mixture was stirred for 3 hours at ambient temperature. The resulting mixture was concentrated under reduced pressure. The residue was purified by silica gel column chromatography, eluted with 1%~25% ethyl acetate in petroleum ether. The desired fractions were collected and concentrated under reduced pressure to afford the title compound as a colorless solid (1.18 g, 88%): $^1$H NMR (400 MHz, DMSO-d₆) δ 9.50 (s, 1H), 8.09 (d, J=2.3 Hz, 1H), 7.80 (d, J=2.3 Hz, 1H), 6.14-6.03 (m, 1H), 5.44 (dq, J=17.3, 1.7 Hz, 1H), 5.26 (dq, J=10.5, 1.5 Hz, 1H), 4.86 (dt, J=5.3, 1.6 Hz, 2H), 3.10 (s, 3H); MS: [(M+1)]⁺=307.00, 309.00.

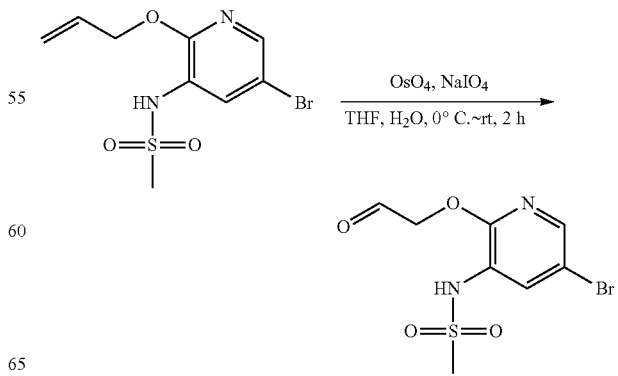

N-[5-Bromo-2-(2-oxoethoxy)pyridin-3-yl]methanesulfonamide: To a stirred mixture of 5-bromo-2-(prop-2-en-1-yloxy)pyridin-3-amine (1.00 g, 4.36 mmol) and sodium periodate (1.07 g, 8.73 mmol) in tetrahydrofuran (10.0 mL) and water (10.0 mL) was added osmium (VIII) oxide (1.70 mL, 0.065 mmol, 1.00 g in 100 mL water) at 0° C. The resulting mixture was stirred for 2 hours at ambient temperature. The reaction was quenched by saturated aqueous sodium thiosulfate solution (10.0 mL). The resulting mixture was extracted with dichloromethane (3×30.0 mL). The combined organic layers was washed with brine (2×30.0 mL) and dried over anhydrous sodium sulfate. After filtration, the filtrate was concentrated under reduced pressure. The residue was purified by silica gel column chromatography, eluted with 50% ethyl acetate in petroleum ether within 10 min quickly. The desired fractions were collected and concentrated under reduced pressure to afford the title compound (700 mg, crude) as a light yellow oil which was used for the next step without further purification: MS: $[(M+1)]^+$ =309.00, 311.00.

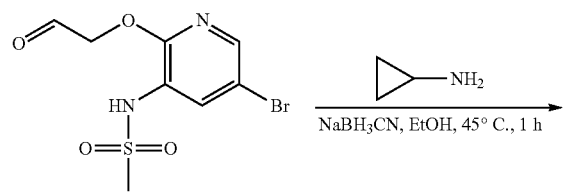

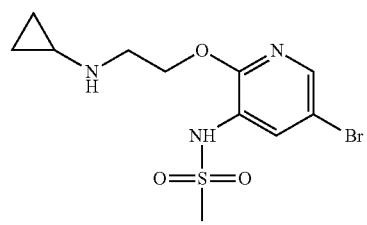

N-(5-Bromo-2-(2-(cyclopropylamino)ethoxy)pyridin-3-yl)methanesulfonamide: To a stirred solution of N-(5-bromo-2-(2-oxoethoxy)pyridin-3-yl)methanesulfonamide (700 mg, crude) and cyclopropanamine (370 mg, 6.47 mmol) in ethanol (20.0 mL) was added sodium cyanoborohydride (204 mg, 3.24 mmol) at ambient temperature. The resulting mixture was stirred for 1 hour at 45° C. The resulting mixture was concentrated under reduced pressure. The residue was purified by silica gel column chromatography, eluted with 2%~6% methanol in dichloromethane. The desired fractions were collected and concentrated under reduced pressure to afford the title compound as an off-white solid (300 mg, 53%): $^1$H NMR (400 MHz, CDCl$_3$) δ 7.95 (d, J=2.2 Hz, 1H), 7.93 (d, J=2.2 Hz, 1H), 4.51 (t, J=5.2 Hz, 2H), 3.49 (s, 1H), 3.16 (t, J=5.2 Hz, 2H), 3.07 (s, 3H), 2.25-2.20 (m, 1H), 0.60-0.51 (m, 2H), 0.49-0.47 (m, J=9.1, 5.0 Hz, 2H); MS: $[(M+1)]^+$=350.1, 352.1.

The following intermediate was prepared according to the procedure described above:

| Structure | Name | MS: $[(M + 1)]^+$ | $^1$H NMR |
|---|---|---|---|
| 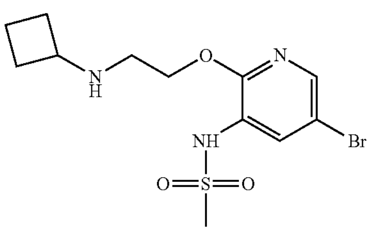 [SMILES: CS(=O)(=O)Nc1cc(Br)cnc1OCCNC1CCC1] | N-(5-Bromo-2-(2-(cyclobutylamino)ethoxy)pyridin-3-yl)methanesulfonamide | 364.10 366.10 | $^1$H NMR (400 MHz, CD$_3$OD) δ 8.11 (d, J = 2.3 Hz, 1H), 8.01 (d, J = 2.3 Hz, 1H), 3.93 (p, J = 8.2 Hz, 1H), 3.54 (t, J = 5.3 Hz, 2H), 3.14-3.07 (m, 5H), 2.10 (s, 2H), 1.89 (p, J = 9.6 Hz, 2H), 1.73-1.63 (m, 2H). |

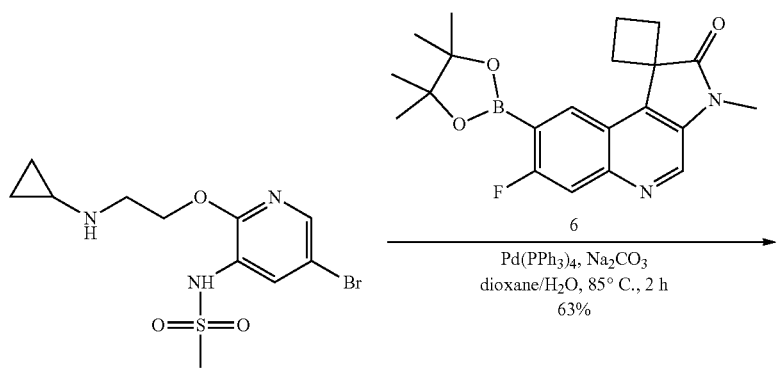

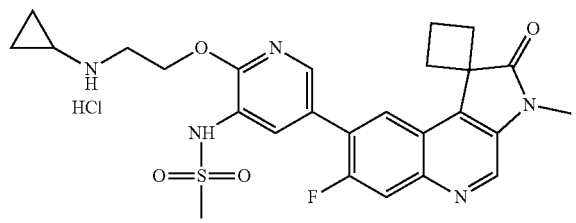

EXAMPLE 376

N-(2-(2-(Cyclopropylamino)ethoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride: To a solution of N-[5-bromo-2-[2-(cyclopropylamino)ethoxy]pyridin-3-yl]methanesulfonamide (85.0 mg, 0.24 mmol) in 1,4-dioxane (7.00 mL) were added water (1.00 mL), 7-fluoro-3-methyl-8-(4,4,5,5-tetramethyl-1,3,2-dioxaborolan-2-yl)-2,3-dihydrospiro[cyclobutane-1,1-pyrrolo[2,3-c]quinolin]-2-one (130 mg, 0.34 mmol), sodium carbonate (38.6 mg, 0.36 mmol) and tetrakis(triphenylphosphine)palladium (0) (Pd(PPh$_3$)$_4$, 42.1 mg, 0.036 mmol). After stirring for 2 hours at 85° C. under nitrogen atmosphere, the resulting mixture was concentrated under reduced pressure. The residue was purified by Prep-TLC (DCM/MeOH=15/1, v/v) to afford the title compound as a yellow solid (80.0 mg, 63%): MS: [(M+1)]$^+$=526.3. A solution of N-[2-[2-(cyclopropylamino)ethoxy]-5-[7-fluoro-3-methyl-2-oxo-2,3-dihydrospiro[cyclobutane-1,1-pyrrolo[2,3-c]quinolin]-8-yl]pyridin-3-yl]methanesulfonamide (80.0 mg, 0.15 mmol) in diluted aqueous HCl (25.3 mL, 0.12 mmol, 0.0046 M) and acetonitrile (3.00 mL) was lyophilized directly to afford the title compound as a light yellow solid (82.4 mg, %%): $^1$H NMR (400 MHz, CD$_3$OD) δ 8.80 (s, 1H), 8.43 (d, J=8.0 Hz, 1H), 8.36 (d, J=2.1 Hz, 1H), 8.25 (d, J=1.8 Hz, 1H), 7.88 (d, J=11.9 Hz, 1H), 4.79 (t, J=5.1 Hz, 2H), 3.69 (t, J=5.1 Hz, 2H), 3.38 (s, 3H), 3.15 (s, 3H), 3.00-2.89 (m, 3H), 2.75-2.66 (m, 2H), 2.66-2.52 (m, 2H), 1.04-0.95 (m, 4H); MS: [(M+1)]$^+$=526.3.

The following compound was prepared according to the procedure described above:

| Example | Structure | Name | MS: [(M + 1)]$^+$ | $^1$H NMR |
|---|---|---|---|---|
| 377 | 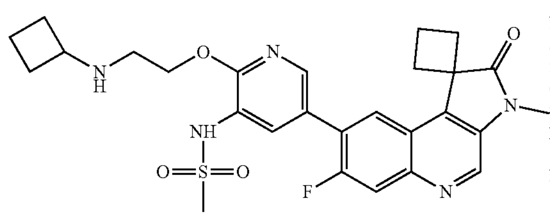 [SMILES: CN1C(=O)C2(CCC2)c2c1cnc1cc(F)c(-c3cnc(OCCNC4CCC4)c(NS(C)(=O)=O)c3)cc21] | N-(2-(2-(Cyclobutylamino)ethoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide | 540.25 | $^1$H NMR (400 MHz, DMSO-d$_6$) δ 8.89 (s, 1H), 8.48 (s, 1H), 8.35 (d, J = 8.3 Hz, 1H), 8.08 (s, 1H), 7.99 (d, J = 12.3 Hz, 1H), 4.18 (p, J = 8.0 Hz, 1H), 3.50 (t, 5.6 Hz, 2H), 3.16 (s, 3H), 3.31 (s, 3H), 3.30-3.26 (m, 1H), 2.98-2.88 (m, 2H), 2.21-2.11 (m, 3H), 2.02-1.91 (m, 2H), 2.60-2.51 (m, 3H), 2.49-2.41 (m, 1H), 1.69-1.60 (m, 2H). |

Synthesis of Example 559

EXAMPLE 559

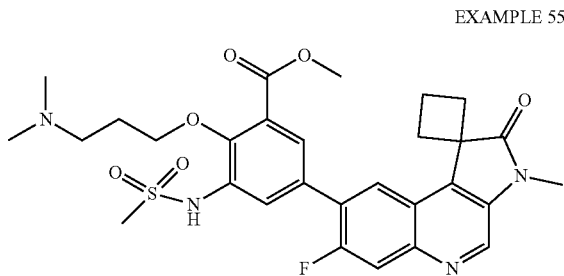

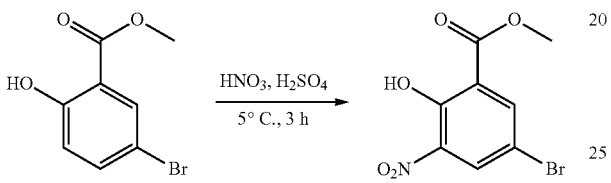

Methyl 5-bromo-2-hydroxy-3-nitrobenzoate: To a mixture of methyl 5-bromo-2-hydroxybenzoate (3.00 g, 13.0 mmol) in concentrated sulfuric acid (6.40 mL) was added a mixture of concentrated nitric acid (1.39 g, 65%) and concentrated sulfuric acid (2.00 mL) dropwise with stirring below 5° C. The resulting mixture was stirred for 3 hours at 5° C. The reaction mixture was poured into ice/water (200 mL). The precipitated solid was collected by filtration, washed with cold water (3×10.0 mL) and dried in vacuum to give the title compound as an off-white solid (2.20 g, 62%): $^1$H NMR (400 MHz, CDCl$_3$) δ 11.88 (s, 1H), 8.28 (d, J=2.5 Hz, 1H), 8.24 (d, J=2.6 Hz, 1H), 4.03 (s, 3H); MS: [(M+1)]$^+$=276.10, 278.10.

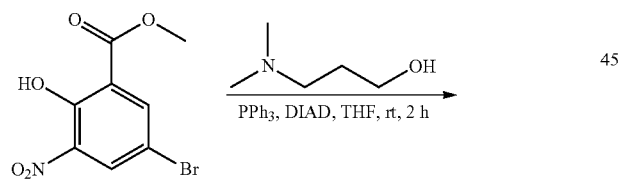

Methyl 5-bromo-2-(3-(dimethylamino)propoxy)-3-nitrobenzoate: To a solution of methyl 5-bromo-2-hydroxy-3-nitrobenzoate (2.20 g, 7.97 mmol), 3-(dimethylamino)propan-1-ol (1.00 g, 9.56 mmol) and triphenylphosphine (2.52 g, 9.56 mmol) in anhydrous tetrahydrofuran (90.0 mL) was added diisopropyl azodicarboxylate (1.93 g, 9.56 mmol) dropwise at 0° C. After stirring for 2 hours at 25° C. the reaction was quenched by water (1.00 mL). The resulting mixture was concentrated under reduced pressure. The residue was purified by silica gel column chromatography, eluted with 1%~10% methanol in dichloromethane. The desired fractions were collected and concentrated under reduced pressure to afford the title compound as a yellow solid (1.86 g, 65%): $^1$H NMR (400 MHz, CDCl$_3$) δ 8.12 (d, J=2.6 Hz, 1H), 8.01 (d, J=2.6 Hz, 1H), 4.14 (t, J=6.5 Hz, 2H), 3.95 (d, J=2.3 Hz, 4H), 2.43 (t, J=7.3 Hz, 2H), 2.24 (s, 7H), 1.97 (p, J=6.7 Hz, 2H); MS: [(M+1)]$^+$=361.00, 363.00.

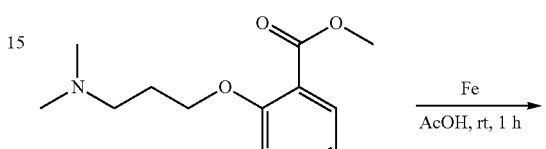

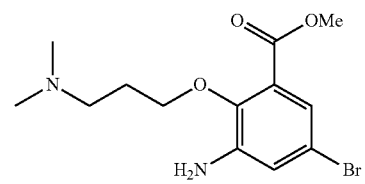

Methyl 3-amino-5-bromo-2-(3-(dimethylamino)propoxy) benzoate: To a solution of methyl 5-bromo-2-(3-(dimethylamino)propoxy)-3-nitrobenzoate (1.20 g, 3.32 mmol) in acetic acid (20.0 mL) was added iron powder (1.50 g, 26.9 mmol) at ambient temperature. After stirring for 1 hour at 25° C., the resulting mixture was filtered and the filtered cake was washed with tetrahydrofuran (4×50.0 mL). The filtrate was concentrated under reduced pressure. The residue was purified by silica gel column chromatography, eluted with 1%~10% methanol in dichloromethane. The desired fractions were collected and concentrated under reduced pressure to afford the title compound as a yellow solid (1.00 g, 91%): $^1$H NMR (400 MHz, CDCl$_3$) δ 7.21 (d, J=2.4 Hz, 1H), 6.95 (d, J=2.4 Hz, 1H), 4.84 (br, 2H), 3.98 (t, J=5.8 Hz, 2H), 3.87 (s, 3H), 2.56 (t, J=6.7 Hz, 2H), 2.27 (s, 6H), 1.96 (p, J=6.0 Hz, 2H); MS: [(M+1)]$^+$=331.10, 333.10.

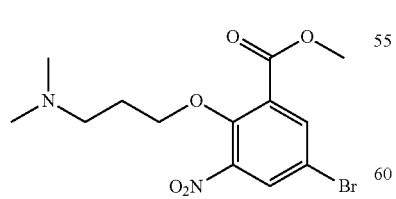

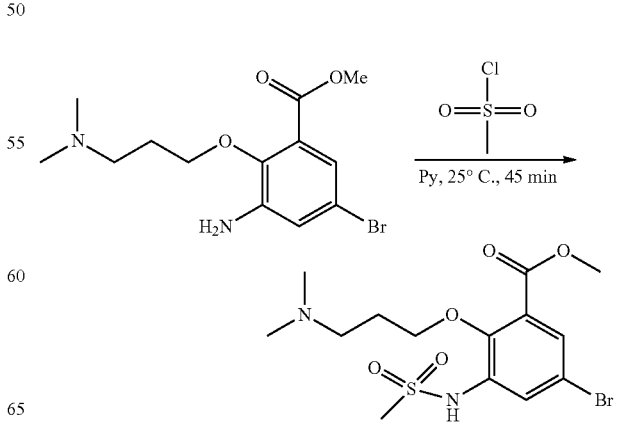

Methyl 5-bromo-2-(3-(dimethylamino)propoxy)-3-(methylsulfonamido)benzoate: To solution of methyl 3-amino-5-bromo-2-(3-(dimethylamino)propoxy)benzoate (950 mg, 2.89 mmol) in pyridine (25.0 mL) were added methanesulfonyl chloride (493 mg, 4.30 mmol) and 4-dimethylaminopyridine (35.0 mg, 0.29 mmol) at ambient temperature. The resulting mixture was stirred under nitrogen atmosphere at 25° C. for 45 minutes. The resulting mixture was concentrated under reduced pressure. The residue was purified by reversed phase flash chromatography with the following conditions: [Column: Spherical C18, 20~40 μm, 120 g; Mobile Phase A: Water (plus 10 mM $NH_4HCO_3$); Mobile Phase B: acetonitrile; Flow rate: 45 mL/min; Gradient (B %): 5%~25%, 5 min; 25%~45%, 25 min; 45~65%, 10 min; 65%~95%; 3 min; 95%, 5 min; Detector: UV 254 nm; Rt: 18 min]. The desired fractions were collected and concentrated under reduced pressure to afford the title compound as a brown solid (400 mg, 35%): $^1$H NMR (400 MHz, $CDCl_3$) δ 7.92 (d, J=1.9 Hz, 1H), 7.50 (d, J=2.0 Hz, 1H), 4.08 (t, J=5.6 Hz, 2H), 3.88 (s, 3H), 2.98 (s, 3H), 2.87 (s, 2H), 2.60 (s, 6H), 2.06 (p, J=6.2 Hz, 2H); MS: $[(M+1)]^+$=409.00, 411.00.

lan-2-yl)-1,3,2-dioxaborolane (497 mg, 1.96 mmol) in 1,4-dioxane (18.0 mL) were added potassium acetate (3.85 g, 3.91 mmol) and 1,1'-bis(diphenylphosphino)ferrocene-palladium(II)dichloride dichloromethane complex (160 mg, 0.20 mmol) at ambient temperature. The resulting mixture was stirred for 2 hours at 90° C. under nitrogen atmosphere. After cooling down to ambient temperature, 8-bromo-3-methyl-2,3-dihydrospiro[cyclobutane-1,1-pyrrolo[2,3-c]quinolin]-2-one (279 mg, 0.88 mmol), water (3.00 mL), sodium carbonate (124 mg, 1.17 mmol) and tetrakis(triphenylphosphine)palladium (136 mg, 0.12 mmol) were added. After stirring for 2 hours at 80° C. under nitrogen atmosphere, the resulting mixture was concentrated under reduced pressure. The residue was purified by reversed phase flash chromatography with the following conditions: [Column: Spherical C18, 20~40 μm, 120 g; Mobile Phase A: Water (plus 10 mM $NH_4HCO_3$); Mobile Phase B: acetonitrile; Flow rate: 45 mL/min; Gradient (B %): 5%~20%, 5 min; 20%~40%, 25 min; 40%~65%, 10 min; 65%~95%; 3 min; 95%, 5 min; Detector: UV 254 nm; Rt: 22 min]. The desired fractions were collected and concentrated under reduced pressure to afford the title compound as a colorless

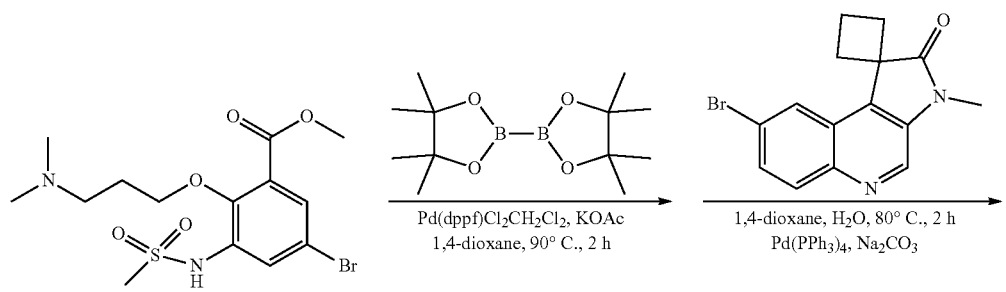

Pd(dppf)Cl₂CH₂Cl₂, KOAc
1,4-dioxane, 90° C., 2 h 1,4-dioxane, H₂O, 80° C., 2 h
Pd(PPh₃)₄, Na₂CO₃

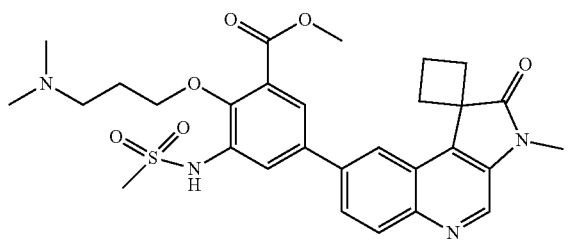

EXAMPLE 559

Methyl 2-(3-(dimethylamino)propoxy)-5-(3'-methyl-2'-oxo-2',3'-dihydrospiro[cyclobutane-1,1'-pyrrolo[2,3-c]quinolin]-8'-yl)-3-(methylsulfonamido)benzoate: To a solution of methyl methyl 5-bromo-2-(3-(dimethylamino)propoxy)-3-(methylsulfonamido)benzoate (400 mg, 0.98 mmol) and 4,4,5,5-tetramethyl-2-(4,4,5,5-tetramethyl-1,3,2-dioxaborosolid (300 mg, 55%): $^1$H NMR (400 MHz, DMSO-$d_6$) δ 8.83 (s, 1H), 8.42 (s, 1H), 8.19 (d, J=2.2 Hz, 1H), 8.15 (d, J=9.0 Hz, 1H), 7.94 (d, J=8.6 Hz, 1H), 7.49 (s, 1H), 4.07 (t, J=5.8 Hz, 2H), 3.86 (s, 3H), 3.31 (s, 3H), 3.13-3.04 (m, 2H), 2.93 (s, 3H), 2.91-2.83 (m, 2H), 2.74 (s, 6H), 2.63-2.54 (m, 4H), 2.10-2.02 (m, 2H); MS: $[(M+1)]^+$=567.25.

Synthesis of Example 399

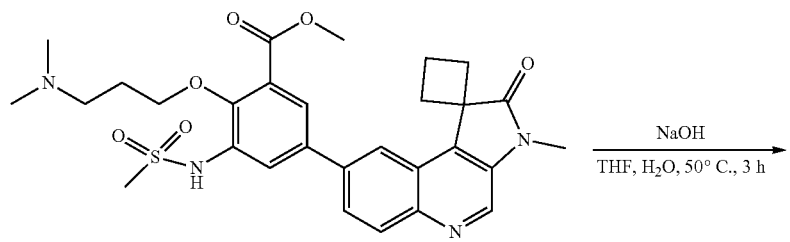

EXAMPLE 559

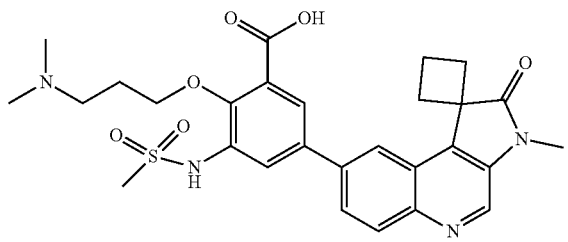

EXAMPLE 399

2-(3-(Dimethylamino)propoxy)-5-(3'-methyl-2'-oxo-2', 3'-dihydrospiro[cyclobutane-1,1'-pyrrolo[2,3-c]quinolin]-8'-yl)-3-(methylsulfonamido)benzoic acid: To a stirred solution of methyl 2-(3-(dimethylamino)propoxy)-5-(3'-methyl-2'-oxo-2',3'-dihydrospiro[cyclobutane-1,1'-pyrrolo[2,3-c]quinolin]-8'-yl)-3-(methylsulfonamido)benzoate (460 mg, 0.81 mmol) in tetrahydrofuran (16.0 mL) were added sodium hydroxide (195 mg, 4.87 mmol) and water (4.00 mL) at ambient temperature. The resulting mixture was stirred under nitrogen atmosphere at 50° C. for 3 hours. The resulting mixture was neutralized with acetic acid (1.00 mL). The resulting mixture was concentrated under reduced pressure. The residue was purified by reversed phase flash chromatography with the following conditions: [Column: Spherical C18, 20~40 μm, 330 g; Mobile Phase A: Water (plus 10 mM $NH_4HCO_3$); Mobile Phase B: acetonitrile; Flow rate: 45 mL/min; Gradient (B %): 5%~25%, 5 min; 25%~45%, 25 min; 45~65%, 10 min; 65%~95%; 3 min; 95%~, 5 min; Detector UV 254 nm; Rt: 20 min]. The desired fractions were collected and concentrated under reduced pressure to afford the title compound as a colorless solid (320 mg, 72%): $^1$H NMR (400 MHz, DMSO-$d_6$) δ 8.84 (s, 1H), 8.41 (s, 1H), 8.17 (d, J=8.8 Hz, 1H), 7.99 (d, J=2.3 Hz, 1H), 7.94 (d, J=9.0 Hz, 1H), 7.81 (d, J=2.3 Hz, 1H), 4.07 (t, J=5.7 Hz, 2H), 3.31 (s, 3H), 3.18 (t, J=5.6 Hz, 2H), 3.08 (s, 3H), 2.88 (q, J=9.7, 8.9 Hz, 2H), 2.80 (s, 6H), 2.65-2.52 (m, 4H), 2.20-2.12 (m, 2H); MS: $[(M+1)]^+$=553.30.

Synthesis of Example 449

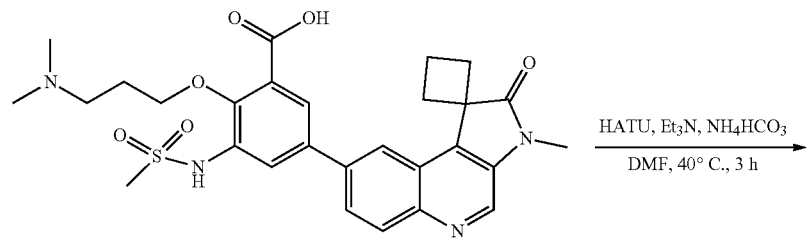

EXAMPLE 399

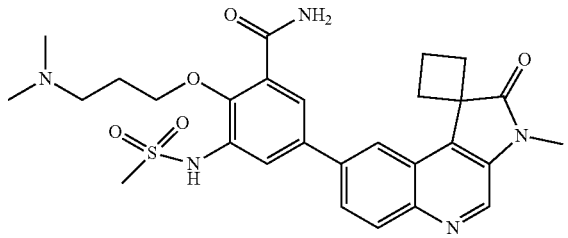

EXAMPLE 449

2-(3-(Dimethylamino)propoxy)-5-(3'-methyl-2'-oxo-2', 3'-dihydrospiro[cyclobutane-1,1'-pyrrolo[2,3-c]quinolin]-8'-yl)-3-(methylsulfonamido)benzamide: To a stirred solution of 2-[3-(dimethylamino)propoxyl]-3-methanesulfonamido-5-[3-methyl-2-oxo-2,3-dihydrospiro[cyclobutane-1,1-pyrrolo[2,3-c]quinolin]-8-yl]benzoic acid (40.0 mg, 0.07 mmol) and triethylamine (14.6 mg, 0.14 mmol) in N,N-dimethylformamide (3.00 mL) was added 0-(7-azabenzotriazol-1-yl)-N,N,N',N'-tetramethyluronium hexafluorophosphate (41.3 mg, 0.11 mmol) at ambient temperature under nitrogen atmosphere. The resulting mixture was stirred for 0.5 hour at ambient temperature under nitrogen atmosphere followed by the addition of ammonium bicarbonate (28.6 mg, 0.36 mmol).

After stirring for additional 3 hours at 40° C. the resulting mixture was purified by reversed phase flash chromatography with the following conditions: [Column: Spherical C18, 20~40 μm, 120 g; Mobile Phase A: Water (plus 10 mM NH₄HCO₃); Mobile Phase B: acetonitrile; Flow rate: 45 mL/min; Gradient (B %): 5%~22%, 4 min; 22%~40%, 20 min; 40%~95%; 2 min; 95%, 5 min; Detector UV 254 nm; Rt: 15 min]. The desired fractions were collected and concentrated under reduced pressure to afford the title compound as a colorless solid (21.2 mg, 54%): $^1$H NMR (400 MHz, DMSO-$d_6$) δ 8.83 (s, 1H), 8.42 (s, 1H), 8.16 (d, J=8.9 Hz, 1H), 8.09 (s, 1H), 7.95 (d, J=9.0 Hz, 1H), 7.81 (s, 1H), 7.49 (d, J=2.2 Hz, 2H), 4.04 (t, J=5.6 Hz, 2H), 3.31 (s, 3H), 3.04-2.98 (m, 2H), 2.% (s, 3H), 2.87 (q, J=9.6 Hz, 2H), 2.66 (s, 6H), 2.64-2.52 (m, 4H), 2.68-2.01 (m, 2H); MS: [(M+1)]⁺=552.30.

The following examples were prepared according to the procedure described above:

| Example | Structure | Name | MS: [(M + 1)]⁺ | $^1$H NMR |
|---|---|---|---|---|
| 564 | 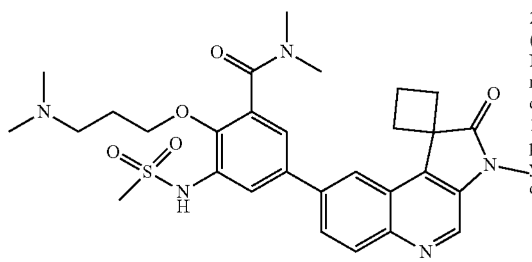 | 2-(3-(Dimethylamino)propoxy)-N,N-dimethyl-5-(3'-methyl-2'-oxo-2',3'-dihydrospiro[cyclobutane-1,1'-pyrrolo[2,3-c]quinolin]-8'-yl)-3-(methylsulfonamido)benzamide | 580.30 | $^1$H NMR (400 MHz, DMSO-$d_6$) δ 8.83 (s, 1H), 8.43-8.38 (m, 1H), 8.14 (d, J = 8.8 Hz, 1H), 8.01 (s, 1H), 7.94 (d, J = 9.0 Hz, 1H), 7.14 (s, 1H), 3.98 (t, J = 5.6 Hz, 2H), 3.32 (s, 3H), 3.04 (s, 3H), 2.99-2.85 (m, 10H), 2.66-2.54 (m, 10 H), 2.02-1.90 (m, 2H). |
| 565 | 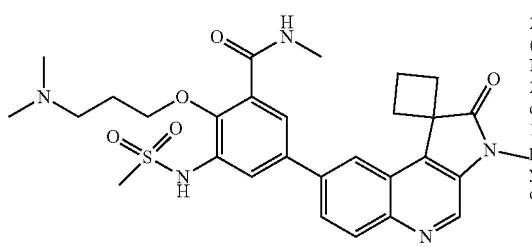 | 2-(3-(Dimethylamino)propoxy)-N-methyl-5-(3'-methyl-2'-oxo-2',3'-dihydrospiro[cyclobutane-1,1'-pyrrolo[2,3-c]quinolin]-8'-yl)-3-(methylsulfonamido)benzamide | 566.35 | $^1$H NMR (400 MHz, DMSO-$d_6$) δ 8.83 (s, 1H), 8.42 (s, 1H), 8.25 (d, J = 5.1 Hz, 1H), 8.15 (d, J = 9.0 Hz, 1H), 8.09 (s, 1H), 7.95 (d, J = 9.1 Hz, 1H), 7.42 (s, 1H), 4.02 (t, J = 5.9 Hz, 2H), 3.31 (s, 3H), 3.01-2.94 (m, 5H), 2.92-2.83 (m, 2H), 2.82 (d, J = 4.6 Hz, 3H), 2.65 (s, 6H), 2.62-2.54 (m, 4H), 2.07-1.99 (m, 2H). |

Synthesis of Example 563

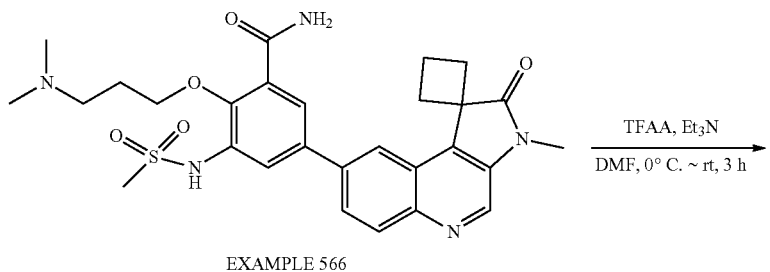

EXAMPLE 566

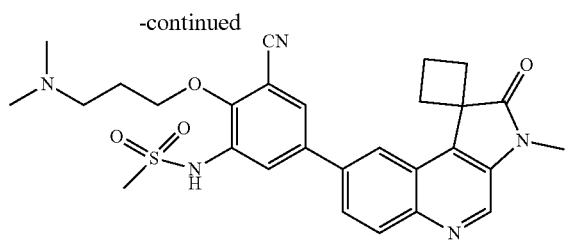

EXAMPLE 563

N-(3-Cyano-2-(3-(dimethylamino)propoxy)-5-(3'-methyl-2'-oxo-2',3'-dihydrospiro[cyclobutane-1,1'-pyrrolo[2,3-c]quinolin]-8'-yl)phenyl)methanesulfonamide: To a stirred solution of 2-(3-(dimethylamino)propoxy)-5-(3'-methyl-2'-oxo-2',3'-dihydrospiro[cyclobutane-1,1'-pyrrolo[2,3-c]quinolin]-8'-yl)-3-(methylsulfonamido)benzamide (40.0 mg, 0.07 mmol) and triethylamine (33.0 mg, 0.33 mmol) in dichloromethane (2.00 mL) was added trifluoroacetic anhydride (30.5 mg, 0.15 mmol) at 0° C. under nitrogen atmosphere. After stirring for 3 hours at 25° C., the resulting mixture was concentrated under reduced pressure. The residue was purified by reversed phase flash chromatography with the following conditions: [Column: Spherical C18, 20~40 μm, 120 g; Mobile Phase A: Water (plus 10 mM NH$_4$HCO$_3$ and 0.05% NH$_3$·H$_2$O); Mobile Phase B: acetonitrile; Flow rate: 45 mL/min; Gradient (B %): 5%~30%, 6 min; 30%~50%, 25 min; 50%~95%; 2 min; 95%, 5 min; Detector: UV 254 nm: Rt: 15 min]. The desired fractions were collected and concentrated under reduced pressure to afford the title compound as a colorless solid (35.2 mg, 91%): $^1$H NMR (400 MHz, DMSO-d$_6$) δ 8.85 (s, 1H), 8.41 (s, 1H), 8.24 (s, 1H), 8.15 (d, J=8.9 Hz, 1H), 7.96 (d, J=9.1 Hz, 1H), 7.55 (s, 1H), 4.16 (t, J=5.8 Hz, 2H), 3.31 (s, 3H), 3.27 (t, J=6.8 Hz, 2H), 2.94-2.86 (m, 5H), 2.86 (s, 6H), 2.62-2.53 (m, 4H), 2.21-2.13 (m, 2H); MS: [(M+1)]$^+$=534.35.

Synthesis of Example 295 and 2%

EXAMPLE 295

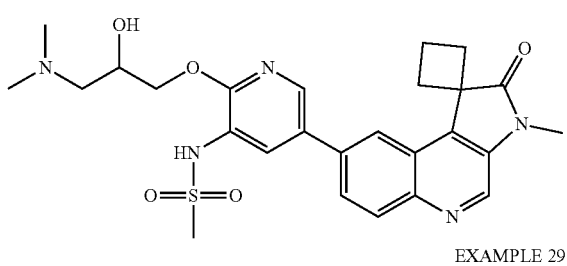

EXAMPLE 296

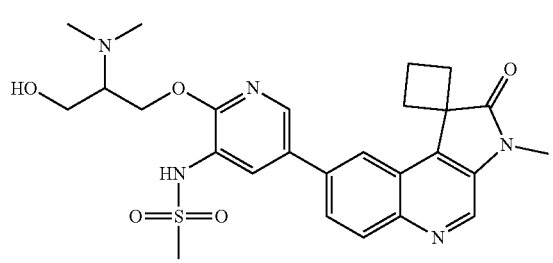

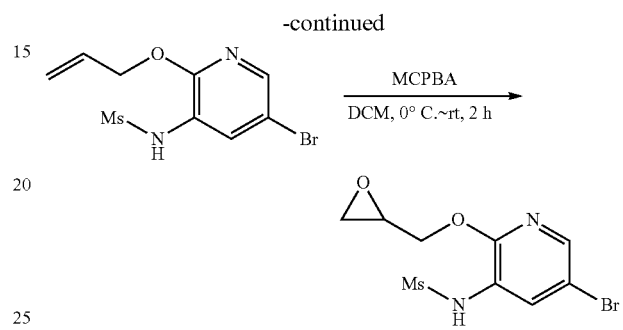

N-(5-Bromo-2-(oxiran-2-ylmethoxy)pyridin-3-yl)methanesulfonamide: To a stirred solution of N-[5-bromo-2-(prop-2-en-1-yloxy)pyridin-3-yl]methanesulfonamide (500 mg, 1.63 mmol) in dichloromethane (15.0 mL) was added meta chloroperbenzoic acid (562 mg, 3.26 mmol,) in portions at 0° C. After stirring for 2 hours at 25° C., the resulting mixture was concentrated under reduced pressure. The residue was purified by reversed phase flash chromatography with the following conditions: [Column: Spherical C18, 20~40 μm; 330 g; Mobile Phase A: Water (plus 10 mM NH$_4$HCO$_3$); Mobile Phase B: acetonitrile; Flow rate: 65 mL/min; Gradient (B %): 5%~23%, 6 min; 23%~43%, 15 min; 43%~95%; 2 min; 95%, 5 min; Detector. UV 254 nm; Rt: 15 min]. The desired fractions were collected and concentrated under reduced pressure to afford the title compound as a colorless solid (500 mg, 96%): $^1$H NMR (400 MHz, DMSO-d$_6$) δ 8.09 (d, J=2.3 Hz, 1H), 7.80 (d, J=2.3 Hz, 1H), 4.64 (dd, J=12.1, 2.7 Hz, 1H), 4.13 (dd, J=12.2, 6.4 Hz, 1H), 3.40-3.35 (m, 1H), 3.12 (s, 3H), 2.85-2.81 (m, 1H), 2.78 (dd, J=5.1, 2.7 Hz, 1H); MS: [(M+1)]$^+$=322.95, 324.95.

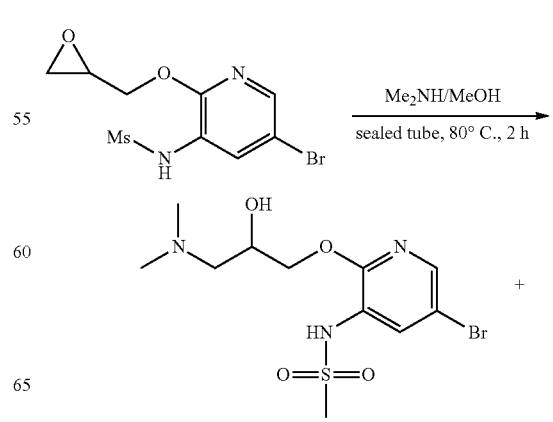

-continued

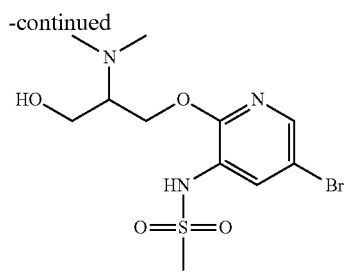

N-(5-Bromo-2-(3-(dimethylamino)-2-hydroxypropoxy)pyridin-3-yl)methanesulfonamide: A mixture of N-(5-bromo-2-(oxiran-2-ylmethoxy)pyridin-3-yl)methanesulfonamide (300 mg, 0.93 mmol) and dimethylamine (4 M in methanol (12 mL) was stirred for 2 hours at 80° C. in a sealed tube. After cooling down to ambient temperature, the resulting mixture was concentrated under reduced pressure to give a mixture of the two intermediate: MS: [(M+1)]$^+$=368.05, 370.05.

5%~25%, 8 min; 25%~45%, 20 min; 47%~95%; 3 min; 95%, 5 min; Detector UV 254 nm; Rt: 17 min]. The desired fractions were collected and concentrated under reduced pressure to afford the title compound as a colorless solid (25.0 mg, 24%, faster eluting isomer): $^1$H NMR (400 MHz, CD$_3$OD) δ 8.74 (s, 1H), 8.51 (d, J=1.9 Hz, 1H), 8.37 (d, J=2.3 Hz, 1H), 8.27 (d, J=2.3 Hz, 1H), 8.18 (d, J=8.9 Hz, 1H), 8.00 (dd, J=9.0, 2.1 Hz, 1H), 4.53 (dd, J=11.0, 3.6 Hz, 1H), 4.37 (dd, J=11.1, 6.3 Hz, 1H), 4.27-4.20 (m, 1H), 3.39 (s, 3H), 3.08 (s, 3H), 3.00 (q, J=9.2, 8.2 Hz, 2H), 2.76-2.61 (m, 6H), 2.44 (s, 6H); MS: [(M+1)]$^+$=526.30; and N-(2-(2-(dimethylamino)-3-hydroxypropoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide as a colorless solid (24.0 mg, 24%, slower eluting isomer): $^1$H NMR (400 MHz, DMSO-d$_6$) δ 9.02 (br, 1H), 8.81 (s, 1H), 8.27 (d, J=1.9 Hz, 1H), 8.14 (d, J=8.8 Hz, 1H), 8.04 (s, 1H), 7.94 (s, 1H), 7.91-7.63 (m, 1H), 5.03 (d, J=5.2 Hz, 1H), 4.56-4.53 (m, 1H), 4.01-3.98 (m, 1H), 3.72-3.66 (m, 1H), 3.31 (s, 6H),

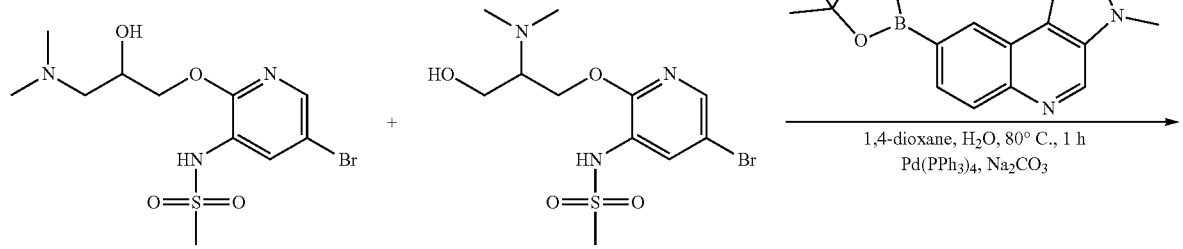

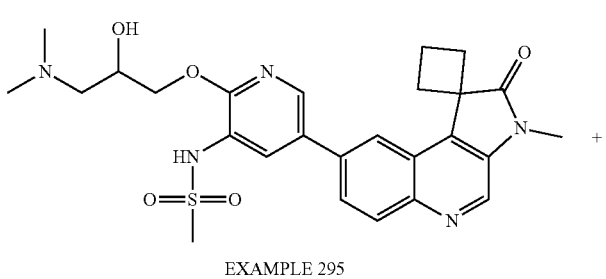

EXAMPLE 295

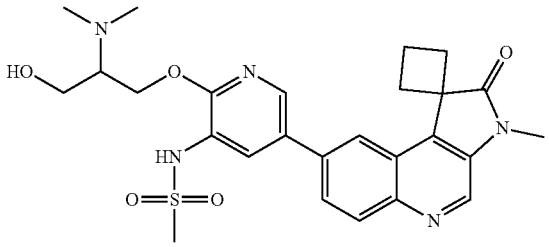

EXAMPLE 296

N-(2-(3-(Dimethylamino)-2-hydroxypropoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide: To a solution of the above mixture (75.0 mg, 0.20 mmol) in 1,4-dioxane (6.00 mL) were added 3-methyl-8-(4,4,5,5-tetramethyl-1,3,2-dioxaborolan-2-yl)-2,3-dihydrospiro[cyclobutane-1,1-pyrrolo[2,3-c]quinolin]-2-one (111 mg, 0.31 mmol), water (1.00 mL), sodium carbonate (25.9 mg, 0.24 mmol) and tetrakis(triphenylphosphine)-palladium (0) (35.3 mg, 0.03 mmol). After stirring for 1 hour at 80° C. under nitrogen atmosphere, the resulting mixture was concentrated under reduced pressure. The residue was purified by reversed phase flash chromatography with the following conditions: [Column: Spherical C18, 20~40 μm, 5 um; 120 g; Mobile Phase A: Water (plus 10 mM NH$_4$HCO$_3$); Mobile Phase B: acetonitrile; Flow rate: 45 min; Gradient (B %):

3.15 (s, 3H), 2.92-2.85 (m, 2H), 2.56-2.60 (m, 1H), 2.55 (s, 3H), 2.41-2.35 (m, 2H); MS: [(M+1)]$^+$=526.30.

Synthesis of Example 7

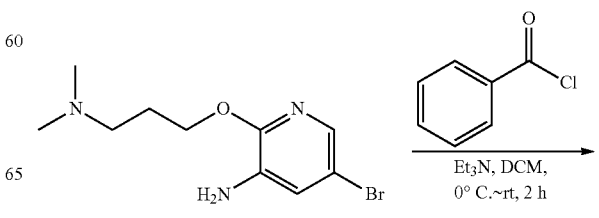

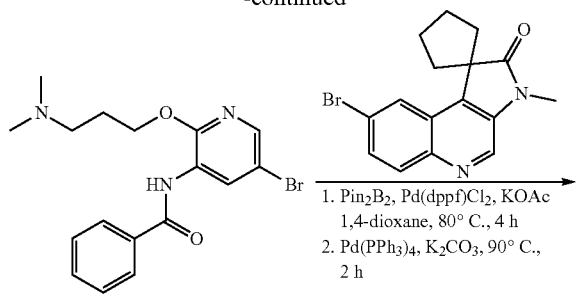

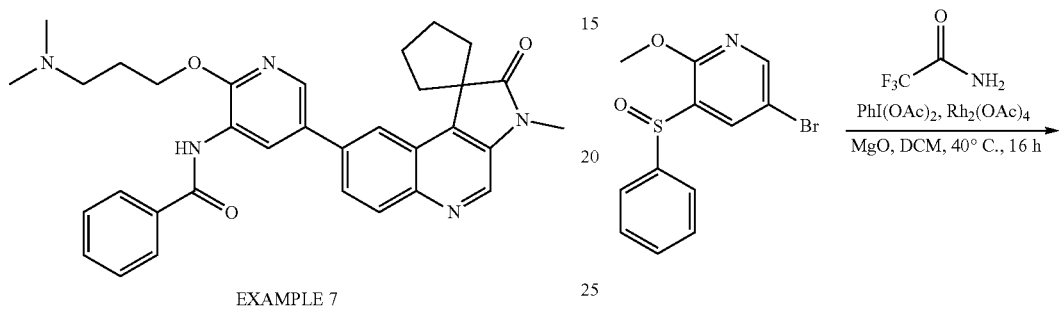

EXAMPLE 7

1-(5-Bromo-2-(3-(dimethylamino)propoxy)pyridin-3-yl) benzamide: To a solution of 5-bromo-2-[3-(dimethylamino)propoxy]pyridin-3-amine (500 mg, 1.82 mmol) in dichloromethane (10.0 mL) were added benzoyl chloride (512 mg, 3.66 mmol) and triethylamine (370 mg, 3.66 mmol) at 0° C. The resulting solution was stirred for 2 h at ambient temperature. The reaction was then quenched by water (20 mL) and extracted with EtOAc (3×100 mL). The combined organic layers was washed with brine (3×100 mL), dried over anhydrous sodium sulfate and filtered. The filtrate was concentrated under reduced pressure. The residue was purified by silica gel column chromatography, eluted with 0%~4% methanol in dichloromethane to afford N-[5-bromo-2-[3-(dimethylamino)propoxy]pyridin-3-yl]benzamide as a colorless solid (300 mg, 43%): $^1$H NMR (300 MHz, DMSO-$d_6$) δ 9.66 (s, 1H), 8.38 (d, J=2.4 Hz, 1H), 8.10 (d, J=2.4 Hz, 1H), 7.97-7.92 (m, 2H), 7.66-7.47 (m, 3H), 4.35 (t, J=6.4 Hz, 2H), 2.45 (t, J=7.1 Hz, 2H), 2.18 (s, 6H), 1.90 (p, J=6.8 Hz, 2H); MS: $[(M+1)]^+$=378.3, 380.3.

Synthesis of Example 151

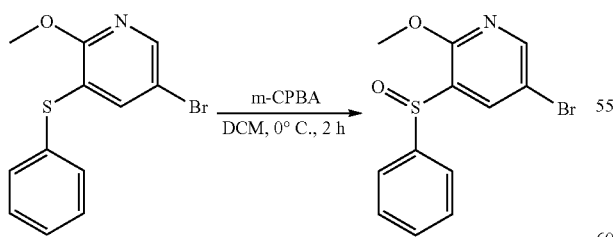

rac-5-Bromo-2-methoxy-3-(phenylsulfinyl)pyridine: To a solution of 5-bromo-2-methoxy-3-(phenylsulfanyl)pyridine (986 mg, 3.33 mmol) in dichloromethane (12.0 mL) was added 3-chloroperbenzoic acid (642 mg, 3.16 mmol) at 0° C. After stirring for 2 hours at 0° C. the mixture was quenched with saturated aqueous sodium sulfite solution (20.0 mL). The resulting mixture extracted with ethyl acetate (3×50.0 mL). The combined organic layers was washed with saturated aqueous sodium bicarbonate (20.0 mL), saturated brine (50.0 mL) and dried over anhydrous sodium d sulfate. After filtration, the filtrate was concentrated under reduced pressure. The residue was purified by silica gel column chromatography with 20% ethyl acetate in petroleum ether to afford the title compound as a yellow solid (700 mg, 68%): $^1$H NMR (300 MHz, CDCl$_3$) δ 8.30 (d, J=2.4 Hz, 1H), 8.21 (d, J=2.4 Hz, 1H), 7.79-7.68 (m, 2H), 7.52-7.41 (m, 3H), 3.92 (s, 3H); MS: $[(M+1)]^+$=312.10, 314.10.

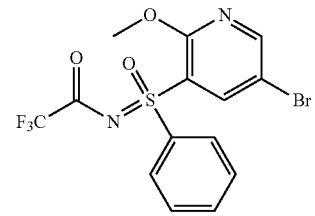

rac-N-((5-Bromo-2-methoxypyridin-3-yl)(oxo)(phenyl)-16-sulfaneylidene)-2,2,2-trifluoroacetamide: To a solution of rac-5-bromo-2-methoxy-3-(phenylsulfinyl)pyridine (700 mg, 2.24 mmol), phenyl-$\lambda^3$-iodanediyl diacetate (1.16 g, 3.59 mmol), dirhodium tetraacetate (99.1 mg, 0.22 mmol) and magnesium oxide (343 mg, 8.52 mmol) in dichloromethane (10.0 mL) was added trifluoroacetamide (507 mg, 4.48 mmol) at 25° C. After stirring for 16 hours at 40° C., the mixture was filtered. The filtrate was concentrated under reduced pressure and the residue was purified by silica gel column chromatography with 20% ethyl acetate in petroleum ether to afford the title compound as a yellow solid (150 mg, 16%): $^1$H NMR (300 MHz, CDCl$_3$) δ 8.62 (d, J=2.4 Hz, 1H), 8.41 (d, J=2.4 Hz, 1H), 8.14-8.04 (m, 2H), 7.77-7.65 (m, 1H), 7.65-7.54 (m, 2H), 3.88 (s, 3H); MS: $[(M+1)]^+$=422.80, 424.80.

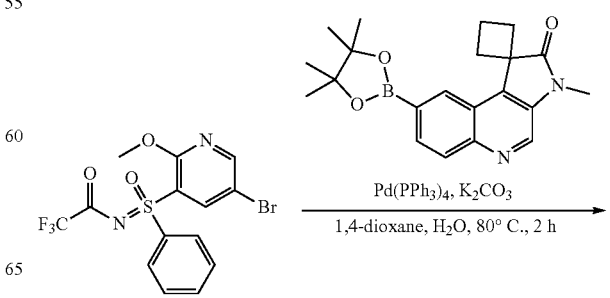

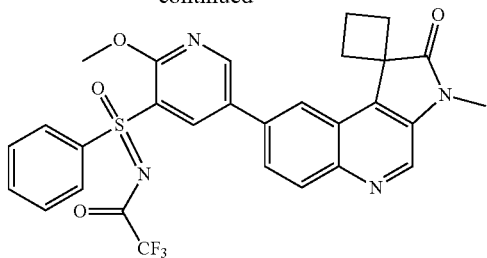

rac-2,2,2-Trifluoro-N-((2-methoxy-5-(3'-methyl-2'-oxo-2',3'-dihydrospiro[cyclobutane-1,1'-pyrrolo[2,3-c]quinolin]-8'-yl)pyridin-3-yl)(oxo)(phenyl)-16-sulfaneylidene)acetamide: To a solution of the crude of 3'-methyl-8'-(4,4,5,5-tetramethyl-1,3,2-dioxaborolan-2-yl)spiro[cyclobutane-1,1'-pyrrolo[2,3-c]quinolin]-2'(3'H)-one (102 mg, 0.28 mmol) and rac-N-((5-bromo-2-methoxypyridin-3-yl)(oxo)(phenyl)-16-sulfaneylidene)-2,2,2-trifluoroacetamide (100 mg, 0.24 mmol) in water (1.00 mL) and 1,4-dioxane (4.00 mL) were added potassium carbonate (65.3 mg, 0.47 mmol) and tetrakis(triphenylphosphine)palladium (0) (27.3 mg, 0.02 mmol). After stirring for 2 hours at 80° C. under nitrogen atmosphere, the resulting mixture was concentrated under reduced pressure. The residue was purified by silica gel column chromatography with 40% ethyl acetate in petroleum ether to afford the title compound afford the title compound as a yellow solid (50.0 mg, 37%): ¹H NMR (400 MHz, CDCl₃) δ 8.92 (d, J=2.4 Hz, 1H), 8.77 (d, J=2.4 Hz, 1H), 8.70 (s, 1H), 8.43 (d, J=2.0 Hz, 1H), 8.32 (d, J=8.8 Hz, 1H), 8.17-8.12 (m, 2H), 7.87 (dd, J=8.8, 2.0 Hz, 1H), 7.59-7.42 (m, 3H), 3.99 (s, 3H), 3.40 (s, 3H), 2.98-2.87 (m, 2H), 2.87-2.66 (m, 2H), 2.62-2.49 (m, 1H); MS: [(M+1)]⁺=581.00.

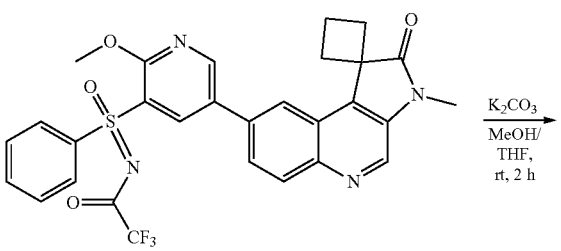

EXAMPLE 151 rac-8'-(6-Methoxy-5-(phenylsulfonimidoyl)pyridin-3-yl)-3'-methylspiro[cyclobutane-1,1'-pyrrolo[2,3-c]quinolin]-2'(3'H)-one: To a solution of rac-2,2,2-Trifluoro-N-((2-methoxy-5-(3'-methyl-2'-oxo-2',3'-dihydrospiro[cyclobutane-1,1'-pyrrolo[2,3-c]quinolin]-8'-yl)pyridin-3-yl)(oxo)(phenyl)-16-sulfaneylidene)acetamide (50.0 mg, 0.09 mmol) in methanol (1.00 mL) and tetrahydrofuran (3.00 mL) was added potassium carbonate (47.6 mg, 0.34 mmol) at 25° C. After stirring for 2 hours at 25° C., the resulting mixture was diluted with ethyl acetate (30.0 mL), washed with water (3×30.0 mL), saturated brine (20.0 mL). The organic layer was dried over anhydrous sodium sulfate. After filtration, the filtrate was concentrated under reduced pressure. The residue was triturated with diethyl ether (15.0 mL) and dried under reduced pressure to give the title compound as a colorless solid (28.0 mg, 68%): ¹H NMR (400 MHz, DMSO-d₆) δ 8.94 (d, J=2.4 Hz, 1H), 8.88 (s, 1H), 8.80 (d, J=2.5 Hz, 1H), 8.46 (d, J=2.0 Hz, 1H), 8.22 (d, J=8.8 Hz, 1H), 8.08-8.01 (m, 3H), 7.69-7.64 (m, 1H), 7.62-7.56 (m, 2H), 5.32 (s, 1H), 3.89 (s, 3H), 3.01-2.91 (m, 2H), 2.61-2.51 (m, 4H); MS: [(M+1)]⁺=485.10.

Synthesis of Example 21 and 27

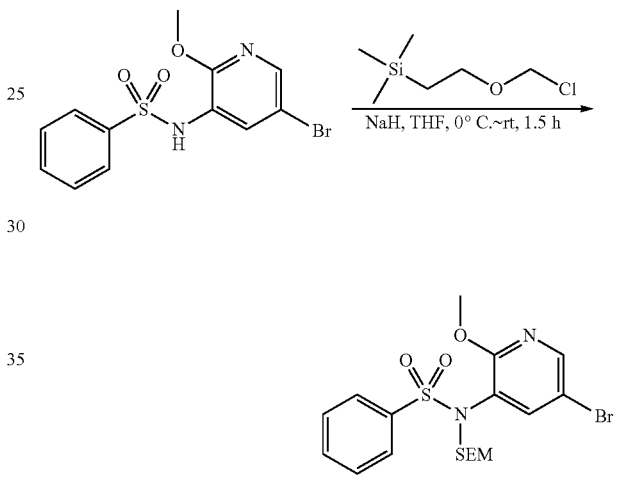

N-(5-Bromo-2-methoxypyridin-3-yl)-N-((2-(trimethylsilyl)ethoxy)methyl)benzenesulfonamide: To a solution of N-(5-bromo-2-methoxypyridin-3-yl)benzenesulfonamide (686 mg, 2.00 mmol) in tetrahydrofuran (30.0 mL) was added sodium hydride (96.0 mg, 2.40 mmol, 60% dispersed in mineral oil) at 0° C. under nitrogen atmosphere. The resulting mixture was stirred for 1 hour at 25° C. followed by the addition of [2-(chloromethoxy)ethyl]trimethylsilane (367 mg, 2.20 mmol) at 0° C. After stirring for additional 1.5 hours at 25° C., the reaction was quenched with saturated aqueous ammonium chloride (3.00 mL). The resulting mixture was diluted with water (30.0 mL) and extracted with ethyl acetate (3×20.0 mL). The combined organic layers was washed with brine (2×30.0 mL) and dried over anhydrous sodium sulfate. After filtration, the filtrate was concentrated under reduced pressure. The residue was purified by silica gel column chromatography, eluted with 2%%~3% ethyl acetate in petroleum ether. The desired fractions were collected and concentrated under reduced pressure to afford the title compound as a light-yellow oil (564 mg, 60%): ¹H NMR (400 MHz, CDCl₃) δ 8.15 (d, J=2.4 Hz, 1H), 7.73 (d, J=2.4 Hz, 1H), 7.66 (dd, J=8.3, 1.3 Hz, 2H), 7.61-7.51 (m, 1H), 7.46 (t, J=7.8 Hz, 2H), 5.04 (s, 2H), 3.73-3.69 (m, 2H), 3.49 (s, 3H), 0.99-0.86 (m, 2H), 0.02 (s, 9H); MS: [(M+1)]⁺=473.20, 475.20.

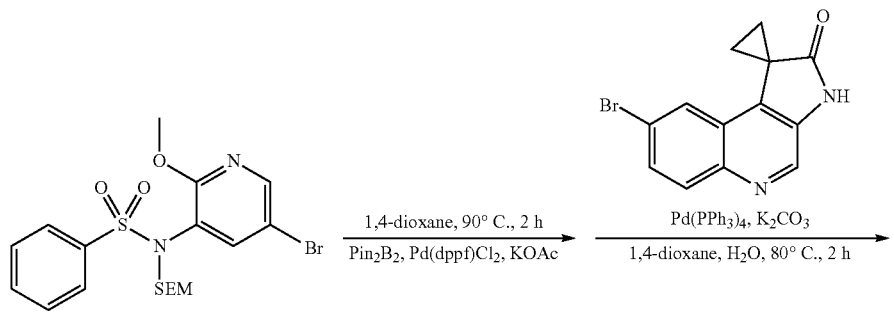

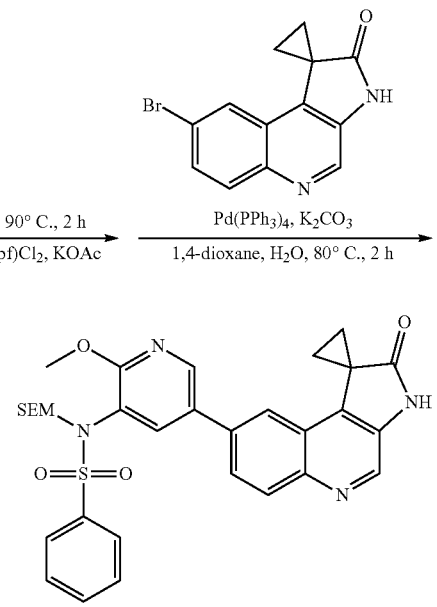

N-(2-Methoxy-5-(2-oxo-2',3'-dihydrospiro[cyclopropane-1,1'-pyrrolo[2,3-c]quinolin]-8'-yl)pyridin-3-yl)-N-((2-(trimethylsilyl)ethoxy)methyl)benzenesulfonamide: To a solution of N-(5-bromo-2-methoxypyridin-3-yl)-N-((2-(trimethylsilyl)ethoxy)methyl)benzenesulfonamide (564 mg, 1.19 mmol) and 4,4,5,5-tetramethyl-2-(tetramethyl-1,3,2-dioxaborolan-2-yl)-1,3,2-dioxaborolane (454 mg, 1.79 mmol) in 1,4-dioxane (40.0 mL) were added potassium acetate (468 mg, 4.77 mmol) and bis(diphenylphosphino)ferrocene-palladium (II) dichloride dichloromethane complex (87.2 mg, 0.12 mmol) at ambient temperature. The resulting mixture was stirred for 2 hours at 90° C. under nitrogen atmosphere. After cooling down to ambient temperature, water (2.00 mL), potassium carbonate (95.5 mg, 0.69 mmol, 1.98 equiv), 8-bromo-2,3-dihydrospiro[cyclopropane-1,1'-pyrrolo[2,3-c]quinolin]-2-one (100 mg, 0.35 mmol) and tetrakis(triphenylphosphine)palladium (0) (137 mg, 0.12 mmol) were added to above mixture. After stirring for 2 hours at 80° C. under nitrogen atmosphere, the resulting mixture was concentrated under reduced pressure. The residue was purified by Prep-TLC (DCM/MeOH=13/1, v/v) to afford the title compound as a light yellow solid (128 mg, 62%): $^1$H NMR (400 MHz, CDCl$_3$) δ 8.78 (s, 1H), 8.40 (d, J=2.4 Hz, 1H), 8.21 (d, J=8.8 Hz, 1H), 7.90 (d, J=2.4 Hz, 1H), 7.77-7.69 (m, 3H), 7.59 (t, J=7.6 Hz, 1H), 7.48 (dd, J=15.6, 8.7 Hz, 4H), 5.13 (s, 2H), 3.78 (t, J=8.2 Hz, 2H), 3.59 (s, 3H), 2.32 (q, J=4.6 Hz, 2H), 2.03 (q, J=4.5 Hz, 2H), 0.98-0.89 (m, 2H), 0.02 (s, 9H); MS: [(M+1)]$^+$=603.20.

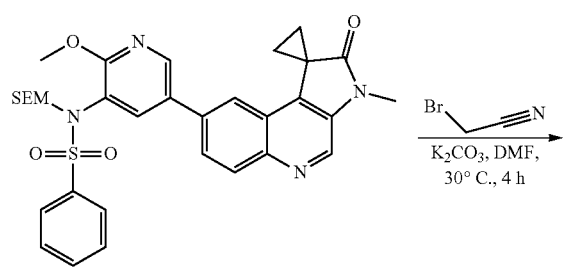

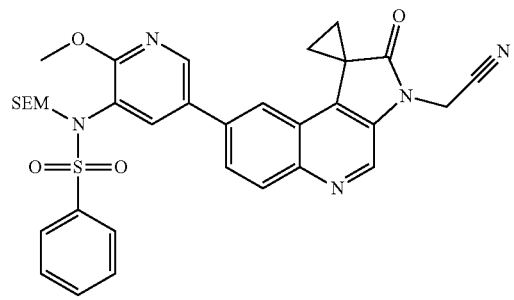

N-(5-(3'-(Cyanomethyl)-2-oxo-2',3'-dihydrospiro[cyclopropane-1,1'-pyrrolo[2,3-c]quinolin]-8'-yl)-2-methoxypyridin-3-yl)-N-((2-(trimethylsilyl)ethoxy)methyl)benzenesulfonamide: A mixture of N-(2-methoxy-5-(2'-oxo-2',3'-dihydrospiro[cyclopropane-1,1'-pyrrolo[2,3-c]quinolin]-8'-yl)pyridin-3-yl)-N-((2-(trimethylsilyl)ethoxy)methyl) benzenesulfonamide (20.0 mg, 0.033 mmol), 2-bromoacetonitrile (4.80 mg, 0.04 mmol) and potassium carbonate (9.20 mg, 0.07 mmol) in N,N-dimethylformamide (5.00 mL) was stirred for 4 hours at 30° C. The resulting solution was diluted with water (10.0 mL) and extracted with ethyl acetate (3×30.0 mL). The combined organic layers was washed with brine (2×30.0 mL) and dried over anhydrous sodium sulfate. After filtration, the filtrate was concentrated under reduced pressure. The residue was purified by Prep-TLC (DCM/MeOH 15/1, v/v) to afford the title compound as yellow solid (18 mg, 85%): $^1$H NMR (400 MHz, CDCl$_3$) δ 8.43 (d, J=16.1 Hz, 1H) 7.96 (s, 1H), 7.71 (d, J=8.3 Hz, 82H), 7.58-7.45 (m, 2H), 7.34 (t, J=7.9 Hz, 2H), 7.10 (J=7.5 Hz, 1H), 7.01 (d, J=8.2 Hz, 2H), 5.12 (s, 3H), 4.95 (s, 1H), 3.78 (t, J=7.9 Hz, 2H), 3.59 (d, J=17.2 Hz, 3H), 2.61-2.55 (m, 2H), 2.36-2.28 (m, 2H), 0.93-0.89 (m, 2H), 0.01 (m, 9H); MS: [(M+1)]$^+$=642.30.

The following intermediate was prepared according to the procedure described above:

| Structure | Name | MS: [(M + 1)]+ | 1H NMR |
|---|---|---|---|
| 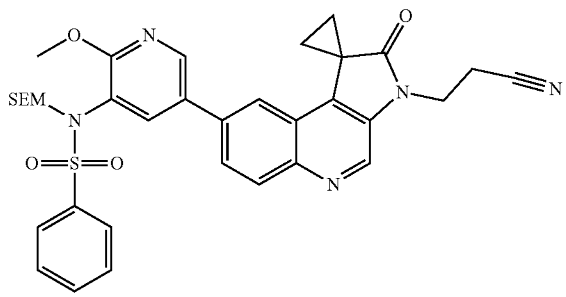 [SMILES: COc1ncc(-c2ccc3ncc4c(c3c2)C2(CC2)C(=O)N4CCC#N)cc1N(COCC[Si](C)(C)C)S(=O)(=O)c1ccccc1] | N-(5-(3'-(2-Cyanoethyl)-2'-oxo-2',3'-dihydrospiro[cyclopropane-1,1'-pyrrolo[2,3-c]quinolin]-8'-yl)-2-methoxypyridin-3-yl)-N-((2-(trimethylsilyl)ethoxy)methyl)benzenesulfonamide | 656.20 | 1H NMR (300 MHz, CDCl3) δ 8.86 (s, 1H), 8.40 (d, J = 2.4 Hz, 1H), 8.29 (d, J - 8.9 Hz, 1H), 7.90 (d, J - 2.4 Hz, 1H), 7.82-7.67 (m, 3H), 7.65-7.43 (m, 4H), 5.13 (s, 2H), 4.30 (t, J = 6.6 Hz, 2H), 3.84-3.72 (m, 2H), 3.60 (s, 3H), 2.99-2.85 (m, 3H), 2.39 (q,J= 4.5, 4.1 Hz, 2H), 2.10 (q, J = 4.4 Hz, 2H), 0.99-0.85 (m, 2H), 0.01 (s, 9H). |

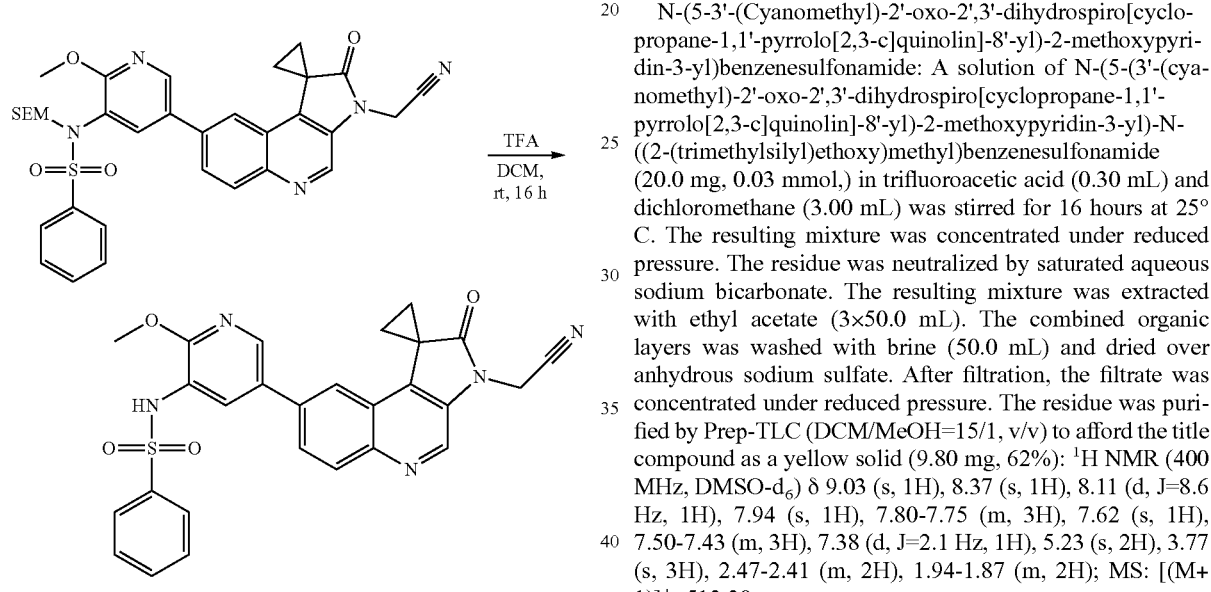

EXAMPLE 21

N-(5-3'-(Cyanomethyl)-2'-oxo-2',3'-dihydrospiro[cyclopropane-1,1'-pyrrolo[2,3-c]quinolin]-8'-yl)-2-methoxypyridin-3-yl)benzenesulfonamide: A solution of N-(5-(3'-(cyanomethyl)-2'-oxo-2',3'-dihydrospiro[cyclopropane-1,1'-pyrrolo[2,3-c]quinolin]-8'-yl)-2-methoxypyridin-3-yl)-N-((2-(trimethylsilyl)ethoxy)methyl)benzenesulfonamide (20.0 mg, 0.03 mmol,) in trifluoroacetic acid (0.30 mL) and dichloromethane (3.00 mL) was stirred for 16 hours at 25° C. The resulting mixture was concentrated under reduced pressure. The residue was neutralized by saturated aqueous sodium bicarbonate. The resulting mixture was extracted with ethyl acetate (3×50.0 mL). The combined organic layers was washed with brine (50.0 mL) and dried over anhydrous sodium sulfate. After filtration, the filtrate was concentrated under reduced pressure. The residue was purified by Prep-TLC (DCM/MeOH=15/1, v/v) to afford the title compound as a yellow solid (9.80 mg, 62%): 1H NMR (400 MHz, DMSO-d6) δ 9.03 (s, 1H), 8.37 (s, 1H), 8.11 (d, J=8.6 Hz, 1H), 7.94 (s, 1H), 7.80-7.75 (m, 3H), 7.62 (s, 1H), 7.50-7.43 (m, 3H), 7.38 (d, J=2.1 Hz, 1H), 5.23 (s, 2H), 3.77 (s, 3H), 2.47-2.41 (m, 2H), 1.94-1.87 (m, 2H); MS: [(M+1)]+=512.20.

The following example was prepared according to the procedure described above:

| Example | Structure | Name | MS: [(M + 1)]+ | 1H NMR |
|---|---|---|---|---|
| 27 | 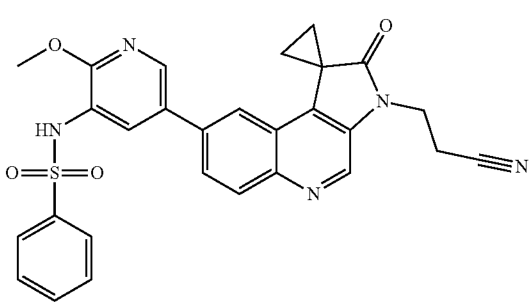 [SMILES: COc1ncc(-c2ccc3ncc4c(c3c2)C2(CC2)C(=O)N4CCC#N)cc1NS(=O)(=O)c1ccccc1] | N-(5-(3'-(2-Cyanoethyl)-2'-oxo-2',3'-dihydrospiro[cyclopropane-1,1'-pyrrolo[2,3-c]quinolin]-8'-yl)-2-methoxypyridin-3-yl)benzenesulfonamide | 526.20 | 1H NMR (300 MHz, DMSO-d6) δ 10.06 (s, 1H), 9.07 (s, 1H), 8.43 (d, J = 2.3 Hz, 1H), 8.13 (d, J = 8.8 Hz, 1H), 7.91 (d, J = 2.3 Hz, 1H), 7.86-7.78 (m, 3H), 7.70-7.55 (m, 3H), 7.50 (d, J = 1.9 Hz, 1H), 4.27 (t, J = 6.6 Hz, 2H), 3.70 (s, 3H), 3.04 (t, J = 6.5 Hz, 2H), 2.50(q, J = 4.4 Hz, 2H) 1.83 (q, J = 4.4 Hz, 2H). |

Synthesis of Example 138

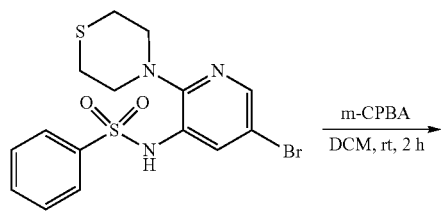

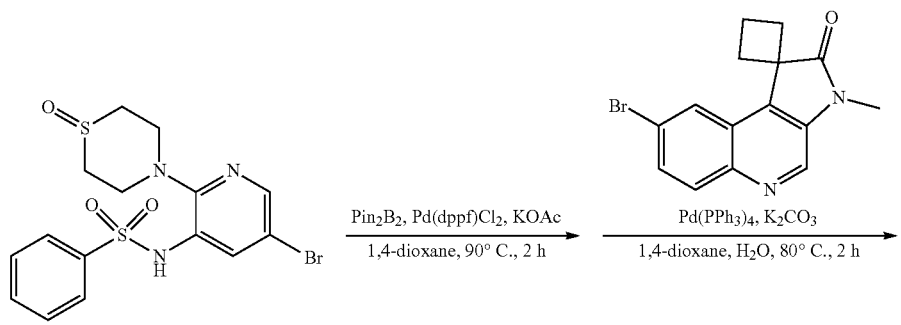

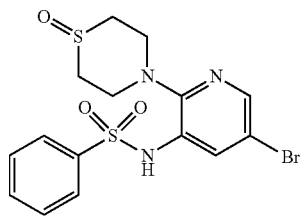

rac-N-(5-Bromo-2-(1-oxidothiomorpholino)pyridin-3-yl)benzenesulfonamide: To a solution of N-(5-bromo-2-thiomorpholinopyridin-3-yl)benzenesulfonamide (1.00 g, 2.41 mmol) in dichloromethane (50.0 mL) was added 3-chloroperbenzoic acid (417 mg, 2.41 mmol) at 0° C. After stirring for 2 hours at ambient temperature, the reaction was quenched with saturated aqueous sodium bicarbonate (20.0 mL) and saturated aqueous sodium sulfite solution (20.0 mL). The resulting mixture was extracted with dichloromethane (3×50.0 mL). The combined organic layers was washed with brine (2×30.0 mL) and dried over anhydrous sodium sulfate. After filtration, the filtrate was concentrated under reduced pressure. The residue was purified by silica gel column chromatography, eluted with 5%~9% methanol in dichloromethane. The desired fractions were collected and concentrated under reduced pressure to afford the title compound as a light yellow solid (980 mg, 95%): $^1$H NMR (400 MHz, CDCl$_3$) δ 8.12 (d, J=2.2 Hz, 1H), 7.99 (d, J=2.2 Hz, 1H), 7.91-7.83 (m, 2H), 7.67-7.58 (m, 1H), 7.53 (dd, J=8.3, 6.9 Hz, 2H), 7.40 (s, 1H), 3.74-3.62 (m, 2H), 3.05-2.93 (m, 2H), 2.87-2.66 (m, 4H); MS: [(M+1)]$^+$=429.95, 431.95.

rac-N-(5-(3'-Methyl-2'-oxo-2',3'-dihydrospiro[cyclobutane-1,1'-pyrrolo[2,3-c]quinolin]-8'-yl)-2-(1-oxidothiomorpholino)pyridin-3-yl)benzenesulfonamide: To a solution of rac-N-(5-bromo-2-(1-oxidothiomorpholino)pyridin-3-yl)benzenesulfonamide (600 mg, 1.39 mmol) and bis(pinacolato)diboron (708 mg, 2.79 mmol) in 1,4-dioxane (20.0 mL) were added potassium acetate (547 mg, 5.58 mmol) and bis(diphenylphosphino)ferrocene-palladium (II) dichloride dichloromethane complex (102 mg, 0.14 mmol) at ambient temperature. After stirring for 2 hours at 90° C. under nitrogen atmosphere. The resulting mixture was cooled down to ambient temperature. Water (2.00 mL), potassium carbonate (385 mg, 2.79 mmol), 8-bromo-3-methyl-2,3-dihydrospiro[cyclobutane-1,1-pyrrolo[2,3-c]quinoline]-2-one (442 mg, 1.39 mmol) and tetrakis(triphenylphosphine)palladium (0) (80.5 mg, 0.07 mmol) were added to the above mixture. After stirring for 2 hours at 80° C. under nitrogen atmosphere, the resulting mixture was concentrated under reduced pressure. The residue was purified by Prep-TLC (DCM/MeOH=10/1, v/v) to afford the title compound as a colorless solid (600 mg, 74%): $^1$H NMR (400 MHz, CDCl$_3$) δ 8.69 (s, 1H), 8.49 (d, J=2.2 Hz, 1H), 8.41 (d, J=1.9 Hz, 1H), 8.31 (d, J=8.8 Hz, 1H), 8.19 (d, J=2.2 Hz, 1H), 7.91 (dd, J=7.1, 1.7 Hz, 2H), 7.81 (dd, J=8.9, 1.9 Hz, 1H), 7.66-7.58 (m, 1H), 7.52 (dd, J=8.4, 7.0 Hz, 2H), 3.79 (t, J=11.9 Hz, 2H), 3.40 (s, 3H), 3.10-2.98 (m, 4H), 2.98-2.66 (m, 7H), 2.65-2.52 (m, 1H); MS: [(M+1)]⁺=588.05.

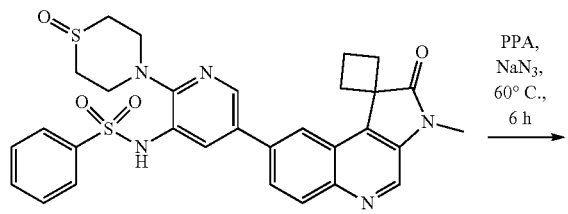

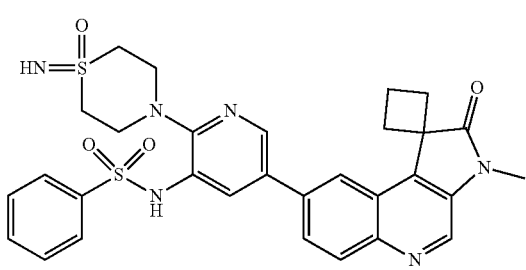

rac-N-(2-(1-Imino-1-oxido-1λ⁶-thiomorpholino)-5-(3'-methyl-2'-oxo-2',3'-dihydrospiro[cyclobutane-1,1'-pyrrolo[2,3-c]quinolin]-8'-yl)pyridin-3-yl)benzenesulfonamide: To a solution of rac-N-(5-(3'-methyl-2-oxo-2',3'-dihydrospiro[cyclobutane-1,1'-pyrrolo[2,3-c]quinolin]-8'-yl)-2-(1-oxido-thiomorpholino)pyridin-3-yl)benzenesulfonamide (250 mg, 0.43 mmol) in polyphosphoric acid (5.00 mL) was added sodium azide (83.0 mg, 1.28 mmol) at ambient temperature. After stirring for 6 hours at 60° C., the reaction was quenched with saturated aqueous sodium bicarbonate (20.0 mL) at 0° C. The resulting mixture was diluted with water (50.0 mL) and extracted with ethyl acetate (3×50.0 mL). The combined organic layers was washed with brine (2×30.0 mL) and dried over anhydrous sodium sulfate. After filtration, the filtrate was concentrated under reduced pressure. The residue was purified by silica gel column chromatography, eluted with 9%~17% methanol in dichloromethane. The desired fractions were collected and concentrated under reduced pressure to afford the title compound as a light yellow solid (100 mg, 39%): MS: [(M+1)]⁺=603.10.

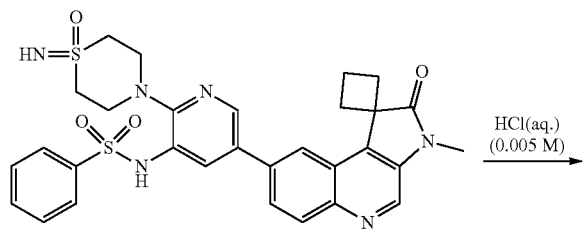

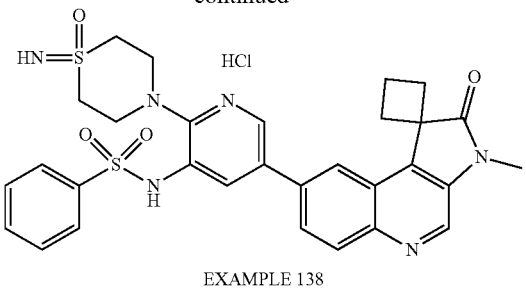

EXAMPLE 138 rac-N-(2-(1-Imino-1-oxido-1λ⁶-thiomorpholino)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride: A solution of rac-N-(2-(1-imino-1-oxido-1λ⁶-thiomorpholino)-5-(3'-methyl-2'-oxo-2',3'-dihydrospiro[cyclobutane-1,1'-pyrrolo[2,3-c]quinolin]-8'-yl)pyridin-3-yl)benzenesulfonamide (140 mg, 0.23 mmol) in HCl (aq.) (0.005 M) (46.0 mL, 0.23 mmol) and acetonitrile (15.0 mL) was lyophilized to afford the title compound as a light yellow solid (144.2 mg, 98%): ¹H NMR (400 MHz, DMSO-d₆) δ 9.99 (s, 1H), 8.86 (s, 1H), 8.66 (d, J=2.1 Hz, 1H), 8.27 (s, 1H), 8.16 (d, J=8.9 Hz, 1H), 7.91-7.77 (m, 4H), 7.71-7.55 (m, 3H), 3.77 (d, J=14.1 Hz, 2H), 3.66 (br, 4H), 3.31 (s, 3H), 3.21-3.15 (m, 2H), 2.91-2.78 (m, 2H), 2.63-2.52 (m, 4H); MS: [(M+1)]⁺=603.10.

Synthesis of Example 140

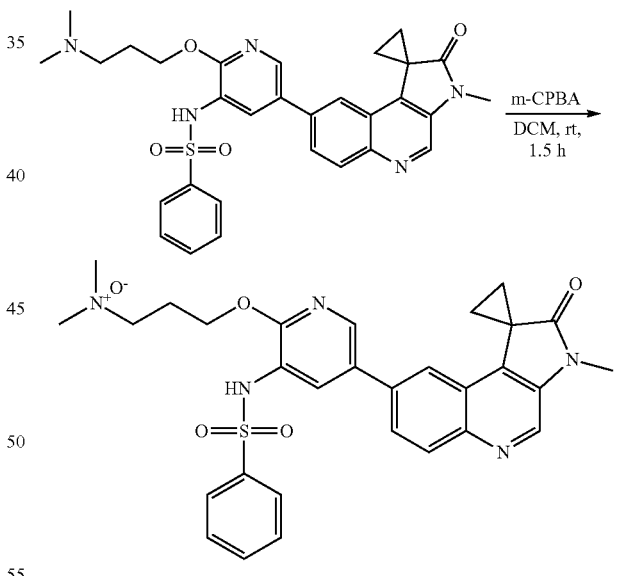

EXAMPLE 140

N,N-Dimethyl-3-((5-(3'-methyl-2'-oxo-2',3'-dihydrospiro[cyclopropane-1,1'-pyrrolo[2,3-c]quinolin]-8'-yl)-3-(phenylsulfonamido)pyridin-2-yl)oxy)propan-1-amine oxide: A mixture of N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide and 3-chloroperbenzoic acid (18.6 mg, 0.11 mmol) in dichloromethane (20.0 mL) was stirred for 1.5 hours at 25° C. The resulting mixture was concentrated under reduced pressure. The residue was purified by Prep-HPLC to afford the title compound as a yellow solid (14.1 mg, 28%): $^1$H NMR (300 MHz, DMSO-d$_6$) δ 8.86 (s, 1H), 8.06 (d, J=8.81 Hz, 1H), 7.92 (s, 1H), 7.79 (dd, J=6.7, 2.9 Hz, 2H), 7.69 (d, J=8.9 Hz, 1H), 7.63 (s, 1H), 7.52-7.43 (m, 4H), 7.32 (s, 1H), 4.28 (t, J=6.2 Hz, 2H), 3.66 (t, J=7.6 Hz, 2H), 3.41 (s, 3H), 3.36 (s, 6H), 2.33-2.16 (m, 4H), 1.80 (q, J=3.9 Hz, 2H); MS: [(M+1)]$^+$=574.20.

Assay of Compounds ATM and DNA-PK Inhibition

ATM in Cell Western Assay:

Plate MCF-7 breast cancer cells at density of 10,000 cells/well in 384 well plate (Corning, #356663), 25 μL cells per well in the morning. Next day, add corresponding concentration of compounds using pin tool (Echo 550), the final top concentration is 1 μM, 3-fold series dilution, total 10 doses. Then add etoposide (Sigma, #E1383) to a final concentration of 100 μM. Incubate at 37° C. for 1 hr. Fix cells by adding 25 μL of fixing solution (8% paraformaldehyde) for 20 minutes at ambient temperature. Permeabilize cells for 5 washes with 1×PBS (phosphate buffered saline) containing 0.1% Triton X-100; each wash is for 5 minutes. Then block cells by adding 50 μL of Odyssey Blocking Buffer (LI-COR, #927-40000) in 384 well plates for 1.5 hours with shaking at ambient temperature. Remove blocking buffer, add 20 μL of anti-pKAP1 antibody (Bethyl Laboratories, #A300-767A) (1/2000) solution to each well of 384-well plate, then incubate overnight at 4° C. The next day, wash the plate 5 times with 1×PBST (1×PBS containing 0.1% Tween-20). Then add 20 μL of secondary antibody (IRDye 800CW Goat anti-Rabbit IgG, LI-COR, #926-32211) (1/5,000) solution containing DNA stain DRAQ5 (CST, #4084L) (1/5,000) to each well of 384 plate, incubate 1 hour with gentle shaking in the dark. Wash the cells for 5 times with 1×PBST (1×PBS containing 0.1% Tween-20) at ambient temperature, using gentle shaking in the dark. After the last wash

| Example Number | nomenclature | ATM (cell) | DNA-PK IC50 |
|---|---|---|---|
| Example 1 | 8'-(6-(3-(Dimethylamino)propoxy)pyridin-3-yl)-3'-methylspiro[cyclopropane-1,1'-pyrrolo[2,3-c]quinolin]-2'(3'H)-one | *** | *** |
| Example 2 | N-(2-(3-(Dimethylamino)propoxy)-5-(3'-methyl-2'-oxo-2',3'-dihydrospiro[cyclopentane-1,1'-pyrrolo[2,3-c]quinolin]-8'-yl)pyridin-3-yl)benzenesulfonamide | *** | *** |
| Example 3 | N-(2-(3-(Dimethylamino)propoxy)-5-(3'-methyl-2'-oxo-2',3'-dihydrospiro[cyclohexane-1,1'-pyrrolo[2,3-c]quinolin]-8'-yl)pyridin-3-yl)benzenesulfonamide | *** | *** |
| Example 4 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | * | * |
| Example 5 | N-(2-(3-(Dimethylamino[propoxy)-5-(3'-methyl-2'-oxo-2',3'-dihydrospiro[cyclobutane-1,1'-pyrrolo[2,3-c]quinolin]-8'-yl)pyridin-3-yl)benzenesulfonamide | *** | * |
| Example 6 | N-(2-(2-(Dimethylamino)ethoxy)-5-(3'-methyl-2'-oxo-2',3'-dihydrospiro[cyclopentane-1,1'-pyrrolo[2,3-c]quinolin]-8'-yl)pyridin-3-yl)benzenesulfonamide | *** | ** |
| Example 7 | N-(2-(3-(Dimethylamino[propoxy)-5-(3'-methyl-2'-oxo-2',3'-dihydrospiro[cyclopentane-1,1'-pyrrolo[2,3-c]quinolin]-8'-yl)pyridin-3-yl)benzamide | **** | |
| Example 8 | N-(2-Methoxy-5-(3'-methyl-2'-oxo-2',3'-dihydrospiro[oxetane-3,1'-pyrrolo[2,3-c]quinolin]-8'-yl)pyridin-3-yl)benzenesulfonamide | *** | * |
| Example 9 | 3-Chloro-N-(2-methoxy-5-(3'-methyl-2'-oxo-2',3'-dihydrospiro[cyclopropane-1,1'-pyrrolo[2,3-c]quinolin]-8'-yl[pyridin-3-yl)benzenesulfonamide | *** | * |
| Example 10 | N-(2-(Dimethylamino)-5-(3'-methyl-2'-oxo-2',3'-dihydrospiro[cyclobutane-1,1'-pyrrolo[2,3-c]quinolin]-8'-yl)pyridin-3-yl)benzenesulfonamide | *** | * |
| Example 11 | N-(5-(3'-((1H-pyrazol-4-yl)methyl)-2'-oxo-2',3'-dihydrospiro[cyclopropane-1,1'-pyrrolo[2,3-c]quinolin]-8'-yl)-2-methoxypyridin-3-yl)benzenesulfonamide | **** | |
| Example 12 | N-(2-Methoxy-5-(3'-methyl-2'-oxo-2',3'-dihydrospiro[cyclopropane-1,1'-pyrrolo[2,3-c]quinolin]-8'-yl)pyridin-3-yl)-4-nitrobenzenesulfonamide | *** | * |
| Example 13 | 3-Acetyl-N-(2-methoxy-5-(3'-methyl-2'-oxo-2',3'-dihydrospiro[cyclopropane-1,1'-pyrrolo[2,3-c]quinolin]-8'-yl)pyridin-3-yl)benzenesulfonamide | *** | * |
| Example 14 | N-(2-Methoxy-5-(3'-methyl-2'-oxo-2',3'-dihydrospiro[cyclopropane-1,1'-pyrrolo[2,3-c]quinolin]-8'-yl)pyridin-3-yl)benzenesulfonamide | *** | * |
| Example 15 | N-(2-Chloro-5-(3'-methyl-2'-oxo-2',3'-dihydrospiro[cyclopropatie-1,1'-pyrrolo[2,3-c]quinolin]-8'-yl)pyridin-3-yl)benzenesulfonamide | *** | * |
| Example 16 | N-(2-Methoxy-5-(3-((1-methyl-1H-pyrazol-3-yl)amino)-4-oxo-4H-pyrido[1,2-a]pyrimidin-7-yl)pyridin-3-yl)benzenesulfonamide | **** | |
| Example 17 | N-(2-Methoxy-5-(3'-(oxetan-3-ylmethyl)-2'-oxo-2',3'-dihydrospiro[cyclopropane-1,1'-pyrrolo[2,3-c]quinolin]-8'-yl)pyridin-3-yl)benzenesulfonamide | **** | |
| Example 18 | 3-(1-Hydroxyethyl)-N-(2-methoxy-5-(3'-methyl-2'-oxo-2',3'-dihydrospiro[cyclopropane-1,1'-pyrrolo[2,3-c]quinolin]-8'-yl)pyridin-3-yl)benzenesulfonamide | *** | * |
| Example 19 | N-(2-Methoxy-5-(2'-oxo-2',3'-dihydrospiro[cyclopropane-1,1'-pyrrolo[2,3-c]quinolin]-8'-yl)pyridin-3-yl)benzenesulfonamide | *** | * |
| Example 20 | 3'-Methy)-8'-(quinolin-3-yl)spiro[cyclopropane-1,1'-pyrrolo[2,3-c]quinolin]-2'(3'H)-one | **** | |
| Example 21 | N-(5-(3'-(Cyanomethyl)-2'-oxo-2',3'-dihydrospiro[cyclopropane-1,1'-pyrrolo[2,3-c]quinolin]-8'-yl)-2-methoxypyridin-3-yl)benzenesulfonamide | *** | * |
| Example 22 | 3'-Methyl-8'-(quinolin-6-yl)spiro[cyclopropane-1,1'-pyrrolo[2,3-c]quinolin]-2'(3'H)-one | *** | *** |
| Example 23 | N-(2-Chloro-5-(1,3-dimethyl-2-oxo-1-(pyridin-4-yl)-2,3-dihydro-1H-pyrrolo[2,3-c]quinolin-8-yl)pyridin-3-yl)benzenesulfonamide | **** | |
| Example 24 | N-(2-Methyl-5-(3'-methyl-2'-oxo-2',3'-dihydrospiro[cyclopropane-1,1'-pyrrolo[2,3-c]quinolin]-8'-yl)pyridin-3-yl)benzenesulfonamide | *** | * |
| Example 25 | 8'-(5-(2-Hydroxypropan-2-yl)pyridin-3-yl)-3'-methylspiro[cyclopropane-1,1'-pyrrolo[2,3-c]quinolin]-2'(3'H)-one | **** | |
| Example 26 | 8'-(5-(2-Hydroxypropan-2-yl)-6-methoxypyridin-3-yl)-3'-methylspiro[cyclopropane-1,1'-pyrrolo[2,3-c]quinolin]-2'(3'H)-one | **** | |
| Example 27 | N-(5-(3'-(2-Cyanoethyl)-2'-oxo-2',3'-dihydrospiro[cyclopropane-1,1'-pyrrolo[2,3-c]quinolin]-8'-yl)-2-methoxypyridin-3-yl)benzenesulfonamide | **** | |

-continued

| Example Number | nomenclature | ATM (cell) | DNA-PK IC50 |
|---|---|---|---|
| Example 28 | 8'-(6-Chloro-5-(2-hydroxypropan-2-yl)pyridin-3-yl)-3'-methylspiro[cyclopropane-1,1'-pyrrolo[2,3-c]quinolin]-2'(3'H)-one | **** | |
| Example 29 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide | *** | *** |
| Example 30 | N-(5'-((1H-pyrazol-4-yl)methyl)-2'-oxo-2',3'-dihydrospiro[cyclopropane-1,1'-pyrrolo[2,3-c]quinolin]-8'-yl)-2-(3-(dimethylamino)propoxy)pyridin-3-yl)benzenesulfonamide | *** | *** |
| Example 31 | N-(2-(3-(Dimethylamino)propoxy)-5-(3'-isopropyl-2'-oxo-2',3'-dihydrospiro[cyclopropane-1,1'-pyrrolo[2,3-c]quinolin]-8'-yl)pyridin-3-yl)benzenesulfonamide | **** | |
| Example 32 | N-(2-(3-(Dimethylamino)propoxy)-5-(3'-methyl-2'-oxo-2',3'-dihydrospiro[oxetane-3,1'-pyrrolo[2,3-c]quinolin]-8'-yl)pyridin-3-yl)benzenesulfonamide | *** | *** |
| Example 33 | N-(2-(3-(Dimethylamino)propoxy)-5-(3'-methyl-2'-oxo-2,2',3,3',5,6-hexahydrospiro[pyran-4,1'-pyrrolo[2,3-c]quinolin]-8'-yl)pyridin-3-yl)benzenesulfonamide | *** | *** |
| Example 34 | 8'-(6-(3-(Dimethylamino)propoxy)-5-(isopropylamino)pyridin-3-yl)-3'-methylspiro[cyclopropane-1,1'-pyrrolo[2,3-c]quinolin]-2'(3'H)-one | **** | |
| Example 35 | N-(4-(Dimethylamino)butoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | *** | ** |
| Example 36 | 8'-(6-Methoxy-5-(phenylsulfonyl)pyridin-3-yl)-3'-methylspiro[cyclopropane-1,1'-pyrrolo[2,3-c]quinolin]-2'(3'H)-one | **** | |
| Example 37 | N-(2-(3-(Dimethylamino)propoxy)-5-(3'-(oxetan-3-ylmethyl)-2'-oxo-2',3'-dihydrospiro[cyclopropane-1,1'-pyrrolo[2,3-c]quinolin]-8'-yl)pyridin-3-yl)benzenesulfonamide | *** | *** |
| Example 38 | 8'-(6-(3-(Dimethylamino)propoxy)-5-isopropoxypyridin-3-yl)-3'-methylspiro[cyclopropane-1,1'-pyrrolo[2,3-c]quinolin]-2'(3'H)-one | **** | |
| Example 39 | 3'-Methyl-8'-(quinoxalin-6-yl)spiro[cyclopropane-1,1'-pyrrolo[2,3-c]quinolin]-2'(3'H)-one | **** | |
| Example 40 | 3'-Methyl-8'-(2-oxo-1,2,4a,8a-tetrahydroquinolin-6-yl)spiro[cyclopropane-1,1'-pyrrolo[2,3-c]quinolin]-2'(3'H)-one | **** | |
| Example 41 | 8'-(2-Chloroquinolin-6-yl)-3'-methylspiro[cyclopropane-1,1'-pyrrolo[2,3-c]quinolin]-2'(3'H)-one | **** | |
| Example 42 | N-(2-(3-(Dimethylamino)propoxy)-5-(3'-ethyl-2'-oxo-2',3'-dihydrospiro[cyclopropane-1,1'-pyrrolo[2,3-c]quinolin]-8'-yl)pyridin-3-yl)benzenesulfonamide | *** | ** |
| Example 43 | N-(5-(3'-Methyl-2'-oxo-2',3'-dihydrospiro[cyclopropane-1,1'-pyrrolo[2,3-c]quinolin]-8'-yl)-2-(2-(methylamino)ethoxy)pyridin-3-yl)benzenesulfonamide | *** | ** |
| Example 44 | 8'-(2-Methoxyquinolin-6-yl)-3'-methylspiro[cyclopropane-1,1'-pyrrolo[2,3-c]quinolin]-2'(3'H)-one | **** | |
| Example 45 | 3'-Methyl-8'-(1-methyl-2-oxo-1,2-dihydroquinolin-6-yl)spiro[cyclopropane-1,1'-pyrrolo[2,3-c]quinolin]-2'(3'H)-one | **** | |
| Example 46 | 3-(1-Cyanoethyl)-N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | *** | * |
| Example 47 | N-(2-(3-(Dimethylamino)propoxy)-5-(3'-methyl-2'-oxo-2',3'-dihydrospiro[oxetane-3,1'-pyrrolo[2,3-c]quinolin]-8'-yl)pyridin-3-yl)cyclopropanesulfonamide | *** | *** |
| Example 48 | 8'-(2-Aminopyrimidin-5-yl)-3'-methylspiro[cyclopropane-1,1'-pyrrolo[2,3-c]quinolin]-2'(3'H)-one | *** | ** |
| Example 49 | N-(5-(3'-Methyl-2'-oxo-2',3'-dihydrospiro[cyclopropane-1,1'-pyrrolo[2,3-c]quinolin]-8'-yl)-2-('4-methylpiperazin-1-yl)pyridin-3-yl)benzenesulfonamide | ** | * |
| Example 50 | 8'-(1H-indazol-4-yl)-3'-methylspiro[cyclopropane-1,1'-pyrrolo[2,3-c]quinolin]-2'(3'H)-one | **** | |
| Example 51 | 3'-Methyl-8'-(pyrimidin-5-yl)spiro[cyclopropane-1,1'-pyrrolo[2,3-c[quinolin]-2'(3'H)-one | **** | |
| Example 52 | 2-(3-(Dimethylamino)propoxy)-5-(3'-methyl-2'-oxo-2',3'-dihydrospiro[cyclopropane-1,1'-pyrrolo[2,3-c]qninolin]-8'-yl)nicotinamide | **** | |
| Example 53 | N-(2-(4-Methyl-1,4-diazepan-1-yl)-5-(3'-methyl-2'-oxo-2',3'-dihydrospiro[cyclopropane-1,1'-pyrrolo[2,3-c]quinolin]-8'-yl)pyridin-3-yl)benzenesulfonamide | *** | *** |
| Example 54 | 8'-(6-(3-(Dimethylamino)propoxy)-5-methoxypyridin-3-yl)-3'-methylspiro[cyclopropane-1,1'-pyrrolo[2,3-c]quinolin]-2'(3'H)-one | ** | **** |
| Example 55 | 8'-(5-Chloro-6-(3-(dimethylamino)propoxy)pyridin-3-yl)-3'-methylspiro[cyclopropane-1,1'-pyrrolo[2,3-c]quinolin]-2'(3'H)-one | **** | |
| Example 56 | N-(2-(4-(Dimethylamino)butoxy)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide | *** | *** |
| Example 57 | 8'-(6-(3-(Dimethylamino)propoxy)-5-methylpyridin-3-yl)-3'-methylspiro[cyclopropane-1,1'-pyrrolo[2,3-c]quinolin]-2'(3'H)-one | *** | *** |
| Example 58 | N-(5-(3'-Methyl-2'-oxo-2',3'-dihydrospiro[cyclopropane-1,1'-pyrrolo[2,3-c]quinolin]-8'-yl)-2-(3-(pyrrolidin-1-yl)propoxy)pyridin-3-yl)benzenesulfonamide | * | * |
| Example 59 | 8'-(5-(Benzyloxy)-6-(3-(dimethylamino)propoxy)pyridin-3-yl)-3'-methylspiro[cyclopropane-1,1'-pyrrolo[2,3-c]quinolin]-2'(3'H)-one | *** | *** |
| Example 60 | N-(5-(3'-Methyl-2'-oxo-2',3'-dihydrospiro[cyclopropane-1,1'-pyrrolo[2,3-c]quinolin]-8'-yl)-2-(3-(pyrrolidin-1-yl)propoxy)pyridin-3-yl)cyclopropanesulfonamide | *** | * |
| Example 61 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)ethanesulfonamide hydrochloride | *** | *** |
| Example 62 | 3'-Methyl-8'-(1,8-naphthyridin-3-yl)spiro[cyclopropane-1,1'-pyrrolo[2,3-c]quinolin]-2'(3'H)-one | *** | *** |

| Example Number | nomenclature | ATM (cell) | DNA-PK IC50 |
|---|---|---|---|
| Example 63 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)phenyl)benzenesulfonamide | ** | *** |
| Example 64 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)methanesulfonamide | *** | * |
| Example 65 | N-(2-(3-(Dimethylamino)propoxy)-5-(7'-fluoro-3'-methyl-2'-oxo-2',3'-dihydrospiro[cyclopropane-1,1'-pyrrolo[2,3-c]quinolin]-8'-yl)pyridin-3-yl)benzenesulfonamide | *** | *** |
| Example 66 | N-(2-(3-(Dimethylamino)propoxy)-5-(7'-fluoro-3'-methyl-2'-oxo-2',3'-dihydrospiro[cyclopropane-1,1'-pyrrolo[2,3-c]quinolin]-8'-yl)pyridin-3-yl)cyclopropanesulfonamide | *** | *** |
| Example 67 | N-(5-(3'-Methyl-2'-oxo-2',3'-dihydrospiro[cyclopropane-1,1'-pyrrolo[2,3-c]quinolin[-8'-yl)-2-(3-(piperidin-1-yl)propoxy)pyridin-3-yl)benzenesulfonamide | ** | * |
| Example 68 | N-(5-(3'-Methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)cyclopropanesulfonamide | *** | * |
| Example 69 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)cyclobutanesulfonamide | *** | *** |
| Example 70 | 8'-(2-((3-(Dimethylamino)propyl)amino)pyrimidin-5-yl)-3'-methylspiro[cyclopropane-1,1'-pyrrolo[2,3-c]quinolin]-2'(3'H)-one | *** | *** |
| Example 71 | 8'-(2-(3-(Dimethylamino)propoxy)pyrimidin-5-yl)-3'-methylspiro[cyclopropane-1,1'-pyrrolo[2,3-c]quinolin]-2'(3'H)-one | *** | **** |
| Example 72 | 8'-(6-(3-(Dimethylamino)propoxy)-5-phenylpyridin-3-yl)-3'-methylspiro[cyclopropane-1,1'-pyrrolo[2,3-c]quinolin]-2'(3'H)-one | **** | |
| Example 73 | N-(2-(3-(Dimethylamino)propoxy)-5-(4-methyl-3-oxo-3,4-dihydro-1H-spire[benzo[f][1,7]naphthyridine-2,1'-cyclobutan]-9-yl)pyridin-3-yl)beozenesulfonamide | *** | *** |
| Example 74 | N-(5-(1,4'-Dimethyl-3'-oxo-3',4'-dihydro-1'H-spiro[cyclopropane-1,2'-pyrazino[2,3-c]quinolin]-9'-yl)-2-(3-(dimethylamino)propoxy)pyridin-3-yl)benzenesulfonamide | **** | |
| Example 75 | N-(5-(3'-Methyl-2'-oxo-2',3'-dihydrospiro[cyclopropane-1,1'-pyrrolo[2,3-c]quinolin]-8'-yl)-2-(4-(methylamino[butoxy)pyridin-3-yl)benzenesulfonamide | *** | *** |
| Example 76 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)oxetane-3-sulfonamide | *** | ** |
| Example 77 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)propane-1-sulfonamide | *** | *** |
| Example 78 | N-(5-(3'-Methyl-2'-oxo-2',3'-dihydrospiro[cyclopropane-1,1'-pyrrolo[2,3-c]quinolin]-8'-yl)-2-(2-(1-methylpyrrolidin-2-yl)ethoxy)pyridin-3-yl)benzenesulfonamide | *** | *** |
| Example 79 | N-(5-(3'-Methyl-2'-oxo-2',3'-dihydrospiro[cyclopropane-1,1'-pyrrolo[2,3-c]quinolin]-8'-yl)-2-(2-(1-methylpyrrolidin-2-yl)ethoxy)pyridin-3-yl)cyclopropanesulfonamide | *** | *** |
| Example 80 | N-(5-(3'-Methyl-2'-oxo-2',3'-dihydrospiro[cyclopropane-1,1'-pyrrolo[2,3-c]quinolin]-8'-yl)-2-(2-(1-methylpiperidin-2-yl)ethoxy)pyridin-3-yl)cyclopropanesulfonamide | *** | *** |
| Example 81 | N-(5-(3'-Methyl-2'-oxo-2',3'-dihydrospiro[cyclopropane-1,1'-pyrrolo[2,3-c]quinolin]-8'-yl)-2-(2-(1-methylpiperidin-2-yl)ethoxy)pyridin-3-yl)benzenesulfonamide | *** | *** |
| Example 82 | N-(2-(3-(Dimethylamino)propoxy)-5-(7'-methoxy-3'-methyl-2'-oxo-2',3'-dihydrospiro[cyclopropane-1,1'-pyrrolo[2,3-c]quinolin]-8'-yl)pyridin-3-yl)benzenesulfonamide | ** | *** |
| Example 83 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-2-methoxyethane-1-sulfonamide | * | *** |
| Example 84 | N-(5-(3'-Methyl-2'-oxo-2',3'-dihydrospiro[cyclopropane-1,1'-pyrrolo[2,3-c]quinolin]-8'-yl)-2-((1-methylpiperidin-3-yl)methoxy)pyridin-3-yl)benzenesulfonamide | *** | *** |
| Example 85 | N-(2-(3-(Dimethylamino[propoxy)-5-(3'-methyl-2'-oxo-2',3'-dihydrospiro[cyclopropane-1,1'-pyrrolo[2,3-c]quinolin]-8'-yl)pyridin-3-yl)pyridine-3-sulfonamide | *** | * |
| Example 86 | N-(5-(3'-Methyl-2'-oxo-2',3'-dihydrospiro[cyclopropane-1,1'-pyrrolo[2,3-c]quinolin]-8'-yl)-2-((1-methylpiperidin-3-yl)methoxy)pyridin-3-yl)cyclopropanesulfonamide | *** | *** |
| Example 87 | N-(2-(3-(Dimethylamino)propoxy)-5-(1'-methyl-3'-oxo-3',4'-dihydro-1'H-spiro[cyclopropane-1,2'-pyrazino[2,3-c]quinolin]-9'-yl)pyridin-3-yl)benzenesulfonamide | **** | |
| Example 88 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-fluorobenzenesulfonamide | ** | * |
| Example 89 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)pyrrolidine-1-sulfonamide hydrochloride | ** | * |
| Example 90 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)phenyl)-3-fluorobenzenesulfonamide | ** | *** |
| Example 91 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-1-methyl-1H-pyrazole-4-sulfonamide | *** | * |
| Example 92 | N-(2-(3-(Dimethylamino)propoxy)-5-(3'-methyl-2-oxo-2',3'-dihydrospiro[cyclopropane-1,1'-pyrrolo[2,3-c]quinolin]-8'-yl)pyridin-3-yl)thiophene-3-sulfonamide | ** | * |
| Example 93 | N-(2-(3-(Dimethylbenzo)propoxy)-5-(3'-methyl-2'-oxo-2',3'-dihydrospiro[cyclopropane-1,1'-pyrrolo[2,3-c]quinolin]-8'-yl)pyridin-3-yl)-4-methoxybenzenesulfonamide | *** | * |
| Example 94 | 8'-(6-((3-(Dimethylamino)propyl)amino)pyridin-3-yl)-3'-methylspiro[cyclopropane-1,1'-pyrrolo[2,3-c]quinolin]-2'(3'H)-one | *** | |
| Example 95 | 8'-(6-(3-(Dimethylamino)propoxy)-5-(1-pbenylethoxy)pyridin-3-yl)-3'-methylspiro[cyclopropane-1,1'-pyrrolo[2,3-c]quinolin]-2'(3'H)-one | **** | |
| Example 96 | 3-Cyano-N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | ** | * |
| Example 97 | N-(2-(3-(Dimethylamino)propoxy)-3-fluoro-5-(3'-methyl-2'-oxo-2',3'-dihydrospiro[cyclopropane-1,1'-pyrrolo[2,3-c]quinolin]-8'-yl)phenyl)benzenesulfonamide | *** | *** |

| Example Number | nomenclature | ATM (cell) | DNA-PK IC50 |
|---|---|---|---|
| Example 98 | 3-Chloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)phenyl)benzenesulfonamide | *** | *** |
| Example 99 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-5-methylisoxazole-4-sulfonamide | **** | |
| Example 100 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-methylbenzenesulfonamide | *** | * |
| Example 101 | N-(4-(N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)sulfamoyl)phenyl)acetamide | *** | |
| Example 102 | N-(2-(3-(Dimethylamino)cyclobutoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | *** | *** |
| Example 103 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-1-phenylmethanesulfonamide | *** | *** |
| Example 104 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-3-methoxybenzenesulfonamide | ** | *** |
| Example 105 | 6-Chloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)pyridine-3-sulfonamide | *** | |
| Example 106 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-3-(trifluoromethyl)benzenesulfonamide | *** | * |
| Example 107 | N-(2-(3-(Dimethylamino)propoxy)-5-(3'-methyl-2-oxo-2',3'-dihydrospiro[cyclopropane-1,1'-pyrrolo[2,3-c]quinolin]-8'-yl)pyridin-3-yl)-2-fluorobenzenesulfonamide | ** | * |
| Example 108 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-(trifluoromethyl)benzenesulfonamide | * | * |
| Example 109 | 8'-{6-[3-(Dimethylamino)propoxy]-5-[(dimethylsulfamoyl)amino]pyridine-3-yl}-3'-methyl-2',3'-dihydrospiro[cyclopropane-1,1'-pyrrolo[2,3-c]quinoline]-2'-one | *** | * |
| Example 110 | N-(5-(3'-Methyl-2'-oxo-2',3'-dihydrospiro[cyclopropane-1,1'-pyrrolo[2,3-c]quinolin]-8'-yl)-2-((1-methylazetidin-3-yl)methoxy)pyridin-3-yl)benzenesulfonamide | **** | |
| Example 111 | 3-Cyano-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-fluorobenzenesulfonamide | *** | * |
| Example 112 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-1-methyl-1H-pyrazole-3-sulfonamide | *** | * |
| Example 113 | N-(2-(4-(Dimethylamino)piperidin-1-yl)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide | * | * |
| Example 114 | N-(2-(3-(Dimethylamino)propoxy)-5-(3'-methyl-2'-oxo-1-phenyl-2',3'-dihydrospiro[azetidine-3,1'-pyrrolo[2,3-c]quinolin]-8'-yl)pyridin-3-yl)benzenesulfonamide | *** | *** |
| Example 115 | N-(2-(4-((Dimethylamino)methyl)piperidin-1-yl)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide | ** | *** |
| Example 116 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-2-(trifluoromethoxy)benzenesulfonamide | ** | ** |
| Example 117 | N-(5-(7'-Fluoro-3'-methyl-2'-oxo-2',3'-dihydrospiro[cyclopropane-1,1'-pyrrolo[2,3-c]quinolin]-8'-yl)-2-(4-methylpiperazin-1-yl)pyridin-3-yl)benzenesulfonamide hydrochloride | *** | *** |
| Example 118 | N-(5-(7'-Fluoro-3'-methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)benzenesulfonamide hydrochloride | *** | *** |
| Example 119 | 4-Methoxy-N-(5-(3'-methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)benzenesulfonamide hydrochloride | *** | * |
| Example 120 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)thiophene-2-sulfonamide | ** | * |
| Example 121 | N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-(trifluoromethoxy)benzenesulfonamide | *** | * |
| Example 122 | N-(2-(3-((Dimethylamino)methyl)azetidin-1-yl)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide | *** | |
| Example 123 | 8'-(6-(3-(Dimethylamino)propoxy)-5-(phenylsulfonamido)pyridin-3-yl)-3'-methyl-2'-oxo-2',3'-dihydrospiro[cyclopropane-1,1'-pyrrolo[2,3-c]quinoline] 5'-oxide | *** | *** |
| Example 124 | N-(5-(7'-Fluoro-3'-methyl-2'-oxo-2',3'-dihydrospiro[cycloproparie-1,1'-pyrrolo[2,3-c]quinolin]-8'-yl)-2-(3-(pyrrolidin-1-yl)propoxy)pyridin-3-yl)benzenesulfonamide | *** | *** |
| Example 125 | 3,5-Dichloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | *** | * |
| Example 126 | 4-(Difluoromethoxy)-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | *** | * |
| Example 127 | 4-(tert-Butyl)-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide | *** | *** |

-continued

| Example Number | nomenclature | ATM (cell) | DNA-PK IC50 |
|---|---|---|---|
| Example 128 | 4-Chloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide hydrochloride | *** | * |
| Example 129 | 4-Chloro-N-(2-(3-(dimethylamino)propoxy)-5-(7'-fluoro-3'-methyl-2'-oxo-2',3'-dihydrospiro[cyclopropane-1,1'-pyrrolo[2,3-c]quinolin]-8'-yl)pyridin-3-yl)benzenesulfonamide hydrochloride | *** | *** |
| Example 130 | 5-Chloro-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyridine-3-sulfonamide hydrochloride | *** | *** |
| Example 131 | N-(5-(3'-Methyl-2'-oxo-2',3'-dihydrospiro[cyclobutane-1,1'-pyrrolo[2,3-c]quinolin]-8'-yl)-2-(3-morpholinopropoxy)pyridin-3-yl)benzenesulfonamide hydrochloride | *** | *** |
| Example 132 | N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)benzenesulfonamide hydrochloride | *** | *** |
| Example 133 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-6-methoxypyridine-3-sulfonamide hydrochloride | *** | ** |
| Example 134 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-(pentafluoro-16-sulfaneyl)benzenesulfonamide | *** | *** |
| Example 135 | N-(2-(1,1-Dioxidothiomorpholino)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride | **** | |
| Example 136 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)morpholine-4-sulfonamide hydrochloride | *** | *** |
| Example 137 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide hydrochloride | *** | *** |
| Example 138 | N-(2-(1-Imino-1-oxido-1l6-thiomorpholino)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride | **** | |
| Example 139 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3,4-dihydroquinoline-1(2H)-sulfonamide | *** | |
| Example 140 | N,N-Dimethyl-3-((5-(3'-methyl-2'-oxo-2',3'-dihydrospiro[cyclopropane-1,1'-pyrrolo[2,3-c]quinolin]-8'-yl)-3-(phenylsulfonamido)pyridin-2-yl)oxy)propan-1-amine oxide | *** | |
| Example 141 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-5-(trifluoromethyl)pyridine-3-sulfonamide hydrochloride | *** | **** |
| Example 142 | 6-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)pyridine-3-sulfonamide hydrochloride | *** | * |
| Example 143 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-(trifluoromethoxy)benzenesulfonamide hydrochloride | *** | |
| Example 144 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methoxybenzenesulfonamide hydrochloride | *** | *** |
| Example 145 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methylbenzenesulfonamide hydrochloride | *** | ** |
| Example 146 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-6-(trifluoromethyl)pyridine-3-sulfonamide hydrochloride | *** | *** |
| Example 147 | 6-Cyano-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyridine-3-sulfonamide hydrochloride | *** | ** |
| Example 148 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyridine-2-sulfonamide hydrochloride | *** | *** |
| Example 149 | 8'-{6-[3-(Dimethylamino)propoxy]-5-[(dimethylsulfamoyl)amino]pyridine-3-yl}-3'-methyl-2',3'-dihydrospiro[cyclobutane-1,1'-pyrrolo[2,3-c]quinoline]-2'-one hydrochloride | * | ** |
| Example 150 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3-(trifluoromethyl)benzenesulfonamide | *** | *** |
| Example 151 | 8'-(6-Methoxy-5-(phenylsulfonimidoyl)pyridin-3-yl)-3'-methylspiro[cyclobutane-1,1'-pyrrolo[2,3-c]quinolin]-2'(3'H)-one | **** | |
| Example 152 | N-(2-(3-(4,4-Difluoropiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride | *** | |
| Example 153 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3,5-difluorobenzenesulfonamide | *** | ** |
| Example 154 | 3-Chloro-N-(2-(3-(dimethylamino)propoxy)-5-(3'-methtyl-2'-oxo-2',3'-dihydrospiro[cyclobutane-1,1'-pyrrolo[2,3-c]quinolin]-8'-yl)pyridin-3-yl)-5-(trifluoromethyl)benzenesulfonamide hydrochloride | *** | *** |
| Example 155 | N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride | *** | ** |

-continued

| Example Number | nomenclature | ATM (cell) | DNA-PK IC50 |
|---|---|---|---|
| Example 156 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3-fluoro-5-(trifluoromethyl)benzenesulfonamide hydrochloride | *** | *** |
| Example 157 | 3,5-Dichloro-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride | *** | *** |
| Example 158 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-fluorobenzenesulfonamide hydrochloride | ** | ** |
| Example 159 | 3-Cyano-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-fluorobenzenesulfonamide hydrochloride | ** | ** |
| Example 160 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)thiazole-4-sulfonamide hydrochloride | *** | * |
| Example 161 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-oxo-1,2-dilydropyridine-4-sulfonamide | *** | |
| Example 162 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methylpiperazine-1-sulfonamide hydrochloride | *** | ** |
| Example 163 | 8'-{6-[3-(Dimethylamino)propoxy]-5-{[ethyl(methyl)sulfamoyl]amino}pyridin-3-yl}-3'-Methyl-2',3'-dihydrospiro[cyclobutane-1,1'-pyrrolo[2,3-c]quinolin]-2'-one | *** | ** |
| Example 164 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)azetidine-1-sulfonamide | *** | * |
| Example 165 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methylpiperidine-1-sulfonamide | *** | *** |
| Example 166 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1-methyl-1H-pyrazole-4-sulfonamide hydrochloride | *** | *** |
| Example 167 | 4-Methyl-N-(5-(3'-methyl-2'-oxo-2',3'-dihydrospiro[cyclobutane-1,1'-pyrrolo[2,3-c]quinolin]-8'-yl)-2-(4-morpholinopiperidin-1-yl)pyridin-3-yl)benzenesulfonamide hydrochloride | *** | *** |
| Example 168 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-fluorobenzenesulfonamide hydrochloride | ** | * |
| Example 169 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)thiazole-5-sulfonamide hydrochloride | *** | * |
| Example 170 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3-methylisothiazole-5-sulfonamide | *** | * |
| Example 171 | 3-Chloro-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-5-fluorobenzenesulfonamide hydrochloride | *** | ** |
| Example 172 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-methylpyrrolidine-1-sulfonamide | *** | *** |
| Example 173 | N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide hydrochloride | * | * |
| Example 174 | 5-Cyano-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyridine-3-sulfonamide hydrochloride | *** | |
| Example 175 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-3-methylpiperidine-1-sulfonamide | *** | *** |
| Example 176 | 8'-(5-{[Butyl(methyl)sulfamoyl]amino}-6-[3-(dimethylamino)propoxy]pyridin-3-yl)-3'-methyl-2',3'-dihydrospiro[cyclobutane-1,1'-pyrrolo[2,3-c]quinolin]-2'-one | *** | |
| Example 177 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)piperazine-1-sulfonamide | *** | * |
| Example 178 | N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)-4-methylbenzenesulfonamide 2,2,2-trifluoroacetate | *** | * |
| Example 179 | N-Methyl-N-(piperidin-4-yl)({2-[3-(dimethylamino)propoxy]-5-{3'-methyl-2'-oxo-2',3'-dihydrospiro[cyclobutane-1,1'-pyrrolo[2,3-c]quinoline]-8'-yl}pyridin-3-yl}amino)sulfonamide 2,2,2-trifluoroacetate | *** | |
| Example 180 | 8'-{5-[(Dimethylsulfamoyl)amino]-6-[3-(piperidin-1-yl)propoxy]pyridin-3-yl}-3'-methyl-2',3'-dihydrospiro[cyclobutane-1,1'-pyrrolo[2,3-c]quinolin]-2'-one hydrochloride | *** | ** |
| Example 181 | 8'-(5-{[Bis(2-methoxyethyl)sulfamoyl]amino}-6-[3-(dimethylamino)propoxy]pyridine-3-yl)-3'-methyl-2',3'-dihydrospiro[cyclobutane-1,1'-pyrrolo[2,3-c]quinoline]-2'-one | *** | *** |
| Example 182 | N-Benzyl-N-methyl({2-[3-(dimethylamino)propoxy]-5-{3'-methyl-2'-oxo-2',3'-dihydrospiro[cyclobutane-1,1'-pyrrolo[2,3-c]quinoline]-8'-yl}pyridin-3-yl}amino)sulfonamide | *** | |
| Example 183 | 8'-{5-[(Diethylsulfamoyl)amino]-6-[3-(dimethylamino)propoxy]pyridine-3-yl}-3'-methyl-2',3'-dihydrospiro[cyclobutane-1,1'-pyrrolo[2,3-c]quinoline]-2'-one | *** | *** |
| Example 184 | N-(2-(3-(Dimethylamino)propoxy)-5-(3'-methyl-2'-oxo-2',3'-dihydrospiro[cyclobutane-1,1-pyrrolo[2,3-c]quinolin]-8'-yl)pyridin-3-yl)-2,6-dimethylmorpholine-4-sulfonamide | *** | *** |

| Example Number | nomenclature | ATM (cell) | DNA-PK IC50 |
|---|---|---|---|
| Example 185 | N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide hydrochloride | *** | ** |
| Example 186 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-(trifluoromethyl)benzenesulfonamide hydrochloride | *** | *** |
| Example 187 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-methoxypiperidine-1-sulfonamide | *** | * |
| Example 188 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)isothiazole-5-sulfonamide hydrochloride | *** | * |
| Example 189 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | *** |
| Example 190 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide | *** | *** |
| Example 191 | N,6-Dimethyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)pyridine-3-sulfonamide 2,2,2-trifluoroacetate | **** | |
| Example 192 | N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-4-methylbenzenesulfonamide hydrochloride | *** | *** |
| Example 193 | N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)thiazole-4-sulfonamide hydrochloride | *** | ** |
| Example 194 | 3-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)isothiazole-5-sulfonamide hydrochloride | *** | * |
| Example 195 | 2-Fluoro-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)benzenesulfonamide hydrochloride | *** | ** |
| Example 196 | 3-Chloro-5-fluoro-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)benzenesulfonamide hydrochloride | *** | *** |
| Example 197 | N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)cyclopropanesulfonamide hydrochloride | *** | ** |
| Example 198 | N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide hydrochloride | *** | * |
| Example 199 | N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)thiazole-5-sulfonamide hydrochloride | *** | * |
| Example 200 | 4-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)piperazine-1-sulfonamide | ** | * |
| Example 201 | 6-Methyl-N-(5-(3'-methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)pyridine-3-sulfonamide | *** | * |
| Example 202 | N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)piperazine-1-sulfonamide | ** | * |
| Example 203 | N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-2-fluorobenzenesulfonamide | *** | ** |
| Example 204 | N-(2-(3-(Dimethylamino)propoxy)-5-(9'-fluoro-3'-methyl-2'-oxo-2',3'-dihydrospiro[cyclobutane-1,1'-pyrrolo[2,3-c]quinolin]-8'-yl)pyridin-3-yl)-4-methylbenzenesulfonamide | *** | ** |
| Example 205 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)oxetane-3-sulfonamide | *** | * |
| Example 206 | N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-2,4-difluorobenzenesulfonamide hydrochloride | *** | * |
| Example 207 | N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide hydrochloride | *** | * |
| Example 208 | 8'-(6-{[1,4'-Bipiperidine]-1'-yl}-5-[(dimethylsulfamoyl)amino]pyridin-3-yl)-3'-methyl-2',3'-dihydrospiro[cyclobutane-1,1'-pyrrolo[2,3-c]quinoline]-2'-one | *** | * |
| Example 209 | 8'-(6-Methoxy-5-(((6-methylpyridin-3-yl)sulfonyl)methyl)pyridin-3-yl)-3'-methylspiro[cyclopropane-1,1'-pyrrolo[2,3-c]quinolin]-2'(3'H)-one | **** | |
| Example 210 | N-(2-(3-(2,6-Dimethylpiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)-6-methylpyridine-3-sulfonamide | *** | |
| Example 211 | 6-Methyl-N-(5-(3'-methyl-2'-oxo-2',3'-dihydrospiro[cyclobutane-1,1'-pyrrolo[2,3-c]quinolin]-8'-yl)-2-(3-(2,2,6,6-tetramethylpiperidin-1-yl)propoxy)pyridin-3-yl)pyridine-3-sulfonamide | **** | |
| Example 212 | 8'-(6-{[1,4'-Bipiperidine]-1'-yl}-5-{[ethyl(methyl)sulfamoyl]amino}pyridin-3-yl)-3'-methyl-2',3'-dihydrospiro[cyclobutane-1,1'-pyrrolo[2,3-c]quinoline]-2'-one | *** | *** |
| Example 213 | N-(2-([1,4'-Bipiperidin]-1'-yl)-5-(3'-methyl-2'-oxo-2',3'-dihydrospiro[cyclopropane-1,1'-pyrrolo[2,3-c]quinolin]-8'-yl)pyridin-3-yl)benzenesulfonamide methanesulfonate | *** | *** |
| Example 214 | 8'-(6-{[1,4'-Bipiperidine]-1'-yl}-5-{[ethyl(methyl)sulfamoyl]amino}pyridin-3-yl)-3'-methyl-2',3'-dihydrospiro[cyclopropane-1,1'-pyrrolo[2,3-c]quinoline]-2'-one | ** | ** |
| Example 215 | N-(2-(3-(Dimethylamino)propoxy)-5-(9'-fluoro-3'-methyl-2'-oxo-2',3'-dihydrospiro[cyclopropane-1,1'-pyrrolo[2,3-c]quinolin]-8'-yl)pyridin-3-yl)-4-methylbenzenesulfonamide | ** | * |

| Example Number | nomenclature | ATM (cell) | DNA-PK IC50 |
|---|---|---|---|
| Example 216 | 3'-Methyl-8'-(1-((6-methylpyridin-3-yl)sulfonyl)-2-(2-(piperidin-1-yl)ethyl)-1H-pyrrolo[3,2-b]pyridin-6-yl)spiro[cyclobutane-1,1'-pyrrolo[2,3-c]quinolin]-2'(3'H)-one | *** | *** |
| Example 217 | N-(5-(7'-Fluoro-3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)-6-methylpyridine-3-sulfonamide hydrochloride | *** | *** |
| Example 218 | N-(2-([1,4'-Bipiperidin]-1'-yl)-5-(3'-methyl-2'-oxo-2',3'-dihydrospiro[cyclopropane-1,1'-pyrrolo[2,3-c]quinolin]-8'-yl)pyridin-3-yl)-6-methylpyridine-3-sulfonamide | *** | * |
| Example 219 | 6-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy-2,2-d2)pyridin-3-yl)pyridine-3-sulfonamide | **** | |
| Example 220 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-hydroxybenzenesulfonamide hydrochloride | *** | * |
| Example 221 | 6-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl-d10)propoxy)pyridin-3-yl)pyridine-3-sulfonamide hydrochloride | *** | ** |
| Example 222 | 8'-{5-{[Ethyl(methyl)sulfamoyl]amino}-6-[3-(piperidin-1-yl)propoxy]pyridin-3-yl}-3'-methyl-2',3'-dihydrospiro[cyclobutane-1,1'-pyrrolo[2,3-c]quinoline]-2'-one | *** | *** |
| Example 223 | 2-Amino-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)ethane-1-sulfonamide | *** | * |
| Example 224 | N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | * |
| Example 225 | N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)methanesulfonamide | *** | * |
| Example 226 | 8'-{6-[4-(Dimethylamino)piperidin-1-yl]-5-[(dimethylsulfamoyl)amino]pyridin-3-yl}-3'-methyl-2',3'-dihydrospiro[cyclobutane-1,1'-pyrrolo[2,3-c]quinoline]-2'-one | ** | * |
| Example 227 | N-(5-(3'-Methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)cyclopropanesulfonamide hydrochloride | ** | * |
| Example 228 | N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide | ** | * |
| Example 229 | N-(5-(3'-Methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)methanesulfonamide | ** | * |
| Example 230 | 8'-{5-[(Dimethylsulfamoyl)amino]-6-(4-methylpiperazin-1-yl)pyridin-3-yl}-3'-methyl-2',3'-dihydrospiro[cyclobutane-1,1'-pyrrolo[2,3-c]quinoline]-2'-one | *** | * |
| Example 231 | N-(2-(3-Methyl(2,2,2-trifluoroethyl)amino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | |
| Example 232 | N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)propoxy)pyridin-3-yl)benzenesulfonamide | *** | ** |
| Example 233 | N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)-3-methylisothiazole-5-sulfonamide | *** | ** |
| Example 234 | 2-(3-(Dimethylamino)propoxy)-N,N-dimethyl-5-(3'-methyl-2'-oxo-2',3'-dihydrospiro[cyclobutane-1,1'-pyrrolo[2,3-c]quinolin]-8'-yl)pyridine-3-sulfonamide | *** | |
| Example 235 | N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)propoxy)pyridin-3-yl)cyclopropanesulfonamide | *** | *** |
| Example 236 | N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)propoxy)pyridin-3-yl)methanesulfonamide | *** | ** |
| Example 237 | N-(2-(3-(Dimethylamino)propoxy)-5-(2'-oxo-2',3'-dihydrospiro[cyclobutane-1,1'-pyrrolo[2,3-c]quinolin]-8'-yl)pyridin-3-yl)methanesulfonamide | *** | *** |
| Example 238 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)ethanesulfonamide | *** | *** |
| Example 239 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1,1,1-trifluoromethanesulfonamide | *** | * |
| Example 240 | N-(5-(3'-Methyl-2'-oxo-2',3'-dihydrospiro[cyclobutane-1,1'-pyrrolo[2,3-c]quinolin]-8'-yl)-2-(3-(methylamino)propoxy)pyridin-3-yl)methanesulfonamide formate | *** | * |
| Example 241 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)propane-1-sulfonamide | *** | *** |
| Example 242 | 8'-{5-[(Dimethylsulfamoyl)amino]-6-[3-(pyrrolidin-1-yl)propoxy]pyridin-3-yl}-3'-methyl-2',3'-dihydrospiro[cyclobutane-1,1'-pyrrolo[2,3-c]quinoline]-2'-one | ** | *** |
| Example 243 | N-(5-(3'-Methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)benzenesulfonamide | *** | *** |
| Example 244 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)pyrrolidine-1-sulfonamide | *** | *** |
| Example 245 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-ethylthiazole-5-sulfonamide | *** | * |
| Example 246 | 3-Methyl-N-(5-(3'-methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)isothiazole-5-sulfonamide | *** | * |
| Example 247 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1,1-difluoromethanesulfonamide | *** | * |
| Example 248 | N-(2-(2-(Ethylamino)ethoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | * |

| Example Number | nomenclature | ATM (cell) | DNA-PK IC50 |
|---|---|---|---|
| Example 249 | N-(5-(3'-Methyl-2'-oxo-2',3'-dihydrospiro[cyclobutane-1,1'-pyrrolo[2,3-c]quinolin]-8'-yl)-2-(2-(methylamino)ethoxy)pyridin-3-yl)methanesulfonamide | *** | * |
| Example 250 | N-(5-(3'-Methyl-2'-oxo-2',3'-dihydrospiro[cyclobulane-1,1'-pyrrolo[2,3-c]quinolin]-8'-yl)-2-(2-(methylamino)ethoxy)pyridin-3-yl)benzenesulfonamide | *** | * |
| Example 251 | N-(2-(3'3-Difluoro-[1,4'-bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | ** |
| Example 252 | N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)pyridine-3-sulfonamide | *** | *** |
| Example 253 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)cyclobutanesulfonamide | *** | *** |
| Example 254 | N-(2-(3-Hydroxypropoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | **** | |
| Example 255 | 2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridine-3-sulfonamide | *** | |
| Example 256 | N-(2-(2,2-Difluoro-3-(piperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | **** | |
| Example 257 | N-(5-(8',9'-dihydrospiro[cyclopentane-1,11'-imidazo[1',2':1,5]pyrrolo[2,3-c]quinolin]-2'-yl)-2-(2-(isopropylamino)ethoxy)pyridin-3-yl)methanesulfonamide | *** | * |
| Example 258 | N-(2-(3-(Dimethylamino)propoxy)-5-(3'-methyl-2',3-dioxo-2',3'-dihydrospiro[cyclobutane-1,1'-pyrrolo[2,3-c]quinolin]-8'-yl)pyridin-3-yl)methanesulfonamide | *** | |
| Example 259 | N-(2-((3-(Dimethylamino)propyl)amino)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | |
| Example 260 | N-(5-(3'-Methyl-2'-oxo-2',3'-dihydrospiro[cyclobutane-1,1'-pyrrolo[2,3-c]quinolin]-8'-yl)-2-(4-methylpiperidin-1-yl)pyridin-3-yl)methanesulfonamide | **** | |
| Example 261 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-(1,3-dioxoisoindolin-2-yl)ethane-1-sulfonamide | *** | |
| Example 262 | N-(2-(3-(Dimethylamino)propoxy)-5-(3-fluoro-3'-methyl-2'-oxo-2',3'-dihydrospiro[cyclobutane-1,1'-pyrrolo[2,3-c]quinolin]-8'-yl)pyridin-3-yl)methanesulfonamide | *** | *** |
| Example 263 | N-(3-(3-(Dimethylamino)propoxy)-6-(3'-methyl-2'-oxo-2',3'-dihydrospiro[cyclobutane-1,1'-pyrrolo[2,3-c]quinolin]-8'-yl)pyrazin-2-yl)methanesulfonamide | *** | |
| Example 264 | 2-(Dimethylamino)-N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)ethane-1-sulfonamide | ** | *** |
| Example 265 | N-(2-((2-(Dimethylamino)ethoxy)methyl)-5-(3'-methyl-2'-oxo-2',3'-dihydrospiro[cyclobutane-1,1'-pyrrolo[2,3-c]quinolin]-8'-yl)pyridin-3-yl)methanesulfonamide | **** | |
| Example 266 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-methoxyethane-1-sulfonamide | *** | *** |
| Example 267 | 2-(3-(Dimethylamino)propoxy)-N-methyl-5-(3'-methyl-2'-oxo-2',3'-dihydrospiro[cyclobutane-1,1'-pyrrolo[2,3-c]quinolin]-8'-yl)pyridine-3-sulfonamide | *** | |
| Example 268 | N-(2-(3-(Dimethylamino)propoxy)-5-(9'-fluoro-3'-methyl-2'-oxo-2',3'-dihydrospiro[cyclobutane-1,1'-pyrrolo[2,3-c]quinolin]-8'-yl)pyridin-3-yl)methanesulfonamide | *** | *** |
| Example 269 | N-(5-(3'-Methyl-2'-oxo-2',3'-dihydrospiro[cyclobutane-1,1'-pyrrolo[2,3-c]quinolin]-8'-yl)-2-(4-(piperidin-1-yl)butyl)pyridin-3-yl)methanesulfonamide | *** | |
| Example 270 | N-(2-(3-(3-Hydroxypiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | *** |
| Example 271 | N-(6'-(Dimethylamino)-5-(3'-methyl-2'-oxo-2',3'-dihydrospiro[cyclobutane-1,1'-pyrrolo[2,3-c]quinolin]-8'-yl)-[2,3'-bipyridin]-3-yl)methanesulfonamide | *** | |
| Example 272 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)thiophene-3-sulfonamide | ** | *** |
| Example 273 | 1-Cyano-N-(2-(3-(dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | * |
| Example 274 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-1-(methylsulfonyl)methanesulfonamide | *** | |
| Example 275 | 2-Ethyl-N-(5-(3'-methyl-2'-oxo-2',3'-dihydrospiro[cyclobutane-1,1'-pyrrolo[2,3-c]quinolin]-8'-yl)-2-(2-(methylamino)ethoxy)pyridin-3-yl)thiazole-5-sulfonamide | *** | |
| Example 276 | N-(1'-Methyl-5-(3'-methyl-2'-oxo-2',3'-dihydrospiro[cyclobutane-1,1'-pyrrolo[2,3-c]quinolin]-8'-yl)-1',2',3',6'-tetrahydro-[2,4'-bipyridin]-3-yl)methanesulfonamide | *** | * |
| Example 277 | N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)azetidin-1-yl)pyridin-3-yl)methanesulfonamide | *** | *** |
| Example 278 | N-(2-(3-((2-Methoxyethyl)(methyl)amino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | ** | *** |
| Example 279 | N-(2-(3-(3-Fluoropyrrolidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | ** |

-continued

| Example Number | nomenclature | ATM (cell) | DNA-PK IC50 |
|---|---|---|---|
| Example 280 | N-(2-(3-(3-Methoxypiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | ** |
| Example 281 | N-(2-(2-(Isopropylamino)ethoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | ** |
| Example 282 | N-(2-(3-(3-Fluoropiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | * |
| Example 283 | N-(2-(3-(3-Methoxypyrrolidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | ** |
| Example 284 | N-(2-(3-Hydroxy-2-(piperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | **** | |
| Example 285 | N-(5-(3'-Methyl-2'-oxo-2',3'-dihydrospiro[cyclobutane-1,1'-pyrrolo[2,3-c]quinolin]-8'-yl)-2-(1-methylpiperidin-4-yl)pyridin-3-yl)methanesulfonamide | *** | *** |
| Example 286 | N-(2-(3-(4-Fluoropiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | * |
| Example 287 | N-(2-(2-Hydroxy-3-(piperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | * |
| Example 288 | 8'-{6-[3-(Dimethylamino)azetidin-1-yl]-5-[(dimethylsulfamoyl)amino]pyridin-3-yl}-3'-methyl-2',3'-dihydrospiro[cyclobutane-1,1'-pyrrolo[2,3-c]quinoline]-2'-one | *** | ** |
| Example 289 | N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-methylthiazole-5-sulfonamide | *** | ** |
| Example 290 | 8'-{6-[3-(Dimethylamino)propoxy]-5-[(dimethylsulfamoyl)amino]pyridin-3-yl}-7'-fluoro-3'-methyl-2',3'-dihydrospiro[cyclobutane-1,1'-pyrrolo[2,3-c]quinoline]-2'-one hydrochloride | *** | ** |
| Example 291 | N-(2-(3-(Dimethylamino)propoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | *** | *** |
| Example 292 | M-(2-(3-(Dimethylamino)butoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | |
| Example 293 | N-(2-(3-((2-Cyanoethyl)(methyl)amino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | **** | **** |
| Example 294 | N-(5-(7'-Fluoro-3'-methyl-2'-oxo-2',3'-dihydrospiro[cyclobutane-1,1'-pyrrolo[2,3-c]quinolin]-8'-yl)-2-((2-methoxyethyl)(methyl)amino)propoxy)pyridin-3-yl)morpholine-4-sulfonamide | *** | *** |
| Example 295 | N-(2-(3-(Dimethylamino)-2-hydroxypropoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | ** |
| Example 296 | N-(2-(2-(Dimethylamino)-3-hydroxypropoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | **** | |
| Example 297 | N-(5-(7'-Fluoro-3'-methyl-2'-oxo-2',3'-dihydrospiro[cyclobutane-1,1'-pyrrolo[2,3-c]quinolin]-8'-yl)-2-(3-(4-fluoropiperidin-1-yl)propoxy)pyridin-3-yl)methanesulfonamide hydrochloride | *** | *** |
| Example 298 | N-(2-(3-(3'3-Difluoropiperidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | **** | |
| Example 299 | N-(5-(3'-Methyl-2'-oxo-2',3'-dihydrospiro[cyclobutane-1,1'-pyrrolo[2,3-c]quinolin]-8'-yl)-2-(3-(4-methylpiperazin-1-yl)propoxy)pyridin-3-yl)methanesulfonamide | *** | *** |
| Example 300 | N-(5-(3'-Methyl-2'-oxo-2',3'-dihydrospiro[cyclobutane-1,1'-pyrrolo[2,3-c]quinolin]-8'-yl)-2-(3-(piperazin-1-yl)propoxy)phenyl)methanesulfonamide hydrochloride | *** | |
| Example 301 | 1-Fluoro-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)methanesulfonamide | *** | |
| Example 302 | 1,1-Difluoro-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)methanesulfonamide | *** | * |
| Example 303 | N-(2-(3-(6-Oxa-3-azabicyclo[3.1.1]heptan-3-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | **** | |
| Example 304 | 8'-{5-[(Dimethylsulfamoyl)amino]-6-[3-(morpholin-4-yl)propoxy]pyridin-3-yl}-3'-methyl-2',3'-dihydrospiro[cyclobutane-1,1'-pyrrolo[2,3-c]quinoline]-2'-one | *** | ** |
| Example 305 | N-(5-(3'-Methyl-2'-oxo-2',3'-dihydrospiro[cyclobutane-1,1'-pyrrolo[2,3-c]quinolin]-8'-yl)-2-(3-morpholinopropoxy)pyridin-3-yl)methanesulfonamide | *** | *** |
| Example 306 | N-(5-(3'-Methyl-2'-oxo-2',3'-dihydrospiro[cyclobutane-1,1'-pyrrolo[2,3-c]quinolin]-8'-yl)-2-(3-morpholinopropoxy)pyridin-3-yl)cyclopropanesulfonamide | *** | *** |
| Example 307 | N-(2-(3-(3,3-Difluoroazetidin-1-yl)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide formate | **** | |
| Example 308 | N-(5-(3'-Ethyl-2'-oxo-2',3'-dihydrospiro[cyclobutane-1,1'-pyrrolo[2,3-c]quinolin]-8'-yl)-2-(2-(methylamino)ethoxy)pyridin-3-yl)methanesulfonamide hydrochloride | *** | |

| Example Number | nomenclature | ATM (cell) | DNA-PK IC50 |
|---|---|---|---|
| Example 309 | N-(2-(2-(tert-Butylamino)ethoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | ** |
| Example 310 | N-(2-(Azetidin-3-ylmethoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide hydrochloride | **** | |
| Example 311 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)-3-methoxyazetidine-1-sulfonamide formate | *** | *** |
| Example 312 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)morpholine-4-sulfonamide hydrochloride | *** | |
| Example 313 | N-(2-(3-(Ethyl(methyl)amino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | *** | |
| Example 314 | N-(5-(7'-Fluoro-3'-methyl-2'-oxo-2',3'-dihydrospiro[cyclobutane-1,1'-pyrrolo[2,3-c]quinolin]-8'-yl)-2-(3-((2-methoxyethyl)(methyl)amino)azetidin-1-yl)pyridin-3-yl)methanesulfonamide hydrochloride | *** | |
| Example 315 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)-2,4-difluorobenzenesulfonamide hydrochloride | *** | *** |
| Example 316 | 8'-{6-[3-(Dimethylamino)azetidin-1-yl]-5-[(dimethylsulfamoyl)amino]pyridin-3-yl}-7'-fluoro-3'-methyl-2',3'-dihydrospiro[cyclobutane-1,1'-pyrrolo[2,3-c]quinoline]-2'-one hydrochloride | *** | *** |
| Example 317 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | *** | *** |
| Example 318 | N-(2-(3-(Dimethylamino)azetidin-1-yl)-5-(3'-methyl-2'-oxo-2',3'-dihydrospiro[cyclobutane-1,1'-pyrrolo[2,3-c]quinolin]-8'-yl)pyridin-3-yl)ethanesulfonamide | *** | ** |
| Example 319 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)cyclopropanesulfonamide hydrochloride | *** | *** |
| Example 320 | N-(2-(3-(Dimethylamino)azetidin-1-yl)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide | *** | *** |
| Example 321 | N-(5-(3'-Methyl-2'-oxo-2',3'-dihydrospiro[cyclobutane-1,1'-pyrrolo[2,3-c]quinolin]-8'-yl)-2-(3-(piperidin-1-yl)azetidin-1-yl)pyridin-3-yl)methanesulfonamide hydrochloride | *** | |
| Example 322 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)-2-fluorobenzenesulfonamide hydrochloride | *** | |
| Example 323 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)-4-methylbenzenesulfonamide hydrochloride | *** | *** |
| Example 324 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)benzenesulfonamide hydrochloride | *** | *** |
| Example 325 | N-(5-(2,3'-Dimethyl-2'-oxo-2',3'-dihydrospiro[cyclobutane-1,1'-pyrrolo[2,3-c]quinolin]-8'-yl)-2-(3-(dimethylamino)azetidin-1-yl)pyridin-3-yl)methanesulfonamide formate | *** | *** |
| Example 326 | N-(2-(3-(Ethyl(methyl)amino)azetidin-1-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide hydrochloride | *** | ** |
| Example 327 | N-(5-(4'-Amino-3'-methyl-2'-oxo-2',3'-dihydrospiro[cyclobutane-1,1'-pyrrolo[2,3-c]quinolin]-8'-yl)-2-(3-(dimethylamino)azetidin-1-yl)pyridin-3-yl)methanesulfonamide hydrochloride | **** | |
| Example 328 | N-(5-(7'-Fluoro-3'-methyl-2'-oxo-2',3'-dihydrospiro[cyclobutane-1,1'-pyrrolo[2,3-c]quinolin]-8'-yl)-2-(3-(isopropylamino)azetidin-1-yl)pyridin-3-yl)methanesulfonamide hydrochloride | *** | |
| Example 329 | N-(5-(3'-Methyl-2'-oxo-2',3'-dihydrospiro[cyclobutane-1,1'-pyrrolo[2,3-c]quinolin]-8'-yl)-2-(3-(methylamino)azetidin-1-yl)pyridin-3-yl)methanesulfonamide formate | *** | * |
| Example 330 | N-(5-(7'-Fluoro-3'-methyl-2'-oxo-2',3'-dihydrospiro[cyclobutane-1,1'-pyrrolo[2,3-c]quinolin]-8'-yl)-2-(3-(methylamino)azetidin-1-yl)pyridin-3-yl)methanesulfonamide formate | *** | ** |
| Example 331 | N-(2-(3-(Ethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide | *** | ** |
| Example 332 | 8'-{5-[(Dimethylsulfamoyl)amino]-6-[3-(methylamino)azetidin-1-yl]pyridin-3-yl}-7'-fluoro-3'-methyl-2',3'-dihydrospiro[cyclobutane-1,1'-pyrrolo[2,3-c]quinoline]-2'-one | *** | *** |
| Example 333 | N-(5-7'-Fluoro-3'-methyl-2'-oxo-2',3'-dihydrospiro[cyclobutane-1,1'-pyrrolo[2,3-c]quinolin]-8'-yl)-2-(3-(methylamino)azetidin-1-yl)pyridin-3-yl)cyclopropanesulfonamide | ** | ** |
| Example 334 | N-(5-(7'-Fluoro-3'-methyl-2'-oxo-2',3'-dihydrospiro[cyclobutane-1,1'-pyrrolo[2,3-c]quinolin]-8'-yl)-2-(3-(methylamino)azetidin-1-yl)pyridin-3-yl)ethanesulfonamide | *** | ** |
| Example 335 | N-(5-(3',7'-Dimethyl-2'-oxo-2',3'-dihydrospiro[cyclobutane-1,1'-pyrrolo[2,3-c]quinolin]-8'-yl)-2-(3-(dimethylamino)azetidin-1-yl)pyridin-3-yl)methanesulfonamide | *** | |

-continued

| Example Number | nomenclature | ATM (cell) | DNA-PK IC50 |
|---|---|---|---|
| Example 336 | N-(2-(3-(Dimethylamino)azetidin-1-yl)-5-(3'-ethyl-2'-oxo-2',3'-dihydrospiro[cyclobutane-1,1'-pyrrolo[2,3-c]quinolin]-8'-yl)pyridin-3-yl)methanesulfonamide | *** | |
| Example 337 | N-(2-(3-(Dimethylamino)azetidin-1-yl)-5-(3'-ethyl-2'-oxo-2',3'-dihydrospiro[cyclobutane-1,1'-pyrrolo[2,3-c]quinolin]-8'-yl)pyridin-3-yl)benzenesulfonamide | *** | |
| Example 338 | N-(2-(3-(Dimethylamino)azetidin-1-yl)-5-(3'-methyl-2'-oxo-2',3'-dihydrospiro[cyclobutane-1,1'-pyrrolo[2,3-c]quinolin]-8'-yl)pyridin-3-yl)-2-methylthiazole-5-sulfonamide | *** | *** |
| Example 339 | 8'-{6-[3-(Dimethylamino)azetidin-1-yl]-5-{[ethyl(methyl)sulfamoyl]amino}pyridin-3-yl}-3'-methyl-2',3'-dihydrospiro[cyclobutane-1,1'-pyrrolo[2,3-c]quinoline]-2'-one | *** | *** |
| Example 340 | 8'-{6-[3-(Dimethylamino)azetidin-1-yl]-5-[(methylsulfamoyl)amino]pyridin-3-yl}-7'-fluoro-3'-methyl-2',3'-dihydrospiro[cyclobutane-1,1'-pyrrolo[2,3-c]quinoline]-2'-one | *** | |
| Example 341 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)-1,1-difluoromethanesulfonamide formate | **** | |
| Example 342 | 1-Cyano-N-(2-(3-(dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | **** | |
| Example 343 | N-(2-(3-(Dimethylamino)azetidin-1-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)ethanesulfonamide formate | *** | *** |
| Example 344 | N-(5-(7'-Fluoro-3'-methyl-2'-oxo-2',3'-dihydrospiro[cyclobutane-1,1'-pyrrolo[2,3-c]quinolin]-8'-yl)-2-(3-(morpholinomethyl)azetidin-1-yl)pyridin-3-yl)methanesulfonamide formate | **** | |
| Example 345 | N-(5-(3'-Methyl-2'-oxo-2',3'-dihydrosprro[cyclobutane-1,1'-pyrrolo[2,3-c]quinolin]-8'-yl)-2-(6-methyl-2,6-diazaspiro[3.3]heptan-2-yl)pyridin-3-yl)methanesulfonamide formate | *** | |
| Example 346 | N-(5-(3'-Methyl-2'-oxo-2',3'-dihydrospiro[cyclobutane-1,1'-pyrrolo[2,3-c]quinolin]-8'-yl)-2-(2,6-diazaspiro[3.3]heptan-2-yl)pyridin-3-yl)methanesulfonamide formate | **** | |
| Example 347 | tert-Butyl 6-(5-(3'-methyl-2'-oxo-2',3'-dihydrospiro[cyclobutane-1,1'-pyrrolo[2,3-c]quinolin]-8'-yl)-3-(methylsulfonamido)pyridin-2-yl)-2,6-diazaspiro[3.3]heptane-2-carboxylate | **** | |
| Example 348 | tert-Butyl 5-(5-(3'-methyl-2'-oxo-2',3'-dihydrospiro[cyclobutane-1,1'-pyrrolo[2,3-c]quinolin]-8'-yl)-3-(methylsulfonamido)pyridin-2-yl)hexahydropyrrolo[3,4-c]pyrrolo-2(1H)-carboxylate | **** | |
| Example 349 | N-(2-(Hexahydropyrrolo[3,4-c]pyrrol-2(1H)-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide formate | *** | |
| Example 350 | N-(5'-(3'-Methyl-2'-oxo-2',3'-dihydrosprro[cyclobutane-1,1'-pyrrolo[2,3-c]quinolin]-8'-yl)-2-(5-methylhexahydropyrrolo[3,4-c]pyrrol-2(1H)-yl)pyridin-3-yl)methanesulfonamide formate | *** | *** |
| Example 351 | N-(2-(3-(Dimethylamino)pyrrolidin-1-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide | *** | *** |
| Example 352 | N-(5-(3'-Methyl-2'-oxo-2',3'-dihydrospiro[cyclobutane-1,1'-pyrrolo[2,3-c]quinolin]-8'-yl)-2-(3-(piperidin-1-yl)pyrrolidin-1-yl)pyridin-3-yl)methanesulfonamide hydrochloride | *** | *** |
| Example 353 | N-(5-(3'-Methyl-2'-oxo-2',3'-dihydrospiro[cyclobutane-1,1'-pyrrolo[2,3-c]quinolin]-8'-yl)-2-(3-methyl-3-(piperidin-1-yl)pyrrolidin-1-yl)pyridin-3-yl)methanesulfonamide hydrochloride | **** | |
| Example 354 | N-(5-(3'-Methyl-2'-oxo-2',3'-dihydrospiro[cyclobutane-1,1'-pyrrolo[2,3-c]quinolin]-8'-yl)-2-(4'-methyl-[1,4'-bipiperidin]-1-yl)pyridin-3-yl)methanesulfonamide | **** | |
| Example 355 | 8'-{5-[(Dimethylsulfamoyl)amino]-6-[4-(morpholin-4-yl)piperidin-1-yl]pyridin-3-yl}-3'-methyl-2',3'-dihydrospiro[cyclobutane-1,1'-pyrrolo[2,3-c]quinoline]-2'-one | *** | *** |
| Example 356 | N-(5-(3'-Methyl-2'-oxo-2',3'-dihydrospiro[cyclobutane-1,1'-pyrrolo[2,3-c]quinolin]-8'-yl)-2-(4-morpholinopiperidin-1-yl)pyridin-3-yl)cyclopropanesulfonamide hydrochloride | * | ** |
| Example 357 | N-(5-(3'-Methyl-2'-oxo-2',3'-dihydrospiro[cyclobutane-1,1'-pyrrolo[2,3-c]quinolin]-8'-yl)-2-(4-morpholinopiperidin-1-yl)pyridin-3-yl)methanesulfonamide hydrochloride | ** | ** |
| Example 358 | N-(2-([1,4'-Bipiperidin]-1'-yl)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | ** | *** |
| Example 359 | tert-Butyl 3-(5-(3'-methyl-2'-oxo-2',3'-dihydrospiro[cyclobutane-1,1'-pyrrolo[2,3-c]quinolin]-8'-yl)-3-(methylsulfonamido)pyridin-2-yl)-3,6-diazabicyclo[3.1.1]heptane-6-carboxylate | **** | |
| Example 360 | N-(2-(3',6-Diazabicyclo[3.1.1]heptan-3-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide formate | **** | |
| Example 361 | N-(5-(3'-Methyl-2'-oxo-2',3'-dihydrospiro[cyclobutatie-1,1'-pyrrolo[2,3-c]quinolin]-8'-yl)-2-(6-methyl-3,6-diazabicyclo[3.1.1]heptan-3-yl)pyridin-3-yl)methanesulfonamide formate | **** | |
| Example 362 | N-(2-((3-(Dimethylamino)propyl)(methyl)amino)-5-(3'-methyl-2'-oxo-2',3'-dihydrospiro[cyclobutane-1,1'-pyrrolo[2,3-c]quinolin]-8'-yl)pyridin-3-yl)methanesulfonamide hydrochloride | *** | |

-continued

| Example Number | nomenclature | ATM (cell) | DNA-PK IC50 |
|---|---|---|---|
| Example 363 | N-(2-((2-(Dimethylamino)ethyl)(methyl)amino)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | **** | |
| Example 364 | 8'-(2-(Dimethylamino)pyrimidin-5-yl)-7'-fluoro-3'-methylspiro[cyclobutane-1,1'-pyrrolo[2,3-c]quinolin]-2'(3'H)-one | **** | |
| Example 365 | N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)cyclopropanesulfonamide hydrochloride | *** | *** |
| Example 366 | N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)-2-methylpropane-2-sulfonamide | *** | ** |
| Example 367 | N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)-1-methylcyclopropane-1-sulfonamide | *** | *** |
| Example 368 | 1,1-Difluoro-N-(5-(7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 369 | 8'-{5-[(Dimethylsulfamoyl)amino]-6-{2-[(propan-2-yl)amino]ethoxy}pyridin-3-yl}-7'-fluoro-3'-methyl-2',3'-dihydrospiro[cyclobutane-1,1'-pyrrolo[2,3-c]quinoline]-2'-one hydrochloride | *** | ** |
| Example 370 | N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)azetidine-1-sulfonamide | *** | *** |
| Example 371 | 3-Fluoro-N-(5-(7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)azetidine-1-sulfonamide | *** | *** |
| Example 372 | 3-Cyano-N-(5-(7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)azetidine-1-sulfonamide | **** | |
| Example 373 | N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)morpholine-4-sulfonamide hydrochloride | *** | *** |
| Example 374 | 1-Cyano-N-(5-(7'-fluoro-3'-methyl-2'-oxo-2',3'-dihydrospiro[cylclobutane-1,1'-pyrrolo[2,3-c]quinolin]-8'-yl)-2-(2-(isopropylamino)ethoxy)pyridin-3-yl)methanesulfonamide hydrochloride | *** | |
| Example 375 | 2-(Dimethylamino)-N-(5-(7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)ethane-1-sulfonamide hydrochloride | *** | *** |
| Example 376 | N-(2-(2-(Cyclopropylamino)ethoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | *** | |
| Example 377 | N-(2-(2-(Cyclobutylamino)ethoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide | **** | |
| Example 378 | N-(5-(7'-Fluoro-3'-methyl-2'-oxo-2',3'-dihydrospiro[cyclobutane-1,1'-pyrrolo[2,3-c]quinolin]-8'-yl)-2-(2-((2,2,2-trifluoroethyl)amino)ethoxy)pyridin-3-yl)methanesulfonamide | **** | |
| Example 379 | N-(2-(2-((2,2-Difluoroethyl)amino)ethoxy)-5-(7'-fluoro-3'-methyl-2'-oxo-2',3'-dihydrospiro[cyclobutane-1,1'-pyrrolo[2,3-c]quinolin]-8'-yl)pyridin-3-yl)methanesulfonamide | **** | |
| Example 380 | N-(5-(7'-Fluoro-3'-methyl-2'-oxo-2',3'-dihydrospiro[cyclobutane-1,1'-pyrrolo[2,3-c]quinolin]-8'-yl)-2-(2-((2-fluoroethyl)amino)ethoxy)pyridin-3-yl)methanesulfonamide hydrochloride | *** | |
| Example 381 | cis-N-(5-(7'-Fluoro-3-hydroxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | *** | |
| Example 382 | trans-N-(5-(7'-Fluoro-3-hydroxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 383 | trans-N-(2-(3-(Dimethylamino)propoxy)-5-(3-hydroxy-3'-methyl-2'-oxo-2',3'-dihydrospiro[cyclobutane-1,1'-pyrrolo[2,3-c]quinolin]-8'-yl)pyridin-3-yl)methanesulfonamide | *** | *** |
| Example 384 | trans-N-(2-(2-(Isopropylamino)ethoxy)-5-(3-methoxy-3'-methyl-2'-oxo-2',3'-dihydrospiro[cyclobutane-1,1'-pyrrolo[2,3-c]quinolin]-8'-yl)pyridin-3-yl)methanesulfonamide hydrochloride | *** | * |
| Example 385 | cis-N-(5-(7'-Fluoro-3-methoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | * |
| Example 386 | trans-N-(5-(7'-Fluoro-3-methoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 387 | cis-N-(5-(7'-Fluoro-3-methoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)cyclopropanesulfonamid | *** | *** |

| Example Number | nomenclature | ATM (cell) | DNA-PK IC50 |
|---|---|---|---|
| Example 388 | trans-N-(5-(7'-Fluoro-3-methoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)cyclopropanesulfonamide | *** | *** |
| Example 389 | cis-8'-{5-[(Dimethylsulfamoyl)amino]-6-{2-[(propan-2-yl)amino]ethoxy}pyridine-3-yl}-7'-fluoro-3-Methoxy-3'-methyl-2',3'-dihydrospiro[cyclobutane-1,1'-pyrrolo[2,3-c]quinoline]-2'-one | *** | *** |
| Example 390 | trans-8'-{5-[(Dimethylsulfamoyl)amino]-6-{2-[(propan-2-yl)amino]ethoxy}pyridine-3-yl}-7'-fluoro-3-Methoxy-3'-methyl-2',3'-dihydrospiro[cyclobutane-1,1'-pyrrolo[2,3-c]quinoline]-2'-one | *** | *** |
| Example 391 | cis-N-(2-([1,4'-Bipiperidin]-1'-yl)-5-(7'-fluoro-3-methoxy-3'-methyl-2'-oxo-2',3'-dihydrospiro[cyclobutane-1,1'-pyrrolo[2,3-c]quinolin]-8'-yl)pyridin-3-yl)methanesulfonamide | *** | *** |
| Example 392 | trans-N-(2-([1,4'-Bipiperidin]-1'-yl)-5-(7'-fluoro-3-methoxy-3'-methyl-2'-oxo-2',3'-dihydrospiro[cyclobutane-1,1'-pyrrolo[2,3-c]quinolin]-8'-yl)pyridin-3-yl)methanesulfonamide | *** | *** |
| Example 393 | cis-N-(5-(3-Ethoxy-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 394 | trans-N-(5-(3-Ethoxy-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 395 | cis-N-(5-(7'-Fluoro-3-isopropoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 396 | trans-N-(5-(7'-Fluoro-3-isopropoxy-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 397 | cri-N-(5-(7'-Fluoro-3'-methyl-2'-oxo-3-(1-phenylethoxy)-2',3'-dihydrospiro[cyclobutane-1,1'-pyrrolo[2,3-c]quinolin]-8'-yl)-2-(2-(isopropylamino)ethoxyl)pyridin-3-yl)methanesulfonamide | *** | * |
| Example 398 | trans-N-(5-(7'-Fluoro-3'-methyl-2'-oxo-3-(1-phenylethoxy)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 399 | 2-(3-(Dimethylamino)propoxy)-5-(3'-methyl-2'-oxo-2',3'-dihydrospiro[cyclobutane-1,1'-pyrrolo[2,3-c]quinolin]-8'-yl)-3-(methylsulfonamido)benzoic acid | **** | |
| Example 400 | cis-N-(5-(7'-Fluoro-3'-methyl-2'-oxo-3-phenoxy-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | ** | *** |
| Example 401 | trans-N-(5-(7'-Fluoro-3'-methyl-2'-oxo-3-phenoxy-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 402 | cis-8'-{5-[(Dimethylsulfamoyl)amino]-6-{2-[(propan-2-yl)amino]ethoxy}pyridine-3-yl}-7'-fluoro-3'-methyl-3-phenoxy-2',3'-dihydrospiro[cyclobutane-1,1'-pyrrolo[2,3-c]quinoline]-2'-one hydrochloride | *** | *** |
| Example 403 | trans-8'-{5-[(Dimethylsulfamoyl)amino]-6-{2-[(propan-2-yl)amino]ethoxy}pyridine-3-yl}-7'-fluoro-3'-methyl-3-phenoxy-2',3'-dihydrospiro[cyclobutane-1,1'-pyrrolo[2,3-c]quinoline]-2'-one hydrochloride | **** | |
| Example 404 | cis-N-(5-(7'-Fluoro-3-(methoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | ** |
| Example 405 | trans-N-(5-(7'-Fluoro-3-(methoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 406 | cis-y-(5-(3-(Ethoxymethyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | ** |
| Example 407 | trans-N-(5-(3-(Ethoxymethyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 408 | trans-N-(5-(7'-Fluoro-3'-methyl-2'-oxo-3-(phenoxymethyl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 409 | cis-N-(5-(7'-Fluoro-3'-methyl-2'-oxo-3-(phenoxymethyl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | * |
| Example 410 | cis-N-(5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | * |
| Example 411 | trans-N-(5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 412 | cis-N-(5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)propane-2-sulfonamide | *** | *** |

| Example Number | nomenclature | ATM (cell) | DNA-PK IC50 |
|---|---|---|---|
| Example 413 | trans-N-(5-(7'-Fluoro-3-(isopropoxymethyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)propane-2-sulfonamide | *** | |
| Example 414 | cis-N-(5-(7'-Fluoro-3'-methyl-2'-oxo-3-phenyl-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | *** | *** |
| Example 415 | trans-N-(5-(7'-Fluoro-3'-methyl-2'-oxo-3-phenyl-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | *** | *** |
| Example 416 | cis-N-(5-(3-(4-Chlorophenyl)-7'-fluoro-3'-methyl-2'-oxo-2',3'-dihydrospiro[cyclobntane-1,1'-pyrrolo[2,3-c]quinolin]-8'-yl)-2-(2-(isopropylamino)ethoxy)pyridin-3-yl)methanesulfonamide | *** | *** |
| Example 417 | trans-Nr-(5-(3-(4-Chlorophenyl)-7'-fluoro-3'-methyl-2'-oxo-2',3'-dihydrospiro[cyclobutane-1,1'-pyrrolo[2,3-c]quinolin]-8'-yl)-(2-(isopropylamino)ethoxy)pyridin-3-yl)methanesulfonamide | **** | *** |
| Example 418 | cis-N-(5-(3-(3-Chlorophenyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 419 | trans-N-(5-(3-(3-Chlorophenyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | *** |
| Example 420 | cis-N-(5-(7'-Fluoro-3-(4-methoxyphenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | *** | *** |
| Example 421 | trans-N-(5-(7'-Fluoro-3-(4-methoxyphenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | **** | *** |
| Example 422 | cis-N-(5-(7'-Fluoro-3-(4-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 423 | trans-N-(5-(7'-Fluoro-3-(4-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 424 | cis-N-(5-(7'-Fluoro-3-(3-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 425 | trans-N-(5-(7'-Fluoro-3-(3-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | *** |
| Example 426 | cis-N-(5-(7'-Fluoro-3-(2-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 427 | trans-N-(5-(7'-Fluoro-3-(2-fluorophenyl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | *** |
| Example 428 | cis-N-(5-(7'-Fluoro-3-(6-methoxypyridin-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 429 | trans-N-(5-(7'-Fluoro-3-(6-methoxypyridin-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 430 | cis-N-(5-(7'-Fluoro-3-(6-methoxypyridin-3-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 431 | trans-N-(5-(7'-Fluoro-3-(6-methoxypyridin-3-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | **** |
| Example 432 | cis-N-(5-(7'-Fluoro-3-(2-methoxypyridin-4-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 433 | trans-N-(5-(7'-Fluoro-3-(2-methoxypyridin-4-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | *** |
| Example 434 | cis-N-Fluoro-3'-methyl-2'-oxo-3-(pyridin-2-yl)-2',3'-dihydrospiro[cyclobutane-1,1'-pyrrolo[-(5-(72,3-c]quinolin]-8'-yl)-2-(2-(isopropylamino)ethoxy)pyridin-3-yl)methanesulfonamide | *** | *** |
| Example 435 | trans-N-(5-(7'-Fluoro-3'-methyl-2'-oxo-3-(pyridin-2-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | *** |
| Example 436 | cis-N-(5-(7'-Fluoro-3'-methyl-2'-oxo-3-(pyridin-3-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 437 | trans-N-(5-(7'-Fluoro-3'-methyl-2'-oxo-3-(pyridin-3-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | *** |

-continued

| Example Number | nomenclature | ATM (cell) | DNA-PK IC50 |
|---|---|---|---|
| Example 438 | cis-N-(5-(7'-Fluoro-3'-methyl-2'-oxo-3-(pyridin-4-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 439 | trans-N-(5-(7'-Fluoro-3'-methyl-2'-oxo-3-(pyridin-4-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | *** |
| Example 440 | cis-N-(5-(7'-Fluoro-3'-methyl-2'-oxo-3-(6-oxo-1,6-dihydropyridin-2-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | *** |
| Example 441 | trans-N-(5-(7'-Fluoro-3'-methyl-2'-oxo-3-(6-oxo-1,6-dihydropyridin-2-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 442 | cis-N-(5-(7'-Fluoro-3'-methyl-2'-oxo-3-(6-oxo-1,6-dihydropyridin-3-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 443 | trans-N-(5-(7'-Fluoro-3'-methyl-2'-oxo-3-(6-oxo-1,6-dihydropyridin-3-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 444 | cis-N-(5-(7'-Fluoro-3'-methyl-2'-oxo-3-(2-oxo-1,2-dihydropyridin-4-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 445 | trans-N-(5-(7'-Fluoro-3'-methyl-2'-oxo-3-(2-oxo-1,2-dihydropyridin-4-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 446 | N-(5-(7'-Fluoro-3,3,3'-trimethyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | * |
| Example 447 | trans-N-(5-(7'-Fluoro-3,3'-dimethyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 448 | cis-N-(5-(7'-Fluoro-3,3'-dimethyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 449 | 2-(3-(Dimethylamino)propoxy)-5-(3'-methyl-2'-oxo-2',3'-dihydrospiro[cyclobutane-1,1'-pyrrolo[2,3-c]quinolin]-8'-yl)-3-(methylsulfonamido)benzamide | *** | |
| Example 450 | trans-N-(5-(3-Benzyl-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 451 | cis-N-(5-(3-Benzyl-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 452 | cis-N-(5-(3-((Dimethylamino)methyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 453 | trans-N-(5-(3-((Dimethylamino)methyl)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 454 | cis-N-(5-(7'-Fluoro-3'-methyl-3-((methylamino)methyl)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 455 | trans-N-(5-(7'-Fluoro-3'-methyl-3-((methylamino)methyl)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | **** | |
| Example 456 | cis-N-(5-(7'-Fluoro-3-(2-hydroxypropan-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 457 | trans-N-(5-(7'-Fluoro-3-(2-hydroxypropan-2-yl)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 458 | N-(5-(7''-Fluoro-3''-methyl-2''-oxo-2'',3''-dihydrodispiro[piperidine-4,1'-cyclobutane-3',1''-pyrrolo[2,3-c]quinolin]-8''-yl)-2-(2-(isopropylamino)ethoxy)pyridin-3-yl)methanesulfonamide | **** | |
| Example 459 | cis-N-(5-(7'-Fluoro-3'-methyl-2'-oxo-3-(phenylamino)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | ** |
| Example 460 | trans-N-(5-(7'-Fluoro-3'-methyl-2'-oxo-3-(phenylamino)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | *** | *** |
| Example 461 | cis-N-(5-(3-((4-Chlorophenyl)amino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | *** |
| Example 462 | trans-N-(5-(3-((4-Chlorophenyl)amino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 463 | cis-N-(5-(7'-Fluoro-3'-methyl-3-(methyl(phenyl)amino)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | * |

-continued

| Example Number | nomenclature | ATM (cell) | DNA-PK IC50 |
|---|---|---|---|
| Example 464 | trans-N-(5-(7'-Fluoro-3'-methyl-3-(methyl(phenyl)amino)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 465 | cis-N-(5-(3-(Dimethylamino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 466 | trans-N-(5-(3-(Dimethylamino)-7'-fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 467 | cis-N-(5-(7'-Fluoro-3'-methyl-2'-oxo-3-(pyrrolidin-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 468 | trans-N-(5-(7'-Fluoro-3'-methyl-2'-oxo-3-(pyrrolidin-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 469 | cis-N-(5-(7'-Fluoro-3'-methyl-2'-oxo-3-(piperidin-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 470 | trans-N-(5-(7'-Fluoro-3'-methyl-2'-oxo-3-(piperidin-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | *** | |
| Example 471 | cis-N-(5-(7'-Fluoro-3'-methyl-3-morpholino-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 472 | trans-N-(5-(7'-Fluoro-3'-methyl-3-morpholino-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 473 | trans-N-(5-(7'-Fluoro-3'-methyl-3-(methylamino)-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 474 | trans-N-(5-(7'-Fluoro-3-((2-methoxyethyl)amino)-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 475 | cis-N-(5-(7'-Fluoro-3'-methyl-2'-oxo-3-(2-oxopyridin-1(2H)-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 476 | cis-N-(5-(7'-Fluoro-3'-methyl-2'-oxo-3-(1H-pyrazol-1-yl)-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 477 | N-(2-(3-(Dimethylamino)propoxy)-5-(3'-methyl-2'-oxo-2',3'-dihydrospiro[azetidine-3,1'-pyrrolo[2,3-c]quinolin]-8'-yl)pyridin-3-yl)methanesulfonamide | **** | |
| Example 478 | N-(5-(1,3'-Dimethyl-2'-oxo-2',3'-dihydrospiro[azetidine-3,1'-pyrrolo[2,3-c]quinolin]-8'-yl)-2-(3-(dimethylamino)propoxy)pyridin-3-yl)methanesulfonamide | *** | *** |
| Example 479 | tert-Butyl 8'-(6-(3-(dimethylamino)propoxy)-5-(methylsulfonamido)pyridin-3-yl)-3'-methyl-2'-oxo-2',3'-dihydrospiro[azetidine-3,1'-pyrrolo[2,3-c]quinoline]-1-carboxylate | *** | |
| Example 480 | N-(2-(3-(Dimethylamino)azetidin-1-yl)-5-(3'-methyl-2'-oxo-1-(2,2,2-trifluoroethyl)-2',3'-dihydrospiro[azetidine-3,1'-pyrrolo[2,3-c]quinolin]-8'-yl)pyridin-3-yl)methanesulfonamide | *** | |
| Example 481 | N-(5-(7'-Fluoro-1,3'-dimethyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | *** | |
| Example 482 | N-(5-(1-Ethyl-7'-fluoro-3'-methyl-2'-oxo-2',3'-dihydrospiro[azeridine-3,1'-pyrrolo[2,3-c]quinolin]-8'-yl)-2-(2-(isopropylamino)ethoxy)pyridin-3-yl)methanesulfonamide | *** | |
| Example 483 | N-(5-(7'-Fluoro-1-isopropyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)ethanesulfonamide | *** | ** |
| Example 484 | N-(5-(7'-Fluoro-1-isopropyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)cyclopropanesulfonamide | *** | *** |
| Example 485 | N-(5-(7'-Fluoro-1-isopropyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)propane-2-sulfonamide | *** | *** |
| Example 486 | N-(2-([1,4'-Bipiperidin]-1'-yl)-5-(7'-fluoro-1-isopropyl-3'-methyl-2'-oxo-2',3'-dihydrospiro[azetidine-3,1'-pyrrolo[2,3-c]quinolin]-8'-yl)pyridin-3-yl)methanesulfonamide | *** | *** |
| Example 487 | N-(5-(1-(sec-Butyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 488 | N-(5-(7'-Fluoro-3'-methyl-2'-oxo-1-propyl-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 489 | N-(5-(1-Butyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 490 | N-(5-(7'-Fluoro-3'-methyl-2'-oxo-1-(pentan-3-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |

-continued

| Example Number | nomenclature | ATM (cell) | DNA-PK IC50 |
|---|---|---|---|
| Example 491 | N-(5-(7'-Fluoro-1-isobutyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 492 | N-(5-(7'-Fluoro-1-isopentyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 493 | (S)-N-(5-(7'-Fluoro-3'-methyl-2'-oxo-1-(1-phenylethyl)-2',3'-dihydrospiro[azetidine-3,1-pyrrolo[2,3-c]quinolin]-8'-yl)-2-(2-(isopropylamino)ethoxy)pyridin-3-yl)methanesulfonamide | *** | |
| Example 494 | (R)-N-(5-(7'-Fluoro-3'-methyl-2'-oxo-1-(1-phenylethyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 495 | N-(5-(1-Benzyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 496 | N-(5-(1-Cyclopropyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 497 | N-(5-(1-Cyclobutyl-7'-fluoro-3'-methyl-2'-oxo-2',3'-dihydrospiro[azetidine-3,1-pyrrolo[2,3-c]quinolin]-8'-yl)-2-(2-(isopropylamino)ethoxy)pyridin-3-yl)methanesulfonamide hydrochloride | *** | *** |
| Example 498 | N-(5-(1-Cyclopentyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | ** |
| Example 499 | N-(5-(1-Cyclohexyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 500 | N-(5-(7'-Fluoro-S'-methyl-2'-oxo-1-(tetrahydro-2H-pyran-4-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | *** | |
| Example 501 | N-(5-(7'-Fluoro-3'-methyl-2'-oxo-1-(piperidin-4-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 502 | N-(5-(7'-Fluoro-3'-methyl-1-(1-methylpiperidin-4-yl)-2'-oxo-2',3'-dihydrospiro[azetidine-3,1'-pyrrolo[2,3-c]quinolin]-8'-yl)-2-(2-(isopropylamino)ethoxy)pyridin-3-yl)melhanesulfonamide | **** | |
| Example 503 | N-(5-(1-(1-Acetylpiperidin-4-yl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 504 | N-(5-(7'-Fluoro-1-(cis-4-hydroxycyclohexyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 505 | N-(5-(7'-Fluoro-1-(trans-4-hydroxycyclohexyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfotiamide | **** | |
| Example 506 | N-(5-(7'-Fluoro-1-(2-hydroxyethyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 507 | N-(5-(7'-Fluoro-1-(2-methoxyethyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 508 | N-(5-(1-(2,2-Difluoroethyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 509 | (R)-N-(5-(1-(2,3-Dihydroxypropyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 510 | (S)-N-(5-(1-(2,3-Dihydroxypropyl)-7'-fluoro-3'-methyl-2'-oxo-2',3'-dihydrospiro[azetidine-3,1'-pytrolo[2,3-c]quinolin]-8'-yl)-2-(2-(isopropylamino)ethoxy)pyridin-3-yl)methanesulfonamide | **** | |
| Example 511 | N-(5-(1-Acetyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 512 | N-(5-(7'-Fluoro-1-isobutylyl-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 513 | Methyl 7'-fluoro-8'-(6-(2-(isopropylamino)ethoxy)-5-(methylsulfonamido)pyridin-3-yl)-3'-methyl-2'-oxo-2',3'-dihydrospiro[azetidine-3,1'-pyrrolo[2,3-c]quinoline]-1-carboxylate | **** | |
| Example 514 | Isopropyl 7'-fluoro-8'-(6-(2-(isopropylamino)ethoxy)-5-(methylsulfonamido)pyridin-3-yl)-3'-methyl-2'-oxo-2',3'-dihydrospiro[azetidine-3,1'-pyrrolo[2,3-c]quinoline]-1-carboxylate | *** | |
| Example 515 | N-(5-(7'-Fluoro-3'-methyl-2'-oxo-1-(phenylsulfonyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 516 | N-(5-(1-Benzoyl-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |

| Example Number | nomenclature | ATM (cell) | DNA-PK IC50 |
|---|---|---|---|
| Example 517 | 7'-Fluoro-8'-(6-(2-(isopropylamino)ethoxy)-5-(methylsulfonamido)pyridin-3-yl)-3'-methyl-2'-oxo-2',3'-dihydrospiro[azetidine-3,1'-pviTolo[2,3-c]quinoline]-1-carboxamide | **** | |
| Example 518 | 7'-Fluoro-8'-(6-(2-(isopropylamino)ethoxy)-5-(methylsulfonamido)pyridin-3-yl)-N,N,3'-trimethyl-2'-oxo-2',3'-dihydrospiro[azetidine-3,1'-pyrrolo[2,3-c]quinoline]-1-carboxamide | **** | |
| Example 519 | N-(5-(7'-Fluoro-3'-methyl-2'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | *** | * |
| Example 520 | N-(5-(7'-Fluoro-3'-methyl-2'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)-2-methylthiazole-5-sulfonamide | *** | *** |
| Example 521 | N-(5-(7'-Fluoro-3'-methyl-1'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)-3-methylisothiazole-5-sulfonamide | *** | |
| Example 522 | N-(5-(7'-Fluoro-3'-methyl-2'-oxo-1-phenyl-2',3'-dihydrospiro[azetidine-3,1'-pyrrolo[2,3-c]quinolin]-8'-yl)-2-(2-(isopropylamino)ethoxy)pyridin-3-yl)ethanesulfonamide hydrochloride | *** | ** |
| Example 523 | N-(5-(1-(4-Chlorophenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | *** | * |
| Example 524 | N-(5-(1-(3-Chlorophenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | *** |
| Example 525 | N-(5-(1-(2-Chiorophenyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | ** |
| Example 526 | N-(5-(7'-Fluoro-3'-methyl-2'-oxo-1-(p-tolyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | *** | * |
| Example 527 | N-(5-(7'-Fluoro-3'-methyl-2'-oxo-1-(m-tolyl)-2',3'-dihy'drospiro[azetidine-3,1'-pyrrolo[2,3-c]quinolin]-8'-yl)-2-(2-(isopropylamino)ethoxy)pyridin-3-yl)methanesulfonamide | *** | *** |
| Example 528 | N-(5-(7'-Fluoro-3'-methyl-2'-oxo-1-(o-tolyl)-2',3'-dihydrospiro[azelidine-3,1'-pyrrolo[2,3-c]quinolin]-8'-yl)-2-(2-(isopropylamino)ethoxy)pyridin-3-yl)methanesulfonamide | *** | * |
| Example 529 | N-(5-(1-(4-Ethylphenyl)-7'-fluoro-3'-methyl-2'-oxo-2',3'-dihydrospiro[azetidine-3,1'-pyrrolo[2,3-c]quinolin]-8'-yl)-2-(2-(isopropylatmino)ethoxy)pyridin-3-yl)methanesulfonamide | *** | *** |
| Example 530 | N-(5-(7'-Fluoro-1-(4-isopropylphenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | ** |
| Example 531 | N-(5-(1-(4-(tert-butyl)phenyl)-7'-fluoro-3'-methyl-2'-oxo-2',3'-dihydrospiro[azetidine-3,1'-pyrrolo[2,3-c]quinolin]-8'-yl)-2-(2-(isopropylannno)ethoxy)pyridin-3-yl)methanesulfonamide | *** | |
| Example 532 | N-(5-(7'-Fluoro-1-(4-(methoxymethyl)phenyl)-3'-methyl-2'-oxo-2',3'-dihydrospiro[azetidine-3,1'-pyrrolo[2,3-c]quinolin]-8'-yl)-2-(2-(isopropylamino)ethoxy)prridin-3-yl)methanesulfonamide | *** | * |
| Example 533 | N-(5-(7'-Fluoro-1-(4-methoxyphenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | *** |
| Example 534 | N-(5-(7'-Fluoro-1-(3-methoxyphenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 535 | N-(5-(7'-Fluoro-1-(2-methoxyphenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | *** |
| Example 536 | N-(5-(7'-Fluoro-3'-methyl-2'-oxo-1-(4-(trifluoromethyl)phenyl)-2',3'-dihydtospiro[azetidine-3,1'-pyrrolo[2,3-c]quinolin]-8'-yl)-2-(2-(isopropylamino)ethoxy)pyridin-3-yl)methanesulfonamide hydrochloride | *** | *** |
| Example 537 | N-(5-(7'-Fluoro-3'-methyl-2'-oxo-1-(3-(trifluoromethyl)phenyl)-2',3'-dihydrospiro[azetidine-3,1'-pyrrolo[2,3-c]quinolin]-8'-yl)-2-(2-(isopropxlamino)ethoxy)pyridin-3-yl)methanesulfonamide | *** | |
| Example 538 | N-(5-(7'-Fluoro-1-(4-fluorophenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | *** | *** |
| Example 539 | N-(5-(7'-Fluoro-1-(3-fluorophenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | * |
| Example 540 | N-(5-(7'-Fluoro-1-(2-fluoropbenyl)-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | * |
| Example 541 | N-(5-(7'-Fluoro-3'-methyl-2'-oxo-1-(4-(trifluoromethoxy)phenyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | *** |

-continued

| Example Number | nomenclature | ATM (cell) | DNA-PK IC50 |
|---|---|---|---|
| Example 542 | N-(5-(7'-Fluoro-3'-methyl-2'-oxo-1-(3-(trifluoromethoxy)phenyl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 543 | N-(5-(1-([1,1'-Biphenyl]-4-yl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | *** |
| Example 544 | N-(5-(1-(Benzo[d][1,3]dioxol-5-yl)-7'-fluoro-3'-methyl-2'-oxo-2',3'-dihydrospiro[azetidine-3,1'-pyrrolo[2,3-c]quinolin]-8'-yl)-2-(2-(isopropxlamino)ethoxy)pyridin-3-yl)methanesulfonamide | *** | * |
| Example 545 | N-(5-(1-(2,3-Dihydrobenzo[b][1,4]dioxin-6-yl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | ** |
| Example 546 | N-(5-(1-(3,4-Dimethoxypheuyl)-7'-fluoro-3'-methyl-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | *** | |
| Example 547 | N-(5-(7'-Fluoro-3'-methyl-2'-oxo-1-(pyridin-4-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 548 | N-(5-(7'-Fluoro-3'-methyl-2'-oxo-1-(pyridin-3-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | *** | |
| Example 549 | N-(5-(7'-Fluoro-3'-methyl-2'-oxo-1-(pyrimidin-5-yl)-2',3'-dihydrospiro[azetidine-3,1 pyrrolo[2,3-c]quinolin]-8'-yl)-2-(2-(isopropylamino)ethoxy)pyridin-3-yl)methanesulfonamide | **** | |
| Example 550 | N-(5-(7'-Fluoro-3'-methyl-2'-oxo-1-(2H-tetrazol-5-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 551 | N-(5-(7'-Fluoro-3'-methyl-2'-oxo-1-(pyrimidin-2-yl)-2',3'-dihydrospiro[azetidine-3,1'-pyrrolo[2,3-c]quinolin]-8'-yl)-2-(2-(isopropylamino)ethoxy)pyridin-3-yl)methanesulfonamide hydrochloride | **** | |
| Example 552 | N-(5-(7'-Fluoro-3'-methyl-1-(2-methyl-2H-tetrazol-5-yl)-2'-oxo-2',3'-dihydrospiro[azetidine-3,1'-pyrrolo[2,3-c]quinolin]-8'-yl)-2-(2-(isopropylamino)ethoxx)pyridin-3-yl)methanesulfonamide | **** | |
| Example 553 | N-(5-(7'-Fluoro-3'-methyl-1-(1-methyl-1H-tetrazol-5-yl)-2'-oxo-2',3'-dihydrospiro[azetidine-3,1'-pyrrolo[2,3-c]quinolin]-8'-yl)-2-(2-(isopropylamino)ethoxy)pyridin-3-yl)methanesulfonamide | **** | |
| Example 554 | N-(5-(3'3-Difluoro-3'-methyl-2'-oxo-2',3'-dihydrospiro[cyclobutane-1,1'-pyrrolo[2,3-c]quinolin]-8'-yl)-2-(3-(dimethylamino)propoxy)pyridin-3-yl)methanesulfonamide | *** | *** |
| Example 555 | N-(5-(7'-Fluoro-3'-methyl-2'-oxo-2',3'-dihydrospiro[oxetane-3,1'-pyrrolo[2,3-c]quinolin]-8'-yl)-2-(2-(isopropylamino)ethoxy)pyridin-3-yl)methanesulfonamide hydrochloride | *** | |
| Example 556 | N-(5-(9'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide hydrochloride | *** | * |
| Example 557 | 8'-{6-[3-(Dimethylamino)propoxy]-5-[(dimethylsulfamoyl)amino]pyridin-3-yl}-6'-fluoro-3'-methyl-2',3'-dihydrospiro[cyclobutane-1,1'-pyrrolo[2,3-c]quinoline]-2'-one | *** | |
| Example 558 | N-(5-(7'-Fluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | **** | |
| Example 559 | Methyl 2-(3-(dimethylamino)propoxy)-5-(3'-methyl-2'-oxo-2',3'-dihydrospiro[cyclobutane-1,1'-pyrrolo[2,3-c]quinolin]-8'-yl)-3-(methylsulfonamido)benzoale | **** | |
| Example 560 | cis-N-(5-(3,7'-Difluoro-3'-methyl-2'-oxo-2',3'-dihydrospiro[cyclobutane-1,1'-pyrrolo[2,3-c]quinolin]-8'-yl)-2-(2-(isopropylamino)ethoxy)pyridin-3-yl)methanesulfonamide | *** | |
| Example 561 | N-(5-[7-Methyl-8-oxo-7,8-dihydrospiro[cyclobutane-1,9-pyrrolo[2,3-c][1,5-naphthyridin]-2-yl]-2-[2-[(propan-2-yl)amino]ethoxy]pyridin-3-yl)methanesulfonamide | *** | |
| Example 562 | N-(2-(2-(Isopropylamino)ethoxy)-5-(3'-methyl-2'-oxo-2',3'-dihydrospiro[cyclobutane-1,1'-pyrrolo[2,3-c][1,7]naphthyridin]-8'-yl)pyridin-3-yl)methanesulfonamide | **** | |
| Example 563 | N-(3-cyano-2-(3-(Dimethylamino)propoxy)-5-(3'-methyl-2'-oxo-2',3'-dihydrospiro[cyclobutane-1,1'-pyrrolo[2,3-c]quinolin]-8'-yl)phenyl)methanesulfonamide | *** | |
| Example 564 | 2-(3-(Dimethylamino)propoxy)-N,N-dimethyl-5-(3'-methyl-2'-oxo-2',3'-dihydrospiro[cyclobutane-1,1'-pyrrolo[2,3-c]quinolin]-8'-yl)-3-(methylsulfonamido)benzamide | **** | |
| Example 565 | 2-(3-(Dimethylamino)propoxy)-N-methyl-5-(3'-methyl-2'-oxo-2',3'-dihydrospiro[cyclobutane-1,1'-pyrrolo[2,3-c]quinolin]-8'-yl)-3-(methylsulfonamido)benzamide | **** | |

Assay potency ranges:
*$IC_{50} < 0.5$ nM; $0.5$ nM $< IC_{50} < 1$ nM; *$1$ nM $< IC_{50} < 100$ nM. ****$IC50 > 100$ nM remove wash solution, turn plate upside down onto a thin paper towel and centrifuge at 1000 rpm for 1 min to absorb all wash buffer. Clean the bottom of plate with moist lint free paper. Scan plate immediately using ODYSSEY CLx (LI-COR) for the best results.

DNA-PK Enzyme-Linked Immunosorbent Assay:

On day one, coat 96-well plate (ThermoFisher. Cat #: 442404) with GST-p53 (1-101) peptide (purified by Pharmaron, BCS department) by diluting 3 µg of GST-p53 each well with 0.1 M $Na_2CO_3/NaHCO_3$, pH 9.6. Incubate the plate overnight at 4° C. The second day, remove coating buffer, wash 2× with PBST (1×PBS containing 0.1% Tween-20). Then add DNA-PK enzyme solution (Invitrogen, #PR9107A; the final DNA-PK concentration is 0.1 µg/mL), series dilution compounds (the final top concentration is 100 nM, 3 fold series dilution, with total 10 doses) and ATP solution (the final ATP concentration is 20 µM) to the 96-well plate. Incubate the plate at 25° C. for 1 hour. Then wash 3× with PBST (1×PBS containing 0.1% Tween-20). Block the plate with PBST+ 1% BSA at 4° C. overnight. The third day, wash 4× with PBST (1×PBS containing 0.1% Tween-20). Then add Phospho-p53 primary antibody (cell signaling Technology, #9286, Phospho-p53 (Ser15) (16G8) Mouse mAb) (1/1000) to each well. Seal with plate and incubate the plate for 1 h at 37° C. Wash 4× with PBST (1×PBS containing 0.1% Tween-20), add 100 µL of HRP-linked secondary antibody (Cell signaling Technology, #7076, Anti-mouse IgG, HRP-linked Antibody) (1/1000) to each well. Seal with tape and incubate the plate for 30 min at 37° C. Wash 4× with PBST (1×PBS containing 0.1% Tween-20), add 100 µL of TMB (Cell signaling Technology, #7004) substrate to each well. Seal with tape and incubate the plate for 10 min at 37° C. Then add 100 µL of Stop solution (Cell signaling Technology, #7002) to each well. Read the plate at 450 nm to detect absorption.

In some embodiments, the compound of the invention is selected from the group consisting of compounds listed in the table below.

Assay Results

It is to be understood that the invention is not limited to the particular embodiments of the invention described above, as variations of the particular embodiments may be made and still fall within the scope of the appended claims.

What is claimed is:

1. A compound of Formula (I):

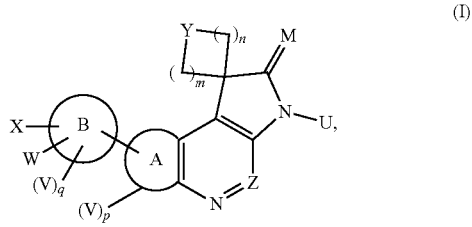

(I)

or a stereoisomer, enantiomer, tautomer thereof or a mixture thereof;
or a pharmaceutically acceptable salt thereof;
wherein
m is 0, 1, 2, 3, or 4;
n is 1, 2, 3, or 4;
p and q are each independently 0, 1, 2, or 3;

is a fused cyclyl, a fused heterocyclyl, a fused aryl or a fused heteroaryl;

is a mono-cyclic or bi-cyclic ring, a mono-heterocyclic or bi-heterocyclic ring, an aryl or heteroaryl;

Y is $-C(R^{1a})H-$, $-C(O)-$, $-O-$, $-N(R^5)-$, $-S(O)_r-$ (where r is 0, 1 or 2), $-S(O)_t(NR^5)-$ (where t is 1 or 2), $-P(O)(R^3)-O-$, $-O-P(O)(R^3)-$, $P(O)(R^3)-N(R^5)-$, $-N(R^5)-P(O)(R^3)-$, $-CHF-$, $-CF_2-$, $-OC(O)-$, $-C(O)O-$, $-C(O)N(R^5)-$ or $-N(R^5)C(O)-$, M is O, S, or $NR^5$;

U is hydrogen or alkyl;

V, W, and X are each independently selected from the group consisting of hydrogen, optionally substituted alkyl, optionally substituted alkenyl, optionally substituted alkynyl, halo, optionally substituted haloalkyl, optionally substituted haloalkenyl, optionally substituted haloalkoxy, optionally substituted cycloalkyl, optionally substituted aryl, optionally substituted heterocyclyl, optionally substituted heteroaryl, $-R^6-$CN, $-R^6-NO_2$, $-R^6-OR^5$, $-R^6-N(R^4)R^5$, $-O-R^6-N(R^4)R^5$, $-N=C(R^4)R^5$, $-S(O)_rR^4$, $-OS(O)_2CF_3$, $-R^6-C(O)R^4$, $-C(S)R^4$, $-R^6-C(O)OR^4$, $-C(S)OR^4$, $-R^6-C(O)N(R^4)R^5$, $-C(S)N(R^4)R^5$, $-N(R^5)C(O)R^4$, $-N(R^5)C(S)R^4$, $-N(R^5)C(O)OR^4$, $-N(R^5)C(S)OR^4$, $-N(R^5)C(O)N(R^4)R^5$, $-N(R^5)C(S)N(R^4)R^5$, $-N(R^5)S(O)_rR^4$, $-N(R^5)S(O)_tN(R^4)R^5$, $-R^6-S(O)_tN(R^4)R^5$, $-O-P(O)(R^4)R^5$, $-O-P(O)R^4O(R^4)$, $-O-P(O)R^4N(R^4)R^5$, $-N(R^5)-P(O)(R^4)R^5$, $-N(R^5)-P(O)R^4O(R^4)$, $-N(R^5)-P(O)R^4N(R^4)R^5$, $-N(R^5)-P(O)O(R^4)N(R^4)R^5$, $-N(R^5)-P(O)N(R^4)R^5N(R^4)R^5$, $-N(R^5)C(=NR^5)R^4$, $-N(R^5)C(=NR^5)N(R^4)R^5$, and $-N(R^5)C(=N-CN)N(R^4)R^5$, wherein each r is independently 0, 1, or 2 and each t is independently 1 or 2;

or two adjacent V, or W, or X together with the carbon ring atoms to which they are directly attached, form a fused ring selected from optionally substituted cycloalkyl, optionally substituted aryl, optionally substituted heterocyclyl, and optionally substituted heteroaryl;

Z is $C(R^{1a})$ or N;

$R^{1a}$ is a hydrogen, optionally substituted alkyl, halo, CN, $NO_2$, or $-OR^5$;

$R^3$ is an optionally substituted alkyl, $-OR^5$, or $-N(R^4)R^5$;

each $R^4$ and $R^5$ is independently selected from group consisting of hydrogen, optionally substituted alkyl, optionally substituted alkenyl, optionally substituted alkynyl, optionally substituted haloalkyl, optionally substituted alkoxyalkyl, optionally substituted cycloalkyl, optionally substituted aryl, optionally substituted heterocyclyl, and optionally substituted heteroaryl;

or when $R^4$ and $R^5$ are each attached to the same nitrogen atom, $R^4$ and $R^5$, together with the nitrogen atom to which they are attached, form a optionally substituted heterocyclyl or optionally substituted heteroaryl; and each $R^6$ is a direct bond or a linear or branched optionally substituted alkylene chain, a linear or branched optionally substituted alkenylene chain, a linear or branched optionally substituted alkynylene chain, or optionally substituted heterocyclylene.

2. The compound according to claim 1, wherein Y is $-C(R^{1a})H-$, $-O-$, $-N(R^5)-$, $-CHF-$, or $-CF_2-$.

3. The compound according to claim 1, wherein Y is $-C(R^{1a})H-$.

4. The compound according to claim 1, wherein M is O.

5. The compound according to claim 1, wherein $R^{1a}$ is a hydrogen, alkyl, halo, CN, or $-OR^5$.

6. The compound according to claim 1, wherein:
V, W, and X are each independently selected from the group consisting of hydrogen, optionally substituted alkyl, halo, optionally substituted cycloalkyl, optionally substituted aryl, optionally substituted heterocyclyl, optionally substituted heteroaryl, —$R^6$—N($R^4$)$R^5$, —O—$R^6$—N($R^4$)$R^5$, —N($R^5$)S(O)$_r$$R^4$, and —N($R^5$)S(O)$_t$N($R^4$)$R^5$, wherein each r is independently 0, 1, or 2, and each t is independently 1 or 2;

or two adjacent V, or W, or X together with the carbon ring atoms to which they are directly attached, form a fused ring selected from optionally substituted cycloalkyl, optionally substituted aryl, optionally substituted heterocyclyl, and optionally substituted heteroaryl.

7. The compound according to claim 1, wherein V, W, and X are each independently selected from the group consisting of hydrogen, optionally substituted alkyl, halo, optionally substituted heterocyclyl, —$R^6$—N($R^4$)$R^5$, —O—$R^6$—N($R^4$)$R^5$, —N($R^5$)S(O)$_r$$R^4$, and —N($R^5$)S(O)$_t$N($R^4$)$R^5$, wherein each r is independently 0, 1, or 2 and each t is independently 1 or 2;

or two adjacent V, or W, or X together with the carbon ring atoms to which they are directly attached, form a fused ring selected from optionally substituted cycloalkyl, optionally substituted aryl, optionally substituted heterocyclyl, and optionally substituted heteroaryl.

8. A compound of Formula (II):

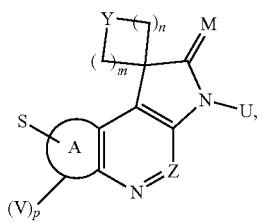

(II)

or a stereoisomer, enantiomer, tautomer thereof or a mixture thereof;
wherein
m is 0, 1, 2, 3, or 4;
n is 1, 2, 3, or 4;
p is 0, 1, 2, 3;

is a fused cyclyl, a fused heterocyclyl, a fused aryl or a fused heteroaryl;
Y is —(C($R^{1a}$)H)—;
M is O;
U is hydrogen or alkyl;
V is selected from the group consisting of nitro, hydrogen, optionally substituted alkyl, optionally substituted alkenyl, optionally substituted alkynyl, halo, optionally substituted haloalkyl, optionally substituted haloalkenyl, optionally substituted haloalkoxy, optionally substituted cycloalkyl, optionally substituted aryl, optionally substituted heterocyclyl, optionally substituted heteroaryl, —$R^6$—CN, —$R^6$—NO$_2$, —$R^6$—O$R^5$, —$R^6$—N($R^4$)$R^5$, —N=C($R^4$)$R^5$, —S(O)$_r$$R^4$ (where r is 0, 1 or 2), —OS(O)$_2$CF$_3$, —$R^6$—C(O)$R^4$, —C(S)$R^4$, —C($R^4$)$_2$C(O)$R^5$, —$R^6$—C(O)O$R^4$, —C(S)O$R^4$, —$R^6$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_r$$R^4$, —N($R^5$)S(O)$_t$N($R^4$)$R^5$, —$R^6$—S(O)$_t$N($R^4$)$R^5$, —N($R^5$)C(=N$R^5$)N($R^4$)$R^5$, and —N($R^5$)C(=N—CN)N($R^4$)$R^5$, wherein each r is independently 0, 1, or 2 and each t is independently 1 or 2;
Z is C($R^{1a}$), or N;
$R^{1a}$ is a hydrogen, alkyl, halo, CN, NO$_2$ or —O$R^5$;
$R^3$ is an alkyl, —O$R^5$, or —N($R^4$)$R^5$;
S is halo, boronate, or boronic acid.

9. The compound according to claim 1, wherein the compound is selected from the group consisting of:
N-(2-(3-(Dimethylamino)propoxy)-5-(3'-methyl-2'-oxo-2',3'-dihydrospiro[cyclopentane-1,1'-pyrrolo[2,3-c]quinolin]-8'-yl)pyridin-3-yl)benzenesulfonamide;
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide;
N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)benzenesulfonamide;
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide;
3-(1-Cyanoethyl)-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide;
N-(5-(3'-Methyl-2'-oxo-2',3'-dihydrospiro[cyclopropane-1,1'-pyrrolo[2,3-c]quinolin]-8'-yl)-2-(4-methylpiperazin-1-yl)pyridin-3-yl)benzenesulfonamide;
N-(5-(3'-Methyl-2'-oxo-2',3'-dihydrospiro[cyclopropane-1,1'-pyrrolo[2,3-c]quinolin]-8'-yl)-2-(3-(pyrrolidin-1-yl)propoxy)pyridin-3-yl)cyclopropanesulfonamide;
N-(5-(3'-Methyl-2'-oxo-2',3'-dihydrospiro[cyclopropane-1,1'-pyrrolo[2,3-c]quinolin]-8'-yl)-2-(3-(piperidin-1-yl)propoxy)pyridin-3-yl)benzenesulfonamide hydrochloride;
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-fluorobenzenesulfonamide;
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)pyrrolidine-1-sulfonamide;
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-1-methyl-1H-pyrazole-4-sulfonamide;
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)thiophene-3-sulfonamide;
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-methoxybenzenesulfonamide hydrochloride;
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-4-methylbenzenesulfonamide;
N-(2-(3-(Dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)-2-fluorobenzenesulfonamide;

N-(2-(4-(Dimethylamino)piperidin-1-yl)-5-(3'-methyl-2'-oxo-2',3'-dihydrospiro[cyclopropane-1,1'-pyrrolo[2,3-c]quinolin]-8'-yl)pyridin-3-yl)cyclopropanesulfonamide;

3,5-Dichloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide;

4-Chloro-N-(2-(3-(dimethylamino)propoxy)-5-(3'-methyl-2'-oxo-2',3'-dihydrospiro[cyclopropane-1,1'-pyrrolo[2,3-c]quinolin]-8'-yl)pyridin-3-yl)benzenesulfonamide hydrochloride;

8'-{6-[3-(Dimethylamino)propoxy]-5-[(dimethylsulfamoyl)amino]pyridine-3-yl}-3'-methyl-2',3'-dihydrospiro[cyclobutane-1,1'-pyrrolo[2,3-c]quinoline]-2'-one hydrochloride;

N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)benzenesulfonamide hydrochloride;

N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-fluorobenzenesulfonamide hydrochloride;

N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)azetidine-1-sulfonamide;

N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-2-fluorobenzenesulfonamide hydrochloride;

N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide hydrochloride;

N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide;

N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide;

2-Fluoro-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)benzenesulfonamide hydrochloride;

N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)thiazole-5-sulfonamide hydrochloride;

4-Methyl-N-(5-(3'-methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)piperazine-1-sulfonamide;

N-(5-(3'-Methyl-2'-oxo-2',3'-dihydrospiro[cyclobutane-1,1'-pyrrolo[2,3-c]quinolin]-8'-yl)-2-(3-(piperidin-1-yl)propoxy)pyridin-3-yl)piperazine-1-sulfonamide;

N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-2-fluorobenzenesulfonamide;

N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)oxetane-3-sulfonamide;

N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)-2,4-difluorobenzenesulfonamide hydrochloride;

N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)cyclopropanesulfonamide hydrochloride;

8'-(6-{[1,4'-Bipiperidine]-1'-yl}-5-[(dimethylsulfamoyl)amino]pyridin-3-yl)-3'-methyl-2',3'-dihydrospiro[cyclobutane-1,1'-pyrrolo[2,3-c]quinoline]-2'-one;

8'-(6-{[1,4'-Bipiperidine]-1'-yl}-5-{[ethyl(methyl)sulfamoyl]amino}pyridin-3-yl)-3'-methyl-2',3'-dihydrospiro[cyclopropane-1,1'-pyrrolo[2,3-c]quinoline]-2'-one;

N-(2-(3-(Dimethylamino)propoxy)-5-(9'-fluoro-3'-methyl-2'-oxo-2',3'-dihydrospiro[cyclopropane-1,1'-pyrrolo[2,3-c]quinolin]-8'-yl)pyridin-3-yl)-4-methylbenzenesulfonamide;

N-(2-([1,4'-Bipiperidin]-1'-yl)-5-(3'-methyl-2'-oxo-2',3'-dihydrospiro[cyclopropane-1,1'-pyrrolo[2,3-c]quinolin]-8'-yl)pyridin-3-yl)-6-methylpyridine-3-sulfonamide;

N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)-4-hydroxybenzenesulfonamide hydrochloride;

N-(2-(4-(Dimethylamino)piperidin-1-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide;

8'-{6-[4-(Dimethylamino)piperidin-1-yl]-5-[(dimethylsulfamoyl)amino]pyridin-3-yl}-3'-methyl-2',3'-dihydrospiro[cyclobutane-1,1'-pyrrolo[2,3-c]quinoline]-2'-one;

N-(5-(3'-Methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)cyclopropanesulfonamide hydrochloride;

N-(2-([1,4'-Bipiperidin]-1'-yl)-5-(3'-methyl-2'-oxo-2',3'-dihydrospiro[cyclobutane-1,1'-pyrrolo[2,3-c]quinolin]-8'-yl)pyridin-3-yl)methanesulfonamide;

N-(5-(3'-Methyl-2'-oxo-2',3'-dihydrospiro[cyclobutane-1,1'-pyrrolo[2,3-c]quinolin]-8'-yl)-2-(4-methylpiperazin-1-yl)pyridin-3-yl)methanesulfonamide;

8'-{5-[(Dimethylsulfamoyl)amino]-6-(4-methylpiperazin-1-yl)pyridin-3-yl}-3'-methyl-2',3'-dihydrospiro[cyclobutane-1,1'-pyrrolo[2,3-c]quinoline]-2'-one;

N-(2-(3-(Methyl(2,2,2-trifluoroethyl)amino)propoxy)-5-(3'-methyl-2'-oxo-2',3'-dihydrospiro[cyclobutane-1,1'-pyrrolo[2,3-c]quinolin]-8'-yl)pyridin-3-yl)methanesulfonamide;

N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)propoxy)pyridin-3-yl)benzenesulfonamide;

N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)propoxy)pyridin-3-yl)cyclopropanesulfonamide;

N-(5-(3'-Methyl-2'-oxo-2',3'-dihydrospiro[cyclobutane-1,1'-pyrrolo[2,3-c]quinolin]-8'-yl)-2-(3-(pyrrolidin-1-yl)propoxy)pyridin-3-yl)methanesulfonamide;

N-(2-(3-(Dimethylamino)propoxy)-5-(3'-methyl-2'-oxo-2',3'-dihydrospiro[cyclobutane-1,1'-pyrrolo[2,3-c]quinolin]-8'-yl)pyridin-3-yl)ethanesulfonamide;

N-(5-(3'-Methyl-2'-oxo-2',3'-dihydrospiro[cyclobutane-1,1'-pyrrolo[2,3-c]quinolin]-8'-yl)-2-(3-(methylamino)propoxy)pyridin-3-yl)methanesulfonamide formate; and 8'-{5-[(Dimethylsulfamoyl)amino]-6-[3-(pyrrolidin-1-yl)propoxy]pyridin-3-yl}-3'-methyl-2',3'-dihydrospiro[cyclobutane-1,1'-pyrrolo[2,3-c]quinoline]-2'-one.

10. The compound according to claim 8, wherein said intermediate is selected from the group consisting of
8'-Bromo-3'-methylspiro[cyclopentane-1,1'-pyrrolo[2,3-c]quinolin]-2'(3'H)-one;
8'-Bromo-3'-methylspiro[cyclohexane-1,1'-pyrrolo[2,3-c]quinolin]-2'(3'H)-one;
8'-Bromo-3'-methyl-2,3,5,6-tetrahydrospiro[pyran-4,1'-pyrrolo[2,3-c]quinolin]-2'(3'H)-one;
8'-Bromo-3'-methyl-3-((tetrahydro-2H-pyran-2-yl)oxy)spiro[cyclobutane-1,1'-pyrrolo[2,3-c]quinolin]-2'(3'H)-one;
8'-Bromo-3'-methylspiro[oxetane-3,1'-pyrrolo[2,3-c]quinolin]-2'(3'H)-one;
8'-Bromo-9'-fluoro-3'-methylspiro[cyclobutane-1,1'-pyrrolo[2,3-c]quinolin]-2'(3'H)-one;
8'-Bromo-7'-fluoro-3'-methylspiro[cyclobutane-1,1'-pyrrolo[2,3-c]quinolin]-2'(3'H)-one; and
8'-Bromo-3'-methylspiro[cyclopropane-1,1'-pyrrolo[2,3-c] quinolin]-2'(3'H)-one.

11. A pharmaceutical composition comprising a therapeutically effective amount of a compound according to claim 1 or a pharmaceutically acceptable salt thereof and a pharmaceutically acceptable carrier or excipient.

12. A method of treating an oncology disease or disorder, comprising administering a therapeutically effective amount of the compound according to claim 1 or a pharmaceutically acceptable salt thereof to a patient in need thereof.

13. A method of treating a disease or disorder, comprising administering a therapeutically effective amount of the compound according to claim 1 or a pharmaceutically acceptable salt thereof to a patient in need thereof.

14. A method of treating an oncology disease or disorder, comprising administering a therapeutically effective amount of compound according to claim 1 or a pharmaceutically acceptable salt thereof to a patient in need thereof, wherein the patient is receiving radiotherapy.

15. The method according to claim 14, wherein the compound is administered to the patient concomitantly with the radiotherapy.

16. The method according to claim 14, wherein the compound is administered to the patient before radiotherapy.

17. The method according to claim 14, wherein the compound is administered to the patient after radiotherapy.

18. The method according to claim 14, wherein the radiotherapy comprises external, internal, brachytherapy, or systemic exposure.

19. A method of treating an oncology disease or disorder, comprising the step of administering a therapeutically effective amount of the compound according to claim 1 or a pharmaceutically acceptable salt thereof to a patient in need thereof, wherein the patient is receiving an anti-tumor agent.

20. The method according to claim 19, wherein the anti-tumor agent is cisplatin, oxaliplatin, carboplatin, valrubicin, idarubicin, calicheamicin, or a PARP inhibitor.

21. The method according to claim 19, wherein the anti-tumor agent is an anti-tumor biological agent or immunotherapy.

22. The method according to claim 19, wherein the compound is administered to the patient concomitantly with the anti-tumor agent.

23. The method according to claim 19, wherein the compound is administered to the patient before the anti-tumor agent.

24. The method according to claim 19, wherein the compound is administered to the patient after the anti-tumor agent.

25. A method of treatment for warm blooded animals in need of such treatment that involves the administration of the compound according to claim 1 or a pharmaceutically acceptable salt thereof in a therapeutically effective amount.

* * * * *